(12) United States Patent
Wacker et al.

(10) Patent No.: US 11,254,663 B2
(45) Date of Patent: Feb. 22, 2022

(54) SUBSTITUTED BICYCLIC COMPOUNDS AS FARNESOID X RECEPTOR MODULATORS

(71) Applicant: BRISTOL-MYERS SQUIBB COMPANY, Princeton, NJ (US)

(72) Inventors: Dean A. Wacker, Yardley, PA (US); Susheel Jethanand Nara, Mumbai (IN); Srinivas Cheruku, Bangalore (IN); Kandhasamy Sarkunam, Hosur (IN); Firoz Ali Jaipuri, Bengaluru, IN (US); Soodamani Thangavel, Krishnagiri (IN); Srinivas Jogi, Bangalore (IN); Pavan Kalyan Kathi, Bangalore (IN)

(73) Assignee: Bristol-Myers Squibb Company, Princeton, NJ (US)

( * ) Notice: Subject to any disclaimer, the term of this patent is extended or adjusted under 35 U.S.C. 154(b) by 15 days.

(21) Appl. No.: 16/789,551

(22) Filed: Feb. 13, 2020

(65) Prior Publication Data
US 2021/0261535 A1    Aug. 26, 2021

Related U.S. Application Data

(60) Provisional application No. 62/806,066, filed on Feb. 15, 2019.

(51) Int. Cl.
| | | |
|---|---|---|
| C07D 413/12 | (2006.01) | |
| C07D 271/06 | (2006.01) | |
| A61P 11/00 | (2006.01) | |

(52) U.S. Cl.
CPC ............ C07D 413/12 (2013.01); A61P 11/00 (2018.01); C07D 271/06 (2013.01)

(58) Field of Classification Search
CPC .......................... C07D 413/12; C07D 271/06
See application file for complete search history.

(56) References Cited

U.S. PATENT DOCUMENTS

| | | |
|---|---|---|
| 8,158,665 B2 | 4/2012 | Caldwell et al. |
| 8,907,095 B2 | 12/2014 | Xia et al. |
| 9,539,244 B2 | 1/2017 | Kinzel et al. |
| 9,751,874 B2 | 9/2017 | Gege et al. |
| 2010/0152166 A1 | 6/2010 | Genin et al. |
| 2011/0034507 A1 | 2/2011 | Akwabi-Ameyaw et al. |
| 2015/0366856 A1 | 12/2015 | Tully et al. |
| 2016/0176861 A1 | 6/2016 | Gege et al. |
| 2017/0298068 A1 | 10/2017 | Gege et al. |
| 2017/0304270 A1 | 10/2017 | Or et al. |
| 2017/0304271 A1 | 10/2017 | Or et al. |
| 2017/0304272 A1 | 10/2017 | Or et al. |
| 2017/0333399 A1 | 11/2017 | Or et al. |
| 2017/0355693 A1 | 12/2017 | Blomgren et al. |
| 2017/0355694 A1 | 12/2017 | Gege |
| 2017/0368038 A1 | 12/2017 | Badman et al. |
| 2019/0002452 A1 | 1/2019 | Zhang et al. |

FOREIGN PATENT DOCUMENTS

| | | |
|---|---|---|
| CN | 106146483 A | 11/2016 |
| CN | 106632294 A | 5/2017 |
| CN | 107021958 A | 8/2017 |
| EP | 3034499 A1 | 6/2016 |
| EP | 3034501 A1 | 6/2016 |
| EP | 3401315 A1 | 11/2018 |
| WO | WO199313101 A1 | 7/1993 |
| WO | WO199817276 A1 | 4/1998 |
| WO | WO03099821 A1 | 12/2003 |
| WO | WO2004046162 | 6/2004 |
| WO | WO2006006490 | 1/2006 |
| WO | WO2007076260 | 7/2007 |
| WO | WO2008051942 | 5/2008 |
| WO | WO2008094556 | 8/2008 |
| WO | WO2009009059 | 1/2009 |
| WO | WO2010058318 | 5/2010 |
| WO | WO2011006935 | 1/2011 |
| WO | WO2011045292 | 4/2011 |
| WO | WO2012087520 | 6/2012 |
| WO | WO2013186159 | 12/2013 |
| WO | WO2014054053 A1 | 4/2014 |
| WO | WO2015172747 A1 | 11/2015 |
| WO | WO2016096115 A1 | 6/2016 |
| WO | WO2017049173 A1 | 3/2017 |
| WO | WO2017133521 A1 | 8/2017 |
| WO | WO2017145040 A1 | 8/2017 |
| WO | WO2017145041 A1 | 8/2017 |

(Continued)

OTHER PUBLICATIONS

Cancer and Metastasis Reviews (1998), 17(1), 91-106.*

(Continued)

*Primary Examiner* — Shawquia Jackson
(74) *Attorney, Agent, or Firm* — Gary Greenblatt

(57) ABSTRACT

Disclosed are compounds of Formula (I):

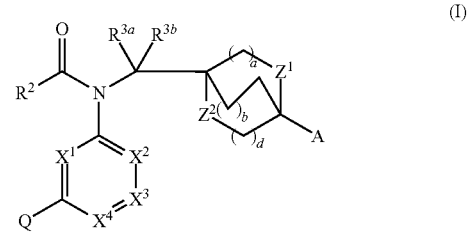

or a stereoisomer, a tautomer, or a salt or solvate thereof, wherein all the variables are as defined herein. These compounds modulate the activity of farnesoid X receptor (FXR), for example, as agonists. Also disclosed are pharmaceutical compositions comprising these compounds and methods of treating a disease, disorder, or condition associated with FXR dysregulation, such as pathological fibrosis, transplant rejection, cancer, osteoporosis, and inflammatory disorders, by using the compounds and pharmaceutical compositions.

26 Claims, 3 Drawing Sheets

(56) References Cited

FOREIGN PATENT DOCUMENTS

| WO | WO2018059314 A1 | 4/2018 |
|----|-----------------|--------|
| WO | WO2018170165 A1 | 9/2018 |
| WO | WO2018170166 A1 | 9/2018 |
| WO | WO2018170167 A1 | 9/2018 |
| WO | WO2018170173 A1 | 9/2018 |
| WO | WO2018170182 A1 | 9/2018 |

OTHER PUBLICATIONS

Science (1999), vol. 286, 531-537.*
Cancer [online], [retrieved on Jul. 6, 2007]. Retrieved from the internet, URL http://www.nlm.nih.gov/medlineplus/cancer.html>.*
Claudel, Thierry et al., "The Farnesoid X Receptor: A Novel Drug Target?", Expert Opin. Investig. Drugs, vol. 13(9), pp. 1135-1148, (2004).
Sepe, Valentina et al., "Farnesoid X Receptor Modulators 2014-present: A Patent Review, Expert Opinion on Therapeutic Patents", vol. 28, No. 5, pp. 351-364 (2018).
Tully, David C. et al., "Discovery of Tropifexor (LJN452), a Highly Potent Non-bile Acid FXR Agonist for the Treatment of Cholestatic Liver Diseases and Nonalcoholic Steatohepatitis (NASH)", Journal of Medicinal Chemistry, vol. 60, pp. 9960-9973 (2017).

* cited by examiner

Scheme 12

Scheme 13

Scheme 15

SUBSTITUTED BICYCLIC COMPOUNDS AS FARNESOID X RECEPTOR MODULATORS

CROSS REFERENCE

This application claims the benefit of U.S. Provisional Application Ser. No. 62/806,066 filed Feb. 15, 2019 which is incorporated herein in its entirety.

DESCRIPTION

The present invention relates generally to compounds useful as farnesoid X receptor (FXR) modulators, pharmaceutical compositions comprising such compounds and to their use in therapy, especially in the treatment or prophylaxis of diseases, disorders, and conditions for which an FXR modulator is indicated.

FXR or NR1H4 (nuclear receptor subfamily 1, group H, member 4) is a nuclear receptor that can activate the expression of specific target genes in a ligand-dependent manner. FXR is expressed in the liver, throughout the gastrointestinal tract, colon, ovary, adrenal gland, kidney, and in the gall bladder and biliary tree in humans. FXR forms a heterodimer with Retinoid X Receptor (RXR) and binds to specific response elements in target genes to regulate gene transcription (B. M. Forman et al., Cell 1995; 81: 687; W. Seol et al., Mol. Endocrinol. 1995; 9: 72). The FXR/RXR heterodimer typically binds to an inverted repeat of a consensus hexanucleotide sequence (AGGTCA) separated by a single nucleotide, i.e. an IR-1 sequence. The relevant physiological ligands of FXR are bile acids including chenodeoxycholic acid and its taurine-conjugate (D. J. Parks et al., Science 1999; 284: 1365; M. Makishima et al., Science 1999; 284: 1362). FXR activation regulates the expression of multiple genes that encode enzymes and transporters involved in bile acid synthesis, influx, and efflux from the liver and intestine resulting in a net decrease in total endogenous bile acids in a negative feedback loop. FXR is involved in paracrine and endocrine signaling by upregulating the expression of the cytokine Fibroblast Growth Factor 15 (rodents) or 19 (primates), which can also contribute to the regulation of bile acid concentrations (Holt et al., Genes Dev. 2003; 17: 1581; Inagaki et al., Cell Metab 2005; 2: 217). Therefore, FXR is considered to be a master regulator of bile acid homeostasis.

One use of FXR agonists is for the treatment of diseases in which bile acids are dysregulated, including cholestatic diseases (e.g. primary biliary cirrhosis and primary sclerosing cholangitis) that can lead to fibrosis, cirrhosis, cholangiocarcinoma, hepatocellular carcinoma, liver failure, and death. While elevated bile acid concentrations in the liver have deleterious effects, bile acids also affect the microflora and integrity of the small intestine. Obstruction of bile flow in humans or rodents causes proliferation of intestinal bacteria and mucosal injury, which can lead to bacterial translocation across the mucosal barrier and systemic infection (Berg, Trends Microbiol. 1995; 3: 149-154). Mice lacking FXR have increased ileal levels of bacteria and a compromised epithelial barrier, while activation of intestinal FXR plays an important role in preventing bacterial overgrowth and maintaining the integrity of the intestinal epithelium (Inagaki et al., Proc Natl Acad Sci 2006; 103: 3920-3925). Over time, FXR null mice spontaneously develop hepatocellular carcinoma, and this can be abrogated by selective re-activation of FXR in the intestine (Degirolamo et al., Hepatology 61: 161-170). Pharmacological activation of FXR with a small molecule agonist or transgenic expression of FXR in the intestine can normalize bile acid concentrations, decrease cellular proliferation in hepatic bile ducts, and reduce inflammatory cell infiltration, necrotic area, and liver fibrosis in rodent models of cholestasis (Liu et al., J. Clin. Invest. 2003; 112:1678-1687; Modica et al., Gastroenterology. 2012; 142: 355-365). Some of these beneficial effects observed in preclinical models of cholestasis have translated to human patients, and the FXR agonist, obeticholic acid (OCA or OCALIVA™), has been approved for the treatment of primary biliary cirrhosis (https://www.fda.gov/newsevents/newsroom/pressannouncements/ucm503964.htm).

In addition to controlling bile acid homeostasis, FXR agonists regulate the hepatic expression of hundreds of genes encoding proteins involved in cholesterol and lipid metabolism and transport, glucose homeostasis, inflammation, chemotaxis, and apoptosis among other pathways (Zhan et al., PLoS One 2014; 9: e105930; Ijssennagger et al., J Hepatol 2016; 64: 1158-1166). Consistent with these broad effects on gene expression, FXR agonists have also been investigated in preclinical models of fibrosis, cancer, inflammatory diseases, and metabolic disorders, including dyslipidemia, obesity, type 2 diabetes, nonalcoholic fatty liver disease (NAFLD) and metabolic syndrome (Crawley, Expert Opin. Ther. Patents 2010; 20:1047-1057).

FXR agonists are also being investigated in human clinical trials for the treatment of NAFLD, a more advanced form of fatty liver disease, nonalcoholic steatohepatitis (NASH), and associated complications. NAFLD is one of the most common causes of chronic liver disease in the world today (Vernon et al., Aliment Pharmacol Ther 2011; 34:274-285). The risk factors for developing NAFLD include obesity, type 2 diabetes mellitus (T2DM), insulin resistance, hypertension, and dyslipidemia. In a 6-week clinical trial in T2DM patients with NAFLD, the FXR agonist OCA statistically significantly improved insulin sensitivity and reduced body weight, showing beneficial effects on some of these risk factors (Mudaliar et al., Gastroenterology 2013; 145: 574-582). NASH is the most severe and progressive form of NAFLD and includes the histological findings of hepatic steatosis, inflammation, and ballooning degeneration with varying amounts of pericellular fibrosis (Sanyal et al., Hepatology 2015; 61:1392-1405). In a 72-week clinical trial in patients with NASH, OCA statistically significantly improved hepatic steatosis, lobular inflammation, hepatocyte ballooning, and fibrosis as assessed by histological analyses of liver biopsies (Neuschwander-Tetri et al., Lancet 2015; 385: 956-965). These data also suggest the potential for FXR agonists to show benefit on clinical outcomes given that NASH is the second leading cause of hepatocellular carcinoma (HCC) and liver transplantation in the United States (Wong et al., Hepatology 2014; 59: 2188-2195).

The present invention provides novel compounds for treating a disease, disorder, or condition associated with farnesoid X receptor (FXR) activity in a patient in need thereof.

SUMMARY OF THE INVENTION

In one aspect, the present invention provides compounds of Formula (I) as well as the subgenera and species thereof, including stereoisomers, tautomers, pharmaceutically acceptable salts, and solvates thereof, which are useful as FXR modulators.

In another aspect, the present invention also provides processes and intermediates for making the compounds of the present invention.

In another aspect, the present invention also provides pharmaceutical compositions comprising a pharmaceutically acceptable carrier and at least one of the compounds of the present invention or stereoisomers, tautomers, pharmaceutically acceptable salts, or solvates thereof.

In another aspect, the compounds of the invention may be used in therapy, either alone or in combination with one or more additional therapeutic agents.

The compounds of the invention may be used in the treatment of a disease, disorder, or condition associated with activity of farnesoid X receptor (FXR) in a patient in need of such treatment by administering a therapeutically effective amount of the compound, or a stereoisomer, a tautomer, or a pharmaceutically acceptable salt or solvate thereof, to the patient. The disease, disorder, or condition may be related to pathological fibrosis. The compounds of the invention can be used alone, in combination with one or more compounds of the present invention, or in combination with one or more, e.g., one to two, other therapeutic agents.

The compounds of the invention may be used, either as a single agent or in combination with other agents, in the treatment of a disease, disorder, or condition selected from nonalcoholic steatohepatitis (NASH), non-alcoholic fatty liver disease (NAFLD), chronic kidney disease, diabetic kidney disease, primary sclerosing cholangitis (PSC), and primary biliary cirrhosis (PBC). The compounds of the invention may be used, either as a single agent or in combination with other agents, in the treatment of idiopathic pulmonary fibrosis (IPF).

The compounds of the invention may be used for the manufacture of a medicament for the treatment of a disease, disorder, or condition in a patient in need of such treatment.

Other features and advantages of the invention will be apparent from the following detailed description and claims.

BRIEF DESCRIPTION OF THE DRAWINGS

The invention is illustrated by reference to the accompanying drawing described below.

DETAILED DESCRIPTION

Figure 1:
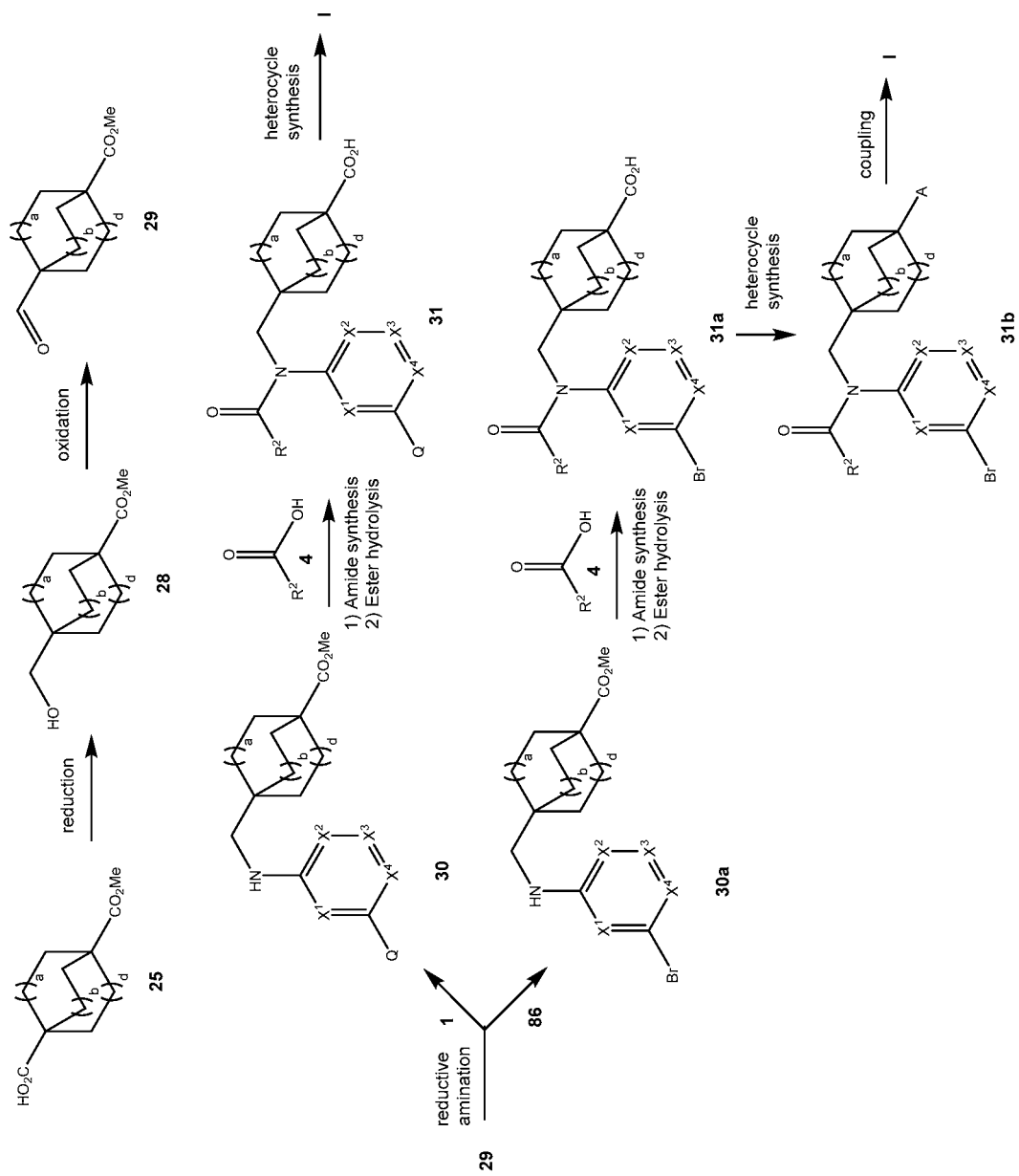
FIG. 1 shows the general reaction Scheme 12.

The present application provides compounds, including all stereoisomers, solvates, prodrugs and pharmaceutically acceptable salt and solvate forms thereof, according to Formula (I). The present application also provides pharmaceutical compositions containing at least one compound according to Formula (I), or a stereoisomer, a tautomer, or a pharmaceutically acceptable salt or a solvate thereof, and optionally at least one additional therapeutic agent. Additionally, the present application provides methods for treating a patient suffering from a FXR-modulated disease or disorder such as for example, biliary fibrosis, liver fibrosis, renal fibrosis, Non-Alcoholic Fatty Liver Disease (NAFLD), Non-Alcoholic Steato-Hepatitis (NASH), primary sclerosing cholangitis (PSC), primary biliary cirrhosis (PBC), and pancreatic fibrosis, by administering to a patient in need of such treatment a therapeutically effective amount of a compound of the present invention, or a stereoisomer, a tautomer, or a pharmaceutically acceptable salt or a solvate thereof, and optionally in combination with at least one additional therapeutic agent.

The first aspect of the present invention provides a compound of Formula (I):

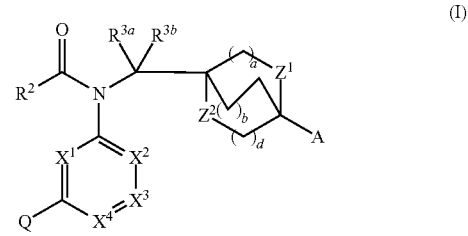

or a stereoisomer, a tautomer, or a salt or solvate thereof, wherein:
$X^1$ is $CR^{5a}$ or N;
$X^2$ is $CR^{5b}$ or N;
$X^3$ is $CR^{5c}$ or N;
$X^4$ is $CR^{5d}$ or N; provided that zero, 1, or 2 of $X^1$, $X^2$, $X^3$, and $X^4$ are N;
$Z^1$ and $Z^2$ are independently $CH_2$ or O; provided that at least one of $Z^1$ and $Z^2$ is $CH_2$;
a is zero or 1;
b is zero, 1, or 2;
d is zero, 1, or 2; provided that $Z^1$ and $Z^2$ are each $CH_2$ when a, b, and d are each zero;
Q is a cyclic group selected from 3- to 8-membered carbocyclyl, 6- to 10-membered aryl, 4- to 10-membered heterocyclyl, and 5- to 10-membered heteroaryl, wherein said cyclic group is substituted with zero to 4 $R^1$;
each $R^1$ is independently hydrogen, halo, cyano, hydroxyl, oxo, $C_{1-6}$ alkyl, $C_{2-6}$ alkenyl, $C_{2-6}$ alkynyl, $C_{1-6}$ alkoxy, —$NH_2$, —$NH(C_{1-6}$ alkyl), —$N(C_{1-6}$ alkyl$)_2$, —$C(O)(C_{1-6}$ alkyl), —$C(O)(C_{3-6}$ cycloalkyl), —$NR^xC(O)R^y$, —$C(O)OR^x$, —$C(O)NR^wR^w$, —$S(O)_2(C_{1-6}$ alkyl), —$S(O)_2(C_{3-6}$ cycloalkyl), —$NR^xS(O)_2(C_{1-6}$ alkyl), —$NR^xS(O)_2(C_{3-6}$ cycloalkyl), —$S(O)_2NR^zR^z$, —$P(O)R^yR^y$, —$(CH_2)_{0-3}$ ($C_{3-6}$ carbocyclyl), —$O(C_{3-6}$ cycloalkyl), —$O(4$- to 6-membered heterocyclyl), —$(CH_2)_{0-3}$(4- to 6-membered heterocyclyl), or —$(CH_2)_{0-3}$(5- or 6-membered heteroaryl), wherein each of said alkyl, alkoxy, alkenyl, and alkynyl is substituted with zero to 4 $R^{1a}$ and each of said cycloalkyl, heterocyclyl, and heteroaryl is substituted with zero to 4 $R^{1b}$;
each $R^{1a}$ is independently halo, hydroxyl, —$NR^wR^w$, oxo, cyano, $C_{1-3}$ alkoxy, $C_{1-3}$ haloalkoxy, —$C(O)OR^x$, —$C(O)NR^wR^w$, or —$NR^xC(O)R^y$;
each $R^{1b}$ is independently halo, oxo, cyano, hydroxyl, —$NH_2$, $C_{1-6}$ alkyl, $C_{1-6}$ alkoxy, —$NH(C_{1-6}$ alkyl), —$N(C_{1-6}$ alkyl$)_2$, or —$NR^xC(O)(C_{1-6}$ alkyl), wherein each of said alkyl and alkoxy is substituted with zero to 6 $R^{1a}$;
$R^2$ is:
(i) $C_{1-6}$ alkyl, $C_{2-6}$ alkenyl, $C_{2-6}$ alkynyl, $C_{1-6}$ alkoxy, or —$NR^vR^v$, wherein each of said alkyl, alkenyl, alkynyl, and alkoxy is substituted with zero to 6 $R^{2a}$;
(ii) $C_{3-5}$ carbocyclyl, $C_{6-8}$ spirobicyclyl, or 4- to 5-membered heterocyclyl, wherein each of said carbocyclyl, spirobicyclyl, and heterocyclyl is substituted with zero to 3 $R^{2b}$; or
(iii) —$CH_2(C_{3-6}$ cycloalkyl), —$CH_2$(4- to 6-membered heterocyclyl), —$NR^x(CH_2)_{0-2}(C_{3-6}$ cycloalkyl), —NR($CH_2)_{0-2}(C_{5-8}$ bicycloalkyl), —NR($CH_2)_{0-2}(C_{5-8}$ spirobicyclyl), —$NR^x(CH_2)_{0-2}$(4- to 6-membered heterocyclyl), —$NR^x(CH_2)_{0-2}$(5- to 6-membered heteroaryl), —$NR^x(CH_2)_{0-2}$(phenyl), —$O(CH_2)_{0-2}(C_{3-6}$ cycloalkyl), —$O(CH_2)_{0-2}(C_{5-8}$ bicycloalkyl), —$O(CH_2)_{0-2}$($C_{5-8}$ spirobicyclyl), —$O(CH_2)_{0-2}$(4- to 6-membered heterocyclyl), —O(CH$_2$)$_{0-2}$(5- to 6-membered heteroaryl), or —O(CH$_2$)$_{0-2}$(phenyl), wherein each of said cycloalkyl, heterocyclyl, bicycloalkyl, spirobicyclyl, aryl, and heteroaryl is substituted with zero to 3 R$^{2b}$;

each R$^{2a}$ is independently halo, cyano, hydroxyl, oxo, C$_{1-3}$ haloalkyl, C$_{1-3}$ alkoxy, C$_{1-3}$ haloalkoxy, —NR$^x$R$^x$, —C(O)(C$_{1-6}$ alkyl), —C(O)(C$_{3-6}$ cycloalkyl), —NR$^x$C(O)R$^y$, —C(O)(C$_{1-6}$ alkyl), —C(O)OR$^x$, —C(O)NR$^w$R$^w$, —S(O)$_2$R$^y$, —S(O)$_2$(C$_{1-3}$ fluoroalkyl), —NR$^x$S(O)$_2$(C$_{1-3}$ alkyl), —NR$^x$S(O)$_2$(C$_{3-6}$ cycloalkyl), —S(O)$_2$NR$^z$R$^z$, or —P(O)R$^y$R$^y$;

each R$^{2b}$ is independently halo, cyano, hydroxyl, oxo, C$_{1-6}$ alkyl, C$_{1-6}$ alkoxy, —NR$^x$R$^x$, —NR$^x$C(O)O(C$_{1-4}$ alkyl), —C(O)(C$_{1-3}$ alkyl), or —S(O)$_2$(C$_{1-3}$ alkyl), wherein each of said alkyl and alkoxy is substituted with zero to 6 R$^{2a}$;

R$^{3a}$ and R$^{3b}$ are independently hydrogen, C$_{1-3}$ alkyl, C$_{1-3}$ haloalkyl, or C$_{3-6}$ cycloalkyl, or R$^{3a}$ and R$^{3b}$, taken together with the carbon atom to which they are attached, form a C$_{3-6}$ cycloalkyl;

A is:
(i) cyano;
(ii) phenyl or a 5- or 10-membered heteroaryl containing 1 to 4 heteroatoms independently selected from N, O, and S, wherein each of said phenyl and heteroaryl is substituted with zero to 3 R$^{4a}$; or
(iii)

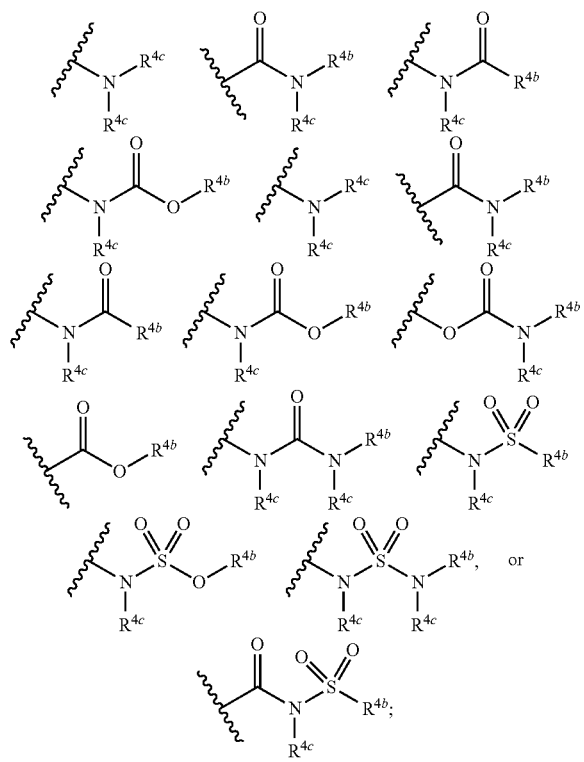

each R$^{4a}$ is independently halo, cyano, hydroxyl, —NH$_2$, C$_{1-6}$ alkyl, C$_{2-6}$ alkenyl, C$_{2-6}$ alkynyl, C$_{1-6}$ alkoxy, —(CH$_2$)$_{0-3}$NH(C$_{1-6}$ alkyl), —(CH$_2$)$_{0-2}$N(C$_{1-6}$ alkyl)$_2$, —(CH$_2$)$_{0-3}$(C$_{3-6}$ cycloalkyl), or —(CH$_2$)$_{0-3}$(4- to 6-membered heterocyclyl), wherein each of said alkyl, alkoxy, alkenyl, and alkynyl is substituted with zero to 6 R$^{4d}$ and each of said cycloalkyl and heterocyclyl is substituted with zero to 3 R$^{4e}$;

R$^{4b}$ is C$_{1-6}$ alkyl, —(CH$_2$)$_{0-3}$(C$_{3-6}$ cycloalkyl), —(CH$_2$)$_{0-3}$(4- to 6-membered heterocyclyl), or —(CH$_2$)$_{0-3}$(phenyl), wherein each of said alkyl is substituted with zero to 6 R$^{4d}$ and each of said cycloalkyl, heterocyclyl, and phenyl is substituted with zero to 3 R$^{4e}$;

each R$^{4c}$ is independently hydrogen, C$_{1-6}$ alkyl, C$_{3-6}$ cycloalkyl, 4- to 6-membered heterocyclyl, phenyl, or 5- to 6-membered heteroaryl;

each R$^{4d}$ is independently halo, hydroxyl, —NR$^x$R$^x$, oxo, cyano, C$_{1-3}$ alkoxy, or C$_{1-3}$ haloalkoxy;

each R$^{4e}$ is independently halo, oxo, cyano, hydroxyl, —NH$_2$, C$_{1-6}$ alkyl, C$_{1-6}$ alkoxy, —NH(C$_{1-6}$ alkyl), or —N(C$_{1-6}$ alkyl)$_2$, wherein each of said alkyl and alkoxy is substituted with zero to 6 R$^{4d}$;

each of R$^{5a}$, R$^{5b}$, R$^{5c}$, and R$^{5d}$ is independently hydrogen, halo, hydroxy, cyano, C$_{1-6}$ alkyl substituted with zero to 6 R$^{5e}$, C$_{1-6}$ alkoxy substituted with zero to 6 R$^{5e}$, —C(O)OR$^x$, —C(O)NR$^w$R$^w$, —S(O)$_2$R$^y$, —S(O)$_2$NR$^z$R$^z$, or phenyl substituted with zero to 3 R$^{5f}$;

each of R$^{5e}$ is independently halo, hydroxyl, —NR$^x$R$^x$, oxo, cyano, C$_{1-3}$ alkoxy, or C$_{1-3}$ haloalkoxy;

each R$^{5f}$ is independently halo, oxo, cyano, hydroxyl, —NH$_2$, C$_{1-6}$ alkyl, C$_{1-6}$ alkoxy, —NH(C$_{1-6}$ alkyl), or —N(C$_{1-6}$ alkyl)$_2$, wherein each of said alkyl and alkoxy is substituted with zero to 6 R$^{5e}$;

each R$^v$ is independently hydrogen, C$_{1-6}$ alkyl, or alternatively, two R$^v$, taken together with the nitrogen atom to which they are attached, form a 4- to 7-membered bicyclic or spirocyclic ring moiety containing zero to 2 additional heteroatoms independently selected from N, O, and S, wherein each ring can be substituted with zero to 6 R$^{2a}$;

each R$^w$ is independently hydrogen, C$_{1-6}$ alkyl, or C$_{3-6}$ cycloalkyl; or alternatively, two R$^w$, taken together with the nitrogen atom to which they are attached, form a 4- to 7-membered ring moiety containing zero to 2 additional heteroatoms independently selected from N, O, and S;

each R$^x$ is independently hydrogen, C$_{1-6}$ alkyl, or C$_{3-6}$ cycloalkyl;

each R$^y$ is independently C$_{1-6}$ alkyl or C$_{3-6}$ cycloalkyl; and each R$^z$ is independently hydrogen, C$_{1-6}$ alkyl, or C$_{3-6}$ cycloalkyl; or alternatively, two R$^z$, taken together with the nitrogen atom to which they are attached, form a 4- to 7-membered ring moiety containing zero to 2 additional heteroatoms independently selected from N, O, and S.

The second aspect of the present invention provides a compound of Formula (I):

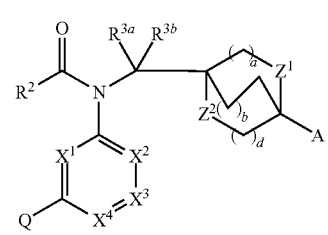

or a stereoisomer, a tautomer, or a salt or solvate thereof, wherein:
X$^1$ is CR$^{5a}$ or N;
X$^2$ is CR$^{5b}$ or N;
X$^3$ is CR$^{5c}$ or N;
X$^4$ is CR$^{5d}$ or N; provided that zero, 1, or 2 of X$^1$, X$^2$, X$^3$, and X$^4$ are N;

$Z^1$ and $Z^2$ are independently $CH_2$ or O; provided that at least one of $Z^1$ and $Z^2$ is $CH_2$;

a is zero or 1;

b is zero, 1, or 2;

d is zero, 1, or 2; provided that $Z^1$ and $Z^2$ are each $CH_2$ when a, b, and d are each zero;

Q is a cyclic group selected from 3- to 8-membered carbocyclyl, 6- to 10-membered aryl, 4- to 10-membered heterocyclyl, and 5- to 10-membered heteroaryl, wherein said cyclic group is substituted with zero to 4 $R^1$;

each $R^1$ is independently hydrogen, halo, cyano, hydroxyl, oxo, $C_{1-6}$ alkyl, $C_{2-6}$ alkenyl, $C_{2-6}$ alkynyl, $C_{1-6}$ alkoxy, —$NH_2$, —$NH(C_{1-6}$ alkyl), —$N(C_{1-6}$ alkyl$)_2$, —$C(O)(C_{1-6}$ alkyl), —$C(O)(C_{3-6}$ cycloalkyl), —$NR^xC(O)R$, —$C(O)OR^x$, —$C(O)NR^wR^w$, —$S(O)_2(C_{1-6}$ alkyl), —$S(O)_2(C_{3-6}$ cycloalkyl), —$NR^xS(O)_2(C_{1-6}$ alkyl), —$NR^xS(O)_2(C_{3-6}$ cycloalkyl), —$S(O)_2NR^zR^z$, —$P(O)R^yR^y$, —$(CH_2)_{0-3}$ $(C_{3-6}$ carbocyclyl), —$O(C_{3-6}$ cycloalkyl), —O(4- to 6-membered heterocyclyl), —$(CH_2)_{0-3}$(4- to 6-membered heterocyclyl), or —$(CH_2)_{0-3}$(5- or 6-membered heteroaryl), wherein each of said alkyl, alkoxy, alkenyl, and alkynyl is substituted with zero to 4 $R^{1a}$ and each of said cycloalkyl, heterocyclyl, and heteroaryl is substituted with zero to 4 $R^{1b}$;

each $R^{1a}$ is independently halo, hydroxyl, —$NR^wR^w$, oxo, cyano, $C_{1-3}$ alkoxy, $C_{1-3}$ haloalkoxy, —$C(O)OR^x$, —$C(O)NR^wR^w$, or —$NR^xC(O)R^y$;

each $R^{1b}$ is independently halo, oxo, cyano, hydroxyl, —$NH_2$, $C_{1-6}$ alkyl, $C_{1-6}$ alkoxy, —$NH(C_{1-6}$ alkyl), —$N(C_{1-6}$ alkyl$)_2$, or —$NR^xC(O)(C_{1-6}$ alkyl), wherein each of said alkyl and alkoxy is substituted with zero to 6 $R^{1a}$;

$R^2$ is:
(i) $C_{1-6}$ alkyl, $C_{2-6}$ alkenyl, $C_{2-6}$ alkynyl, $C_{1-6}$ alkoxy, or —$NR^vR^v$, wherein each of said alkyl, alkenyl, alkynyl, and alkoxy is substituted with zero to 6 $R^{2a}$;
(ii) $C_{3-5}$ carbocyclyl, $C_{6-8}$ spirobicyclyl, or 4- to 5-membered heterocyclyl, wherein each of said carbocyclyl, spirobicyclyl, and heterocyclyl is substituted with zero to 3 $R^{2b}$; or
(iii) —$CH_2(C_{3-6}$ cycloalkyl), —$CH_2$(4- to 6-membered heterocyclyl), —$NR^x(CH_2)_{0-2}(C_{3-6}$cycloalkyl), —$NR^x$ $(CH_2)_{0-2}(C_{5-8}$ bicycloalkyl), —$NR^x(CH_2)_{0-2}(C_{5-8}$ spirobicyclyl), —$NR^x(CH_2)_{0-2}$(4- to 6-membered heterocyclyl), —$NR^x(CH_2)_{0-2}$(5- to 6-membered heteroaryl), —$NR^x(CH_2)_{0-2}$(phenyl), —$O(CH_2)_{0-2}(C_{3-6}$ cycloalkyl), —$O(CH_2)_{0-2}(C_{5-8}$ bicycloalkyl), —$O(CH_2)_{0-2}$ $(C_{5-8}$ spirobicyclyl), —$O(CH_2)_{0-2}$(4- to 6-membered heterocyclyl), —$O(CH_2)_{0-2}$(5- to 6-membered heteroaryl), or —$O(CH_2)_{0-2}$(phenyl), wherein each of said cycloalkyl, heterocyclyl, bicycloalkyl, spirobicyclyl, aryl, and heteroaryl is substituted with zero to 3 $R^{2b}$;

each $R^{2a}$ is independently halo, cyano, hydroxyl, oxo, $C_{1-3}$ haloalkyl, $C_{1-3}$ alkoxy, $C_{1-3}$ haloalkoxy, —$NR^xR^x$, —$C(O)(C_{1-6}$ alkyl), —$C(O)(C_{3-6}$ cycloalkyl), —$NR^xC$ $(O)R^y$, —$C(O)(C_{1-6}$ alkyl), —$C(O)OR^x$, —$C(O)NR^wR^w$, —$S(O)_2R^y$, —$S(O)_2(C_{1-3}$ fluoroalkyl), —$NR^xS(O)_2(C_{1-3}$ alkyl), —$NR^xS(O)_2(C_{3-6}$ cycloalkyl), —$S(O)_2NR^zR^z$, or —$P(O)R^yR^y$;

each $R^{2b}$ is independently halo, cyano, hydroxyl, oxo, $C_{1-6}$ alkyl, $C_{1-6}$ alkoxy, —$NR^xR^x$, —$NR^xC(O)O(C_{1-3}$ alkyl), —$C(O)(C_{1-3}$ alkyl), or —$S(O)_2(C_{1-3}$ alkyl), wherein each of said alkyl and alkoxy is substituted with zero to 6 $R^{2a}$;

$R^{3a}$ and $R^{3b}$ are independently hydrogen, $C_{1-3}$ alkyl, $C_{1-3}$ haloalkyl, or $C_{3-6}$ cycloalkyl, or $R^{3a}$ and $R^{3b}$, taken together with the carbon atom to which they are attached, form a $C_{3-6}$ cycloalkyl;

A is:
(i) cyano;
(ii) phenyl or a 5- or 10-membered heteroaryl containing 1 to 4 heteroatoms independently selected from N, O, and S, wherein each of said phenyl and heteroaryl is substituted with zero to 3 $R^{4a}$; or
(iii)

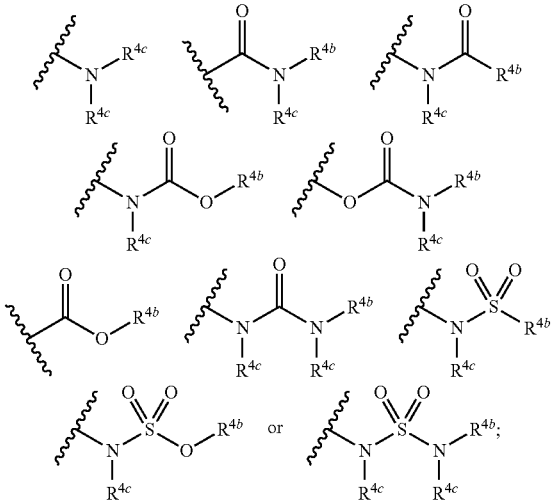

each $R^{4a}$ is independently halo, cyano, hydroxyl, —$NH_2$, $C_{1-6}$ alkyl, $C_{2-6}$ alkenyl, $C_{2-6}$ alkynyl, $C_{1-6}$ alkoxy, —$(CH_2)_{0-3}NH(C_{1-6}$ alkyl), —$(CH_2)_{0-2}N(C_{1-6}$ alkyl$)_2$, —$(CH_2)_{0-3}(C_{3-6}$ cycloalkyl), or —$(CH_2)_{0-3}$(4- to 6-membered heterocyclyl), wherein each of said alkyl, alkoxy, alkenyl, and alkynyl is substituted with zero to 6 $R^{4d}$ and each of said cycloalkyl and heterocyclyl is substituted with zero to 3 $R^{4e}$;

$R^{4b}$ is $C_{1-6}$ alkyl, —$(CH_2)_{0-3}(C_{3-6}$ cycloalkyl), or —$(CH_2)_{0-3}$(4- to 6-membered heterocyclyl), wherein each of said alkyl is substituted with zero to 6 $R^{4d}$ and each of said cycloalkyl and heterocyclyl is substituted with zero to 3 $R^{4e}$;

each $R^{4c}$ is independently hydrogen, $C_{1-6}$ alkyl, $C_{3-6}$ cycloalkyl, 4- to 6-membered heterocyclyl, phenyl, or 5- to 6-membered heteroaryl;

each $R^{4d}$ is independently halo, hydroxyl, —$NR^xR^x$, oxo, cyano, $C_{1-3}$ alkoxy, or $C_{1-3}$ haloalkoxy;

each $R^{4e}$ is independently halo, oxo, cyano, hydroxyl, —$NH_2$, $C_{1-6}$ alkyl, $C_{1-6}$ alkoxy, —$NH(C_{1-6}$ alkyl), or —$N(C_{1-6}$ alkyl$)_2$, wherein each of said alkyl and alkoxy is substituted with zero to 6 $R^{4d}$;

each of $R^{5a}$, $R^{5b}$, $R^{5c}$, and $R^{5d}$ is independently hydrogen, halo, hydroxy, cyano, $C_{1-6}$ alkyl substituted with zero to 6 $R^{5e}$, $C_{1-6}$ alkoxy substituted with zero to 6 $R^{5e}$, —$C(O)$ $OR^x$, —$C(O)NR^wR^w$, —$S(O)_2R^y$, —$S(O)_2NR^zR^z$, or phenyl substituted with zero to 3 $R^{5f}$;

each of $R^{5e}$ is independently halo, hydroxyl, —$NR^xR^x$, oxo, cyano, $C_{1-3}$ alkoxy, or $C_{1-3}$ haloalkoxy;

each $R^{5f}$ is independently halo, oxo, cyano, hydroxyl, —$NH_2$, $C_{1-6}$ alkyl, $C_{1-6}$ alkoxy, —$NH(C_{1-6}$ alkyl), or —$N(C_{1-6}$ alkyl$)_2$, wherein each of said alkyl and alkoxy is substituted with zero to 6 $R^{5e}$;

each $R^v$ is independently hydrogen, $C_{1-6}$ alkyl, or alternatively, two $R^v$, taken together with the nitrogen atom to which they are attached, form a 4- to 7-membered bicyclic or spirocyclic ring moiety containing zero to 2 additional heteroatoms independently selected from N, O, and S, wherein each ring can be substituted with zero to 6 $R^{2a}$;

each $R^w$ is independently hydrogen, $C_{1-6}$ alkyl, or $C_{3-6}$ cycloalkyl; or alternatively, two $R^w$, taken together with the nitrogen atom to which they are attached, form a 4- to 7-membered ring moiety containing zero to 2 additional heteroatoms independently selected from N, O, and S;

each $R^x$ is independently hydrogen, $C_{1-6}$ alkyl, or $C_{3-6}$ cycloalkyl;

each $R^y$ is independently $C_{1-6}$ alkyl or $C_{3-6}$ cycloalkyl; and each $R^z$ is independently hydrogen, $C_{1-6}$ alkyl, or $C_{3-6}$ cycloalkyl; or alternatively, two $R^z$, taken together with the nitrogen atom to which they are attached, form a 4- to 7-membered ring moiety containing zero to 2 additional heteroatoms independently selected from N, O, and S.

In one embodiment, a compound of Formula (I) or a stereoisomer, a tautomer, or a salt or solvate thereof is provided, wherein $X^1$ is $CR^{5a}$; $X^2$ is $CR^{5b}$; $X^3$ is $CR^{5c}$; $X^4$ is $CR^{5d}$. Compounds of this embodiment have the structure:

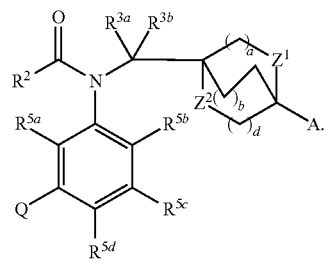

Included in this embodiment are compounds in which one of $R^{5a}$, $R^{5b}$, $R^{5c}$, and $R^{5d}$ is F, Cl, cyano, or —OCH$_3$; and three of $R^{5a}$, $R^{5b}$, $R^{5c}$, and $R^{5d}$ are hydrogen.

One embodiment provides a compound of Formula (I) or a stereoisomer, a tautomer, or a pharmaceutically acceptable salt or solvate thereof, wherein: $X^1$ is N; $X^2$ is $CR^{5b}$; $X^3$ is $CR^{5c}$; and $X^4$ is $CR^{5d}$. Compounds of this embodiment have the structure:

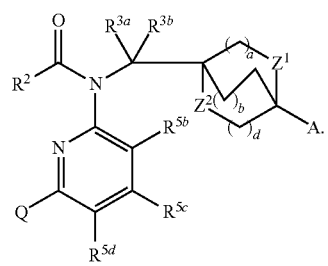

One embodiment provides a compound of Formula (I) or a stereoisomer, a tautomer, or a pharmaceutically acceptable salt or solvate thereof, wherein: $X^1$ is $CR^{5a}$; $X^2$ is N; $X^3$ is $CR^{5c}$; and $X^4$ is $CR^{5d}$. Compounds of this embodiment have the structure:

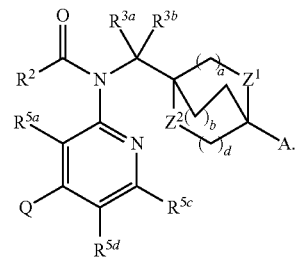

One embodiment provides a compound of Formula (I) or a stereoisomer, a tautomer, or a pharmaceutically acceptable salt or solvate thereof, wherein: $X^1$ is $CR^{5a}$; $X^2$ is $CR^{5b}$; $X^3$ is N; and $X^4$ is $CR^{5d}$. Compounds of this embodiment have the structure:

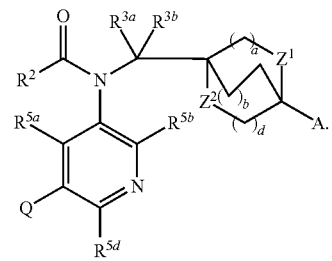

One embodiment provides a compound of Formula (I) or a stereoisomer, a tautomer, or a pharmaceutically acceptable salt or solvate thereof, wherein: $X^1$ is $CR^{5a}$; $X^2$ is $CR^{5b}$; $X^3$ is $CR^{5c}$; and $X^4$ is N. Compounds of this embodiment have the structure:

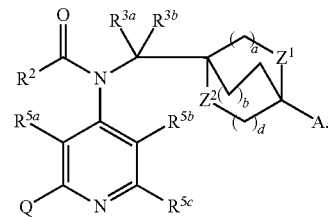

One embodiment provides a compound of Formula (I) or a stereoisomer, a tautomer, or a pharmaceutically acceptable salt or solvate thereof, wherein: $X^1$ is $CR^{5a}$; $X^2$ is N; $X^3$ is CRC; and $X^4$ is N. Compounds of this embodiment have the structure:

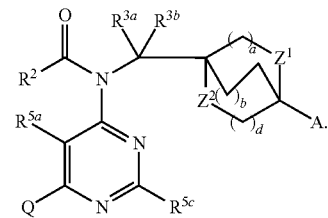

One embodiment provides a compound of Formula (I) or a stereoisomer, a tautomer, or a pharmaceutically acceptable salt or solvate thereof, wherein: $X^1$ is N; $X^2$ is $CR^{5b}$; $X^3$ is CRC; and $X^4$ is N. Compounds of this embodiment have the structure:

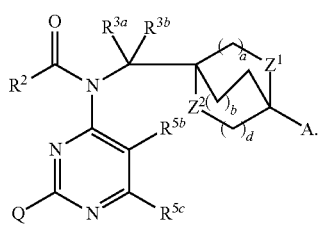

One embodiment provides a compound of Formula (I) or a stereoisomer, a tautomer, or a pharmaceutically acceptable salt or solvate thereof, wherein: $X^1$ is N; $X^2$ is N; $X^3$ is CRC; and $X^4$ is $CR^{5d}$. Compounds of this embodiment have the structure:

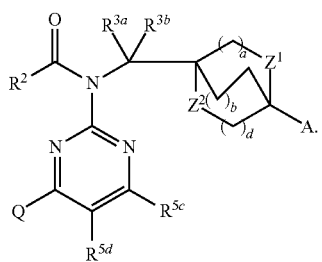

One embodiment provides a compound of Formula (I) or a stereoisomer, a tautomer, or a pharmaceutically acceptable salt or solvate thereof, wherein: $X^1$ is $CR^{5a}$; $X^2$ is N; $X^3$ is N; and $X^4$ is $CR^{5d}$. Compounds of this embodiment have the structure:

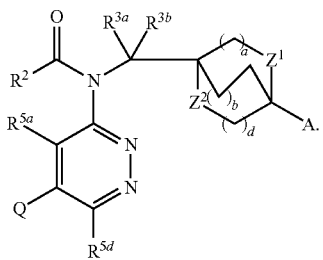

One embodiment provides a compound of Formula (I) or a stereoisomer, a tautomer, or a pharmaceutically acceptable salt or solvate thereof, wherein: $X^1$ is $CR^{5a}$; $X^2$ is $CR^{5b}$; $X^3$ is N; and $X^4$ is N. Compounds of this embodiment have the structure:

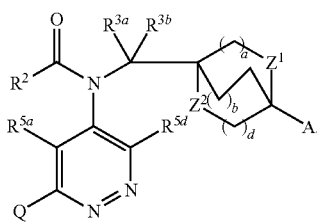

One embodiment provides a compound of Formula (I) or a stereoisomer, a tautomer, or a pharmaceutically acceptable salt or solvate thereof, wherein: $X^1$ is $CR^{5a}$; $X^2$ is $CR^{5b}$; $X^3$ is $CR^{5c}$; $X^4$ is $CR^{5d}$; and $Z^1$ and $Z^2$ are each $CH_2$. Compounds of this embodiment have the structure:

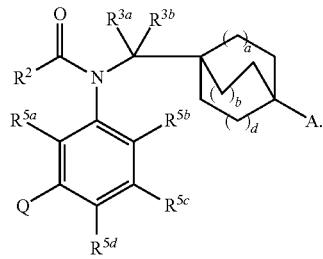

One embodiment provides a compound of Formula (I) or a stereoisomer, a tautomer, or a pharmaceutically acceptable salt or solvate thereof, wherein: $X^1$ is $CR^{5a}$; $X^2$ is $CR^{5b}$; $X^3$ is $CR^{5c}$; $X^4$ is $CR^{5d}$; $Z^1$ and $Z^2$ are each $CH_2$; and a, b, and d are each 1.

Compounds of this embodiment have the structure:

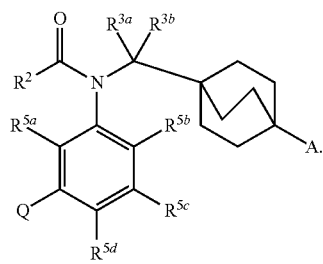

One embodiment provides a compound of Formula (I) or a stereoisomer, a tautomer, or a pharmaceutically acceptable salt or solvate thereof, wherein: a is 1; b is 1; and d is 1. Compounds of this embodiment have the structure:

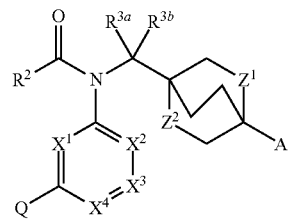

Included in this embodiment are compounds in which $X^1$ is $CR^{5a}$ or N; $X^2$ is $CR^{5b}$ or N; $X^3$ is $CR^{5c}$ or N; and $X^4$ is $CR^{5d}$ or N; provided that zero or 1 of $X^1$, $X^2$, $X^3$, and $X^4$ is N. Also included in this embodiment are compounds in which $X^1$ is $CR^{5a}$; $X^2$ is $CR^{5b}$; $X^3$ is $CR^{5c}$; and $X^4$ is $CR^{5d}$. Additionally, included in this embodiment are compounds in which $R^{5a}$, $R^{5b}$, $R^{5c}$, and $R^{5d}$ are selected from hydrogen and F, provided that zero or 1 of $R^{5a}$, $R^{5b}$, $R^{5c}$, and $R^{5d}$ is F.

One embodiment provides a compound of Formula (I) or a stereoisomer, a tautomer, or a pharmaceutically acceptable salt or solvate thereof, wherein: a is 1; b is 1; d is 1; $Z^1$ is $CH_2$; and $Z^2$ is $CH_2$. Compounds of this embodiment have the structure:

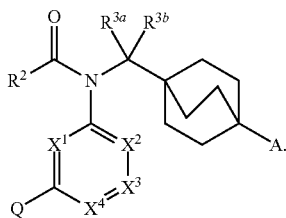

Included in this embodiment are compounds in which $X^1$ is $CR^{5a}$ or N; $X^2$ is $CR^{5b}$ or N; $X^3$ is $CR^{5c}$ or N; and $X^4$ is $CR^{5d}$ or N; provided that zero or 1 of $X^1$, $X^2$, $X^3$, and $X^4$ is N. Also included in this embodiment are compounds in which $R^{5a}$, $R^{5b}$, $R^{5c}$, and $R^{5d}$ are selected from hydrogen and F, provided that zero or 1 of $R^{5a}$, $R^{5b}$, $R^{5c}$, and $R^{5d}$ is F.

One embodiment provides a compound of Formula (I) or a stereoisomer, a tautomer, or a pharmaceutically acceptable salt or solvate thereof, wherein: a is 1; b is 1; d is 1; $Z^1$ is $CH_2$; and $Z^2$ is O. Compounds of this embodiment have the structure:

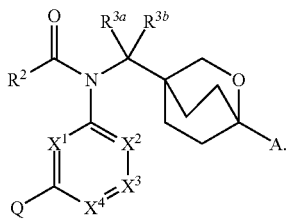

Included in this embodiment are compounds in which $X^1$ is $CR^{5a}$ or N; $X^2$ is $CR^{5b}$ or N; $X^3$ is $CR^{5c}$ or N; and $X^4$ is $CR^{5d}$ or N; provided that zero or 1 of $X^1$, $X^2$, $X^3$, and $X^4$ is N. Also included in this embodiment are compounds in which $X^1$ is $CR^{5a}$; $X^2$ is $CR^{5b}$; $X^3$ is $CR^{5c}$; and $X^4$ is $CR^{5d}$. Additionally, included in this embodiment are compounds in which $R^{5a}$, $R^{5b}$, $R^{5c}$, and $R^{5d}$ are selected from hydrogen and F, provided that zero or 1 of $R^{5a}$, $R^{5b}$, $R^{5c}$, and $R^{5d}$ is F.

One embodiment provides a compound of Formula (I) or a stereoisomer, a tautomer, or a pharmaceutically acceptable salt or solvate thereof, wherein: a is 1; b is 1; d is 1; $Z^1$ is O; and $Z^2$ is $CH_2$. Compounds of this embodiment have the structure:

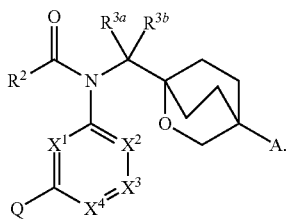

Included in this embodiment are compounds in which $X^1$ is $CR^{5a}$ or N; $X^2$ is $CR^{5b}$ or N; $X^3$ is $CR^{5c}$ or N; and $X^4$ is $CR^{5d}$ or N; provided that zero or 1 of $X^1$, $X^2$, $X^3$, and $X^4$ is N. Also included in this embodiment are compounds in which $X^1$ is $CR^{5a}$; $X^2$ is $CR^{5b}$; $X^3$ is $CR^{5c}$; and $X^4$ is $CR^{5d}$. Additionally, included in this embodiment are compounds in which $R^{5a}$, $R^{5b}$, $R^{5c}$, and $R^{5d}$ are selected from hydrogen and F, provided that zero or 1 of $R^{5a}$, $R^{5b}$, $R^{5c}$, and $R^{5d}$ is F.

One embodiment provides a compound of Formula (I) or a stereoisomer, a tautomer, or a pharmaceutically acceptable salt or solvate thereof, wherein Q is a cyclic group selected from 3- to 8-membered carbocyclyl, phenyl, 4- to 10-membered heterocyclyl, and 5- to 10-membered heteroaryl, wherein said cyclic group is substituted with zero to 3 $R^1$;

One embodiment provides a compound of Formula (I) or a stereoisomer, a tautomer, or a pharmaceutically acceptable salt or solvate thereof, wherein Q is a 3- to 8-membered carbocyclyl substituted with zero to 4 $R^1$. Included in this embodiment are compounds in which Q is $C_{3-6}$ cycloalkyl, spiro[2.3]hexanyl, spiro[2.4]heptanyl, spiro[3.3]heptanyl, spiro[3.3]heptenyl, spiro[3.4]octanyl, or oxaazaspiro[3.3]heptanyl, each substituted with zero to 4 $R^1$.

One embodiment provides a compound of Formula (I) or a stereoisomer, a tautomer, or a pharmaceutically acceptable salt or solvate thereof, wherein Q is a 6- to 10-membered aryl substituted with zero to 4 $R^1$. Included in this embodiment are compounds in which Q is phenyl or naphthalenyl, each substituted with zero to 4 $R^1$. Also included in this embodiment are compounds in which Q is phenyl substituted with zero to 3 $R^1$.

One embodiment provides a compound of Formula (I) or a stereoisomer, a tautomer, or a pharmaceutically acceptable salt or solvate thereof, wherein Q is a 4- to 10-membered heterocyclyl substituted with zero to 4 $R^1$. Included in this embodiment are compounds in which Q is a 4- to 6-membered heterocyclyl substituted with zero to 4 $R^1$. Also included in this embodiment are compounds in which Q is azetidinyl, pyrrolidinyl, piperazinyl, piperidinyl, or morpholinyl.

One embodiment provides a compound of Formula (I) or a stereoisomer, a tautomer, or a pharmaceutically acceptable salt or solvate thereof, wherein Q is a 5- to 10-membered heteroaryl substituted with zero to 4 $R^1$. Included in this embodiment are compounds in which Q is a 5- to 6-membered heteroaryl substituted with zero to 4 $R^1$. Also included in this embodiment are compounds in which Q is pyrazolyl, imidazolyl, isoxazolyl, oxazolyl, oxadiazolyl, thiazolyl, triazolyl, pyridinyl, pyrimidinyl, pyrazinyl, pyridazinyl, indolyl, indazolyl, indolinyl, quinolinyl, isoquinolinyl, [1,2,4]triazolo[1,5-a]pyridinyl, [1,2,4]triazolo[4,3-a]pyridinyl, 1H-pyrazolo[3,4-b]pyridinyl, 2,3-dihydrobenzo[d]oxazolyl, 7,8-dihydro-5H-pyrano[4,3-b]pyridinyl, benzo[d][1,3]dioxolyl, benzo[d]oxazolyl, benzo[d]thiazolyl, imidazo[1,2-a]pyridinyl, imidazo[1,2-b]pyridazinyl, pyrrolo[2,1-f] [1,2,4]triazinyl, thiazolo[4,5-b]pyridinyl, thiazolo[5,4-b]pyridinyl, or thieno[3,2-b]pyridinyl.

One embodiment provides a compound of Formula (I) or a stereoisomer, a tautomer, or a pharmaceutically acceptable salt or solvate thereof, wherein A is phenyl or a 5- or 10-membered heteroaryl containing 1 to 4 heteroatoms independently selected from N, O, and S, wherein each of said phenyl and heteroaryl is substituted with zero to 3 $R^{4a}$.

One embodiment provides a compound of Formula (I) or a stereoisomer, a tautomer, or a pharmaceutically acceptable salt or solvate thereof, wherein A is phenyl or a 5- or 6-membered heteroaryl containing 1 to 4 heteroatoms independently selected from N, O, and S, wherein each of said phenyl and heteroaryl is substituted with zero to 3 $R^{4a}$. Included in this embodiment are compounds in which A is oxadiazolyl, oxazolyl, phenyl, pyrazolyl, pyridinyl, pyrimidinyl, thiadiazolyl, or thiazolyl, each substituted with zero to 2 $R^{4a}$. Also included in this embodiment are compounds in which A is a 5- or 6-membered heteroaryl containing 1 to 3 heteroatoms independently selected from N, O, and S, wherein said heteroaryl is substituted with zero to 3 $R^{4a}$.

Additionally, included in this embodiment are compounds in which A is phenyl substituted with zero to 2 $R^{4a}$.

One embodiment provides a compound of Formula (I) or a stereoisomer, a tautomer, or a pharmaceutically acceptable salt or solvate thereof, wherein A is:

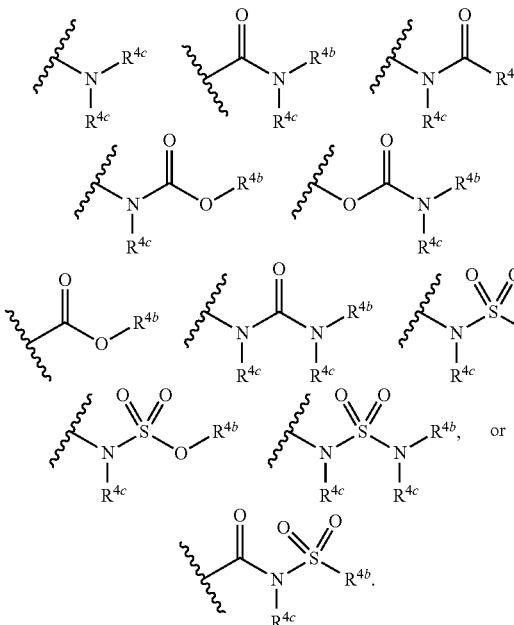

Included in this embodiment are compounds in which A is:

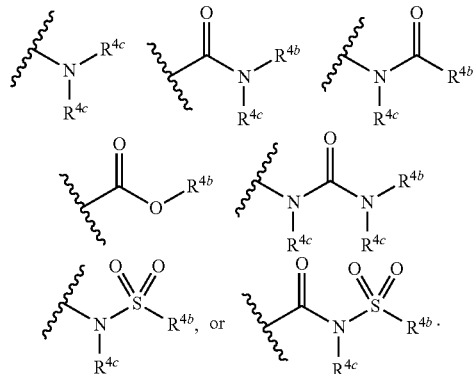

Also included in this embodiment are compounds in which A is —C(O)NH(cyclopropyl), —NHS(O)$_2$CF$_3$, —NHC(O)OCH(CH$_3$)$_2$, —NHC(O)NHCH(CH$_3$)$_2$, or —C(O)NHS(O)$_2$(cyclopropyl).

One embodiment provides a compound of Formula (I) or a stereoisomer, a tautomer, or a pharmaceutically acceptable salt or solvate thereof, wherein A is:

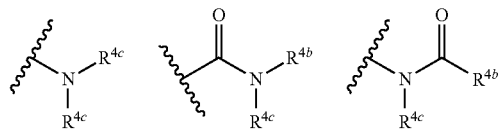

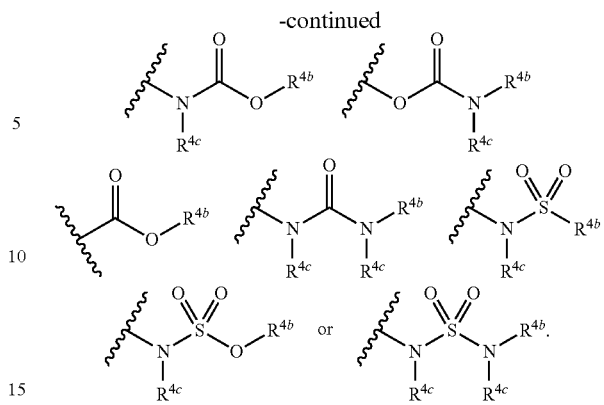

Included in this embodiment are compounds in which A is:

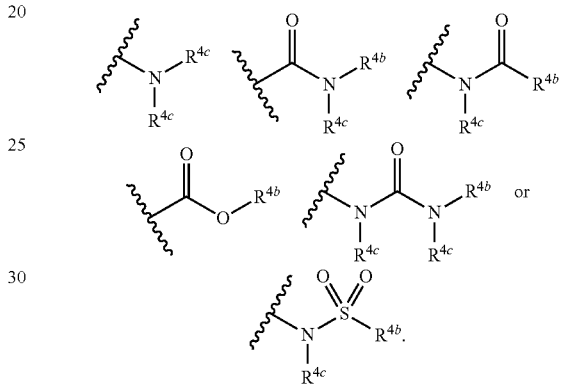

Also included in this embodiment are compounds in which A is —C(O)NH(cyclopropyl), —NHS(O)$_2$CF$_3$, —NHC(O)OCH(CH$_3$)$_2$, or —NHC(O)NHCH(CH$_3$)$_2$.

One embodiment provides a compound of Formula (I) or a stereoisomer, a tautomer, or a pharmaceutically acceptable salt or solvate thereof, wherein $R^2$ is $C_{1-6}$ alkyl, $C_{2-6}$ alkenyl, $C_{2-6}$ alkynyl, $C_{1-6}$ alkoxy, or —NR$^v$R$^v$, wherein each of said alkyl, alkenyl, alkynyl, and alkoxy is substituted with zero to 6 $R^{2a}$. Included in this embodiment are compounds in which $R^2$ is $C_{1-4}$ alkyl, $C_{1-5}$ alkoxy, or —NH($C_{1-6}$ alkyl), wherein each of said alkyl and alkoxy is substituted with zero to 4 $R^{2a}$. Also included in this embodiment are compounds in which $R^2$ is —CH(CH$_3$)$_2$, —NHCH$_2$CH$_3$, or —NHCH$_2$C(CH$_3$)$_3$.

One embodiment provides a compound of Formula (I) or a stereoisomer, a tautomer, or a pharmaceutically acceptable salt or solvate thereof, wherein $R^2$ is $C_{3-5}$ carbocyclyl, $C_{6-8}$ spirobicyclyl, or 4- to 5-membered heterocyclyl, wherein each of said carbocyclyl, spirobicyclyl, and heterocyclyl is substituted with zero to 3 $R^{2b}$. Included in this embodiment are compounds in which $R^2$ is $C_{3-5}$ carbocyclyl, $C_{6-8}$ spirobicyclyl, or 4- to 5-membered heterocyclyl, wherein each of said carbocyclyl, spirobicyclyl, and heterocyclyl is substituted with zero to 2 $R^{2b}$. Also included in this embodiment are compounds in which $R^2$ is $C_{3-5}$ cycloalkyl, azetidinyl, oxetanyl, pyrrolidinyl, and bicyclo[1.1.1]pentyl, each cyclic group substituted with zero to 2 substituents independently selected from F, hydroxyl, —CH$_3$, —CHF$_2$, —CF$_3$, —OCH$_3$, —OCH$_2$CH$_3$, —NH$_2$, —N(CH$_3$)$_2$, —NHC(O)OC(CH$_3$)$_3$, and —C(O)CF$_3$.

One embodiment provides a compound of Formula (I) or a stereoisomer, a tautomer, or a pharmaceutically acceptable salt or solvate thereof, wherein $R^2$ is:

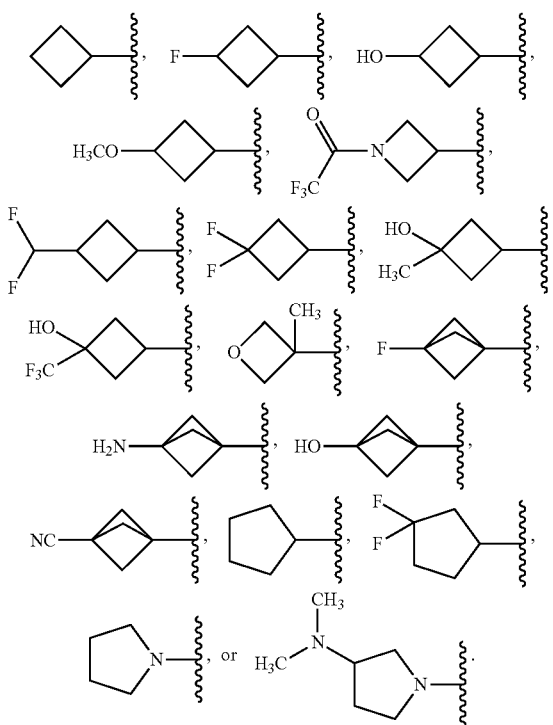

One embodiment provides a compound of Formula (I) or a stereoisomer, a tautomer, or a pharmaceutically acceptable salt or solvate thereof, wherein $R^2$ is —$CH_2(C_{3-6}$ cycloalkyl), —$CH_2$(4- to 6-membered heterocyclyl), —$NR^x$ $(CH_2)_{0-2}(C_{3-6}$ cycloalkyl), —$NR^x(CH_2)_{0-2}(C_{5-8}$ bicycloalkyl), —$NR^x(CH_2)_{0-2}(C_{5-8}$ spirobicyclyl), —$NR^x(CH_2)_{0-2}$(4- to 6-membered heterocyclyl), —$NR^x(CH_2)_{0-2}$(5- to 6-membered heteroaryl), —$NR^x(CH_2)_{0-2}$(phenyl), —$O(CH_2)_{0-2}$ $(C_{3-6}$ cycloalkyl), —$O(CH_2)_{0-2}(C_{5-8}$ bicycloalkyl), —$O(CH_2)_{0-2}(C_{5-8}$ spirobicyclyl), —$O(CH_2)_{0-2}$(4- to 6-membered heterocyclyl), —$O(CH_2)_{0-2}$(5- to 6-membered heteroaryl), or —$O(CH_2)_{0-2}$(phenyl), wherein each of said cycloalkyl, heterocyclyl, bicycloalkyl, spirobicyclyl, aryl, and heteroaryl is substituted with zero to 3 $R^{2b}$. Included in this embodiment are compounds in which $R^2$ is —$CH_2(C_{3-5}$ cycloalkyl), —$CH_2$(4- to 6-membered heterocyclyl), —$NR$ $(CH_2)_{0-2}(C_{3-5}$ cycloalkyl), —$NR^x(CH_2)_{0-2}$(4- to 6-membered heterocyclyl), —$NR^x(CH_2)_{0-2}$(phenyl), —$O$(phenyl), or —$O$(pyridinyl), wherein each of said cycloalkyl, heterocyclyl, phenyl, and pyridinyl is substituted with zero to 3 $R^{2b}$. Also included in this embodiment are compounds in which $R^2$ is —NH(methyl cyclopropyl) or —NH(methoxyphenyl).

One embodiment provides a compound of Formula (I) or a stereoisomer, a tautomer, or a pharmaceutically acceptable salt or solvate thereof, wherein $R^2$ is —$CH_2(C_{3-5}$ cycloalkyl), —$CH_2$(4- to 6-membered heterocyclyl), —$NR^x$ $(CH_2)_{0-2}(C_{3-6}$ cycloalkyl), —$NR^x(CH_2)_{0-2}(C_{6-8}$ spirobicyclyl), —$NR^x(CH_2)_{0-2}$(4- to 6-membered heterocyclyl), —$NR^x(CH_2)_{0-2}$(phenyl), —O(4- to 6-membered heterocyclyl), —O(phenyl), or —O(pyridinyl), wherein each of said cycloalkyl, spirobicyclyl, heterocyclyl, phenyl, and pyridinyl is substituted with zero to 3 $R^{2b}$. Included in this embodiment are compounds in which $R^2$ is —$CH_2(C_{3-5}$ cycloalkyl), —$CH_2$(4- to 6-membered heterocyclyl), —$NR^x$ $(CH_2)_{0-2}(C_{3-6}$ cycloalkyl), —$NR(CH_2)_{0-2}(C_{6-8}$ spirobicyclyl), —$NR^x(CH_2)_{0-2}$(4- to 6-membered heterocyclyl), —$NR^x(CH_2)_{0-2}$(phenyl), —O(tetrahydropyranyl), —O(phenyl), or —O(pyridinyl), wherein each of said cycloalkyl, spirobicyclyl, heterocyclyl, phenyl, and pyridinyl is substituted with zero to 3 $R^{2b}$.

One embodiment provides a compound of Formula (I) or a stereoisomer, a tautomer, or a pharmaceutically acceptable salt or solvate thereof, wherein $R^{3a}$ and $R^{3b}$ are independently hydrogen, $C_{1-3}$ alkyl, $C_{1-3}$ fluoroalkyl, or $C_{3-6}$ cycloalkyl, or $R^{3a}$ and $R^{3b}$, taken together with the carbon atom to which they are attached, form a $C_{3-6}$ cycloalkyl. Included in this embodiment are compounds in which $R^{3a}$ and $R^{3b}$ are independently hydrogen, $C_{1-2}$ alkyl, $C_{1-2}$ fluoroalkyl, or $C_{3-6}$ cycloalkyl. Also included in this embodiment are compounds in which $R^{3a}$ and $R^{3b}$ are independently hydrogen, —$CH_3$, or —$CF_3$. Additionally, included in this embodiment are compounds in which one of $R^{3a}$ and $R^{3b}$ is hydrogen and the other of $R^{3a}$ and $R^{3b}$ is hydrogen or —$CH_3$.

One embodiment provides a compound of Formula (I) or a stereoisomer, a tautomer, or a pharmaceutically acceptable salt or solvate thereof, wherein each $R^{1a}$ is independently F, Cl, hydroxyl, —$NR^wR^w$, oxo, cyano, $C_{1-3}$ alkoxy, $C_{1-3}$ fluoroalkoxy, or —C(O)OH. Included in this embodiment are compounds in which each $R^{1a}$ is independently F, hydroxyl, —$NR^xR^x$, cyano, $C_{1-2}$ alkoxy, $C_{1-2}$ fluoroalkoxy, or —C(O)OH.

One embodiment provides a compound of Formula (I) or a stereoisomer, a tautomer, or a pharmaceutically acceptable salt or solvate thereof, wherein each $R^{1b}$ is independently halo, oxo, cyano, hydroxyl, —$NH_2$, $C_{1-6}$ alkyl, $C_{1-6}$ alkoxy, —NH($C_{1-6}$ alkyl), —N($C_{1-6}$ alkyl)$_2$, or —$NR^xC(O)(C_{1-6}$ alkyl), wherein each of said alkyl and alkoxy is substituted with zero to 6 $R^{1a}$. Included in this embodiment are compounds in which each $R^{1b}$ is independently F, Cl, oxo, cyano, hydroxyl, —$NH_2$, $C_{1-4}$ alkyl, $C_{1-4}$ alkoxy, —NH($C_{1-4}$ alkyl), —N($C_{1-4}$ alkyl)$_2$, or —$NR^xC(O)(C_{1-6}$ alkyl), wherein each of said alkyl and alkoxy is substituted with zero to 6 $R^{1a}$. Also included in this embodiment are compounds in which each $R^{1a}$ is independently F, cyano, hydroxyl, or —$OCH_3$.

One embodiment provides a compound of Formula (I) or a stereoisomer, a tautomer, or a pharmaceutically acceptable salt or solvate thereof, wherein each $R^{1b}$ is independently F, Cl, Br, oxo, cyano, hydroxyl, —$NH_2$, $C_{1-6}$ alkyl, $C_{1-4}$ alkoxy, —NH($C_{1-4}$ alkyl), —N($C_{1-4}$ alkyl)$_2$, or —$NR^xC(O)$ ($C_{1-6}$ alkyl), wherein each of said alkyl and alkoxy is substituted with zero to 6 $R^{1a}$. Included in this embodiment are compounds in which each $R^{1b}$ is independently F, Cl, oxo, cyano, hydroxyl, —$NH_2$, $C_{1-4}$ alkyl, $C_{1-4}$ alkoxy, —NH ($C_{1-4}$ alkyl), —N($C_{1-4}$ alkyl)$_2$, or —$NR^xC(O)(C_{1-4}$ alkyl), wherein each of said alkyl and alkoxy is substituted with zero to 6 $R^{1a}$. Also included in this embodiment are compounds in which each $R^{1b}$ is independently F, Cl, cyano, hydroxyl, —$CH_3$, or —$OCH_3$.

One embodiment provides a compound of Formula (I) or a stereoisomer, a tautomer, or a pharmaceutically acceptable salt or solvate thereof, wherein each $R^w$ is independently hydrogen, $C_{1-4}$ alkyl, or $C_{3-6}$ cycloalkyl; or alternatively, two $R^w$, taken together with the nitrogen atom to which they are attached, form a 4- to 7-membered ring moiety containing zero to 2 additional heteroatoms independently selected from N, O, and S.

One embodiment provides a compound of Formula (I) or a stereoisomer, a tautomer, or a pharmaceutically acceptable salt or solvate thereof, wherein each $R^w$ is independently hydrogen, $C_{1-6}$ alkyl, or $C_{3-6}$ cycloalkyl. Included in this embodiment are compounds in which each $R^w$ is independently hydrogen, $C_{1-4}$ alkyl, or $C_{3-6}$ cycloalkyl. Also included in this embodiment are compounds in which each $R^w$ is independently hydrogen or $C_{1-3}$ alkyl.

One embodiment provides a compound of Formula (I) or a stereoisomer, a tautomer, or a pharmaceutically acceptable salt or solvate thereof, wherein each $R^x$ is independently hydrogen, $C_{1-4}$ alkyl, or $C_{3-6}$ cycloalkyl. Included in this embodiment are compounds in which each $R^x$ is independently hydrogen or $C_{1-4}$ alkyl.

One embodiment provides a compound of Formula (I) or a stereoisomer, a tautomer, or a pharmaceutically acceptable salt or solvate thereof, wherein each $R^y$ is independently $C_{1-4}$ alkyl or $C_{3-6}$ cycloalkyl. Included in this embodiment are compounds in which each $R^y$ is independently $C_{1-4}$ alkyl.

One embodiment provides a compound of Formula (I) or a stereoisomer, a tautomer, or a pharmaceutically acceptable salt or solvate thereof, wherein each $R^z$ is independently hydrogen, $C_{1-4}$ alkyl, or $C_{3-6}$ cycloalkyl; or alternatively, two $R^z$, taken together with the nitrogen atom to which they are attached, form a 4- to 7-membered ring moiety containing zero to 2 additional heteroatoms independently selected from N, O, and S.

One embodiment provides a compound of Formula (I) or a stereoisomer, a tautomer, or a pharmaceutically acceptable salt or solvate thereof, wherein each $R^z$ is independently hydrogen, $C_{1-6}$ alkyl, or $C_{3-6}$ cycloalkyl. Included in this embodiment are compounds in which each $R^w$ is independently hydrogen, $C_{1-4}$ alkyl, or $C_{3-6}$ cycloalkyl. Also included in this embodiment are compounds in which each $R^z$ is independently hydrogen or $C_{1-3}$ alkyl.

One embodiment provides a compound of Formula (I) or a stereoisomer, a tautomer, or a pharmaceutically acceptable salt or solvate thereof, wherein each $R^{2a}$ is independently F, Cl, hydroxyl, —$NR^xR^x$, oxo, cyano, $C_{1-3}$ alkoxy, $C_{1-3}$ haloalkoxy, or —C(O)OH. Included in this embodiment are compounds in which each $R^{2a}$ is independently F, Cl, hydroxyl, —$NR^xR^x$, cyano, $C_{1-3}$ alkoxy, $C_{1-3}$ haloalkoxy, or —C(O)OH.

One embodiment provides a compound of Formula (I) or a stereoisomer, a tautomer, or a pharmaceutically acceptable salt or solvate thereof, wherein each $R^{2a}$ is independently F, Cl, Br, cyano, hydroxyl, oxo, $C_{1-3}$ alkoxy, $C_{1-3}$ fluoroalkoxy, or —$NR^wR^w$. Included in this embodiment are compounds in which each $R^{2a}$ is independently F, Cl, cyano, hydroxyl, $C_{1-3}$ alkoxy, $C_{1-3}$ fluoroalkoxy, or —$NR^xR^x$. Also included in this embodiment are compounds in which each $R^{2a}$ is independently F, cyano, hydroxyl, $C_{1-2}$ alkoxy, or —$NR^xR^x$.

One embodiment provides a compound of Formula (I) or a stereoisomer, a tautomer, or a pharmaceutically acceptable salt or solvate thereof, wherein each $R^{2b}$ is independently F, Cl, cyano, hydroxyl, $C_{1-4}$ alkyl, $C_{1-3}$ alkoxy, —$NR^xR^x$, —$NR^xC(O)O(C_{1-4}$ alkyl), —C(O)($C_{1-2}$ alkyl), or —$S(O)_2$($C_{1-2}$ alkyl), wherein each of said alkyl and alkoxy is substituted with zero to 4 $R^{2a}$.

One embodiment provides a compound of Formula (I) or a stereoisomer, a tautomer, or a pharmaceutically acceptable salt or solvate thereof, wherein each $R^{2b}$ is independently F, Cl, cyano, hydroxyl, $C_{1-3}$ alkyl, $C_{1-3}$ alkoxy, —$NR^xR^x$, —$NR^xC(O)O(C_{1-3}$ alkyl), —C(O)($C_{1-2}$ alkyl), or —$S(O)_2$($C_{1-2}$ alkyl), wherein each of said alkyl and alkoxy is substituted with zero to 4 $R^{2a}$. Included in this embodiment are compounds in which each $R^{2b}$ is independently F, cyano, hydroxyl, $C_{1-3}$ alkyl, $C_{1-2}$ fluoroalkyl, $C_{1-3}$ hydroxyalkyl, $C_{1-2}$ alkoxy, —$NR^xR^x$, —$NR^xC(O)O(C_{1-3}$ alkyl), —C(O)($C_{1-2}$ alkyl), —C(O)($C_{1-2}$ fluoroalkyl), or —$S(O)_2$($C_{1-2}$ alkyl).

One embodiment provides a compound of Formula (I) or a stereoisomer, a tautomer, or a pharmaceutically acceptable salt or solvate thereof, wherein each $R^{4a}$ is independently F, Cl, Br, cyano, hydroxyl, —$NH_2$, $C_{1-6}$ alkyl, $C_{1-4}$ alkoxy, —$(CH_2)_{0-3}NH(C_{1-4}$ alkyl), —$(CH_2)_{0-2}N(C_{1-4}$ alkyl)$_2$, —$(CH_2)_{0-3}(C_{3-6}$ cycloalkyl), or —$(CH_2)_{0-3}$(4- to 6-membered heterocyclyl), wherein each of said alkyl and alkoxy is substituted with zero to 6 $R^{4d}$ and each of said cycloalkyl and heterocyclyl is substituted with zero to 3 $R^{4e}$. Included in this embodiment are compounds in which each $R^{4a}$ is independently F, Cl, cyano, hydroxyl, —$NH_2$, $C_{1-4}$ alkyl, $C_{1-4}$ alkoxy, —$(CH_2)_{0-3}NH(C_{1-6}$ alkyl), —$(CH_2)_{0-3}N(C_{1-6}$ alkyl)$_2$, —$(CH_2)_{0-3}(C_{3-6}$ cycloalkyl), or —$(CH_2)_{0-3}$(4- to 6-membered heterocyclyl), wherein each of said alkyl and alkoxy is substituted with zero to 4 $R^{4d}$; and each of said cycloalkyl and heterocyclyl is substituted with zero to 3 $R^{4e}$. Also included in this embodiment are compounds in which each $R^{4a}$ is independently cyano, —$CH_3$, —$CH(CH_3)_2$, —$C(CH_3)_3$, —$CHF_2$, —$CF_3$, —$C(CH_3)_2F$, —$C(CH_3)_2OH$, —$C(CH_3)_2CN$, —$OCH_3$, —$C(O)N(CH_3)_2$, —$CH_2$(cyclopropyl), cyclopropyl, fluorocyclopropyl, methylcyclopropyl, cyanocyclopropyl, trifluoromethylcyclopropyl, difluorocyclopropyl, methyloxetanyl, tetrahydropyranyl, or fluorobicyclo[1.1.1]pentyl.

One embodiment provides a compound of Formula (I) or a stereoisomer, a tautomer, or a pharmaceutically acceptable salt or solvate thereof, wherein $R^{4b}$ is $C_{1-4}$ alkyl, —$(CH_2)_{0-3}(C_{3-6}$ cycloalkyl), —$(CH_2)_{0-3}$(4- to 6-membered heterocyclyl), or —$(CH_2)_{0-3}$(phenyl), wherein each of said alkyl is substituted with zero to 6 $R^{4d}$ and each of said cycloalkyl, heterocyclyl, and phenyl is substituted with zero to 3 $R^{4e}$.

One embodiment provides a compound of Formula (I) or a stereoisomer, a tautomer, or a pharmaceutically acceptable salt or solvate thereof, wherein $R^{4b}$ is $C_{1-4}$ alkyl, —$(CH_2)_{0-3}(C_{3-6}$ cycloalkyl), or —$(CH_2)_{0-3}$(4- to 6-membered heterocyclyl), wherein each of said alkyl is substituted with zero to 6 $R^{4d}$ and each of said cycloalkyl and heterocyclyl is substituted with zero to 3 $R^{4e}$. Included in this embodiment are compounds in which $R^{4b}$ is $C_{1-4}$ alkyl, —$(CH_2)_{0-3}(C_{3-6}$ cycloalkyl), or —$(CH_2)_{0-3}$(4- to 6-membered heterocyclyl), wherein each of said alkyl is substituted with zero to 4 $R^{4d}$ and each of said cycloalkyl and heterocyclyl is substituted with zero to 3 $R^{4e}$.

One embodiment provides a compound of Formula (I) or a stereoisomer, a tautomer, or a pharmaceutically acceptable salt or solvate thereof, wherein each $R^{4c}$ is independently hydrogen, $C_{1-4}$ alkyl, or $C_{3-6}$ cycloalkyl. Included in this embodiment are compounds in which each $R^{4c}$ is independently hydrogen, $C_{1-3}$ alkyl, or $C_{3-6}$ cycloalkyl. Also included in this embodiment are compounds in which each $R^{4c}$ is independently hydrogen or —$CH_3$.

One embodiment provides a compound of Formula (I) or a stereoisomer, a tautomer, or a pharmaceutically acceptable salt or solvate thereof, wherein each $R^{4d}$ is independently F, Cl, hydroxyl, —$NR^xR^x$, cyano, $C_{1-3}$ alkoxy, or $C_{1-3}$ haloalkoxy. Included in this embodiment are compounds in which each $R^{4d}$ is independently F, Cl, hydroxyl, —$NR^xR^x$, oxo, cyano, $C_{1-3}$ alkoxy, or $C_{1-3}$ fluoroalkoxy.

One embodiment provides a compound of Formula (I) or a stereoisomer, a tautomer, or a pharmaceutically acceptable salt or solvate thereof, wherein each $R^{4e}$ is independently F, Cl, oxo, cyano, hydroxyl, —$NH_2$, $C_{1-4}$ alkyl, $C_{1-4}$ alkoxy, —$NH(C_{1-4}$ alkyl), or —$N(C_{1-4}$ alkyl)$_2$, wherein each of said alkyl and alkoxy is substituted with zero to 6 $R^{4d}$. Included in this embodiment are compounds in which each $R^{4e}$ is independently F, Cl, oxo, cyano, hydroxyl, —$NH_2$, $C_{1-4}$ alkyl, $C_{1-4}$ alkoxy, or —$NH(C_{1-6}$ alkyl), or —$N(C_{1-6}$ alkyl)$_2$, wherein each of said alkyl and alkoxy is substituted with zero to 4 $R^{4d}$.

One embodiment provides a compound of Formula (I) or a stereoisomer, a tautomer, or a pharmaceutically acceptable salt or solvate thereof, wherein $R^2$ is:

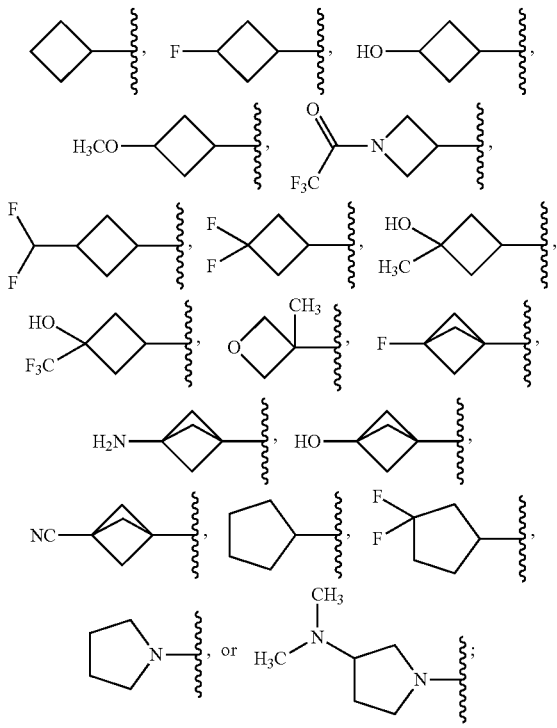

and A is oxadiazolyl substituted with zero to 2 $R^{4a}$. Included in this embodiment are compounds in which Q is phenyl substituted with 1 to 2 $R^1$. Also included in this embodiment are compounds in which Q is oxadiazolyl substituted with zero to 2 $R^1$.

One embodiment provides a compound of Formula (I) or a stereoisomer, a tautomer, or a pharmaceutically acceptable salt or solvate thereof, wherein: Q is a cyclic group selected from 3- to 8-membered carbocyclyl, phenyl, 4- to 10-membered heterocyclyl, and 5- to 10-membered heteroaryl, wherein said cyclic group is substituted with zero to 3 $R^1$; each $R^1$ is independently F, Cl, Br, cyano, hydroxyl, oxo, $-NR^xR^x$, $C_{1-5}$ alkyl, $C_{1-4}$ alkoxy, $-NR^x(C_{1-4}$ alkyl), $-NR^xC(O)R^y$, $-C(O)(C_{1-4}$ alkyl), $-C(O)OR^x$, $-C(O)NR^wR^w$, $-S(O)_2(C_{1-4}$ alkyl), $-S(O)_2(C_{3-6}$ cycloalkyl), $-NR^xS(O)_2(C_{1-4}$ alkyl), $-NR^xS(O)_2(C_{3-6}$ cycloalkyl), $-S(O)_2NR^zR^z$, $-P(O)R^yR^y$, $-(CH_2)_{0-3}(C_{3-6}$ carbocyclyl), $-O(C_{3-6}$ cycloalkyl), $-O(4-$ to 6-membered heterocyclyl), $-(CH_2)_{0-3}(4-$ to 6-membered heterocyclyl), or $-(CH_2)_{0-3}$(5- or 6-membered heteroaryl), wherein each of said alkyl and alkoxy is substituted with zero to 4 $R^{1a}$ and each of said cycloalkyl, heterocyclyl, and heteroaryl is substituted with zero to 3 $R^{1b}$; each $R^{1a}$ is independently F, Cl, hydroxyl, $-NR^wR^w$, oxo, cyano, $C_{1-3}$ alkoxy, $C_{1-3}$ haloalkoxy, or $-C(O)OH$; each $R^{1b}$ is independently F, Cl, cyano, hydroxyl, oxo, $-NH_2$, $C_{1-4}$ alkyl, $C_{1-4}$ alkoxy, $-NH(C_{1-4}$ alkyl), $-N(C_{1-4}$ alkyl)$_2$, or $-NR^xC(O)$ $(C_{1-6}$ alkyl), wherein each of said alkyl and alkoxy is substituted with zero to 6 $R^{1a}$; $R^2$ is: (i) $C_{1-4}$ alkyl, $C_{1-5}$ alkoxy, or $-NR^vR^v$, wherein each of said alkyl and alkoxy is substituted with zero to 4 $R^{2a}$; (ii) $C_{3-5}$ carbocyclyl, $C_{6-8}$ spirobicyclyl, or 4- to 5-membered heterocyclyl, wherein each of said carbocyclyl, spirobicyclyl, and heterocyclyl is substituted with zero to 3 $R^{2b}$; or (iii) $-CH_2(C_{3-5}$ cycloalkyl), $-CH_2$(4- to 6-membered heterocyclyl), $-NR^x(CH_2)_{0-2}(C_{3-6}$ cycloalkyl), $-NR^x(CH_2)_{0-2}(C_{6-8}$ spirobicyclyl), $-NR^x(CH_2)_{0-2}$(4- to 6-membered heterocyclyl), $-NR^x(CH_2)_{0-2}$(phenyl), $-O$(4- to 6-membered heterocyclyl), $-O$(phenyl), or $-O$(pyridinyl), wherein each of said cycloalkyl, spirobicyclyl, heterocyclyl, phenyl, and pyridinyl is substituted with zero to 3 $R^{2b}$; each $R^{2a}$ is independently F, Cl, hydroxyl, $-NR^xR^x$, oxo, cyano, $C_{1-3}$ alkoxy, $C_{1-3}$ haloalkoxy, or $-C(O)OH$; each $R^{2b}$ is independently F, Cl, cyano, hydroxyl, $C_{1-4}$ alkyl, $C_{1-3}$ alkoxy, $-NR^xR^x$, $-NR^xC(O)O(C_{1-4}$ alkyl), $-C(O)(C_{1-2}$ alkyl), or $-S(O)_2(C_{1-2}$ alkyl), wherein each of said alkyl and alkoxy is substituted with zero to 4 $R^{2a}$; A is: (i) cyano; (ii) phenyl or a 5- or 6-membered heteroaryl containing 1 to 4 heteroatoms independently selected from N, O, and S, wherein each of said phenyl and heteroaryl is substituted with zero to 3 $R^{4a}$; or
(iii)

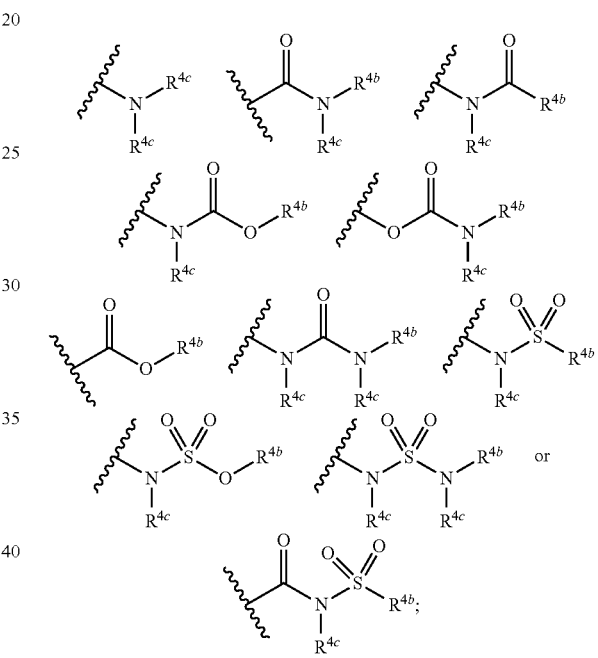

each $R^{4a}$ is independently F, Cl, cyano, hydroxyl, $-NH_2$, $C_{1-4}$ alkyl, $C_{1-4}$ alkoxy, $-(CH_2)_{0-3}NH(C_{1-6}$ alkyl), $-(CH_2)_{0-3}N(C_{1-6}$ alkyl)$_2$, $-(CH_2)_{0-3}(C_{3-6}$ cycloalkyl), or $-(CH_2)_{0-3}$(4- to 6-membered heterocyclyl), wherein each of said alkyl and alkoxy is substituted with zero to 4 $R^{4d}$; and each of said cycloalkyl and heterocyclyl is substituted with zero to 3 $R^{4e}$; $R^{4b}$ is $C_{1-4}$ alkyl, $-(CH_2)_{0-3}(C_{3-6}$ cycloalkyl), $-(CH_2)_{0-3}$(4- to 6-membered heterocyclyl), or $-(CH_2)_{0-3}$(phenyl), wherein each of said alkyl is substituted with zero to 6 $R^{4d}$ and each of said cycloalkyl, heterocyclyl, and phenyl is substituted with zero to 3 $R^{4e}$; each $R^{4c}$ is independently hydrogen, $C_{1-3}$ alkyl, or $C_{3-6}$ cycloalkyl; each $R^{4d}$ is independently F, Cl, hydroxyl, $-NR^xR^x$, oxo, $C_{1-3}$ alkoxy, or $C_{1-3}$ fluoroalkoxy; each $R^{4e}$ is independently F, Cl, oxo, cyano, hydroxyl, $-NH_2$, $C_{1-4}$ alkyl, $C_{1-4}$ alkoxy, or $-NH(C_{1-6}$ alkyl), or $-N(C_{1-6}$ alkyl)$_2$, wherein each of said alkyl and alkoxy is substituted with zero to 4 $R^{4d}$; each of $R^{5a}$, $R^{5b}$, $R^{5c}$, and $R^{5d}$ is independently hydrogen, F, Cl, hydroxy, cyano, $C_{1-3}$ alkyl substituted with zero to 4 $R^{5e}$, $C_{1-3}$ alkoxy substituted with zero to 4 $R^{5e}$, $-C(O)OR^x$, $-C(O)NR^wR^w$, $-S(O)_2R^y$, $-S(O)_2NR^zR^z$, or phenyl substituted with zero to 3 $R^{5f}$; each $R^w$ is independently hydrogen, $C_{1-4}$ alkyl, or $C_{3-6}$ cycloalkyl; or alternatively, two $R^w$, taken together with the nitrogen atom to which they are attached, form a 4- to 7-membered ring moiety containing zero to 2 additional heteroatoms independently selected from N, O, and S; each $R^x$ is independently H, $C_{1-4}$ alkyl, or $C_{3-6}$ cycloalkyl; $R^y$ is $C_{1-4}$ alkyl or $C_{3-6}$ cycloalkyl; and each $R^z$ is independently hydrogen, $C_{1-4}$ alkyl, or $C_{3-6}$ cycloalkyl; or alternatively, two $R^z$, taken together with the nitrogen atom to which they are attached, form a 4- to 7-membered ring moiety containing zero to 2 additional heteroatoms independently selected from N, O, and S.

One embodiment provides a compound of Formula (I) or a stereoisomer, a tautomer, or a pharmaceutically acceptable salt or solvate thereof, wherein: each $R^1$ is independently hydrogen, F, Cl, Br, cyano, hydroxyl, oxo, —$NR^xR^x$, $C_{1-5}$ alkyl, $C_{1-4}$ alkoxy, —$NR^x(C_{1-4}$ alkyl), —$NR^xC(O)R^y$, —$C(O)(C_{1-4}$ alkyl), —$C(O)OR^x$, —$C(O)NR^wR^w$, —$S(O)_2R$, —$S(O)_2(C_{1-2}$ fluoroalkyl), —$NR^xS(O)_2(C_{1-3}$ alkyl), —$NR^xS(O)_2(C_{3-6}$ cycloalkyl), —$S(O)_2NR^zR^z$, —$P(O)R^yR^y$, —$(CH_2)_{0-3}(C_{3-6}$ carbocyclyl), —$O(C_{3-6}$ cycloalkyl), —$O(4-$ to 6-membered heterocyclyl), —$(CH_2)_{0-3}(4-$ to 6-membered heterocyclyl), or —$(CH_2)_{0-3}$ (5- or 6-membered heteroaryl), wherein each of said alkyl and alkoxy is substituted with zero to 4 $R^{1a}$ and each of said cycloalkyl, heterocyclyl, and heteroaryl is substituted with zero to 3 $R^{1b}$; each $R^{1a}$ is independently F, Cl, hydroxyl, —$NR^xR^x$, oxo, cyano, $C_{1-3}$ alkoxy, $C_{1-3}$ haloalkoxy, or —$C(O)OH$; each $R^{1b}$ is independently F, Cl, oxo, cyano, hydroxyl, —$NH_2$, $C_{1-4}$ alkyl, $C_{1-4}$ alkoxy, —$NH(C_{1-4}$ alkyl), —$N(C_{1-4}$ alkyl)$_2$, or —$NR^xC(O)$ $(C_{1-6}$ alkyl), wherein each of said alkyl and alkoxy is substituted with zero to 6 $R^{1a}$; each $R^w$ is independently hydrogen, $C_{1-4}$ alkyl, or $C_{3-6}$ cycloalkyl; or alternatively, two $R^w$, taken together with the nitrogen atom to which they are attached, form a 4- to 7-membered ring moiety containing zero to 2 additional heteroatoms independently selected from N, O, and S; each $R^x$ is independently hydrogen, $C_{1-4}$ alkyl, or $C_{3-6}$ cycloalkyl; each $R^y$ is independently $C_{1-4}$ alkyl or $C_{3-6}$ cycloalkyl; each $R^z$ is independently hydrogen, $C_{1-4}$ alkyl, or $C_{3-6}$ cycloalkyl; or alternatively, two $R^z$, taken together with the nitrogen atom to which they are attached, form a 4- to 7-membered ring moiety containing zero to 2 additional heteroatoms independently selected from N, O, and S; $R^2$ is: (i) $C_{1-4}$ alkyl, $C_{1-4}$ alkoxy, or —$NH(C_{1-6}$ alkyl), wherein each of said alkyl and alkoxy is substituted with zero to 4 $R^{2a}$; (ii) $C_{3-5}$ carbocyclyl, $C_{6-8}$ spirobicyclyl, or 4- to 5-membered heterocyclyl, wherein each of said carbocyclyl, spirobicyclyl, and heterocyclyl is substituted with zero to 3 $R^{2b}$; or (iii) —$CH_2(C_{3-5}$ cycloalkyl), —$CH_2(4-$ to 6-membered heterocyclyl), —$NR^x(CH_2)_{0-2}(C_{3-5}$ cycloalkyl), —$NR^x(CH_2)_{0-2}(4-$ to 6-membered heterocyclyl), —$NR^x(CH_2)_{0-2}$(phenyl), —$O$(phenyl), or —$O$(pyridinyl), wherein each of said cycloalkyl, heterocyclyl, phenyl, and pyridinyl is substituted with zero to 3 $R^{2b}$; each $R^{2a}$ is independently F, Cl, cyano, hydroxyl, $C_{1-3}$ alkoxy, $C_{1-3}$ fluoroalkoxy, or —$NR^xR^x$; each $R^{2b}$ is independently F, Cl, cyano, hydroxyl, $C_{1-4}$ alkyl, $C_{1-3}$ alkoxy, —$NR^xR^x$, —$NR^xC(O)O(C_{1-3}$ alkyl), —$C(O)(C_{1-2}$ alkyl), or —$S(O)_2(C_{1-2}$ alkyl), wherein each of said alkyl and alkoxy is substituted with zero to 4 $R^{2a}$; each $R^{4a}$ is independently F, Cl, cyano, hydroxyl, —$NH_2$, $C_{1-4}$ alkyl, $C_{1-4}$ alkoxy, —$(CH_2)_{0-3}NH(C_{1-6}$ alkyl), —$(CH_2)_{0-3}N(C_{1-6}$ alkyl)$_2$, —$(CH_2)_{0-3}(C_{3-6}$ cycloalkyl), or —$(CH_2)_{0-3}(4-$ to 6-membered heterocyclyl), wherein each of said alkyl and alkoxy is substituted with zero to 4 $R^{4d}$; and each of said cycloalkyl and heterocyclyl is substituted with zero to 3 $R^{4e}$; $R^{4b}$ is $C_{1-4}$ alkyl, —$(CH_2)_{0-3}(C_{3-6}$ cycloalkyl), or —$(CH_2)_{0-3}(4-$ to 6-membered heterocyclyl), wherein each of said alkyl is substituted with zero to 4 $R^{4d}$ and each of said cycloalkyl and heterocyclyl is substituted with zero to 3 $R^{4e}$; each $R^{4c}$ is independently hydrogen, $C_{1-3}$ alkyl, or $C_{3-6}$ cycloalkyl; each $R^{4d}$ is independently F, Cl, hydroxyl, —$NR^xR^x$, oxo, cyano, $C_{1-3}$ alkoxy, or $C_{1-3}$ fluoroalkoxy; each $R^{4e}$ is independently F, Cl, oxo, cyano, hydroxyl, —$NH_2$, $C_{1-4}$ alkyl, $C_{1-4}$ alkoxy, or —$NH(C_{1-6}$ alkyl), or —$N(C_{1-6}$ alkyl)$_2$, wherein each of said alkyl and alkoxy is substituted with zero to 4 $R^{4d}$; and each of $R^{5a}$, $R^{5b}$, $R^{5c}$, and $R^{5d}$ is independently hydrogen, F, Cl, hydroxy, cyano, $C_{1-3}$ alkyl substituted with zero to 4 $R^{5e}$, $C_{1-3}$ alkoxy substituted with zero to 4 $R^{5e}$, —$C(O)OR^x$, —$C(O)NR^wR^w$, —$S(O)_2R^y$, —$S(O)_2NR^zR^z$, or phenyl substituted with zero to 3 $R^{5f}$.

One embodiment provides a compound of Formula (I) or a stereoisomer, a tautomer, or a pharmaceutically acceptable salt or solvate thereof, wherein $X^1$ is $CR^{5a}$; $X^2$ is $CR^{5b}$ or N; $X^3$ is CRC or N; $X^4$ is $CR^{5d}$ or N; provided that zero or 1 of $X^2$, $X^3$, and $X^4$ is N; $Z^1$ and $Z^2$ are independently $CH_2$ or O; provided that at least one of $Z^1$ and $Z^2$ is $CH_2$; a is 1; b is 1; d is 1; Q is a cyclic group selected from cyclopropyl, spiro[3.3]heptenyl, phenyl, azetidinyl, morpholinyl, oxaazaspiro[3.3]heptanyl, piperazinyl, piperidinyl, [1,2,4]triazolo[1,5-a] pyridinyl, [1,2,4]triazolo[4,3-a]pyridinyl, 1H-pyrazolo[3,4-b]pyridinyl, 2,3-dihydrobenzo[d]oxazolyl, 7,8-dihydro-5H-pyrano[4,3-b]pyridinyl, benzo[d][1,3]dioxolyl, benzo[d]oxazolyl, benzo[d]thiazolyl, imidazo[1,2-a]pyridinyl, imidazo[1,2-b]pyridazinyl, imidazolyl, indazolyl, indolinyl, isoxazolyl, oxadiazolyl, oxazolyl, pyrazinyl, pyrazolyl, pyridazinyl, pyridinyl, pyrimidinyl, pyrrolo[2,1-f][1,2,4]triazinyl, quinolinyl, thiazolo[4,5-b]pyridinyl, thiazolo[5,4-b]pyridinyl, thiazolyl, thieno[3,2-b]pyridinyl, and triazolyl, wherein said cyclic group is substituted with zero to 2 $R^1$; A is: (i) pyrazolyl, oxazolyl, thiazolyl, oxadiazolyl, thiadiazolyl, phenyl, pyridinyl, or pyrimidinyl, each substituted with zero to 2 $R^{4a}$; or (ii) —$C(O)NH$(cyclopropyl), —$NHS(O)_2CF_3$, —$NHC(O)OCH(CH_3)_2$, or —$NHC(O)NHCH(CH_3)_2$; each $R^1$ is independently hydrogen, F, Cl, Br, cyano, hydroxyl, oxo, $C_{1-4}$ alkyl, $C_{1-2}$ fluoroalkyl, —$CH_2Cl$, $C_{1-4}$ hydroxyalkyl, —$CH_2OCH_3$, $C_{1-3}$ alkoxy, $C_{1-2}$ fluoroalkoxy, —$OC(CH_3)_2CN$, —$C(O)OCH_2CH_3$, —$O$(cyclopropyl), —$CH_2$(cyclopropyl), —$NHC(O)CH_3$, —$NHS(O)_2CH_3$, —$NHS(O)_2CH(CH_3)_2$, —$NHS(O)_2CF_3$, —$NHS(O)_2$(cyclopropyl), —$S(O)_2CH_3$, —$S(O)_2$(cyclopropyl), —$S(O)_2$ $NH_2$, acetamidocyclopropyl, cyanocyclopropyl, difluorocyclopropyl, hydroxycyclopropyl, methoxycyclopropyl, cyclohexenyl, dihydropyranyl, oxetanyl, methyloxetanyl, tetrahydropyranyl, pyridinyl, or fluorobicyclo[1.1.1]pentyl; $R^2$ is: (i) $C_{1-4}$ alkyl, $C_{1-4}$ alkoxy, or —$NH(C_{1-6}$ alkyl), wherein each of said alkyl and alkoxy is substituted with zero to 4 $R^{2a}$; (ii) $C_{3-5}$ carbocyclyl, $C_{6-8}$ spirobicyclyl, or 4- to 5-membered heterocyclyl, wherein each of said carbocyclyl, spirobicyclyl, and heterocyclyl is substituted with zero to 3 $R^{2b}$; or (iii) —$CH_2(C_{3-5}$ cycloalkyl), —$CH_2$ (4- to 6-membered heterocyclyl), —$NR^x(CH_2)_{0-2}(C_{3-5}$ cycloalkyl), —$NR^x(CH_2)_{0-2}(4-$ to 6-membered heterocyclyl), —$NR^x(CH_2)_{0-2}$(phenyl), —$O$(phenyl), or —$O$(pyridinyl), wherein each of said cycloalkyl, heterocyclyl, phenyl, and pyridinyl is substituted with zero to 3 $R^{2b}$; each $R^{2a}$ is independently F, cyano, hydroxyl, $C_{1-2}$ alkoxy, or —$NR^xR^x$; each $R^{2b}$ is independently F, cyano, hydroxyl, $C_{1-3}$ alkyl, $C_{1-2}$ fluoroalkyl, $C_{1-3}$ hydroxyalkyl, $C_{1-2}$ alkoxy, —$NR^xR^x$, —$NR^xC(O)O(C_{1-3}$ alkyl), —$C(O)(C_{1-2}$ alkyl), —$C(O)(C_{1-2}$ fluoroalkyl), or —$S(O)_2(C_{1-2}$ alkyl); one of $R^{3a}$ and $R^{3b}$ is hydrogen and the other of $R^{3a}$ and $R^{3b}$ is hydrogen or —$CH_3$; each $R^{4a}$ is independently cyano, —$CH_3$, —$CH(CH_3)_2$, —$C(CH_3)_3$, —$CHF_2$, —$CF_3$, —$C(CH_3)_2F$, —$C(CH_3)_2OH$, —$C(CH_3)_2CN$, —$OCH_3$, —$C(O)N(CH_3)_2$, —CH$_2$(cyclopropyl), cyclopropyl, fluorocyclopropyl, methylcyclopropyl, cyanocyclopropyl, trifluoromethylcyclopropyl, difluorocyclopropyl, methyloxetanyl, tetrahydropyranyl, or fluorobicyclo[1.1.1]pentyl; and each of R$^{5a}$, R$^{5b}$, R$^{5c}$, and R$^{5d}$ is hydrogen.

One embodiment provides a compound of Formula (I) or a stereoisomer, a tautomer, or a pharmaceutically acceptable salt or solvate thereof, wherein X$^1$ is CR$^{5a}$; X$^2$ is CR$^{5b}$ or N; X$^3$ is CR$^{5c}$ or N; X$^4$ is CR$^{5d}$ or N; provided that zero, 1, or 2 of X$^2$, X$^3$, and X$^4$ is N; Z$^1$ and Z$^2$ are independently CH$_2$ or O; provided that at least one of Z$^1$ and Z$^2$ is CH$_2$; a is 1; b is 1; d is 1; Q is a cyclic group selected from cyclopropyl, spiro[3.3]heptenyl, bicyclo[2.2.2]octanyl, phenyl, azetidinyl, morpholinyl, oxaazaspiro[3.3]heptanyl, piperazinyl, piperidinyl, [1,2,4]triazolo[1,5-a] pyridinyl, [1,2,4]triazolo[4,3-a]pyridinyl, 1H-pyrazolo[3,4-b] pyridinyl, 2,3-dihydrobenzo[d]oxazolyl, 7,8-dihydro-5H-pyrano[4,3-b] pyridinyl, benzo[d][1,3]dioxolyl, benzo[d]oxazolyl, benzo[d]thiazolyl, imidazo[1,2-a]pyridinyl, imidazo[1,2-b]pyridazinyl, imidazolyl, indazolyl, indolinyl, isoxazolyl, oxadiazolyl, oxazolyl, pyrazinyl, pyrazolyl, pyridazinyl, pyridinyl, pyrimidinyl, pyrrolo[2,1-f][1,2,4]triazinyl, quinolinyl, tetrahydropyridinyl, thiazolo[4,5-b]pyridinyl, thiazolo[5,4-b] pyridinyl, thiazolyl, thieno[3,2-b]pyridinyl, and triazolyl, wherein said cyclic group is substituted with zero to 2 R$^1$; each R$^1$ is independently hydrogen, F, Cl, Br, cyano, hydroxyl, oxo, C$_{1-4}$ alkyl, C$_{1-2}$ fluoroalkyl, —CH$_2$Cl, C$_{1-4}$ hydroxyalkyl, —C(CH$_3$)$_2$CN, —CH(OH)CHF$_2$, —CH$_2$OCH$_3$, C$_{1-4}$ alkoxy, C$_{1-2}$ fluoroalkoxy, —OCF$_2$Cl, —OC(CH$_3$)$_2$CN, —C(CH$_3$)$_2$OCHF$_2$, —OC(CH$_3$)$_2$C(O)NH$_2$, —C(O)OH, —C(O)O(C$_{1-2}$ alkyl), —C(O)NH$_2$, —O(cyclopropyl), —CH$_2$(cyclopropyl), —CH$_2$(oxetanyl), —NHC(O)CH$_3$, —NHS(O)$_2$CH$_3$, —NHS(O)$_2$CH(CH$_3$)$_2$, —NHS(O)$_2$CF$_3$, —NHS(O)$_2$(cyclopropyl), —S(O)$_2$CH$_3$, —S(O)$_2$(cyclopropyl), —S(O)$_2$NH$_2$, cyclopropyl, acetamidocyclopropyl, cyanocyclopropyl, difluorocyclobutyl, hydroxycyclopropyl, methoxycyclopropyl, cyclohexenyl, dihydropyranyl, oxetanyl, methyloxetanyl, tetrahydropyranyl, aminooxadiazolyl, pyridinyl, or fluorobicyclo[1.1.1]pentyl; R$^2$ is: (i) C$_{1-4}$ alkyl, C$_{1-5}$ alkoxy, or —NH(C$_{1-6}$ alkyl), wherein each of said alkyl and alkoxy is substituted with zero to 4 R$^{2a}$; (ii) C$_{3-5}$ carbocyclyl, C$_{6-8}$ spirobicyclyl, or 4- to 5-membered heterocyclyl, wherein each of said carbocyclyl, spirobicyclyl, and heterocyclyl is substituted with zero to 3 R$^{2b}$; or (iii) —CH$_2$(C$_{3-5}$ cycloalkyl), —CH$_2$(4- to 6-membered heterocyclyl), —NR(CH$_2$)$_{0-2}$(C$_{3-6}$ cycloalkyl), —NR(CH$_2$)$_{0-2}$ (C$_{6-8}$ spirobicyclyl), —NR(CH$_2$)$_{0-2}$(4- to 6-membered heterocyclyl), —NR$^x$(CH$_2$)$_{0-2}$(phenyl), —O(tetrahydropyranyl), —O(phenyl), or —O(pyridinyl), wherein each of said cycloalkyl, spirobicyclyl, heterocyclyl, phenyl, and pyridinyl is substituted with zero to 3 R$^{2b}$; each R$^{2a}$ is independently F, cyano, hydroxyl, C$_{1-2}$ alkoxy, or —NR$^x$R$^x$; each R$^{2b}$ is independently F, cyano, hydroxyl, C$_{1-3}$ alkyl, C$_{1-2}$ fluoroalkyl, C$_{1-3}$ hydroxyalkyl, C$_{1-2}$ alkoxy, C$_{1-2}$ fluoroalkoxy, —NR$^x$R$^x$, —NR$^x$C(O)O(C$_{1-4}$ alkyl), —C(O)(C$_{1-2}$ alkyl), —C(O)(C$_{1-2}$ fluoroalkyl), or —S(O)$_2$ (C$_{1-2}$ alkyl); one of R$^{3a}$ and R$^{3b}$ is hydrogen and the other of R$^{3a}$ and R$^{3b}$ is hydrogen or —CH$_3$; A is: (i) pyrazolyl, oxazolyl, thiazolyl, oxadiazolyl, thiadiazolyl, phenyl, pyridinyl, or pyrimidinyl, each substituted with zero to 2 R$^{4a}$; or (ii) —C(O)NH(cyclopropyl), —NHS(O)$_2$CF$_3$, —NHC(O)OCH(CH$_3$)$_2$, or —NHC(O)NHCH(CH$_3$)$_2$, or —C(O)NHS(O)$_2$(cyclopropyl); each R$^{4a}$ is independently cyano, —CH$_3$, —CH(CH$_3$)$_2$, —C(CH$_3$)$_3$, —CHF$_2$, —CF$_3$, —CF$_2$CH$_3$, —C(CH$_3$)$_2$F, —C(CH$_3$)$_2$OH, —C(CH$_3$)$_2$CN, —OCH$_3$, —C(O)N(CH$_3$)$_2$, —CH$_2$(cyclopropyl), cyclopropyl, fluorocyclopropyl, methylcyclopropyl, cyanocyclopropyl, trifluoromethylcyclopropyl, difluorocyclopropyl, methyloxetanyl, tetrahydropyranyl, or fluorobicyclo[1.1.1]pentyl; and each of R$^{5a}$, R$^{5b}$, R$^{5c}$, and R$^{5d}$ is hydrogen.

One embodiment provides a compound of Formula (I) or a stereoisomer, a tautomer, or a pharmaceutically acceptable salt or solvate thereof, wherein X$^1$ is CH; X$^2$ is CH or N; X$^3$ is CH or N; X$^4$ is CH; provided that zero or 1 or X$^2$ and X$^3$ are N; Z$^1$ and Z$^2$ are independently CH$_2$ or O; provided that at least one of Z$^1$ and Z$^2$ is CH$_2$; a is 1; b is 1; d is 1; Q is a cyclic group selected from cyclopropyl, azetidinyl, imidazolyl, isoxazolyl, oxazolyl, oxadiazolyl, pyrazolyl, thiazolyl, triazolyl, morpholinyl, piperazinyl, phenyl, pyrazinyl, pyridazinyl, pyridinyl, pyrimidinyl, indazolyl, indolinyl, [1,2,4]triazolo[1,5-a]pyridinyl, [1,2,4]triazolo[4,3-a]pyridinyl, 1H-pyrazolo[3,4-b]pyridinyl, 2,3-dihydrobenzo[d]oxazolyl, 7,8-dihydro-5H-pyrano[4,3-b]pyridinyl, benzo[d]dioxolyl, benzo[d]thiazolyl, imidazo[1,2-a]pyridinyl, imidazo[1,2-b] pyridazinyl, pyrrolo[2,1-f][1,2,4]triazinyl, thiazolo[4,5-b]pyridinyl, thiazolo[5,4-b] pyridinyl, thieno[3,2-b]pyridinyl, and quinolinyl, wherein said cyclic group is substituted with zero to 2 R$^1$; A is —C(O)NH(cyclopropyl), phenyl, or a 5- to 6-membered heteroaryl selected from oxadiazolyl, oxazolyl, pyrazolyl, pyridinyl, pyrimidinyl, thiadiazolyl, and thiazolyl, wherein each of said phenyl and heteroaryl is substituted with zero to 2 substituents independently selected from cyano, fluorobicyclo[1.1.1]pentyl, C$_{1-4}$ alkyl, C$_{1-2}$ fluoroalkyl, —C(CH$_3$)$_2$CN, —C(CH$_3$)$_2$OH, —OCH$_3$, —C(O)N(CH$_3$)$_2$, —CH$_2$(cyclopropyl), cyclopropyl, fluorocyclopropyl, difluorocyclopropyl, trifluoromethylcyclopropyl, cyanocyclopropyl, methylcyclopropyl, methyl oxetanyl, and tetrahydropyranyl; R$^2$ is —CH(CH$_3$)$_2$, —NHCH$_2$CH$_3$, —NHCH$_2$C(CH$_3$)$_3$, —NH(methyl cyclopropyl), —NH(methoxyphenyl), or a cyclic group selected from C$_{3-5}$ cycloalkyl, azetidinyl, oxetanyl, pyrrolidinyl, and bicyclo[1.1.1]pentyl, each cyclic group substituted with zero to 2 substituents independently selected from F, hydroxyl, cyano, —CH$_3$, —CHF$_2$, —CF$_3$, —C(CH$_3$)$_2$OH, —OCH$_3$, —OCH$_2$CH$_3$, —NH$_2$, —N(CH$_3$)$_2$, —NHC(O)OC(CH$_3$)$_3$, and —C(O)CF$_3$; each R$^1$ is independently C$_{1-4}$ alkyl, —CHF$_2$, —CF$_3$, —CH$_2$CF$_3$, —CF$_2$CH$_3$, —CH$_2$CHF$_2$, —CH$_2$Cl, —C(CH$_3$)$_2$OH, —CH$_2$OCH$_3$, —C(CH$_3$)$_2$OCH$_3$, —OCH$_3$, —OCH$_2$CH$_3$, —C(O)OCH$_3$, —C(O)OCH$_2$CH$_3$, —CH$_2$(cyclopropyl), —S(O)$_2$CH$_3$, —S(O)$_2$(cyclopropyl), oxo, difluorocyclobutyl, fluorobicyclo[1.1.1]pentyl, oxetanyl, methyl oxetanyl, pyridinyl tetrahydropyranyl, or cyclopropyl substituted with zero to 1 substituent selected from hydroxyl, —CH$_3$, —OCH$_3$, and —NHC(O)CH$_3$; R$^{3a}$ is hydrogen or —CH$_3$; and R$^{3b}$ is hydrogen.

One embodiment provides a compound of Formula (I) or a stereoisomer, a tautomer, or a pharmaceutically acceptable salt or solvate thereof, wherein X$^1$ is CH; X$^2$ is CH; X$^3$ is CH; X$^4$ is CH; Z$^1$ is CH$_2$; Z$^2$ is CH$_2$; a is 1; b is 1; d is 1; A is oxadiazolyl substituted with one R$^{4a}$; R$^2$ is cyclobutyl substituted with zero to two R$^{2b}$; and each R$^{2b}$ is independently F, hydroxyl, cyano, —CHF$_2$, —CF$_3$, —C(CH$_3$)$_2$OH, —OCH$_3$, or —OCH$_2$CH$_3$. Included in this embodiment are compounds in which Q is benzo[d]thiazolyl, imidazolyl, isoxazolyl, oxazolyl, phenyl, pyrazolyl, pyridinyl, or pyrimidinyl, each substituted with zero to 2 R$^1$. Also included in this embodiment are compounds in which Q is oxadiazolyl, oxazolyl, phenyl, or pyrimidinyl, each substituted with zero to 2 R$^1$.

One embodiment provides a compound of Formula (I) or a stereoisomer, a tautomer, or a pharmaceutically acceptable salt or solvate thereof, wherein R$^2$ is C$_{1-6}$ alkoxy substituted with zero to 6 R$^{2a}$. Included in this embodiment are compounds in which $R^2$ is $C_{2-4}$ alkoxy substituted with zero to 3 $R^{2a}$. Also included in this embodiment are compounds in which $R^2$ is —$OCH_2CH_3$, —$OCH(CH_3)_2$, —$OCH_2CH(CH_3)_2$, —$OC(CH_3)_2CN$, and —$OC(CH_3)_2CF_3$. Additionally, included in this embodiment are compounds in which $R^2$ is —$OC(CH_3)_2CN$ and —$OC(CH_3)_2CF_3$; A is oxadiazolyl substituted with zero to 2 $R^{4a}$; and Q is phenyl, oxazolyl, or oxadiazolyl substituted with zero to 2 $R^{1b}$.

One embodiment provides a compound of Formula (I) or a stereoisomer, a tautomer, or a pharmaceutically acceptable salt or solvate thereof, wherein said compound has the structure:

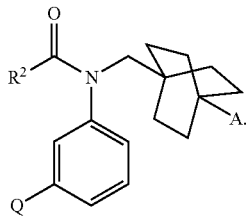

wherein $R^2$ is $C_{2-4}$ alkoxy substituted with zero to 3 $R^{2a}$. Included in this embodiment are compounds in which $R^2$ is —$OC(CH_3)_2CN$ and —$OC(CH_3)_2CF_3$. Also included in this embodiment are compounds in which A is oxadiazolyl substituted with zero to 2 $R^{4a}$; and Q is phenyl, oxazolyl, or oxadiazolyl substituted with zero to 2 $R^{1b}$.

One embodiment provides a compound of Formula (I) or a stereoisomer, a tautomer, or a pharmaceutically acceptable salt or solvate thereof, wherein said compound has the structure:

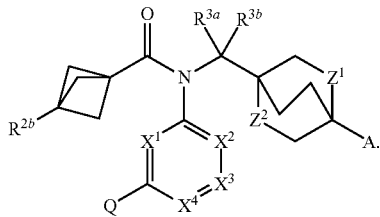

Included in this embodiment are compounds in which $R^{2b}$ is F, cyano, or —$C(CH_3)_2OH$. Also included in this embodiment are compounds in which $X^1$ is $CR^{5a}$; $X^2$ is $CR^{5b}$; $X^3$ is $CR^{5c}$; $X^4$ is $CR^{5d}$; and one of $R^{5a}$, $R^{5b}$, $R^{5c}$, and $R^{5d}$ is hydrogen, F, Cl, cyano, or —$OCH_3$, and the other three of $R^{5a}$, $R^{5b}$, $R^{5c}$, and $R^{5d}$ are each hydrogen. Additionally, included in this embodiment are compounds in which $Z^1$ is $CH_2$ and $Z^2$ is $CH_2$.

One embodiment provides a compound of Formula (I) or a stereoisomer, a tautomer, or a pharmaceutically acceptable salt or solvate thereof, wherein said compound has the structure:

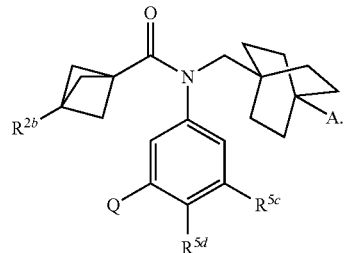

Included in this embodiment are compounds in which $R^{2b}$ is F, cyano, or —$C(CH_3)_2OH$. Also included in this embodiment are compounds in which one of $R^{5c}$ and $R^{5d}$ is hydrogen, F, Cl, cyano, or —$OCH_3$, and the other $R^{5c}$ and $R^{5d}$ is hydrogen. Additionally, included in this embodiment are compounds in which $R^{2b}$ is F; $R^{5c}$ is hydrogen; and $R^{5d}$ is hydrogen.

One embodiment provides a compound of Formula (I) or a stereoisomer, a tautomer, or a pharmaceutically acceptable salt or solvate thereof, wherein said compound has the structure:

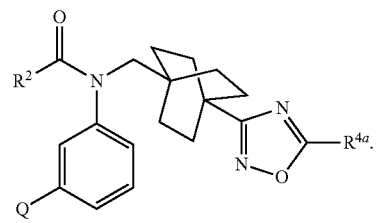

One embodiment provides a compound of Formula (I) or a stereoisomer, a tautomer, or a pharmaceutically acceptable salt or solvate thereof, wherein said compound has the structure:

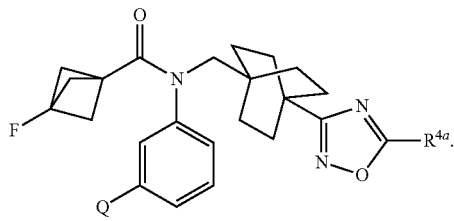

Included in this embodiment are compounds in which $R^{4a}$ is —$CH(CH_3)_2$, —$CH_2F$, —$CF_3$, —$CF_2CH_3$, cyclopropyl, fluorocyclopropyl, or methylcyclopropyl. Also included in this embodiment are compounds in which Q is phenyl or oxadiazolyl substituted with 1 to 2 $R^1$. Additionally, included in this embodiment are compounds in which Q is phenyl substituted with —$C(CH_3)_2OH$, —$C(CH_3)_2OCHF_2$, —$OCH(CH_3)_2$, or —$OC(CH_3)_2CN$, or cyanocyclopropyl.

One embodiment provides a compound of Formula (I) or a stereoisomer, a tautomer, or a pharmaceutically acceptable salt or solvate thereof, wherein said compound has the structure:

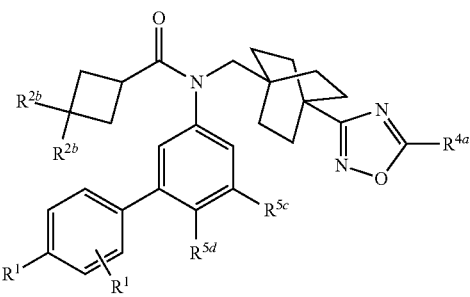

wherein one of $R^{5c}$ and $R^{5d}$ is hydrogen and the other of $R^{5c}$ and $R^{5d}$ is hydrogen or F; one $R^{2b}$ is hydroxyl and the other $R^{2b}$ is —$CH_3$, —$CH_2CH_3$, or —$CF_3$; $R^1$ is —$C(CH_3)_2OH$, —$C(CH_3)_2OCHF_2$, —$OCH(CH_3)_2$, —$OC(CH_3)_2CN$, or cyanocyclopropyl; and $R^{4a}$ is —$CF_2CH_3$, —$CH(CH_3)_2$, —$C(CH_3)_2F$, cyclopropyl, or fluorocyclopropyl. Included in this embodiment are compound in which one $R^{2b}$ is hydroxyl and the other $R^{2b}$ is —$CH_3$ or —$CH_2CH_3$. Also included in this embodiment are compounds in which one $R^{2b}$ is hydroxyl and the other $R^{2b}$ is —$CF_3$.

One embodiment provides a compound of Formula (I) or a stereoisomer, a tautomer, or a pharmaceutically acceptable salt or solvate thereof, wherein said compound has the structure:

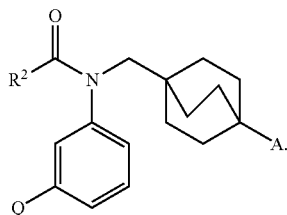

Included in this embodiment are compound in which Q is phenyl substituted with $R^{4a}$. Additionally, included in this embodiment are compounds in which Q is phenyl; A is oxadiazolyl substituted with $R^{4a}$; and $R^2$ is: (i) $C_{1-4}$ alkyl, $C_{1-5}$ alkoxy, or —NH($C_{1-6}$ alkyl), wherein each of said alkyl and alkoxy is substituted with zero to 4 $R^{2a}$; or (ii) $C_{3-5}$ cycloalkyl substituted with zero to 3 $R^{2b}$.

One embodiment provides a compound of Formula (I) or a stereoisomer, a tautomer, or a pharmaceutically acceptable salt or solvate thereof, wherein said compound has the structure:

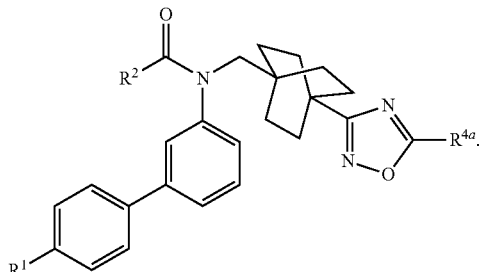

Included in this embodiment are compounds in which $R^2$ is: (i) $C_{1-5}$ alkoxy or —NH($C_{1-6}$ alkyl), wherein each of said alkyl and alkoxy is substituted with zero to 4 $R^{2a}$; or (ii) cyclobutyl substituted with 1 to 3 $R^{2b}$. Also included in this embodiment are compounds in which $R^{4a}$ is $C_{2-3}$ alkyl substituted with 1 to 6 $R^{4d}$; each $R^{4d}$ is F; $R^1$ is $C_{2-3}$ alkyl substituted with one $R^{1a}$; and $R^{1a}$ is hydroxyl. Additionally, included in this embodiment are compounds in which $R^{4a}$ is —$CF_3$ or —$C(CH_3)_2F$. Furthermore, included in this embodiment are compounds in which $R^1$ is —$C(CH_3)_2OH$.

One embodiment provides a compound of Formula (I) or a stereoisomer, a tautomer, or a pharmaceutically acceptable salt or solvate thereof, wherein said compound has the structure:

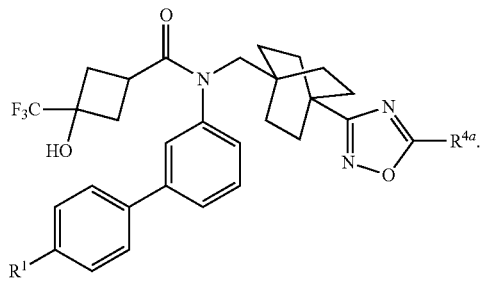

Included in this embodiment are compounds in which $R^{4a}$ is cyano, —$CH_3$, —$CH(CH_3)_2$, —$C(CH_3)_3$, —$CHF_2$, —$CF_3$, —$C(CH_3)_2F$, —$C(CH_3)_2OH$, —$C(CH_3)_2CN$, —$OCH_3$, —$C(O)N(CH_3)_2$, —$CH_2$(cyclopropyl), cyclopropyl, fluorocyclopropyl, methylcyclopropyl, cyanocyclopropyl, trifluoromethylcyclopropyl, difluorocyclopropyl, methyloxetanyl, tetrahydropyranyl, or fluorobicyclo[1.1.1]pentyl. Also included in this embodiment are compounds in which each $R^1$ is independently hydrogen, F, oxo, $C_{1-3}$ alkyl, —$CHF_2$, —$C(CH_3)_2OH$, —$CH_2OCH_3$, $C_{1-3}$ alkoxy, —$OCHF_2$, —$OC(CH_3)_2CN$, —O(cyclopropyl), —$CH_2$(cyclopropyl), —$NHS(O)_2CH_3$, cyclopropyl, cyanocyclopropyl, dihydropyranyl, or tetrahydropyranyl.

One embodiment provides a compound of Formula (I) or a stereoisomer, a tautomer, or a pharmaceutically acceptable salt or solvate thereof, wherein said compound has the structure:

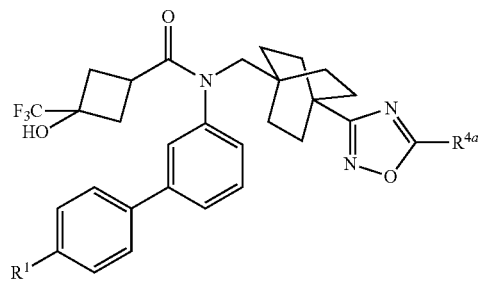

wherein $R^{4a}$ is $C_{1-3}$ alkyl substituted with zero to 6 $R^{4d}$; each $R^{4d}$ is F; $R^1$ is $C_{1-3}$ alkyl substituted with zero to 2 $R^{1a}$; and each $R^{1a}$ is hydroxyl. Included in this embodiment are compounds in which $R^{4a}$ is $C_{2-3}$ alkyl substituted with 1 to 6 $R^{4d}$; each $R^{4d}$ is F; $R^1$ is $C_{2-3}$ alkyl substituted with one $R^{1a}$; and $R^{1a}$ is hydroxyl. Additionally, included in this embodiment are compounds in which $R^{4a}$ is —$CF_3$ or —$C(CH_3)_2F$. Furthermore, included in this embodiment are compounds in which $R^1$ is —$C(CH_3)_2OH$.

One embodiment provides a compound of Formula (I) or a stereoisomer, a tautomer, or a pharmaceutically acceptable salt or solvate thereof, wherein said compound has the structure:

31

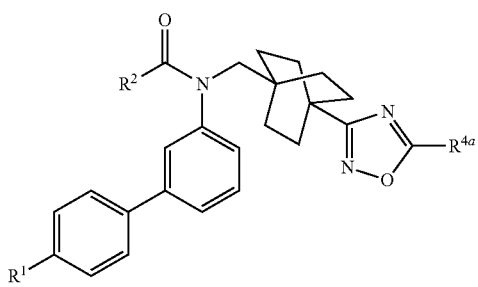

wherein $R^2$ is —NH($C_{1-6}$ alkyl), wherein said alkyl is substituted with zero to 4 $R^{2a}$. Included in this embodiment are compounds in which $R^2$ is —NH($C_{2-4}$ alkyl), wherein said alkyl is substituted with zero to 2 $R^{2a}$. Also included in this embodiment are compounds in which $R^2$ is —NH($CH_2CH_3$), —NH(CH($CH_3$)$_2$), —NH($CH_2CH(CH_3)_2$), or —NH(C($CH_3$)$_3$). Additionally, included in this embodiment are compounds in which $R^2$ is —NH($CH_2CH_3$), —NH(CH($CH_3$)$_2$), —NH($CH_2CH(CH_3)_2$), or —NH(C($CH_3$)$_3$); and $R^1$ is C($CH_3$)$_2$OH.

One embodiment provides a compound of Formula (I) or a stereoisomer, a tautomer, or a pharmaceutically acceptable salt or solvate thereof, wherein said compound has the structure:

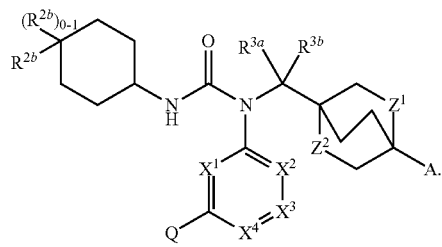

Included in this embodiment are compounds in which $R^{2b}$ is hydroxyl, —$CH_3$, or —$CF_3$. Also included in this embodiment are compounds in which $X^1$ is $CR^{5a}$; $X^2$ is $CR^{5b}$; $X^3$ is $CR^{5c}$; $X^4$ is $CR^{5d}$; and one of $R^{5a}$, $R^{5b}$, $R^{5c}$, and $R^{5d}$ is hydrogen, F, Cl, cyano, or —$OCH_3$, and the other three of $R^{5a}$, $R^{5b}$, $R^{5c}$, and $R^{5d}$ are each hydrogen; and $Z^1$ is $CH_2$ and $Z^2$ is $CH_2$. Included in this embodiment are compounds having the structures:

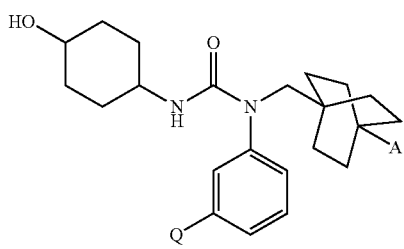

32

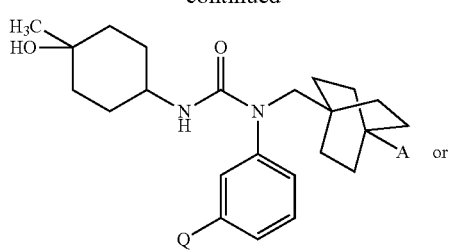

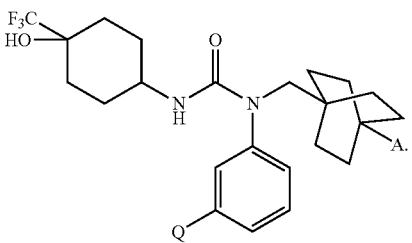

One embodiment provides a compound of Formula (I) or a pharmaceutically acceptable salt, wherein said compound is:

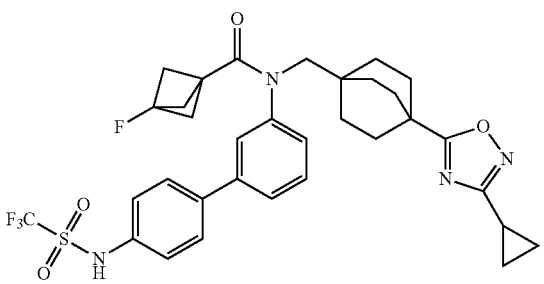

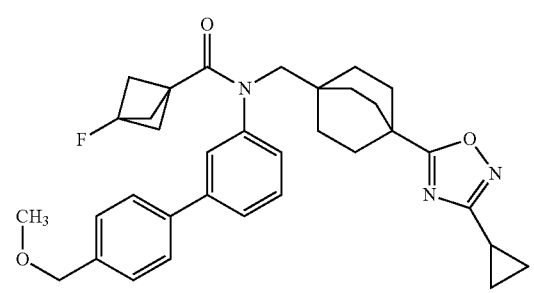

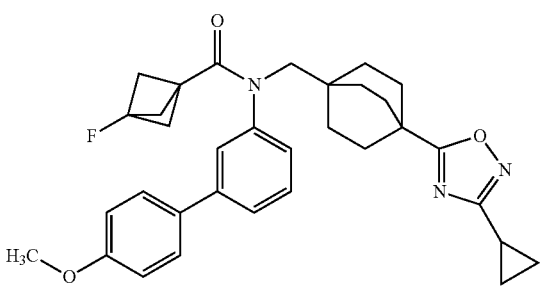

-continued
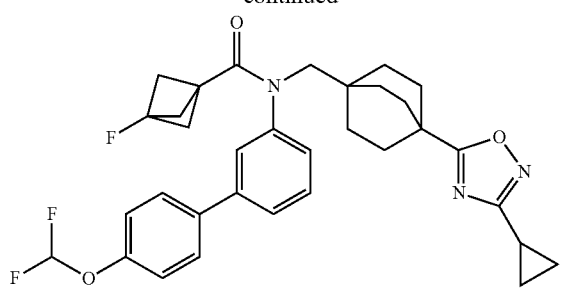
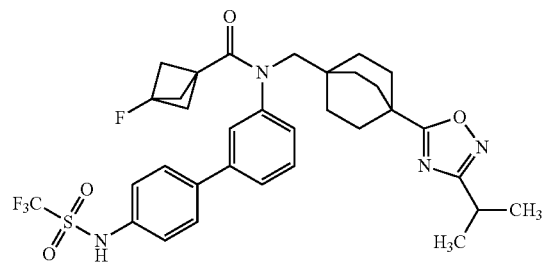
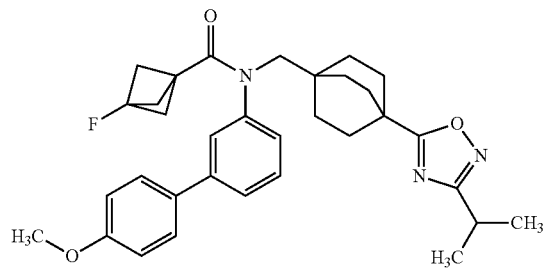
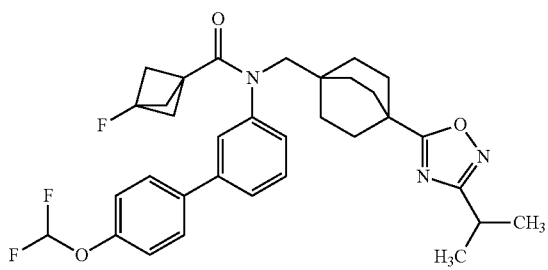
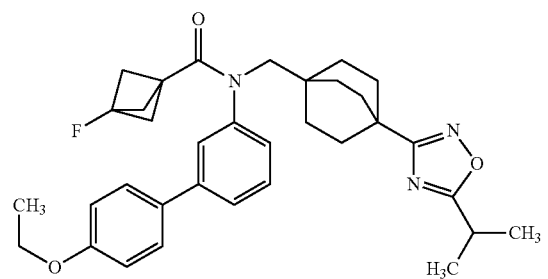
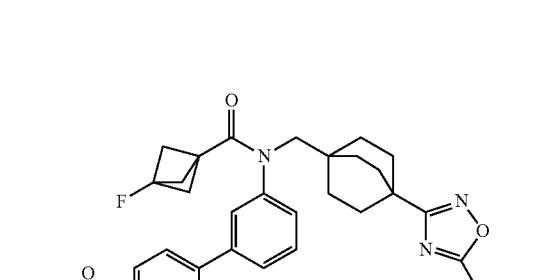
-continued
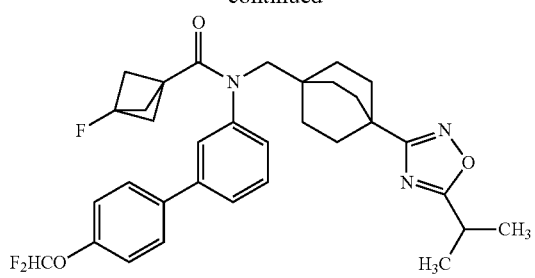
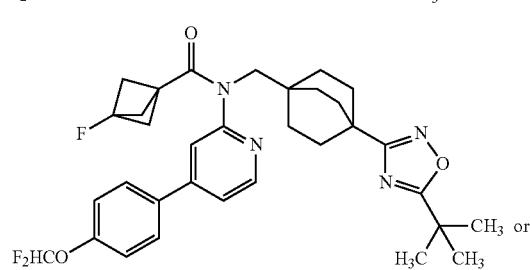
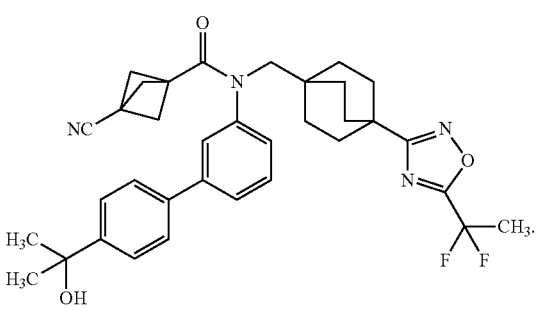
or
One embodiment provides a compound of Formula (I) or a pharmaceutically acceptable salt, wherein said compound is:
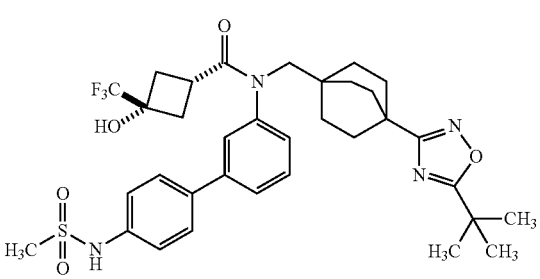
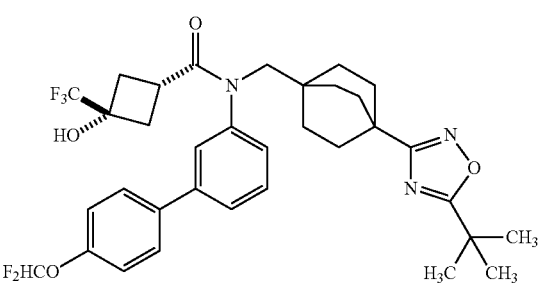

-continued

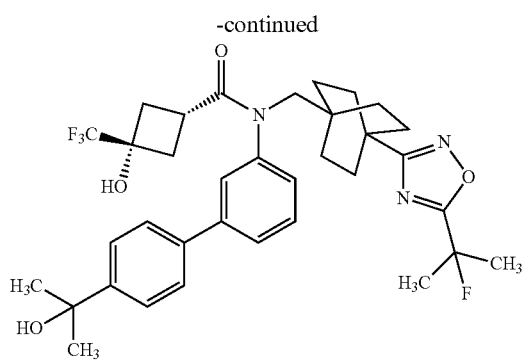

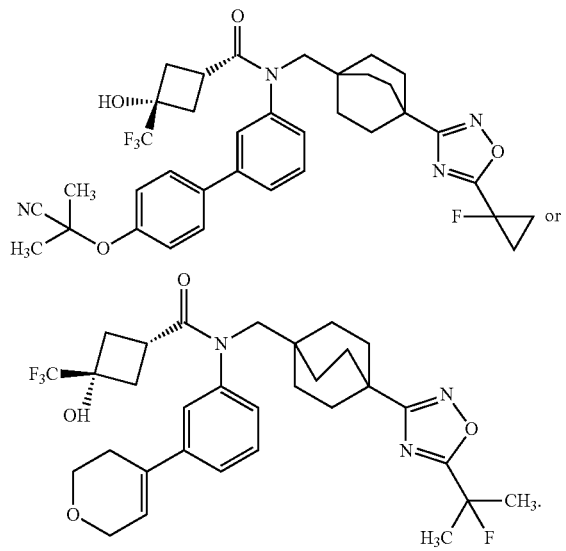

One embodiment provides a compound of Formula (I) or a pharmaceutically acceptable salt, wherein said compound is:

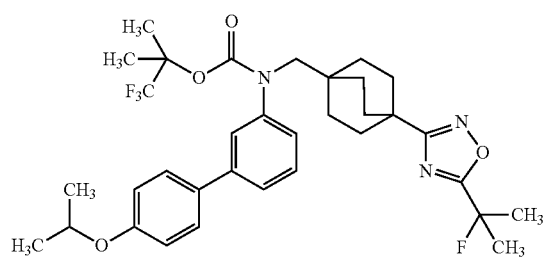

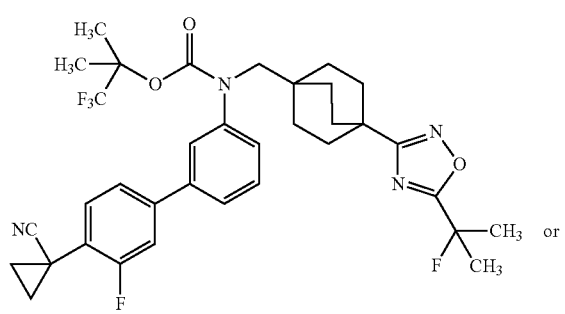

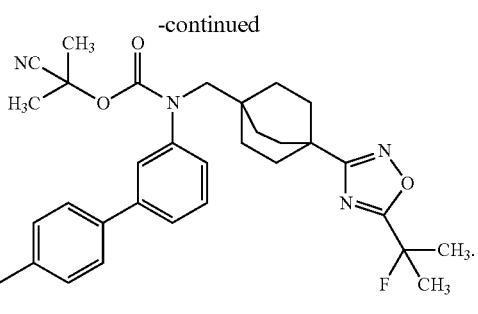

One embodiment provides a compound of Formula (I) or a pharmaceutically acceptable salt, wherein said compound is:

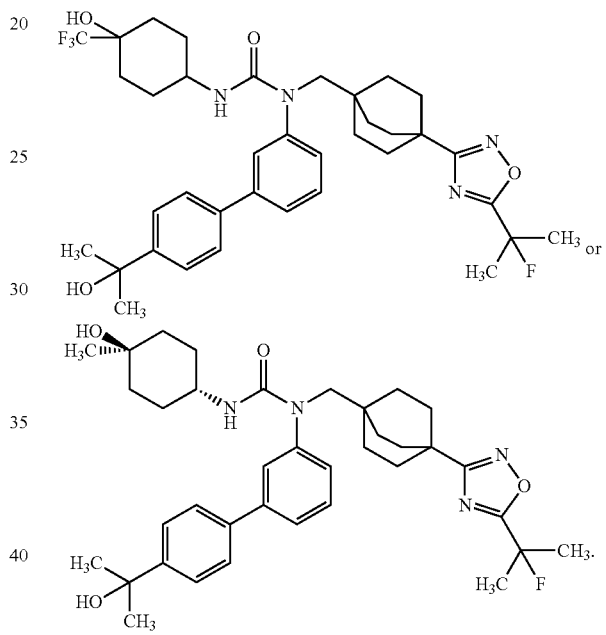

One embodiment provides a compound of Formula (I) or a stereoisomer, a tautomer, or a pharmaceutically acceptable salt or solvate thereof, wherein said compound has the structure:

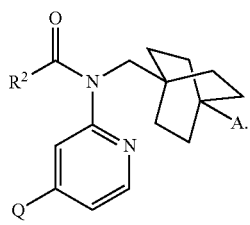

Included in this embodiment are compound in which Q is phenyl substituted with $R^{4a}$. Also included in this embodiment are compounds in which Q is phenyl; A is oxadiazolyl or pyridinyl substituted with $R^{4a}$; and $R^2$ is: (i) $C_{1-4}$ alkyl, $C_{1-5}$ alkoxy, or —NH($C_{1-6}$ alkyl), wherein each of said alkyl and alkoxy is substituted with zero to 4 $R^{2a}$; or (ii) $C_{3-5}$ cycloalkyl substituted with zero to 3 $R^{2b}$. Additionally, included in this embodiment are compounds in which A is oxadiazolyl or pyridinyl substituted with —CF$_2$CH$_3$.

One embodiment provides a compound of Formula (I) or a stereoisomer, a tautomer, or a pharmaceutically acceptable salt or solvate thereof, wherein said compound has the structure:

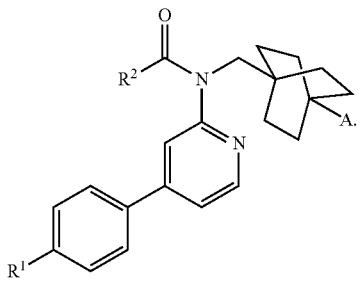

Included in this embodiment are compounds in which R$^2$ is C$_{1-5}$ alkoxy, wherein said alkoxy is substituted with zero to 4 R$^{2a}$. Also included in this embodiment are compounds in which R$^1$ is —C(CH$_3$)$_2$OH. Additionally, included in this embodiment are compounds in which A is oxadiazolyl or pyridinyl, each substituted with —CF$_2$CH$_3$; R$^1$ is —C(CH$_3$)$_2$ OH; and R$^2$ is —OC(CH$_3$)$_2$CF$_3$.

In one embodiment, the present invention provides a compound or a stereoisomer, a tautomer, or a pharmaceutically acceptable salt or solvate thereof, wherein said compound is:

N-((4-(4-cyclopropylphenyl)bicyclo[2.2.2]octan-1-yl) methyl)-N-(3-(3-methyl-1,2,4-oxadiazol-5-yl)phenyl) isobutyramide (1);

N-((4-(4-cyclopropylphenyl)bicyclo[2.2.2]octan-1-yl) methyl)-N-(3-(3-methyl-1,2,4-oxadiazol-5-yl)phenyl)cyclopropanecarboxamide (2);

N-(3-(3-ethyl-1,2,4-oxadiazol-5-yl)phenyl)-3-fluoro-N-((4-(3-methyl-1,2,4-oxadiazol-5-yl)bicyclo[2.2.2]octan-1-yl) methyl)bicyclo[1.1.1]pentane-1-carboxamide (3);

N-((4-(3-cyclopropyl-1,2,4-oxadiazol-5-yl)bicyclo[2.2.2] octan-1-yl)methyl)-3-(difluoromethyl)-N-(3-(3-ethyl-1,2,4-oxadiazol-5-yl)phenyl)cyclobutane-1-carboxamide (4);

(1s, 3s)-N-((4-(3-cyclopropyl-1,2,4-oxadiazol-5-yl)bicyclo [2.2.2]octan-1-yl)methyl)-N-(3-(3-ethyl-1,2,4-oxadiazol-5-yl)phenyl)-3-hydroxy-3-(trifluoromethyl)cyclobutane-1-carboxamide (5);

N-((4-(3-cyclopropyl-1,2,4-oxadiazol-5-yl)bicyclo[2.2.2] octan-1-yl)methyl)-N-(3-(3-ethyl-1,2,4-oxadiazol-5-yl) phenyl)-3-fluorobicyclo[1.1.1]pentane-1-carboxamide (6);

N-((4-(3-cyclopropyl-1,2,4-oxadiazol-5-yl)bicyclo[2.2.2] octan-1-yl)methyl)-N-(3-(2-ethoxyoxazol-5-yl)phenyl)-3-fluorobicyclo[1.1.1]pentane-1-carboxamide (7);

N-((4-(3-cyclopropyl-1,2,4-oxadiazol-5-yl)bicyclo[2.2.2] octan-1-yl)methyl)-N-(3-(3-cyclopropyl-1,2,4-oxadiazol-5-yl)phenyl)-3-fluorobicyclo[1.1.1]pentane-1-carboxamide (8);

(1s, 3s)-N-((4-(3-cyclopropyl-1,2,4-oxadiazol-5-yl)bicyclo [2.2.2]octan-1-yl)methyl)-N-(3-(3-cyclopropyl-1,2,4-oxadiazol-5-yl)phenyl)-3-hydroxy-3-(trifluoromethyl)cyclobutane-1-carboxamide (9);

N-((4-(3-cyclopropyl-1,2,4-oxadiazol-5-yl)bicyclo[2.2.2] octan-1-yl)methyl)-N-(3-(3-cyclopropyl-1,2,4-oxadiazol-5-yl)phenyl)-3,3-difluorocyclobutane-1-carboxamide (10);

N-((4-(3-cyclopropyl-1,2,4-oxadiazol-5-yl)bicyclo[2.2.2] octan-1-yl)methyl)-N-(3-(3-cyclopropyl-1,2,4-oxadiazol-5-yl)phenyl)-3,3-difluorocyclopentane-1-carboxamide (11);

ethyl 2-(3-(3-fluoro-N-((4-(3-methyl-1,2,4-oxadiazol-5-yl) bicyclo[2.2.2]octan-1-yl) methyl)bicyclo[1.1.1]pentane-1-carboxamido)phenyl)oxazole-4-carboxylate (12);

ethyl 2-(3-(N-((4-(3-cyclopropyl-1,2,4-oxadiazol-5-yl)bicyclo[2.2.2]octan-1-yl)methyl)-3-fluorobicyclo[1.1.1]pentane-1-carboxamido)phenyl)oxazole-4-carboxylate (13);

N-(3-(4-(chloromethyl)oxazol-2-yl)phenyl)-N-((4-(3-cyclopropyl-1,2,4-oxadiazol-5-yl)bicyclo[2.2.2]octan-1-yl) methyl)-3-fluorobicyclo[1.1.1]pentane-1-carboxamide (14);

N-((4-(3-cyclopropyl-1,2,4-oxadiazol-5-yl)bicyclo[2.2.2] octan-1-yl)methyl)-3-fluoro-N-(3-(4-(2-hydroxypropan-2-yl)oxazol-2-yl)phenyl)bicyclo[1.1.1]pentane-1-carboxamide (15);

N-((4-(3-cyclopropyl-1,2,4-oxadiazol-5-yl)bicyclo[2.2.2] octan-1-yl)methyl)-3,3-difluoro-N-(3-(4-(2-hydroxypropan-2-yl)oxazol-2-yl)phenyl)cyclobutane-1-carboxamide (16);

N-((4-(3-cyclopropyl-1,2,4-oxadiazol-5-yl)bicyclo[2.2.2] octan-1-yl)methyl)-3-(difluoromethyl)-N-(3-(4-(2-hydroxypropan-2-yl)oxazol-2-yl)phenyl)cyclobutane-1-carboxamide (17);

N-((4-(3-cyclopropyl-1,2,4-oxadiazol-5-yl)bicyclo[2.2.2] octan-1-yl)methyl)-3,3-difluoro-N-(3-(4-(2-hydroxypropan-2-yl)oxazol-2-yl)phenyl)cyclopentane-1-carboxamide (18);

(1S,3S)—N-((4-(3-cyclopropyl-1,2,4-oxadiazol-5-yl)bicyclo[2.2.2]octan-1-yl)methyl)-3-hydroxy-N-(3-(3-(2-hydroxypropan-2-yl)-1,2,4-oxadiazol-5-yl)phenyl)-3-(trifluoromethyl)cyclobutane-1-carboxamide (19);

N-((4-(3-cyclopropyl-1,2,4-oxadiazol-5-yl)bicyclo[2.2.2] octan-1-yl)methyl)-N-(3-(2-cyclopropyloxazol-5-yl)phenyl)cyclobutanecarboxamide (20);

(1S,3S)—N-((4-(3-cyclopropyl-1,2,4-oxadiazol-5-yl)bicyclo[2.2.2]octan-1-yl)methyl)-N-(3-(2-cyclopropyloxazol-5-yl)phenyl)-3-hydroxy-3-(trifluoromethyl)cyclobutane-1-carboxamide (21);

N-((4-(3-cyclopropyl-1,2,4-oxadiazol-5-yl)bicyclo[2.2.2] octan-1-yl)methyl)-N-(3-(2-cyclopropyloxazol-5-yl)phenyl)-3,3-difluorocyclobutane-1-carboxamide (22);

N-((4-(3-cyclopropyl-1,2,4-oxadiazol-5-yl)bicyclo[2.2.2] octan-1-yl)methyl)-N-(3-(2-cyclopropyloxazol-5-yl)phenyl)-3-fluorobicyclo[1.1.1]pentane-1-carboxamide (23);

N-((4-(3-cyclopropyl-1,2,4-oxadiazol-5-yl)bicyclo[2.2.2] octan-1-yl)methyl)-N-(3-(2-cyclopropyloxazol-5-yl)phenyl)-3-(difluoromethyl)cyclobutane-1-carboxamide (24);

N-((4-(3-cyclopropyl-1,2,4-oxadiazol-5-yl)bicyclo[2.2.2] octan-1-yl)methyl)-N-(3-(5-ethoxyisoxazol-3-yl)phenyl)-3-fluorobicyclo[1.1.1]pentane-1-carboxamide (25);

N-((4-(3-cyclopropyl-1,2,4-oxadiazol-5-yl)bicyclo[2.2.2] octan-1-yl)methyl)-3-fluoro-N-(3-(2-propyloxazol-5-yl) phenyl)bicyclo[1.1.1]pentane-1-carboxamide (26);

N-((4-(3-cyclopropyl-1,2,4-oxadiazol-5-yl)bicyclo[2.2.2] octan-1-yl)methyl)-3,3-difluoro-N-(3-(2-propyloxazol-5-yl)phenyl)cyclobutane-1-carboxamide (27);

N-((4-(3-cyclopropyl-1,2,4-oxadiazol-5-yl)bicyclo[2.2.2] octan-1-yl)methyl)-3-(difluoromethyl)-N-(3-(2-propyloxazol-5-yl)phenyl)cyclobutane-1-carboxamide (28);

ethyl 4-(3-(N-((4-(3-cyclopropyl-1,2,4-oxadiazol-5-yl)bicyclo[2.2.2]octan-1-yl)methyl)-3-fluorobicyclo[1.1.1]pentane-1-carboxamido)phenyl)thiazole-2-carboxylate (29);

N-(3-(2-(chloromethyl)thiazol-4-yl)phenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide (30);

N-((4-(3-cyclopropyl-1,2,4-oxadiazol-5-yl)bicyclo[2.2.2]octan-1-yl)methyl)-3-fluoro-N-(3-(2-(2-hydroxypropan-2-yl)thiazol-4-yl)phenyl)bicyclo[1.1.1]pentane-1-carboxamide (31);

N-(3-(3-cyclopropyl-1,2,4-oxadiazol-5-yl)phenyl)-3-fluoro-N-((4-(2-methylpyridin-4-yl)bicyclo[2.2.2]octan-1-yl)methyl)bicyclo[1.1.1]pentane-1-carboxamide (32);

N-(3-(3-cyclopropyl-1,2,4-oxadiazol-5-yl)phenyl)-3,3-difluoro-N-((4-(2-methylpyridin-4-yl)bicyclo[2.2.2]octan-1-yl)methyl)cyclopentane-1-carboxamide (33);

3-Fluoro-N-((4-(3-methyl-1,2,4-oxadiazol-5-yl)bicyclo[2.2.2]octan-1-yl)methyl)-N-(3-(2-(tetrahydro-2H-pyran-4-yl)oxazol-5-yl)phenyl)bicyclo[1.1.1]pentane-1-carboxamide (34);

N-((4-(3-cyclopropyl-1,2,4-oxadiazol-5-yl)bicyclo[2.2.2]octan-1-yl)methyl)-3-fluoro-N-(3-(2-(tetrahydro-2H-pyran-4-yl)oxazol-5-yl)phenyl)bicyclo[1.1.1]pentane-1-carboxamide (35);

N-((4-(3-cyclopropyl-1,2,4-oxadiazol-5-yl)bicyclo[2.2.2]octan-1-yl)methyl)-3,3-difluoro-N-(3-(2-(tetrahydro-2H-pyran-4-yl)oxazol-5-yl)phenyl)cyclobutane-1-carboxamide (36);

N-(3-(3-cyclopropyl-1,2,4-oxadiazol-5-yl)phenyl)-3-fluoro-N-((4-(5-methyloxazol-2-yl)bicyclo[2.2.2]octan-1-yl)methyl)bicyclo[1.1.1]pentane-1-carboxamide (37);

(1S,3S)—N-(3-(3-cyclopropyl-1,2,4-oxadiazol-5-yl)phenyl)-3-hydroxy-N-((4-(5-methyloxazol-2-yl)bicyclo[2.2.2]octan-1-yl)methyl)-3-(trifluoromethyl)cyclobutane-1-carboxamide (38);

N-(3-(3-cyclopropyl-1,2,4-oxadiazol-5-yl)phenyl)-3,3-difluoro-N-((4-(5-methyloxazol-2-yl)bicyclo[2.2.2]octan-1-yl)methyl)cyclopentane-1-carboxamide (39);

N-((4-(3-cyclopropyl-1,2,4-oxadiazol-5-yl)bicyclo[2.2.2]octan-1-yl)methyl)-N-(3-(4-(difluoromethyl)oxazol-2-yl)phenyl)-3-fluorobicyclo[1.1.1]pentane-1-carboxamide (40);

N-((4-(3-cyclopropyl-1,2,4-oxadiazol-5-yl)bicyclo[2.2.2]octan-1-yl)methyl)-N-(3-(4-(difluoromethyl)oxazol-2-yl)phenyl)-3,3-difluorocyclobutane-1-carboxamide (41);

(1s, 3s)-N-((4-(3-cyclopropyl-1,2,4-oxadiazol-5-yl)bicyclo[2.2.2]octan-1-yl)methyl)-N-(3-(4-(difluoromethyl)oxazol-2-yl)phenyl)-3-hydroxy-3-(trifluoromethyl)cyclobutane-1-carboxamide (42);

N-((4-(3-cyclopropyl-1,2,4-oxadiazol-5-yl)bicyclo[2.2.2]octan-1-yl)methyl)-3-(difluoromethyl)-N-(3-(4-(difluoromethyl)oxazol-2-yl)phenyl)cyclobutane-1-carboxamide (43);

N-((4-(3-cyclopropyl-1,2,4-oxadiazol-5-yl)bicyclo[2.2.2]octan-1-yl)methyl)-N-(3-(4-(difluoromethyl)oxazol-2-yl)phenyl)-3,3-difluorocyclopentane-1-carboxamide (44);

N-(3-(4-(difluoromethyl)oxazol-2-yl)phenyl)-3-fluoro-N-((4-(5-methyloxazol-2-yl) bicyclo[2.2.2]octan-1-yl)methyl)bicyclo[1.1.1]pentane-1-carboxamide (45);

(cis)-N-(3-(4-(difluoromethyl)oxazol-2-yl)phenyl)-3-hydroxy-N-((4-(5-methyloxazol-2-yl)bicyclo[2.2.2]octan-1-yl)methyl)-3-(trifluoromethyl)cyclobutane-1-carboxamide (46);

N-((1-(4-(2-cyanopropan-2-yl)phenyl)-2-oxabicyclo[2.2.2]octan-4-yl)methyl)-N-(3-(3-ethyl-1,2,4-oxadiazol-5-yl)phenyl)-3-fluorobicyclo[1.1.1]pentane-1-carboxamide (47);

N-((1-(4-(2-cyanopropan-2-yl)phenyl)-2-oxabicyclo[2.2.2]octan-4-yl)methyl)-N-(3-(3-ethyl-1,2,4-oxadiazol-5-yl)phenyl)cyclobutanecarboxamide (48);

N-(3-(3-cyclopropyl-1,2,4-oxadiazol-5-yl)phenyl)-3,3-difluoro-N-((4-(4-(trifluoromethyl)pyridin-2-yl)bicyclo[2.2.2]octan-1-yl)methyl)cyclobutane-1-carboxamide (49);

N-(3-(3-cyclopropyl-1,2,4-oxadiazol-5-yl)phenyl)-3-fluoro-N-((4-(4-(trifluoromethyl)pyridin-2-yl)bicyclo[2.2.2]octan-1-yl)methyl)bicyclo[1.1.1]pentane-1-carboxamide (50);

N-((1-(4-(2-cyanopropan-2-yl)phenyl)-2-oxabicyclo[2.2.2]octan-4-yl)methyl)-N-(3-(2-ethoxyoxazol-5-yl)phenyl)-3-fluorobicyclo[1.1.1]pentane-1-carboxamide (51);

3-fluoro-N-(3-(2-propyloxazol-5-yl)phenyl)-N-((4-(4-(trifluoromethyl)pyridin-2-yl) bicyclo[2.2.2]octan-1-yl)methyl)bicyclo[1.1.1]pentane-1-carboxamide (52);

N-((4-(3-cyclopropyl-1,2,4-oxadiazol-5-yl)bicyclo[2.2.2]octan-1-yl)methyl)-N-(3-(5-ethoxy-1,3,4-oxadiazol-2-yl)phenyl)-3-fluorobicyclo[1.1.1]pentane-1-carboxamide (53);

N-((4-(3-cyclopropyl-1,2,4-oxadiazol-5-yl)bicyclo[2.2.2]octan-1-yl)methyl)-N-(3-(5-ethoxy-1,3,4-oxadiazol-2-yl)phenyl)cyclobutanecarboxamide (54);

N-((4-(3-cyclopropyl-1,2,4-oxadiazol-5-yl)bicyclo[2.2.2]octan-1-yl)methyl)-N-(3-(5-ethoxy-1,3,4-oxadiazol-2-yl)phenyl)-3,3-difluorocyclopentane-1-carboxamide (55);

N-((4-(3-cyclopropyl-1,2,4-oxadiazol-5-yl)bicyclo[2.2.2]octan-1-yl)methyl)-3-(difluoromethyl)-N-(3-(5-ethoxy-1,3,4-oxadiazol-2-yl)phenyl)cyclobutane-1-carboxamide (56);

N-((4-(3-cyclopropyl-1,2,4-oxadiazol-5-yl)bicyclo[2.2.2]octan-1-yl)methyl)-N-(3-(5-cyclopropylisoxazol-3-yl)phenyl)-3-fluorobicyclo[1.1.1]pentane-1-carboxamide (57);

N-((4-(3-cyclopropyl-1,2,4-oxadiazol-5-yl)bicyclo[2.2.2]octan-1-yl)methyl)-N-(3-(5-cyclopropylisoxazol-3-yl)phenyl)-3-(difluoromethyl)cyclobutane-1-carboxamide (58);

N-((4-(3-cyclopropyl-1,2,4-oxadiazol-5-yl)bicyclo[2.2.2]octan-1-yl)methyl)-N-(3-(5-cyclopropylisoxazol-3-yl)phenyl)-3,3-difluorocyclopentane-1-carboxamide (59);

N-((4-(3-cyclopropyl-1,2,4-oxadiazol-5-yl)bicyclo[2.2.2]octan-1-yl)methyl)-N-(3-(5-cyclopropylisoxazol-3-yl)phenyl)-3,3-difluorocyclobutane-1-carboxamide (60);

N-((4-(3-(cyclopropylmethyl)-1,2,4-oxadiazol-5-yl)bicyclo[2.2.2]octan-1-yl)methyl)-N-(3-(3-(cyclopropylmethyl)-1,2,4-oxadiazol-5-yl)phenyl)-3-fluorobicyclo[1.1.1]pentane-1-carboxamide (61);

N-((4-(3-(cyclopropylmethyl)-1,2,4-oxadiazol-5-yl)bicyclo[2.2.2]octan-1-yl)methyl)-N-(3-(3-(cyclopropylmethyl)-1,2,4-oxadiazol-5-yl)phenyl)-3,3-difluorocyclopentane-1-carboxamide (62);

N-((4-(3-(cyclopropylmethyl)-1,2,4-oxadiazol-5-yl)bicyclo[2.2.2]octan-1-yl)methyl)-N-(3-(3-(cyclopropylmethyl)-1,2,4-oxadiazol-5-yl)phenyl)-3,3-difluorocyclobutane-1-carboxamide (63);

N-((4-(3-(cyclopropylmethyl)-1,2,4-oxadiazol-5-yl)bicyclo[2.2.2]octan-1-yl)methyl)-N-(3-(3-(cyclopropylmethyl)-1,2,4-oxadiazol-5-yl)phenyl)cyclobutanecarboxamide (64);

N-((4-(3-cyclopropyl-1,2,4-oxadiazol-5-yl)bicyclo[2.2.2]octan-1-yl)methyl)-N-(3-(3-(cyclopropylmethyl)-1,2,4-oxadiazol-5-yl)phenyl)-3-fluorobicyclo[1.1.1]pentane-1-carboxamide (65);

N-((4-(3-cyclopropyl-1,2,4-oxadiazol-5-yl)bicyclo[2.2.2]octan-1-yl)methyl)-N-(3-(3-(cyclopropylmethyl)-1,2,4-oxadiazol-5-yl)phenyl)cyclobutanecarboxamide (66);

N-((4-(3-cyclopropyl-1,2,4-oxadiazol-5-yl)bicyclo[2.2.2]octan-1-yl)methyl)-N-(3-(3-(cyclopropylmethyl)-1,2,4-oxadiazol-5-yl)phenyl)-3,3-difluorocyclopentane-1-carboxamide (67);

N-(3-(3-cyclopropyl-1,2,4-oxadiazol-5-yl)phenyl)-N-((4-(3-(cyclopropylmethyl)-1,2,4-oxadiazol-5-yl)bicyclo[2.2.2]octan-1-yl)methyl)-3-fluorobicyclo[1.1.1]pentane-1-carboxamide (68);

N-(3-(3-cyclopropyl-1,2,4-oxadiazol-5-yl)phenyl)-N-((4-(3-(cyclopropylmethyl)-1,2,4-oxadiazol-5-yl)bicyclo[2.2.2]octan-1-yl)methyl)-3,3-difluorocyclopentane-1-carboxamide (69);

N-(3-(3-cyclopropyl-1,2,4-oxadiazol-5-yl)phenyl)-N-((4-(3-(cyclopropylmethyl)-1,2,4-oxadiazol-5-yl)bicyclo[2.2.2]octan-1-yl)methyl)-3,3-difluorocyclobutane-1-carboxamide (70);

N-(3-(3-cyclopropyl-1,2,4-oxadiazol-5-yl)phenyl)-N-((4-(3-(cyclopropylmethyl)-1,2,4-oxadiazol-5-yl)bicyclo[2.2.2]octan-1-yl)methyl)cyclobutanecarboxamide (71);

N-((4-(3-cyclopropyl-1,2,4-oxadiazol-5-yl)bicyclo[2.2.2]octan-1-yl)methyl)-3-fluoro-N-(3-(2-(methoxymethyl)thiazol-4-yl)phenyl)bicyclo[1.1.1]pentane-1-carboxamide (72);

N-((4-(3-cyclopropyl-1,2,4-oxadiazol-5-yl)bicyclo[2.2.2]octan-1-yl)methyl)-3-(difluoromethyl)-N-(3-(2-(methoxymethyl)thiazol-4-yl)phenyl)cyclobutane-1-carboxamide (73);

N-((4-(3-cyclopropyl-1,2,4-oxadiazol-5-yl)bicyclo[2.2.2]octan-1-yl)methyl)-3,3-difluoro-N-(3-(2-(methoxymethyl)thiazol-4-yl)phenyl)cyclopentane-1-carboxamide (74);

N-((4-(3-cyclopropyl-1,2,4-oxadiazol-5-yl)bicyclo[2.2.2]octan-1-yl)methyl)-N-(3-(5-cyclopropyl-1-methyl-1H-pyrazol-3-yl)phenyl)-3-fluorobicyclo[1.1.1]pentane-1-carboxamide (75);

N-((4-(3-cyclopropyl-1,2,4-oxadiazol-5-yl)bicyclo[2.2.2]octan-1-yl)methyl)-N-(3-(5-cyclopropyl-1-methyl-1H-pyrazol-3-yl)phenyl)-3,3-difluorocyclobutane-1-carboxamide (76);

N-((4-(3-cyclopropyl-1,2,4-oxadiazol-5-yl)bicyclo[2.2.2]octan-1-yl)methyl)-N-(3-(5-cyclopropyl-1-methyl-1H-pyrazol-3-yl)phenyl)-3,3-difluorocyclopentane-1-carboxamide (77);

N-((4-(3-cyclopropyl-1,2,4-oxadiazol-5-yl)bicyclo[2.2.2]octan-1-yl)methyl)-N-(3-(5-cyclopropyl-1-methyl-1H-pyrazol-3-yl)phenyl)-3-(difluoromethyl)cyclobutane-1-carboxamide (78);

N-((4-(3-cyclopropyl-1,2,4-oxadiazol-5-yl)bicyclo[2.2.2]octan-1-yl)methyl)-3-fluoro-N-(3-(4-(2-methoxypropan-2-yl)oxazol-2-yl)phenyl)bicyclo[1.1.1]pentane-1-carboxamide (79);

N-((4-(3-cyclopropyl-1,2,4-oxadiazol-5-yl)bicyclo[2.2.2]octan-1-yl)methyl)-N-(3-(3-ethyl-2-oxo-2,3-dihydrooxazol-5-yl)phenyl)-3-fluorobicyclo[1.1.1]pentane-1-carboxamide (80);

N-((4-(3-cyclopropyl-1,2,4-oxadiazol-5-yl)bicyclo[2.2.2]octan-1-yl)methyl)-N-(3-(3-ethyl-2-oxo-2,3-dihydrooxazol-5-yl)phenyl)-3,3-difluorocyclobutane-1-carboxamide (81);

N-((4-(4-cyclopropyloxazol-2-yl)bicyclo[2.2.2]octan-1-yl)methyl)-N-(3-(2-cyclopropyloxazol-5-yl)phenyl)-3-fluorobicyclo[1.1.1]pentane-1-carboxamide (82);

N-((4-(4-cyclopropyloxazol-2-yl)bicyclo[2.2.2]octan-1-yl)methyl)-N-(3-(2-cyclopropyloxazol-5-yl)phenyl)-3,3-difluorocyclobutane-1-carboxamide (83);

N-((4-(3-cyclopropyl-1,2,4-oxadiazol-5-yl)bicyclo[2.2.2]octan-1-yl)methyl)-3,3-difluoro-N-(3-(4-(methoxymethyl)oxazol-2-yl)phenyl)cyclobutane-1-carboxamide (84);

N-((4-(3-cyclopropyl-1,2,4-oxadiazol-5-yl)bicyclo[2.2.2]octan-1-yl)methyl)-3-fluoro-N-(3-(4-(methoxymethyl)oxazol-2-yl)phenyl)bicyclo[1.1.1]pentane-1-carboxamide (85);

N-((4-(3-cyclopropyl-1,2,4-oxadiazol-5-yl)bicyclo[2.2.2]octan-1-yl)methyl)-N-(3-(5-cyclopropyl-1,3,4-oxadiazol-2-yl)phenyl)-3-fluorobicyclo[1.1.1]pentane-1-carboxamide (86);

N-((4-(3-cyclopropyl-1,2,4-oxadiazol-5-yl)bicyclo[2.2.2]octan-1-yl)methyl)-N-(3-(5-cyclopropyl-1,3,4-oxadiazol-2-yl)phenyl)-3,3-difluorocyclobutane-1-carboxamide (87);

N-((4-(3-(tert-butyl)-1,2,4-oxadiazol-5-yl)bicyclo[2.2.2]octan-1-yl)methyl)-N-(3-(3-cyclopropyl-1,2,4-oxadiazol-5-yl)phenyl)-3-fluorobicyclo[1.1.1]pentane-1-carboxamide (88);

N-(3-(3-cyclopropyl-1,2,4-oxadiazol-5-yl)phenyl)-3-fluoro-N-((4-(3-isopropyl-1,2,4-oxadiazol-5-yl)bicyclo[2.2.2]octan-1-yl)methyl)bicyclo[1.1.1]pentane-1-carboxamide (89);

N-(3-(3-cyclopropyl-1,2,4-oxadiazol-5-yl)phenyl)-3-fluoro-N-((4-(3-(tetrahydro-2H-pyran-4-yl)-1,2,4-oxadiazol-5-yl)bicyclo[2.2.2]octan-1-yl)methyl)bicyclo[1.1.1]pentane-1-carboxamide (90);

N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)pyrrolidine-1-carboxamide (91);

1-((4-(3-cyclopropyl-1,2,4-oxadiazol-5-yl)bicyclo[2.2.2]octan-1-yl)methyl)-1-(3-(3-cyclopropyl-1,2,4-oxadiazol-5-yl)phenyl)-3-neopentylurea (92);

(S)—N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)-3-(dimethylamino)pyrrolidine-1-carboxamide (93);

1-((4-(3-cyclopropyl-1,2,4-oxadiazol-5-yl)bicyclo[2.2.2]octan-1-yl)methyl)-1-(3-(3-cyclopropyl-1,2,4-oxadiazol-5-yl)phenyl)-3-(1-methylcyclopropyl)urea (94);

1-((4-(3-cyclopropyl-1,2,4-oxadiazol-5-yl)bicyclo[2.2.2]octan-1-yl)methyl)-1-(3-(3-cyclopropyl-1,2,4-oxadiazol-5-yl)phenyl)-3-ethylurea (95);

1-((4-(3-cyclopropyl-1,2,4-oxadiazol-5-yl)bicyclo[2.2.2]octan-1-yl)methyl)-1-(3-(3-cyclopropyl-1,2,4-oxadiazol-5-yl)phenyl)-3-(4-methoxyphenyl)urea (96);

N-(3-(2-cyclopropyloxazol-5-yl)phenyl)-N-((4-(4-cyclopropylthiazol-2-yl)bicyclo[2.2.2]octan-1-yl)methyl)-3-fluorobicyclo[1.1.1]pentane-1-carboxamide (97);

N-(3-(2-cyclopropyloxazol-4-yl)phenyl)-N-((4-(4-cyclopropylthiazol-2-yl)bicyclo[2.2.2]octan-1-yl)methyl)-3,3-difluorocyclobutane-1-carboxamide (98);

N-(3-(2-cyclopropyloxazol-4-yl)phenyl)-N-((4-(4-cyclopropylthiazol-2-yl)bicyclo[2.2.2]octan-1-yl)methyl)-3,3-difluorocyclopentane-1-carboxamide (99);

N-(3-(3-cyclopropyl-1,2,4-oxadiazol-5-yl)phenyl)-N-((4-(4-cyclopropylthiazol-2-yl)bicyclo[2.2.2]octan-1-yl)methyl)-3-fluorobicyclo[1.1.1]pentane-1-carboxamide (100);

N-(3-(3-cyclopropyl-1,2,4-oxadiazol-5-yl)phenyl)-N-((4-(4-cyclopropylthiazol-2-yl)bicyclo[2.2.2]octan-1-yl)methyl)-3,3-difluorocyclobutane-1-carboxamide (101);

N-((4-(3-cyclopropyl-1,2,4-oxadiazol-5-yl)bicyclo[2.2.2]octan-1-yl)methyl)-3-fluoro-N-(3-(5-(3-fluorobicyclo[1.1.1]pentan-1-yl)-1,2,4-oxadiazol-3-yl)phenyl)bicyclo[1.1.1]pentane-1-carboxamide (102);

N-((4-(3-cyclopropyl-1,2,4-oxadiazol-5-yl)bicyclo[2.2.2]octan-1-yl)methyl)-N-(3-(5-(3,3-difluorocyclobutyl)-1,2,4-oxadiazol-3-yl)phenyl)-3-fluorobicyclo[1.1.1]pentane-1-carboxamide (103);

N-(3-(5-cyclopropyl-1,2,4-oxadiazol-3-yl)phenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide (104);

N-((4-(3-cyclopropyl-1,2,4-oxadiazol-5-yl)bicyclo[2.2.2]octan-1-yl)methyl)-N-(3-(5-(difluoromethyl)-1,2,4-oxadiazol-3-yl)phenyl)-3-fluorobicyclo[1.1.1]pentane-1-carboxamide (105);

N-((4-(3-cyclopropyl-1,2,4-oxadiazol-5-yl)bicyclo[2.2.2]octan-1-yl)methyl)-3-fluoro-N-(3-(5-(1-methylcyclopropyl)-1,2,4-oxadiazol-3-yl)phenyl)bicyclo[1.1.1]pentane-1-carboxamide (106);

N-(3-(5-(tert-butyl)-1,2,4-oxadiazol-3-yl)phenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide (107);

N-((4-(3-cyclopropyl-1,2,4-oxadiazol-5-yl)bicyclo[2.2.2]octan-1-yl)methyl)-3-fluoro-N-(3-(5-(trifluoromethyl)-1,2,4-oxadiazol-3-yl)phenyl)bicyclo[1.1.1]pentane-1-carboxamide (108);

N-((4-(3-cyclopropyl-1,2,4-oxadiazol-5-yl)bicyclo[2.2.2]octan-1-yl)methyl)-3-fluoro-N-(3-(5-isopropyl-1,2,4-oxadiazol-3-yl)phenyl)bicyclo[1.1.1]pentane-1-carboxamide (109);

N-((4-(3-cyclopropyl-1,2,4-oxadiazol-5-yl)bicyclo[2.2.2]octan-1-yl)methyl)-3-fluoro-N-(3-(5-(1-hydroxycyclopropyl)-1,2,4-oxadiazol-3-yl)phenyl)bicyclo[1.1.1]pentane-1-carboxamide (110);

N-(3-(5-(1-acetamidocyclopropyl)-1,2,4-oxadiazol-3-yl)phenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide (111);

N-((4-(3-cyclopropyl-1,2,4-oxadiazol-5-yl)bicyclo[2.2.2]octan-1-yl)methyl)-N-(3-(5-(1,1-difluoroethyl)-1,2,4-oxadiazol-3-yl)phenyl)-3-fluorobicyclo[1.1.1]pentane-1-carboxamide (112);

N-((4-(3-cyclopropyl-1,2,4-oxadiazol-5-yl)bicyclo[2.2.2]octan-1-yl)methyl)-3-fluoro-N-(3-(5-(3-methyloxetan-3-yl)-1,2,4-oxadiazol-3-yl)phenyl)bicyclo[1.1.1]pentane-1-carboxamide (113);

N-(3-(3-cyclopropyl-1,2,4-oxadiazol-5-yl)phenyl)-3-fluoro-N-((4-(5-(3-fluorobicyclo[1.1.1]pentan-1-yl)-1,2,4-oxadiazol-3-yl)bicyclo[2.2.2]octan-1-yl)methyl) bicyclo[1.1.1]pentane-1-carboxamide (114);

N-(3-(3-cyclopropyl-1,2,4-oxadiazol-5-yl)phenyl)-3-fluoro-N-((4-(5-(1-methylcyclopropyl)-1,2,4-oxadiazol-3-yl)bicyclo[2.2.2]octan-1-yl)methyl) bicyclo[1.1.1]pentane-1-carboxamide (115);

N-((4-(5-cyclopropyl-1,2,4-oxadiazol-3-yl)bicyclo[2.2.2]octan-1-yl)methyl)-N-(3-(3-cyclopropyl-1,2,4-oxadiazol-5-yl)phenyl)-3-fluorobicyclo[1.1.1]pentane-1-carboxamide (116);

N-(3-(3-cyclopropyl-1,2,4-oxadiazol-5-yl)phenyl)-N-((4-(5-(difluoromethyl)-1,2,4-oxadiazol-3-yl)bicyclo[2.2.2]octan-1-yl)methyl)-3-fluorobicyclo[1.1.1]pentane-1-carboxamide (117);

N-(3-(3-cyclopropyl-1,2,4-oxadiazol-5-yl)phenyl)-3-fluoro-N-((4-(5-(1-(trifluoromethyl)cyclopropyl)-1,2,4-oxadiazol-3-yl)bicyclo[2.2.2]octan-1-yl)methyl) bicyclo[1.1.1]pentane-1-carboxamide (118);

N-((4-(5-(tert-butyl)-1,2,4-oxadiazol-3-yl)bicyclo[2.2.2]octan-1-yl)methyl)-N-(3-(3-cyclopropyl-1,2,4-oxadiazol-5-yl)phenyl)-3-fluorobicyclo[1.1.1]pentane-1-carboxamide (119);

N-(3-(3-cyclopropyl-1,2,4-oxadiazol-5-yl)phenyl)-3-fluoro-N-((4-(5-isopropyl-1,2,4-oxadiazol-3-yl)bicyclo[2.2.2]octan-1-yl)methyl)bicyclo[1.1.1]pentane-1-carboxamide (120);

N-(3-(3-cyclopropyl-1,2,4-oxadiazol-5-yl)phenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide (121);

N-(3-(3-cyclopropyl-1,2,4-oxadiazol-5-yl)phenyl)-3-fluoro-N-((4-(5-(3-methyloxetan-3-yl)-1,2,4-oxadiazol-3-yl)bicyclo[2.2.2]octan-1-yl)methyl)bicyclo[1.1.1]pentane-1-carboxamide (122);

N-(3-(3-cyclopropyl-1,2,4-oxadiazol-5-yl)phenyl)-N-((4-(5-(2,2-difluorocyclopropyl)-1,2,4-oxadiazol-3-yl)bicyclo[2.2.2]octan-1-yl)methyl)-3-fluorobicyclo[1.1.1]pentane-1-carboxamide (123);

N-(3-(3-cyclopropyl-1,2,4-oxadiazol-5-yl)phenyl)-N-((4-(5-cyclopropyl-1-methyl-1H-pyrazol-3-yl)bicyclo[2.2.2]octan-1-yl)methyl)-3-fluorobicyclo[1.1.1]pentane-1-carboxamide (124);

N-(3-(3-cyclopropyl-1,2,4-oxadiazol-5-yl)phenyl)-N-((4-(5-cyclopropyl-1-methyl-1H-pyrazol-3-yl)bicyclo[2.2.2]octan-1-yl)methyl)-3,3-difluorocyclobutane-1-carboxamide (125);

N-(3-(3-cyclopropyl-1,2,4-oxadiazol-5-yl)phenyl)-N-((4-(3-cyclopropyl-1-methyl-1H-pyrazol-5-yl)bicyclo[2.2.2]octan-1-yl)methyl)-3-fluorobicyclo[1.1.1]pentane-1-carboxamide (126);

N-(3-(3-cyclopropyl-1,2,4-oxadiazol-5-yl)phenyl)-N-((4-(3-cyclopropyl-1-methyl-1H-pyrazol-5-yl)bicyclo[2.2.2]octan-1-yl)methyl)-3,3-difluorocyclobutane-1-carboxamide (127);

N-(3-(3-cyclopropyl-1,2,4-oxadiazol-5-yl)phenyl)-3-fluoro-N-((1-(4-methoxyphenyl)-2-oxabicyclo[2.2.2]octan-4-yl)methyl)bicyclo[1.1.1]pentane-1-carboxamide (128);

N-(3-(3-cyclopropyl-1,2,4-oxadiazol-5-yl)phenyl)-3,3-difluoro-N-((1-(4-methoxyphenyl)-2-oxabicyclo[2.2.2]octan-4-yl)methyl)cyclobutane-1-carboxamide (129);

N-((4-(3-cyclopropyl-1,2,4-oxadiazol-5-yl)bicyclo[2.2.2]octan-1-yl)methyl)-N-(3-(2-cyclopropyl-1-methyl-1H-imidazol-4-yl)phenyl)-3-fluorobicyclo[1.1.1]pentane-1-carboxamide (130);

N-((4-(3-cyclopropyl-1,2,4-oxadiazol-5-yl)bicyclo[2.2.2]octan-1-yl)methyl)-N-(3-(2-cyclopropyl-1-methyl-1H-imidazol-4-yl)phenyl)-3,3-difluorocyclobutane-1-carboxamide (131);

N-((4-(3-cyclopropyl-1,2,4-oxadiazol-5-yl)bicyclo[2.2.2]octan-1-yl)methyl)-N-(3-(5-cyclopropyl-4-methyl-4H-1,2,4-triazol-3-yl)phenyl)-3-fluorobicyclo[1.1.1]pentane-1-carboxamide (132);

N-((4-(5-cyclopropyl-1,3,4-oxadiazol-2-yl)bicyclo[2.2.2]octan-1-yl)methyl)-N-(3-(5-cyclopropyl-1,3,4-oxadiazol-2-yl)phenyl)-3,3-difluorocyclopentane-1-carboxamide (133);

N-((4-(5-cyclopropyl-1,3,4-oxadiazol-2-yl)bicyclo[2.2.2]octan-1-yl)methyl)-N-(3-(5-cyclopropyl-1,3,4-oxadiazol-2-yl)phenyl)-3-(difluoromethyl)cyclobutane-1-carboxamide (134);

N-((4-(5-cyclopropyl-1,3,4-oxadiazol-2-yl)bicyclo[2.2.2]octan-1-yl)methyl)-N-(3-(5-cyclopropyl-1,3,4-oxadiazol-2-yl)phenyl)-3,3-difluorocyclobutane-1-carboxamide (135);

N-((4-(5-cyclopropyl-1,3,4-oxadiazol-2-yl)bicyclo[2.2.2]octan-1-yl)methyl)-N-(3-(5-cyclopropyl-1,3,4-oxadiazol-2-yl)phenyl)-3-fluorobicyclo[1.1.1]pentane-1-carboxamide (136);

N-(3-(3-cyclopropyl-1,2,4-oxadiazol-5-yl)phenyl)-N-((4-(5-cyclopropyl-1,3,4-oxadiazol-2-yl)bicyclo[2.2.2]octan-1-yl)methyl)-3-fluorobicyclo[1.1.1]pentane-1-carboxamide (137);

N-(3-(3-cyclopropyl-1,2,4-oxadiazol-5-yl)phenyl)-N-((4-(5-cyclopropyl-1,3,4-oxadiazol-2-yl)bicyclo[2.2.2]octan-1-yl)methyl)-3,3-difluorocyclobutane-1-carboxamide (138);

N-(3-(3-cyclopropyl-1,2,4-oxadiazol-5-yl)phenyl)-N-((4-(5-cyclopropyl-1,3,4-oxadiazol-2-yl)bicyclo[2.2.2]octan-1-yl)methyl)-3-(difluoromethyl)cyclobutane-1-carboxamide (139);

N-(3-(3-cyclopropyl-1,2,4-oxadiazol-5-yl)phenyl)-3-fluoro-N-((1-(2-methoxypyrimidin-5-yl)-2-oxabicyclo[2.2.2]octan-4-yl)methyl)bicyclo[1.1.1]pentane-1-carboxamide (140);

N-((1-(4-(1-cyanocyclopropyl)phenyl)-2-oxabicyclo[2.2.2]octan-4-yl)methyl)-N-(3-(3-cyclopropyl-1,2,4-oxadiazol-5-yl)phenyl)-3-(difluoromethyl)cyclobutane-1-carboxamide (141);

N-((1-(4-(1-cyanocyclopropyl)phenyl)-2-oxabicyclo[2.2.2]octan-4-yl)methyl)-N-(3-(3-cyclopropyl-1,2,4-oxadiazol-5-yl)phenyl)-3,3-difluorocyclobutuane-1-carboxamide (142);

N-((1-(4-(1-cyanocyclopropyl)phenyl)-2-oxabicyclo[2.2.2]octan-4-yl)methyl)-N-(3-(3-cyclopropyl-1,2,4-oxadiazol-5-yl)phenyl)-3-fluorobicyclo[1.1.1]pentane-1-carboxamide (143);

N-((1-(4-(1-Cyanocyclopropyl)phenyl)-2-oxabicyclo[2.2.2]octan-4-yl)methyl)-N-(3-(5-cyclopropyl-1,3,4-oxadiazol-2-yl)phenyl)-3-(difluoromethyl)cyclobutane-1-carboxamide (144);

N-((1-(4-(1-cyanocyclopropyl)phenyl)-2-oxabicyclo[2.2.2]octan-4-yl)methyl)-N-(3-(3-cyclopropyl-1,2,4-oxadiazol-5-yl)phenyl)-3,3-difluorocyclobutane-1-carboxamide (145);

N-((1-(4-(1-cyanocyclopropyl)phenyl)-2-oxabicyclo[2.2.2]octan-4-yl)methyl)-N-(3-(3-cyclopropyl-1,2,4-oxadiazol-5-yl)phenyl)-3-fluorobicyclo[1.1.1]pentane-1-carboxamide (146);

N-((4-(3-cyclopropyl-1,2,4-oxadiazol-5-yl)bicyclo[2.2.2]octan-1-yl)methyl)-3-fluoro-N-(3-(5-(1-methoxycyclopropyl)-1,2,4-oxadiazol-3-yl)phenyl)bicyclo[1.1.1]pentane-1-carboxamide (147);

N-(3-(3-cyclopropyl-1,2,4-oxadiazol-5-yl)phenyl)-3-fluoro-N-((4-(2-methoxypyrimidin-4-yl)bicyclo[2.2.2]octan-1-yl)methyl)bicyclo[1.1.1]pentane-1-carboxamide (148);

N-((4-(3-cyclopropyl-1,2,4-oxadiazol-5-yl)bicyclo[2.2.2]octan-1-yl)methyl)-3-fluoro-N-(3-(1-(oxetan-3-yl)-1H-pyrazol-3-yl)phenyl)bicyclo[1.1.1]pentane-1-carboxamide (149);

N-((4-(3-cyclopropyl-1,2,4-oxadiazol-5-yl)bicyclo[2.2.2]octan-1-yl)methyl)-3-fluoro-N-(3-(1-(oxetan-3-yl)-1H-pyrazol-4-yl)phenyl)bicyclo[1.1.1]pentane-1-carboxamide (150);

N-((4-(3-cyclopropyl-1,2,4-oxadiazol-5-yl)bicyclo[2.2.2]octan-1-yl)methyl)-3-fluoro-N-(3-(4-methylthiazol-2-yl)phenyl)bicyclo[1.1.1]pentane-1-carboxamide (151);

N-((4-(3-cyclopropyl-1,2,4-oxadiazol-5-yl)bicyclo[2.2.2]octan-1-yl)methyl)-3-fluoro-N-(3-(1-(pyridin-3-yl)-1H-pyrazol-4-yl)phenyl)bicyclo[1.1.1]pentane-1-carboxamide (152);

N-((4-(3-(tert-butyl)-1,2,4-oxadiazol-5-yl)bicyclo[2.2.2]octan-1-yl)methyl)-N-(3-(5-cyclopropyl-1,3,4-oxadiazol-2-yl)phenyl)-3-fluorobicyclo[1.1.1]pentane-1-carboxamide (153);

N-(3-(5-cyclopropyl-1,3,4-oxadiazol-2-yl)phenyl)-3-fluoro-N-((4-(5-(1-methylcyclopropyl)-1,2,4-oxadiazol-3-yl)bicyclo[2.2.2]octan-1-yl)methyl) bicyclo[1.1.1]pentane-1-carboxamide (154);

N-(3-(5-cyclopropyl-1,3,4-oxadiazol-2-yl)phenyl)-3-fluoro-N-((4-(5-(3-methyloxetan-3-yl)-1,2,4-oxadiazol-3-yl)bicyclo[2.2.2]octan-1-yl)methyl)bicyclo[1.1.1]pentane-1-carboxamide (155);

N-(3-(5-cyclopropyl-1,3,4-oxadiazol-2-yl)phenyl)-N-((4-(5-(difluoromethyl)-1,2,4-oxadiazol-3-yl)bicyclo[2.2.2]octan-1-yl)methyl)-3-fluorobicyclo[1.1.1]pentane-1-carboxamide (156);

N-((4-(5-(tert-butyl)-1,2,4-oxadiazol-3-yl)bicyclo[2.2.2]octan-1-yl)methyl)-N-(3-(5-cyclopropyl-1,3,4-oxadiazol-2-yl)phenyl)-3-fluorobicyclo[1.1.1]pentane-1-carboxamide (157);

N-((4-(3-cyclopropyl-1,2,4-oxadiazol-5-yl)bicyclo[2.2.2]octan-1-yl)methyl)-N-(3-(1-(cyclopropyl sulfonyl)-1H-pyrazol-4-yl)phenyl)-3-fluorobicyclo[1.1.1]pentane-1-carboxamide (158);

N-((4-(3-cyclopropyl-1,2,4-oxadiazol-5-yl)bicyclo[2.2.2]octan-1-yl)methyl)-3-fluoro-N-(3-(1-(methylsulfonyl)-1H-pyrazol-4-yl)phenyl)bicyclo[1.1.1]pentane-1-carboxamide (159);

N-((4-(3-cyclopropyl-1,2,4-oxadiazol-5-yl)bicyclo[2.2.2]octan-1-yl)methyl)-N-(3-(1-(difluoromethyl)-1H-pyrazol-4-yl)phenyl)-3-fluorobicyclo[1.1.1]pentane-1-carboxamide (160);

N-((4-(3-cyclopropyl-1,2,4-oxadiazol-5-yl)bicyclo[2.2.2]octan-1-yl)methyl)-N-(3-(1-(2,2-difluoroethyl)-1H-pyrazol-4-yl)phenyl)-3-fluorobicyclo[1.1.1]pentane-1-carboxamide (161);

N-((4-(3-cyclopropyl-1,2,4-oxadiazol-5-yl)bicyclo[2.2.2]octan-1-yl)methyl)-3-fluoro-N-(3-(1-(2,2,2-trifluoroethyl)-1H-pyrazol-4-yl)phenyl)bicyclo[1.1.1]pentane-1-carboxamide (162);

N-((4-(3-cyclopropyl-1-methyl-1H-pyrazol-5-yl)bicyclo[2.2.2]octan-1-yl)methyl)-3-fluoro-N-(3-(5-isopropyl-1,2,4-oxadiazol-3-yl)phenyl)bicyclo[1.1.1]pentane-1-carboxamide (163);

N-((4-(3-cyclopropyl-1-methyl-1H-pyrazol-5-yl)bicyclo[2.2.2]octan-1-yl)methyl)-N-(3-(5-(difluoromethyl)-1,2,4-oxadiazol-3-yl)phenyl)-3-fluorobicyclo[1.1.1]pentane-1-carboxamide (164);

N-(3-(5-(tert-butyl)-1,2,4-oxadiazol-3-yl)phenyl)-N-((4-(3-cyclopropyl-1-methyl-1H-pyrazol-5-yl)bicyclo[2.2.2]octan-1-yl)methyl)-3-fluorobicyclo[1.1.1]pentane-1-carboxamide (165);

N-((4-(3-cyclopropyl-1-methyl-1H-pyrazol-5-yl)bicyclo[2.2.2]octan-1-yl)methyl)-3-fluoro-N-(3-(5-(1-methylcyclopropyl)-1,2,4-oxadiazol-3-yl)phenyl)bicyclo[1.1.1]pentane-1-carboxamide (166);

N-(3-(5-(tert-butyl)-1,2,4-oxadiazol-3-yl)phenyl)-N-((4-(5-cyclopropyl-1-methyl-1H-pyrazol-3-yl)bicyclo[2.2.2]octan-1-yl)methyl)-3-fluorobicyclo[1.1.1]pentane-1-carboxamide (167);

N-((4-(5-cyclopropyl-1-methyl-1H-pyrazol-3-yl)bicyclo[2.2.2]octan-1-yl)methyl)-N-(3-(5-(difluoromethyl)-1,2,4-oxadiazol-3-yl)phenyl)-3-fluorobicyclo[1.1.1]pentane-1-carboxamide (168);

N-((4-(5-cyclopropyl-1-methyl-1H-pyrazol-3-yl)bicyclo[2.2.2]octan-1-yl)methyl)-3-fluoro-N-(3-(5-isopropyl-1,2,4-oxadiazol-3-yl)phenyl)bicyclo[1.1.1]pentane-1-carboxamide (169);

N-(3-(5-cyclopropyl-1,2,4-oxadiazol-3-yl)phenyl)-N-((4-(5-cyclopropyl-1-methyl-1H-pyrazol-3-yl)bicyclo[2.2.2]octan-1-yl)methyl)-3-fluorobicyclo[1.1.1]pentane-1-carboxamide (170);

N-((4-(3-(tert-butyl)-1,2,4-oxadiazol-5-yl)bicyclo[2.2.2]octan-1-yl)methyl)-N-(3-(5-cyclopropyl-1,2,4-oxadiazol-3-yl)phenyl)-3-fluorobicyclo[1.1.1]pentane-1-carboxamide (171);

N-(3-(5-cyclopropyl-1,2,4-oxadiazol-3-yl)phenyl)-N-((4-(3-(difluoromethyl)-1,2,4-oxadiazol-5-yl)bicyclo[2.2.2]octan-1-yl)methyl)-3-fluorobicyclo[1.1.1]pentane-1-carboxamide (172);

N-((4-(3-(difluoromethyl)-1,2,4-oxadiazol-5-yl)bicyclo[2.2.2]octan-1-yl)methyl)-3-fluoro-N-(3-(5-(3-methyloxetan-3-yl)-1,2,4-oxadiazol-3-yl)phenyl)bicyclo[1.1.1]pentane-1-carboxamide (173);

N-((4-(3-(tert-butyl)-1,2,4-oxadiazol-5-yl)bicyclo[2.2.2]octan-1-yl)methyl)-3-fluoro-N-(3-(5-(3-methyloxetan-3-yl)-1,2,4-oxadiazol-3-yl)phenyl)bicyclo[1.1.1]pentane-1-carboxamide (174);

3-fluoro-N-((4-(3-isopropyl-1,2,4-oxadiazol-5-yl)bicyclo[2.2.2]octan-1-yl)methyl)-N-(3-(5-(1-methylcyclopropyl)-1,2,4-oxadiazol-3-yl)phenyl)bicyclo[1.1.1]pentane-1-carboxamide (175);

N-((4-(3-(tert-butyl)-1,2,4-oxadiazol-5-yl)bicyclo[2.2.2]octan-1-yl)methyl)-3-fluoro-N-(3-(5-(1-methylcyclopropyl)-1,2,4-oxadiazol-3-yl)phenyl)bicyclo[1.1.1]pentane-1-carboxamide (176);

N-((4-(5-(tert-butyl)-1,2,4-oxadiazol-3-yl)bicyclo[2.2.2]octan-1-yl)methyl)-3-fluoro-N-(3-(5-(1-methylcyclopropyl)-1,2,4-oxadiazol-3-yl)phenyl)bicyclo[1.1.1]pentane-1-carboxamide (177);

N-((4-(5-(difluoromethyl)-1,2,4-oxadiazol-3-yl)bicyclo[2.2.2]octan-1-yl)methyl)-3-fluoro-N-(3-(5-(1-methylcyclopropyl)-1,2,4-oxadiazol-3-yl)phenyl)bicyclo[1.1.1]pentane-1-carboxamide (178);

N-((4-(5-(1,1-difluoroethyl)-1,2,4-oxadiazol-3-yl)bicyclo[2.2.2]octan-1-yl)methyl)-3-fluoro-N-(3-(5-(1-methylcyclopropyl)-1,2,4-oxadiazol-3-yl)phenyl)bicyclo[1.1.1]pentane-1-carboxamide (179);

3-fluoro-N-(3-(5-(1-methylcyclopropyl)-1,2,4-oxadiazol-3-yl)phenyl)-N-((4-(5-(3-methyloxetan-3-yl)-1,2,4-oxadiazol-3-yl)bicyclo[2.2.2]octan-1-yl)methyl) bicyclo[1.1.1]pentane-1-carboxamide (180);

N-(3-(5-(tert-butyl)-1,2,4-oxadiazol-3-yl)phenyl)-3-fluoro-N-((1-(2-(trifluoromethyl) pyrimidin-5-yl)-2-oxabicyclo[2.2.2]octan-4-yl) methyl)bicyclo[1.1.1]pentane-1-carboxamide (181);

N-(3-(5-(difluoromethyl)-1,2,4-oxadiazol-3-yl)phenyl)-3-fluoro-N-((1-(2-(trifluoromethyl)pyrimidin-5-yl)-2-oxabicyclo[2.2.2]octan-4-yl)methyl) bicyclo[1.1.1]pentane-1-carboxamide (182);

N-((4-(5-(tert-butyl)-1,2,4-oxadiazol-3-yl)bicyclo[2.2.2]octan-1-yl)methyl)-N-(3-(5-(tert-butyl)-1,2,4-oxadiazol-3-yl)phenyl)-3-fluorobicyclo[1.1.1]pentane-1-carboxamide (183);

N-((4-(5-(difluoromethyl)-1,2,4-oxadiazol-3-yl)bicyclo[2.2.2]octan-1-yl)methyl)-N-(3-(5-(difluoromethyl)-1,2,4-oxadiazol-3-yl)phenyl)-3-fluorobicyclo[1.1.1]pentane-1-carboxamide (184);

N-(3-(5-cyclopropyl-1,2,4-oxadiazol-3-yl)phenyl)-3-fluoro-N-((4-(5-(trifluoromethyl) pyridin-2-yl)bicyclo[2.2.2]octan-1-yl)methyl)bicyclo[1.1.1]pentane-1-carboxamide (185);

3-fluoro-N-(3-(5-(1-methylcyclopropyl)-1,2,4-oxadiazol-3-yl)phenyl)-N-((4-(5-(trifluoromethyl)pyridin-2-yl)bicyclo[2.2.2]octan-1-yl)methyl)bicyclo[1.1.1]pentane-1-carboxamide (186);

3-fluoro-N-(3-(5-isopropyl-1,2,4-oxadiazol-3-yl)phenyl)-N-((4-(5-(trifluoromethyl)pyridin-2-yl)bicyclo[2.2.2]octan-1-yl)methyl)bicyclo[1.1.1]pentane-1-carboxamide (187);

N-(3-(5-(tert-butyl)-1,2,4-oxadiazol-3-yl)phenyl)-3-fluoro-N-((4-(5-(trifluoromethyl)pyridin-2-yl)bicyclo[2.2.2]octan-1-yl)methyl)bicyclo[1.1.1]pentane-1-carboxamide (188);

N-(3-(5-(difluoromethyl)-1,2,4-oxadiazol-3-yl)phenyl)-3-fluoro-N-((4-(5-(trifluoromethyl)pyridin-2-yl)bicyclo[2.2.2]octan-1-yl)methyl)bicyclo[1.1.1]pentane-1-carboxamide (189);

N-(3-(5-(1,1-difluoroethyl)-1,2,4-oxadiazol-3-yl)phenyl)-3-fluoro-N-((4-(5-(trifluoromethyl)pyridin-2-yl)bicyclo[2.2.2]octan-1-yl)methyl)bicyclo[1.1.1]pentane-1-carboxamide (190);

N-((4-(3-(tert-butyl)-1,2,4-oxadiazol-5-yl)bicyclo[2.2.2]octan-1-yl)methyl)-N-(3-(3-cyclopropyl-1,2,4-oxadiazol-5-yl)phenyl)-3-methyloxetane-3-carboxamide (191);

(1S,3S)—N-((4-(3-(tert-butyl)-1,2,4-oxadiazol-5-yl)bicyclo[2.2.2]octan-1-yl)methyl)-N-(3-(3-cyclopropyl-1,2,4-oxadiazol-5-yl)phenyl)-3-methoxycyclobutane-1-carboxamide (192);

N-((4-(3-(tert-butyl)-1,2,4-oxadiazol-5-yl)bicyclo[2.2.2]octan-1-yl)methyl)-N-(3-(3-cyclopropyl-1,2,4-oxadiazol-5-yl)phenyl)-1-(2,2,2-trifluoroacetyl)azetidine-3-carboxamide (193);

N-((4-(5-(tert-butyl)-1,2,4-oxadiazol-3-yl)bicyclo[2.2.2]octan-1-yl)methyl)-3-fluoro-N-(3-(1-(methylsulfonyl)-1H-pyrazol-4-yl)phenyl)bicyclo[1.1.1]pentane-1-carboxamide (194);

N-((4-(5-(tert-butyl)-1,2,4-oxadiazol-3-yl)bicyclo[2.2.2]octan-1-yl)methyl)-N-(3-(1-(cyclopropyl sulfonyl)-1H-pyrazol-4-yl)phenyl)-3-fluorobicyclo[1.1.1]pentane-1-carboxamide (195);

N-((1-(3-cyclopropyl-1,2,4-oxadiazol-5-yl)-2-oxabicyclo[2.2.2]octan-4-yl)methyl)-N-(3-(3-cyclopropyl-1,2,4-oxadiazol-5-yl)phenyl)-3-fluorobicyclo[1.1.1]pentane-1-carboxamide (196);

N-((1-(3-cyclopropyl-1,2,4-oxadiazol-5-yl)-2-oxabicyclo[2.2.2]octan-4-yl)methyl)-N-(3-(3-cyclopropyl-1,2,4-oxadiazol-5-yl)phenyl)-3,3-difluorocyclobutane-1-carboxamide (197);

N-((1-(3-cyclopropyl-1,2,4-oxadiazol-5-yl)-2-oxabicyclo[2.2.2]octan-4-yl)methyl)-N-(3-(3-cyclopropyl-1,2,4-oxadiazol-5-yl)phenyl)-3-(difluoromethyl)cyclobutane-1-carboxamide (198);

N-((1-(3-cyclopropyl-1,2,4-oxadiazol-5-yl)-2-oxabicyclo[2.2.2]octan-4-yl)methyl)-N-(3-(5-cyclopropylisoxazol-3-yl)phenyl)-3-fluorobicyclo[1.1.1]pentane-1-carboxamide (199);

N-((1-(3-cyclopropyl-1,2,4-oxadiazol-5-yl)-2-oxabicyclo[2.2.2]octan-4-yl)methyl)-N-(3-(5-cyclopropylisoxazol-3-yl)phenyl)-3,3-difluorocyclobutane-1-carboxamide (200);

N-((1-(3-cyclopropyl-1,2,4-oxadiazol-5-yl)-2-oxabicyclo [2.2.2]octan-4-yl)methyl)-N-(3-(5-cyclopropylisoxazol-3-yl)phenyl)-3-(difluoromethyl)cyclobutane-1-carboxamide (201);

N-((1-(3-cyclopropyl-1,2,4-oxadiazol-5-yl)-2-oxabicyclo [2.2.2]octan-4-yl)methyl)-N-(3-(5-cyclopropylisoxazol-3-yl)phenyl)-3,3-difluorocyclopentane-1-carboxamide (202);

N-((1-(3-cyclopropyl-1,2,4-oxadiazol-5-yl)-2-oxabicyclo [2.2.2]octan-4-yl)methyl)-N-(3-(5-cyclopropylisoxazol-3-yl)phenyl)-3-fluorobicyclo[1.1.1]pentane-1-carboxamide (203);

N-((1-(3-cyclopropyl-1,2,4-oxadiazol-5-yl)-2-oxabicyclo [2.2.2]octan-4-yl)methyl)-N-(3-(5-(difluoromethyl)-1,2,4-oxadiazol-3-yl)phenyl)-3-fluorobicyclo[1.1.1]pentane-1-carboxamide (204);

N-(5-(3-cyclopropyl-1,2,4-oxadiazol-5-yl)pyridin-3-yl)-N-((4-(3-cyclopropyl-1-methyl-1H-pyrazol-5-yl)bicyclo[2.2.2]octan-1-yl)methyl)-3-fluorobicyclo[1.1.1]pentane-1-carboxamide (205);

N-((4-(5-(tert-butyl)-1,2,4-oxadiazol-3-yl)bicyclo[2.2.2]octan-1-yl)methyl)-N-(5-(3-cyclopropyl-1,2,4-oxadiazol-5-yl)pyridin-3-yl)-3-fluorobicyclo[1.1.1]pentane-1-carboxamide (206);

N-((4-(3-(tert-butyl)-1,2,4-oxadiazol-5-yl)bicyclo[2.2.2]octan-1-yl)methyl)-N-(5-(3-cyclopropyl-1,2,4-oxadiazol-5-yl)pyridin-3-yl)-3-fluorobicyclo[1.1.1]pentane-1-carboxamide (207);

N-((4-(3-(tert-butyl)-1,2,4-oxadiazol-5-yl)-2-oxabicyclo [2.2.2]octan-1-yl)methyl)-N-(3-(1-(cyclopropylsulfonyl)-1H-pyrazol-4-yl)phenyl)-3-fluorobicyclo[1.1.1]pentane-1-carboxamide (208);

N-(3-(1H-pyrazol-4-yl)phenyl)-3-fluoro-N-((4-(5-(1-(trifluoromethyl)cyclopropyl)-1,2,4-oxadiazol-3-yl)bicyclo[2.2.2]octan-1-yl)methyl)bicyclo[1.1.1]pentane-1-carboxamide (209);

N-((4-(5-(tert-butyl)-1,2,4-oxadiazol-3-yl)bicyclo[2.2.2]octan-1-yl)methyl)-N-(4-(3-cyclopropyl-1,2,4-oxadiazol-5-yl)pyridin-2-yl)-3-fluorobicyclo[1.1.1]pentane-1-carboxamide (210);

N-(4-(1H-pyrazol-4-yl)pyridin-2-yl)-N-((4-(5-(tert-butyl)-1,2,4-oxadiazol-3-yl) bicyclo[2.2.2]octan-1-yl)methyl)-3-fluorobicyclo[1.1.1]pentane-1-carboxamide (211);

N-((4-(5-(tert-butyl)-1,2,4-oxadiazol-3-yl)bicyclo[2.2.2]octan-1-yl)methyl)-N-(4-(1-(difluoromethyl)-1H-pyrazol-4-yl)pyridin-2-yl)-3-fluorobicyclo[1.1.1]pentane-1-carboxamide (212);

N-((4-(5-(tert-butyl)-1,2,4-oxadiazol-3-yl)bicyclo[2.2.2]octan-1-yl)methyl)-N-(3-(3-(tert-butyl)-1-methyl-1H-pyrazol-5-yl)phenyl)-3-fluorobicyclo[1.1.1]pentane-1-carboxamide (213);

N-((4-(5-(tert-butyl)-1,2,4-oxadiazol-3-yl)bicyclo[2.2.2]octan-1-yl)methyl)-N-(3-(5-(tert-butyl)-1-methyl-1H-pyrazol-3-yl)phenyl)-3-fluorobicyclo[1.1.1]pentane-1-carboxamide (214);

N-(1-(4-(3-cyclopropyl-1,2,4-oxadiazol-5-yl)bicyclo[2.2.2]octan-1-yl)ethyl)-N-(3-(2-cyclopropyloxazol-5-yl)phenyl)-3-fluorobicyclo[1.1.1]pentane-1-carboxamide (215-216);

N-(1-(4-(3-cyclopropyl-1,2,4-oxadiazol-5-yl)bicyclo[2.2.2] octan-1-yl)ethyl)-N-(3-(3-cyclopropyl-1,2,4-oxadiazol-5-yl)phenyl)-3-fluorobicyclo[1.1.1]pentane-1-carboxamide (217-218);

N-((4-(3-cyclopropyl-1,2,4-oxadiazol-5-yl)bicyclo[2.2.2] octan-1-yl)methyl)-N-(3-(4-cyclopropyl-1H-1,2,3-triazol-1-yl)phenyl)-3-fluorobicyclo[1.1.1]pentane-1-carboxamide (219);

3,3-Difluoro-N-(3'-methoxy-[1,1'-biphenyl]-3-yl)-N-((4-(3-methyl-1,2,4-oxadiazol-5-yl)bicyclo[2.2.2]octan-1-yl)methyl)cyclobutane-1-carboxamide (220);

3-fluoro-N-(3'-methoxy-[1,1'-biphenyl]-3-yl)-N-((4-(3-methyl-1,2,4-oxadiazol-5-yl) bicyclo[2.2.2]octan-1-yl)methyl)bicyclo[1.1.1]pentane-1-carboxamide (221);

N-((1-(4-(2-cyanopropan-2-yl)phenyl)-2-oxabicyclo[2.2.2] octan-4-yl)methyl)-3-fluoro-N-(3-(2-methoxypyridin-4-yl)phenyl)bicyclo[1.1.1]pentane-1-carboxamide (222);

N-((1-(4-(2-cyanopropan-2-yl)phenyl)-2-oxabicyclo[2.2.2] octan-4-yl)methyl)-N-(3-(2-methoxypyridin-4-yl)phenyl) cyclobutanecarboxamide (223);

N-((1-(4-(2-cyanopropan-2-yl)phenyl)-2-oxabicyclo[2.2.2] octan-4-yl)methyl)-N-(3-(2-methoxypyridin-4-yl)phenyl) cyclopentanecarboxamide (224);

N-((4-(3-cyclopropyl-1,2,4-oxadiazol-5-yl)bicyclo[2.2.2] octan-1-yl)methyl)-N-(3-(4-ethoxypyridin-2-yl)phenyl)-3-fluorobicyclo[1.1.1]pentane-1-carboxamide (225);

N-((4-(3-cyclopropyl-1,2,4-oxadiazol-5-yl)bicyclo[2.2.2] octan-1-yl)methyl)-N-(3-(2-ethoxypyridin-4-yl)phenyl)-3-fluorobicyclo[1.1.1]pentane-1-carboxamide (226);

3-fluoro-N-(3-(2-methoxypyridin-4-yl)phenyl)-N-((4-(3-(tetrahydro-2H-pyran-4-yl)-1,2,4-oxadiazol-5-yl)bicyclo [2.2.2]octan-1-yl)methyl)bicyclo[1.1.1]pentane-1-carboxamide (227);

3-fluoro-N-(3-(2-methoxypyridin-4-yl)phenyl)-N-((4-(3-methyl-1,2,4-oxadiazol-5-yl) bicyclo[2.2.2]octan-1-yl)methyl)bicyclo[1.1.1]pentane-1-carboxamide (228);

N-((4-(3-cyclopropyl-1,2,4-oxadiazol-5-yl)bicyclo[2.2.2] octan-1-yl)methyl)-3-fluoro-N-(3-(2-methoxypyridin-4-yl)phenyl)bicyclo[1.1.1]pentane-1-carboxamide (229);

3-fluoro-N-(3-(2-methoxypyridin-4-yl)phenyl)-N-((4-(5-methyl-1,3,4-oxadiazol-2-yl) bicyclo[2.2.2]octan-1-yl)methyl)bicyclo[1.1.1]pentane-1-carboxamide (230);

N-(3-(2-methoxypyridin-4-yl)phenyl)-N-((4-(5-methyl-1,3,4-oxadiazol-2-yl) bicyclo[2.2.2]octan-1-yl)methyl)cyclobutanecarboxamide (231);

3-fluoro-N-(3-(2-methoxypyridin-4-yl)phenyl)-N-((4-(5-methyl-1,3,4-thiadiazol-2-yl) bicyclo[2.2.2]octan-1-yl)methyl)bicyclo[1.1.1]pentane-1-carboxamide (232);

N-(3-(2-methoxypyridin-4-yl)phenyl)-N-((4-(5-methyl-1,3,4-thiadiazol-2-yl) bicyclo[2.2.2]octan-1-yl)methyl)cyclopentanecarboxamide (233);

3,3-difluoro-N-(3-(2-methoxypyridin-4-yl)phenyl)-N-((4-(5-methyl-1,3,4-thiadiazol-2-yl)bicyclo[2.2.2]octan-1-yl)methyl)cyclobutane-1-carboxamide (234);

3,3-difluoro-N-(3-(2-methoxypyridin-4-yl)phenyl)-N-((4-(5-methyl-1,3,4-thiadiazol-2-yl)bicyclo[2.2.2]octan-1-yl)methyl)cyclopentane-1-carboxamide (235);

(1S,3S)-3-hydroxy-N-(3-(2-methoxypyridin-4-yl)phenyl)-N-((4-(5-methyl-1,3,4-thiadiazol-2-yl)bicyclo[2.2.2]octan-1-yl)methyl)-3-(trifluoromethyl)cyclobutane-1-carboxamide (236);

3,3-difluoro-N-(3-(2-methoxypyridin-4-yl)phenyl)-N-((4-(2-methylpyridin-4-yl) bicyclo[2.2.2]octan-1-yl)methyl) cyclobutane-1-carboxamide (237);

3-fluoro-N-(3-(2-methoxypyridin-4-yl)phenyl)-N-((4-(2-methylpyridin-4-yl) bicyclo[2.2.2]octan-1-yl)methyl)bicyclo[1.1.1]pentane-1-carboxamide (238);

3-fluoro-N-(3-(2-methoxypyridin-4-yl)phenyl)-N-((4-(6-methylpyridin-2-yl) bicyclo[2.2.2]octan-1-yl)methyl)bicyclo[1.1.1]pentane-1-carboxamide (239);

N-(3-(2-methoxypyridin-4-yl)phenyl)-N-((4-(4-(trifluoromethyl)pyridin-2-yl) bicyclo[2.2.2]octan-1-yl)methyl)cyclobutanecarboxamide (240);

3-fluoro-N-(3-(2-methoxypyridin-4-yl)phenyl)-N-((4-(4-(trifluoromethyl)pyridin-2-yl)bicyclo[2.2.2]octan-1-yl)methyl)bicyclo[1.1.1]pentane-1-carboxamide (241);

N-((4-(3-cyclopropyl-1,2,4-oxadiazol-5-yl)bicyclo[2.2.2]octan-1-yl)methyl)-3-fluoro-N-(3-(2-methoxypyrimidin-4-yl)phenyl)bicyclo[1.1.1]pentane-1-carboxamide (242);

N-((4-(3-cyclopropyl-1,2,4-oxadiazol-5-yl)bicyclo[2.2.2]octan-1-yl)methyl)-3,3-difluoro-N-(3-(2-methoxypyrimidin-4-yl)phenyl)cyclobutane-1-carboxamide (243);

N-((4-(3-cyclopropyl-1,2,4-oxadiazol-5-yl)bicyclo[2.2.2]octan-1-yl)methyl)-N-(3-(2-methoxypyrimidin-4-yl)phenyl)cyclobutanecarboxamide (244);

N-((4-(3-cyclopropyl-1,2,4-oxadiazol-5-yl)bicyclo[2.2.2]octan-1-yl)methyl)-3,3-difluoro-N-(3-(2-methoxypyrimidin-4-yl)phenyl)cyclopentane-1-carboxamide (245);

N-((4-(3-cyclopropyl-1,2,4-oxadiazol-5-yl)bicyclo[2.2.2]octan-1-yl)methyl)-3-fluoro-N-(4'-(methylsulfonamido)-[1,1'-biphenyl]-3-yl)bicyclo[1.1.1]pentane-1-carboxamide (246);

N-((4-(3-cyclopropyl-1,2,4-oxadiazol-5-yl)bicyclo[2.2.2]octan-1-yl)methyl)-3-fluoro-N-(3-(6-fluoro-5-methylpyridin-3-yl)phenyl)bicyclo[1.1.1]pentane-1-carboxamide (247);

N-((4-(3-cyclopropyl-1,2,4-oxadiazol-5-yl)bicyclo[2.2.2]octan-1-yl)methyl)-3-fluoro-N-(3-(2-methoxypyrimidin-5-yl)phenyl)bicyclo[1.1.1]pentane-1-carboxamide (248);

N-((4-(3-cyclopropyl-1,2,4-oxadiazol-5-yl)bicyclo[2.2.2]octan-1-yl)methyl)-3-fluoro-N-(3-(6-methoxypyridin-3-yl)phenyl)bicyclo[1.1.1]pentane-1-carboxamide (249);

N-((4-(3-cyclopropyl-1,2,4-oxadiazol-5-yl)bicyclo[2.2.2]octan-1-yl)methyl)-N-(3',5'-dichloro-[1,1'-biphenyl]-3-yl)-3-fluorobicyclo[1.1.1]pentane-1-carboxamide (250);

N-((4-(3-cyclopropyl-1,2,4-oxadiazol-5-yl)bicyclo[2.2.2]octan-1-yl)methyl)-3-fluoro-N-(4'-(trifluoromethoxy)-[1,1'-biphenyl]-3-yl)bicyclo[1.1.1]pentane-1-carboxamide (251);

N-((4-(3-cyclopropyl-1,2,4-oxadiazol-5-yl)bicyclo[2.2.2]octan-1-yl)methyl)-3-fluoro-N-(3'-(trifluoromethyl)-[1,1'-biphenyl]-3-yl)bicyclo[1.1.1]pentane-1-carboxamide (252);

N-((4-(3-cyclopropyl-1,2,4-oxadiazol-5-yl)bicyclo[2.2.2]octan-1-yl)methyl)-3-fluoro-N-(4'-(trifluoromethyl)-[1,1'-biphenyl]-3-yl)bicyclo[1.1.1]pentane-1-carboxamide (253);

N-(3'-acetamido-[1,1'-biphenyl]-3-yl)-N-((4-(3-cyclopropyl-1,2,4-oxadiazol-5-yl) bicyclo[2.2.2]octan-1-yl)methyl)-3-fluorobicyclo[1.1.1]pentane-1-carboxamide (254);

N-(3-(benzo[d][1,3]dioxol-5-yl)phenyl)-N-((4-(3-cyclopropyl-1,2,4-oxadiazol-5-yl) bicyclo[2.2.2]octan-1-yl)methyl)-3-fluorobicyclo[1.1.1]pentane-1-carboxamide (255);

N-((4-(3-cyclopropyl-1,2,4-oxadiazol-5-yl)bicyclo[2.2.2]octan-1-yl)methyl)-3-fluoro-N-(3'-(methylsulfonamido)-[1,1'-biphenyl]-3-yl)bicyclo[1.1.1]pentane-1-carboxamide (256);

N-((4-(3-cyclopropyl-1,2,4-oxadiazol-5-yl)bicyclo[2.2.2]octan-1-yl)methyl)-3-fluoro-N-(3'-sulfamoyl-[1,1'-biphenyl]-3-yl)bicyclo[1.1.1]pentane-1-carboxamide (257);

N-(3'-cyano-[1,1'-biphenyl]-3-yl)-N-((4-(3-cyclopropyl-1,2,4-oxadiazol-5-yl) bicyclo[2.2.2]octan-1-yl)methyl)-3-fluorobicyclo[1.1.1]pentane-1-carboxamide (258);

N-((4-(3-cyclopropyl-1,2,4-oxadiazol-5-yl)bicyclo[2.2.2]octan-1-yl)methyl)-3-fluoro-N-(3'-(trifluoromethoxy)-[1,1'-biphenyl]-3-yl)bicyclo[1.1.1]pentane-1-carboxamide (259);

N-((4-(3-cyclopropyl-1,2,4-oxadiazol-5-yl)bicyclo[2.2.2]octan-1-yl)methyl)-3-fluoro-N-(4'-fluoro-3'-methoxy-[1,1'-biphenyl]-3-yl)bicyclo[1.1.1]pentane-1-carboxamide (260);

N-((4-(3-cyclopropyl-1,2,4-oxadiazol-5-yl)bicyclo[2.2.2]octan-1-yl)methyl)-3-fluoro-N-(3-(2-oxo-2,3-dihydrobenzo[d]oxazol-6-yl)phenyl)bicyclo[1.1.1]pentane-1-carboxamide (261);

N-((4-(3-cyclopropyl-1,2,4-oxadiazol-5-yl)bicyclo[2.2.2]octan-1-yl)methyl)-3-fluoro-N-(3-(2-(trifluoromethyl)pyrimidin-5-yl)phenyl)bicyclo[1.1.1]pentane-1-carboxamide (262);

N-((4-(3-cyclopropyl-1,2,4-oxadiazol-5-yl)bicyclo[2.2.2]octan-1-yl)methyl)-3-fluoro-N-(3-(8-(trifluoromethyl)-[1,2,4]triazolo[1,5-a]pyridin-6-yl)phenyl)bicyclo[1.1.1]pentane-1-carboxamide (263);

N-((4-(3-cyclopropyl-1,2,4-oxadiazol-5-yl)bicyclo[2.2.2]octan-1-yl)methyl)-3-fluoro-N-(3-(8-methoxy-[1,2,4]triazolo[1,5-a]pyridin-6-yl)phenyl)bicyclo[1.1.1]pentane-1-carboxamide (264);

N-((4-(3-cyclopropyl-1,2,4-oxadiazol-5-yl)bicyclo[2.2.2]octan-1-yl)methyl)-N-(3-(2,8-dimethyl-[1,2,4]triazolo[1,5-a]pyridin-6-yl)phenyl)-3-fluorobicyclo[1.1.1]pentane-1-carboxamide (265);

N-((4-(3-cyclopropyl-1,2,4-oxadiazol-5-yl)bicyclo[2.2.2]octan-1-yl)methyl)-3-fluoro-N-(3-(8-methyl-[1,2,4]triazolo[1,5-a]pyridin-6-yl)phenyl)bicyclo[1.1.1]pentane-1-carboxamide (266);

N-((4-(3-cyclopropyl-1,2,4-oxadiazol-5-yl)bicyclo[2.2.2]octan-1-yl)methyl)-3-fluoro-N-(4'-((trifluoromethyl)sulfonamido)-[1,1'-biphenyl]-3-yl)bicyclo[1.1.1]pentane-1-carboxamide (267);

N-((4-(3-cyclopropyl-1,2,4-oxadiazol-5-yl)bicyclo[2.2.2]octan-1-yl)methyl)-3-fluoro-N-(4'-((1-methylethyl)sulfonamido)-[1,1'-biphenyl]-3-yl)bicyclo[1.1.1]pentane-1-carboxamide (268);

N-(4'-(cyclopropanesulfonamido)-[1,1'-biphenyl]-3-yl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide (269);

N-((4-(3-cyclopropyl-1,2,4-oxadiazol-5-yl)bicyclo[2.2.2]octan-1-yl)methyl)-3-fluoro-N-(3-(6-(methylsulfonamido)pyridin-3-yl)phenyl)bicyclo[1.1.1]pentane-1-carboxamide (270);

N-((4-(3-cyclopropyl-1,2,4-oxadiazol-5-yl)bicyclo[2.2.2]octan-1-yl)methyl)-N-(3-(2-cyclopropylpyrimidin-5-yl)phenyl)-3-fluorobicyclo[1.1.1]pentane-1-carboxamide (271);

N-((4-(3-cyclopropyl-1,2,4-oxadiazol-5-yl)bicyclo[2.2.2]octan-1-yl)methyl)-3-fluoro-N-(3-(2-(methylsulfonamido)pyrimidin-5-yl)phenyl)bicyclo[1.1.1]pentane-1-carboxamide (272);

N-((4-(3-cyclopropyl-1,2,4-oxadiazol-5-yl)bicyclo[2.2.2]octan-1-yl)methyl)-3-fluoro-N-(4'-(methoxymethyl)-[1,1'-biphenyl]-3-yl)bicyclo[1.1.1]pentane-1-carboxamide (273);

N-((4-(3-cyclopropyl-1,2,4-oxadiazol-5-yl)bicyclo[2.2.2]octan-1-yl)methyl)-3-fluoro-N-(3-(6-(methoxymethyl)pyridin-3-yl)phenyl)bicyclo[1.1.1]pentane-1-carboxamide (274);

N-((4-(3-cyclopropyl-1,2,4-oxadiazol-5-yl)bicyclo[2.2.2]octan-1-yl)methyl)-3-fluoro-N-(3-(2-methylbenzo[d]oxazol-6-yl)phenyl)bicyclo[1.1.1]pentane-1-carboxamide (275);

N-((4-(3-cyclopropyl-1,2,4-oxadiazol-5-yl)bicyclo[2.2.2]
octan-1-yl)methyl)-N-(3-(2-cyclopropylthiazolo[4,5-b]
pyridin-6-yl)phenyl)-3-fluorobicyclo[1.1.1]pentane-1-
carboxamide (276);

N-(3-(benzo[d]thiazol-6-yl)phenyl)-N-((4-(3-cyclopropyl-
1,2,4-oxadiazol-5-yl) bicyclo[2.2.2]octan-1-yl)methyl)-
3-fluorobicyclo[1.1.1]pentane-1-carboxamide (277);

N-((4-(3-cyclopropyl-1,2,4-oxadiazol-5-yl)bicyclo[2.2.2]
octan-1-yl)methyl)-3-fluoro-N-(3-(2-methylthiazolo[4,5-
b]pyridin-6-yl)phenyl)bicyclo[1.1.1]pentane-1-carbox-
amide (278);

N-(4'-(1-cyanocyclopropyl)-[1,1'-biphenyl]-3-yl)-N-((4-(3-
cyclopropyl-1,2,4-oxadiazol-5-yl)bicyclo[2.2.2]octan-1-
yl)methyl)-3-fluorobicyclo[1.1.1]pentane-1-carboxamide
(279);

N-((4-(3-cyclopropyl-1,2,4-oxadiazol-5-yl)bicyclo[2.2.2]
octan-1-yl)methyl)-3-fluoro-N-(3-(6-(trifluoromethyl)
pyridin-3-yl)phenyl)bicyclo[1.1.1]pentane-1-carboxam-
ide (280);

N-((4-(3-cyclopropyl-1,2,4-oxadiazol-5-yl)bicyclo[2.2.2]
octan-1-yl)methyl)-N-(3-(6-ethoxypyridin-3-yl)phenyl)-
3-fluorobicyclo[1.1.1]pentane-1-carboxamide (281);

N-((4-(3-cyclopropyl-1,2,4-oxadiazol-5-yl)bicyclo[2.2.2]
octan-1-yl)methyl)-3-fluoro-N-(4'-methoxy-[1,1'-biphe-
nyl]-3-yl)bicyclo[1.1.1]pentane-1-carboxamide (282);

N-((4-(3-cyclopropyl-1,2,4-oxadiazol-5-yl)bicyclo[2.2.2]
octan-1-yl)methyl)-N-(3-(6-ethoxypyridazin-3-yl)phe-
nyl)-3-fluorobicyclo[1.1.1]pentane-1-carboxamide (283);

N-((4-(3-cyclopropyl-1,2,4-oxadiazol-5-yl)bicyclo[2.2.2]
octan-1-yl)methyl)-N-(3-(2,2-difluorobenzo[d][1,3]di-
oxol-5-yl)phenyl)-3-fluorobicyclo[1.1.1]pentane-1-car-
boxamide (284);

N-((4-(3-cyclopropyl-1,2,4-oxadiazol-5-yl)bicyclo[2.2.2]
octan-1-yl)methyl)-N-(4'-ethyl-[1,1'-biphenyl]-3-yl)-3-
fluorobicyclo[1.1.1]pentane-1-carboxamide (285);

N-((4-(3-cyclopropyl-1,2,4-oxadiazol-5-yl)bicyclo[2.2.2]
octan-1-yl)methyl)-N-(3',4'-dichloro-[1,1'-biphenyl]-3-
yl)-3-fluorobicyclo[1.1.1]pentane-1-carboxamide (286);

N-((4-(3-cyclopropyl-1,2,4-oxadiazol-5-yl)bicyclo[2.2.2]
octan-1-yl)methyl)-3-fluoro-N-(3-(5-fluoropyridin-2-yl)
phenyl)bicyclo[1.1.1]pentane-1-carboxamide (287);

N-((4-(3-cyclopropyl-1,2,4-oxadiazol-5-yl)bicyclo[2.2.2]
octan-1-yl)methyl)-3-fluoro-N-(3-(imidazo[1,2-a]pyri-
din-7-yl)phenyl)bicyclo[1.1.1]pentane-1-carboxamide
(288);

N-((4-(3-cyclopropyl-1,2,4-oxadiazol-5-yl)bicyclo[2.2.2]
octan-1-yl)methyl)-N-(3-(2-ethoxypyrimidin-5-yl)phe-
nyl)-3-fluorobicyclo[1.1.1]pentane-1-carboxamide (289);

N-((4-(3-cyclopropyl-1,2,4-oxadiazol-5-yl)bicyclo[2.2.2]
octan-1-yl)methyl)-N-(4'-ethoxy-[1,1'-biphenyl]-3-yl)-3-
fluorobicyclo[1.1.1]pentane-1-carboxamide (290);

N-((4-(3-cyclopropyl-1,2,4-oxadiazol-5-yl)bicyclo[2.2.2]
octan-1-yl)methyl)-3-fluoro-N-(3-(4-(trifluoromethyl)py-
rimidin-2-yl)phenyl)bicyclo[1.1.1]pentane-1-carboxam-
ide (291);

N-(3-(6-cyanopyridin-2-yl)phenyl)-N-((4-(3-cyclopropyl-1,
2,4-oxadiazol-5-yl) bicyclo[2.2.2]octan-1-yl)methyl)-3-
fluorobicyclo[1.1.1]pentane-1-carboxamide (292);

N-((4-(3-cyclopropyl-1,2,4-oxadiazol-5-yl)bicyclo[2.2.2]
octan-1-yl)methyl)-3-fluoro-N-(3-(3-fluoro-6-(trifluo-
romethyl)pyridin-2-yl)phenyl)bicyclo[1.1.1]pentane-1-
carboxamide (293);

N-(3'-cyano-4'-fluoro-[1,1'-biphenyl]-3-yl)-N-((4-(3-cyclo-
propyl-1,2,4-oxadiazol-5-yl)bicyclo[2.2.2]octan-1-yl)
methyl)-3-fluorobicyclo[1.1.1]pentane-1-carboxamide
(294);

N-((4-(3-cyclopropyl-1,2,4-oxadiazol-5-yl)bicyclo[2.2.2]
octan-1-yl)methyl)-3-fluoro-N-(3-(6-methylpyridazin-3-
yl)phenyl)bicyclo[1.1.1]pentane-1-carboxamide (295);

N-(3'-cyano-4'-methoxy-[1,1'-biphenyl]-3-yl)-N-((4-(3-cy-
clopropyl-1,2,4-oxadiazol-5-yl)bicyclo[2.2.2]octan-1-yl)
methyl)-3-fluorobicyclo[1.1.1]pentane-1-carboxamide
(296);

N-(3-(5-cyanopyridin-2-yl)phenyl)-N-((4-(3-cyclopropyl-1,
2,4-oxadiazol-5-yl) bicyclo[2.2.2]octan-1-yl)methyl)-3-
fluorobicyclo[1.1.1]pentane-1-carboxamide (297);

N-(3-([1,2,4]triazolo[1,5-a]pyridin-7-yl)phenyl)-N-((4-(3-
cyclopropyl-1,2,4-oxadiazol-5-yl)bicyclo[2.2.2]octan-1-
yl)methyl)-3-fluorobicyclo[1.1.1]pentane-1-carboxamide
(298);

N-((4-(3-cyclopropyl-1,2,4-oxadiazol-5-yl)bicyclo[2.2.2]
octan-1-yl)methyl)-3-fluoro-N-(3'-(1,1,2,2-tetrafluoro-
ethoxy)-[1,1'-biphenyl]-3-yl)bicyclo[1.1.1]pentane-1-
carboxamide (299);

N-((4-(3-cyclopropyl-1,2,4-oxadiazol-5-yl)bicyclo[2.2.2]
octan-1-yl)methyl)-3-fluoro-N-(3-(4-methylpyrimidin-2-
yl)phenyl)bicyclo[1.1.1]pentane-1-carboxamide (300);

N-((4-(3-cyclopropyl-1,2,4-oxadiazol-5-yl)bicyclo[2.2.2]
octan-1-yl)methyl)-N-(3',4'-dimethoxy-[1,1'-biphenyl]-3-
yl)-3-fluorobicyclo[1.1.1]pentane-1-carboxamide (301);

N-(4'-cyano-[1,1'-biphenyl]-3-yl)-N-((4-(3-cyclopropyl-1,2,
4-oxadiazol-5-yl) bicyclo[2.2.2]octan-1-yl)methyl)-3-
fluorobicyclo[1.1.1]pentane-1-carboxamide (302);

N-((4-(3-cyclopropyl-1,2,4-oxadiazol-5-yl)bicyclo[2.2.2]
octan-1-yl)methyl)-3-fluoro-N-(3-(2-methylbenzo[d]thi-
azol-5-yl)phenyl)bicyclo[1.1.1]pentane-1-carboxamide
(303);

N-((4-(3-cyclopropyl-1,2,4-oxadiazol-5-yl)bicyclo[2.2.2]
octan-1-yl)methyl)-3-fluoro-N-(3-(1-methyl-1H-indazol-
5-yl)phenyl)bicyclo[1.1.1]pentane-1-carboxamide (304);

N-((4-(3-cyclopropyl-1,2,4-oxadiazol-5-yl)bicyclo[2.2.2]
octan-1-yl)methyl)-3-fluoro-N-(3-(2-methylbenzo[d]oxa-
zol-5-yl)phenyl)bicyclo[1.1.1]pentane-1-carboxamide
(305);

N-(3-(3-cyanoimidazo[1,2-b]pyridazin-6-yl)phenyl)-N-((4-
(3-cyclopropyl-1,2,4-oxadiazol-5-yl)bicyclo[2.2.2]octan-
1-yl)methyl)-3-fluorobicyclo[1.1.1]pentane-1-carboxam-
ide (306);

N-(3-([1,2,4]triazolo[4,3-a]pyridin-7-yl)phenyl)-N-((4-(3-
cyclopropyl-1,2,4-oxadiazol-5-yl)bicyclo[2.2.2]octan-1-
yl)methyl)-3-fluorobicyclo[1.1.1]pentane-1-carboxamide
(307);

N-((4-(3-cyclopropyl-1,2,4-oxadiazol-5-yl)bicyclo[2.2.2]
octan-1-yl)methyl)-N-(4'-(difluoromethoxy)-[1,1'-biphe-
nyl]-3-yl)-3-fluorobicyclo[1.1.1]pentane-1-carboxamide
(308);

N-(3-([1,2,4]triazolo[1,5-a]pyridin-8-yl)phenyl)-N-((4-(3-
cyclopropyl-1,2,4-oxadiazol-5-yl)bicyclo[2.2.2]octan-1-
yl)methyl)-3-fluorobicyclo[1.1.1]pentane-1-carboxamide
(309);

N-((4-(3-cyclopropyl-1,2,4-oxadiazol-5-yl)bicyclo[2.2.2]
octan-1-yl)methyl)-3-fluoro-N-(3-(5-methylpyrazin-2-yl)
phenyl)bicyclo[1.1.1]pentane-1-carboxamide (310);

N-(3-(8-cyanoquinolin-5-yl)phenyl)-N-((4-(3-cyclopropyl-
1,2,4-oxadiazol-5-yl) bicyclo[2.2.2]octan-1-yl)methyl)-
3-fluorobicyclo[1.1.1]pentane-1-carboxamide (311);

N-((4-(3-cyclopropyl-1,2,4-oxadiazol-5-yl)bicyclo[2.2.2]
octan-1-yl)methyl)-N-(3-(7,8-dimethyl-[1,2,4]triazolo[1,
5-a]pyridin-6-yl)phenyl)-3-fluorobicyclo[1.1.1]pentane-
1-carboxamide (312);

N-(3-(5-cyano-1-methyl-1H-pyrazolo[3,4-b]pyridin-6-yl)phenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide (313);

N-(3-(7-cyanoimidazo[1,2-b]pyridazin-3-yl)phenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide (314);

N-(3-(2-chloropyrrolo[2,1-f][1,2,4]triazin-4-yl)phenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide (315);

N-(3-(6-cyanothieno[3,2-b]pyridin-5-yl)phenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide (316);

N-((4-(3-cyclopropyl-1,2,4-oxadiazol-5-yl)bicyclo[2.2.2]octan-1-yl)methyl)-3-fluoro-N-(3-(8-fluoroimidazo[1,2-a]pyridin-6-yl)phenyl)bicyclo[1.1.1]pentane-1-carboxamide (317);

N-((4-(3-cyclopropyl-1,2,4-oxadiazol-5-yl)bicyclo[2.2.2]octan-1-yl)methyl)-3-fluoro-N-(3-(imidazo[1,2-b]pyridazin-3-yl)phenyl)bicyclo[1.1.1]pentane-1-carboxamide (318);

N-((4-(3-cyclopropyl-1,2,4-oxadiazol-5-yl)bicyclo[2.2.2]octan-1-yl)methyl)-3-fluoro-N-(3-(7-methylimidazo[1,2-b]pyridazin-3-yl)phenyl)bicyclo[1.1.1]pentane-1-carboxamide (319);

N-((4-(3-cyclopropyl-1,2,4-oxadiazol-5-yl)bicyclo[2.2.2]octan-1-yl)methyl)-N-(3-(2,7-dimethylimidazo[1,2-a]pyridin-6-yl)phenyl)-3-fluorobicyclo[1.1.1]pentane-1-carboxamide (320);

N-((4-(3-cyclopropyl-1,2,4-oxadiazol-5-yl)bicyclo[2.2.2]octan-1-yl)methyl)-3-fluoro-N-(3-(2-methyl-8-(trifluoromethyl)-[1,2,4]triazolo[1,5-a]pyridin-6-yl)phenyl)bicyclo[1.1.1]pentane-1-carboxamide (321);

N-((4-(3-cyclopropyl-1,2,4-oxadiazol-5-yl)bicyclo[2.2.2]octan-1-yl)methyl)-N-(3-(2,8-dimethylimidazo[1,2-a]pyridin-6-yl)phenyl)-3-fluorobicyclo[1.1.1]pentane-1-carboxamide (322);

N-(3-([1,2,4]triazolo[4,3-a]pyridin-6-yl)phenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide (323);

N-((4-(3-cyclopropyl-1,2,4-oxadiazol-5-yl)bicyclo[2.2.2]octan-1-yl)methyl)-3-fluoro-N-(3-(2-methyl-[1,2,4]triazolo[1,5-a]pyridin-6-yl)phenyl)bicyclo[1.1.1]pentane-1-carboxamide (324);

N-((4-(3-cyclopropyl-1,2,4-oxadiazol-5-yl)bicyclo[2.2.2]octan-1-yl)methyl)-3-fluoro-N-(3-(5-methylpyridin-2-yl)phenyl)bicyclo[1.1.1]pentane-1-carboxamide (325);

N-(3-(6-bromo-[1,2,4]triazolo[1,5-a]pyridin-8-yl)phenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide (326);

N-((4-(3-cyclopropyl-1,2,4-oxadiazol-5-yl)bicyclo[2.2.2]octan-1-yl)methyl)-3-fluoro-N-(3-(7-methylthiazolo[5,4-b]pyridin-5-yl)phenyl)bicyclo[1.1.1]pentane-1-carboxamide (327);

N-(3-(3-cyano-7,8-dihydro-5H-pyrano[4,3-b]pyridin-2-yl)phenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide (328);

N-(3-(7-chloroimidazo[1,2-b]pyridazin-3-yl)phenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide (329);

N-((4-(3-cyclopropyl-1,2,4-oxadiazol-5-yl)bicyclo[2.2.2]octan-1-yl)methyl)-3-fluoro-N-(3-(imidazo[1,2-a]pyridin-8-yl)phenyl)bicyclo[1.1.1]pentane-1-carboxamide (330);

N-((4-(3-cyclopropyl-1,2,4-oxadiazol-5-yl)bicyclo[2.2.2]octan-1-yl)methyl)-3-fluoro-N-(3-(2-hydroxyquinolin-6-yl)phenyl)bicyclo[1.1.1]pentane-1-carboxamide (331);

N-((4-(3-cyclopropyl-1,2,4-oxadiazol-5-yl)bicyclo[2.2.2]octan-1-yl)methyl)-3-fluoro-N-(3-(2-oxoindolin-5-yl)phenyl)bicyclo[1.1.1]pentane-1-carboxamide (332);

N-((4-(3-cyclopropyl-1,2,4-oxadiazol-5-yl)bicyclo[2.2.2]octan-1-yl)methyl)-N-(3-(5-ethoxypyrimidin-2-yl)phenyl)-3-fluorobicyclo[1.1.1]pentane-1-carboxamide (333);

N-((4-(3-cyclopropyl-1,2,4-oxadiazol-5-yl)bicyclo[2.2.2]octan-1-yl)methyl)-3-fluoro-N-(3-(5-methoxypyrimidin-2-yl)phenyl)bicyclo[1.1.1]pentane-1-carboxamide (334);

N-((4-(3-cyclopropyl-1,2,4-oxadiazol-5-yl)bicyclo[2.2.2]octan-1-yl)methyl)-N-(3-(5-(difluoromethoxy)pyrimidin-2-yl)phenyl)-3-fluorobicyclo[1.1.1]pentane-1-carboxamide (335);

N-(3-(2-acetamidoimidazo[1,2-b]pyridazin-6-yl)phenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide (336);

N-(3-(2-cyclopropoxypyrimidin-4-yl)phenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide (337);

N-(3-(2-cyclopropoxypyrimidin-4-yl)phenyl)-N-((4-(3-cyclopropyl-1,2,4-oxadiazol-5-yl)bicyclo[2.2.2]octan-1-yl)methyl)-3,3-difluorocyclobutane-1-carboxamide (338);

N-((1-(3-cyclopropyl-1,2,4-oxadiazol-5-yl)-2-oxabicyclo[2.2.2]octan-4-yl)methyl)-3-fluoro-N-(3-(2-methoxypyridin-4-yl)phenyl)bicyclo[1.1.1]pentane-1-carboxamide (339);

N-((4-(3-cyclopropyl-1,2,4-oxadiazol-5-yl)bicyclo[2.2.2]octan-1-yl)methyl)-3-fluoro-N-(2'-methoxy-[4,4'-bipyridin]-2-yl)bicyclo[1.1.1]pentane-1-carboxamide (340);

N-((4-(5-cyclopropyl-1,3,4-oxadiazol-2-yl)bicyclo[2.2.2]octan-1-yl)methyl)-3-fluoro-N-(3-(2-methoxypyrimidin-5-yl)phenyl)bicyclo[1.1.1]pentane-1-carboxamide (341);

N-((4-(5-cyclopropyl-1,3,4-oxadiazol-2-yl)bicyclo[2.2.2]octan-1-yl)methyl)-3-fluoro-N-(3-(2-methoxypyridin-4-yl)phenyl)bicyclo[1.1.1]pentane-1-carboxamide (342);

N-((4-(5-cyclopropyl-1,3,4-oxadiazol-2-yl)bicyclo[2.2.2]octan-1-yl)methyl)-3-fluoro-N-(3-(6-methoxypyridin-3-yl)phenyl)bicyclo[1.1.1]pentane-1-carboxamide (343);

N-((4-(5-cyclopropyl-1,3,4-oxadiazol-2-yl)bicyclo[2.2.2]octan-1-yl)methyl)-3-fluoro-N-(4'-(methylsulfonamido)-[1,1'-biphenyl]-3-yl)bicyclo[1.1.1]pentane-1-carboxamide (344);

N-((1-(4-(1-Cyanocyclopropyl)phenyl)-2-oxabicyclo[2.2.2]octan-4-yl)methyl)-3-fluoro-N-(4'-(methylsulfonamido)-[1,1'-biphenyl]-3-yl)bicyclo[1.1.1]pentane-1-carboxamide (345);

N-((1-(4-(1-cyanocyclopropyl)phenyl)-2-oxabicyclo[2.2.2]octan-4-yl)methyl)-3-fluoro-N-(3-(2-methylbenzo[d]thiazol-6-yl)phenyl)bicyclo[1.1.1]pentane-1-carboxamide (346);

N-((1-(4-(1-cyanocyclopropyl)phenyl)-2-oxabicyclo[2.2.2]octan-4-yl)methyl)-3-fluoro-N-(3-(2-methylbenzo[d]oxazol-6-yl)phenyl)bicyclo[1.1.1]pentane-1-carboxamide (347);

N-((1-(4-(1-cyanocyclopropyl)phenyl)-2-oxabicyclo[2.2.2]octan-4-yl)methyl)-3-fluoro-N-(3-(2-methoxypyridin-4-yl)phenyl)bicyclo[1.1.1]pentane-1-carboxamide (348);

N-((1-(4-(1-cyanocyclopropyl)phenyl)-2-oxabicyclo[2.2.2]octan-4-yl)methyl)-3-fluoro-N-(4'-methoxy-[1,1'-biphenyl]-3-yl)bicyclo[1.1.1]pentane-1-carboxamide (349);

N-((1-(4-(1-cyanocyclopropyl)phenyl)-2-oxabicyclo[2.2.2]octan-4-yl)methyl)-3-fluoro-N-(3-(6-methoxypyridin-3-yl)phenyl)bicyclo[1.1.1]pentane-1-carboxamide (350);

N-((1-(4-(1-cyanocyclopropyl)phenyl)-2-oxabicyclo[2.2.2]octan-4-yl)methyl)-3-fluoro-N-(3-(2-methoxypyrimidin-5-yl)phenyl)bicyclo[1.1.1]pentane-1-carboxamide (351);

N-((1-(4-(1-cyanocyclopropyl)phenyl)-2-oxabicyclo[2.2.2]octan-4-yl)methyl)-N-(3-(2-ethoxypyrimidin-5-yl)phenyl)-3-fluorobicyclo[1.1.1]pentane-1-carboxamide (352);

N-((1-(3-cyclopropyl-1,2,4-oxadiazol-5-yl)-2-oxabicyclo[2.2.2]octan-4-yl)methyl)-N-(3-(2-ethoxypyrimidin-5-yl)phenyl)-3-fluorobicyclo[1.1.1]pentane-1-carboxamide (353);

N-(4'-(cyclopropanesulfonamido)-[1,1'-biphenyl]-3-yl)-3-fluoro-N-((4-(4-(trifluoromethyl)pyridin-2-yl)bicyclo[2.2.2]octan-1-yl)methyl)bicyclo[1.1.1]pentane-1-carboxamide (354);

3-fluoro-N-(4'-(methylsulfonamido)-[1,1'-biphenyl]-3-yl)-N-((4-(4-(trifluoromethyl) pyridin-2-yl)bicyclo[2.2.2]octan-1-yl)methyl)bicyclo[1.1.1]pentane-1-carboxamide (355);

3-fluoro-N-(3-(2-methylbenzo[d]thiazol-6-yl)phenyl)-N-((4-(4-(trifluoromethyl)pyridin-2-yl)bicyclo[2.2.2]octan-1-yl)methyl)bicyclo[1.1.1]pentane-1-carboxamide (356);

N-((4-(3-(tert-butyl)-1,2,4-oxadiazol-5-yl)bicyclo[2.2.2]octan-1-yl)methyl)-N-(3-(2-ethoxypyrimidin-5-yl)phenyl)-3-fluorobicyclo[1.1.1]pentane-1-carboxamide (357);

N-((4-(3-(tert-butyl)-1,2,4-oxadiazol-5-yl)bicyclo[2.2.2]octan-1-yl)methyl)-N-(3-(2-cyclopropylpyrimidin-5-yl)phenyl)-3-fluorobicyclo[1.1.1]pentane-1-carboxamide (358);

N-((4-(3-(tert-butyl)-1,2,4-oxadiazol-5-yl)bicyclo[2.2.2]octan-1-yl)methyl)-N-(4'-ethoxy-[1,1'-biphenyl]-3-yl)-3-fluorobicyclo[1.1.1]pentane-1-carboxamide (359);

N-((4-(3-(tert-butyl)-1,2,4-oxadiazol-5-yl)bicyclo[2.2.2]octan-1-yl)methyl)-N-(3-(6-ethoxypyridin-3-yl)phenyl)-3-fluorobicyclo[1.1.1]pentane-1-carboxamide (360);

N-((4-(3-(tert-butyl)-1,2,4-oxadiazol-5-yl)bicyclo[2.2.2]octan-1-yl)methyl)-3-fluoro-N-(4'-(methylsulfonamido)-[1,1'-biphenyl]-3-yl)bicyclo[1.1.1]pentane-1-carboxamide (361);

N-((4-(3-(tert-butyl)-1,2,4-oxadiazol-5-yl)bicyclo[2.2.2]octan-1-yl)methyl)-3-fluoro-N-(3-(2-methylbenzo[d]thiazol-6-yl)phenyl)bicyclo[1.1.1]pentane-1-carboxamide (362);

N-((4-(3-(tert-butyl)-1,2,4-oxadiazol-5-yl)bicyclo[2.2.2]octan-1-yl)methyl)-3-fluoro-N-(3-(2-methoxypyrimidin-5-yl)phenyl)bicyclo[1.1.1]pentane-1-carboxamide (363);

N-((4-(3-(tert-butyl)-1,2,4-oxadiazol-5-yl)bicyclo[2.2.2]octan-1-yl)methyl)-3-fluoro-N-(3-(6-(methylsulfonamido)pyridin-3-yl)phenyl)bicyclo[1.1.1]pentane-1-carboxamide (364);

N-((4-(3-(tert-butyl)-1,2,4-oxadiazol-5-yl)bicyclo[2.2.2]octan-1-yl)methyl)-3-fluoro-N-(3-(2-methylthiazolo[4,5-b]pyridin-6-yl)phenyl)bicyclo[1.1.1]pentane-1-carboxamide (365);

N-((4-(3-(tert-butyl)-1,2,4-oxadiazol-5-yl)bicyclo[2.2.2]octan-1-yl)methyl)-3-fluoro-N-(3-(2-(trifluoromethyl)pyrimidin-5-yl)phenyl)bicyclo[1.1.1]pentane-1-carboxamide (366);

N-((4-(3-(tert-butyl)-1,2,4-oxadiazol-5-yl)bicyclo[2.2.2]octan-1-yl)methyl)-3-fluoro-N-(3-(2-(methylsulfonamido)pyrimidin-5-yl)phenyl)bicyclo[1.1.1]pentane-1-carboxamide (367);

N-((4-(3-(tert-butyl)-1,2,4-oxadiazol-5-yl)bicyclo[2.2.2]octan-1-yl)methyl)-N-(4'-(difluoromethoxy)-[1,1'-biphenyl]-3-yl)-3-fluorobicyclo[1.1.1]pentane-1-carboxamide (368);

N-((4-(3-(tert-butyl)-1,2,4-oxadiazol-5-yl)bicyclo[2.2.2]octan-1-yl)methyl)-3-fluoro-N-(3-(5-methoxypyrimidin-2-yl)phenyl)bicyclo[1.1.1]pentane-1-carboxamide (369);

N-((4-(3-(tert-butyl)-1,2,4-oxadiazol-5-yl)bicyclo[2.2.2]octan-1-yl)methyl)-N-(3-(5-ethoxypyrimidin-2-yl)phenyl)-3-fluorobicyclo[1.1.1]pentane-1-carboxamide (370);

N-((4-(3-(tert-butyl)-1,2,4-oxadiazol-5-yl)bicyclo[2.2.2]octan-1-yl)methyl)-N-(3-(5-(difluoromethoxy)pyrimidin-2-yl)phenyl)-3-fluorobicyclo[1.1.1]pentane-1-carboxamide (371);

N-((4-(3-(tert-butyl)-1,2,4-oxadiazol-5-yl)bicyclo[2.2.2]octan-1-yl)methyl)-3-fluoro-N-(4'-((trifluoromethyl)sulfonamido)-[1,1'-biphenyl]-3-yl)bicyclo[1.1.1]pentane-1-carboxamide (372);

N-((4-(3-(tert-butyl)-1,2,4-oxadiazol-5-yl)bicyclo[2.2.2]octan-1-yl)methyl)-N-(3-(5-(difluoromethoxy)pyridin-2-yl)phenyl)-3-fluorobicyclo[1.1.1]pentane-1-carboxamide (373);

N-(3-(2-ethoxypyrimidin-5-yl)phenyl)-3-fluoro-N-((4-(3-isopropyl-1,2,4-oxadiazol-5-yl)bicyclo[2.2.2]octan-1-yl)methyl)bicyclo[1.1.1]pentane-1-carboxamide (374);

N-(4'-ethoxy-[1,1'-biphenyl]-3-yl)-3-fluoro-N-((4-(3-isopropyl-1,2,4-oxadiazol-5-yl) bicyclo[2.2.2]octan-1-yl)methyl)bicyclo[1.1.1]pentane-1-carboxamide (375);

3-fluoro-N-((4-(3-isopropyl-1,2,4-oxadiazol-5-yl)bicyclo[2.2.2]octan-1-yl)methyl)-N-(4'-(methylsulfonamido)-[1,1'-biphenyl]-3-yl)bicyclo[1.1.1]pentane-1-carboxamide (376);

3-fluoro-N-((4-(3-isopropyl-1,2,4-oxadiazol-5-yl)bicyclo[2.2.2]octan-1-yl)methyl)-N-(4'-methoxy-[1,1'-biphenyl]-3-yl)bicyclo[1.1.1]pentane-1-carboxamide (377);

3-fluoro-N-((4-(3-isopropyl-1,2,4-oxadiazol-5-yl)bicyclo[2.2.2]octan-1-yl)methyl)-N-(3-(2-methylbenzo[d]thiazol-6-yl)phenyl)bicyclo[1.1.1]pentane-1-carboxamide (378);

N-(4'-(cyclopropanesulfonamido)-[1,1'-biphenyl]-3-yl)-3-fluoro-N-((4-(3-isopropyl-1,2,4-oxadiazol-5-yl)bicyclo[2.2.2]octan-1-yl)methyl)bicyclo[1.1.1]pentane-1-carboxamide (379);

3-fluoro-N-((4-(3-isopropyl-1,2,4-oxadiazol-5-yl)bicyclo[2.2.2]octan-1-yl)methyl)-N-(4'-(trifluoromethyl)-[1,1'-biphenyl]-3-yl)bicyclo[1.1.1]pentane-1-carboxamide (380);

N-(3-(6-ethoxypyridin-3-yl)phenyl)-3-fluoro-N-((4-(3-isopropyl-1,2,4-oxadiazol-5-yl)bicyclo[2.2.2]octan-1-yl)methyl)bicyclo[1.1.1]pentane-1-carboxamide (381);

3-fluoro-N-((4-(3-isopropyl-1,2,4-oxadiazol-5-yl)bicyclo[2.2.2]octan-1-yl)methyl)-N-(3-(6-methoxypyridin-3-yl)phenyl)bicyclo[1.1.1]pentane-1-carboxamide (382);

3-fluoro-N-((4-(3-isopropyl-1,2,4-oxadiazol-5-yl)bicyclo[2.2.2]octan-1-yl)methyl)-N-(3-(2-methoxypyrimidin-5-yl)phenyl)bicyclo[1.1.1]pentane-1-carboxamide (383);

3-fluoro-N-((4-(3-isopropyl-1,2,4-oxadiazol-5-yl)bicyclo[2.2.2]octan-1-yl)methyl)-N-(3-(2-(trifluoromethyl)pyrimidin-5-yl)phenyl)bicyclo[1.1.1]pentane-1-carb oxamide (384);

N-(3-(2-cyclopropylpyrimidin-5-yl)phenyl)-3-fluoro-N-((4-(3-isopropyl-1,2,4-oxadiazol-5-yl)bicyclo[2.2.2]octan-1-yl)methyl)bicyclo[1.1.1]pentane-1-carboxamide (385);

N-(3-(2,2-difluorobenzo[d][1,3]dioxol-5-yl)phenyl)-3-fluoro-N-((4-(3-isopropyl-1,2,4-oxadiazol-5-yl)bicyclo[2.2.2]octan-1-yl)methyl)bicyclo[1.1.1]pentane-1-carboxamide (386);

N-(4'-(difluoromethoxy)-[1,1'-biphenyl]-3-yl)-3-fluoro-N-((4-(3-isopropyl-1,2,4-oxadiazol-5-yl)bicyclo[2.2.2]octan-1-yl)methyl)bicyclo[1.1.1]pentane-1-carboxamide (387);

3-fluoro-N-((4-(3-isopropyl-1,2,4-oxadiazol-5-yl)bicyclo[2.2.2]octan-1-yl)methyl)-N-(3-(6-(trifluoromethyl)pyridin-3-yl)phenyl)bicyclo[1.1.1]pentane-1-carboxamide (388);

3-fluoro-N-((4-(3-isopropyl-1,2,4-oxadiazol-5-yl)bicyclo[2.2.2]octan-1-yl)methyl)-N-(3-(2-methylthiazolo[4,5-b]pyridin-6-yl)phenyl)bicyclo[1.1.1]pentane-1-carboxamide (389);

3-fluoro-N-((4-(3-isopropyl-1,2,4-oxadiazol-5-yl)bicyclo[2.2.2]octan-1-yl)methyl)-N-(4'-((trifluoromethyl)sulfonamido)-[1,1'-biphenyl]-3-yl)bicyclo[1.1.1]pentane-1-carboxamide (390);

3-fluoro-N-((4-(3-isopropyl-1,2,4-oxadiazol-5-yl)bicyclo[2.2.2]octan-1-yl)methyl)-N-(3-(6-(methoxymethyl)pyridin-3-yl)phenyl)bicyclo[1.1.1]pentane-1-carboxamide (391);

3-fluoro-N-((4-(3-isopropyl-1,2,4-oxadiazol-5-yl)bicyclo[2.2.2]octan-1-yl)methyl)-N-(4'-(methoxymethyl)-[1,1'-biphenyl]-3-yl)bicyclo[1.1.1]pentane-1-carboxamide (392);

3-fluoro-N-((4-(3-isopropyl-1,2,4-oxadiazol-5-yl)bicyclo[2.2.2]octan-1-yl)methyl)-N-(3-(5-methylpyrimidin-2-yl)phenyl)bicyclo[1.1.1]pentane-1-carboxamide (393);

N-(3-(5-ethylpyrimidin-2-yl)phenyl)-3-fluoro-N-((4-(3-isopropyl-1,2,4-oxadiazol-5-yl)bicyclo[2.2.2]octan-1-yl)methyl)bicyclo[1.1.1]pentane-1-carboxamide (394);

N-(3-(5-ethoxypyrimidin-2-yl)phenyl)-3-fluoro-N-((4-(3-isopropyl-1,2,4-oxadiazol-5-yl)bicyclo[2.2.2]octan-1-yl)methyl)bicyclo[1.1.1]pentane-1-carboxamide (395);

N-(3-(2-ethoxypyrimidin-5-yl)phenyl)-3-fluoro-N-((4-(5-(1-methylcyclopropyl)-1,2,4-oxadiazol-3-yl)bicyclo[2.2.2]octan-1-yl)methyl)bicyclo[1.1.1]pentane-1-carboxamide (396);

N-(4'-(cyclopropanesulfonamido)-[1,1'-biphenyl]-3-yl)-3-fluoro-N-((4-(5-(1-methylcyclopropyl)-1,2,4-oxadiazol-3-yl)bicyclo[2.2.2]octan-1-yl)methyl) bicyclo[1.1.1]pentane-1-carboxamide (397);

3-fluoro-N-((4-(5-(1-methylcyclopropyl)-1,2,4-oxadiazol-3-yl)bicyclo[2.2.2]octan-1-yl) methyl)-N-(4'-(methylsulfonamido)-[1,1'-biphenyl]-3-yl)bicyclo[1.1.1]pentane-1-carboxamide (398);

N-(4'-ethoxy-[1,1'-biphenyl]-3-yl)-3-fluoro-N-((4-(5-(1-methylcyclopropyl)-1,2,4-oxadiazol-3-yl)bicyclo[2.2.2]octan-1-yl)methyl)bicyclo[1.1.1]pentane-1-carboxamide (399);

3-fluoro-N-(3-(2-methoxypyrimidin-5-yl)phenyl)-N-((4-(5-(1-methylcyclopropyl)-1,2,4-oxadiazol-3-yl)bicyclo[2.2.2]octan-1-yl)methyl)bicyclo[1.1.1]pentane-1-carboxamide (400);

N-(3-(6-ethoxypyridin-3-yl)phenyl)-3-fluoro-N-((4-(5-(1-methylcyclopropyl)-1,2,4-oxadiazol-3-yl)bicyclo[2.2.2]octan-1-yl)methyl)bicyclo[1.1.1]pentane-1-carboxamide (401);

3-fluoro-N-(3-(2-methylbenzo[d]thiazol-6-yl)phenyl)-N-((4-(5-(1-methylcyclopropyl)-1,2,4-oxadiazol-3-yl)bicyclo[2.2.2]octan-1-yl)methyl)bicyclo[1.1.1]pentane-1-carboxamide (402);

N-(3-(2-cyclopropylpyrimidin-5-yl)phenyl)-3-fluoro-N-((4-(5-(1-methylcyclopropyl)-1,2,4-oxadiazol-3-yl)bicyclo[2.2.2]octan-1-yl)methyl)bicyclo[1.1.1]pentane-1-carboxamide (403);

3-fluoro-N-((4-(5-(1-methylcyclopropyl)-1,2,4-oxadiazol-3-yl)bicyclo[2.2.2]octan-1-yl)methyl)-N-(3-(2-(trifluoromethyl)pyrimidin-5-yl)phenyl)bicyclo[1.1.1]pentane-1-carboxamide (404);

N-(4'-(difluoromethoxy)-[1,1'-biphenyl]-3-yl)-3-fluoro-N-((4-(5-(1-methylcyclopropyl)-1,2,4-oxadiazol-3-yl)bicyclo[2.2.2]octan-1-yl)methyl)bicyclo[1.1.1]pentane-1-carboxamide (405);

N-((4-(5-cyclopropyl-1-methyl-1H-pyrazol-3-yl)bicyclo[2.2.2]octan-1-yl)methyl)-3-fluoro-N-(4'-(methylsulfonamido)-[1,1'-biphenyl]-3-yl)bicyclo[1.1.1]pentane-1-carboxamide (406);

N-((4-(5-cyclopropyl-1-methyl-1H-pyrazol-3-yl)bicyclo[2.2.2]octan-1-yl)methyl)-N-(3-(2-ethoxypyrimidin-5-yl)phenyl)-3-fluorobicyclo[1.1.1]pentane-1-carboxamide (407);

N-((4-(5-cyclopropyl-1-methyl-1H-pyrazol-3-yl)bicyclo[2.2.2]octan-1-yl)methyl)-3-fluoro-N-(4'-methoxy-[1,1'-biphenyl]-3-yl)bicyclo[1.1.1]pentane-1-carboxamide (408);

N-((4-(5-cyclopropyl-1-methyl-1H-pyrazol-3-yl)bicyclo[2.2.2]octan-1-yl)methyl)-3-fluoro-N-(3-(2-methylbenzo[d]thiazol-6-yl)phenyl)bicyclo[1.1.1]pentane-1-carboxamide (409);

N-((4-(5-cyclopropyl-1-methyl-1H-pyrazol-3-yl)bicyclo[2.2.2]octan-1-yl)methyl)-N-(3-(2-cyclopropylthiazolo[4,5-b]pyridin-6-yl)phenyl)-3-fluorobicyclo[1.1.1]pentane-1-carboxamide (410);

N-((4-(5-cyclopropyl-1-methyl-1H-pyrazol-3-yl)bicyclo[2.2.2]octan-1-yl)methyl)-3-fluoro-N-(3-(2-oxo-2,3-dihydrobenzo[d]oxazol-6-yl)phenyl)bicyclo[1.1.1]pentane-1-carboxamide (411);

N-((4-(3-cyclopropyl-1-methyl-1H-pyrazol-5-yl)bicyclo[2.2.2]octan-1-yl)methyl)-3-fluoro-N-(4'-(methylsulfonamido)-[1,1'-biphenyl]-3-yl)bicyclo[1.1.1]pentane-1-carboxamide (412);

N-((4-(3-cyclopropyl-1-methyl-1H-pyrazol-5-yl)bicyclo[2.2.2]octan-1-yl)methyl)-N-(3-(2-ethoxypyrimidin-5-yl)phenyl)-3-fluorobicyclo[1.1.1]pentane-1-carboxamide (413);

N-((4-(3-cyclopropyl-1-methyl-1H-pyrazol-5-yl)bicyclo[2.2.2]octan-1-yl)methyl)-3-fluoro-N-(4'-methoxy-[1,1'-biphenyl]-3-yl)bicyclo[1.1.1]pentane-1-carboxamide (414);

N-((4-(3-cyclopropyl-1-methyl-1H-pyrazol-5-yl)bicyclo[2.2.2]octan-1-yl)methyl)-3-fluoro-N-(3-(2-methylbenzo[d]thiazol-6-yl)phenyl)bicyclo[1.1.1]pentane-1-carboxamide (415);

N-((4-(3-cyclopropyl-1,2,4-oxadiazol-5-yl)bicyclo[2.2.2]octan-1-yl)methyl)-3-fluoro-N-(3-(4-methylpiperazin-1-yl)phenyl)bicyclo[1.1.1]pentane-1-carboxamide (416);

N-((4-(3-cyclopropyl-1,2,4-oxadiazol-5-yl)bicyclo[2.2.2]octan-1-yl)methyl)-3-fluoro-N-(3-morpholinophenyl)bicyclo[1.1.1]pentane-1-carboxamide (417);

N-(3-(2-ethoxypyrimidin-5-yl)phenyl)-3-fluoro-N-((1-(2-(trifluoromethyl)pyrimidin-5-yl)-2-oxabicyclo[2.2.2]octan-4-yl)methyl)bicyclo[1.1.1]pentane-1-carboxamide (418);

3-fluoro-N-(4'-(methylsulfonamido)-[1,1'-biphenyl]-3-yl)-N-((1-(2-(trifluoromethyl) pyrimidin-5-yl)-2-oxabicyclo[2.2.2]octan-4-yl)methyl)bicyclo[1.1.1]pentane-1-carboxamide (419);

3-fluoro-N-(4'-methoxy-[1,1'-biphenyl]-3-yl)-N-((1-(2-(trifluoromethyl)pyrimidin-5-yl)-2-oxabicyclo[2.2.2]octan-4-yl)methyl)bicyclo[1.1.1]pentane-1-carboxamide (420);

3-fluoro-N-(3-(2-methylbenzo[d]thiazol-6-yl)phenyl)-N-((1-(2-(trifluoromethyl) pyrimidin-5-yl)-2-oxabicyclo[2.2.2]octan-4-yl)methyl)bicyclo[1.1.1]pentane-1-carboxamide (421);

N-(4'-ethoxy-[1,1'-biphenyl]-3-yl)-3-fluoro-N-((1-(2-(trifluoromethyl)pyrimidin-5-yl)-2-oxabicyclo[2.2.2]octan-4-yl)methyl)bicyclo[1.1.1]pentane-1-carboxamide (422);

N-((4-(3-cyclopropyl-1,2,4-oxadiazol-5-yl)bicyclo[2.2.2]octan-1-yl)methyl)-N-(5-(2-ethoxypyrimidin-5-yl)pyridin-3-yl)-3-fluorobicyclo[1.1.1]pentane-1-carboxamide (423);

N-((4-(3-cyclopropyl-1,2,4-oxadiazol-5-yl)bicyclo[2.2.2]octan-1-yl)methyl)-N-(5-(4-ethoxyphenyl)pyridin-3-yl)-3-fluorobicyclo[1.1.1]pentane-1-carboxamide (424);

N-((4-(3-cyclopropyl-1,2,4-oxadiazol-5-yl)bicyclo[2.2.2]octan-1-yl)methyl)-3-fluoro-N-(5-(2-methylbenzo[d]thiazol-6-yl)pyridin-3-yl)bicyclo[1.1.1]pentane-1-carboxamide (425);

N-((4-(3-cyclopropyl-1,2,4-oxadiazol-5-yl)bicyclo[2.2.2]octan-1-yl)methyl)-N-(6'-ethoxy-[3,3'-bipyridin]-5-yl)-3-fluorobicyclo[1.1.1]pentane-1-carboxamide (426);

N-((4-(3-cyclopropyl-1,2,4-oxadiazol-5-yl)bicyclo[2.2.2]octan-1-yl)methyl)-3-fluoro-N-(5-(2-(trifluoromethyl)pyrimidin-5-yl)pyridin-3-yl)bicyclo[1.1.1]pentane-1-carboxamide (427);

N-((4-(3-cyclopropyl-1,2,4-oxadiazol-5-yl)bicyclo[2.2.2]octan-1-yl)methyl)-3-fluoro-N-(5-(2-(trifluoromethyl)pyrimidin-5-yl)pyridin-3-yl)bicyclo[1.1.1]pentane-1-carboxamide (428);

N-(3-(2-ethoxypyrimidin-5-yl)phenyl)-3-fluoro-N-((4-(5-isopropyl-1,2,4-oxadiazol-3-yl)bicyclo[2.2.2]octan-1-yl)methyl)bicyclo[1.1.1]pentane-1-carboxamide (429);

3-fluoro-N-((4-(5-isopropyl-1,2,4-oxadiazol-3-yl)bicyclo[2.2.2]octan-1-yl)methyl)-N-(4'-(methylsulfonamido)-[1,1'-biphenyl]-3-yl)bicyclo[1.1.1]pentane-1-carboxamide (430);

N-(4'-ethoxy-[1,1'-biphenyl]-3-yl)-3-fluoro-N-((4-(5-isopropyl-1,2,4-oxadiazol-3-yl) bicyclo[2.2.2]octan-1-yl)methyl)bicyclo[1.1.1]pentane-1-carboxamide (431);

N-(3-(6-ethoxypyridin-3-yl)phenyl)-3-fluoro-N-((4-(5-isopropyl-1,2,4-oxadiazol-3-yl)bicyclo[2.2.2]octan-1-yl)methyl)bicyclo[1.1.1]pentane-1-carboxamide (432);

3-fluoro-N-((4-(5-isopropyl-1,2,4-oxadiazol-3-yl)bicyclo[2.2.2]octan-1-yl)methyl)-N-(3-(2-methylbenzo[d]thiazol-6-yl)phenyl)bicyclo[1.1.1]pentane-1-carboxamide (433);

N-(3-(2-cyclopropylpyrimidin-5-yl)phenyl)-3-fluoro-N-((4-(5-isopropyl-1,2,4-oxadiazol-3-yl)bicyclo[2.2.2]octan-1-yl)methyl)bicyclo[1.1.1]pentane-1-carboxamide (434);

3-fluoro-N-((4-(5-isopropyl-1,2,4-oxadiazol-3-yl)bicyclo[2.2.2]octan-1-yl)methyl)-N-(3-(2-(trifluoromethyl)pyrimidin-5-yl)phenyl)bicyclo[1.1.1]pentane-1-carboxamide (435);

N-(4'-(difluoromethoxy)-[1,1'-biphenyl]-3-yl)-3-fluoro-N-((4-(5-isopropyl-1,2,4-oxadiazol-3-yl)bicyclo[2.2.2]octan-1-yl)methyl)bicyclo[1.1.1]pentane-1-carboxamide (436);

N-((4-(5-(tert-butyl)-1,2,4-oxadiazol-3-yl)bicyclo[2.2.2]octan-1-yl)methyl)-N-(3-(2-ethoxypyrimidin-5-yl)phenyl)-3-fluorobicyclo[1.1.1]pentane-1-carboxamide (437);

N-((4-(5-(tert-butyl)-1,2,4-oxadiazol-3-yl)bicyclo[2.2.2]octan-1-yl)methyl)-3-fluoro-N-(4'-(methylsulfonamido)-[1,1'-biphenyl]-3-yl)bicyclo[1.1.1]pentane-1-carboxamide (438);

N-((4-(5-(tert-butyl)-1,2,4-oxadiazol-3-yl)bicyclo[2.2.2]octan-1-yl)methyl)-N-(4'-ethoxy-[1,1'-biphenyl]-3-yl)-3-fluorobicyclo[1.1.1]pentane-1-carboxamide (439);

N-((4-(5-(tert-butyl)-1,2,4-oxadiazol-3-yl)bicyclo[2.2.2]octan-1-yl)methyl)-N-(3-(6-ethoxypyridin-3-yl)phenyl)-3-fluorobicyclo[1.1.1]pentane-1-carboxamide (440);

N-((4-(5-(tert-butyl)-1,2,4-oxadiazol-3-yl)bicyclo[2.2.2]octan-1-yl)methyl)-3-fluoro-N-(3-(2-methylbenzo[d]thiazol-6-yl)phenyl)bicyclo[1.1.1]pentane-1-carboxamide (441);

N-((4-(5-(tert-butyl)-1,2,4-oxadiazol-3-yl)bicyclo[2.2.2]octan-1-yl)methyl)-N-(3-(2-cyclopropylpyrimidin-5-yl)phenyl)-3-fluorobicyclo[1.1.1]pentane-1-carboxamide (442);

N-((4-(5-(tert-butyl)-1,2,4-oxadiazol-3-yl)bicyclo[2.2.2]octan-1-yl)methyl)-3-fluoro-N-(3-(2-(trifluoromethyl)pyrimidin-5-yl)phenyl)bicyclo[1.1.1]pentane-1-carboxamide (443);

N-((4-(5-(tert-butyl)-1,2,4-oxadiazol-3-yl)bicyclo[2.2.2]octan-1-yl)methyl)-N-(4'-(difluoromethoxy)-[1,1'-biphenyl]-3-yl)-3-fluorobicyclo[1.1.1]pentane-1-carboxamide (444);

N-((4-(5-(tert-butyl)-1,2,4-oxadiazol-3-yl)bicyclo[2.2.2]octan-1-yl)methyl)-3-fluoro-N-(4'-(trifluoromethyl)-[1,1'-biphenyl]-3-yl)bicyclo[1.1.1]pentane-1-carboxamide (445);

N-((4-(5-(tert-butyl)-1,2,4-oxadiazol-3-yl)bicyclo[2.2.2]octan-1-yl)methyl)-3-fluoro-N-(4'-((trifluoromethyl)sulfonamido)-[1,1'-biphenyl]-3-yl)bicyclo[1.1.1]pentane-1-carboxamide (446);

N-((4-(5-(tert-butyl)-1,2,4-oxadiazol-3-yl)bicyclo[2.2.2]octan-1-yl)methyl)-3-fluoro-N-(3-(2-oxo-2,3-dihydrobenzo[d]oxazol-6-yl)phenyl)bicyclo[1.1.1]pentane-1-carboxamide (447);

N-((4-(5-(tert-butyl)-1,2,4-oxadiazol-3-yl)bicyclo[2.2.2]octan-1-yl)methyl)-3-fluoro-N-(4'-((1-methylethyl)sulfonamido)-[1,1'-biphenyl]-3-yl)bicyclo[1.1.1]pentane-1-carboxamide (448);

N-((4-(5-(tert-butyl)-1,2,4-oxadiazol-3-yl)bicyclo[2.2.2]octan-1-yl)methyl)-3-fluoro-N-(3-(2-methylthiazolo[4,5-b]pyridin-6-yl)phenyl)bicyclo[1.1.1]pentane-1-carboxamide (449);

N-((4-(5-(tert-butyl)-1,2,4-oxadiazol-3-yl)bicyclo[2.2.2]octan-1-yl)methyl)-3-fluoro-N-(3-(5-methoxypyrimidin-2-yl)phenyl)bicyclo[1.1.1]pentane-1-carboxamide (450);

N-((4-(5-(tert-butyl)-1,2,4-oxadiazol-3-yl)bicyclo[2.2.2]octan-1-yl)methyl)-N-(3-(5-ethoxypyrimidin-2-yl)phenyl)-3-fluorobicyclo[1.1.1]pentane-1-carboxamide (451);

N-((4-(5-(tert-butyl)-1,2,4-oxadiazol-3-yl)bicyclo[2.2.2]octan-1-yl)methyl)-N-(3-(5-(difluoromethoxy)pyrimidin-2-yl)phenyl)-3-fluorobicyclo[1.1.1]pentane-1-carboxamide (452);

N-((4-(5-(tert-butyl)-1,2,4-oxadiazol-3-yl)bicyclo[2.2.2]octan-1-yl)methyl)-N-(3-(5-ethylpyrimidin-2-yl)phenyl)-3-fluorobicyclo[1.1.1]pentane-1-carboxamide (453);

N-((4-(5-(tert-butyl)-1,2,4-oxadiazol-3-yl)bicyclo[2.2.2]octan-1-yl)methyl)-3-fluoro-N-(3-(5-methylpyrimidin-2-yl)phenyl)bicyclo[1.1.1]pentane-1-carboxamide (454);

N-((4-(5-(tert-butyl)-1,2,4-oxadiazol-3-yl)bicyclo[2.2.2]octan-1-yl)methyl)-N-(3-(5-(difluoromethoxy)pyridin-2-yl)phenyl)-3-fluorobicyclo[1.1.1]pentane-1-carboxamide (455);

N-((4-(5-(tert-butyl)-1,2,4-oxadiazol-3-yl)bicyclo[2.2.2]octan-1-yl)methyl)-N-(4'-ethyl-[1,1'-biphenyl]-3-yl)-3-fluorobicyclo[1.1.1]pentane-1-carboxamide (456);

N-((4-(5-(tert-butyl)-1,2,4-oxadiazol-3-yl)bicyclo[2.2.2]octan-1-yl)methyl)-N-(3-(2,2-difluorobenzo[d][1,3]dioxol-5-yl)phenyl)-3-fluorobicyclo[1.1.1]pentane-1-carboxamide (457);

N-((4-(5-(tert-butyl)-1,2,4-oxadiazol-3-yl)bicyclo[2.2.2]octan-1-yl)methyl)-N-(4'-ethyl-[1,1'-biphenyl]-3-yl)-3-fluorobicyclo[1.1.1]pentane-1-carboxamide (458);

N-((4-(5-(tert-butyl)-1,2,4-oxadiazol-3-yl)bicyclo[2.2.2]octan-1-yl)methyl)-N-(3-(2,2-difluorobenzo[d][1,3]dioxol-5-yl)phenyl)-3-fluorobicyclo[1.1.1]pentane-1-carboxamide (457);

N-((4-(5-(tert-butyl)-1,2,4-oxadiazol-3-yl)bicyclo[2.2.2]octan-1-yl)methyl)-N-(3-(2-cyclopropylthiazolo[4,5-b]pyridin-6-yl)phenyl)-3-fluorobicyclo[1.1.1]pentane-1-carboxamide (458);

N-((4-(5-(difluoromethyl)-1,2,4-oxadiazol-3-yl)bicyclo[2.2.2]octan-1-yl)methyl)-N-(3-(2-ethoxypyrimidin-5-yl)phenyl)-3-fluorobicyclo[1.1.1]pentane-1-carboxamide (459);

N-((4-(5-(difluoromethyl)-1,2,4-oxadiazol-3-yl)bicyclo[2.2.2]octan-1-yl)methyl)-3-fluoro-N-(4'-(methylsulfonamido)-[1,1'-biphenyl]-3-yl)bicyclo[1.1.1]pentane-1-carboxamide (460);

N-((4-(5-(difluoromethyl)-1,2,4-oxadiazol-3-yl)bicyclo[2.2.2]octan-1-yl)methyl)-N-(4'-ethoxy-[1,1'-biphenyl]-3-yl)-3-fluorobicyclo[1.1.1]pentane-1-carboxamide (460);

N-((4-(5-(difluoromethyl)-1,2,4-oxadiazol-3-yl)bicyclo[2.2.2]octan-1-yl)methyl)-3-fluoro-N-(3-(2-methylbenzo[d]thiazol-6-yl)phenyl)bicyclo[1.1.1]pentane-1-carboxamide (462);

N-(3-(2-cyclopropylpyrimidin-5-yl)phenyl)-N-((4-(5-(difluoromethyl)-1,2,4-oxadiazol-3-yl)bicyclo[2.2.2]octan-1-yl)methyl)-3-fluorobicyclo[1.1.1]pentane-1-carboxamide (463);

N-((4-(5-(difluoromethyl)-1,2,4-oxadiazol-3-yl)bicyclo[2.2.2]octan-1-yl)methyl)-3-fluoro-N-(3-(2-(trifluoromethyl)pyrimidin-5-yl)phenyl)bicyclo[1.1.1]pentane-1-carboxamide (464);

N-(4'-(difluoromethoxy)-[1,1'-biphenyl]-3-yl)-N-((4-(5-(difluoromethyl)-1,2,4-oxadiazol-3-yl)bicyclo[2.2.2]octan-1-yl)methyl)-3-fluorobicyclo[1.1.1]pentane-1-carboxamide (465);

N-(3-(2-cyclopropylpyrimidin-5-yl)phenyl)-N-((4-(3-(difluoromethyl)-1,2,4-oxadiazol-5-yl)bicyclo[2.2.2]octan-1-yl)methyl)-3-fluorobicyclo[1.1.1]pentane-1-carboxamide (466);

N-((4-(3-(difluoromethyl)-1,2,4-oxadiazol-5-yl)bicyclo[2.2.2]octan-1-yl)methyl)-3-fluoro-N-(3-(2-(trifluoromethyl)pyrimidin-5-yl)phenyl)bicyclo[1.1.1]pentane-1-carboxamide (467);

N-(4'-(difluoromethoxy)-[1,1'-biphenyl]-3-yl)-N-((4-(3-(difluoromethyl)-1,2,4-oxadiazol-5-yl)bicyclo[2.2.2]octan-1-yl)methyl)-3-fluorobicyclo[1.1.1]pentane-1-carboxamide (468);

N-((4-(3-(difluoromethyl)-1,2,4-oxadiazol-5-yl)bicyclo[2.2.2]octan-1-yl)methyl)-3-fluoro-N-(4'-(methylsulfonamido)-[1,1'-biphenyl]-3-yl)bicyclo[1.1.1]pentane-1-carboxamide (469);

N-((4-(3-(difluoromethyl)-1,2,4-oxadiazol-5-yl)bicyclo[2.2.2]octan-1-yl)methyl)-N-(3-(2-ethoxypyrimidin-5-yl)phenyl)-3-fluorobicyclo[1.1.1]pentane-1-carboxamide (470);

N-((4-(3-(difluoromethyl)-1,2,4-oxadiazol-5-yl)bicyclo[2.2.2]octan-1-yl)methyl)-3-fluoro-N-(3-(2-methylbenzo[d]thiazol-6-yl)phenyl)bicyclo[1.1.1]pentane-1-carboxamide (471);

N-((4-(3-(tert-butyl)-1,2,4-oxadiazol-5-yl)bicyclo[2.2.2]octan-1-yl)methyl)-N-(5-(2-ethoxypyrimidin-5-yl)pyridin-3-yl)-3-fluorobicyclo[1.1.1]pentane-1-carboxamide (472);

N-((4-(3-(tert-butyl)-1,2,4-oxadiazol-5-yl)bicyclo[2.2.2]octan-1-yl)methyl)-N-(5-(2-cyclopropylpyrimidin-5-yl)pyridin-3-yl)-3-fluorobicyclo[1.1.1]pentane-1-carboxamide (473);

N-((4-(3-(tert-butyl)-1,2,4-oxadiazol-5-yl)bicyclo[2.2.2]octan-1-yl)methyl)-3-fluoro-N-(5-(2-methylbenzo[d]thiazol-6-yl)pyridin-3-yl)bicyclo[1.1.1]pentane-1-carboxamide (474);

N-((4-(3-(tert-butyl)-1,2,4-oxadiazol-5-yl)bicyclo[2.2.2]octan-1-yl)methyl)-3-fluoro-N-(5-(4-(methylsulfonamido)phenyl)pyridin-3-yl)bicyclo[1.1.1]pentane-1-carboxamide (475);

N-((4-(3-(tert-butyl)-1,2,4-oxadiazol-5-yl)bicyclo[2.2.2]octan-1-yl)methyl)-N-(5-(4-ethoxyphenyl)pyridin-3-yl)-3-fluorobicyclo[1.1.1]pentane-1-carboxamide (476);

N-((4-(3-(tert-butyl)-1,2,4-oxadiazol-5-yl)bicyclo[2.2.2]octan-1-yl)methyl)-N-(6'-ethoxy-[3,3'-bipyridin]-5-yl)-3-fluorobicyclo[1.1.1]pentane-1-carboxamide (477);

N-((4-(5-(tert-butyl)-1,2,4-oxadiazol-3-yl)bicyclo[2.2.2]octan-1-yl)methyl)-N-(5-(2-ethoxypyrimidin-5-yl)pyridin-3-yl)-3-fluorobicyclo[1.1.1]pentane-1-carboxamide (478);

N-((4-(5-(tert-butyl)-1,2,4-oxadiazol-3-yl)bicyclo[2.2.2]octan-1-yl)methyl)-3-fluoro-N-(5-(2-oxo-2,3-dihydrobenzo[d]oxazol-6-yl)pyridin-3-yl)bicyclo[1.1.1]pentane-1-carboxamide (479);

N-((4-(5-(tert-butyl)-1,2,4-oxadiazol-3-yl)bicyclo[2.2.2]octan-1-yl)methyl)-N-(5-(2-cyclopropylthiazolo[4,5-b]pyridin-6-yl)pyridin-3-yl)-3-fluorobicyclo[1.1.1]pentane-1-carboxamide (480);

N-((4-(5-(tert-butyl)-1,2,4-oxadiazol-3-yl)bicyclo[2.2.2]octan-1-yl)methyl)-3-fluoro-N-(5-(4-(methylsulfonamido)phenyl)pyridin-3-yl)bicyclo[1.1.1]pentane-1-carboxamide (481);

N-((4-(5-(tert-butyl)-1,2,4-oxadiazol-3-yl)bicyclo[2.2.2]octan-1-yl)methyl)-N-(5-(4-ethoxyphenyl)pyridin-3-yl)-3-fluorobicyclo[1.1.1]pentane-1-carboxamide (482);

N-((4-(5-(tert-butyl)-1,2,4-oxadiazol-3-yl)bicyclo[2.2.2]octan-1-yl)methyl)-N-(5-(4-(difluoromethoxy)phenyl)pyridin-3-yl)-3-fluorobicyclo[1.1.1]pentane-1-carboxamide (483);

N-((4-(5-(tert-butyl)-1,2,4-oxadiazol-3-yl)bicyclo[2.2.2]octan-1-yl)methyl)-3-fluoro-N-(5-(2-methylbenzo[d]thiazol-6-yl)pyridin-3-yl)bicyclo[1.1.1]pentane-1-carboxamide (484);

N-((4-(5-(tert-butyl)-1,2,4-oxadiazol-3-yl)bicyclo[2.2.2]octan-1-yl)methyl)-N-(5-(5-(difluoromethoxy)pyrimidin-2-yl)pyridin-3-yl)-3-fluorobicyclo[1.1.1]pentane-1-carboxamide (485);

N-((4-(5-(tert-butyl)-1,2,4-oxadiazol-3-yl)bicyclo[2.2.2]octan-1-yl)methyl)-N-(5-(difluoromethoxy)-[2,3'-bipyridin]-5'-yl)-3-fluorobicyclo[1.1.1]pentane-1-carboxamide (486);

N-(3-(2-ethoxypyrimidin-5-yl)phenyl)-3-fluoro-N-((4-(5-(trifluoromethyl)pyridin-2-yl)bicyclo[2.2.2]octan-1-yl)methyl)bicyclo[1.1.1]pentane-1-carboxamide (487);

3-fluoro-N-(4'-(methylsulfonamido)-[1,1'-biphenyl]-3-yl)-N-((4-(5-(trifluoromethyl)pyridin-2-yl)bicyclo[2.2.2]octan-1-yl)methyl)bicyclo[1.1.1]pentane-1-carboxamide (488);

N-(4'-ethoxy-[1,1'-biphenyl]-3-yl)-3-fluoro-N-((4-(5-(trifluoromethyl)pyridin-2-yl) bicyclo[2.2.2]octan-1-yl)methyl)bicyclo[1.1.1]pentane-1-carboxamide (489);

N-(3-(2-cyclopropylpyrimidin-5-yl)phenyl)-3-fluoro-N-((4-(5-(trifluoromethyl)pyridin-2-yl)bicyclo[2.2.2]octan-1-yl)methyl)bicyclo[1.1.1]pentane-1-carboxamide (490);

3-fluoro-N-((4-(5-(trifluoromethyl)pyridin-2-yl)bicyclo[2.2.2]octan-1-yl)methyl)-N-(3-(2-(trifluoromethyl)pyrimidin-5-yl)phenyl)bicyclo[1.1.1]pentane-1-carboxamide (491);

N-(3-(6-ethoxypyridin-3-yl)phenyl)-3-fluoro-N-((4-(5-(trifluoromethyl)pyridin-2-yl) bicyclo[2.2.2]octan-1-yl)methyl)bicyclo[1.1.1]pentane-1-carboxamide (492);

N-(4'-(difluoromethoxy)-[1,1'-biphenyl]-3-yl)-3-fluoro-N-((4-(5-(trifluoromethyl) pyridin-2-yl)bicyclo[2.2.2]octan-1-yl)methyl)bicyclo[1.1.1]pentane-1-carboxamide (493);

3-fluoro-N-(3-(2-methoxypyrimidin-5-yl)phenyl)-N-((4-(5-(trifluoromethyl)pyridin-2-yl)bicyclo[2.2.2]octan-1-yl)methyl)bicyclo[1.1.1]pentane-1-carboxamide (494);

N-(3-(5-(difluoromethoxy)pyridin-2-yl)phenyl)-3-fluoro-N-((4-(5-(trifluoromethyl) pyridin-2-yl)bicyclo[2.2.2]octan-1-yl)methyl)bicyclo[1.1.1]pentane-1-carboxamide (495);

N-(3-(5-ethylpyrimidin-2-yl)phenyl)-3-fluoro-N-((4-(5-(trifluoromethyl)pyridin-2-yl) bicyclo[2.2.2]octan-1-yl)methyl)bicyclo[1.1.1]pentane-1-carboxamide (496);

N-(4'-ethyl-[1,1'-biphenyl]-3-yl)-3-fluoro-N-((4-(5-(trifluoromethyl)pyridin-2-yl) bicyclo[2.2.2]octan-1-yl)methyl)bicyclo[1.1.1]pentane-1-carboxamide (497);

N-(3-(5-ethoxypyrimidin-2-yl)phenyl)-3-fluoro-N-((4-(5-(trifluoromethyl)pyridin-2-yl)bicyclo[2.2.2]octan-1-yl)methyl)bicyclo[1.1.1]pentane-1-carboxamide (498);

N-(3-(5-(difluoromethoxy)pyrimidin-2-yl)phenyl)-3-fluoro-N-((4-(5-(trifluoromethyl) pyridin-2-yl)bicyclo[2.2.2]octan-1-yl)methyl)bicyclo[1.1.1]pentane-1-carboxamide (499);

3-fluoro-N-(3-(5-methoxypyrimidin-2-yl)phenyl)-N-((4-(5-(trifluoromethyl)pyridin-2-yl)bicyclo[2.2.2]octan-1-yl)methyl)bicyclo[1.1.1]pentane-1-carboxamide (500);

N-((4-(3-(tert-butyl)-1,2,4-oxadiazol-5-yl)bicyclo[2.2.2]octan-1-yl)methyl)-N-(3-(2-ethoxypyrimidin-5-yl)phenyl)-3-hydroxycyclobutane-1-carboxamide (501);

(1S,3S)—N-((4-(3-(tert-butyl)-1,2,4-oxadiazol-5-yl)bicyclo[2.2.2]octan-1-yl)methyl)-N-(3-(2-ethoxypyrimidin-5-yl)phenyl)-3-methoxycyclobutane-1-carboxamide (502);

N-((4-(3-(tert-butyl)-1,2,4-oxadiazol-5-yl)bicyclo[2.2.2]octan-1-yl)methyl)-N-(3-(2-ethoxypyrimidin-5-yl)phenyl)-3-methyloxetane-3-carboxamide (503);

(1S,3S)—N-((4-(3-(tert-butyl)-1,2,4-oxadiazol-5-yl)bicyclo[2.2.2]octan-1-yl)methyl)-N-(3-(2-ethoxypyrimidin-5-yl)phenyl)-3-hydroxy-3-methylcyclobutane-1-carboxamide (504);

tert-butyl (3-(((4-(3-(tert-butyl)-1,2,4-oxadiazol-5-yl)bicyclo[2.2.2]octan-1-yl)methyl) (3-(2-ethoxypyrimidin-5-yl)phenyl)carbamoyl)bicyclo[1.1.1]pentan-1-yl)carbamate (505);

3-amino-N-((4-(3-(tert-butyl)-1,2,4-oxadiazol-5-yl)bicyclo[2.2.2]octan-1-yl)methyl)-N-(3-(2-ethoxypyrimidin-5-yl)phenyl)bicyclo[1.1.1]pentane-1-carboxamide (506);

(1S,3S)—N-((4-(3-(tert-butyl)-1,2,4-oxadiazol-5-yl)bicyclo[2.2.2]octan-1-yl)methyl)-N-(3-(2-ethoxypyrimidin-5-yl)phenyl)-3-hydroxy-3-(trifluoromethyl)cyclobutane-1-carboxamide (507);

(cis)-N-((4-(5-(tert-butyl)-1,2,4-oxadiazol-3-yl)bicyclo[2.2.2]octan-1-yl)methyl)-N-(3-(2-ethoxypyrimidin-5-yl)phenyl)-3-hydroxy-3-methylcyclobutane-1-carboxamide (508);

(1S,3S)—N-((4-(5-(tert-butyl)-1,2,4-oxadiazol-3-yl)bicyclo[2.2.2]octan-1-yl)methyl)-N-(3-(2-ethoxypyrimidin-5-yl)phenyl)-3-hydroxy-3-(trifluoromethyl)cyclobutane-1-carboxamide (509);

N-((4-(5-(tert-butyl)-1,2,4-oxadiazol-3-yl)bicyclo[2.2.2]octan-1-yl)methyl)-N-(3-(2-ethoxypyrimidin-5-yl)phenyl)-3-methyloxetane-3-carboxamide (510);

(1S,3S)—N-((4-(5-(tert-butyl)-1,2,4-oxadiazol-3-yl)bicyclo[2.2.2]octan-1-yl)methyl)-N-(3-(2-ethoxypyrimidin-5-yl)phenyl)-3-methoxycyclobutane-1-carboxamide (511);

(cis)-N-((4-(5-(tert-butyl)-1,2,4-oxadiazol-3-yl)bicyclo[2.2.2]octan-1-yl)methyl)-3-hydroxy-3-methyl-N-(4'-(methylsulfonamido)-[1,1'-biphenyl]-3-yl)cyclobutane-1-carboxamide (512);

(1S,3S)—N-((4-(5-(tert-butyl)-1,2,4-oxadiazol-3-yl)bicyclo[2.2.2]octan-1-yl)methyl)-3-hydroxy-N-(4'-(methylsulfonamido)-[1,1'-biphenyl]-3-yl)-3-(trifluoromethyl)cyclobutane-1-carboxamide (513);

(1S,3S)—N-((4-(5-(tert-butyl)-1,2,4-oxadiazol-3-yl)bicyclo[2.2.2]octan-1-yl)methyl)-3-methoxy-N-(4'-(methylsulfonamido)-[1,1'-biphenyl]-3-yl)cyclobutane-1-carboxamide (514);

N-((4-(5-(tert-butyl)-1,2,4-oxadiazol-3-yl)bicyclo[2.2.2]octan-1-yl)methyl)-N-(4'-(difluoromethoxy)-[1,1'-biphenyl]-3-yl)-3-methyl oxetane-3-carboxamide (515);

(1S,3S)—N-((4-(5-(tert-butyl)-1,2,4-oxadiazol-3-yl)bicyclo[2.2.2]octan-1-yl)methyl)-N-(4'-(difluoromethoxy)-[1,1'-biphenyl]-3-yl)-3-hydroxy-3-(trifluoromethyl)cyclobutane-1-carboxamide (516);

(1S,3S)—N-((4-(5-(tert-butyl)-1,2,4-oxadiazol-3-yl)bicyclo[2.2.2]octan-1-yl)methyl)-N-(4'-(difluoromethoxy)-[1,1'-biphenyl]-3-yl)-3-hydroxy-3-methylcyclobutane-1-carboxamide (517);

(cis)-N-(3-(2-ethoxypyrimidin-5-yl)phenyl)-3-methoxy-N-((4-(5-(3-methyloxetan-3-yl)-1,2,4-oxadiazol-3-yl)bicyclo[2.2.2]octan-1-yl)methyl)cyclobutane-1-carboxamide (518);

(1S,3S)—N-(3-(2-ethoxypyrimidin-5-yl)phenyl)-3-hydroxy-3-methyl-N-((4-(5-(3-methyloxetan-3-yl)-1,2,4-oxadiazol-3-yl)bicyclo[2.2.2]octan-1-yl)methyl)cyclobutane-1-carboxamide (519);

(1S,3S)—N-(3-(2-ethoxypyrimidin-5-yl)phenyl)-3-hydroxy-N-((4-(5-(3-methyloxetan-3-yl)-1,2,4-oxadiazol-3-yl)bicyclo[2.2.2]octan-1-yl)methyl)-3-(trifluoromethyl)cyclobutane-1-carboxamide (520);

N-(4'-ethoxy-[1,1'-biphenyl]-3-yl)-3-fluoro-N-((4-(5-(1-(trifluoromethyl)cyclopropyl)-1,2,4-oxadiazol-3-yl)bicyclo[2.2.2]octan-1-yl)methyl)bicyclo[1.1.1]pentane-1-carboxamide (521);

N-(4'-(difluoromethoxy)-[1,1'-biphenyl]-3-yl)-3-fluoro-N-((4-(5-(1-(trifluoromethyl) cyclopropyl)-1,2,4-oxadiazol-3-yl)bicyclo[2.2.2]octan-1-yl)methyl)bicyclo[1.1.1]pentane-1-carboxamide (522);

3-fluoro-N-(4'-(methylsulfonamido)-[1,1'-biphenyl]-3-yl)-N-((4-(5-(1-(trifluoromethyl) cyclopropyl)-1,2,4-oxadiazol-3-yl)bicyclo[2.2.2]octan-1-yl)methyl)bicyclo[1.1.1]pentane-1-carboxamide (523);

3-fluoro-N-(3-(2-methylbenzo[d]thiazol-6-yl)phenyl)-N-((4-(5-(1-(trifluoromethyl) cyclopropyl)-1,2,4-oxadiazol-3-yl)bicyclo[2.2.2]octan-1-yl)methyl)bicyclo[1.1.1]pentane-1-carboxamide (524);

N-(3-(2-ethoxypyrimidin-5-yl)phenyl)-3-fluoro-N-((4-(5-(1-(trifluoromethyl) cyclopropyl)-1,2,4-oxadiazol-3-yl)bicyclo[2.2.2]octan-1-yl)methyl)bicyclo[1.1.1]pentane-1-carboxamide (525);

N-(3-(2-cyclopropylthiazolo[4,5-b]pyridin-6-yl)phenyl)-3-fluoro-N-((4-(5-(1-(trifluoromethyl)cyclopropyl)-1,2,4-oxadiazol-3-yl)bicyclo[2.2.2]octan-1-yl)methyl) bicyclo[1.1.1]pentane-1-carboxamide (526);

N-((4-(5-(1,1-difluoroethyl)-1,2,4-oxadiazol-3-yl)bicyclo[2.2.2]octan-1-yl)methyl)-N-(4'-ethoxy-[1,1'-biphenyl]-3-yl)-3-fluorobicyclo[1.1.1]pentane-1-carboxamide (527);

N-((4-(5-(1,1-difluoroethyl)-1,2,4-oxadiazol-3-yl)bicyclo[2.2.2]octan-1-yl)methyl)-N-(4'-(difluoromethoxy)-[1,1'-biphenyl]-3-yl)-3-fluorobicyclo[1.1.1]pentane-1-carboxamide (528);

N-((4-(5-(1,1-difluoroethyl)-1,2,4-oxadiazol-3-yl)bicyclo[2.2.2]octan-1-yl)methyl)-N-(3-(2-ethoxypyrimidin-5-yl)phenyl)-3-fluorobicyclo[1.1.1]pentane-1-carboxamide (529);

N-(3-(2-cyclopropylthiazolo[4,5-b]pyridin-6-yl)phenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide (530);

N-((4-(5-(tert-butyl)-1,2,4-oxadiazol-3-yl)bicyclo[2.2.2]octan-1-yl)methyl)-N-(4-(2-ethoxypyrimidin-5-yl)pyridin-2-yl)-3-fluorobicyclo[1.1.1]pentane-1-carboxamide (531);

N-((4-(5-(tert-butyl)-1,2,4-oxadiazol-3-yl)bicyclo[2.2.2]octan-1-yl)methyl)-N-(4-(4-ethoxyphenyl)pyridin-2-yl)-3-fluorobicyclo[1.1.1]pentane-1-carboxamide (532);

N-((4-(5-(tert-butyl)-1,2,4-oxadiazol-3-yl)bicyclo[2.2.2]octan-1-yl)methyl)-N-(4-(4-(difluoromethoxy)phenyl)pyridin-2-yl)-3-fluorobicyclo[1.1.1]pentane-1-carboxamide (533);

N-((4-(5-(tert-butyl)-1,2,4-oxadiazol-3-yl)bicyclo[2.2.2]octan-1-yl)methyl)-3-fluoro-N-(4-(4-(methylsulfonamido)phenyl)pyridin-2-yl)bicyclo[1.1.1]pentane-1-carboxamide (534);

N-((4-(5-(tert-butyl)-1,2,4-oxadiazol-3-yl)bicyclo[2.2.2]octan-1-yl)methyl)-N-(4-(2-cyclopropylthiazolo[4,5-b]pyridin-6-yl)pyridin-2-yl)-3-fluorobicyclo[1.1.1]pentane-1-carboxamide (535);

N-((4-(5-(tert-butyl)-1,2,4-oxadiazol-3-yl)bicyclo[2.2.2]octan-1-yl)methyl)-N-(6-ethoxy-[3,4'-bipyridin]-2'-yl)-3-fluorobicyclo[1.1.1]pentane-1-carboxamide (536);

N-((4-(5-(tert-butyl)-1,2,4-oxadiazol-3-yl)bicyclo[2.2.2]octan-1-yl)methyl)-3-fluoro-N-(4-(2-methylbenzo[d]thiazol-6-yl)pyridin-2-yl)bicyclo[1.1.1]pentane-1-carboxamide (537);

N-((4-(5-(tert-butyl)-1,2,4-oxadiazol-3-yl)bicyclo[2.2.2]octan-1-yl)methyl)-3-fluoro-N-(4-(2-methoxypyrimidin-5-yl)pyridin-2-yl)bicyclo[1.1.1]pentane-1-carboxamide (538);

N-((4-(5-(tert-butyl)-1,2,4-oxadiazol-3-yl)bicyclo[2.2.2]octan-1-yl)methyl)-N-(4-(2-cyclopropylpyrimidin-5-yl)pyridin-2-yl)-3-fluorobicyclo[1.1.1]pentane-1-carboxamide (539);

N-((4-(5-(tert-butyl)-1,2,4-oxadiazol-3-yl)bicyclo[2.2.2]octan-1-yl)methyl)-3-fluoro-N-(4-(2-oxo-2,3-dihydrobenzo[d]oxazol-6-yl)pyridin-2-yl)bicyclo[1.1.1]pentane-1-carboxamide (540);

N-((4-(5-(tert-butyl)-1,2,4-oxadiazol-3-yl)bicyclo[2.2.2]octan-1-yl)methyl)-N-(4-(5-(difluoromethoxy)pyrimidin-2-yl)pyridin-2-yl)-3-fluorobicyclo[1.1.1]pentane-1-carboxamide (541);

N-((4-(5-(tert-butyl)-1,2,4-oxadiazol-3-yl)bicyclo[2.2.2]octan-1-yl)methyl)-N-(4-(5-ethoxypyrimidin-2-yl)pyridin-2-yl)-3-fluorobicyclo[1.1.1]pentane-1-carboxamide (542);

N-((4-(5-(tert-butyl)-1,2,4-oxadiazol-3-yl)bicyclo[2.2.2]octan-1-yl)methyl)-N-(4-(5-ethylpyrimidin-2-yl)pyridin-2-yl)-3-fluorobicyclo[1.1.1]pentane-1-carboxamide (543);

N-((4-(5-(tert-butyl)-1,2,4-oxadiazol-3-yl)bicyclo[2.2.2]octan-1-yl)methyl)-N-(5-(difluoromethoxy)-[2,4'-bipyridin]-2'-yl)-3-fluorobicyclo[1.1.1]pentane-1-carboxamide (544);

N-((4-(3-cyclopropyl-1-methyl-1H-pyrazol-5-yl)bicyclo[2.2.2]octan-1-yl)methyl)-N-(4-(4-(difluoromethoxy)phenyl)pyridin-2-yl)-3-fluorobicyclo[1.1.1]pentane-1-carboxamide (545);

N-((4-(3-cyclopropyl-1-methyl-1H-pyrazol-5-yl)bicyclo[2.2.2]octan-1-yl)methyl)-3-fluoro-N-(4-(2-methylbenzo[d]thiazol-6-yl)pyridin-2-yl)bicyclo[1.1.1]pentane-1-carboxamide (546);

N-((4-(3-cyclopropyl-1-methyl-1H-pyrazol-5-yl)bicyclo[2.2.2]octan-1-yl)methyl)-3-fluoro-N-(4-(4-(methylsulfonamido)phenyl)pyridin-2-yl)bicyclo[1.1.1]pentane-1-carboxamide (547);

N-((4-(3-cyclopropyl-1,2,4-oxadiazol-5-yl)bicyclo[2.2.2]octan-1-yl)methyl)-N-(4-(2-ethoxypyrimidin-5-yl)pyridin-2-yl)-3-fluorobicyclo[1.1.1]pentane-1-carboxamide (548);

N-((4-(3-cyclopropyl-1,2,4-oxadiazol-5-yl)bicyclo[2.2.2]octan-1-yl)methyl)-3-fluoro-N-(4-(2-methylbenzo[d]thiazol-6-yl)pyridin-2-yl)bicyclo[1.1.1]pentane-1-carboxamide (549);

N-((4-(3-cyclopropyl-1,2,4-oxadiazol-5-yl)bicyclo[2.2.2]octan-1-yl)methyl)-3-fluoro-N-(4-(2-methylbenzo[d]oxazol-6-yl)pyridin-2-yl)bicyclo[1.1.1]pentane-1-carboxamide (550);

N-((4-(3-(tert-butyl)-1,2,4-oxadiazol-5-yl)bicyclo[2.2.2]octan-1-yl)methyl)-3-fluoro-N-(4-(2-methylbenzo[d]thiazol-6-yl)pyridin-2-yl)bicyclo[1.1.1]pentane-1-carboxamide (551);

N-(3-(2-ethoxypyrimidin-5-yl)phenyl)-3-fluoro-N-((4-(5-methoxypyrimidin-2-yl)bicyclo[2.2.2]octan-1-yl)methyl)bicyclo[1.1.1]pentane-1-carboxamide (552);

N-((4-(3-(tert-butyl)-1,2,4-oxadiazol-5-yl)-2-oxabicyclo[2.2.2]octan-1-yl)methyl)-N-(3-(2-ethoxypyrimidin-5-yl)phenyl)-3-fluorobicyclo[1.1.1]pentane-1-carboxamide (553);

N-((4-(3-cyclopropyl-1,2,4-oxadiazol-5-yl)bicyclo[2.2.2]octan-1-yl)methyl)-3,3-difluoro-N-(3-(2-methylbenzo[d]thiazol-6-yl)phenyl)cyclobutane-1-carboxamide (554);

N-((4-(3-cyclopropyl-1,2,4-oxadiazol-5-yl)bicyclo[2.2.2]octan-1-yl)methyl)-3-fluoro-N-(3-(2-methylbenzo[d]thiazol-6-yl)phenyl)bicyclo[1.1.1]pentane-1-carboxamide (555);

3-fluoro-N-((1-(4-methoxyphenyl)-2-oxabicyclo[2.2.2]octan-4-yl)methyl)-N-(3-(2-methylbenzo[d]thiazol-6-yl)phenyl)bicyclo[1.1.1]pentane-1-carboxamide (556);

3,3-difluoro-N-((1-(4-methoxyphenyl)-2-oxabicyclo[2.2.2]octan-4-yl)methyl)-N-(3-(2-methylbenzo[d]thiazol-6-yl)phenyl)cyclobutane-1-carboxamide (557);

3-fluoro-N-((1-(2-methoxypyrimidin-5-yl)-2-oxabicyclo[2.2.2]octan-4-yl)methyl)-N-(3-(2-methylbenzo[d]thiazol-6-yl)phenyl)bicyclo[1.1.1]pentane-1-carboxamide (558);

N-((4-(3-cyclopropyl-1,2,4-oxadiazol-5-yl)bicyclo[2.2.2]octan-1-yl)methyl)-3-fluoro-N-(3-(5-fluorobenzo[d]oxazol-2-yl)phenyl)bicyclo[1.1.1]pentane-1-carboxamide (559);

N-((4-(3-cyclopropyl-1,2,4-oxadiazol-5-yl)bicyclo[2.2.2]octan-1-yl)methyl)-3,3-difluoro-N-(3-(5-fluorobenzo[d]oxazol-2-yl)phenyl)cyclobutane-1-carboxamide (560);

N-((4-(5-cyclopropyl-1,3,4-oxadiazol-2-yl)bicyclo[2.2.2]octan-1-yl)methyl)-3-fluoro-N-(3-(2-methylbenzo[d]thiazol-6-yl)phenyl)bicyclo[1.1.1]pentane-1-carboxamide (561);

N-((4-(5-cyclopropyl-1,3,4-oxadiazol-2-yl)bicyclo[2.2.2]octan-1-yl)methyl)-3-(difluoromethyl)-N-(3-(2-methylbenzo[d]thiazol-6-yl)phenyl)cyclobutane-1-carboxamide (562);

N-((4-(5-cyclopropyl-1,3,4-oxadiazol-2-yl)bicyclo[2.2.2]octan-1-yl)methyl)-3,3-difluoro-N-(3-(2-methylbenzo[d]thiazol-6-yl)phenyl)cyclopentane-1-carboxamide (563);

N-((1-(3-cyclopropyl-1,2,4-oxadiazol-5-yl)-2-oxabicyclo[2.2.2]octan-4-yl)methyl)-3-fluoro-N-(3-(2-methylbenzo[d]thiazol-6-yl)phenyl)bicyclo[1.1.1]pentane-1-carboxamide (564);

N-((1-(3-cyclopropyl-1,2,4-oxadiazol-5-yl)-2-oxabicyclo[2.2.2]octan-4-yl)methyl)-3,3-difluoro-N-(3-(2-methylbenzo[d]thiazol-6-yl)phenyl)cyclobutane-1-carboxamide (565);

N-((1-(3-cyclopropyl-1,2,4-oxadiazol-5-yl)-2-oxabicyclo[2.2.2]octan-4-yl)methyl)-3-(difluoromethyl)-N-(3-(2-methylbenzo[d]thiazol-6-yl)phenyl)cyclobutane-1-carboxamide (566);

N-((1-(3-cyclopropyl-1,2,4-oxadiazol-5-yl)-2-oxabicyclo[2.2.2]octan-4-yl)methyl)-3,3-difluoro-N-(3-(2-methylbenzo[d]thiazol-6-yl)phenyl)cyclopentane-1-carboxamide (567);

N-((1-(4-cyanophenyl)-2-oxabicyclo[2.2.2]octan-4-yl)methyl)-3-fluoro-N-(3-(2-methylbenzo[d]thiazol-6-yl)phenyl)bicyclo[1.1.1]pentane-1-carboxamide (376);

N-((1-(4-(dimethylcarbamoyl)phenyl)-2-oxabicyclo[2.2.2]octan-4-yl)methyl)-3-fluoro-N-(3-(2-methylbenzo[d]thiazol-6-yl)phenyl)bicyclo[1.1.1]pentane-1-carboxamide (377);

N-cyclopropyl-4-((3-fluoro-N-(3-(2-methoxypyridin-4-yl)phenyl)bicyclo[1.1.1]pentane-1-carboxamido)methyl)bicyclo[2.2.2]octane-1-carboxamide (570);

N-(3-cyclopropylphenyl)-N-((4-(5-(1,1-difluoroethyl)-1,2,4-oxadiazol-3-yl) bicyclo[2.2.2]octan-1-yl)methyl)-3-fluorobicyclo[1.1.1]pentane-1-carboxamide (571);

N-(3-cyclopropylphenyl)-3-fluoro-N-((4-(5-(trifluoromethyl)-1,2,4-oxadiazol-3-yl) bicyclo[2.2.2]octan-1-yl)methyl)bicyclo[1.1.1]pentane-1-carboxamide (572):

N-(3-cyclopropylphenyl)-3-fluoro-N-((4-(5-(1-fluorocyclopropyl)-1,2,4-oxadiazol-3-yl)bicyclo[2.2.2]octan-1-yl)methyl)bicyclo[1.1.1]pentane-1-carboxamide (573);

N-(3-cyclopropyl-4-fluorophenyl)-N-((4-(5-(1,1-difluoroethyl)-1,2,4-oxadiazol-3-yl) bicyclo[2.2.2]octan-1-yl)methyl)-3-fluorobicyclo[1.1.1]pentane-1-carboxamide (574);

N-(3-(azetidin-1-yl)-4-fluorophenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide (575);

(cis)-N-((4-(5-(2-fluoropropan-2-yl)-1,2,4-oxadiazol-3-yl)bicyclo[2.2.2]octan-1-yl) methyl)-3-hydroxy-N-(4'-(2-hydroxypropan-2-yl)-[1,1'-biphenyl]-3-yl)-3-(trifluoromethyl)cyclobutane-1-carboxamide (576);

(cis)-N-((4-(5-(2-fluoropropan-2-yl)-1,2,4-oxadiazol-3-yl)bicyclo[2.2.2]octan-1-yl) methyl)-3-hydroxy-N-(4'-(2-hydroxypropan-2-yl)-[1,1'-biphenyl]-3-yl)-3-methylcyclobutane-1-carboxamide (577);

(cis)-N-(4'-(1-cyanocyclopropyl)-3'-fluoro-[1,1'-biphenyl]-3-yl)-N-((4-(5-(1-fluorocyclopropyl)-1,2,4-oxadiazol-3-yl)bicyclo[2.2.2]octan-1-yl)methyl)-3-hydroxy-3-(trifluoromethyl)cyclobutane-1-carboxamide (578);

N-(3-(2-cyclopropylpyrimidin-5-yl)phenyl)-3-fluoro-N-((4-(5-(1-fluorocyclopropyl)-1,2,4-oxadiazol-3-yl)bicyclo[2.2.2]octan-1-yl)methyl)bicyclo[1.1.1]pentane-1-carboxamide (579);

N-(3-(2-cyclopropylpyrimidin-5-yl)phenyl)-3-fluoro-N-((4-(5-(trifluoromethyl)-1,2,4-oxadiazol-3-yl)bicyclo[2.2.2]octan-1-yl)methyl)bicyclo[1.1.1]pentane-1-carboxamide (580);

(cis)-N-(6-fluoro-4'-isopropoxy-[1,1'-biphenyl]-3-yl)-N-((4-(5-(1-fluorocyclopropyl)-1,2,4-oxadiazol-3-yl)bicyclo[2.2.2]octan-1-yl)methyl)-3-hydroxy-3-(trifluoromethyl) cyclobutane-1-carboxamide (581);

(cis)-N-(4'-((2-cyanopropan-2-yl)oxy)-6-fluoro-[1,1'-biphenyl]-3-yl)-N-((4-(5-(2-fluoropropan-2-yl)-1,2,4-oxadiazol-3-yl)bicyclo[2.2.2]octan-1-yl)methyl)-3-hydroxy-3-(trifluoromethyl)cyclobutane-1-carboxamide (582);

(cis)-N-(4'-((2-cyanopropan-2-yl)oxy)-[1,1'-biphenyl]-3-yl)-N-((4-(5-(1-fluorocyclopropyl)-1,2,4-oxadiazol-3-yl)bicyclo[2.2.2]octan-1-yl)methyl)-3-hydroxy-3-(trifluoromethyl)cyclobutane-1-carboxamide (583);

1,1,1-trifluoro-2-methylpropan-2-yl ((4-(5-(2-fluoropropan-2-yl)-1,2,4-oxadiazol-3-yl)bicyclo[2.2.2]octan-1-yl)methyl)(4'-isopropoxy-[1,1'-biphenyl]-3-yl)carbamate (584);

3-cyano-N-((4-(5-(1,1-difluoroethyl)-1,2,4-oxadiazol-3-yl)bicyclo[2.2.2]octan-1-yl) methyl)-N-(4'-(2-hydroxypropan-2-yl)-[1,1'-biphenyl]-3-yl)bicyclo[1.1.1]pentane-1-carboxamide (585);

3-(tert-butyl)-1-(6-fluoro-4'-isopropoxy-[1,1'-biphenyl]-3-yl)-1-((4-(5-(1-fluorocyclopropyl)-1,2,4-oxadiazol-3-yl)bicyclo[2.2.2]octan-1-yl)methyl)urea (586);

(cis)-N-((4-(5-(2-fluoropropan-2-yl)-1,2,4-oxadiazol-3-yl)bicyclo[2.2.2]octan-1-yl) methyl)-3-hydroxy-N-(4'-(2-hydroxypropan-2-yl)-2',3',4',5'-tetrahydro-[1,1'-biphenyl]-3-yl)-3-(trifluoromethyl)cyclobutane-1-carboxamide (587);

(cis)-N-(3-(3,6-dihydro-2H-pyran-4-yl)phenyl)-N-((4-(5-(2-fluoropropan-2-yl)-1,2,4-oxadiazol-3-yl)bicyclo[2.2.2]octan-1-yl)methyl)-3-hydroxy-3-(trifluoromethyl)cyclobutane-1-carboxamide (588);

N-((4-(5-(1,1-difluoroethyl)-1,2,4-oxadiazol-3-yl)bicyclo[2.2.2]octan-1-yl)methyl)-3-fluoro-N-(3-(4-hydroxypiperidin-1-yl)phenyl)bicyclo[1.1.1]pentane-1-carb oxamide (589);

(cis)-N-((4-(5-(2-fluoropropan-2-yl)-1,2,4-oxadiazol-3-yl)bicyclo[2.2.2]octan-1-yl) methyl)-3-hydroxy-N-(3-(6-(2-hydroxypropan-2-yl)spiro[3.3]hept-1-en-2-yl)phenyl)-3-(trifluoromethyl)cyclobutane-1-carboxamide (590);

1,1,1-trifluoro-2-methylpropan-2-yl (4'-(1-cyanocyclopropyl)-3'-fluoro-[1,1'-biphenyl]-3-yl)((4-(5-(2-fluoropropan-2-yl)-1,2,4-oxadiazol-3-yl)bicyclo[2.2.2]octan-1-yl) methyl) carbamate (591);

(cis)-N-(3-(2-oxa-6-azaspiro[3.3]heptan-6-yl)phenyl)-N-((4-(5-(2-fluoropropan-2-yl)-1,2,4-oxadiazol-3-yl)bicyclo[2.2.2]octan-1-yl)methyl)-3-hydroxy-3-(trifluoromethyl) cyclobutane-1-carboxamide (592);

(cis)-N-((4-(5-(2-fluoropropan-2-yl)-1,2,4-oxadiazol-3-yl)bicyclo[2.2.2]octan-1-yl) methyl)-3-hydroxy-N-(3-(6-(2-hydroxypropan-2-yl)pyridazin-3-yl)phenyl)-3-(trifluoromethyl)cyclobutane-1-carboxamide (593);

3-fluoro-N-((4-(5-(2-fluoropropan-2-yl)-1,2,4-oxadiazol-3-yl)bicyclo[2.2.2]octan-1-yl) methyl)-N-(3-(6-oxo-1,6-dihydropyridazin-4-yl)phenyl)bicyclo[1.1.1]pentane-1-carboxamide (594);

(cis)-N-((4-(5-(2-fluoropropan-2-yl)-1,2,4-oxadiazol-3-yl)bicyclo[2.2.2]octan-1-yl) methyl)-3-hydroxy-N-(6-(4-(2-hydroxypropan-2-yl)phenyl)pyridin-2-yl)-3-(trifluoromethyl)cyclobutane-1-carboxamide (595);

N-((4-(5-(tert-butyl)-1,2,4-oxadiazol-3-yl)bicyclo[2.2.2]octan-1-yl)methyl)-N-(2-(2-ethoxypyrimidin-5-yl)pyridin-4-yl)-3-fluorobicyclo[1.1.1]pentane-1-carboxamide (596);

N-((4-(5-(tert-butyl)-1,2,4-oxadiazol-3-yl)bicyclo[2.2.2]octan-1-yl)methyl)-N-(2-(2-cyclopropylpyrimidin-5-yl)pyridin-4-yl)-3-fluorobicyclo[1.1.1]pentane-1-carboxamide (597);

2-cyanopropan-2-yl((4-(5-(2-fluoropropan-2-yl)-1,2,4-oxadiazol-3-yl) bicyclo[2.2.2]octan-1-yl)methyl)(4'-(2-hydroxypropan-2-yl)-[1,1'-biphenyl]-3-yl) carbamate (598);

1-((4-(5-(2-fluoropropan-2-yl)-1,2,4-oxadiazol-3-yl)bicyclo[2.2.2]octan-1-yl)methyl)-3-((trans)-4-hydroxy-4-methylcyclohexyl)-1-(4'-(2-hydroxypropan-2-yl)-[1,1'-biphenyl]-3-yl) urea (599);

1-((4-(5-(2-fluoropropan-2-yl)-1,2,4-oxadiazol-3-yl)bicyclo[2.2.2]octan-1-yl) methyl)-3-(4-hydroxy-4-(trifluoromethyl) cyclohexyl)-1-(4'-(2-hydroxypropan-2-yl)-[1,1'-biphenyl]-3-yl)urea (600-601);

isopropyl (4-(((cis)-3-hydroxy-N-(4'-(2-hydroxypropan-2-yl)-[1,1'-biphenyl]-3-yl)-3-(trifluoromethyl)cyclobutane-1-carboxamido)methyl)bicyclo[2.2.2]octan-1-yl)carbamate (602);

(cis)-N-(4'-(difluoromethoxy)-[1,1'-biphenyl]-3-yl)-3-hydroxy-3-(trifluoromethyl)-N-((4-(((trifluoromethyl)sulfonamido)bicyclo[2.2.2]octan-1-yl)methyl)cyclobutane-1-carboxamide (603);

(cis)-3-hydroxy-N-(4'-isopropoxy-[1,1'-biphenyl]-3-yl)-N-((4-(3-isopropylureido) bicyclo[2.2.2]octan-1-yl)methyl)-3-(trifluoromethyl)cyclobutane-1-carboxamide (604);

1,1,1-trifluoro-2-methylpropan-2-yl((4-(5-(1,1-difluoroethyl) pyridin-2-1) bicyclo[2.2.2]octan-1-yl)methyl)(4-(4-(2-hydroxypropan-2-yl)phenyl)pyridin-2-yl)carbamate (605);

1,1,1-trifluoro-2-methylpropan-2-yl (4-(4-((2-cyanopropan-2-yl)oxy)phenyl)pyridin-2-yl)((4-(5-(1,1-difluoroethyl)pyridin-2-yl)bicyclo[2.2.2]octan-1-yl)methyl)carbamate (606);

1,1,1-trifluoro-2-methylpropan-2-yl ((4-(5-(1,1-difluoroethyl)pyridin-2-yl) bicyclo[2.2.2]octan-1-yl)methyl)(5-(2-hydroxypropan-2-yl)-[2,4'-bipyridin]-2'-yl)carbamate (607);

1,1,1-trifluoro-2-methylpropan-2-yl ((4-(5-(1,1-difluoroethyl)pyridin-2-yl) bicyclo[2.2.2]octan-1-yl)methyl)(4-(5-(2-hydroxypropan-2-yl)pyrimidin-2-yl)pyridin-2-yl) carbamate (608);

1,1,1-trifluoro-2-methylpropan-2-yl((4-(5-(1,1-difluoroethyl)-1,2,4-oxadiazol-3-yl) bicyclo[2.2.2]octan-1-yl)methyl)(4-(4-(2-hydroxypropan-2-yl)phenyl)pyridin-2-yl) carbamate (609);

1,1,1-trifluoro-2-methylpropan-2-yl ((4-(5-(1,1-difluoroethyl)-1,2,4-oxadiazol-3-yl) bicyclo[2.2.2]octan-1-yl)methyl)(4-(4-isopropoxyphenyl)pyridin-2-yl)carbamate (610);

3-(tert-butyl)-1-(4'-(2-hydroxypropan-2-yl)-[1,1'-biphenyl]-3-yl)-1-((4-(5-(trifluoromethyl)-1,2,4-oxadiazol-3-yl)bicyclo[2.2.2]octan-1-yl)methyl) urea (611);

3-(tert-butyl)-1-(4'-(difluoromethoxy)-[1,1'-biphenyl]-3-yl)-1-((4-(5-(trifluoromethyl)-1,2,4-oxadiazol-3-yl)bicyclo[2.2.2]octan-1-yl)methyl)urea (612);

3-(tert-butyl)-1-(4'-(2-(difluoromethoxy)propan-2-yl)-[1,1'-biphenyl]-3-yl)-1-((4-(5-(trifluoromethyl)-1,2,4-oxadiazol-3-yl)bicyclo[2.2.2]octan-1-yl)methyl)urea (613);

1-(4'-(2-hydroxypropan-2-yl)-[1,1'-biphenyl]-3-yl)-3-(spiro[2.3]hexan-5-ylmethyl)-1-((4-(5-(trifluoromethyl)-1,2,4-oxadiazol-3-yl)bicyclo[2.2.2]octan-1-yl)methyl)urea (614);

1,1,1-trifluoro-2-methylpropan-2-yl (4-(4-(chlorodifluoromethoxy)phenyl)pyridin-2-yl) ((4-(5-(1,1-difluoroethyl)-1,2,4-oxadiazol-3-yl)bicyclo[2.2.2]octan-1-yl) methyl)carbamate (615);

1,1,1-trifluoro-2-methylpropan-2-yl((4-(3-cyclopropyl-1,2,4-oxadiazol-5-yl) bicyclo[2.2.2]octan-1-yl)methyl)(5-fluoro-4-(4-(2-hydroxypropan-2-yl)phenyl) pyridin-2-yl) carbamate (616);

1,1,1-trifluoro-2-methylpropan-2-yl ((4-(3-cyclopropyl-1,2,4-oxadiazol-5-yl) bicyclo[2.2.2]octan-1-yl)methyl)(5-fluoro-4-(4-isopropoxyphenyl)pyridin-2-yl)carbamate (617);

1,1,1-trifluoro-2-methylpropan-2-yl((4-(3-cyclopropyl-1,2,4-oxadiazol-5-yl) bicyclo[2.2.2]octan-1-yl)methyl)(5-fluoro-4-(3-fluoro-4-(2-hydroxypropan-2-yl)phenyl) pyridin-2-yl) carbamate (618);

neopentyl ((4-(5-(1,1-difluoroethyl)-1,2,4-oxadiazol-3-yl) bicyclo[2.2.2]octan-1-yl) methyl)(5-fluoro-4-(4-(2-hydroxypropan-2-yl) phenyl) pyridin-2-yl)carbamate (619);

1,1,1-trifluoro-2-methylpropan-2-yl(5-fluoro-4-(4-(2-hydroxypropan-2-yl)phenyl) pyridin-2-yl)((4-(5-(2-fluoropropan-2-yl)-1,2,4-oxadiazol-3-yl)bicyclo[2.2.2]octan-1-yl) methyl)carbamate (620);

1,1,1-trifluoro-2-methylpropan-2-yl(5-fluoro-4-(1-(oxetan-3-ylmethyl)-1H-pyrazol-4-yl) pyridin-2-yl)((4-(5-(2-fluoropropan-2-yl)-1,2,4-oxadiazol-3-yl)bicyclo[2.2.2] octan-1-yl) methyl)carbamate (621);

1,1,1-trifluoro-2-methylpropan-2-yl(4-(4-((2-cyanopropan-2-yl)oxy)phenyl)pyridin-2-yl)((4-(3-cyclopropyl-1,2,4-oxadiazol-5-yl)bicyclo[2.2.2]octan-1-yl)methyl)carbamate (622);

1,1,1-trifluoro-2-methylpropan-2-yl((4-(3-cyclopropyl-1,2,4-oxadiazol-5-yl) bicyclo[2.2.2]octan-1-yl)methyl)(4'-(2-hydroxypropan-2-yl)-[1,1'-biphenyl]-3-yl)carbamate (623);

1,1,1-trifluoro-2-methylpropan-2-yl(4-(4-(difluoromethoxy)phenyl)pyridin-2-yl)((4-(5-(1-fluorocyclopropyl)-1,2,4-oxadiazol-3-yl)bicyclo[2.2.2]octan-1-yl) methyl)carbamate (624);

1,1,1-trifluoro-2-methylpropan-2-yl(4-(4-((2-cyanopropan-2-yl)oxy)phenyl)pyridin-2-yl)((4-(5-(1-fluorocyclopropyl)-1,2,4-oxadiazol-3-yl)bicyclo[2.2.2]octan-1-yl) methyl) carbamate (625);

N-((4-(5-(1,1-difluoroethyl)-1,2,4-oxadiazol-3-yl)bicyclo[2.2.2]octan-1-yl)methyl)-N-(4-(4-isopropoxyphenyl) pyridin-2-yl)morpholine-4-carboxamide (626);

tetrahydro-2H-pyran-4-yl((4-(3-cyclopropyl-1,2,4-oxadiazol-5-yl)bicyclo[2.2.2]octan-1-yl)methyl)(4-(4-isopropoxyphenyl)pyridin-2-yl)carbamate (627);

(cis)-N-(4'-(2,2-difluoro-1-hydroxyethyl)-[1,1'-biphenyl]-3-yl)-N-((4-(5-(1,1-difluoroethyl)-1,2,4-oxadiazol-3-yl)bicyclo[2.2.2]octan-1-yl)methyl)-3-hydroxy-3-(trifluoromethyl) cyclobutane-1-carboxamide (628);

(cis)-3-hydroxy-3-(trifluoromethyl)cyclobutyl (4-(4-(difluoromethoxy)phenyl)-5-fluoropyridin-2-yl)((4-(5-(2-fluoropropan-2-yl)-1,2,4-oxadiazol-3-yl)bicyclo[2.2.2]octan-1-yl)methyl)carbamate (629);

3,3-difluorocyclobutyl(4-(4-(difluoromethoxy)phenyl)-5-fluoropyridin-2-yl)((4-(5-(2-fluoropropan-2-yl)-1,2,4-oxadiazol-3-yl)bicyclo[2.2.2]octan-1-yl)methyl)carbamate (630);

4,4-difluorocyclohexyl (4-(4-(difluoromethoxy) phenyl)-5-fluoropyridin-2-yl) ((4-(5-(2-fluoropropan-2-yl)-1,2,4-oxadiazol-3-yl)bicyclo[2.2.2]octan-1-yl) methyl)carbamate (631);

3-(trifluoromethyl)oxetan-3-yl ((4-(5-(2-fluoropropan-2-yl)-1,2,4-oxadiazol-3-yl) bicyclo[2.2.2]octan-1-yl)methyl)(4'-isopropoxy-[1,1'-biphenyl]-3-yl)carbamate (632);

3-(bicyclo[1.1.1]pentan-1-yl)-1-((4-(5-(1,1-difluoroethyl)-1,2,4-oxadiazol-3-yl) bicyclo[2.2.2]octan-1-yl)methyl)-1-(4-fluoro-3-(1-(2-hydroxy-2-methylpropyl)-1H-pyrazol-4-yl)phenyl)urea (633);

1,1,1-trifluoro-2-methylpropan-2-yl((4-(5-(2-fluoropropan-2-yl)-1,2,4-oxadiazol-3-yl) bicyclo[2.2.2]octan-1-yl)methyl)(4-(4-(2-hydroxypropan-2-yl)phenyl)pyridin-2-yl) carbamate (634);

1,1,1-trifluoro-2-methylpropan-2-yl ((4-(5-(2-fluoropropan-2-yl)-1,2,4-oxadiazol-3-yl)bicyclo[2.2.2]octan-1-yl)methyl)(2-(4-(2-hydroxypropan-2-yl)phenyl)pyrimidin-4-yl) carbamate (635);

1,1,1-trifluoro-2-methylpropan-2-yl ((4-(5-(2-fluoropropan-2-yl)-1,2,4-oxadiazol-3-yl)bicyclo[2.2.2]octan-1-yl)methyl)(4-isopropoxyphenyl)pyrimidin-2-yl)carbamate (636);

N-(4-(((cis)-N-(4'-(difluoromethoxy)-[1,1'-biphenyl]-3-yl)-3-hydroxy-3-(trifluoromethyl)cyclobutane-1-carboxamido) methyl)bicyclo[2.2.2]octan-1-yl)-4-fluorobenzamide (637);

N-(cyclopropylsulfonyl)-4-(((cis)-N-(4'-(difluoromethoxy)-[1,1'-biphenyl]-3-yl)-3-hydroxy-3-(trifluoromethyl)cyclobutane-1-carboxamido)methyl)bicyclo[2.2.2]octane-1-carboxamide (638);

(cis)-N-(4'-(difluoromethoxy)-[1,1'-biphenyl]-3-yl)-N-((4-(5-(4-fluorophenyl)-1,2,4-oxadiazol-3-yl)bicyclo[2.2.2]octan-1-yl)methyl)-3-hydroxy-3-(trifluoromethyl)cyclobutane-1-carboxamide (639);

(cis)-N-((4-(5-(1,1-difluoroethyl)pyridin-2-yl)bicyclo[2.2.2]octan-1-yl)methyl)-3-(difluoromethoxy)-N-(4-(4-isopropoxyphenyl)pyridin-2-yl)-3-methylcyclobutane-1-carboxamide (640);

N-((4-(5-(2-fluoropropan-2-yl)-1,2,4-oxadiazol-3-yl)bicyclo[2.2.2]octan-1-yl)methyl)-N-(4'-(2-hydroxypropan-2-yl)-[1,1'-biphenyl]-3-yl)-2-thia-6-azaspiro[3.3]heptane-6-carboxamide 2,2-dioxide (641);

1-((4-(5-(2-fluoropropan-2-yl)-1,2,4-oxadiazol-3-yl)bicyclo[2.2.2]octan-1-yl)methyl)-1-(4'-(2-hydroxypropan-2-yl)-[1,1'-biphenyl]-3-yl)-3-((1-methylsulfonyl)cyclopropyl)methyl) urea (642);

N-((4-(5-(2-fluoropropan-2-yl)-1,2,4-oxadiazol-3-yl)bicyclo[2.2.2]octan-1-yl)methyl)-3-hydroxy-N-(4'-(2-hydroxypropan-2-yl)-[1,1'-biphenyl]-3-yl)-3-(trifluoromethyl)azetidine-1-carboxamide (643);

3-(1,1-dioxidotetrahydro-2H-thiopyran-4-yl)-1-((4-(5-(2-fluoropropan-2-yl)-1,2,4-oxadiazol-3-yl)bicyclo[2.2.2]octan-1-yl)methyl)-1-(4'-(2-hydroxypropan-2-yl)-[1,1'-biphenyl]-3-yl)urea (644);

3-(2,2-difluoro-3-hydroxypropyl)-1-((4-(5-(2-fluoropropan-2-yl)-1,2,4-oxadiazol-3-yl)bicyclo[2.2.2]octan-1-yl)methyl)-1-(4'-(2-hydroxypropan-2-yl)-[1,1'-biphenyl]-3-yl)urea (646);

1-((4-(5-(2-fluoropropan-2-yl)-1,2,4-oxadiazol-3-yl)bicyclo[2.2.2]octan-1-yl)methyl)-3-((4-(hydroxymethyl)tetrahydro-2H-pyran-4-yl)methyl)-1-(4'-(2-hydroxypropan-2-yl)-[1,1'-biphenyl]-3-yl)urea (647);

1-((4-(5-(2-fluoropropan-2-yl)-1,2,4-oxadiazol-3-yl)bicyclo[2.2.2]octan-1-yl)methyl)-3-((1-hydroxycyclopropyl)methyl)-1-(4'-(2-hydroxypropan-2-yl)-[1,1'-biphenyl]-3-yl)urea (648);

1-((4-(5-(2-fluoropropan-2-yl)-1,2,4-oxadiazol-3-yl)bicyclo[2.2.2]octan-1-yl)methyl)-1-(4'-(2-hydroxypropan-2-yl)-[1,1'-biphenyl]-3-yl)-3-(2-morpholinoethyl)urea (649);

1-((4-(5-(2-fluoropropan-2-yl)-1,2,4-oxadiazol-3-yl)bicyclo[2.2.2]octan-1-yl)methyl)-3-(2-(1-hydroxycyclopentyl)ethyl)-1-(4'-(2-hydroxypropan-2-yl)-[1,1'-biphenyl]-3-yl)urea (650);

N-(4'-((2-cyanopropan-2-yl)oxy)-[1,1'-biphenyl]-3-yl)-N-((4-(5-(2-fluoropropan-2-yl)-1,2,4-oxadiazol-3-yl)bicyclo[2.2.2]octan-1-yl)methyl)-4-(2-hydroxypropan-2-yl)piperidine-1-carboxamide (651);

1-((4-(5-(1,1-difluoroethyl)-1,2,4-oxadiazol-3-yl)bicyclo[2.2.2]octan-1-yl)methyl)-1-(4'-isopropoxy-[1,1'-biphenyl]-3-yl)-3-(tetrahydro-2H-pyran-4-yl)urea (652);

3-((trans)-4-(difluoromethoxy)-4-methylcyclohexyl)-1-(6-fluoro-4'-isopropoxy-[1,1'-biphenyl]-3-yl)-1-((4-(5-(2-fluoropropan-2-yl)-1,2,4-oxadiazol-3-yl)bicyclo[2.2.2]octan-1-yl)methyl)urea (653);

(cis)-N-(4'-((1-amino-2-methyl-1-oxopropan-2-yl)oxy)-[1,1'-biphenyl]-3-yl)-N-((4-(5-(2-fluoropropan-2-yl)-1,2,4-oxadiazol-3-yl)bicyclo[2.2.2]octan-1-yl)methyl)-3-hydroxy-3-(trifluoromethyl)cyclobutane-1-carboxamide (654);

(cis)-N-(4'-((2-cyanopropan-2-yl)oxy)-[1,1'-biphenyl]-3-yl)-N-((4-(5-(2-fluoropropan-2-yl)-1,2,4-oxadiazol-3-yl)bicyclo[2.2.2]octan-1-yl)methyl)-3-hydroxy-3-(trifluoromethyl) cyclobutane-1-carboxamide (654A);

1,1,1-trifluoro-2-methylpropan-2-yl ((4-(3-(1-fluorocyclopropyl)-1-methyl-1H-pyrazol-5-yl)bicyclo[2.2.2]octan-1-yl)methyl)(4'-isopropoxy-[1,1'-biphenyl]-3-yl)carbamate (655);

1,1,1-trifluoro-2-methylpropan-2-yl ((4-(5-(1,1-difluoroethyl)isoxazol-3-yl) bicyclo[2.2.2]octan-1-yl)methyl)(4'-isopropoxy-[1,1'-biphenyl]-3-yl)carbamate (656);

1,1,1-trifluoro-2-methylpropan-2-yl ((4-(3-(1,1-difluoroethyl)-1-methyl-1H-pyrazol-5-yl)bicyclo[2.2.2]octan-1-yl)methyl)(4-(4-isopropoxyphenyl)pyridin-2-yl)carbamate (657);

1,1,1-trifluoro-2-methylpropan-2-yl ((4-(5-(1,1-difluoroethyl)-1-methyl-1H-pyrazol-3-yl)bicyclo[2.2.2]octan-1-yl)methyl)(4'-isopropoxy-[1,1'-biphenyl]-3-yl)carbamate (658);

3-(tert-butyl)-1-((4-(3-(1,1-difluoroethyl)-1-methyl-1H-pyrazol-5-yl) bicyclo[2.2.2]octan-1-yl)methyl)-1-(4'-isopropoxy-[1,1'-biphenyl]-3-yl)urea (659);

3-(tert-butyl)-1-(5-(4-(difluoromethoxy)phenyl)pyridazin-3-yl)-1-((4-(5-(2-fluoropropan-2-yl)-1,2,4-oxadiazol-3-yl)bicyclo[2.2.2]octan-1-yl)methyl)urea (660);

1,1,1-trifluoro-2-methylpropan-2-yl (4-(4-(2-hydroxypropan-2-yl)phenyl)pyridin-2-yl) ((4-(3-isopropyl-1-methyl-1H-pyrazol-5-yl)bicyclo[2.2.2]octan-1-yl)methyl)carbamate (661);

(cis)-N-(4'-(4-amino-1,2,5-oxadiazol-3-yl)-[1,1'-biphenyl]-3-yl)-N-((4-(5-(2-fluoropropan-2-yl)-1,2,4-oxadiazol-3-yl)bicyclo[2.2.2]octan-1-yl)methyl)-3-hydroxy-3-(trifluoromethyl)cyclobutane-1-carboxamide (662);

3-fluoro-N-((4-(5-(2-fluoropropan-2-yl)-1,2,4-oxadiazol-3-yl)bicyclo[2.2.2]octan-1-yl) methyl)-N-(3-(1-(2-hydroxy-2-methylpropyl)-1,2,3,6-tetrahydropyridin-4-yl)phenyl) bicyclo[1.1.1]pentane-1-carboxamide (663);

tert-butyl 4-(3-(3-fluoro-N-((4-(5-(2-fluoropropan-2-yl)-1,2,4-oxadiazol-3-yl) bicyclo[2.2.2]octan-1-yl)methyl)bicyclo[1.1.1]pentane-1-carboxamido)phenyl)-3,6-dihydropyridine-1 (2H)-carboxylate (663C);

3-fluoro-N-((4-(5-(2-fluoropropan-2-yl)-1,2,4-oxadiazol-3-yl)bicyclo[2.2.2]octan-1-yl) methyl)-N-(3-(1,2,3,6-tetrahydropyridin-4-yl) phenyl)bicyclo[1.1.1]pentane-1-carboxamide (663D);

1-((4-(5-(2-fluoropropan-2-yl)-1,2,4-oxadiazol-3-yl)bicyclo [2.2.2]octan-1-yl) methyl)-1-(4'-(2-hydroxypropan-2-yl)-[1,1'-biphenyl]-3-yl)-3-((2S,4S,6S)-6-hydroxyspiro[3.3] heptan-2-yl)urea (664);

1,1,1-trifluoro-2-methylpropan-2-yl (4-(4-cyanobicyclo [2.2.2]octan-1-yl)pyrimidin-2-yl)((4-(3-cyclopropyl-1,2, 4-oxadiazol-5-yl)bicyclo[2.2.2]octan-1-yl)methyl)carbamate (665);

methyl 4-(2-(((4-(3-cyclopropyl-1,2,4-oxadiazol-5-yl)bicyclo[2.2.2]octan-1-yl)methyl) (((1,1,1-trifluoro-2-methylpropan-2-yl) oxy)carbonyl)amino)pyrimidin-4-yl)bicyclo [2.2.2]octane-1-carboxylate (665E);

4-(2-(((4-(3-cyclopropyl-1,2,4-oxadiazol-5-yl)bicyclo [2.2.2]octan-1-yl)methyl) (((1,1,1-trifluoro-2-methylpropan-2-yl)oxy)carbonyl) amino)pyrimidin-4-yl) bicyclo [2.2.2]octane-1-carboxylic acid (665F);

1,1,1-trifluoro-2-methylpropan-2-yl (4-(4-carbamoylbicyclo [2.2.2]octan-1-yl) pyrimidin-2-yl)((4-(3-cyclopropyl-1,2, 4-oxadiazol-5-yl)bicyclo[2.2.2]octan-1-yl)methyl) carbamate (665G); or 1,1,1-trifluoro-2-methylpropan-2-yl ((4-(3-cyclopropyl-1,2, 4-oxadiazol-5-yl) bicyclo[2.2.2]octan-1-yl)methyl)(4-(4-(2-hydroxypropan-2-yl)bicyclo[2.2.2]octan-1-yl) pyrimidin-2-yl)carbamate (666).

II. Pharmaceutical Compositions, Therapeutic Utilities, and Combinations

In another embodiment, the present invention provides a composition comprising at least one of the compounds of the present invention, or a stereoisomer, a tautomer, or a pharmaceutically acceptable salt or a solvate thereof.

In another embodiment, the present invention provides a pharmaceutical composition comprising a pharmaceutically acceptable carrier and at least one of the compounds of the present invention or a stereoisomer, a tautomer, or a pharmaceutically acceptable salt or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, or a pharmaceutically acceptable salt or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising one or more additional therapeutic agents.

In another embodiment, the present invention provides a method for the treatment of a disease, disorder, or condition associated with dysregulation of bile acids in a patient in need of such treatment, and the method comprises administering a therapeutically effective amount of a compound of the present invention, or a stereoisomer, a tautomer, or a pharmaceutically acceptable salt or solvate thereof, to the patient.

In another embodiment, the present invention provides a method for the treatment of a disease, disorder, or condition associated with activity of farnesoid X receptor (FXR) in a patient in need of such treatment comprising administering a therapeutically effective amount of a compound of the present invention, or a stereoisomer, a tautomer, or a pharmaceutically acceptable salt or solvate thereof, to the patient.

In another embodiment, the present invention provides a method for the treatment of the disease, disorder, or condition comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for eliciting an farnesoid X receptor (FXR) agonizing effect in a patient comprising administering a therapeutically effective amount of a compound of the present invention, or a stereoisomer, a tautomer, or a pharmaceutically acceptable salt or solvate thereof, to the patient.

In some embodiments, the disease, disorder, or condition is associated with FXR dysfunction include pathological fibrosis, cancer, inflammatory disorders, metabolic, or cholestatic disorders.

In some embodiments, the disease, disorder, or condition is associated with fibrosis, including liver, biliary, renal, cardiac, dermal, ocular, and pancreatic fibrosis.

In other embodiments, the disease, disorder, or condition is associated with cell-proliferative disorders, such as cancer. In some embodiments, the cancer includes solid tumor growth or neoplasia. In other embodiments, the cancer includes tumor metastasis. In some embodiments, the cancer is of the liver, gall bladder, small intestine, large intestine, kidney, prostate, bladder, blood, bone, brain, breast, central nervous system, cervix, colon, endometrium, esophagus, genitalia, genitourinary tract, head, larynx, lung, muscle tissue, neck, oral or nasal mucosa, ovary, pancreas, skin, spleen, stomach, testicle, or thyroid. In other embodiments, the cancer is a carcinoma, sarcoma, lymphoma, leukemia, melanoma, mesothelioma, multiple myeloma, or seminoma.

Examples of diseases, disorders, or conditions associated with the activity of FXR that can be prevented, modulated, or treated according to the present invention include, but are not limited to, transplant injection, fibrotic disorders (e. g., liver fibrosis, kidney fibrosis), inflammatory disorders (e.g., acute hepatitis, chronic hepatitis, non-alcoholic steatohepatitis (NASH), irritable bowel syndrome (IBS), inflammatory bowel disease (IBD)), as well as cell-proliferative disorders (e.g., cancer, myeloma, fibroma, hepatocellular carcinoma, colorectal cancer, prostate cancer, leukemia, Kaposi's sarcoma, solid tumors).

The fibrotic disorders, inflammatory disorders, as well as cell-proliferative disorders that are suitable to be prevented or treated by the compounds of the present invention include, but are not limited to, non-alcoholic fatty liver disease (NAFLD), alcoholic or non-alcoholic steatohepatitis (NASH), acute hepatitis, chronic hepatitis, liver cirrhosis, primary biliary cirrhosis, primary sclerosing cholangitis, drug-induced hepatitis, biliary cirrhosis, portal hypertension, regenerative failure, liver hypofunction, hepatic blood flow disorder, nephropathy, irritable bowel syndrome (IBS), inflammatory bowel disease (IBD), abnormal pancreatic secretion, benign prostatic hyperplasia, neuropathic bladder disease, diabetic nephropathy, focal segmental glomerulosclerosis, IgA nephropathy, nephropathy induced by drugs or transplantation, autoimmune nephropathy, lupus nephritis, liver fibrosis, kidney fibrosis, chronic kidney disease (CKD), diabetic kidney disease (DKD), skin fibrosis, keloids, systemic sclerosis, scleroderma, virally-induced fibrosis, idiopathic pulmonary fibrosis (IPF), interstitial lung disease, non-specific interstitial pneumonia (NSIP), usual interstitial pneumonia (UIP), radiation-induced fibrosis, familial pulmonary fibrosis, airway fibrosis, chronic obstructive pulmonary disease (COPD), spinal cord tumor, hernia of intervertebral disk, spinal canal stenosis, heart failure, cardiac fibrosis, vascular fibrosis, perivascular fibrosis, foot-and-mouth disease, cancer, myeloma, fibroma, hepatocellular carcinoma, colorectal cancer, prostate cancer, leukemia, chronic lymphocytic leukemia, Kaposi's sarcoma, solid tumors, cerebral infarction, cerebral hemorrhage, neuropathic pain, peripheral neuropathy, age-related macular degeneration (AMD), glaucoma, ocular fibrosis, corneal scarring, diabetic retinopathy, proliferative vitreoretinopathy (PVR), cicatricial pemphigoid glaucoma filtration surgery scarring, Crohn's disease or systemic lupus erythematosus; keloid formation resulting from abnormal wound healing; fibrosis occurring after organ transplantation, myelofibrosis, and fibroids. In one embodiment, the present invention provides a method for the treatment of a fibrotic disorder, an inflammatory disorder, or a cell-proliferative disorder, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of a fibrotic disorder, an inflammatory disorder, or a cell-proliferative disorder thereof.

In another embodiment, the present invention also provides the use of a compound of the present invention for the manufacture of a medicament for the treatment of a fibrotic disorder, an inflammatory disorder, or a cell-proliferative disorder thereof.

In another embodiment, the present invention provides a method for the treatment of a fibrotic disorder, an inflammatory disorder, or a cell-proliferative disorder, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of a fibrotic disorder, an inflammatory disorder, or a cell-proliferative disorder.

The compounds of the present invention may be employed in combination with additional therapeutic agent(s), such as one or more anti-fibrotic and/or anti-inflammatory therapeutic agents.

In one embodiment, additional therapeutic agent(s) used in combined pharmaceutical compositions or combined methods or combined uses, are selected from one or more, preferably one to three, of the following therapeutic agents: TGFβ receptor inhibitors (for example, galunisertib), inhibitors of TGFβ synthesis (for example, pirfenidone), inhibitors of vascular endothelial growth factor (VEGF), platelet-derived growth factor (PDGF) and fibroblast growth factor (FGF) receptor kinases (for example, nintedanib), humanized anti-$α_v β6$ integrin monoclonal antibody (for example, 3G9), human recombinant pentraxin-2, recombinant human Serum Amyloid P, recombinant human antibody against TGFβ-1, -2, and -3, endothelin receptor antagonists (for example, macitentan), interferon gamma, c-Jun amino-terminal kinase (JNK) inhibitor (for example, 4-[[9-[(3S)-tetrahydro-3-furanyl]-8-[(2,4,6-trifluorophenyl)amino]-9H-purin-2-yl]amino]-trans-cyclohexanol, 3-pentylbenzeneacetic acid (PBI-4050), tetra-substituted porphyrin derivative containing manganese (III), monoclonal antibody targeting eotaxin-2, interleukin-13 (IL-13) antibody (for example, lebrikizumab, tralokinumab), bispecific antibody targeting interleukin 4 (IL-4) and interleukin 13 (IL-13), NK1 tachykinin receptor agonist (for example, $Sar^9$, $Met(O_2)^{11}$-Substance P), Cintredekin Besudotox, human recombinant DNA-derived, IgG1 kappa monoclonal antibody to connective growth factor, and fully human IgG1 kappa antibody, selective for CC-chemokine ligand 2 (for example, carlumab, CCX140), antioxidants (for example, N-acetylcysteine), phosphodiesterase 5 (PDE5) inhibitors (for example, sildenafil), agents for treatment of obstructive airway diseases such as muscarinic antagonists (for example, tiotropium, ipatropium bromide), adrenergic β2 agonists (for example, salbutamol, salmeterol), corticosteroids (for example, triamcinolone, dexamethasone, fluticasone), immunosuppressive agents (for example, tacrolimus, rapamycin, pimecrolimus), and therapeutic agents useful for the treatment of fibrotic conditions, such as liver, biliary, and kidney fibrosis, Non-Alcoholic Fatty Liver Disease (NALFD), Non-Alcoholic Steato-Hepatitis (NASH), cardiac fibrosis, Idiopathic Pulmonary Fibrosis (IPF), and systemic sclerosis. The therapeutic agents useful for the treatment of such fibrotic conditions include, but are not limited to, FXR agonists (for example OCA, GS-9674, and LJN452), LOXL2 inhibitors (for example simtuzumab), LPA1 antagonists (for example, BMS-986020 and SAR 100842), PPAR modulators (for example, elafibrinor, pioglitazone, and saroglitazar, IVA337), SSAO/VAP-1 inhibitors (for example, PXS-4728A and SZE5302), ASK-1 inhibitors (for example GS-4997 or selonsertib), ACC inhibitors (for example, CP-640186 and NDI-010976 or GS-0976), FGF21 mimetics (for example, LY2405319 and BMS-986036), caspase inhibitors (for example, emricasan), NOX4 inhibitors (for example, GKT137831), MGAT2 inhibitor (for example, BMS-963272), αV integrin inhibitors (for example, abituzumab) and bile acid/fatty acid conjugates (for example aramchol). The FXR agonists of various embodiments of the present invention may also be used in combination with one or more therapeutic agents such as CCR2/5 inhibitors (for example, cenicriviroc), Galectin-3 inhibitors (for example, TD-139, GR-MD-02), leukotriene receptor antagonists (for example, tipelukast, montelukast), SGLT2 inhibitors (for example, dapagliflozin, remogliflozin), GLP-1 receptor agonists (for example, liraglutide and semaglutide), FAK inhibitors (for example, GSK-2256098), CB1 inverse agonists (for example, JD-5037), CB2 agonists (for example, APD-371 and JBT-101), autotaxin inhibitors (for example, GLPG1690), prolyl t-RNA synthetase inhibitors (for example, halofugenone), FPR2 agonists (for example, ZK-994), and THR agonists (for example, MGL:3196). In another embodiment, additional therapeutic agent(s) used in combined pharmaceutical compositions or combined methods or combined uses, are selected from one or more, preferably one to three, of immunoncology agents, such as Alemtuzumab, Atezolizumab, Ipilimumab, Nivolumab, Ofatumumab, Pembrolizumab, and Rituximab.

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and nonaqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 18th Edition (1990).

The terms "treating" or "treatment" as used herein refer to an approach for obtaining beneficial or desired results, including clinical results, by using a compound or a composition of the present invention. For purposes of this invention, beneficial or desired clinical results include, but are not limited to, one or more of the following: decreasing the severity and/or frequency one or more symptoms resulting from the disease, disorder, or condition; diminishing the extent of or causing regression of the disease, disorder, or condition; stabilizing the disease, disorder, or condition (e.g., preventing or delaying the worsening of the disease, disorder, or condition); delay or slowing the progression of the disease, disorder, or condition; ameliorating the disease, disorder, or condition state; decreasing the dose of one or more other medications required to treat the disease, disorder, or condition; and/or increasing the quality of life.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.01 to about 1000 mg per day, and most preferably between about 0.01 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 0.1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., ASK-1 inhibitors, CCR2/5 antagonists, autotaxin inhibitors, LPA1 receptor antagonists or other pharmaceutically active material.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The compounds of the present invention are also useful as standard or reference compounds, for example as a quality standard or control, in tests or assays involving FXR agonists. Such compounds may be provided in a commercial kit, for example, for use in pharmaceutical research involving FXR agonist activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof, and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of fibrosis and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

III. Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds and/or salts thereof" refers to at least one compound, at least one salt of the compounds, or a combination thereof. For example, compounds of Formula (I) and/or salts thereof includes a compound of Formula (I); two compounds of Formula (I); a salt of a compound of Formula (I); a compound of Formula (I) and one or more salts of the compound of Formula (I); and two or more salts of a compound of Formula (I).

Unless otherwise indicated, any atom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.
The term "hydroxy" refers to the group —OH.
The term "amino" refers to the group —NH$_2$.
The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-4}$ alkyl" denotes straight and branched chain alkyl groups with one to four carbon atoms.

The term "haloalkyl" as used herein is intended to include both branched and straight-chain saturated aliphatic hydrocarbon groups substituted with one or more halo atoms. For example, "$C_{1-4}$ haloalkyl" is intended to include $C_1$, $C_2$, $C_3$, and $C_4$ alkyl groups substituted with one or more halo atoms. Representative examples of haloalkyl groups include, but are not limited to, —CF$_3$, —CCl$_3$, —CHF$_2$, and —CF$_2$CCl$_3$.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "hydroxyalkyl" as used herein is intended to include both branched and straight-chain saturated aliphatic hydrocarbon groups substituted with one or more hydroxyl groups. For example, "$C_{1-4}$ hydroxyalkyl" is intended to include $C_1$, $C_2$, $C_3$, and $C_4$ alkyl groups substituted with one or more hydroxyl groups. Representative examples of fluoroalkyl groups include, but are not limited to, —CH$_2$OH, —CH$_2$CH$_2$OH, and —C(CH$_3$)$_2$OH.

The term "alkenyl" refers to a straight or branched chain hydrocarbon radical containing from 2 to 12 carbon atoms and at least one carbon-carbon double bond. Exemplary such groups include ethenyl or allyl. For example, "$C_{2-6}$ alkenyl" denotes straight and branched chain alkenyl groups with two to six carbon atoms.

The term "alkynyl" refers to a straight or branched chain hydrocarbon radical containing from 2 to 12 carbon atoms and at least one carbon to carbon triple bond. Exemplary such groups include ethynyl. For example, "$C_{2-6}$ alkynyl" denotes straight and branched chain alkynyl groups with two to six carbon atoms.

The term "alkoxy" as used herein, refers to an alkyl group attached to the parent molecular moiety through an oxygen atom, for example, methoxy group (—OCH$_3$). For example, "$C_{1-3}$ alkoxy" denotes alkoxy groups with one to three carbon atoms.

The terms "haloalkoxy" and "—O(haloalkyl)" represent a haloalkyl group as defined above attached through an oxygen linkage (—O—). For example, "$C_{1-4}$ haloalkoxy" is intended to include $C_1$, $C_2$, $C_3$, and $C_4$ haloalkoxy groups.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The terms "carbocyclo", "carbocyclic" or "carbocyclyl" may be used interchangeably and refer to cyclic groups having at least one saturated or partially saturated non-aromatic ring wherein all atoms of all rings are carbon, and includes groups having one or more bridged rings in which the bridged ring occurs when one or more carbon atoms link two non-adjacent carbon atoms. The term includes nonaromatic rings such as for example, cycloalkyl and cycloalkenyl, bicyclo[1.1.1]pentyl, bicyclo[2.2.2]octanyl, adamantyl, and tetrahydronaphthyl.

The term "bicycloalkyl," as used herein, refers to a carbocyclyl group having at least one bridge. Representative examples of bicycloalkyl groups include, but are not limited to, bicyclo[1.1.1]pentyl, bicyclo[2.2.2]octanyl, and adamantyl.

The term "aryl" as used herein, refers to a group of atoms derived from a molecule containing aromatic ring(s) by removing one hydrogen that is bonded to the aromatic ring(s). Representative examples of aryl groups include, but are not limited to, phenyl and naphthyl. The aryl ring may be unsubstituted or may contain one or more substituents as valence allows.

The term "heteroatom" refers to oxygen (O), sulfur (S), and nitrogen (N).

The terms "heterocyclo", "heterocyclic", or "heterocyclyl" may be used interchangeably and refer to cyclic groups having at least saturated or partially saturated non-aromatic ring and wherein one or more of the rings have at least one heteroatom (O, S or N), said heteroatom containing ring preferably having 1 to 3 heteroatoms independently selected from O, S, and/or N. The ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The heterocyclo group may be attached at any available nitrogen or carbon atom. The heterocyclo ring may be unsubstituted or may contain one or more substituents as valence allows.

Exemplary monocyclic heterocyclyl groups include pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane, tetrahydro-1,1-dioxothienyl, dihydroisoindolyl, and tetrahydroquinolinyl.

The terms "spirobicyclyl" and spirobicyclo" may be used interchangeably and refer to bicyclic groups in which the two rings are attached at a single carbon atom that is a member of each of the two rings. The term includes both spirobicycloalkyls, in which the two rings are cycloalkyl rings attached at a single carbon atom that is a member of each of the two rings, and spirobicycloheteroalkyls, in which one ring is a heterocyclyl ring and the other ring is a cycloalkyl ring attached at a single carbon atom that is a member of each of the two rings, or in which both rings are heterocyclyl rings attached at a single carbon atom that is a member of each of the two rings. Examples of spirobicyclyl groups include spiro[3.3]heptenyl, spiro[3.4]octanyl, azaspiro[3.3]heptanyl, oxaazaspiro[3.3]heptanyl, oxaazaspiro[3.3]heptanyl, and azaspiro[3.4]octanyl.

The term "heteroaryl" refers to substituted and unsubstituted aromatic 5- or 6-membered monocyclic groups and 9- or 10-membered bicyclic groups that have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group are aromatic and may contain only carbon atoms. The nitrogen and sulfur atoms may optionally be oxidized and the nitrogen atoms may optionally be quaternized. Bicyclic heteroaryl groups must include only aromatic rings. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazinyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, and pyrrolopyridyl.

The term "glycosyl" means a monovalent free radical or substituent moiety obtained by removing the hemiacetal hydroxyl group from the cyclic form of a monosaccharide and, by extension, of a lower oligosaccharide. In one embodiment, the glycosyl group has the following structure:

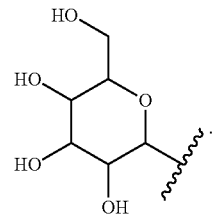

As used herein, the term "tautomer" refers to each of two or more isomers of a compound that exist together in equilibrium, and are readily interchanged by migration of an atom or group within the molecule. For example, one skilled in the art would readily understand that a 1,2,3-triazole exists in two tautomeric forms as defined above:

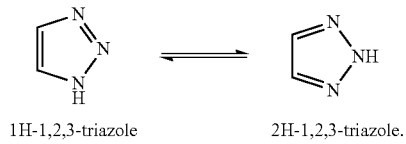

1H-1,2,3-triazole      2H-1,2,3-triazole.

Thus, this disclosure is intended to cover all possible tautomers even when a structure depicts only one of them. For example, the compounds of Formula (Ia) wherein when $R^{5c}$ is hydroxy and each of $R^{5a}$, $R^{5b}$, and $R^{5d}$ are hydrogen, can exist in tautomeric forms:

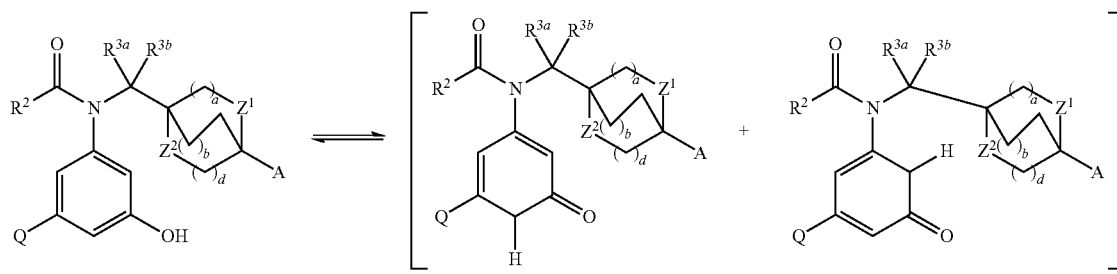

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can form salts which are also within the scope of this invention. Unless otherwise indicated, reference to an inventive compound is understood to include reference to one or more salts thereof. The term "salt(s)" denotes acidic and/or basic salts formed with inorganic and/or organic acids and bases. In addition, the term "salt(s) may include zwitterions (inner salts), e.g., when a compound of Formula (I) contains both a basic moiety, such as an amine or a pyridine or imidazole ring, and an acidic moiety, such as a carboxylic acid. Pharmaceutically acceptable (i.e., non-toxic, physiologically acceptable) salts are preferred, such as, for example, acceptable metal and amine salts in which the cation does not contribute significantly to the toxicity or biological activity of the salt. However, other salts may be useful, e.g., in isolation or purification steps which may be employed during preparation, and thus, are contemplated within the scope of the invention. Salts of the compounds of the formula (I) may be formed, for example, by reacting a compound of the Formula (I) with an amount of acid or base, such as an equivalent amount, in a medium such as one in which the salt precipitates or in an aqueous medium followed by lyophilization. Lists of suitable salts are found in *Remington's Pharmaceutical Sciences*, 18th Edition, Mack Publishing Company, Easton, Pa. (1990), the disclosure of which is hereby incorporated by reference.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, maleates (formed with maleic acid), 2-hydroxyethanesulfonates, lactates, methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

Exemplary basic salts include ammonium salts, alkali metal salts such as sodium, lithium, and potassium salts; alkaline earth metal salts such as calcium and magnesium salts; barium, zinc, and aluminum salts; salts with organic bases (for example, organic amines) such as trialkylamines such as triethylamine, procaine, dibenzylamine, N-benzyl-β-phenethylamine, 1-ephenamine, N,N'-dibenzylethylenediamine, dehydroabietylamine, N-ethylpiperidine, benzylamine, dicyclohexylamine or similar pharmaceutically acceptable amines and salts with amino acids such as arginine, lysine and the like. Basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others. Preferred salts include monohydrochloride, hydrogensulfate, methanesulfonate, phosphate or nitrate salts.

The compounds of Formula (I) can be provided as amorphous solids or crystalline solids. Lyophilization can be employed to provide the compounds of Formula (I) as a solid.

It should further be understood that solvates (e.g., hydrates) of the Compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

e) Rautio, J. et al., *Nature Review Drug Discovery*, 17, 559-587, (2018).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an agonist of FXR, or effective to treat or prevent disorders associated with dysregulation of bile acids, such as pathological fibrosis, cancer, inflammatory disorders, metabolic, or cholestatic disorders.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

In another embodiment, the present invention provides a composition comprising at least one of the compounds of the present invention, or a stereoisomer, a tautomer, or a pharmaceutically acceptable salt or a solvate thereof.

In another embodiment, the present invention provides a pharmaceutical composition comprising a pharmaceutically acceptable carrier and at least one of the compounds of the present invention or a stereoisomer, a tautomer, or a pharmaceutically acceptable salt or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, or a pharmaceutically acceptable salt or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising one or more additional therapeutic agents.

Utility

In one embodiment, the present invention provides a method for the treatment of a disease, disorder, or condition associated with dysregulation of bile acids in a patient in need of such treatment, and the method comprises administering a therapeutically effective amount of a compound of the present invention, or a stereoisomer, a tautomer, or a pharmaceutically acceptable salt or solvate thereof, to the patient.

In another embodiment, the present invention provides a method for the treatment of a disease, disorder, or condition associated with activity of farnesoid X receptor (FXR) in a patient in need of such treatment comprising administering a therapeutically effective amount of a compound of the present invention, or a stereoisomer, a tautomer, or a pharmaceutically acceptable salt or solvate thereof, to the patient.

In another embodiment, the present invention provides a method for the treatment of the disease, disorder, or condition comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a method for eliciting an farnesoid X receptor (FXR) agonizing effect in a patient comprising administering a therapeutically effective amount of a compound of the present invention, or a stereoisomer, a tautomer, or a pharmaceutically acceptable salt or solvate thereof, to the patient.

In some embodiments, the disease, disorder, or condition is associated with FXR dysfunction include pathological fibrosis, cancer, inflammatory disorders, metabolic, or cholestatic disorders.

In some embodiments, the disease, disorder, or condition is associated with fibrosis, including liver, biliary, renal, cardiac, dermal, ocular, and pancreatic fibrosis.

In other embodiments, the disease, disorder, or condition is associated with cell-proliferative disorders, such as cancer. In some embodiments, the cancer includes solid tumor growth or neoplasia. In other embodiments, the cancer includes tumor metastasis. In some embodiments, the cancer is of the liver, gall bladder, small intestine, large intestine, kidney, prostate, bladder, blood, bone, brain, breast, central nervous system, cervix, colon, endometrium, esophagus, genitalia, genitourinary tract, head, larynx, lung, muscle tissue, neck, oral or nasal mucosa, ovary, pancreas, skin, spleen, stomach, testicle, or thyroid. In other embodiments, the cancer is a carcinoma, sarcoma, lymphoma, leukemia, melanoma, mesothelioma, multiple myeloma, or seminoma.

Examples of diseases, disorders, or conditions associated with the activity of FXR that can be prevented, modulated, or treated according to the present invention include, but are not limited to, transplant injection, fibrotic disorders (e. g., liver fibrosis, kidney fibrosis), inflammatory disorders (e.g., acute hepatitis, chronic hepatitis, non-alcoholic steatohepatitis (NASH), irritable bowel syndrome (IBS), inflammatory bowel disease (IBD)), as well as cell-proliferative disorders (e.g., cancer, myeloma, fibroma, hepatocellular carcinoma, colorectal cancer, prostate cancer, leukemia, Kaposi's sarcoma, solid tumors).

The fibrotic disorders, inflammatory disorders, as well as cell-proliferative disorders that are suitable to be prevented or treated by the compounds of the present invention include, but are not limited to, non-alcoholic fatty liver disease (NAFLD), alcoholic or non-alcoholic steatohepatitis (NASH), acute hepatitis, chronic hepatitis, liver cirrhosis, primary biliary cirrhosis, primary sclerosing cholangitis, drug-induced hepatitis, biliary cirrhosis, portal hypertension, regenerative failure, liver hypofunction, hepatic blood flow disorder, nephropathy, irritable bowel syndrome (IBS), inflammatory bowel disease (IBD), abnormal pancreatic secretion, benign prostatic hyperplasia, neuropathic bladder disease, diabetic nephropathy, focal segmental glomerulosclerosis, IgA nephropathy, nephropathy induced by drugs or transplantation, autoimmune nephropathy, lupus nephritis, liver fibrosis, kidney fibrosis, chronic kidney disease (CKD), diabetic kidney disease (DKD), skin fibrosis, keloids, systemic sclerosis, scleroderma, virally-induced fibrosis, idiopathic pulmonary fibrosis (IPF), interstitial lung disease, non-specific interstitial pneumonia (NSIP), usual interstitial pneumonia (UIP), radiation-induced fibrosis, familial pulmonary fibrosis, airway fibrosis, chronic obstructive pulmonary disease (COPD), spinal cord tumor, hernia of intervertebral disk, spinal canal stenosis, heart failure, cardiac fibrosis, vascular fibrosis, perivascular fibrosis, foot-and-mouth disease, cancer, myeloma, fibroma, hepatocellular carcinoma, colorectal cancer, prostate cancer, leukemia, chronic lymphocytic leukemia, Kaposi's sarcoma, solid tumors, cerebral infarction, cerebral hemorrhage, neuropathic pain, peripheral neuropathy, age-related macular degeneration (AMD), glaucoma, ocular fibrosis, corneal scarring, diabetic retinopathy, proliferative vitreoretinopathy (PVR), cicatricial pemphigoid glaucoma filtration surgery scarring, Crohn's disease or systemic lupus erythematosus; keloid formation resulting from abnormal wound healing; fibrosis occurring after organ transplantation, myelofibrosis, and fibroids. In one embodiment, the present invention provides a method for the treatment of a fibrotic disorder, an inflammatory disorder, or a cell-proliferative disorder, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of a fibrotic disorder, an inflammatory disorder, or a cell-proliferative disorder thereof.

In another embodiment, the present invention also provides the use of a compound of the present invention for the manufacture of a medicament for the treatment of a fibrotic disorder, an inflammatory disorder, or a cell-proliferative disorder thereof.

In another embodiment, the present invention provides a method for the treatment of a fibrotic disorder, an inflammatory disorder, or a cell-proliferative disorder, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of a fibrotic disorder, an inflammatory disorder, or a cell-proliferative disorder.

The compounds of the present invention may be employed in combination with additional therapeutic agent(s), such as one or more anti-fibrotic and/or anti-inflammatory therapeutic agents.

In one embodiment, additional therapeutic agent(s) used in combined pharmaceutical compositions or combined methods or combined uses, are selected from one or more, preferably one to three, of the following therapeutic agents: TGFβ receptor inhibitors (for example, galunisertib), inhibitors of TGFβ synthesis (for example, pirfenidone), inhibitors of vascular endothelial growth factor (VEGF), platelet-derived growth factor (PDGF) and fibroblast growth factor (FGF) receptor kinases (for example, nintedanib), humanized anti-$\alpha_v\beta6$ integrin monoclonal antibody (for example, 3G9), human recombinant pentraxin-2, recombinant human Serum Amyloid P, recombinant human antibody against TGFβ-1, -2, and -3, endothelin receptor antagonists (for example, macitentan), interferon gamma, c-Jun amino-terminal kinase (JNK) inhibitor (for example, 4-[[9-[(3S)-tetrahydro-3-furanyl]-8-[(2,4,6-trifluorophenyl)amino]-9H-purin-2-yl]amino]-trans-cyclohexanol, 3-pentylbenzeneacetic acid (PBI-4050), tetra-substituted porphyrin derivative containing manganese (III), monoclonal antibody targeting eotaxin-2, interleukin-13 (IL-13) antibody (for example, lebrikizumab, tralokinumab), bispecific antibody targeting interleukin 4 (IL-4) and interleukin 13 (IL-13), NK1 tachykinin receptor agonist (for example, $Sar^9$, $Met(O_2)^{11}$-Substance P), Cintredekin Besudotox, human recombinant DNA-derived, IgG1 kappa monoclonal antibody to connective growth factor, and fully human IgG1 kappa antibody, selective for CC-chemokine ligand 2 (for example, carlumab, CCX140), antioxidants (for example, N-acetyl-cysteine), phosphodiesterase 5 (PDE5) inhibitors (for example, sildenafil), agents for treatment of obstructive airway diseases such as muscarinic antagonists (for example, tiotropium, ipatropium bromide), adrenergic β2 agonists (for example, salbutamol, salmeterol), corticosteroids (for example, triamcinolone, dexamethasone, fluticasone), immunosuppressive agents (for example, tacrolimus, rapamycin, pimecrolimus), and therapeutic agents useful for the treatment of fibrotic conditions, such as liver, biliary, and kidney fibrosis, Non-Alcoholic Fatty Liver Disease (NALFD), Non-Alcoholic Steato-Hepatitis (NASH), cardiac fibrosis, Idiopathic Pulmonary Fibrosis (IPF), and systemic sclerosis. The therapeutic agents useful for the treatment of such fibrotic conditions include, but are not limited to, FXR agonists (for example OCA, GS-9674, and LJN452), LOXL2 inhibitors (for example simtuzumab), LPA1 antagonists (for example, BMS-986020 and SAR 100842), PPAR modulators (for example, elafibrinor, pioglitazone, and saroglitazar, IVA337), SSAO/VAP-1 inhibitors (for example, PXS-4728A and SZE5302), ASK-1 inhibitors (for example GS-4997 or selonsertib), ACC inhibitors (for example, CP-640186 and NDI-010976 or GS-0976), FGF21 mimetics (for example, LY2405319 and BMS-986036), caspase inhibitors (for example, emricasan), NOX4 inhibitors (for example, GKT137831), MGAT2 inhibitor (for example, BMS-963272), αV integrin inhibitors (for example, abituzumab) and bile acid/fatty acid conjugates (for example aramchol). The FXR agonists of various embodiments of the present invention may also be used in combination with one or more therapeutic agents such as CCR2/5 inhibitors (for example, cenicriviroc), Galectin-3 inhibitors (for example, TD-139, GR-MD-02), leukotriene receptor antagonists (for example, tipelukast, montelukast), SGLT2 inhibitors (for example, dapagliflozin, remogliflozin), GLP-1 receptor agonists (for example, liraglutide and semaglutide), FAK inhibitors (for example, GSK-2256098), CB1 inverse agonists (for example, JD-5037), CB2 agonists (for example, APD-371 and JBT-101), autotaxin inhibitors (for example, GLPG1690), prolyl t-RNA synthetase inhibitors (for example, halofugenone), FPR2 agonists (for example, ZK-994), and THR agonists (for example, MGL:3196). In another embodiment, additional therapeutic agent(s) used in combined pharmaceutical compositions or combined methods or combined uses, are selected from one or more, preferably one to three, of immunoncology agents, such as Alemtuzumab, Atezolizumab, Ipilimumab, Nivolumab, Ofatumumab, Pembrolizumab, and Rituximab.

The compounds of this invention can be administered for any of the uses described herein by any suitable means, for example, orally, such as tablets, capsules (each of which includes sustained release or timed release formulations), pills, powders, granules, elixirs, tinctures, suspensions, syrups, and emulsions; sublingually; bucally; parenterally, such as by subcutaneous, intravenous, intramuscular, or intrasternal injection, or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories. They can be administered alone, but generally will be administered with a pharmaceutical carrier selected on the basis of the chosen route of administration and standard pharmaceutical practice.

The term "pharmaceutical composition" means a composition comprising a compound of the invention in combination with at least one additional pharmaceutically acceptable carrier. A "pharmaceutically acceptable carrier" refers to media generally accepted in the art for the delivery of biologically active agents to animals, in particular, mammals, including, i.e., adjuvant, excipient or vehicle, such as diluents, preserving agents, fillers, flow regulating agents, disintegrating agents, wetting agents, emulsifying agents, suspending agents, sweetening agents, flavoring agents, perfuming agents, anti-bacterial agents, anti-fungal agents, lubricating agents and dispensing agents, depending on the nature of the mode of administration and dosage forms. Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, well known to those of ordinary skill in the art. Descriptions of suitable pharmaceutically acceptable carriers, and factors involved in their selection, are found in a variety of readily available sources such as, for example, *Remington's Pharmaceutical Sciences*, 18th Edition (1990).

The terms "treating" or "treatment" as used herein refer to an approach for obtaining beneficial or desired results, including clinical results, by using a compound or a composition of the present invention. For purposes of this invention, beneficial or desired clinical results include, but are not limited to, one or more of the following: decreasing the severity and/or frequency one or more symptoms resulting from the disease, disorder, or condition; diminishing the extent of or causing regression of the disease, disorder, or condition; stabilizing the disease, disorder, or condition (e.g., preventing or delaying the worsening of the disease, disorder, or condition); delay or slowing the progression of the disease, disorder, or condition; ameliorating the disease, disorder, or condition state; decreasing the dose of one or more other medications required to treat the disease, disorder, or condition; and/or increasing the quality of life.

Pharmaceutically acceptable carriers are formulated according to a number of factors well within the purview of those of ordinary skill in the art. These include, without limitation: the type and nature of the active agent being formulated; the subject to which the agent-containing composition is to be administered; the intended route of administration of the composition; and the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, well known to those of ordinary skill in the art. Descriptions of suitable pharmaceutically acceptable carriers, and factors involved in their selection, are found in a variety of readily available sources such as, for example, Allen, L. V. Jr. et al. *Remington: The Science and Practice of Pharmacy* (2 *Volumes*), 22nd Edition (2012), Pharmaceutical Press.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired.

By way of general guidance, the daily oral dosage of each active ingredient, when used for the indicated effects, will range between about 0.01 to about 5000 mg per day, preferably between about 0.01 to about 1000 mg per day, and most preferably between about 0.01 to about 250 mg per day. Intravenously, the most preferred doses will range from about 0.01 to about 10 mg/kg/minute during a constant rate infusion. Compounds of this invention may be administered in a single daily dose, or the total daily dosage may be administered in divided doses of two, three, or four times daily.

The compounds are typically administered in admixture with suitable pharmaceutical diluents, excipients, or carriers (collectively referred to herein as pharmaceutical carriers) suitably selected with respect to the intended form of administration, e.g., oral tablets, capsules, elixirs, and syrups, and consistent with conventional pharmaceutical practices.

Dosage forms (pharmaceutical compositions) suitable for administration may contain from about 1 milligram to about 2000 milligrams of active ingredient per dosage unit. In these pharmaceutical compositions the active ingredient will ordinarily be present in an amount of about 0.1-95% by weight based on the total weight of the composition.

A typical capsule for oral administration contains at least one of the compounds of the present invention (250 mg), lactose (75 mg), and magnesium stearate (15 mg). The mixture is passed through a 60 mesh sieve and packed into a No. 1 gelatin capsule.

A typical injectable preparation is produced by aseptically placing at least one of the compounds of the present invention (250 mg) into a vial, aseptically freeze-drying and sealing. For use, the contents of the vial are mixed with 2 mL of physiological saline, to produce an injectable preparation.

The present invention includes within its scope pharmaceutical compositions comprising, as an active ingredient, a therapeutically effective amount of at least one of the compounds of the present invention, alone or in combination with a pharmaceutical carrier. Optionally, compounds of the present invention can be used alone, in combination with other compounds of the invention, or in combination with one or more, preferably one to three, other therapeutic agent(s), e.g., ASK-1 inhibitors, CCR2/5 antagonists, autotaxin inhibitors, LPA1 receptor antagonists or other pharmaceutically active material.

The above other therapeutic agents, when employed in combination with the compounds of the present invention may be used, for example, in those amounts indicated in the *Physicians' Desk Reference*, as in the patents set out above, or as otherwise determined by one of ordinary skill in the art.

Particularly when provided as a single dosage unit, the potential exists for a chemical interaction between the combined active ingredients. For this reason, when the compound of the present invention and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but rather is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

The compounds of the present invention can be administered alone or in combination with one or more, preferably one to three, additional therapeutic agents. By "administered in combination" or "combination therapy" it is meant that the compound of the present invention and one or more, preferably one to three, additional therapeutic agents are administered concurrently to the mammal being treated. When administered in combination, each component may be administered at the same time or sequentially in any order at different points in time. Thus, each component may be administered separately but sufficiently closely in time so as to provide the desired therapeutic effect.

The combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment). Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

The compounds of the present invention are also useful as standard or reference compounds, for example as a quality standard or control, in tests or assays involving FXR agonists. Such compounds may be provided in a commercial kit, for example, for use in pharmaceutical research involving FXR agonist activity. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising a compound of the present invention or a pharmaceutically acceptable salt form thereof; and, (c) a package insert stating that the pharmaceutical composition can be used for the treatment of dyslipidemias and the sequelae thereof. In another embodiment, the package insert states that the pharmaceutical composition can be used in combination (as defined previously) with a second therapeutic agent for the treatment of fibrosis and the sequelae thereof. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic) on which the desired information has been formed (e.g., printed or applied).

Methods of Preparation

The compounds of the present invention may be synthesized by many methods available to those skilled in the art of organic chemistry. General synthetic schemes for preparing compounds of the present invention are described below. These schemes are illustrative and are not meant to limit the possible techniques one skilled in the art may use to prepare the compounds disclosed herein. Different methods to prepare the compounds of the present invention will be evident to those skilled in the art. Examples of compounds of the present invention prepared by methods described in the general schemes are given in the Examples section set out hereinafter. Preparation of homochiral examples may be carried out by techniques known to one skilled in the art. For example, homochiral compounds may be prepared by separation of racemic products or diastereomers by chiral phase preparative HPLC. Alternatively, the example compounds may be prepared by methods known to give enantiomerically or diastereomerically enriched products.

The reactions and techniques described in this section are performed in solvents appropriate to the reagents and materials employed and are suitable for the transformations being effected. Also, in the description of the synthetic methods given below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art, with alternatives required when incompatible substituents are present. This will sometimes require a judgment to modify the order of the synthetic steps or to select one particular process scheme over another in order to obtain a compound of the invention. It will also be recognized that another major consideration in the planning of any synthetic route in this field is the judicious choice of a protecting group used for protection of reactive functional groups present in the compounds described in this invention. An authoritative account describing the many alternatives to the trained practitioner is Wuts and Greene, *Greene's Protective Groups in Organic Synthesis*, Fourth Edition, Wiley and Sons (2007).

EXAMPLES

The following examples illustrate the particular and preferred embodiments of the present invention and do not limit the scope of the present invention. Chemical abbreviations and symbols as well as scientific abbreviations and symbols have their usual and customary meanings unless otherwise specified. Additional abbreviations employed in the Examples and elsewhere in this application are defined below. Common intermediates are generally useful for the preparation of more than one Example and are identified sequentially (e.g., Intermediate 1, Intermediate 2) and are abbreviated as Int. 1 or I1, Int. 2 or I2. Compounds of the Examples are identified by the example and STEP in which they were prepared (e.g., "1-A" denotes the Example 1, STEP A), or by the example only where the compound is the title compound of the example (for example, "1" denotes the title compound of Example 1). In some instances, alternate preparations of intermediates or examples are described. Frequently chemists skilled in the art of synthesis may devise alternative preparations which may be desirable based on one or more considerations such as shorter reaction time, less expensive starting materials, ease of operation or isolation, improved yield, amenable to catalysis, avoidance of toxic reagents, accessibility of specialized instrumentation, and decreased number of linear STEPs. The intent of describing alternative preparations is to further enable the preparation of the examples of this invention. In some instances, some functional groups in the outlined examples and claims may be replaced by well-known bioisosteric replacements known in the art, for example, replacement of a carboxylic acid group with a tetrazole or a phosphate moiety. $^1$H NMR data collected in deuterated dimethyl sulfoxide used water suppression in the data processing. The reported spectra are uncorrected for the effects of water suppression. Protons adjacent to the water suppression frequency of 3.35 ppm exhibit diminished signal intensity.

Abbreviations

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "L" for microliter or microliters, "N" for normal, "M" for molar, "mmol" for millimole or millimoles, "min" for minute or minutes, "h" for hour or hours, "rt" for room temperature, "RBF" for round bottom flask, "atm" for atmosphere, "psi" for pounds per square inch, "conc." for concentrated, "RCM" for ring-closing metathesis, "sat" or "sat'd" for saturated, "SFC" for supercritical fluid chromatography, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "nOe" for nuclear Overhauser effect spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

The following abbreviations are employed in the Schemes, Examples and elsewhere herein:
EtOAc=ethyl acetate
PE=petroleum ether
DMF=dimethylformamide
THF=tetrahydrofuran
$K_2CO_3$=potassium carbonate
$Na_2CO_3$=sodium carbonate
$MgSO_4$=magnesium sulfate
DCM=$CH_2Cl_2$=methylene chloride
DCE=1,2-dichloroethane
MeOH=methanol
HCl=hydrochloric acid
AcOH=acetic acid Cs$_2$CO$_3$=cesium carbonate
DMSO=dimethylsulfoxide
TEA=triethylamine
BOP=(benzotriazol-1-yloxy)tris(dimethylamino)phosphonium hexafluorophosphate
DMAc=dimethyl acetamide
DMAP=4-dimethylaminopyridine
2-DMAP=2-dimethylaminopyridine
PCC=pyridinium chlorochromate
PDC=pyridinium dichromate
DIBAL-H=diisobutylaluminium hydride
rotovap=rotary evaporation
min=minute(s)
h or hr=hour(s)
d=day(s)

that all proposed reaction conditions, including solvent, reaction atmosphere, reaction temperature, duration of the experiment and workup procedures, are chosen to be the conditions standard for that reaction, which should be readily recognized by one skilled in the art. One skilled in the art of organic synthesis understands that the functionality present on various portions of the edict molecule must be compatible with the reagents and reactions proposed. Not all compounds of Formula I falling into a given class may be compatible with some of the reaction conditions required in some of the methods described. Such restrictions to the substituents, which are compatible with the reaction conditions, will be readily apparent to one skilled in the art and alternate methods must be used.

SCHEME 1

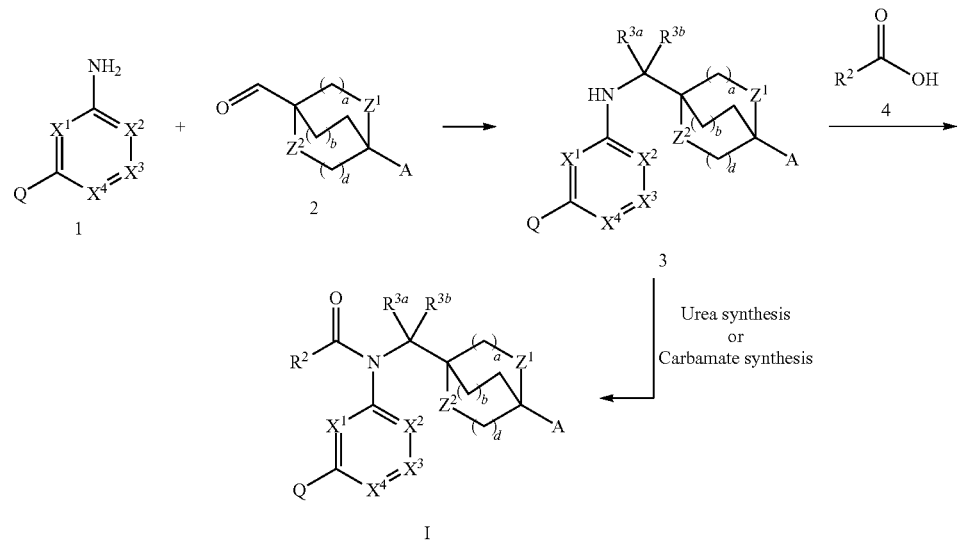

rt=room temperature
mL=milliliter
g=gram(s)
mg=milligram(s)
mmol=millimole(s)
LRMS=low resolution mass spectrometry
NMR=nuclear magnetic resonance
HPLC=high performance liquid chromatography Synthesis The compounds of the present invention can be prepared in a number of ways well known to one skilled in the art of organic synthesis. The compounds of the present invention can be synthesized using the methods described below, together with synthetic methods known in the art of organic chemistry, or variations thereon as appreciated by those skilled in the art. Preferred methods include, but are not limited to, those described below. All references cited herein are hereby incorporated in their entirety by reference.

The novel compounds of Formula I may be prepared using the reactions and techniques described in this section. The reactions are performed in solvents appropriate to the reagents and materials employed and are suitable for the transformations being effected. Also, in the description of the synthetic methods described below, it is to be understood Scheme 1 describes the synthesis of compounds of Formula I. Intermediate 3 can be synthesized by treating intermediate 1 and intermediate 2 under reductive amination conditions which are known methods recognizable by one skilled in the art. The imine synthesis can occur in presence of acid such as acetic acid in a suitable polar protic solvent (e.g. MeOH or EtOH) at room temperature or reflux temperature followed by reduction of imine with reducing agents (e.g. sodium cyanoborohydride or sodium triacetoxyborohydride) to afford intermediate 3. Intermediate 3 can be subjected to a variety of different transformations using numerous known methods recognized by one skilled in the art, including but not limited to the following methods to afford variations of Formula I:

Amides: Intermediate 4 can be obtained from commercial sources or can be synthesized by known methods readily recognizable by one skilled in the art. Intermediate 4 can be activated for acylation using any number of reagents recognizable by one skilled in the art (e.g. phosphorus oxychloride, thionyl chloride, oxalyl chloride, and methyl or ethylchloroformate), in a polar aprotic solvent (e.g. DCM or THF), at temperatures ranging between 130° C. to 0° C. The activated acid intermediate can then be reacted with intermediate 3 in presence of a base (e.g. 2-(dimethylamino)pyridine, N-methylmorpholine, pyridine, or DMAP) to generate compounds of Formula I.

Ureas: Intermediate 3 can be subjected to treatment with isocyanates in presence of base (e.g. Et₃N, DIPEA, or pyridine) in polar aprotic solvent (e.g. DCM or DCE) at room temperature to afford ureas represented by formula I. Alternatively, the intermediate 3 can be treated with triphosgene in presence of base (e.g. Et₃N or DIPEA) in solvent (e.g. DCM or DCE) at 0° C. to room temperature, followed by treatment with an amine in presence of base (e.g. Et₃N or DIPEA) in solvent (e.g. DCM or DCE) at room temperature to afford ureas represented by formula I.

Carbamates: Intermediate 3 can be treated with chloroformates (or alcohols, activated as carbonates) in presence of base (e.g. Et₃N, DIPEA, or pyridine) in polar aprotic solvent (e.g. DCM, DCE, or THF) at 0° C. to room temperature to afford carbamates represented by formula I.

Intermediates 1(a-n) (Scheme 1) can be accessed in various ways as depicted in Schemes 2-10 using numerous known methods recognized by the one skilled in the art including but not limited to the following methods.

SCHEME 3

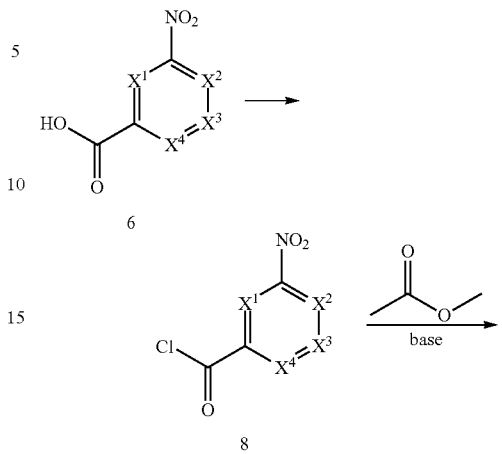

SCHEME 2

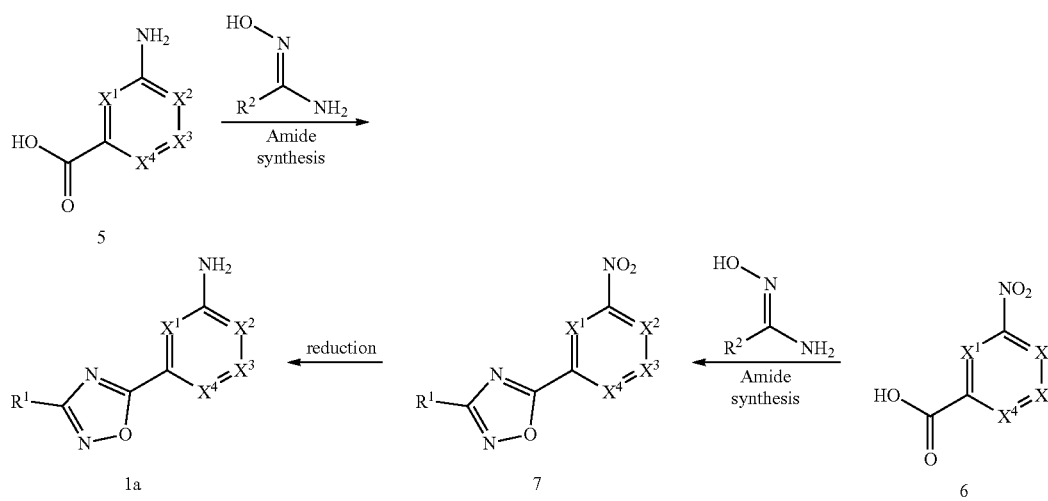

Scheme 2 describes the synthesis of intermediate 1a. Intermediates 5 and 6 can be obtained from commercial sources or can be synthesized by known methods readily recognizable by one skilled in the art. Intermediate 5 or 6 can be coupled with various substituted amide oximes (derived from the corresponding nitriles by reaction with hydroxylamine; see Hirawat, S., et al. WO 2006/110483) using an amide bond coupling reagent (e.g. CDI, BOP, and EDC) in a polar aprotic solvent (e.g. THF, 1,4-dioxane, or DMF) at room temperature. The acyclic intermediate can be subsequently cyclized at elevated temperatures (60° C. to 100° C.) to obtain intermediates 1a or intermediate 7. Alternatively, in situ cyclization can be accomplished by conducting the coupling of compound 5 or 6 with amide oximes at elevated temperatures (60° C. to 100° C.). The nitro intermediate 7 so obtained can be reduced using the conditions recognized by one skilled in the art including but not limited to reduction in presence of catalyst such as Pd and hydrogen gas at ambient pressure and temperature to yield intermediate 1a.

-continued

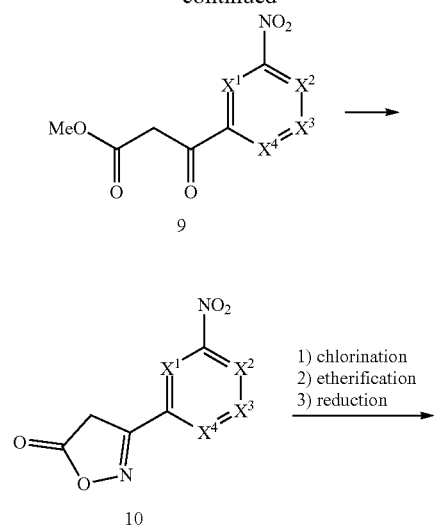

-continued

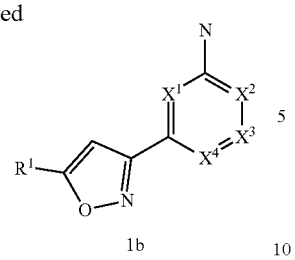

1b

-continued

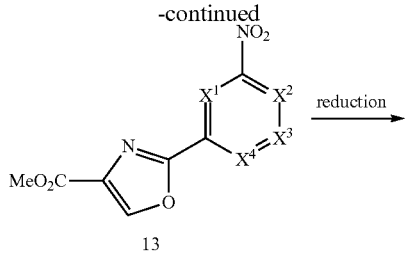

13

Scheme 3 describes the synthesis of intermediates 1b. Intermediate 8 can be prepared from intermediate 6 by using any number of reagents recognizable by one skilled in the art but not limited to the ones described here (e.g. phosphorus oxychloride, thionyl chloride, oxalyl chloride, methylchloroformate, or ethylchloroformate), in a polar aprotic solvent (e.g. DCM or THF), at temperatures ranging between −30° C. to reflux. Intermediate 8 can be treated with methyl acetate pre-treated with base such as n-BuLi in a solvent such as but not limited to THF or ether to afford intermediate 9 (as described by Douglass, T. et al. *J. Am. Chem. Soc.*, 1987, 109, 7488-7494). Alternatively, intermediate 9 can be synthesized as described in France, S. et al. *Org. Lett.* 2016, 18, 4218-4221. Intermediate 9 can be treated with hydroxylamine hydrochloride in polar protic solvent such as MeOH, EtOH or water in presence of base such as $K_2CO_3$ to afford intermediates represented by formula 10 (as described in Wittman, M. D., et al. WO 2015/195880 A1). Intermediate 10 can be treated with reagents such as $POCl_3$ and $SOCl_2$ in presence of base such as $Et_3N$ or DIPEA for chlorination (as described in Wittman, M. D., et al. WO 2015/195880 A1) followed by treatment with metal alkoxides to afford corresponding substituted intermediates which can be reduced in presence of catalyst such as Pd and hydrogen gas at ambient pressure and temperature to yield intermediate 1b.

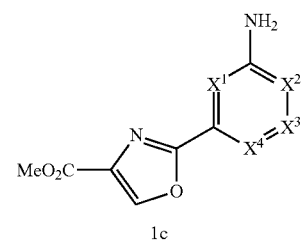

1c

Scheme 4 describes the synthesis of intermediates 1c. Intermediate 11 can be obtained from commercial sources or can be synthesized by known methods readily recognizable by one skilled in the art. Intermediate 11 can be condensed with serine ester in presence of base (e.g. $Et_3N$ or DIPEA) and dehydrating agent such as $MgSO_4$ to afford intermediate 12. Intermediate 12 can be converted to intermediate 13 by treatment with $BrCCl_3$ and base such as DBU in chlorinated solvent ($CH_2Cl_2$ or DCE) at ambient temperature as described in Graham, T. H., *Org. Lett.*, 2010, 12, 3614-3617. The nitro intermediate 13 can be reduced, using the conditions recognized by one skilled in the art including but not limited to reduction in presence of catalyst such as Pd and hydrogen gas at ambient pressure and temperature to yield intermediates 1c.

SCHEME 4

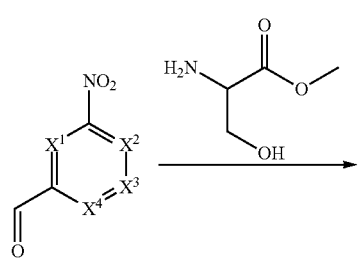

11

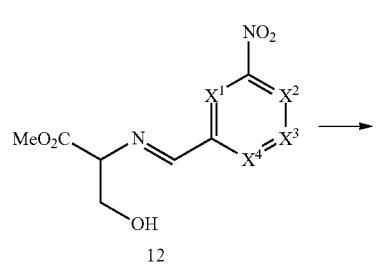

12

SCHEME 5

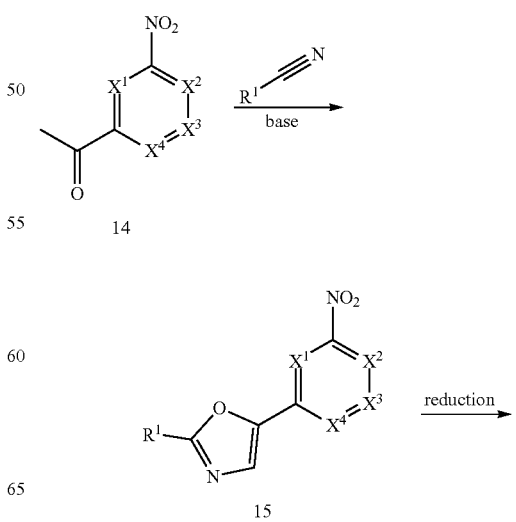

-continued

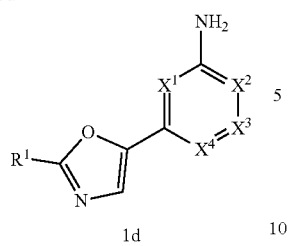

1d

-continued

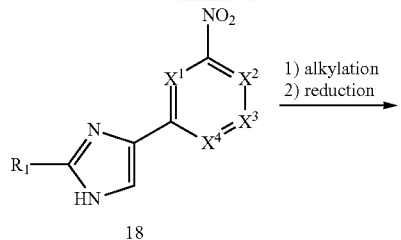

1) alkylation
2) reduction

18

Scheme 5 describes the synthesis of intermediates 1d. Intermediates 14 can be obtained from commercial sources or can be synthesized by known methods readily recognizable by one skilled in the art. Intermediates 14 can be treated with iodobenzene diacetate in presence of trifluoromethane sulfonic acid and substituted nitrile to afford oxazoles as described in Varma, R. S. et al *J. Heterocyclic Chem.* 1998, 35, 1533. The nitro intermediate 15 so obtained can be reduced, using the conditions recognized by one skilled in the art, including but not limited to reduction in presence of catalyst such as Pd and hydrogen gas at ambient pressure and temperature to yield intermediates 1d.

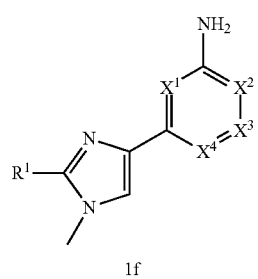

1f

SCHEME 6

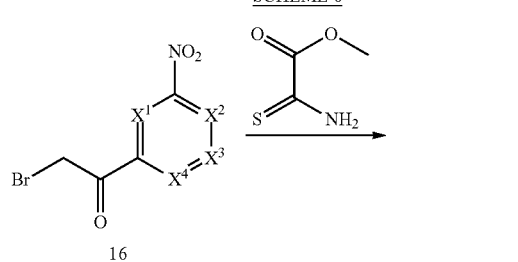

16

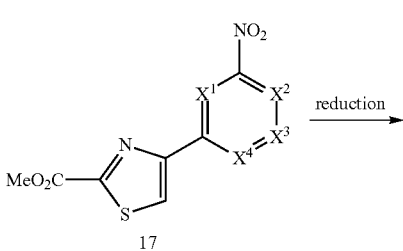

17

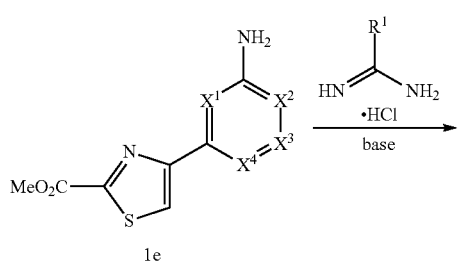

1e

Scheme 6 describes the synthesis of intermediates 1e and 1f. Intermediate 16 can be obtained from commercial sources or can be synthesized by known methods or their modifications readily recognizable by one skilled in the art (described as in *Bioorg. & Med. Chem. Lett.*, 2017, 27, 2192-2196). Intermediate 16 can be treated with methyl thiooxamate under heating conditions in protic polar solvent (e.g. MeOH or EtOH) to afford compounds represented by intermediate 17 as described in Wright, S. W., *J. Med. Chem.* 2002, 45, 3865-3877. The nitro intermediate 17 so obtained can be reduced, using the conditions recognized by one skilled in the art, including but not limited to reduction in presence of catalyst such as Pd and hydrogen gas at ambient pressure and temperature to yield intermediates 1e. Alternatively, intermediate 16 can be treated with an amidine in polar aprotic solvent (MeCN or DMF) in presence of base such as $K_2CO_3$ under heating conditions to afford intermediate 18. Intermediate 18 can be alkylated, using numerous known methods recognized by one skilled in the art, including but not limited to, treatment under basic conditions in presence of alkylating agent to generate N-alkyl imidazole intermediate which can be reduced in presence of catalyst such as Pd and hydrogen gas at ambient pressure and temperature to yield intermediate 1f.

SCHEME 7

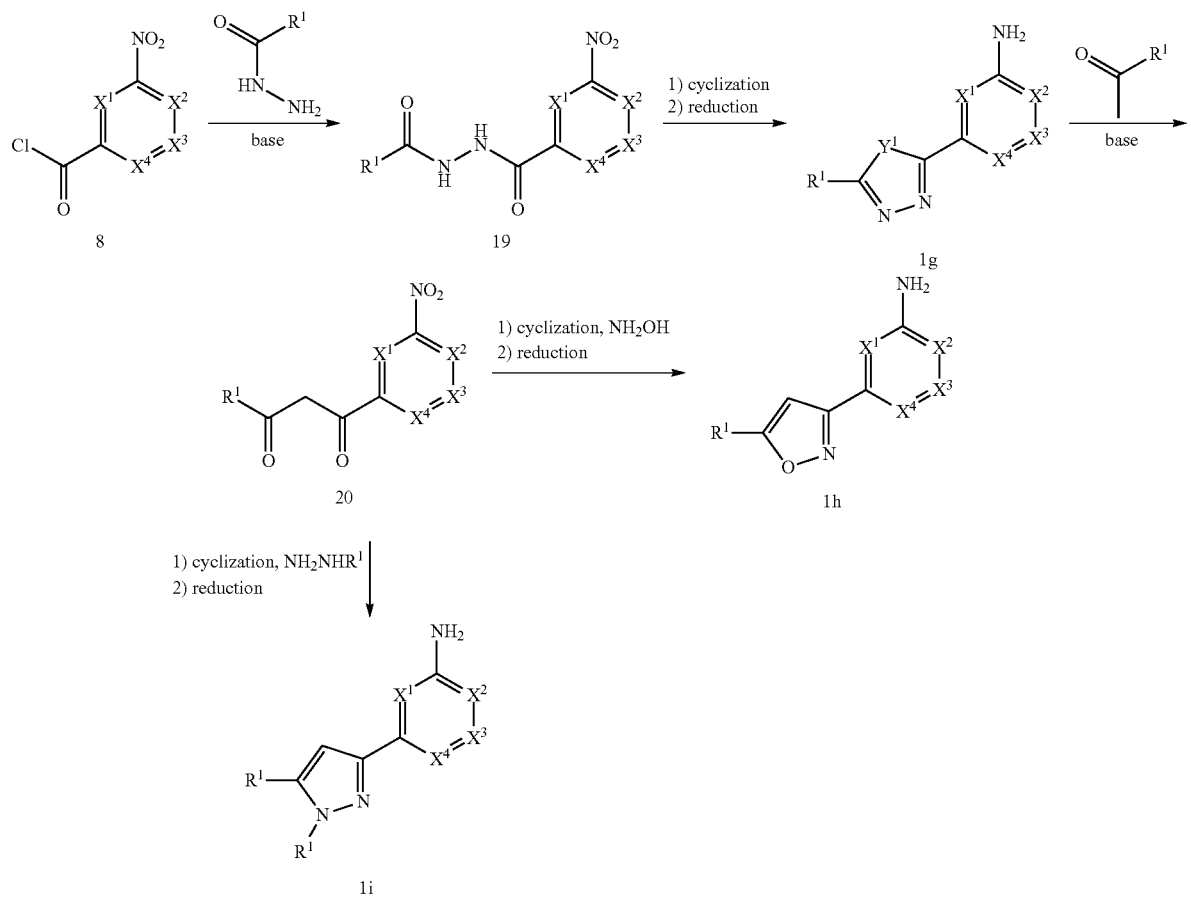

Intermediates 1g, 1h, or 1i can be synthesized from intermediate 8 following the synthetic procedures outlined in Scheme 7. Intermediate 8 can be coupled with acid hydrazide in a polar aprotic solvent (e.g. THF, 1,4-dioxane DMF, or MeCN) and in presence of base (e.g. $Et_3N$ or DIPEA) to obtain intermediate 19. Intermediate 19 can then be cyclized to either 1,3,4-oxadiazole or 1,3,4-thiadiazole using respectively, 4-toluenesulfonic acid (Stabile, P. et al. *Tetrahedron Lett.* 2010, 51, 4801-4805) or Laweson's reagent (Kitamura, S., et al. PCT Int. Appl., 2008011130, 2008). The cyclized intermediate so obtained can be reduced in presence of catalyst such as Pd and hydrogen gas at ambient pressure and temperature to yield intermediate 1g.

Methyl ketones can be pre-treated with base and then reacted with intermediate 8 to afford intermediate 20 as described in France, S. et al. *Org. Lett.* 2016, 18, 4218-4221. Intermediate 20 can be treated with a hydrazine salt in polar protic solvent (such as MeOH and EtOH) under heating conditions to afford a pyrazole. (As described in Cadilla, R., et al. WO 03/074495 A1). The nitro intermediate so obtained can be reduced in presence of catalyst such as Pd and hydrogen gas at ambient pressure and temperature to yield intermediate 1i.

The intermediate 20 can also be subjected to reaction with hydroxyl amine hydrochloride salt in polar protic solvent such as ethanol at reflux temperature to afford substituted isoxazole (as described in Cadilla, R., et al. WO 03/074495 A1). The nitro intermediate so obtained can be reduced in presence of catalyst such as Pd and hydrogen gas at ambient pressure and temperature to yield intermediate 1h.

SCHEME 8

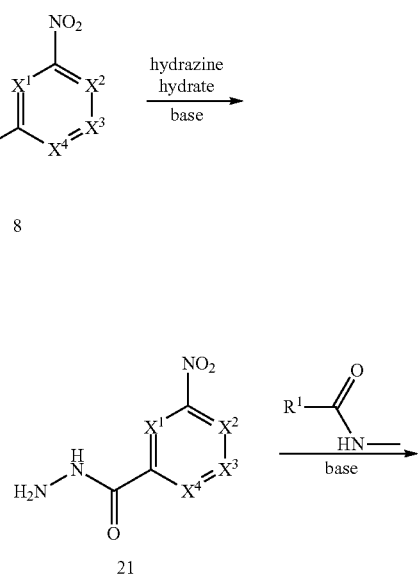

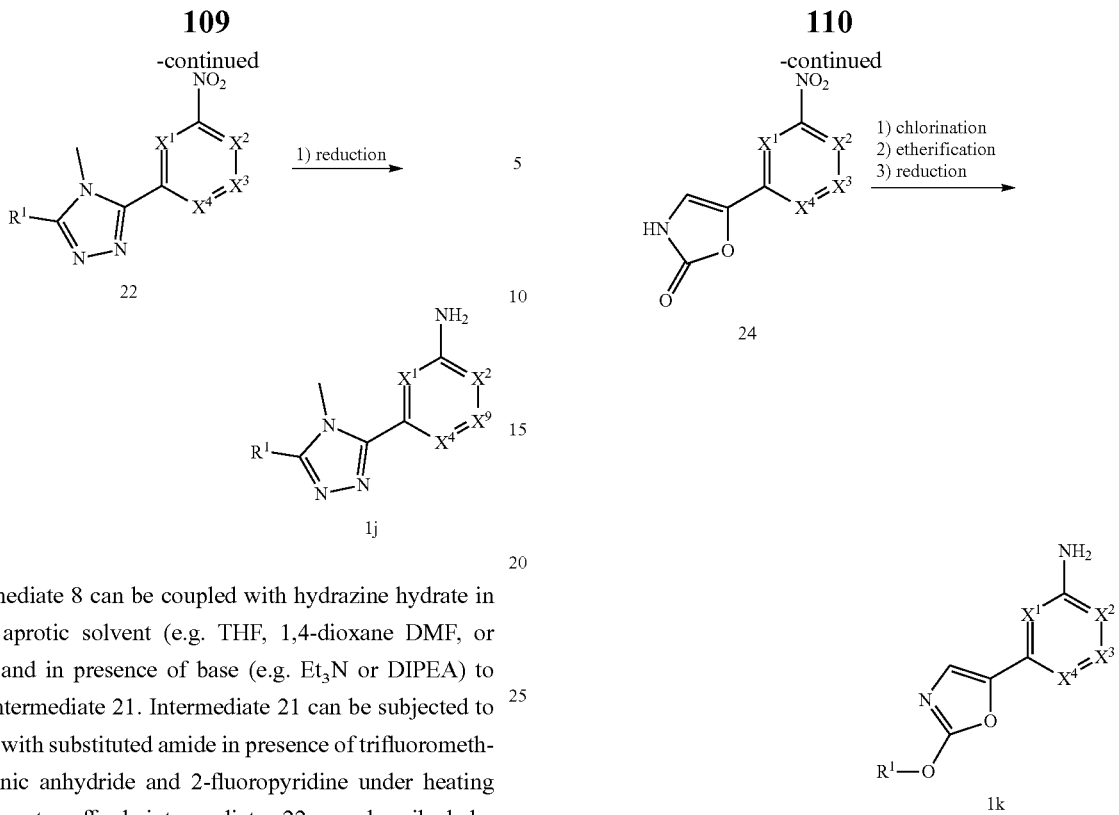

Intermediate 8 can be coupled with hydrazine hydrate in a polar aprotic solvent (e.g. THF, 1,4-dioxane DMF, or MeCN) and in presence of base (e.g. Et$_3$N or DIPEA) to obtain intermediate 21. Intermediate 21 can be subjected to reaction with substituted amide in presence of trifluoromethanesulfonic anhydride and 2-fluoropyridine under heating conditions to afford intermediate 22 as described by Charette, A. B. et al. *Org. Lett.*, 2015, 17, 1184-1187. Intermediate 22 so obtained can be reduced, using the conditions recognized by one skilled in the art including but not limited to reduction in the presence of a catalyst such as Pd and hydrogen gas at ambient pressure and temperature to yield intermediate 1j.

SCHEME 9

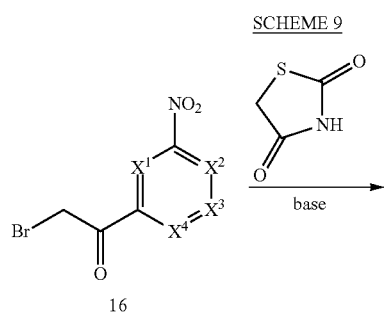

Scheme 9 describes the synthesis of intermediates 1k. Intermediate 16 can be obtained from commercial sources or can be synthesized by known methods or their modifications readily recognizable by one skilled in the art (described as in *Bioorg. & Med. Chem. Lett.*, 2017, 27, 2192-2196). Intermediate 16 can be treated with thiazolidinedione in polar solvents such as DMF or DMAc in presence of base such as K$_2$CO$_3$ and Na$_2$CO$_3$ at room temperature or heating conditions to afford intermediate 24 (as described in Brown, M. L. et al. WO 2004/032882 A2). Intermediate 24 can be treated with reagents such as POCl$_3$ or SOCl$_2$ in presence of base such as Et$_3$N and DIPEA for chlorination (as described in Brown, M. L. et al. WO 2004/032882 A2) followed by treatment with metal alkoxides to afford corresponding substituted intermediates which upon reduction as described in Scheme 3 afford intermediate 1k.

SCHEME 10A

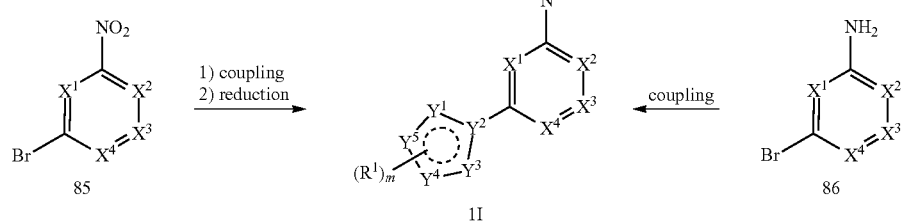

Scheme 10A describes synthesis of intermediates 11 (where $Y^2$ is 'N'-atom). Intermediates 85 and 86 can be obtained from commercial sources or can be synthesized by known methods readily recognizable by one skilled in the art. Intermediates 85 and 86 can be subjected to various metal catalyzed reactions (including but not limited to reactions such as Ullmann and Buchwald reactions) in presence of metal catalyst (e.g. CuI, CuBr, Cu(OAc)$_2$, Cu$_2$O, Pd(OAc)$_2$, Pd$_2$(dba)$_3$, or Pd(dppf)Cl$_2$) and appropriate ligand (including but not limited to ligands such as 1,10-phenanthroline, L-proline, tricyclohexylphosphine, dppf, or β-ketoesters) when necessary. The Ullmann and Buchwald coupling reactions of intermediate 85 and 86 can be carried out with various coupling partners including but not limited to substituted or unsubstituted pyrrole, pyrazole, imidazole, triazole, indole, indazole, benzimidazole, benzotriazole, and cyclic amides. The coupling reactions can be carried out in presence of base whenever necessary (bases including but not limited to Na$_2$CO$_3$, K$_2$CO$_3$, Cs$_2$CO$_3$, K$_3$PO$_4$, NaOtBu, or DBU) and solvent (e.g. dioxane, THF, DME, MeCN, DMSO, DMF, or MeOH) under heating conditions to afford intermediate 11 from intermediate 86. The coupled N-linked heteroaryl nitro intermediate obtained from 85 can be subjected to reduction using the conditions recognized by one skilled in the art including but not limited to reduction in presence of catalyst such as Pd and hydrogen gas or Zn and ammonium chloride or Fe and acetic acid to yield intermediate 11.

presence of metal catalyst (e.g. CuBr, Pd(OAc)$_2$, Pd$_2$(dba)$_3$, Pd(PPh$_3$)$_4$, Pd(PPh$_3$)$_2$Cl$_2$, or Pd(dppf)Cl$_2$) and appropriate ligand (including but not limited to ligands such as proline, 1,10-phenanthroline, tricyclohexylphosphine, and dppf) as and when required. The Ullmann and Buchwald coupling reactions of intermediate 86 can be carried out with various coupling partners such as heterocyclyl or heteroaryl amines. The Suzuki, Chan-Lam coupling reaction of intermediate 88 and 89 can be carried out with various coupling partners such as cycloalkenyl, aryl halides, heteroaryl halides, and triflates. Intermediate 86 can be subjected to Suzuki and Stille cross couplings with coupling partners such as cycloalkyl or alkenyl or aryl or heteroaryl boronic acids, boronic acid esters, and organotin reagents. The coupling reactions can be carried out in presence of base as necessary (including but not limited to Na$_2$CO$_3$, K$_2$CO$_3$, NaHCO$_3$, K$_3$PO$_4$, or NaOtBu) and solvent (e.g. dioxane, THF, DME, toluene, methanol, DMF, or water or the mixture of two or three of these solvents) under heating conditions to afford intermediate 1m. Alternatively, intermediate 86 can be converted to organotin reagent using hexamethylditin in presence of a palladium catalyst and in solvent (e.g. toluene or THF) at reflux temperature, which upon coupling with suitable coupling partners such as cycloalkenyl, aryl or heteroaryl halides, and triflates in a Stille coupling (Sherer, B., et al. PCT Int. Appl., 2016/039734, 2016) to afford

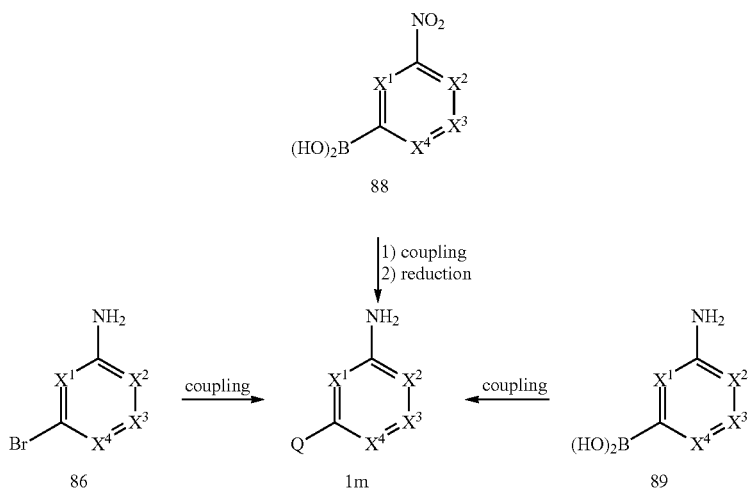

SCHEME 10B

Intermediate 1m can be accessed in various ways as depicted in Scheme 10B. Intermediates 86, 88 and 89 can be obtained from commercial sources or can be synthesized by known methods readily recognizable by one skilled in the art. Intermediates 86, 88 and 89 can be subjected to metal catalyzed cross coupling reactions using numerous known methods recognized by the one skilled in the art including but not limited to the ones described in Metal-Catalyzed Cross-Coupling Reactions, Armin de Meijere, François Diederich, 2 Volumes, Second, Revised and Enlarged Edition, 2004, ISBN: 3-527-30518-1, Wiley-VCH and references cited therein. Intermediate 86, 88 and 89 can be subjected to various metal catalyzed reactions (including but not limited to reactions such as Ullmann, Buchwald, Suzuki, and Stille coupling). These coupling reactions can be carried out in intermediate 1m. Intermediate 86 can be converted to organoboron reagent using bis(pinacolato)diboron and bis (neopentyl glycolato)diboron, for example, in presence of a palladium catalyst such as Pd(dppf)Cl$_2$ and base such as potassium acetate in solvent (e.g. dioxane or DMSO) at reflux temperature, which then can be coupled with suitable coupling partners such as cycloalkenyl, aryl halides, heteroaryl halides, and triflates in a Suzuki coupling to afford intermediate 1m. Intermediate 88 followed by the coupling reactions as described above afforded the nitro intermediate, which can be reduced using the conditions recognized by one skilled in the art including but not limited to reduction in presence of catalyst such as Pd and hydrogen gas at ambient pressure and temperature to yield intermediate 1m.

SCHEME 10C

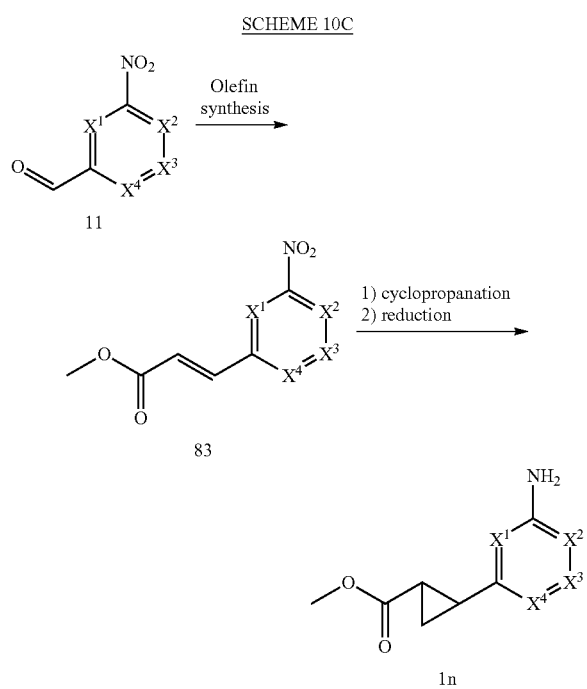

Scheme 10C describes the synthesis of intermediates 1n. Intermediate 11 can be obtained from commercial sources or can be synthesized by known methods readily recognizable by one skilled in the art. Intermediate 11 can be subjected to reaction with alkyl 2-(dimethoxyphosphoryl)acetate in presence of a base (e.g. $K_2CO_3$ or $Na_2CO_3$) in polar protic solvent (e.g. water, methanol or ethanol) to afford intermediate 83. Intermediate 83 can be subjected to cyclopropanation reaction by treating it with diazomethane solution at −78° C. in solvent mixture containing diethyl ether and DCM in presence of $Pd(OAc)_2$ to afford nitro intermediate, which can be reduced to intermediate 1n using the conditions recognized by one skilled in the art including but not limited to one described such as heating in presence of reagent such as tin(II) chloride in polar protic solvent. Intermediate in can be converted to compounds of formula I by using steps described in Scheme 1.

Intermediates 2 (Scheme 1) can be accessed in various ways as depicted in Scheme 11 using numerous known methods recognized by the one skilled in the art including but not limited to the following methods.

SCHEME 11

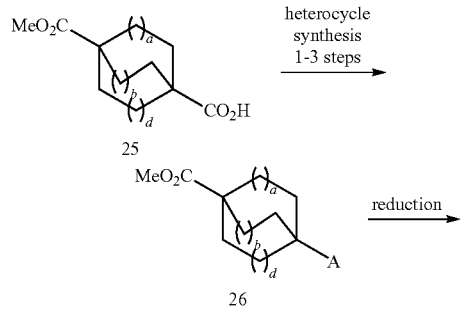

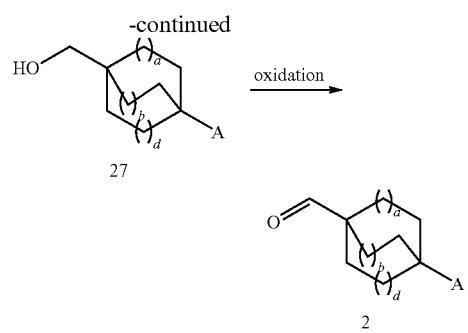

Scheme 11 describes the synthesis of intermediate 2. Commercially available 4-(methoxycarbonyl)bicyclo[2.2.2]octane-1-carboxylic acid 25 can be subjected to heterocycle ring synthesis to afford compounds of intermediate 26.

Heterocycle formation (A). The carboxylic acid moiety of compound 25 can be converted to various heterocycles (A) using numerous known methods recognized by one skilled in the art, including but not limited to the following methods:

A=1,2,4-oxadiazole. Intermediate 25 can be coupled with various amide oximes (derived from the corresponding nitriles by reaction with hydroxylamine; see Hirawat, S., et al. WO 2006/110483) using an amide bond coupling reagent (e.g. CDI, BOP, or EDC) in a polar aprotic solvent (e.g. THF, 1,4-dioxane, or DMF) at room temperature. The acyclic intermediate can be subsequently cyclized at elevated temperatures (60° C. to 100° C.). Alternatively, in situ cyclization can be accomplished by conducting the coupling of acid 25 with amide oximes at elevated temperatures (60° C. to 100° C.).

A=1,2,5-oxadiazole. Intermediate 25 can be converted to 1,2,5-oxadiazole as described in Broström, J. et al. *J. Med. Chem.* 2012, 55, 1817-1830 and references described therein.

A=1,3,4-oxadiazole or A=1,3,4-thiadiazole. Intermediate 25 can be coupled with acetic acid hydrazide (described in WO 2014/071247, Bradner, J. E., et al.), using an amide bond coupling reagent (e.g. CDI, BOP, or EDC) in a polar aprotic solvent (e.g. THF, 1,4-dioxane DMF, or MeCN). The acyclic hydrazide intermediate can then be cyclized to either 1,3,4-oxadiazole or 1,3,4-thiadiazole using respectively, 4-toluenesulfonic acid (Stabile, P. et al. *Tetrahedron Lett.* 2010, 51, 4801-4805) or Lawesson's reagent (Kitamura, S., et al. PCT Int. Appl., 2008011130, 2008).

A=3-substituted 5-alkyl-1-methyl-1H-pyrazole. Methyl ketones can be treated with base and acid chloride of intermediate 25 to afford a diketone, which upon reaction with substituted or unsubstituted hydrazine salt in polar protic solvent such as ethanol at reflux temperature afforded ester 26 where A is alkyl substituted or unsubstituted pyrazole. (As described in Cadilla, R., et al. WO 03/074495 A1).

A=Isoxazole. The diketone prepared from intermediate 25 as described above can be upon reaction with hydroxyl amine hydrochloride salt in polar protic solvent such as ethanol at reflux temperature afforded ester 26 where A is alkyl substituted isoxazole (as described in Cadilla, R., et al. WO 03/074495 A1).

A=5-(3-alkyl-1-methyl-1H-pyrazole). The diketone prepared from intermediate 25 as described above can be upon reaction with alkyl hydrazine in polar protic solvent such as ethanol at reflux temperature afforded ester 26 where A is alkyl substituted pyrazole.

A=substituted heteroaryl. Intermediate 25 can be subjected to Minisci reaction with substituted heteroaryl compounds (including but not limited to heteroaryl rings such as pyridine, pyrimidine, pyridazine, pyrazine, quinoline, pyrazole) in presence of silver nitrate and potassium persulfate or ammonium persulfate in DCM (or any other conditions that can be used to generate carbon-centered radical) and water mixture as a solvent at ambient temperature to afford ester 26 (as described in Ling-Bo, Qu et al. *Org. Biomol. Chem.*, 2015, 13, 2750-2755 and Review: Duncton, M. A. *J. Med. Chem. Commun.*, 2011, 2, 1135-1161 and references described therein).

A=2-Benzothiazole. Method A: Intermediate 25 can be coupled with substituted 2-aminobenzenethiol (See generally Chedekel, M. R., et al. *Synth. Commun.* 1980, 10, 167-173; synthesis of various 2-aminobenzenethiols), using an amide bond coupling reagent (e.g. BOP, $T_3P$, or EDC) in a polar aprotic solvent (e.g. DCE or THF). The coupling reaction can be conducted at elevated temperatures (60° C. to 80° C.) thereby accomplishing the in situ formation of the cyclized 2-benzothiazole.

Method B: Alternatively, intermediate 25 can be coupled with substituted 2-chloroaniline (commercial available) using an amide bond coupling reagent (e.g. T3P or BOP), or by activating intermediate 25 for acylation using any number of reagents (e.g. oxalyl chloride or $POCl_3$). The resultant carboxamide can be treated with Lawesson's reagent at elevated temperature (120° C.), thereby accomplishing an in situ cyclization to 2-benzothiazole.

A=2-Benzoxazole. Intermediate 25 can be coupled with substituted 2-aminophenol (commercial available) using an amide bond coupling reagent (e.g. BOP or EDC), in a polar aprotic solvent (e.g. DMF or THF). Cyclization can be accomplished in refluxing toluene in the presence of tosic acid.

A=2-Benzimidazole. Intermediate 25 can be coupled with ethyl 3,4-diaminobenzoate using an amide bond coupling reagent (e.g. TBTU, T3P, or PyBOP) in a polar aprotic solvent (e.g. DMF or NMP), then cyclized to the 2-benzimidazole under acidic conditions (AcOH neat) at elevated temperatures (115° C.).

A=2-Quinazoline. Intermediate 25 can be coupled with 4-amino-3-(aminomethyl)benzoate dihydrochloride (Pascal, R. et al. *Eur. J. Org. Chem.* 2000, 22, 3755-3761), using an amide bond coupling reagent (e.g. HBTU, EDC, or PyBOP) in a polar aprotic solvent (e.g. MeCN or THF). Cyclization can be accomplished under acidic conditions (AcOH neat) at elevated temperatures (115° C.). The resultant dihydroquinazoline intermediate can be oxidized to the 2-quinazoline using an oxidizing agent such as DDQ.

A=1-triazole. Intermediate 25 can be converted to corresponding amine via Curtius rearrangement (as described in Shioiri, T. et al. *J. Am. Chem. Soc.* 1972, 94, 6203-6205). The amine upon treatment with reagent such asp-toluene sulfonyl azide can be converted to corresponding azide which upon reaction with suitable alkyne (as described in Boren, B. C. et al *J. Am. Chem. Soc.*, 2008, 130, 8923-8930) afforded triazole.

A=Substituted 1,2,4-triazole. Intermediate 25 can be converted to corresponding hydrazide and can be subjected to reaction with substituted carboxamide in presence of trifluoromethanesulfonic anhydride and 2-fluoropyridine under heating conditions as described by Charette, A. B. et al. *Org. Lett.*, 2015, 17, 1184-1187. 'A' can be other heterocycles such as substituted as well as unsubstituted oxazoles, thiazoles imidazoles, isoxazoles, triazoles, pyrazoles and can be synthesized as described in reference: Wlochal, J. et al *Org. Lett.* 2014, 16, 4094-4097 and references cited therein. Alternatively, acid functional group of intermediate 25 can be converted to heterocycles as described in schemes 2-9 using methods and literature references described therein.

Intermediate 26 can be subjected to reduction by a reducing agent (e.g. LAH, DIBAL-H, or $NaBH_4$) in chlorinated or ethereal solvent (e.g. DCM, ether, 1,4-dioxane, or THF) to afford intermediate 27. Intermediate 27 can be oxidized by methodologies recognized by one skilled in the art using oxidation conditions (e.g. Dess-Martin periodane, Swern oxidation conditions, or PDC) to afford intermediate 2.

Scheme 12 (FIG. 1) describes an alternative synthesis of compounds of Formula I with the modified sequence of steps. Commercially available 4-(methoxycarbonyl) bicyclo [2.2.2]octane-1-carboxylic acid 25 can be subjected to reduction in presence of hydride based reducing agent (e.g. LAH, DIBAL-H, or $NaBH_4$) to afford intermediate 28. Intermediate 28 can be oxidized to intermediate 29, by methodologies recognized by one skilled in the art using oxidation conditions (e.g. Dess-Martin periodane, Swern oxidation conditions, PDC, or PCC). The intermediate 1 and intermediate 29 can be reacted in presence of acid such as acetic acid in a suitable polar protic solvent (e.g. MeOH or EtOH) at room temperature or reflux temperature followed by reduction with reducing agents (e.g. sodium cyanoborohydride or sodium triacetoxyborohydride) to afford intermediate 30. Intermediate 4 can be activated for acylation using any number of reagents recognizable by one skilled in the art (e.g. thionyl chloride, phosphorus oxychloride, oxalyl chloride, methylchloroformate, or ethylchloroformate), in a polar aprotic solvent (e.g. DCM or THF), at temperatures ranging between −30° C. to 0° C. The activated acid intermediate can be reacted with intermediate 30 in presence of a base to generate corresponding amide. Subsequent hydrolysis of the methyl ester with an alkali hydroxide base can provide intermediate 31. Intermediate 31 can be converted to various heterocycles (A) using numerous known methods recognized by one skilled in the art, including but not limited to the methods described in Scheme 11 to afford compounds of formula I.

Alternatively, intermediate 29 and intermediate 86 can be subjected to reductive amination using numerous known methods recognizable by one skilled in the art. The imine synthesis in presence of acid such as acetic acid in a suitable polar protic solvent (e.g. MeOH or EtOH) at room temperature or reflux temperature followed by reduction of imine with reducing agents (e.g. sodium cyanoborohydride or sodium triacetoxyborohydride) afforded intermediate 30a. Intermediate 4 can be activated for acylation using any number of reagents recognizable by one skilled in the art (e.g. thionyl chloride, phosphorus oxychloride, oxalyl chloride, methylchloroformate, or ethylchloroformate), in a polar aprotic solvent (e.g. DCM or THF), at temperatures ranging between −30° C. to 0° C. The activated acid intermediate can be reacted with intermediate 30a in presence of a base to generate corresponding amide. Subsequent hydrolysis of the methyl ester with an alkali hydroxide base can provide intermediate 31a. Intermediate 31a can be converted to various heterocycles (A) using numerous known methods recognized by one skilled in the art, including but not limited to the methods described in Scheme 11 to afford intermediate 31b. Intermediate 31b can be subjected to metal catalyzed cross coupling reactions using numerous known methods recognized by one skilled in the art including but not limited to the ones described in Metal-Catalyzed Cross-Coupling Reactions, Armin de Meijere, François Diederich, 2 Volumes, Second, Revised and Enlarged Edition, 2004, ISBN: 3-527-30518-1, Wiley-VCH and references cited therein. Intermediate 31b can also be subjected to various metal catalyzed reactions (including but not limited to reactions such as Ullmann, Buchwald, Suzuki and Stille coupling). These coupling reactions can be carried out in presence of metal catalyst (e.g. CuBr, Pd (OAc)$_2$, Pd$_2$(dba)$_3$, Pd(PPh$_3$)$_4$, Pd(PPh$_3$)$_2$Cl$_2$, or Pd(dppf)Cl$_2$) and appropriate ligand (including but not limited to ligands such as proline, 1,10-phenanthroline, tricyclohexylphosphine, and dppf) as and when required. The Ullmann and Buchwald coupling reactions of intermediate 31b can be carried out with various coupling partners such as heterocyclyl amines and heteroaryl amines. Intermediate 31b can be subjected to Suzuki and Stille cross couplings with coupling partners such as cycloalkyl boronic acids, alkenyl boronic acids, aryl boronic acids, heteroaryl boronic acids, boronic acid esters, and organotin reagents, for example. The coupling reactions can be carried out in presence of base as necessary (including but not limited to Na$_2$CO$_3$, K$_2$CO$_3$, NaHCO$_3$, K$_3$PO$_4$, or NaOtBu) and solvent (e.g. dioxane, THF, DME, toluene, methanol, DMF, or water or the mixture of two or three of these solvents) under heating conditions to afford compounds of formula I. Alternatively, intermediate 31b can be converted to organotin reagent using hexamethylditin in presence of a palladium catalyst and in solvent (e.g. toluene or THF) at reflux temperature, which upon coupling with suitable coupling partners such as cycloalkenyl, aryl or heteroaryl halides, and triflates in a Stille coupling (Sherer, B., et al. PCT Int. Appl., 2016/039734, 2016) afforded compounds represented by formula I. Intermediate 31b can be converted to organoboron reagent using bis(pinacolato)diboron or bis(neopentyl glycolato)diboron, for example, in presence of a palladium catalyst such as Pd(dppf)Cl$_2$ and base such as potassium acetate in solvent (e.g. dioxane or DMSO) at reflux temperature, which upon coupling with suitable coupling partners such as cycloalkenyl, aryl or heteroaryl halides, and triflates in a Suzuki coupling afforded compounds represented by formula I.

Figure 2:
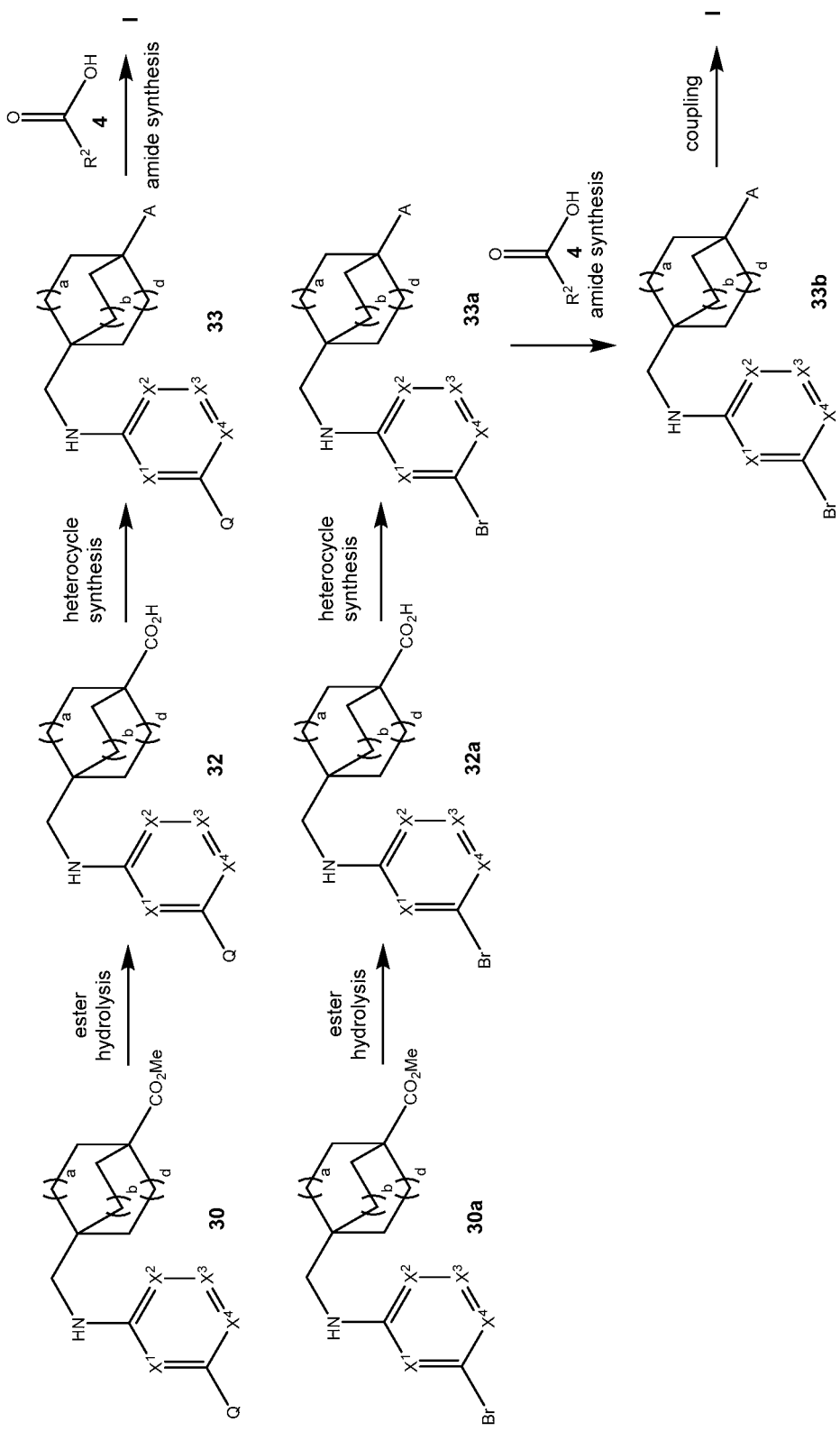
FIG. 2 shows the general reaction Scheme 13.

Scheme 13 (FIG. 2) describes an alternative synthesis of compounds of Formula I with the modified sequence of steps.

Intermediate 30 (described in Scheme 12) can be subjected to hydrolysis of the methyl ester with an alkali hydroxide base to provide intermediate 32. Intermediate 32 can be converted to various heterocycles (A) using numerous known methods recognized by one skilled in the art, including but not limited to the methods described in Scheme 11 to afford compounds of formula 33. Intermediate 4 can be activated for acylation using any number of reagents recognizable by one skilled in the art (e.g. thionyl chloride, phosphorus oxychloride, oxalyl chloride, methylchloroformate, or ethylchloroformate), in a polar aprotic solvent (e.g. DCM or THF), at temperatures ranging between −30° C. to 0° C. The activated acid intermediate can be reacted with intermediate 33 in presence of a base to generate compounds of formula I.

Alternatively, intermediate 30a (described in Scheme 12) can be subjected to hydrolysis of the methyl ester with an alkali hydroxide base to provide intermediate 32a. Intermediate 32a can be converted to various heterocycles (A) using numerous known methods recognized by one skilled in the art, including but not limited to the methods described in Scheme 11 to afford compounds of formula 33a. Intermediate 4 can be activated for acylation using any number of reagents recognizable by one skilled in the art (e.g. thionyl chloride, phosphorus oxychloride, oxalyl chloride, methylchloroformate or ethylchloroformate), in a polar aprotic solvent (e.g. DCM or THF), at temperatures ranging between −30° C. to 0° C. The activated acid intermediate can be reacted with intermediate 33a in presence of a base to generate intermediate 33b. Intermediate 33b can be subjected to metal catalyzed cross coupling reactions using numerous known methods recognized by the one skilled in the art including but not limited to the ones described in Metal-Catalyzed Cross-Coupling Reactions, Armin de Meijere, François Diederich, 2 Volumes, Second, Revised and Enlarged Edition, 2004, ISBN: 3-527-30518-1, Wiley-VCH and references cited therein. The amide intermediate can be subjected to various metal catalyzed reactions (including but not limited to reactions such as Ullmann, Buchwald, Suzuki, and Stille couplings). These coupling reactions can be carried out in presence of metal catalyst (e.g. CuBr, Pd(OAc)$_2$, Pd$_2$(dba)$_3$, Pd(PPh$_3$)$_4$, Pd(PPh$_3$)$_2$Cl$_2$, or Pd(dppf)Cl$_2$) and appropriate ligand (including but not limited to ligands such as proline, 1,10-phenanthroline, tricyclohexylphosphine, or dppf) as and when required. The Ullmann and Buchwald coupling reactions of intermediate 33b can be carried out with various coupling partners such as heterocyclyl amines and heteroaryl amines. Intermediate 33b can be subjected to Suzuki and Stille cross couplings with coupling partners such as cycloalkyl or alkenyl or aryl or heteroaryl boronic acids, boronic acid esters, and organotin reagents. The coupling reactions can be carried out in presence of base as necessary (including but not limited to Na$_2$CO$_3$, K$_2$CO$_3$, NaHCO$_3$, K$_3$PO$_4$, or NaOtBu) and solvent (e.g. dioxane, THF, DME, toluene, methanol, DMF, or water or the mixture of two or three of these solvents) under heating conditions to afford compounds of formula I. Alternatively, intermediate 33b can be converted to organotin reagent using hexamethylditin in presence of a palladium catalyst and in solvent (e.g. toluene and THF) at reflux temperature, which upon coupling with suitable coupling partners such as cycloalkenyl halides, aryl halides, heteroaryl halides, and triflates in a Stille coupling (Sherer, B., et al. PCT Int. Appl., 2016/039734, 2016) afforded compounds represented by formula I. Intermediate 33b can be converted to organoboron reagent using bis(pinacolato)diboron or bis(neopentyl glycolato)diboron, for examples, in presence of a palladium catalyst such as Pd(dppf)Cl$_2$ and base such as potassium acetate in solvent (e.g. dioxane or DMSO) at reflux temperature, which upon coupling with suitable coupling partners such as cycloalkenyl halides, aryl halides, heteroaryl halides, and triflates in a Suzuki coupling afforded compounds represented by formula I.

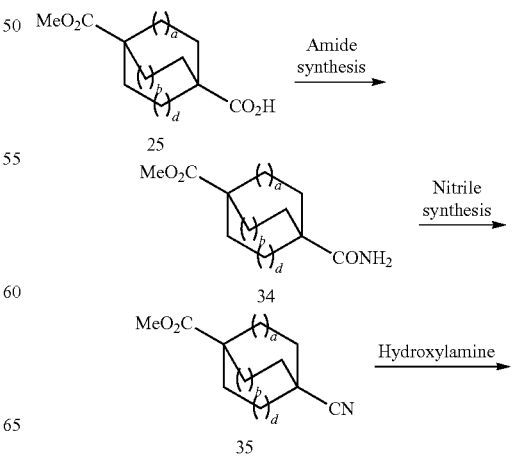

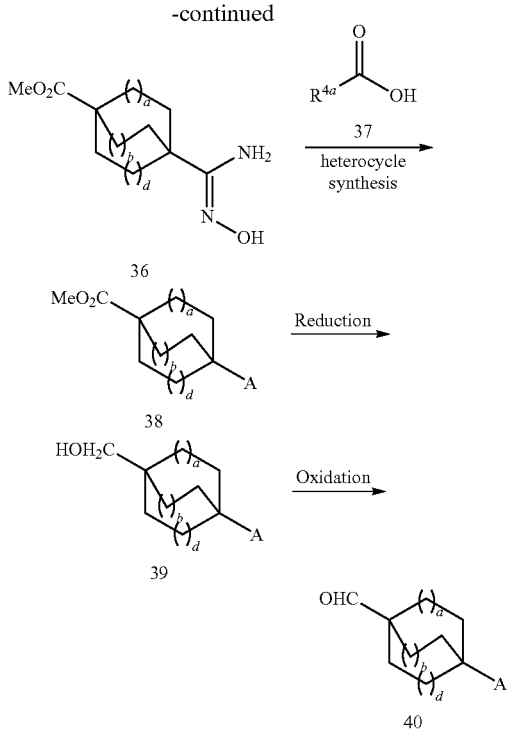

Scheme 14 describes the synthesis of intermediate 40 where A is 3-(5-substituted-1,2,4-oxadiazolyl) ring. Commercially available 4-(methoxycarbonyl)bicyclo[2.2.2]octane-1-carboxylic acid 25 can be subjected to amide synthesis by treating with activation agent such as BOP or HATU in presence of solvent such as DCM and DMF and an organic base such as $Et_3N$ or DIPEA at ambient temperature in presence of ammonium chloride to afford intermediate 34. Intermediate 34 can be converted to intermediate 35 by treatment with trifluoroacetic anhydride in pyridine at 0° C. or by treatment with $POCl_3$ and a base such as imidazole. Intermediate 36 can be synthesized by reaction of intermediate 35 with hydroxylamine; see Hirawat, S., et al. WO 2006/110483. Variously substituted intermediates 37 can be coupled with intermediates 36 using an amide bond coupling reagent (e.g. CDI, BOP, or EDC) in a polar aprotic solvent (e.g. THF, 1,4-dioxane, or DMF) at room temperature. The acyclic intermediate can be subsequently cyclized at elevated temperatures (60° C. to 100° C.). Alternatively, in situ cyclization can be accomplished by conducting the coupling of acids 37 with amide oximes 36 at elevated temperatures (60° C. to 100° C.) to afford intermediates of formula 38. Subsequent hydrolysis of the intermediate 38 with an alkali hydroxide base can provide acid, which can be subjected to reduction in presence of hydride based reducing agents (e.g. LAH, DIBAL-H, or $NaBH_4$) in chlorinated or ethereal solvent such as DCM, ether, 1,4-dioxane, or THF to afford intermediate 39. Intermediate 39 can be oxidized to intermediate 40, by methodologies recognized by one skilled in the art using oxidation conditions (e.g. Dess-Martin periodane, Swern oxidation conditions, PDC, or PCC). Intermediates 40 can be converted to compounds of formula I by steps described in Scheme 1.

Figure 3:
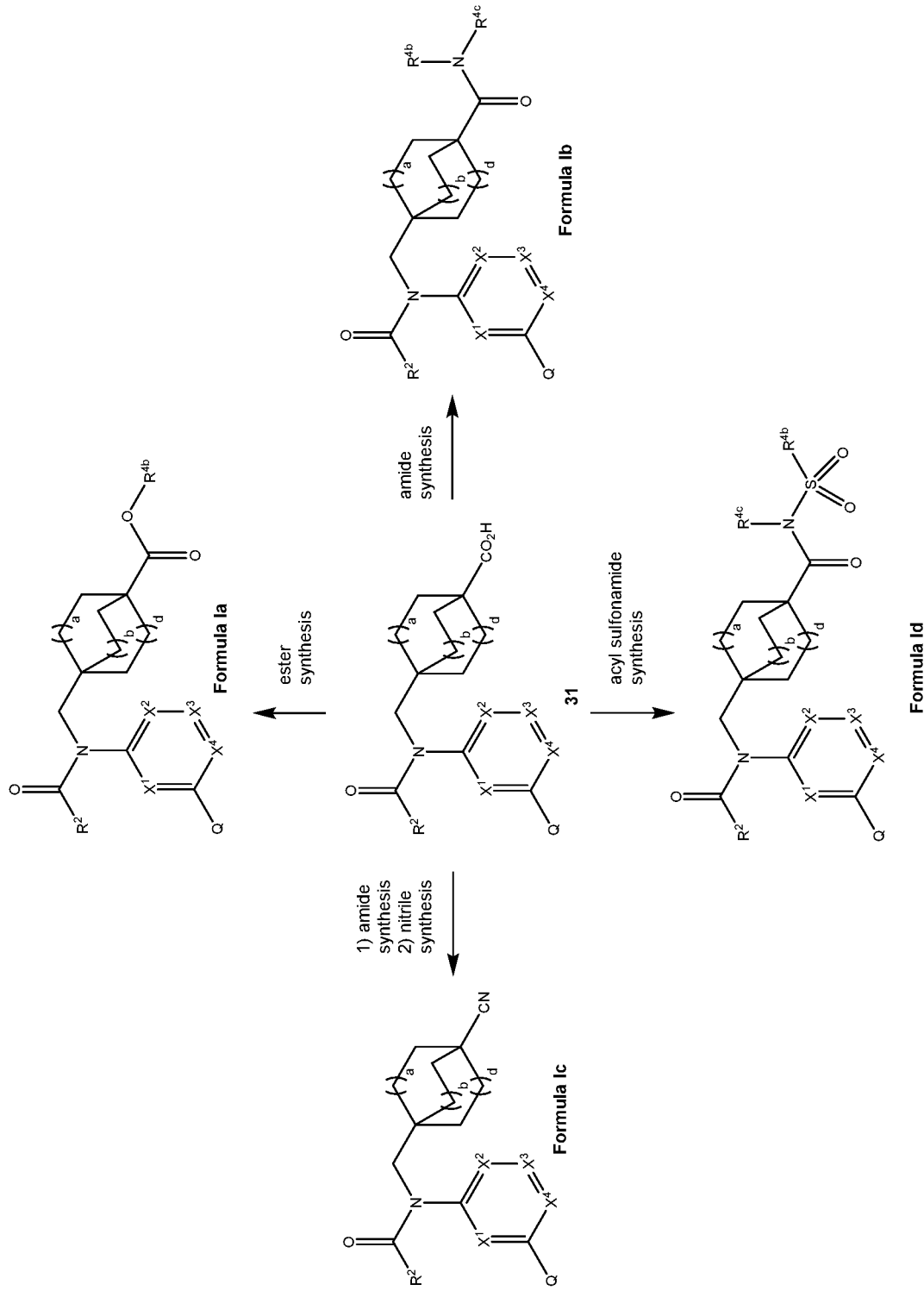
FIG. 3 shows the general reaction Scheme 15.

Scheme 15 (FIG. 3) describes the synthesis of compounds of formula I(a-d). The intermediates represented by formula 31 (synthesis described in Scheme 12) can be subjected to esterification. Intermediate 31 can be activated for acylation using any number of reagents recognizable by one skilled in the art (e.g. thionyl chloride, phosphorus oxychloride, oxalyl chloride, methylchloroformate, or ethylchloroformate), in a polar aprotic solvent (e.g. DCM or THF), at temperatures ranging between −30° C. to 0° C. The activated acid intermediate can be reacted with alcohols in presence of a base to generate compounds of formula Ia. Intermediate 31 can be subjected to amide synthesis by activating the acid with an activation agent (e.g. BOP, CDI, or HATU) in solvent (e.g. DCM or DMF) in presence of base (e.g. $Et_3N$ or DIPEA) at ambient temperature or heating conditions in presence of ammonium chloride or substituted amine (e.g. alkyl, cycloalkyl, aryl, and heteroaryl) to afford amides of formula Ib. Intermediate 31 can be subjected to primary amide synthesis by treating with activation agent (e.g. BOP, CDI, or HATU) in solvent (e.g. DCM or DMF) in presence of base (e.g. $Et_3N$ or DIPEA) and ammonium chloride at ambient temperature. The primary amide so obtained can be treated with i) trifluoroacetic anhydride in pyridine at 0° C. or ii) $POCl_3$ and imidazole to afford nitriles of formula Ic. Intermediate 31 can be activated using any number of reagents recognizable by one skilled in the art (e.g. thionyl chloride, phosphorus oxychloride, oxalyl chloride, methylchloroformate, and ethylchloroformate), in a polar aprotic solvent (e.g. DCM or THF), at temperatures ranging between −30° C. to 0° C. The activated acid intermediate can be reacted with a sulfonamides in presence of a base (e.g. pyridine, DMAP, 2-(dimethylamino)pyridine, or N-methylmorpholine) in a polar aprotic solvent (e.g. DCM or THF), at temperatures ranging between 0° C. to 90° C. to generate acyl sulfonamides of formula Id.

SCHEME 16

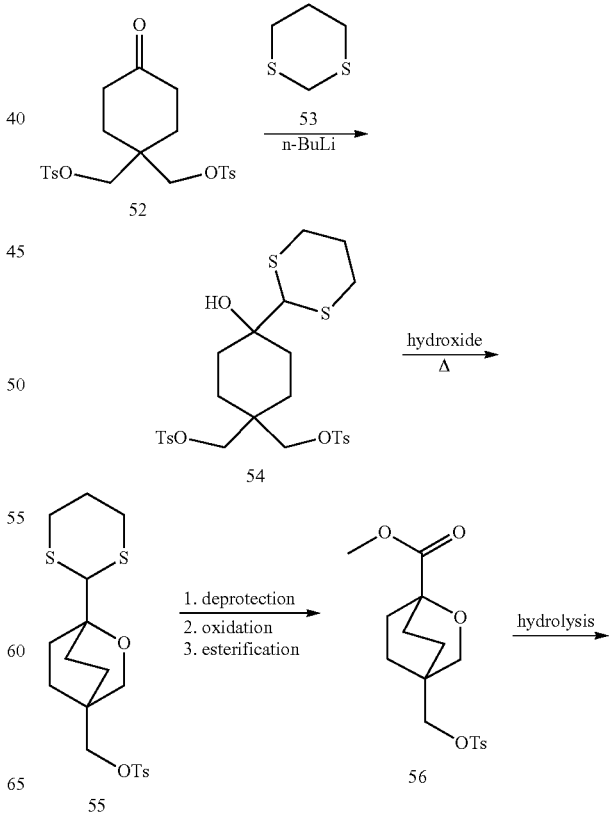

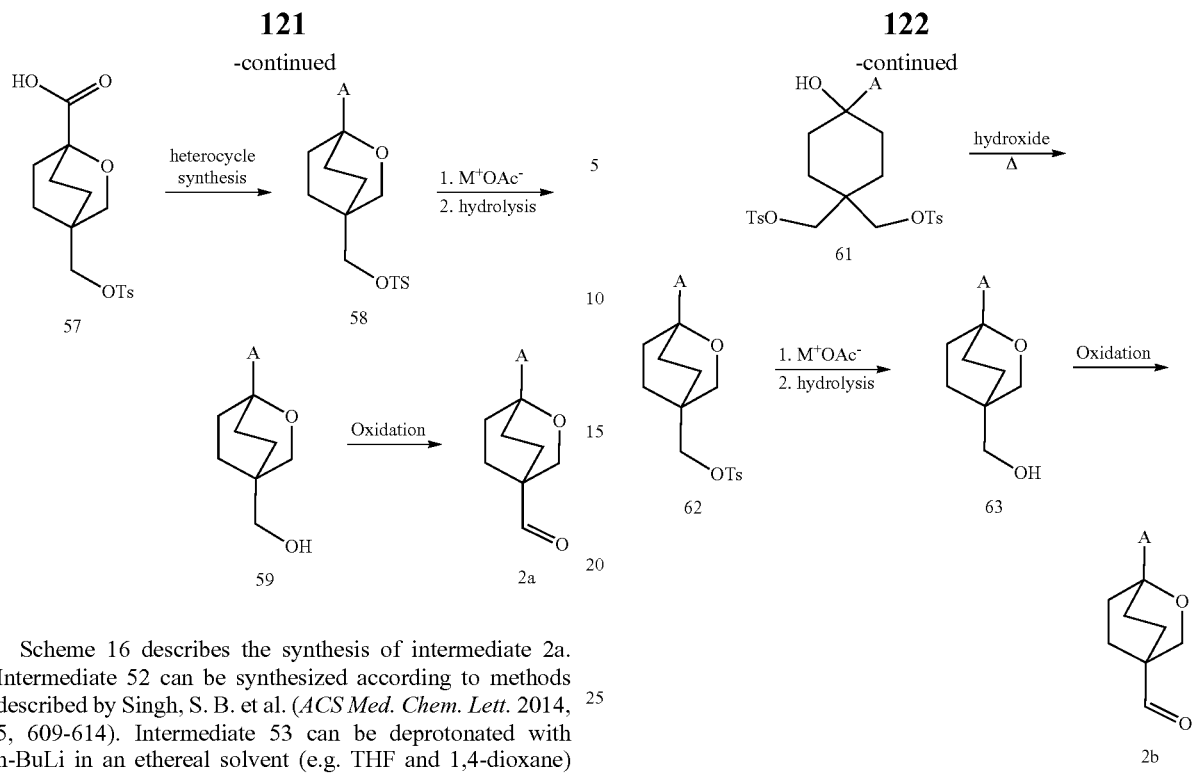

Scheme 16 describes the synthesis of intermediate 2a. Intermediate 52 can be synthesized according to methods described by Singh, S. B. et al. (*ACS Med. Chem. Lett.* 2014, 5, 609-614). Intermediate 53 can be deprotonated with n-BuLi in an ethereal solvent (e.g. THF and 1,4-dioxane) with temperature varying between −78° C. and 0° C., and then reacted with intermediate 52 to yield intermediate 54. Intermediate 54 can be cyclized in the presence of an alkali hydroxide base at elevated temperature (70° C.) to form intermediate 55. Thioacetal deprotection can be accomplished using any number of reagents (e.g. NCS, Hg(ClO$_4$)$_2$, or DDQ) to provide the aldehyde, which can be oxidized to the acid using an oxidizing agent (NaClO$_2$, PCC, PDC, or KMnO$_4$) and then subsequently esterified by reaction with iodomethane to provide intermediate 56. Subsequent hydrolysis of the intermediate 56 with an alkali hydroxide base can provide intermediate 57. Intermediate 57 can be converted to various heterocycles (A) using numerous known methods recognized by one skilled in the art, including but not limited to the methods described in Scheme 11 to afford compounds of intermediate 58. Intermediate 58 can be treated with an acetate salt (e.g. CsOAc or KOAc) in a polar aprotic solvent (e.g. DMF or NMP) at elevated temperatures (120° C.) to provide corresponding acetate, which upon subsequent hydrolysis under acidic conditions (HCl) afforded intermediate 59. Intermediate 59 can be oxidized by methodologies recognized by one skilled in the art using oxidation conditions (e.g. Dess-Martin periodane, Swern oxidation conditions, PDC, or PCC) to afford compounds of formula 2a. The intermediates 2a can be converted to compounds of formula I by using steps described in Scheme 1.

Scheme 17 describes an alternative synthesis of intermediate 2b. Intermediate 52 can be synthesized according to methods described by Singh, S. B. et al. (*ACS Med. Chem. Lett.* 2014, 5, 609-614). Halogenated heterocycles, 60, (commercially available or obtained by methods known by one skilled in the art) can be treated with base such as (e.g. n-BuLi, s-BuLi, or MeLi) in an ethereal solvent (e.g. THF or 1,4-dioxane) with temperature varying between −78° C. and 0° C., and then reacted with ketone 52 to afford intermediate 61. Intermediate 61 can be cyclized in the presence of an alkali hydroxide base at elevated temperature (70° C.) to afford intermediate 62. Intermediate 62 can be treated with an acetate salt (e.g. CsOAc or KOAc) in a polar aprotic solvent (e.g. DMF or NMP) at elevated temperatures (120° C.) to provide corresponding acetate, which upon subsequent hydrolysis under acidic conditions (HCl) afforded intermediate 63. Intermediate 63 can be oxidized by methodologies recognized by one skilled in the art using oxidation conditions (e.g. Dess-Martin periodane, Swern oxidation conditions, PDC, or PCC) to afford intermediate 2b. Intermediate 2b can be converted to compounds of formula I by using steps described in Scheme 1.

SCHEME 17

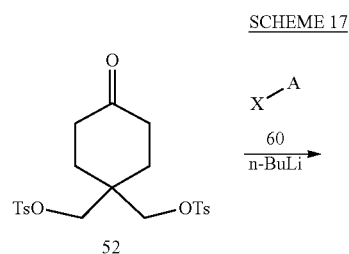

SCHEME 18A

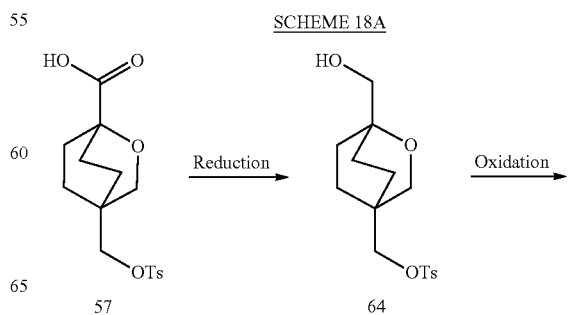

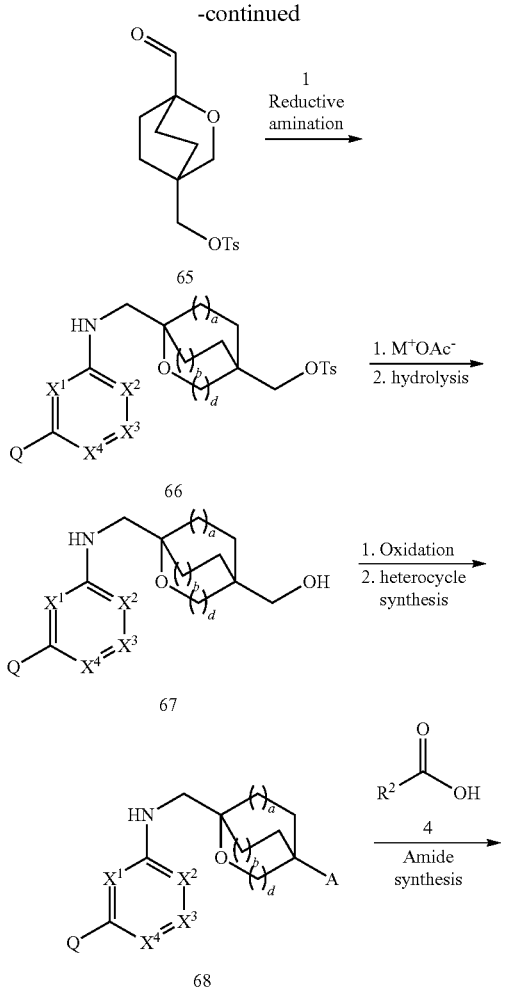

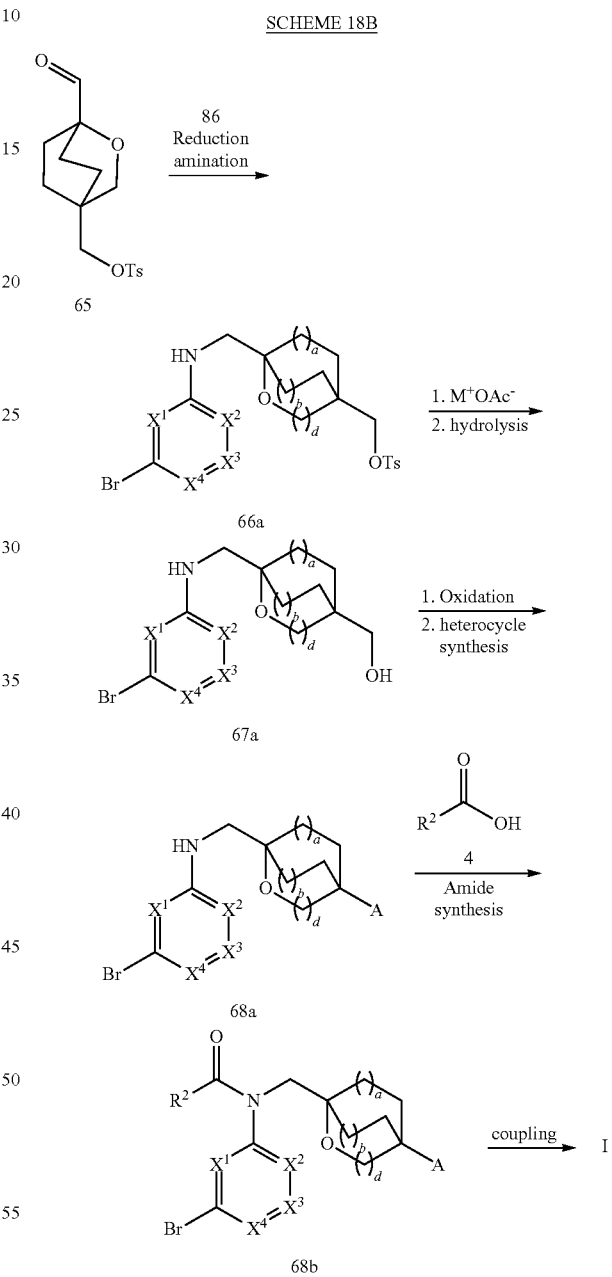

Scheme 18A describes an alternative synthesis of compounds of Formula I. Intermediate 57 (synthesis described in Scheme 16) can be subjected to reduction in presence of hydride based reducing agent (e.g. LAH, DIBAL-H, or NaBH$_4$) to afford intermediate 64. The intermediate 64 can be oxidized to aldehyde 65, by methodologies recognized by one skilled in the art using oxidation conditions (e.g. Dess-Martin periodane, Swern oxidation conditions, PDC, or PCC). The intermediate 1 and intermediate 65 can be subjected to reductive amination, using numerous known methods recognizable by one skilled in the arts, in presence of acid such as acetic acid in a suitable polar protic solvent (e.g. MeOH or EtOH) at room temperature or reflux temperature followed by reduction of imine with reducing agents (e.g. sodium cyanoborohydride or sodium triacetoxyborohydride) afforded intermediate 66. Intermediate 66 can be treated with an acetate salt (e.g. CsOAc or KOAc) in a polar aprotic solvent (e.g. DMF or NMP) at elevated temperatures (120° C.) to provide corresponding acetate, which upon subsequent hydrolysis under acidic conditions (HCl) afforded intermediate 67. The intermediate 67 can be oxidized to the acid by use of an oxidizing agent (NaClO$_2$, PCC, PDC, or KMnO) followed by synthesis of various heterocycles (A) using numerous known methods recognized by one skilled in the art, including but not limited to the methods described in Scheme 11 to afford intermediate 68. Intermediate 4 can be activated for acylation using any number of reagents recognizable by one skilled in the art (e.g. thionyl chloride, phosphorus oxychloride, oxalyl chloride, methylchloroformate, or ethylchloroformate), in a polar aprotic solvent (e.g. DCM or THF), at temperatures ranging between −30° C. to 0° C. The activated acid intermediate can be reacted with intermediate 68 in presence of a base to generate compounds of formula I.

SCHEME 18B

Scheme 18B describes an alternative synthesis of compounds of Formula I. Intermediate 86 and intermediate 65 (as described in Scheme 18A) can be subjected to reductive amination, using numerous known methods recognizable by one skilled in the art, in presence of acid such as acetic acid in a suitable polar protic solvent (e.g. MeOH or EtOH) at room temperature or reflux temperature followed by reduction of imine with reducing agents (e.g. sodium cyanoborohydride or sodium triacetoxyborohydride) to afford intermediate 66a. Intermediate 66a can be treated with an acetate salt (e.g. CsOAc or KOAc) in a polar aprotic solvent (e.g. DMF or NMP) at elevated temperatures (120° C.) to provide corresponding acetate, which upon subsequent hydrolysis under acidic conditions (HCl) afforded intermediate 67a. The intermediate 67a can be oxidized to the acid using an oxidizing agent (NaClO$_2$, PCC, PDC, or KMnO$_4$) followed by synthesis of various heterocycles (A) using numerous known methods recognized by one skilled in the art, including but not limited to the methods described in Scheme 11 to afford intermediate 68a. Intermediate 68a can be converted to compounds of formula I by following steps described in Scheme 13.

SCHEME 19

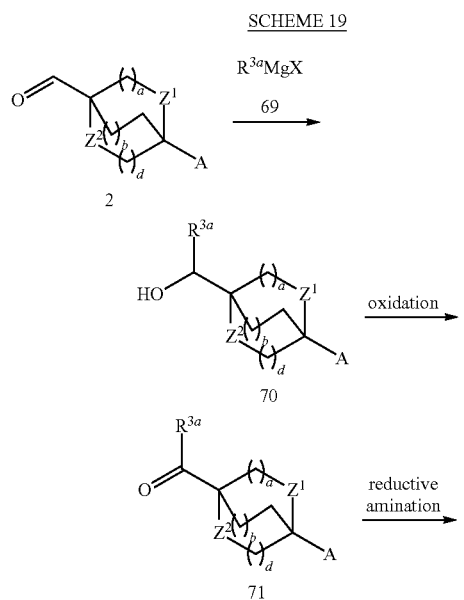

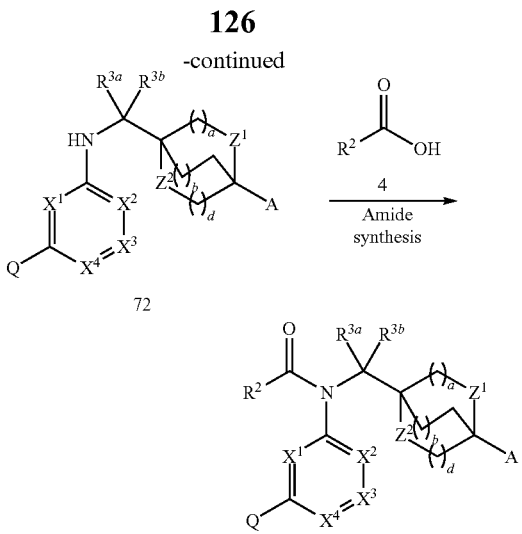

Scheme 19 describes an alternative synthesis of compounds of Formula I. Intermediate 2 can be subjected to treatment with organo magnesium reagents in ethereal solvent (such as Et$_2$O or THF) with temperature varying between −78° C. and 0° C. to afford intermediate 70. The intermediate 70 can be oxidized to intermediate 71, by methodologies recognized by one skilled in the art under oxidation conditions using oxidizing agents such as Dess-Martin periodane, PDC, or PCC. Intermediate 71 and intermediate 1 in polar protic solvent such as MeOH or EtOH, can be treated with triethyl silane and indium chloride at ambient temperature to afford intermediates of formula 72. Intermediate 4 can be activated for acylation using any number of reagents recognizable by one skilled in the art (e.g. thionyl chloride, phosphorus oxychloride, oxalyl chloride, methylchloroformate, or ethylchloroformate), in a polar aprotic solvent (e.g. DCM or THF), at temperatures ranging between −30° C. to 0° C. The activated acid intermediate can be reacted with intermediate 72 in presence of a base to generate compounds of formula I.

SCHEME 20

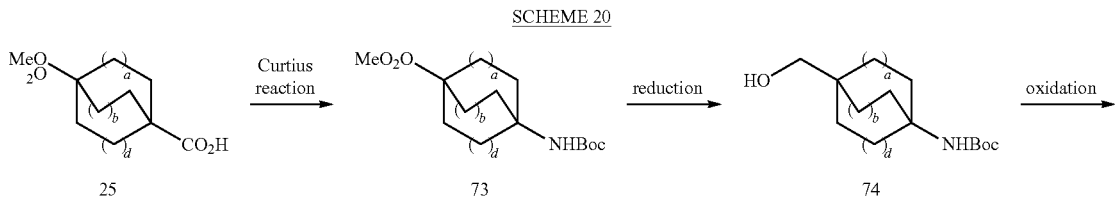

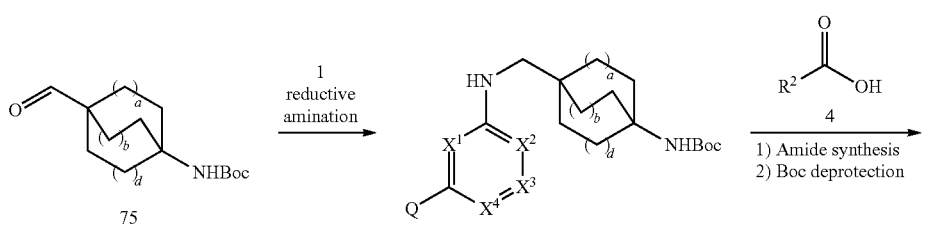

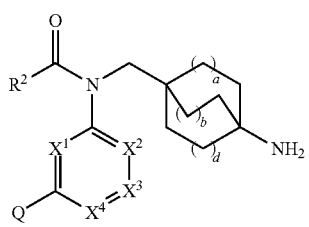

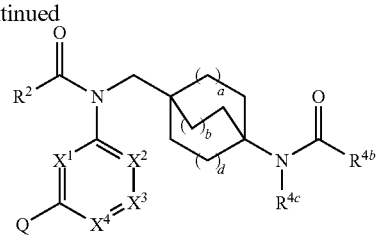

77

Formula Ie

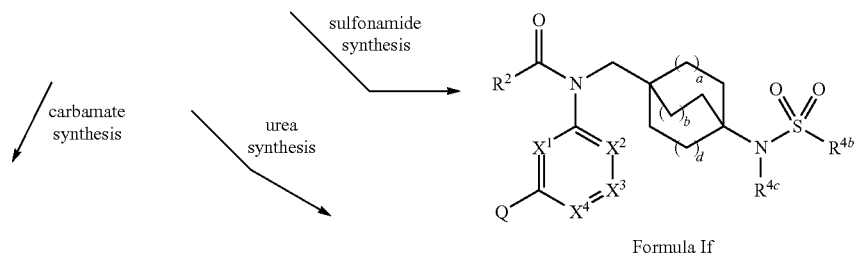

Formula If

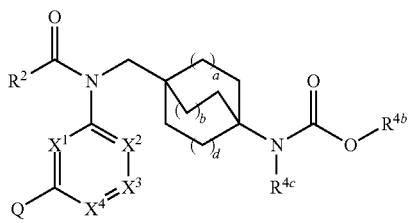

Formula Ih

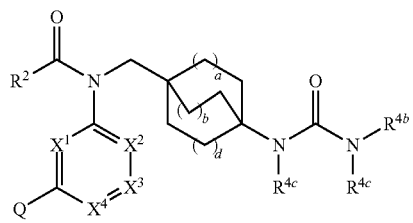

Formula Ig

Scheme 20 describes synthesis of compounds of formula I(e-g) (where 'A' is amide, sulfonamide, urea or carbamate). Intermediate 25 can be converted to intermediate 73 via Curtius rearrangement (as described in Shioiri, T. et al. *J. Am. Chem. Soc.* 1972, 94, 6203-6205). Intermediate 73 can be subjected to reduction in presence of hydride based reducing agent (e.g. LAH, DIBAL-H, or NaBH$_4$) to afford intermediate 74. Intermediate 74 can be oxidized to aldehyde 75, by methodologies recognized by one skilled in the art using oxidation conditions (e.g. Dess-Martin periodane, Swern oxidation conditions, PDC, or PCC). Intermediate 1 and intermediate 75 can be subjected to reductive amination, using numerous known methods recognizable by one skilled in the art, in presence of acid such as acetic acid in a suitable polar protic solvent (e.g. MeOH or EtOH) at room temperature or reflux temperature followed by reduction of imine with reducing agents (e.g. sodium cyanoborohydride or sodium triacetoxyborohydride) to afford intermediate 76. Intermediate 4 can be activated for acylation using any number of reagents recognizable by one skilled in the art (e.g. thionyl chloride, phosphorus oxychloride, oxalyl chloride, methylchloroformate, or ethylchloroformate), in a polar aprotic solvent (e.g. DCM or THF), at temperatures ranging between −30° C. to 0° C. The activated acid intermediate can be reacted with intermediate 76 in presence of a base to generate corresponding amide. The amide intermediate can be subjected to Boc-deprotection in polar aprotic solvent (e.g. DCM or THF) using trifluoroacetic acid at room temperature to afford intermediate 77. Intermediate 77 can be subjected to a variety of different transformations using numerous known methods recognized by one skilled in the art, including but not limited to the following methods to afford variations of Formula I.

Amides: Intermediate 77 can be reacted with activated acid intermediates in presence of base (e.g. pyridine, DMAP, 2-(dimethylamino)pyridine, or N-methylmorpholine) in polar aprotic solvent (e.g. DCM or THF) to generate amides of Formula Ie.

Sulfonamides: Intermediate 77 can be treated with sulfonyl chlorides in presence of a base (e.g. pyridine, DMAP, 2-(dimethylamino)pyridine, or N-methylmorpholine) in a polar aprotic solvent (e.g. DCM or THF), at temperatures ranging between 0° C. to 90° C. to generate sulfonamides of Formula If.

Ureas: Intermediate 77 can be subjected to treatment with isocyanates in presence of base (e.g. Et$_3$N, DIPEA, or pyridine) in polar aprotic solvent (e.g. DCM or DCE) at room temperature to afford ureas represented by formula Ig. Alternatively, intermediate 77 can be activated by treatment with triphosgene in presence of base (e.g. Et$_3$N or DIPEA) in solvent (e.g. DCM or DCE) at 0° C. to room temperature. The activated intermediate 3 can then be treated with substituted alkyl amine, aryl amine, or heteroaryl amine in presence of base (e.g. Et$_3$N or DIPEA) in solvent (e.g. DCM or DCE) at room temperature to afford ureas represented by formula Ig.

Carbamates: Intermediate 77 can be treated with chloroformates in presence of base (e.g. Et$_3$N, DIPEA, or pyridine) in polar aprotic solvent (e.g. DCM, DCE, or THF) at 0° C. to room temperature to afford carbamates represented by formula Ih.

SCHEME 21

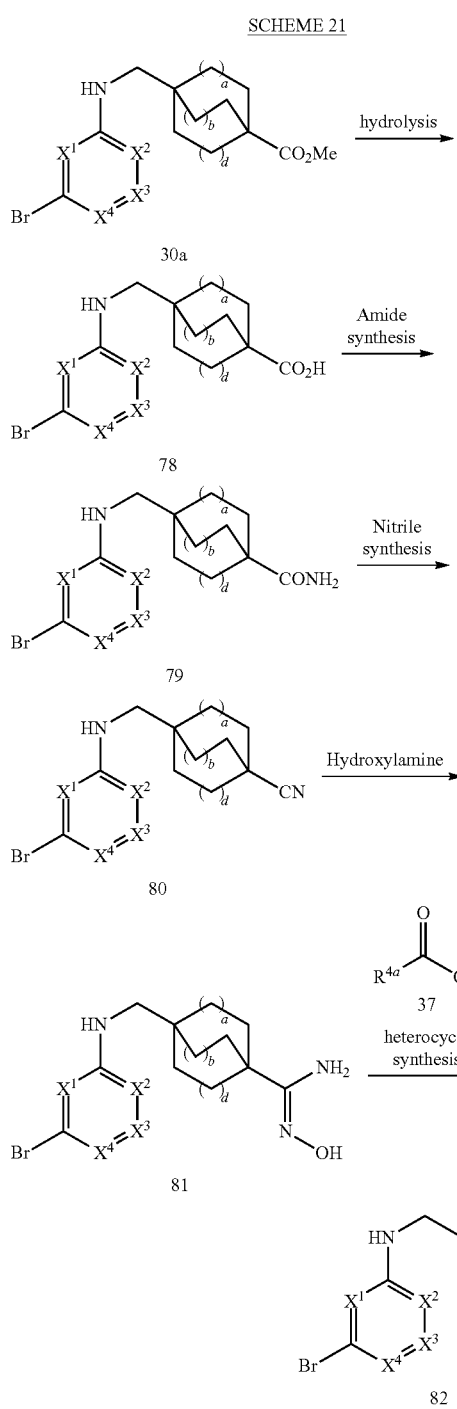

SCHEME 22

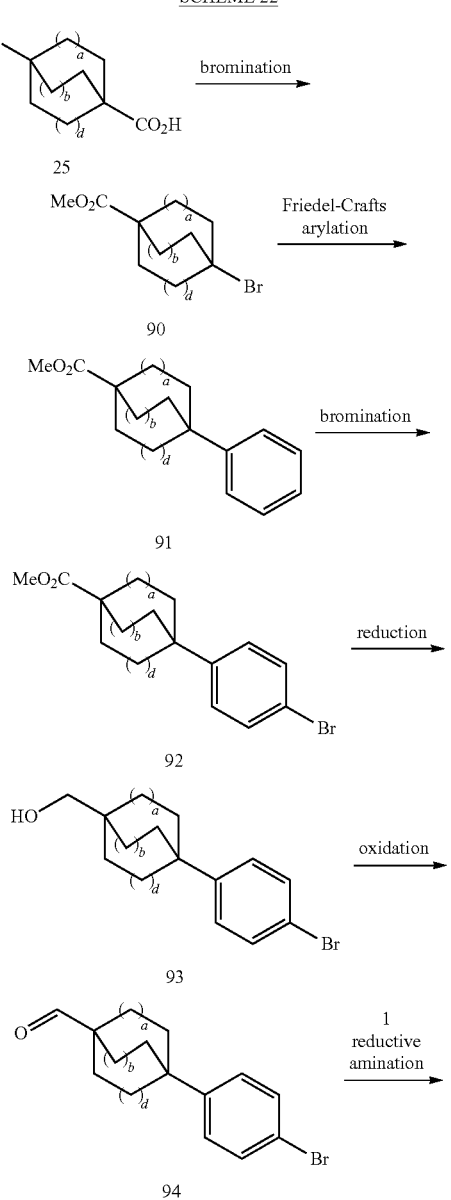

with reagent (e.g. POCl₃, SOCl₂, or TFAA) and base (e.g. imidazole, Et₃N, and DIPEA). Intermediate 81 can be synthesized by reaction of intermediate 80 with hydroxylamine; see Hirawat, S., et al. WO 2006/110483. Intermediate 37 can be obtained from commercial sources or can be synthesized by known methods readily recognizable by one skilled in the art. Intermediates 37 can be coupled with intermediates 81 using an amide bond coupling reagent (e.g. CDI, BOP, or EDC) in a polar aprotic solvent (e.g. THF, 1,4-dioxane, or DMF) at room temperature. The acyclic intermediate can be subsequently cyclized at elevated temperatures (60° C. to 100° C.). Alternatively, in situ cyclization can be accomplished by conducting the coupling of intermediates 37 with intermediates 81 at elevated temperatures (60° C. to 100° C.) to afford oxadiazoles 82. Intermediates 82 can be converted to compounds of formula I via a sequential amide synthesis and coupling as described in Scheme 13.

Scheme 21 describes the synthesis of intermediates 82 where A is 3-(5-substituted-1,2,4-oxadiazolyl) ring. Intermediate 30a (synthesized as described in Scheme 12) can be hydrolyzed with an alkali hydroxide base to afford intermediate 78. Intermediate 78 can be subjected to primary amide synthesis by activating acid with activation agent (e.g. BOP, CDI, or HATU) in polar aprotic solvent (e.g. DCM or DMF) in presence of base (e.g. Et₃N or DIPEA) at ambient temperature in presence of ammonium chloride to afford intermediate 79. Intermediate 79 can be converted to intermediate 80 using various methods recognized by those skilled in the art including but not limited to the treatment

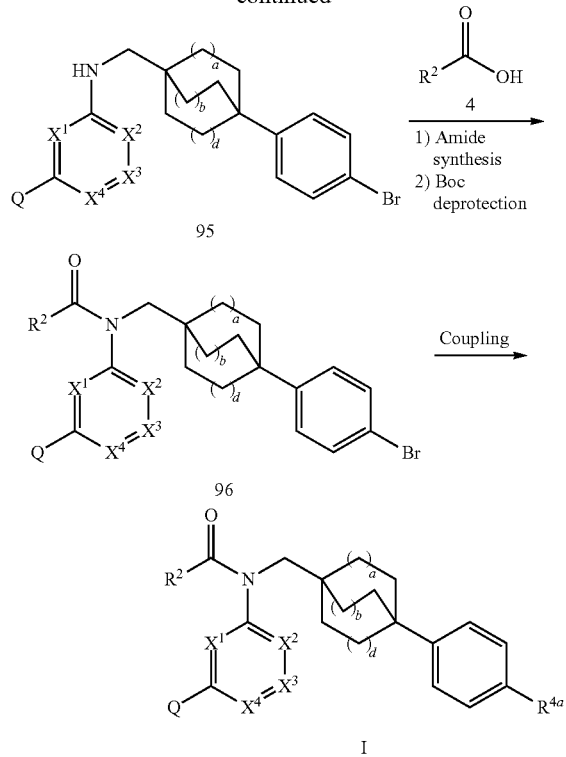

Scheme 22 describes synthesis of compounds of formula I (where 'A' is aryl). Commercially available 4-(methoxycarbonyl)bicyclo[2.2.2]octane-1-carboxylic acid 25 can be subjected to bromination reaction with bromine in presence of mercuric oxide in dibromomethane as a solvent under heating conditions to afford intermediate 90 (as described by Owen et. al. PCT Int. Appl., 2014113485, 2014). Intermediate 90 can be converted to intermediate 91 in benzene in presence of AlCl₃ under conditions described by Piyasena et.

Intermediate 93 can be oxidized to aldehyde 94, by methodologies recognized by one skilled in the art using oxidation conditions (e.g. Dess-Martin periodane, Swern oxidation conditions, PDC, or PCC). Intermediate 1 and intermediate 94 can be subjected to reductive amination, using numerous known methods recognizable by one skilled in the art, in presence of acid such as acetic acid in a suitable polar protic solvent (e.g. MeOH or EtOH) at room temperature or reflux temperature followed by reduction of imine with reducing agents (e.g. sodium cyanoborohydride or sodium triacetoxyborohydride) afforded intermediate 95. Intermediate 4 can be activated for acylation using any number of reagents recognizable by one skilled in the art (e.g. thionyl chloride, phosphorus oxychloride, oxalyl chloride, methylchloroformate, or ethylchloroformate), in a polar aprotic solvent (e.g. DCM or THF), at temperatures ranging between −30° C. to 0° C. The activated acid intermediate can be reacted with intermediate 95 in presence of a base to generate intermediate 96. Intermediate 96 can be subjected to various metal catalyzed reactions (including but not limited to reactions such as Ullmann, Suzuki, Buchwald, and Stille coupling) in presence of metal catalyst (e.g. CuBr, Pd(OAc)₂, Pd₂(dba)₃, Pd(PPh₃)₄, Pd(PPh₃)₂Cl₂, or Pd(dppf)Cl₂) and appropriate ligand (including but not limited to ligands such as tricyclohexylphosphine or dppf) when necessary. The Ullmann and Buchwald coupling reactions of intermediate 96 can be carried out with various coupling partners such as alkyl amines, aryl amines, heteroaryl amines, thiols, and alcohols. The Suzuki or Stille coupling reaction of intermediate 96 can be carried out with various coupling partners such as alkenyl boronic acids, aryl boronic acids, heteroaryl boronic acids, boronic acid esters, and organotin reagents. The coupling reactions can be carried out in presence of base whenever necessary (including but not limited to Na₂CO₃, K₂CO₃, NaHCO₃, K₃PO₄, or NaOtBu) and solvent (e.g. dioxane, THF, DME, toluene, methanol, DMF, or water or the mixture of two or three of these solvents) under heating conditions to afford compounds of Formula I.

SCHEME 23

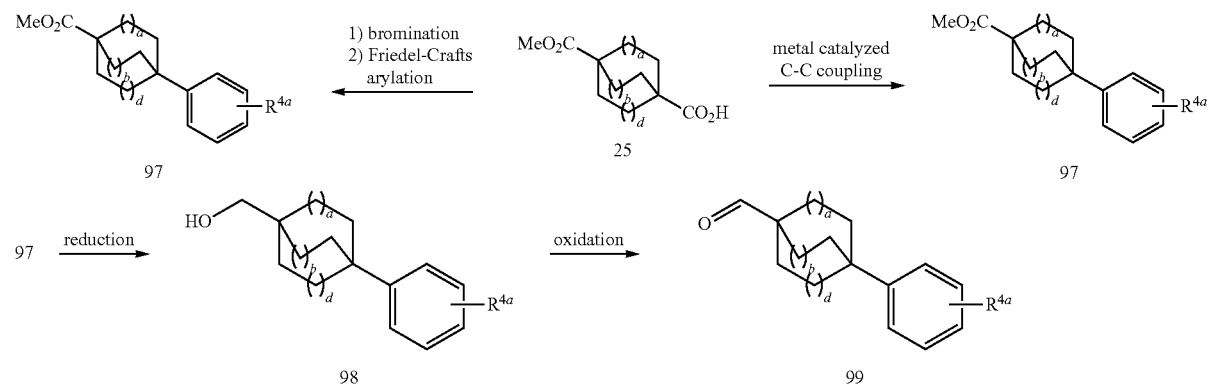

al. PCT Int. Appl., 2015005901, 2015. Intermediate 91 can be subjected to bromination in presence of silver trifluoroacetate and bromine in CHCl₃ at room temperature to afford intermediate 92 (described by Piyasena et. al. PCT Int. Appl., 2015005901, 2015). Intermediate 92 can be subjected to reduction in presence of hydride based reducing agent (e.g. LAH, DIBAL-H, or NaBH₄) to afford intermediate 93.

Scheme 23 describes the synthesis of intermediates 99. Commercially available 4-(methoxycarbonyl)bicyclo[2.2.2]octane-1-carboxylic acid 25 can be subjected to bromination followed by Friedel-Crafts arylation in presence of suitably substituted arenes as described in Scheme 22 to afford intermediate 97. Alternatively, intermediate 97 can be synthesized via decarboxylative Negishi- or Suzuki type cross coupling reactions. Intermediate 25 can be activated as N-hydroxyphthalimide ester or N-hydroxybenzotriazole ester, as redox-active ester and can be treated with organozincs or organoboronic acids or Grignard reagents of variously substituted aryls in presence of metal catalysts (e.g. Fe(acac)$_3$, FeCl$_3$, or NiCl$_2$.glyme) as described by Torriyama, F. et al *J. Am. Chem. Soc.* 2016, 138, 11132-11135 and references cited therein to afford intermediate 97. Intermediate 97 can be subjected to reduction in presence of hydride based reducing agent (e.g. LAH, DIBAL-H, or NaBH$_4$) to afford intermediate 98. Intermediate 98 can be oxidized to aldehyde 99, by methodologies recognized by one skilled in the art using oxidation conditions (e.g. Dess-Martin periodane, Swern oxidation conditions, PDC, or PCC). Intermediate 99 can be converted to compounds of formula I (where 'A' is aryl) by using steps described in Scheme 1.

The sequence of the steps involving installation of groups 'Q' and 'A' can be interchangeably performed in the schemes as appropriate.

Example 1

N-((4-(4-cyclopropylphenyl)bicyclo[2.2.2]octan-1-yl)methyl)-N-(3-(3-methyl-1,2,4-oxadiazol-5-yl)phenyl)isobutyramide

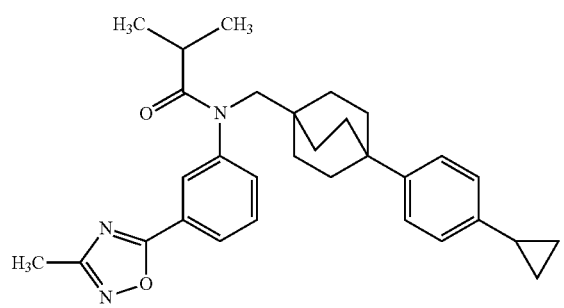

(1)

Step A. Intermediate 1A. Preparation of 3-methyl-5-(3-nitrophenyl)-1,2,4-oxadiazole

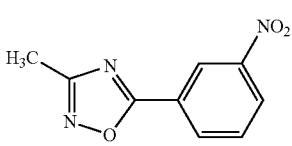

To a solution of 3-nitrobenzoic acid (1 g, 5.98 mmol) in DMF (10 mL) were added (E)-N'-hydroxyacetimidamide (0.887 g, 11.97 mmol) (commercially available), BOP (2.65 g, 5.98 mmol) followed by TEA (2.502 mL, 17.95 mmol). The reaction mixture was stirred for 1 h at room temperature and then heated to 100° C. and stirred for 2 h. The reaction mixture was poured into water (10 mL) and extracted with EtOAc (2×30 mL). The organic layer was washed with brine solution, dried over anhydrous sodium sulphate, filtered and concentrated under reduced pressure to obtain the crude material which was purified by flash chromatography (Silica gel, 0-20% EtOAc/PE). The fractions containing the compound were concentrated under reduced pressure to afford the title compound (0.3 g, 1.389 mmol, 23% yield) as a white solid. $^1$H NMR (400 MHz, DMSO-d$_6$) δ 8.75 (s, 1H), 8.50-8.54 (m, 2H), 7.94 (t, J=8.00 Hz, 1H), 2.47 (s, 3H).

Step B. Intermediate 1B. Preparation of 3-(3-methyl-1,2,4-oxadiazol-5-yl)aniline

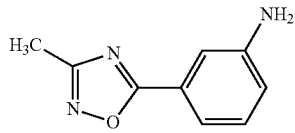

To a solution of Intermediate 1A (0.15 g, 0.731 mmol) in ethanol (5 mL) and water (0.2 mL) was added tin(II) chloride (0.693 g, 3.66 mmol). The reaction mixture was stirred at 90° C. for 2 h. The reaction mixture was cooled to room temperature and concentrated under reduced pressure to obtain the crude material. The crude material was dissolved in EtOAc (30 mL) and washed with 10% aqueous NaHCO$_3$ (10 mL) and with brine solution (25 mL). The organic layer was dried over anhydrous sodium sulphate, filtered and concentrated under reduced pressure. The crude material was purified by flash column chromatography (Silica gel, 0-20% EtOAc/PE) to afford the title compound (0.13 g, 0.705 mmol, 96% yield) as an off-white solid. $^1$H NMR (400 MHz, DMSO-d$_6$) δ 7.35-7.15 (m, 3H), 6.83 (ddd, J=7.8, 2.3, 1.3 Hz, 1H), 5.54 (s, 2H), 2.39 (s, 3H). MS (ESI) 176 (M+H).

Step C. Intermediate 1C. Preparation of methyl 4-bromobicyclo[2.2.2]octane-1-carboxylate

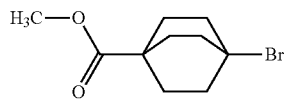

To a stirred solution of 4-(methoxycarbonyl)bicyclo[2.2.2]octane-1-carboxylic acid (1 g, 4.71 mmol) in CH$_2$Br$_2$ (10 mL) was added red mercuric oxide (1.735 g, 8.01 mmol) and heated to 80° C. To the above reaction mixture, bromine (0.364 mL, 7.07 mmol) was added dropwise and the reaction mixture was stirred for 3 h. The reaction mixture was cooled to room temperature, filtered and the solids were washed with dibromomethane. The filtrate was concentrated under reduced pressure to afford the title compound (1 g, 4.05 mmol, 86% yield). $^1$H NMR (300 MHz, DMSO-d$_6$) δ 3.56 (s, 3H), 2.25-2.15 (m, 6H), 1.94-1.85 (m, 6H).

Step D. Intermediate 1D. Preparation of methyl 4-phenylbicyclo[2.2.2]octane-1-carboxylate

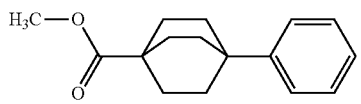

Aluminum chloride (2.70 g, 20.23 mmol) was transferred to a 2-neck 50 mL round bottom flask under nitrogen and cooled to −10° C. Benzene (12.72 mL, 142 mmol) was added to the reaction flask and the resulting mixture was stirred for 5 min. A solution of Intermediate 1C (1 g, 4.05 mmol) in benzene (12.72 mL, 142 mmol) was then added to the reaction mixture at −10° C. and the reaction mixture was warmed up to room temperature and stirred for 12 h. The reaction mixture was poured into crushed ice and the layers were separated. The organic phase was dried over MgSO$_4$, filtered and concentrated under reduced pressure to afford the title compound (0.82 g, 2.097 mmol, 52% yield). $^1$H NMR (300 MHz, CHLOROFORM-d) δ 7.34-7.30 (m, 4H), 7.21 (dt, J=5.8, 2.6 Hz, 1H), 3.73 (s, 3H), 1.99-1.84 (m, 12H). MS (ESI) 445 (M+H).

Step E. Intermediate 1E. Preparation of methyl 4-(4-bromophenyl)bicyclo[2.2.2]octane-1-carboxylate

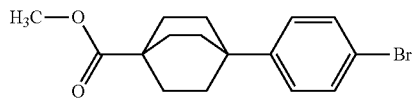

Intermediate 1D (0.8 g, 3.27 mmol) was transferred to a 2-neck 50 mL round bottom flask under nitrogen atmosphere at room temperature and CHCl$_3$ (20 mL) was added. To the stirred reaction mixture, silver trifluoroacetate (0.868 g, 3.93 mmol) was added and stirred for 5 min. A solution of Br$_2$ (0.169 mL, 3.27 mmol) in CHCl$_3$ (40 mL) was added to the reaction mixture and the reaction was stirred at room temperature for 2 h. The mixture was filtered through a pad of celite and the celite pad was washed with CHCl$_3$ (50 mL). The filtrate was concentrated under reduced pressure and the solids were triturated with n-hexane to afford the title compound (0.74 g, 1.580 mmol, 48% yield). MS (ESI) 323 (M+H). $^1$H NMR (300 MHz, chloroform-d) δ 7.43 (d, J=8.7 Hz, 2H), 7.20 (d, J=8.7 Hz, 2H), 3.69 (s, 3H), 1.99-1.78 (m, 12H).

Step F. Intermediate 1F. Preparation of methyl 4-(4-cyclopropylphenyl)bicyclo[2.2.2]octane-1-carboxylate

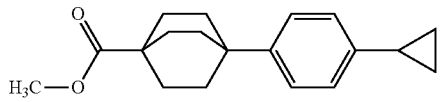

The stirred suspension of Intermediate 1E (500 mg, 1.547 mmol), cyclopropylboronic acid (199 mg, 2.320 mmol) and potassium phosphate tribasic (985 mg, 4.64 mmol) in 1,4-dioxane (10 mL) was degassed and back filled with argon for 10 min. To this mixture, palladium(II) acetate (34.7 mg, 0.155 mmol) and tricyclohexylphosphine (87 mg, 0.309 mmol) was added. The reaction mixture was stirred at 100° C. for 12 h. The reaction mixture was cooled to room temperature and then poured into cold water. The aqueous layer was extracted with EtOAc (2×50 mL) and the combined organic layers were dried over MgSO$_4$. The solvent was removed under reduced pressure and the crude material was purified by flash column chromatography (Combiflash, 12 g silica, 0-20% EtOAc/PE) to afford the title compound (330 mg, 0.580 mmol, 38% yield). MS (ESI) 285 (M+H).

Step G. Intermediate 1G. Preparation of (4-(4-cyclopropylphenyl)bicyclo[2.2.2]octan-1-yl) methanol

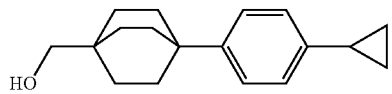

Intermediate 1F (330 mg, 1.160 mmol) was taken into a 2-neck round bottom flask under nitrogen atmosphere and THF (10 mL) was added. The solution was cooled to −78° C. and then DIBAL-H (2.3 mL, 2.321 mmol) was added. After stirring for 2 h, the reaction mixture was poured into aqueous saturated NH$_4$Cl solution. The aqueous layer was extracted with EtOAc (2×50 mL) and the combined organic layers were dried over MgSO$_4$. The solvent was removed under reduced pressure and the crude material was purified by flash column chromatography (Combiflash, 12 g silica, 0-20% EtOAc/PE) to afford the title compound (250 mg, 0.975 mmol, 84% yield). $^1$H NMR (400 MHz, DMSO-d$_6$) δ 7.17 (d, J=8.3 Hz, 2H), 6.96 (d, J=8.3 Hz, 2H), 4.34 (d, J=5.5 Hz, 1H), 3.07 (d, J=5.4 Hz, 2H), 1.91-1.79 (m, 1H), 1.78-1.64 (m, 6H), 1.49-1.36 (m, 6H), 0.89 (dd, J=2.2, 8.4 Hz, 2H), 0.65-0.51 (m, 2H).

Step H. Intermediate 1H. Preparation of 4-(4-cyclopropylphenyl)bicyclo[2.2.2]octane-1-carbaldehyde

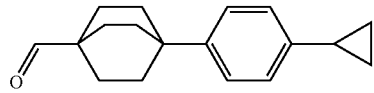

To a stirred solution of Intermediate 1G (260 mg, 1.014 mmol) in DCM (10 mL) was added Dess-Martin periodinane (516 mg, 1.217 mmol) at 0° C. The reaction mixture was stirred at room temperature for 2 h. The reaction mixture was filtered through a celite pad and the filtrate was concentrated under reduced pressure. The crude material was purified by flash column chromatography (Combiflash, 12 g silica, 0-20% EtOAc/PE) to afford the title compound (200 mg, 0.786 mmol, 78% yield). $^1$H NMR (400 MHz, Chloroform-d) δ 9.61-9.42 (m, 1H), 7.20 (d, J=8.3 Hz, 2H), 7.02 (d, J=8.3 Hz, 2H), 1.91-1.83 (m, 7H), 1.81-1.73 (m, 6H), 0.95-0.91 (m, 2H), 0.67 (dd, J=1.6, 5.0 Hz, 2H).

Step I. Intermediate 1I. Preparation of N-((4-(4-cyclopropylphenyl)bicyclo[2.2.2]octan-1-yl)methyl)-3-(3-methyl-1,2,4-oxadiazol-5-yl)aniline

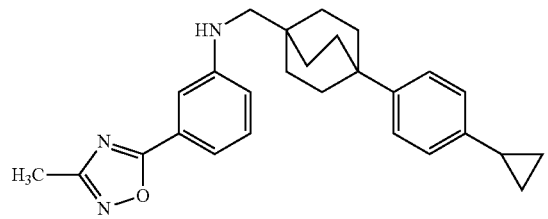 [SMILES: Cc1noc(-c2cccc(NCC34CCC(c5ccc(C6CC6)cc5)(CC3)CC4)c2)n1]

To a stirred solution of Intermediate 1B (34.4 mg, 0.197 mmol) and Intermediate 1H (50 mg, 0.197 mmol) in MeOH, AcOH (5.63 μl, 0.098 mmol) was added followed by molecular sieves 4 Å (5 mg). The reaction mixture was heated to 60° C. and stirred for 16 h. The reaction mixture was cooled to 0° C. and sodium cyanoborohydride (37.1 mg, 0.590 mmol) was added and stirred for 30 min. The reaction mixture was concentrated under reduced pressure and the residue was dissolved in EtOAc (10 mL). The EtOAc solution was poured into cold water (5 mL) and the aqueous layer was extracted with EtOAc (2×10 mL). The combined organic layers were dried over MgSO$_4$, filtered and concentrated under reduced pressure to afford a residue. The residue was purified by column chromatography (4 g silica cartridge, gradient of 0-30% EtOAC in hexane as eluent) to afford the title compound (45 mg, 0.074 mmol, 38% yield). MS (ESI) 414 (M−H).

Step J. Example 1. Preparation of N-((4-(4-cyclopropylphenyl)bicyclo[2.2.2]octan-1-yl)methyl)-N-(3-(3-methyl-1,2,4-oxadiazol-5-yl)phenyl)isobutyramide To a solution of Intermediate 1I (15 mg, 0.036 mmol) in anhydrous DCM (2 mL), Et$_3$N (0.020 mL, 0.145 mmol) was added and the resulting mixture was stirred for 5 minutes. Isobutyryl chloride (7.73 mg, 0.073 mmol) was added to the above reaction mixture and stirring was continued for 2 h at room temperature. The reaction mixture was concentrated and the crude material was purified via preparative LC/MS with the following conditions: Column: Waters XBridge C18, 19×150 mm, 5-μm particles; Mobile Phase A: 10-mM ammonium acetate; Mobile Phase B: acetonitrile; Gradient: 40-80% B over 25 minutes, then a 5-minute hold at 100% B; Flow: 15 mL/min. Fractions containing the desired product were combined and dried via centrifugal evaporation to afford the title compound (4.9 mg, 10.1 μmol, 28%). $^1$H NMR (400 MHz, DMSO-d$_6$) δ 8.04 (s, 2H), 7.82-7.63 (m, 2H), 7.12 (d, J=8.1 Hz, 2H), 6.94 (d, J=8.1 Hz, 2H), 3.64 (br. s., 2H), 2.44 (s, 3H), 1.91-1.75 (m, 1H), 1.73-1.55 (m, 6H), 1.49-1.30 (m, 6H), 1.02-0.76 (m, 9H), 0.64-0.47 (m, 2H). FXR EC$_{50}$ (nM) 1826; MS (ESI) 484 (M+H).

The following compound was synthesized according to the method described for the synthesis of Example 1 by substituting Intermediate 1I and the corresponding acid chloride.

Example 3

N-(3-(3-ethyl-1,2,4-oxadiazol-5-yl)phenyl)-3-fluoro-N-((4-(3-methyl-1,2,4-oxadiazol-5-yl)bicyclo[2.2.2]octan-1-yl)methyl)bicyclo[1.1.1]pentane-1-carboxamide

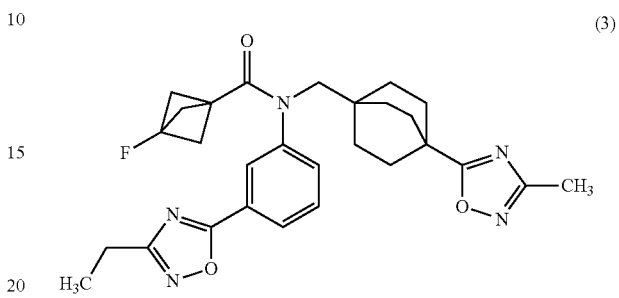

(3)

Step A. Intermediate 3A. Preparation of methyl 4-(3-methyl-1,2,4-oxadiazol-5-yl) bicycle [2.2.2] octane-1-carboxylate

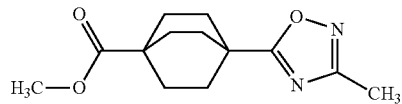

To a solution of 4-(methoxycarbonyl)bicyclo[2.2.2]octane-1-carboxylic acid (2 g, 9.42 mmol) in DMF (20 mL) was added (E)-N'-hydroxyacetimidamide (1.396 g, 18.85 mmol), BOP (4.17 g, 9.42 mmol) followed by TEA (3.94 mL, 28.3 mmol). The reaction mixture was stirred at room temperature for 2 h, and then heated to 110° C. overnight. The reaction mixture was cooled down to room temperature and poured into water. The aqueous layer was extracted with EtOAc (2×30 mL). The combined organic layers were washed with brine solution, dried over anhydrous sodium sulphate, filtered and concentrated. The crude product was purified by flash column chromatography (Combiflash, 12 g

| Ex. No. | Structure | MS (ESI) (M + H) | FXR EC$_{50}$ (nM) |
|---|---|---|---|
| 2 | 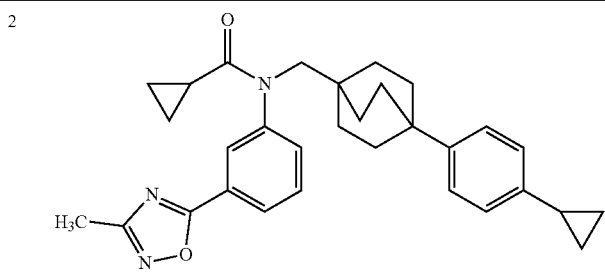 | 482 | 3063 |

2   $^1$H NMR (400 MHz, DMSO-d$_6$) δ 8.08 (s, 1H), 8.01 (d, J = 7.3 Hz, 1H), 7.79 (d, J = 9.0 Hz, 1H), 7.75-7.62 (m, 1H), 7.20-7.02 (m, J = 8.1 Hz, 2H), 6.99-6.81 (m, J = 8.6 Hz, 2H), 3.71 (br. s., 2H), 2.44 (s, 3H), 1.86-1.78 (m, 1H), 1.69-1.58 (m, 6H), 1.47-1.32 (m, 7H), 0.92-0.79 (m, 4H), 0.66 (br. s., 2H), 0.61-0.53 (m, 2H)

Silica gel, 0-30% EtOAc/PE). The fractions containing the desired product were combined together and concentrated under reduced pressure to afford the title compound (0.6 g, 2.277 mmol, 24% yield) as a white solid. $^1$H NMR (400 MHz, DMSO-$d_6$) δ 3.60 (s, 3H), 2.29 (s, 3H), 1.95-1.86 (m, 6H), 1.86-1.78 (m, 6H).

Step B. Intermediate 3B. Preparation of (4-(3-methyl-1,2,4-oxadiazol-5-yl) bicyclo[2.2.2]octan-1-yl)methanol

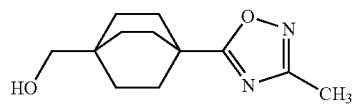

The title compound was synthesized according to the method described for the synthesis of Intermediate 1G by substituting Intermediate 3A where appropriate. The crude was purified by flash column chromatography (Combiflash, 4 g silica, 0-30% EtOAc/pet-ether) to afford the desired product (0.58 g, 2.348 mmol, 98% yield) as an off-white solid. $^1$H NMR (400 MHz, DMSO-$d_6$) δ 4.41 (br. s., 1H), 3.08 (s, 2H), 2.29 (s, 3H), 1.90-1.80 (m, 6H), 1.50-1.40 (m, 6H).

Step C. Intermediate 3C. Preparation of 4-(3-methyl-1,2,4-oxadiazol-5-yl) bicyclo[2.2.2]octane-1-carbaldehyde

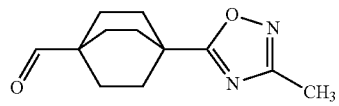

To a solution of Intermediate 3B (0.58 g, 2.61 mmol) in dichloromethane (10 mL) at 0° C., Dess-Martin periodinane (2.213 g, 5.22 mmol) was added under nitrogen atmosphere and stirred for 1 h at 0° C. The reaction mixture was filtered through celite bed and the filtrate was washed with aqueous 10% sodium bicarbonate solution (2×50 mL). The organic layer was dried over sodium sulphate and concentrated under reduced pressure to obtain the crude product, which was purified by flash column chromatography (Combiflash, Silica gel 12 g, 0-20% EtOAc/PE). Fractions containing the desired product were combined together and concentrated to afford the title compound (0.46 g, 1.984 mmol, 76% yield) as white solid. $^1$H NMR (400 MHz, DMSO-$d_6$) δ 9.46 (s, 1H), 2.30 (s, H), 1.96-1.84 (m, 6H), 1.73-1.66 (m, 6H).

Step D. Intermediate 3D. Preparation of 3-ethyl-5-(3-nitrophenyl)-1,2,4-oxadiazole

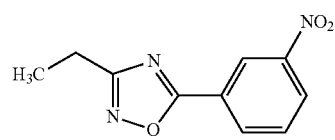 [SMILES: CCc1noc(-c2cccc([N+](=O)[O-])c2)n1]

To a stirred solution of (E)-N'-hydroxypropionimidamide (0.522 g, 5.93 mmol) and DIPEA (1.882 mL, 10.78 mmol) in dichloromethane (10 mL), was added 3-nitrobenzoyl chloride (1 g, 5.39 mmol) at 0° C. and the reaction mixture was warmed to room temperature and stirred for 16 h. The reaction mixture was concentrated under reduced pressure and the crude material was dissolved in EtOAc. The organic solution was washed with water followed by brine solution. The organic layer was dried over anhydrous sodium sulphate, filtered and concentrated under reduced pressure. A solution of the residue obtained above in tetrahydrofuran (10 mL) was cooled to 0° C. A solution of 1 M TBAF in THF (5.06 mL, 5.06 mmol) was added under nitrogen and the reaction mixture was stirred overnight at room temperature. The reaction mixture was concentrated under reduced pressure. The crude material was purified by flash column chromatography (Combiflash, 24 g Silica gel, 0-15% EtOAc/PE). Fractions containing the desired compound were combined together and concentrated under reduced pressure to afford the title compound (0.8 g, 3.47 mmol, 69% yield) as white solid. $^1$H NMR (400 MHz, DMSO-$d_6$) δ 8.78-8.74 (m, 1H), 8.57-8.50 (m, 2H), 7.98-7.91 (m, 1H), 2.90-2.80 (m, 2H), 1.37-1.28 (m, 3H).

Step E. Intermediate 3E. Preparation of 3-(3-ethyl-1,2,4-oxadiazol-5-yl)aniline

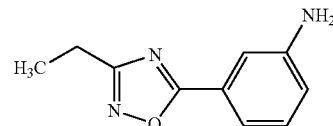

To a solution of Intermediate 3D (1 g, 4.56 mmol) in ethanol (10 mL) was added tin(II) chloride (2.60 g, 13.69 mmol) at room temperature. The reaction mixture was heated at 90° C. and stirred for 3 h. The reaction mixture was concentrated under reduced pressure. The residue was dissolved in EtOAc and washed with 10% aqueous NaHCO$_3$ solution followed by brine solution. The organic layer was dried over anhydrous sodium sulphate, filtered and concentrated under reduced pressure to afford the title compound (0.6 g, 2.85 mmol, 63% yield) as an off-white solid. $^1$H NMR (400 MHz, DMSO-$d_6$) δ 7.33-7.29 (m, 1H), 7.27-7.17 (m, 2H), 6.88-6.80 (m, 1H), 5.53 (s, 2H), 2.78 (q, J=7.5 Hz, 2H), 1.28 (t, J=7.5 Hz, 3H). MS (ESI) 190 (M+H).

Step F. Intermediate 3F. Preparation of 3-(3-ethyl-1,2,4-oxadiazol-5-yl)-N-((4-(3-methyl-1,2,4-oxadiazol-5-yl)bicyclo[2.2.2]octan-1-yl)methyl)aniline

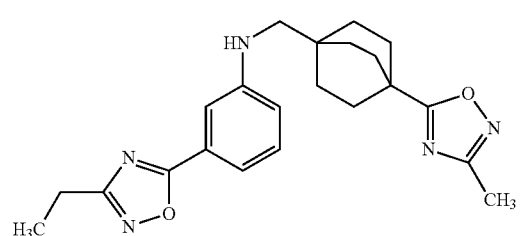

The title compound was synthesized according to the method described for the synthesis of Intermediate 1I by substituting Intermediate 3E and Intermediate 3C where appropriate: (0.13 g, 0.297 mmol, 52% yield) as an off-white solid. $^1$H NMR (400 MHz, DMSO-d$_6$) δ 7.34-7.24 (m, 2H), 7.22-7.17 (m, 1H), 6.92 (dd, J=7.9, 1.8 Hz, 1H), 5.99 (t, J=5.5 Hz, 1H), 2.89 (d, J=5.9 Hz, 2H), 2.78 (q, J=7.6 Hz, 2H), 2.30 (s, 3H), 1.95-1.85 (m, 6H), 1.65-1.55 (m, 6H), 1.28 (t, J=7.6 Hz, 3H). MS (ESI) 394 (M+H).

Step G. Example 3: Preparation of N-(3-(3-ethyl-1,2,4-oxadiazol-5-yl)phenyl)-3-fluoro-N-((4-(3-methyl-1,2,4-oxadiazol-5-yl)bicyclo[2.2.2]octan-1-yl)methyl) bicyclo[1.1.1]pentane-1-carboxamide To a solution of Intermediate 3F (20 mg, 0.051 mmol) and 3-fluorobicyclo[1.1.1]pentane-1-carboxylic acid (6.61 mg, 0.051 mmol) (synthesized as described in Organic & Biomolecular Chemistry, 2015, 13, 11597-11601) in dichloromethane (2 mL) was added pyridine (0.012 mL, 0.152 mmol). The reaction mixture was cooled to 0° C. and POCl$_3$ (9.47 µL, 0.102 mmol) was added. The reaction mixture was gradually warmed to room temperature and stirred for 1 h. The reaction mixture was diluted with DCM, washed with 10% aqueous sodium bicarbonate solution followed by brine solution. The organic layer was dried over sodium sulphate, filtered, concentrated under reduced pressure. The crude material was purified by prep HPLC (Column: Waters XBridge C18, 19×150 mm, 5-µm particles; Mobile Phase A: 10-mM ammonium acetate; Mobile Phase B: acetonitrile; Gradient: 10-45% B over 25 minutes, then a 5-minute hold at 100% B; Flow: 15 mL/min). Fractions containing the desired product were combined and dried via centrifugal evaporation to afford the title compound (20 mg, 0.040 mmol, 78% yield) as an off-white solid (40 mg, 0.079 mmol, 89% yield). $^1$H NMR (400 MHz, DMSO-d$_6$) δ 8.15-8.08 (m, 1H), 8.06 (t, J=1.6 Hz, 1H), 7.79-7.67 (m, 2H), 3.63 (br. s., 2H), 2.83 (q, J=7.5 Hz, 2H), 2.28 (s, 3H), 1.89 (br. s., 6H), 1.85-1.73 (m, 6H), 1.53-1.37 (m, 6H), 1.31 (t, J=7.6 Hz, 3H). FXR EC$_{50}$ (nM) 346; MS (ESI) 506 (M+H).

Example 4

N-((4-(3-cyclopropyl-1,2,4-oxadiazol-5-yl)bicyclo[2.2.2]octan-1-yl)methyl)-3-(difluoromethyl)-N-(3-(3-ethyl-1,2,4-oxadiazol-5-yl)phenyl)cyclobutane-1-carboxamide (4)

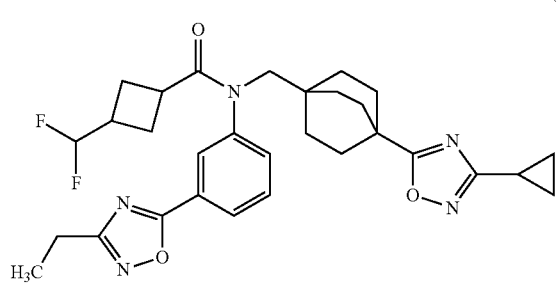

Step A. Intermediate 4A. Preparation of methyl 4-(3-cyclopropyl-1,2,4-oxadiazol-5-yl) bicyclo[2.2.2]octane-1-carboxylate

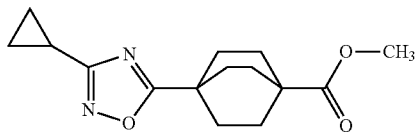 [SMILES: COC(=O)C12CCC(c3nc(C4CC4)no3)(CC1)CC2]

The title compound was synthesized according to the method described for the synthesis of Intermediate 3A by substituting 4-(methoxycarbonyl)bicyclo[2.2.2]octane-1-carboxylic acid and (Z)—N'-hydroxycyclopropanecarboximidamide (commercially available). The crude material was purified by flash column chromatography (Combiflash, 12 g silica gel, 0-30% EtOAc/PE) to afford the title compound (490 mg, 1.667 mmol, 71% yield). MS (ESI) 277 (M+H).

Step B. Intermediate 4B. Preparation of (4-(3-cyclopropyl-1,2,4-oxadiazol-5-yl) bicyclo[2.2.2]octan-1-yl)methanol

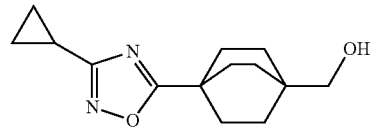 [SMILES: OCC12CCC(c3nc(C4CC4)no3)(CC1)CC2]

The title compound was synthesized according to the method described for the synthesis of Intermediate 1G by substituting Intermediate 4A where appropriate: (500 mg, 1.087 mmol, 61% yield). MS (ESI) 249 (M+H).

Step C. Intermediate 4C. Preparation of 4-(3-cyclopropyl-1,2,4-oxadiazol-5-yl) bicyclo[2.2.2]octane-1-carbaldehyde

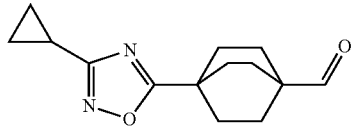

The title compound was synthesized according to the method described for the synthesis of Intermediate 3C by substituting Intermediate 4B where appropriate: (350 mg, 1.421 mmol, 71% yield). MS (ESI) 247 (M+H).

Step D. Intermediate 4D. Preparation of N-((4-(3-cyclopropyl-1,2,4-oxadiazol-5-yl) bicyclo[2.2.2]octan-1-yl)methyl)-3-(3-ethyl-1,2,4-oxadiazol-5-yl)aniline

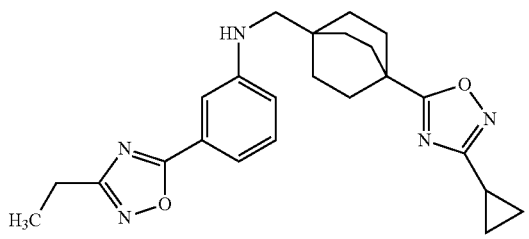 [SMILES: CCc1noc(-c2cccc(NCC34CCC(c5nc(C6CC6)no5)(CC3)CC4)c2)n1]

The title compound was synthesized according to the method described for the synthesis of Intermediate 1I by substituting Intermediate 3E and Intermediate 4C where appropriate: (40 mg, 0.086 mmol, 42% yield) as an off-white solid. $^1$H NMR (400 MHz, DMSO-d$_6$) δ 7.35-7.22 (m, 2H), 7.22-7.15 (m, 1H), 6.91 (dd, J=7.5, 2.0 Hz, 1H), 5.95 (t, J=6.0 Hz, 1H), 2.87 (d, J=6.0 Hz, 2H), 2.77 (q, J=7.5 Hz, 2H), 2.11-2.01 (m, 1H), 1.92-1.80 (m, 6H), 1.63-1.52 (m, 6H), 1.28 (t, J=8.00 Hz, 3H), 1.07-0.98 (m, 2H), 0.88-0.82 (m, 2H). MS (ESI) 420 (M+H).

Step E. Example 4. Preparation of N-((4-(3-cyclopropyl-1,2,4-oxadiazol-5-yl) bicyclo[2.2.2]octan-1-yl)methyl)-3-(difluoromethyl)-N-(3-(3-ethyl-1,2,4-oxadiazol-5-yl)phenyl)cyclobutane-1-carboxamide The title compound was synthesized according to the method described for the synthesis of Example 3 by substituting Intermediate 4D and the corresponding acid where appropriate: (17 mg, 0.031 mmol, 64.6% yield). $^1$H NMR (400 MHz, DMSO-d$_6$) δ 8.08-7.94 (m, 2H), 7.81-7.57 (m, 2H), 6.23-5.68 (m, 1H), 3.71-3.60 (m, 2H), 3.16-2.96 (m, 1H), 2.90-2.75 (m, 2H), 2.30 (br. s., 1H), 2.16-1.95 (m, 2H), 1.82-1.58 (m, 9H), 1.41 (d, J=7.1 Hz, 6H), 1.31 (td, J=7.6, 0.7 Hz, 3H), 1.09-0.93 (m, 2H), 0.91-0.69 (m, 2H). FXR EC$_{50}$ (nM) 322. MS (ESI) 552 (M+H).

The following compounds were synthesized according to the method described for the synthesis of Example 3 by substituting Intermediate 4D and the corresponding acids where appropriate:

| Ex. No. | Structure & Name | MS (ESI) (M + H) | FXR EC$_{50}$ (nM) |
|---|---|---|---|
| 5 | | 586 | 182 |
| 6 | | 532 | 135 |

5 $^1$H NMR (400 MHz, DMSO-d$_6$) δ 8.06 (br. s., 2H), 7.76 (d, J = 7.3 Hz, 1H), 7.70 (t, J = 7.5 Hz, 1H), 6.54 (s, 1H), 3.67 (br. s., 2H), 2.91-2.78 (m, 2H), 2.77-2.63 (m, 1H), 2.41-2.29 (m, 2H), 2.05 (td, J = 8.4, 3.8 Hz, 3H), 1.76 (d, J = 8.1 Hz, 6H), 1.41 (br. s., 6H), 1.33-1.24 (m, 3H), 1.08-0.94 (m, 2H), 0.91-0.72 (m, 2H).

6 $^1$H NMR (400 MHz, DMSO-d$_6$), δ 8.16-8.07 (m, 1H), 8.07-8.02 (m, 1H), 7.85-7.61 (m, 2H), 3.61 (br. s., 2H), 2.83 (q, J = 7.5 Hz, 2H), 2.11-1.99 (m, 1H), 1.89 (br. s., 6H), 1.81-1.67 (m, 6H), 1.53-1.35 (m, 6H), 1.31 (t, J = 7.6 Hz, 3H), 1.12-0.95 (m, 2H), 0.90-0.75 (m, 2H).

Example 7

N-((4-(3-cyclopropyl-1,2,4-oxadiazol-5-yl)bicyclo[2.2.2]octan-1-yl)methyl)-N-(3-(2-ethoxyoxazol-5-yl)phenyl)-3-fluorobicyclo[1.1.1]pentane-1-carboxamide (7)

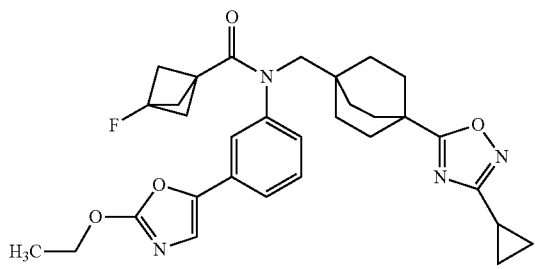

Step A. Intermediate 7A. Preparation of 5-(3-nitrophenyl)oxazol-2(3H)-one

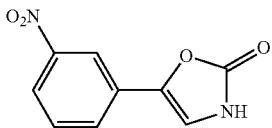 [SMILES: O=c1[nH]cc(-c2cccc([N+](=O)[O-])c2)o1]

To a stirred solution of 2-bromo-1-(3-nitrophenyl)ethan-1-one (5.0 g, 20.49 mmol) and thiazolidine-2,4-dione (2.78 g, 23.77 mmol) in DMF (22 mL) was added potassium carbonate (3.96 g, 28.7 mmol) and stirred for 1.5 h at room temperature. The reaction mixture was poured into ice cold water (200 mL). The solution was filtered, the solids were washed with water (100 mL) and was dried under high vacuum. The solids obtained were dissolved in water (45 mL) and THF (45 mL) and lithium hydroxide monohydrate (3.44 g, 82 mmol) was added to it. The reaction mixture was stirred for 30 min at room temperature. The resulting reaction mixture was poured into acetic acid (4.69 mL, 82 mmol) in ice water (200 mL), The solution was filtered and the solids were washed with water (50 mL) and dried in vacuum to afford the title compound (2.2 g, 10.67 mmol, 52% yield) as yellow solid. $^1$H NMR (400 MHz, DMSO-$d_6$) δ 11.07 (br. s, 1H), 8.29 (t, J=2.0 Hz, 1H), 8.13-8.09 (m, 1H), 7.93 (d, J=8.0 Hz, 1H), 7.85 (s, 1H), 7.74-7.69 (m, 1H). MS (ESI) 205 (M−H).

Step B. Intermediate 7B. Preparation of 2-chloro-5-(3-nitrophenyl)oxazole

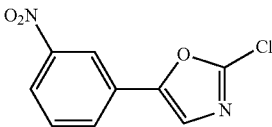

To a stirred solution of Intermediate 7A (1.0 g, 4.85 mmol) in acetonitrile (10 mL) was added tetraethylammonium chloride (1.929 g, 11.64 mmol) and N,N'-diethylaniline (0.724 g, 4.85 mmol). Next, phosphorus oxychloride (4.61 g, 30.1 mmol) was added drop wise, and then refluxed overnight. The reaction mixture was concentrated under reduced pressure to yield crude material. The material was added to crushed ice and extracted with ethyl acetate (2×50 mL). The organic layer was washed with water (50 mL) followed by saturated brine solution (50 mL), dried over anhydrous sodium sulfate, filtered and concentrated under reduced pressure to afford the title compound (220 mg, 0.980 mmol, 20% yield) as pale yellow solid. $^1$H NMR (400 MHz, DMSO-$d_6$) δ 8.49 (t, J=2.0 Hz, 1H), 8.25 (dt, J=7.4, 1.6 Hz, 1H), 8.16-8.13 (m, 1H), 8.08 (s, 1H), 7.80 (t, J=8.0 Hz, 1H). MS (ESI) 226 (M+H).

Step C. Intermediate 7C. Preparation of 2-ethoxy-5-(3-nitrophenyl)oxazole

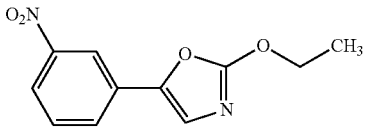 [SMILES: CCOc1ncc(-c2cccc([N+](=O)[O-])c2)o1]

To a cooled (0-5° C.) and stirred solution of sodium ethoxide (144 mg, 0.445 mmol) in THF (1.0 mL) was added a dropwise solution of Intermediate 7B (100 mg, 0.445 mmol) in THF (1.0 mL) and allowed to stir at room temperature for 30 min. The reaction mixture was quenched with water (1 mL) and concentrated under reduced pressure. The residue obtained was diluted with ethyl acetate (10 mL), washed with water (5 mL) and brine solution (5 mL). The organic layer was dried over sodium sulphate, filtered and concentrated under reduced pressure to afford the title compound (80 mg, 0.342 mmol, 77% yield) as white solid. $^1$H NMR (400 MHz, DMSO-$d_6$) δ 8.34 (t, J=2.0 Hz, 1H), 8.16-8.09 (m, 1H), 8.04-7.97 (m, 1H), 7.77-7.68 (m, 2H), 4.49 (q, J=7.0 Hz, 2H), 1.39 (t, J=7.0 Hz, 3H). MS (ESI) 235 (M+H).

Step D. Intermediate 7D. Preparation of 3-(2-ethoxyoxazol-5-yl)aniline

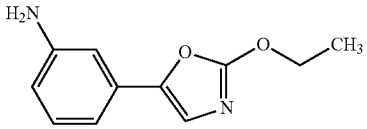

Intermediate 7C (80 mg, 0.342 mmol) was dissolved in a mixture of ethanol (0.8 mL), THF (0.4 mL) and water (0.2 mL). To the stirred reaction mixture, zinc (335 mg, 5.12 mmol) was added, followed by ammonium chloride (274 mg, 5.12 mmol). The reaction mixture was stirred overnight at room temperature. The reaction mixture was concentrated under reduced pressure and the residue was diluted with water (2 mL). The aqueous layer was extracted with ethyl acetate (2×10 mL). The combined organic layers were washed with water (5 mL), followed by brine solution (5 mL), dried over sodium sulfate, filtered and concentrated under reduced pressure to afford the title compound (60 mg, 0.294 mmol, 86% yield) as brown solid. $^1$H NMR (400 MHz, DMSO-$d_6$) δ 7.19 (s, 1H), 7.05 (t, J=7.8 Hz, 1H), 6.77-6.69 (m, 2H), 6.50 (ddd, J=8.0, 2.0, 1.0 Hz, 1H), 5.20 (s, 2H), 4.43 (q, J=7.0 Hz, 2H), 1.38 (t, J=7.3 Hz, 3H). MS (ESI) 205 (M+H).

Step E. Intermediate 7E. Preparation of N-((4-(3-cyclopropyl-1,2,4-oxadiazol-5-yl) bicyclo[2.2.2]octan-1-yl)methyl)-3-(2-ethoxyoxazol-5-yl)aniline

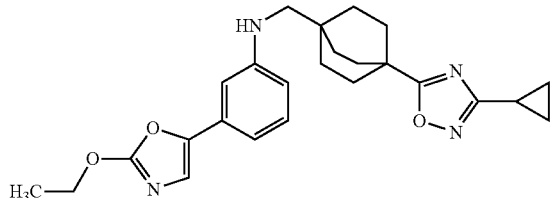

The title compound was synthesized according to the method described for the synthesis of Intermediate 1I by substituting Intermediate 7D and Intermediate 4C where appropriate: (50 mg, 0.115 mmol, 59% yield) as brown wax. $^1$H NMR (400 MHz, DMSO-d$_6$) δ 7.25 (s, 1H), 7.07 (t, J=7.9 Hz, 1H), 6.80-6.74 (m, 1H), 6.70 (d, J=7.6 Hz, 1H), 6.56 (d, J=9.8 Hz, 1H), 5.61 (t, J=6.0 Hz, 1H), 4.43 (q, J=7.0 Hz, 2H), 2.84 (d, J=6.1 Hz, 2H), 2.12-2.00 (m, 1H), 1.91-1.77 (m, 6H), 1.62-1.51 (m, 6H), 1.37 (t, J=7.1 Hz, 3H), 1.07-0.98 (m, 2H), 0.89-0.81 (m, 2H). MS (ESI) 435 (M+H).

Step F. Example 7: Preparation of N-((4-(3-cyclopropyl-1,2,4-oxadiazol-5-yl) bicyclo[2.2.2]octan-1-yl)methyl)-N-(3-(2-ethoxyoxazol-5-yl)phenyl)-3-fluorobicyclo[1.1.1]pentane-1-carboxamide The title compound was synthesized according to the method described for the synthesis of Example 3 by substituting Intermediate 7E and the corresponding acid where appropriate: (12.8 mg, 0.023 mmol, 25.4% yield). $^1$H NMR (400 MHz, DMSO-d$_6$) δ 7.64-7.54 (m, 3H), 7.54-7.43 (m, 1H), 7.32 (d, J=7.6 Hz, 1H), 4.47 (q, J=7.1 Hz, 2H), 3.57 (d, J=5.1 Hz, 2H), 2.09-2.01 (m, 1H), 1.87 (br. s., 6H), 1.82-1.67 (m, 6H), 1.51-1.30 (m, 9H), 1.07-0.96 (m, 2H), 0.92-0.79 (m, 2H). FXR EC$_{50}$ (nM) 22. MS (ESI) 547 (M+H).

Example 8

N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)-3-fluorobicyclo[1.1.1]pentane-1-carboxamide (8)

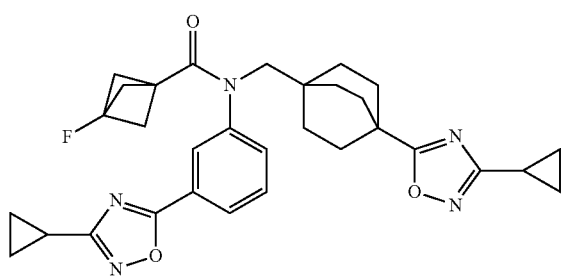

Step A. Intermediate 8A. Preparation of 3-(3-cyclopropyl-1,2,4-oxadiazol-5-yl)aniline

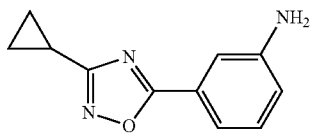 [SMILES: Nc1cccc(-c2nc(C3CC3)no2)c1]

The title compound was synthesized according to the method described for the synthesis of Intermediate 3A by substituting 3-aminobenzoic acid and (Z)—N'-hydroxycyclopropanecarboximidamide where appropriate: (2.3 g, 10.40 mmol, 71% yield) as solid. $^1$H NMR (400 MHz, DMSO-d$_6$) δ 7.30-7.21 (m, 2H), 7.14 (d, J=7.5 Hz, 1H), 6.89 (dd, J=8.3, 1.8 Hz, 1H), 5.95 (t, J=6.0 Hz, 1H), 2.86 (d, J=6.0 Hz, 2H), 2.20-2.12 (m, 1H), 2.10-2.02 (m, 1H), 1.91-1.81 (m, 6H), 1.62-1.52 (m, 6H), 1.13-1.06 (m, 2H), 1.06-0.99 (m, 2H), 0.99-0.94 (m, 2H), 0.89-0.82 (m, 2H), MS (ESI) 432 (M+H).

Step B. Intermediate 8B. Preparation of 3-(3-cyclopropyl-1,2,4-oxadiazol-5-yl)-N-((4-(3-cyclopropyl-1,2,4-oxadiazol-5-yl)bicyclo[2.2.2]octan-1-yl)methyl)aniline

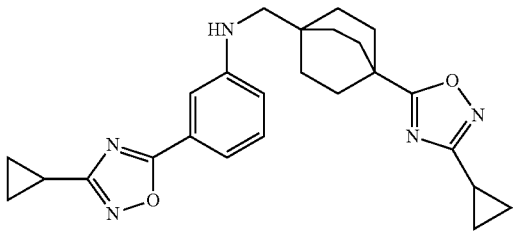 [SMILES: c1cc(NCC23CCC(c4nc(C5CC5)no4)(CC2)CC3)cc(-c2nc(C3CC3)no2)c1]

The title compound was synthesized according to the method described for the synthesis of Intermediate 1I by substituting Intermediate 8A and Intermediate 4C where appropriate: (100 mg, 0.232 mmol, 57% yield) as white solid. $^1$H NMR (400 MHz, DMSO-d$_6$) δ 7.30-7.21 (m, 2H), 7.14 (d, J=7.5 Hz, 1H), 6.89 (dd, J=8.3, 1.8 Hz, 1H), 5.95 (t, J=6.0 Hz, 1H), 2.86 (d, J=6.0 Hz, 2H), 2.20-2.12 (m, 1H), 2.10-2.02 (m, 1H), 1.91-1.81 (m, 6H), 1.62-1.52 (m, 6H), 1.13-1.06 (m, 2H), 1.06-0.99 (m, 2H), 0.99-0.94 (m, 2H), 0.89-0.82 (m, 2H). MS (ESI) 432 (M+H).

Step C. Example 8: Preparation of N-((4-(3-cyclopropyl-1,2,4-oxadiazol-5-yl) bicyclo[2.2.2]octan-1-yl)methyl)-N-(3-(3-cyclopropyl-1,2,4-oxadiazol-5-yl)phenyl)-3-fluorobicyclo[1.1.1]pentane-1-carboxamide The title compound was synthesized according to the method described for the synthesis of Example 3 by substituting Intermediate 8B and the corresponding acid where appropriate: (15 mg, 0.028 mmol, 59.5% yield). $^1$H NMR (400 MHz, DMSO-d$_6$) δ 8.06 (d, J=7.6 Hz, 1H), 8.01 (s, 1H), 7.81-7.64 (m, 2H), 3.63 (br. s., 2H), 2.30-2.15 (m, 1H), 2.11-2.00 (m, 1H), 1.88 (br. s., 6H), 1.82-1.69 (m, 6H), 1.54-1.31 (m, 6H), 1.14 (dd, J=8.4, 2.6 Hz, 2H), 1.08-0.92 (m, 4H), 0.88-0.77 (m, 2H). FXR EC$_{50}$ (nM) 137. MS (ESI) 544 (M+H).

The following compounds were synthesized according to the method described for the synthesis of Example 3 by substituting Intermediate 8B and the corresponding acids.

| Ex. No. | Structure | MS (ESI) (M + H) | FXR EC$_{50}$ (nM) |
|---|---|---|---|
| 9 | | 598 | 153 |
| 10 | | 550 | 425 |
| 11 | | 564 | 282 |

9 $^1$H NMR (400 MHz, DMSO-d$_6$) δ 8.12-7.94 (m, 2H), 7.75 (d, J = 7.8 Hz, 1H), 7.68 (t, J = 7.9 Hz, 1H), 6.54 (s, 1H), 3.66 (br. s., 2H), 2.78-2.69 (m, 1H), 2.37-2.28 (m, 2H), 2.24-2.16 (m, 1H), 2.14-1.96 (m, 3H), 1.85-1.68 (m, 6H), 1.51-1.29 (m, 6H), 1.19-1.08 (m, 2H), 1.08-0.90 (m, 4H), 0.87-0.76 (m, 2H).

10 $^1$H NMR (400 MHz, DMSO-d$_6$) δ 8.13-7.94 (m, 2H), 7.75 (d, J = 8.1 Hz, 1H), 7.68 (t, J = 7.7 Hz, 1H), 3.66 (br. s., 2H), 2.97-2.70 (m, 3H), 2.34 (br. s., 2H), 2.24-2.14 (m, 1H), 2.10-1.98 (m, 1H), 1.88-1.65 (m, 6H), 1.53-1.28 (m, 6H), 1.17-1.08 (m, 2H), 1.07-0.88 (m, 4H), 0.87-0.79 (m, 2H).

11 $^1$H NMR (400 MHz, DMSO-d$_6$) δ 8.16-7.89 (m, 2H), 7.78 (d, J = 7.6 Hz, 1H), 7.68 (t, J = 7.6 Hz, 1H), 3.64 (br. s., 2H), 2.98-2.80 (m, 1H), 2.31-2.16 (m, 2H), 2.15-1.96 (m, 3H), 1.94-1.69 (m, 8H), 1.65 (br. s., 1H), 1.50-1.29 (m, 6H), 1.12 (dd, J = 8.2, 2.6 Hz, 2H), 1.07-0.88 (m, 4H), 0.88-0.70 (m, 2H).

Example 12

Ethyl 2-(3-(3-fluoro-N-((4-(3-methyl-1,2,4-oxadiazol-5-yl)bicyclo[2.2.2]octan-1-yl) methyl)bicyclo[1.1.1]pentane-1-carboxamido)phenyl)oxazole-4-carboxylate (12)

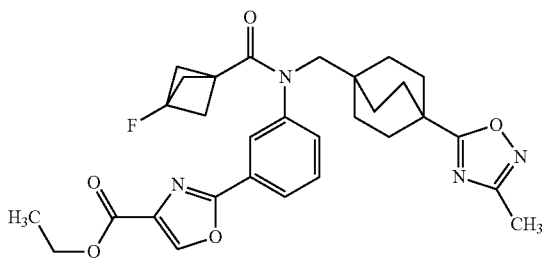

Step A. Intermediate 12A. Preparation of ethyl (Z)-3-hydroxy-2-((3-nitrobenzylidene) amino)propanoate

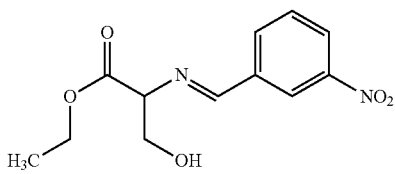 [SMILES: CCOC(=O)C(CO)/N=C/c1cccc([N+](=O)[O-])c1]

To a stirred solution of L-serine ethyl ester hydrochloride (2.81 g, 16.54 mmol) in THF (160 mL) at room temperature was added Et$_3$N (4.61 mL, 33.1 mmol), magnesium sulfate (1.991 g, 16.54 mmol) and 3-nitrobenzaldehyde (2.5 g, 16.54 mmol) (commercially available). The reaction mixture was stirred at room temperature for 12 h.

The reaction mixture was filtered over a celite pad and residue was washed with MTBE (10 mL). The filtrate was concentrated under reduced pressure to afford the title compound (4.5 g, 8.28 mmol, 50% yield), which was used as is in the next STEP without further purification. MS (ESI) 265 (M−H).

Step B. Intermediate 12B. Preparation of ethyl 2-(3-nitrophenyl)oxazole-4-carboxylate

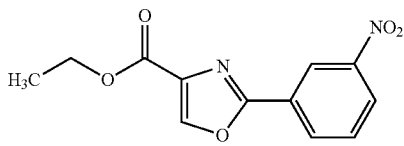 [SMILES: CCOC(=O)c1coc(-c2cccc([N+](=O)[O-])c2)n1]

To a stirred solution of Intermediate 12A (5 g, 18.78 mmol) in DCM (160 mL), were added bromotrichloromethane (5.58 mL, 56.3 mmol) and DBU (8.49 mL, 56.3 mmol) at 0° C. The reaction mixture was stirred at room temperature for 12 h. The reaction mixture was poured into cold water and the aqueous layer was extracted with EtOAc (2×100 mL). The combined organic layers were dried over MgSO$_4$, filtered and concentrated under reduced pressure. The residue was purified by flash column chromatography (Combiflash, 120 g silica, 0-50% EtOAc/PE) to afford the title compound (3 g, 11.33 mmol, 60% yield). MS (ESI) 263 (M+H).

Step C. Intermediate 12C. Preparation of ethyl 2-(3-aminophenyl)oxazole-4-carboxylate

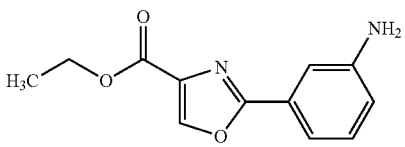

To a stirred solution of Intermediate 12B (1 g, 3.81 mmol) in 1,4-dioxane (20 mL) was added 10% Pd on carbon (0.203 g, 1.907 mmol) and stirred at room temperature for 12 h under ambient hydrogen atmosphere. The reaction mixture was filtered through celite pad and the residue was washed with ethyl acetate. The ethyl acetate solution was concentrated under reduced pressure to yield the title compound (800 mg, 3.31 mmol, 87% yield). MS (ESI) 233 (M+H).

Step D. Intermediate 12D. Preparation of ethyl 2-(3-(((4-(3-methyl-1,2,4-oxadiazol-5-yl)bicyclo[2.2.2]octan-1-yl)methyl)amino)phenyl)oxazole-4-carboxylate

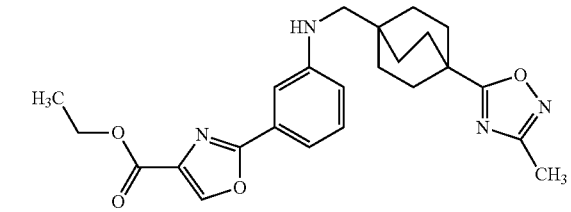 [SMILES: CCOC(=O)c1coc(-c2cccc(NCC34CCC(c5nc(C)no5)(CC3)CC4)c2)n1]

The title compound was synthesized according to the method described for the synthesis of Intermediate 1I by substituting Intermediate 12C and Intermediate 3C where appropriate: (40 mg, 0.092 mmol, 27% yield). MS (ESI) 437 (M+H).

Step E. Example 12. Preparation of Ethyl 2-(3-(3-fluoro-N-((4-(3-methyl-1,2,4-oxadiazol-5-yl)bicyclo[2.2.2]octan-1-yl) methyl)bicyclo[1.1.1]pentane-1-carboxamido) phenyl)oxazole-4-carboxylate The title compound was synthesized according to the method described for the synthesis of Example 3 by substituting Intermediate 12D and 3-fluorobicyclo[1.1.1]pentane-1-carboxylic acid where appropriate: (3.5 mg, 6.38 µmol, 14% yield). $^1$H NMR (400 MHz, DMSO-d$_6$) δ 9.01 (s, 1H), 8.03 (d, J=6.8 Hz, 1H), 7.96 (s, 1H), 7.71-7.61 (m, 2H), 4.35 (q, J=7.3 Hz, 2H), 3.65 (br. s., 1H), 3.59 (br. s., 1H), 2.28 (s, 3H), 1.89 (br. s., 6H), 1.85-1.73 (m, 6H), 1.46 (d, J=8.1 Hz, 6H), 1.33 (t, J=7.1 Hz, 3H); FXR EC$_{50}$ (nM) 1714; MS (ESI) 549 (M+H).

Example 13

Ethyl 2-(3-(N-((4-(3-cyclopropyl-1,2,4-oxadiazol-5-yl)bicyclo[2.2.2]octan-1-yl)methyl)-3-fluorobicyclo[1.1.1]pentane-1-carboxamido)phenyl)oxazole-4-carboxylate (13)

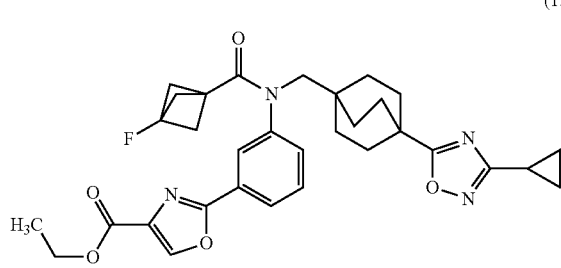

Step A. Intermediate 13A. Preparation of ethyl 2-(3-(((4-(3-cyclopropyl-1,2,4-oxadiazol-5-yl)bicyclo[2.2.2]octan-1-yl)methyl)amino)phenyl)oxazole-4-carboxylate

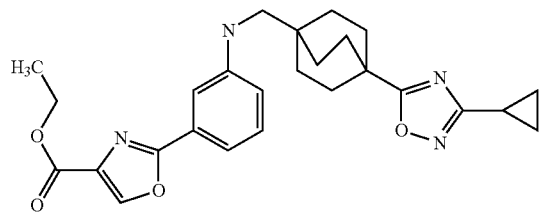 [SMILES: CCOC(=O)c1coc(-c2cccc(NCC34CCC(c5nc(C6CC6)no5)(CC3)CC4)c2)n1]

The title compound was synthesized according to the method described for the synthesis of Intermediate 1I by substituting Intermediate 12C and Intermediate 4C where appropriate: (550 mg, 1.153 mmol, 54% yield). MS (ESI) 463 (M+H).

Step B. Example 13. Preparation of Ethyl 2-(3-(N-((4-(3-cyclopropyl-1,2,4-oxadiazol-5-yl)bicyclo[2.2.2]octan-1-yl)methyl)-3-fluorobicyclo[1.1.1]pentane-1-carboxamido) phenyl)oxazole-4-carboxylate The title compound was synthesized according to the method described for the synthesis of Example 3 by substituting Intermediate 13A and 3-fluorobicyclo[1.1.1]pentane-1-carboxylic acid where appropriate: (13.9 mg, 0.24 mmol, 55% yield). $^1$H NMR (400 MHz, DMSO-$d_6$) δ 9.00 (s, 1H), 8.03 (d, J=7.3 Hz, 1H), 7.95 (s, 1H), 7.72-7.60 (m, 2H), 4.35 (q, J=7.0 Hz, 2H), 3.64 (br. s., 2H), 2.11-2.00 (m, 1H), 1.89 (br. s., 6H), 1.82-1.67 (m, 6H), 1.53-1.36 (m, 6H), 1.33 (t, J=7.1 Hz, 3H), 1.08-0.97 (m, 2H), 0.88-0.76 (m, 2H); FXR $EC_{50}$ (nM) 512; MS (ESI) 575 (M+H).

Example 14

N-(3-(4-(chloromethyl)oxazol-2-yl)phenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide (14)

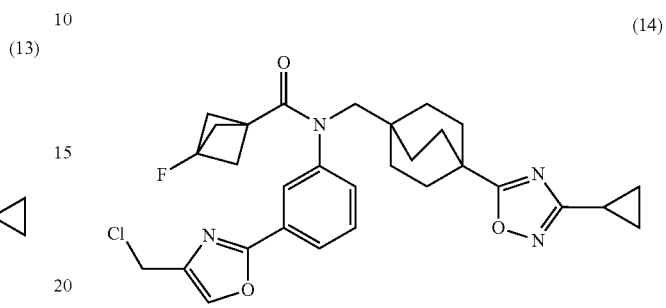

Step A. Intermediate 14A. Preparation of (2-(3-(((4-(3-cyclopropyl-1,2,4-oxadiazol-5-yl)bicyclo[2.2.2]octan-1-yl)methyl)amino)phenyl)oxazol-4-yl)methanol

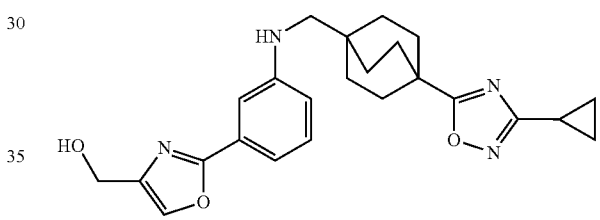

To a stirred solution of Intermediate 13A (100 mg, 0.216 mmol) in THF (5 mL) cooled at −78° C., DIBAL-H (0.432 mL, 0.432 mmol) was added and stirred for 1 h. The reaction mixture was poured into saturated aqueous ammonium chloride solution and the aqueous layer was extracted with EtOAc (2×50 mL). The combined organic layers were dried over MgSO$_4$, filtered and concentrated under reduced pressure. The residue was purified by flash column chromatography (Combiflash, 24 g silica, 0-50% EtOAc/PE) to afford the title compound (60 mg, 0.110 mmol, 51% yield). MS (ESI) 421 (M+H).

Step B. Example 14. Preparation of N-(3-(4-(chloromethyl)oxazol-2-yl)phenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide To a stirred solution of Intermediate 14A (40 mg, 0.095 mmol) and 3-fluorobicyclo[1.1.1]pentane-1-carboxylic acid (12.38 mg, 0.095 mmol) in DCM (2 mL) at room temperature were added pyridine (0.046 mL, 0.571 mmol) and POCl$_3$ (0.027 mL, 0.285 mmol). The reaction mixture was stirred at room temperature for 3 h and the solvent was removed under reduced pressure. The crude material was purified via preparative LC/MS using the following conditions: Column: Waters XBridge C18, 150 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 15% B, 15-70% B over 25 minutes, then a 5-minute hold at 100% B; Flow Rate: 15 mL/min; Column Temperature: 25 C. Fraction collection was triggered by MS signals. Fractions containing the desired product were combined and dried via centrifugal evaporation to yield the title compound (5.6 mg, 10.03 μmol, 11% yield). $^1$H NMR (400 MHz, DMSO-$d_6$) δ 8.34 (s, 1H), 8.00 (d, J=7.6 Hz, 1H), 7.91 (s, 1H), 7.70-7.57 (m, 2H), 4.78 (s, 2H), 3.63 (br. s., 1H), 3.58 (br. s., 1H), 2.08-2.00 (m, 1H), 1.89 (br. s., 6H), 1.82-1.70 (m, 6H), 1.50-1.34 (m, 6H), 1.06-0.96 (m, 2H), 0.87-0.79 (m, 2H); FXR $EC_{50}$ (nM) 166; MS (ESI) 551 (M+H).

Example 15

N-((4-(3-cyclopropyl-1,2,4-oxadiazol-5-yl)bicyclo[2.2.2]octan-1-yl)methyl)-3-fluoro-N-(3-(4-(2-hydroxypropan-2-yl)oxazol-2-yl)phenyl)bicyclo[1.1.1]pentane-1-carboxamide (15)

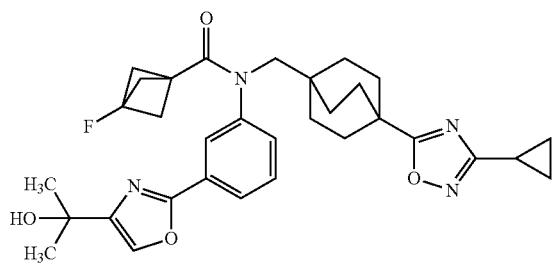

Step A. Intermediate 15A. Preparation of 2-(2-(3-(((4-(3-cyclopropyl-1,2,4-oxadiazol-5-yl)bicyclo[2.2.2]octan-1-yl)methyl)amino)phenyl)oxazol-4-yl)propan-2-ol

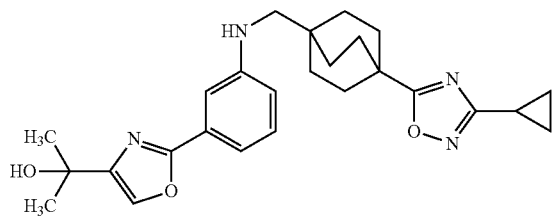 [SMILES: CC(C)(O)c1coc(-c2cccc(NCC34CCC(c5nc(C6CC6)no5)(CC3)CC4)c2)n1]

To a stirred solution of Intermediate 13A (50 mg, 0.108 mmol) in THF (2 mL) was added methylmagnesium bromide (0.108 mL, 0.324 mmol) at 0° C. The reaction mixture was stirred at 0° C. for 1 h. The reaction mixture was poured into saturated aqueous ammonium chloride solution and the aqueous layer was extracted with EtOAc (2×50 mL). The combined organic layers were dried over $MgSO_4$, filtered and concentrated under reduced pressure to afford the title compound (30 mg, 0.067 mmol, 62% yield). MS (ESI) 449 (M+H).

Step B. Example 15. Preparation of N-((4-(3-cyclopropyl-1,2,4-oxadiazol-5-yl) bicyclo[2.2.2]octan-1-yl)methyl)-3-fluoro-N-(3-(4-(2-hydroxypropan-2-yl) oxazol-2-yl) phenyl)bicyclo[1.1.1]pentane-1-carboxamide The title compound was synthesized according to the method described for the synthesis of Example 3 by substituting Intermediate 15A and 3-fluorobicyclo[1.1.1]pentane-1-carboxylic acid where appropriate: (3.0 mg, 5.14 μmol, 12% yield). $^1$H NMR (400 MHz, DMSO-$d_6$) δ 8.03-7.95 (m, 2H), 7.86 (s, 1H), 7.62 (t, J=7.9 Hz, 1H), 7.57 (d, J=8.1 Hz, 1H), 5.15 (s, 1H), 3.75-3.48 (m, 2H), 2.07-2.01 (m, 1H), 1.89 (br.s., 6H), 1.82-1.65 (m, 6H), 1.53-1.34 (m, 12H), 1.06-0.97 (m, 2H), 0.88-0.78 (m, 2H); FXR $EC_{50}$ (nM) 88; MS (ESI) 561 (M+H).

The following compounds were synthesized according to the method described for the synthesis of Example 3 by substituting Intermediate 15A and the corresponding acids where appropriate:

| Ex. No. | Structure & Name | MS (ESI) (M + H) | FXR $EC_{50}$ (nM) |
|---|---|---|---|
| 16 | | 567 | 318 |

| Ex. No. | Structure & Name | MS (ESI) (M + H) | FXR EC$_{50}$ (nM) |
|---|---|---|---|
| 17 | 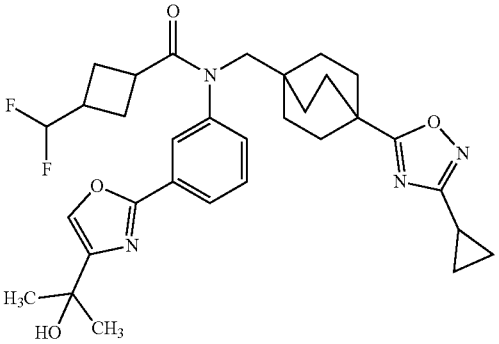 [SMILES: CC(C)(O)c1coc(-c2cccc(N(CC34CCC(c5nc(C6CC6)no5)(CC3)CC4)C(=O)C3CC(C(F)F)C3)c2)n1] | 581 | 309 |
| 18 | 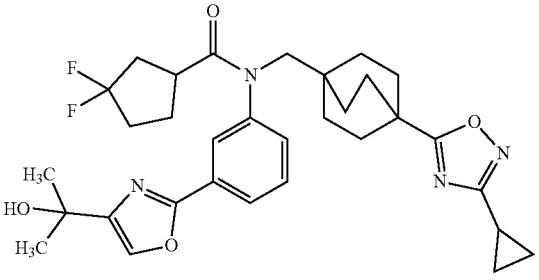 [SMILES: CC(C)(O)c1coc(-c2cccc(N(CC34CCC(c5nc(C6CC6)no5)(CC3)CC4)C(=O)C3CCC(F)(F)C3)c2)n1] | 581 | 154 |
| 19 | 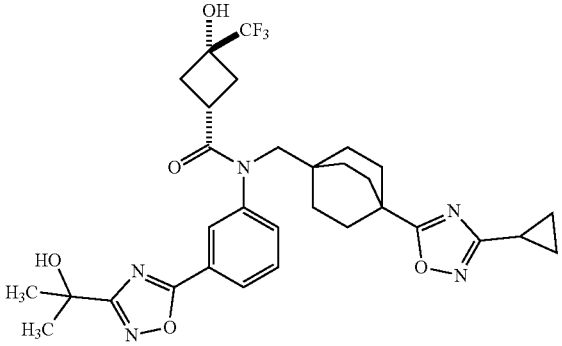 | 615 | 327 |
16 $^1$H NMR (400 MHz, DMSO-d$_6$) δ 7.97 (s, 1H), 7.94 (d, J = 7.6 Hz, 1H), 7.88 (s, 1H), 7.64-7.53 (m, 2H), 5.15 (s, 1H), 3.66 (br. s., 2H), 2.94-2.73 (m, 3H), 2.34 (d, J =2.0 Hz, 2H), 2.08-2.01 (m, 1H), 1.83-1.72 (m, 6H), 1.46 (s, 6H), 1.44-1.35 (m, 6H), 1.03-0.97 (m, 2H), 0.86-0.79 (m, 2H)
17 $^1$H NMR (400 MHz, DMSO-d$_6$) δ 7.97 (s, 1H), 7.92 (d, J = 5.9 Hz, 1H), 7.85-7.76 (m, 1H), 7.61-7.45 (m, 2H), 6.01 (t, J = 56 Hz, 1H), 5.14 (s, 1H), 3.63 (br. s., 2H), 3.02 (d, J = 9.0 Hz, 1H), 2.27 (s, 1H), 2.14-2.01 (m, 2H), 1.76 (d, J = 8.8 Hz, 8H), 1.68 (br. s., 1H), 1.52-1.31 (m, 12H), 1.01 (dd, J = 8.2, 2.6 Hz, 2H), 0.89-0.78 (m, 2H)
18 $^1$H NMR (400 MHz, DMSO-d$_6$) δ 8.00-7.92 (m, 2H), 7.90 (s, 1H), 7.62 (d, J = 4.2 Hz, 2H), 5.15 (s, 1H), 3.62 (br. s., 2H), 2.29 (br. s., 1H), 2.18-1.99 (m, 3H), 1.92 (br. s., 1H), 1.89-1.59 (m, 9H), 1.52-1.32 (m, 12H), 1.07-0.97 (m, 2H), 0.89-0.76 (m, 2H)
19 $^1$H NMR (400 MHz, DMSO-d$_6$) δ 7.97 (s, 1H), 7.92 (d, J = 7.3 Hz, 1H), 7.85 (s, 1H), 7.65-7.50 (m, 2H), 6.57 (s, 1H), 5.15 (s, 1H), 3.66 (br. s., 1H), 3.60 (s, 1H), 2.76-2.69 (m, 1H), 2.40-2.34 (m, 2H), 2.18-1.97 (m, 3H), 1.87-1.68 (m, 6H), 1.52-1.28 (m, 12H), 1.06-0.94 (m, 2H), 0.89-0.72 (m, 2H)

Example 20

N-((4-(3-cyclopropyl-1,2,4-oxadiazol-5-yl)bicyclo[2.2.2]octan-1-yl)methyl)-N-(3-(2-cyclopropyloxazol-5-yl)phenyl)cyclobutanecarboxamide

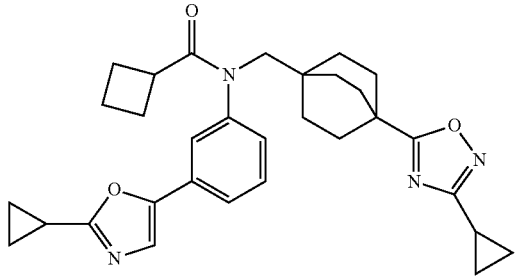
(20)

Step A. Intermediate 20A. Preparation of 2-cyclopropyl-5-(3-nitrophenyl)oxazole

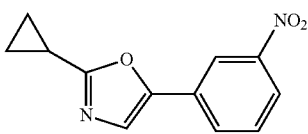 [SMILES: O=[N+]([O-])c1cccc(-c2cnc(C3CC3)o2)c1]

To a stirred solution of (diacetoxyiodo)benzene (1170 mg, 3.63 mmol) in cyclopropanecarbonitrile (50 mL) was added trifluoromethanesulfonic acid (2045 mg, 13.62 mmol) and stirred for 20 min at room temperature. To the reaction mixture, 1-(3-nitrophenyl)ethan-1-one (500 mg, 3.03 mmol) was added and refluxed for 2 h. The reaction mixture was concentrated under reduced pressure and the residue obtained was diluted with DCM (100 mL) and washed with 10% brine solution (5×30 mL). The organic layer was dried over sodium sulphate, filtered and concentrated under reduced pressure. The crude material was purified by flash column chromatography (Combiflash, 40 g silica, 0-40% EtOAc/PE) to afford the title compound (800 mg, 0.556 mmol, 18% yield) as an orange red liquid. $^1$H NMR (400 MHz, DMSO-$d_6$) δ 8.42 (t, J=2.0 Hz, 1H), 8.18-8.13 (m, 1H), 8.13-8.06 (m, 1H), 7.81-7.70 (m, 2H), 1.93 (dd, J=7.8, 6.8 Hz, 1H), 1.16-1.01 (m, 2H), 0.97-0.88 (m, 2H). MS (ESI) 231 (M+H).

Step B. Intermediate 20B. Preparation of 3-(2-cyclopropyloxazol-5-yl)aniline

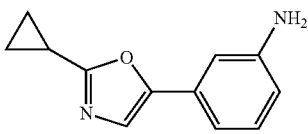 [SMILES: Nc1cccc(-c2cnc(C3CC3)o2)c1]

Intermediate 20A (300 mg, 1.303 mmol) was dissolved in a mixture of ethanol (8 mL), THF (2 mL) and water (4 mL). To the stirred reaction mixture was added zinc (1278 mg, 19.55 mmol) followed by ammonium chloride (1046 mg, 19.55 mmol) and the reaction mixture was stirred overnight at room temperature. The reaction mixture was concentrated under reduced pressure and the residue was suspended in water (10 mL) and EtOAc (10 mL). The organic layer was separated and the aqueous layer was extracted with ethyl acetate (2×10 mL). The combined organic layers were washed with water (10 mL) followed by brine solution (10 mL), dried over sodium sulfate, filtered and concentrated under reduced pressure to afford the title compound (220 mg, 1.099 mmol, 84% yield). $^1$H NMR (400 MHz, DMSO-$d_6$) δ 7.29 (s, 1H), 7.07 (t, J=7.8 Hz, 1H), 6.85-6.77 (m, 2H), 6.52 (dt, J=8.0, 1.3 Hz, 1H), 5.21 (s, 2H), 2.18-2.08 (m, 1H), 1.11-1.02 (m, 2H), 1.02-0.93 (m, 2H). MS (ESI) 201 (M+H).

Step C. Intermediate 20C. Preparation of N-((4-(3-cyclopropyl-1,2,4-oxadiazol-5-yl) bicyclo[2.2.2]octan-1-yl)methyl)-3-(2-cyclopropyloxazol-5-yl)aniline


The title compound was synthesized according to the method described for the synthesis of Intermediate 1I by substituting Intermediate 20B and Intermediate 4C where appropriate: (220 mg, 0.511 mmol, 68% yield) as brown wax. $^1$H NMR (400 MHz, DMSO-$d_6$) δ 7.34 (s, 1H), 7.10 (t, J=8.0 Hz, 1H), 6.87 (d, J=1.5 Hz, 1H), 6.77 (d, J=7.5 Hz, 1H), 6.58 (dd, J=8.0, 1.5 Hz, 1H), 5.62 (t, J=5.8 Hz, 1H), 2.85 (d, J=6.0 Hz, 2H), 2.19-2.10 (m, 1H), 2.10-2.03 (m, 1H), 1.92-1.79 (m, 6H), 1.64-1.53 (m, 6H), 1.11-0.94 (m, 6H), 0.88-0.83 (m, 2H). MS (ESI) 431 (M+H).

Step D. Example 20. Preparation of N-((4-(3-cyclopropyl-1,2,4-oxadiazol-5-yl) bicyclo[2.2.2]octan-1-yl)methyl)-N-(3-(2-cyclopropyloxazol-5-yl)phenyl) cyclobutanecarboxamide The title compound was synthesized according to the method described for the synthesis of Example 3 by substituting Intermediate 20C and the corresponding acid where appropriate: (11.5 mg, 0.022 mmol, 47.8% yield). $^1$H NMR (400 MHz, DMSO-$d_6$) δ 7.65-7.54 (m, 3H), 7.48 (t, J=8.1 Hz, 1H), 7.29 (d, J=8.8 Hz, 1H), 3.61 (s, 2H), 3.09 (d, J=7.6 Hz, 1H), 2.22-1.98 (m, 4H), 1.82-1.71 (m, 6H), 1.64 (m, 4H), 1.46-1.34 (m, 6H), 1.12-0.94 (m, 6H), 0.87-0.78 (m, 2H). FXR $EC_{50}$ (nM) 138; MS (ESI) 513 (M+H).

The following compounds were synthesized according to the method described for the synthesis of Example 3 by substituting Intermediate 20C and the corresponding acids where appropriate:

| Ex. No. | Structure | MS (ESI) (M + H) | FXR EC$_{50}$ (nM) |
|---|---|---|---|
| 21 | 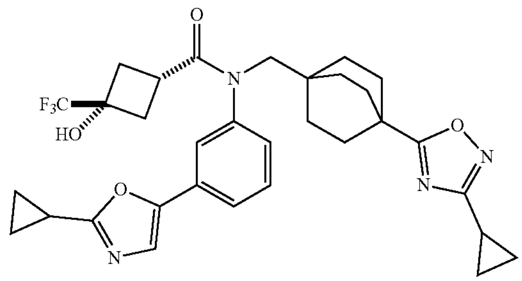 | 597 | 80 |
| 22 | 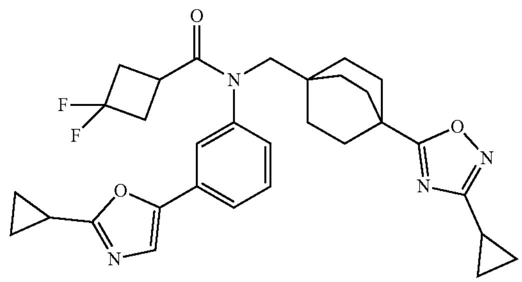 [SMILES: O=C(C1CC(F)(F)C1)N(CC12CCC(c3nc(C4CC4)no3)(CC1)CC2)c1cccc(-c2cnc(C3CC3)o2)c1] | 549 | 133 |
| 23 | 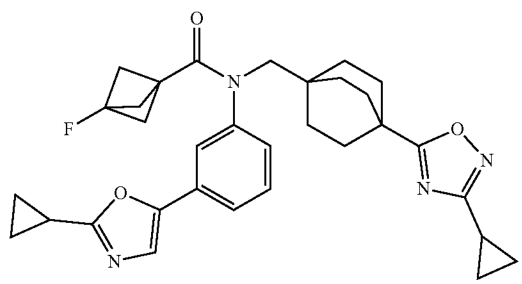 [SMILES: O=C(N(CC12CCC(c3nc(C4CC4)no3)(CC1)CC2)c1cccc(-c2cnc(C3CC3)o2)c1)C12CC(F)(C1)C2] | 543 | 72 |
| 24 | 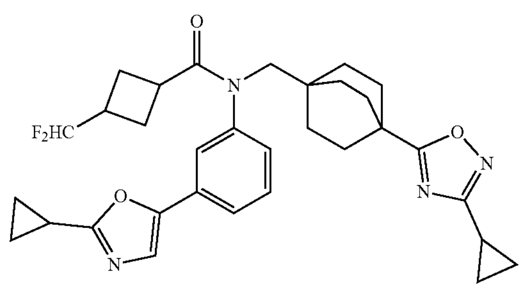 [SMILES: O=C(C1CC(C(F)F)C1)N(CC12CCC(c3nc(C4CC4)no3)(CC1)CC2)c1cccc(-c2cnc(C3CC3)o2)c1] | 563 | 281 |

21 $^1$H NMR (400 MHz, DMSO-d$_6$) δ 7.67 (s, 1H), 7.65-7.57 (m, 2H), 7.50 (t, J = 7.7 Hz, 1H), 7.35 (d, J = 7.3 Hz, 1H), 6.55 (s, 1H), 3.64 (br. s., 2H), 2.80-2.73 (m, 1H), 2.34 (t, J = 11.4 Hz, 2H), 2.21-2.14 (m, 1H), 2 11-2.00 (m, 3H), 1.84-1.67 (m, 6H), 1.41 (br. s., 6H), 1.12-0.98 (m, 6H), 0.87-0.79 (m, 2H).

22 $^1$H NMR (400 MHz, DMSO-d$_6$) δ 7.69 (s, 1H), 7.64-7.55 (m, 2H), 7.51 (t, J = 7.8 Hz, 1H), 7.35 (d, J = 8.6 Hz, 1H), 3.64 (br. s., 2H), 2.96-2.83 (m, 1H), 2.83-2.69 (m, 2H), 2.34 (br. s., 2H), 2.23-2.12 (m, 1H), 2.10-1.99 (m, 1H), 1.87-1.66 (m, 6H), 1.53-1.30 (m, 6H), 1.13-0.96 (m, 6H), 0.89-0.76 (m, 2H).

23 $^1$H NMR (400 MHz, DMSO-d$_6$) δ 7.76-7.60 (m, 3H), 7.52 (t, J = 7.8 Hz, 1H), 7.36 (d, J = 7.8 Hz, 1H), 3.72-3.58 (m, 1H), 3.58-3.44 (m, 1H), 2.24-2.13 (m, 1H), 2.10-1.99 (m, 1H), 1.87 (s, 6H), 1.77 (t, J = 7.7 Hz, 6H), 1.54-1.27 (m, 6H), 1.16-0.93 (m, 6H), 0.89-0.74 (m, 2H).

24 $^1$H NMR (400 MHz, DMSO-d$_6$) δ 7.63-7.54 (m, 2H), 7.49 (t, J = 7.9 Hz, 1H), 7.36-7.26 (m, 1H), 5.90 (d, J = 3.9 Hz, 1H), 3.61 (br. s., 2H), 3.14-3.00 (m, 1H), 2.30 (d, J = 8.8 Hz, 1H), 2.18 (d, J = 4.9 Hz, 1H), 2.11-2.00 (m, 3H), 1.82-1.72 (m, 6H), 1.68 (d, J = 11.5 Hz, 2H), 1.40 (m, 6H), 1.14-0.95 (m, 6H), 0.89-0.77 (m, 2H). (1H was buried under DMSO peak)

Example 25

N-((4-(3-cyclopropyl-1,2,4-oxadiazol-5-yl)bicyclo[2.2.2]octan-1-yl)methyl)-N-(3-(5-ethoxyisoxazol-3-yl)phenyl)-3-fluorobicyclo[1.1.1]pentane-1-carboxamide

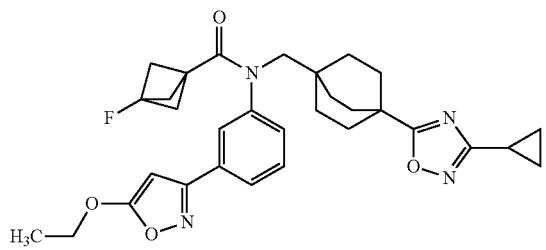
(25)

Step A. Intermediate 25A. Preparation of 3-(3-nitrophenyl)isoxazol-5(4H)-one

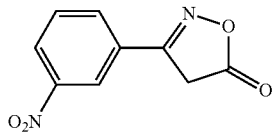 [SMILES: O=C1CC(c2cccc([N+](=O)[O-])c2)=NO1]

To a stirred solution of methyl 3-(3-nitrophenyl)-3-oxo-propanoate (1.0 g, 4.48 mmol) in ethanol (8 mL) was added hydroxylamine hydrochloride (0.342 g, 4.93 mmol) in water (8 mL) and stirred overnight at room temperature. The reaction mixture was concentrated under reduced pressure and the residue obtained was diluted with water (50 mL), and then filtered. The solids were washed with water (50 mL) and dried under reduced pressure to afford the title compound (800 mg, 3.88 mmol, 87% yield) as yellow solid. $^1$H NMR (400 MHz, DMSO-$d_6$) δ 8.58-8.50 (m, 1H), 8.35 (br. s., 1H), 8.22 (d, J=7.5 Hz, 1H), 7.88-7.78 (m, 1H), 5.93 (br. s., 1H), 4.44 (br. s., 1H). MS (ESI) 207 (M+H).

Step B. Intermediate 25B. Preparation of 5-chloro-3-(3-nitrophenyl)isoxazole

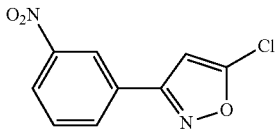 [SMILES: O=[N+]([O-])c1cccc(-c2cc(Cl)on2)c1]

To a stirred solution of Intermediate 25A (0.8 g, 3.88 mmol) in POCl$_3$ (2.170 ml, 23.28 mmol) was added TEA (0.595 ml, 4.27 mmol) and stirred at 120° C. for 2 h. The reaction mixture was concentrated under reduced pressure and the residue obtained was added to crushed ice and then extracted with ethyl acetate (2×20 mL). The combined organic layers were washed with water (20 mL) followed by saturated aqueous brine solution (20 mL), dried over sodium sulfate, filtered and concentrated under reduced pressure. The crude material was purified using flash column chromatography (Combiflash, 12 g silica gel, 0-30% EtOAc/PE) to afford the title compound (130 mg, 0.579 mmol, 15% yield) as white solid. $^1$H NMR (400 MHz, DMSO-$d_6$) δ 8.66 (t, J=2.0 Hz, 1H), 8.41 (ddd, J=8.3, 2.3, 1.0 Hz, 1H), 8.34 (dt, J=7.9, 1.3 Hz, 1H), 7.87 (t, J=8.0 Hz, 1H), 7.60 (s, 1H). MS (ESI) 242 (M+H).

Step C. Intermediate 25C. Preparation of 5-ethoxy-3-(3-nitrophenyl)isoxazole

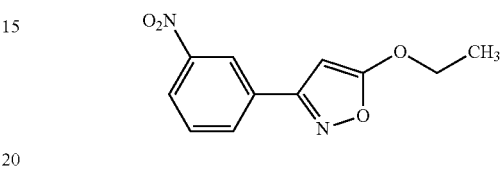

To a cooled (0-5° C.) and stirred solution of sodium ethoxide (151 mg, 2.226 mmol) in THF (5 mL) was added drop wise a solution of Intermediate 25B (500 mg, 2.226 mmol) in THF (5 mL) and the reaction mixture was allowed to stir at room temperature for 30 min. The reaction mixture was quenched with water (1 mL) and concentrated under reduced pressure. The residue was diluted with ethyl acetate (5 mL), washed with water (5 mL) followed by brine solution (5 mL). The organic layer was dried over sodium sulphate, filtered and concentrated under reduced pressure to afford the title compound (450 mg, 1.921 mmol, 86% yield) as yellow solid. $^1$H NMR (400 MHz, DMSO-$d_6$) δ 8.58 (t, J=2.0 Hz, 1H), 8.34 (d, J=1.0 Hz, 1H), 8.30-8.23 (m, 1H), 7.82 (t, J=8.0 Hz, 1H), 6.45 (s, 1H), 4.38 (q, J=7.0 Hz, 2H), 1.42 (t, J=7.0 Hz, 3H). MS (ESI) 235 (M+H).

Step D. Intermediate 25D. Preparation of 3-(5-ethoxyisoxazol-3-yl)aniline

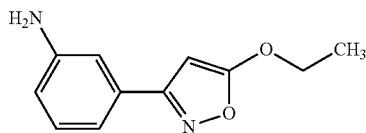

Intermediate 25C (450 mg, 1.921 mmol) was dissolved in a mixture of ethanol (4 mL), THF (1 mL) and water (2 mL). To the stirred reaction mixture, zinc (1884 mg, 28.8 mmol) was added followed by the addition of ammonium chloride (1542 mg, 28.8 mmol). The reaction mixture was stirred overnight at room temperature. The reaction mixture was filtered through celite pad and the celite pad was washed with methanol (5 mL). The combined filtrate was evaporated under reduced pressure to obtain residue which was diluted in ethyl acetate (10 mL). The subsequent solution was washed with water (2×5 mL), brine solution (10 mL), then dried over sodium sulfate, filtered and concentrated under reduced pressure to afford the title compound (220 mg, 1.077 mmol, 56% yield) as brown wax. $^1$H NMR (400 MHz, DMSO-$d_6$) δ 7.15-7.07 (m, 1H), 7.00 (t, J=2.0 Hz, 1H), 6.91-6.86 (m, 1H), 6.69-6.62 (m, 1H), 5.96 (s, 1H), 5.25 (s, 2H), 4.32 (q, J=7.0 Hz, 2H), 1.42 (t, J=7.0 Hz, 3H). MS (ESI) 205 (M+H).

Step E. Intermediate 25E. Preparation of N-((4-(3-cyclopropyl-1,2,4-oxadiazol-5-yl) bicyclo[2.2.2]octan-1-yl)methyl)-3-(5-ethoxyisoxazol-3-yl)aniline

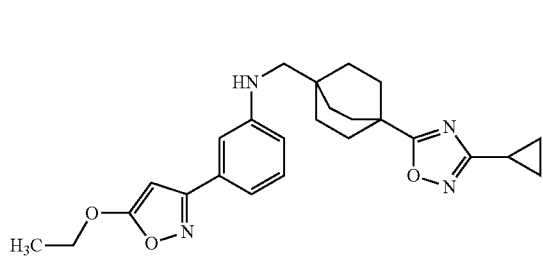 [SMILES: CCOc1cc(-c2cccc(NCC34CCC(c5nc(C6CC6)no5)(CC3)CC4)c2)no1]

The title compound was synthesized according to the method described for the synthesis of Intermediate 1I by substituting Intermediate 25D and Intermediate 4C where appropriate: (200 mg, 0.460 mmol, 63% yield) as brown wax. MS (ESI) 435 (M+H).

Step F. Example 25. Preparation of N-((4-(3-cyclopropyl-1,2,4-oxadiazol-5-yl) bicyclo[2.2.2]octan-1-yl)methyl)-N-(3-(5-ethoxyisoxazol-3-yl)phenyl)-3-fluorobicyclo[1.1.1]pentane-1-carboxamide The title compound was synthesized according to the method described for the synthesis of Example 3 by substituting Intermediate 25E and the corresponding acid where appropriate: (2.1 mg, 3.84 μmol, 8% yield). ¹H NMR (400 MHz, DMSO-d$_6$) δ 7.83 (d, J=7.6 Hz, 1H), 7.79 (s, 1H), 7.59 (t, J=7.7 Hz, 1H), 7.54 (d, J=8.3 Hz, 1H), 6.33 (s, 1H), 4.36 (q, J=7.1 Hz, 2H), 3.59 (s, 2H), 2.09-1.96 (m, 1H), 1.86 (s, 6H), 1.81-1.67 (m, 6H), 1.52-1.36 (m, 9H), 1.08-0.97 (m, 2H), 0.88-0.76 (m, 2H). FXR EC$_{50}$ (nM)=87; MS (ESI) 547 (M+H).

Example 26

N-((4-(3-cyclopropyl-1,2,4-oxadiazol-5-yl)bicyclo[2.2.2]octan-1-yl)methyl)-3-fluoro-N-(3-(2-propyloxazol-5-yl)phenyl)bicyclo[1.1.1]pentane-1-carboxamide (26)

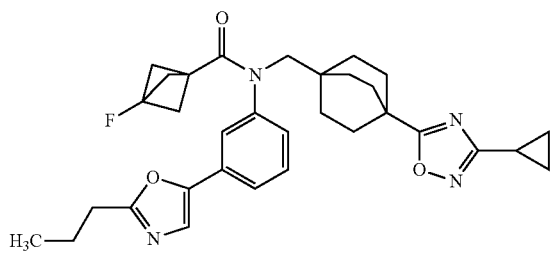

Step A. Intermediate 26A. Preparation of 5-(3-nitrophenyl)-2-propyloxazole

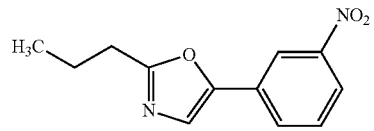

To a stirred solution of (diacetoxyiodo)benzene (2.340 g, 7.27 mmol) in butyronitrile (10 mL) was added trifluoromethanesulfonic acid (4.09 g, 27.2 mmol) and the reaction mixture was stirred at room temperature for 20 min. To the reaction mixture, 1-(3-nitrophenyl)ethan-1-one (1.0 g, 6.06 mmol) was added and the reaction mixture was refluxed for 2 h. The reaction mixture was concentrated under reduced pressure and the residue was diluted with DCM (100 mL). The subsequent organic solution was washed with 10% aqueous brine solution (3×50 mL). The organic layer was dried over sodium sulfate and concentrated under reduced pressure. The crude material was purified by flash column chromatography (Combiflash, 24 g silica, 0-50% EtOAc/PE, gradient elution) to afford the title compound (300 mg, 1.292 mmol, 21% yield) as brown liquid.

¹H NMR (400 MHz, DMSO-d$_6$) δ 8.76 (s, 1H), 8.59-8.53 (m, 1H), 8.24-8.11 (m, 2H), 7.73 (t, J=8.0 Hz, 1H), 2.80 (t, J=7.5 Hz, 2H), 1.82-1.70 (m, 2H), 0.97 (t, J=7.3 Hz, 3H). MS (ESI) 233 (M+H).

Step B. Intermediate 26B. Preparation of 3-(2-propyloxazol-5-yl)aniline

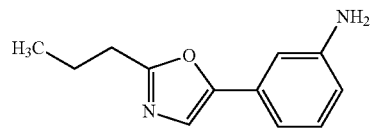 [SMILES: CCCc1ncc(-c2cccc([N+](=O)[O-])c2)o1]

Intermediate 26A (300 mg, 1.292 mmol) was dissolved in a mixture of ethanol (8 mL), THF (2 mL), and water (4 mL). To the stirred reaction mixture, zinc (1267 mg, 19.38 mmol) was added followed by the addition of ammonium chloride (1036 mg, 19.38 mmol) and stirred overnight at room temperature. The reaction mixture was concentrated under reduced pressure and the residue was diluted with water (10 mL) and extracted with ethyl acetate (2×10 mL). The combined organic layers were washed with water (10 mL), followed by brine solution (10 mL), dried over sodium sulfate, filtered and concentrated under reduced pressure to afford the title compound (220 mg, 1.088 mmol, 84% yield). ¹H NMR (400 MHz, DMSO-d$_6$) δ 8.29 (s, 1H), 7.09-6.97 (m, 2H), 6.91-6.84 (m, 1H), 6.52-6.46 (m, 1H), 5.12 (s, 2H), 2.75 (t, J=7.3 Hz, 2H), 1.74 (q, J=7.4 Hz, 2H), 0.96 (t, J=7.3 Hz, 3H). MS (ESI) 203 (M+H).

Step C. Intermediate 26C. Preparation of N-((4-(3-cyclopropyl-1,2,4-oxadiazol-5-yl) bicyclo[2.2.2]octan-1-yl)methyl)-3-(2-propyloxazol-5-yl)aniline

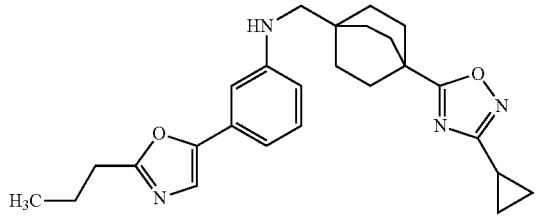 [SMILES: CCCc1ncc(-c2cccc(NCC34CCC(c5nc(C6CC6)no5)(CC3)CC4)c2)o1]

The title compound was synthesized according to the method described for the synthesis of Intermediate 1I by substituting Intermediate 26B and Intermediate 4C where appropriate: (140 mg, 0.324 mmol, 66% yield) as a brown wax. $^1$H NMR (400 MHz, DMSO-$d_6$) δ 8.33 (s, 1H), 7.10-7.06 (m, 1H), 7.04 (d, J=5.5 Hz, 1H), 6.87 (d, J=7.5 Hz, 1H), 6.56 (dd, J=8.3, 1.8 Hz, 1H), 5.53 (t, J=6.0 Hz, 1H), 2.85 (d, J=5.5 Hz, 2H), 2.76 (t, J=7.3 Hz, 2H), 2.11-2.03 (m, 1H), 1.92-1.82 (m, 6H), 1.80-1.69 (m, 2H), 1.63-1.54 (m, 6H), 1.07-1.00 (m, 2H), 0.96 (t, J=7.3 Hz, 3H), 0.89-0.83 (m, 2H). MS (ESI) 433 (M+H).

Step D. Example 26. Preparation of N-((4-(3-cyclopropyl-1,2,4-oxadiazol-5-yl) bicyclo[2.2.2]octan-1-yl)methyl)-3-fluoro-N-(3-(2-propyloxazol-5-yl)phenyl) bicyclo[1.1.1]pentane-1-carboxamide The title compound was synthesized according to the method described for the synthesis of Example 3 by substituting Intermediate 26C and the corresponding acid where appropriate: (8.2 mg, 0.015 mmol, 33% yield). $^1$H NMR (400 MHz, DMSO-$d_6$) δ 8.63 (s, 1H), 7.78 (d, J=7.8 Hz, 1H), 7.72 (s, 1H), 7.51 (t, J=7.8 Hz, 1H), 7.33 (d, J=7.1 Hz, 1H), 3.59 (br. s., 2H), 2.79 (t, J=7.5 Hz, 2H), 2.10-2.01 (m, 1H), 1.87 (s, 6H), 1.82-1.69 (m, 8H), 1.52-1.35 (m, 6H), 1.04-0.92 (m, 5H), 0.87-0.79 (m, 2H). FXR EC$_{50}$ (nM)=72; MS (ESI) 545 (M+H).

The title compounds were synthesized according to the method described for the synthesis of Example 3 by substituting Intermediate 26C and the corresponding acids where appropriate:

| Ex. No | Structure | MS (ESI) (M + H) | FXR EC$_{50}$ (nM) |
|---|---|---|---|
| 27 | 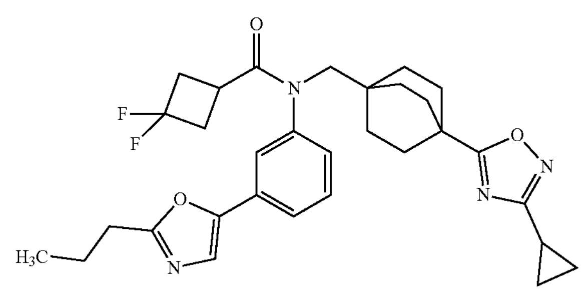 [SMILES: CCCc1ncc(-c2cccc(N(CC34CCC(c5nc(C6CC6)no5)(CC3)CC4)C(=O)C3CC(F)(F)C3)c2)o1] | 551 | 148 |
| 28 | 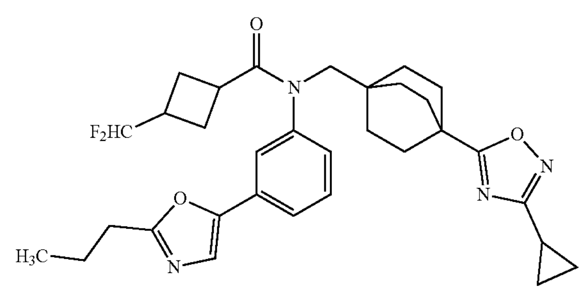 [SMILES: CCCc1ncc(-c2cccc(N(CC34CCC(c5nc(C6CC6)no5)(CC3)CC4)C(=O)C3CC(C(F)F)C3)c2)o1] | 565 | 248 |

27 $^1$H NMR (400 MHz, DMSO-$d_6$) δ 8.59 (s, 1H), 7.80-7.68 (m, 2H), 7.50 (t, J = 7.9 Hz, 1H), 7.33 (d, J = 7.1 Hz, 1H), 3.64 (br. s., 2H), 2.94-2.82 (m, 1H), 2.82-2.69 (m, 4H), 2.39-2.32 (m, 2H), 2.09-2.00 (m, 1H), 1.76 (q, J = 7.3 Hz, 8H), 1.48-1.36 (m, 6H), 1.05-0.99 (m, 2H), 0.97 (t, J = 7.3 Hz, 3H), 0.88-0.79 (m, 2H)

28 $^1$H NMR (400 MHz, DMSO-$d_6$) δ 8.57 (d, J = 6.1 Hz, 1H), 7.76-7.63 (m, 2H), 7.48 (t, J = 7.8 Hz, 1H), 7.29 (dd, J = 14.7, 8.3 Hz, 1H), 6 2-5.7 (m, 1H), 3.61 (br. s., 2H), 3.12-3.02 (m, 1H), 2.78 (t, J = 7.3 Hz, 2H), 2.33-2.21 (m, 1H), 2.11-1.94 (m, 3H), 1.84-1.55 (m, 10H), 1.49-1.33 (m, 6H), 1.08-0.90 (m, 5H), 0.89-0.79 (m, 2H)

Example 29

Ethyl 4-(3-(N-((4-(3-cyclopropyl-1,2,4-oxadiazol-5-yl)bicyclo[2.2.2]octan-1-yl)methyl)-3-fluorobicyclo[1.1.1]pentane-1-carboxamido)phenyl)thiazole-2-carboxylate

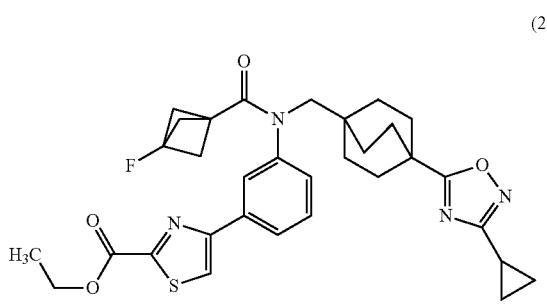

(29)

Step A. Intermediate 29A. Preparation of ethyl 4-(3-nitrophenyl)thiazole-2-carboxylate

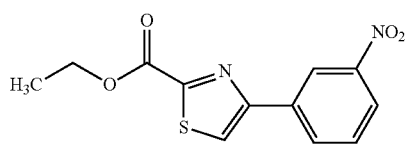 [SMILES: CCOC(=O)c1nc(-c2cccc([N+](=O)[O-])c2)cs1]

To a stirred solution of 2-bromo-1-(3-nitrophenyl)ethan-1-one (1.5 g, 6.15 mmol) in EtOH (15 mL) at room temperature was added ethyl thiooxamate (0.818 g, 6.15 mmol) and the reaction mixture was stirred for 2 h at 90° C. The reaction mixture was concentrated and the residue was suspended in cold water. The aqueous layer was extracted with EtOAc (2×50 mL) and the combined organic layers were dried over MgSO$_4$, filtered and concentrated under reduced pressure to afford the title compound (1.2 g, 4.23 mmol, 69% yield). MS (ESI) 279 (M+H).

Step B. Intermediate 29B. Preparation of ethyl 4-(3-aminophenyl)thiazole-2-carboxylate

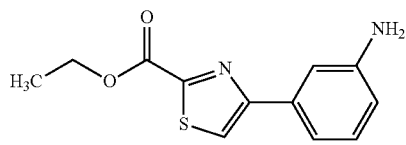 [SMILES: CCOC(=O)c1nc(-c2cccc(N)c2)cs1]

To a stirred solution of Intermediate 29A (500 mg, 1.797 mmol) in EtOH (10 mL), were added tin(II) chloride dihydrate (1338 mg, 5.93 mmol) and conc. HCl (1.8 mL, 59.2 mmol) at 0° C. The reaction mixture was stirred at 90° C. for 2 h. The reaction mixture was concentrated and cold water was added. The aqueous solution was basified with 10% aqueous sodium bicarbonate solution and the aqueous layer was extracted with EtOAc (2×70 mL). The combined organic layers were dried over MgSO$_4$, filtered and concentrated under reduced pressure to afford the title compound (250 mg, 0.886 mmol, 49% yield). MS (ESI) 249 (M+H).

Step C. Intermediate 29C. Preparation of ethyl 4-(3-(((4-(3-cyclopropyl-1,2,4-oxadiazol-5-yl)bicyclo[2.2.2]octan-1-yl)methyl)amino)phenyl)thiazole-2-carboxylate

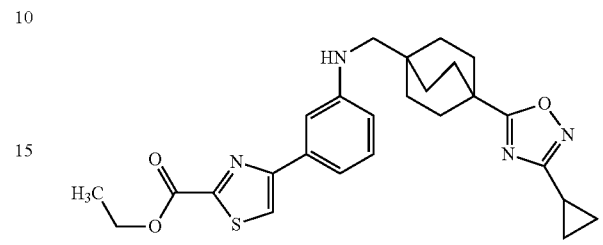

The title compound was synthesized according to the method described for the synthesis of Intermediate 1I by substituting Intermediate 29B and Intermediate 4C where appropriate: (Combiflash, 12 g silica gel, 0-30% EtOAc/PE) to afford the title compound (240 mg, 0.466 mmol, 58% yield). MS (ESI) 479 (M+H).

Step D. Example 29. Preparation of Ethyl 4-(3-(N-((4-(3-cyclopropyl-1,2,4-oxadiazol-5-yl)bicyclo[2.2.2]octan-1-yl)methyl)-3-fluorobicyclo[1.1.1]pentane-1-carboxamido) phenyl)thiazole-2-carboxylate The title compound was synthesized according to the method described for the synthesis of Example 3 by substituting Intermediate 29C and the corresponding acid where appropriate: (15 mg, 0.025 mmol, 60% yield). $^1$H NMR (400 MHz, DMSO-d$_6$) δ 8.70 (s, 1H), 8.04 (d, J=8.1 Hz, 1H), 7.99 (d, J=1.7 Hz, 1H), 7.58 (t, J=7.8 Hz, 1H), 7.45 (d, J=7.6 Hz, 1H), 4.44 (q, J=7.1 Hz, 2H), 3.66 (br. s., 1H), 3.57 (br. s., 1H), 2.07-1.99 (m, 1H), 1.88 (br. s., 6H), 1.83-1.70 (m, 6H), 1.46 (d, J=8.1 Hz, 6H), 1.37 (t, J=7.1 Hz, 3H), 1.09-0.95 (m, 2H), 0.91-0.76 (m, 2H); FXR EC$_{50}$ (nM) 1094; MS (ESI) 591 (M+H).

Example 30

N-(3-(2-(chloromethyl)thiazol-4-yl)phenyl)-N-((4-(3-cyclopropyl-1,2,4-oxadiazol-5-yl) bicyclo[2.2.2]octan-1-yl)methyl)-3-fluorobicyclo[1.1.1]pentane-1-carboxamide

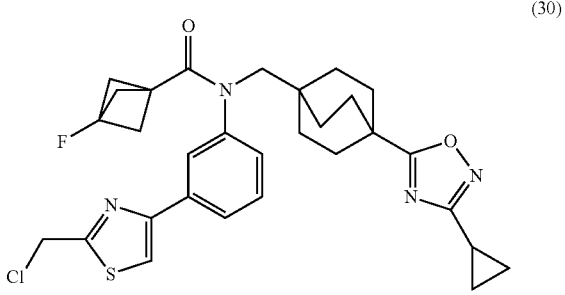 [SMILES: O=C(N(CC12CCC(c3nc(C4CC4)no3)(CC1)CC2)c1cccc(-c2csc(CCl)n2)c1)C12CC(F)(C1)C2]

(30)

Step A. Intermediate 30A. Preparation of (4-(3-(((4-(3-cyclopropyl-1,2,4-oxadiazol-5-yl)bicyclo[2.2.2]octan-1-yl)methyl)amino)phenyl)thiazol-2-yl)methanol

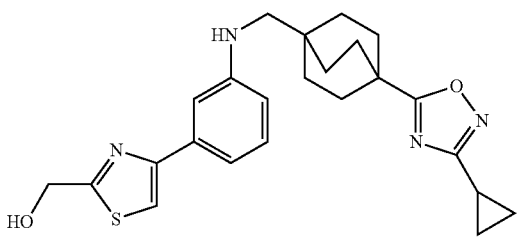 [SMILES: OCc1nc(-c2cccc(NCC34CCC(c5nc(C6CC6)no5)(CC3)CC4)c2)cs1]

To a stirred solution of Intermediate 29C (110 mg, 0.230 mmol) in THF (5 mL) cooled at −78° C., DIBAL-H (0.460 mL, 0.460 mmol) was added and stirred for 1 h. The reaction mixture was poured into a biphasic mixture of saturated aqueous ammonium chloride solution and EtOAc (50 mL) and the layers were separated. The aqueous layer was further extracted with EtOAc (2×50 mL). The combined organic layers were dried over MgSO$_4$, filtered and concentrated under reduced pressure. The residue was purified by flash column chromatography (Combiflash, 24 g silica, 0-50% EtOAc/PE) to afford the title compound (70 mg, 0.151 mmol, 66% yield). MS (ESI) 437 (M+H).

Step B. Example 30. Preparation of N-(3-(2-(chloromethyl)thiazol-4-yl)phenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide To a stirred solution of Intermediate 30A (40 mg, 0.092 mmol) and 3-fluorobicyclo[1.1.1]pentane-1-carboxylic acid (11.92 mg, 0.092 mmol) in DCM (2 mL) at room temperature were added pyridine (0.044 mL, 0.550 mmol) and POCl$_3$ (0.026 mL, 0.275 mmol). The reaction mixture was stirred at room temperature for 3 h. The solvent was removed under reduced pressure and the crude material was purified via preparative LC/MS using following conditions: Column: Waters XBridge C18, 150 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 15% B, 15-70% B over 25 minutes, then a 5-minute hold at 100% B; Flow Rate: 15 mL/min; Column Temperature: 25° C. Fraction collection was triggered by MS signals. Fractions containing the desired product were combined and dried via centrifugal evaporation to yield the title compound (9.4 mg, 0.016 mmol, 17% yield). $^1$H NMR (400 MHz, DMSO-d$_6$) δ 8.37 (s, 1H), 7.99 (d, J=8.3 Hz, 1H), 7.93 (s, 1H), 7.55 (t, J=7.8 Hz, 1H), 7.40 (d, J=8.1 Hz, 1H), 5.19 (s, 2H), 3.63 (br. s., 1H), 3.57 (br. s., 1H), 2.09-2.00 (m, 1H), 1.88 (br. s., 6H), 1.82-1.69 (m, 6H), 1.46 (d, J=7.8 Hz, 6H), 1.07-0.96 (m, 2H), 0.88-0.78 (m, 2H); FXR EC$_{50}$ (nM) 112; MS (ESI) 567 (M+H).

Example 31

N-((4-(3-cyclopropyl-1,2,4-oxadiazol-5-yl)bicyclo[2.2.2]octan-1-yl)methyl)-3-fluoro-N-(3-(2-(2-hydroxypropan-2-yl)thiazol-4-yl)phenyl)bicyclo[1.1.1]pentane-1-carboxamide (31)

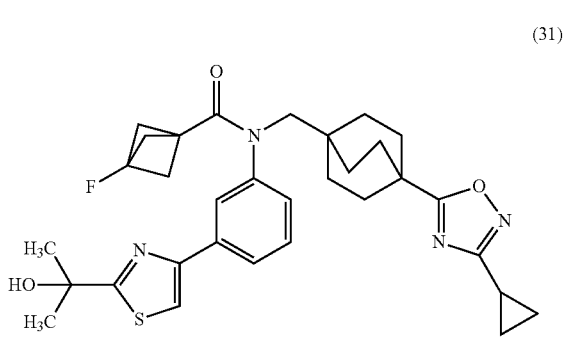 [SMILES: CC(C)(O)c1nc(-c2cccc(N(CC34CCC(c5nc(C6CC6)no5)(CC3)CC4)C(=O)C34CC(F)(C3)C4)c2)cs1]

Step A. Intermediate 31A. Preparation of 2-(4-(3-(((4-(3-cyclopropyl-1,2,4-oxadiazol-5-yl)bicyclo[2.2.2]octan-1-yl)methyl)amino)phenyl)thiazol-2-yl)propan-2-ol

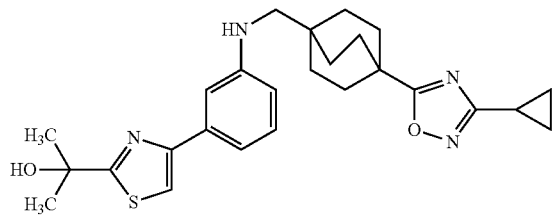 [SMILES: CC(C)(O)c1nc(-c2cccc(NCC34CCC(c5nc(C6CC6)no5)(CC3)CC4)c2)cs1]

To a stirred solution of Intermediate 29C (60 mg, 0.125 mmol) in THF (2 mL) cooled to 0° C. was added methylmagnesium bromide (0.251 mL, 0.752 mmol) and the reaction mixture was stirred at for 12 h. The reaction mixture was poured into saturated aqueous ammonium chloride solution and the aqueous layer was extracted with EtOAc (2×50 mL). The combined organic layers were dried over MgSO$_4$, filtered, and concentrated under reduced pressure. The residue was purified by flash column chromatography (Combiflash, 24 g silica, 0-50% EtOAc/PE) to afford the title compound (40 mg, 0.067 mmol, 54% yield). MS (ESI) 465 (M+H).

Step B. Example 64. Preparation of N-((4-(3-cyclopropyl-1,2,4-oxadiazol-5-yl) bicyclo[2.2.2]octan-1-yl)methyl)-3-fluoro-N-(3-(2-(2-hydroxypropan-2-yl)thiazol-4-yl)phenyl)bicyclo[1.1.1]pentane-1-carboxamide The title compound was synthesized according to the method described for the synthesis of Example 3 by substituting Intermediate 31A and the corresponding acid where appropriate: (7.2 mg, 0.012 mmol, 28% yield). $^1$H NMR (400 MHz, DMSO-d$_6$) δ 8.13 (s, 1H), 7.97 (d, J=8.1 Hz, 1H), 7.90 (s, 1H), 7.52 (t, J=7.8 Hz, 1H), 7.35 (d, J=5.1 Hz, 1H), 6.06 (s, 1H), 3.60 (br. s., 2H), 2.10-2.01 (m, 1H), 1.89

(br. s., 6H), 1.82-1.68 (m, 6H), 1.58 (s, 6H), 1.50-1.35 (m, 6H), 1.05-0.96 (m, 2H), 0.87-0.78 (m, 2H); FXR EC$_{50}$ (nM) 260; MS (ESI) 577 (M+H).

Example 32

N-(3-(3-cyclopropyl-1,2,4-oxadiazol-5-yl)phenyl)-3-fluoro-N-((4-(2-methylpyridin-4-yl)bicyclo[2.2.2]octan-1-yl)methyl)bicyclo[1.1.1]pentane-1-carboxamide (32)

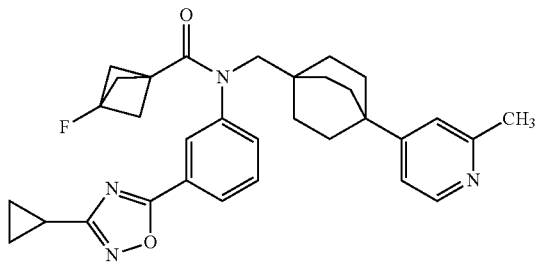

Step A. Intermediate 32A1 & 32A2. Preparation of methyl 4-(6-methylpyridin-2-yl) bicyclo[2.2.2]octane-1-carboxylate & methyl 4-(2-methylpyridin-4-yl) bicyclo[2.2.2]octane-1-carboxylate

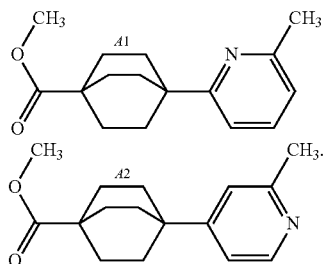

To a stirred solution of 4-(methoxycarbonyl)bicyclo[2.2.2]octane-1-carboxylic acid (2 g, 9.42 mmol) and 2-methylpyridine (1.053 g, 11.31 mmol) in DCM (60 mL) and water (60 mL) was added silver nitrate (0.320 g, 1.885 mmol) followed by potassium persulfate (2.55 g, 9.42 mmol) and stirred at room temperature overnight. The reaction mixture was diluted with DCM (30 mL) and the organic layer was washed with water (2×50 mL). The organic layer was dried over sodium sulfate, filtered and concentrated under reduced pressure. The crude material was purified by flash column chromatography (Combiflash, 24 g silica, 0-50% EtOAc/PE) to afford the Intermediate 66A1 (200 mg, 0.771 mmol). $^1$H NMR (400 MHz, DMSO-d$_6$) δ 7.61-7.54 (m, 1H), 7.10 (d, J=8.0 Hz, 1H), 7.04 (d, J=7.5 Hz, 1H), 3.60 (s, 3H), 2.43 (s, 3H), 1.90-1.77 (m, 12H). MS (ESI) 260 (M+H) and Intermediate 32A2 (650 mg, 2.506 mmol). $^1$H NMR (400 MHz, DMSO-d$_6$) δ 8.32 (d, J=5.5 Hz, 1H), 7.20 (d, J=2.0 Hz, 1H), 7.12 (dd, J=5.3, 1.8 Hz, 1H), 3.60 (s, 3H), 2.43 (s, 3H), 1.87-1.73 (m, 12H). MS (ESI) 260 (M+H).

Step B. Intermediate 32B1 & 32B2. Preparation of 4-(2-methylpyridin-4-yl) bicyclo[2.2.2]octane-1-carbaldehyde & (4-(2-methylpyridin-4-yl)bicyclo[2.2.2]octan-1-yl)methanol

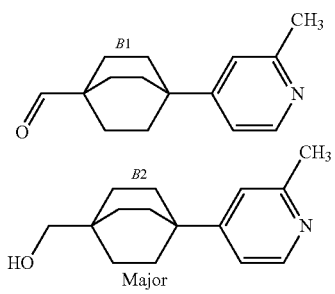

A stirred solution of Intermediate 32A2 (650 mg, 2.506 mmol) in DCM (20 mL) was cooled to −78° C. DIBAL-H in heptane (5.22 mL, 6.27 mmol) was added and the reaction mixture was stirred at −78° C. for 20 minutes. The reaction mixture was quenched with saturated aqueous ammonium chloride solution and stirred for 2 h. The DCM layer was separated and the aqueous layer was extracted with DCM (2×25 mL). The combined organic layers were dried over sodium sulfate, filtered and concentrated under reduced pressure. The crude material was purified by flash chromatography to afford Intermediate 32B1 (110 mg, 0.480 mmol, 19% yield). $^1$H NMR (400 MHz, DMSO-d$_6$) δ 9.48 (s, 1H), 8.33 (d, J=5.5 Hz, 1H), 7.21 (s, 1H), 7.15-7.12 (m, 1H), 2.43 (s, 3H), 1.83-1.77 (m, 6H), 1.73-1.66 (m, 6H). MS (ESI) 230 (M+H) and Intermediate 32B2 (250 mg, 1.081 mmol, 43% yield). $^1$H NMR (400 MHz, DMSO-d$_6$) δ 8.30 (d, J=5.0 Hz, 1H), 7.21-7.15 (m, 1H), 7.11 (dd, J=5.5, 1.5 Hz, 1H), 4.39 (t, J=5.5 Hz, 1H), 3.09 (d, J=5.5 Hz, 2H), 2.43 (s, 3H), 1.79-1.68 (m, 6H), 1.51-1.39 (m, 6H). MS (ESI) 232 (M+H).

Step C. Intermediate 32C. Preparation of 3-(3-cyclopropyl-1,2,4-oxadiazol-5-yl)-N-((4-(2-methylpyridin-4-yl)bicyclo[2.2.2]octan-1-yl)methyl)aniline

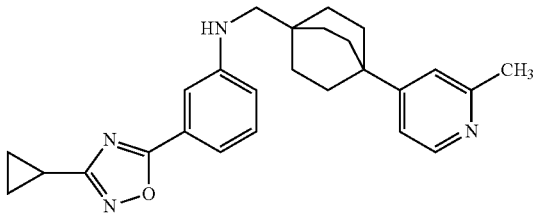 [SMILES: Cc1cc(C23CCC(CNc4cccc(-c5nc(C6CC6)no5)c4)(CC2)CC3)ccn1]

The title compound was synthesized according to the method described for the synthesis of Intermediate 1I by substituting Intermediate 8A and Intermediate 32B1 where appropriate: (70 mg, 0.169 mmol, 43% yield). $^1$H NMR (400 MHz, DMSO-d$_6$) δ 8.31 (d, J=5.0 Hz, 1H), 7.32-7.23 (m, 2H), 7.19 (s, 1H), 7.17-7.11 (m, 2H), 6.93-6.88 (m, 1H), 6.00-5.95 (m, 1H), 2.87 (d, J=5.5 Hz, 2H), 2.44 (s, 3H), 2.22-2.16 (m, 1H), 1.77 (m, 6H), 1.64-1.56 (m, 6H), 1.14-1.08 (m, 2H), 1.00-0.95 (m, 2H). MS (ESI) 415 (M+H).

Step D. Example 32. Preparation of N-(3-(3-cyclopropyl-1,2,4-oxadiazol-5-yl)phenyl)-3-fluoro-N-((4-(2-methylpyridin-4-yl)bicyclo[2.2.2]octan-1-yl)methyl) bicyclo[1.1.1]pentane-1-carboxamide The title compound was synthesized according to the method described for the synthesis of Example 3 by substituting Intermediate 32C and the corresponding acid where appropriate: (8 mg, 0.0151 mmol, 41% yield). $^1$H NMR (400 MHz, DMSO-d$_6$) δ 8.26 (d, J=5.4 Hz, 1H), 8.06 (dt, J=7.3, 1.5 Hz, 1H), 7.99 (t, J=1.6 Hz, 1H), 7.78-7.63 (m, 2H), 7.12 (s, 1H), 7.05 (dd, J=5.4, 1.5 Hz, 1H), 2.39 (s, 3H), 2.26-2.15 (m, 1H), 1.99-1.75 (m, 6H), 1.73-1.54 (m, 6H), 1.50-1.31 (m, 6H), 1.07-0.91 (m, 4H). 2 Protons buried under moisture peak. FXR EC$_{50}$ (nM)=756; MS (ESI) 527 (M+H).

The title compound was synthesized according to the method described for the synthesis of Example 3 by substituting Intermediate 32C and the corresponding acids where appropriate:

| Ex. No. | Structure | MS (ESI) (M + H) | FXR EC$_{50}$ (nM) |
|---|---|---|---|
| 33 | | 547 | 4315 |

33 $^1$H NMR (400 MHz, DMSO-d$_6$) δ 8.27 (d, J = 5.4 Hz, 1H), 8.12-7.89 (m, 2H), 7.79 (d, J = 8.1 Hz, 1H), 7.70 (t, J = 7.8 Hz, 1H), 7.13 (s, 1H), 7.05 (dd, J = 5.4, 1.5 Hz, 1H), 3.65 (br. s., 2H), 2.93 (t, J = 8.4 Hz, 1H), 2.44-2.35 (m, 3H), 2.35-2.16 (m, 2H), 2.14-1.96 (m, 4H), 1.95-1.77 (m, 1H), 1.74-1.53 (m, 6H), 1.49-1.29 (m, 6H), 1.20-1.08 (m, 2H), 1.05-0.93 (m, 2H)

Example 34

3-Fluoro-N-((4-(3-methyl-1,2,4-oxadiazol-5-yl)bicyclo[2.2.2]octan-1-yl)methyl)-N-(3-(2-(tetrahydro-2H-pyran-4-yl)oxazol-5-yl)phenyl)bicyclo[1.1.1]pentane-1-carboxamide (34)

Step A. Intermediate 34A. Preparation of 5-(3-nitrophenyl)-2-(tetrahydro-2H-pyran-4-yl)oxazole

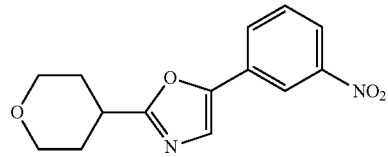 [SMILES: O=[N+]([O-])c1cccc(-c2cnc(C3CCOCC3)o2)c1]

To a stirred solution of (diacetoxyiodo)benzene (1170 mg, 3.63 mmol) in oxane-4-carbonitrile (10 mL) was added trifluoromethanesulfonic acid (2045 mg, 13.62 mmol) and stirred at room temperature for 20 min. To the reaction mixture, 1-(3-nitrophenyl) ethan-1-one (500 mg, 3.03 mmol) was added and the reaction mixture was refluxed for 2 h. The reaction mixture was concentrated under reduced pressure and the residue was diluted with DCM (100 mL) and washed with 10% aqueous brine solution (3×50 mL). The organic layer was dried over sodium sulfate and concentrated under reduced pressure. The residue was purified by flash column chromatography (Combiflash, 24 g silica, 0-60% EtOAc/PE) to afford the title compound (200 mg, 0.729 mmol, 24% yield) as a brown wax. MS (ESI) 275 (M+H).

Step B. Intermediate 34B. Preparation of 3-(2-(tetrahydro-2H-pyran-4-yl)oxazol-5-yl) aniline

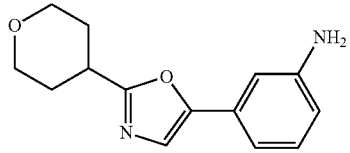 [SMILES: Nc1cccc(-c2cnc(C3CCOCC3)o2)c1]

Intermediate 34A (200 mg, 0.729 mmol) was dissolved in a mixture of ethanol (4 mL), THF (2 mL) and water (1 mL). To the stirred reaction mixture was added zinc (715 mg, 10.94 mmol) followed by ammonium chloride (585 mg, 10.94 mmol) and stirred overnight at room temperature. The reaction mixture was filtered over a celite pad and the filtrate was concentrated under reduced pressure. The residue was diluted with ethyl acetate (50 mL). The organic layer was washed with water (20 mL), followed by 10% aqueous sodium bicarbonate solution (20 mL) and brine solution (20 mL). The organic layer was dried over sodium sulfate, concentrated under reduced pressure. The residue was purified by flash column chromatography (Combiflash, 12 g silica, 0-70% EtOAc/PE) to afford the title compound (100 mg, 0.409 mmol, 56% yield) as brown wax. MS (ESI) 245 (M+H).

Step C. Intermediate 34C. Preparation of N-((4-(3-methyl-1,2,4-oxadiazol-5-yl) bicyclo[2.2.2]octan-1-yl)methyl)-3-(2-(tetrahydro-2H-pyran-4-yl)oxazol-5-yl)aniline

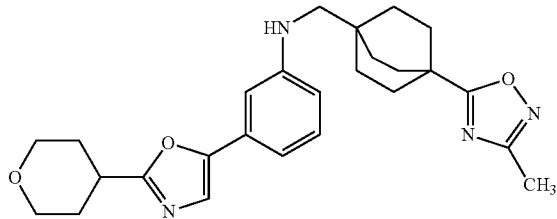 [SMILES: Cc1noc(C23CCC(CNc4cccc(-c5cnc(C6CCOCC6)o5)c4)(CC2)CC3)n1]

The title compound was synthesized according to the method described for the synthesis of Intermediate 1I by substituting Intermediate 34B and Intermediate 3C where appropriate: (40 mg, 0.089 mmol, 44% yield) as a brown wax. MS (ESI) 449 (M+H).

Step D. Example 34. Preparation of 3-Fluoro-N-((4-(3-methyl-1,2,4-oxadiazol-5-yl) bicyclo[2.2.2]octan-1-yl)methyl)-N-(3-(2-(tetrahydro-2H-pyran-4-yl)oxazol-5-yl)phenyl) bicyclo[1.1.1]pentane-1-carboxamide The title compound was synthesized according to the method described for the synthesis of Example 3 by substituting Intermediate 34C and the corresponding acid where appropriate: (6.4 mg, 0.011 mmol, 26% yield). $^1$H NMR (400 MHz, DMSO-d$_6$) δ 7.73 (s, 2H), 7.69 (d, J=7.8 Hz, 1H), 7.55 (t, J=7.8 Hz, 1H), 7.39 (d, J=9.0 Hz, 1H), 3.95-3.88 (m, 2H), 3.66 (d, J=13.9 Hz, 1H), 3.49 (td, J=11.3, 2.1 Hz, 2H), 3.23-3.14 (m, 2H), 2.28 (s, 3H), 1.99 (d, J=11.2 Hz, 2H), 1.88 (m, 6H), 1.85-1.74 (m, 8H), 1.46 (m, 6H); FXR EC$_{50}$ (nM)=1523; MS (ESI) 561 (M+H).

Example 35

N-((4-(3-cyclopropyl-1,2,4-oxadiazol-5-yl)bicyclo[2.2.2]octan-1-yl)methyl)-3-fluoro-N-(3-(2-(tetrahydro-2H-pyran-4-yl)oxazol-5-yl)phenyl)bicyclo[1.1.1]pentane-1-carboxamide

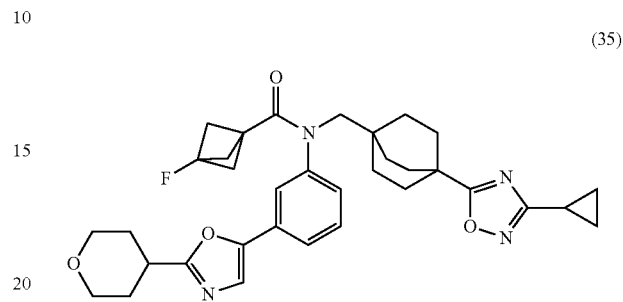

(35)

Step A. Intermediate 35A. Preparation of N-((4-(3-cyclopropyl-1,2,4-oxadiazol-5-yl) bicyclo[2.2.2]octan-1-yl)methyl)-3-(2-(tetrahydro-2H-pyran-4-yl)oxazol-5-yl)aniline

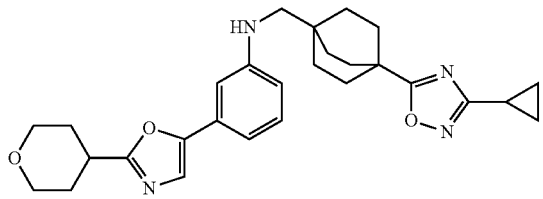 [SMILES: c1cc(NCC23CCC(c4nc(C5CC5)no4)(CC2)CC3)cc(-c2cnc(C3CCOCC3)o2)c1]

The title compound was synthesized according to the method described for the synthesis of Intermediate 1I by substituting Intermediate 34B and Intermediate 4C where appropriate: (60 mg, 0.126 mmol, 62% yield) as brown wax. MS (ESI) 475 (M+H).

Step B. Example 35. Preparation of N-((4-(3-cyclopropyl-1,2,4-oxadiazol-5-yl) bicyclo[2.2.2]octan-1-yl)methyl)-3-fluoro-N-(3-(2-(tetrahydro-2H-pyran-4-yl)oxazol-5-yl)phenyl)bicyclo[1.1.1]pentane-1-carboxamide The title compound was synthesized according to the method described for the synthesis of Example 3 by substituting Intermediate 35A and the corresponding acid where appropriate: (4.2 mg, 7.16 µmol, 17% yield). $^1$H NMR (400 MHz, DMSO-d$_6$) δ 7.73 (s, 2H), 7.69 (d, J=7.8 Hz, 1H), 7.54 (t, J=7.7 Hz, 1H), 7.38 (d, J=7.6 Hz, 1H), 3.91 (d, J=11.0 Hz, 2H), 3.63 (br. s., 1H), 3.55-3.44 (m, 3H), 3.23-3.15 (m, 1H), 2.09-1.96 (m, 3H), 1.88 (m, 6H), 1.82-1.72 (m, 8H), 1.44 (m, 6H), 1.05-0.98 (m, 2H), 0.87-0.80 (m, 2H); FXR EC$_{50}$ (nM)=251; MS (ESI) 587 (M+H).

Example 36

N-((4-(3-cyclopropyl-1,2,4-oxadiazol-5-yl)bicyclo[2.2.2]octan-1-yl)methyl)-3,3-difluoro-N-(3-(2-(tetrahydro-2H-pyran-4-yl)oxazol-5-yl)phenyl)cyclobutane-1-carboxamide

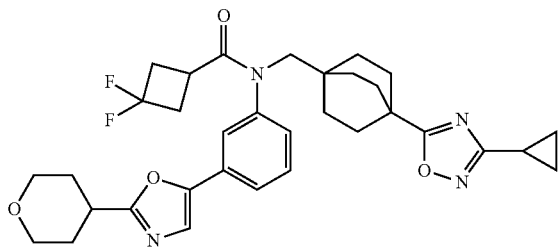

(36)

The title compound was synthesized according to the method described for the synthesis of Example 3 by substituting Intermediate 35A and the corresponding acid where appropriate: (1.9 mg, 3.21 μmol, 8% yield). $^1$H NMR (400 MHz, DMSO-d$_6$) δ 7.74 (s, 1H), 7.69 (s, 1H), 7.66 (d, J=8.6 Hz, 1H), 7.54 (t, J=7.8 Hz, 1H), 7.38 (d, J=9.0 Hz, 1H), 3.91 (d, J=10.5 Hz, 2H), 3.65 (br. s., 2H), 3.54-3.42 (m, 2H), 3.24-3.12 (m, 2H), 2.90 (m, 1H), 2.76 (d, J=18.3 Hz, 2H), 2.34 (d, J=2.0 Hz, 1H), 2.08-1.90 (m, 3H), 1.83-1.69 (m, 6H), 1.52-1.30 (m, 6H), 1.06-0.96 (m, 2H), 0.88-0.78 (m, 2H), Note: 2H merged in DMSO peak. FXR EC$_{50}$ (nM)= 497. MS (ESI) 593 (M+H).

Example 37

N-(3-(3-cyclopropyl-1,2,4-oxadiazol-5-yl)phenyl)-3-fluoro-N-((4-(5-methyloxazol-2-yl)bicyclo[2.2.2]octan-1-yl)methyl)bicyclo[1.1.1]pentane-1-carboxamide

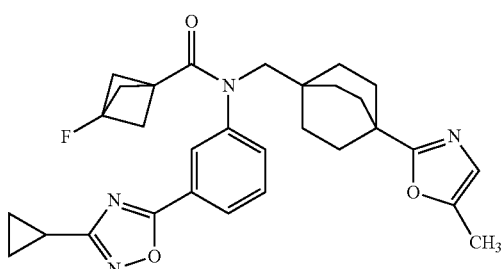

(37)

Step A. Intermediate 37A. Preparation of Methyl 4-((2-hydroxypropyl)carbamoyl)bicyclo[2.2.2]octane-1-carboxylate

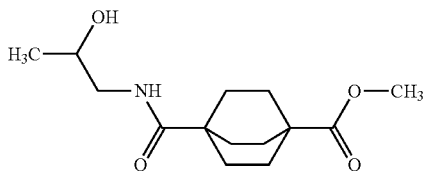 [SMILES: COC(=O)C12CCC(C(=O)NCC(C)O)(CC1)CC2]

A solution of 4-(methoxycarbonyl)bicyclo[2.2.2]octane-1-carboxylic acid (1 g, 4.71 mmol), 1-hydroxybenzotriazole hydrate (0.722 g, 4.71 mmol), and 1-(3-dimethylaminopropyl)-3-ethylcarbodiimide hydrochloride (1.806 g, 9.42 mmol) in DCM (20 mL) was stirred at 0° C. for 30 min. To the reaction mixture, 1-aminopropan-2-ol (0.369 mL, 4.71 mmol) was added. The resulting mixture was stirred at 0° C. for 2 hours and overnight at room temperature. The reaction mixture was concentrated under reduced pressure. The residue was diluted with water (10 mL) and EtOAc (30 mL) and the layers separated. The organic layer was washed with brine, dried over Na$_2$SO$_4$, filtered and concentrated under reduced pressure. The residue was purified by flash column chromatography (Combiflash, 24 g silica, 0-50% EtOAc/PE) to afford the title compound (1.2 g, 4.37 mmol, 93% yield) was obtained from the reaction mixture. MS (ESI) 268 (M−H).

Step B. Intermediate 37B. Preparation of Methyl 4-((2-oxopropyl)carbamoyl)bicyclo[2.2.2]octane-1-carboxylate

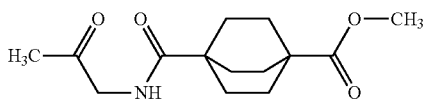 [SMILES: COC(=O)C12CCC(C(=O)NCC(C)=O)(CC1)CC2]

To a stirred solution of Intermediate 37A (1.2 g, 4.46 mmol) in DCM (15 mL), Dess-Martin periodinane (1.701 g, 4.01 mmol) was added and the reaction mixture was stirred at room temperature for 1 h. The reaction mixture was diluted with DCM (15 mL) and washed with saturated aqueous NaHCO$_3$ solution (3×10 mL). The organic layer was dried over Na$_2$SO$_4$, filtered and concentrated under reduced pressure. The residue was purified by flash column chromatography (Combiflash, 24 g silica, 0-50% EtOAc/PE) to afford the title compound (950 mg, 80% yield). MS (ESI) 268 (M+H).

Step C. Intermediate 37C. Preparation of N-(3-(2-methoxypyridin-4-yl)phenyl) pyrimidin-2-amine

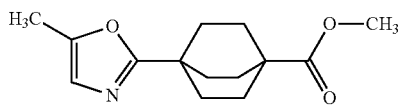

A solution of Intermediate 37B (0.4 g, 1.496 mmol) in DCM (10 mL) and POCl$_3$ (5.58 mL, 59.9 mmol) was heated to reflux for 2 h. The reaction mixture was cooled to room temperature and concentrated under reduced pressure to remove all the volatiles. The residue was diluted with EtOAc (30 mL) and washed with saturated aqueous NaHCO₃ (2×20 mL) solution. The organic layer was washed with brine, dried over Na₂SO₄, filtered and concentrated in vacuum to afford the title compound (0.25 g, 0.842 mmol, 56% yield) which was used further without any purification. ¹H NMR (400 MHz, DMSO-d₆) δ 6.77 (s, 1H), 3.59 (s, 3H), 2.24 (s, 3H), 1.9-1.7 (m, 12H). MS (ESI) 250 (M+H).

Step D. Intermediate 37D. Preparation of (4-(5-methyloxazol-2-yl)bicyclo[2.2.2]octan-1-yl)methanol

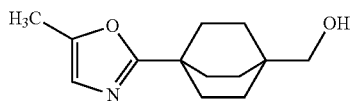 [SMILES: Cc1cnc(C23CCC(CO)(CC2)CC3)o1]

The title compound was synthesized according to the method described for the synthesis of Intermediate 1G by substituting Intermediate 37C where appropriate: (65 mg, 0.294 mmol, 73% yield). ¹H NMR (400 MHz, DMSO-d₆) δ 6.57 (s, 1H), 3.77 (s, 2H), 3.32 (s, 1H), 2.24 (s, 3H), 1.9-1.7 (m, 12H). MS (ESI) 222 (M+H).

Step E. Intermediate 37E: Preparation of 4-(5-methyloxazol-2-yl)bicyclo[2.2.2]octane-1-carbaldehyde

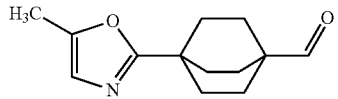

The title compound was synthesized according to the method described for the synthesis of Intermediate 1H by substituting Intermediate 37D where appropriate: (110 mg, 0.477 mmol, 56% yield). ¹H NMR (400 MHz, DMSO-d₆) δ 9.45 (s, 1H), 6.68 (s, 1H), 2.24 (s, 3H), 1.87-1.83 (m, 6H), 1.68-1.65 (m, 6H). MS (ESI) 220 (M+H).

Step F. Intermediate 37F: Preparation of 3-(3-cyclopropyl-1,2,4-oxadiazol-5-yl)-N-((4-(5-methyloxazol-2-yl)bicyclo[2.2.2]octan-1-yl)methyl)aniline

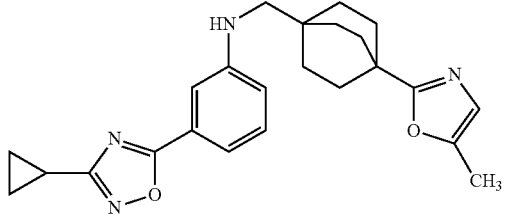 [SMILES: Cc1cnc(C23CCC(CNc4cccc(-c5nc(C6CC6)no5)c4)(CC2)CC3)o1]

The title compound was synthesized according to the method described for the synthesis of Intermediate 1I by substituting Intermediate 8A and Intermediate 37E where appropriate: (105 mg, 0.259 mmol, 81% yield). ¹H NMR (400 MHz, DMSO-d₆) δ 7.29-7.08 (m, 3H), 6.89-6.83 (m, 1H), 6.65 (s, 1H), 5.95 (s, 1H), 3.32 (s, 2H), 2.33 (s, 3H), 2.23-2.16 (m, 1H), 1.84-1.80 (m, 6H), 1.57-1.53 (m, 6H), 1.11-1.08 (m, 4H). MS (ESI) 405 (M+H).

Step G. Example 37. Preparation of N-(3-(3-cyclopropyl-1,2,4-oxadiazol-5-yl)phenyl)-3-fluoro-N-((4-(5-methyloxazol-2-yl)bicyclo[2.2.2]octan-1-yl)methyl) bicyclo[1.1.1]pentane-1-carboxamide The title compound was synthesized according to the method described for the synthesis of Example 3 by substituting Intermediate 37F and the corresponding acid where appropriate: (12.5 mg, 0.024 mmol, 49% yield). ¹H NMR (400 MHz, DMSO-d₆) δ 8.05 (d, J=7.3 Hz, 1H), 7.98 (s, 1H), 7.76-7.62 (m, 2H), 6.60 (d, J=1.2 Hz, 1H), 3.61-3.55 (m, 2H), 2.25-2.12 (m, 4H), 1.87 (br. s., 6H), 1.77-1.61 (m, 6H), 1.49-1.28 (m, 6H), 1.12 (dd, J=8.1, 2.4 Hz, 2H), 1.05-0.94 (m, 2H). FXR EC₅₀ (nM) 82; MS (ESI) 517 (M+H).

The title compound was synthesized according to the method described for the synthesis of Example 3 by substituting Intermediate 74F and the corresponding acids where appropriate:

| Ex. No. | Structure | MS (ESI) (M + H) | FXR EC₅₀ (nM) |
|---|---|---|---|
| 38 | 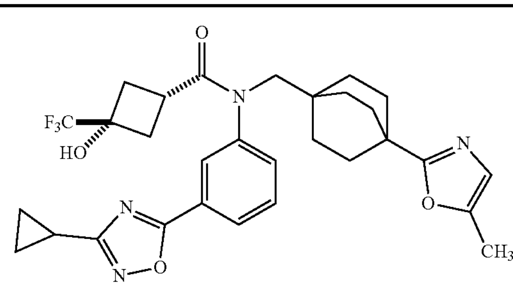 | 632 | 571 |

-continued

| Ex. No. | Structure | MS (ESI) (M + H) | FXR EC$_{50}$ (nM) |
|---|---|---|---|
| 38 | | 308 | 537 |

38  $^1$H NMR (400 MHz, DMSO-d$_6$) δ 8.00 (br s, 2H), 7.76 (d, J = 8.1 Hz, 1H), 7.68 (t, J = 8.1 Hz, 1H), 6.62 (d, J = 1.2 Hz, 1H), 6.56 (s, 1H), 3.65 (m, 2H), 2.73 (t, J = 8.7 Hz, 1H), 2.40-2.30 (m, 2H), 2.27-2.15 (m, 4H), 2.09 (br. s., 2H), 1.82-1.60 (m, 6H), 1.50-1.29 (m, 6H), 1.18-1.10 (m, 2H), 1.05-0.96 (m, 2H).
39  $^1$H NMR (400 MHz, DMSO-d$_6$) δ 8.11-7.94 (m, 2H), 7.79 (d, J = 7.8 Hz, 1H), 7.69 (t, J = 7.8 Hz, 1H), 6.62 (d, J = 1.2 Hz, 1H), 3.63 (br. s., 2H), 2.97-2.86 (m, 1H), 2.35-2.16 (m, 5H), 2.06 (dd, J = 10.8, 4.6 Hz, 2H), 1.97-1.77 (m, 2H), 1.77-1.51 (m, 7H), 1.49-1.26 (m, 6H), 1.19-1.08 (m, 2H), 1.05-0.92 (m, 2H)

Example 40

N-((4-(3-cyclopropyl-1,2,4-oxadiazol-5-yl)bicyclo[2.2.2]octan-1-yl)methyl)-N-(3-(4-(difluoromethyl)oxazol-2-yl)phenyl)-3-fluorobicyclo[1.1.1]pentane-1-carboxamide

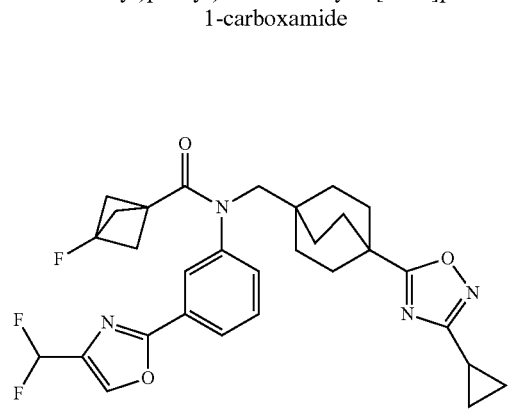

(40)

Intermediate 40A. Preparation of (2-(3-nitrophenyl)oxazol-4-yl)methanol

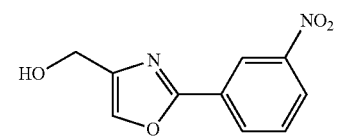 [SMILES: O=[N+]([O-])c1cccc(-c2nc(CO)co2)c1]

To a stirred solution of Intermediate 12B (1 g, 3.81 mmol) in THF (30 mL) at −78° C., DIBAL-H (7.63 mL, 7.63 mmol) was added and the reaction mixture was stirred for 1 h. The reaction mixture was poured into saturated aqueous ammonium chloride solution (10 mL) and EtOAc (50 mL) and the layers were separated. The aqueous layer was extracted further with EtOAc (2×50 mL). The combined organic layers were dried over MgSO$_4$, filtered and concentrated under reduced pressure. The residue was purified by flash column chromatography (Combiflash, 24 g silica, 0-50% EtOAc/PE) to afford the title compound (400 mg, 1.798 mmol, 47% yield). MS (ESI) 221 (M+H).

Step B. Intermediate 40B. Preparation of 2-(3-nitrophenyl)oxazole-4-carbaldehyde

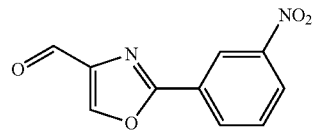 [SMILES: O=Cc1coc(-c2cccc([N+](=O)[O-])c2)n1]

To a stirred solution of Intermediate 40A (400 mg, 1.817 mmol) in DCM (15 mL) at 0° C. was added Dess-Martin periodinane (925 mg, 2.180 mmol). The reaction mixture was warmed up to room temperature and stirred for 1 h. The reaction mixture was poured into saturated aqueous sodium bicarbonate solution and the aqueous layer was extracted with EtOAc (2×50 mL). The combined organic layers were dried over MgSO$_4$, filtered and concentrated under reduced pressure. The residue was purified by flash column chromatography (Combiflash, 24 g silica, 0-50% EtOAc/PE) to yield the title compound (370 mg, 1.594 mmol, 88% yield). MS (ESI) 219 (M+H).

Step C. Intermediate 40C. Preparation of 4-(difluoromethyl)-2-(3-nitrophenyl)oxazole

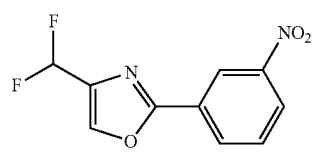 [SMILES: O=[N+]([O-])c1cccc(-c2nc(C(F)F)co2)c1]

To a stirred solution of Intermediate 40B (370 mg, 1.696 mmol) in DCM (10 mL) at −78° C. was added DAST (0.560 mL, 4.24 mmol). The reaction mixture was stirred at room temperature for 12 h. The reaction mixture was quenched with cold water and the aqueous layer was extracted with EtOAc (2×50 mL). The combined organic layers were dried over MgSO$_4$, filtered and concentrated under reduced pressure. The residue was purified by flash column chromatography (Combiflash, 24 g silica, 0-50% EtOAc/PE) to afford the title compound (330 mg, 1.374 mmol, 81% yield). $^1$H NMR; 400 MHz, DMSO-d$_6$: δ 8.91 (s, 1H), 8.33-8.41 (m, 2H), 8.01 (d, J=4.00 Hz, 1H), 7.69 (t, J=16.00 Hz, 1H), 6.74 (t, J=54.00 Hz, 1H).

Step D. Intermediate 40D. Preparation of 3-(4-(difluoromethyl)oxazol-2-yl)aniline

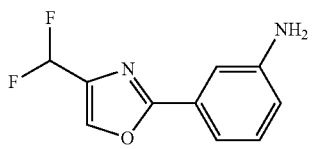 [SMILES: Nc1cccc(-c2nc(C(F)F)co2)c1]

To a stirred solution of Intermediate 40C (50 mg, 0.208 mmol) in EtOH (2.5 mL) at 0° C. was added tin(II) chloride dihydrate (164 mg, 0.729 mmol) and conc. HCl (0.190 mL, 6.25 mmol). The reaction mixture was stirred at 90° C. for 2 h. The reaction mixture was neutralized with aqueous sodium bicarbonate solution and the aqueous layer was extracted with EtOAc (2×50 mL). The combined organic layers were dried over MgSO$_4$, filtered and concentrated under reduced pressure to afford the title compound (30 mg, 0.131 mmol, 63% yield). MS (ESI) 211 (M+H).

Step E. Intermediate 40E. Preparation of N-((4-(3-cyclopropyl-1,2,4-oxadiazol-5-yl) bicyclo[2.2.2]octan-1-yl)methyl)-3-(4-(difluoromethyl)oxazol-2-yl)aniline

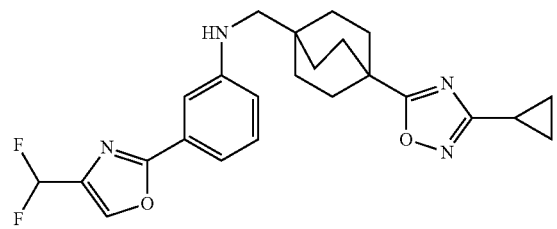 [SMILES: FC(F)c1coc(-c2cccc(NCC34CCC(c5nc(C6CC6)no5)(CC3)CC4)c2)n1]

The title compound was synthesized according to the method described for the synthesis of Intermediate 1I by substituting Intermediate 40D and Intermediate 4C where appropriate: (290 mg, 0.658 mmol, 69% yield). MS (ESI) 441 (M+H).

Step F. Example 40. Preparation of N-((4-(3-cyclopropyl-1,2,4-oxadiazol-5-yl) bicyclo[2.2.2]octan-1-yl)methyl)-N-(3-(4-(difluoromethyl)oxazol-2-yl) phenyl)-3-fluorobicyclo[1.1.1]pentane-1-carboxamide The title compound was synthesized according to the method described for the synthesis of Example 3 by substituting Intermediate 40E and the corresponding acid where appropriate: $^1$H NMR (400 MHz, DMSO-d$_6$) δ 8.70 (t, J=2.6 Hz, 1H), 8.03 (d, J=7.1 Hz, 1H), 7.94 (s, 1H), 7.70-7.59 (m, 2H), 7.16 (t J=54 Hz, 1H), 3.61 (d, J=15.9 Hz, 2H), 2.10-1.99 (m, 1H), 1.89 (br. s., 6H), 1.82-1.68 (m, 6H), 1.53-1.34 (m, 6H), 1.05-0.96 (m, 2H), 0.86-0.76 (m, 2H). FXR EC$_{50}$ (nM) 243; MS (ESI) 553 (M+H).

The title compounds were synthesized according to the method described for the synthesis of Example 3 by substituting Intermediate 40E and the corresponding acids where appropriate:

| Ex. No. | Structure | MS (ESI) (M + H) | FXR EC$_{50}$ (nM) |
|---|---|---|---|
| 41 | 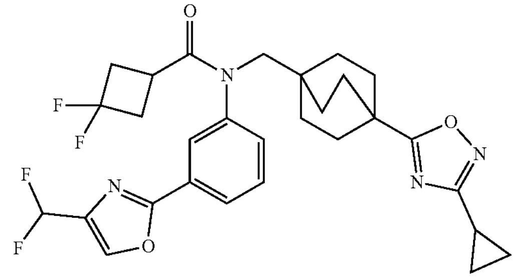 [SMILES: O=C(C1CC(F)(F)C1)N(CC12CCC(c3nc(C4CC4)no3)(CC1)CC2)c1cccc(-c2nc(C(F)F)co2)c1] | 559 | 465 |

-continued

| Ex. No. | Structure | MS (ESI) (M + H) | FXR EC$_{50}$ (nM) |
|---|---|---|---|
| 42 | 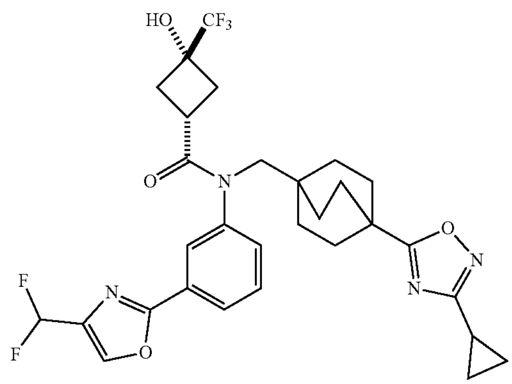 | 607 | 613 |
| 43 | 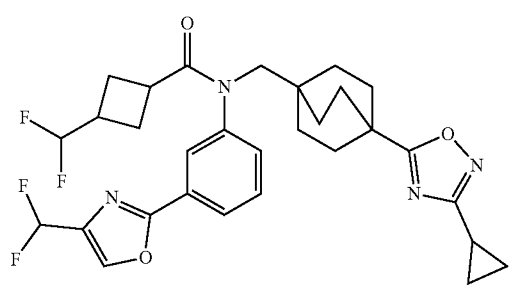 [SMILES: O=C(C1CC(C(F)F)C1)N(CC12CCC(c3nc(C4CC4)no3)(CC1)CC2)c1cccc(-c2nc(C(F)F)co2)c1] | 573 | 851 |
| 44 | 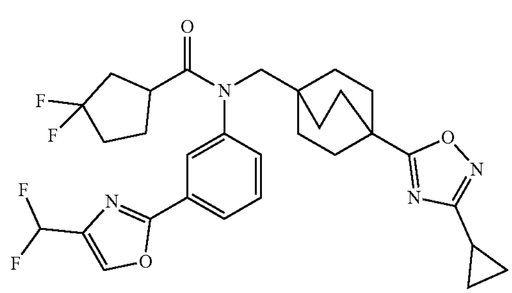 [SMILES: O=C(C1CCC(F)(F)C1)N(CC12CCC(c3nc(C4CC4)no3)(CC1)CC2)c1cccc(-c2nc(C(F)F)co2)c1] | 573 | 646 |

41 $^1$H NMR (400 MHz, DMSO-d$_6$) δ 8.76-8.64 (m, 1H), 8.10-7.89 (m, 2H), 7.72-7.56 (m, 2H), 7.16 (dd, J = 53.1, 51.1 Hz, 1H), 3.67 (br. s., 2H), 2.96-2.85 (m, 1H), 2.84-2.70 (m, 2H), 2.34 (br. s., 2H), 2.10-1.98 (m, 1H), 1.86-1.62 (m, 6H), 1.52-1.30 (m, 6H), 1.08-0.92 (m, 2H), 0.89-0.70 (m, 2H)

42 $^1$H NMR (400 MHz, DMSO-d$_6$) δ 8.69 (t, J = 2.7 Hz, 1H), 8.05-7.85 (m, 2H), 7.64 (d, J = 4.4 Hz, 2H), 7.15 (dd, J = 55.3, 51.1 Hz, 1H), 6.56 (s, 1H), 3.66 (br. s., 2H), 2.77-2.71 (m, 1H), 2.34 (br. s., 2H), 2.16-1.96 (m, 3H), 1.86-1.66 (m, 6H), 1.42 (d, J = 7.8 Hz, 6H), 1.08-0.95 (m, 2H), 0.90-0.77 (m, 2H)

43 $^1$H NMR (400 MHz, DMSO-d$_6$) δ 8.68 (t, J = 2.7 Hz, 1H), 7.96 (d, J = 7.3 Hz, 1H), 7.91 (d, J = 8.3 Hz, 1H), 7.72-7.55 (m, 2H), 7.15 (t, J = 54 Hz, 1H), 6.19-5.69 (m, 1H), 3.63 (br. s., 2H), 3.07 (dt, J = 18.6, 9.0 Hz, 1H), 2.33-2.23 (m, 1H), 2.11-1.99 (m, 2H), 1.82-1.56 (m, 8H), 1.51-1.29 (m, 6H), 1.10-0.95 (m, 2H), 0.89-0.73 (m, 2H)

44 $^1$H NMR (400 MHz, DMSO-d$_6$) δ 8.69 (s, 1H), 8.00 (br. s., 2H), 7.72-7.53 (m, 2H), 7.16 (dd, J = 54.0, 52.6 Hz, 1H), 3.63 (br. s., 2H), 3.00-2.89 (m, 1H), 2.16-1.98 (m, 3H), 1.91 (br. s., 1H), 1.88-1.71 (m, 7H), 1.67 (br. s., 1H), 1.52-1.30 (m, 6H), 1.25 (s, 1H), 1.09-0.92 (m, 2H), 0.91-0.71 (m, 2H)

Example 45

N-(3-(4-(difluoromethyl)oxazol-2-yl)phenyl)-3-fluoro-N-((4-(5-methyloxazol-2-yl) bicyclo[2.2.2]octan-1-yl)methyl)bicyclo[1.1.1]pentane-1-carboxamide (45)

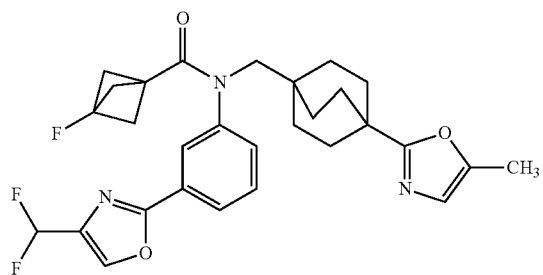

Step A. Intermediate 45A. Preparation of 3-(4-(difluoromethyl)oxazol-2-yl)-N-((4-(5-methyloxazol-2-yl)bicyclo[2.2.2]octan-1-yl)methyl)aniline

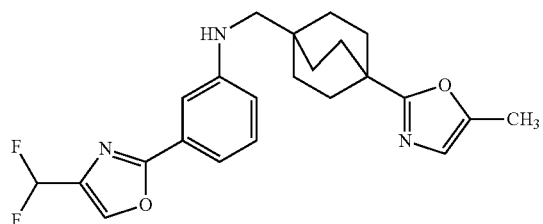 [SMILES: Cc1cnc(C23CCC(CNc4cccc(-c5nc(C(F)F)co5)c4)(CC2)CC3)o1]

The title compound was synthesized according to the method described for the synthesis of Intermediate 1I by substituting Intermediate 40D and Intermediate 37E where appropriate: (45 mg, 0.109 mmol, 57% yield). MS (ESI) 414 (M+H).

Step B. Example 45. Preparation of N-(3-(4-(difluoromethyl)oxazol-2-yl)phenyl)-3-fluoro-N-((4-(5-methyloxazol-2-yl)bicyclo[2.2.2]octan-1-yl)methyl)bicyclo[1.1.1]pentane-1-carboxamide The title compound was synthesized according to the method described for the synthesis of Example 3 by substituting Intermediate 45A and the corresponding acid where appropriate: (12.6 mg, 0.024 mmol, 40% yield). $^1$H NMR (400 MHz, DMSO-$d_6$) δ 8.70 (t, J=2.6 Hz, 1H), 8.03 (d, J=7.3 Hz, 1H), 7.94 (s, 1H), 7.72-7.57 (m, 2H), 7.16 (t, J=54.0 Hz, 1H), 6.63 (d, J=1.2 Hz, 1H), 3.63 (br. s., 1H), 3.58 (br. s., 1H), 2.21 (d, J=1.2 Hz, 3H), 1.89 (br. s., 6H), 1.78-1.61 (m, 6H), 1.50-1.29 (m, 6H); FXR EC$_{50}$ (nM) 258; MS (ESI) 526 (M+H).

Example 46

(cis)-N-(3-(4-(difluoromethyl)oxazol-2-yl)phenyl)-3-hydroxy-N-((4-(5-methyloxazol-2-yl)bicyclo[2.2.2]octan-1-yl)methyl)-3-(trifluoromethyl)cyclobutane-1-carboxamide (46)

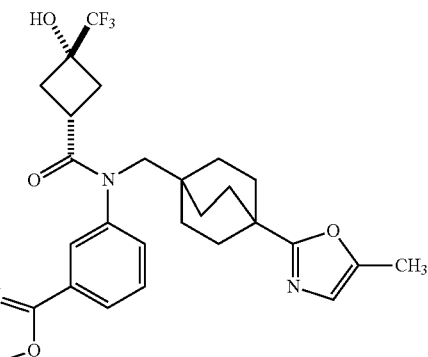

The title compound was synthesized according to the method described for the synthesis of Example 3 by substituting Intermediate 45A and the corresponding acid where appropriate: (5.6 mg, 9.57 µmol, 16% yield). $^1$H NMR (400 MHz, DMSO-$d_6$) δ 8.73-8.64 (m, 1H), 8.02-7.86 (m, 2H), 7.64 (d, J=4.2 Hz, 2H), 7.15 (t, J=54.5 Hz, 1H), 6.62 (d, J=1.2 Hz, 1H), 6.55 (s, 1H), 3.65 (br. s., 2H), 2.74 (t, J=9.2 Hz, 1H), 2.37-2.28 (m, 2H), 2.21 (d, J=1.0 Hz, 3H), 2.09 (br. s., 2H), 1.80-1.60 (m, 6H), 1.49-1.29 (m, 6H); FXR EC$_{50}$ (nM) 437 MS (ESI) 580 (M+H).

Example 47

N-((1-(4-(2-cyanopropan-2-yl)phenyl)-2-oxabicyclo[2.2.2]octan-4-yl)methyl)-N-(3-(3-ethyl-1,2,4-oxadiazol-5-yl)phenyl)-3-fluorobicyclo[1.1.1]pentane-1-carboxamide (47)

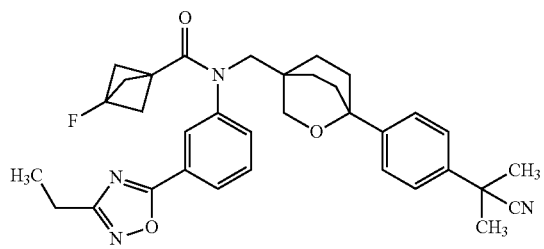

Step A. Intermediate 47A. Preparation of (4-(4-(2-cyanopropan-2-yl)phenyl)-4-hydroxycyclohexane-1,1-diyl)bis(methylene) bis(4-methylbenzenesulfonate)

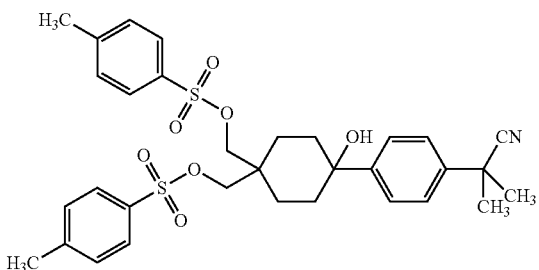

To a stirred solution of 2-(4-bromophenyl)-2-methylpropanenitrile (1.441 g, 6.43 mmol) in THF (25 mL) at −78° C. was added n-butyl lithium (2.79 mL, 6.97 mmol) and stirred for 1 h. To the above mixture, a solution of (4-oxocyclohexane-1,1-diyl)bis(methylene) bis(4-methylbenzenesulfonate) (synthesized as described in ACS Med. Chem. Lett. 2014, 5, 609-614) (2.5 g, 5.36 mmol) in THF (12 mL) was added dropwise and stirred at −78° C. for 4 h. The reaction mixture was quenched with saturated aqueous ammonium chloride solution (20 mL) and extracted with ethyl acetate (2×50 mL). The combined organic layers were dried over sodium sulfate and concentrated under reduced pressure to afford the title compound (3.2 g, 2.93 mmol, 55% yield) as brown solid. $^1$H NMR (400 MHz, DMSO-$d_6$) δ 7.83-7.81 (m, 2H), 7.78-7.76 (m, 2H), 7.50 (d, J=8.0 Hz, 6H), 7.29-7.24 (m, 2H), 4.79 (s, 1H), 4.01 (s, 2H), 3.75 (s, 2H), 2.45-2.42 (m, 3H), 2.36 (s, 3H), 1.70-1.65 (m, 6H), 1.62-1.54 (m, 2H), 1.34-1.21 (m, 6H). MS (ESI) 629 (M+H) NH$_3$ adduct.

Step B. Intermediate 47B. Preparation of (1-(4-(2-cyanopropan-2-yl)phenyl)-2-oxabicyclo[2.2.2]octan-4-yl)methyl 4-methylbenzenesulfonate

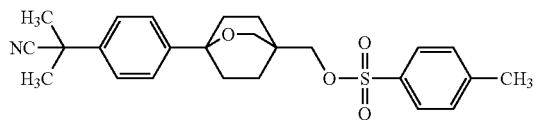 [SMILES: Cc1ccc(S(=O)(=O)OCC23CCC(c4ccc(C(C)(C)C#N)cc4)(CC2)OC3)cc1]

To a stirred solution of Intermediate 47A (3.6 g, 5.88 mmol) in THF (100 mL) was added NaOH (0.706 g, 17.65 mmol) and refluxed overnight. The reaction mixture was diluted with water (100 mL) and extracted with ethyl acetate (2×100 mL). The combined organic layers were dried over sodium sulfate and concentrated under reduced pressure. The residue was purified by flash column chromatography (Combiflash, 24 g silica, 0-50% EtOAc/PE) to afford the title compound (1.4 g, 2.61 mmol, 44% yield) as an off-white solid (1.4 g, 2.61 mmol, 44% yield). $^1$H NMR (400 MHz, DMSO-$d_6$) δ 7.81-7.79 (m, 2H), 7.50 (d, J=8.0 Hz, 2H), 7.45-7.37 (m, 4H), 3.81 (s, 2H), 3.70 (s, 2H), 2.43 (s, 3H), 2.08-1.99 (m, 2H), 1.82-1.75 (m, 2H), 1.65 (s, 6H), 1.61-1.58 (m, 4H). MS (ESI) 440 (M+H).

Step C. Intermediate 47C. Preparation of (1-(4-(2-cyanopropan-2-yl)phenyl)-2-oxabicyclo[2.2.2]octan-4-yl)methyl acetate

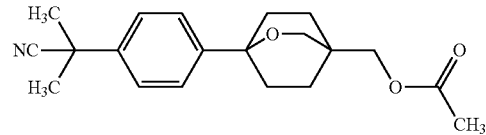

To a stirred solution of Intermediate 47B (1.35 g, 3.07 mmol) in DMF (20 mL) was added cesium acetate (1.474 g, 7.68 mmol) and heated to 120° C. for 6 h. The reaction mixture was concentrated under reduced pressure and the residue was diluted with water (25 mL) and extracted with ethyl acetate (2×30 mL). The combined organic layers were dried over sodium sulfate and concentrated under reduced pressure to afford the title compound (1.0 g, 2.93 mmol, 95% yield) as brown gummy solid. $^1$H NMR (400 MHz, DMSO-$d_6$) δ 7.46-7.40 (m, 4H), 3.81 (s, 4H), 2.11-2.04 (m, 2H), 2.03 (s, 3H) 1.88-1.78 (m, 2H), 1.70-1.65 (m, 4H), 1.66 (s, 6H) MS (ESI) 345 (M+H) NH$_3$ adduct.

Step D. Intermediate 47D. Preparation of 2-(4-(4-(hydroxymethyl)-2-oxabicyclo[2.2.2]octan-1-yl)phenyl)-2-methylpropanenitrile

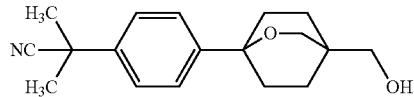

To a stirred solution of Intermediate 47C (1.1 g, 3.36 mmol) in THF (15 mL) was added sodium methoxide (0.073 g, 0.336 mmol) and stirred at room temperature for 2 h. The reaction mixture was diluted with DCM (25 mL) and the organic layer was washed with water (15 mL) followed by brine solution (25 mL). The organic layer was dried over sodium sulphate and concentrated under reduced pressure. The residue was purified by flash column chromatography (Combiflash, 24 g silica, 0-50% EtOAc/PE) to afford title compound (600 mg, 2.081 mmol, 62% yield) as white solid. $^1$H NMR (400 MHz, DMSO-$d_6$) δ 7.43 (s, 4H), 4.53 (t, J=5.5 Hz, 1H), 3.80 (s, 2H), 3.16 (d, J=5.0 Hz, 2H), 2.10-2.01 (m, 2H), 1.85-1.76 (m, 2H), 1.70-1.62 (m, 8H), 1.56-1.50 (m, 2H). MS (ESI) 286 (M+H).

Step E. Intermediate 47E. Preparation of 2-(4-(4-formyl-2-oxabicyclo[2.2.2]octan-1-yl) phenyl)-2-methylpropanenitrile

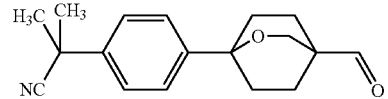

The title compound was synthesized according to the method described for the synthesis of Intermediate 1H by substituting Intermediate 47D where appropriate: (430 mg, 1.517 mmol, 77% yield) as white solid. $^1$H NMR (400 MHz, DMSO-d$_6$) δ 9.50 (s, 1H), 7.46-7.40 (m, 5H), 4.00 (s, 2H), 2.16-2.08 (m, 2H), 1.92-1.85 (m, 6H), 1.66 (s, 6H). MS (ESI) 284 (M+H).

Step F. Intermediate 47F. Preparation of 2-(4-(4-(((3-(3-ethyl-1,2,4-oxadiazol-5-yl) phenyl)amino)methyl)-2-oxabicyclo[2.2.2]octan-1-yl)phenyl)-2-methyl propanenitrile

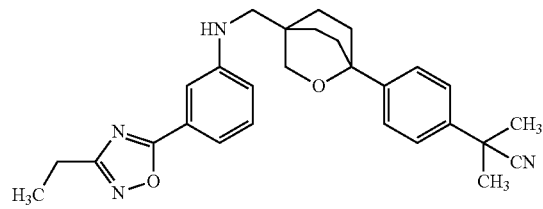 [SMILES: CCc1noc(-c2cccc(NCC34CCC(c5ccc(C(C)(C)C#N)cc5)(CC3)OC4)c2)n1]

The title compound was synthesized according to the method described for the synthesis of Intermediate 1I by substituting Intermediate 3E and Intermediate 47E where appropriate: (60 mg, 0.106 mmol, 60% yield) as a yellow gummy liquid. $^1$H NMR (400 MHz, DMSO-d$_6$) δ 7.47-7.41 (m, 4H), 7.35-7.27 (m, 2H), 7.24-7.20 (m, 1H), 6.96-6.92 (m, 1H), 6.02 (t, J=5.8 Hz, 1H), 3.90 (s, 2H), 2.95 (d, J=6.0 Hz, 2H), 2.83-2.75 (m, 2H), 2.15-2.04 (m, 2H), 1.88-1.72 (m, 6H), 1.67 (s, 6H), 1.31-1.26 (m, 3H). MS (ESI) 457 (M+H).

Step G. Example 47. Preparation of N-((1-(4-(2-cyanopropan-2-yl)phenyl)-2-oxabicyclo [2.2.2]octan-4-yl)methyl)-N-(3-(3-ethyl-1,2,4-oxadiazol-5-yl)phenyl)-3-fluorobicyclo[1.1.1]pentane-1-carboxamide The title compound was synthesized according to the method described for the synthesis of Example 3 by substituting Intermediate 47F and the corresponding acid where appropriate: (9 mg, 0.016 mmol, 24% yield). $^1$H NMR (400 MHz, DMSO-d$_6$) δ 8.20-8.08 (m, 2H), 7.87-7.78 (m, 1H), 7.77-7.68 (m, 1H), 7.40 (q, J=8.8 Hz, 4H), 3.71 (s, 2H), 3.66 (br. s., 2H), 2.83 (q, J=7.6 Hz, 2H), 2.07-1.96 (m, 2H), 1.90 (br. s., 6H), 1.81-1.70 (m, 2H), 1.65 (s, 8H), 1.59 (d, J=12.7 Hz, 2H), 1.31 (t, J=7.5 Hz, 3H). FXR EC$_{50}$ (nM)=299; MS (ESI) 569 (M+H).

Example 48

N-((1-(4-(2-cyanopropan-2-yl)phenyl)-2-oxabicyclo [2.2.2]octan-4-yl)methyl)-N-(3-(3-ethyl-1,2,4-oxadiazol-5-yl)phenyl)cyclobutanecarboxamide (48)

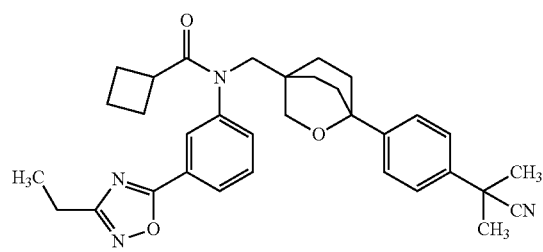

The title compound was synthesized according to the method described for the synthesis of Example 3 by substituting Intermediate 47F and the corresponding acid where appropriate: (0.7 mg). $^1$H NMR (400 MHz, DMSO-d6) δ 8.10-7.95 (m, 2H), 7.80-7.58 (m, 2H), 7.47-7.30 (m, 4H), 3.67 (br. s., 4H), 3.08 (br. s., 2H), 2.81 (q, J=7.6 Hz, 2H), 2.14 (br. s., 2H), 1.98 (t, J=10.9 Hz, 2H), 1.72 (d, J=11.2 Hz, 3H), 1.67-1.43 (m, 12H), 1.30 (t, J=7.5 Hz, 3H). FXR EC$_{50}$ (nM)=299; MS (ESI) 539 (M+H).

Example 49

N-(3-(3-cyclopropyl-1,2,4-oxadiazol-5-yl)phenyl)-3,3-difluoro-N-((4-(4-(trifluoromethyl)pyridin-2-yl)bicyclo[2.2.2]octan-1-yl)methyl)cyclobutane-1-carboxamide (49)

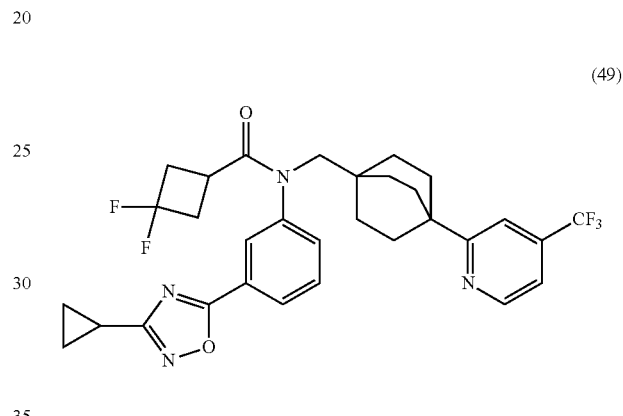

Step A. Intermediate 49A. Preparation of methyl 4-(4-(trifluoromethyl)pyridin-2-yl) bicyclo[2.2.2]octane-1-carboxylate

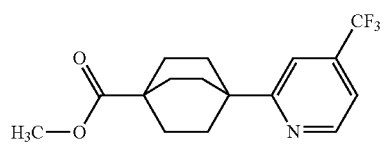

To a stirred solution of 4-(methoxycarbonyl)bicyclo [2.2.2]octane-1-carboxylic acid (1 g, 4.71 mmol) and 4-(trifluoromethyl)pyridine (0.832 g, 5.65 mmol) in a mixture of DCM (30 mL) and water (30 mL) at room temperature was added silver nitrate (0.160 g, 0.942 mmol) followed by potassium persulfate (0.160 g, 0.942 mmol). The reaction mixture was stirred overnight at room temperature and then diluted with DCM (25 mL) and filtered through celite. The organic layer was separated and washed with brine solution (25 mL), dried over Na$_2$SO$_4$, filtered and concentrated under reduced pressure. The crude material was purified by flash column chromatography (Combiflash, 24 g silica, 0-30% EtOAc/PE) to afford the title compound (600 mg, 1.915 mmol, 41% yield) as brown solid. $^1$H NMR (400 MHz, DMSO-d$_6$) δ 8.79 (d, J=5.0 Hz, 1H), 7.64 (d, J=1.0 Hz, 1H), 7.59 (d, J=5.0 Hz, 1H), 3.61 (s, 3H), 1.96-1.88 (m, 6H), 1.88-1.81 (m, 6H). MS (ESI) 314 (M+H).

Step B. Intermediate 49B. Preparation of (4-(4-(trifluoromethyl)pyridin-2-yl) bicyclo[2.2.2]octan-1-yl)methanol

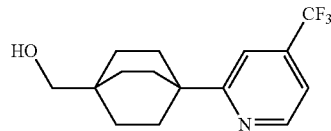 [SMILES: OCC12CCC(c3cc(C(F)(F)F)ccn3)(CC1)CC2]

The title compound was synthesized according to the method described for the synthesis of Intermediate 1G by substituting Intermediate 49A where appropriate: (370 mg, 1.271 mmol, 80% yield) as a brown gummy solid. $^1$H NMR (400 MHz, DMSO-$d_6$) δ 8.78 (d, J=5.0 Hz, 1H), 7.62-7.51 (m, 2H), 4.36 (t, J=5.5 Hz, 1H), 3.10 (d, J=5.5 Hz, 2H), 1.93-1.80 (m, 6H), 1.52-1.41 (m, 6H). MS (ESI) 286 (M+H).

Step C. Intermediate 49C. Preparation of 4-(4-(trifluoromethyl)pyridin-2-yl) bicyclo[2.2.2]octane-1-carbaldehyde

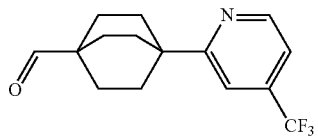

The title compound was synthesized according to the method described for the synthesis of Intermediate 3C by substituting Intermediate 49B where appropriate: (220 mg, 0.777 mmol, 60% yield) as colorless gummy solid. $^1$H NMR (300 MHz, DMSO-$d_6$) δ 9.45 (s, 1H), 78 (d, J=5.0 Hz, 1H), 7.62-7.51 (m, 2H), 1.93-1.80 (m, 6H), 1.52-1.41 (m, 6H). MS (ESI) 284 (M+H).

Step D. Intermediate 49D. Preparation of 3-(3-cyclopropyl-1,2,4-oxadiazol-5-yl)-N-((4-(4-(trifluoromethyl)pyridin-2-yl)bicyclo[2.2.2]octan-1-yl)methyl)aniline

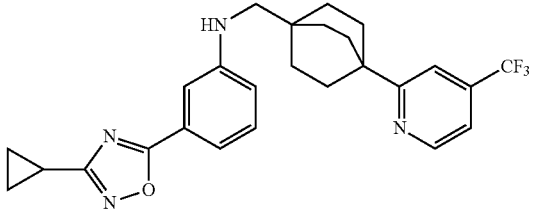 [SMILES: FC(F)(F)c1ccnc(C23CCC(CNc4cccc(-c5nc(C6CC6)no5)c4)(CC2)CC3)c1]

The title compound was synthesized according to the method described for the synthesis of Intermediate 1I by substituting Intermediate 8A and Intermediate 49C where appropriate: (80 mg, 0.155 mmol, 63% yield) as a brown gummy solid. MS (ESI) 469 (M+H).

Step E. Example 49. Preparation of N-(3-(3-cyclopropyl-1,2,4-oxadiazol-5-yl)phenyl)-3,3-difluoro-N-((4-(4-(trifluoromethyl)pyridin-2-yl)bicyclo[2.2.2]octan-1-yl)methyl) cyclobutane-1-carboxamide The title compound was synthesized according to the method described for the synthesis of Example 3 by substituting Intermediate 49D and 3,3-difluorocyclobutane-1-carboxylic acid where appropriate: (9.9 mg, 0.017 mmol, 40% yield). $^1$H NMR (400 MHz, DMSO-$d_6$) δ 8.74 (d, J=4.9 Hz, 1H), 8.08-7.94 (m, 2H), 7.75 (d, J=8.1 Hz, 1H), 7.68 (t, J=7.9 Hz, 1H), 7.59-7.47 (m, 2H), 3.68 (br. s., 2H), 2.98-2.85 (m, 1H), 2.83-2.65 (m, 2H), 2.42-2.25 (m, 2H), 2.24-2.16 (m, 1H), 1.90-1.68 (m, 6H), 1.52-1.35 (m, 6H), 1.18-1.08 (m, 2H), 1.05-0.93 (m, 2H). FXR EC$_{50}$ (nM)=1374; MS (ESI) 587 (M+H).

The following compound was synthesized according to the method described for the synthesis of Example 3 by substituting Intermediate 49D and the corresponding acid where appropriate:

| Ex. No. | Structure | MS (ESI) (M + H) | FXR EC50 (nM) |
|---|---|---|---|
| 50 | | 581 | 462 |

$^1$HNMR (400 MHz, DMSO-$d_6$) δ 8.76 (d, J = 5.1 Hz, 1H), 8.07 (d, J = 7.8 Hz, 1H), 8.01 (s, 1H), 7.81-7.65 (m, 2H), 7.61-7.48 (m, 2H), 3.66 (br. s., 2H), 2.26-2.20 (m, 1H), 1.89 (br. s., 6H), 1.85-1.72 (m, 6H), 1.46 (d, J = 8.3 Hz, 6H), 1.14 (dd, J = 8.1, 2.4 Hz, 2H), 1.01 (d, J = 2.2 Hz, 2H)

Example 51

N-((1-(4-(2-cyanopropan-2-yl)phenyl)-2-oxabicyclo[2.2.2]octan-4-yl)methyl)-N-(3-(2-ethoxyoxazol-5-yl)phenyl)-3-fluorobicyclo[1.1.1]pentane-1-carboxamide (51)

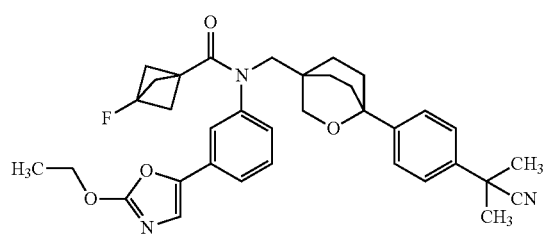

Step A. Intermediate 51A. Preparation of 2-(4-(4-(((3-(4-ethoxyoxazol-2-yl)phenyl)amino)methyl)-2-oxabicyclo[2.2.2]octan-1-yl)phenyl)-2-methyl propanenitrile

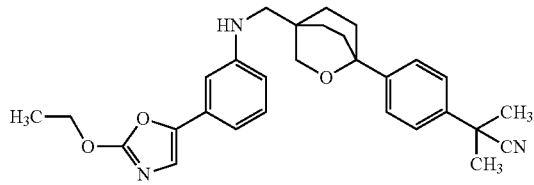 [SMILES: CCOc1ncc(-c2cccc(NCC34CCC(c5ccc(C(C)(C)C#N)cc5)(CC3)OC4)c2)o1]

The title compound was synthesized according to the method described for the synthesis of Intermediate 1I by substituting Intermediate 7D and Intermediate 47E where appropriate: (30 mg, 0.064 mmol, 45% yield) as a gummy liquid. MS (ESI) 471 (M+H).

Step B. Example 51. Preparation of N-((1-(4-(2-cyanopropan-2-yl)phenyl)-2-oxabicyclo[2.2.2]octan-4-yl)methyl)-N-(3-(2-ethoxyoxazol-5-yl)phenyl)-3-fluorobicyclo[1.1.1]pentane-1-carboxamide The title compound was synthesized according to the method described for the synthesis of Example 3 by substituting Intermediate 51A and the corresponding acid where appropriate: (1.8 mg, 0.00308 mmol, 6% yield). $^1$H NMR (400 MHz, DMSO-$d_6$) δ 7.62 (s, 1H), 7.60-7.54 (m, 2H), 7.51 (t, J=7.8 Hz, 1H), 7.45-7.23 (m, 4H), 4.46 (q, J=6.9 Hz, 2H), 3.70 (s, 2H), 3.59 (s, 2H), 2.07-1.93 (m, 2H), 1.88 (br.s., 6H), 1.80-1.70 (m, 2H), 1.69-1.45 (m, 11H), 1.43-1.33 (m, 3H). FXR $EC_{50}$ (nM)=25. MS (ESI) 584 (M+H).

Example 52

3-fluoro-N-(3-(2-propyloxazol-5-yl)phenyl)-N-((4-(4-(trifluoromethyl)pyridin-2-yl)bicyclo[2.2.2]octan-1-yl)methyl)bicyclo[1.1.1]pentane-1-carboxamide (52)

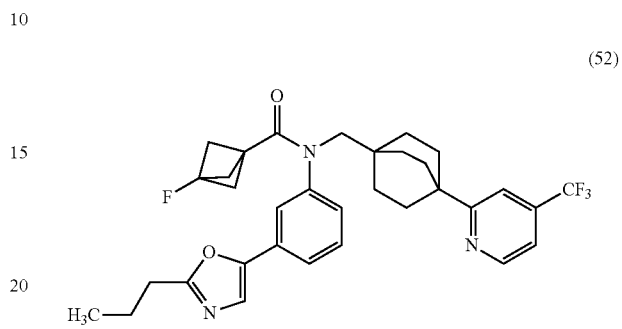

Step A. Intermediate 52A. Preparation of 3-(2-propyloxazol-5-yl)-N-((4-(4-(trifluoromethyl)pyridin-2-yl)bicyclo[2.2.2]octan-1-yl)methyl)aniline

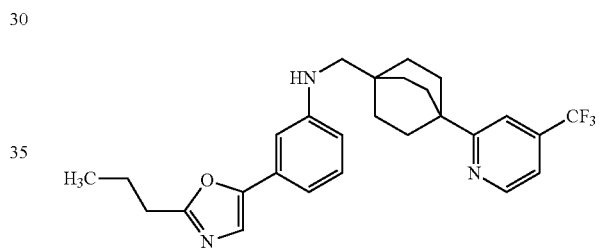

The title compound was synthesized according to the method described for the synthesis of Intermediate 1I by substituting Intermediate 26B and Intermediate 49C where appropriate: (78 mg, 0.158 mmol, 64% yield) as a brown gummy solid. MS (ESI) 470 (M+H).

Step B. Example 52. Preparation of 3-fluoro-N-(3-(2-propyloxazol-5-yl)phenyl)-N-((4-(4-(trifluoromethyl)pyridin-2-yl)bicyclo[2.2.2]octan-1-yl)methyl)bicyclo[1.1.1]pentane-1-carboxamide The title compound was synthesized according to the method described for the synthesis of Example 3 by substituting Intermediate 52A and 3-fluorobicyclo[1.1.1]pentane-1-carboxylic acid where appropriate: (17.5 mg, 0.03 mmol, 40% yield). $^1$H NMR (400 MHz, DMSO-$d_6$) δ 8.76 (d, J=4.9 Hz, 1H), 8.64 (s, 1H), 7.78 (d, J=8.3 Hz, 1H), 7.74 (d, J=1.7 Hz, 1H), 7.61-7.45 (m, 3H), 7.34 (d, J=8.8 Hz, 1H), 3.61 (s, 2H), 2.79 (t, J=7.3 Hz, 2H), 1.88 (br. s., 6H), 1.78 (td, J=15.0, 7.7 Hz, 8H), 1.54-1.39 (m, 6H), 0.98 (t, J=7.3 Hz, 3H). FXR $EC_{50}$ (nM)=242; MS (ESI) 582 (M+H).

Example 53

N-((4-(3-cyclopropyl-1,2,4-oxadiazol-5-yl)bicyclo[2.2.2]octan-1-yl)methyl)-N-(3-(5-ethoxy-1,3,4-oxadiazol-2-yl)phenyl)-3-fluorobicyclo[1.1.1]pentane-1-carboxamide (53)

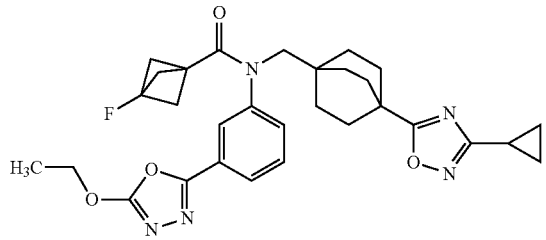

Step A. Intermediate 53A. Preparation of ethyl 2-(3-nitrobenzyl)hydrazine-1-carboxylate

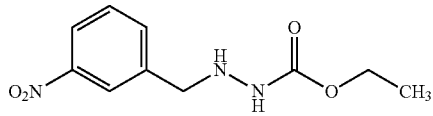 [SMILES: CCOC(=O)NNCc1cccc([N+](=O)[O-])c1]

To a stirred solution of 1-(chloromethyl)-3-nitrobenzene (2 g, 11.66 mmol) and ethyl hydrazinecarboxylate (1.214 g, 11.66 mmol) in DMF (40 mL) at room temperature was added $K_2CO_3$ (1.772 g, 12.82 mmol) followed by sodium iodide (0.349 g, 2.331 mmol). The reaction mixture was stirred overnight at room temperature and then diluted with ethyl acetate (25 mL). The organic solution was washed with ice cold water (2×50 mL) followed by brine solution (30 mL). The organic layer was dried over sodium sulfate, filtered and concentrated under reduced pressure. The crude material was purified by flash column chromatography (Combiflash, 24 g silica, 0-30% EtOAc/PE) to afford the title compound (1.05 g, 4.39 mmol, 38% yield) as a colorless gummy solid. $^1$H NMR (400 MHz, DMSO-$d_6$) δ 8.53 (br. s., 1H), 8.22 (br. s., 1H), 8.14-8.09 (m, 1H), 7.78 (d, J=7.6 Hz, 1H), 7.64-7.58 (m, 1H), 5.22 (q, J=4.2 Hz, 1H), 4.05-3.95 (m, 4H), 1.13 (t, J=7.1 Hz, 3H). MS (ESI) 240 (M+H).

Step B. Intermediate 53B. Preparation of 2-ethoxy-5-(3-nitrophenyl)-1,3,4-oxadiazole

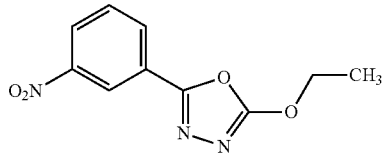 [SMILES: CCOc1nnc(-c2cccc([N+](=O)[O-])c2)o1]

To a stirred solution of Intermediate 53A (0.9 g, 3.76 mmol) in MeCN (90 mL) heated to 40° C. was added iodobenzene diacetate (2.67 g, 8.28 mmol) and continued heating for 2 h. The reaction mixture was diluted with ethyl acetate (10 mL) and washed with brine solution (2×10 mL). The organic layer was dried over sodium sulfate, filtered and concentrated under reduced pressure to yield crude material which was purified by flash chromatography to afford the title compound (700 mg, 2.68 mmol, 71% yield) as a brown gummy solid. $^1$H NMR (400 MHz, DMSO-$d_6$) δ 8.58-8.54 (m, 1H), 8.42 (dd, J=8.4, 1.1 Hz, 1H), 8.34-8.29 (m, 1H), 7.88 (t, J=8.1 Hz, 1H), 4.60 (q, J=7.3 Hz, 3H), 1.45 (t, J=7.20 Hz, 3H). MS (ESI) 236 (M+H).

Step C. Intermediate 53C. Preparation of 3-(5-ethoxy-1,3,4-oxadiazol-2-yl)aniline

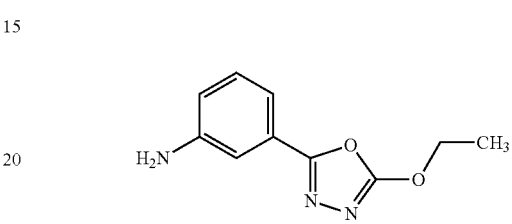

To a stirred solution of Intermediate 53B (600 mg, 2.55 mmol) in ethanol (6 mL) was added a solution of ammonium chloride (2047 mg, 38.3 mmol) in water (6 mL) followed by zinc (2502 mg, 38.3 mmol). The reaction mixture was stirred overnight at room temperature and then diluted with DCM (20 mL) and filtered through celite. The filtrate was washed with water (10 mL) followed by brine solution. The organic layer was dried over sodium sulfate, filtered and concentrated under reduced pressure to afford the title compound (480 mg, 2.199 mmol, 86% yield) as brown solid. $^1$H NMR (400 MHz, DMSO-$d_6$) δ 7.17 (t, J=7.8 Hz, 1H), 7.11-7.06 (m, 1H), 7.01-6.95 (m, 1H), 6.73 (dt, J=8.0, 1.3 Hz, 1H), 5.44 (br. s., 2H), 4.53 (q, J=7.0 Hz, 2H), 1.42 (t, J=7.0 Hz, 3H). MS (ESI) 206 (M+H).

Step D. Intermediate 53D. Preparation of N-((4-(3-cyclopropyl-1,2,4-oxadiazol-5-yl) bicyclo[2.2.2]octan-1-yl)methyl)-3-(5-ethoxy-1,3,4-oxadiazol-2-yl)aniline

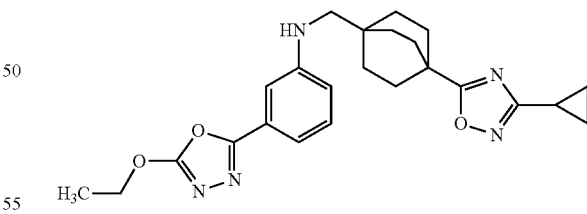

The title compound was synthesized according to the method described for the synthesis of 1I by substituting Intermediate 53C and Intermediate 4C where appropriate: (320 mg, 0.735 mmol, 60% yield) as a brown gummy solid. $^1$H NMR (400 MHz, DMSO-$d_6$) δ 7.25-7.16 (m, 1H), 7.11 (d, J=1.7 Hz, 1H), 6.98 (d, J=6.8 Hz, 1H), 6.83-6.78 (m, 1H), 4.54 (q, J=7.0 Hz, 2H), 2.86 (d, J=6.1 Hz, 2H), 2.10-2.01 (m, 1H), 1.90-1.80 (m, 6H), 1.61-1.51 (m, 6H), 1.42 (t, J=7.0 Hz, 3H), 1.06-1.00 (m, 2H), 0.89-0.82 (m, 2H). MS (ESI) 206 (M+H).

Step E. Example 53. Preparation of N-((4-(3-cyclopropyl-1,2,4-oxadiazol-5-yl) bicyclo[2.2.2]octan-1-yl)methyl)-N-(3-(5-ethoxy-1,3,4-oxadiazol-2-yl) phenyl)-3-fluorobicyclo[1.1.1]pentane-1-carboxamide The title compound was synthesized according to the method described for the synthesis of Example 3 by substituting Intermediate 53D and 3-fluorobicyclo[1.1.1]pentane-1-carboxylic acid where appropriate: (7.9 mg, 0.014 mmol, 18% yield). $^1$H NMR (400 MHz, DMSO-d6) δ 7.89 (d, J=6.6 Hz, 1H), 7.84 (s, 1H), 7.70-7.57 (m, 2H), 4.58 (q, J=7.1 Hz, 2H), 3.60 (br. s., 2H), 2.08-2.02 (m, 1H), 1.88 (br. s., 6H), 1.81-1.68 (m, 6H), 1.54-1.32 (m, 9H), 1.24 (s, 1H), 1.07-0.96 (m, 2H), 0.86-0.80 (m, 2H). FXR EC$_{50}$ (nM)=81; MS (ESI) 548 (M+H).

The following compounds were synthesized according to the method described for the synthesis of Example 3 by substituting Intermediate 53D and the corresponding acids where appropriate:

| Ex. No. | Structure | MS (ESI) (M + H) | FXR EC$_{50}$ (nM) |
|---|---|---|---|
| 54 | 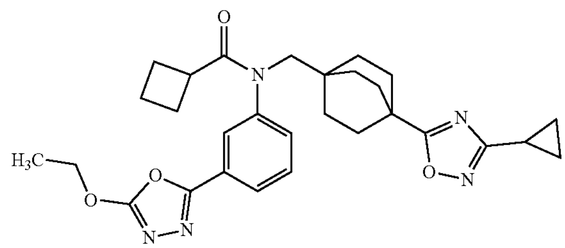 [SMILES: CCOc1nnc(-c2cccc(N(CC34CCC(c5nc(C6CC6)no5)(CC3)CC4)C(=O)C3CCC3)c2)o1] | 518 | 215 |
| 55 | 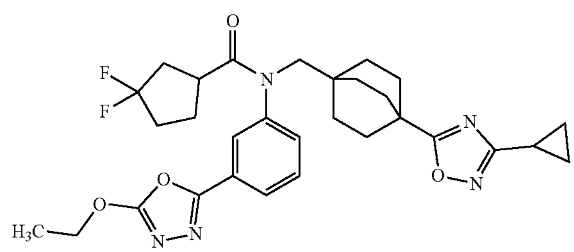 [SMILES: CCOc1nnc(-c2cccc(N(CC34CCC(c5nc(C6CC6)no5)(CC3)CC4)C(=O)C3CCC(F)(F)C3)c2)o1] | 568 | 127 |
| 56 | 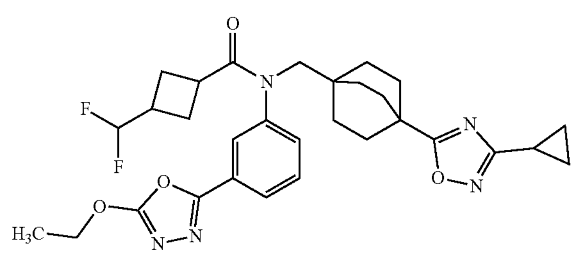 [SMILES: CCOc1nnc(-c2cccc(N(CC34CCC(c5nc(C6CC6)no5)(CC3)CC4)C(=O)C3CC(C(F)F)C3)c2)o1] | 568 | 275 |

54 $^1$HNMR (400 MHz, DMSO-d$_6$) δ 7.82 (d, J = 7.3 Hz, 1H), 7.77 (s, 1H), 7.67-7.53 (m, 2H), 4.58 (q, J = 7.1 Hz, 2H), 3.62 (s, 2H), 3.05 (br. s, 1H), 2.20-2.08 (m, 2H), 2.07-1.98 (m, 1H), 1.83-1.71 (m, 6H), 1.64 (br. s., 4H), 1.51-1.31 (m, 9H), 1.07-0.97 (m, 2H), 0.89-0.77 (m, 2H)

55 $^1$HNMR (400 MHz, DMSO-d$_6$) δ 8.01-7.79 (m, 2H), 7.77-7.51 (m, 2H), 4.58 (q, J = 6.9 Hz, 2H), 3.79-3.50 (m, 2H), 2.92-2.96 (m, 1H), 2.39-2.20 (m, 1H), 2.19-1.97 (m, 3H), 1.88-1.71 (m, 9H), 1.71-1.64 (m, 1H), 1.52-1.26 (m, 9H), 1.07-0.94 (m, 2H), 0.89-0.74 (m, 2H)

56 $^1$HNMR (400 MHz, DMSO-d$_6$) δ 7.90-7.73 (m, 2H), 7.67-7 48 (m, 2H), 5.95-5.78 (m, 1H), 4.57 (q, J = 7.0 Hz, 2H), 3.62 (d, J = 5.6 Hz, 2H), 3.11-2.95 (m, 1H), 2.13-1.98 (m, 2H), 1.74 (d, J = 8.6 Hz, 6H), 1.67 (br. s., 2H), 1.50-1.27 (m, 9H), 1.00 (dd, J = 8.3, 2.4 Hz, 2H), 0.90-0.75 (m, 2H)

Example 57

N-((4-(3-cyclopropyl-1,2,4-oxadiazol-5-yl)bicyclo[2.2.2]octan-1-yl)methyl)-N-(3-(5-cyclopropylisoxazol-3-yl)phenyl)-3-fluorobicyclo[1.1.1]pentane-1-carboxamide

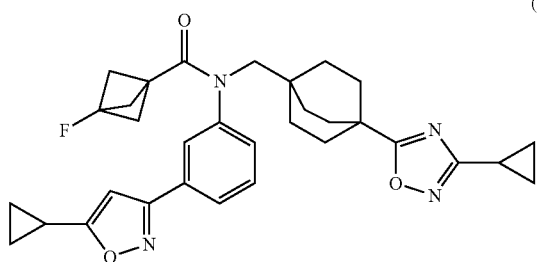

(57)

Step A. Intermediate 57A. Preparation of 1-cyclopropyl-3-(3-nitrophenyl)propane-1,3-dione

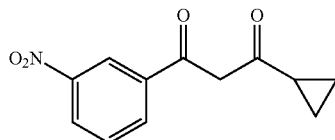

To a stirred solution of LiHMDS in THF (1M solution) at −78° C. (23.78 mL, 23.78 mmol) was added 1-cyclopropylethan-1-one (1.0 g, 11.89 mmol) and stirred for 45 min. A solution of 3-nitrobenzoyl chloride (2.101 g, 11.32 mmol) in THF (11 mL) was added to the reaction mixture dropwise over 20 min and the reaction mixture was stirred for 1 h at −78° C. The reaction mixture was quenched with saturated aqueous ammonium chloride solution (50 mL) and extracted with ethyl acetate (2×50 mL). The combined organic layers were washed with water (50 mL) followed by saturated brine solution (50 mL) and dried over sodium sulphate. The solution was filtered and concentrated under reduced pressure. The crude material was purified by flash column chromatography (Combiflash, 24 g silica, 0-30% EtOAc/PE) to afford the title compound (1.6 g, 6.86 mmol, 61% yield) as a yellow solid. $^1$H NMR (400 MHz, CHLOROFORM-d) δ 16.16 (br. s., 1H), 8.75-8.60 (m, 1H), 8.43-8.27 (m, 1H), 8.20 (dt, J=7.9, 1.3 Hz, 1H), 7.65 (t, J=7.8 Hz, 1H), 6.36 (s, 1H), 1.90-1.77 (m, 1H), 1.28-1.15 (m, 2H), 1.06 (dq, J=7.8, 3.7 Hz, 2H). MS (ESI) 232 (M−H).

Step B. Intermediate 57B. Preparation of 5-cyclopropyl-3-(3-nitrophenyl)isoxazole

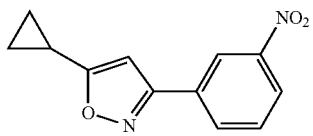 [SMILES: O=[N+]([O-])c1cccc(-c2cc(C3CC3)on2)c1]

To a stirred solution of Intermediate 57A (0.8 g, 3.43 mmol) in MeOH (30 mL) was added hydroxylamine hydrochloride (0.953 g, 13.72 mmol) and stirred at room temperature for 48 h. The reaction mixture was concentrated under reduced pressure and the residue was diluted with water (30 mL) and extracted with ethyl acetate (2×20 mL). The combined organic layers were washed with saturated brine solution (40 mL), dried over sodium sulfate, filtered and concentrated under reduced pressure. The crude material was purified by flash column chromatography (Combiflash, 24 g silica, 0-30% EtOAc/PE) to afford the title compound (600 mg, 2.61 mmol, 76% yield) as a brown oil. $^1$H NMR (400 MHz, DMSO-$d_6$) δ 8.60-8.56 (m, 1H), 8.36-8.31 (m, 1H), 8.30-8.23 (m, 1H), 7.86-7.79 (m, 1H), 6.98 (s, 1H), 2.26-2.18 (m, 1H), 1.17-1.11 (m, 2H), 1.00-0.94 (m, 2H). MS (ESI) 231 (M+H).

Step C. Intermediate 57C. Preparation of 3-(5-cyclopropylisoxazol-3-yl)aniline

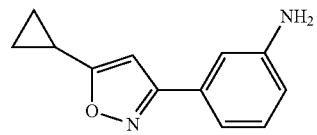

To a stirred solution of Intermediate 57B (700 mg, 3.04 mmol) in a mixture of ethanol (8 mL), THF (4 mL) and water (2 mL) was added zinc (2982 mg, 45.6 mmol) followed by ammonium chloride (2440 mg, 45.6 mmol). The reaction mixture was stirred overnight at room temperature. The reaction mixture was concentrated under reduced pressure and the residue was diluted with ethyl acetate (10 mL). The solution was filtered through celite bed and the residue was washed with ethyl acetate (10 mL).

The filtrate obtained was concentrated under reduced pressure. The crude material was purified by flash column chromatography (Combiflash, 24 g silica, 0-30% EtOAc/PE) to afford the title compound (200 mg, 0.999 mmol, 33% yield) as a brown wax. $^1$H NMR (400 MHz, DMSO-$d_6$) δ 7.10 (t, J=8.0 Hz, 1H), 7.03-6.99 (m, 1H), 6.88 (d, J=7.5 Hz, 1H), 6.64 (dd, J=8.0, 1.5 Hz, 1H), 6.57-6.51 (m, 1H), 5.24 (s, 2H), 2.20-2.09 (m, 1H), 1.12-1.04 (m, 2H), 0.96-0.88 (m, 2H). MS (ESI) 201 (M+H).

Step D. Intermediate 57D. Preparation of N-((4-(3-cyclopropyl-1,2,4-oxadiazol-5-yl) bicyclo[2.2.2]octan-1-yl)methyl)-3-(5-cyclopropylisoxazol-3-yl)aniline

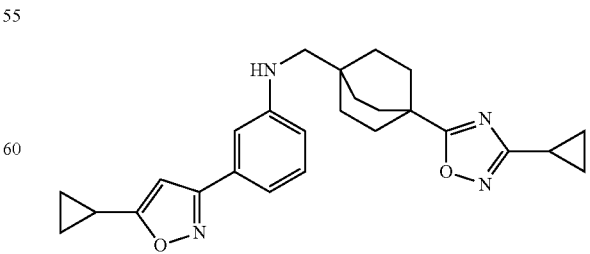

The title compound was synthesized according to the method described for the synthesis of Intermediate 1I by substituting Intermediate 57C and Intermediate 4C where appropriate: (350 mg, 0.813 mmol, 81% yield) as a brown wax. MS (ESI) 431 (M+H).

Step E. Example 57. Preparation of N-((4-(3-cyclopropyl-1,2,4-oxadiazol-5-yl) bicyclo[2.2.2]octan-1-yl)methyl)-N-(3-(5-cyclopropylisoxazol-3-yl)phenyl)-3-fluorobicyclo[1.1.1]pentane-1-carboxamide The title compound was synthesized according to the method described for the synthesis of Example 3 by substituting Intermediate 57D and the corresponding acid where appropriate: (19.7 mg, 52% yield). $^1$H NMR (400 MHz, DMSO-$d_6$) δ 7.84 (d, J=7.8 Hz, 1H), 7.80 (s, 1H), 7.64-7.56 (m, 1H), 7.56-7.49 (m, 1H), 6.88 (s, 1H), 3.59 (s, 2H), 2.26-2.15 (m, 1H), 2.12-2.00 (m, 1H), 1.86 (br. s., 6H), 1.81-1.71 (m, 6H), 1.50-1.36 (m, 6H), 1.17-1.07 (m, 2H), 1.05-0.98 (m, 2H), 0.98-0.91 (m, 2H), 0.88-0.79 (m, 2H). FXR EC$_{50}$ (nM)=19.80 MS (ESI) 543 (M+H).

The following compounds were synthesized according to the method described for the synthesis of Example 3 by substituting Intermediate 57D and the corresponding acid where appropriate:

| Ex. No. | Structure | MS (ESI) (M + H) | FXR EC$_{50}$ (nM) |
|---|---|---|---|
| 58 | 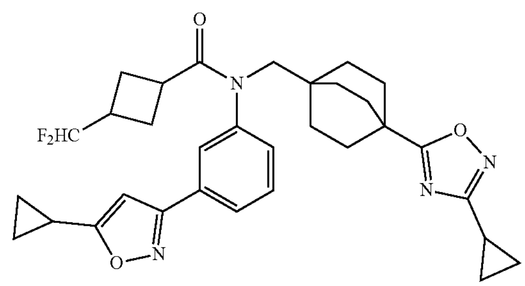 [SMILES: O=C(C1CC(C(F)F)C1)N(CC12CCC(c3nc(C4CC4)no3)(CC1)CC2)c1cccc(-c2cc(C3CC3)on2)c1] | 563 | 39 |
| 59 | 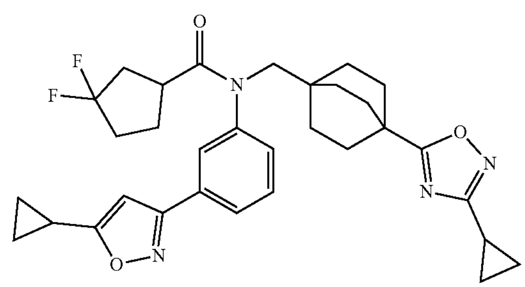 [SMILES: O=C(C1CCC(F)(F)C1)N(CC12CCC(c3nc(C4CC4)no3)(CC1)CC2)c1cccc(-c2cc(C3CC3)on2)c1] | 563 | 70 |
| 60 | 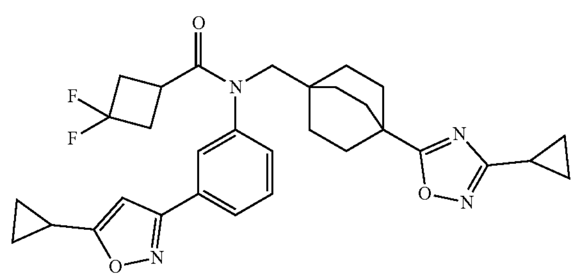 [SMILES: O=C(C1CC(F)(F)C1)N(CC12CCC(c3nc(C4CC4)no3)(CC1)CC2)c1cccc(-c2cc(C3CC3)on2)c1] | 549 | 230 |

58 $^1$H NMR (400 MHz, DMSO-$d_6$) δ 7.84-7.67 (m, 2H), 7.60-7.40 (m, 2H), 6.90-6.81 (m, 1H), 6.18-5.81 (m, 1H), 3.62 (br. s., 2H), 3.13-2.99 (m, 1H), 2.30 (br. s., 1H), 2.23-2.15 (m, 1H), 2.12-1.97 (m, 2H), 1.86-1.70 (m, 6H), 1.65 (d, J = 10.3 Hz, 2H), 1.41 (d, J = 4.2 Hz, 6H), 1.18-1.07 (m, 2H), 1.05-0.97 (m, 2H), 0.97-0.89 (m, 2H), 0.88-0.75 (m, 2H) (1H- buried under DMSO peak)

59 $^1$H NMR (400 MHz, DMSO-$d_6$) δ 7.94-7.73 (m, 2H), 7.66-7.49 (m, 2H), 6.86 (s, 1H), 3.65 (br. s., 2H), 2.94 (t, J = 8.7 Hz, 1H), 2.29 (br. s., 1H), 2.20 (ddd, J = 13.4, 8.3, 5.1 Hz, 1H), 2.15-1.97 (m, 3H), 1.90-1.71 (m, 8H), 1.67 (m, 1H), 1.50-1.32 (m, 6H), 1.18-1.07 (m, 2H), 1.06-0.98 (m, 2H), 0.98-0.90 (m, 2H), 0.87-0.75 (m, 2H)

60 $^1$H NMR (400 MHz, DMSO-$d_6$) δ 7.89-7.72 (m, 2H), 7.58 (t, J = 7.9 Hz, 1H), 7.54-7.45 (m, 1H), 6.84 (s, 1H), 3.65 (s, 2H), 2.95-2.84 (m, 1H), 2.81-2.70 (m, 2H), 2.34 (d, J = 2.0 Hz, 2H), 2.22-2.14 (m, 1H), 2.08-2.01 (m, 1H), 1.86-1.68 (m, 6H), 1.51-1.32 (m, 6H), 1.16-1.09 (m, 2H), 1.06-0.98 (m, 2H), 0.98-0.91 (m, 2H), 0.88-0.77 (m, 2H)

Example 61

N-((4-(3-(cyclopropylmethyl)-1,2,4-oxadiazol-5-yl)bicyclo[2.2.2]octan-1-yl)methyl)-N-(3-(3-(cyclopropylmethyl)-1,2,4-oxadiazol-5-yl)phenyl)-3-fluorobicyclo[1.1.1]pentane-1-carboxamide (61)

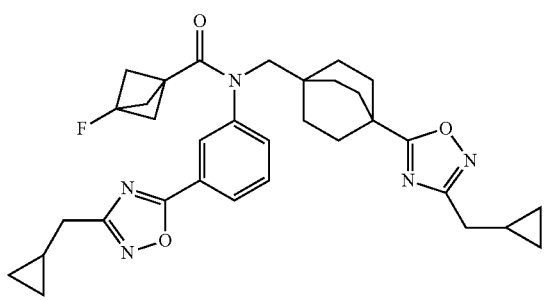

Step A. Intermediate 61A. Preparation of (E)-2-cyclopropyl-N'-hydroxyacetimidamide

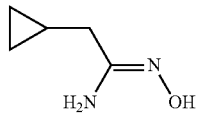

To a stirred solution of 2-cyclopropylacetonitrile (1.111 mL, 12.33 mmol) in ethanol (10 mL) was added hydroxylamine (3.78 mL, 61.6 mmol) and stirred under reflux for 1 h. The reaction mixture was concentrated under reduced pressure, diluted with water and filtered to afford the title compound (1200 mg, 10.51 mmol, 85% yield) as a pale gray solid. $^1$H NMR (400 MHz, DMSO-$d_6$) δ 8.70 (s, 1H), 5.32 (br. s., 2H), 1.84 (d, J=7.0 Hz, 2H), 1.00-0.87 (m, 1H), 0.48-0.33 (m, 2H), 0.14-0.07 (m, 2H). MS (ESI) 115 (M+H).

Step B. Intermediate 61B. Preparation of 3-(3-(cyclopropylmethyl)-1,2,4-oxadiazol-5-yl)aniline

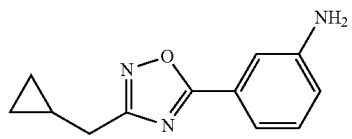 [SMILES: Nc1cccc(-c2nc(CC3CC3)no2)c1]

The title compound was synthesized according to the method described for the synthesis of Intermediate 1B by substituting Intermediate 57A and 3-aminobenzoic acid where appropriate: (350 mg, 1.593 mmol, 87% yield) as yellow gummy liquid. $^1$H NMR (400 MHz, DMSO-$d_6$) δ 7.31 (t, J=1.8 Hz, 1H), 7.27-7.17 (m, 2H), 6.87-6.80 (m, 1H), 5.55 (s, 2H), 2.68 (d, J=6.80 Hz, 2H), 1.15-1.07 (m, 1H), 0.57-0.48 (m, 2H), 0.30-0.22 (m, 2H). MS (ESI) 216 (M+H).

Step C. Intermediate 57C. Preparation of methyl 4-(3-(cyclopropylmethyl)-1,2,4-oxadiazol-5-yl)bicyclo[2.2.2]octane-1-carboxylate

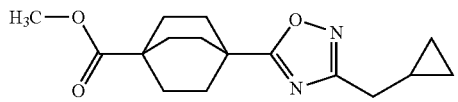 [SMILES: COC(=O)C12CCC(c3nc(CC4CC4)no3)(CC1)CC2]

The title compound was synthesized according to the method described for the synthesis of Intermediate 1F by substituting Intermediate 57A and 4-(methoxycarbonyl)bicyclo[2.2.2]octane-1-carboxylic acid where appropriate: (1000 mg, 2.411 mmol, 68% yield). $^1$H NMR (400 MHz, DMSO-$d_6$) δ 3.60 (s, 3H), 2.58 (d, J=7.0 Hz, 2H), 1.97-1.87 (m, 6H), 1.87-1.77 (m, 6H), 1.09-0.98 (m, 1H), 0.52-0.45 (m, 2H), 0.23-0.16 (m, 2H). MS (ESI) 291 (M+H).

Step D. Intermediate 61D. Preparation of (4-(3-(cyclopropylmethyl)-1,2,4-oxadiazol-5-yl)bicyclo[2.2.2]octan-1-yl)methanol

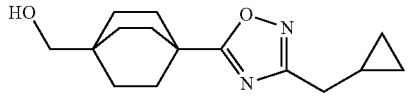 [SMILES: OCC12CCC(c3nc(CC4CC4)no3)(CC1)CC2]

The title compound was synthesized according to the method described for the synthesis of Intermediate 1G by substituting Intermediate 61C where appropriate: (650 mg, 2.478 mmol, 80% yield). MS (ESI) 263 (M+H).

Step E. Intermediate 61E. Preparation of 4-(3-(cyclopropylmethyl)-1,2,4-oxadiazol-5-yl)bicyclo[2.2.2]octane-1-carbaldehyde

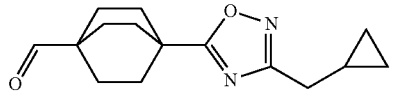

The title compound was synthesized according to the method described for the synthesis of Intermediate 3C by substituting Intermediate 61D where appropriate: (500 mg, 1.921 mmol, 78% yield). $^1$H NMR (400 MHz, DMSO-$d_6$) δ 9.47 (s, 1H), 1.97-1.88 (m, 6H), 1.84-1.76 (m, 2H), 1.74-1.66 (m, 6H), 1.09-1.01 (m, 1H), 0.53-0.46 (m, 2H), 0.23-0.18 (m, 2H). MS (ESI) 261 (M+H).

Step F. Intermediate 61F. Preparation of 3-(3-(cyclopropylmethyl)-1,2,4-oxadiazol-5-yl)-N-((4-(3-(cyclopropylmethyl)-1,2,4-oxadiazol-5-yl)bicyclo[2.2.2]octan-1-yl)methyl)aniline

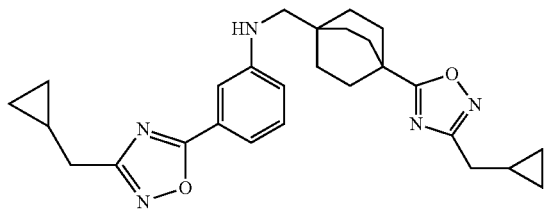 [SMILES: c1cc(NCC23CCC(c4nc(CC5CC5)no4)(CC2)CC3)cc(-c2nc(CC3CC3)no2)c1]

The title compound was synthesized according to the method described for the synthesis of Intermediate 1I by substituting Intermediate 61B and 61E where appropriate: (180 mg, 0.392 mmol, 73% yield). ¹H NMR (400 MHz, DMSO-d₆) δ 7.35-7.15 (m, 2H), 6.92 (dd, J=7.7, 2.1 Hz, 1H), 6.83 (ddd, J=7.6, 2.4, 1.5 Hz, 1H), 6.00 (s, 1H), 2.89 (d, J=5.9 Hz, 2H), 2.68 (dd, J=7.0, 3.3 Hz, 2H), 2.59 (d, J=6.8 Hz, 2H), 1.95-1.85 (m, 6H), 1.84-1.75 (m, 1H), 1.64-1.54 (m, 6H), 1.17-0.98 (m, 1H), 0.58-0.42 (m, 4H), 0.30-0.17 (m, 4H). MS (ESI) 460 (M+H).

Step G. Example 61. Preparation of N-((4-(3-(cyclopropylmethyl)-1,2,4-oxadiazol-5-yl)bicyclo[2.2.2]octan-1-yl)methyl)-N-(3-(3-(cyclopropylmethyl)-1,2,4-oxadiazol-5-yl) phenyl)-3-fluorobicyclo[1.1.1]pentane-1-carboxamide The title compound was synthesized according to the method described for the synthesis of Example 3 by substituting Intermediate 61F and the corresponding acid where appropriate: (9.6 mg, 0.017 mmol, 26% yield). ¹H NMR (400 MHz, DMSO-d₆) δ 8.10 (d, J=7.6 Hz, 1H), 8.05 (s, 1H), 7.83-7.63 (m, 2H), 3.62 (br s, 2H), 2.73 (d, J=6.8 Hz, 2H), 2.55 (d, J=6.8 Hz, 2H), 1.89 (br. s., 6H), 1.84-1.64 (m, 6H), 1.59-1.33 (m, 6H), 1.14 (ddd, J=12.2, 7.4, 4.6 Hz, 1H), 1.06-0.88 (m, 1H), 0.64-0.40 (m, 4H), 0.36-0.23 (m, 2H), 0.17 (q, J=4.6 Hz, 2H) FXR EC$_{50}$ (nM)=99; MS (ESI) 572 (M+H).

The following compounds were synthesized according to the method described for the synthesis of Example 3 by substituting Intermediate 61F and the corresponding acids where appropriate:

| Ex. No. | Structure | MS (ESI) (M + H) | FXR EC$_{50}$ (nM) |
|---|---|---|---|
| 62 | 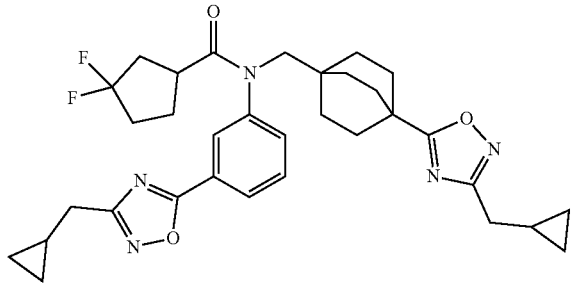 [SMILES: O=C(C1CCC(F)(F)C1)N(CC12CCC(c3nc(CC4CC4)no3)(CC1)CC2)c1cccc(-c2nc(CC3CC3)no2)c1] | 592 | 363 |
| 63 | 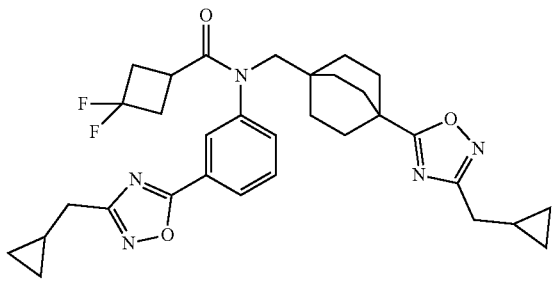 [SMILES: O=C(C1CC(F)(F)C1)N(CC12CCC(c3nc(CC4CC4)no3)(CC1)CC2)c1cccc(-c2nc(CC3CC3)no2)c1] | 578 | 562 |

| Ex. No. | Structure | MS (ESI) (M + H) | FXR EC$_{50}$ (nM) |
|---|---|---|---|
| 64 | | 542 | 523.96 |

| | |
|---|---|
| 62 | $^1$H NMR (400 MHz, DMSO-d$_6$) δ 8.12 (s, 1H), 8.09 (d, J = 7.8 Hz, 1H), 7.82 (d, J = 8.3 Hz, 1H), 7.72 (t, J = 7.7 Hz, 1H), 3.66 (br. s., 2H), 3.01-2.90 (m, 1H), 2.73 (d, J = 7.1 Hz, 2H), 2.56 (d, J = 6.8 Hz, 2H), 2.29 (br. s., 1H), 2.08 (br. s., 2H), 1.96-1.75 (m, 8H), 1.52-1.35 (m, 6H), 119-1.10 (m, 1H), 1.08-0.97 (m, 2H), 0.59-0.51 (m, 2H), 0.51-0.42 (m, 2H), 0.33-0.25 (m, 2H), 0.23-0.15 (m, 2H) |
| 63 | $^1$H NMR (400 MHz, DMSO-d$_6$) δ 8.15-8.04 (m, 2H), 7.77 (d, J = 7.6 Hz, 1H), 7.71 (t, J = 7.8 Hz, 1H), 3.68 (br. s., 2H), 2.91 (d, J = 5.9 Hz, 1H), 2.73 (d, J = 7.1 Hz, 3H), 2.56 (d, J = 7.1 Hz, 2H), 2.40-2.27 (m, 3H), 1.91-1.72 (m, 6H), 1.56-1.32 (m, 6H), 1.21-1.10 (m, 1H), 1.06-0.96 (m, 1H), 0.60-0.52 (m, 2H), 0.52-0.44 (m, 2H), 0.33-0.25 (m, 2H), 0.23-0.14 (m, 2H) |
| 64 | $^1$H NMR (400 MHz, DMSO-d$_6$) δ 8.04 (d, J = 6.6 Hz, 1H), 8.00 (s, 1H), 7.75-7.62 (m, 2H), 3.65 (s, 2H), 3.08 (br. s., 1H), 2.73 (d, J = 7.1 Hz, 2H), 2.56 (d, J = 7.1 Hz, 2H), 2.14 (br. s., 2H), 1.90-1.75 (m, 6H), 1.65 (br. s., 4H), 1.49-1.32 (m, 6H), 1.19-1.09 (m, 1H), 1 06-0.91 (m, 1H), 0.59-0.52 (m, 2H), 0.51-0.43 (m, 2H), 0.34-0.25 (m, 2H), 0.24-0.14 (m, 2H) |

Example 65

N-((4-(3-cyclopropyl-1,2,4-oxadiazol-5-yl)bicyclo[2.2.2]octan-1-yl)methyl)-N-(3-(3-(cyclopropylmethyl)-1,2,4-oxadiazol-5-yl)phenyl)-3-fluorobicyclo[1.1.1]pentane-1-carboxamide (65)

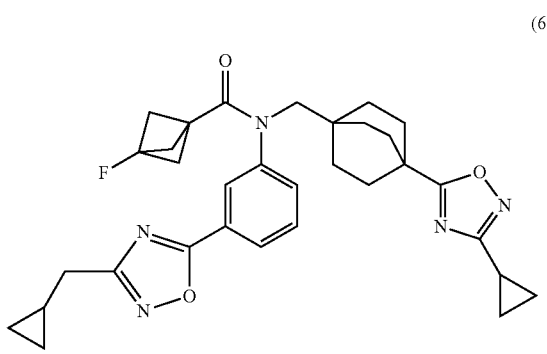

Step A. Intermediate 65A. Preparation of N-((4-(3-cyclopropyl-1,2,4-oxadiazol-5-yl) bicyclo[2.2.2]octan-1-yl)methyl)-3-(3-(cyclopropylmethyl)-1,2,4-oxadiazol-5-yl)aniline

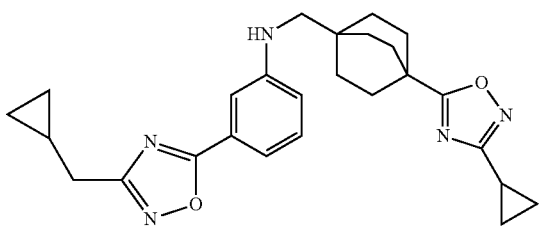 [SMILES: c1cc(NCC23CCC(c4nc(C5CC5)no4)(CC2)CC3)cc(-c2nc(CC3CC3)no2)c1]

The title compound was synthesized according to the method described for the synthesis of Intermediate 1I by substituting Intermediates 61B and 4C where appropriate: (180 mg, 0.404 mmol, 71% yield). MS (ESI) 446 (M+H).

Step B. Example 65. Preparation of N-((4-(3-cyclopropyl-1,2,4-oxadiazol-5-yl) bicyclo[2.2.2]octan-1-yl)methyl)-N-(3-(3-(cyclopropylmethyl)-1,2,4-oxadiazol-5-yl) phenyl)-3-fluorobicyclo[1.1.1]pentane-1-carboxamide The title compound was synthesized according to the method described for the synthesis of Example 3 by substituting Intermediate 65A and the corresponding acid where appropriate: (20.4 mg, 0.036 mmol, 40% yield). $^1$H NMR (400 MHz, DMSO-d$_6$) δ 8.11 (d, J=7.3 Hz, 1H), 8.06 (s, 1H), 7.82-7.64 (m, 2H), 3.62 (br. s., 2H), 2.74 (d, J=7.1 Hz, 2H), 2.12-2.00 (m, 1H), 1.90 (br. s., 6H), 1.82-1.60 (m, 6H), 1.56-1.32 (m, 6H), 1.21-1.09 (m, 1H), 1.07-0.92 (m, 2H), 0.90-0.73 (m, 2H), 0.62-0.49 (m, 2H), 0.37-0.22 (m, 2H). FXR EC$_{50}$ (nM)=142; MS (ESI) 558 (M+H).

The following compounds were synthesized according to the method described for the synthesis of Example 3 by substituting Intermediate 65A and the corresponding acids where appropriate:

| Ex. No. | Structure | MS (ESI) (M + H) | FXR EC$_{50}$ (nM) |
|---|---|---|---|
| 66 | | 528 | 303 |
| 67 | | 578 | 202 |

66  $^1$H NMR (400 MHz, DMSO-d$_6$) δ 8.04 (d, J = 6.6 Hz, 1H), 7.99 (s, 1H), 7.76-7.63 (m, 2H), 3.64 (s, 2H), 3.07 (br. s., 1H), 2.73 (d, J = 7.1 Hz, 2H), 2.14 (br. s., 2H), 2.07-2.00 (m, 1H), 1.84-1.70 (m, 6H), 1.65 (br. s., 4H), 1.47-1.30 (m, 6H), 1.18-1.08 (m, 1H), 1.07-0.95 (m, 2H), 0.88-0.73 (m, 2H), 0.61-0.50 (m, 2H), 0.32-0.24 (m, 2H)

67  $^1$H NMR (400 MHz, DMSO-d$_6$) δ 8 18-8.01 (m, 2H), 7.80 (d, J = 8.1 Hz, 1H), 7.72 (t, J = 7.8 Hz, 1H), 3.65 (br. s., 2H), 2.95 (t, J = 8.3 Hz, 1H), 2.73 (d, J = 6.8 Hz, 2H), 2.41-2.22 (m, 2H), 2.17-1.97 (m, 3H), 1.91 (br. s., 1H), 1.88-1.71 (m, 6H), 1.67 (br. s., 1H), 1.53-1.31 (m, 6H), 1.20-1.09 (m, 1H), 1.06-0.97 (m, 2H), 0.89-0.79 (m, 2H), 0.61-0.48 (m, 2H), 0.33-0.24 (m, 2H)

Example 68

N-(3-(3-cyclopropyl-1,2,4-oxadiazol-5-yl)phenyl)-N-((4-(3-(cyclopropylmethyl)-1,2,4-oxadiazol-5-yl)bicyclo[2.2.2]octan-1-yl)methyl)-3-fluorobicyclo[1.1.1]pentane-1-carboxamide

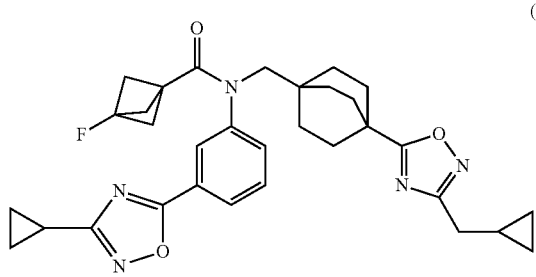

(68)

Step A. Intermediate 68A. Preparation of 3-(3-cyclopropyl-1,2,4-oxadiazol-5-yl)-N-((4-(3-(cyclopropylmethyl)-1,2,4-oxadiazol-5-yl)bicyclo[2.2.2]octan-1-yl)methyl)aniline

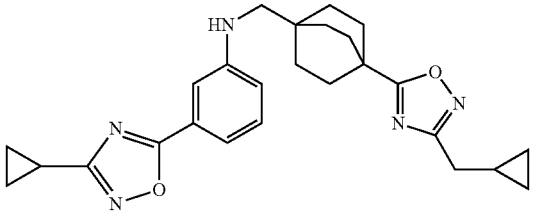 [SMILES: c1cc(NCC23CCC(c4nc(CC5CC5)no4)(CC2)CC3)cc(-c2nc(C3CC3)no2)c1]

The title compound was synthesized according to the method described for the synthesis of Intermediate 1I by substituting Intermediate 8A and Intermediate 61E where appropriate: (180 mg, 0.404 mmol, 70% yield) as pale brown solid. $^1$H NMR (400 MHz, DMSO-d$_6$) δ 7.32-7.21 (m, 2H), 7.15 (d, J=7.8 Hz, 1H), 6.90 (dd, J=8.2, 1.6 Hz, 1H), 5.98 (t, J=5.5 Hz, 1H), 2.88 (d, J=5.9 Hz, 2H), 2.60-2.56 (m, 2H), 2.23-2.11 (m, 1H), 1.97-1.83 (m, 6H), 1.65-1.53 (m, 6H), 1.13-1.06 (m, 2H), 1.00-0.93 (m, 2H), 0.89-0.83 (m, 1H), 0.53-0.45 (m, 2H), 0.23-0.18 (m, 2H). MS (ESI) 446 (M+H).

Step B. Example 68. Preparation of N-(3-(3-cyclopropyl-1,2,4-oxadiazol-5-yl)phenyl)-N-((4-(3-(cyclopropylmethyl)-1,2,4-oxadiazol-5-yl)bicyclo[2.2.2]octan-1-yl)methyl)-3-fluorobicyclo[1.1.1]pentane-1-carboxamide The title compound was synthesized according to the method described for the synthesis of Example 3 by substituting Intermediate 68A and the corresponding acid where appropriate: (8.4 mg, 0.015 mmol, 22% yield). $^1$H NMR (400 MHz, DMSO-$d_6$) δ 8.07 (d, J=7.3 Hz, 1H), 8.02 (s, 1H), 7.79-7.73 (m, 1H), 7.73-7.64 (m, 1H), 3.64 (br. s., 1H), 3.58 (br. s., 1H), 2.56 (d, J=7.1 Hz, 2H), 2.22 (tt, J=8.6, 4.2 Hz, 1H), 1.89 (br. s., 6H), 1.84-1.68 (m, 6H), 1.55-1.34 (m, 6H), 1.14 (dd, J=8.2, 2.6 Hz, 2H), 1.08-0.94 (m, 3H), 0.54-0.41 (m, 2H), 0.25-0.12 (m, 2H). FXR EC$_{50}$ (nM)=110. MS (ESI) 558 (M+H).

The following compounds were synthesized according to the method described for the synthesis of Example 3 by substituting Intermediate 68A and the corresponding acids where appropriate:

| Ex. No. | Structure | MS (ESI) (M + H) | FXR EC$_{50}$ (nM) |
|---|---|---|---|
| 69 | | 578 | 474 |
| 70 | | 564 | 598 |
| 71 | | 528 | 406 |

69 $^1$H NMR (400 MHz, DMSO-$d_6$) δ 8.07 (s, 1H), 8.03 (d, J = 7.3 Hz, 1H), 7.80 (d, J = 6.6 Hz, 1H), 7.75-7.62 (m, 1H), 3.68 (br. s., 2H), 3.00-2.88 (m, 1H), 2.56 (d, J = 7.1 Hz, 2H), 2.33-2.18 (m, 2H), 2.08 (br. s., 2H), 1.96-1.73 (m, 8H), 1.66 (br. s., 1H), 1.62-1.34 (m, 6H), 1.19-1.09 (m, 2H), 1.07-0.94 (m, 3H), 0.55-0.41 (m, 2H), 0.29-0.10 (m, 2H)

70 $^1$H NMR (400 MHz, DMSO-$d_6$) δ 8.13-7.96 (m, 2H), 7.75 (d, J = 8.1 Hz, 1H), 7.69 (t, J = 7.7 Hz, 1H), 3.67 (br. s., 2H), 3.18 (d, J = 5.4 Hz, 1H), 2.95-2.85 (m, 1H), 2.83-2.69 (m, 2H), 2.56 (d, J = 7.1 Hz, 2H), 2.40-2.29 (m, 2H), 2.26-2.13 (m, 1H), 1.93-1.69 (m, 6H), 1.56-1.30 (m, 6H), 1.18-1.08 (m, 2H), 1.07-0.93 (m, 2H), 0.53-0.42 (m, 2H), 0.23-0.12 (m, 2H)

71 $^1$H NMR (400 MHz, DMSO-$d_6$) δ 7.99 (d, J = 7.1 Hz, 1H), 7.95 (s, 1H), 7.74-7.59 (m, 2H), 3.64 (s, 2H), 3.07 (br. s., 1H), 2.56 (d, J = 7.1 Hz, 2H), 2.26-2.19 (m, 1H), 2.12 (d, J = 9.8 Hz, 2H), 1.88-1.73 (m, 6H), 1.64 (br. s., 4H), 1.49-1.30 (m, 6H), 1.17-1.09 (m, 2H), 1.07-0.93 (m, 3H), 0.53-0.41 (m, 2H), 0.23-0.14 (m, 2H)

Example 72

N-((4-(3-cyclopropyl-1,2,4-oxadiazol-5-yl)bicyclo[2.2.2]octan-1-yl)methyl)-3-fluoro-N-(3-(2-(methoxymethyl)thiazol-4-yl)phenyl)bicyclo[1.1.1]pentane-1-carboxamide (72)

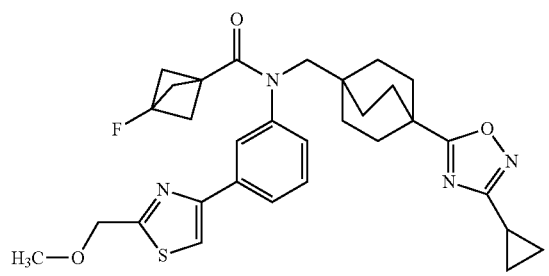

Step A. Intermediate 72A. Preparation of (4-(3-nitrophenyl)thiazol-2-yl)methanol

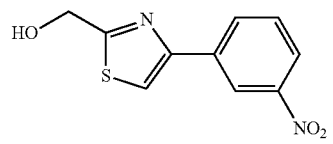 [SMILES: O=[N+]([O-])c1cccc(-c2csc(CO)n2)c1]

To a stirred solution of Intermediate 29A (750 mg, 2.70 mmol) in THF (20 mL) at −78° C., DIBAL-H (10.78 mL, 10.78 mmol) was added and the reaction mixture was stirred for 2 h. The reaction mixture was poured into a biphasic mixture of saturated aqueous ammonium chloride solution (10 mL) and EtOAc (50 mL) and the layers were separated. The aqueous layer was further extracted with EtOAc (2×50 mL). The combined organic layers were dried over MgSO$_4$, filtered and concentrated under reduced pressure. The crude material was purified by flash column chromatography (Combiflash, 24 g silica, 0-30% EtOAc/PE) to afford the title compound (400 mg, 1.693 mmol, 63% yield). MS (ESI) 237 (M+H).

Step B. Intermediate 72B. Preparation of 2-(methoxymethyl)-4-(3-nitrophenyl)thiazole

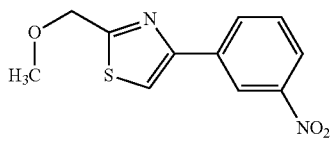 [SMILES: COCc1nc(-c2cccc([N+](=O)[O-])c2)cs1]

To a stirred solution of Intermediate 72A (400 mg, 1.693 mmol) in DMF (10 mL) at 0° C., NaH (135 mg, 3.39 mmol) and MeI (0.212 mL, 3.39 mmol) were added. The reaction mixture was stirred at room temperature for 2 h. The reaction was quenched with cold water and the aqueous layer was extracted with EtOAc (2×50 mL). The combined organic layers were dried over MgSO$_4$, filtered and concentrated under reduced pressure. The crude material was purified by flash column chromatography (Combiflash, 24 g silica, 0-30% EtOAc/PE) to afford the title compound (380 mg, 1.488 mmol, 88% yield). MS (ESI) 251 (M+H).

Step C. Intermediate 72C. Preparation of 3-(2-(methoxymethyl)thiazol-4-yl)aniline

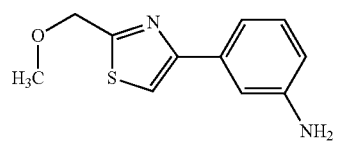

To a stirred solution of Intermediate 72B (380 mg, 1.518 mmol) in EtOH (10 mL) at room temperature were added tin(II) chloride dihydrate (1199 mg, 5.31 mmol) and conc. HCl (1.384 mL, 45.6 mmol). The reaction mixture was stirred at 90° C. for 2 h and concentrated. The residue was basified with saturated aqueous NaHCO$_3$ solution and extracted with EtOAc (2×100 mL). The combined organic layers were dried over Na$_2$SO$_4$, filtered and concentrated to afford the title compound (325 mg, 1.416 mmol, 93% yield). MS (ESI) 221 (M+H).

Step D. Intermediate 72D. Preparation of N-((4-(3-cyclopropyl-1,2,4-oxadiazol-5-yl) bicyclo[2.2.2]octan-1-yl)methyl)-3-(2-(methoxymethyl)thiazol-4-yl)aniline

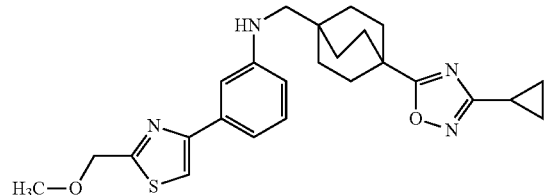

The title compound was synthesized according to the method described for the synthesis of Intermediate 1I by substituting Intermediate 72C and Intermediate 4C where appropriate: (250 mg, 0.388 mmol, 43% yield). MS (ESI) 451 (M+H).

Step E. Example 72. Preparation of N-((4-(3-cyclopropyl-1,2,4-oxadiazol-5-yl) bicyclo[2.2.2]octan-1-yl)methyl)-3-fluoro-N-(3-(2-(methoxymethyl)thiazol-4-yl)phenyl) bicyclo[1.1.1]pentane-1-carboxamide The title compound was synthesized according to the method described for the synthesis of Example 3 by substituting Intermediate 72D and the corresponding acid where appropriate: (11.3 mg, 0.020 mmol, 36% yield). $^1$H NMR (400 MHz, DMSO-d$_6$) δ 8.28 (s, 1H), 7.98 (d, J=8.1 Hz, 1H), 7.94-7.88 (m, 1H), 7.53 (t, J=7.8 Hz, 1H), 7.37 (d, J=9.0 Hz, 1H), 4.79 (s, 2H), 3.60 (d, J=16.4 Hz, 2H), 3.46 (s, 3H), 2.11-1.98 (m, 1H), 1.95-1.82 (m, 6H), 1.82-1.70 (m, 6H), 1.54-1.36 (m, 6H), 1.11-0.91 (m, 2H), 0.88-0.77 (m, 2H); FXR EC$_{50}$ (nM) 166; MS (ESI) 563 (M+H).

The following compounds were synthesized according to the method described for the synthesis of Example 8 by substituting Intermediate 72D and the corresponding acids where appropriate:

| Ex. No. | Structure | MS (ESI) (M + H) | FXR EC$_{50}$ (nM) |
|---|---|---|---|
| 73 | 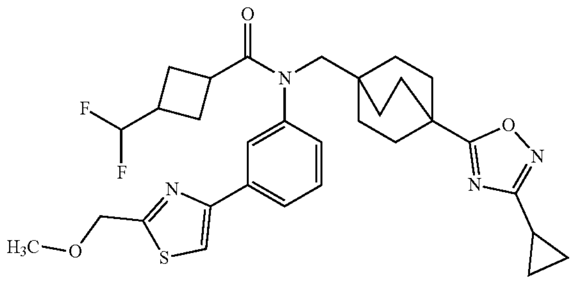 [SMILES: COCc1nc(-c2cccc(N(CC34CCC(c5nc(C6CC6)no5)(CC3)CC4)C(=O)C3CC(C(F)F)C3)c2)cs1] | 583 | 341 |
| 74 | | 583 | 220 |

7  $^1$H NMR (400 MHz, DMSO-d$_6$) δ 8.25 (d, J = 7.1 Hz, 1H), 7.99-7.79 (m, 2H), 7.50 (t, J = 7.7 Hz, 1H), 7.33 (dd, J = 15.0, 7.9 Hz, 1H), 5.95-5.78 (m, 1H), 4.83-4.73 (m, 2H), 3.63 (br. s., 2H), 3.49-3.42 (m, 3H), 3.15-2.98 (m, 1H), 2.34-2.26 (m, 1H), 2.15-1.99 (m, 2H), 1.87 (d, J = 9.5 Hz, 1H), 1.82-1.72 (m, 6H), 1.67 (d, J = 8.8 Hz, 1H), 1.60 (d, J = 7.1 Hz, 1H), 1.43 (d, J = 3.7 Hz, 6H), 1.09-0.94 (m, 2H), 0.92-0.78 (m, 2H)

74 $^1$H NMR (400 MHz, DMSO-d$_6$) δ 8.27 (s, 1H), 8.01-7.89 (m, 2H), 7.53 (t, J = 7.9 Hz, 1H), 7.42 (d, J = 7.6 Hz, 1H), 4.79 (s, 2H), 3.68 (br. s., 2H), 3.45 (s, 3H), 3.02-2.91 (m, 1H), 2.27 (d, J = 9.3 Hz, 1H), 2.18-1.99 (m, 3H), 1.97-1.73 (m, 8H), 1.70 (br. s., 1H), 1.53-1.35 (m, 6H), 1.08-0.96 (m, 2H), 0.89-0.78 (m, 2H)

Example 75

N-((4-(3-cyclopropyl-1,2,4-oxadiazol-5-yl)bicyclo[2.2.2]octan-1-yl)methyl)-N-(3-(5-cyclopropyl-1-methyl-1H-pyrazol-3-yl)phenyl)-3-fluorobicyclo[1.1.1]pentane-1-carboxamide (75)

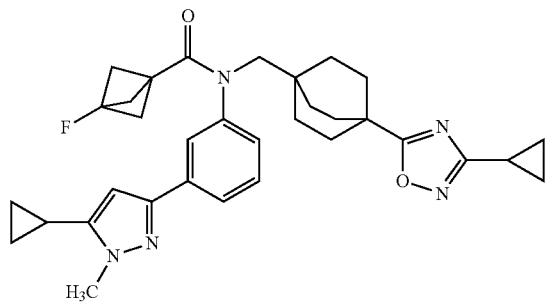

Step A. Intermediate 75A. Preparation of 5-cyclopropyl-3-(3-nitrophenyl)-1H-pyrazole

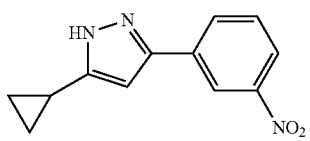

To a stirred solution of Intermediate 57A (0.8 g, 3.43 mmol) in ethanol (5 mL) were added hydrazine hydrate (0.343 g, 6.86 mmol), acetic acid (10 mL) and stirred for 3 h at 80° C. The reaction mixture was concentrated under reduced pressure and the residue was diluted water (10 mL) and extracted with ethyl acetate (2×10 mL). The combined organic layers were washed with brine solution (10 mL), dried over sodium sulfate, filtered and concentrated under reduced pressure. The crude material was purified by flash column chromatography (Combiflash, 24 g silica, 0-30% EtOAc/PE) to afford the title compound (700 mg, 3.05 mmol, 89% yield) as yellow solid. MS (ESI) 230 (M+H).

Step B. Intermediate 75B. Preparation of 5-cyclopropyl-1-methyl-3-(3-nitrophenyl)-1H-pyrazole

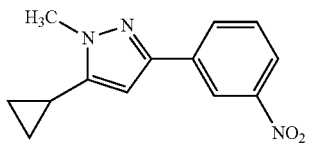 [SMILES: Cn1nc(-c2cccc([N+](=O)[O-])c2)cc1C1CC1]

To a stirred solution of Intermediate 75A (700 mg, 3.05 mmol) in DMF (7 mL) was added $Cs_2CO_3$ (2985 mg, 9.16 mmol) and methyl iodide (0.382 mL, 6.11 mmol). The reaction mixture was stirred overnight at room temperature and then diluted with ethyl acetate (20 mL). The organic solution was washed with saturated brine solution (5×20 mL), dried over $Na_2SO_4$, filtered and concentrated under reduced pressure. The crude material was purified by flash column chromatography (Combiflash, 24 g silica, 0-50% EtOAc/PE) to afford the title compound (450 mg, 1.850 mmol, 61% yield) as Brown solid, MS (ESI) 244 (M+H).

Step C. Intermediate 75C. Preparation of 3-(5-cyclopropyl-1-methyl-1H-pyrazol-3-yl) aniline

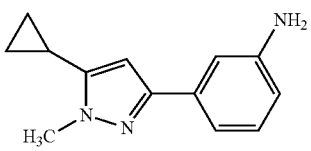

To a stirred solution of Intermediate 75B (450 mg, 1.850 mmol) in a mixture of ethanol (4 mL), THF (2 mL), and water (1 mL) was added zinc (1814 mg, 27.7 mmol) followed by ammonium chloride (1484 mg, 27.7 mmol) and stirred overnight at room temperature. The reaction mixture was concentrated under reduced pressure and the residue was diluted with ethyl acetate (10 mL). The organic solution was filtered through a celite bed and the celite bed was washed with ethyl acetate (10 mL). The filtrate was washed with saturated brine solution (10 mL), dried over sodium sulphate, filtered and concentrated under reduced pressure. The crude material was purified by flash column chromatography (Combiflash, 24 g silica, 0-60% EtOAc/PE) to afford the title compound (350 mg, 1.641 mmol, 89% yield) as a brown wax. MS (ESI) 214 (M+H).

Step D. Intermediate 75D. Preparation of N-((4-(3-cyclopropyl-1,2,4-oxadiazol-5-yl) bicyclo[2.2.2]octan-1-yl)methyl)-3-(5-cyclopropyl-1-methyl-1H-pyrazol-3-yl)aniline

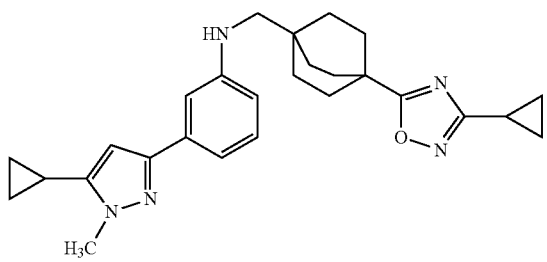 [SMILES: Cn1nc(-c2cccc(NCC34CCC(c5nc(C6CC6)no5)(CC3)CC4)c2)cc1C1CC1]

The title compound was synthesized according to the method described for the synthesis of Intermediate 1I by substituting Intermediate 75C and Intermediate 4C where appropriate: (230 mg, 0.518 mmol, 55% yield) as brown wax. MS (ESI) 444 (M+H).

Step E. Example 75. Preparation of N-((4-(3-cyclopropyl-1,2,4-oxadiazol-5-yl) bicyclo[2.2.2]octan-1-yl)methyl)-N-(3-(5-cyclopropyl-1-methyl-1H-pyrazol-3-yl) phenyl)-3-fluorobicyclo[1.1.1]pentane-1-carboxamide The title compound was synthesized according to the method described for the synthesis of Example 3 by substituting Intermediate 75D and the corresponding acid where appropriate: (17.2 mg, 0.029 mmol, 33% yield). $^1$H NMR (400 MHz, DMSO-$d_6$) δ 7.73 (d, J=7.6 Hz, 1H), 7.66 (s, 1H), 7.44 (t, J=7.8 Hz, 1H), 7.26 (d, J=7.8 Hz, 1H), 6.48 (s, 1H), 3.89 (s, 3H), 3.58 (br. s., 2H), 2.08-2.00 (m, 1H), 1.95-1.82 (m, 7H), 1.82-1.70 (m, 6H), 1.50-1.35 (m, 6H), 1.07-0.96 (m, 4H), 0.88-0.79 (m, 2H), 0.74-0.64 (m, 2H); FXR $EC_{50}$ (nM)=247; MS (ESI) 556 (M+H).

The following compounds were synthesized according to the method described for the synthesis of Example 3 by substituting Intermediate 75D and the corresponding acid where appropriate:

| Ex. No. | Structure | MS (ESI) (M + H) | FXR $EC_{50}$ (nM) |
|---|---|---|---|
| 76 | 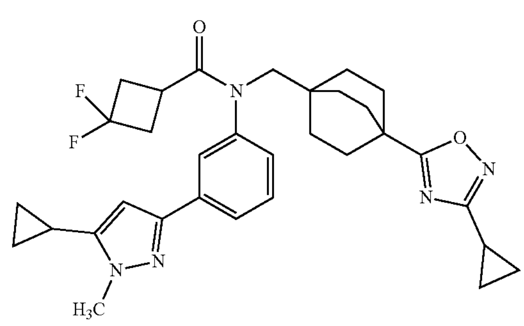 [SMILES: Cn1nc(-c2cccc(N(CC34CCC(c5nc(C6CC6)no5)(CC3)CC4)C(=O)C3CC(F)(F)C3)c2)cc1C1CC1] | 562 | 610 |

| Ex. No. | Structure | MS (ESI) (M + H) | FXR EC$_{50}$ (nM) |
|---|---|---|---|
| 77 | | 576 | 429 |
| 78 | | 576 | 607 |

76 $^1$H NMR (400 MHz, DMSO-d$_6$) δ 7.71 (d, J = 7.6 Hz, 1H), 7.67 (s, 1H), 7.44 (t, J = 7.8 Hz, 1H), 7.27 (d, J = 8.3 Hz, 1H), 6.46 (s, 1H), 3.88 (s, 3H), 3.64 (br. s., 2H), 2.93-2.83 (m, 1H), 2.81-2.68 (m, 2H), 2.38-2.28 (m, 2H), 2.10-2.00 (m, 1H), 1.97-1.88 (m, 1H), 1.84-1.65 (m, 6H), 1.51-1.32 (m, 6H), 1.07-0.92 (m, 4H), 0.89-0.78 (m, 2H), 0.76-0.67 (m, 2H)

77 $^1$H NMR (400 MHz, DMSO-d$_6$) δ 7.79-7.57 (m, 2H), 7.43 (t, J = 7.8 Hz, 1H), 7.30 (d, J = 7.3 Hz, 1H), 6.46 (s, 1H), 3.98-3.80 (m, 3H), 3.56 (s, 2H), 3.02-2.81 (m, 1H), 2.25 (d, J = 13.7 Hz, 1H), 2.16-1.97 (m, 3H), 1.97-1.70 (m, 9H), 1.66 (m, 1H), 1.41 (br. s., 6H), 0.99 (t, J = 8.3 Hz, 4H), 0.90-0.75 (m, 2H), 0.68 (d, J = 4.9 Hz, 2H)

78 $^1$H NMR (400 MHz, DMSO-d$_6$) δ 7.68 (d, J = 7.6 Hz, 1H), 7.62 (d, J = 10.8 Hz, 1H), 7.41 (td, J = 7.9, 1.8 Hz, 1H), 7.28-7.14 (m, 1H), 6.45 (d, J = 7.1 Hz, 1H), 3.93-3.84 (m, 3H), 3.61 (br. s., 2H), 3.13-3.00 (m, 1H), 2.33-2.21 (m, 1H), 2.11-1.97 (m, 3H), 1.95-1.88 (m, 1H), 1.83-1.70 (m, 7H), 1.65 (d, J = 10.0 Hz, 1H), 1.42 (d, J = 4.9 Hz, 6H), 1.07-0.93 (m, 4H), 0.88-0.78 (m, 2H), 0.73-0.63 (m, 2H) (Note: 1H is buried under DMSO peak)

Example 79

N-((4-(3-cyclopropyl-1,2,4-oxadiazol-5-yl)bicyclo[2.2.2]octan-1-yl)methyl)-3-fluoro-N-(3-(4-(2-methoxypropan-2-yl)oxazol-2-yl)phenyl)bicyclo[1.1.1]pentane-1-carboxamide (79)

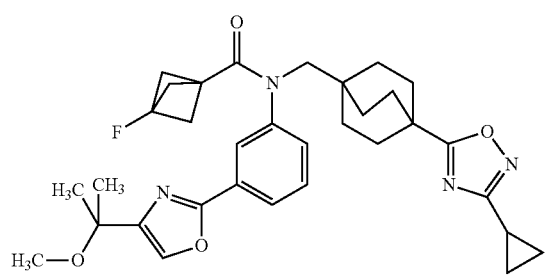

To a stirred solution of Example 15 (15 mg, 0.027 mmol) in DMF (1 mL) at 0° C. were added NaH (2.140 mg, 0.054 mmol) and MeI (3.35 μL, 0.054 mmol). The reaction mixture was stirred at room temperature for 2 h and concentrated under reduced pressure. The crude material was purified via preparative LC/MS using following conditions: Column: Waters XBridge C18, 150 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 15% B, 15-60% B over 25 minutes, then a 5-minute hold at 100% B; Flow Rate: 15 mL/min; Column Temperature: 25 C. Fraction collection was triggered by signals. Fractions containing the desired product were combined and dried via centrifugal evaporation to yield the title compound (9.1 mg, 0.016 mmol, 59% yield). $^1$H NMR (400 MHz, DMSO-d$_6$) δ 8.18 (s, 1H), 7.99 (d, J=7.6 Hz, 1H), 7.88 (s, 1H), 7.68-7.53 (m, 2H), 3.66 (br. s., 1H), 3.57 (br. s., 1H), 3.06 (s, 3H), 2.09-2.00 (m, 1H), 1.89 (br. s., 6H), 1.83-1.65 (m, 6H), 1.50 (s, 6H), 1.44 (d, J=7.8 Hz, 6H), 1.07-0.95 (m, 2H), 0.87-0.76 (m, 2H); FXR EC$_{50}$ (nM) 194; MS (ESI) 575 (M+H).

Example 80

N-((4-(3-cyclopropyl-1,2,4-oxadiazol-5-yl)bicyclo[2.2.2]octan-1-yl)methyl)-N-(3-(3-ethyl-2-oxo-2,3-dihydrooxazol-5-yl)phenyl)-3-fluorobicyclo[1.1.1]pentane-1-carboxamide (80)

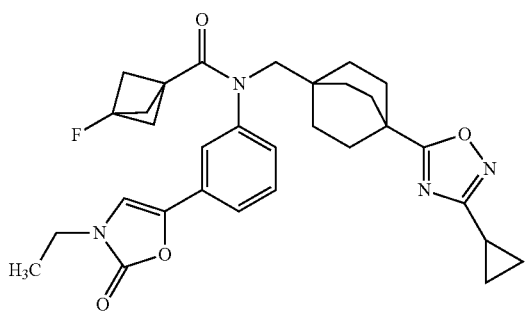

Step A. Intermediate 80A. Preparation of 3-ethyl-5-(3-nitrophenyl)oxazol-2(3H)-one

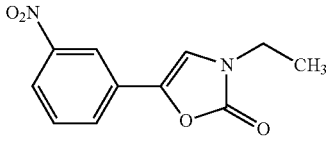 [SMILES: CCn1cc(-c2cccc([N+](=O)[O-])c2)oc1=O]

To a stirred solution of Intermediate 7A (500 mg, 2.425 mmol) in DMF (5 mL) was added iodoethane (0.388 mL, 4.85 mmol) followed by potassium carbonate (670 mg, 4.85 mmol). The reaction mixture was heated to 80° C. and stirred overnight. The reaction mixture was concentrated, diluted with water and extracted with ethyl acetate (2×20 mL). The combined organic layers were dried over sodium sulfate, filtered and concentrated under reduced pressure. The crude material was purified by flash column chromatography (Combiflash, 24 g silica, 0-30% EtOAc/PE) to afford the title compound (440 mg, 1.879 mmol, 77% yield) as yellow solid. $^1$H NMR (400 MHz, DMSO-$d_6$) δ 8.26 (t, J=1.8 Hz, 1H), 8.11 (dt, J=8.2, 1.2 Hz, 1H), 8.01 (s, 1H), 7.96-7.86 (m, 1H), 7.77-7.66 (m, 1H), 3.63 (q, J=7.5 Hz, 2H), 1.28 (t, J=4.00 Hz, 3H). MS (ESI) 235 (M+H).

Step B. Intermediate 80B. Preparation of 5-(3-aminophenyl)-3-ethyloxazol-2(3H)-one

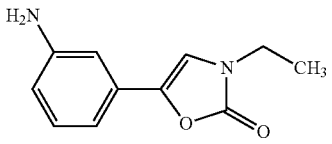

To a stirred solution of Intermediate 80A (440 mg, 1.879 mmol) in ethanol (5 mL) was added zinc (1842 mg, 28.2 mmol) and ammonium chloride (1507 mg, 28.2 mmol) in water (5 mL). The reaction mixture was stirred overnight at room temperature. The reaction mixture was diluted with DCM (30 mL), filtered through celite and concentrated under reduced pressure to afford the title compound (300 mg, 1.469 mmol, 78% yield)) as yellow solid. $^1$H NMR (400 MHz, DMSO-$d_6$) δ 7.49 (s, 1H), 7.04 (t, J=7.8 Hz, 1H), 6.71-6.62 (m, 2H), 6.48 (ddd, J=8.0, 2.0, 1.0 Hz, 1H), 5.23 (br. s., 2H), 3.58 (q, J=7.0 Hz, 2H), 1.24 (t, J=7.3 Hz, 3H). MS (ESI) 205 (M+H).

Step C. Intermediate 80C. Preparation of 5-(3-(((4-(3-cyclopropyl-1,2,4-oxadiazol-5-yl)bicyclo[2.2.2]octan-1-yl)methyl)amino)phenyl)-3-ethyloxazol-2(3H)-one

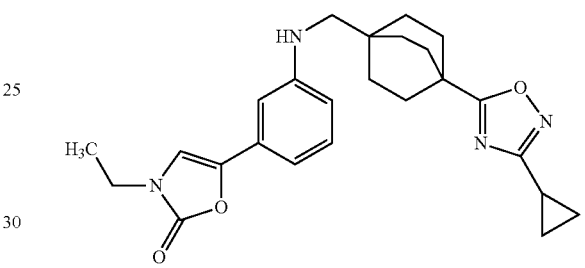

The title compound was synthesized according to the method described for the synthesis of Intermediate 1I by substituting Intermediate 80B and Intermediate 4C where appropriate: (160 mg, 0.368 mmol, 61% yield) as yellow solid. $^1$H NMR (400 MHz, DMSO-$d_6$) δ 7.54 (s, 1H), 7.07 (t, J=7.8 Hz, 1H), 6.71 (s, 1H), 6.64 (d, J=7.5 Hz, 1H), 6.58-6.54 (m, 1H), 5.63 (t, J=6.0 Hz, 1H), 3.58 (q, J=7.0 Hz, 2H), 2.84 (d, J=6.0 Hz, 2H), 2.11-2.03 (m, 1H), 1.94-1.79 (m, 6H), 1.60-1.53 (m, 6H), 1.25 (t, J=7.3 Hz, 3H), 1.06-1.00 (m, 2H), 0.89-0.84 (m, 2H). MS (ESI) 435 (M+H).

Step D. Example 80. Preparation of N-((4-(3-cyclopropyl-1,2,4-oxadiazol-5-yl) bicyclo[2.2.2]octan-1-yl)methyl)-N-(3-(3-ethyl-2-oxo-2,3-dihydrooxazol-5-yl)phenyl)-3-fluorobicyclo[1.1.1]pentane-1-carboxamide The title compound was synthesized according to the method described for the synthesis of Example 3 by substituting Intermediate 80C and the corresponding acid where appropriate: (18.7 mg, 0.034 mmol, 50% yield). $^1$H NMR (400 MHz, DMSO-$d_6$) δ 7.83 (s, 1H), 7.50 (d, J=4.2 Hz, 3H), 7.37-7.27 (m, 1H), 3.62 (q, J=7.4 Hz, 2H), 3.57 (s, 2H), 2.09-2.01 (m, 1H), 1.88 (s, 6H), 1.82-1.67 (m, 6H), 1.51-1.35 (m, 6H), 1.32-1.22 (m, 3H), 1.08-0.97 (m, 2H), 0.88-0.81 (m, 2H). FXR $EC_{50}$ (nM)=265; MS (ESI) 547 (M+H).

The following compound was synthesized according to the method described for the synthesis of Example 3 by substituting Intermediate 80C and the corresponding acid where appropriate:

| Ex. No. | Structure | MS (ESI) (M + H) | FXR EC$_{50}$ (nM) |
|---|---|---|---|
| 81 | | 553 | 945 |

81 $^1$H NMR (400 MHz, DMSO-d$_6$) δ 7.78 (s, 1H), 7.60-7.40 (m, 3H), 7.31 (d, J = 7.1 Hz, 1H), 3.62 (q, J = 7.2 Hz, 4H), 2.95-2.84 (m, 1H), 2.84-2.69 (m, 2H), 2.34 (br. s., 2H), 2.10-1.99 (m, 1H), 1.89-1.67 (m, 6H), 1.53-1.33 (m, 6H), 1.32-1.23 (m, 3H), 1.08-0.96 (m, 2H), 0.90-0.76 (m, 2H)

Example 82

N-((4-(4-cyclopropyloxazol-2-yl)bicyclo[2.2.2]octan-1-yl)methyl)-N-(3-(2-cyclopropyloxazol-5-yl)phenyl)-3-fluorobicyclo[1.1.1]pentane-1-carboxamide

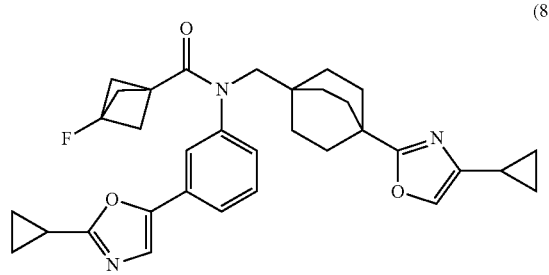

(82)

Step A. Intermediate 82A. Preparation of methyl 4-(4-cyclopropyloxazol-2-yl)bicyclo[2.2.2]octane-1-carboxylate

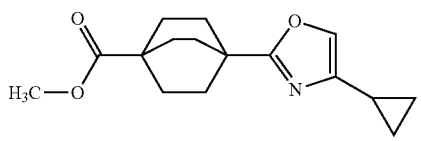 [SMILES: COC(=O)C12CCC(c3nc(C4CC4)co3)(CC1)CC2]

To a solution of Intermediate 206A (78 mg, 0.368 mmol) in toluene (2 mL) was added 2-bromo-1-cyclopropylethan-1-one (50 mg, 0.307 mmol) and the reaction mixture was heated at 100° C. and stirred overnight. The reaction mixture was cooled to room temperature and concentrated under reduced pressure. The crude material was purified by flash column chromatography (Combiflash, 24 g silica, 0-30% EtOAc/PE) to afford the title compound (25 mg, 0.091 mmol, 30% yield). $^1$H NMR (400 MHz, DMSO-d$_6$) δ 7.68 (s, 1H), 3.58 (s, 3H), 1.91-1.71 (m, 12H), 1.30-1.21 (m, 1H), 0.80-0.62 (m, 4H).

Step B. Intermediate 82B. Preparation of (4-(4-cyclopropyloxazol-2-yl) bicyclo[2.2.2]octan-1-yl)methanol

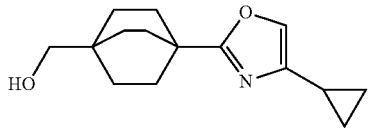 [SMILES: OCC12CCC(c3nc(C4CC4)co3)(CC1)CC2]

The title compound was synthesized according to the method described for the synthesis of Intermediate 1G by substituting Intermediate 139A where appropriate: (40 mg, 0.162 mmol, 56% yield). MS (ESI) 248 (M+H).

Step C Intermediate 82C. Preparation of 4-(4-cyclopropyloxazol-2-yl)bicyclo[2.2.2]octane-1-carbaldehyde

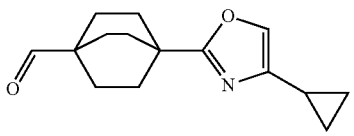

The title compound was synthesized according to the method described for the synthesis of Intermediate 3C by substituting Intermediate 82B where appropriate: (35 mg, 71% yield). MS (ESI) 246 (M+H).

Step D. Intermediate 82D. Preparation of N-((4-(4-cyclopropyloxazol-2-yl)bicyclo [2.2.2]octan-1-yl) methyl)-3-(2-cyclopropyloxazol-5-yl)aniline

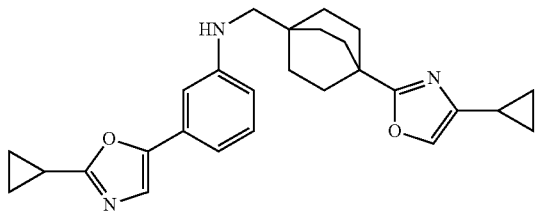 [SMILES: c1cc(NCC23CCC(c4nc(C5CC5)co4)(CC2)CC3)cc(-c2cnc(C3CC3)o2)c1]

The title compound was synthesized according to the method described for the synthesis of Intermediate 1I by substituting Intermediate 20B and Intermediate 82C where appropriate: (20 mg, 0.047 mmol, 57% yield). $^1$H NMR (400 MHz, DMSO-d$_6$) δ 7.67 (s, 1H), 7.33 (s, 1H), 7.1-7.08 (m, 1H), 6.89-6.73 (m, 2H), 6.65 (s, 1H), 5.75 (s, 1H), 2.81-2.75 (m, 2H), 2.15-2.06 (m, 1H), 1.84-1.52 (m, 12H), 1.11-0.71 (m, 8H). MS (ESI) 430 (M+H).

Step E. Example 82. Preparation of N-((4-(4-cyclopropyloxazol-2-yl) bicyclo[2.2.2]octan-1-yl) methyl)-N-(3-(2-cyclopropyloxazol-5-yl)phenyl)-3-fluorobicyclo[1.1.1]pentane-1-carboxamide The title compound was synthesized according to the method described for the synthesis of Example 3 by substituting Intermediate 82D and the corresponding acid where appropriate: (3.8 mg, 7.02 μmol, 30% yield). $^1$H NMR (400 MHz, DMSO-d$_6$) δ 7.78-7.59 (m, 4H), 7.52 (t, J=7.6 Hz, 1H), 7.35 (d, J=8.3 Hz, 1H), 3.62 (br. s., 1H), 3.52 (br. s., 1H), 2.19 (ddd, J=13.0, 8.1, 5.1 Hz, 1H), 1.88 (br. s., 6H), 1.78-1.57 (m, 7H), 1.41 (br. s., 6H), 1.14-1.00 (m, 4H), 0.84-0.71 (m, 2H), 0.64-0.50 (m, 2H). FXR EC$_{50}$ (nM) 48; MS (ESI) 542 (M+H).

Example 83

N-((4-(4-cyclopropyloxazol-2-yl)bicyclo[2.2.2]octan-1-yl)methyl)-N-(3-(2-cyclopropyloxazol-5-yl)phenyl)-3,3-difluorocyclobutane-1-carboxamide (83)

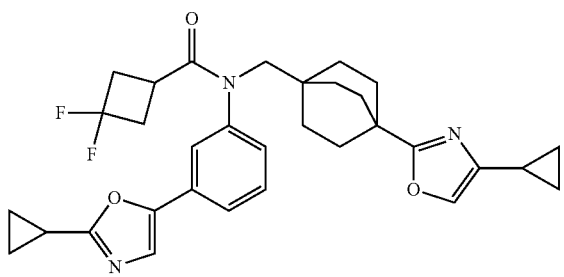

The title compound was synthesized according to the method described for the synthesis of Example 3 by substituting Intermediate 82D and the corresponding acid where appropriate: (7 mg, 0.013 mmol, 54% yield). $^1$H NMR (400 MHz, DMSO-d$_6$) 7.75-7.55 (m, 4H), 7.50 (t, J=7.8 Hz, 1H), 7.33 (d, J=7.8 Hz, 1H), 3.62 (br. s., 2H), 2.89 (dd, J=8.2, 5.5 Hz, 1H), 2.82-2.66 (m, 2H), 2.33 (br. s., 2H), 2.22-2.09 (m, 1H), 1.85-1.55 (m, 7H), 1.50-1.23 (m, 6H), 1.15-0.93 (m, 4H), 0.84-0.69 (m, 2H), 0.66-0.46 (m, 2H). FXR EC$_{50}$ (nM) 590; MS (ESI) 548 (M+H).

Example 84

N-((4-(3-cyclopropyl-1,2,4-oxadiazol-5-yl)bicyclo [2.2.2]octan-1-yl)methyl)-3,3-difluoro-N-(3-(4-(methoxymethyl)oxazol-2-yl)phenyl)cyclobutane-1-carboxamide (84)

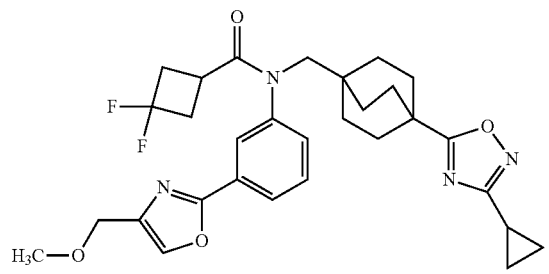

Step A. Intermediate 84A. Preparation of (2-(3-nitrophenyl)oxazol-4-yl)methanol

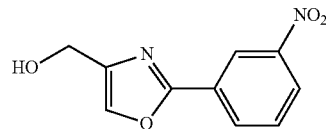 [SMILES: O=[N+]([O-])c1cccc(-c2nc(CO)co2)c1]

To a stirred solution of Intermediate 12B (1 g, 3.81 mmol) in THF (30 mL) at −78° C., DIBAL-H (7.63 mL, 7.63 mmol) was added, and then the reaction mixture was stirred for 1 h at −78° C. The reaction mixture was poured into a biphasic mixture of aqueous ammonium chloride solution (10 mL) and EtOAc (50 mL) and the layers were separated. The aqueous layer was further extracted with EtOAc (2×50 mL). The combined organic layers were dried over MgSO$_4$, filtered and concentrated under reduced pressure. The crude material was purified by flash column chromatography (Combiflash, 24 g silica, 0-30% EtOAc/PE) to yield the title compound (400 mg, 1.798 mmol, 47% yield). MS (ESI) 221 (M+H).

Step B. Intermediate 84B. Preparation of 4-(methoxymethyl)-2-(3-nitrophenyl)oxazole

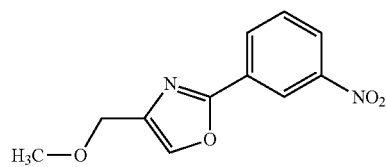 [SMILES: COCc1coc(-c2cccc([N+](=O)[O-])c2)n1]

To a stirred solution of Intermediate 84A (370 mg, 1.680 mmol) in DMF (6 mL) at 0° C., NaH (134 mg, 3.36 mmol) and MeI (0.210 mL, 3.36 mmol) were added. After stirring for 1 h, the reaction mixture was poured into cold water and the aqueous layer was extracted with EtOAc (2×50 mL). The combined organic layers were dried over MgSO$_4$, filtered and concentrated under reduced pressure. The crude material was purified by flash column chromatography (Combi-flash, 24 g silica, 0-30% EtOAc/PE) to afford the title compound (350 mg, 1.464 mmol, 87% yield). MS (ESI) 235 (M+H).

Step C. Intermediate 84C. Preparation of 3-(4-(methoxymethyl)oxazol-2-yl)aniline

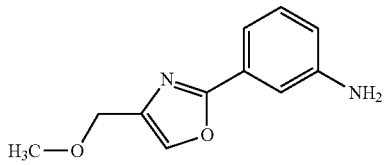

To a stirred solution of Intermediate 84B (360 mg, 1.537 mmol) in EtOH (10 mL) at 0° C. were added tin(II) chloride dihydrate (1214 mg, 5.38 mmol) and conc. HCl (1.401 mL, 46.1 mmol). The reaction mixture was stirred at 90° C. for 2 h and concentrated under reduced pressure. The residue was basified with saturated aqueous NaHCO$_3$ solution and extracted with EtOAc (2×100 mL). The combined organic layers were dried over Na$_2$SO$_4$, filtered and concentrated under reduced pressure to afford the title compound (310 mg, 1.427 mmol, 93% yield). MS (ESI) 205 (M+H).

Step D. Intermediate 84D. Preparation of N-((4-(3-cyclopropyl-1,2,4-oxadiazol-5-yl) bicyclo[2.2.2]octan-1-yl)methyl)-3-(4-(methoxymethyl)oxazol-2-yl)aniline

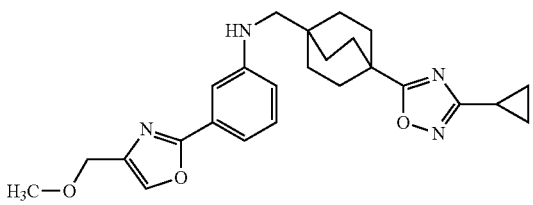 [SMILES: COCc1coc(-c2cccc(NCC34CCC(c5nc(C6CC6)no5)(CC3)CC4)c2)n1]

The title compound was synthesized according to the method described for the synthesis of Intermediate 1I by substituting Intermediate 84C and Intermediate 4C where appropriate: (260 mg, 0.592 mmol, 61% yield). MS (ESI) 435 (M+H).

Step E. Example 84. Preparation of N-((4-(3-cyclopropyl-1,2,4-oxadiazol-5-yl)bicyclo [2.2.2]octan-1-yl)methyl)-3,3-difluoro-N-(3-(4-(methoxymethyl) oxazol-2-yl)phenyl) cyclobutane-1-carboxamide The title compound was synthesized according to the method described for the synthesis of Example 3 by substituting Intermediate 84D and the corresponding acid where appropriate: (15 mg, 0.027 mmol, 47% yield). $^1$H NMR (400 MHz, DMSO-d$_6$) δ 8.22 (s, 1H), 8.02-7.87 (m, 2H), 7.69-7.52 (m, 2H), 4.39 (s, 2H), 3.66 (br. s., 2H), 3.33 (s, 3H), 2.89 (d, J=6.4 Hz, 1H), 2.86-2.71 (m, 2H), 2.38-2.29 (m, 2H), 2.08-2.00 (m, 1H), 1.86-1.70 (m, 6H), 1.51-1.33 (m, 6H), 1.07-0.95 (m, 2H), 0.88-0.76 (m, 2H); FXR EC$_{50}$ (nM) 948; MS (ESI) 553 (M+H).

The following compound was synthesized according to the method described for the synthesis of Example 3 by substituting Intermediate 84D and the corresponding acids where appropriate:

| Ex. No. | Structure | MS (ESI) (M + H) | FXR EC$_{50}$ (nM) |
|---|---|---|---|
| 85 | ![structure] | 547 | 137 |

85 $^1$H NMR (400 MHz, DMSO-d$_6$) δ 8.22 (s, 1H), 7.97 (d, J = 7.6 Hz, 1H), 7.89(s, 1H), 7.62 (t, J = 7.8 Hz, 1H), 7.57 (d, J = 7.8 Hz, 1H), 4.38 (s, 2H), 3.60 (br. s., 2H), 3.33 (s, 3H), 2.07-2.00 (m, 1H), 1.88 (br. s., 6H), 1.80-1.72 (m, 6H), 1.48-1.36 (m, 6H), 1.05-0.98 (m, 2H), 0.86-0.79 (m, 2H)

Example 86

N-((4-(3-cyclopropyl-1,2,4-oxadiazol-5-yl)bicyclo[2.2.2]octan-1-yl)methyl)-N-(3-(5-cyclopropyl-1,3,4-oxadiazol-2-yl)phenyl)-3-fluorobicyclo[1.1.1]pentane-1-carboxamide

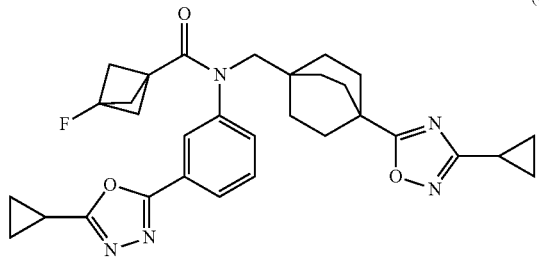

(86)

Step A. Intermediate 86A. Preparation of 3-nitrobenzohydrazide

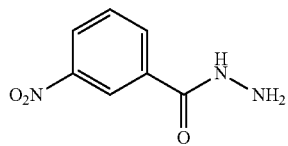 [SMILES: NNC(=O)c1cccc([N+](=O)[O-])c1]

To a stirred solution of methyl 3-nitrobenzoate (5 g, 27.6 mmol) in ethanol (75 mL) was added hydrazine hydrate (6.77 mL, 138 mmol) and refluxed for 6 h. The solids were filtered and washed with ethanol (5 mL) and dried in vacuum to afford the title compound (4.2 g, 23.19 mmol, 84% yield) as an off-white solid. $^1$H NMR (400 MHz, DMSO-$d_6$) δ 10.17 (br. s., 1H), 8.65 (t, J=2.0 Hz, 1H), 8.37 (ddd, J=8.3, 2.3, 1.0 Hz, 1H), 8.31-8.23 (m, 1H), 7.78 (t, J=8.0 Hz, 1H), 4.63 (s, 2H).

Step B. Intermediate 86B. Preparation of N'-(cyclopropanecarbonyl)-3-nitrobenzohydrazide

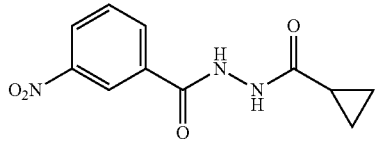 [SMILES: O=C(NNC(=O)C1CC1)c1cccc([N+](=O)[O-])c1]

To a stirred solution of Intermediate 86A (3 g, 16.56 mmol) in DCM (45 mL) at 0° C. was added pyridine (2.68 mL, 33.1 mmol) followed by cyclopropanecarbonyl chloride (2.077 g, 19.87 mmol) and stirred at 0° C. for 1 h. The reaction mixture was diluted with DCM (25 mL) and washed with water (2×25 mL), 1.5 N aqueous HCl solution (2×25 mL) and brine solution (2×25 mL). The organic layer was dried over sodium sulfate, filtered and concentrated under reduced pressure. The crude material was purified by flash column chromatography (Combiflash, 24 g silica, 0-30% EtOAc/PE) to afford the title compound (3.8 g, 14.33 mmol, 87% yield) as a white solid. $^1$H NMR (400 MHz, DMSO-$d_6$) δ 10.76 (d, J=1.5 Hz, 1H), 10.29 (d, J=1.5 Hz, 1H), 8.72-8.67 (m, 1H), 8.49-8.40 (m, 1H), 8.34-8.27 (m, 1H), 7.83 (t, J=8.0 Hz, 1H), 1.77-1.66 (m, 1H), 0.86-0.70 (m, 4H). MS (ESI) 250 (M+H).

Step C. Intermediate 86C. Preparation of 2-cyclopropyl-5-(3-nitrophenyl)-1,3,4-oxadiazole

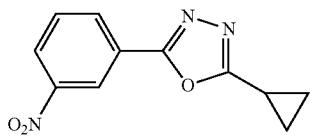

To a stirred solution of Intermediate 86B (3.3 g, 13.24 mmol) in acetonitrile (70 mL) was added CCl$_4$ (1.533 mL, 15.89 mmol) followed by triphenylphosphine (7.29 g, 27.8 mmol) and refluxed for 2 days. The reaction mixture was diluted with ethyl acetate (50 mL) and washed with water (2×50 mL) followed by brine solution (30 mL). The organic layer was dried over sodium sulfate, filtered and concentrated under reduced pressure. The crude material was purified by flash column chromatography (Combiflash, 24 g silica, 0-30% EtOAc/PE) to afford the title compound (1.5 g, 6.49 mmol, 49% yield) as white solid. MS (ESI) 232 (M+H).

Step D. Intermediate 86D. Preparation of 3-(5-cyclopropyl-1,3,4-oxadiazol-2-yl) aniline

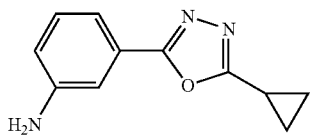 [SMILES: O=[N+]([O-])c1cccc(-c2nnc(C3CC3)o2)c1]

To a stirred solution of Intermediate 86C (1.5 g, 6.49 mmol) in ethanol (15 mL) was added zinc (6.36 g, 97 mmol) followed by a solution of ammonium chloride (5.21 g, 97 mmol) in water (15 mL) and stirred overnight. The reaction mixture was diluted with DCM (50 mL) and filtered through celite. The filtrate was washed with brine solution (50 mL), dried over sodium sulfate, filtered and concentrated under reduced pressure. The crude material was purified by flash column chromatography (Combiflash, 24 g silica, 0-30% EtOAc/PE) to afford the title compound (650 mg, 3.00 mmol, 46% yield) as yellow solid. $^1$H NMR (400 MHz, DMSO-$d_6$) δ 7.15-7.21 (m, 2H), 7.04-7.08 (m, 1H), 6.72-6.76 (m, 1H), 5.47 (s, 2H), 2.24-2.25 (m, 1H), 1.10-1.20 (m, 4H). MS (ESI) 202 (M+H).

235

Step E. Intermediate 86E. Preparation of N-((4-(3-cyclopropyl-1,2,4-oxadiazol-5-yl) bicyclo[2.2.2]octan-1-yl)methyl)-3-(5-cyclopropyl-1,3,4-oxadiazol-2-yl)aniline

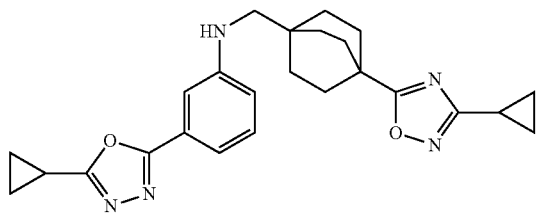 [SMILES: c1cc(NCC23CCC(c4nc(C5CC5)no4)(CC2)CC3)cc(-c2nnc(C3CC3)o2)c1]

The title compound was synthesized according to the method described for the synthesis of Intermediate 1I by substituting Intermediate 86D and Intermediate 4C where appropriate: (350 mg, 0.706 mmol, 58% yield) as a white solid. $^1$H NMR (400 MHz, DMSO-$d_6$) δ 7.26-7.19 (m, 2H), 7.07-7.04 (m, 1H), 6.82 (dd, J=8.0, 2.0 Hz, 1H), 5.88 (t, J=6.0 Hz, 1H), 2.87 (d, J=5.5 Hz, 2H), 2.32-2.25 (m, 1H), 2.11-2.03 (m, 1H), 1.92-1.80 (m, 6H), 1.63-1.54 (m, 6H), 1.47-1.40 (m, 1H), 1.21-1.14 (m, 2H), 1.12-1.07 (m, 2H), 1.06-1.01 (m, 2H), 0.89-0.84 (m, 2H). MS (ESI) 432 (M+H).

Step F. Example 86. Preparation of N-((4-(3-cyclopropyl-1,2,4-oxadiazol-5-yl) bicyclo[2.2.2]octan-1-yl)methyl)-N-(3-(5-cyclopropyl-1,3,4-oxadiazol-2-yl)phenyl)-3-fluorobicyclo[1.1.1]pentane-1-carboxamide The title compound was synthesized according to the method described for the synthesis of Example 3 by substituting Intermediate 86E and 3-fluorobicyclo[1.1.1]pentane-1-carboxylic acid where appropriate: (20 mg, 0.037 mmol, 53% yield). $^1$H NMR (400 MHz, DMSO-$d_6$) δ 8.00-7.94 (m, 1H), 7.92 (s, 1H), 7.75-7.60 (m, 2H), 3.61 (br. s., 2H), 2.37-2.27 (m, 1H), 2.08-2.01 (m, 1H), 1.89 (br. s., 6H), 1.83-1.68 (m, 6H), 1.53-1.33 (m, 6H), 1.29-1.11 (m, 4H), 1.07-0.96 (m, 2H), 0.88-0.75 (m, 2H). FXR EC$_{50}$ (nM)=123; MS (ESI) 544 (M+H).

The following compound was synthesized according to the method described for the synthesis of Example 3 by substituting Intermediate 86E and the corresponding acids where appropriate:

236

Example 88

N-((4-(3-(tert-butyl)-1,2,4-oxadiazol-5-yl)bicyclo[2.2.2]octan-1-yl)methyl)-N-(3-(3-cyclopropyl-1,2,4-oxadiazol-5-yl)phenyl)-3-fluorobicyclo[1.1.1]pentane-1-carboxamide (88)

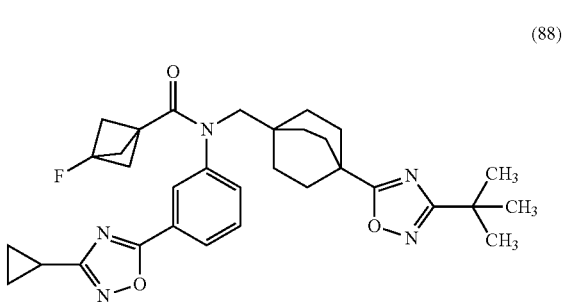 [SMILES: CC(C)(C)c1noc(C23CCC(CN(C(=O)C45CC(F)(C4)C5)c4cccc(-c5nc(C6CC6)no5)c4)(CC2)CC3)n1]

Step A. Intermediate 88A. Preparation of methyl 4-(hydroxymethyl)bicyclo[2.2.2]octane-1-carboxylate

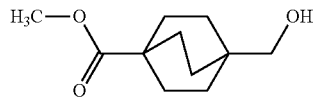

To a stirred solution of 4-(methoxycarbonyl)bicyclo[2.2.2]octane-1-carboxylic acid (10 g, 47.1 mmol) in THF (100 mL) at 0° C. was added BH$_3$.DMS (14.28 mL, 141 mmol). The reaction mixture was allowed to slowly warm up to room temperature and stirring continued for 2 h at room temperature. The reaction mixture was quenched by slow addition of methanol at 0° C. and allowed to stir overnight at room temperature. The reaction mixture was concentrated, and the residue was diluted with water. The aqueous solution was extracted with ethyl acetate (2×50 mL). The combined organic layers were dried over sodium sulfate, filtered, and concentrated under reduced pressure. The crude material was purified by flash column chromatography (Combiflash, 40 g silica, 0-40% EtOAc/PE) to

| Ex. No. | Structure | MS (ESI) (M + H) | FXR EC$_{50}$ (nM) |
|---|---|---|---|
| 87 | ![structure] | 550 | 712 |

87 $^1$HNMR (400 MHz, DMSO-$d_6$) δ 8.03-7.83 (m, 2H), 7.65 (d, J = 4.9 Hz, 2H), 3.66 (br. s., 2H), 2.94-2.84 (m, 1H), 2.84-2.71 (m, 2H), 2.39-2.29 (m, 3H), 2.10-2.00 (m, 1H), 1 87-1.65 (m, 6H), 1.52-1.31 (m, 6H), 1.25-1.11 (m, 4H), 1.07-0.92 (m, 2H), 0.89-0.76 (m, 2H).

afford the title compound (7 g, 35.3 mmol, 75% yield). $^1$H NMR (400 MHz, DMSO-$d_6$): δ 4.12 (dd, J=2.8, 4.0 Hz, 1H), 3.65 (s, 3H), 3.29 (s, 2H), 1.82-1.77 (m, 6H), 1.47-1.42 (m, 6H)

Step B. Intermediate 88B. Preparation of methyl 4-formylbicyclo[2.2.2]octane-1-carboxylate

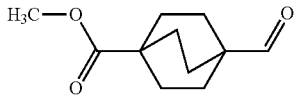

The title compound was synthesized according to the method described for the synthesis of Intermediate 3C by substituting Intermediate 88A where appropriate: (900 mg, 4.59 mmol, 91% yield) as a gummy solid. $^1$H NMR (400 MHz, DMSO-$d_6$) δ 9.43 (s, 1H), 3.59 (s, 3H), 1.78-1.57 (m, 12H). MS (ESI) 197 (M+H).

Step C. Intermediate 88C. Preparation of methyl 4-(((3-(3-cyclopropyl-1,2,4-oxadiazol-5-yl)phenyl) amino)methyl)bicyclo[2.2.2]octane-1-carboxylate

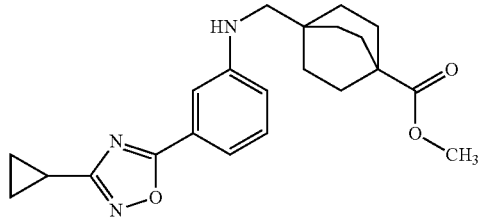 [SMILES: COC(=O)C12CCC(CNc3cccc(-c4nc(C5CC5)no4)c3)(CC1)CC2]

The title compound was synthesized according to the method described for the synthesis of Intermediate 1I by substituting Intermediate 8A and Intermediate 88B where appropriate: (550 mg, 1.298 mmol, 67% yield) as a gummy liquid. MS (ESI) 382 (M+H).

Step D. Intermediate 88D. Preparation of methyl 4-((N-(3-(3-cyclopropyl-1,2,4-oxadiazol-5-yl)phenyl)-3-fluorobicyclo[1.1.1]pentane-1-carboxamido) methyl) bicyclo[2.2.2]octane-1-carboxylate

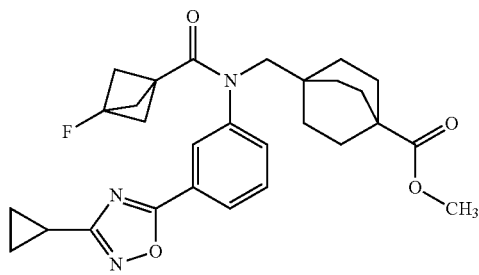 [SMILES: COC(=O)C12CCC(CN(C(=O)C34CC(F)(C3)C4)c3cccc(-c4nc(C5CC5)no4)c3)(CC1)CC2]

The title compound was synthesized according to the method described for the synthesis of Example 3 by substituting Intermediate 88C and 3-fluorobicyclo[1.1.1]pentane-1-carboxylic acid where appropriate: (480 mg, 0.632 mmol, 44% yield) as a gummy liquid. MS (ESI) 494 (M+H).

Step E. Intermediate 88E. Preparation of 4-((N-(3-(3-cyclopropyl-1,2,4-oxadiazol-5-yl) phenyl)-3-fluorobicyclo[1.1.1]pentane-1-carboxamido)methyl) bicyclo[2.2.2]octane-1-carboxylic acid

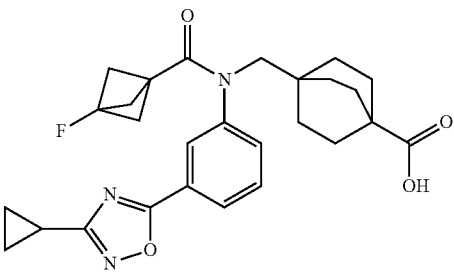 [SMILES: O=C(O)C12CCC(CN(C(=O)C34CC(F)(C3)C4)c3cccc(-c4nc(C5CC5)no4)c3)(CC1)CC2]

To a stirred solution of Intermediate 88D (480 mg, 0.972 mmol) in MeOH (5 mL) at room temperature was added a solution of NaOH (194 mg, 4.86 mmol) in H$_2$O (2 mL) and stirred overnight. The reaction mixture was concentrated and the residue was diluted with water. The aqueous solution was acidified with 1.5N aqueous HCl and extracted with ethyl acetate (2×20 mL). The combined organic layers were dried over sodium sulfate, filtered and concentrated under reduced pressure to afford the title compound (400 mg, 0.751 mmol, 77% yield) as white fluffy solid. MS (ESI) 480 (M+H).

Step F. Intermediate 88F. Preparation of N'-hydroxypivalimidamide

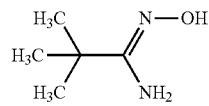

To a stirred solution of pivalonitrile (20 g, 241 mmol) in ethanol (200 mL) was added 50% aqueous hydroxylamine (73.7 mL, 1203 mmol) and refluxed for 1 h. The reaction mixture was concentrated under reduced pressure and the residue was diluted with water. The mixture was stirred for 15 min and the solids were filtered off. The product was dried under high vacuum to afford (E)-N'-hydroxypivalimidamide (22 g, 189 mmol, 79% yield) as white solid. MS (ESI) 117 (M+H).

Step G. Example 88. Preparation of N-((4-(3-(tert-butyl)-1,2,4-oxadiazol-5-yl) bicyclo[2.2.2]octan-1-yl)methyl)-N-(3-(3-cyclopropyl-1,2,4-oxadiazol-5-yl)phenyl)-3-fluorobicyclo[1.1.1]pentane-1-carboxamide The title compound was synthesized according to the method described for the synthesis of Intermediate 3A by substituting Intermediate 88E and Intermediate 88F where appropriate: (13 mg, 0.023 mmol, 37% yield). $^1$H NMR (400 MHz, DMSO-$d_6$) δ 8.11-8.04 (m, 1H), 8.04-7.97 (m, 1H), 7.79-7.62 (m, 2H), 3.63 (br. s., 2H), 2.28-2.16 (m, 1H), 1.89 (br. s., 6H), 1.84-1.69 (m, 6H), 1.53-1.35 (m, 6H), 1.33-1.20 (m, 9H), 1.14 (dd, J=8.2, 2.6 Hz, 2H), 1.04-0.93 (m, 2H). FXR EC$_{50}$ (nM)=86; MS (ESI) 560 (M+H).

The following compounds were synthesized according to the method described for the synthesis of Intermediate 3A by substituting Intermediate 88E and the corresponding amidoximes where appropriate:

| Ex. No. | Structure | MS (ESI) (M + H) | FXR EC$_{50}$ (nM) |
|---|---|---|---|
| 89 | 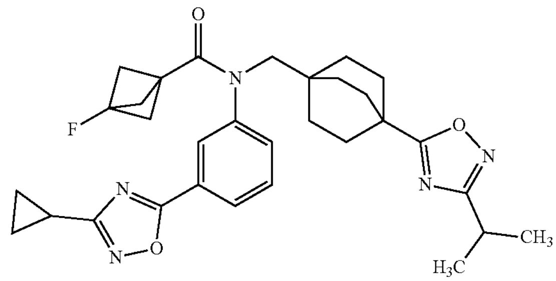 [SMILES: CC(C)c1noc(C23CCC(CN(C(=O)C45CC(F)(C4)C5)c4cccc(-c5nc(C6CC6)no5)c4)(CC2)CC3)n1] | 546 | 47 |
| 90 | 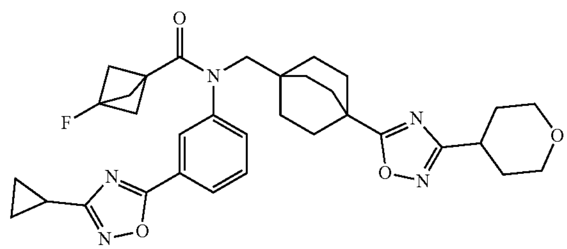 [SMILES: O=C(N(CC12CCC(c3nc(C4CCOCC4)no3)(CC1)CC2)c1cccc(-c2nc(C3CC3)no2)c1)C12CC(F)(C1)C2] | 588 | 121 |

89 $^1$H NMR (400 MHz, DMSO-d$_6$) δ 8.12-8.04 (m, 1H), 8.04-7.95 (m, 1H), 7.80-7.73 (m, 1H), 7.73-7.64 (m, 1H), 3.62 (br. s., 2H), 2.99 (quin, J = 7.0 Hz, 1H), 2.28-2.18 (m, 1H), 1.89 (br. s., 6H), 1.84-1.67 (m, 6H), 1.53-1.34 (m, 6H), 1.28-1.19 (m, 6H), 1.14 (dd, J = 8.2, 2.6 Hz, 2H), 1.06-0.93 (m, 2H)

90 $^1$H NMR (400 MHz, DMSO-d$_6$) δ 8.07 (d, J = 7.3 Hz, 1H), 8.01 (s, 1H), 7.76 (d, J = 8.6 Hz, 1H), 7.70 (t, J = 7.8 Hz, 1H), 3.93-3.80 (m, 2H), 3.63 (br. s., 1H), 3.48-3.38 (m, 2H), 3.18 (d, J = 5.1 Hz, 1H), 3.01 (tt, J = 11.2, 3.8 Hz, 1H), 2.27-2.17 (m, 1H), 1.99-1.72 (m, 14H), 1.71-1.57 (m, 2H), 1.54-1.34 (m, 6H), 1.14 (dd, J = 8.2, 2.3 Hz, 2H), 1.06-0.96 (m, 2H)

Example 91

N-((4-(3-cyclopropyl-1,2,4-oxadiazol-5-yl)bicyclo[2.2.2]octan-1-yl)methyl)-N-(3-(3-cyclopropyl-1,2,4-oxadiazol-5-yl)phenyl)pyrrolidine-1-carboxamide (91)

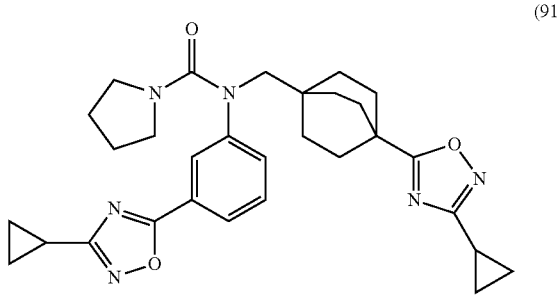

To a stirred solution of Intermediate 8B (30 mg, 0.070 mmol) in DCM (1 mL) at 0° C. was added triphosgene (22.69 mg, 0.076 mmol) and the reaction mixture was stirred overnight at room temperature. To the stirred reaction mixture was added a solution of pyrrolidone (4.97 mg, 0.070 mmol) in DCM (1 mL) followed by TEA (0.058 mL, 0.417 mmol). The reaction mixture was stirred at room temperature for 1 h. The reaction mixture was concentrated and the crude material was purified via preparative LC/MS using following conditions: Column: Waters XBridge C18, 150 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 30% B, 30-67% B over 20 minutes, then a 5-minute hold at 100% B; Flow Rate: 15 mL/min; Column Temperature: 25 C. Fraction collection was triggered by MS signals. Fractions containing the desired product were combined and dried via centrifugal evaporation to afford the title compound (18.8 mg, 0.034 mmol, 49% yield). $^1$H NMR (400 MHz, DMSO-d$_6$) δ 7.72 (d, J=7.6 Hz, 1H), 7.61 (s, 1H), 7.54 (t, J=7.9 Hz, 1H), 7.31 (dd, J=8.2, 1.6 Hz, 1H), 3.49 (s, 2H), 3.08 (s, 4H), 2.26-2.13 (m, 1H), 2.12-2.00 (m, 1H), 1.97-1.74 (m, 6H), 1.74-1.59 (m, 4H), 1.59-1.39 (m, 6H), 1.17-1.06 (m, 2H), 1.06-0.92 (m, 4H), 0.89-0.81 (m, 2H); FXR EC$_{50}$ (nM)=322; MS (ESI) 529 (M+H).

The following compounds were synthesized according to the method described for the synthesis of Example 91 by substituting Intermediate 8B and the corresponding amines where appropriate:

| Ex. No. | Structure | MS (ESI) (M + H) | FXR EC$_{50}$ (nM) |
|---|---|---|---|
| 92 | 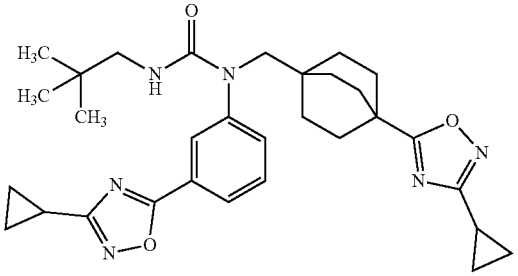 [SMILES: CC(C)(C)CNC(=O)N(CC12CCC(c3nc(C4CC4)no3)(CC1)CC2)c1cccc(-c2nc(C3CC3)no2)c1] | 545 | 420 |
| 93 | 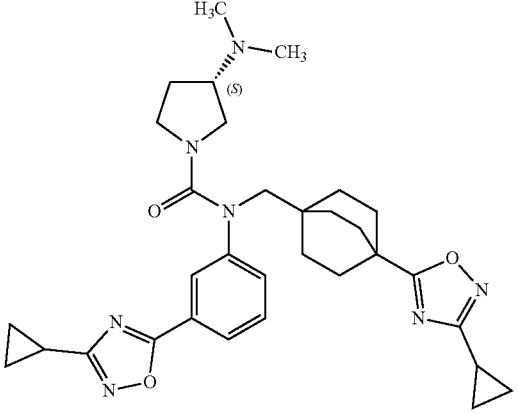 | 572 | 2692 |
| 94 | 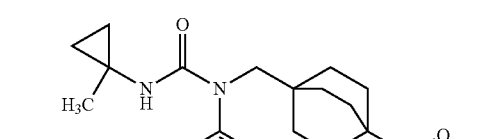 | 529 | 265 |
92 $^1$H NMR (400 MHz, DMSO-d$_6$) δ 7.96 (s, 1H), 7.89 (dt, J = 7.0, 1.5 Hz, 1H), 7.69-7.59 (m, 2H), 5.72 (t, J = 6.3 Hz, 1H), 3.60 (s, 2H), 2.83 (d, J = 6.0 Hz, 2H), 2.24-2.15 (m, 1H), 2.09-1.98 (m, 1H), 1.80-1.69 (m, 6H), 1.44-1.33 (m, 6H), 1.16-1.08 (m, 2H), 1.04-0.95 (m, 4H), 0.85-0.74 (m, 11H).
93 $^1$H NMR (400 MHz, DMSO-d$_6$) δ 7.73 (d, J = 7.5 Hz, 1H), 7.61 (s, 1H), 7.55 (t, J = 7.8 Hz, 1H), 7.33 (d, J = 8.0 Hz, 1H), 3.62 (d, J = 14.6 Hz, 1H), 3.28-3.19 (m, 1H), 3.06-2.96 (m, 1H), 2.84 (br. s., 1H), 2.20 (ddd, J = 13.1, 8.0, 5.0 Hz, 1H), 2.11-1.99 (m, 6H), 1.85 (t, J = 7.8 Hz, 6H), 1.52 (d, J = 6.5 Hz, 6H), 1.17-1.08 (m, 2H), 1.06-0.96 (m, 4H), 0.89-0.81 (m, 2H) (6 Protons are buried under solvent peaks).
94 $^1$H NMR (400 MHz, DMSO-d$_6$) δ 7.87-7.80 (m, 2H), 7.59-7.51 (m, 2H), 6.28 (s, 1H), 3.54 (s, 2H), 2.23-2.15 (m, 1H), 2.01 (td, J = 8.7, 4.3 Hz, 1H), 1.78-1.68 (m, 6H), 1.40-1.32 (m, 6H), 1.23 (s, 3H), 1.14-1.07 (m, 2H), 1.02-0.95 (m, 4H), 0.84-0.78 (m, 2H), 0.59-0.52 (m, 2H), 0.47-0.41 (m, 2H).

Example 95

1-((4-(3-cyclopropyl-1,2,4-oxadiazol-5-yl)bicyclo[2.2.2]octan-1-yl)methyl)-1-(3-(3-cyclopropyl-1,2,4-oxadiazol-5-yl)phenyl)-3-ethylurea (165)

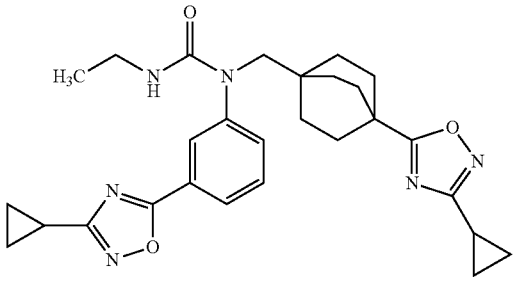

To a stirred solution of Intermediate 8B (20 mg, 0.046 mmol) in DCM (1 mL) was added ethyl isocyanate (3.67 µL, 0.046 mmol) and stirred at room temperature for 2 h. The reaction mixture was concentrated under reduced pressure and the crude material was purified via preparative LC/MS using following conditions: Column: Waters XBridge C18, 150 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 30% B, 30-60% B over 20 minutes, then a 5-minute hold at 100% B; Flow Rate: 15 mL/min; Column Temperature: 25 C. Fraction collection was triggered by MS signals. Fractions containing the desired product were combined and dried via centrifugal evaporation to afford the title compound (3.6 mg, 6.68 µmol, 14% yield). $^1$H NMR (400 MHz, DMSO-$d_6$) δ 7.95-7.83 (m, 2H), 7.71-7.56 (m, 2H), 6.00-5.92 (m, 1H), 3.59 (s, 2H), 3.02 (dt, J=13.1, 6.5 Hz, 2H), 2.24-2.18 (m, 1H), 2.09-2.01 (m, 1H), 1.84-1.64 (m, 6H), 1.47-1.30 (m, 6H), 1.13 (dd, J=8.1, 2.2 Hz, 2H), 1.06-0.90 (m, 7H), 0.88-0.77 (m, 2H); FXR EC$_{50}$ (nM)=590; MS (ESI) 503 (M+H).

Example 96

1-((4-(3-cyclopropyl-1,2,4-oxadiazol-5-yl)bicyclo[2.2.2]octan-1-yl)methyl)-1-(3-(3-cyclopropyl-1,2,4-oxadiazol-5-yl)phenyl)-3-(4-methoxyphenyl)urea (96)

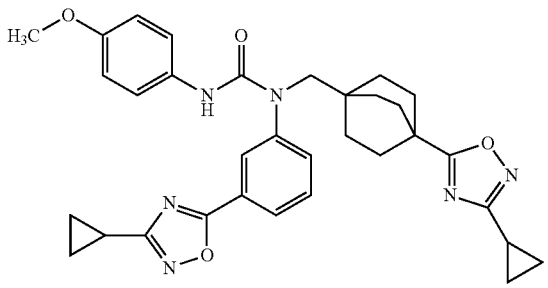

The title compound was synthesized according to the method described for the synthesis of Example 95 by substituting Intermediate 8B and the corresponding isocyanate where appropriate: (7.4 mg, 0.0127 mmol, 18% yield). $^1$H NMR (400 MHz, DMSO-$d_6$) δ 8.00 (s, 1H), 7.95-7.86 (m, 2H), 7.74-7.67 (m, 1H), 7.67-7.59 (m, 1H), 7.32-7.22 (m, 2H), 6.86-6.73 (m, 2H), 3.70 (s, 3H), 3.68 (s, 2H), 2.24-2.18 (m, 1H), 2.09-2.01 (m, 1H), 1.83-1.69 (m, 6H), 1.51-1.37 (m, 6H), 1.18-1.10 (m, 2H), 1.07-0.95 (m, 4H), 0.86-0.80 (m, 2H). FXR EC$_{50}$ (nM)=647; MS (ESI) 581 (M+H).

Example 97

N-(3-(2-cyclopropyloxazol-5-yl)phenyl)-N-((4-(4-cyclopropylthiazol-2-yl)bicyclo[2.2.2]octan-1-yl)methyl)-3-fluorobicyclo[1.1.1]pentane-1-carboxamide (97)

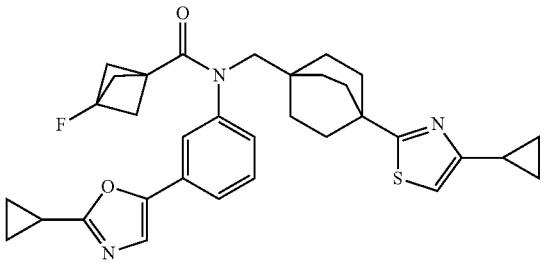

Step A. Intermediate 97A. Preparation of methyl 4-carbamothioylbicyclo[2.2.2]octane-1-carboxylate

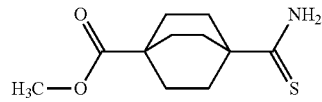

To a solution of Intermediate 213A (850 mg, 4.02 mmol) in THF (10 mL), Lawesson's reagent (976 mg, 2.414 mmol) was added and the reaction mixture was stirred at room temperature for 1 h. The reaction mixture was evaporated to dryness and the residue was diluted with EtOAc (50 mL). The organic layer was washed with saturated aqueous NaHCO$_3$ solution followed by brine. The organic layer was dried over Na$_2$SO$_4$, filtered and concentrated under reduced pressure. The crude material was purified by flash column chromatography (Combiflash, 24 g silica, 0-30% EtOAc/PE) to afford the title compound (0.65 g, 2.86 mmol, 71% yield). MS (ESI) 228 (M+H).

Step B. Intermediate 97B. Preparation of methyl 4-(4-cyclopropylthiazol-2-yl)bicyclo[2.2.2]octane-1-carboxylate

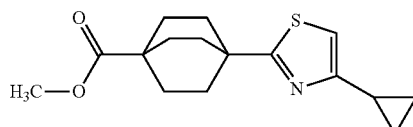

Intermediate 97A (150 mg, 0.660 mmol) was transferred to a reaction vial and toluene (3 mL) was added. To this solution, 2-bromo-1-cyclopropylethan-1-one (161 mg, 0.990 mmol) was added and the reaction mixture was heated to 100° C. and stirred at the same temperature overnight. The reaction mixture was concentrated under reduced pressure and the crude material was purified by flash column chromatography (Combiflash, 24 g silica, 0-20% EtOAc/PE) to afford the title compound (120 mg, 0.412 mmol, 62% yield). $^1$H NMR (400 MHz, DMSO-$d_6$) δ 7.05 (s, 1H), 3.58 (s, 3H), 2.76-2.71 (m, 1H), 1.87-1.79 (m, 12H), 0.87-0.67 (m, 4H). MS (ESI) 292 (M+H).

Step C. Intermediate 97C. Preparation of (4-(4-cyclopropylthiazol-2-yl) bicyclo[2.2.2]octan-1-yl)methanol

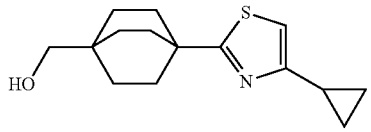 [SMILES: OCC12CCC(c3nc(C4CC4)cs3)(CC1)CC2]

The title compound was synthesized according to the method described for the synthesis of Intermediate 1G by substituting Intermediate 97B where appropriate: (95 mg, 0.321 mmol, 62% yield). $^1$H NMR (400 MHz, DMSO-$d_6$) δ 7.02 (s, 1H), 4.38 (s, 1H), 3.07 (s, 2H), 1.99-1.97 (m, 1H), 1.82-1.77 (m, 6H), 1.46-1.41 (m, 6H), 0.87-0.67 (m, 4H). MS (ESI) 264 (M+H).

Step D. Intermediate 97D. Preparation of 4-(4-cyclopropylthiazol-2-yl)bicycle[2.2.2]octane-1-carbaldehyde

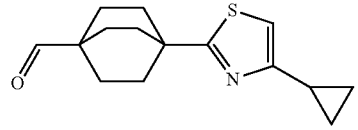 [SMILES: O=CC12CCC(c3nc(C4CC4)cs3)(CC1)CC2]

The title compound was synthesized according to the method described for the synthesis of Intermediate 3C by substituting Intermediate 97C where appropriate: (50 mg, 0.191 mmol, 72% yield). MS (ESI) 262 (M+H)

Step E. Intermediate 97E. Preparation of 3-(2-cyclopropyloxazol-5-yl)-N-((4-(4-cyclopropyl thiazol-2-yl)bicyclo[2.2.2]octan-1-yl)methyl)aniline

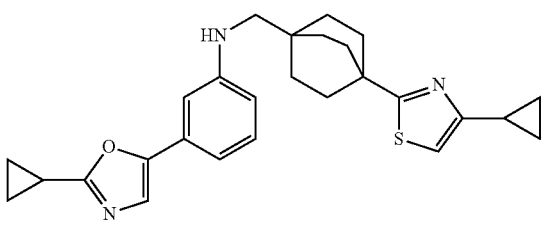

The title compound was synthesized according to the method described for the synthesis of Intermediate 1I by substituting Intermediate 20B and Intermediate 97D where appropriate: (25 mg, 0.046 mmol, 60% yield) was obtained from the reaction mixture. MS (ESI) 446 (M+H).

Step F. Example 97. Preparation of N-(3-(2-cyclopropyloxazol-5-yl)phenyl)-N-((4-(4-cyclopropylthiazol-2-yl)bicyclo[2.2.2]octan-1-yl)methyl)-3-fluorobicyclo[1.1.1]pentane-1-carboxamide The title compound was synthesized according to the method described for the synthesis of Example 3 by substituting Intermediate 97E and the corresponding acid where appropriate: (4 mg, 7.17 μmol, 32% yield). $^1$H NMR (400 MHz, DMSO-$d_6$) δ 7.77-7.59 (m, 3H), 7.52 (t, J=7.8 Hz, 1H), 7.36 (d, J=7.8 Hz, 1H), 7.02 (s, 1H), 3.65 (d, J=12.2 Hz, 1H), 3.51 (d, J=13.0 Hz, 1H), 2.25-2.11 (m, 1H), 2.03-1.95 (m, 1H), 1.87 (br. s., 6H), 1.75 (t, J=7.7 Hz, 6H), 1.57-1.28 (m, 6H), 0.90-0.79 (m, 2H), 0.78-0.65 (m, 2H). FXR EC$_{50}$ (nM) 70; MS (ESI) 558 (M+H).

The following compounds were synthesized according to the method described for the synthesis of Example 3 by substituting Intermediate 97E and the corresponding acid where appropriate:

| Ex. No. | Structure | MS (ESI) (M + H) | FXR EC$_{50}$ (nM) |
| --- | --- | --- | --- |
| 98 | 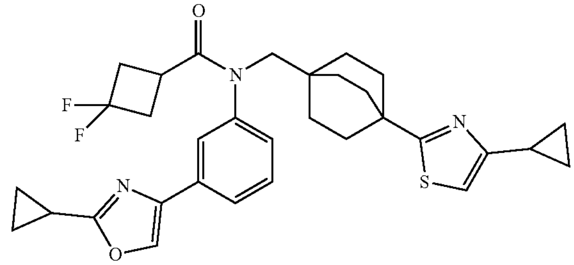 [SMILES: O=C(C1CC(F)(F)C1)N(CC12CCC(c3nc(C4CC4)cs3)(CC1)CC2)c1cccc(-c2coc(C3CC3)n2)c1] | 513 | 564 |

| Ex. No. | Structure | MS (ESI) (M + H) | FXR EC$_{50}$ (nM) |
|---|---|---|---|
| 99 | | 560 | 578 |

98  $^1$H NMR (400 MHz, DMSO-d$_6$) δ 7.69 (s, 1H), 7.65-7.57 (m, 2H), 7.52 (t, J = 7.8 Hz, 1H), 7.36 (d, J = 8.3 Hz, 1H), 7.02 (s, 1H), 3.64 (br. s., 2H), 2.89 (br. s., 1H), 2.76 (d, J = 18.1 Hz, 2H), 2.23-2.13 (m, 1H), 2.03-1.93 (m, 1H), 1.81-1.64 (m, 6H), 1.44 (d, J = 8.3 Hz, 6H), 0.84 (dd, J = 8.2, 2.3 Hz, 2H)

99  $^1$H NMR (400 MHz, DMSO-d$_6$) δ 7.72 (s, 1H), 7.67-7.60 (m, 2H), 7.52 (t, J = 7.8 Hz, 1H), 7.40 (d, J = 6.4 Hz, 1H), 7.02 (s, 1H), 3.64 (s, 3H), 2.99-2.91 (m, 1H), 2.30 (d, J = 5.6 Hz, 1H), 2.18 (ddd, J = 13.2, 8.3, 4.9 Hz, 2H), 2.09 (s, 2H), 2.03-1.95 (m, 2H), 1.82 (d, J = 10.0 Hz, 2H), 1.80-1.61 (m, 7H), 1.43 (br. s., 6H), 1.13-1.00 (m, 4H), 0.87-0.80 (m, 2H), 0.76-0.67 (m, 2H).

Example 100

N-(3-(3-cyclopropyl-1,2,4-oxadiazol-5-yl)phenyl)-N-((4-(4-cyclopropylthiazol-2-yl)bicyclo[2.2.2]octan-1-yl)methyl)-3-fluorobicyclo[1.1.1]pentane-1-carboxamide (100)

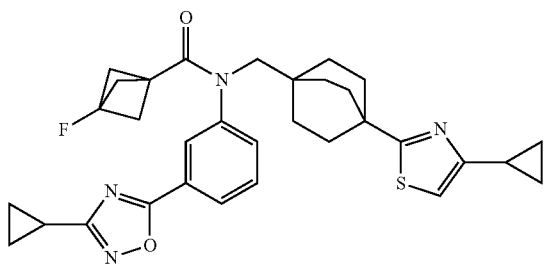

Step A. Intermediate 100A. Preparation of 3-(3-cyclopropyl-1,2,4-oxadiazol-5-yl)-N-((4-(4-cyclopropylthiazol-2-yl)bicyclo[2.2.2]octan-1-yl)methyl) aniline

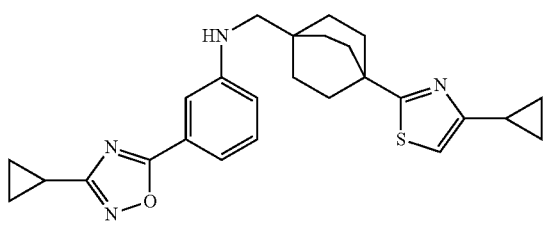 [SMILES: c1cc(NCC23CCC(c4nc(C5CC5)cs4)(CC2)CC3)cc(-c2nc(C3CC3)no2)c1]

The title compound was synthesized according to the method described for the synthesis of Intermediate 1I by substituting Intermediate 8A and Intermediate 97D where appropriate: (55 mg, 0.101 mmol, 66% yield). $^1$H NMR (400 MHz, DMSO-d$_6$) δ 7.4-7.1 (m, 3H), 7.05 (s, 1H), 6.98-6.92 (m, 1H), 2.85 (s, 2H), 2.21-1.95 (m, 2H), 1.85-1.56 (m, 12H), 1.11-0.71 (m, 8H). MS (ESI) 447 (M+H).

Step B. Example 100. Preparation of N-(3-(3-cyclopropyl-1,2,4-oxadiazol-5-yl)phenyl)-N-((4-(4-cyclopropylthiazol-2-yl)bicyclo[2.2.2]octan-1-yl)methyl)-3-fluorobicyclo[1.1.1]pentane-1-carboxamide The title compound was synthesized according to the method described for the synthesis of Example 3 by substituting Intermediate 100A and the corresponding acid where appropriate: (6.3 mg, 0.011 mmol, 25% yield). $^1$H NMR (400 MHz, DMSO-d$_6$) δ 8.06 (d, J=7.6 Hz, 1H), 8.01 (s, 1H), 7.76 (d, J=8.1 Hz, 1H), 7.70 (t, J=7.8 Hz, 1H), 7.01 (s, 1H), 3.65 (br. s., 1H), 3.56 (br. s., 1H), 2.27-2.17 (m, 1H), 2.04-1.96 (m, 1H), 1.88 (br. s., 6H), 1.82-1.58 (m, 6H), 1.54-1.30 (m, 6H), 1.14 (dd, J=8.2, 2.3 Hz, 2H), 1.01 (d, J=2.7 Hz, 2H), 0.90-0.78 (m, 2H), 0.78-0.66 (m, 2H). FXR EC$_{50}$ (nM) 164; MS (ESI) 559 (M+H).

The below compound was synthesized according to the method described for the synthesis of Example 3 by substituting Intermediate 100A and the corresponding acid where appropriate:

| Ex. No. | Structure | MS (ESI) (M + H) | FXR EC$_{50}$ (nM) |
|---|---|---|---|
| 101 | | 565 | 635 |

101 $^1$H NMR (400 MHz, DMSO-d$_6$) δ 8.10-7.99 (m, 2H), 7.75 (d, J = 8.3 Hz, 1H), 7.69 (t, J = 8.1 Hz, 1H), 7.02 (s, 1H), 3.66 (br. s., 2H), 2.94-2.84 (m, 2H), 2.83-2.70 (m, 3H), 2.34 (d, J = 2.0 Hz, 3H), 2.22 (ddd, J = 12.9, 8.3, 4.8 Hz, 1H), 2.01-1.93 (m, 1H), 1.82-1.65 (m, 6H), 1.48-1.32 (m, 6H), 1.17-1.09 (m, 2H), 1.06-0.96 (m, 2H), 0.88-0.76 (m, 2H), 0.75-0.69 (m, 2H)

Example 102

N-((4-(3-cyclopropyl-1,2,4-oxadiazol-5-yl)bicyclo[2.2.2]octan-1-yl)methyl)-3-fluoro-N-(3-(5-(3-fluorobicyclo[1.1.1]pentan-1-yl)-1,2,4-oxadiazol-3-yl)phenyl)bicyclo[1.1.1]pentane-1-carboxamide (102)

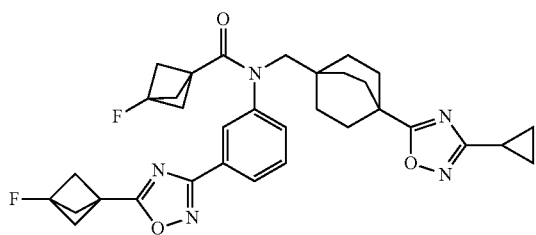

Step A. Intermediate 102A. Preparation of 3-(((4-(3-cyclopropyl-1,2,4-oxadiazol-5-yl)bicyclo[2.2.2]octan-1-yl)methyl)amino)benzonitrile

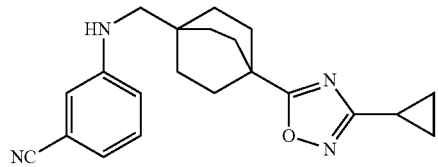 [SMILES: N#Cc1cccc(NCC23CCC(c4nc(C5CC5)no4)(CC2)CC3)c1]

The title compound was synthesized according to the method described for the synthesis of Intermediate 1I by substituting 3-aminobenzonitrile and Intermediate 4C where appropriate: (600 mg, 1.636 mmol, 67% yield) as an off-white solid. MS (ESI) 349 (M+H).

Step B. Intermediate 102B. Preparation of N-(3-cyanophenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide

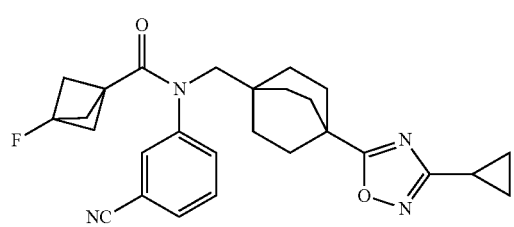

The title compound was synthesized according to the method described for the synthesis of Example 3 by substituting Intermediate 102A and the corresponding acid where appropriate: (300 mg, 0.619 mmol, 86% yield) as an off-white solid. MS (ESI) 461 (M+H).

Step C. Intermediate 102C. Preparation of (Z)—N-((4-(3-cyclopropyl-1,2,4-oxadiazol-5-yl)bicyclo[2.2.2]octan-1-yl)methyl)-3-fluoro-N-(3-(N'-hydroxycarbamimidoyl) phenyl) bicyclo[1.1.1]pentane-1-carboxamide

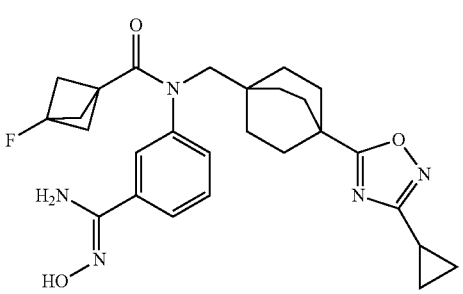 [SMILES: N/C(=N\O)c1cccc(N(CC23CCC(c4nc(C5CC5)no4)(CC2)CC3)C(=O)C23CC(F)(C2)C3)c1]

The title compound was synthesized according to the method described for the synthesis of Intermediate 88F by substituting Intermediate 102B where appropriate: (250 mg, 0.481 mmol, 85% yield) as a white solid. MS (ESI) 494 (M+H).

Step D. Example 102. Preparation of N-((4-(3-cyclopropyl-1,2,4-oxadiazol-5-yl) bicyclo[2.2.2]octan-1-yl)methyl)-3-fluoro-N-(3-(5-(3-fluorobicyclo[1.1.1]pentan-1-yl)-1,2,4-oxadiazol-3-yl)phenyl)bicyclo[1.1.1]pentane-1-carboxamide The title compound was synthesized according to the method described for the synthesis of Intermediate 3A by substituting Intermediate 102C and 3-fluorobicyclo[1.1.1]pentane-1-carboxylic acid where appropriate: (17 mg, 0.029 mmol, 57% yield). $^1$H NMR (400 MHz, DMSO-d$_6$) δ 8.09-7.99 (m, 1H), 7.91 (d, J=1.2 Hz, 1H), 7.66 (d, J=5.4 Hz, 2H), 3.63 (br. s., 1H), 3.56 (br. s., 1H), 2.70 (d, J=2.2 Hz, 6H), 2.09-1.97 (m, 1H), 1.87 (br. s., 6H), 1.81-1.65 (m, 6H), 1.52-1.33 (m, 6H), 1.08-0.95 (m, 2H), 0.84-0.80 (m, 2H). FXR EC$_{50}$ (nM) 1040; MS (ESI) 588 (M+H).

The following compounds were synthesized according to the method described for the synthesis of Intermediate 3A by substituting Intermediate 102C and the corresponding acids where appropriate:

| Ex. No. | Structure | MS (ESI) (M + H) | FXR EC$_{50}$ (nM) |
|---|---|---|---|
| 103 | 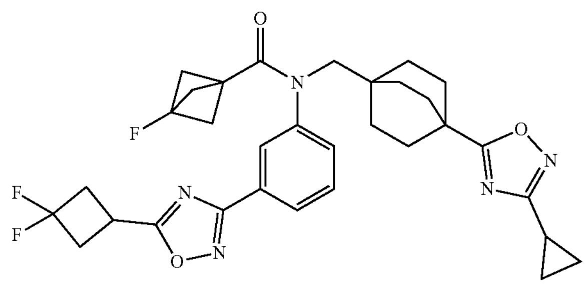 [SMILES: O=C(N(CC12CCC(c3nc(C4CC4)no3)(CC1)CC2)c1cccc(-c2noc(C3CC(F)(F)C3)n2)c1)C12CC(F)(C1)C2] | 594 | 227 |
| 104 | 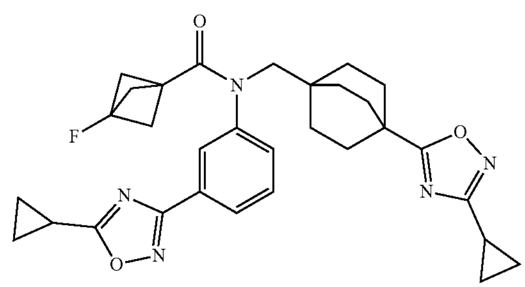 [SMILES: O=C(N(CC12CCC(c3nc(C4CC4)no3)(CC1)CC2)c1cccc(-c2noc(C3CC3)n2)c1)C12CC(F)(C1)C2] | 544 | 60 |
| 105 | 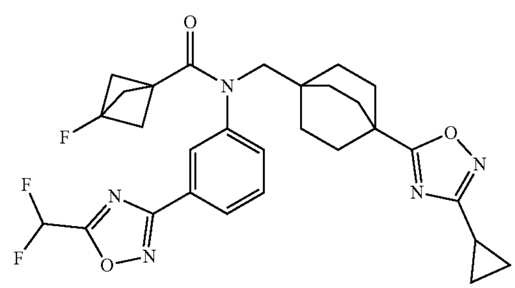 [SMILES: O=C(N(CC12CCC(c3nc(C4CC4)no3)(CC1)CC2)c1cccc(-c2noc(C(F)F)n2)c1)C12CC(F)(C1)C2] | 554 | 57 |
| 106 | 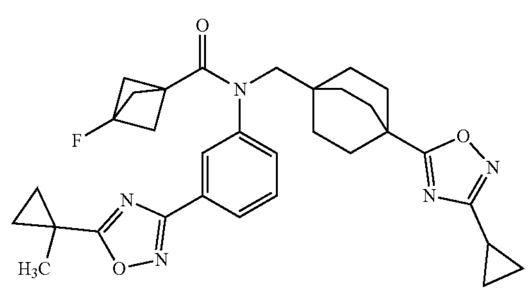 [SMILES: CC1(c2nc(-c3cccc(N(CC45CCC(c6nc(C7CC7)no6)(CC4)CC5)C(=O)C45CC(F)(C4)C5)c3)no2)CC1] | 558 | 58 |

-continued

| Ex. No. | Structure | MS (ESI) (M + H) | FXR EC$_{50}$ (nM) |
|---|---|---|---|
| 107 | 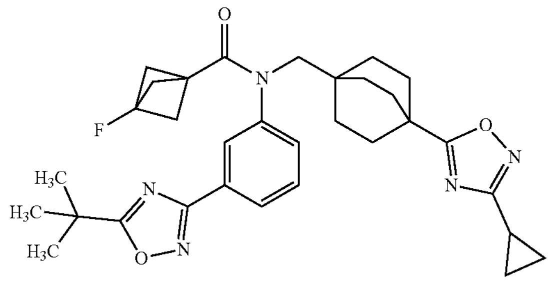 [SMILES: CC(C)(C)c1nc(-c2cccc(N(CC34CCC(c5nc(C6CC6)no5)(CC3)CC4)C(=O)C34CC(F)(C3)C4)c2)no1] | 560 | 18 |
| 108 | 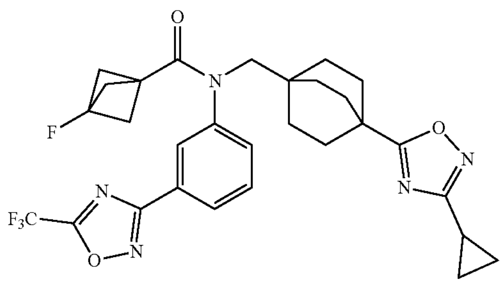 [SMILES: O=C(N(CC12CCC(c3nc(C4CC4)no3)(CC1)CC2)c1cccc(-c2noc(C(F)(F)F)n2)c1)C12CC(F)(C1)C2] | 572 | 144 |
| 109 | 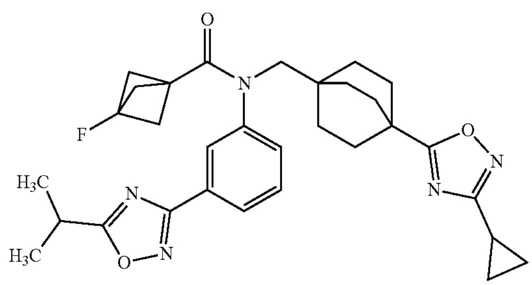 [SMILES: CC(C)c1nc(-c2cccc(N(CC34CCC(c5nc(C6CC6)no5)(CC3)CC4)C(=O)C34CC(F)(C3)C4)c2)no1] | 546 | 55 |
| 110 | 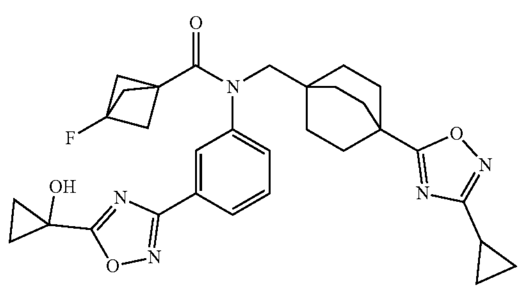 [SMILES: O=C(N(CC12CCC(c3nc(C4CC4)no3)(CC1)CC2)c1cccc(-c2noc(C3(O)CC3)n2)c1)C12CC(F)(C1)C2] | 560 | 88 |
| 111 | 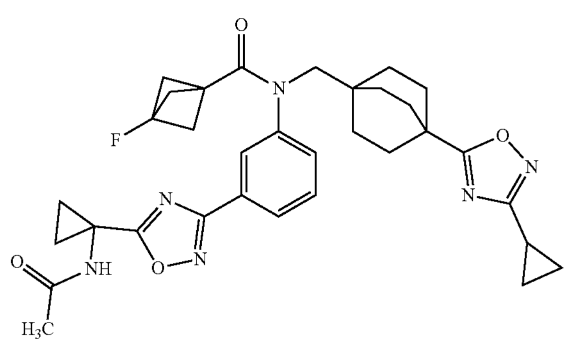 [SMILES: CC(=O)NC1(c2nc(-c3cccc(N(CC45CCC(c6nc(C7CC7)no6)(CC4)CC5)C(=O)C45CC(F)(C4)C5)c3)no2)CC1] | 601 | 120 |

| Ex. No. | Structure | MS (ESI) (M + H) | FXR EC$_{50}$ (nM) |
|---|---|---|---|
| 112 | | 568 | 68 |
| 113 | | 574 | 121 |

103 $^1$H NMR (400 MHz, DMSO-d$_6$) δ 8.16-7.99 (m, 1H), 7.94 (s, 1H), 7.75-7.58 (m, 2H), 3.96-3.85 (m, 1H), 3.61 (br. s., 2H), 3.26-3.02 (m, 4H), 2.11-1.99 (m, 1H), 1.88 (br. s., 6H), 1.82-1.61 (m, 6H), 1.54-1.33 (m, 6H), 1.08-0.96 (m, 2H), 0.91-0.75 (m, 2H).

104 $^1$H NMR (400 MHz, DMSO-d$_6$) δ 8.05-7.92 (m, 1H), 7.87 (s, 1H), 7.74-7.59 (m, 2H), 3.60 (br. s., 2H), 2.48-2.39 (m, 1H), 2.09-2.00 (m, 1H), 1.87 (br. s., 6H), 1.81-1.65 (m, 6H), 1.53-1.36 (m, 6H), 1.35-1.11 (m, 4H), 1.06-0.94 (m, 2H), 0.89-0.78 (m, 2H).

105 $^1$H NMR (400 MHz, DMSO-d$_6$) δ 8.15-8.03 (m, 1H), 7.99 (s, 1H), 7.78-7.64 (m, 2H), 7.58 (s, 1H), 3.61 (s, 2H), 2.08-2.01 (m, 1H), 1.89 (br. s., 6H), 1.82-1.66 (m, 6H), 1.54-1.34 (m, 6H), 1.07-0.97 (m, 2H), 0.88-0.77 (m, 2H).

106 $^1$H NMR (400 MHz, DMSO-d$_6$) δ 8.06-7.94 (m, 1H), 7.87 (s, 1H), 7.73-7.55 (m, 2H), 3.60 (br. s., 2H), 2.12-2.00 (m, 1H), 1.88 (br. s., 6H), 1.83-1.65 (m, 6H), 1.58 (s, 3H), 1.51-1.30 (m, 8H), 1.20-1.10 (m, 2H), 1.06-0.96 (m, 2H), 0.90-0.77 (m, 2H).

107 $^1$H NMR (400 MHz, DMSO-d$_6$) δ 8.01-7.99 (m, 1H), 7.91 (s, 1H), 7.75-7.58 (m, 2H), 3.60 (br. s., 2H), 2.09-2.01 (m, 1H), 1.89 (br. s., 6H), 1.84-1.65 (m, 6H), 1.56-1.27 (m, 15H), 1.08-0.95 (m, 2H), 0.88-0.74 (m, 2H).

108 $^1$H NMR (400 MHz, DMSO-d$_6$) δ 8.09-8.05 (m, 1H), 8.01 (s, 1H), 7.75-7.69 (m, 2H), 3.62 (s, 2H), 2.11-1.98 (m, 1H), 1.89 (br. s., 6H), 1.82-1.65 (m, 6H), 1.55-1.33 (m, 6H), 1.01-0.99 (m, 2H), 0.83-0.80 (m, 2H).

109 $^1$H NMR (400 MHz, DMSO-d$_6$) δ 8.02-7.99 (m, 1H), 7.90 (s, 1H), 7.67-7.62 (m, 2H), 3.60 (br. s., 2H), 3.46-3.35 (m, 1H), 2.11-1.99 (m, 1H), 1.88 (br. s., 6H), 1.82-1.67 (m, 6H), 1.53-1.32 (m, 12H), 1.07-0.96 (m, 2H), 0.89-0.75 (m, 2H).

110 $^1$H NMR (400 MHz, DMSO-d$_6$) δ 8.04-7.94 (m, 1H), 7.88 (d, J = 1.0 Hz, 1H), 7.75-7.59 (m, 2H), 7.06 (s, 1H), 3.62 (br. s., 1H), 3.57 (br. s., 1H), 2.11-2.00 (m, 1H), 1.87 (br. s., 6H), 1.83-1.66 (m, 6H), 1.56-1.29 (m, 10H), 1.09-0.96 (m, 2H), 0.89-0.74 (m, 2H).

111 $^1$H NMR (400 MHz, DMSO-d$_6$) δ 9.02 (s, 1H), 8.05-7.93 (m, 1H), 7.85 (s, 1H), 7.65 (d, J = 5.4 Hz, 2H), 3.62 (br. s., 1H), 3.56 (br. s., 1H), 2.08-2.01 (m, 1H), 1.94-1.83 (m, 9H), 1.83-1.72 (m, 6H), 1.68 (br. s., 2H), 1.51-1.27 (m, 8H), 1.07-0.95 (m, 2H), 0.89-0.77 (m, 2H)

112 $^1$H NMR (400 MHz, DMSO-d$_6$) δ 8.07 (br. s., 1H), 7.99 (br. s., 1H), 7.72 (br. s., 2H), 4.00-3.85 (m, 1H), 3.62 (br. s., 2H), 2.34-2.17 (m, 3H), 2.05 (d, J = 5.1 Hz, 2H), 1.89 (br. s., 6H), 1.77 (br. s., 6H), 1.59-1.34 (m, 6H), 1.02 (d, J = 2.7 Hz, 2H), 0.83 (br. s., 2H)

113 $^1$H NMR (400 MHz, DMSO-d$_6$) δ 8.11-8.00 (m, 1H), 7.95 (s, 1H), 7.75-7.62 (m, 2H), 5.01 (d, J = 6.1 Hz, 2H), 4.61 (d, J = 6.1 Hz, 2H), 3.62 (br. s., 2H), 2.12-2.00 (m, 1H), 1.98-1.82 (m, 9H), 1.82-1.63 (m, 6H), 1.55-1.32 (m, 6H), 1.08-0.92 (m, 2H), 0.90-0.72 (m, 2H)

Example 114

N-(3-(3-cyclopropyl-1,2,4-oxadiazol-5-yl)phenyl)-3-fluoro-N-((4-(5-(3-fluorobicyclo[1.1.1]pentan-1-yl)-1,2,4-oxadiazol-3-yl)bicyclo[2.2.2]octan-1-yl)methyl)bicyclo[1.1.1]pentane-1-carboxamide

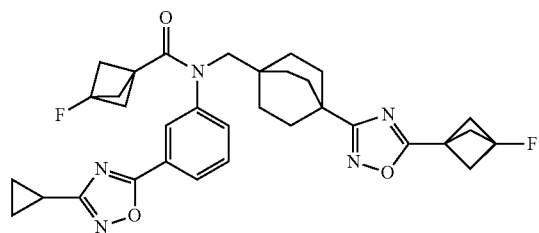

(114)

Step A. Intermediate 114A. Preparation of 4-((N-(3-(3-cyclopropyl-1,2,4-oxadiazol-5-yl)phenyl)-3-fluorobicyclo[1.1.1]pentane-1-carboxamido)methyl)bicyclo[2.2.2]octane-1-carboxamide

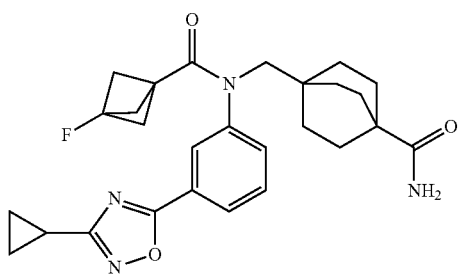 [SMILES: NC(=O)C12CCC(CN(C(=O)C34CC(F)(C3)C4)c3cccc(-c4nc(C5CC5)no4)c3)(CC1)CC2]

To a stirred solution of Intermediate 88E (200 mg, 0.417 mmol) in DMF (5 mL) at room temperature were added ammonium chloride (26.8 mg, 0.500 mmol), TEA (0.174 mL, 1.251 mmol) and BOP (203 mg, 0.459 mmol). The reaction mixture was stirred at room temperature for 1 h and then concentrated under reduced pressure. The residue was diluted with water and extracted with ethyl acetate (2×10 mL). The combined organic layers were dried over sodium sulfate, filtered and concentrated under reduced pressure to afford the title compound (200 mg, 0.418 mmol, 100% yield). MS (ESI) 479 (M+H).

Step B. Intermediate 114B. Preparation of N-((4-cyanobicyclo[2.2.2]octan-1-yl) methyl)-N-(3-(3-cyclopropyl-1,2,4-oxadiazol-5-yl)phenyl)-3-fluoro-bicyclo[1.1.1]pentane-1-carboxamide

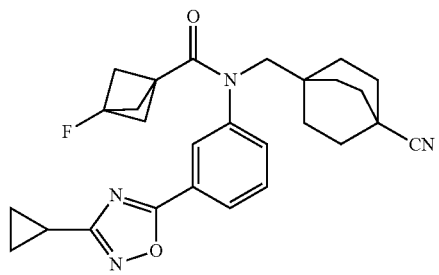 [SMILES: N#CC12CCC(CN(C(=O)C34CC(F)(C3)C4)c3cccc(-c4nc(C5CC5)no4)c3)(CC1)CC2]

To a stirred solution of Intermediate 114A (200 mg, 0.418 mmol) in pyridine (5 mL) at 0° C. was added TFAA (0.295 mL, 2.090 mmol) and stirred at room temperature for 30 min. The reaction mixture was diluted with cold water and extracted with DCM (2×10 mL). The combined organic layers were dried over sodium sulfate, filtered and concentrated under reduced pressure. The crude material was purified by flash column chromatography (Combiflash, 12 g silica, 0-40% EtOAc/PE) to afford the title compound (70 mg, 0.149 mmol, 36% yield) as pale white solid. MS (ESI) 461 (M+H).

Step C. Intermediate 114C. Preparation of (E)-N-(3-(3-cyclopropyl-1,2,4-oxadiazol-5-yl)phenyl)-3-fluoro-N-((4-(N'-hydroxycarbamimidoyl)bicyclo[2.2.2]octan-1-yl)methyl) bicyclo[1.1.1]pentane-1-carboxamide

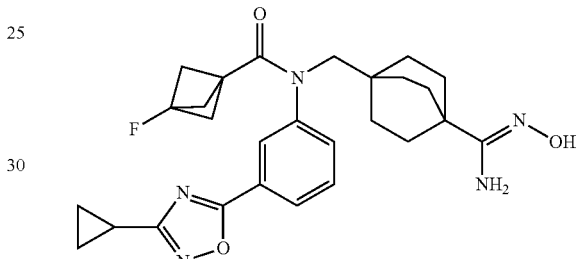

The title compound was synthesized according to the method described for the synthesis of Intermediate 88F by substituting Intermediate 114B where appropriate: (60 mg, 0.122 mmol, 80% yield) as pale gray solid. MS (ESI) 494 (M+H).

Step D. Example 114. Preparation of N-(3-(3-cyclopropyl-1,2,4-oxadiazol-5-yl) phenyl)-3-fluoro-N-((4-(5-(3-fluorobicyclo[1.1.1]pentan-1-yl)-1,2,4-oxadiazol-3-yl) bicyclo[2.2.2]octan-1-yl)methyl)bicyclo[1.1.1]pentane-1-carboxamide The title compound was synthesized according to the method described for the synthesis of Intermediate 3A by substituting Intermediate 114C and the corresponding acid where appropriate: (11.8 mg, 0.020 mmol, 33% yield). $^1$H NMR (400 MHz, DMSO-$d_6$) δ 7.75 (d, J=7.6 Hz, 1H), 7.70 (s, 1H), 7.45 (d, J=8.6 Hz, 1H), 7.39 (t, J 7.8 Hz, 1H), 3.34 (br. s., 2H), 2.27 (d, J=2.2 Hz, 6H), 1.96-1.87 (m, 1H), 1.57 (br. s., 6H), 1.48-1.32 (m, 6H), 1.19-1.02 (m, 6H), 0.83 (dd, J=8.1, 2.7 Hz, 2H), 0.75-0.67 (m, 2H); FXR EC$_{50}$ (nM)=177; MS (ESI) 588 (M+H).

The following compounds were synthesized according to the method described for the synthesis of Intermediate 3A by substituting Intermediate 114C and the corresponding acids where appropriate:

| Ex. No. | Structure | MS (ESI) (M + H) | FXR EC$_{50}$ (nM) |
|---|---|---|---|
| 115 | 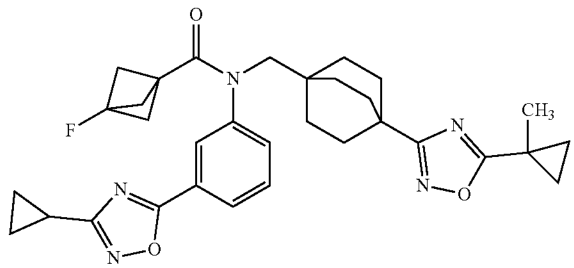 [SMILES: CC1(c2nc(C34CCC(CN(C(=O)C56CC(F)(C5)C6)c5cccc(-c6nc(C7CC7)no6)c5)(CC3)CC4)no2)CC1] | 558 | 35 |
| 116 | 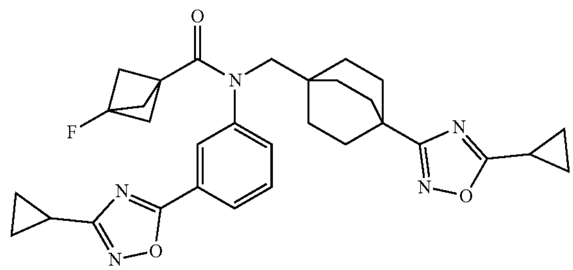 [SMILES: O=C(N(CC12CCC(c3noc(C4CC4)n3)(CC1)CC2)c1cccc(-c2nc(C3CC3)no2)c1)C12CC(F)(C1)C2] | 544 | 117 |
| 117 | 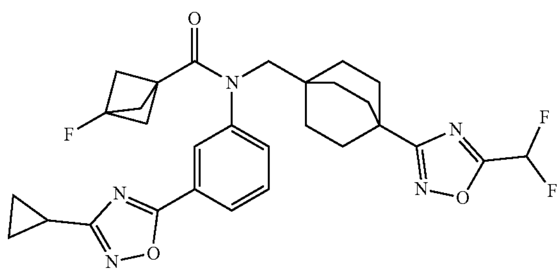 [SMILES: O=C(N(CC12CCC(c3noc(C(F)F)n3)(CC1)CC2)c1cccc(-c2nc(C3CC3)no2)c1)C12CC(F)(C1)C2] | 554 | 12 |
| 118 | 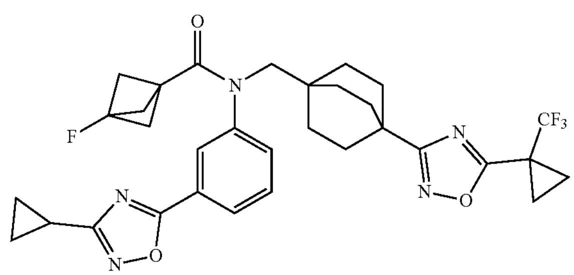 [SMILES: O=C(N(CC12CCC(c3noc(C4(C(F)(F)F)CC4)n3)(CC1)CC2)c1cccc(-c2nc(C3CC3)no2)c1)C12CC(F)(C1)C2] | 612 | 30 |
| 119 | 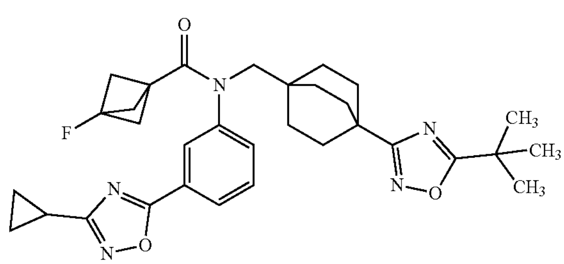 [SMILES: CC(C)(C)c1nc(C23CCC(CN(C(=O)C45CC(F)(C4)C5)c4cccc(-c5nc(C6CC6)no5)c4)(CC2)CC3)no1] | 560 | 15 |

-continued

| Ex. No. | Structure | MS (ESI) (M + H) | FXR EC₅₀ (nM) |
|---|---|---|---|
| 120 | 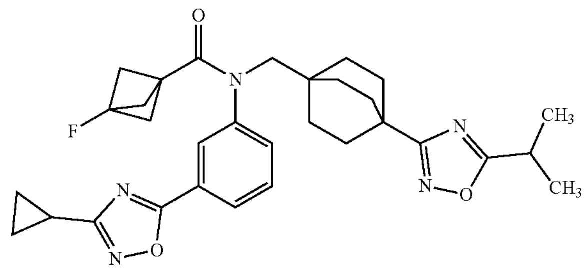 [SMILES: CC(C)c1nc(C23CCC(CN(C(=O)C45CC(F)(C4)C5)c4cccc(-c5nc(C6CC6)no5)c4)(CC2)CC3)no1] | 546 | 15 |
| 121 | 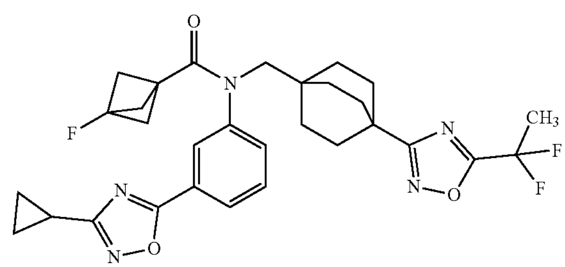 [SMILES: CC(F)(F)c1nc(C23CCC(CN(C(=O)C45CC(F)(C4)C5)c4cccc(-c5nc(C6CC6)no5)c4)(CC2)CC3)no1] | 568 | 22 |
| 122 | 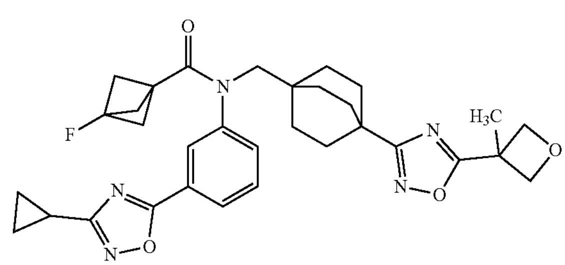 [SMILES: CC1(c2nc(C34CCC(CN(C(=O)C56CC(F)(C5)C6)c5cccc(-c6nc(C7CC7)no6)c5)(CC3)CC4)no2)COC1] | 574 | 28 |

| Ex. No. | Structure | MS (ESI) (M + H) | FXR EC₅₀ (nM) |
|---|---|---|---|
| 123 | | 580 | 73 |

115  ¹H NMR (400 MHz, DMSO-d₆) δ 8.06 (d, J = 7.6 Hz, 1H), 8.01 (s, 1H), 7.81-7.74 (m, 1H), 7.73-7.63 (m, 1H), 3.65 (br. s., 2H), 3.54 (d, J = 4.4 Hz, 2H), 2.28-2.16 (m, 1H), 1.88 (br. s., 6H), 1.79-1.60 (m, 6H), 1.49-1.28 (m, 6H), 1.26-1.19 (m, 3H), 1.14 (dd, J = 8.2, 2.6 Hz, 2H), 1.08-0.93 (m, 4H)

116  ¹H NMR (400 MHz, DMSO-d₆) δ 8.06 (d, J = 7.3 Hz, 1H), 8.01 (s, 1H), 7.75 (s, 1H), 7.72-7.64 (m, 1H), 3.64 (s, 2H), 2.24 (dd, J = 9.0, 4.9 Hz, 2H), 1.88 (br. s., 6H), 1.69 (d, J = 8.6 Hz, 6H), 1.41 (d, J = 6.4 Hz, 6H), 1.21-1.09 (m, 4H), 1.02 (d, J = 3.9 Hz, 4H)

117  ¹H NMR (400 MHz, DMSO-d₆) δ 8.07 (d, J = 7.6 Hz, 1H), 8.04-7.99 (m, 1H), 7.77 (d, J = 8.3 Hz, 1H), 7.70 (t, J = 7.8 Hz, 1H), 7.42 (s, 1H), 3.59 (br. s., 2H), 2.29-2.15 (m, 1H), 1.89 (br. s., 6H), 1.85-1.65 (m, 6H), 1.56-1.33 (m, 6H), 1.21-1.09 (m, 2H), 1.06-0.96 (m, 2H)

118  ¹H NMR (400 MHz, DMSO-d₆) δ 8.06 (d, J = 7.8 Hz, 1H), 8.01 (s, 1H), 7.76 (d, J = 7.8 Hz, 1H), 7.70 (t, J = 7.8 Hz, 1H), 3.64 (br. s., 1H), 3.58 (br. s., 1H), 2.28-2.16 (m, 1H), 1.88 (br. s., 6H), 1.82-1.56 (m, 10H), 1.52-1.30 (m, 6H), 1.14 (dd, J = 8.4, 2.8 Hz, 2H), 1.07-0.95 (m, 2H)

119  ¹H NMR (400 MHz, DMSO-d₆) δ 8.06 (d, J = 7.3 Hz, 1H), 8.01 (s, 1H), 7.76 (d, J = 8.6 Hz, 1H), 7.70 (t, J = 7.8 Hz, 1H), 3.64 (br. s., 2H), 2.30-2.16 (m, 1H), 1.88 (br. s., 6H), 1.79-1.61 (m, 6H), 1.46-1.36 (m, 6H), 1.33 (s, 9H), 1.19-1.10 (m, 2H), 1.06-0.96 (m, 2H)

120  ¹H NMR (400 MHz, DMSO-d₆) δ 8.06 (d, J = 7.8 Hz, 1H), 8.01 (t, J = 1.7 Hz, 1H), 7.81-7.72 (m, 1H), 7.72-7.65 (m, 1H), 3.65 (br. s., 2H), 3.24-3.17 (m, 1H), 2.29-2.16 (m, 1H), 1.88 (br. s., 6H), 1.78-1.57 (m, 6H), 1.53-1.33 (m, 6H), 1.32-1.20 (m, 6H), 1.14 (dd, J = 8.1, 2.7 Hz, 2H), 1.05-0.95 (m, 2H)

121  ¹H NMR (400 MHz, DMSO-d₆) δ 8.07 (d, J = 7.8 Hz, 1H), 8.04-7.98 (m, 1H), 7.82-7.73 (m, 1H), 7.73-7.65 (m, 1H), 3.65 (br. s., 1H), 3.59 (br. s., 1H), 2.27-2.20 (m, 1H), 2.14 (t, J = 19.7 Hz, 3H), 1.89 (br. s., 6H), 1.84-1.60 (m, 6H), 1.57-1.31 (m, 6H), 1.14 (dd, J = 8.2, 2.6 Hz, 2H), 1.07-0.93 (m, 2H)

122  ¹H NMR (400 MHz, DMSO-d₆) δ 8.07 (d, J = 7.8 Hz, 1H), 8.01 (t, J = 1.6 Hz, 1H), 7.79-7.74 (m, 1H), 7.74-7.62 (m, 1H), 4.84 (d, J = 6.1 Hz, 2H), 4.52 (d, J = 6.1 Hz, 2H), 3.65 (br. s., 1H), 3.54 (br. s., 1H), 2.28-2.16 (m, 1H), 1.89 (br. s., 6H), 1.82-1.60 (m, 9H), 1.55-1.33 (m, 6H), 1.20-1.07 (m, 2H), 1.06-0.92 (m, 2H)

123  ¹H NMR (400 MHz, DMSO-d₆) δ 8.15-7.93 (m, 2H), 7.84-7.56 (m, 2H), 3.76-3.48 (m, 4H), 2.26-2.13 (m, 2H), 1.88 (br. s., 6H), 1.82-1.59 (m, 6H), 1.51-1.35 (m, 6H), 1.18-1.08 (m, 2H), 1.07-0.91 (m, 2H)

Example 124

N-(3-(3-cyclopropyl-1,2,4-oxadiazol-5-yl)phenyl)-N-((4-(5-cyclopropyl-1-methyl-1H-pyrazol-3-yl)bicyclo[2.2.2]octan-1-yl)methyl)-3-fluorobicyclo[1.1.1]pentane-1-carboxamide (124)

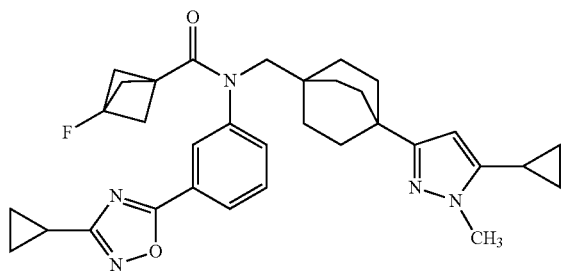

Step A. Intermediate 124A. Preparation of methyl 4-(chlorocarbonyl)bicyclo[2.2.2]octane-1-carboxylate

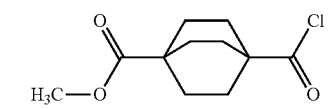

4-(methoxycarbonyl)bicyclo[2.2.2]octane-1-carboxylic acid was taken in SOCl₂ and refluxed for 2 h at 60° C. Progress of the reaction was monitored by TLC (small amount was quenched with MeOH and checked TLC) showed completion of acid. The reaction mixture was concentrated under reduced pressure. The crude was so-distilled twice with DCM to afford the title compound (1.8 g, 7.80 mmol) as an off-white solid.

Step B. Intermediate 124B. Preparation of methyl 4-(3-cyclopropyl-3-oxopropanoyl) bicyclo[2.2.2]octane-1-carboxylate

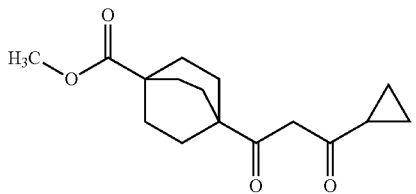 [SMILES: COC(=O)C12CCC(C(=O)CC(=O)C3CC3)(CC1)CC2]

To a stirred solution of LiHMDS (9.10 mL, 9.10 mmol) in THF at −78° C. was added 1-cyclopropylethan-1-one (0.383 g, 4.55 mmol) and the reaction mixture was stirred for 45 min. A solution of Intermediate 124A (1 g, 4.33 mmol) in tetrahydrofuran (10 mL) was added to the reaction mixture and stirred for additional 1 h at same temperature. The reaction mixture was quenched with saturated aqueous ammonium chloride solution (20 mL) and extracted with EtOAc (2×50 mL). The combined organic layers were dried over anhydrous sodium sulphate, filtered and concentrated under reduced pressure. The crude material was purified by flash column chromatography (Combiflash, 24 g silica, 0-30% EtOAc/PE) to afford the title compound (800 mg, 2.73 mmol, 63% yield) as an oil. MS (ESI) 279 (M+H).

Step C. Intermediate 124C$_1$ and 124C2. Preparation of methyl 4-(5-cyclopropyl-1-methyl-1H-pyrazol-3-yl)bicyclo[2.2.2]octane-1-carboxylate and methyl 4-(3-cyclopropyl-1-methyl-1H-pyrazol-5-yl)bicyclo[2.2.2]octane-1-carboxylate

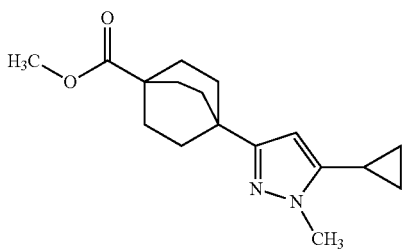

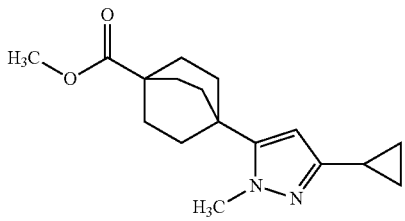

To a solution of Intermediate 124B (800 mg, 2.87 mmol) in methanol (10 mL) was added methylhydrazine sulfate (1036 mg, 7.19 mmol). The reaction mixture was stirred overnight at 80° C. The reaction mixture was concentrated under reduced pressure; the crude was poured into water and extracted with EtOAc. The organic layer was washed with brine, dried over anhydrous sodium sulfate and concentrated under reduced pressure. The crude was purified by flash chromatography (Combiflash, 24 g Silica gel column) using 0-20% EtOAc in pet-ether as eluents. The compound containing fractions were concentrated to yield mixture of compounds. The same was purified by prep-HPLC to yield the individual regio isomers. The isolated one of the isomer was confirmed by NMR (NOE) studies. The first eluting isomer (RT=4.31 min or peak-1) Intermediate 124C$_1$ (270 mg, 0.889 mmol, 31% yield). $^1$H NMR (400 MHz, DMSO-d$_6$) δ 5.65 (s, 1H), 3.71 (s, 3H), 3.57 (s, 3H), 1.69-1.81 (m, 13H), 0.88-0.91 (m, 2H), 0.52-0.57 (m, 2H) and second eluting isomer (RT=4.90 min or peak-2) Intermediate 124C2 (320 mg, 1.054 mmol, 37% yield). MS (ESI) 289 (M+H). $^1$H NMR (400 MHz, DMSO-d$_6$) δ 5.67 (s, 1H), 3.76 (s, 3H), 3.59 (s, 3H), 1.75-1.83 (m, 12H), 1.69-1.74 (m, 1H), 0.73-0.78 (m, 2H), 0.56-0.57 (m, 2H).

Step D. Intermediate 124D. Preparation of (4-(5-cyclopropyl-1-methyl-1H-pyrazol-3-yl) bicyclo[2.2.2]octan-1-yl)methanol

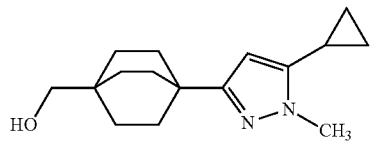

The title compound was synthesized according to the method described for the synthesis of Intermediate 1G by substituting Intermediate 124C1 where appropriate: (160 mg, 0.584 mmol, 67% yield) as an off-white solid. $^1$H NMR (400 MHz, DMSO-d$_6$) δ 5.63 (s, 1H), 4.30 (t, J=7.20 Hz, 1H), 3.33 (s, 3H), 3.04 (d, J=7.20 Hz, 2H), 1.74-1.79 (m, 1H), 1.62-1.65 (m, 6H), 1.34-1.39 (m, 6H), 0.86-0.91 (m, 2H), 0.57-0.60 (m, 2H).

Step E. Intermediate 124E. Preparation of 4-(5-cyclopropyl-1-methyl-1H-pyrazol-3-yl) bicyclo[2.2.2]octane-1-carbaldehyde

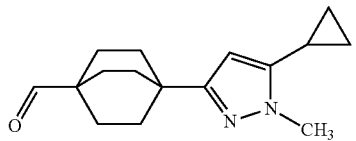 [SMILES: Cn1nc(C23CCC(C=O)(CC2)CC3)cc1C1CC1]

The title compound was synthesized according to the method described for the synthesis of Intermediate 3C by substituting Intermediate 124D where appropriate: (160 mg, 0.557 mmol, 91% yield) as an off-white solid. $^1$H NMR (400 MHz, DMSO-d$_6$) δ 9.44 (s, 1H), 5.67 (s, 1H), 3.72 (s, 3H), 1.59-1.76 (m, 13H), 0.88-0.92 (m, 2H), 0.57-0.60 (m, 2H).

Step F. Intermediate 124F. Preparation of 3-(3-cyclopropyl-1,2,4-oxadiazol-5-yl)-N-((4-(5-cyclopropyl-1-methyl-1H-pyrazol-3-yl)bicyclo[2.2.2]octan-1-yl)methyl)aniline

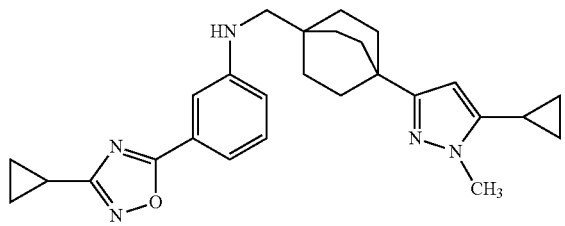 [SMILES: Cn1nc(C23CCC(CNc4cccc(-c5nc(C6CC6)no5)c4)(CC2)CC3)cc1C1CC1]

The title compound was synthesized according to the method described for the synthesis of Intermediate 1I by substituting Intermediate 8A and Intermediate 124E where appropriate: (95 mg, 0.203 mmol, 33% yield) as an off-white solid. MS (ESI) 444 (M+H).

Step G. Example 124. Preparation of N-(3-(3-cyclopropyl-1,2,4-oxadiazol-5-yl) phenyl)-N-((4-(5-cyclopropyl-1-methyl-1H-pyrazol-3-yl)bicyclo[2.2.2]octan-1-yl) methyl)-3-fluorobicyclo[1.1.1]pentane-1-carboxamide The title compound was synthesized according to the method described for the synthesis of Example 3 by substituting Intermediate 124F and the corresponding acid where appropriate: (14 mg, 0.025 mmol, 44% yield). $^1$H NMR (400 MHz, DMSO-$d_6$) δ 8.06 (d, J=7.3 Hz, 1H), 7.98 (s, 1H), 7.78-7.65 (m, 2H), 5.59 (s, 1H), 3.69 (s, 3H), 3.61 (br. s., 1H), 3.53 (br. s., 1H), 2.26-2.18 (m, 1H), 1.88 (br. s., 6H), 1.79-1.72 (m, 1H), 1.67-1.47 (m, 6H), 1.44-1.25 (m, 6H), 1.14 (dd, J=8.3, 2.7 Hz, 2H), 1.04-0.96 (m, 2H), 0.91-0.81 (m, 2H), 0.58-0.49 (m, 2H). FXR EC$_{50}$ (nM) 89; MS (ESI) 556.3 (M+H).

The following compound was synthesized according to the method described for the synthesis of Example 3 by substituting intermediate 124F and the corresponding acids where appropriate:

Example 126

N-(3-(3-cyclopropyl-1,2,4-oxadiazol-5-yl)phenyl)-N-((4-(3-cyclopropyl-1-methyl-1H-pyrazol-5-yl)bicyclo[2.2.2]octan-1-yl)methyl)-3-fluorobicyclo[1.1.1]pentane-1-carboxamide (126)

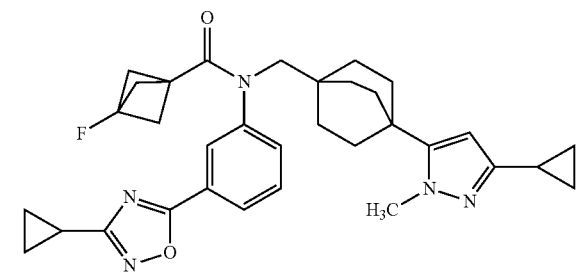

Step A. Intermediate 126A. Preparation of (4-(3-cyclopropyl-1-methyl-1H-pyrazol-5-yl)bicyclo[2.2.2]octan-1-yl)methanol

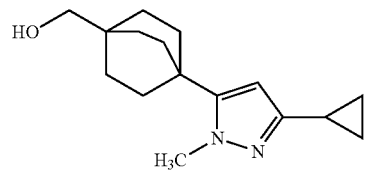

The title compound was synthesized according to the method described for the synthesis of Intermediate 1G by substituting Intermediate 124C2 where appropriate: (120 mg, 0.438 mmol, 42% yield) as pale yellow oil. $^1$H NMR (400 MHz, DMSO-$d_6$): δ 5.65 (s, 1H), 3.75 (s, 3H), 3.05 (s, 2H), 1.68-1.79 (m, 7H), 1.35-1.44 (m, 6H), 0.72-0.78 (m, 2H), 0.50-0.56 (m, 2H).

| Ex. No. | Structure | MS (ESI) (M + H) | FXR EC$_{50}$ (nM) |
|---|---|---|---|
| 125 | 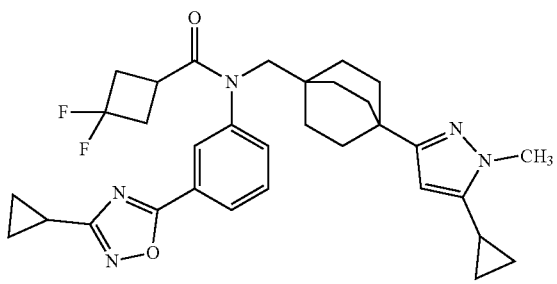 [SMILES: Cn1nc(C23CCC(CN(C(=O)C4CC(F)(F)C4)c4cccc(-c5nc(C6CC6)no5)c4)(CC2)CC3)cc1C1CC1] | 562 | 480 |

125 $^1$H NMR (400 MHz, DMSO-$d_6$) δ 8.10-7.94 (m, 2H), 7.74 (d, J = 8.1 Hz, 1H), 7.68 (t, J = 7.9 Hz, 1H), 5.59 (s, 1H), 3.69 (s, 3H), 3.63 (br. s., 2H), 2.97-2.84 (m, 1H), 2.84-2.68 (m, 2H), 2.34 (d, J = 1.7 Hz, 2H), 2.26-2.14 (m, 1H), 1.80-1.68 (m, 1H), 1.68-1.46 (m, 6H), 1.46-1.28 (m, 6H), 1.19-1.09 (m, 2H), 1.06-0.95 (m, 2H), 0.94-0.80 (m, 2H), 0.60-0.47 (m, 2H).

Step B. Intermediate 126B. Preparation of 4-(3-cyclopropyl-1-methyl-1H-pyrazol-5-yl) bicyclo[2.2.2]octane-1-carbaldehyde

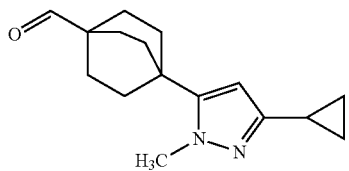 [SMILES: Cn1nc(C2CC2)cc1C12CCC(C=O)(CC1)CC2]

The title compound was synthesized according to the method described for the synthesis of Intermediate 3C by substituting Intermediate 126A where appropriate: (90 mg, 0.348 mmol, 76% yield) as an off-white solid. $^1$H NMR (400 MHz, DMSO-$d_6$): δ 9.45 (s, 1H), 5.69 (s, 1H), 3.77 (s, 3H), 1.68-1.79 (m, 7H), 1.55-1.61 (m, 6H), 0.73-0.79 (m, 2H), 0.53-0.58 (m, 2H).

Step C. Intermediate 126C. Preparation of 3-(3-cyclopropyl-1,2,4-oxadiazol-5-yl)-N-((4-(3-cyclopropyl-1-methyl-1H-pyrazol-5-yl)bicyclo[2.2.2]octan-1-yl)methyl)aniline

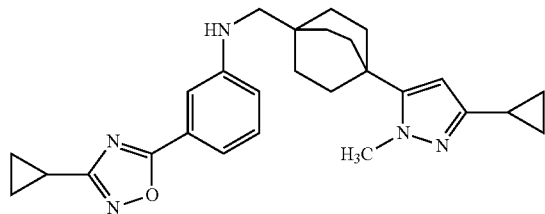 [SMILES: Cn1nc(C2CC2)cc1C12CCC(CNc3cccc(-c4nc(C5CC5)no4)c3)(CC1)CC2]

The title compound was synthesized according to the method described for the synthesis of Intermediate 1I by substituting Intermediate 8A and Intermediate 126B where appropriate: (70 mg, 0.142 mmol, 41% yield) as an off-white solid. MS (ESI) 444 (M+H).

Step D. Example 126. Preparation of N-(3-(3-cyclopropyl-1,2,4-oxadiazol-5-yl) phenyl)-N-((4-(3-cyclopropyl-1-methyl-1H-pyrazol-5-yl)bicyclo[2.2.2]octan-1-yl) methyl)-3-fluorobicyclo[1.1.1]pentane-1-carboxamide The title compound was synthesized according to the method described for the synthesis of Example 3 by substituting Intermediate 126C and the corresponding acid where appropriate: (20.5 mg, 0.037 mmol, 65% yield). $^1$H NMR (400 MHz, DMSO-$d_6$) δ 8.06 (d, J=7.6 Hz, 1H), 8.03-7.97 (m, 1H), 7.75 (d, J=8.3 Hz, 1H), 7.70 (t, J=7.7 Hz, 1H), 5.62 (s, 1H), 3.72 (s, 3H), 3.63 (br. s., 1H), 3.55 (br. s., 1H), 2.27-2.18 (m, 1H), 1.88 (br. s., 6H), 1.78-1.58 (m, 7H), 1.41 (d, J=7.1 Hz, 6H), 1.14 (dd, J=8.2, 2.8 Hz, 2H), 1.06-0.96 (m, 2H), 0.79-0.69 (m, 2H), 0.59-0.48 (m, 2H). FXR EC$_{50}$ (nM) 87; MS (ESI) 556 (M+H).

The following compound was synthesized according to the method described for the synthesis of Example 3 by substituting Intermediate 126C and the corresponding acid where appropriate:

| Ex. No. | Structure & Name | MS (ESI) (M+H) | FXR EC$_{50}$ (nM) |
|---|---|---|---|
| 127 | | 562 | 374 |

127 $^1$H NMR (400 MHz, DMSO-$d_6$) δ 8.12-8.01 (m, 2H), 7.75 (d, J = 7.6 Hz, 1H), 7.69 (t, J = 8.1 Hz, 1H), 5.62 (s, 1H), 3.72 (s, 3H), 3.65 (br. s., 2H), 2.96-2.83 (m, 1H), 2.82-2.69 (m, 2H), 2.34 (d, J = 1.7 Hz, 2H), 2.21 (td, J = 8.6, 4.2 Hz, 1H), 1.81-1.57 (m, 7H), 1.50-1.26 (m, 6H), 1.18-1.07 (m, 2H), 1.06-0.94 (m, 2H), 0.81-0.70 (m, 2H), 0.57-0.48 (m, 2H).

Example 128

N-(3-(3-Cyclopropyl-1,2,4-oxadiazol-5-yl)phenyl)-3-fluoro-N-((1-(4-methoxyphenyl)-2-oxabicyclo[2.2.2]octan-4-yl)methyl)bicyclo[1.1.1]pentane-1-carboxamide (128)

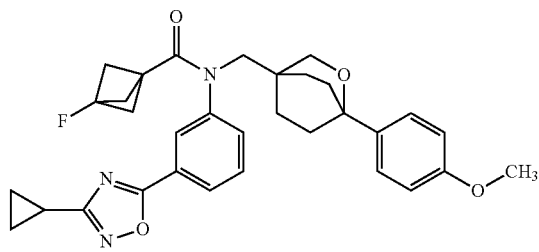

Step A. Intermediate 128A. Preparation of (4-hydroxy-4-(4-methoxyphenyl) cyclohexane-1,1-diyl) bis(methylene) bis(4-methylbenzenesulfonate)

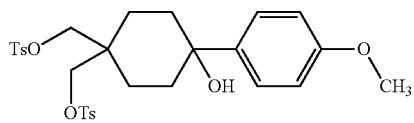 [SMILES: COc1ccc(C2(O)CCC(COS(=O)(=O)c3ccc(C)cc3)(COS(=O)(=O)c3ccc(C)cc3)CC2)cc1]

To a solution of (4-oxocyclohexane-1,1-diyl)bis(methylene) bis(4-methylbenzenesulfonate) (0.5 g, 1.072 mmol) in THF (15 mL) at −78° C. was added (4-methoxyphenyl) magnesium bromide (3.21 mL, 3.21 mmol). The reaction mixture was allowed to warm to room temperature and stirred for 2 h. The reaction mixture was quenched with saturated aqueous ammonium chloride solution (20 mL) and extracted with EtOAc (50 mL). The organic layer was dried over anhydrous sodium sulphate and concentrated under reduced pressure. The crude material was purified by flash column chromatography (Combiflash, 24 g silica, 0-30% EtOAc/PE) to afford the title compound (0.6 g, 0.992 mmol, 93% yield) as white solid. $^1$H NMR (400 MHz, CHLOROFORM-d) δ 7.81-7.71 (m, 4H), 7.37 (d, J=8.5 Hz, 4H), 7.27-7.24 (m, 2H), 6.90-6.83 (m, 2H), 4.00 (s, 1H), 3.84-3.77 (m, 5H), 2.49-2.44 (m, 6H), 1.70-1.60 (m, 5H), 1.58-1.48 (m, 2H), 1.30-1.27 (m, 1H).

Step B. Intermediate 128B. Preparation of (1-(4-methoxyphenyl)-2-oxabicyclo[2.2.2]octan-4-yl) methyl 4-methylbenzenesulfonate

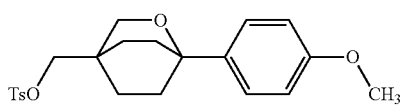 [SMILES: COc1ccc(C23CCC(COS(=O)(=O)c4ccc(C)cc4)(CC2)CO3)cc1]

To a solution of Intermediate 128A (0.6 g, 1.044 mmol) in anhydrous 1,2-dimethoxyethane (20 mL) at 0° C. was added sodium hydride (0.125 g, 3.13 mmol). The reaction mixture was stirred for 30 minutes at 0° C. and the refluxed overnight. The reaction mixture was quenched with saturated aqueous ammonium chloride solution (10 mL) and extracted with EtOAc (2×30 mL). The combined organic layers were dried over anhydrous sodium sulphate, filtered and concentrated under reduced pressure. The crude material was purified by flash column chromatography (Combiflash, 12 g silica, 0-50% EtOAc/PE) to afford the title compound (0.4 g, 0.944 mmol, 90% yield) as white solid. MS (ESI) 403 (M+H).

Step C. Intermediate 128C. Preparation of (1-(4-methoxyphenyl)-2-oxabicyclo[2.2.2]octan-4-yl) methyl acetate

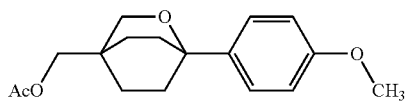

To a solution of Intermediate 128B (0.4 g, 0.994 mmol) in DMF (5 mL) was added cesium acetate (0.572 g, 2.98 mmol). The reaction mixture was heated at 120° C. and stirred overnight in a sealed tube. The reaction mixture was cooled to room temperature and poured into water (10 mL). The aqueous layer was extracted with EtOAc (2×30 mL). The combined organic layers were washed with brine solution, dried over anhydrous sodium sulphate, filtered and concentrated under reduced pressure. The crude material was purified by flash column chromatography (Combiflash, 24 g silica, 0-30% EtOAc/PE) to afford the title compound (0.3 g, 0.982 mmol, 99% yield) as an off-white solid. MS (ESI) 291 (M+H).

Step D. Intermediate 128D. Preparation of (1-(4-methoxyphenyl)-2-oxabicyclo[2.2.2]octan-4-yl) methanol

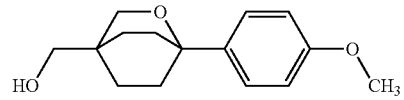

To a solution of Intermediate 128C (0.3 g, 1.033 mmol) in methanol (5 mL) at 0° C. was added a solution of potassium carbonate (0.714 g, 5.17 mmol) in water (7 mL) and the reaction mixture was stirred at room temperature for 2 h. Methanol was removed under reduced pressure and the aqueous solution was extracted with EtOAc (containing 5% MeOH) (2×30 mL). The combined organic layers were washed with brine, dried over anhydrous sodium sulphate, filtered and concentrated under reduced pressure to afford title compound (0.25 g, 0.906 mmol, 88% yield) as an off-white solid. MS (ESI) 249 (M+H).

Step E. Intermediate 128E. Preparation of 1-(4-methoxyphenyl)-2-oxabicyclo[2.2.2]octane-4-carbaldehyde

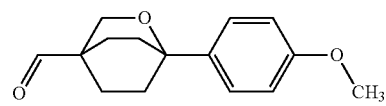

The title compound was synthesized according to the method described for the synthesis of Intermediate 3C by substituting Intermediate 128D where appropriate: (0.1 g, 0.386 mmol, 96% yield) as an off-white solid. ¹H NMR (400 MHz, DMSO-d₆) δ 9.51 (s, 1H), 7.32-7.25 (m, 2H), 6.89-6.81 (m, 2H), 3.98 (s, 2H), 3.73 (s, 3H), 2.14-2.00 (m, 2H), 1.93-1.83 (m, 6H).

Step F. Intermediate 128F: Preparation of 3-(3-cyclopropyl-1,2,4-oxadiazol-5-yl)-N-((1-(4-methoxyphenyl)-2-oxabicyclo[2.2.2]octan-4-yl)methyl)aniline

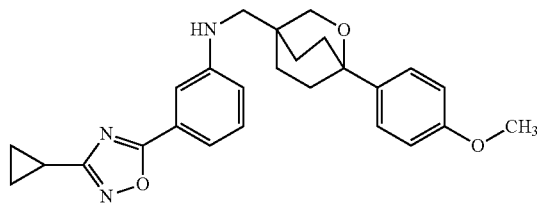 [SMILES: COc1ccc(C23CCC(CNc4cccc(-c5nc(C6CC6)no5)c4)(CC2)CO3)cc1]

The title compound was synthesized according to the method described for the synthesis of Intermediate 1I by substituting Intermediate 8A and Intermediate 128E where appropriate: (75 mg, 0.099 mmol, 61% yield) as a brown gummy solid. MS (ESI) 432 (M+H).

Step G. Example 128. Preparation of N-(3-(3-Cyclopropyl-1,2,4-oxadiazol-5-yl) phenyl)-3-fluoro-N-((1-(4-methoxyphenyl)-2-oxabicyclo[2.2.2]octan-4-yl)methyl) bicyclo[1.1.1]pentane-1-carboxamide The title compound was synthesized according to the method described for the synthesis of Example 3 by substituting Intermediate 128F and the corresponding acid where appropriate: (11.6 mg, 0.021 mmol, 37% yield). ¹H NMR (400 MHz, DMSO-d₆) δ 8.08 (d, J=7.8 Hz, 1H), 8.05 (d, J=1.7 Hz, 1H), 7.82-7.76 (m, 1H), 7.76-7.67 (m, 1H), 7.30-7.16 (m, 2H), 6.87-6.73 (m, 2H), 3.71-3.68 (m, 7H), 2.28-2.17 (m, 1H), 2.02-1.92 (m, 2H), 1.89 (br. s., 6H), 1.80-1.68 (m, 2H), 1.62 (br. s., 2H), 1.55 (d, J=7.3 Hz, 2H), 1.14 (dd, J=8.2, 2.6 Hz, 2H), 1.02 (dd, J=4.6, 2.4 Hz, 2H); FXR EC₅₀ (nM)=403; MS (ESI) 544 (M+H).

Example 129

N-(3-(3-Cyclopropyl-1,2,4-oxadiazol-5-yl)phenyl)-3,3-difluoro-N-((1-(4-methoxyphenyl)-2-oxabicyclo[2.2.2]octan-4-yl)methyl)cyclobutane-1-carboxamide (129)

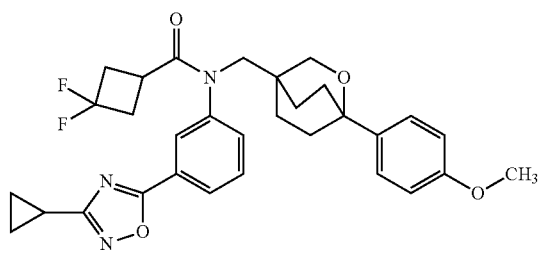

The title compound was synthesized according to the method described for the synthesis of Example 3 by substituting Intermediate 128F and the corresponding acid where appropriate: (13.8 mg, 0.025 mmol, 43% yield). ¹H NMR (400 MHz, DMSO-d₆) δ 8.08 (s, 1H), 8.04 (d, J=8.1 Hz, 1H), 7.79 (d, J=7.8 Hz, 1H), 7.70 (t, J=7.8 Hz, 1H), 7.30-7.14 (m, J=9.0 Hz, 2H), 6.92-6.75 (m, J=9.0 Hz, 2H), 3.79-3.59 (m, 7H), 2.96-2.71 (m, 3H), 2.34 (br. s., 2H), 2.25-2.17 (m, 1H), 2.00-1.87 (m, 2H), 1.74 (br.s., 2H), 1.66-1.57 (m, 2H), 1.53 (d, J=7.1 Hz, 2H), 1.17-1.10 (m, 2H), 1.05-0.92 (m, 2H); FXR EC₅₀ (nM)=1136; MS (ESI) 550 (M+H).

Example 130

N-((4-(3-cyclopropyl-1,2,4-oxadiazol-5-yl)bicyclo[2.2.2]octan-1-yl)methyl)-N-(3-(2-cyclopropyl-1-methyl-1H-imidazol-4-yl)phenyl)-3-fluorobicyclo[1.1.1]pentane-1-carboxamide (130)

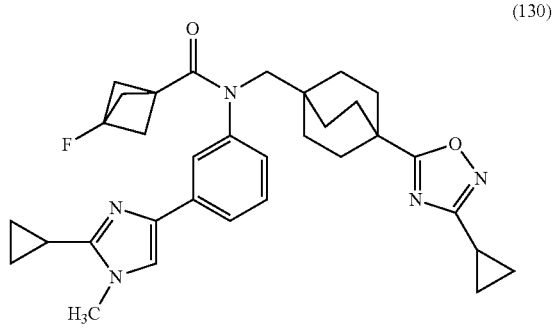 [SMILES: Cn1cc(-c2cccc(N(CC34CCC(c5nc(C6CC6)no5)(CC3)CC4)C(=O)C34CC(F)(C3)C4)c2)nc1C1CC1]

Step A. Intermediate 130A. Preparation of 2-cyclopropyl-4-(3-nitrophenyl)-1H-imidazole

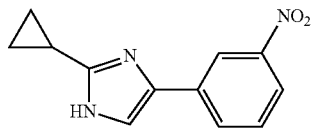 [SMILES: O=[N+]([O-])c1cccc(-c2c[nH]c(C3CC3)n2)c1]

To a stirred solution of 2-bromo-1-(3-nitrophenyl)ethan-1-one (4 g, 16.39 mmol) and cyclopropanecarboximidamide hydrochloride (2.372 g, 19.67 mmol) in acetonitrile (60 mL) was added K₂CO₃ (6.80 g, 49.2 mmol) and the reaction mixture was stirred for 3 h at 90° C. in a microwave reactor. The reaction mixture was poured into saturated aqueous NaHCO₃ solution and the aqueous layer was extracted with EtOAc (2×50 mL). The combined organic layers were dried over MgSO₄, filtered and concentrated under reduced pressure to afford the title compound (3.0 g, 13.09 mmol, 80% yield). MS (ESI) 230 (M+H).

Step B. Intermediate 130B. Preparation of 2-cyclopropyl-1-methyl-4-(3-nitrophenyl)-1H-imidazole

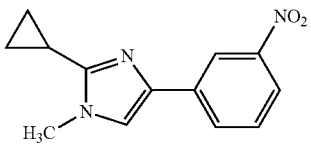

To a stirred solution of Intermediate 130A (0.35 g, 1.527 mmol) and NaH (0.073 g, 1.832 mmol) in DMF (5 mL) at 0° C. was added iodomethane (0.099 mL, 1.527 mmol). After stirring the reaction for 1 h at room temperature, the reaction mixture was poured into ice-water and the aqueous layer was extracted with EtOAc (2×50 mL). The combined organic layers were dried over MgSO₄, filtered and concentrated under reduced pressure. The crude material was purified by flash column chromatography (Combiflash, 24 g silica, 0-50% EtOAc/PE) to afford the title compound (200 mg, 0.822 mmol, 54% yield). MS (ESI) 244 (M+H).

Step C. Intermediate 130C. Preparation of 3-(2-cyclopropyl-1-methyl-1H-imidazol-4-yl)aniline

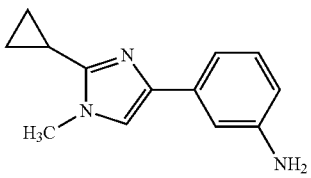 [SMILES: Cn1cc(-c2cccc(N)c2)nc1C1CC1]

To a stirred solution of Intermediate 130B (250 mg, 1.028 mmol) in EtOH (2 mL) at 0° C. was added tin(II) chloride dihydrate (812 mg, 3.60 mmol) and conc. HCl (0.468 mL, 15.42 mmol). The reaction mixture was heated at 90° C. and stirred for 2 h. The reaction mixture was concentrated under reduced pressure and the residue was basified with saturated aqueous NaHCO₃ and extracted with EtOAc (2×100 mL). The combined organic layers were dried over anhydrous sodium sulphate, filtered and concentrated under reduced pressure to afford the title compound (210 mg, 0.985 mmol, 96% yield). MS (ESI) 214 (M+H).

Step D. Intermediate 130D. Preparation of N-((4-(3-cyclopropyl-1,2,4-oxadiazol-5-yl) bicyclo[2.2.2]octan-1-yl)methyl)-3-(2-cyclopropyl-1-methyl-1H-imidazol-4-yl)aniline

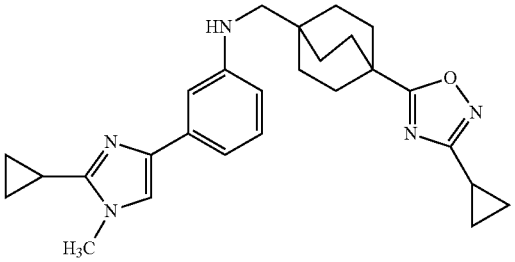 [SMILES: Cn1cc(-c2cccc(NCC34CCC(c5nc(C6CC6)no5)(CC3)CC4)c2)nc1C1CC1]

The title compound was synthesized according to the method described for the synthesis of Intermediate 1I by substituting Intermediate 130C and Intermediate 4C where appropriate: (220 mg, 0.496 mmol, 71% yield). MS (ESI) 444 (M+H).

Step E. Example 130. Preparation of N-((4-(3-cyclopropyl-1,2,4-oxadiazol-5-yl) bicyclo[2.2.2]octan-1-yl)methyl)-N-(3-(2-cyclopropyl-1-methyl-1H-imidazol-4-yl) phenyl)-3-fluorobicyclo[1.1.1]pentane-1-carboxamide The title compound was synthesized according to the method described for the synthesis of Example 3 by substituting Intermediate 130D and the corresponding acid where appropriate: (6.4 mg, 0.012 mmol, 17% yield). $^1$H NMR (400 MHz, DMSO-d₆) δ 7.68 (d, J=7.8 Hz, 1H), 7.64 (s, 1H), 7.58 (s, 1H), 7.39 (t, J=7.8 Hz, 1H), 7.15 (d, J=8.1 Hz, 1H), 3.70 (s, 3H), 3.56 (br. s., 2H), 2.11-1.96 (m, 2H), 1.86 (br. s., 6H), 1.81-1.67 (m, 6H), 1.53-1.31 (m, 6H), 1.06-0.98 (m, 2H), 0.98-0.85 (m, 4H), 0.85-0.76 (m, 2H); FXR EC₅₀ (nM) 585; MS (ESI) 556 (M+H).

The following compound was synthesized according to the method described for the synthesis of Example 3 by substituting Intermediate 130D and the corresponding acid where appropriate:

| Ex. No. | Structure | MS (ESI) (M + H) | FXR EC₅₀ (nM) |
|---|---|---|---|
| 131 | | 562 | 1440 |

131 $^1$H NMR (400 MHz, DMSO-d₆) δ 7.70-7.53 (m, 3H), 7.38 (t, J = 7.8 Hz, 1H), 7.15 (d, J = 7.6 Hz, 1H), 3.70 (s, 3H), 3.62 (s, 2H), 2.91-2.69 (m, 3H), 2.41-2.28 (m, 2H), 2.10-1.92 (m, 2H), 1.92-1.64 (m, 6H), 1.55-1.28 (m, 6H), 1.07-0.97 (m, 2H), 0.94 (d, J = 8.1 Hz, 2H), 0.91-0.86 (m, 2H), 0.86-0.76 (m, 2H)

Example 132

N-((4-(3-cyclopropyl-1,2,4-oxadiazol-5-yl)bicyclo[2.2.2]octan-1-yl)methyl)-N-(3-(5-cyclopropyl-4-methyl-4H-1,2,4-triazol-3-yl)phenyl)-3-fluorobicyclo[1.1.1]pentane-1-carboxamide

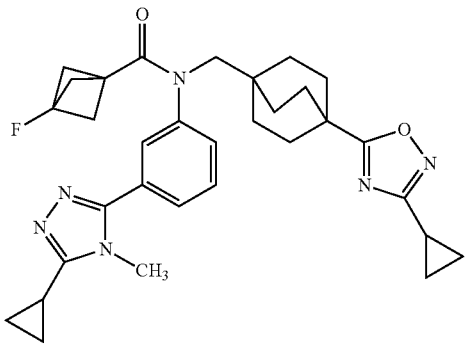

(132)

Step A. Intermediate 132A. Preparation of N-methylcyclopropanecarboxamide

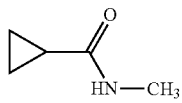

To a stirred solution of cyclopropanecarbonyl chloride (2.174 mL, 23.92 mmol) in THF (20 mL) at room temperature was added methanamine (33.5 mL, 67.0 mmol) and the reaction mixture was stirred for 12 h at room temperature. The reaction mixture was poured into saturated aqueous sodium bicarbonate solution (30 mL) and the aqueous layer was extracted with EtOAc (2×50 mL). The combined organic layers were dried over MgSO$_4$, filtered and concentrated under reduced pressure to afford the title compound (1.6 g, 16.14 mmol, 68% yield). $^1$H NMR (400 MHz, DMSO-d$_6$) δ 7.96 (br. s., 1H), 2.58 (d, J=4.6 Hz, 3H), 1.57-1.43 (m, 1H), 0.70-0.54 (m, 4H).

Step B. Intermediate 132B. Preparation of 3-cyclopropyl-4-methyl-5-(3-nitrophenyl)-4H-1,2,4-triazole

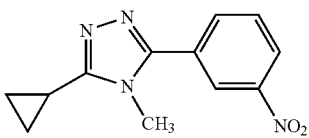 [SMILES: Cn1c(-c2cccc([N+](=O)[O-])c2)nnc1C1CC1]

To a stirred solution of Intermediate 86A (704 mg, 3.88 mmol) in DCE (12 mL) at 0° C. were added 2-fluoropyridine (0.343 mL, 3.88 mmol), trifluoromethanesulfonic anhydride (0.685 mL, 3.88 mmol) and N-methylcyclopropanecarboxamide (350 mg, 3.53 mmol). The reaction mixture was stirred for 10 min at room temperature and then stirred for 2 h at 140° C. in a microwave reactor. The reaction mixture was then poured into water and the aqueous layer was extracted with EtOAc (2×25 mL). The combined organic layers were dried over MgSO$_4$, filtered and concentrated under reduced pressure. The crude material was purified by flash column chromatography (Combiflash, 24 g silica, 0-30% EtOAc/PE) to afford the title compound (550 mg, 2.252 mmol, 64% yield). MS (ESI) 245 (M+H).

Step C. Intermediate 132C. Preparation of 3-(5-cyclopropyl-4-methyl-4H-1,2,4-triazol-3-yl)aniline

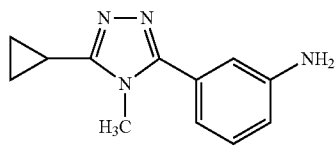 [SMILES: Cn1c(-c2cccc(N)c2)nnc1C1CC1]

To a stirred solution of Intermediate 132B (250 mg, 1.024 mmol) in EtOH (10 mL) at 0° C. was added tin(II) chloride dihydrate (808 mg, 3.58 mmol) and conc. HCl (0.466 mL, 15.35 mmol). The reaction mixture was heated to 90° C. and stirred for 2 h. The reaction mixture was concentrated under reduced pressure and the residue was basified with saturated aqueous NaHCO$_3$ solution and extracted with EtOAc (2×100 mL). The combined organic layers were dried over anhydrous sodium sulphate, filtered and concentrated under reduced pressure to afford the title compound (200 mg, 0.924 mmol, 90% yield). MS (ESI) 215 (M+H).

Step D. Intermediate 132D. Preparation of N-((4-(3-cyclopropyl-1,2,4-oxadiazol-5-yl) bicyclo[2.2.2]octan-1-yl)methyl)-3-(5-cyclopropyl-4-methyl-4H-1,2,4-triazol-3-yl)aniline

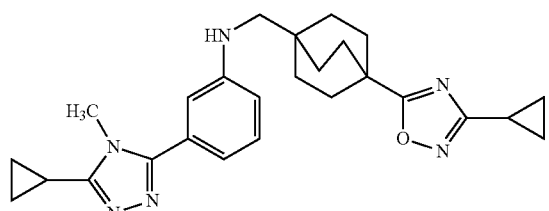

The title compound was synthesized according to the method described for the synthesis of Intermediate 1I by substituting Intermediate 132C and Intermediate 4C where appropriate: (140 mg, 0.220 mmol, 32% yield). MS (ESI) 445 (M+H).

Step E. Example 132. Preparation of N-((4-(3-cyclopropyl-1,2,4-oxadiazol-5-yl) bicyclo[2.2.2]octan-1-yl)methyl)-N-(3-(5-cyclopropyl-4-methyl-4H-1,2,4-triazol-3-yl) phenyl)-3-fluorobicyclo[1.1.1]pentane-1-carboxamide The title compound was synthesized according to the method described for the synthesis of Example 3 by substituting Intermediate 132D and the corresponding acid where appropriate: (11.5 mg, 0.020 mmol, 30% yield). $^1$H NMR (400 MHz, DMSO-$d_6$) δ 7.76-7.66 (m, 2H), 7.63 (t, J=8.1 Hz, 1H), 7.59-7.48 (m, 1H), 3.77-3.67 (m, 3H), 3.59 (s, 2H), 2.11-2.00 (m, 2H), 1.99-1.82 (m, 6H), 1.82-1.64 (m, 6H), 1.52-1.31 (m, 6H), 1.10-0.99 (m, 4H), 0.99-0.90 (m, 2H), 0.89-0.76 (m, 2H); FXR EC$_{50}$ (nM) 4413; MS (ESI) 557 (M+H).

Example 133

N-((4-(5-cyclopropyl-1,3,4-oxadiazol-2-yl)bicyclo[2.2.2]octan-1-yl)methyl)-N-(3-(5-cyclopropyl-1,3,4-oxadiazol-2-yl)phenyl)-3,3-difluorocyclopentane-1-carboxamide (Racemate)

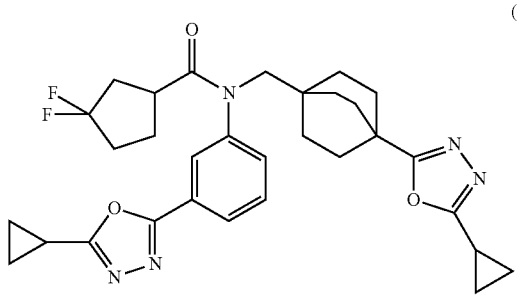

(133)

Step A. Intermediate 133A. Preparation of methyl 4-(2-(cyclopropanecarbonyl) hydrazine-1-carbonyl) bicyclo[2.2.2]octane-1-carboxylate

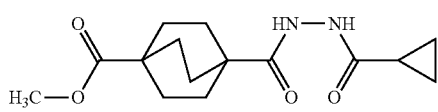

To a stirred solution of 4-(methoxycarbonyl)bicyclo[2.2.2]octane-1-carboxylic acid (2.0 g, 9.42 mmol) in DMF (20 mL) at room temperature were added cyclopropanecarbohydrazide (1.038 g, 10.37 mmol), DIPEA (4.94 mL, 28.3 mmol) followed by HATU (4.658 g, 12.25 mmol) and stirred over night at room temperature. The reaction mixture was concentrated, diluted with water (50 mL) and extracted with ethyl acetate (2×100 mL). The combined organic layers were dried over anhydrous sodium sulphate and concentrated under reduced pressure. The crude material was purified by flash column chromatography (Combiflash, 40 g silica, 0-30% EtOAc/PE) to afford the title compound (2.2 g, 7.47 mmol, 79% yield) as white solid. MS (ESI) 295 (M+H).

Step B. Intermediate 133B. Preparation of methyl 4-(5-cyclopropyl-1,3,4-oxadiazol-2-yl)bicyclo[2.2.2]octane-1-carboxylate

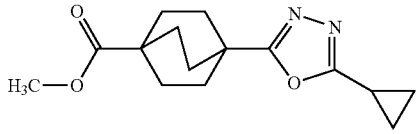 [SMILES: COC(=O)C12CCC(c3nnc(C4CC4)o3)(CC1)CC2]

To a stirred solution of Intermediate 133A (1.200 g, 4.08 mmol) in acetonitrile (12 mL) was added CCl$_4$ (0.433 mL, 4.48 mmol) followed by triphenylphosphine (2.246 g, 8.56 mmol) and the reaction mixture was heated at 90° C. and stirred overnight. The reaction mixture was concentrated under reduced pressure, diluted with water, and extracted with ethyl acetate (2×100 mL). The combined organic layers were dried over anhydrous sodium sulfate, filtered and concentrated under reduced pressure. The crude material was purified by flash column chromatography (Combiflash, 24 g silica, 0-80% EtOAc/PE) to afford the title compound (800 mg, 2.90 mmol, 71% yield) as gray solid. MS (ESI) 277 (M+H).

Step C. Intermediate 133C. Preparation of (4-(5-cyclopropyl-1,3,4-oxadiazol-2-yl) bicyclo[2.2.2]octan-1-yl)methanol

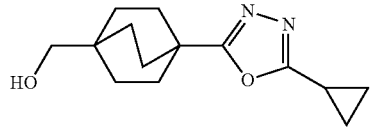 [SMILES: OCC12CCC(c3nnc(C4CC4)o3)(CC1)CC2]

The title compound was synthesized according to the method described for the synthesis of Intermediate 1G by substituting Intermediate 133B where appropriate: (500 mg, 2.013 mmol, 62% yield) as a white gummy solid. MS (ESI) 249 (M+H).

Step D. Intermediate 133D. Preparation of 4-(5-cyclopropyl-1,3,4-oxadiazol-2-yl) bicyclo[2.2.2]octane-1-carbaldehyde

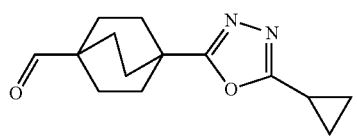 [SMILES: O=CC12CCC(c3nnc(C4CC4)o3)(CC1)CC2]

The title compound was synthesized according to the method described for the synthesis of Intermediate 3C by substituting Intermediate 133C where appropriate: (380 mg, 1.543 mmol, 77% yield) as a white solid. $^1$H NMR (400 MHz, DMSO-$d_6$): δ 9.46 (s, 1H), 2.15-2.20 (m, 1H), 1.66-1.77 (m, 6H), 1.85-1.92 (m, 6H), 1.10-1.11 (m, 4H).

Step E. Intermediate 133E. Preparation of 3-(5-cyclopropyl-1,3,4-oxadiazol-2-yl)-N-((4-(5-cyclopropyl-1,3,4-oxadiazol-2-yl)bicyclo[2.2.2]octan-1-yl)methyl)aniline

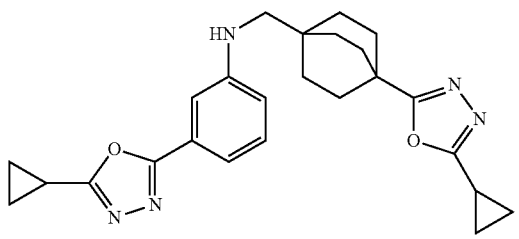 [SMILES: c1cc(NCC23CCC(c4nnc(C5CC5)o4)(CC2)CC3)cc(-c2nnc(C3CC3)o2)c1]

The title compound was synthesized according to the method described for the synthesis of Intermediate 1I by substituting Intermediate 86D and Intermediate 133D where appropriate: (120 mg, 0.278 mmol, 86% yield) as gummy liquid. MS (ESI) 432 (M+H).

Step F. Example 133. Preparation of N-((4-(5-cyclopropyl-1,3,4-oxadiazol-2-yl) bicyclo[2.2.2]octan-1-yl)methyl)-N-(3-(5-cyclopropyl-1,3,4-oxadiazol-2-yl)phenyl)-3,3-difluorocyclopentane-1-carboxamide (Racemate)

The title compound was synthesized according to the method described for the synthesis of Example 3 by substituting Intermediate 133E and the corresponding acid where appropriate: (4.8 mg, 8.02 μmol, 14% yield). $^1$H NMR (400 MHz, DMSO-$d_6$) δ 7.98 (s, 1H), 7.94 (d, J=7.8 Hz, 1H), 7.79-7.59 (m, 2H), 3.62 (s, 2H), 2.93 (t, J=8.3 Hz, 1H), 2.36-2.27 (m, 2H), 2.19-1.98 (m, 3H), 1.97-1.79 (m, 2H), 1.79-1.66 (m, 6H), 1.60 (br. s., 1H), 1.52-1.30 (m, 6H), 1.24-1.11 (m, 4H), 1.11-1.01 (m, 2H), 0.99-0.85 (m, 2H); FXR $EC_{50}$ (nM)=293; MS (ESI) 564 (M+H).

The following compounds were synthesized according to the method described for the synthesis of Example 3 by substituting Intermediate 133E and the corresponding acids where appropriate:

| Ex. No. | Structure | MS (ESI) (M + H) | FXR $EC_{50}$ (nM) |
|---|---|---|---|
| 134 | 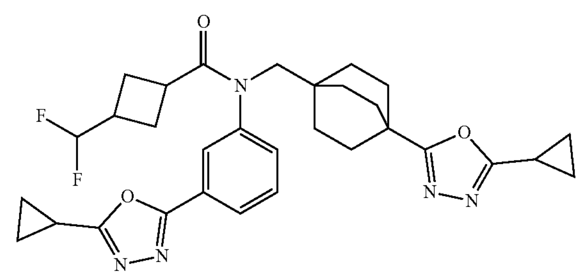 [SMILES: O=C(C1CC(C(F)F)C1)N(CC12CCC(c3nnc(C4CC4)o3)(CC1)CC2)c1cccc(-c2nnc(C3CC3)o2)c1] | 564 | 636 |
| 135 | 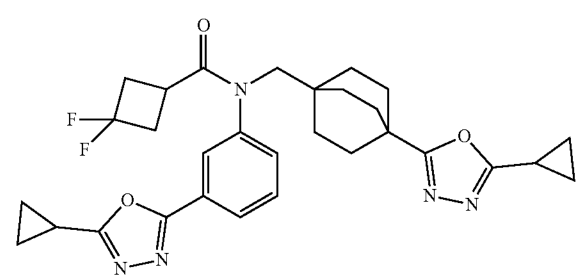 [SMILES: O=C(C1CC(F)(F)C1)N(CC12CCC(c3nnc(C4CC4)o3)(CC1)CC2)c1cccc(-c2nnc(C3CC3)o2)c1] | 550 | 1109 |

| Ex. No. | Structure | MS (ESI) (M + H) | FXR EC$_{50}$ (nM) |
|---|---|---|---|
| 136 | | 544 | 141 |

134 $^1$H NMR (400 MHz, DMSO-d$_6$) δ 8.00-7.84 (m, 2H), 7.71-7.52 (m, 2H), 6.16-5.96 (m, 1H), 5.96-5.82 (m, 1H), 3.63 (d, J = 3.7 Hz, 2H), 3.04 (dd, J = 19.1, 9.0 Hz, 1H), 2.39-2.29 (m, 2H), 2.19-2.02 (m, 2H), 1.85-1.57 (m, 8H), 1.40 (d, J = 4.6 Hz, 6H), 1.24-1.11 (m, 4H), 1.10-1.02 (m, 2H), 0.97-0.86 (m, 2H)

135 $^1$H NMR (400 MHz, DMSO-d$_6$) δ 8.01-7.87 (m, 2H), 7.66 (d, J = 5.1 Hz, 2H), 3.77- 3.56 (m, 2H), 2.96-2.69 (m, 3H), 2.41-2.25 (m, 3H), 2.17-2.03 (m, 1H), 1.86-1.63 (m, 6H), 1.52-1.29 (m, 6H), 1.23-1.11 (m, 4H), 1.11-1.01 (m, 2H), 0.98-0.86 (m, 2H)

136 $^1$H NMR (400 MHz, DMSO-d$_6$) δ 8.00-7.94 (m, 1H), 7.93 (s, 1H), 7.66 (d, J = 5.1 Hz, 2H), 3.60 (d, J = 16.9 Hz, 2H), 2.39-2.28 (m, 1H), 2.21-2.09 (m, 1H), 1.88 (br. s., 6H), 1.79-1.62 (m, 6H), 1.52-1.33 (m, 6H), 1.29-1.11 (m, 4H), 1.11-1.02 (m, 2H), 0.98-0.87 (m, 2H)

Example 137

N-(3-(3-cyclopropyl-1,2,4-oxadiazol-5-yl)phenyl)-N-((4-(5-cyclopropyl-1,3,4-oxadiazol-2-yl)bicyclo[2.2.2]octan-1-yl)methyl)-3-fluorobicyclo[1.1.1]pentane-1-carboxamide (137)

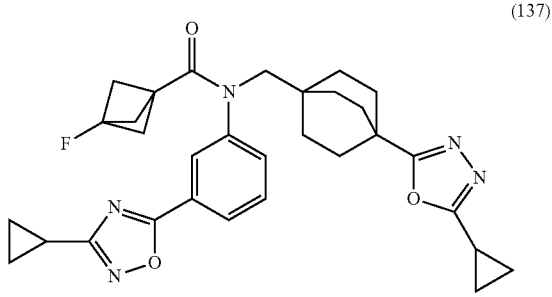 [SMILES: O=C(N(CC12CCC(c3nnc(C4CC4)o3)(CC1)CC2)c1cccc(-c2nc(C3CC3)no2)c1)C12CC(F)(C1)C2]

Step A. Intermediate 137A. Preparation of 3-(3-cyclopropyl-1,2,4-oxadiazol-5-yl)-N-((4-(5-cyclopropyl-1,3,4-oxadiazol-2-yl)bicyclo[2.2.2]octan-1-yl)methyl)aniline

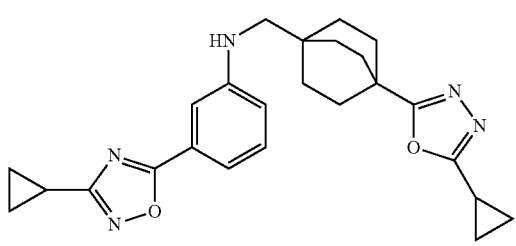 [SMILES: c1cc(NCC23CCC(c4nnc(C5CC5)o4)(CC2)CC3)cc(-c2nc(C3CC3)no2)c1]

The title compound was synthesized according to the method described for the synthesis of Intermediate 1I by substituting Intermediate 8A and Intermediate 133D where appropriate: (70 mg, 0.162 mmol, 100% yield) as a gummy liquid. MS (ESI) 432 (M+H).

Step B. Example 137. Preparation of N-(3-(3-cyclopropyl-1,2,4-oxadiazol-5-yl)phenyl)-N-((4-(5-cyclopropyl-1,3,4-oxadiazol-2-yl)bicyclo[2.2.2]octan-1-yl)methyl)-3-fluorobicyclo[1.1.1]pentane-1-carboxamide The title compound was synthesized according to the method described for the synthesis of Example 3 by substituting Intermediate 137A and the corresponding acid where appropriate: (7.2 mg, 0.013 mmol, 19% yield). $^1$H NMR (400 MHz, DMSO-d$_6$) δ 8.05 (d, J=7.6 Hz, 1H), 8.00 (s, 1H), 7.75 (d, J=8.6 Hz, 1H), 7.69 (t, J=7.8 Hz, 1H), 3.63 (br. s., 1H), 3.55 (br. s., 1H), 2.26-2.17 (m, 1H), 2.17-2.08 (m, 1H), 1.87 (br. s., 6H), 1.80-1.60 (m, 6H), 1.51-1.31 (m, 6H), 1.12 (dd, J=8.2, 2.6 Hz, 2H), 1.09-1.03 (m, 2H), 1.03-0.96 (m, 2H), 0.95-0.82 (m, 2H); FXR EC$_{50}$ (nM)=43; MS (ESI) 544 (M+H).

The following compounds were synthesized according to the method described for the synthesis of Example 3 by substituting Intermediate 137A and the corresponding acid where appropriate:

| Ex. No. | Structure | MS (ESI) (M + H) | FXR EC$_{50}$ (nM) |
|---|---|---|---|
| 138 | 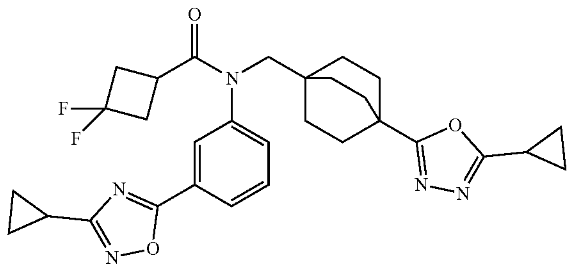 [SMILES: O=C(C1CC(F)(F)C1)N(CC12CCC(c3nnc(C4CC4)o3)(CC1)CC2)c1cccc(-c2nc(C3CC3)no2)c1] | 550 | 158 |
| 139 | 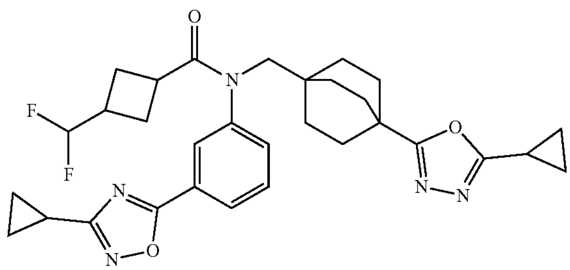 [SMILES: O=C(C1CC(C(F)F)C1)N(CC12CCC(c3nnc(C4CC4)o3)(CC1)CC2)c1cccc(-c2nc(C3CC3)no2)c1] | 564 | 384 |

138  $^1$H NMR (400 MHz, DMSO-d$_6$) δ 8.12-7.91 (m, 2H), 7.75 (d, J = 7.8 Hz, 1H), 7.69 (t, J = 7.9 Hz, 1H), 3.66 (br. s., 2H), 2.96-2.69 (m, 3H), 2.34 (br. s., 2H), 2.25-2.17 (m, 1H), 2.17-2.08 (m, 1H), 1.85-1.60 (m, 6H), 1.51-1.29 (m, 6H), 1.19-1.11 (m, 2H), 1.11-1.03 (m, 2H), 1.03-0.97 (m, 2H), 0.97-0.83 (m, 2H)

139  $^1$H NMR (400 MHz, DMSO-d$_6$) δ 8.10-7.87 (m, 2H), 7.80-7.54 (m, 2H), 6.18-5.65 (m, 1H), 3.62 (br. s., 2H), 3.14-2.96 (m, 1H), 2.34-2.26 (m, 1H), 2.24-2.16 (m, 1H), 2.16-1.98 (m, 2H), 1.82-1.67 (m, 7H), 1.64 (d, J = 9.8 Hz, 1H), 1.49-1.35 (m, 6H), 1.32 (br. s., 1H), 1.18-1.09 (m, 2H), 1.09-1.02 (m, 2H), 1.02-0.95 (m, 2H), 0.95-0.81 (m, 2H)

Example 140

N-(3-(3-Cyclopropyl-1,2,4-oxadiazol-5-yl)phenyl)-3-fluoro-N-((1-(2-methoxypyrimidin-5-yl)-2-oxabicyclo[2.2.2]octan-4-yl)methyl)bicyclo[1.1.1]pentane-1-carboxamide (140)

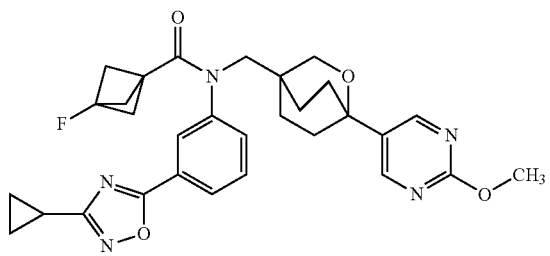

Step A. Intermediate 140A. Preparation of (4-hydroxy-4-(2-methoxypyrimidin-5-yl) cyclohexane-1,1-diyl)bis(methylene) bis(4-methylbenzenesulfonate)

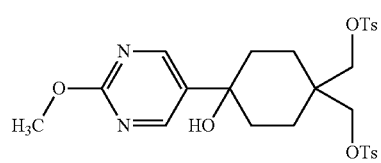 [SMILES: COc1ncc(C2(O)CCC(COS(=O)(=O)c3ccc(C)cc3)(COS(=O)(=O)c3ccc(C)cc3)CC2)cn1]

To a stirred solution of 5-bromo-2-methoxypyrimidine (1.519 g, 8.04 mmol) in THF (50 mL) at −78° C. was added n-butyl lithium (3.43 mL, 8.57 mmol) and stirred for 10 minutes. To the above reaction mixture was added a solution of (4-oxocyclohexane-1,1-diyl)bis(methylene) bis(4-methylbenzenesulfonate) (2.5 g, 5.36 mmol) in THF (12 mL) and the reaction mixture was stirred at −78° C. for 1 h. The reaction mixture was quenched with saturated aqueous ammonium chloride solution (10 mL) and extracted with ethyl acetate (2×50 mL). The combined organic layers were dried over anhydrous sodium sulfate, filtered and concentrated under reduced pressure. The crude material was purified by flash column chromatography (Combiflash, 24 g silica, 0-30% EtOAc/PE) to afford the title compound (1.4 g, 1.360 mmol, 25% yield) as white solid. MS (ESI) 577 (M+H).

Step B. Intermediate 140B. Preparation of (1-(2-methoxypyrimidin-5-yl)-2-oxabicyclo [2.2.2]octan-4-yl)methyl 4-methylbenzenesulfonate

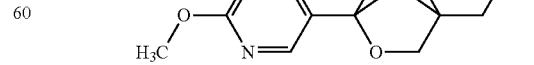

To a stirred solution of Intermediate 140A (1.35 g, 2.341 mmol) in THF (40 mL) at room temperature was added NaOH (0.281 g, 7.02 mmol) and refluxed overnight. The reaction mixture was cooled to room temperature, diluted with water (20 mL) and extracted with ethyl acetate (2×50 mL). The combined organic layers were dried over anhydrous sodium sulfate and concentrated under reduced pressure. The crude material was purified by flash column chromatography (Combiflash, 24 g silica, 0-30% EtOAc/PE) to afford the title compound (120 mg, 0.291 mmol, 12% yield) as a brown solid. MS (ESI) 405 (M+H).

Step C. Intermediate 140C. Preparation of (1-(2-methoxypyrimidin-5-yl)-2-oxabicyclo [2.2.2]octan-4-yl)methyl acetate

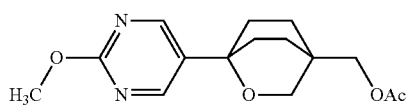

To a stirred solution of Intermediate 140B (120 mg, 0.297 mmol) in DMF (2 mL) was added cesium acetate (142 mg, 0.742 mmol) and heated to 120° C. and stirred for 6 h. The reaction mixture was concentrated under reduced pressure, the residue was diluted with water (25 mL) and extracted with ethyl acetate (2×30 mL). The combined organic layers were dried over anhydrous sodium sulfate and concentrated under reduced pressure to afford the title compound (75 mg, 0.233 mmol, 79% yield) as a brown gummy solid. MS (ESI) 293 (M+H).

Step D. Intermediate 140D. Preparation of (1-(2-methoxypyrimidin-5-yl)-2-oxabicyclo [2.2.2]octan-4-yl)methanol

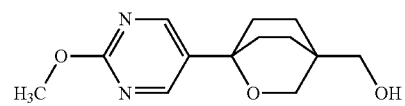

To a stirred solution of Intermediate 140C (70 mg, 0.239 mmol) in methanol (2 mL) at room temperature was added solution of sodium methoxide (5.48 µL, 0.024 mmol) in methanol. After stirring the reaction mixture for 2 h, it was diluted with DCM (25 mL) and washed with water (15 mL) followed by brine solution (25 mL). The organic layer was dried over anhydrous sodium sulphate, filtered and concentrated under reduced pressure. The crude material was purified by flash column chromatography (Combiflash, 24 g silica, 0-30% EtOAc/PE) to afford the title compound (60 mg, 0.209 mmol, 87% yield) as white solid. MS (ESI) 251 (M+H).

Step E. Intermediate 140E. Preparation of 1-(2-methoxypyrimidin-5-yl)-2-oxabicyclo[2.2.2]octane-4-carbaldehyde

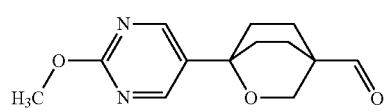

The title compound was synthesized according to the method described for the synthesis of Intermediate 3C by substituting Intermediate 140D where appropriate: (50 mg, 0.201 mmol, 84% yield) as brown gummy solid. MS (ESI) 249 (M+H).

Step F. Intermediate 140F. Preparation of 3-(3-cyclopropyl-1,2,4-oxadiazol-5-yl)-N-((1-(2-methoxypyrimidin-5-yl)-2-oxabicyclo[2.2.2]octan-4-yl)methyl)aniline

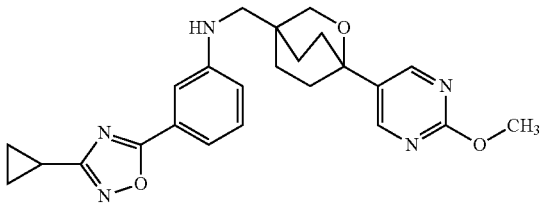 [SMILES: COc1ncc(C23CCC(CNc4cccc(-c5nc(C6CC6)no5)c4)(CC2)CO3)cn1]

The title compound was synthesized according to the method described for the synthesis of Intermediate 1I by substituting Intermediate 8A and Intermediate 140E where appropriate: (20 mg, 0.046 mmol, 38% yield) as a brown gummy solid. $^1$H NMR (400 MHz, DMSO-$d_6$) δ 8.59 (s, 2H), 7.33-7.24 (m, 2H), 7.18 (d, J=7.5 Hz, 1H), 6.93-6.92 (m, 1H), 6.01 (br. s., 1H), 3.93-3.87 (m, 5H), 2.94 (d, J=5.0 Hz, 2H), 2.18-2.09 (m, 5H), 1.93-1.88 (m, 2H), 1.75 (br. s., 2H), 1.14-1.07 (m, 2H), 1.00-0.96 (m, 2H). MS (ESI) 434 (M+H).

Step G. Example 140. Preparation of N-(3-(3-Cyclopropyl-1,2,4-oxadiazol-5-yl) phenyl)-3-fluoro-N-((1-(2-methoxypyrimidin-5-yl)-2-oxabicyclo[2.2.2]octan-4-yl) methyl)bicyclo[1.1.1]pentane-1-carboxamide The title compound was synthesized according to the method described for the synthesis of Example 3 by substituting Intermediate 140F and the corresponding acid where appropriate: (11.3 mg, 0.021 mmol, 44% yield). $^1$H NMR (400 MHz, DMSO-$d_6$) δ 8.52 (s, 2H), 8.15-7.98 (m, 2H), 7.79 (d, J=8.1 Hz, 1H), 7.71 (t, J=7.8 Hz, 1H), 3.88 (s, 3H), 3.71 (br. s., 3H), 3.61 (br. s., 1H), 2.27-2.17 (m, 1H), 2.08-1.97 (m, 2H), 1.89 (br. s., 6H), 1.82 (br. s., 2H), 1.65 (br. s., 2H), 1.56 (d, J=6.1 Hz, 2H), 1.14 (dd, J=8.3, 2.7 Hz, 2H), 1.07-0.90 (m, 2H); FXR $EC_{50}$ (nM)=582; MS (ESI) 546 (M+H).

Example 141

N-((1-(4-(1-Cyanocyclopropyl)phenyl)-2-oxabicyclo[2.2.2]octan-4-yl)methyl)-N-(3-(3-cyclopropyl-1,2,4-oxadiazol-5-yl)phenyl)-3-(difluoromethyl)cyclobutane-1-carboxamide (141)

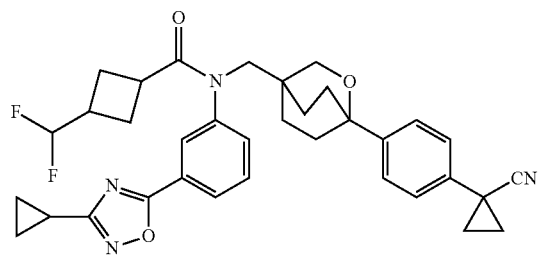

Step A. Intermediate 141A. Preparation of (4-(4-(1-cyanocyclopropyl)phenyl)-4-hydroxy cyclohexane-1,1-diyl)bis(methylene) bis(4-methylbenzene-sulfonate)

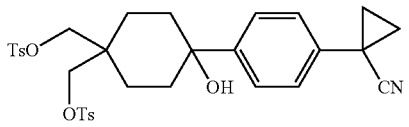 [SMILES: Cc1ccc(S(=O)(=O)OCC2(COS(=O)(=O)c3ccc(C)cc3)CCC(O)(c3ccc(C4(C#N)CC4)cc3)CC2)cc1]

To a stirred solution of 1-(4-bromophenyl)cyclopropane-1-carbonitrile (1.785 g, 8.04 mmol) in THF (25 mL), cooled to −78° C., was added n-butyl lithium (3.43 mL, 8.57 mmol) and gradually allowed to warm up to room temperature over 1 h. The reaction mixture was again cooled to −78° C. and added a solution of (4-oxocyclohexane-1,1-diyl)bis(methylene) bis(4-methylbenzenesulfonate) (2.5 g, 5.36 mmol) in THF (12 mL). After stirring for 3 h, the reaction mixture was quenched with saturated aqueous ammonium chloride solution (10 mL) and extracted with ethyl acetate (2×50 mL). The combined organic layers were dried over sodium sulfate and concentrated under reduced pressure. The crude material was purified by flash column chromatography (Combiflash, 24 g silica, 0-30% EtOAc/PE) to afford the title compound (2.4 g, 3.62 mmol, 67% yield) as white solid. MS (ESI) 609 (M+H). $^1$H NMR (400 MHz, DMSO-$d_6$) δ 7.83 (d, J=8.3 Hz, 2H), 7.80-7.74 (m, 2H), 7.50 (d, J=8.1 Hz, 4H), 7.27-7.19 (m, 4H), 4.81 (s, 1H), 4.01 (s, 2H), 3.74 (s, 2H), 2.45 (s, 3H), 2.37 (s, 3H), 1.77-1.70 (m, 2H), 1.64-1.52 (m, 2H), 1.50-1.44 (m, 2H), 1.31-1.21 (m, 6H).

Step B. Intermediate 141B. Preparation of (1-(4-(1-cyanocyclopropyl)phenyl)-2-oxabicyclo[2.2.2]octan-4-yl)methyl 4-methylbenzenesulfonate

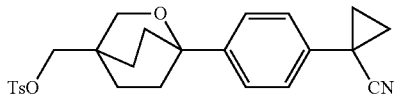

To a stirred solution of Intermediate 141A (2.4 g, 3.94 mmol) in THF (70 mL) at room temperature was added NaOH (0.472 g, 11.81 mmol) and refluxed overnight. The reaction mixture was cooled to room temperature, diluted with water (100 mL) and extracted with ethyl acetate (2×100 mL). The combined organic layers were dried over sodium sulfate and concentrated under reduced pressure. The crude material was purified by flash column chromatography (Combiflash, 24 g silica, 0-30% EtOAc/PE) to afford the title compound (1.5 g, 2.54 mmol, 65% yield) as white solid. $^1$H NMR (400 MHz, DMSO-$d_6$) δ 7.81 (d, J=8.3 Hz, 2H), 7.51 (d, J=8.1 Hz, 2H), 7.36 (d, J=8.6 Hz, 2H), 7.24 (d, J=8.3 Hz, 2H), 3.81 (s, 2H), 3.70 (s, 2H), 2.44 (s, 3H), 2.08-1.98 (m, 2H), 1.83-1.68 (m, 4H), 1.66-1.50 (m, 4H), 1.49-1.43 (m, 2H).

Step C. Intermediate 141C. Preparation of (1-(4-(1-cyanocyclopropyl)phenyl)-2-oxabicyclo[2.2.2]octan-4-yl)methyl acetate

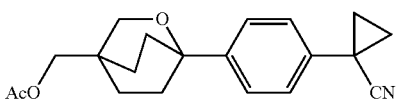 [SMILES: CC(=O)OCC12CCC(c3ccc(C4(C#N)CC4)cc3)(CC1)OC2]

To a stirred solution of Intermediate 141B (1.40 g, 3.20 mmol) in DMF (20 mL) was added cesium acetate (1.535 g, 8.00 mmol) and heated to 120° C. After stirring for 3 h, the reaction mixture was concentrated under reduced pressure and the residue was diluted with water (25 mL) and extracted with ethyl acetate (2×50 mL). The combined organic layers were dried over anhydrous sodium sulfate and concentrated under reduced pressure to afford the title compound (1.1 g, 3.01 mmol, 94% yield) as brown solid. MS (ESI) 326 (M+H). $^1$H NMR (400 MHz, DMSO-$d_6$) δ 7.38 (d, J=8.6 Hz, 2H), 7.25 (d, J=8.6 Hz, 2H), 3.80 (s, 4H), 2.11-2.01 (m, 5H), 1.85-1.75 (m, 2H), 1.74-1.57 (m, 6H), 1.50-1.44 (m, 2H).

Step D. Intermediate 141D. Preparation of 1-(4-(4-(hydroxymethyl)-2-oxabicyclo[2.2.2]octan-1-yl)phenyl)cyclopropane-1-carbonitrile

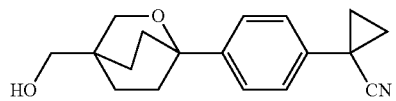 [SMILES: N#CC1(c2ccc(C34CCC(CO)(CC3)CO4)cc2)CC1]

To a stirred solution of Intermediate 141C (1.2 g, 3.69 mmol) in THF (15 mL) at room temperature was added sodium methoxide (0.084 mL, 0.369 mmol) and stirred for 2 h. The reaction mixture was diluted with DCM (25 mL) and washed with water (15 mL) followed by brine solution (25 mL). The organic layer was dried over sodium sulphate, filtered and concentrated under reduced pressure. The crude material was purified by flash column chromatography (Combiflash, 24 g silica, 0-30% EtOAc/PE) to afford the title compound (500 mg, 1.747 mmol, 47% yield) as white solid. $^1$H NMR (400 MHz, DMSO-$d_6$) δ 7.42-7.36 (m, J=9.0 Hz, 2H), 7.28-7.23 (m, J=8.5 Hz, 2H), 4.54 (t, J=5.3 Hz, 1H), 3.79 (s, 2H), 3.15 (d, J=5.5 Hz, 2H), 2.09-1.99 (m, 2H), 1.83-1.70 (m, 4H), 1.65 (td, J=10.8, 4.0 Hz, 2H), 1.59-1.44 (m, 4H). MS (ESI) 284 (M+H).

Step E. Intermediate 141E. Preparation of 1-(4-(4-formyl-2-oxabicyclo[2.2.2]octan-1-yl)phenyl)cyclopropane-1-carbonitrile

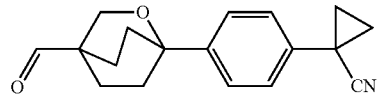 [SMILES: N#CC1(c2ccc(C34CCC(C=O)(CC3)CO4)cc2)CC1]

The title compound was synthesized according to the method described for the synthesis of Intermediate 3C by substituting Intermediate 141D where appropriate: (400 mg, 1.123 mmol, 66% yield) as a white solid. MS (ESI) 282 (M+H). $^1$H NMR (400 MHz, DMSO-$d_6$) δ 9.50 (s, 1H), 7.43-7.33 (m, 2H), 7.30-7.20 (m, 2H), 3.99 (s, 2H), 2.10 (d, J=11.7 Hz, 1H), 2.04-1.96 (m, 1H), 1.93-1.82 (m, 4H), 1.79-1.61 (m, 4H), 1.50-1.43 (m, 2H).

Step F. Intermediate 141F. Preparation of 1-(4-(4-(((3-(3-cyclopropyl-1,2,4-oxadiazol-5-yl)phenyl)amino)methyl)-2-oxabicyclo[2.2.2]octan-1-yl)phenyl)cyclopropane-1-carbonitrile

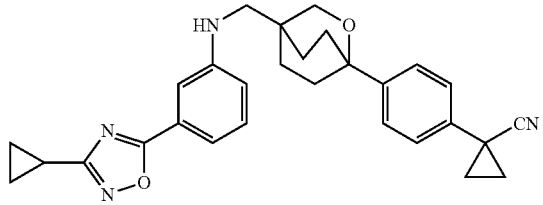 [SMILES: N#CC1(c2ccc(C34CCC(CNc5cccc(-c6nc(C7CC7)no6)c5)(CC3)CO4)cc2)CC1]

The title compound was synthesized according to the method described for the synthesis of Intermediate 1I by substituting Intermediate 8A and Intermediate 141E where appropriate: (70 mg, 0.120 mmol, 84% yield) as white solid. MS (ESI) 467 (M+H).

Step G. Example 141. Preparation of N-((1-(4-(1-Cyanocyclopropyl)phenyl)-2-oxabicyclo[2.2.2]octan-4-yl)methyl)-N-(3-(3-cyclopropyl-1,2,4-oxadiazol-5-yl)phenyl)-3-(difluoromethyl)cyclobutane-1-carboxamide The title compound was synthesized according to the method described for the synthesis of Example 3 by substituting Intermediate 141F and the corresponding acid where appropriate: (7.3 mg, 0.012 mmol, 28% yield). $^1$H NMR (400 MHz, DMSO-$d_6$) δ 8.08-7.96 (m, 2H), 7.82-7.61 (m, 2H), 7.38-7.28 (m, J=8.6 Hz, 2H), 7.27-7.14 (m, J=8.6 Hz, 2H), 6.21-5.74 (m, 1H), 3.68 (br. s., 4H), 3.15-3.01 (m, 1H), 2.43-2.41 (m, 1H), 2.34 (br. s., 1H), 2.27-2.18 (m, 1H), 2.14-2.04 (m, 1H), 2.02-1.89 (m, 2H), 1.79-1.52 (m, 10H), 1.47-1.42 (m, 2H), 1.17-1.09 (m, 2H), 1.01 (br. s., 2H). FXR EC$_{50}$ (nM)=643; MS (ESI) 599 (M+H).

The following compounds were synthesized according to the method described for the synthesis of Example 3 by substituting Intermediate 141F and the corresponding acid where appropriate:

| Ex. No. | Structure | MS (ESI) (M + H) | FXR EC$_{50}$ (nM) |
|---|---|---|---|
| 142 | | 585 | 583 |
| 143 | | 579 | 89 |

142 $^1$H NMR (400 MHz, DMSO-$d_6$) δ 8.08 (s, 1H), 8.04 (d, J = 7.3 Hz, 1H), 7.79 (d, J = 7.6 Hz, 1H), 7.70 (t, J = 7.8 Hz, 1H), 7.42-7.30 (m, J = 8.3 Hz, 2H), 7.27-7.14 (m, J = 8.3 Hz, 2H), 3.70 (br. s., 4H), 2.96-2.71 (m, 3H), 2.34 (br. s., 2H), 2.25-2.18 (m, 1H), 2.07-1.89 (m, 2H), 1.80-1.67 (m, 4H), 1.66-1.48 (m, 4H), 1.48-1.41 (m, 2H), 1.18-1.08 (m, 2H), 1.05-0.94 (m, 2H)

143 $^1$H NMR (400 MHz, DMSO-$d_6$) δ 8.15-8.00 (m, 2H), 7.79 (d, J = 7.8 Hz, 1H), 7.71 (t, J = 8.1 Hz, 1H), 7.39-7.28 (m, J = 8.3 Hz, 2H), 7.27-7.14 (m, J = 8.3 Hz, 2H), 3.70 (br. s., 4H), 2.28-2.19 (m, 1H), 2.04-1.93 (m, 2H), 1.89 (br. s., 6H), 1.79-1.67 (m, 4H), 1.67-1.59 (m, 2H), 1.55 (br. s., 2H), 1.49-1.40 (m, 2H), 1.14 (d, J = 8.3 Hz, 2H), 1.02 (br. s., 2H)

Example 144

N-((1-(4-(1-Cyanocyclopropyl)phenyl)-2-oxabicyclo[2.2.2]octan-4-yl)methyl)-N-(3-(5-cyclopropyl-1,3,4-oxadiazol-2-yl)phenyl)-3-(difluoromethyl)cyclobutane-1-carboxamide

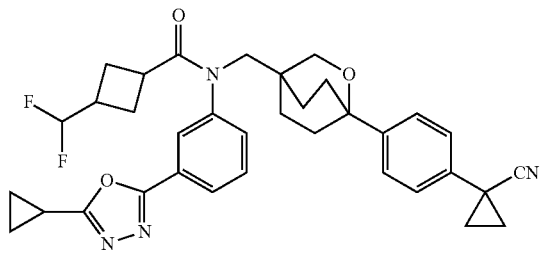
(144)

Step A. Intermediate 144A. Preparation of 1-(4-(4-(((3-(5-cyclopropyl-1,3,4-oxadiazol-2-yl)phenyl)amino)methyl)-2-oxabicyclo[2.2.2]octan-1-yl)phenyl)cyclopropane-1-carbonitrile

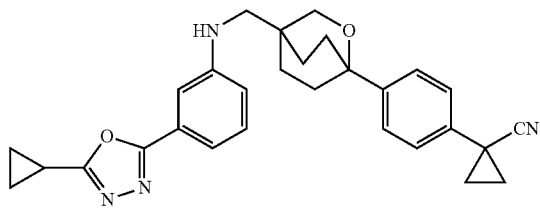 [SMILES: N#CC1(c2ccc(C34CCC(CNc5cccc(-c6nnc(C7CC7)o6)c5)(CC3)CO4)cc2)CC1]

The title compound was synthesized according to the method described for the synthesis of Intermediate 1I by substituting Intermediate 86D and Intermediate 141E where appropriate: (65 mg, 0.116 mmol, 81% yield) as a white solid. MS (ESI) 467 (M+H).

Step B. Example 144. Preparation of N-((1-(4-(1-Cyanocyclopropyl)phenyl)-2-oxabicyclo[2.2.2]octan-4-yl)methyl)-N-(3-(5-cyclopropyl-1,3,4-oxadiazol-2-yl)phenyl)-3-(difluoromethyl)cyclobutane-1-carboxamide The title compound was synthesized according to the method described for the synthesis of Example 3 by substituting Intermediate 144A and the corresponding acid where appropriate: (7.2 mg, 0.012 mmol, 28% yield). $^1$H NMR (400 MHz, DMSO-$d_6$) δ 7.91 (s, 1H), 7.94 (s, 1H), 7.75-7.59 (m, 2H), 7.40-7.30 (m, J=8.6 Hz, 2H), 7.27-7.14 (m, J=8.3 Hz, 2H), 6.24-5.72 (m, 1H), 3.76-3.60 (m, 4H), 3.06 (dd, J=18.1, 9.0 Hz, 1H), 2.43-2.41 9m, 1H), 2.36-2.30 (m, 2H), 2.16-2.02 (m, 1H), 2.02-1.90 (m, 2H), 1.81-1.67 (m, 6H), 1.67-1.48 (m, 4H), 1.48-1.42 (m, 2H), 1.29-1.05 (m, 4H); FXR EC$_{50}$ (nM)=2157; MS (ESI) 599 (M+H).

The following compounds were synthesized according to the method described for the synthesis of Example 3 by substituting Intermediate 144A and the corresponding acid where appropriate:

| Ex. No. | Structure | MS (ESI) (M + H) | FXR EC$_{50}$ (nM) |
|---|---|---|---|
| 145 | ![structure] | 585 | 4316 |

| Ex. No. | Structure | MS (ESI) (M + H) | FXR EC$_{50}$ (nM) |
|---|---|---|---|
| 146 | | 579 | 334 |

145 $^1$H NMR (400 MHz, DMSO-d$_6$) δ 8.07-7.88 (m, 2H), 7.76-7.58 (m, 2H), 7.41-7.29 (m, J = 8.6 Hz, 2H), 7.28-7.17 (m, J = 8.3 Hz, 2H), 3.70 (br. s., 4H), 2.97-2.72 (m, 3H), 2.37-2.24 (m, 3H), 2.03-1.90 (m, 2H), 1.81-1.59 (m, 4H), 1.56-1.53 (m, J = 8.6 Hz, 4H), 1.49-1.39 (m, 2H), 1.27-1.09 (m, 4H)

146 $^1$H NMR (400 MHz, DMSO-d$_6$) δ 7.97 (s, 2H), 7.69 (s, 2H), 7.39-7.29 (m, J = 7.8 Hz, 2H), 7.29-7.17 (m, J = 8.3 Hz, 2H), 3.70 (br. s., 2H), 3.62 (br. s., 2H), 2.33 (br. s., 1H), 1.98 (d, J = 9.8 Hz, 2H), 1.90 (br. s., 6H), 1.78-1.67 (m, 4H), 1.67-1.50 (m, 4H), 1.46 (t, J = 6.0 Hz, 2H), 1.27-1.09 (m, 4H)

Example 147

N-((4-(3-cyclopropyl-1,2,4-oxadiazol-5-yl)bicyclo[2.2.2]octan-1-yl)methyl)-3-fluoro-N-(3-(5-(1-methoxycyclopropyl)-1,2,4-oxadiazol-3-yl)phenyl)bicyclo[1.1.1]pentane-1-carboxamide

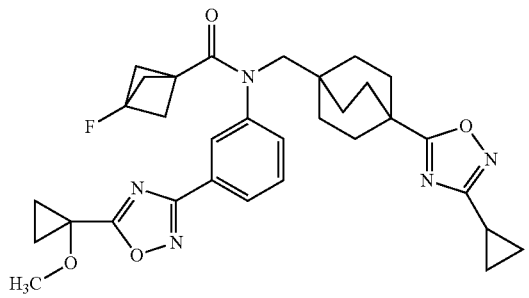
(147)

To a stirred solution of Example 110 (25 mg, 0.045 mmol) in DMF (1 mL) at 0° C., NaH (2.68 mg, 0.067 mmol) and MeI (4.19 μL, 0.067 mmol) were added. The reaction mixture was stirred at room temperature for 2 h and the concentrated under reduced pressure. The crude material was purified via preparative LC/MS using following conditions: Column: Waters XBridge C18, 150 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 15% B, 15-60% B over 25 minutes, then a 5-minute hold at 100% B; Flow Rate: 15 mL/min; Column Temperature: 25° C. Fraction collection was triggered by signals. Fractions containing the desired product were combined and dried via centrifugal evaporation to afford the title compound (8 mg, 0.014 mmol, 31% yield). $^1$H NMR (400 MHz, DMSO-d$_6$) δ 8.05-7.95 (m, 1H), 7.91 (s, 1H), 7.67 (d, J=5.1 Hz, 2H), 3.61 (br. s., 2H), 3.49 (s, 3H), 2.10-2.00 (m, 1H), 1.88 (br. s., 6H), 1.84-1.65 (m, 6H), 1.59-1.38 (m, 10H), 1.08-0.98 (m, 2H), 0.87-0.77 (m, 2H); FXR EC$_{50}$ (nM) 79; MS (ESI) 574 (M+H).

Example 148

N-(3-(3-cyclopropyl-1,2,4-oxadiazol-5-yl)phenyl)-3-fluoro-N-((4-(2-methoxypyrimidin-4-yl)bicyclo[2.2.2]octan-1-yl)methyl)bicyclo[1.1.1]pentane-1-carboxamide

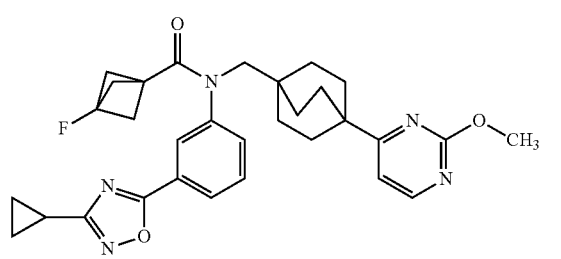
(148)

Step A. Intermediate 148A. Preparation of methyl 4-(2-chloropyrimidin-4-yl)bicyclo[2.2.2]octane-1-carboxylate

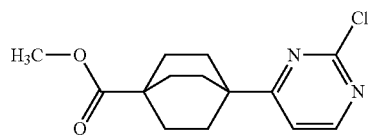 [SMILES: COC(=O)C12CCC(c3ccnc(Cl)n3)(CC1)CC2]

To a stirred solution of 2-chloropyrimidine (1 g, 8.73 mmol) and 4-(methoxycarbonyl)bicyclo[2.2.2]octane-1-carboxylic acid (1.483 g, 6.98 mmol) in a mixture of DCM (50 mL) and H₂O (50 mL) at room temperature were added potassium persulfate (2.360 g, 8.73 mmol) and silver nitrate (0.297 g, 1.746 mmol). After stirring the reaction mixture for 12 h, it was poured into EtOAc (100 mL) and the layers were separated. The aqueous layer was further extracted with EtOAc (2×50 mL). The combined organic layers were dried over MgSO₄, filtered and concentrated under reduced pressure. The crude material was purified by flash column chromatography (Combiflash, 24 g silica, 0-50% EtOAc/PE) to afford the title compound (800 mg, 2.85 mmol, 33% yield). MS (ESI) 281 (M+H).

Step B. Intermediate 148B. Preparation of (4-(2-chloropyrimidin-4-yl) bicyclo[2.2.2]octan-1-yl)methanol

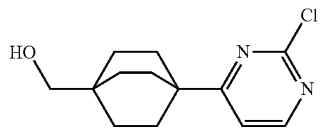 [SMILES: OCC12CCC(c3ccnc(Cl)n3)(CC1)CC2]

The title compound was synthesized according to the method described for the synthesis of Intermediate 1G by substituting Intermediate 148A where appropriate: (1 g, 3.96 mmol, 79% yield). MS (ESI) 253 (M+H).

Step C. Intermediate 148C. Preparation of 4-(2-chloropyrimidin-4-yl)bicyclo[2.2.2]octane-1-carbaldehyde

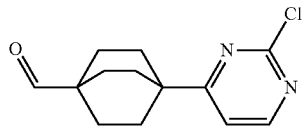

The title compound was synthesized according to the method described for the synthesis of Intermediate 3C by substituting Intermediate 148B where appropriate: (30 mg, 0.120 mmol, 30% yield). ¹H NMR (400 MHz, DMSO-d₆): δ 9.47 (s, 1H), 8.68 (d, J=8.00 Hz, 1H), 7.54 (d, J=6.80 Hz, 1H), 1.83-1.89 (m, 6H), 1.66-1.71 (m, 6H).

Step D. Intermediate 148D. Preparation of N-((4-(2-chloropyrimidin-4-yl)bicyclo [2.2.2]octan-1-yl)methyl)-3-(3-cyclopropyl-1,2,4-oxadiazol-5-yl)aniline

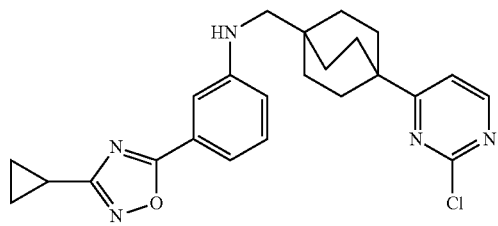 [SMILES: Clc1nccc(C23CCC(CNc4cccc(-c5nc(C6CC6)no5)c4)(CC2)CC3)n1]

The title compound was synthesized according to the method described for the synthesis of Intermediate 1I by substituting Intermediate 8A and Intermediate 148C where appropriate: (20 mg, 0.046 mmol, 37% yield). MS (ESI) 436 (M+H).

Step E. Intermediate 148E. Preparation of N-((4-(2-chloropyrimidin-4-yl) bicyclo[2.2.2]octan-1-yl)methyl)-N-(3-(3-cyclopropyl-1,2,4-oxadiazol-5-yl)phenyl)-3-fluorobicyclo[1.1.1]pentane-1-carboxamide

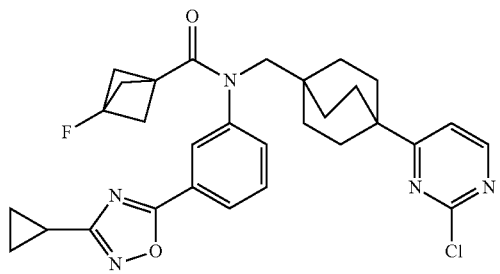 [SMILES: O=C(N(CC12CCC(c3ccnc(Cl)n3)(CC1)CC2)c1cccc(-c2nc(C3CC3)no2)c1)C12CC(F)(C1)C2]

The title compound was synthesized according to the method described for the synthesis of Example 3 by substituting Intermediate 148D and the corresponding acid where appropriate: (20 mg, 0.036 mmol, 64% yield). MS (ESI) 548 (M+H).

Step F. Example 148. Preparation of N-(3-(3-cyclopropyl-1,2,4-oxadiazol-5-yl)phenyl)-3-fluoro-N-((4-(2-methoxypyrimidin-4-yl)bicyclo[2.2.2]octan-1-yl)methyl) bicyclo[1.1.1]pentane-1-carboxamide A stirred solution of Intermediate 148E (20 mg, 0.036 mmol) in MeOH (2 mL) at room temperature was added sodium methoxide (15.77 mg, 0.073 mmol). The reaction mixture was stirred at room temperature for 3 h. The solvent was removed under reduced pressure. The crude material was purified via preparative LC/MS using following conditions: Column: Waters XBridge C18, 150 mm×19 mm, 5-μm particles; Mobile Phase A: 5:95 methanol:water with 10-mM ammonium acetate; Mobile Phase B: 95:5 methanol:water with 10-Mm ammonium acetate; Gradient: a 2-minute hold at 18% B, 18-75% B over 25 minutes, then a 5-minute hold at 100% B; Flow Rate: 15 mL/min; Column Temperature: 25° C. Fraction collection was triggered by MS signals. Fractions containing the desired product were combined and dried via centrifugal evaporation to afford the title compound (9 mg, 0.017 mmol, 45% yield). ¹H NMR (400 MHz, DMSO-d₆) δ 8.45 (d, J=5.4 Hz, 1H), 8.07 (d, J=7.6 Hz, 1H), 8.01 (s, 1H), 7.76 (d, J=8.8 Hz, 1H), 7.70 (t, J=7.9 Hz, 1H), 7.01 (d, J=5.4 Hz, 1H), 3.86 (s, 3H), 3.67 (br. s., 1H), 3.57 (br. s., 1H), 2.28-2.17 (m, 1H), 1.89 (br. s., 6H), 1.79-1.63 (m, 6H), 1.52-1.32 (m, 6H), 1.14 (dd, J=8.4, 2.6 Hz, 2H), 1.07-0.95 (m, 2H). FXR EC₅₀ (nM) 687; MS (ESI) 544 (M+H).

Example 149

N-((4-(3-cyclopropyl-1,2,4-oxadiazol-5-yl)bicyclo[2.2.2]octan-1-yl)methyl)-3-fluoro-N-(3-(1-(oxetan-3-yl)-1H-pyrazol-3-yl)phenyl)bicyclo[1.1.1]pentane-1-carboxamide (149)

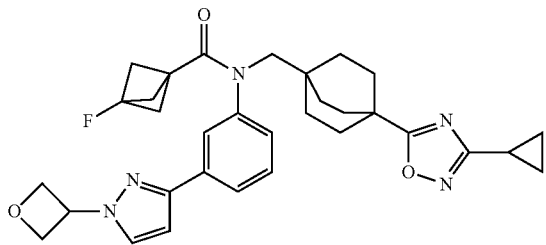

Step A. Intermediate 149A. Preparation of 3-bromo-N-((4-(3-cyclopropyl-1,2,4-oxadiazol-5-yl)bicyclo[2.2.2]octan-1-yl)methyl)aniline

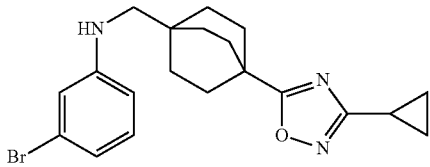 [SMILES: Brc1cccc(NCC23CCC(c4nc(C5CC5)no4)(CC2)CC3)c1]

The title compound was synthesized according to the method described for the synthesis of Intermediate 1I by substituting 3-bromoaniline and Intermediate 4C where appropriate: (700 mg, 1.740 mmol, 86% yield) as brown gummy solid. $^1$H NMR (400 MHz, DMSO-$d_6$) δ 7.02-6.92 (m, 1H), 6.76 (s, 1H), 6.59 (dd, J=8.0, 2.0 Hz, 2H), 5.80-5.70 (m, 1H), 2.79 (d, J=6.0 Hz, 2H), 2.05 (m, 1H), 1.89-1.77 (m, 6H), 1.59-1.48 (m, 6H), 1.02 (m, 2H), 0.89-0.80 (m, 2H). MS (ESI) 402 (M+H).

Step B. Intermediate 149B. Preparation of N-(3-bromophenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide

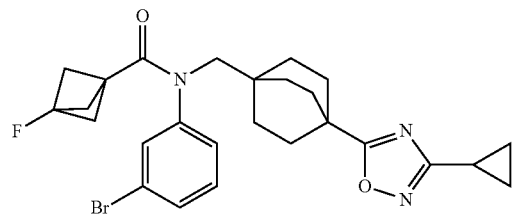

The title compound was synthesized according to the method described for the synthesis of Example 3 by substituting Intermediate 149A and the corresponding acid where appropriate: (320 mg, 0.603 mmol, 38% yield) as white solid. $^1$H NMR (400 MHz, DMSO-$d_6$) δ 7.69 (s, 1H), 7.60 (d, J=7.0 Hz, 1H), 7.45-7.39 (m, 2H), 3.56 (br. s., 1H), 3.48 (br. s., 1H), 2.08-2.00 (m, 1H), 1.86 (br. s., 6H), 1.81-1.72 (m, 6H), 1.40 (br. s., 6H), 1.01 (m, 2H), 0.86-0.79 (m, 2H). MS (ESI) 514 (M+H).

Step C. Intermediate 149C. Preparation of N-((4-(3-cyclopropyl-1,2,4-oxadiazol-5-yl)bicyclo[2.2.2]octan-1-yl)methyl)-N-(3-(5,5-dimethyl-1,3,2-dioxaborinan-2-yl)phenyl)-3-fluorobicyclo[1.1.1]pentane-1-carboxamide

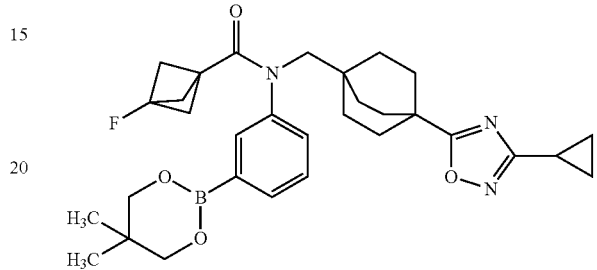

To a stirred solution of Intermediate 149B (50 mg, 0.097 mmol) in dioxane (1 mL) was added bis(neopentyl glycolato)diboron (43.9 mg, 0.194 mmol) followed by potassium acetate (42.9 mg, 0.437 mmol). The reaction mixture was then degassed and back-filled with argon and PdCl$_2$(dppf) (3.56 mg, 4.86 μmol) was added. The reaction mixture was heated to 110° C. and stirred for 3 h. The reaction mixture was then diluted with ethyl acetate (25 mL) and washed with water (2×50 mL) followed by brine solution (30 mL). The organic layer was dried over anhydrous sodium sulphate, filtered and concentrated under reduced pressure. The crude material was purified by flash column chromatography (Combiflash, 4 g silica, 0-50% EtOAc/PE) to afford the title compound (45 mg, 0.082 mmol, 85% yield) as brown gummy solid. $^1$H NMR (400 MHz, DMSO-$d_6$) δ 7.68 (s, 1H), 7.55-7.53 (m, 1H), 7.49-7.43 (m, 2H), 3.79 (s, 4H), 2.05-2.00 (m, 1H), 1.84-1.70 (m, 12H), 1.41 (br. s., 6H), 1.01-1.00 (m, 2H), 0.97 (s, 6H), 0.87-0.80 (m, 2H) (2 Protons buried under solvent peak).

Step D. Intermediate 149D. Preparation of 3-bromo-1-(oxetan-3-yl)-1H-pyrazole

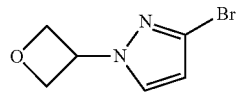

To a stirred solution of 3-bromo-1H-pyrazole (50 mg, 0.340 mmol) in DMF (2 mL) were added cesium carbonate (149 mg, 0.680 mmol), 3-iodooxetane (62.6 mg, 0.340 mmol) and heated at 150° C. in a microwave reactor for 30 min. The reaction mixture was then diluted with ethyl acetate (5 mL), washed with water (2×5 mL) and saturated brine solution (5 mL). The organic layer was dried over anhydrous sodium sulfate, filtered and concentrated under reduced pressure. The crude material was purified by flash column chromatography (Combiflash, 4 g silica, 0-50% EtOAc/PE) to afford the title compound (25 mg, 0.123 mmol, 36% yield) as white solid, MS (ESI) 205 (M+2H).

Step E. Example 149. Preparation of N-((4-(3-cyclopropyl-1,2,4-oxadiazol-5-yl) bicyclo[2.2.2]octan-1-yl)methyl)-3-fluoro-N-(3-(1-(oxetan-3-yl)-1H-pyrazol-3-yl)phenyl) bicyclo[1.1.1]pentane-1-carboxamide To a stirred solution of Intermediate 149C (30 mg, 0.055 mmol) in 1,4-dioxane (1 mL) was added Intermediate 149D (11.13 mg, 0.055 mmol), potassium carbonate (15.15 mg, 0.110 mmol) in water (0.250 mL). The resulting reaction mixture was degassed and back-filled with argon and [1,1'-bis(diphenylphosphino)ferrocene]dichloro palladium(II) (2.005 mg, 2.74 µmol) then was added. The reaction mixture was heated at 100° C. and stirred overnight. The reaction mixture was concentrated under reduced pressure and the residue was diluted with ethyl acetate (5 mL), washed with water (5 mL) followed by brine solution (5 mL). The organic layer was dried over sodium sulfate, filtered and concentrated under reduced pressure. The crude material was purified via preparative LC/MS using following conditions: Column: Waters XBridge C18, 150 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 2-minute hold at 18% B, 18-62% B over 25 minutes, then a 5-minute hold at 100% B; Flow Rate: 15 mL/min; Column Temperature: 25° C. Fraction collection was triggered by MS signals. Fractions containing the desired product were combined and dried via centrifugal evaporation to afford the title compound (9.5 mg, 0.017 mmol, 31% yield). $^1$H NMR (400 MHz, DMSO-$d_6$) δ 8.00 (d, J=2.4 Hz, 1H), 7.88 (d, J=7.8 Hz, 1H), 7.79 (s, 1H), 7.50 (t, J=7.8 Hz, 1H), 7.34 (d, J=8.1 Hz, 1H), 6.92 (d, J=2.4 Hz, 1H), 5.72-5.58 (m, 1H), 5.08-4.87 (m, 4H), 3.60 (d, J=19.3 Hz, 2H), 2.10-2.00 (m, 1H), 1.89 (br. s., 6H), 1.84-1.63 (m, 6H), 1.46 (d, J=7.6 Hz, 6H), 1.09-0.94 (m, 2H), 0.90-0.74 (m, 2H); FXR EC$_{50}$ (nM)=111; MS (ESI) 558 (M+H).

The following compounds were synthesized according to the method described for the synthesis of Example 149 by substituting Intermediate 149C and the corresponding Hetero aryl/Aryl halides where appropriate:

| Ex. No. | Structure | MS (ESI) (M + H) | FXR EC$_{50}$ (nM) |
| --- | --- | --- | --- |
| 150 | 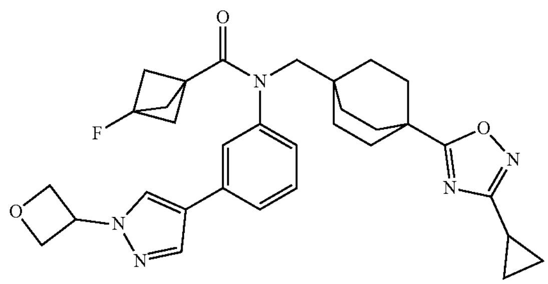 [SMILES: O=C(N(CC12CCC(c3nc(C4CC4)no3)(CC1)CC2)c1cccc(-c2cnn(C3COC3)c2)c1)C12CC(F)(C1)C2] | 558 | 87 |
| 151 | 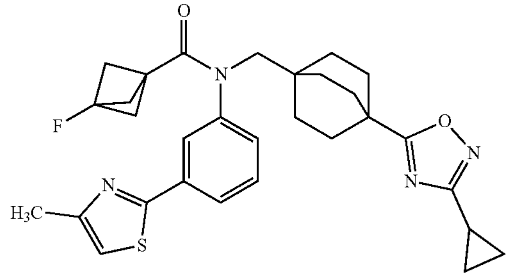 [SMILES: Cc1csc(-c2cccc(N(CC34CCC(c5nc(C6CC6)no5)(CC3)CC4)C(=O)C34CC(F)(C3)C4)c2)n1] | 533 | 79 |

| Ex. No. | Structure | MS (ESI) (M + H) | FXR EC$_{50}$ (nM) |
|---|---|---|---|
| 152 | 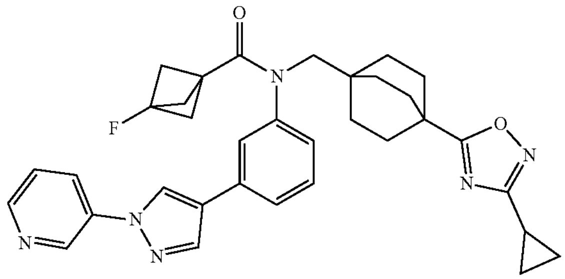 [SMILES: O=C(N(CC12CCC(c3nc(C4CC4)no3)(CC1)CC2)c1cccc(-c2cnn(-c3cccnc3)c2)c1)C12CC(F)(C1)C2] | 579 | 162 |

150  $^1$H NMR (400 MHz, DMSO-d$_6$) δ 8.51 (s, 1H), 8.14 (s, 1H), 7.75-7.57 (m, 2H), 7.44 (t, J = 7.8 Hz, 1H), 7.21 (d, J = 7.6 Hz, 1H), 5.59 (t, J = 7.1 Hz, 1H), 5.07-4.84 (m, 4H), 3.58 (s, 2H), 2.10-2.00 (m, 1H), 1.87 (br. s., 6H), 1.83-1.59 (m, 6H), 1.55-1.31 (m, 6H), 1.08-0.96 (m, 2H), 0.90-0.76 (m, 2H)

151  $^1$H NMR (400 MHz, DMSO-d$_6$) δ 7.91 (d, J = 7.6 Hz, 1H), 7.85 (s, 1H), 7.58 (t, J = 7.8 Hz, 1H), 7.51 (d, J = 7.9 Hz, 1H), 7.41 (s, 1H), 3.63 (br. s., 1H), 3.56 (br. s., 1H), 2.45 (s, 3H), 2.09-2.00 (m, 1H), 1.89 (br. s., 6H), 1.83-1.72 (m, 6H), 1.44 (br. s., 6H), 1.01 (d, J = 7.7 Hz, 2H), 0.86-0.79 (m, 2H).

152  $^1$H NMR (400 MHz, DMSO-d$_6$) δ 9.22 (s, 1H), 9.17 (s, 1H), 8.57 (d, J = 4.5 Hz, 1H), 8.43 (s, 1H), 8.29 (d, J = 8.3 Hz, 1H), 7.77 (br. s., 2H), 7.60 (dd, J = 8.1, 4.8 Hz, 1H), 7.50 (t, J = 7.9 Hz, 1H), 7.29 (d, J = 7.7 Hz, 1H), 3.61 (d, J = 9.2 Hz, 2H), 2.09-2.00 (m, 1H), 1.89 (br. s., 6H), 1.83-1.73 (m, 6H), 1.53-1.39 (m, 6H), 1.01 (d, J = 7.8 Hz, 2H), 0.83 (br. s., 2H).

Example 153

N-((4-(3-(tert-butyl)-1,2,4-oxadiazol-5-yl)bicyclo[2.2.2]octan-1-yl)methyl)-N-(3-(5-cyclopropyl-1,3,4-oxadiazol-2-yl)phenyl)-3-fluorobicyclo[1.1.1]pentane-1-carboxamide (153)

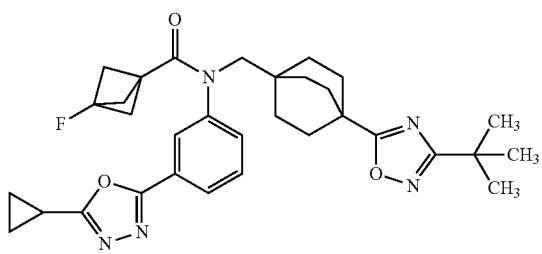

Step A. Intermediate 153A. Preparation of methyl 4-(((3-(5-cyclopropyl-1,3,4-oxadiazol-2-yl)phenyl)amino)methyl)bicyclo[2.2.2]octane-1-carboxylate

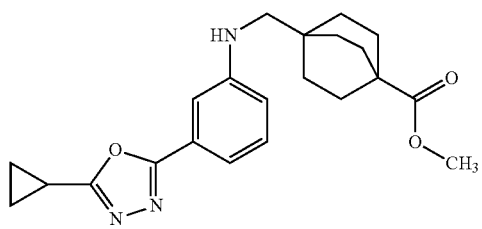 [SMILES: COC(=O)C12CCC(CNc3cccc(-c4nnc(C5CC5)o4)c3)(CC1)CC2]

The title compound was synthesized according to the method described for the synthesis of Intermediate 1I by substituting Intermediate 86D and Intermediate 88B where appropriate: (250 mg, 0.655 mmol, 86% yield) as gummy liquid. MS (ESI) 382 (M+H).

Step B. Intermediate 153B. Preparation of methyl 4-((N-(3-(5-cyclopropyl-1,3,4-oxadiazol-2-yl)phenyl)-3-fluorobicyclo[1.1.1]pentane-1-carboxamido)methyl)bicycle [2.2.2]octane-1-carboxylate

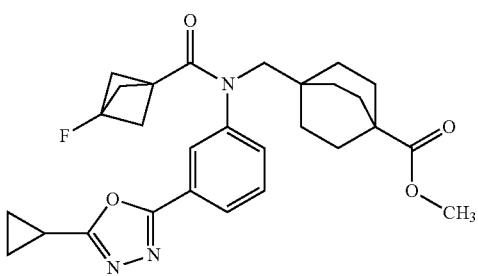 [SMILES: COC(=O)C12CCC(CN(C(=O)C34CC(F)(C3)C4)c3cccc(-c4nnc(C5CC5)o4)c3)(CC1)CC2]

The title compound was synthesized according to the method described for the synthesis of Example 3 by substituting Intermediate 153A and the corresponding acid where appropriate: (180 mg, 0.365 mmol, 56% yield) as gummy solid. MS (ESI) 494 (M+H).

Step C. Intermediate 153C. Preparation of 4-((N-(3-(5-cyclopropyl-1,3,4-oxadiazol-2-yl)phenyl)-3-fluorobicyclo[1.1.1]pentane-1-carboxamido)methyl)bicyclo[2.2.2]octane-1-carboxylic acid

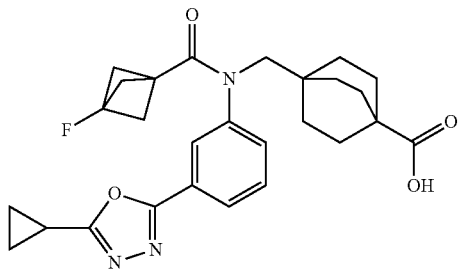 [SMILES: O=C(O)C12CCC(CN(C(=O)C34CC(F)(C3)C4)c3cccc(-c4nnc(C5CC5)o4)c3)(CC1)CC2]

To a stirred solution of Intermediate 153B (180 mg, 0.365 mmol) in MeOH (5 mL) at room temperature was added a solution of NaOH (72.9 mg, 1.823 mmol) in $H_2O$ (2.5 mL) and stirred overnight. The reaction mixture was concentrated under reduced pressure and the residue was diluted with water (10 mL). The aqueous solution was acidified with 1.5 N aqueous HCl and extracted with ethyl acetate (2×10 mL). The combined organic layers were dried over anhydrous sodium sulphate, filtered, and concentrated under reduced pressure to afford the title compound (160 mg, 0.334 mmol, 91% yield) as white puffy solid. MS (ESI) 480 (M+H).

Step D. Example 153. Preparation of N-((4-(3-(tert-butyl)-1,2,4-oxadiazol-5-yl) bicyclo[2.2.2]octan-1-yl)methyl)-N-(3-(5-cyclopropyl-1,3,4-oxadiazol-2-yl)phenyl)-3-fluorobicyclo[1.1.1]pentane-1-carboxamide The title compound was synthesized according to the method described for the synthesis of Intermediate 3A by substituting Intermediate 153C and Intermediate 88F where appropriate: (3.4 mg, 6.07 µmol, 19% yield). $^1$H NMR (400 MHz, DMSO-$d_6$) δ 8.01-7.94 (m, 1H), 7.93 (s, 1H), 7.72-7.58 (m, 2H), 3.62 (br. s., 2H), 2.38-2.27 (m, 1H), 1.89 (br. s., 6H), 1.86-1.70 (m, 6H), 1.55-1.32 (m, 6H), 1.32-1.22 (m, 9H), 1.22-1.09 (m, 4H); FXR $EC_{50}$ (nM)=73; MS (ESI) 560 (M+H).

Example 154

N-(3-(5-cyclopropyl-1,3,4-oxadiazol-2-yl)phenyl)-3-fluoro-N-((4-(5-(1-methylcyclopropyl)-1,2,4-oxadiazol-3-yl)bicyclo[2.2.2]octan-1-yl)methyl) bicyclo[1.1.1]pentane-1-carboxamide (154)

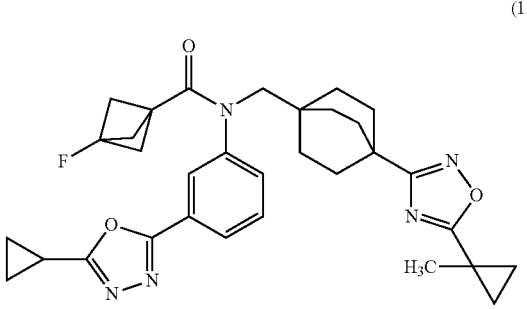

Step A. Intermediate 154A. Preparation of 4-((N-(3-(5-cyclopropyl-1,3,4-oxadiazol-2-yl)phenyl)-3-fluorobicyclo[1.1.1]pentane-1-carboxamido)methyl)bicyclo[2.2.2]octane-1-carboxamide

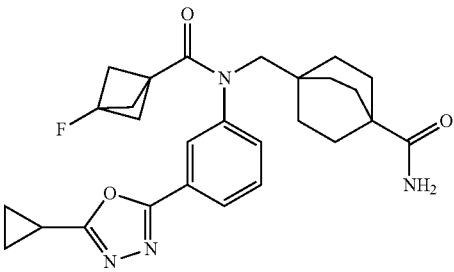 [SMILES: NC(=O)C12CCC(CN(C(=O)C34CC(F)(C3)C4)c3cccc(-c4nnc(C5CC5)o4)c3)(CC1)CC2]

The title compound was synthesized according to the method described for the synthesis of Intermediate 114A by substituting Intermediate 153C where appropriate: (160 mg, 0.147 mmol, 50% yield). MS (ESI) 479 (M+H).

Step B. Intermediate 154B. Preparation of N-((4-cyanobicyclo[2.2.2]octan-1-yl) methyl)-N-(3-(5-cyclopropyl-1,3,4-oxadiazol-2-yl)phenyl)-3-fluoro-bicyclo[1.1.1]pentane-1-carboxamide

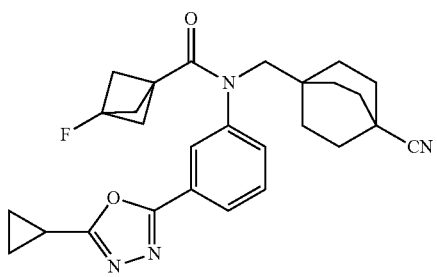 [SMILES: N#CC12CCC(CN(C(=O)C34CC(F)(C3)C4)c3cccc(-c4nnc(C5CC5)o4)c3)(CC1)CC2]

The title compound was synthesized according to the method described for the synthesis of Intermediate 114B by substituting Intermediate 154A where appropriate: (100 mg, 0.217 mmol, 65% yield) as pale yellow solid. MS (ESI) 461 (M+H).

Step C. Intermediate 154C. Preparation of (E)-N-(3-(5-cyclopropyl-1,3,4-oxadiazol-2-yl)phenyl)-3-fluoro-N-((4-(N'-hydroxycarbamimidoyl)bicyclo[2.2.2]octan-1-yl)methyl) bicyclo[1.1.1]pentane-1-carboxamide

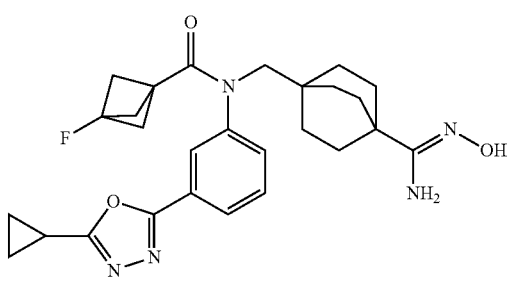 [SMILES: N/C(=N\O)C12CCC(CN(C(=O)C34CC(F)(C3)C4)c3cccc(-c4nnc(C5CC5)o4)c3)(CC1)CC2]

The title compound was synthesized according to the method described for the synthesis of Intermediate 88F by substituting Intermediate 154B where appropriate: (70 mg, 0.142 mmol, 59% yield) as white solid. MS (ESI) 494 (M+H).

Step D. Example 154. Preparation of N-(3-(5-cyclopropyl-1,3,4-oxadiazol-2-yl) phenyl)-3-fluoro-N-((4-(5-(1-methylcyclopropyl)-1,2,4-oxadiazol-3-yl)bicyclo[2.2.2]octan-1-yl)methyl)bicyclo[1.1.1]pentane-1-carboxamide The title compound was synthesized according to the method described for the synthesis of Intermediate 3A by substituting Intermediate 154C and 1-methylcyclopropane-1-carboxylic acid where appropriate: (6.5 mg, 0.012 mmol, 38% yield). $^1$H NMR (400 MHz, DMSO-d$_6$) δ 7.99-7.94 (m, 1H), 7.92 (s, 1H), 7.71-7.61 (m, 2H), 3.61 (br. s., 2H), 2.38-2.27 (m, 1H), 1.89 (br. s., 6H), 1.79-1.59 (m, 6H), 1.52-1.31 (m, 9H), 1.26-1.10 (m, 6H), 1.07-1.00 (m, 2H); FXR EC$_{50}$ (nM)=27; MS (ESI) 558 (M+H).

The following compounds were synthesized according to the method described for the synthesis of Intermediate 3A by substituting Intermediate 154C and the corresponding acids where appropriate:

| Ex. No. | Structure | MS (ESI) (M + H) | FXR EC$_{50}$ (nM) |
|---|---|---|---|
| 155 | 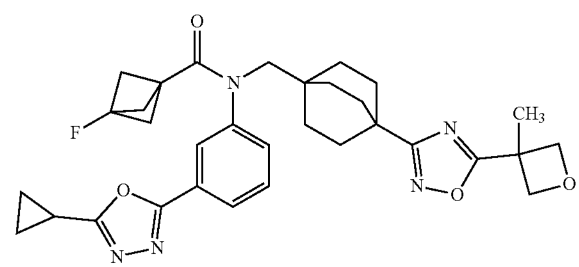 [SMILES: CC1(c2nc(C34CCC(CN(C(=O)C56CC(F)(C5)C6)c5cccc(-c6nnc(C7CC7)o6)c5)(CC3)CC4)no2)COC1] | 574 | 72 |
| 156 | 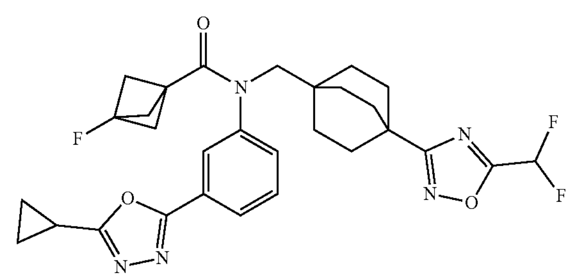 [SMILES: O=C(N(CC12CCC(c3noc(C(F)F)n3)(CC1)CC2)c1cccc(-c2nnc(C3CC3)o2)c1)C12CC(F)(C1)C2] | 554 | 103 |
| 157 | 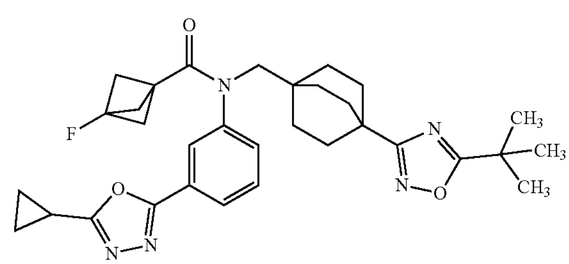 [SMILES: CC(C)(C)c1nc(C23CCC(CN(C(=O)C45CC(F)(C4)C5)c4cccc(-c5nnc(C6CC6)o5)c4)(CC2)CC3)no1] | 560 | 43 |

155 $^1$H NMR (400 MHz, DMSO-d$_6$) δ 7.99-7.95 (m, 1H), 7.93 (s, 1H), 7.67 (d, J = 5.4 Hz, 2H), 4.84 (d, J = 6.1 Hz, 2H), 4.52 (d, J = 6.1 Hz, 2H), 3.62 (br. s., 2H), 2.36-2.31 (m, 1H), 1.89 (br. s., 6H), 1.83-1.62 (m, 9H), 1.54-1.34 (m, 6H), 1.24-1.05 (m, 4H)

156 $^1$H NMR (400 MHz, DMSO-d$_6$) δ 8.02-7.87 (m, 2H), 7.67 (d, J = 5.1 Hz, 2H), 7.42 (s, 1H), 3.63 (br. s., 2H), 2.38-2.29 (m, 1H), 1.89 (br. s., 6H), 1.84-1.68 (m, 6H), 1.55-1.36 (m, 6H), 1.30-1.07 (m, 4H)

157 $^1$H NMR (400 MHz, DMSO-d$_6$) δ 8.01-7.94 (m, 1H), 7.92 (s, 1H), 7.72-7.59 (m, 2H), 3.60 (d, J = 7.8 Hz, 2H), 2.36-2.30 (m, 1H), 1.89 (br. s., 6H), 1.81-1.62 (m, 6H), 1.49-1.36 (m, 6H), 1.33 (s, 9H), 1.23-1.09 (m, 4H)

Example 158

N-((4-(3-cyclopropyl-1,2,4-oxadiazol-5-yl)bicyclo[2.2.2]octan-1-yl)methyl)-N-(3-(1-(cyclopropylsulfonyl)-1H-pyrazol-4-yl)phenyl)-3-fluorobicyclo[1.1.1]pentane-1-carboxamide

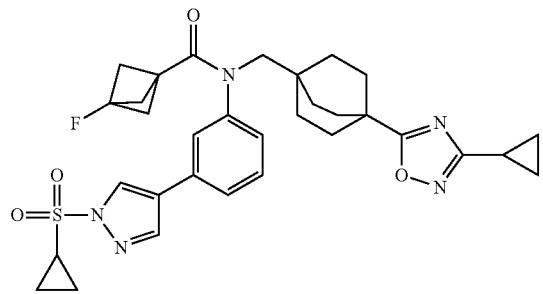

(158)

Step A. Intermediate 158A. Preparation of 1-(cyclopropylsulfonyl)-4-(4,4,5,5-tetramethyl-1,3,2-dioxaborolan-2-yl)-1H-pyrazole

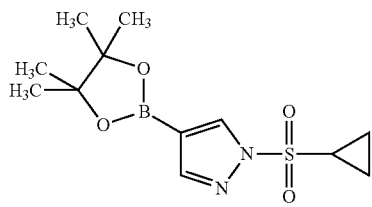 [SMILES: CC1(C)OB(c2cnn(S(=O)(=O)C3CC3)c2)OC1(C)C]

To a stirred solution of 4-(4,4,5,5-tetramethyl-1,3,2-dioxaborolan-2-yl)-1H-pyrazole (1 g, 5.15 mmol) in DMF (15 mL) was added NaH (0.309 g, 7.73 mmol) and stirred for 5 min at room temperature. To the reaction mixture was added cyclopropanesulfonyl chloride (0.797 g, 5.67 mmol) drop wise and stirred for 6 h at room temperature. The reaction mixture was then quenched with saturated aqueous ammonium chloride solution (20 mL) and extracted with ethyl acetate (2×50 mL). The combined organic extracts were washed with water (50 mL) and saturated brine solution (2×50 mL). The organic layer was then dried over anhydrous sodium sulfate, filtered and concentrated under reduced pressure. The crude material was purified by flash column chromatography (Combiflash, 24 g silica, 0-80% EtOAc/PE) to afford 1-(cyclopropylsulfonyl)-4-(4,4,5,5-tetramethyl-1,3,2-dioxaborolan-2-yl)-1H-pyrazole (750 mg, 2.52 mmol, 49% yield) as a white solid. $^1$H NMR (400 MHz, DMSO-$d_6$) δ 8.36 (s, 1H), 8.30 (s, 1H), 3.17-0.00 (m, 1H), 1.31-1.25 (m, 14H), 1.21-1.17 (m, 2H).

Step B. Example 158. Preparation of N-((4-(3-cyclopropyl-1,2,4-oxadiazol-5-yl) bicyclo[2.2.2]octan-1-yl)methyl)-N-(3-(1-(cyclopropylsulfonyl)-1H-pyrazol-4-yl) phenyl)-3-fluorobicyclo[1.1.1]pentane-1-carboxamide The title compound was synthesized according to the method described for the synthesis of Example 149 by substituting Intermediate 149B and Intermediate 158A where appropriate: (17.9 mg, 0.029 mmol, 30% yield). $^1$H NMR (400 MHz, DMSO-$d_6$) δ 8.96 (s, 1H), 8.57 (s, 1H), 7.92-7.84 (m, 1H), 7.80 (d, J=7.8 Hz, 1H), 7.48 (t, J=7.9 Hz, 1H), 7.36-7.24 (m, 1H), 3.67-3.51 (m, 2H), 3.22-3.13 (m, 1H), 2.10-1.99 (m, 1H), 1.87 (d, J=5.9 Hz, 6H), 1.83-1.58 (m, 6H), 1.56-1.35 (m, 6H), 1.35-1.28 (m, 2H), 1.26-1.19 (m, 2H), 1.05-0.96 (m, 2H), 0.87-0.77 (m, 2H); FXR EC$_{50}$ (nM)=43; MS (ESI) 606 (M+H).

Example 159

N-((4-(3-cyclopropyl-1,2,4-oxadiazol-5-yl)bicyclo[2.2.2]octan-1-yl)methyl)-3-fluoro-N-(3-(1-(methylsulfonyl)-1H-pyrazol-4-yl)phenyl)bicyclo[1.1.1]pentane-1-carboxamide

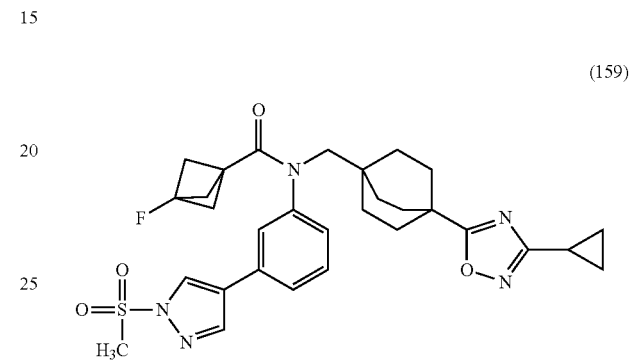

(159)

Step A. Intermediate 159A. Preparation of 1-(methylsulfonyl)-4-(4,4,5,5-tetramethyl-1,3,2-dioxaborolan-2-yl)-1H-pyrazole

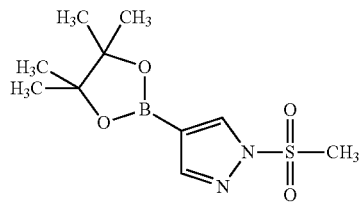

The title compound was synthesized according to the method described for the synthesis of Intermediate 158A by substituting 4-(4,4,5,5-tetramethyl-1,3,2-dioxaborolan-2-yl)-1H-pyrazole and methanesulfonyl chloride where appropriate: (2 g, 7.35 mmol, 57% yield) as colorless oil. $^1$H NMR (400 MHz, DMSO-$d_6$) δ 8.31 (s, 1H), 8.01 (s, 1H), 3.31 (s, 3H), 1.31 (s, 12H).

Step B. Example 159. Preparation of N-((4-(3-cyclopropyl-1,2,4-oxadiazol-5-yl) bicyclo[2.2.2]octan-1-yl)methyl)-3-fluoro-N-(3-(1-(methylsulfonyl)-1H-pyrazol-4-yl) phenyl)bicyclo[1.1.1]pentane-1-carboxamide The title compound was synthesized according to the method described for the synthesis of Example 149 by substituting Intermediate 149B and Intermediate 159A where appropriate: (8.4 mg, 0.014 mmol, 14% yield). $^1$H NMR (400 MHz, DMSO-$d_6$) δ 8.95 (s, 1H), 8.57 (s, 1H), 7.88 (s, 1H), 7.80 (d, J=8.3 Hz, 1H), 7.48 (t, J=7.8 Hz, 1H), 7.30 (d, J=9.0 Hz, 1H), 3.66-3.48 (m, 5H), 2.08-2.01 (m, 1H), 1.87 (br. s., 6H), 1.83-1.61 (m, 6H), 1.55-1.33 (m, 6H), 1.06-0.95 (m, 2H), 0.89-0.76 (m, 2H); FXR EC$_{50}$ (nM)=73; MS (ESI) 580 (M+H).

The following compounds were synthesized according to the method described for the synthesis of Example 149 by substituting Intermediate 149B and the corresponding hetero aryl boronates where appropriate:

| Ex. No. | Structure | MS (ESI) (M + H) | FXR EC$_{50}$ (nM) |
|---|---|---|---|
| 160 | 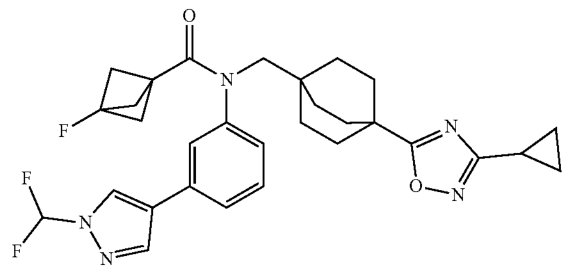 [SMILES: O=C(N(CC12CCC(c3nc(C4CC4)no3)(CC1)CC2)c1cccc(-c2cnn(C(F)F)c2)c1)C12CC(F)(C1)C2] | 552 | 43 |
| 161 | 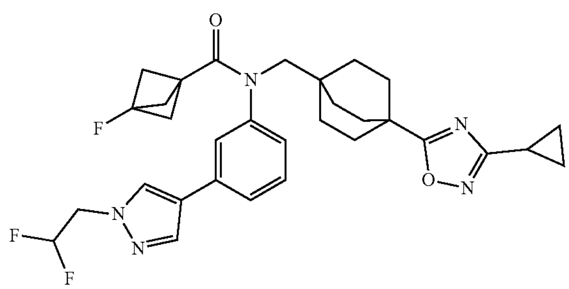 [SMILES: O=C(N(CC12CCC(c3nc(C4CC4)no3)(CC1)CC2)c1cccc(-c2cnn(CC(F)F)c2)c1)C12CC(F)(C1)C2] | 566 | 96 |
| 162 | 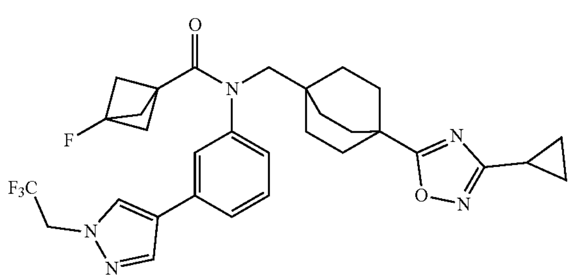 [SMILES: O=C(N(CC12CCC(c3nc(C4CC4)no3)(CC1)CC2)c1cccc(-c2cnn(CC(F)(F)F)c2)c1)C12CC(F)(C1)C2] | 584 | 116 |

160 $^{1}$H NMR (400 MHz, DMSO-d$_6$) δ 8.86 (s, 1H), 8.39 (s, 1H), 8.00-7.65 (m, 3H), 7.48 (t, J =7.8 Hz, 1H), 7.34-7.22 (m, 1H), 3.59 (d, J = 6.8 Hz, 2H), 2.08-2.00 (m, 1H), 1.87 (br. s., 6H), 1.83-1.54 (m, 6H), 1.54-1.33 (m, 6H), 1.05-0.96 (m, 2H), 0.88-0.77 (m, 2H).

161 $^{1}$H NMR (400 MHz, DMSO-d$_6$) δ 8.35 (s, 1H), 8.10 (s, 1H), 7.71-7.53 (m, 2H), 7.44 (t, J = 7.8 Hz, 1H), 7.21 (d, J = 7.6 Hz, 1H), 6.41 (t, J = 3.7 Hz, 1H), 4.65 (td, J = 15.2, 3.7 Hz, 2H), 3.58 (d, J = 9.3 Hz, 2H), 2.13-1.99 (m, 1H), 1.99-1.83 (m, 6H), 1.83-1.58 (m, 6H), 1.57-1.33 (m, 6H), 1.10-0.93 (m, 2H), 0.90-0.75 (m, 2H).

162 $^{1}$H NMR (400 MHz, DMSO-d$_6$) δ 8.41 (s, 1H), 8.16 (s, 1H), 7.72-7.55 (m, 2H), 7.45 (t, J = 7.8 Hz, 1H), 7.23 (d, J = 9.0 Hz, 1H), 5.17 (q, J = 9.0 Hz, 2H), 3.71-3.58 (m, 1H), 3.58-3.43 (m, 1H), 2.10-1.99 (m, 1H), 1.98-1.83 (m, 6H), 1.83-1.59 (m, 6H), 1.55-1.33 (m, 6H), 1.08-0.96 (m, 2H), 0.87-0.78 (m, 2H)

Example 163

N-((4-(3-cyclopropyl-1-methyl-1H-pyrazol-5-yl)bicyclo[2.2.2]octan-1-yl)methyl)-3-fluoro-N-(3-(5-isopropyl-1,2,4-oxadiazol-3-yl)phenyl)bicyclo[1.1.1]pentane-1-carboxamide (163)

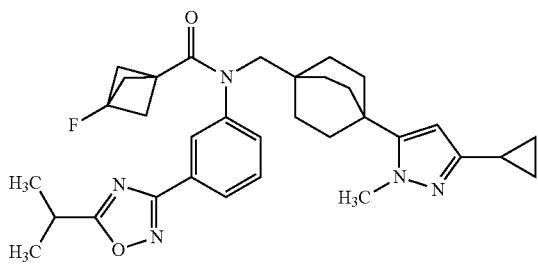

Step A. Intermediate 163A. Preparation of 3-(((4-(3-cyclopropyl-1-methyl-1H-pyrazol-5-yl)bicyclo[2.2.2]octan-1-yl)methyl)amino)benzonitrile

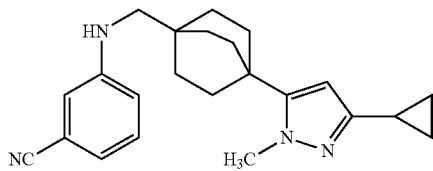 [SMILES: Cn1nc(C2CC2)cc1C12CCC(CNc3cccc(C#N)c3)(CC1)CC2]

The title compound was synthesized according to the method described for the synthesis of Intermediate 1I by substituting 3-aminobenzonitrile and Intermediate 126B where appropriate: (135 mg, 0.356 mmol, 71% yield) as an off-white solid. MS (ESI) 361 (M+H).

Step B. Intermediate 163B. Preparation of N-(3-cyanophenyl)-N-((4-(3-cyclopropyl-1-methyl-1H-pyrazol-5-yl)bicyclo[2.2.2]octan-1-yl)methyl)-3-fluorobicyclo[1.1.1]pentane-1-carboxamide

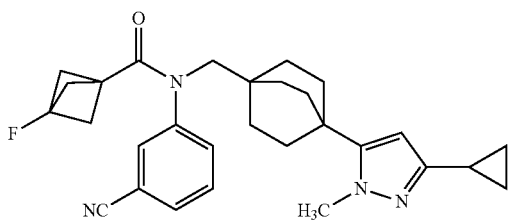 [SMILES: Cn1nc(C2CC2)cc1C12CCC(CN(C(=O)C34CC(F)(C3)C4)c3cccc(C#N)c3)(CC1)CC2]

The title compound was synthesized according to the method described for the synthesis of Example 3 by substituting Intermediate 163A and the corresponding acid where appropriate: (110 mg, 0.221 mmol, 61% yield) as an off-white solid. MS (ESI) 473 (M+H).

Step C. Intermediate 163C. Preparation of (Z)—N-((4-(3-cyclopropyl-1-methyl-1H-pyrazol-5-yl)bicyclo[2.2.2]octan-1-yl)methyl)-3-fluoro-N-(3-(N'-hydroxycarbamimidoyl) phenyl)bicyclo[1.1.1]pentane-1-carboxamide

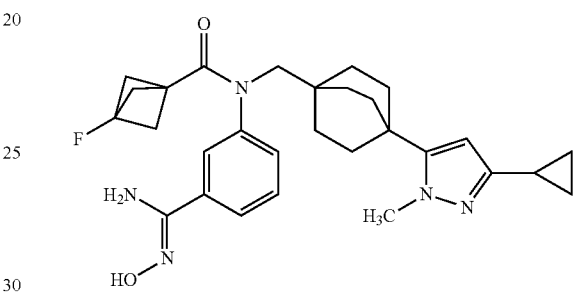

The title compound was synthesized according to the method described for the synthesis of Intermediate 88F by substituting Intermediate 163B where appropriate: (120 mg, 0.225 mmol, 76% yield) as an off-white solid. MS (ESI) 506 (M+H).

Step D. Example 163. Preparation of N-((4-(3-cyclopropyl-1-methyl-1H-pyrazol-5-yl)bicyclo[2.2.2]octan-1-yl)methyl)-3-fluoro-N-(3-(5-isopropyl-1,2,4-oxadiazol-3-yl)phenyl)bicyclo[1.1.1]pentane-1-carboxamide The title compound was synthesized according to the method described for the synthesis of Intermediate 3A by substituting Intermediate 163C and the corresponding acid where appropriate: (7.8 mg, 0.014 mmol, 35% yield). $^1$H NMR (400 MHz, DMSO-$d_6$) δ 8.02-7.99 (m, 1H), 7.89 (s, 1H), 7.66-7.64 (m, 2H), 5.61 (s, 1H), 3.72 (s, 3H), 3.58 (br. s., 2H), 3.42-3.36 (m, 1H), 1.88 (br. s., 6H), 1.79-1.59 (m, 7H), 1.50-1.31 (m, 12H), 0.74-0.72 (m, 2H), 0.53-0.51 (m, 2H). FXR EC$_{50}$ (nM) 156; MS (ESI) 558 (M+H).

The following compounds were synthesized according to the method described for the synthesis of Intermediate 3A by substituting Intermediate 163C and the corresponding acids where appropriate:

| Ex. No. | Structure | MS (ESI) (M + H) | FXR EC$_{50}$ (nM) |
|---|---|---|---|
| 164 | 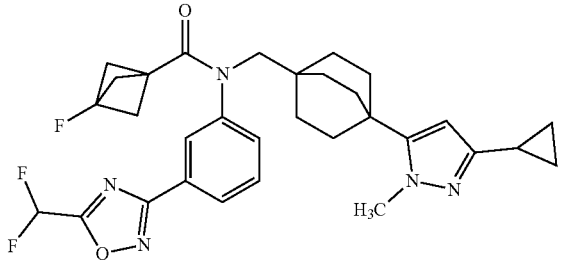 [SMILES: Cn1nc(C2CC2)cc1C12CCC(CN(C(=O)C34CC(F)(C3)C4)c3cccc(-c4noc(C(F)F)n4)c3)(CC1)CC2] | 566 | 104 |
| 165 | 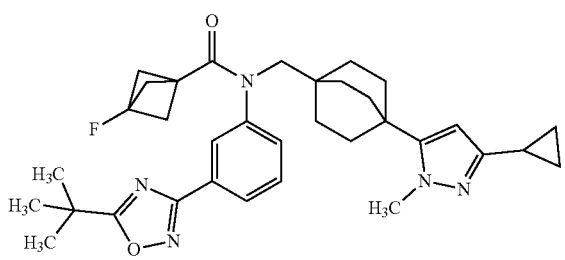 [SMILES: Cn1nc(C2CC2)cc1C12CCC(CN(C(=O)C34CC(F)(C3)C4)c3cccc(-c4noc(C(C)(C)C)n4)c3)(CC1)CC2] | 572 | 124 |
| 166 | 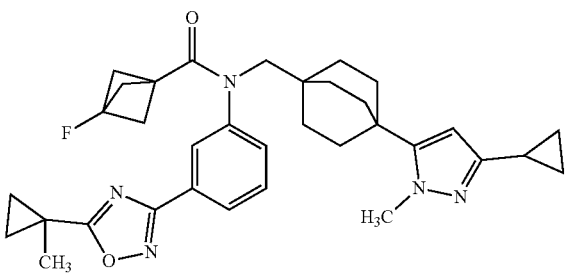 [SMILES: Cn1nc(C2CC2)cc1C12CCC(CN(C(=O)C34CC(F)(C3)C4)c3cccc(-c4noc(C5(C)CC5)n4)c3)(CC1)CC2] | 570 | 82 |
164 $^1$H NMR (400 MHz, DMSO-d$_6$) δ 8.07-8.05 (m, 1H), 7.97 (d, J = 1.0 Hz, 1H), 7.71-7.69 (m, 2H), 7.56 (t, J = 51.60 Hz, 1H), 5.61 (s, 1H), 3.72 (s, 3H), 3.59 (s, 2H), 1.89 (br. s., 6H), 1.77-1.61 (m, 7H), 1.49-1.30 (m, 6H), 0.74-0.71 (m, 2H), 0.53-0.51 (m, 2H).
165 $^1$H NMR (400 MHz, DMSO-d$_6$) δ 8.02-8.00 (m, 1H), 7.90 (s, 1H), 7.66-7.65 (m, 2H), 5.61 (s, 1H), 3.72 (s, 3H), 3.20 (br. s., 2H), 1.89 (br. s., 6H), 1.80-1.57 (m, 7H), 1.47 (s, 9H), 1.45-1.28 (m, 6H), 0.76-0.71 (m, 2H), 0.54-0.50 (m, 2H).
166 $^1$H NMR (400 MHz, DMSO-d$_6$) δ 7.98-7.96 (m, 1H), 7.86 (s, 1H), 7.64-7.63 (m, 2H), 5.61 (s, 1H), 3.72 (s, 3H), 3.58 (br. s., 2H), 1.88 (br. s., 6H), 1.78-1.61 (m, 7H), 1.58 (s, 3H), 1.47-1.31 (m, 8H), 1.20-1.11 (m, 2H), 0.74-0.71 (m, 2H), 0.53-0.51 (m, 2H).

Example 167

N-(3-(5-(tert-butyl)-1,2,4-oxadiazol-3-yl)phenyl)-N-((4-(5-cyclopropyl-1-methyl-1H-pyrazol-3-yl)bicyclo[2.2.2]octan-1-yl)methyl)-3-fluorobicyclo[1.1.1]pentane-1-carboxamide

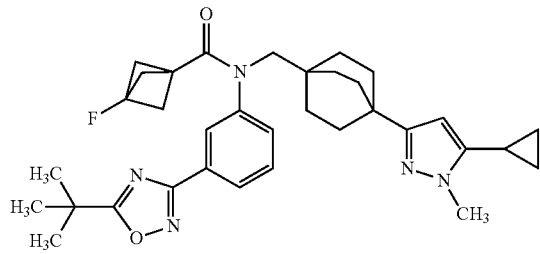

(167)

Step A. Intermediate 167A. Preparation of 3-(((4-(5-cyclopropyl-1-methyl-1H-pyrazol-3-yl)bicyclo[2.2.2]octan-1-yl)methyl)amino)benzonitrile

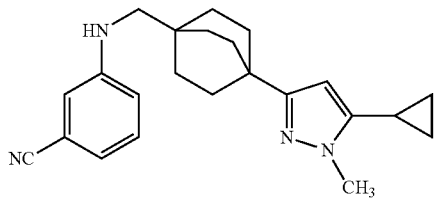 [SMILES: Cn1nc(C23CCC(CNc4cccc(C#N)c4)(CC2)CC3)cc1C1CC1]

The title compound was synthesized according to the method described for the synthesis of Intermediate 1I by substituting 3-aminobenzonitrile and Intermediate 124E where appropriate: (130 mg, 0.361 mmol, 72% yield) as an off-white solid. (ESI) 361 (M+H).

Step B. Intermediate 167B. Preparation of N-(3-cyanophenyl)-N-((4-(5-cyclopropyl-1-methyl-1H-pyrazol-3-yl)bicyclo[2.2.2]octan-1-yl)methyl)-3-fluorobicyclo[1.1.1]pentane-1-carboxamide

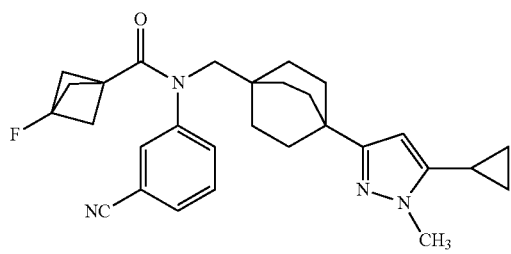

The title compound was synthesized according to the method described for the synthesis of Example 3 by substituting Intermediate 167A and the corresponding acid where appropriate: (95 mg, 0.201 mmol, 56% yield) as an off-white solid. MS (ESI) 473 (M+H).

Step C. Intermediate 167C. Preparation of (E)-N-((4-(5-cyclopropyl-1-methyl-1H-pyrazol-3-yl)bicyclo[2.2.2]octan-1-yl)methyl)-3-fluoro-N-(3-(N'-hydroxycarbamimidoyl) phenyl)bicyclo[1.1.1]pentane-1-carboxamide The title compound was synthesized according to the method described for the synthesis of Intermediate 88F by substituting Intermediate 167B where appropriate: (100 mg, 0.188 mmol, 93% yield) as an off-white solid. (ESI) 506 (M+H).

Step D. Example 167. Preparation of N-(3-(5-(tert-butyl)-1,2,4-oxadiazol-3-yl)phenyl)-N-((4-(5-cyclopropyl-1-methyl-1H-pyrazol-3-yl)bicyclo[2.2.2]octan-1-yl)methyl)-3-fluorobicyclo[1.1.1]pentane-1-carboxamide The title compound was synthesized according to the method described for the synthesis of Intermediate 3A by substituting Intermediate 167C and the corresponding acid where appropriate: (9.7 mg, 0.017 mmol, 43% yield). $^1$H NMR (400 MHz, DMSO-$d_6$) δ 8.01 (d, J=7.1 Hz, 1H), 7.88 (s, 1H), 7.72-7.56 (m, 2H), 5.59 (s, 1H), 3.69 (s, 3H), 3.57 (br. s., 2H), 1.88 (br. s., 6H), 1.75-1.72 (m, 1H), 1.70-1.50 (m, 6H), 1.47 (s, 9H), 1.41-1.29 (m, 6H), 0.94-0.82 (m, 2H), 0.60-0.45 (m, 2H). FXR EC$_{50}$ (nM) 69; MS (ESI) 572 (M+H).

The following compounds were synthesized according to the method described for the synthesis of Intermediate 3A by substituting Intermediate 167C and the corresponding acid where appropriate:

| Ex. No. | Structure | MS (ESI) (M + H) | FXR EC$_{50}$ (nM) |
|---|---|---|---|
| 168 | 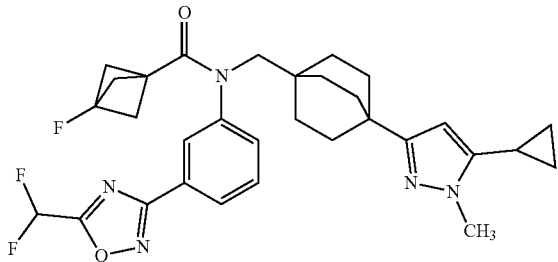 [SMILES: Cn1nc(C23CCC(CN(C(=O)C45CC(F)(C4)C5)c4cccc(-c5noc(C(F)F)n5)c4)(CC2)CC3)cc1C1CC1] | 566 | 111 |
| 169 | 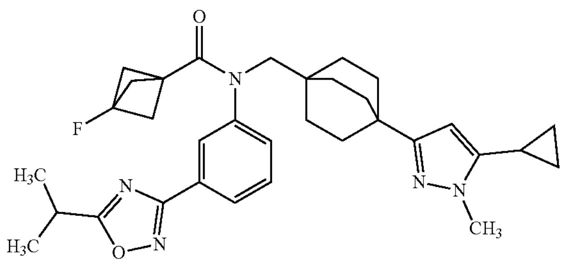 [SMILES: CC(C)c1nc(-c2cccc(N(CC34CCC(c5cc(C6CC6)n(C)n5)(CC3)CC4)C(=O)C34CC(F)(C3)C4)c2)no1] | 558 | 98 |
| 170 | 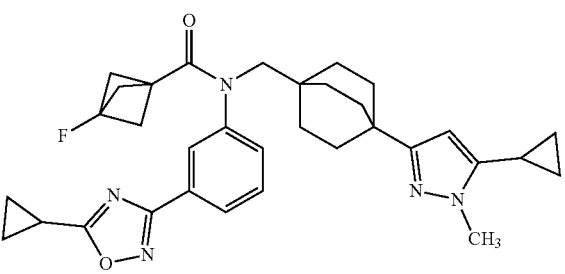 [SMILES: Cn1nc(C23CCC(CN(C(=O)C45CC(F)(C4)C5)c4cccc(-c5noc(C6CC6)n5)c4)(CC2)CC3)cc1C1CC1] | 556 | 74 |
168  $^1$H NMR (400 MHz, DMSO-d$_6$) δ 8.06-80.5 (m, 1H), 7.95 (s, 1H), 7.73-7.68 (m, 2H), 7.56 (t, J = 51.60 Hz, 1H), 5.59 (s, 1H), 3.69 (s, 3H), 3.58 (s, 2H), 1.96-1.81 (m, 6H), 1.78-1.70 (m, 1H), 1.66-1.52 (m, 6H), 1.45-1.30 (m, 6H), 0.90-0.82 (m, 2H), 0.56-0.49 (m, 2H).
169  $^1$H NMR (400 MHz, DMSO-d$_6$) δ 8.02-8.00 (m, 1H), 7.89-7.88 (m, 1H), 7.67-7.61 (m, 2H), 5.59 (s, 1H), 3.69 (s, 3H), 3.57 (br. s., 2H), 3.43-3.35 (m, 1H), 1.88 (br. s., 6H), 1.79-1.70 (m, 1H), 1.67-1.51 (m, 6H), 1.48-1.28 (m, 12H), 1.24 (s, 1H), 0.88-0.86 (m, 2H), 0.54-0.52 (m, 2H).
170  $^1$H NMR (400 MHz, DMSO-d$_6$) δ 7.97-7.95 (m, 1H), 7.90-7.85 (m, 1H), 7.64-7.61 (m, 2H), 5.59 (s, 1H), 3.69 (s, 3H), 3.56 (s, 2H), 2.47-2.40 (m, 1H), 1.87 (br. s., 6H), 1.79-1.70 (m, 1H), 1.68-1.45 (m, 6H), 1.45-1.25 (m, 8H), 1.25-1.15 (m, 2H), 0.94-0.82 (m, 2H), 0.60-0.48 (m, 2H).

Example 171

N-((4-(3-(tert-butyl)-1,2,4-oxadiazol-5-yl)bicyclo[2.2.2]octan-1-yl)methyl)-N-(3-(5-cyclopropyl-1,2,4-oxadiazol-3-yl)phenyl)-3-fluorobicyclo[1.1.1]pentane-1-carboxamide (171)

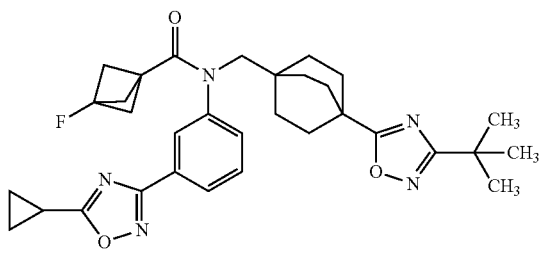

Step A. Intermediate 171A. Preparation of methyl 4-(((3-cyanophenyl) amino)methyl) bicyclo[2.2.2]octane-1-carboxylate

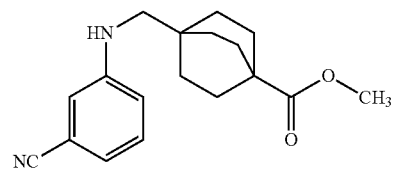 [SMILES: COC(=O)C12CCC(CNc3cccc(C#N)c3)(CC1)CC2]

The title compound was synthesized according to the method described for the synthesis of Intermediate 1I by substituting 3-aminobenzonitrile and Intermediate 88B where appropriate: (575 mg, 1.908 mmol, 45% yield). MS (ESI) 299 (M+H).

Step B. Intermediate 171B. Preparation of methyl 4-((N-(3-cyanophenyl)-3-fluorobicyclo[1.1.1]pentane-1-carboxamido)methyl)bicyclo[2.2.2]octane-1-carboxylate

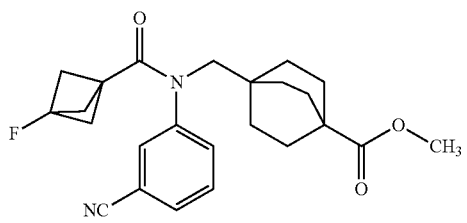 [SMILES: COC(=O)C12CCC(CN(C(=O)C34CC(F)(C3)C4)c3cccc(C#N)c3)(CC1)CC2]

The title compound was synthesized according to the method described for the synthesis of Example 3 by substituting Intermediate 171A and the corresponding acid where appropriate: (600 mg, 1.432 mmol, 75% yield). MS (ESI) 411 (M+H).

Step C. Intermediate 171C. Preparation of methyl (Z)-4-((3-fluoro-N-(3-(N'-hydroxy carbamimidoyl)phenyl)bicyclo[1.1.1]pentane-1-carboxamido)methyl)bicyclo[2.2.2]octane-1-carboxylate

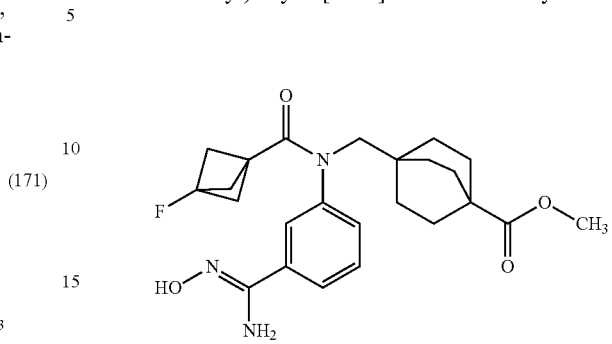

The title compound was synthesized according to the method described for the synthesis of Intermediate 88F by substituting Intermediate 171B where appropriate: (470 mg, 1.060 mmol, 95% yield). MS (ESI) 444 (M+H).

Step D. Intermediate 171D. Preparation of methyl 4-((N-(3-(5-cyclopropyl-1,2,4-oxadiazol-3-yl)phenyl)-3-fluorobicyclo[1.1.1]pentane-1-carboxamido)methyl) bicyclo[2.2.2]octane-1-carboxylate

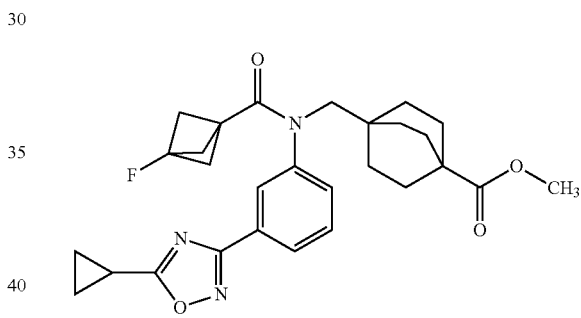

The title compound was synthesized according to the method described for the synthesis of Intermediate 3A by substituting Intermediate 171C and the corresponding acid where appropriate: (300 mg, 0.583 mmol, 70% yield). MS (ESI) 494 (M+H).

Step E. Intermediate 171E. Preparation of 4-((N-(3-(5-cyclopropyl-1,2,4-oxadiazol-3-yl)phenyl)-3-fluorobicyclo[1.1.1]pentane-1-carboxamido)methyl) bicyclo[2.2.2]octane-1-carboxylic acid

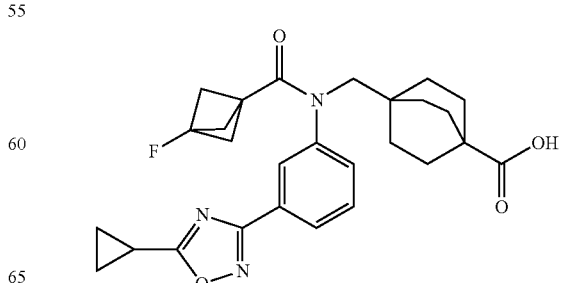

To a stirred solution of Intermediate 171D (250 mg, 0.507 mmol) in a mixture of THF (5 mL), MeOH (5 mL) and water (2 mL), was added LiOH (36.4 mg, 1.520 mmol) at room temperature, and then the reaction mixture was stirred for 12 h. The reaction mixture was concentrated under reduced pressure and the residue was reconstituted in cold water. The aqueous solution was acidified with 1.5 N aqueous HCl till the solution attained pH=2. The aqueous solution was extracted with EtOAc (2×50 mL). The combined organic extracts were dried over $MgSO_4$, filtered and concentrated under reduced pressure to afford the title compound (200 mg, 0.400 mmol, 96% yield). MS (ESI) 480 (M+H).

Step F. Example 171. Preparation of N-((4-(3-(tert-butyl)-1,2,4-oxadiazol-5-yl) bicyclo[2.2.2]octan-1-yl)methyl)-N-(3-(5-cyclopropyl-1,2,4-oxadiazol-3-yl)phenyl)-3-fluorobicyclo[1.1.1]pentane-1-carboxamide The title compound was synthesized according to the method described for the synthesis of Intermediate 3A by substituting Intermediate 171E and Intermediate 88F where appropriate: (17.7 mg, 0.031 mmol, 60% yield). $^1$H NMR (400 MHz, DMSO-$d_6$) δ 7.97 (td, J=4.1, 2.1 Hz, 1H), 7.87 (s, 1H), 7.72-7.56 (m, 2H), 3.60 (br. s., 2H), 2.47-2.40 (m, 1H), 1.88 (br. s., 6H), 1.84-1.68 (m, 6H), 1.54-1.37 (m, 6H), 1.36-1.28 (m, 2H), 1.28-1.13 (m, 11H); FXR $EC_{50}$ (nM) 37.58 MS (ESI) 560.1 (M+H).

Example 172

N-(3-(5-cyclopropyl-1,2,4-oxadiazol-3-yl)phenyl)-N-((4-(3-(difluoromethyl)-1,2,4-oxadiazol-5-yl)bicyclo[2.2.2]octan-1-yl)methyl)-3-fluorobicyclo[1.1.1]pentane-1-carboxamide (172)

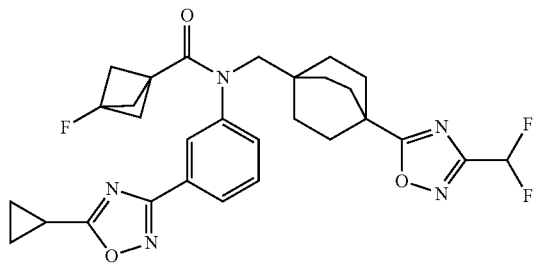

The title compound was synthesized according to the method described for the synthesis of Intermediate 3A by substituting Intermediate 171E and (E)-2,2-difluoro-N'-hydroxyacetimidamide where appropriate: (12.8 mg, 0.023 mmol, 44% yield). $^1$HNMR (400 MHz, DMSO-$d_6$) δ 7.97 (td, J=4.5, 1.6 Hz, 1H), 7.88 (d, J=1.0 Hz, 1H), 7.70-7.58 (m, 2H), 7.31 (m, 1H), 3.61 (br. s., 2H), 2.47-2.40 (m, 1H), 2.00-1.74 (m, 12H), 1.58-1.37 (m, 6H), 1.35-1.28 (m, 2H), 1.27-1.16 (m, 2H); FXR $EC_{50}$ (nM) 153.69 MS (ESI) 554.3 (M+H).

Example 173

N-((4-(3-(difluoromethyl)-1,2,4-oxadiazol-5-yl)bicyclo[2.2.2]octan-1-yl)methyl)-3-fluoro-N-(3-(5-(3-methyloxetan-3-yl)-1,2,4-oxadiazol-3-yl)phenyl)bicyclo[1.1.1]pentane-1-carboxamide (173)

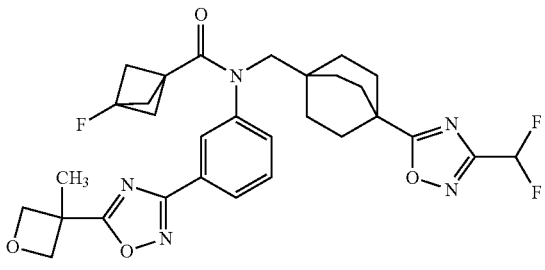

Step A. Intermediate 173A. Preparation of methyl 4-((3-fluoro-N-(3-(5-(3-methyloxetan-3-yl)-1,2,4-oxadiazol-3-yl)phenyl)bicyclo[1.1.1]pentane-1-carboxamido) methyl)bicyclo[2.2.2]octane-1-carboxylate

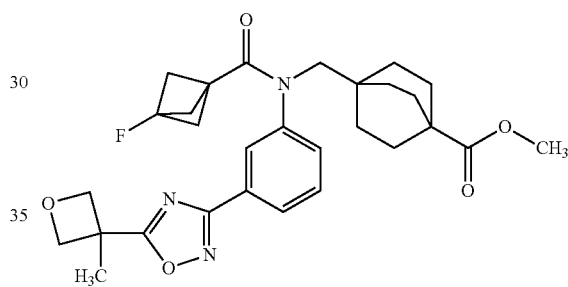

The title compound was synthesized according to the method described for the synthesis of Intermediate 3A by substituting Intermediate 171C and the corresponding acid where appropriate: (100 mg, 0.189 mmol, 56% yield). MS (ESI) 524 (M+H).

Step B. Intermediate 173B. Preparation of 4-((3-fluoro-N-(3-(5-(3-methyloxetan-3-yl)-1,2,4-oxadiazol-3-yl)phenyl)bicyclo[1.1.1]pentane-1-carboxamido)methyl)bicyclo[2.2.2]octane-1-carboxylic acid

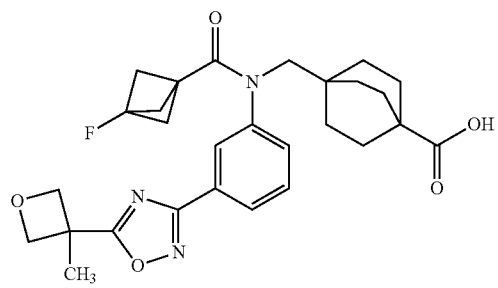 [SMILES: CC1(c2nc(-c3cccc(N(CC45CCC(C(=O)O)(CC4)CC5)C(=O)C45CC(F)(C4)C5)c3)no2)COC1]

The title compound was synthesized according to the method described for the synthesis of Intermediate 171E by substituting Intermediate 173A where appropriate: (100 mg, 0.192 mmol, 40% yield). MS (ESI) 510 (M+H).

Step C. Example 173. Preparation of N-((4-(3-(difluoromethyl)-1,2,4-oxadiazol-5-yl) bicyclo[2.2.2]octan-1-yl)methyl)-3-fluoro-N-(3-(5-(3-methyloxetan-3-yl)-1,2,4-oxadiazol-3-yl)phenyl)bicyclo[1.1.1]pentane-1-carboxamide The title compound was synthesized according to the method described for the synthesis of Intermediate 3A by substituting Intermediate 173B and (E)-2,2-difluoro-N'-hydroxyacetimidamide where appropriate: (11.4 mg, 0.019 mmol, 39% yield). $^1$H NMR (400 MHz, DMSO-$d_6$) δ 8.09-8.02 (m, 1H), 7.96 (d, J=1.0 Hz, 1H), 7.74-7.61 (m, 2H), 7.32 (m, 1H), 5.00 (d, J=6.1 Hz, 2H), 4.61 (d, J=6.1 Hz, 2H), 3.63 (br. s., 2H), 2.00-1.75 (m, 15H), 1.56-1.39 (m, 6H); FXR $EC_{50}$ (nM) 139; MS (ESI) 584.1 (M+H).

Example 174

N-((4-(3-(tert-butyl)-1,2,4-oxadiazol-5-yl)bicyclo[2.2.2]octan-1-yl)methyl)-3-fluoro-N-(3-(5-(3-methyloxetan-3-yl)-1,2,4-oxadiazol-3-yl)phenyl)bicyclo[1.1.1]pentane-1-carboxamide (174)

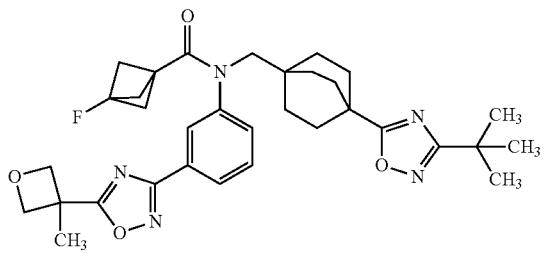

The title compound was synthesized according to the method described for the synthesis of Intermediate 3A by substituting Intermediate 173B and Intermediate 88F where appropriate: (18.8 mg, 0.032 mmol, 65% yield). $^1$H NMR (400 MHz, DMSO-$d_6$) δ 8.11-8.01 (m, 1H), 7.95 (s, 1H), 7.76-7.55 (m, 2H), 5.00 (d, J=6.1 Hz, 2H), 4.61 (d, J=6.1 Hz, 2H), 3.62 (br. s., 2H), 2.00-1.86 (m, 6H), 1.86-1.70 (m, 9H), 1.56-1.34 (m, 6H), 1.33-1.17 (m, 9H); FXR $EC_{50}$ (nM) 40; MS (ESI) 590 (M+H).

Example 175

3-fluoro-N-((4-(3-isopropyl-1,2,4-oxadiazol-5-yl)bicyclo[2.2.2]octan-1-yl)methyl)-N-(3-(5-(1-methylcyclopropyl)-1,2,4-oxadiazol-3-yl)phenyl)bicyclo[1.1.1]pentane-1-carboxamide (175)

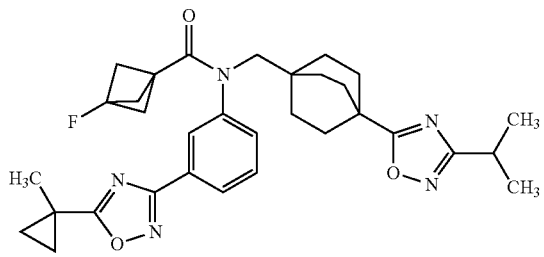

Step A. Intermediate 175A. Preparation of methyl 4-((3-fluoro-N-(3-(5-(1-methyl cyclopropyl)-1,2,4-oxadiazol-3-yl)phenyl)bicyclo[1.1.1]pentane-1-carboxamido)methyl) bicyclo[2.2.2]octane-1-carboxylate

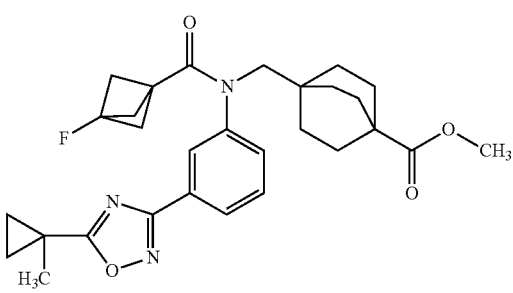 [SMILES: COC(=O)C12CCC(CN(C(=O)C34CC(F)(C3)C4)c3cccc(-c4noc(C5(C)CC5)n4)c3)(CC1)CC2]

The title compound was synthesized according to the method described for the synthesis of Intermediate 3A by substituting Intermediate 171C and the corresponding acid where appropriate: (260 mg, 0.512 mmol, 87% yield) as a gummy solid. MS (ESI) 508 (M+H).

Step B. Intermediate 175B. Preparation of 4-((3-fluoro-N-(3-(5-(1-methylcyclopropyl)-1,2,4-oxadiazol-3-yl)phenyl)bicyclo[1.1.1]pentane-1-carboxamido)methyl) bicyclo[2.2.2]octane-1-carboxylic acid

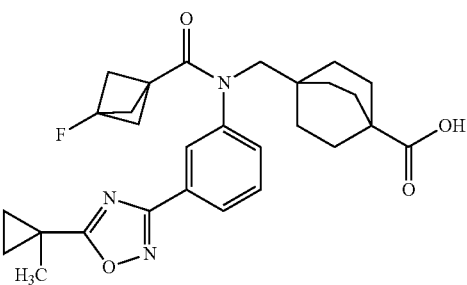 [SMILES: CC1(c2nc(-c3cccc(N(CC45CCC(C(=O)O)(CC4)CC5)C(=O)C45CC(F)(C4)C5)c3)no2)CC1]

To a stirred solution of Intermediate 175A (260 mg, 0.512 mmol) in MeOH (3 mL) was added a solution of NaOH (102 mg, 2.56 mmol) in $H_2O$ (1.5 mL) and stirred for 1 h at 60° C. The reaction mixture was concentrated under reduced pressure and diluted with water (10 mL). The aqueous solution was acidified with 1.5 N aqueous HCl and extracted with ethyl acetate (2×20 mL). The combined organic extracts were dried over anhydrous sodium sulfate, filtered and concentrated under reduced pressure to afford the title compound (250 mg, 0.507 mmol, 99% yield) as a brownish gummy solid. MS (ESI) 494 (M+H).

Step C. Example 175. Preparation of 3-fluoro-N-((4-(3-isopropyl-1,2,4-oxadiazol-5-yl) bicyclo[2.2.2]octan-1-yl)methyl)-N-(3-(5-(1-methylcyclopropyl)-1,2,4-oxadiazol-3-yl) phenyl)bicyclo[1.1.1]pentane-1-carboxamide The title compound was synthesized according to the method described for the synthesis of Intermediate 3A by substituting Intermediate 175B and (Z)—N'-hydroxyisobutyrimidamide where appropriate: (22 mg, 0.039 mmol, 78% yield). $^1$H NMR (400 MHz, DMSO-$d_6$): δ 7.99-7.96 (m, 1H), 7.87 (s, 1H), 7.65 (d, J=6.00 Hz, 2H), 3.60 (s, 2H), 3.00-2.97 (m, 1H), 1.88-1.78 (m, 12H), 1.58 (s, 3H), 1.46-1.40 (m, 8H), 1.24-1.16 (m, 8H); FXR $EC_{50}$ (nM)=54; MS (ESI) 560 (M+H).

The following compound was synthesized according to the method described for the synthesis of Intermediate 3A by substituting Intermediate 175B and the corresponding N'-hydroxyimidamides where appropriate:

| Ex. No. | Structure | MS (ESI) (M + H) | FXR $EC_{50}$ (nM) |
|---|---|---|---|
| 176 | | 574 | 24 |

176 $^1$H NMR (400 MHz, DMSO-$d_6$) δ 8.00-7.95 (m, 1H), 7.87 (s, 1H), 7.68-7.62 (m, 2H), 3.61 (br. s., 2H), 1.88 (br. s., 6H), 1.84-1.73 (m, 6H), 1.58 (s, 3H), 1.53-1.31 (m, 8H), 1.31-1.20 (m, 9H), 1.19-1.15 (m, 2H)

Example 177

N-((4-(5-(tert-butyl)-1,2,4-oxadiazol-3-yl)bicyclo[2.2.2]octan-1-yl)methyl)-3-fluoro-N-(3-(5-(1-methylcyclopropyl)-1,2,4-oxadiazol-3-yl)phenyl)bicyclo[1.1.1]pentane-1-carboxamide (177)

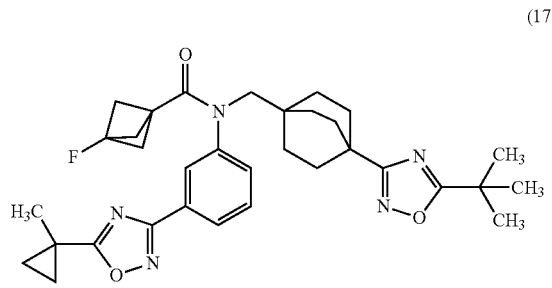

Step A. Intermediate 177A. Preparation of 4-((3-fluoro-N-(3-(5-(1-methylcyclopropyl)-1,2,4-oxadiazol-3-yl)phenyl)bicyclo[1.1.1]pentane-1-carboxamido)methyl)bicyclo[2.2.2]octane-1-carboxamide

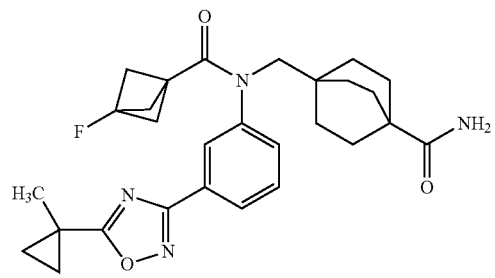 [SMILES: CC1(c2nc(-c3cccc(N(CC45CCC(C(N)=O)(CC4)CC5)C(=O)C45CC(F)(C4)C5)c3)no2)CC1]

The title compound was synthesized according to the method described for the synthesis of Intermediate 114A by substituting Intermediate 175B where appropriate: (250 mg, 0.508 mmol, 100% yield). MS (ESI) 493 (M+H).

Step B. Intermediate 175B. Preparation of N-((4-cyanobicyclo[2.2.2]octan-1-yl) methyl)-3-fluoro-N-(3-(5-(1-methylcyclopropyl)-1,2,4-oxadiazol-3-yl) phenyl) bicyclo[1.1.1]pentane-1-carboxamide

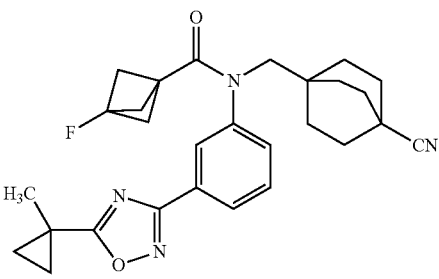 [SMILES: CC1(c2nc(-c3cccc(N(CC45CCC(C#N)(CC4)CC5)C(=O)C45CC(F)(C4)C5)c3)no2)CC1]

The title compound was synthesized according to the method described for the synthesis of Intermediate 114B by substituting Intermediate 177A where appropriate: (100 mg, 0.211 mmol, 52% yield) as a white gummy solid. MS (ESI) 475 (M+H).

Step C. Intermediate 177C. Preparation of 3-fluoro-N-((4-(N'-hydroxycarbamimidoyl) bicyclo[2.2.2]octan-1-yl)methyl)-N-(3-(5-(1-methylcyclopropyl)-1,2,4-oxadiazol-3-yl) phenyl)bicyclo[1.1.1]pentane-1-carboxamide

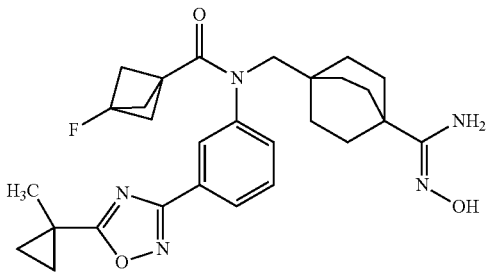 [SMILES: CC1(c2nc(-c3cccc(N(CC45CCC(/C(N)=N/O)(CC4)CC5)C(=O)C45CC(F)(C4)C5)c3)no2)CC1]

The title compound was synthesized according to the method described for the synthesis of Intermediate 88F by substituting Intermediate 177B where appropriate: (100 mg, 0.197 mmol, 100% yield) as a white solid. MS (ESI) 508 (M+H).

Step D. Example 177. Preparation of N-((4-(5-(tert-butyl)-1,2,4-oxadiazol-3-yl) bicyclo[2.2.2]octan-1-yl)methyl)-3-fluoro-N-(3-(5-(1-methylcyclopropyl)-1,2,4-oxadiazol-3-yl)phenyl)bicyclo[1.1.1]pentane-1-carboxamide The title compound was synthesized according to the method described for the synthesis of Intermediate 3A by substituting Intermediate 177C and the corresponding acid where appropriate: (11.5 mg, 0.020 mmol, 41% yield). $^1$H NMR (400 MHz, DMSO-$d_6$) δ 8.02-7.93 (m, 1H), 7.91-7.83 (m, 1H), 7.69-7.59 (m, 2H), 3.60 (br. s., 2H), 1.88 (br. s., 6H), 1.80-1.63 (m, 6H), 1.58 (s, 3H), 1.46-1.36 (m, 8H), 1.36-1.30 (m, 9H), 1.20-1.12 (m, 2H); FXR EC$_{50}$ (nM)=33; MS (ESI) 574 (M+H).

The following compounds were synthesized according to the method described for the synthesis of Intermediate 3A by substituting Intermediate 177C and the corresponding acids where appropriate:

| Ex. No. | Structure | MS (ESI) (M + H) | FXR EC$_{50}$ (nM) |
|---|---|---|---|
| 178 | | 568 | 73 |
| 179 | | 582 | 58 |
| 180 | | 588 | 83 |

178 $^1$H NMR (400 MHz, DMSO-$d_6$) δ 7.98 (td, J = 4.5, 1.6 Hz, 1H), 7.88 (d, J = 1.0 Hz, 1H), 7.72-7.59 (m, 2H), 7.42 (s, 1H), 3.61 (br. s., 2H), 1.88 (br. s., 6H), 1.83-1.67 (m, 6H), 1.58 (s, 3H), 1.53-1.32 (m, 8H), 1.20-1.12 (m, 2H)

179 $^1$H NMR (400 MHz, DMSO-$d_6$) δ 7.98 (td, J = 4.4, 1.5 Hz, 1H), 7.88 (d, J = 1.2 Hz, 1H), 7.71-7.57 (m, 2H), 3.61 (br. s., 2H), 2.25-2.04 (m, 3H), 1.88 (br. s., 6H), 1.82-1.64 (m, 6H), 1.58 (s, 3H), 1.51-1.31 (m, 8H), 1.20-1.12 (m, 2H)

180 $^1$H NMR (400 MHz, DMSO-$d_6$) δ 7.98 (td, J = 4.4, 1.5 Hz, 1H), 7.87 (d, J = 1.2 Hz, 1H), 7.73-7.53 (m, 2H), 4.84 (d, J = 5.9 Hz, 2H), 4.52 (d, J = 6.1 Hz, 2H), 3.61 (br. s., 2H), 1.88 (br. s., 6H), 1.80-1.63 (m, 9H), 1.58 (s, 3H), 1.52-1.31 (m, 8H), 1.21-1.12 (m, 2H)

Example 181

N-(3-(5-(tert-butyl)-1,2,4-oxadiazol-3-yl)phenyl)-3-fluoro-N-((1-(2-(trifluoromethyl)pyrimidin-5-yl)-2-oxabicyclo[2.2.2]octan-4-yl)methyl)bicyclo[1.1.1]pentane-1-carboxamide (181)

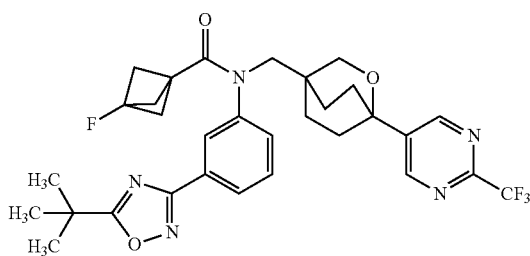

Step A. Intermediate 181A. Preparation of (4-hydroxy-4-(2-(trifluoromethyl)pyrimidin-5-yl)cyclohexane-1,1-diyl)bis(methylene) bis(4-methylbenzenesulfonate)

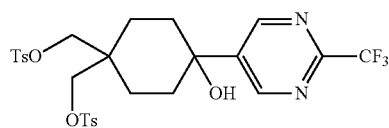 [SMILES: Cc1ccc(S(=O)(=O)OCC2(COS(=O)(=O)c3ccc(C)cc3)CCC(O)(c3cnc(C(F)(F)F)nc3)CC2)cc1]

The title compound was synthesized according to the method described for the synthesis of Intermediate 141A by substituting 5-bromo-2-(trifluoromethyl)pyrimidine where appropriate: (brown gummy solid; 2.5 g, 1.139 mmol, 27% yield). MS (ESI) 614 (M+H).

Step B. Intermediate 181B. Preparation of (1-(2-(trifluoromethyl)pyrimidin-5-yl)-2-oxabicyclo[2.2.2]octan-4-yl)methyl 4-methylbenzenesulfonate

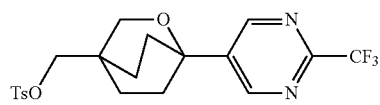

The title compound was synthesized according to the method described for the synthesis of Intermediate 141B by substituting Intermediate 181A where appropriate: (An off white solid; 450 mg, 1.017 mmol, 28% yield). MS (ESI) 443 (M+H).

Step C. Intermediate 181C. Preparation of (1-(2-(trifluoromethyl)pyrimidin-5-yl)-2-oxabicyclo[2.2.2]octan-4-yl)methyl acetate

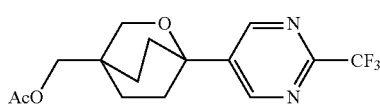 [SMILES: CC(=O)OCC12CCC(c3cnc(C(F)(F)F)nc3)(CC1)OC2]

The title compound was synthesized according to the method described for the synthesis of Intermediate 141C by substituting Intermediate 181B where appropriate: (brown gummy solid; 300 mg, 0.881 mmol, 89% yield). MS (ESI) 331 (M+H). $^1$H NMR (400 MHz, DMSO-d$_6$) δ 9.07 (s, 2H), 3.86 (d, J=11.5 Hz, 4H), 2.28-2.18 (m, 2H), 2.05 (s, 3H), 2.01-1.90 (m, 2H), 1.80-1.63 (m, 4H).

Step D. Intermediate 181D. Preparation of (1-(2-(trifluoromethyl)pyrimidin-5-yl)-2-oxabicyclo[2.2.2]octan-4-yl)methanol

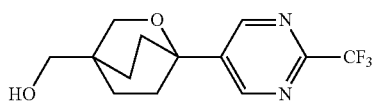

The title compound was synthesized according to the method described for the synthesis of Intermediate 141D by substituting Intermediate 181C where appropriate: (brown solid; 250 mg, 0.824 mmol, 91% yield). MS (ESI) 289 (M+H). $^1$H NMR (400 MHz, DMSO-d$_6$) δ 9.07 (s, 2H), 4.59 (t, J=5.3 Hz, 1H), 3.85 (s, 2H), 3.19 (d, J=5.0 Hz, 2H), 2.26-2.14 (m, 2H), 1.91 (d, J=4.0 Hz, 2H), 1.76-1.66 (m, 2H), 1.60 (d, J=8.0 Hz, 2H).

Step E. Intermediate 181E. Preparation of 1-(2-(trifluoromethyl)pyrimidin-5-yl)-2-oxabicyclo[2.2.2]octane-4-carbaldehyde

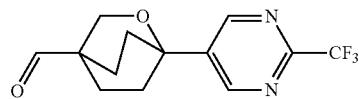 [SMILES: O=CC12CCC(c3cnc(C(F)(F)F)nc3)(CC1)OC2]

The title compound was synthesized according to the method described for the synthesis of Intermediate 3C by substituting Intermediate 181D where appropriate: (brown solid; 150 mg, 0.524 mmol, 60% yield). MS (ESI) 287 (M+H). $^1$H NMR (400 MHz, DMSO-d$_6$) δ 9.53 (s, 1H), 9.09 (s, 2H), 4.06 (s, 2H), 2.36-2.22 (m, 2H), 2.06-1.88 (m, 6H).

Step F. Intermediate 181F. Preparation of 3-(((1-(2-(trifluoromethyl)pyrimidin-5-yl)-2-oxabicyclo[2.2.2]octan-4-yl)methyl)amino)benzonitrile

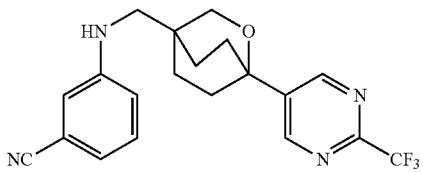 [SMILES: N#Cc1cccc(NCC23CCC(c4cnc(C(F)(F)F)nc4)(CC2)OC3)c1]

The title compound was synthesized according to the method described for the synthesis of Intermediate 1I by substituting 3-aminobenzonitrile and Intermediate 181E where appropriate: (brown solid; 60 mg, 0.057 mmol, 33% yield). MS (ESI) 389 (M+H). $^1$H NMR (400 MHz, DMSO-$d_6$) δ 9.07 (s, 1H), 7.28-7.15 (m, 1H), 7.00-6.94 (m, 1H), 6.92-6.83 (m, 2H), 5.59 (s, 1H), 3.91 (s, 2H), 2.96 (d, J=6.0 Hz, 2H), 2.28-2.18 (m, 2H), 1.99-1.89 (m, 2H), 1.77 (d, J=5.0 Hz, 4H).

Step G. Intermediate 181G. Preparation of N-(3-cyanophenyl)-3-fluoro-N-((1-(2-(trifluoromethyl)pyrimidin-5-yl)-2-oxabicyclo[2.2.2]octan-4-yl)methyl) bicyclo[1.1.1]pentane-1-carboxamide

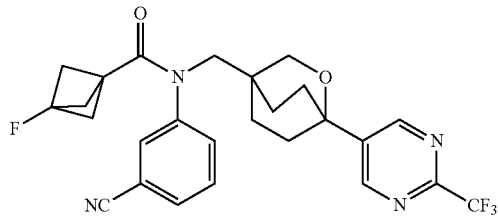 [SMILES: N#Cc1cccc(N(CC23CCC(c4cnc(C(F)(F)F)nc4)(CC2)OC3)C(=O)C23CC(F)(C2)C3)c1]

The title compound was synthesized according to the method described for the synthesis of Example 3 by substituting Intermediate 181F and the corresponding acid where appropriate: (brown gummy solid; 45 mg, 0.080 mmol, 57% yield). MS (ESI) 501 (M+H). $^1$H NMR (400 MHz, DMSO-$d_6$) δ 9.02 (s, 2H), 8.09 (s, 1H), 7.90 (d, J=7.5 Hz, 1H), 7.85 (d, J=8.5 Hz, 1H), 7.71-7.65 (m, 1H), 3.73 (s, 2H), 3.63 (br. s., 2H), 2.20-2.10 (m, 2H), 1.94-1.82 (m, 6H), 1.72-1.61 (m, 2H), 1.58 (br. s., 2H) (2 protons are buried under solvent peak)

Step H. Intermediate 181H. Preparation of 3-fluoro-N-(3-(N'-hydroxycarbamimidoyl) phenyl)-N-((1-(2-(trifluoromethyl)pyrimidin-5-yl)-2-oxabicyclo[2.2.2]octan-4-yl)methyl) bicyclo[1.1.1]pentane-1-carboxamide

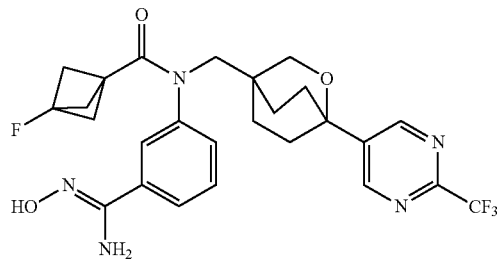 [SMILES: N/C(=N\O)c1cccc(N(CC23CCC(c4cnc(C(F)(F)F)nc4)(CC2)OC3)C(=O)C23CC(F)(C2)C3)c1]

The title compound was synthesized according to the method described for the synthesis of Intermediate 88F by substituting Intermediate 181G where appropriate: (white solid, 30 mg, 0.050 mmol, 56% yield). MS (ESI) 534 (M+H).

Step I. Example 181. Preparation of N-(3-(5-(tert-butyl)-1,2,4-oxadiazol-3-yl)phenyl)-3-fluoro-N-((1-(2-(trifluoromethyl)pyrimidin-5-yl)-2-oxabicyclo[2.2.2]octan-4-yl)methyl) bicyclo[1.1.1]pentane-1-carboxamide The title compound was synthesized according to the method described for the synthesis of Intermediate 3A by substituting Intermediate 181H and the corresponding acid where appropriate: (6.7 mg, 10.84 μmol, 39% yield). $^1$H NMR (400 MHz, DMSO-$d_6$) δ 9.01 (s, 2H), 8.09-8.00 (m, 1H), 7.95 (s, 1H), 7.76-7.61 (m, 2H), 3.76 (s, 2H), 3.66 (br. s., 2H), 2.23-2.09 (m, 2H), 2.01-1.75 (m, 8H), 1.74-1.52 (m, 4H), 1.50-1.40 (m, 9H); FXR EC$_{50}$ (nM)=828; MS (ESI) 600 (M+H).

The following compounds were synthesized according to the method described for the synthesis of Intermediate 3A by substituting Intermediate 181H and the corresponding acid where appropriate:

| Ex. No. | Structure | MS (ESI) (M + H) | FXR EC$_{50}$ (nM) |
|---|---|---|---|
| 182 | (structure shown) | 594 | 2000 |

182 $^1$H NMR (400 MHz, DMSO-$d_6$) δ 9.01 (s, 2H), 8.10 (dt, J = 7.0, 1.6 Hz, 1H), 8.06-7.99 (m, 1H), 7.82-7.43 (m, 3H), 3.77 (s, 2H), 3.67 (s, 2H), 2.23-2.07 (m, 2H), 2.01-1.80 (m, 8H), 1.77-1.65 (m, 2H), 1.65-1.54 (m, 2H).

Example 183

N-((4-(5-(tert-butyl)-1,2,4-oxadiazol-3-yl)bicyclo[2.2.2]octan-1-yl)methyl)-N-(3-(5-(tert-butyl)-1,2,4-oxadiazol-3-yl)phenyl)-3-fluorobicyclo[1.1.1]pentane-1-carboxamide (183)

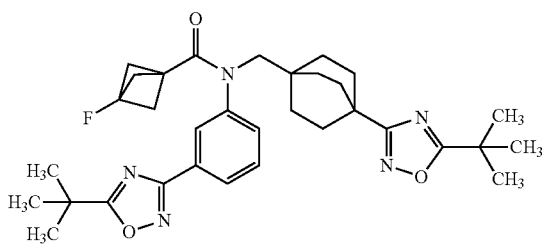

Step A. Intermediate 183A. Preparation of 4-((N-(3-carbamoylphenyl)-3-fluorobicyclo[1.1.1]pentane-1-carboxamido)methyl)bicyclo[2.2.2]octane-1-carboxylic acid

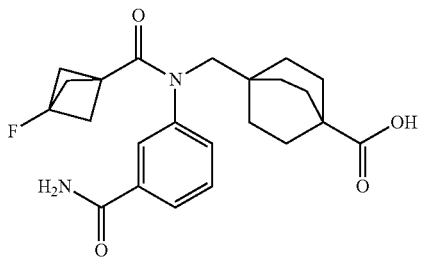 [SMILES: NC(=O)c1cccc(N(CC23CCC(C(=O)O)(CC2)CC3)C(=O)C23CC(F)(C2)C3)c1]

To a solution of Intermediate 171B (200 mg, 0.487 mmol) in mixture of methanol (2 mL), tetrahydrofuran (2 mL) and water (2 mL) at room temperature was added sodium hydroxide (195 mg, 4.87 mmol) and stirred overnight. The reaction mixture was concentrated under reduced pressure. The residue was acidified with 1.5N aqueous HCl solution ~pH=2 and extracted with EtOAc (2×25 mL). The combined organic layers were dried over anhydrous sodium sulphate, filtered and concentrated under reduced pressure to afford the title compound (170 mg, 0.369 mmol, 76% yield) as pale yellow oil. MS (ESI) 415 (M+H).

Step B. Intermediate 183B. Preparation of 4-((N-(3-carbamoylphenyl)-3-fluorobicyclo[1.1.1]pentane-1-carboxamido)methyl)bicyclo[2.2.2]octane-1-carboxamide

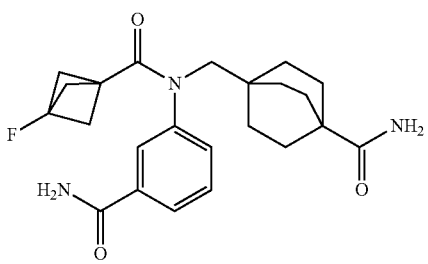 [SMILES: NC(=O)c1cccc(N(CC23CCC(C(N)=O)(CC2)CC3)C(=O)C23CC(F)(C2)C3)c1]

The title compound was synthesized according to the method described for the synthesis of Intermediate 114A by substituting Intermediate 183A where appropriate: (90 mg, 0.174 mmol, 43% yield) as pale yellow oil. MS (ESI) 414 (M+H).

Step C. Intermediate 183C. Preparation of N-((4-cyanobicyclo[2.2.2]octan-1-yl)methyl)-N-(3-cyanophenyl)-3-fluorobicyclo[1.1.1]pentane-1-carboxamide

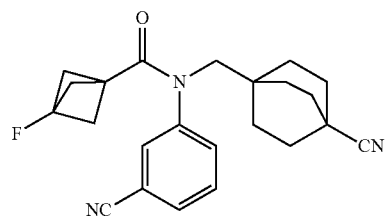 [SMILES: N#Cc1cccc(N(CC23CCC(C#N)(CC2)CC3)C(=O)C23CC(F)(C2)C3)c1]

The title compound was synthesized according to the method described for the synthesis of Intermediate 114B by substituting Intermediate 183B where appropriate: (90 mg, 0.227 mmol, 62% yield). MS (ESI) 378 (M+H).

Step D. Intermediate 183D. Preparation of 3-fluoro-N-((4-((E)-N'-hydroxycarbamimidoyl)bicyclo[2.2.2]octan-1-yl)methyl)-N-(3-((Z)—N'-hydroxycarbamimidoyl)phenyl)bicycle[1.1.1]pentane-1-carboxamide

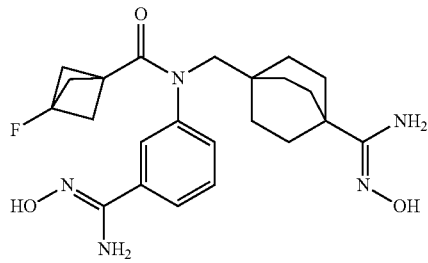 [SMILES: N/C(=N\O)c1cccc(N(CC23CCC(/C(N)=N/O)(CC2)CC3)C(=O)C23CC(F)(C2)C3)c1]

The title compound was synthesized according to the method described for the synthesis of Intermediate 88F by substituting Intermediate 183C where appropriate: (60 mg, 0.122 mmol, 51% yield) as an off-white solid. MS (ESI) 444 (M+H).

Step E. Example 183. Preparation of N-((4-(5-(tert-butyl)-1,2,4-oxadiazol-3-yl) bicyclo[2.2.2]octan-1-yl)methyl)-N-(3-(5-(tert-butyl)-1,2,4-oxadiazol-3-yl)phenyl)-3-fluorobicyclo[1.1.1]pentane-1-carboxamide The title compound was synthesized according to the method described for the synthesis of Intermediate 3A by substituting Intermediate 183D and the corresponding acid where appropriate: (13.5 mg, 0.023 mmol, 42% yield). $^1$H NMR (400 MHz, DMSO-$d_6$) δ 8.01 (dd, J=6.2, 2.6 Hz, 1H), 7.90 (s, 1H), 7.66-7.64 (m, 2H), 3.61 (br. s., 2H), 1.89 (br. s., 6H), 1.81-1.67 (m, 6H), 1.62 (s, 9H), 1.54-1.36 (m, 6H), 1.33 (s, 9H). FXR EC$_{50}$ (nM) 18; MS (ESI) 576 (M+H).

Example 184

N-((4-(5-(difluoromethyl)-1,2,4-oxadiazol-3-yl)bicyclo[2.2.2]octan-1-yl)methyl)-N-(3-(5-(difluoromethyl)-1,2,4-oxadiazol-3-yl)phenyl)-3-fluorobicyclo[1.1.1]pentane-1-carboxamide

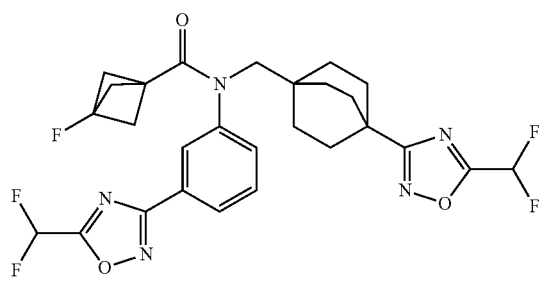
(184)

The title compound was synthesized according to the method described for the synthesis of Intermediate 3A by substituting Intermediate 183D and the corresponding acid where appropriate: (10.83 mg, 0.113 mmol). $^1$H NMR (400 MHz, DMSO-$d_6$) δ 8.07-8.05 (m, 1H), 7.99 (s, 1H), 7.71-7.69 (m, 2H), 7.56 (t, J=52.00 Hz, 1H), 7.40 (t, J=48.00 Hz, 1H), 3.62 (s, 2H), 1.89-1.81 (m, 6H), 1.79-1.75 (m, 6H), 1.46-1.42 (m, 6H). FXR $EC_{50}$ (nM) 58; MS (ESI) 564 (M+H).

Example 185

N-(3-(5-cyclopropyl-1,2,4-oxadiazol-3-yl)phenyl)-3-fluoro-N-((4-(5-(trifluoromethyl) pyridin-2-yl)bicyclo[2.2.2]octan-1-yl)methyl)bicyclo[1.1.1]pentane-1-carboxamide

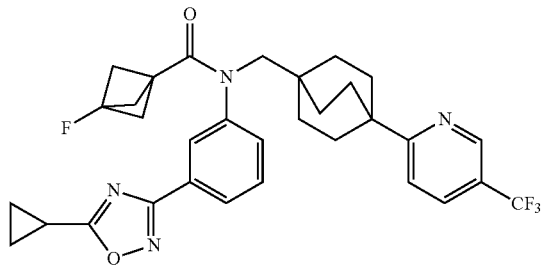
(185)

Step A. Intermediate 185A. Preparation of methyl 4-(5-(trifluoromethyl)pyridin-2-yl) bicyclo[2.2.2]octane-1-carboxylate

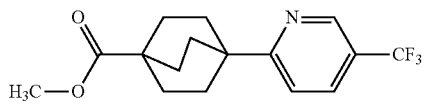

To a stirred solution of 4-(methoxycarbonyl)bicyclo[2.2.2]octane-1-carboxylic acid (3 g, 14.13 mmol) and 3-(trifluoromethyl)pyridine (2.495 g, 16.96 mmol) in DCM (90 mL) and water (90 mL) was added ammonium persulfate (3.23 g, 14.13 mmol) followed by silver nitrate (0.480 g, 2.83 mmol). After stirring overnight at room temperature, the reaction mixture was diluted with DCM (25 mL) and filtered through celite. The organic layer was separated and washed with brine solution (25 mL), dried over anhydrous sodium sulphate, filtered and concentrated under reduced pressure. The crude material was purified by flash column chromatography (Combiflash, 40 g silica, 0-50% EtOAc/PE) to afford the title compound (2.2 g, 6.95 mmol, 49% yield) as white solid. MS (ESI) 314 (M+H).

Step B. Intermediate 185B. Preparation of (4-(5-(trifluoromethyl)pyridin-2-yl)bicyclo [2.2.2]octan-1-yl)methanol

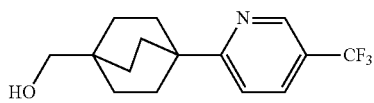 [SMILES: OCC12CCC(c3ccc(C(F)(F)F)cn3)(CC1)CC2]

The title compound was synthesized according to the method described for the synthesis of Intermediate 1G by substituting Intermediate 258A where appropriate: (1.6 g, 5.05 mmol, 79% yield) as white solid. MS (ESI) 286 (M+H).

Step C. Intermediate 185C. Preparation of 4-(5-(trifluoromethyl)pyridin-2-yl) bicyclo[2.2.2]octane-1-carbaldehyde

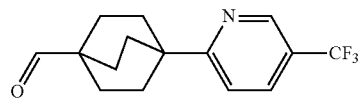

The title compound was synthesized according to the method described for the synthesis of Intermediate 3C by substituting Intermediate 185B where appropriate: (1.2 g, 4.24 mmol, 78% yield) as a white solid. MS (ESI) 284 (M+H). $^1$H NMR (400 MHz, DMSO-$d_6$) δ 9.48 (s, 1H), 8.89 (dd, J=2.5, 1.0 Hz, 1H), 8.18-8.07 (m, 1H), 7.60 (d, J=8.5 Hz, 1H), 1.98-1.83 (m, 6H), 1.76-1.65 (m, 6H).

Step D. Intermediate 185D. Preparation of 3-(((4-(5-(trifluoromethyl)pyridin-2-yl) bicyclo[2.2.2]octan-1-yl)methyl)amino)benzonitrile

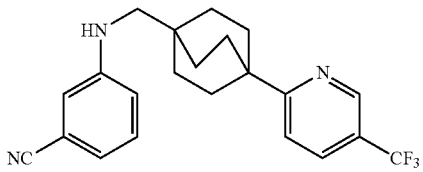 [SMILES: N#Cc1cccc(NCC23CCC(c4ccc(C(F)(F)F)cn4)(CC2)CC3)c1]

The title compound was synthesized according to the method described for the synthesis of Intermediate 1I by substituting 3-aminobenzonitrile and Intermediate 185C where appropriate: (180 mg, 0.462 mmol, 66% yield) as a brown solid. MS (ESI) 386 (M+H). ¹H NMR (400 MHz, DMSO-d₆) δ 8.91-8.86 (m, 1H), 8.10 (dd, J=8.5, 2.5 Hz, 1H), 7.59 (d, J=8.5 Hz, 1H), 7.22 (t, J=7.8 Hz, 1H), 6.99-6.92 (m, 2H), 6.85 (dt, J=7.5, 1.3 Hz, 1H), 6.01 (t, J=5.8 Hz, 1H), 2.87 (d, J=5.5 Hz, 2H), 1.93-1.84 (m, 6H), 1.63-1.56 (m, 6H).

Step E. Intermediate 185E. Preparation of N-(3-cyanophenyl)-3-fluoro-N-((4-(5-(trifluoromethyl)pyridin-2-yl)bicyclo[2.2.2]octan-1-yl)methyl)bicyclo[1.1.1]pentane-1-carboxamide

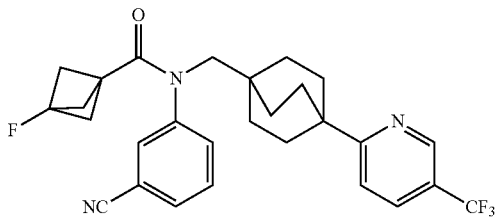 [SMILES: N#Cc1cccc(N(CC23CCC(c4ccc(C(F)(F)F)cn4)(CC2)CC3)C(=O)C23CC(F)(C2)C3)c1]

The title compound was synthesized according to the method described for the synthesis of Example 3 by substituting Intermediate 185D and the corresponding acid where appropriate: (190 mg, 0.378 mmol, 81% yield) as a brown solid. MS (ESI) 498 (M+H). ¹H NMR (400 MHz, DMSO-d₆) δ 8.85 (s, 1H), 8.12-8.02 (m, 2H), 7.88 (d, J=7.5 Hz, 1H), 7.84-7.78 (m, 1H), 7.70-7.63 (m, 1H), 7.53 (d, J=8.5 Hz, 1H), 3.61 (br. s., 2H), 1.94-1.84 (m, 6H), 1.84-1.75 (m, 6H), 1.48-1.37 (m, 6H).

Step F. Intermediate 185F. Preparation of 3-fluoro-N-(3-(N'-hydroxycarbamimidoyl) phenyl)-N-((4-(5-(trifluoromethyl)pyridin-2-yl)bicyclo[2.2.2]octan-1-yl)methyl) bicyclo[1.1.1]pentane-1-carboxamide

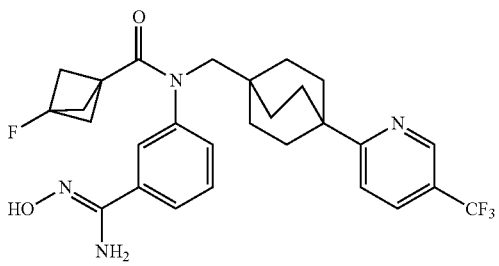 [SMILES: N/C(=N\O)c1cccc(N(CC23CCC(c4ccc(C(F)(F)F)cn4)(CC2)CC3)C(=O)C23CC(F)(C2)C3)c1]

The title compound was synthesized according to the method described for the synthesis of Intermediate 88F by substituting Intermediate 185E where appropriate (190 mg, 0.347 mmol, 96% yield) as a white solid. MS (ESI) 531 (M+H). ¹H NMR (400 MHz, DMSO-d₆) δ 9.78 (s, 1H), 8.85 (s, 1H), 8.08 (dd, J=8.5, 2.5 Hz, 1H), 7.71 (d, J=8.0 Hz, 1H), 7.65 (t, J=1.8 Hz, 1H), 7.53 (d, J=8.5 Hz, 1H), 7.50-7.44 (m, 1H), 7.42-7.38 (m, 1H), 5.95 (s, 2H), 3.72-3.65 (m, 1H), 3.54-3.47 (m, 1H), 1.92-1.76 (m, 12H), 1.45 (d, J=4.5 Hz, 6H).

Step G. Example 185. Preparation of N-(3-(5-cyclopropyl-1,2,4-oxadiazol-3-yl)phenyl)-3-fluoro-N-((4-(5-(trifluoromethyl)pyridin-2-yl)bicyclo[2.2.2]octan-1-yl)methyl)bicyclo[1.1.1]pentane-1-carboxamide The title compound was synthesized according to the method described for the synthesis of Intermediate 3A by substituting Intermediate 185F and the corresponding acid where appropriate: (15.6 mg, 0.027 mmol, 47% yield). ¹H NMR (400 MHz, DMSO-d₆) δ 8.85 (s, 1H), 8.07 (dd, J=8.6, 2.0 Hz, 1H), 7.98 (ddd, J=5.3, 3.5, 1.5 Hz, 1H), 7.88 (s, 1H), 7.71-7.57 (m, 2H), 7.52 (d, J=8.6 Hz, 1H), 3.62 (s, 2H), 2.47-2.40 (m, 1H), 1.88 (br. s., 6H), 1.85-1.63 (m, 6H), 1.57-1.36 (m, 6H), 1.34-1.27 (m, 2H), 1.25-1.17 (m, 2H); FXR EC₅₀ (nM)=508; MS (ESI) 581 (M+H).

The following compounds were synthesized according to the method described for the synthesis of Intermediate 3A by substituting Intermediate 185F and the corresponding acid where appropriate:

| Ex. No. | Structure | MS (ESI) (M + H) | FXR EC₅₀ (nM) |
|---|---|---|---|
| 186 | 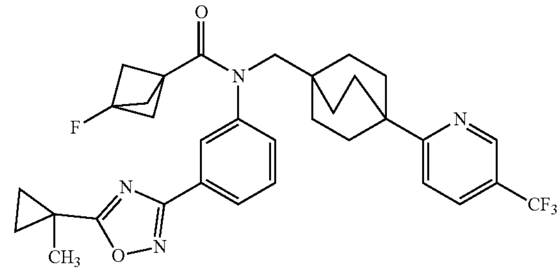 [SMILES: CC1(c2nc(-c3cccc(N(CC45CCC(c6ccc(C(F)(F)F)cn6)(CC4)CC5)C(=O)C45CC(F)(C4)C5)c3)no2)CC1] | 595 | 625 |

| Ex. No. | Structure | MS (ESI) (M + H) | FXR EC$_{50}$ (nM) |
|---|---|---|---|
| 187 | 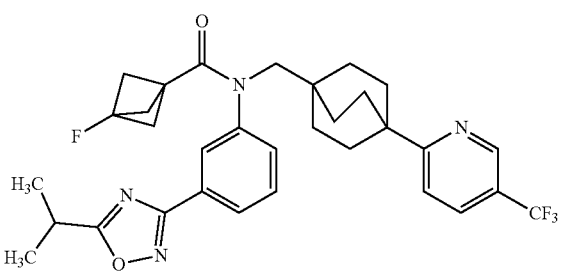 [SMILES: CC(C)c1nc(-c2cccc(N(CC34CCC(c5ccc(C(F)(F)F)cn5)(CC3)CC4)C(=O)C34CC(F)(C3)C4)c2)no1] | 583 | 605 |
| 188 | 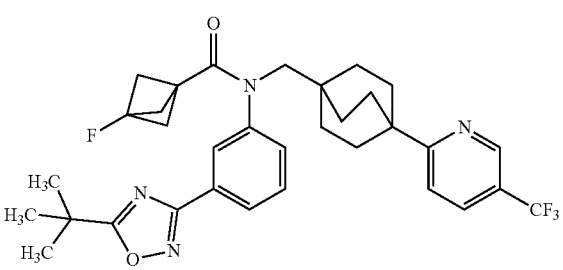 [SMILES: CC(C)(C)c1nc(-c2cccc(N(CC34CCC(c5ccc(C(F)(F)F)cn5)(CC3)CC4)C(=O)C34CC(F)(C3)C4)c2)no1] | 597 | 304 |
| 189 | 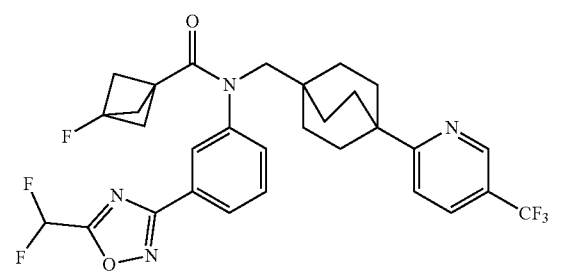 [SMILES: O=C(N(CC12CCC(c3ccc(C(F)(F)F)cn3)(CC1)CC2)c1cccc(-c2noc(C(F)F)n2)c1)C12CC(F)(C1)C2] | 591 | 691 |
| 190 | 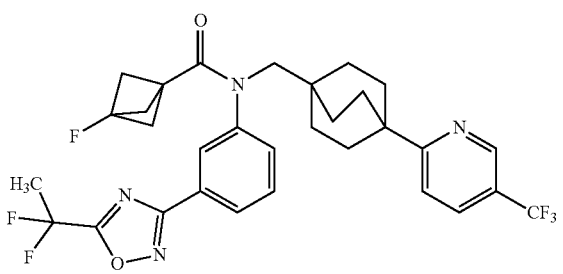 [SMILES: CC(F)(F)c1nc(-c2cccc(N(CC34CCC(c5ccc(C(F)(F)F)cn5)(CC3)CC4)C(=O)C34CC(F)(C3)C4)c2)no1] | 605 | 281 |
186 $^1$H NMR (400 MHz, DMSO-d$_6$) δ 8.84 (s, 1H), 8.07 (dd, J = 8.8, 2.4 Hz, 1H), 8.03-7.94 (m, 1H), 7.88 (s, 1H), 7.72-7.59 (m, 2H), 7.52 (d, J = 8.6 Hz, 1H), 3.62 (br. s., 2H), 1.88 (br. s., 6H), 1.85-1.65 (m, 6H), 1.58 (s, 3H), 1.53-1.33 (m, 8H), 1.20-1.11 (m, 2H)
187 $^1$H NMR (400 MHz, DMSO-d$_6$) δ 8.84 (s, 1H), 8.07 (dd, J = 8.6, 2.4 Hz, 1H), 8.04-7.96 (m, 1H), 7.92 (s, 1H), 7.77-7.59 (m, 2H), 7.52 (d, J = 8.3 Hz, 1H), 3.63 (br. s., 2H), 3.45-3.35 (m, 1H), 1.89 (br. s., 6H), 1.85-1.71 (m, 6H), 1.55-1.31 (m, 12H)
188 $^1$H NMR (400 MHz, DMSO-d$_6$) δ 8.92-8.78 (m, 1H), 8.07 (dd, J = 8.6, 2.0 Hz, 1H), 8.04-7.96 (m, 1H), 7.91 (s, 1H), 7.76-7.57 (m, 2H), 7.52 (d, J = 8.6 Hz, 1H), 3.63 (br. s., 2H), 1.89 (br. s., 6H), 1.85-1.70 (m, 6H), 1.58-1.36 (m, 15H)
189 $^1$H NMR (400 MHz, DMSO-d$_6$) δ 8.84 (s, 1H), 8.19-8.03 (m, 2H), 8.01-7.95 (m, 1H), 7.81-7.64 (m, 2H), 7.64-7.48 (m, 2H), 3.64 (s, 2H), 1.90 (br. s., 6H), 1.86-1.59 (m, 6H), 1.57-1.35 (m, 6H)
190 $^1$H NMR (400 MHz, DMSO-d$_6$) δ 8.91-8.79 (m, 1H), 8.15-8.02 (m, 2H), 7.99 (s, 1H), 7.79-7.62 (m, 2H), 7.52 (d, J = 8.3 Hz, 1H), 3.64 (br. s., 2H), 2.25 (t, J = 19.8 Hz, 3H), 1.90 (br. s., 6H), 1.86-1.59 (m, 6H), 1.55-1.34 (m, 6H)

Example 191

N-((4-(3-(tert-butyl)-1,2,4-oxadiazol-5-yl)bicyclo[2.2.2]octan-1-yl)methyl)-N-(3-(3-cyclopropyl-1,2,4-oxadiazol-5-yl)phenyl)-3-methyloxetane-3-carboxamide (191)

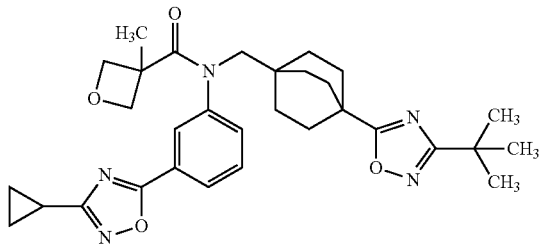

Step A. Intermediate 191A. Preparation of methyl 4-(3-(tert-butyl)-1,2,4-oxadiazol-5-yl)bicyclo[2.2.2]octane-1-carboxylate

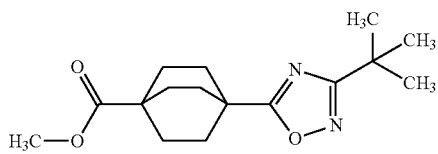

The title compound was synthesized according to the method described for the synthesis of Intermediate 3A by substituting 4-(methoxycarbonyl)bicyclo[2.2.2]octane-1-carboxylic acid and Intermediate 88F where appropriate: (2.2 g, 7.52 mmol, 97% yield) as white solid. MS (ESI) 293 (M+H). $^1$H NMR (400 MHz, DMSO-$d_6$) δ 3.61 (s, 3H), 1.96-1.87 (m, 6H), 1.87-1.79 (m, 6H), 1.29 (s, 9H).

Step B. Intermediate 191B. Preparation of (4-(3-(tert-butyl)-1,2,4-oxadiazol-5-yl) bicyclo[2.2.2]octan-1-yl)methanol

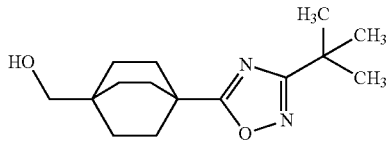 [SMILES: CC(C)(C)c1noc(C23CCC(CO)(CC2)CC3)n1]

The title compound was synthesized according to the method described for the synthesis of Intermediate 1G by substituting Intermediate 191A where appropriate: (1.5 g, 5.62 mmol, 75% yield) as white solid. MS (ESI) 265 (M+H). $^1$H NMR (400 MHz, DMSO-$d_6$) δ 4.43 (t, J=5.5 Hz, 1H), 3.09 (d, J=5.5 Hz, 2H), 1.94-1.79 (m, 6H), 1.52-1.39 (m, 6H), 1.29 (s, 9H).

Step C. Intermediate 191C. Preparation of 4-(3-(tert-butyl)-1,2,4-oxadiazol-5-yl) bicyclo[2.2.2]octane-1-carbaldehyde

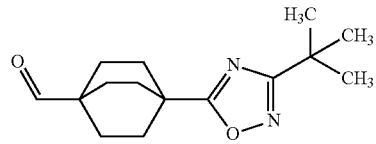 [SMILES: CC(C)(C)c1noc(C23CCC(C=O)(CC2)CC3)n1]

The title compound was synthesized according to the method described for the synthesis of Intermediate 3C by substituting Intermediate 191B where appropriate: (1.1 g, 3.44 mmol, 61% yield) as a white solid. MS (ESI) 263 (M+H). $^1$H NMR (400 MHz, DMSO-$d_6$) δ 9.47 (s, 1H), 1.97-1.88 (m, 6H), 1.76-1.65 (m, 6H), 1.29 (s, 9H).

Step D. Intermediate 191D. Preparation of N-((4-(3-(tert-butyl)-1,2,4-oxadiazol-5-yl) bicyclo[2.2.2]octan-1-yl)methyl)-3-(3-cyclopropyl-1,2,4-oxadiazol-5-yl)aniline

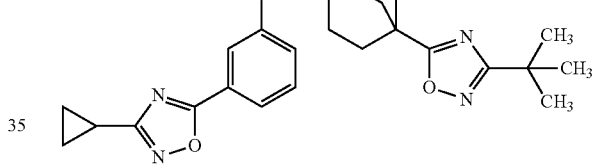

The title compound was synthesized according to the method described for the synthesis of Intermediate 1I by substituting Intermediate 8A and Intermediate 191C where appropriate: (3 g, 6.70 mmol, 70% yield) as a brown solid. MS (ESI) 448 (M+H).

Step E. Example 191. Preparation of N-((4-(3-(tert-butyl)-1,2,4-oxadiazol-5-yl) bicyclo[2.2.2]octan-1-yl)methyl)-N-(3-(3-cyclopropyl-1,2,4-oxadiazol-5-yl)phenyl)-3-methyloxetane-3-carboxamide The title compound was synthesized according to the method described for the synthesis of Example 3 by substituting Intermediate 191D and the corresponding acid where appropriate: (8 mg, 0.014 mmol, 22% yield). $^1$H NMR (400 MHz, DMSO-$d_6$) δ 8.05 (t, J=1.7 Hz, 1H), 8.01 (dd, J=9.0, 1.2 Hz, 1H), 7.79 (d, J=8.6 Hz, 1H), 7.67 (t, J=7.9 Hz, 1H), 4.51 (br. s., 2H), 3.74-3.44 (m, 4H), 2.27-2.15 (m, 1H), 1.88-1.72 (m, 6H), 1.59 (s, 3H), 1.48-1.34 (m, 6H), 1.32-1.16 (m, 9H), 1.16-1.08 (m, 2H), 1.06-0.97 (m, 2H); FXR $EC_{50}$ (nM)=824; MS (ESI) 546 (M+H).

The following compounds were synthesized according to the method described for the synthesis of Example 3 by substituting Intermediate 191D and the corresponding acid where appropriate:

| Ex. No. | Structure | MS (ESI) (M + H) | FXR EC$_{50}$ (nM) |
|---|---|---|---|
| 192 | 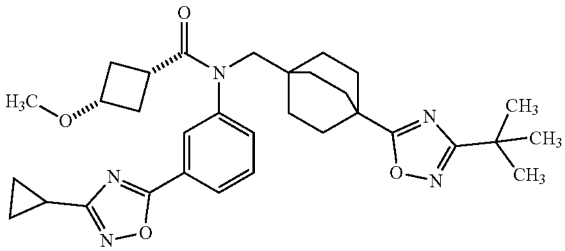 | 560 | 449 |
| 193 | 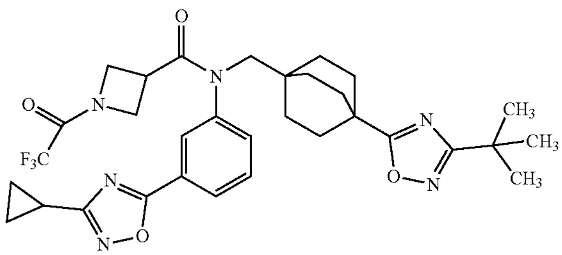 [SMILES: CC(C)(C)c1noc(C23CCC(CN(C(=O)C4CN(C(=O)C(F)(F)F)C4)c4cccc(-c5nc(C6CC6)no5)c4)(CC2)CC3)n1] | 627 | 4871 |

192 $^1$H NMR (400 MHz, DMSO-d$_6$) δ 7.98 (t, J = 18.40 Hz, 3H), 7.71-7.64 (m, 2H), 3.63 (s, 2H), 3.44-3.51 (m, 1H), 3.02 (s, 3H), 2.20 (m, 1H), 1.96-1.92 (m, 4H), 1.80-1.76 (m, 6H), 1.41-1.37 (m, 6H), 1.25 (s, 9H), 1.13-1.11 (m, 2H), 1.02-0.99 (m, 2H).

193 $^1$H NMR (400 MHz, DMSO-d$_6$) δ 8.14-7.90 (m, 2H), 7.79-7.60 (m, 2H), 4.55-4.39 (m, 1H), 4.20-3.95 (m, 2H), 3.80-3.61 (m, 2H), 3.61-3.46 (m, 2H), 2.28-2.17 (m, 1H), 1.88-1.68 (m, 6H), 1.54-1.30 (m, 6H), 1.30-1.17 (m, 9H), 1.17-1.07 (m, 2H), 1.04-0.93 (m, 2H)

Example 194

N-((4-(5-(tert-butyl)-1,2,4-oxadiazol-3-yl)bicyclo[2.2.2]octan-1-yl)methyl)-3-fluoro-N-(3-(1-(methylsulfonyl)-1H-pyrazol-4-yl)phenyl)bicyclo[1.1.1]pentane-1-carboxamide (194)

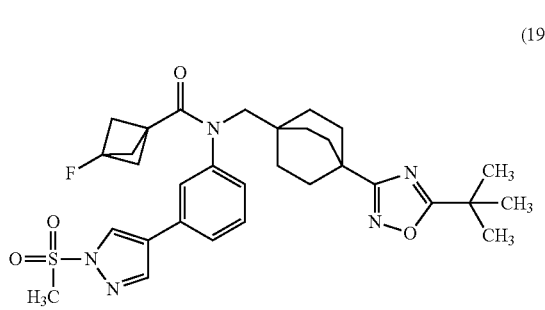

Step A. Intermediate 194A. Preparation of methyl 4-(((3-bromophenyl)amino)methyl)bicyclo[2.2.2]octane-1-carboxylate

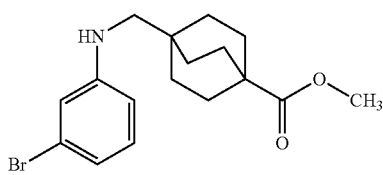 [SMILES: COC(=O)C12CCC(CNc3cccc(Br)c3)(CC1)CC2]

The title compound was synthesized according to the method described for the synthesis of Intermediate 1I by substituting 3-bromoaniline and Intermediate 88B where appropriate: (2.0 g, 5.68 mmol, 81% yield) as brown wax, MS (ESI) 352 (M+H).

Step B. Intermediate 194B. Preparation of 4-(((3-bromophenyl)amino)methyl) bicyclo[2.2.2]octane-1-carboxylic acid

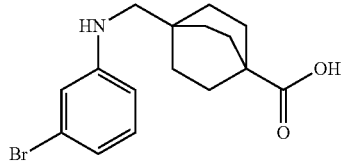

The title compound was synthesized according to the method described for the synthesis of Intermediate 175B by substituting Intermediate 194A where appropriate: (1.9 g, 5.62 mmol, 99% yield) as white solid. MS (ESI) 338 (M+H).

Step C. Intermediate 194C. Preparation of 4-(((3-bromophenyl)amino)methyl) bicyclo[2.2.2]octane-1-carboxamide

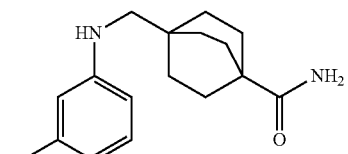

The title compound was synthesized according to the method described for the synthesis of Intermediate 184A by substituting Intermediate 194B where appropriate: (2.0 g, 5.93 mmol, 100% yield). MS (ESI) 338 (M+H).

Step D. Intermediate 194D. Preparation of 4-(((3-bromophenyl)amino)methyl) bicyclo[2.2.2]octane-1-carbonitrile

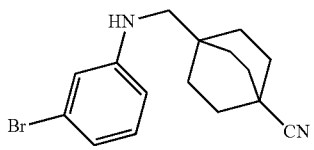 [SMILES: N#CC12CCC(CNc3cccc(Br)c3)(CC1)CC2]

To a stirred solution of Intermediate 194C (2.0 g, 5.93 mmol) in pyridine (50 mL) was added imidazole (1.009 g, 14.83 mmol) and cooled 0-5° C. To the cooled solution was added POCl₃ (0.608 mL, 6.52 mmol) drop wise and gradually allowed to warm to room temperature over 5 h. The reaction mixture was diluted with ice cold water (100 mL) and extracted with ethyl acetate (2×70 mL). The combined organic layers were washed with 1.5N aqueous HCl solution (4×50 mL), water (100 mL) and saturated brine solution (100 mL). The organic layer was then dried over anhydrous sodium sulfate, filtered and concentrated under reduced pressure. The crude material was purified by flash column chromatography (Combiflash, 40 g silica, 0-60% EtOAc/PE) to afford the title compound (1.0 g, 3.13 mmol, 53% yield) as white solid. MS (ESI) 336 (M+18) (NH₃ adduct).

Step E. Intermediate 194E. Preparation of (Z)-4-(((3-bromophenyl)amino)methyl)-N'-hydroxybicyclo[2.2.2]octane-1-carboximidamide

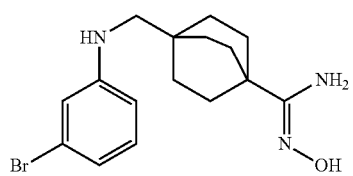 [SMILES: N/C(=N\O)C12CCC(CNc3cccc(Br)c3)(CC1)CC2]

The title compound was synthesized according to the method described for the synthesis of Intermediate 88F by substituting Intermediate 194D where appropriate: (1.0 g, 2.84 mmol, 91% yield) as white solid. MS (ESI) 352 (M+H).

Step F. Intermediate 194F. Preparation of 3-bromo-N-((4-(5-(tert-butyl)-1,2,4-oxadiazol-3-yl)bicyclo[2.2.2]octan-1-yl)methyl)aniline

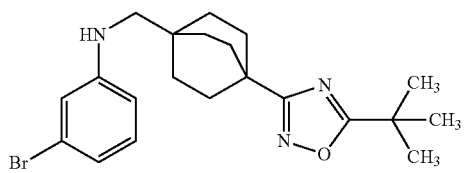 [SMILES: CC(C)(C)c1nc(C23CCC(CNc4cccc(Br)c4)(CC2)CC3)no1]

The title compound was synthesized according to the method described for the synthesis of Intermediate 3A by substituting Intermediate 194E and the corresponding acid where appropriate: (900 mg, 2.151 mmol, 95% yield) as brown wax. MS (ESI) 420 (M+2).

Step G. Intermediate 194G. Preparation of N-(3-bromophenyl)-N-((4-(5-(tert-butyl)-1,2,4-oxadiazol-3-yl)bicyclo[2.2.2]octan-1-yl)methyl)-3-fluorobicyclo[1.1.1]pentane-1-carboxamide

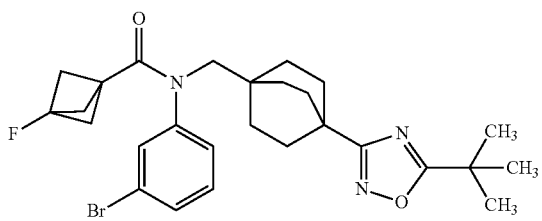 [SMILES: CC(C)(C)c1nc(C23CCC(CN(C(=O)C45CC(F)(C4)C5)c4cccc(Br)c4)(CC2)CC3)no1]

The title compound was synthesized according to the method described for the synthesis of Example 3 by substituting Intermediate 194F and the corresponding acid where appropriate: (300 mg, 0.566 mmol, 49% yield) as brown wax. MS (ESI) 530 (M+H).

Step H. Example 194. Preparation of N-((4-(5-(tert-butyl)-1,2,4-oxadiazol-3-yl) bicyclo[2.2.2]octan-1-yl)methyl)-3-fluoro-N-(3-(1-(methylsulfonyl)-1H-pyrazol-4-yl) phenyl)bicyclo[1.1.1]pentane-1-carboxamide The title compound was synthesized according to the method described for the synthesis of Example 149 by substituting Intermediate 194G and 1-(methylsulfonyl)-4-(4,4,5,5-tetramethyl-1,3,2-dioxaborolan-2-yl)-1H-pyrazole where appropriate: (4.8 mg, 8.06 µmol, 17% yield). ¹H NMR (400 MHz, DMSO-d₆) δ 8.97 (s, 1H), 8.59 (s, 1H), 7.94-7.85 (m, 1H), 7.81 (d, J=8.0 Hz, 1H), 7.49 (t, J=7.8 Hz, 1H), 7.31 (d, J=8.0 Hz, 1H), 3.72-3.45 (m, 5H), 1.87 (br. s., 6H), 1.79-1.62 (m, 6H), 1.56-1.37 (m, 6H), 1.33 (s, 9H). FXR EC₅₀ (nM)=16; MS (ESI) 596 (M+H).

The following compound was synthesized according to the method described for the synthesis of Example 149 by substituting Intermediate 194G and the corresponding hetero aryl boronate where appropriate:

| Ex. No. | Structure | MS (ESI) (M + H) | FXR EC$_{50}$ (nM) |
|---|---|---|---|
| 195 | 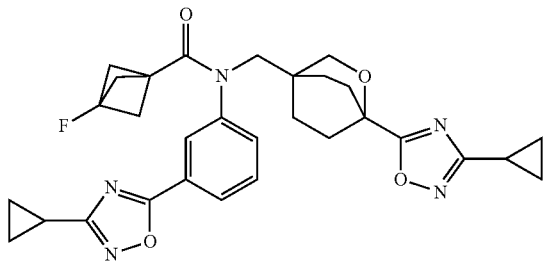 | 622 | 20 |

195 $^1$H NMR (400 MHz, DMSO-d$_6$) δ 8.98 (s, 1H), 8.62-8.54 (m, 1H), 7.89 (s, 1H), 7.81 (d, J = 8.1 Hz, 1H), 7.49 (t, J = 7.8 Hz, 1H), 7.32 (d, J = 8.8 Hz, 1H), 3.64 (d, J = 13.4 Hz, 1H), 3.54 (d, J = 13.7 Hz, 1H), 3.22-3.14 (m, 1H), 1.87 (d, J = 6.6 Hz, 6H), 1.79-1.58 (m, 6H), 1.57-1.36 (m, 6H), 1.36-1.27 (m, 11H), 1.26-1.20 (m, 2H).

Example 196

N-((1-(3-cyclopropyl-1,2,4-oxadiazol-5-yl)-2-oxabicyclo[2.2.2]octan-4-yl)methyl)-N-(3-(3-cyclopropyl-1,2,4-oxadiazol-5-yl)phenyl)-3-fluorobicyclo[1.1.1]pentane-1-carboxamide (196)

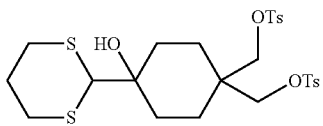 [SMILES: Cc1ccc(S(=O)(=O)OCC2(COS(=O)(=O)c3ccc(C)cc3)CCC(O)(C3SCCCS3)CC2)cc1]

Step A. Intermediate 196A. Preparation of (4-(1,3-dithian-2-yl)-4-hydroxycyclohexane-1,1-diyl)bis(methylene) bis(4-methylbenzenesulfonate)

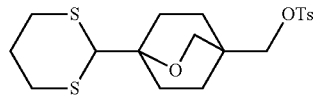

To a stirred solution of 1,3-dithiane (4.33 g, 36.0 mmol) in THF (60 mL) at −78° C. was added n-butyl lithium (15.60 mL, 39.0 mmol) and allowed to warm up to 0° C. over 1 h. The reaction mixture was cooled again to −78° C. and then a solution of (4-oxocyclohexane-1,1-diyl)bis(methylene) bis(4-methylbenzenesulfonate) (7.0 g, 15.00 mmol) in THF (20 mL) was added. The reaction mixture was allowed to warm up to 0° C. over 1 h. The reaction mixture was quenched with saturated aqueous ammonium chloride solution (100 mL) and extracted with EtOAc (3×100 mL). The combined organic layers were washed with water (100 mL) followed by saturated brine solution (100 mL). The organic layer was dried over anhydrous sodium sulphate, filtered and concentrated under reduced pressure. The crude material was purified by flash column chromatography (Combiflash, 220 g silica, 0-60% EtOAc/PE) to afford the title compound (5.5 g, 9.37 mmol, 63% yield) as white solid. MS (ESI) 604 (M+18) (NH$_3$ adduct).

Step B. Intermediate 196B. Preparation of (1-(1,3-dithian-2-yl)-2-oxabicyclo[2.2.2]octan-4-yl)methyl 4-methylbenzenesulfonate

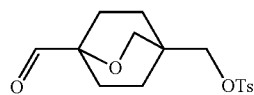

The title compound was synthesized according to the method described for the synthesis of Intermediate 141B by substituting Intermediate 196A where appropriate: (2.5 g, 6.0 mmol, 71%) as brown wax. MS (ESI) 432 (M+18) (NH$_3$ adduct).

Step C. Intermediate 196C. Preparation of (1-formyl-2-oxabicyclo[2.2.2]octan-4-yl) methyl 4-methylbenzenesulfonate To a stirred solution of Intermediate 196B (2.3 g, 5.55 mmol) in DCM (90 mL) was added a solution of N-chlorosuccinimide (2.59 g, 19.42 mmol) in H$_2$O (10 mL) and stirred for 2 h at room temperature. The reaction mixture was then diluted with DCM (100 mL) and washed with water (2×50 mL), followed by saturated brine solution (50 mL). The organic layer was dried over anhydrous sodium sulphate, filtered and concentrated under reduced pressure to afford the title compound (3 g, Crude) as white wax. MS (ESI) 325 (M+H).

Step D. Intermediate 196D. Preparation of 4-((tosyloxy)methyl)-2-oxabicyclo[2.2.2]octane-1-carboxylic acid

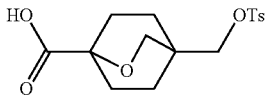

To a stirred solution of Intermediate 196C (2.0 g, 6.17 mmol) in tert-butanol (60 mL) was added 2-methyl-2-butene (1.297 g, 18.50 mmol) followed by sodium chlorite (2.79 g, 30.8 mmol) and then a solution of sodium dihydrogen phosphate monohydrate (8.51 g, 61.7 mmol) in water (20 mL) was added. After stirring the reaction overnight at room temperature, the reaction mixture was concentrated under reduced pressure and the residue was diluted with water (50 mL). The aqueous solution was acidified with 1.5 N aqueous HCl and extracted with EtOAc (2×50 mL). The combined organic extracts were washed with water (50 mL), saturated brine solution (50 mL), dried over sodium sulphate, filtered and concentrated under reduced pressure to afford the title compound (1.5 g, 4.41 mmol, 72% yield). MS (ESI) 341 (M+H).

Since intermediate 196D so obtained was not pure, it was subjected to esterification in STEP E and purification. The Intermediate 196E was then subjected to hydrolysis in STEP F to afford pure acid Intermediate 196F as described below.

Step E. Intermediate 196E. Preparation of methyl 4-((tosyloxy)methyl)-2-oxabicyclo[2.2.2]octane-1-carboxylate

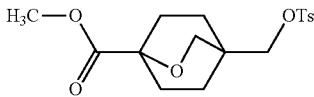

To a stirred solution of Intermediate 196D (2.5 g, 7.34 mmol) in DMF (20 mL) at room temperature was added potassium carbonate (2.030 g, 14.69 mmol) and stirred for 5 min. To the resulting solution, methyl iodide (0.918 mL, 14.69 mmol) was added and stirred for 1 h at room temperature. The reaction mixture was then diluted with ethyl acetate (100 mL) and washed with water (2×50 mL), followed by saturated brine solution (2×50 mL). The organic layer was dried over anhydrous sodium sulphate, filtered and concentrated under reduced pressure. The crude material was purified by flash column chromatography (Combiflash, 24 g silica, 0-50% EtOAc/PE) to afford the title compound (1.4 g, 3.95 mmol, 54% yield) as white solid. MS (ESI) 372 (M+18) $NH_3$ adduct.

Step F. Intermediate 196F. Preparation of 4-((tosyloxy)methyl)-2-oxabicyclo[2.2.2]octane-1-carboxylic acid

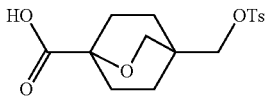 [SMILES: Cc1ccc(S(=O)(=O)OCC23CCC(C(=O)O)(CC2)OC3)cc1]

To a stirred solution of Intermediate 196E (1 g, 2.82 mmol) in a mixture of THF (4 mL) and MeOH (2 mL) was added a solution of sodium hydroxide (0.226 g, 5.64 mmol) in water (1 mL). After stirring overnight at room temperature, the reaction mixture was concentrated under reduced pressure and the residue was diluted with water (40 mL). The aqueous solution was acidified with 1.5 N aqueous HCl (5 mL) and extracted with ethyl acetate (2×50 mL). The combined organic layers were washed with brine solution (20 mL), dried over anhydrous sodium sulphate, filtered and concentrated under reduced pressure to afford the title compound (900 mg, 2.64 mmol, 94% yield) as white solid. MS (ESI) 358 (M+18) $NH_3$ adduct.

Step G. Intermediate 196G. Preparation of (Z)-(1-((((amino(cyclopropyl) methylene) amino)oxy)carbonyl)-2-oxabicyclo[2.2.2]octan-4-yl)methyl 4-methylbenzenesulfonate

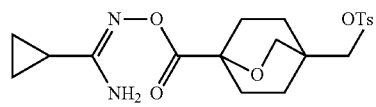 [SMILES: Cc1ccc(S(=O)(=O)OCC23CCC(C(=O)O/N=C(\N)C4CC4)(CC2)OC3)cc1]

To a stirred solution of Intermediate 196F (800 mg, 2.350 mmol) in DMF (8 mL) was added TEA (1.310 mL, 9.40 mmol), (Z)—N'-hydroxycyclopropanecarboximidamide (706 mg, 7.05 mmol), BOP (1143 mg, 2.59 mmol) and stirred for 1 h at room temperature. The reaction mixture was stirred overnight at 110° C. After cooling down to room temperature, the reaction mixture was diluted with ethyl acetate (20 mL) and washed with water (2×5 mL) followed by brine solution (10 mL). The organic layer was dried over sodium sulfate, filtered and concentrated under reduced pressure to afford the title compound (1.5 g, crude), which was used as is for the next STEP without further purification. MS (ESI) 423 (M+1).

Step H. Intermediate 196H. Preparation of (1-(3-cyclopropyl-1,2,4-oxadiazol-5-yl)-2-oxabicyclo[2.2.2]octan-4-yl)methyl 4-methylbenzenesulfonate

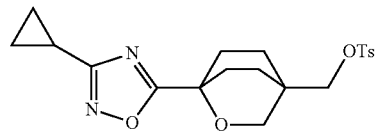 [SMILES: Cc1ccc(S(=O)(=O)OCC23CCC(c4nc(C5CC5)no4)(CC2)OC3)cc1]

To a stirred solution of Intermediate 196G (1.0 g, 2.367 mmol) in THF (20 mL) at 0° C. was added a solution of 1M TBAF in THF (14.20 mL, 14.20 mmol) at following time points: 2 eq each at 0, 4 h, and 8 h. After stirring for an additional 8 h, the reaction mixture was concentrated under reduced pressure and the residue was diluted with ethyl acetate (50 mL). The organic solution was washed with water (20 mL) followed by saturated brine solution (20 mL). The organic layer was dried over anhydrous sodium sulphate, filtered and concentrated under reduced pressure. The crude material was purified by flash column chromatography (Combiflash, 12 g silica, 0-60% EtOAc/PE) to afford the title compound (600 mg, 1.483 mmol, 63% yield) as brown wax. MS (ESI) 405 (M+1).

353

Step I. Intermediate 196I. Preparation of (1-(3-cyclopropyl-1,2,4-oxadiazol-5-yl)-2-oxabicyclo[2.2.2]octan-4-yl)methyl acetate

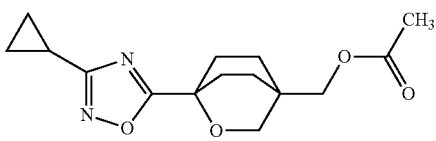 [SMILES: CC(=O)OCC12CCC(c3nc(C4CC4)no3)(CC1)OC2]

The title compound was synthesized according to the method described for the synthesis of Intermediate 141C by substituting Intermediate 196H where appropriate: (420 mg, 1.437 mmol, 89% yield) as brown oil. MS (ESI) 293 (M+1).

Step J. Intermediate 196J. Preparation of (1-(3-cyclopropyl-1,2,4-oxadiazol-5-yl)-2-oxabicyclo[2.2.2]octan-4-yl)methanol

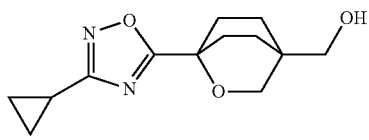 [SMILES: OCC12CCC(c3nc(C4CC4)no3)(CC1)OC2]

The title compound was synthesized according to the method described for the synthesis of Intermediate 141D by substituting Intermediate 196I where appropriate: (280 mg, 1.119 mmol, 91% yield) as white solid. MS (ESI) 251 (M+1).

Step K. Intermediate 196K. Preparation of 1-(3-cyclopropyl-1,2,4-oxadiazol-5-yl)-2-oxabicyclo[2.2.2]octane-4-carbaldehyde

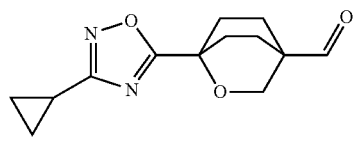 [SMILES: O=CC12CCC(c3nc(C4CC4)no3)(CC1)OC2]

354

The title compound was synthesized according to the method described for the synthesis of Intermediate 3C by substituting Intermediate 196J where appropriate: (200 mg, 0.806 mmol, 67% yield) as white solid. MS (ESI) 249.2 (M+1), $^1$H NMR (400 MHz, DMSO-$d_6$) δ 9.47 (s, 1H), 3.95 (s, 2H), 2.30-2.20 (m, 1H), 2.15-2.02 (m, 4H), 1.93-1.86 (m, 4H), 1.10-1.01 (m, 2H), 0.90-0.84 (m, 2H).

Step L. Intermediate 196L. Preparation of 3-(3-cyclopropyl-1,2,4-oxadiazol-5-yl)-N-((1-(3-cyclopropyl-1,2,4-oxadiazol-5-yl)-2-oxabicyclo[2.2.2]octan-4-yl)methyl)aniline

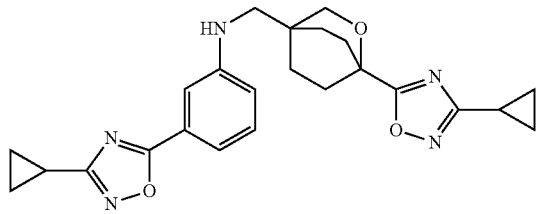 [SMILES: c1cc(NCC23CCC(c4nc(C5CC5)no4)(CC2)OC3)cc(-c2nc(C3CC3)no2)c1]

The title compound was synthesized according to the method described for the synthesis of Intermediate 1I by substituting Intermediate 8A and Intermediate 196K where appropriate: (24 mg, 0.053 mmol, 65% yield) as an off-white solid. MS (ESI) 434 (M+H).

Step M. Example 196. Preparation of N-((1-(3-cyclopropyl-1,2,4-oxadiazol-5-yl)-2-oxabicyclo[2.2.2]octan-4-yl)methyl)-N-(3-(3-cyclopropyl-1,2,4-oxadiazol-5-yl)phenyl)-3-fluorobicyclo[1.1.1]pentane-1-carboxamide The title compound was synthesized according to the method described for the synthesis of Example 3 by substituting Intermediate 196L and the corresponding acid where appropriate: (14.9 mg, 0.027 mmol, 47% yield). $^1$H NMR (400 MHz, DMSO-$d_6$) δ 8.17-7.96 (m, 2H), 7.79 (d, J=8.1 Hz, 1H), 7.71 (t, J=7.8 Hz, 1H), 3.65 (br. s., 4H), 2.27-2.19 (m, 1H), 2.18-2.03 (m, 3H), 2.02-1.76 (m, 8H), 1.65 (d, J=9.8 Hz, 2H), 1.57 (d, J=7.3 Hz, 2H), 1.14 (dd, J=8.2, 2.6 Hz, 2H), 1.08-0.90 (m, 4H), 0.90-0.80 (m, 2H). FXR EC$_{50}$ (nM) 205; MS (ESI) 546 (M+H).

The following compounds were synthesized according to the method described for the synthesis of Example 3 by substituting Intermediate 196L and the corresponding acids where appropriate:

| Ex. No. | Structure | MS (ESI) (M + H) | FXR EC$_{50}$ (nM) |
|---|---|---|---|
| 197 | 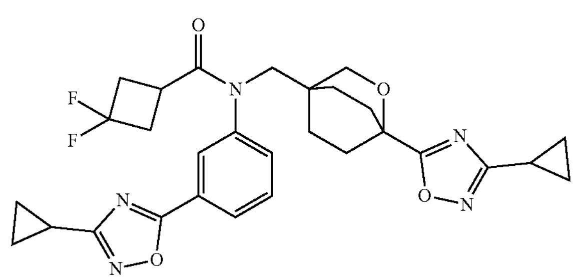 [SMILES: O=C(C1CC(F)(F)C1)N(CC12CCC(c3nc(C4CC4)no3)(CC1)OC2)c1cccc(-c2nc(C3CC3)no2)c1] | 552 | 965 |

| Ex. No. | Structure | MS (ESI) (M + H) | FXR EC$_{50}$ (nM) |
|---|---|---|---|
| 198 | 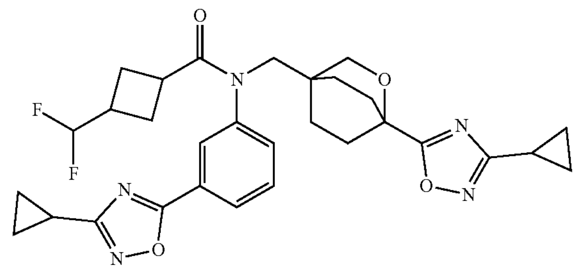 [SMILES: O=C(C1CC(C(F)F)C1)N(CC12CCC(c3nc(C4CC4)no3)(CC1)OC2)c1cccc(-c2nc(C3CC3)no2)c1] | 566 | 909 |

197 $^1$H NMR (400 MHz, DMSO-d$_6$) δ 8.08 (s, 1H), 8.04 (d, J = 7.8 Hz, 1H), 7.78 (d, J = 8.1 Hz, 1H), 7.70 (t, J = 7.8 Hz, 1H), 3.80-3.55 (m, 4H), 2.97-2.70 (m, 3H), 2.39-2.28 (m, 2H), 2.26-2.19 (m, 1H), 2.16-1.99 (m, 3H), 1.98-1.86 (m, 2H), 1.72-1.60 (m, 2H), 1.55 (d, J = 6.8 Hz, 2H), 1.20-1.10 (m, 2H), 1.09-0.95 (m, 4H), 0.93-0.78 (m, 2H).

198 $^1$H NMR (400 MHz, DMSO-d$_6$) δ 8.10-7.95 (m, 2H), 7.82-7.55 (m, 2H), 6.2-5.7 (m, 1H), 3.75-3.59 (m, 4H), 3.05 (dq, J = 16.9, 8.5 Hz, 1H), 2.34-2.26 (m, 1H), 2.26-2.16 (m, 2H), 2.15-2.00 (m, 4H), 1.99-1.86 (m, 2H), 1.79-1.70 (m, 1H), 1.70-1.58 (m, 3H), 1.54 (d, J = 8.3 Hz, 2H), 1.19-1.09 (m, 2H), 1.08-0.94 (m, 4H), 0.89-0.78 (m, 2H). (1H is buried under solvent peak)

Example 199

N-((1-(3-cyclopropyl-1,2,4-oxadiazol-5-yl)-2-oxabicyclo[2.2.2]octan-4-yl)methyl)-N-(3-(5-cyclopropylisoxazol-3-yl)phenyl)-3-fluorobicyclo[1.1.1]pentane-1-carboxamide

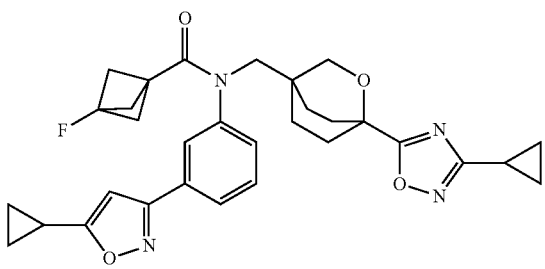

(199)

Step A. Intermediate 199A. Preparation of N-((1-(3-cyclopropyl-1,2,4-oxadiazol-5-yl)-2-oxabicyclo[2.2.2]octan-4-yl)methyl)-3-(5-cyclopropylisoxazol-3-yl)aniline

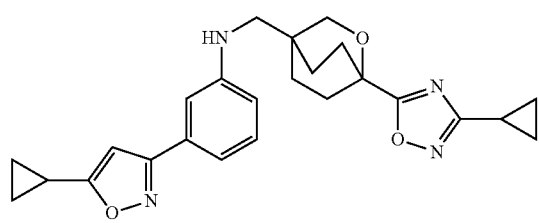 [SMILES: c1cc(NCC23CCC(c4nc(C5CC5)no4)(CC2)OC3)cc(-c2cc(C3CC3)on2)c1]

The title compound was synthesized according to the method described for the synthesis of Intermediate 1I by substituting Intermediate 57C and Intermediate 196K where appropriate: (20 mg, 0.046 mmol, 46% yield) as brown wax. MS (ESI) 433 (M+1).

Step B. Example 199. Preparation of N-((1-(3-cyclopropyl-1,2,4-oxadiazol-5-yl)-2-oxabicyclo[2.2.2]octan-4-yl)methyl)-N-(3-(5-cyclopropylisoxazol-3-yl)phenyl)-3-fluorobicyclo[1.1.1]pentane-1-carboxamide The title compound was synthesized according to the method described for the synthesis of Example 3 by substituting Intermediate 199A and the corresponding acid where appropriate: (10.9 mg, 0.019 mmol, 41% yield). $^1$H NMR (400 MHz, DMSO-d$_6$) δ 7.94-7.76 (m, 2H), 7.67-7.50 (m, 2H), 6.88 (s, 1H), 3.75-3.53 (m, 4H), 2.24-2.16 (m, 1H), 2.16-2.01 (m, 3H), 2.00-1.77 (m, 8H), 1.74-1.61 (m, 2H), 1.61-1.42 (m, 2H), 1.17-1.08 (m, 2H), 1.08-1.00 (m, 2H), 1.00-0.90 (m, 2H), 0.89-0.74 (m, 2H); FXR EC$_{50}$ (nM)=281; MS (ESI) 545 (M+H).

The following compounds were synthesized according to the method described for the synthesis of Example 3 by substituting Intermediate 199A and the corresponding acid where appropriate:

| Ex. No. | Structure | MS (ESI) (M + H) | FXR EC$_{50}$ (nM) |
|---|---|---|---|
| 200 | | 551 | 526 |
| 201 | | 565 | 384 |
| 202 | | 565 | 299 |

200 $^1$H NMR (400 MHz, DMSO-d$_6$) δ 7.88-7.78 (m, 2H), 7.63-7.48 (m, 2H), 6.84 (s, 1H), 3.67 (d, J = 6.6 Hz, 4H), 2.96-2.69 (m, 3H), 2.39-2.29 (m, 2H), 2.26-2.16 (m, 1H), 2.14-2.01 (m, 3H), 1.97-1.85 (m, 2H), 1.72-1.60 (m, 2H), 1.56 (d, J = 5.9 Hz, 2H), 1.18-1.09 (m, 2H), 1.07-0.99 (m, 2H), 0.98-0.89 (m, 2H), 0.88-0.79 (m, 2H)

201 $^1$H NMR (400 MHz, DMSO-d$_6$) δ 7.89-7.70 (m, 2H), 7.64-7.40 (m, 2H), 6.92-6.76 (m, 1H), 3.74-3.56 (m, 4H), 3.14-3.02 (m, 1H), 2.44 (br. s., 1H), 2.34-2.27 (m, 1H), 2.24-2.17 (m, 1H), 2.15-2.01 (m, 4H), 1.99-1.83 (m, 2H), 1.73 (m, 1H), 1.65 (t, J = 10.0 Hz, 3H), 1.54 (m, 2H), 1.18-1.07 (m, 2H), 1.07-1.00 (m, 2H), 0.96-0.89 (m, 2H), 0.89-0.80 (m, 2H), (1H is buried under DMSO peak).

202 $^1$H NMR (400 MHz, DMSO-d$_6$) δ 7.97-7.75 (m, 2H), 7.60 (d, J = 4.4 Hz, 2H), 6.86 (s, 1H), 3.65 (s, 4H), 2.94 (t, J = 8.3 Hz, 1H), 2.32-2.16 (m, 2H), 2.16-1.99 (m, 5H), 1.99-1.76 (m, 4H), 1.66 (m, 3H), 1.56 (d, J = 8.8 Hz, 2H), 1.17-1.09 (m, 2H), 1.09-0.97 (m, 2H), 0.97-0.89 (m, 2H), 0.89-0.76 (m, 2H)

Example 203

N-((1-(3-cyclopropyl-1,2,4-oxadiazol-5-yl)-2-oxabicyclo[2.2.2]octan-4-yl)methyl)-N-(3-(5-cyclopropylisoxazol-3-yl)phenyl)-3-fluorobicyclo[1.1.1]pentane-1-carboxamide

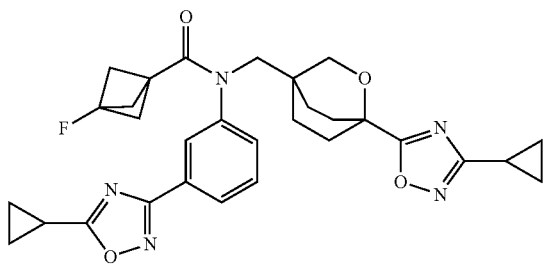

(203)

Step A. Intermediate 203A. Preparation of 3-(((1-(3-cyclopropyl-1,2,4-oxadiazol-5-yl)-2-oxabicyclo[2.2.2]octan-4-yl)methyl)amino)benzonitrile

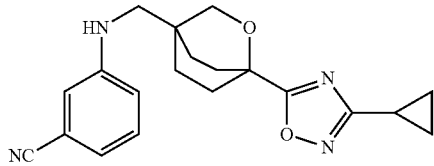 [SMILES: N#Cc1cccc(NCC23CCC(c4nc(C5CC5)no4)(CC2)OC3)c1]

The title compound was synthesized according to the method described for the synthesis of Intermediate 1I by substituting 3-aminobenzonitrile and Intermediate 196K where appropriate: (30 mg, 0.086 mmol, 25% yield) as white solid. MS (ESI) 351 (M+H).

Step B. Intermediate 203B. Preparation of N-(3-cyanophenyl)-N-((1-(3-cyclopropyl-1,2,4-oxadiazol-5-yl)-2-oxabicyclo[2.2.2]octan-4-yl)methyl)-3-fluorobicyclo[1.1.1]pentane-1-carboxamide

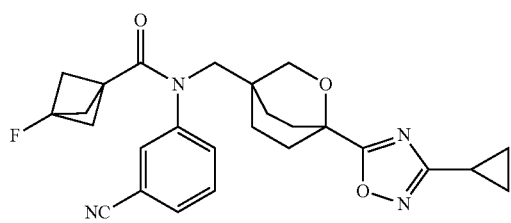 [SMILES: N#Cc1cccc(N(CC23CCC(c4nc(C5CC5)no4)(CC2)OC3)C(=O)C23CC(F)(C2)C3)c1]

The title compound was synthesized according to the method described for the synthesis of Example 3 by substituting Intermediate 203A and the corresponding acid where appropriate: (30 mg, 0.065 mmol, 76% yield) as brown wax. MS (ESI) 463 (M+H).

Step C. Intermediate 203C. Preparation of (Z)—N-((1-(3-cyclopropyl-1,2,4-oxadiazol-5-yl)-2-oxabicyclo[2.2.2]octan-4-yl)methyl)-3-fluoro-N-(3-(N'-hydroxycarbamimidoyl) phenyl)bicyclo[1.1.1]pentane-1-carboxamide

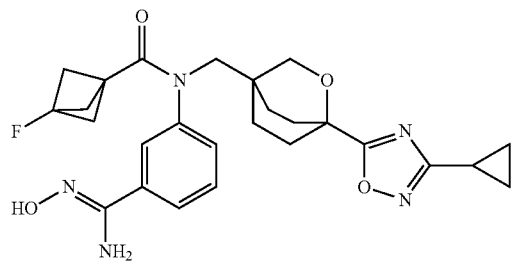 [SMILES: N/C(=N\O)c1cccc(N(CC23CCC(c4nc(C5CC5)no4)(CC2)OC3)C(=O)C23CC(F)(C2)C3)c1]

The title compound was synthesized according to the method described for the synthesis of Intermediate 88F by substituting Intermediate 203B where appropriate: (40 mg, 0.081 mmol, 93% yield) as brown wax. MS (ESI) 496 (M+H).

Step D. Example 203. Preparation of N-((1-(3-cyclopropyl-1,2,4-oxadiazol-5-yl)-2-oxabicyclo[2.2.2]octan-4-yl)methyl)-N-(3-(5-cyclopropylisoxazol-3-yl)phenyl)-3-fluorobicyclo[1.1.1]pentane-1-carboxamide The title compound was synthesized according to the method described for the synthesis of Intermediate 3A by substituting Intermediate 203C and the corresponding acid where appropriate: (3.8 mg, 6.96 μmol, 17% yield). $^1$H NMR (400 MHz, DMSO-$d_6$) δ 8.03-7.95 (m, 1H), 7.91 (s, 1H), 7.72-7.60 (m, 2H), 3.75-3.52 (m, 4H), 2.47-2.42 (m, 1H), 2.17-2.03 (m, 3H), 2.01-1.91 (m, 2H), 2.0-1.88 (m, 6H), 1.66-1.56 (m., 2H), 1.60-1.49 (m, 2H), 1.38-1.2 (m, 4H), 1.09-0.99 (m, 2H), 0.90-0.79 (m, 2H); FXR EC$_{50}$ (nM)=74; MS (ESI) 546 (M+H).

Example 204

N-((1-(3-cyclopropyl-1,2,4-oxadiazol-5-yl)-2-oxabicyclo[2.2.2]octan-4-yl)methyl)-N-(3-(5-(difluoromethyl)-1,2,4-oxadiazol-3-yl)phenyl)-3-fluorobicyclo[1.1.1]pentane-1-carboxamide

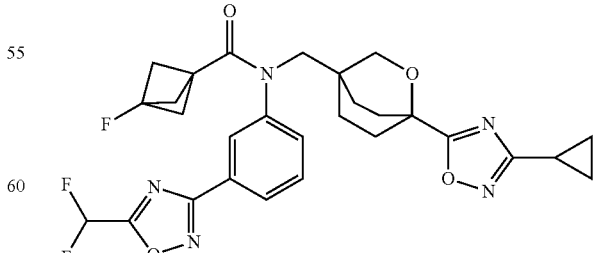

(204)

The title compound was synthesized according to the method described for the synthesis of Intermediate 3A by substituting Intermediate 203C and the corresponding acid where appropriate: (9.3 mg, 0.017 mmol, 42% yield). $^1$H NMR (400 MHz, DMSO-$d_6$) δ 8.14-8.05 (m, 1H), 8.05-7.99 (m, 1H), 7.79-7.44 (m, 3H), 3.65 (d, J=10.0 Hz, 4H), 2.18-2.03 (m, 3H), 2.03-1.76 (m, 8H), 1.67-1.62 (m, 2H), 1.61-1.49 (m, 2H), 1.09-0.99 (m, 2H), 0.90-0.75 (m, 2H); FXR EC$_{50}$ (nM)=371; MS (ESI) 556 (M+H).

Example 205

N-(5-(3-cyclopropyl-1,2,4-oxadiazol-5-yl)pyridin-3-yl)-N-((4-(3-cyclopropyl-1-methyl-1H-pyrazol-5-yl)bicyclo[2.2.2]octan-1-yl)methyl)-3-fluorobicyclo[1.1.1]pentane-1-carboxamide (205)

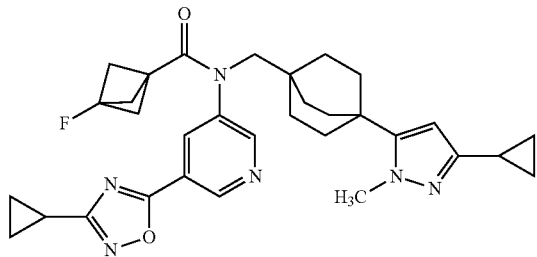

Step A. Intermediate 205A. Preparation of 5-(3-cyclopropyl-1,2,4-oxadiazol-5-yl)pyridin-3-amine

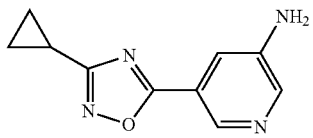 [SMILES: Nc1cncc(-c2nc(C3CC3)no2)c1]

The title compound was synthesized according to the method described for the synthesis of Intermediate 3A by substituting 5-aminonicotinic acid (cis)-N-((4-(3-(tertbutyl)-1,2,4-oxadiazol-5-yl)bicyclo[2.2.2]octan-1-yl)methyl)-N-(3-(3-cyclopropyl-1,2,4-oxadiazol-5-yl)phenyl)-3-methoxycyclobutane-1-carboxamide and (Z)—N'-hydroxycyclopropane carboximidamide where appropriate: (700 mg, 3.46 mmol, 80% yield) as brown solid. MS (ESI) 203 (M+H).

Step B. Intermediate 205B. Preparation of 5-(3-cyclopropyl-1,2,4-oxadiazol-5-yl)-N-((4-(3-cyclopropyl-1-methyl-1H-pyrazol-5-yl)bicyclo[2.2.2]octan-1-yl)methyl)pyridin-3-amine

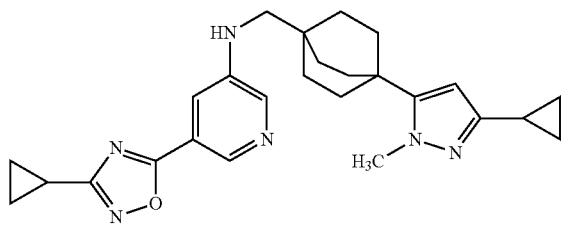 [SMILES: Cn1nc(C2CC2)cc1C12CCC(CNc3cncc(-c4nc(C5CC5)no4)c3)(CC1)CC2]

The title compound was synthesized according to the method described for the synthesis of Intermediate 1I by substituting Intermediate 205A and Intermediate 126B where appropriate: (20 mg, 0.045 mmol, 30% yield) as brown wax. MS (ESI) 445 (M+H).

Step C. Example 205. Preparation of N-(5-(3-cyclopropyl-1,2,4-oxadiazol-5-yl)pyridin-3-yl)-N-((4-(3-cyclopropyl-1-methyl-1H-pyrazol-5-yl)bicyclo[2.2.2]octan-1-yl)methyl)-3-fluorobicyclo[1.1.1]pentane-1-carboxamide To a stirred solution of Intermediate 205B (20 mg, 0.045 mmol) in DCM (2 mL) was added 2-dimethylaminopyridine (16.49 mg, 0.135 mmol) and 3-fluorobicyclo[1.1.1]pentane-1-carboxylic acid (8.78 mg, 0.067 mmol). After cooling the reaction mixture to 0° C., POCl$_3$ (8.39 μL, 0.090 mmol) was added and the reaction was stirred at room temperature for 1 h. The reaction mixture was quenched with ice cold water (2 mL) and extracted with DCM (5 mL). The organic layer was washed with water (5 mL), saturated brine solution (5 mL), dried over sodium sulphate, filtered and concentrated under reduced pressure. The crude material was purified via preparative LC/MS using following conditions: Column: Waters XBridge C18, 150 mm×19 mm, 5-μm particles; Mobile Phase A: 5:95 acetonitrile:water with 10-mM ammonium acetate; Mobile Phase B: 95:5 acetonitrile:water with 10 mM ammonium acetate; Gradient: a 0-minute hold at 15% B, 15-75% B over 25 minutes, then a 5-minute hold at 100% B; Flow Rate: 15 mL/min; Column Temperature: 25° C. Fraction collection was triggered by signals. Fractions containing the desired product were combined and dried via centrifugal evaporation to afford the title compound (4.7 mg, 8.11 μmol, 18% yield). $^1$H NMR (400 MHz, DMSO-$d_6$) δ 9.18 (d, J=1.7 Hz, 1H), 8.95 (d, J=2.4 Hz, 1H), 8.50 (t, J=2.3 Hz, 1H), 5.62 (s, 1H), 3.72 (s, 5H), 2.30-2.21 (m, 1H), 1.92 (br. s., 6H), 1.76-1.64 (m, 7H), 1.54-1.27 (m, 6H), 1.19-1.10 (m, 2H), 1.08-0.98 (m, 2H), 0.80-0.69 (m, 2H), 0.59-0.45 (m, 2H); FXR EC$_{50}$ (nM)=218; MS (ESI) 557 (M+H).

Example 206

N-((4-(5-(tert-butyl)-1,2,4-oxadiazol-3-yl)bicyclo[2.2.2]octan-1-yl)methyl)-N-(5-(3-cyclopropyl-1,2,4-oxadiazol-5-yl)pyridin-3-yl)-3-fluorobicyclo[1.1.1]pentane-1-carboxamide (206)

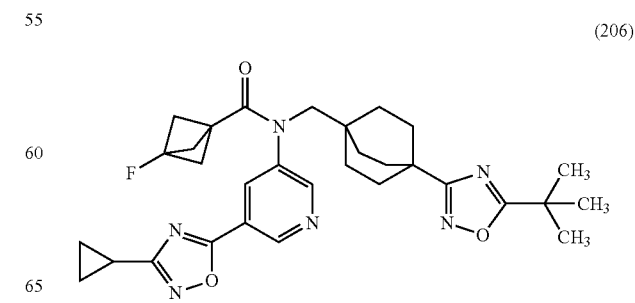

Step A. Intermediate 206A. Preparation of methyl 4-carbamoylbicyclo[2.2.2]octane-1-carboxylate

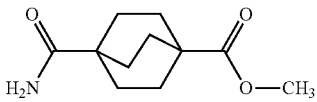

The title compound was synthesized according to the method described for the synthesis of Intermediate 114A by substituting 4-(methoxycarbonyl)bicyclo[2.2.2]octane-1-carboxylic acid where appropriate: (9.0 g, 42.6 mmol, 90% yield). MS (ESI) 212 (M+1).

Step B. Intermediate 206B. Preparation of methyl 4-cyanobicyclo[2.2.2]octane-1-carboxylate

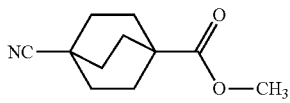

The title compound was synthesized according to the method described for the synthesis of Intermediate 114B by substituting Intermediate 206A where appropriate: (4.3 g, 22.25 mmol, 47% yield) as white solid. MS (ESI) 211 (M+18) $NH_3$ adduct.

Step C. Intermediate 206C. Preparation of methyl 4-(N'-hydroxycarbamimidoyl)bicyclo[2.2.2]octane-1-carboxylate

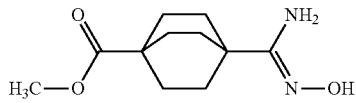

The title compound was synthesized according to the method described for the synthesis of Intermediate 88F by substituting Intermediate 206B where appropriate: (530 mg, 2.342 mmol, 91% yield) as white solid. MS (ESI) 227 (M+H).

Step D. Intermediate 206D. Preparation of methyl 4-(5-(tert-butyl)-1,2,4-oxadiazol-3-yl)bicyclo[2.2.2]octane-1-carboxylate

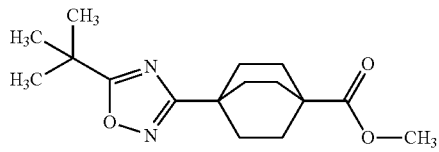 [SMILES: COC(=O)C12CCC(c3noc(C(C)(C)C)n3)(CC1)CC2]

The title compound was synthesized according to the method described for the synthesis of Intermediate 3A by substituting Intermediate 206C and the corresponding acid where appropriate: (650 mg, 2.223 mmol, 95% yield). MS (ESI) 293 (M+H).

Step E. Intermediate 280E. Preparation of (4-(5-(tert-butyl)-1,2,4-oxadiazol-3-yl) bicyclo[2.2.2]octan-1-yl)methanol

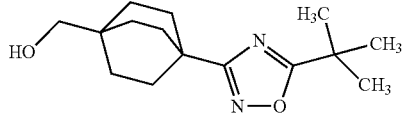 [SMILES: CC(C)(C)c1nc(C23CCC(CO)(CC2)CC3)no1]

The title compound was synthesized according to the method described for the synthesis of Intermediate 1G by substituting Intermediate 206D where appropriate: (500 mg, 1.891 mmol, 89% yield) as white solid. MS (ESI) 265 (M+H).

Step F. Intermediate 206F. Preparation of 4-(5-(tert-butyl)-1,2,4-oxadiazol-3-yl) bicyclo[2.2.2]octane-1-carbaldehyde

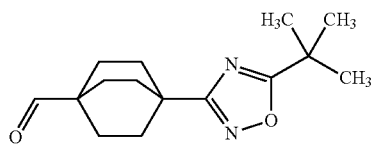 [SMILES: CC(C)(C)c1nc(C23CCC(C=O)(CC2)CC3)no1]

The title compound was synthesized according to the method described for the synthesis of Intermediate 3C by substituting Intermediate 206E where appropriate: (390 mg, 1.487 mmol, 82% yield) as a pale yellow solid. $^1$HNMR (400 MHz, DMSO-$d_6$): δ 9.45 (s, 1H), 1.88-1.84 (m, 6H), 1.70-1.66 (m, 6H), 1.35 (s, 9H), Step G. Intermediate 206G. Preparation of N-((4-(5-(tert-butyl)-1,2,4-oxadiazol-3-yl) bicyclo[2.2.2]octan-1-yl)methyl)-5-(3-cyclopropyl-1,2,4-oxadiazol-5-yl)pyridin-3-amine

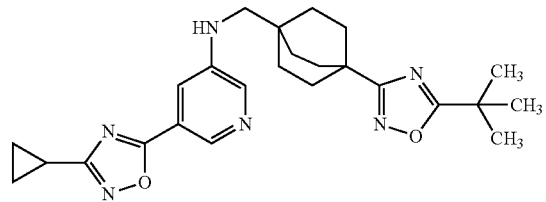 [SMILES: CC(C)(C)c1nc(C23CCC(CNc4cncc(-c5nc(C6CC6)no5)c4)(CC2)CC3)no1]

The title compound was synthesized according to the method described for the synthesis of Intermediate 1I by substituting Intermediate 205A and Intermediate 206F where appropriate: (20 mg, 0.045 mmol, 27% yield) as brown wax. MS (ESI) 449 (M+H).

Step H. Example 206. Preparation of N-((4-(5-(tert-butyl)-1,2,4-oxadiazol-3-yl) bicyclo[2.2.2]octan-1-yl)methyl)-N-(5-(3-cyclopropyl-1,2,4-oxadiazol-5-yl)pyridin-3-yl)-3-fluorobicyclo[1.1.1]pentane-1-carboxamide The title compound was synthesized according to the method described for the synthesis of Example 205 by substituting Intermediate 206G and the corresponding acid where appropriate: (5.2 mg, 9.27 µmol, 21% yield). $^1$H NMR (400 MHz, DMSO-d$_6$) δ 9.19 (d, J=1.7 Hz, 1H), 8.96 (d, J=2.2 Hz, 1H), 8.51 (d, J=2.0 Hz, 1H), 3.72 (m, 2H), 2.28-2.23 (m, 1H), 1.92 (br. s., 6H), 1.82-1.63 (m, 6H), 1.52-1.36 (m, 6H), 1.36-1.29 (m, 9H), 1.15 (dd, J=8.1, 2.4 Hz, 2H), 1.06-0.99 (m, 2H); FXR EC$_{50}$ (nM)=49; MS (ESI) 561.3 (M+H).

Example 207

N-((4-(3-(tert-butyl)-1,2,4-oxadiazol-5-yl)bicyclo[2.2.2]octan-1-yl)methyl)-N-(5-(3-cyclopropyl-1,2,4-oxadiazol-5-yl)pyridin-3-yl)-3-fluorobicyclo[1.1.1]pentane-1-carboxamide (207)

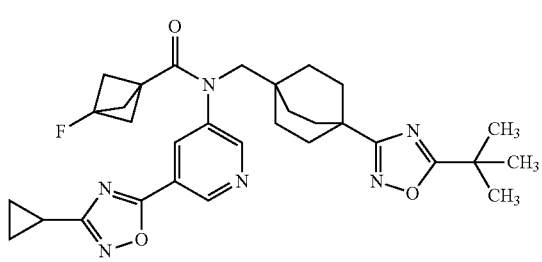

Step A. Intermediate 207A. Preparation of methyl 4-(((5-(3-cyclopropyl-1,2,4-oxadiazol-5-yl)pyridin-3-yl)amino)methyl)bicyclo[2.2.2]octane-1-carboxylate

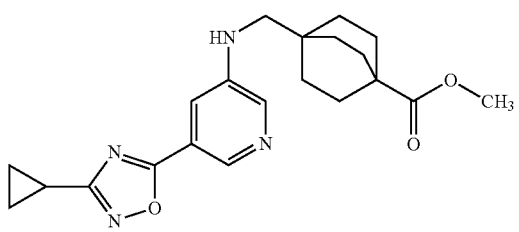 [SMILES: COC(=O)C12CCC(CNc3cncc(-c4nc(C5CC5)no4)c3)(CC1)CC2]

The title compound was synthesized according to the method described for the synthesis of Intermediate 1I by substituting Intermediate 205A and Intermediate 88B where appropriate: (250 mg, 0.654 mmol, 44% yield). MS (ESI) 383 (M+H).

Step B. Intermediate 207B. Preparation of 4-(((5-(3-cyclopropyl-1,2,4-oxadiazol-5-yl) pyridin-3-yl)amino)methyl)bicyclo[2.2.2]octane-1-carboxylic acid

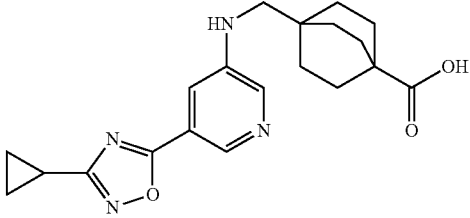 [SMILES: O=C(O)C12CCC(CNc3cncc(-c4nc(C5CC5)no4)c3)(CC1)CC2]

The title compound was synthesized according to the method described for the synthesis of Intermediate 175B by substituting Intermediate 207A where appropriate: (50 mg, 0.115 mmol, 67% yield). MS (ESI) 369 (M+H).

Step C. Intermediate 207C. Preparation of N-((4-(3-(tert-butyl)-1,2,4-oxadiazol-5-yl) bicyclo[2.2.2]octan-1-yl)methyl)-5-(3-cyclopropyl-1,2,4-oxadiazol-5-yl)pyridin-3-amine

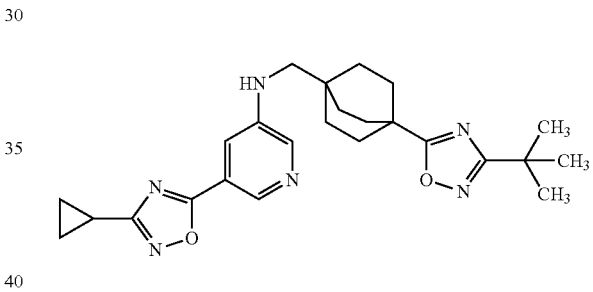

The title compound was synthesized according to the method described for the synthesis of Intermediate 3A by substituting Intermediate 207B and Intermediate 88F where appropriate: (20 mg, 0.045 mmol, 55% yield). MS (ESI) 449 (M+H).

Step D. Example 207. Preparation of N-((4-(3-(tert-butyl)-1,2,4-oxadiazol-5-yl) bicyclo[2.2.2]octan-1-yl)methyl)-N-(5-(3-cyclopropyl-1,2,4-oxadiazol-5-yl)pyridin-3-yl)-3-fluorobicyclo[1.1.1]pentane-1-carboxamide The title compound was synthesized according to the method described for the synthesis of Example 3 by substituting Intermediate 207C and the corresponding acid where appropriate: (1 mg, 1.784 µmol, 3% yield). $^1$H NMR (400 MHz, DMSO-d$_6$) δ 9.19 (d, J=2.2 Hz, 1H), 8.96 (d, J=2.7 Hz, 1H), 8.51 (s, 1H), 3.3-3.18 (s, 2H), 2.29-2.23 (m, 1H), 1.92 (br. s., 6H), 1.84-1.77 (m, 6H), 1.45 (br. s., 6H), 1.26 (s, 9H), 1.19-1.13 (m, 2H), 1.03 (br. s., 2H). FXR EC$_{50}$ (nM) 571; MS (ESI) 561 (M+H).

Example 208

N-((4-(3-(tert-butyl)-1,2,4-oxadiazol-5-yl)-2-oxabi-cyclo[2.2.2]octan-1-yl)methyl)-N-(3-(1-(cyclopropylsulfonyl)-1H-pyrazol-4-yl)phenyl)-3-fluorobicyclo[1.1.1]pentane-1-carboxamide

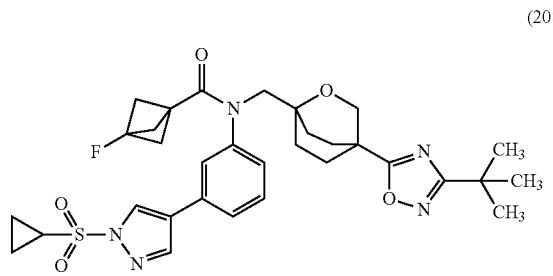

(208)

Step A. Intermediate 208A. Preparation of (1-(hydroxymethyl)-2-oxabicyclo[2.2.2]octan-4-yl)methyl 4-methylbenzenesulfonate

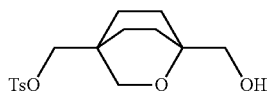

The title compound was synthesized according to the method described for the synthesis of Intermediate 88A by substituting Intermediate 196F where appropriate: (900 mg, 2.76 mmol, 52% yield) as white solid. MS (ESI) 344 (M+18) $NH_3$ adduct.

Step B. Intermediate 208B. Preparation of (1-formyl-2-oxabicyclo[2.2.2]octan-4-yl) methyl 4-methylbenzenesulfonate

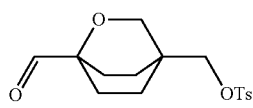

To a stirred solution of oxalyl chloride (0.402 mL, 4.60 mmol) in DCM (2 mL) at −78° C. was added DMSO (0.326 mL, 4.60 mmol) in DCM (1.7 mL) drop wise over 5 min. After stirring the reaction for 15 min, a solution of Intermediate 208A (600.0 mg, 1.838 mmol) in DCM (4 mL) was added drop wise over 10 min and the reaction mixture was stirred for 2.5 h at −78° C. To the above reaction mixture, TEA (1.794 mL, 12.87 mmol) was added drop wise over 5 min and the reaction was stirred for additional 5 min at −78° C. The reaction mixture was warmed up to room temperature and stirred for additional 1 h. The reaction was quenched with water (20 mL) and extracted with DCM (2×20 mL). The combined organic layers were washed with brine solution (20 mL), dried over sodium sulfate, filtered and concentrated under reduced pressure. The crude material was purified by flash column chromatography (Combi-flash, 24 g silica, 0-90% EtOAc/PE) to afford the title compound (430 mg, 1.326 mmol, 72% yield) as white solid. MS (ESI) 342 (M+18) $NH_3$ adduct.

Step C. Intermediate 208C. Preparation of (1-(((3-bromophenyl)amino)methyl)-2-oxabicyclo[2.2.2]octan-4-yl)methyl 4-methylbenzenesulfonate

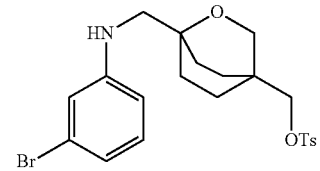 [SMILES: Cc1ccc(S(=O)(=O)OCC23CCC(CNc4cccc(Br)c4)(CC2)OC3)cc1]

The title compound was synthesized according to the method described for the synthesis of Intermediate 1I by substituting 3-bromoaniline and Intermediate 208B where appropriate: (440 mg, 0.916 mmol, 79% yield) as brown wax. MS (ESI) 480 (M+H).

Step D. Intermediate 208D. Preparation of (1-((N-(3-bromophenyl)-3-fluorobicyclo[1.1.1]pentane-1-carboxamido)methyl)-2-oxabicyclo[2.2.2]octan-4-yl) methyl 4-methylbenzenesulfonate

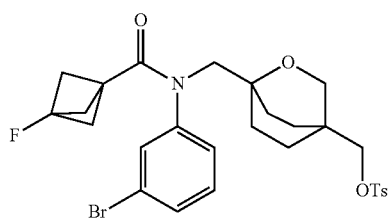 [SMILES: Cc1ccc(S(=O)(=O)OCC23CCC(CN(C(=O)C45CC(F)(C4)C5)c4cccc(Br)c4)(CC2)OC3)cc1]

The title compound was synthesized according to the method described for the synthesis of Example 3 by substituting Intermediate 208C and the corresponding acid where appropriate: (330 mg, 0.557 mmol, 61% yield)) as brown wax. MS (ESI) 592 (M+H).

Step E. Intermediate 208E. Preparation of (1-((N-(3-bromophenyl)-3-fluorobicyclo[1.1.1]pentane-1-carboxamido)methyl)-2-oxabicyclo[2.2.2]octan-4-yl) methyl acetate

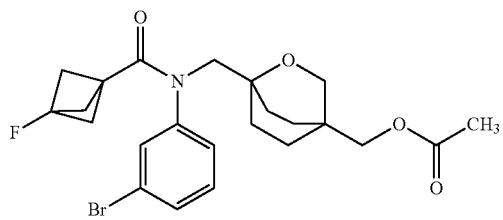 [SMILES: CC(=O)OCC12CCC(CN(C(=O)C34CC(F)(C3)C4)c3cccc(Br)c3)(CC1)OC2]

The title compound was synthesized according to the method described for the synthesis of Intermediate 141C by substituting Intermediate 208D where appropriate: (230 mg, 0.479 mmol, 92% yield) as white solid. MS (ESI) 480 (M+H).

Step F. Intermediate 208F. Preparation of N-(3-bromophenyl)-3-fluoro-N-((4-(hydroxymethyl)-2-oxabicyclo[2.2.2]octan-1-yl)methyl)bicyclo[1.1.1]pentane-1-carboxamide

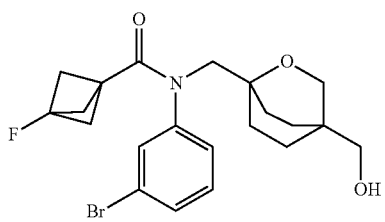 [SMILES: O=C(N(CC12CCC(CO)(CC1)CO2)c1cccc(Br)c1)C12CC(F)(C1)C2]

The title compound was synthesized according to the method described for the synthesis of Intermediate 141D by substituting Intermediate 208E where appropriate: (180 mg, 0.411 mmol, 86% yield). MS (ESI) 438 (M+H).

Step G. Intermediate 208G. Preparation of 1-((N-(3-bromophenyl)-3-fluorobicyclo[1.1.1]pentane-1-carboxamido)methyl)-2-oxabicyclo[2.2.2]octane-4-carboxylic acid

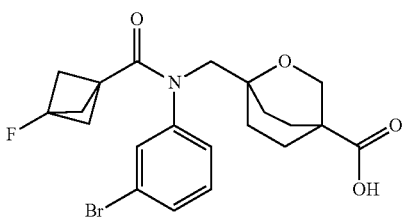 [SMILES: O=C(O)C12CCC(CN(C(=O)C34CC(F)(C3)C4)c3cccc(Br)c3)(CC1)OC2]

To a stirred solution of Intermediate 208F (160 mg, 0.365 mmol) in acetone (2 mL) at 0° C. was added chromium trioxide (0.365 mL, 0.730 mmol) and the reaction mixture was stirred for 15 min at 0° C. The reaction mixture was quenched with isopropanol (5 mL) and concentrated under reduced pressure. The residue was diluted with water (10 mL) and extracted with ethyl acetate (2×20 mL). The combined organic extracts were washed with water (10 mL), saturated brine solution (10 mL), dried over anhydrous sodium sulfate, filtered and concentrated under reduced pressure to afford the title compound (160 mg, 0.354 mmol, 97% yield). MS (ESI) 452 (M+H).

Step H. Intermediate 208H. Preparation of N-(3-bromophenyl)-N-((4-(3-(tert-butyl)-1,2,4-oxadiazol-5-yl)-2-oxabicyclo[2.2.2]octan-1-yl)methyl)-3-fluorobicyclo[1.1.1]pentane-1-carboxamide

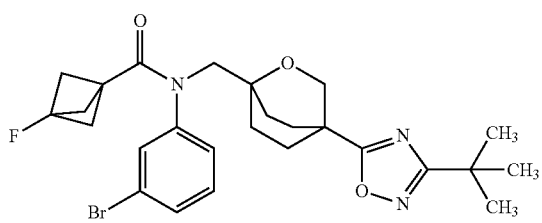 [SMILES: CC(C)(C)c1noc(C23CCC(CN(C(=O)C45CC(F)(C4)C5)c4cccc(Br)c4)(CC2)OC3)n1]

The title compound was synthesized according to the method described for the synthesis of Intermediate 3A by substituting Intermediate 208G and (Z)—N'-hydroxypivalimidamide where appropriate: (130 mg, 0.244 mmol, 69% yield) as brown wax. MS (ESI) 532 (M+H).

Step I. Example 208. Preparation of N-((4-(3-(tert-butyl)-1,2,4-oxadiazol-5-yl)-2-oxabicyclo[2.2.2]octan-1-yl)methyl)-N-(3-(1-(cyclopropylsulfonyl)-1H-pyrazol-4-yl) phenyl)-3-fluorobicyclo[1.1.1]pentane-1-carboxamide The title compound was synthesized according to the method described for the synthesis of Example 149 by substituting Intermediate 208H and the corresponding boronate ester where appropriate: (4.5 mg, 7.05 μmol, 15% yield). $^1$H NMR (400 MHz, DMSO-$d_6$) δ 8.93 (s, 1H), 8.55 (s, 1H), 7.89-7.71 (m, 2H), 7.46 (t, J=7.8 Hz, 1H), 7.29 (d, J=8.8 Hz, 1H), 3.85 (br. s., 2H), 3.72 (d, J=17.4 Hz, 2H), 3.21-3.13 (m, 1H), 2.03 (br. s., 4H), 1.87 (br. s., 8H), 1.83-1.66 (m, 2H), 1.39-1.30 (m, 2H), 1.30-1.11 (m, 11H). FXR EC$_{50}$ (nM) 618; MS (ESI) 624 (M+H).

Example 209

N-(3-(1H-pyrazol-4-yl)phenyl)-3-fluoro-N-((4-(5-(1-(trifluoromethyl)cyclopropyl)-1,2,4-oxadiazol-3-yl)bicyclo[2.2.2]octan-1-yl)methyl)bicyclo[1.1.1]pentane-1-carboxamide (209)

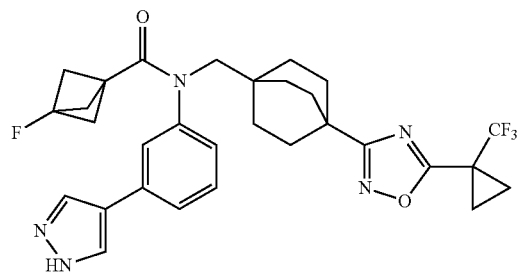

Step A. Intermediate 209A. Preparation of 3-bromo-N-((4-(5-(1-(trifluoromethyl) cyclopropyl)-1,2,4-oxadiazol-3-yl)bicyclo[2.2.2]octan-1-yl)methyl)aniline

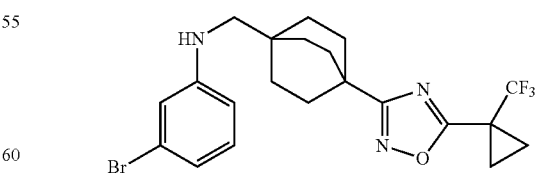

The title compound was synthesized according to the method described for the synthesis of Intermediate 3A by substituting Intermediate 194E and the corresponding acid where appropriate: (450 mg, 0.957 mmol, 96% yield) as yellow solid. MS (ESI) 470 (M+H).

Step B. Intermediate 209B. Preparation of N-(3-bromophenyl)-3-fluoro-N-((4-(5-(1-(trifluoromethyl)cyclopropyl)-1,2,4-oxadiazol-3-yl)bicyclo[2.2.2]octan-1-yl)methyl) bicyclo[1.1.1]pentane-1-carboxamide

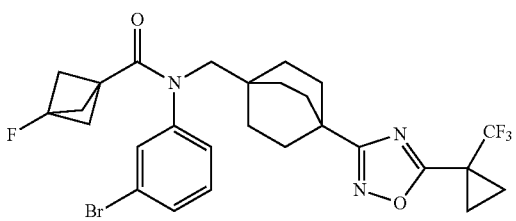 [SMILES: O=C(N(CC12CCC(c3noc(C4(C(F)(F)F)CC4)n3)(CC1)CC2)c1cccc(Br)c1)C12CC(F)(C1)C2]

The title compound was synthesized according to the method described for the synthesis of Example 3 by substituting Intermediate 209A and the corresponding acid where appropriate: (400 mg, 0.687 mmol, 77% yield). MS (ESI) 582 (M+H).

Step C. Example 209. Preparation of N-(3-(1H-pyrazol-4-yl)phenyl)-3-fluoro-N-((4-(5-(1-(trifluoromethyl)cyclopropyl)-1,2,4-oxadiazol-3-yl)bicyclo[2.2.2]octan-1-yl)methyl) bicyclo[1.1.1]pentane-1-carboxamide The title compound was synthesized according to the method described for the synthesis of Example 149 by substituting Intermediate 209B and the corresponding boronate ester where appropriate: (7.9 mg, 0.0138 mmol, 26% yield). $^1$H NMR (400 MHz, DMSO-$d_6$) δ 13.00 (br. s., 1H), 8.31 (br. s., 1H), 8.03 (br. s., 1H), 7.71-7.54 (m, 2H), 7.41 (t, J=8.1 Hz, 1H), 7.18 (d, J=8.3 Hz, 1H), 3.67-3.49 (m, 2H), 1.87 (br. s., 6H), 1.80-1.57 (m, 10H), 1.55-1.35 (m, 6H). FXR EC$_{50}$ (nM) 152; MS (ESI) 570 (M+H).

Example 210

N-((4-(5-(tert-butyl)-1,2,4-oxadiazol-3-yl)bicyclo[2.2.2]octan-1-yl)methyl)-N-(4-(3-cyclopropyl-1,2,4-oxadiazol-5-yl)pyridin-2-yl)-3-fluorobicyclo[1.1.1]pentane-1-carboxamide (210)

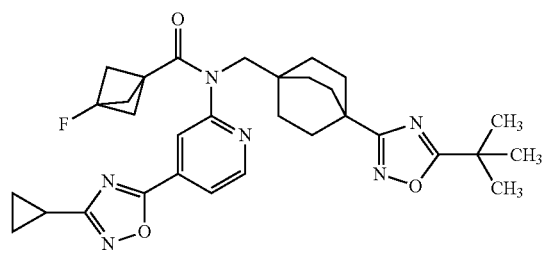

Step A. Intermediate 210A. Preparation of 4-(3-cyclopropyl-1,2,4-oxadiazol-5-yl)pyridin-2-amine

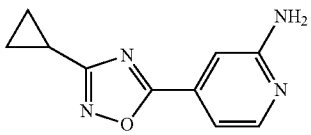

The title compound was synthesized according to the method described for the synthesis of Intermediate 3A by substituting 2-aminoisonicotinic acid and N'-hydroxycyclopropanecarboximidamide where appropriate: (200 mg, 0.920 mmol, 25% yield) as yellow solid. MS (ESI) 203 (M+H). $^1$H NMR (400 MHz, DMSO-$d_6$) δ 8.13 (d, J=5.0 Hz, 1H), 7.06 (s, 1H), 7.00 (dd, J=5.0, 1.5 Hz, 1H), 6.42 (s, 2H), 2.25-2.17 (m, 1H), 1.17-1.09 (m, 2H), 1.01-0.95 (m, 2H).

Step B. Intermediate 210B. Preparation of N-((4-(5-(tert-butyl)-1,2,4-oxadiazol-3-yl) bicyclo[2.2.2]octan-1-yl)methyl)-4-(3-cyclopropyl-1,2,4-oxadiazol-5-yl)pyridin-2-amine

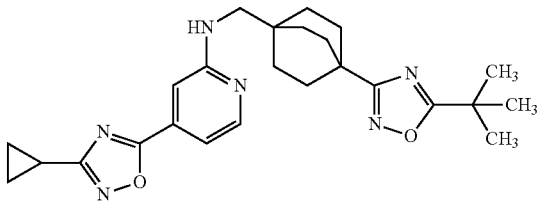 [SMILES: CC(C)(C)c1nc(C23CCC(CNc4cc(-c5nc(C6CC6)no5)ccn4)(CC2)CC3)no1]

The title compound was synthesized according to the method described for the synthesis of Intermediate 1I by substituting Intermediate 210A and Intermediate 206F where appropriate: (30 mg, 0.067 mmol, 35% yield) as brown solid. $^1$H NMR (400 MHz, DMSO-$d_6$) δ 8.15 (d, J=4.5 Hz, 1H), 7.21 (s, 1H), 6.93 (dd, J=5.3, 1.3 Hz, 2H), 4.38 (t, J=5.3 Hz, 2H), 2.22-2.19 (m, 1H), 1.86-1.75 (m, 6H), 1.57-1.49 (m, 3H), 1.47-1.40 (m, 3H), 1.35 (s, 9H), 1.14-1.12 (m, 2H), 1.00-0.95 (m, 2H). MS (ESI) 449 (M+H).

Step C. Example 210. Preparation of N-((4-(5-(tert-butyl)-1,2,4-oxadiazol-3-yl) bicyclo[2.2.2]octan-1-yl)methyl)-N-(4-(3-cyclopropyl-1,2,4-oxadiazol-5-yl)pyridin-2-yl)-3-fluorobicyclo[1.1.1]pentane-1-carboxamide To a stirred solution of 3-fluorobicyclo[1.1.1]pentane-1-carboxylic acid (17.40 mg, 0.134 mmol) in acetonitrile (1 mL) was added Intermediate 210B (30 mg, 0.067 mmol). The reaction mixture was cooled to 0° C. and 4-methylmorpholine (0.038 mL, 0.334 mmol) was added, followed by POCl$_3$ (0.016 mL, 0.167 mmol). The reaction mixture was gradually warmed up to room temperature and stirred at room temperature for 2 h. The reaction mixture was diluted with ethyl acetate (30 mL) and the organic solution was washed with 10% aqueous citric acid solution (25 mL), 10% aqueous sodium bicarbonate solution (25 mL) followed by brine solution (2×20 mL). The organic layer was dried over anhydrous sodium sulphate, filtered and concentrated under reduced pressure. The crude material was purified via preparative LC/MS using following conditions: Column: Waters XBridge C18, 150 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 2-minute hold at 25% B, 25-70% B over 25 minutes, then a 5-minute hold at 100% B; Flow Rate: 15 mL/min; Column Temperature: 25° C. Fraction collection was triggered by MS signals. Fractions containing the desired product were combined and dried via centrifugal evaporation to afford the title compound (6.2 mg, 0.011 mmol, 17% yield). FXR $EC_{50}$ (nM)=48; MS (ESI) 561 (M+H).

Example 211

N-(4-(1H-pyrazol-4-yl)pyridin-2-yl)-N-((4-(5-(tert-butyl)-1,2,4-oxadiazol-3-yl) bicyclo[2.2.2]octan-1-yl)methyl)-3-fluorobicyclo[1.1.1]pentane-1-carboxamide (211)

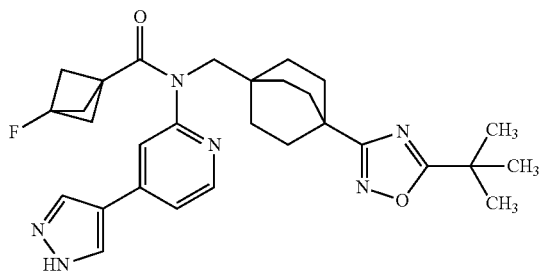

Step A. Intermediate 211A. Preparation of 4-bromo-N-((4-(5-(tert-butyl)-1,2,4-oxadiazol-3-yl) bicyclo[2.2.2]octan-1-yl)methyl)pyridin-2-amine

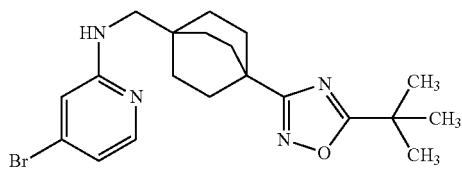 [SMILES: CC(C)(C)c1nc(C23CCC(CNc4cc(Br)ccn4)(CC2)CC3)no1]

The title compound was synthesized according to the method described for the synthesis of Intermediate 1I by substituting 4-bromopyridin-2-amine and Intermediate 206F where appropriate: (250 mg, 0.596 mmol, 41% yield) as colorless liquid. MS (ESI) 419 (M+H).

Step B. Intermediate 211B. Preparation of N-(4-bromopyridin-2-yl)-N-((4-(5-(tert-butyl)-1,2,4-oxadiazol-3-yl)bicyclo[2.2.2]octan-1-yl)methyl)-3-fluorobicyclo[1.1.1]pentane-1-carboxamide

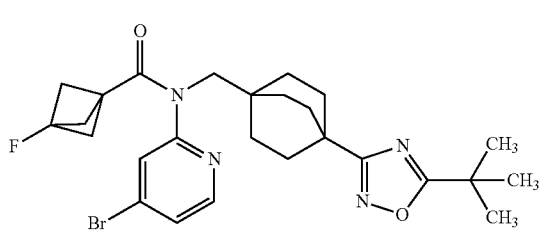 [SMILES: CC(C)(C)c1nc(C23CCC(CN(C(=O)C45CC(F)(C4)C5)c4cc(Br)ccn4)(CC2)CC3)no1]

The title compound was synthesized according to the method described for the synthesis of Example 210 by substituting Intermediate 211A and the corresponding acid where appropriate: (130 mg, 0.245 mmol, 57% yield) as colorless liquid. MS (ESI) 531 (M+H).

Step C. Example 211. Preparation of N-(4-(1H-pyrazol-4-yl)pyridin-2-yl)-N-((4-(5-(tert-butyl)-1,2,4-oxadiazol-3-yl)bicyclo[2.2.2]octan-1-yl)methyl)-3-fluorobicyclo[1.1.1]pentane-1-carboxamide The title compound was synthesized according to the method described for the synthesis of Example 149 by substituting Intermediate 211B and the corresponding boronate ester where appropriate: (2.9 mg, 0.006 mmol, 10% yield). $^1$H NMR (400 MHz, DMSO-$d_6$) δ 13.25 (br. s., 1H), 8.55 (s, 1H), 8.45 (d, J=5.1 Hz, 1H), 8.21 (s, 1H), 7.75 (s, 1H), 7.66 (dd, J=5.3, 1.6 Hz, 1H), 3.67 (s, 2H), 1.91 (d, J=2.7 Hz, 6H), 1.80-1.60 (m, 6H), 1.50-1.35 (m, 6H), 1.33 (s, 9H). FXR $EC_{50}$ (nM) 17; MS (ESI) 519 (M+H).

Example 212

N-((4-(5-(tert-butyl)-1,2,4-oxadiazol-3-yl)bicyclo[2.2.2]octan-1-yl)methyl)-N-(4-(1-(difluoromethyl)-1H-pyrazol-4-yl)pyridin-2-yl)-3-fluorobicyclo[1.1.1]pentane-1-carboxamide (212)

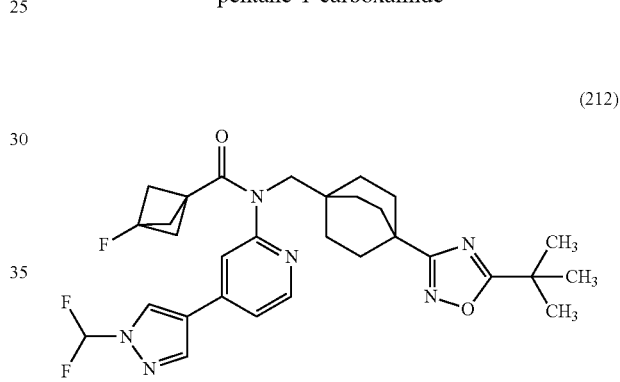

The title compound was synthesized according to the method described for the synthesis of Example 149 by substituting Intermediate 211B and the corresponding boronate ester where appropriate: (22.9 mg, 0.0402 mmol, 71% yield). $^1$H NMR (400 MHz, DMSO-$d_6$) δ 9.09 (s, 1H), 8.63-8.46 (m, 2H), 7.90 (s, 2H), 7.84-7.67 (m, 1H), 3.69 (s, 2H), 1.91 (d, J=2.4 Hz, 6H), 1.80-1.54 (m, 6H), 1.52-1.36 (m, 6H), 1.36-1.16 (m, 9H). FXR $EC_{50}$ (nM) 11; MS (ESI) 569 (M+H).

Example 213

N-((4-(5-(tert-butyl)-1,2,4-oxadiazol-3-yl)bicyclo[2.2.2]octan-1-yl)methyl)-N-(3-(3-(tert-butyl)-1-methyl-1H-pyrazol-5-yl)phenyl)-3-fluorobicyclo[1.1.1]pentane-1-carboxamide (213)

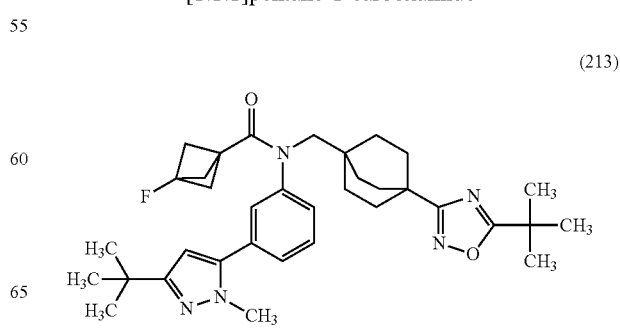

Step A. Intermediate 213A. Preparation of 4,4-dimethyl-1-(3-nitrophenyl)pentane-1,3-dione

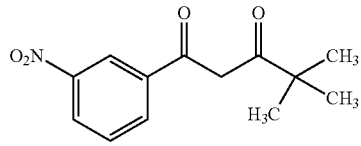 [SMILES: CC(C)(C)C(=O)CC(=O)c1cccc([N+](=O)[O-])c1]

To a stirred solution of 1 M LiHMDS in THF (140 mL, 140 mmol) at −78° C. was added 3,3-dimethylbutan-2-one (7.0 g, 69.9 mmol) and stirred for 45 min, To the resulting solution, a solution of 3-nitrobenzoyl chloride (12.35 g, 66.6 mmol) in THF (20 mL) was added dropwise over 20 min and stirred for 1 h at −78° C. The reaction mixture was quenched with saturated aqueous ammonium chloride solution (50 mL) and extracted with ethyl acetate (2×50 mL). The combined organic layers were washed with water (50 mL), saturated brine solution (50 mL), dried over sodium sulphate, filtered and concentrated under reduced pressure. The crude material was purified by flash column chromatography (Combiflash, 40 g silica, 0-30% EtOAc/PE) to afford the title compound (8.0 g, 32.1 mmol, 48% yield) as yellow solid. MS (ESI) 252 (M+H).

Step B. Intermediate 213B1 and 213B2. Preparation of 3-(tert-butyl)-1-methyl-5-(3-nitrophenyl)-1H-pyrazole and 5-(tert-butyl)-1-methyl-3-(3-nitrophenyl)-1H-pyrazole

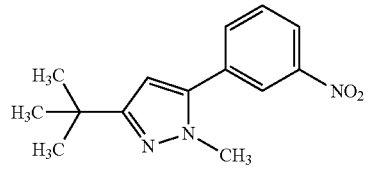

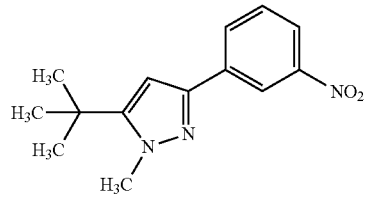

To a stirred solution of Intermediate 213A (3.0 g, 12.04 mmol) in MeOH (30 mL) at room temperature was added methylhydrazine sulfate (3.47 g, 24.07 mmol) and heated to 80° C. After stirring for 3 h, the reaction mixture was concentrated under reduced pressure and the residue was diluted with water (50 mL). The aqueous solution was extracted with ethyl acetate (2×50 mL). The combined organic layers were washed with brine solution (50 mL), dried over anhydrous sodium sulfate, filtered and concentrated under reduced pressure. The crude material was purified by flash column chromatography (Combiflash, 40 g silica, 0-50% EtOAc/PE) to afford the mixture of isomers. The regioisomers were separated by preparative HPLC to afford Intermediate 294B1 (900 mg, 3.47 mmol, 29% yield). $^1$H NMR (400 MHz, DMSO-d$_6$) δ 8.29-8.24 (m, 2H), 8.01-7.99 (m, 1H), 7.77 (t, J=8.00 Hz, 1H), 6.46 (s, 1H), 3.83 (s, 3H), 1.28 (s, 9H); MS (ESI) 260 (M+H) as yellow solid and Intermediate 294B2 (800 mg, 3.09 mmol, 26% yield)$^1$H NMR (400 MHz, DMSO-d$_6$) δ 8.54-8.53 (m, 1H), 8.20-8.18 (m, 1H), 8.12-8.09 (m, 1H), 7.66 (t, J=8.00 Hz, 1H), 6.72 (s, 1H), 3.98 (s, 3H), 1.38 (s, 9H); MS (ESI) 260 (M+H) as yellow solid.

Step C. Intermediate 213C. Preparation of 3-(3-(tert-butyl)-1-methyl-1H-pyrazol-5-yl) aniline

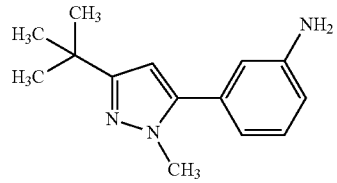 [SMILES: Cn1nc(C(C)(C)C)cc1-c1cccc(N)c1]

To a stirred solution of Intermediate 213B1 (700 mg, 2.70 mmol) in a mixture of ethanol (8 mL) and THF (4 mL) was added zinc (2.65 g, 40.5 mmol) followed by a solution of ammonium chloride (2.167 g, 40.5 mmol) in water (2 mL). After stirring the reaction overnight at room temperature, the reaction mixture was concentrated under reduced pressure and the residue was diluted with water (20 mL). The aqueous solution was extracted with ethyl acetate (2×20 mL) and the combined organic layers were washed with water (20 mL) followed by saturated brine solution (20 mL). The organic layer was then dried over sodium sulfate, filtered and concentrated under reduced pressure. The crude material was purified by flash column chromatography (Combiflash, 12 g silica, 0-80% EtOAc/PE) to afford the title compound (250 mg, 1.090 mmol, 40% yield) as brown wax. MS (ESI) 230 (M+H).

Step D. Intermediate 213D. Preparation of N-((4-(5-(tert-butyl)-1,2,4-oxadiazol-3-yl) bicyclo[2.2.2]octan-1-yl)methyl)-3-(3-(tert-butyl)-1-methyl-1H-pyrazol-5-yl)aniline

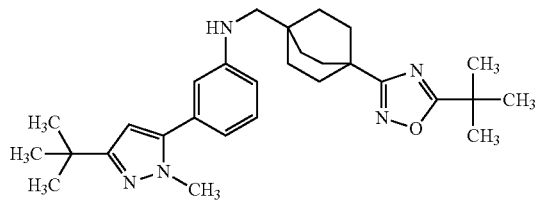 [SMILES: Cn1nc(C(C)(C)C)cc1-c1cccc(NCC23CCC(c4noc(C(C)(C)C)n4)(CC2)CC3)c1]

The title compound was synthesized according to the method described for the synthesis of Intermediate 1I by substituting Intermediate 213C and Intermediate 206F where appropriate: (60 mg, 0.126 mmol, 72% yield) as brown wax. MS (ESI) 476 (M+H).

Step E. Example 213. Preparation of N-((4-(5-(tert-butyl)-1,2,4-oxadiazol-3-yl) bicyclo[2.2.2]octan-1-yl)methyl)-N-(3-(3-(tert-butyl)-1-methyl-1H-pyrazol-5-yl)phenyl)-3-fluorobicyclo[1.1.1]pentane-1-carboxamide The title compound was synthesized according to the method described for the synthesis of Example 3 by substituting Intermediate 213D and the corresponding acid where appropriate: (14.2 mg, 0.024 mmol, 19% yield). $^1$H NMR (400 MHz, DMSO-$d_6$) δ 7.63-7.49 (m, 3H), 7.48-7.40 (m, 1H), 6.36 (s, 1H), 3.81 (s, 3H), 3.73 (d, J=15.4 Hz, 1H), 3.43 (d, J=13.2 Hz, 1H), 1.92 (br. s., 3H), 1.84 (br. s., 3H), 1.74 (t, J=7.9 Hz, 6H), 1.57-1.36 (m, 6H), 1.36-1.30 (m, 9H), 1.30-1.20 (m, 9H); FXR EC$_{50}$ (nM)=198; MS (ESI) 588 (M+H).

Example 214

N-((4-(5-(tert-butyl)-1,2,4-oxadiazol-3-yl)bicyclo[2.2.2]octan-1-yl)methyl)-N-(3-(5-(tert-butyl)-1-methyl-1H-pyrazol-3-yl)phenyl)-3-fluorobicyclo[1.1.1]pentane-1-carboxamide (214)

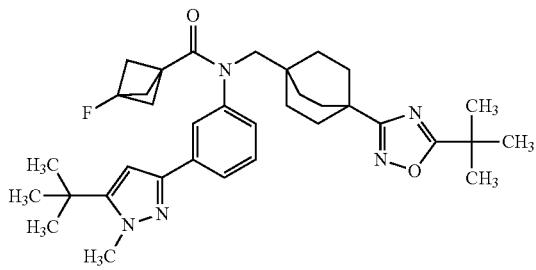

Step A. Intermediate 214A. Preparation of 3-(5-(tert-butyl)-1-methyl-1H-pyrazol-3-yl) aniline

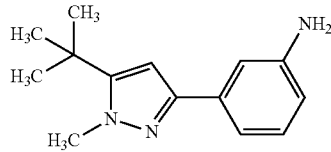

The title compound was synthesized according to the method described for the synthesis of Intermediate 213C by substituting Intermediate 213B2 where appropriate: (240 mg, 1.047 mmol, 45% yield) as brown wax. MS (ESI) 230 (M+H).

Step B. Intermediate 214B. Preparation of N-((4-(5-(tert-butyl)-1,2,4-oxadiazol-3-yl) bicyclo[2.2.2]octan-1-yl)methyl)-3-(5-(tert-butyl)-1-methyl-1H-pyrazol-3-yl)aniline

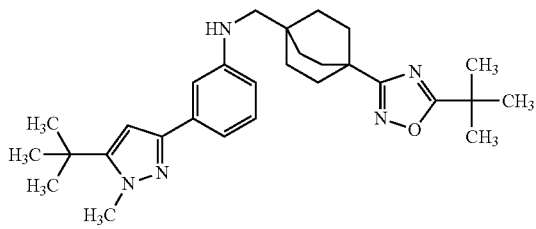 [SMILES: Cn1nc(-c2cccc(NCC34CCC(c5noc(C(C)(C)C)n5)(CC3)CC4)c2)cc1C(C)(C)C]

The title compound was synthesized according to the method described for the synthesis of Intermediate 1I by substituting Intermediate 214A and Intermediate 206F where appropriate: (50 mg, 0.105 mmol, 60% yield) as brown wax. MS (ESI) 476 (M+H).

Step C. Example 214. Preparation of N-((4-(5-(tert-butyl)-1,2,4-oxadiazol-3-yl) bicyclo[2.2.2]octan-1-yl)methyl)-N-(3-(5-(tert-butyl)-1-methyl-1H-pyrazol-3-yl)phenyl)-3-fluorobicyclo[1.1.1]pentane-1-carboxamide The title compound was synthesized according to the method described for the synthesis of Example 3 by substituting Intermediate 214B and the corresponding acid where appropriate: (26 mg, 0.044 mmol, 42% yield). $^1$H NMR (400 MHz, DMSO-$d_6$) δ 7.76 (d, J=8.1 Hz, 1H), 7.71 (t, J=1.7 Hz, 1H), 7.45 (t, J=7.8 Hz, 1H), 7.32-7.24 (m, 1H), 6.63 (s, 1H), 3.97 (s, 3H), 3.62 (br. s., 1H), 3.55 (br. s., 1H), 1.87 (d, J=2.2 Hz, 6H), 1.78-1.67 (m, 6H), 1.51-1.41 (m, 6H), 1.39 (s, 9H), 1.33 (s, 9H); FXR EC$_{50}$ (nM)=89; MS (ESI) 588 (M+H).

Examples 215 and 216

N-(1-(4-(3-cyclopropyl-1,2,4-oxadiazol-5-yl)bicyclo[2.2.2]octan-1-yl)ethyl)-N-(3-(2-cyclopropyloxazol-5-yl)phenyl)-3-fluorobicyclo[1.1.1]pentane-1-carboxamide (215-216)

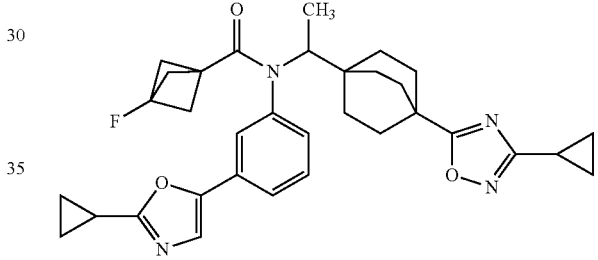

Step A. Intermediate 215A. 1-(4-(3-cyclopropyl-1,2,4-oxadiazol-5-yl) bicyclo[2.2.2]octan-1-yl)ethan-1-ol

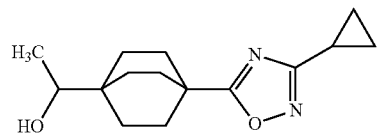 [SMILES: CC(O)C12CCC(c3nc(C4CC4)no3)(CC1)CC2]

A solution of Intermediate 4C (1.5 g, 6.09 mmol) in dry tetrahydrofuran (15 mL) was cooled to −78° C. and 3 M methyl magnesium bromide in diethyl ether (3.04 mL, 9.13 mmol) was added under inert atmosphere. The reaction mixture was slowly allowed to warm up to room temperature and stirred for 1 h at room temperature. The reaction mixture was cooled to 0° C. and quenched with saturated aqueous NH$_4$Cl solution (50 mL). The aqueous solution was extracted with EtOAc (2×50 mL). The combined organic extracts were washed with brine, dried over anhydrous sodium sulfate and concentrated under reduced pressure to afford a residue. The residue was purified by flash column chromatography (24 g silica cartridge, gradient of 0-50% EtOAc in PE as eluent) to afford the title compound (1.25 g, 4.53 mmol, 74% yield) as clear oil. $^1$H-NMR (400 MHz, DMSO-$d_6$) δ 4.29 (d, J=6.80 Hz, 1H), 3.21-3.25 (m, 1H), 2.05-2.11 (m, 1H), 1.78-1.83 (m, 6H), 1.35-1.58 (m, 6H), 1.05-1.10 (m, 2H), 0.94 (d, J=8.40 Hz, 3H), 0.86-0.90 (m, 2H).

Step B. Intermediate 215B. 1-(4-(3-cyclopropyl-1,2,4-oxadiazol-5-yl) bicyclo[2.2.2]octan-1-yl)ethan-1-one

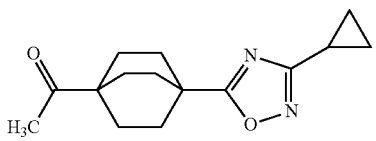 [SMILES: CC(=O)C12CCC(c3nc(C4CC4)no3)(CC1)CC2]

To a solution of Intermediate 215A (1.2 g, 4.57 mmol) in dichloromethane (20 mL) was added Dess-Martin periodinane (4.85 g, 11.43 mmol) at 0° C. Then the reaction mixture was allowed to room temperature and stirred for 1 h. The reaction mixture was diluted with DCM and washed with aqueous 10% NaHCO$_3$ solution, followed by brine. The organic layer was concentrated under reduced pressure; crude was purified by flash chromatography (Combiflash, 12 g Silica gel column) using 0-30% EtOAc in pet-ether as eluents. The compound containing fractions were concentrated to afford the title compound (1 g, 3.65 mmol, 80% yield) as white solid. $^1$H-NMR (400 MHz, DMSO-d$_6$) δ 2.51 (s, 3H), 2.50-2.51 (m, 1H), 1.89-1.99 (m, 6H), 1.71-1.76 (m, 6H), 1.00-1.06 (m, 2H), 0.84-0.88 (m, 2H).

Step C. Intermediate 215C. Preparation of N-(1-(4-(3-cyclopropyl-1,2,4-oxadiazol-5-yl) bicyclo[2.2.2]octan-1-yl)ethyl)-3-(2-cyclopropyloxazol-5-yl)aniline

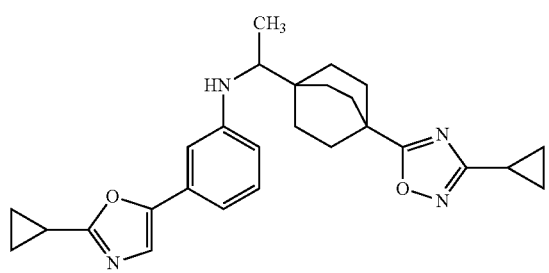 [SMILES: CC(Nc1cccc(-c2cnc(C3CC3)o2)c1)C12CCC(c3nc(C4CC4)no3)(CC1)CC2]

To a stirred solution of Intermediate 20B (0.25 g, 0.960 mmol) in methanol (3 mL) at room temperature was added Intermediate 215B (0.192 g, 0.960 mmol). The reaction mixture was stirred at room temperature for 1 h and then triethylsilane (0.307 mL, 1.921 mmol) was added followed by indium (III) chloride (0.021 g, 0.096 mmol). The reaction mixture was stirred overnight at room temperature and then concentrated under reduced pressure to afford a residue. The residue was dissolved in EtOAc (50 mL) and the EtOAc solution was washed with water (10 mL) followed by brine (10 mL). The organic layer was dried over anhydrous sodium sulfate and concentrated under reduced pressure to afford crude product. The crude was purified by flash column chromatography (12 g silica cartridge, gradient of 0-40% EtOAc in PE as eluent) to afford the title compound (0.25 g, 0.534 mmol, 56% yield) as pale yellow oil. MS (ESI) 445 (M+H).

Step D. Examples 215 and 216. Preparation of N-(1-(4-(3-cyclopropyl-1,2,4-oxadiazol-5-yl)bicyclo[2.2.2]octan-1-yl)ethyl)-N-(3-(2-cyclopropyloxazol-5-yl)phenyl)-3-fluorobicyclo[1.1.1]pentane-1-carboxamide To a solution of Intermediate 215C (100 mg, 0.225 mmol) in pyridine (4 mL) was added freshly prepared solution of 3-fluorobicyclo[1.1.1]pentane-1-carbonyl chloride (234 mg, 1.575 mmol) in pyridine (1 mL). To the above mixture DMAP (27.5 mg, 0.225 mmol) was added and the reaction mixture was heated to 90° C. and stirred for 12 h. The reaction mixture was poured into water (10 mL) and extracted with DCM (2×20 mL). The combined organic extracts were dried over anhydrous sodium sulfate, filtered and concentrated under reduced pressure to afford a residue. The residue was purified by flash column chromatography (12 g silica cartridge, gradient of 0-40% EtOAc in PE as eluent) to afford the desired product as racemate, which was submitted to chiral SFC to get individual enantiomers. Column: Lux Cellulose-4 (250×4.6) 5.0 μm; Isocratic Mode, Co-Solvent: 0.2% NH$_4$OH in MeOH+CAN (1:1); Co-Solvent percentage: 20%, Column Temperature: 30° C.; Back Pressure: 100 bars; Total Flow: 4 g/min. Example 215-Enantiomer 1 (24 mg, 0.041 mmol, 18% yield): RT=5.5 min; $^1$H NMR (400 MHz, DMSO-d$_6$): δ 7.70-7.72 (m, 1H), 7.62-7.64 (m, 1H), 7.47-7.56 (m, 2H), 7.22 (d, J=8.00 Hz, 1H), 4.78 (s, 1H), 2.15-2.21 (m, 1H), 2.03-2.07 (m, 1H), 1.74-1.83 (m, 12H), 1.55 (s, 6H), 1.01-1.07 (m, 9H), 0.84-0.86 (m, 2H), FXR EC$_{50}$ (nM) 269; MS (ESI) 557 (M+H). Example 216-Enantiomer 2 (34 mg, 0.058 mmol, 26% yield): RT=7.5 min; $^1$H NMR (400 MHz, DMSO-d$_6$): δ 7.70-7.72 (m, 1H), 7.62-7.64 (m, 1H), 7.47-7.56 (m, 2H), 7.22 (d, J=8.00 Hz, 1H), 4.78 (s, 1H), 2.15-2.21 (m, 1H), 2.03-2.07 (m, 1H), 1.74-1.83 (m, 12H), 1.55 (s, 6H), 1.01-1.07 (m, 9H), 0.84-0.86 (m, 2H), FXR EC$_{50}$ (nM) 511; MS (ESI) 557 (M+H).

Examples 217 and 218

N-(1-(4-(3-cyclopropyl-1,2,4-oxadiazol-5-yl)bicyclo[2.2.2]octan-1-yl)ethyl)-N-(3-(3-cyclopropyl-1,2,4-oxadiazol-5-yl)phenyl)-3-fluorobicyclo[1.1.1]pentane-1-carboxamide (217-218)

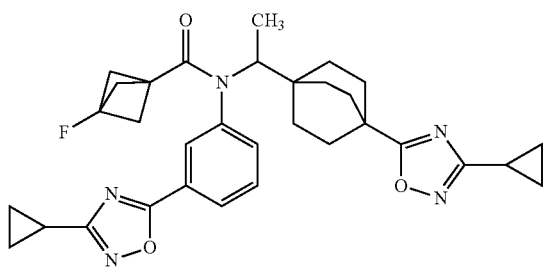

Step A. Intermediate 217A. Preparation of 3-(3-cyclopropyl-1,2,4-oxadiazol-5-yl)-N-(1-(4-(3-cyclopropyl-1,2,4-oxadiazol-5-yl)bicyclo[2.2.2]octan-1-yl)ethyl)aniline

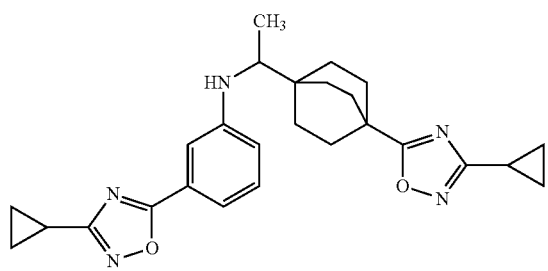 [SMILES: CC(Nc1cccc(-c2nc(C3CC3)no2)c1)C12CCC(c3nc(C4CC4)no3)(CC1)CC2]

The title compound was synthesized according to the method described for the synthesis of Intermediate 215C by substituting Intermediate 215B and Intermediate 8A where appropriate: (0.26 g, 0.584 mmol, 61% yield) as pale yellow oil. MS (ESI) 446.4 (M+H).

Step B. Examples 217 and 218. Preparation of N-(1-(4-(3-cyclopropyl-1,2,4-oxadiazol-5-yl)bicyclo[2.2.2]octan-1-yl)ethyl)-N-(3-(3-cyclopropyl-1,2,4-oxadiazol-5-yl)phenyl)-3-fluorobicyclo[1.1.1]pentane-1-carboxamide The title compound was synthesized according to the method described for the synthesis of Example 215 by substituting Intermediate 217A and 3-fluorobicyclo[1.1.1]pentane-1-carbonyl chloride where appropriate: The racemate was purified by chiral SFC to afford individual enantiomers. Column: Lux Cellulose-4 (250×4.6) 5.0 μm; Isocratic Mode, Co-Solvent: 0.2% NH$_4$OH in MeOH+CAN (1:1); Co-Solvent percentage: 20%, Column Temperature: 30° C.; Back Pressure: 100 bars; Total Flow: 4 g/min.

Example 217: Enantiomer 1 (21.6 mg, 0.037 mmol, 17% yield): $^1$H NMR (400 MHz, DMSO-d$_6$): δ 8.12-8.14 (m, 1H), 7.85-7.88 (m, 1H), 7.62-7.64 (m, 2H), 4.78 (br. s., 1H), 2.18-2.23 (m, 1H), 2.05-2.09 (m, 1H), 1.74-1.83 (m, 12H), 1.53 (br. s., 6H), 1.12-1.15 (m, 2H), 1.01-1.12 (m, 7H), 0.84-0.86 (m, 2H), FXR EC$_{50}$ (nM) 1435; MS (ESI) 558 (M+H).

Example 218: Enantiomer 2 (16.8 mg, 0.028 mmol, 12.35% yield): $^1$H NMR (400 MHz, DMSO-d$_6$): δ 8.12-8.14 (m, 1H), 7.85-7.88 (m, 1H), 7.62-7.64 (m, 2H), 4.78 (br. s., 1H), 2.18-2.23 (m, 1H), 2.05-2.09 (m, 1H), 1.74-1.83 (m, 12H), 1.53 (br. s., 6H), 1.12-1.15 (m, 2H), 1.01-1.12 (m, 7H), 0.84-0.86 (m, 2H), FXR EC$_{50}$ (nM) 1116; MS (ESI) 558 (M+H).

Example 219

N-((4-(3-cyclopropyl-1,2,4-oxadiazol-5-yl)bicyclo[2.2.2]octan-1-yl)methyl)-N-(3-(4-cyclopropyl-1H-1,2,3-triazol-1-yl)phenyl)-3-fluorobicyclo[1.1.1]pentane-1-carboxamide

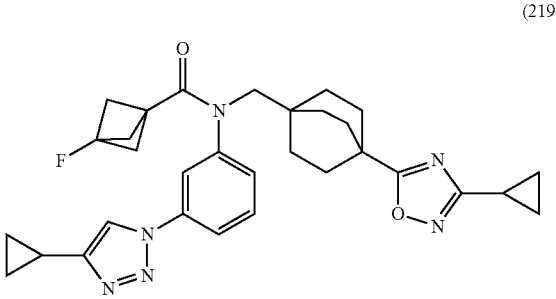

(219)

Step A. Intermediate 219A. Preparation of 3-bromo-N-((4-(3-cyclopropyl-1,2,4-oxadiazol-5-yl)bicyclo[2.2.2]octan-1-yl)methyl)aniline

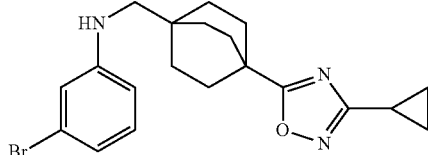

The title compound was synthesized according to the method described for the synthesis of Intermediate 1I by substituting 3-bromoaniline and Intermediate 4C where appropriate: (700 mg, 1.740 mmol, 86% yield) as brown gummy solid. MS (ESI) 402.2 (M+H); $^1$H NMR (400 MHz, DMSO-d$_6$) δ 7.02-6.92 (m, 1H), 6.76 (s, 1H), 6.59 (dd, J=8.0, 2.0 Hz, 2H), 5.80-5.70 (m, 1H), 2.79 (d, J=6.0 Hz, 2H), 2.05 (m, 1H), 1.89-1.77 (m, 6H), 1.59-1.48 (m, 6H), 1.02 (m, 2H), 0.89-0.80 (m, 2H).

Step B. Intermediate 219B. Preparation of N-(3-bromophenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide

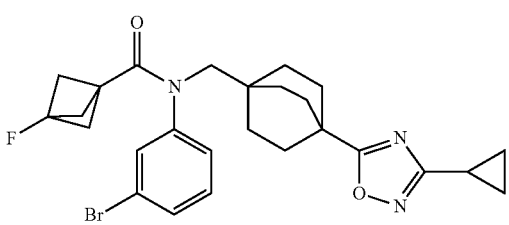 [SMILES: O=C(N(CC12CCC(c3nc(C4CC4)no3)(CC1)CC2)c1cccc(Br)c1)C12CC(F)(C1)C2]

The following compounds were synthesized according to the method described for the synthesis of Example 3 by substituting Intermediate 219A and the corresponding acid where appropriate: (320 mg, 0.603 mmol, 36% yield) as a white solid. MS (ESI) 514.0 (M+H); ¹H NMR (400 MHz, DMSO-d₆) δ 7.69 (s, 1H), 7.60 (d, J=7.0 Hz, 1H), 7.45-7.39 (m, 2H), 3.56 (br. s., 1H), 3.48 (br. s., 1H), 2.08-2.00 (m, 1H), 1.86 (br. s., 6H), 1.81-1.72 (m, 6H), 1.40 (br. s., 6H), 1.01 (m, 2H), 0.86-0.79 (m, 2H).

Step C. Intermediate 219C: Preparation of N-(3-azidophenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide

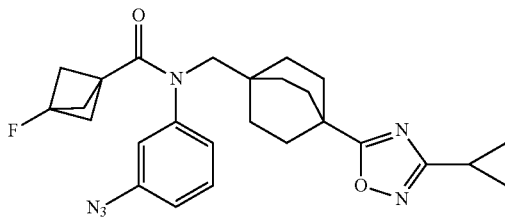 [SMILES: [N-]=[N+]=Nc1cccc(N(CC23CCC(c4nc(C5CC5)no4)(CC2)CC3)C(=O)C23CC(F)(C2)C3)c1]

To a stirred solution of Intermediate 219B (100 mg, 0.194 mmol) in DMF (0.6 mL) at room temperature were added sodium azide (63.2 mg, 0.972 mmol), sodium ascorbate (7.70 mg, 0.039 mmol), trans-N,N'-dimethylcyclohexane-1,2-diamine (11.06 mg, 0.078 mmol) and copper(I) iodide (7.40 mg, 0.039 mmol). After stirring for 3 h at 60° C., the reaction mixture was poured into a biphasic mixture of water (10 mL) and EtOAc (25 mL) and the layers were separated. The aqueous layer was further extracted with EtOAc (2×50 mL) and the combined organic layers were dried over MgSO₄, filtered and concentrated under reduced pressure to afford the title compound (25 mg, 0.052 mmol, 27% yield). MS (ESI) 477 (M+H).

Step D. Example 219. Preparation of N-((4-(3-cyclopropyl-1,2,4-oxadiazol-5-yl) bicyclo[2.2.2]octan-1-yl)methyl)-N-(3-(4-cyclopropyl-1H-1,2,3-triazol-1-yl)phenyl)-3-fluorobicyclo[1.1.1]pentane-1-carboxamide To a stirred solution of Intermediate 219C (20 mg, 0.042 mmol) in DMF (2 mL) at room temperature was added ethynylcyclopropane (5.55 mg, 0.084 mmol). After stirring at room temperature for 3 h, the reaction mixture was concentrated under reduced pressure. The crude material was purified via preparative LC/MS using following conditions: Column: Waters XBridge C18, 150 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 3-minute hold at 19% B, 19-65% B over 25 minutes, then a 5-minute hold at 100% B; Flow Rate: 15 mL/min; Column Temperature: 25° C. Fraction collection was triggered by MS signals. Fractions containing the desired product were combined and dried via centrifugal evaporation to yield the title compound (6.0 mg, 0.011 mmol, 26% yield). ¹H NMR (400 MHz, DMSO-d₆) δ 8.64 (s, 1H), 7.99-7.86 (m, 2H), 7.65 (t, J=8.3 Hz, 1H), 7.56-7.46 (m, 1H), 3.61 (d, J=6.4 Hz, 2H), 2.08-2.02 (m, 2H), 1.91 (br. s., 6H), 1.83-1.67 (m, 6H), 1.55-1.33 (m, 6H), 1.08-0.93 (m, 4H), 0.89-0.74 (m, 4H). FXR EC₅₀ (nM) 98.36 MS (ESI) 543.1 (M+H).

Example 220

3,3-Difluoro-N-(3'-methoxy-[1,1'-biphenyl]-3-yl)-N-((4-(3-methyl-1,2,4-oxadiazol-5-yl)bicyclo[2.2.2]octan-1-yl)methyl)cyclobutane-1-carboxamide

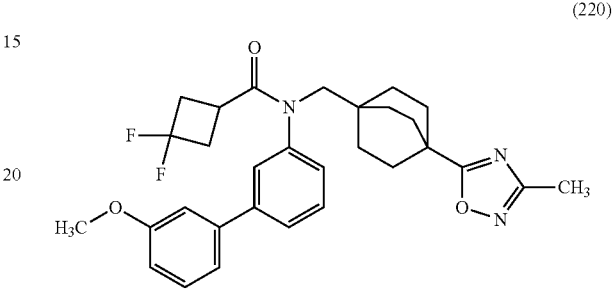

(220)

Step A. Intermediate 220A. Preparation of 3-methoxy-3'-nitro-1,1'-biphenyl

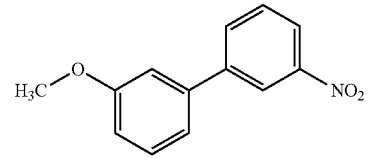 [SMILES: COc1cccc(-c2cccc([N+](=O)[O-])c2)c1]

To a stirred solution of 1-bromo-3-methoxybenzene (0.5 g, 2.67 mmol) in toluene (5 mL) and ethanol (2 mL) was added (3-nitrophenyl)boronic acid (0.535 g, 3.21 mmol). The reaction mixture was degassed and back-filled with argon. A solution of Na₂CO₃ (0.850 g, 8.02 mmol) in water (0.3 mL) was added to the reaction mass, degassed and back-filled with argon. Tetrakis(triphenylphosphine) palladium(0) (0.154 g, 0.134 mmol) was added and the reaction was stirred at 110° C. for overnight. The reaction was cooled to room temperature, diluted with water (20 mL) and extracted with EtOAc (3×10 mL). The organic layers were combined, washed with brine solution (10 mL), dried over anhydrous sodium sulphate and concentrated under reduced pressure. The crude material was purified by flash column chromatography (12 g silica gel cartridge; A=Hex, B=EtOAc; 20 min grad.; 0% B to 15% B; flow rate=30 mL/min). The pure fractions were combined, concentrated and dried in vacuo to afford the title compound (0.48 g, 1.885 mmol, 70% yield) as white solid. ¹H NMR (400 MHz, DMSO-d₆) δ 8.44 (t, J=2.1 Hz, 1H), 8.23 (dt, J=8.3, 1.1 Hz, 1H), 8.20-8.13 (m, 1H), 7.77 (t, J=7.9 Hz, 1H), 7.49-7.41 (m, 1H), 7.38-7.29 (m, 2H), 7.04 (dd, J=8.1, 2.4 Hz, 1H), 3.85 (s, 3H).

Step B. Intermediate 220B. Preparation of 3'-methoxy-[1,1'-biphenyl]-3-amine

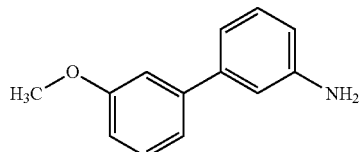

A solution of Intermediate 220A (0.48 g, 2.094 mmol) in methanol (10 mL) was purged and flushed with nitrogen. Pd—C(0.111 g, 0.105 mmol) was added to the reaction and stirred under hydrogen (1 atm, balloon) for overnight. The reaction was filtered through Celite and the filtrate was concentrated under reduced pressure. The crude material was purified by flash column chromatography (24 g silica gel cartridge; A=Hex, B=EtOAc; 20 min grad.; 0% B to 20% B; flow rate=30 mL/min). The pure fractions were combined, concentrated and dried in vacuo to afford the title compound (0.38 g, 1.812 mmol, 87% yield) as oil. $^1$H NMR (400 MHz, DMSO-d$_6$) δ 7.37-7.31 (m, 1H), 7.14-7.05 (m, 3H), 6.90 (ddd, J=8.0, 2.5, 1.0 Hz, 1H), 6.84 (t, J=2.0 Hz, 1H), 6.80-6.75 (m, 1H), 6.61-6.53 (m, 1H), 5.13 (s, 2H), 3.81 (s, 3H). MS (ESI) 200 (M+H).

Step C. Intermediate 220C. Preparation of 3'-methoxy-N-((4-(3-methyl-1,2,4-oxadiazol-5-yl)bicyclo[2.2.2]octan-1-yl)methyl)-[1,1'-biphenyl]-3-amine

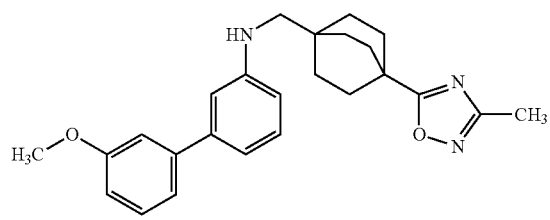

The title compound was synthesized according to the method described for the synthesis of Intermediate 1I by substituting Intermediate 220B and Intermediate 3C where appropriate: compound (0.13 g, 0.29 mmol, 51% yield) as an off-white solid. MS (ESI) 404 (M+H).

Step D. Example 220. 3,3-Difluoro-N-(3'-methoxy-[1,1'-biphenyl]-3-yl)-N-((4-(3-methyl-1,2,4-oxadiazol-5-yl)bicyclo[2.2.2]octan-1-yl)methyl)cyclobutane-1-carboxamide The title compound was synthesized according to the method described for the synthesis of Example 3 by substituting Intermediate 220C and the corresponding acid where appropriate: (2 mg, 3.83 μmol, 7.74% yield). $^1$H NMR (400 MHz, DMSO-d$_6$) δ 7.71 (s, 1H), 7.67 (d, J=7.6 Hz, 1H), 7.52 (t, J=7.8 Hz, 1H), 7.45-7.35 (m, 2H), 7.29 (d, J=7.8 Hz, 1H), 7.25 (s, 1H), 6.97 (dd, J=8.3, 1.7 Hz, 1H), 3.83 (s, 3H), 3.66 (br. s., 2H), 2.98-2.87 (m, 1H), 2.84-2.69 (m, 2H), 2.32 (d, J=1.7 Hz, 2H), 2.26 (s, 3H), 1.92-1.67 (m, 6H), 1.58-1.31 (m, 6H). FXR EC$_{50}$ (nM) 547; MS (ESI) 522 (M+H).

The following Example was prepared according to the method described for the preparation of Example 3 by substituting Intermediate 220C and the corresponding acid chlorides.

| Ex. No. | Structure | MS (ESI) (M + H) | FXR EC$_{50}$ (nM) |
|---|---|---|---|
| 221 | 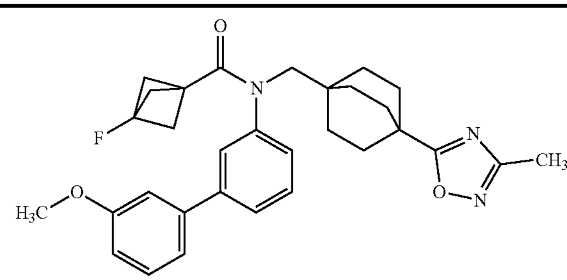 | 516 | 506 |
| 222 | $^1$H NMR (400 MHz, DMSO-d$_6$) δ 7.78-7.65 (m, 2H), 7.54 (t, J = 7.7 Hz, 1H), 7.46-7.36 (m, 2H), 7.31 (d, J = 7.8 Hz, 1H), 7.26 (d, J = 2.0 Hz, 1H), 6.99 (dd, J = 7.8, 2.0 Hz, 1H), 3.85 (s, 3H), 3.65 (br. s., 1H), 3.57 (br. s., 1H), 2.28 (s, 3H), 1.96-1.74 (m, 12H), 1.48 (d, J = 4.9 Hz, 6H). | | |

Example 222

N-((1-(4-(2-cyanopropan-2-yl)phenyl)-2-oxabicyclo[2.2.2]octan-4-yl)methyl)-3-fluoro-N-(3-(2-methoxypyridin-4-yl)phenyl)bicyclo[1.1.1]pentane-1-carboxamide (222)

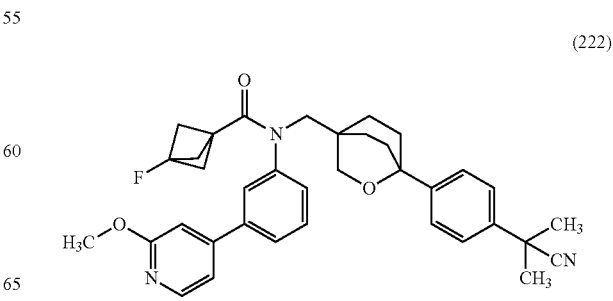

Step A. Intermediate 222A. Preparation of 3-(2-methoxypyridin-4-yl)aniline

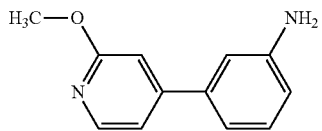

To a stirred solution of 4-bromo-2-methoxypyridine (5 g, 26.6 mmol) in toluene (50 mL) was added (3-aminophenyl) boronic acid (4.4 g, 31.9 mmol). The reaction mixture was degassed and back-filled with argon. A solution of Na₂CO₃ (0.85 g, 8.02 mmol) in water (0.5 mL) was added and degassed and back-filled with argon. Tetrakis(triphenylphosphine) palladium(0) (1.536 g, 1.330 mmol) was added and the reaction mixture was stirred at 110° C. for overnight. The reaction mixture was cooled to room temperature, diluted with water (50 mL) and extracted with EtOAc (3×25 mL). The organic layers were combined, washed with brine solution (30 mL), dried over anhydrous sodium sulphate and concentrated under reduced pressure. The crude material was purified by flash column chromatography (40 g silica gel cartridge; A=Hex, B=EtOAc; 20 min grad.; 0% B to 20% B; flow rate=30 mL/min). The pure fractions were combined, concentrated and dried in vacuo to afford the title compound (6 g, 27 mmol, 100% yield) as yellow solid. ¹H NMR (400 MHz, DMSO-d₆) δ 8.19 (d, J=5.5 Hz, 1H), 7.22-7.10 (m, 2H), 6.98-6.83 (m, 3H), 6.66 (ddd, J=8.0, 2.0, 1.0 Hz, 1H), 5.23 (s, 2H), 3.88 (s, 3H). MS (ESI) 201 (M+H).

Step B. Intermediate 222B. Preparation of 2-(4-(4-(((3-(2-methoxypyridin-4-yl)phenyl) amino)methyl)-2-oxabicyclo[2.2.2]octan-1-yl)phenyl)-2-methylpropanenitrile

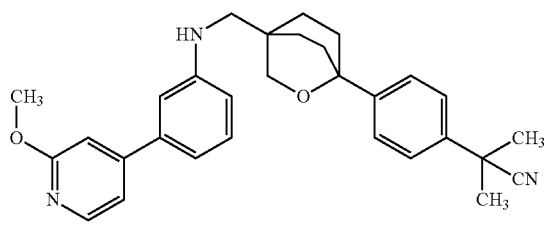 [SMILES: COc1cc(-c2cccc(NCC34CCC(c5ccc(C(C)(C)C#N)cc5)(CC3)OC4)c2)ccn1]

The title compound was prepared according to the method described for the synthesis of Intermediate 1I by substituting Intermediate 222A and Intermediate 47E where appropriate. (130 mg, 0.247 mmol, 70% yield) as brown gummy solid. ¹H NMR (400 MHz, DMSO-d₆) 8.20 (d, J=5.0 Hz, 1H), 7.45 (s, 5H), 7.23 (dd, J=5.0, 1.5 Hz, 1H), 7.18 (t, J=7.8 Hz, 1H), 7.01 (s, 1H), 6.96 (s, 1H), 6.88 (d, J=7.5 Hz, 1H), 6.74 (d, J=8.0 Hz, 1H), 5.70-5.65 (m, 2H), 3.92-3.88 (m, 3H), 2.97 (d, J=6.0 Hz, 2H), 2.08 (d, J=9.0 Hz, 2H), 1.89-1.72 (m, 6H), 1.67 (s, 6H). MS (ESI) 468 (M+H).

Step C. Example 222: N-((1-(4-(2-cyanopropan-2-yl)phenyl)-2-oxabicyclo[2.2.2]octan-4-yl)methyl)-3-fluoro-N-(3-(2-methoxypyridin-4-yl)phenyl)bicyclo[1.1.1]pentane-1-carboxamide The title compound was synthesized according to the method described for the synthesis of Example 3 by substituting Intermediate 222B and the corresponding acid where appropriate: (10 mg, 0.017 mmol, 32% yield). ¹HNMR (400 MHz, DMSO-d₆) δ 8.27 (d, J=5.4 Hz, 1H), 7.90 (s, 1H), 7.85 (d, J=7.6 Hz, 1H), 7.67-7.57 (m, 1H), 7.56-7.50 (m, 1H), 7.47-7.31 (m, 5H), 7.24 (s, 1H), 3.92 (s, 3H), 3.73 (br.s., 2H), 3.64 (d, J=12.2 Hz, 2H), 2.05-1.95 (m, 2H), 1.86-1.90 (m, 6H), 1.82-1.72 (m, 2H), 1.71-1.51 (m, 10H). FXR EC₅₀ (nM)=285; MS (ESI) 580 (M+H).

The following examples were prepared according to the method described for the synthesis of Example 3 by substituting Intermediate 222B and the corresponding acids where appropriate.

| Ex. No. | Structure | MS (ESI) (M + H) | FXR EC₅₀ (nM) |
|---|---|---|---|
| 223 | 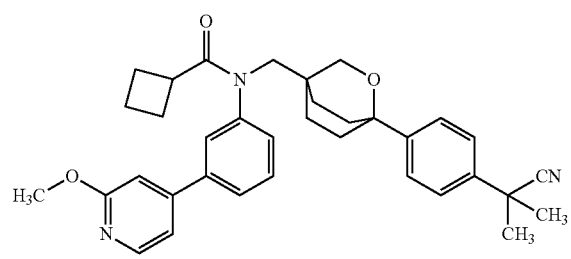 [SMILES: COc1cc(-c2cccc(N(CC34CCC(c5ccc(C(C)(C)C#N)cc5)(CC3)OC4)C(=O)C3CCC3)c2)ccn1] | 550 | 313 |

-continued

| Ex. No. | Structure | MS (ESI) (M + H) | FXR EC$_{50}$ (nM) |
|---|---|---|---|
| 224 | 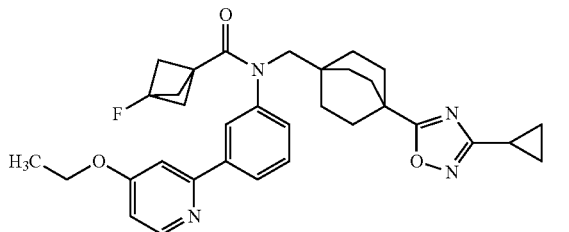 | 564 | 894 |

| 223 | $^1$HNMR (400 MHz, DMSO-d$_6$) δ 8.26 (d, J = 5.4 Hz, 1H), 7.81 (s, 1H), 7.77 (d, J = 8.1 Hz, 1H), 7.57 (t, J = 7.8 Hz, 1H), 7.46 (d, J = 8.6 Hz, 1H), 7.43-7.32 (m, 5H), 7.22 (s, 1H), 3.94-3.89 (m, 3H), 3.69 (br. s., 4H), 3.19-3.06 (m, 1H), 2.14 (d, J = 8.6 Hz, 2H), 2.04-1.95 (m, 3H), 1.73 (d, J = 10.8 Hz, 1H), 1.70-1.62 (m, 12H), 1.57 (d, J = 11.0 Hz, 2H). |
|---|---|
| 224 | $^1$HNMR (400 MHz, DMSO-d$_6$) δ 8.26 (d, J = 5.4 Hz, 1H), 7.85 (s, 1H), 7.78 (d, J = 7.1 Hz, 1H), 7.59 (t, J = 7.9 Hz, 1H), 7.52 (d, J = 7.6 Hz, 1H), 7.39 (q, J = 8.8 Hz, 5H), 7.22 (s, 1H), 3.92 (s, 3H), 3.70 (s, 4H), 2.65 (d, J = 6.1 Hz, 1H), 2.06-1.95 (m, 2H), 1.81-1.70 (m, 3H), 1.65 (s, 8H), 1.62-1.48 (m, 7H), 1.36 (br. s., 2H). |

Example 225

N-((4-(3-cyclopropyl-1,2,4-oxadiazol-5-yl)bicyclo[2.2.2]octan-1-yl)methyl)-N-(3-(4-ethoxypyridin-2-yl)phenyl)-3-fluorobicyclo[1.1.1]pentane-1-carboxamide

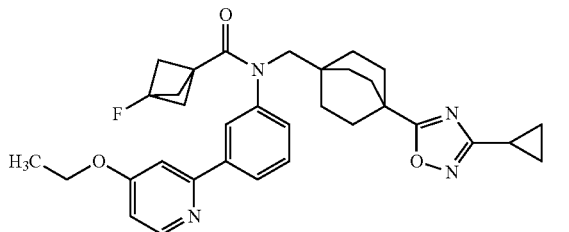

(225)

Step A. Intermediate 225A. Preparation of 2-chloro-4-ethoxypyridine

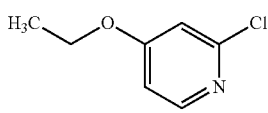

To a stirred solution of 4-bromo-2-chloropyridine (500 mg, 2.60 mmol) in ethanol (5 mL) was added sodium ethoxide in ethanol (1.4 g, 5.20 mmol) under nitrogen. The reaction mixture was stirred at room temperature for overnight. The solvent was removed under reduced pressure and the residue was diluted with water (20 mL) and extracted with EtOAc (2×10 mL). The organic layers were combined, washed with brine (10 mL), dried over anhydrous sodium sulphate and concentrated under reduced pressure. The crude material was purified by flash chromatography (24 g silica gel cartridge; A=Hex, B=EtOAc; 20 min grad.; 0% B to 20% B; flow rate=30 mL/min). The pure fractions were combined, concentrated and dried in vacuo to afford the title compound (270 mg, 1.45 mmol, 56% yield) as pale yellow oil. MS (ESI) 158 (M+H).

Step B. Intermediate 225B. Preparation of 4-ethoxy-2-(3-nitrophenyl)pyridine

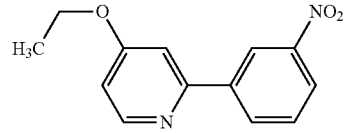 [SMILES: CCOc1ccnc(-c2cccc([N+](=O)[O-])c2)c1]

To a stirred solution of Intermediate 225A (270 mg, 1.71 mmol) in toluene (3 mL) and ethanol (3 mL) were added (3-nitrophenyl)boronic acid (286 mg, 1.71 mmol) and Na$_2$CO$_3$ (545 mg, 5.14 mmol) in water (2 mL). The reaction mixture was degassed and back-filled with argon. Tetrakis(triphenylphosphine) palladium(0) (98 mg, 0.085 mmol) was added and the resulting reaction mass was heated at 110° C. for overnight. The reaction mixture was cooled to room temperature, diluted with water (10 mL) and extracted with EtOAc (2×10 mL). The organic layers were combined, washed with brine solution (10 mL), dried over anhydrous sodium sulphate and concentrated under reduced pressure. The crude material was purified by flash column chromatography (12 g silica gel cartridge; A=Hex, B=EtOAc; 20 min grad.; 0% B to 20% B; flow rate=30 mL/min). The pure fractions were combined, concentrated and dried in vacuo to afford the title compound (200 mg, 0.778 mmol, 45% yield) as an off-white solid. $^1$H NMR (400 MHz, DMSO-d$_6$) δ 8.96-8.92 (m, 1H), 8.59-8.52 (m, 2H), 8.32-8.26 (m, 1H), 7.79 (t, J=8.0 Hz, 1H), 7.68 (d, J=2.0 Hz, 1H), 7.06-7.01 (m, 1H), 4.26 (q, J=7.0 Hz, 2H), 1.40 (t, J=7.0 Hz, 3H). MS (ESI) 245 (M+H).

Step C. Intermediate 225C. Preparation of 3-(4-ethoxypyridin-2-yl)aniline

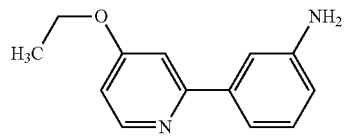 [SMILES: CCOc1ccnc(-c2cccc(N)c2)c1]

A solution of Intermediate 225B (200 mg, 0.819 mmol) in methanol (10 mL) was purged and flushed with nitrogen. Pd—C(43.6 mg, 0.041 mmol) was added to the reaction and stirred under hydrogen (1 atm, balloon) for overnight. The reaction mixture was filtered through Celite and the filtrate was concentrated to afford title compound (150 mg, 0.665 mmol, 81% yield) as pale yellow oil. $^1$H NMR (400 MHz, DMSO-$d_6$) δ 8.41 (d, J=6.0 Hz, 1H), 7.32 (t, J=2.0 Hz, 1H), 7.27 (d, J=2.5 Hz, 1H), 7.19-7.15 (m, 1H), 7.12-7.07 (m, 1H), 6.88 (dd, J=5.5, 2.5 Hz, 1H), 6.64-6.59 (m, 1H), 5.13 (s, 2H), 4.19 (q, J=7.0 Hz, 2H), 1.37 (t, J=7.0 Hz, 3H). MS (ESI) 215 (M+H).

Step D. Intermediate 225D. Preparation of 3-(4-ethoxypyridin-2-yl)aniline

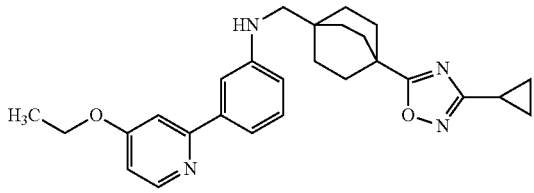 [SMILES: CCOc1ccnc(-c2cccc(NCC34CCC(c5nc(C6CC6)no5)(CC3)CC4)c2)c1]

The title compound was prepared according to the method described for the synthesis of Intermediate 1I by substituting Intermediate 225C and Intermediate 4C where appropriate. (110 mg, 0.235 mmol, 58% yield) as white solid. $^1$H NMR (400 MHz, DMSO-$d_6$) δ 8.42 (d, J=6.0 Hz, 1H), 7.36-7.28 (m, 2H), 7.18-7.09 (m, 2H), 6.91-6.86 (m, 1H), 6.67 (dt, J=7.8, 1.6 Hz, 1H), 5.52 (t, J=6.0 Hz, 1H), 4.19 (q, J=6.9 Hz, 2H), 2.88 (d, J=6.0 Hz, 2H), 2.10-2.02 (m, 1H), 1.90-1.82 (m, 6H), 1.63-1.53 (m, 6H), 1.37 (t, J=7.0 Hz, 3H), 1.06-0.98 (m, 2H), 0.89-0.82 (m, 2H). MS (ESI) 445 (M+H).

Step E. Example 225. Preparation of N-((4-(3-cyclopropyl-1,2,4-oxadiazol-5-yl) bicyclo[2.2.2]octan-1-yl)methyl)-N-(3-(4-ethoxypyridin-2-yl)phenyl)-3-fluorobicyclo[1.1.1]pentane-1-carboxamide The title compound was prepared according to the method described for the synthesis of Example 3 by substituting Intermediate 225D and the corresponding acid where appropriate. (20 mg, 0.036 mmol, 80% yield). $^1$H NMR (400 MHz, DMSO-$d_6$) δ 8.53 (d, J=5.6 Hz, 1H), 8.17-8.05 (m, 2H), 7.64 (s, 1H), 7.58 (t, J=7.8 Hz, 1H), 7.49 (d, J=7.3 Hz, 1H), 7.06 (br. s., 1H), 4.27 (q, J=7.3 Hz, 2H), 3.62 (d, J=17.1 Hz, 2H), 2.07-2.00 (m, 1H), 1.87 (s, 6H), 1.82-1.68 (m, 6H), 1.53-1.34 (m, 9H), 1.05-0.96 (m, 2H), 0.87-0.77 (m, 2H). FXR EC$_{50}$ (nM) 241; MS (ESI) 557 (M+H).

Example 226

N-((4-(3-cyclopropyl-1,2,4-oxadiazol-5-yl)bicyclo[2.2.2]octan-1-yl)methyl)-N-(3-(2-ethoxypyridin-4-yl)phenyl)-3-fluorobicyclo[1.1.1]pentane-1-carboxamide (226)

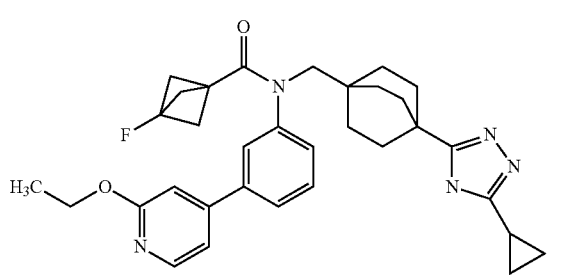

Step A. Intermediate 226A. Preparation of 2-chloro-4-(3-nitrophenyl) pyridine

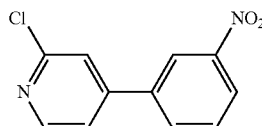

To a stirred solution of 4-bromo-2-chloropyridine (0.25 g, 1.30 mmol) in toluene (5 mL) and ethanol (2 mL) were added (3-nitrophenyl)boronic acid (0.260 g, 1.56 mmol) and Na$_2$CO$_3$ (0.413 g, 3.90 mmol) in water (0.2 mL). The reaction mass was degassed and back-filled with argon. Tetrakis(triphenylphosphine) palladium(0) (0.075 g, 0.065 mmol) was added and the reaction mixture was heated at 90° C. for overnight. The reaction mixture was cooled to room temperature, diluted with water (10 mL) and extracted with EtOAc (2×10 mL). The organic layers were combined, washed with brine solution (10 mL), dried over anhydrous sodium sulphate and concentrated under reduced pressure. The crude material was purified by flash column chromatography (12 g silica gel cartridge; A=Hex, B=EtOAc; 20 min grad.; 0% B to 20% B; flow rate=30 mL/min). The pure fractions were combined, concentrated and dried in vacuo to afford the title compound (0.15 g, 0.607 mmol, 47% yield) as white solid. $^1$H NMR (400 MHz, DMSO-$d_6$) δ 8.65 (t, J=2.0 Hz, 1H), 8.57-8.54 (m, 1H), 8.38-8.31 (m, 2H), 8.05-8.03 (m, 1H), 7.90 (dd, J=5.3, 1.8 Hz, 1H), 7.85 (t, J=8.0 Hz, 1H). MS (ESI) 235 (M+H).

Step B. Intermediate 226B. Preparation of 2-ethoxy-4-(3-nitrophenyl)pyridine

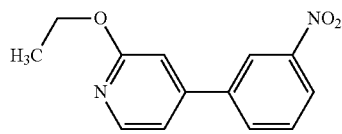 [SMILES: CCOc1cc(-c2cccc([N+](=O)[O-])c2)ccn1]

To a stirred solution of Intermediate 226A (0.15 g, 0.639 mmol) in ethanol (3 mL) was added sodium ethoxide in ethanol (0.29 g, 0.639 mmol) under inert atmosphere. The reaction mixture was stirred at room temperature for overnight. The solvent was removed under reduced pressure and the residue was diluted with water (10 mL) and extracted with EtOAc (2×10 mL). The organic layers were combined, washed with brine (10 mL), dried over anhydrous sodium sulphate and concentrated under reduced pressure. The crude material was purified by flash chromatography (12 g silica gel cartridge; A=Hex, B=EtOAc; 20 min grad.; 0% B to 20% B; flow rate=30 mL/min). The pure fractions were combined, concentrated and dried in vacuo to afford the title compound (110 mg, 0.428 mmol, 67% yield) as pale yellow oil. $^1$H NMR (400 MHz, DMSO-$d_6$) δ 8.53 (t, J=2.0 Hz, 1H), 8.35-8.21 (m, 3H), 7.80 (t, J=7.8 Hz, 1H), 7.41 (dd, J=5.3, 1.8 Hz, 1H), 7.22 (d, J=1.0 Hz, 1H), 4.37 (q, J=7.2 Hz, 2H), 1.35 (t, J=7.0 Hz, 3H). MS (ESI) 245 (M+H).

Step C. Intermediate 226C. Preparation of 3-(2-ethoxypyridin-4-yl)aniline

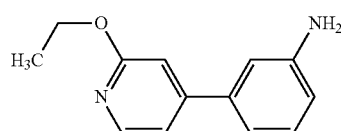

A solution of Intermediate 226B (100 mg, 0.409 mmol) in methanol (5 mL) was purged and flushed with nitrogen. Pd—C(21.79 mg, 0.020 mmol) was added to the reaction and stirred under hydrogen (1 atm, balloon) at room temperature for overnight. The reaction mixture was filtered through Celite and the filtrate was concentrated to afford title compound (80 mg, 0.355 mmol, 87% yield) as pale yellow oil. $^1$H NMR (400 MHz, DMSO-$d_6$) δ 8.19-8.15 (m, 1H), 7.17-7.14 (m, 1H), 7.13 (d, J=7.5 Hz, 1H), 6.93-6.90 (m, 2H), 6.89-6.85 (m, 1H), 6.65 (ddd, J=8.0, 2.0, 1.0 Hz, 1H), 5.22 (s, 2H), 4.34 (q, J=7.0 Hz, 2H), 1.34 (t, J=7.0 Hz, 3H). MS (ESI) 215 (M+H).

Step D. Intermediate 226D. Preparation of N-((4-(3-cyclopropyl-1,2,4-oxadiazol-5-yl) bicyclo[2.2.2]octan-1-yl)methyl)-3-(2-ethoxypyridin-4-yl)aniline

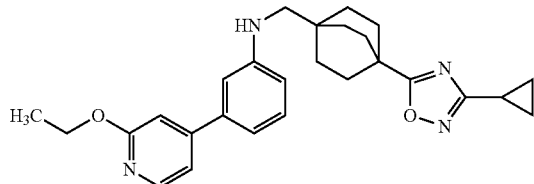

The title compound was prepared according to the method described for the synthesis of Intermediate 1I by substituting Intermediate 226C and Intermediate 4C where appropriate. (60 mg, 0.121 mmol, 60% yield) as pale yellow oil. $^1$H NMR (400 MHz, DMSO-$d_6$) δ 8.17 (d, J=6.0 Hz, 1H), 7.23-7.11 (m, 2H), 6.98-6.91 (m, 2H), 6.85 (d, J=8.0 Hz, 1H), 6.71 (dd, J=8.3, 1.8 Hz, 1H), 5.61 (t, J=6.0 Hz, 1H), 4.35 (q, J=7.0 Hz, 2H), 2.90 (d, J=6.0 Hz, 2H), 2.12-2.03 (m, 1H), 1.93-1.81 (m, 6H), 1.64-1.51 (m, 6H), 1.34 (t, J=7.0 Hz, 3H), 1.07-0.99 (m, 2H), 0.90-0.81 (m, 2H). MS (ESI) 445 (M+H).

Step E. Example 226. Preparation of N-((4-(3-cyclopropyl-1,2,4-oxadiazol-5-yl) bicyclo[2.2.2]octan-1-yl)methyl)-N-(3-(2-ethoxypyridin-4-yl)phenyl)-3-fluorobicyclo[1.1.1]pentane-1-carboxamide The title compound was prepared according to the method described for the synthesis of Example 3 by substituting Intermediate 226D and the corresponding acid where appropriate. (12.8 mg, 0.023 mmol, 51.1% yield). $^1$H NMR (400 MHz, DMSO-$d_6$) δ 8.25 (d, J=5.4 Hz, 1H), 7.86 (s, 1H), 7.83 (d, J=7.8 Hz, 1H), 7.58 (t, J=7.9 Hz, 1H), 7.48 (d, J=8.3 Hz, 1H), 7.39 (dd, J=5.4, 1.5 Hz, 1H), 7.21 (s, 1H), 4.37 (q, J=7.1 Hz, 2H), 3.67-3.54 (m, 2H), 2.11-2.01 (m, 1H), 1.95-1.70 (m, 12H), 1.46 (d, J=5.6 Hz, 6H), 1.36 (t, J=7.1 Hz, 3H), 1.08-0.96 (m, 2H), 0.88-0.77 (m, 2H). FXR EC$_{50}$ (nM) 219; MS (ESI) 557 (M+H).

Example 227

3-Fluoro-N-(3-(2-methoxypyridin-4-yl)phenyl)-N-((4-(3-(tetrahydro-2H-pyran-4-yl)-1,2,4-oxadiazol-5-yl)bicyclo[2.2.2]octan-1-yl)methyl)bicyclo[1.1.1]pentane-1-carboxamide (227)

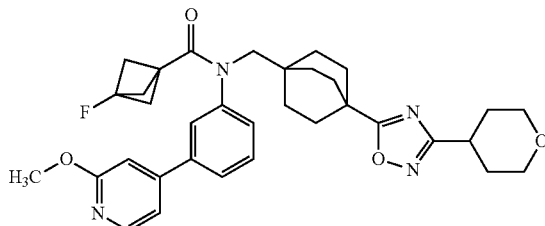

Step A. Intermediate 227A. Preparation of methyl 4-(((3-(2-methoxypyridin-4-yl) phenyl)amino)methyl)bicyclo[2.2.2]octane-1-carboxylate

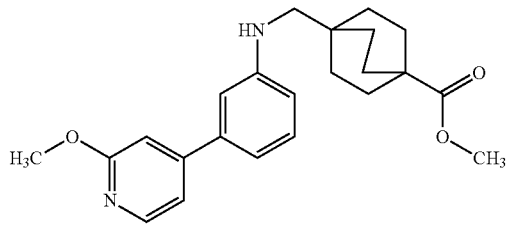

The title compound was prepared according to the method described for the synthesis of Intermediate 1I by substituting Intermediate 222A and Intermediate 88B where appropriate. (1.4 g, 3.24 mmol, 71% yield) as brown solid. $^1$H NMR (400 MHz, DMSO-$d_6$) δ 8.18 (d, J=5.0 Hz, 1H), 7.23-7.10 (m, 2H), 6.97 (d, J=1.0 Hz, 1H), 6.92 (t, J=2.0 Hz, 1H), 6.84 (d, J=7.5 Hz, 1H), 6.69 (dd, J=8.0, 1.5 Hz, 1H), 5.56 (t, J=5.8 Hz, 1H), 3.90 (s, 3H), 3.57 (s, 3H), 2.84 (d, J=6.0 Hz, 2H), 1.77-1.65 (m, 6H), 1.53-1.44 (m, 6H). MS (ESI) 381 (M+H).

Step B. Intermediate 227B. Preparation of methyl 4-((3-fluoro-N-(3-(2-methoxy pyridin-4-yl)phenyl)bicyclo[1.1.1]pentane-1-carboxamido)methyl)bicyclo[2.2.2]octane-1-carboxylate

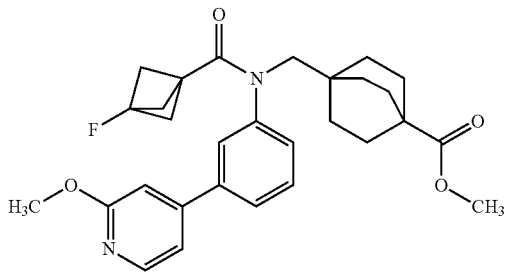

The title compound was prepared according to the method described for the synthesis of Example 3 by substituting Intermediate 227A and the corresponding acid where appropriate. (220 mg, 0.447 mmol, 85% yield). $^1$H NMR (400 MHz, DMSO-d$_6$) δ 8.27 (d, J=5.4 Hz, 1H), 7.89-7.75 (m, 2H), 7.57 (t, J=8.2 Hz, 1H), 7.47 (d, J=7.6 Hz, 1H), 7.39 (dd, J=5.4, 1.5 Hz, 1H), 7.21 (s, 1H), 3.92 (s, 3H), 3.59 (br. s., 2H), 3.54 (s, 3H), 1.83 (s, 3H), 1.87 (s, 3H), 1.72-1.53 (m, 6H), 1.44-1.28 (m, 6H). MS (ESI) 493 (M+H).

Step C. Intermediate 227C. Preparation of 4-((3-fluoro-N-(3-(2-methoxypyridin-4-yl) phenyl)bicyclo[1.1.1]pentane-1-carboxamido)methyl)bicyclo[2.2.2]octane-1-carboxylic acid

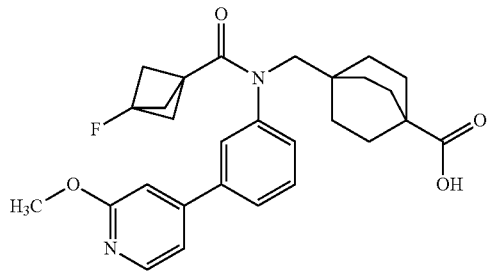 [SMILES: COc1cc(-c2cccc(N(CC34CCC(C(=O)O)(CC3)CC4)C(=O)C34CC(F)(C3)C4)c2)ccn1]

To a stirred solution of Intermediate 227B (330 mg, 0.66 mmol) in methanol (10 mL) was added NaOH (133 mg, 3.3 mmol) in H$_2$O (5 mL). The reaction mixture was stirred at room temperature for overnight. The reaction mixture was concentrated under reduced pressure. The residue was diluted with water, acidified by using aqueous 1.5 N HCl (pH ~3) and extracted with ethyl acetate (2×20 mL). The organic layers were combined, dried over sodium sulphate and concentrated under reduced pressure to afford the title compound. (8.2 mg, 0.0172 mmol, 52% yield). $^1$H NMR (400 MHz, DMSO-d$_6$) δ 8.27 (d, J=5.4 Hz, 1H), 7.90-7.74 (m, 2H), 7.58 (t, J=8.1 Hz, 1H), 7.47 (d, J=7.6 Hz, 1H), 7.39 (dd, J=5.4, 1.7 Hz, 1H), 7.21 (s, 1H), 3.92 (s, 3H), 3.64-3.58 (m, 1H), 3.53 (s, 1H) 1.94-1.76 (m, 6H), 1.67-1.54 (m, 6H), 1.35 (d, J=5.1 Hz, 6H). MS (ESI) 479 (M+H).

Step D. Intermediate 227D. Preparation of N'-hydroxytetrahydro-2H-pyran-4-carboximidamide

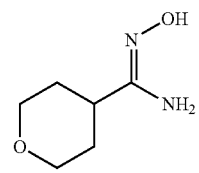

To a stirred solution of tetrahydro-2H-pyran-4-carbonitrile (0.988 mL, 9.00 mmol) in ethanol (12 mL) was added 50% hydroxylamine in water (2.76 mL, 45.0 mmol). The reaction mixture was heated at reflux for 2 h. The reaction mixture was concentrated under reduced pressure, diluted with water (15 mL) and stirred for 10 min. The precipitated solid was filtered and dried in vacuo to afford the title compound (1.28 g, 6.21 mmol, 69% yield) as white puffy solid. MS (ESI) 145 (M+H).

Step E. Example 227. Preparation of 3-fluoro-N-(3-(2-methoxypyridin-4-yl)phenyl)-N-((4-(3-(tetrahydro-2H-pyran-4-yl)-1,2,4-oxadiazol-5-yl)bicyclo[2.2.2]octan-1-yl) methyl)bicyclo[1.1.1]pentane-1-carboxamide The title compound was prepared according to the method described for the synthesis of Intermediate 3A by substituting Intermediate 227C and Intermediate 227D where appropriate. (7.1 mg, 0.012 mmol, 39% yield). $^1$H NMR (400 MHz, DMSO-d$_6$) δ 8.27 (d, J=5.1 Hz, 1H), 7.91-7.77 (m, 2H), 7.59 (t, J=7.8 Hz, 1H), 7.50 (d, J=7.1 Hz, 1H), 7.41 (dd, J=5.5, 1.6 Hz, 1H), 7.22 (s, 1H), 3.92 (s, 3H), 3.89-3.81 (m, 2H), 3.61 (d, J=15.4 Hz, 2H), 3.43 (td, J=11.4, 2.0 Hz, 2H), 3.06-2.95 (m, 1H), 1.95-1.75 (m, 12H), 1.71-1.58 (m, 2H), 1.48 (d, J=6.4 Hz, 6H), 1.25 (s, 2H). FXR EC$_{50}$ (nM)=377; MS (ESI) 587 (M+H).

The following compounds were prepared according to the method described for the synthesis of Intermediate 3A by substituting Intermediate 227C and the corresponding imidamide where appropriate.

| Ex. No. | Structure | MS (ESI) (M + H) | FXR EC$_{50}$ (nM) |
|---|---|---|---|
| 228 | | 517 | 442 |
| 229 | | 543 | 154 |

228  $^1$H NMR (400 MHz, DMSO-d$_6$) δ 8.27 (d, J = 5.6 Hz, 1H), 7.91-7.73 (m, 2H), 7.59 (t, J = 7.9 Hz, 1H), 7.50 (d, J = 8.3 Hz, 1H), 7.40 (dd, J = 5.5, 1.3 Hz, 1H), 7.22 (s, 1H), 3.92 (s, 3H), 3.64 (br. s., 2H), 2.28 (s, 3H), 1.96-1.71 (m, 12H), 1.46 (br. s., 6H).

229  $^1$H NMR (400 MHz, DMSO-d$_6$) δ 8.27 (d, J = 5.4 Hz, 1H), 7.91-7.75 (m, 2H), 7.58 (t, J = 7.7 Hz, 1H), 7.53-7.45 (m, 1H), 7.40 (dd, J = 5.4, 1.5 Hz, 1H), 7.22 (s, 1H), 3.92 (s, 3H), 3.61 (d, J = 15.4 Hz, 2H), 2.05 (ddd, J = 13.4, 8.5, 5.5 Hz, 1H), 1.95-1.69 (m, 12H), 1.46 (d, J = 8.6 Hz, 6H), 1.06-0.94 (m, 2H), 0.87-0.75 (m, 2H).

Example 230

3-Fluoro-N-(3-(2-methoxypyridin-4-yl)phenyl)-N-((4-(5-methyl-1,3,4-oxadiazol-2-yl)bicyclo[2.2.2]octan-1-yl)methyl)bicyclo[1.1.1]pentane-1-carboxamide (230)

Step A. Intermediate 230A. Preparation of methyl 4-(2-acetylhydrazine-1-carbonyl)bicyclo[2.2.2]octane-1-carboxylate

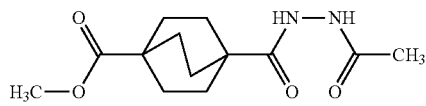

To a stirred solution of 4-(methoxycarbonyl)bicyclo[2.2.2]octane-1-carboxylic acid (500 mg, 2.356 mmol) in DMF (6 mL) were added acetohydrazide (192 mg, 2.59 mmol), DIPEA (1.234 mL, 7.07 mmol) followed by HATU (1164 mg, 3.06 mmol). The reaction mixture was stirred at room temperature for overnight. The reaction mixture was concentrated under reduced pressure, residue was diluted with water and extracted with ethyl acetate (2×10 ml). The organic layers were combined, dried over anhydrous sodium sulphate and concentrated under reduced pressure. The crude material was purified by flash chromatography (24 g silica gel cartridge; A=Hex, B=EtOAc; 20 min grad.; 0% B to 30% B; flow rate=30 mL/min). The pure fractions were combined, concentrated and dried in vacuo to afford the title compound (850 mg, 2.313 mmol, 98% yield) as white solid. $^1$H NMR (400 MHz, DMSO-d$_6$) δ 8.18 (br. s., 2H), 3.57 (s, 3H), 1.82 (s, 3H), 1.75-1.67 (m, 6H), 1.31-1.20 (m, 6H). MS (ESI) 269 (M+H).

Step B. Intermediate 230B. Preparation of methyl 4-(5-methyl-1,3,4-oxadiazol-2-yl) bicyclo[2.2.2]octane-1-carboxylate

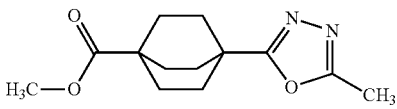

A solution of Intermediate 230A (350 mg, 1.304 mmol) in toluene (5 mL) was stirred at 100° C. for 20 h. The reaction mixture was concentrated under reduced pressure, diluted with water (10 mL) and extracted with ethyl acetate (2×10 mL). The organic layers were combined, dried over anhydrous sodium sulphate and concentrated under reduced pressure. The crude material was purified by flash chromatography (24 g silica gel cartridge; A=Hex, B=EtOAc; 20 min grad.; 0% B to 40% B; flow rate=30 mL/min). The pure fractions were combined, concentrated and dried in vacuo to afford the title compound (280 mg, 1.119 mmol, 86% yield). $^1$H NMR (400 MHz, DMSO-d$_6$) δ 3.61 (s, 3H), 2.45 (s, 3H), 1.85 (m, 12H). MS (ESI) 251 (M+H).

Step C. Intermediate 230C. Preparation of (4-(5-methyl-1,3,4-oxadiazol-2-yl) bicyclo[2.2.2]octan-1-yl)methanol

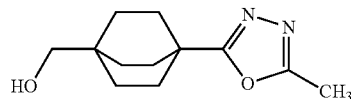

A stirred solution of Intermediate 230B (280 mg, 1.119 mmol) in DCM (6 mL) was cooled to −78° C. Diisobutylaluminium hydride in heptane (2.80 mL, 2.80 mmol) was added drop wise to the reaction mixture. The reaction mixture was allowed to warm to 0° C. and stirred for 1 h. The reaction was quenched with aqueous 1.5 N HCl, diluted with water (10 mL) and extracted with DCM (2×20 mL). The organic layers were combined, dried over anhydrous sodium sulphate and concentrated under reduced pressure. The crude material was purified by flash chromatography (24 g silica gel cartridge; A=Hex, B=EtOAc; 20 min grad.; 0% B to 60% B; flow rate=30 mL/min). The pure fractions were combined, concentrated and dried in vacuo to afford the title compound (190 mg, 0.701 mmol, 63% yield). $^1$H NMR (400 MHz, DMSO-d$_6$) δ 4.40 (br. s., 1H), 3.08 (s, 2H), 2.41 (s, 3H), 1.88-1.77 (m, 6H), 1.49-1.40 (m, 6H). MS (ESI) 223 (M+H).

Step D. Intermediate 230D. Preparation of 4-(5-methyl-1,3,4-oxadiazol-2-yl) bicyclo[2.2.2]octane-1-carbaldehyde

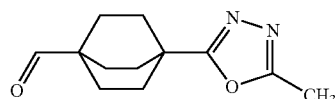

A stirred solution of oxalyl chloride (0.217 mL, 2.479 mmol) in DCM (4 mL) was cooled to −78° C. DMSO (0.15 mL, 2.02 mmol) in DCM (0.1 mL) was added drop wise to the reaction mass and stirred for 15 min. at the same temperature. Intermediate 230C (180 mg, 0.810 mmol) as a solution in DCM (2 mL) was added followed by TEA (0.79 mL, 5.67 mmol). The reaction mixture was allowed to warm to room temperature and stirred for 2 h. The reaction mixture was diluted with water and extracted with DCM (2×20 mL). The organic layers were combined, dried over anhydrous sodium sulphate and concentrated under reduced pressure. The crude material was purified by flash chromatography (12 g silica gel cartridge; A=Hex, B=EtOAc; 20 min grad.; 0% B to 20% B; flow rate=30 mL/min). The pure fractions were combined, concentrated and dried in vacuo to afford the title compound (100 mg, 0.454 mmol, 56% yield). $^1$H NMR (400 MHz, DMSO-d$_6$) δ 9.45 (s, 1H), 2.44 (s, 3H), 1.93-1.86 (m, 6H), 1.73-1.65 (m, 6H). MS (ESI) 221 (M+H).

Step E. Intermediate 230E. Preparation of 3-(2-methoxypyridin-4-yl)-N-((4-(5-methyl-1,3,4-oxadiazol-2-yl)bicyclo[2.2.2]octan-1-yl)methyl)aniline

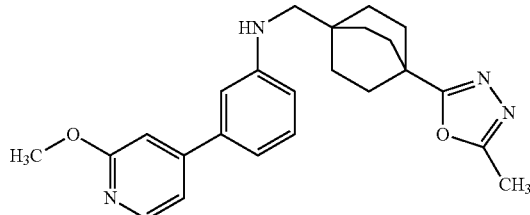

The title compound was prepared according to the method described for the synthesis of Intermediate 1I by substituting Intermediate 222A and Intermediate 230D where appropriate. (110 mg, 0.245 mmol, 60% yield). $^1$H NMR (400 MHz, DMSO-d$_6$) δ 8.20 (d, J=5.5 Hz, 1H), 7.24-7.20 (m, 1H), 7.16 (t, J=8.0 Hz, 1H), 7.00 (d, J=1.5 Hz, 1H), 6.96-6.94 (m, 1H), 6.85 (d, J=8.0 Hz, 1H), 6.72 (dd, J=8.0, 1.5 Hz, 1H), 5.65 (t, J=5.8 Hz, 1H), 3.89 (s, 3H), 2.90 (d, J=5.5 Hz, 2H), 2.45 (s, 3H), 1.90-1.82 (m, 6H), 1.63-1.55 (m, 6H). MS (ESI) 405 (M+H).

Step F. Example 230. Preparation of 3-fluoro-N-(3-(2-methoxypyridin-4-yl)phenyl)-N-((4-(5-methyl-1,3,4-oxadiazol-2-yl)bicyclo[2.2.2]octan-1-yl)methyl)bicyclo[1.1.1]pentane-1-carboxamide The title compound was prepared according to the method described for the synthesis of Example 3 by substituting Intermediate 230E and the corresponding acid where appropriate. (0.4 mg, 0.774 μmol, 1.5% yield). $^1$H NMR (400 MHz, DMSO-d$_6$) δ 8.26 (d, J=5.1 Hz, 1H), 7.81 (s, 1H), 7.76 (d, J=8.3 Hz, 1H), 7.56 (t, J=7.9 Hz, 1H), 7.46 (d, J=8.6 Hz, 1H), 7.37 (dd, J=5.5, 1.6 Hz, 1H), 7.19 (s, 1H), 3.91 (s, 3H), 3.58 (br. s., 2H), 2.42 (s, 3H), 1.83-1.71 (m, 6H), 1.42-1.21 (m, 10H), 0.86 (d, J=12.7 Hz, 2H). FXR EC$_{50}$ (nM)=988; MS (ESI) 517 (M+H).

Example 231

N-(3-(2-methoxypyridin-4-yl)phenyl)-N-((4-(5-methyl-1,3,4-oxadiazol-2-yl) bicyclo[2.2.2]octan-1-yl)methyl)cyclobutanecarboxamide

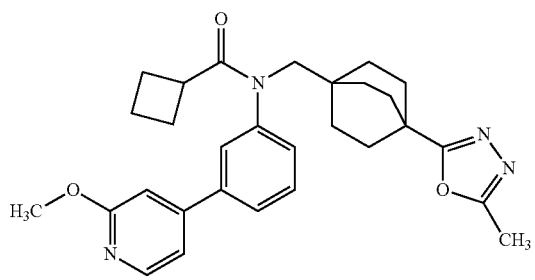

(231)

The title compound was prepared according to the method described for the synthesis of Example 3 by substituting Intermediate 230E and the corresponding acid where appropriate. (7.9 mg, 0.016 mmol, 32% yield). $^1$H NMR (400 MHz, DMSO-$d_6$) δ 8.26 (d, J=5.4 Hz, 1H), 7.82-7.67 (m, 2H), 7.55 (t, J=7.8 Hz, 1H), 7.43 (d, J=8.3 Hz, 1H), 7.39 (dd, J=5.4, 1.5 Hz, 1H), 7.20 (s, 1H), 3.91 (s, 3H), 3.65 (s, 2H), 3.12 (d, J=7.3 Hz, 1H), 2.42 (s, 3H), 2.12 (d, J=9.5 Hz, 2H), 2.09 (s, 2H), 1.82-1.69 (m, 6H), 1.62 (br. s., 2H), 1.49-1.35 (m, 6H). FXR EC$_{50}$ (nM)=592; MS (ESI) 487 (M+H).

Example 232

3-Fluoro-N-(3-(2-methoxypyridin-4-yl)phenyl)-N-((4-(5-methyl-1,3,4-thiadiazol-2-yl) bicyclo[2.2.2]octan-1-yl)methyl)bicyclo[1.1.1]pentane-1-carboxamide (232)

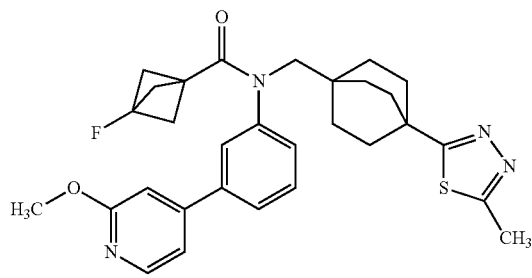

Step A. Intermediate 232A. Preparation of methyl 4-(5-methyl-1,3,4-thiadiazol-2-yl) bicyclo[2.2.2]octane-1-carboxylate

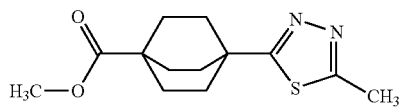

To a stirred solution of Intermediate 230A (1.2 g, 4.47 mmol) in toluene (12 mL) was added Lawesson's reagent (2 g, 4.92 mmol). The reaction mixture was heated at 100° C. for overnight. The reaction mixture was washed with aqueous sodium bicarbonate solution (10 mL) followed by water (10 mL). The aqueous layer was extracted with ethyl acetate (2×30 mL). The organic layers were combined, dried over anhydrous sodium sulphate and concentrated under reduced pressure. The crude material was purified by flash chromatography (40 g silica gel cartridge; A=Hex, B=EtOAc; 30 min grad.; 0% B to 40% B; flow rate=40 mL/min). The pure fractions were combined, concentrated and dried in vacuo to afford the title compound (700 mg, 2.63 mmol, 59% yield) as white solid. $^1$H NMR (400 MHz, DMSO-$d_6$) δ 3.60 (s, 3H), 2.69 (s, 3H), 1.95-1.80 (m, 12H). MS (ESI) 267 (M+H).

Step B. Intermediate 232B. Preparation of (4-(5-methyl-1,3,4-thiadiazol-2-yl) bicyclo[2.2.2]octan-1-yl)methanol

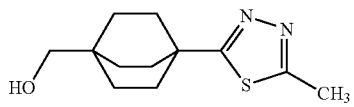

The title compound was prepared according to the method described for the synthesis of Intermediate 230C by substituting Intermediate 232A where appropriate. (360 mg, 1.510 mmol, 50% yield). $^1$H NMR (400 MHz, DMSO-$d_6$) δ 4.40 (t, J=5.3 Hz, 1H), 3.08 (d, J=5.0 Hz, 2H), 2.63 (s, 3H), 1.90-1.82 (m, 6H), 1.53-1.41 (m, 6H). MS (ESI) 239 (M+H).

Step C. Intermediate 232C. Preparation of 4-(5-methyl-1,3,4-thiadiazol-2-yl) bicyclo[2.2.2]octane-1-carbaldehyde

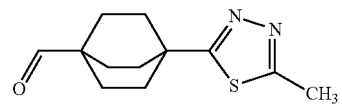

The title compound was prepared according to the method described for the synthesis of Intermediate 230D, by substituting Intermediate 232B where appropriate. (240 mg, 1.016 mmol, 69% yield), $^1$H NMR (400 MHz, DMSO-$d_6$) δ 9.46 (s, 1H), 2.67 (s, 3H), 1.97-1.89 (m, 6H), 1.76-1.67 (m, 6H). MS (ESI) 237 (M+H).

Step D. Intermediate 232D. Preparation of 3-(2-methoxypyridin-4-yl)-N-((4-(5-methyl-1,3,4-thiadiazol-2-yl)bicyclo[2.2.2]octan-1-yl)methyl)aniline

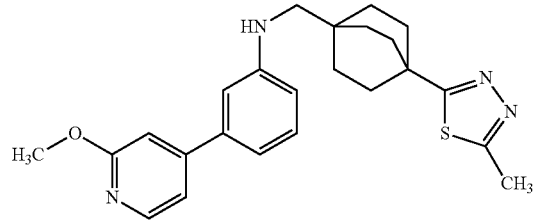 [SMILES: COc1cc(-c2cccc(NCC34CCC(c5nnc(C)o5)(CC3)CC4)c2)ccn1]

The title compound was prepared according to the method described for the synthesis of Intermediate 1I by substituting Intermediate 222A and Intermediate 232C where appropriate. (240 mg, 0.571 mmol, 54% yield). $^1$H NMR (400 MHz, DMSO-$d_6$) δ 8.20 (d, J=5.5 Hz, 1H), 7.22 (d, J=5.0 Hz, 1H), 7.16 (t, J=8.0 Hz, 1H), 7.00 (s, 1H), 6.95 (s, 1H), 6.85 (d, J=8.0 Hz, 1H), 6.72 (d, J=8.5 Hz, 1H), 5.65 (s, 1H), 3.89 (s, 3H), 2.90 (d, J=5.5 Hz, 2H), 2.70 (s, 3H), 1.94-1.88 (m, 6H), 1.66-1.58 (m, 6H). MS (ESI) 421 (M+H).

Step E. Example 232. 3-Fluoro-N-(3-(2-methoxypyridin-4-yl)phenyl)-N-((4-(5-methyl-1,3,4-thiadiazol-2-yl)bicyclo[2.2.2]octan-1-yl)methyl)bicyclo[1.1.1]pentane-1-carboxamide The title compound was prepared according to the method described for the synthesis of Example 3 by substituting Intermediate 232D and the corresponding acid where appropriate. (5.6 mg, 0.01051 mmol, 22.11% yield). $^1$H NMR (400 MHz, DMSO-$d_6$) δ 8.27 (d, J=5.4 Hz, 1H), 7.86 (s, 1H), 7.83 (d, J=7.8 Hz, 1H), 7.59 (t, J=7.8 Hz, 1H), 7.53-7.47 (m, 1H), 7.41 (dd, J=5.5, 1.6 Hz, 1H), 7.23 (s, 1H), 3.92 (s, 3H), 3.65 (s, 2H), 2.65 (s, 3H), 1.92-1.77 (m, 12H), 1.49 (br. s., 6H). FXR EC$_{50}$ (nM) 465; MS (ESI) 533 (M+H).

The following compounds were prepared according to the method described for the synthesis of Example 3 by substituting Intermediate 232D and the corresponding acid where appropriate.

| Ex. No. | Structure | MS (ESI) (M + H) | FXR EC$_{50}$ (nM) |
|---|---|---|---|
| 233 | 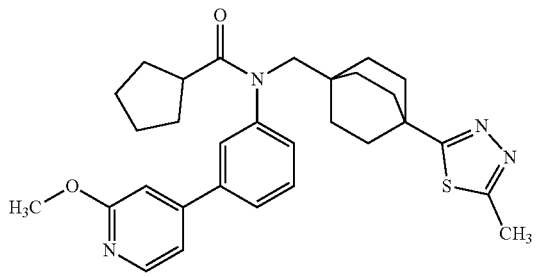 [SMILES: COc1cc(-c2cccc(N(CC34CCC(c5nnc(C)s5)(CC3)CC4)C(=O)C3CCCC3)c2)ccn1] | 517 | 1102 |
| 234 | 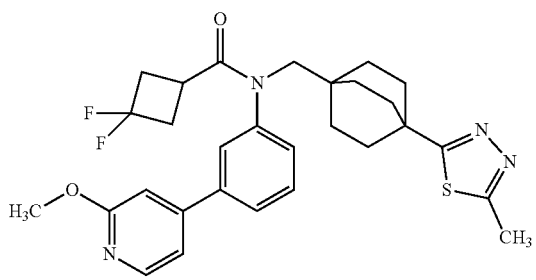 [SMILES: COc1cc(-c2cccc(N(CC34CCC(c5nnc(C)s5)(CC3)CC4)C(=O)C3CC(F)(F)C3)c2)ccn1] | 539 | 1756 |
| 235 | 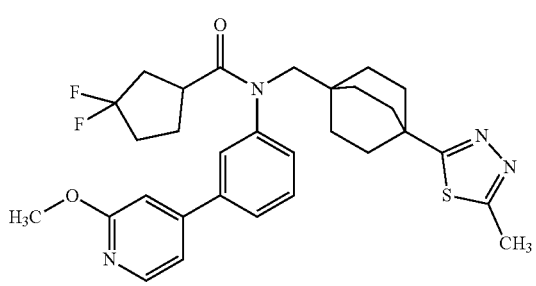 [SMILES: COc1cc(-c2cccc(N(CC34CCC(c5nnc(C)s5)(CC3)CC4)C(=O)C3CCC(F)(F)C3)c2)ccn1] | 553 | 895 |
| 236 | 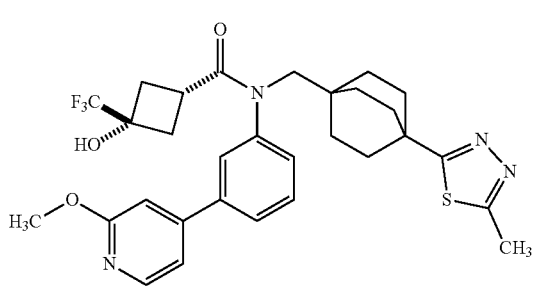 | 587 | 1542 |
233 $^{1}$H NMR (400 MHz, DMSO-d$_6$) δ 8.26 (d, J = 5.6 Hz, 1H), 7.83 (s, 1H), 7.76 (d, J = 6.8 Hz, 1H), 7.62-7.53 (m, 1H), 7.53-7.45 (m, 1H), 7.39 (d, J = 5.4 Hz, 1H), 7.21 (s, 1H), 3.91 (s, 3H), 3.65 (s, 2H), 2.67-2.58 (m, 4H), 1.90-1.73 (m, 6H), 1.72-1.63 (m, 2H), 1.57 (d, J = 6.4 Hz, 4H), 1.52-1.40 (m, 6H), 1.35 (br. s., 2H)
234 $^{1}$H NMR (400 MHz, DMSO-d$_6$) δ 8.26 (d, J = 5.4 Hz, 1H), 7.87 (s, 1H), 7.79 (d, J = 7.3 Hz, 1H), 7.58 (t, J = 7.8 Hz, 1H), 7.50 (d, J = 7.8 Hz, 1H), 7.41 (dd, J = 5.6, 1.5 Hz, 1H), 7.23 (s, 1H), 3.91 (s, 3H), 3.69 (br. s., 2H), 2.65 (s, 3H), 1.87-1.71 (m, 6H), 1.55-1.37 (m, 6H), 1.40-1.27 (m, 4H), 1.15-1.04 (m, 1H)
235 $^{1}$H NMR (400 MHz, DMSO-d$_6$) δ 8.25 (d, J = 5.4 Hz, 1H), 7.89 (s, 1H), 7.78 (d, J = 7.6 Hz, 1H), 7.63-7.47 (m, 2H), 7.39 (dd, J = 5.3, 1.1 Hz, 1H), 7.22 (s, 1H), 3.90 (s, 3H), 3.66 (br. s, 2H), 3.01-2.90 (m, 2H), 2.64 (s, 3H), 2.35-2.25 (m, 1H), 2.18-1.98 (m, 2H), 1.96-1.72 (m, 8H), 1.55-1.37 (m, 6H).

| Ex. No. | Structure | MS (ESI) (M + H) | FXR EC$_{50}$ (nM) |
|---|---|---|---|
| 236 | $^1$H NMR (400 MHz, DMSO-d$_6$) δ 8.25 (d, J = 5.4 Hz, 1H), 7.86 (s, 1H), 7.76 (d, J = 7.6 Hz, 1H), 7.60-7.51 (m, 1H), 7.51-7.40 (m, 1H), 7.38 (dd, J = 5.4, 1.5 Hz, 1H), 7.20 (s, 1H), 6.53 (d, J = 6.8 Hz, 1H), 3.97-3.83 (m, 3H), 3.68 (br. s., 2H), 2.82 (t, J = 9.2 Hz, 1H), 2.63 (s, 3H), 2.36-2.31 (m, 2H), 2.03 (br. s., 2H), 1.85-1.68 (m, 6H), 1.52-1.39 (m, 6H) | | |

Example 237

3,3-Difluoro-N-(3-(2-methoxypyridin-4-yl)phenyl)-N-((4-(2-methylpyridin-4-yl) bicyclo[2.2.2]octan-1-yl)methyl)cyclobutane-1-carboxamide

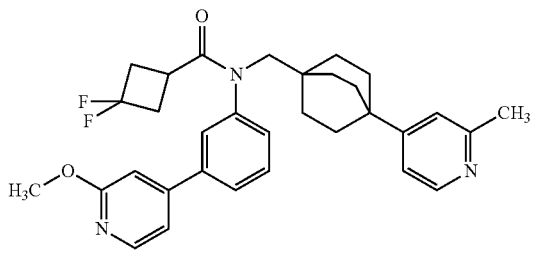

(237)

Step A. Intermediate 237A1 & 237A2. Preparation of methyl 4-(6-methylpyridin-2-yl) bicyclo[2.2.2]octane-1-carboxylate & methyl 4-(2-methylpyridin-4-yl) bicyclo[2.2.2]octane-1-carboxylate

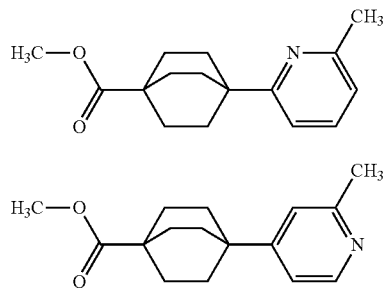

(I-237A1)

(I-237A2)

To a stirred solution of 4-(methoxycarbonyl)bicyclo[2.2.2]octane-1-carboxylic acid (2 g, 9.42 mmol) and 2-methylpyridine (1.053 g, 11.31 mmol) in DCM (60 mL) and water (60 mL) was added silver nitrate (0.320 g, 1.885 mmol) followed by potassium persulfate (2.55 g, 9.42 mmol) and stirred at room temperature overnight. The reaction mixture was diluted with DCM (30 mL) and the organic layer was washed with water (2×50 mL). The organic layer was dried over sodium sulfate, filtered and concentrated under reduced pressure. The crude material was purified by flash column chromatography (24 g silica gel cartridge; A=Hex, B=EtOAc; 30 min grad.; 0% B to 20% B; flow rate=30 mL/min). The pure fractions were combined, concentrated and dried in vacuo to afford the title compound Intermediate 237A1 (200 mg, 0.771 mmol). $^1$H NMR (400 MHz, DMSO-d$_6$) δ 7.61-7.54 (m, 1H), 7.10 (d, J=8.0 Hz, 1H), 7.04 (d, J=7.5 Hz, 1H), 3.60 (s, 3H), 2.43 (s, 3H), 1.90-1.77 (m, 12H). MS (ESI) 260 (M+H) and Intermediate 237A2 (650 mg, 2.506 mmol). $^1$H NMR (400 MHz, DMSO-d$_6$) δ 8.32 (d, J=5.5 Hz, 1H), 7.20 (d, J=2.0 Hz, 1H), 7.12 (dd, J=5.3, 1.8 Hz, 1H), 3.60 (s, 3H), 2.43 (s, 3H), 1.87-1.73 (m, 12H). MS (ESI) 260 (M+H).

Step B. Intermediate 237B1 & 237B2. Preparation of 4-(2-methylpyridin-4-yl) bicyclo[2.2.2]octane-1-carbaldehyde and (4-(2-methylpyridin-4-yl)bicyclo[2.2.2]octan-1-yl)methanol

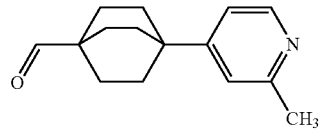

(I-237B1)

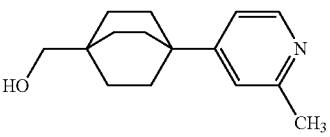

(I-237B2)

A stirred solution of Intermediate 237A2 (650 mg, 2.506 mmol) in DCM (20 mL) was cooled to −78° C. and stirred for 5 min. DIBAL-H in heptane (5.22 mL, 6.27 mmol) was added to the reaction mass and stirred at −78° C. for 20 min. The reaction was quenched with ammonium chloride solution and stirred for 2 h. The organic layer was separated and the aqueous layer was extracted with DCM (2×25 mL). The organic layers were combined, dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated and dried in vacuo to afford the title compound 4-(2-methylpyridin-4-yl)bicyclo[2.2.2]octane-1-carbaldehyde (110 mg, 0.48 mmol, 19% yield). $^1$H NMR (400 MHz, DMSO-d$_6$) δ 9.48 (s, 1H), 8.33 (d, J=5.5 Hz, 1H), 7.21 (s, 1H), 7.15-7.12 (m, 1H), 2.43 (s, 3H), 1.83-1.77 (m, 6H), 1.73-1.66 (m, 6H). MS (ESI) 230 (M+H) Intermediate 237B1 and (4-(2-methylpyridin-4-yl)bicyclo[2.2.2]octan-1-yl)methanol (250 mg, 1.081 mmol, 43% yield). $^1$H NMR (400 MHz, DMSO-d$_6$) δ 8.30 (d, J=5.0 Hz, 1H), 7.21-7.15 (m, 1H), 7.11 (dd, J=5.5, 1.5 Hz, 1H), 4.39 (t, J=5.5 Hz, 1H), 3.09 (d, J=5.5 Hz, 2H), 2.43 (s, 3H), 1.79-1.68 (m, 6H), 1.51-1.39 (m, 6H). MS (ESI) 232 (M+H) Intermediate 237B2.

Step C. Intermediate 237C. Preparation of 3-(2-methoxypyridin-4-yl)-N-((4-(2-methylpyridin-4-yl)bicyclo[2.2.2]octan-1-yl)methyl)aniline

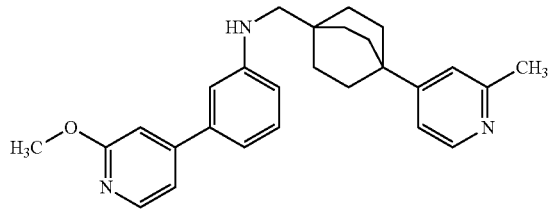

The title compound was prepared according to the method described for the synthesis of Intermediate 1I by substituting Intermediate 222A and Intermediate 237B1 where appropriate. (140 mg, 0.33 mmol, 77% yield) as brown gummy solid. $^1$H NMR (400 MHz, DMSO-$d_6$) δ 8.31 (d, J=5.5 Hz, 1H), 8.20 (d, J=6.0 Hz, 1H), 7.24-7.11 (m, 4H), 7.00 (d, J=1.5 Hz, 1H), 6.96 (s, 1H), 6.85 (d, J=7.5 Hz, 1H), 6.72 (d, J=9.5 Hz, 1H), 5.77 (s, 1H), 5.63 (t, J=5.5 Hz, 1H), 3.89 (s, 3H), 2.90 (d, J=6.0 Hz, 2H), 2.43 (s, 3H), 1.81-1.74 (m, 6H), 1.65-1.57 (m, 6H). MS (ESI) 414 (M+H).

Step D. Example 237. Preparation of 3,3-difluoro-N-(3-(2-methoxypyridin-4-yl) phenyl)-N-((4-(2-methylpyridin-4-yl)bicyclo[2.2.2]octan-1-yl)methyl)cyclobutane-1-carboxamide The title compound was prepared according to the method described for the synthesis of Example 3 by substituting Intermediate 237C and 3,3-difluorocyclobutane-1-carboxylic acid where appropriate. (2 mg, 3.72 μmol, 8% yield). $^1$H NMR (400 MHz, DMSO-$d_6$) δ 8.32-8.23 (m, 2H), 7.86 (s, 1H), 7.79 (d, J=8.3 Hz, 1H), 7.58 (t, J=7.9 Hz, 1H), 7.49 (d, J=8.1 Hz, 1H), 7.41 (dd, J=5.5, 1.3 Hz, 1H), 7.23 (s, 1H), 7.13 (s, 1H), 7.05 (d, J=5.4 Hz, 1H), 3.91 (s, 3H), 3.69 (br. s., 2H), 3.01-2.91 (m, 1H), 2.75 (br. s., 2H), 2.40 (s, 3H), 2.34 (d, J=2.0 Hz, 1H), 1.74-1.56 (m, 6H), 1.52-1.35 (m, 6H). FXR EC$_{50}$ (nM)=541; MS (ESI) 532 (M+H).

Example 238

3-Fluoro-N-(3-(2-methoxypyridin-4-yl)phenyl)-N-((4-(2-methylpyridin-4-yl) bicyclo[2.2.2]octan-1-yl)methyl)bicyclo[1.1.1]pentane-1-carboxamide (238)

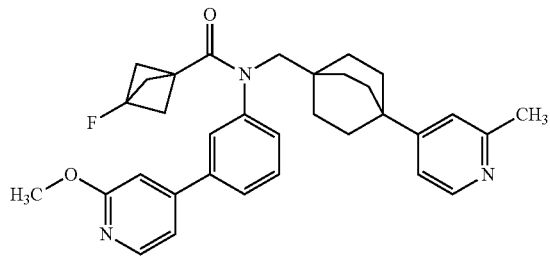

The title compound was prepared according to the method described for the synthesis of Example 3 by substituting Intermediate 237C and the corresponding acid where appropriate. (2 mg, 3.72 μmol, 8% yield). $^1$HNMR (400 MHz, DMSO-$d_6$) δ 8.28 (dd, J=5.3, 3.5 Hz, 2H), 7.89-7.78 (m, 2H), 7.59 (t, J=7.7 Hz, 1H), 7.52-7.44 (m, 1H), 7.41 (dd, J=5.4, 1.5 Hz, 1H), 7.23 (d, J=1.0 Hz, 1H), 7.13 (s, 1H), 7.06 (d, J=5.4 Hz, 1H), 3.92 (s, 3H), 3.70-3.62 (m, 1H), 3.60-3.51 (m, 1H), 2.41 (s, 3H), 2.09 (s, 1H), 1.96-1.77 (m, 6H), 1.73-1.58 (m, 6H), 1.46 (d, J=5.4 Hz, 6H). FXR EC$_{50}$ (nM)=517. MS (ESI) 526 (M+H).

Example 239

3-Fluoro-N-(3-(2-methoxypyridin-4-yl)phenyl)-N-((4-(6-methylpyridin-2-yl) bicyclo[2.2.2]octan-1-yl)methyl)bicyclo[1.1.1]pentane-1-carboxamide (239)

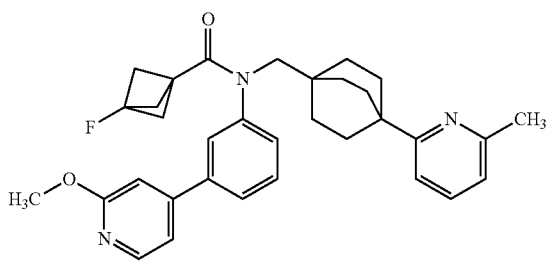

Step A. Intermediate 239A. Preparation of (4-(6-methylpyridin-2-yl)bicyclo[2.2.2]octan-1-yl)methanol

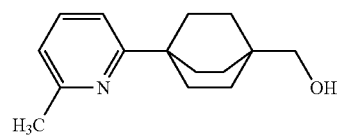

The title compound was prepared according to the method described for the synthesis of Intermediate 1G by substituting Intermediate 237A1 where appropriate. (120 mg, 0.514 mmol, 83% yield) as brown gummy solid. MS (ESI) 232 (M+H).

Step B. Intermediate 239B. Preparation of 4-(6-methylpyridin-2-yl)bicyclo[2.2.2]octane-1-carbaldehyde

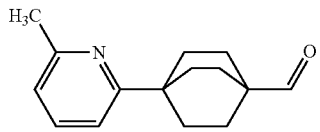 [SMILES: Cc1cccc(C23CCC(C=O)(CC2)CC3)n1]

The title compound was prepared according to the method described for the synthesis of Intermediate 3C by substituting Intermediate 239A where appropriate. (70 mg, 59% yield). $^1$H NMR (400 MHz, DMSO-$d_6$) δ 9.49 (s, 1H), 7.59

(t, J=7.8 Hz, 1H), 7.12 (d, J=7.5 Hz, 1H), 7.04 (d, J=7.5 Hz, 1H), 2.40 (s, 3H), 1.92-1.83 (m, 6H), 1.74-1.64 (m, 6H). MS (ESI) 230 (M+H).

Step C. Intermediate 239C. Preparation of 3-(2-methoxypyridin-4-yl)-N-((4-(6-methylpyridin-2-yl)bicyclo[2.2.2]octan-1-yl)methyl)aniline

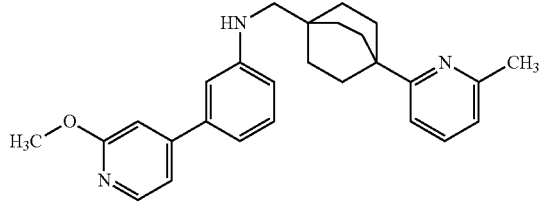

The title compound was prepared according to the method described for the synthesis of Intermediate 1I by substituting Intermediate 222A and Intermediate 239B where appropriate. (50 mg, 0.12 mmol, 40% yield). $^1$H NMR (400 MHz, DMSO-$d_6$) δ 8.20 (d, J=6.0 Hz, 1H), 7.57 (t, J=7.8 Hz, 1H), 7.23 (dd, J=5.5, 1.5 Hz, 1H), 7.11 (d, J=8.0 Hz, 1H), 7.16 (d, J=7.5 Hz, 1H), 7.04-6.99 (m, 2H), 6.96 (s, 1H), 6.85 (d, J=7.5 Hz, 1H), 6.73 (d, J=7.5 Hz, 1H), 5.61 (s, 1H), 3.89 (s, 3H), 2.89 (d, J=6.0 Hz, 2H), 2.43 (s, 3H), 1.90-1.81 (m, 6H), 1.64-1.56 (m, 6H). MS (ESI) 414 (M+H).

Step D. Example 239. Preparation of 3-fluoro-N-(3-(2-methoxypyridin-4-yl)phenyl)-N-((4-(6-methylpyridin-2-yl)bicyclo[2.2.2]octan-1-yl)methyl)bicyclo[1.1.1]pentane-1-carboxamide The title compound was prepared according to the method described for the synthesis of Example 3 by substituting Intermediate 239C and the corresponding acid where appropriate. (4.5 mg, 8.56 μmol, 24% yield). $^1$H NMR (400 MHz, DMSO-$d_6$) δ 8.27 (d, J=5.4 Hz, 1H), 7.88-7.78 (m, 2H), 7.63-7.47 (m, 3H), 7.41 (dd, J=5.4, 1.5 Hz, 1H), 7.23 (s, 1H), 7.04 (d, J=7.8 Hz, 1H), 7.00 (d, J=7.6 Hz, 1H), 3.92 (s, 3H), 3.65 (s, 2H), 2.40 (s, 3H), 1.89 (br. s., 3H), 1.84 (br. s., 3H), 1.75 (t, J=8.1 Hz, 6H), 1.46 (br. s., 6H). FXR EC$_{50}$ (nM)= 1317; MS (ESI) 526 (M+H).

Example 240

N-(3-(2-methoxypyridin-4-yl)phenyl)-N-((4-(4-(trifluoromethyl)pyridin-2-yl) bicyclo[2.2.2]octan-1-yl)methyl)cyclobutanecarboxamide

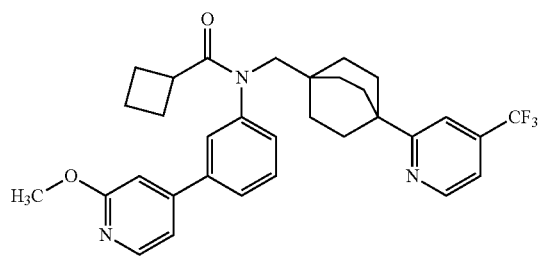

(240)

Step A. Intermediate 240A. Preparation of methyl 4-(4-(trifluoromethyl)pyridin-2-yl) bicyclo[2.2.2]octane-1-carboxylate

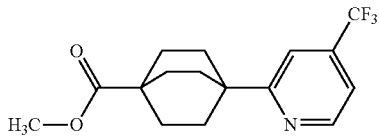

To a stirred solution of 4-(methoxycarbonyl)bicyclo[2.2.2]octane-1-carboxylic acid (1 g, 4.71 mmol) in DCM (30 mL) and water (30 mL) were added 4-(trifluoromethyl)pyridine (0.83 g, 5.65 mmol), silver nitrate (0.16 g, 0.94 mmol) followed by potassium persulfate (0.160 g, 0.94 mmol). The reaction mixture was stirred at room temperature for overnight. The reaction mixture was diluted with DCM (25 mL) and filtered through Celite. The organic layer was separated, washed with brine solution (25 mL), dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated and dried in vacuo to afford the title compound (600 mg, 1.91 mmol, 40% yield) as brown solid. $^1$H NMR (400 MHz, DMSO-$d_6$) δ 8.79 (d, J=5.0 Hz, 1H), 7.64 (d, J=1.0 Hz, 1H), 7.59 (d, J=5.0 Hz, 1H), 3.61 (s, 3H), 1.96-1.88 (m, 6H), 1.88-1.81 (m, 6H). MS (ESI) 314 (M+H).

Step B. Intermediate 240B. Preparation of (4-(4-(trifluoromethyl)pyridin-2-yl) bicyclo[2.2.2]octan-1-yl)methanol

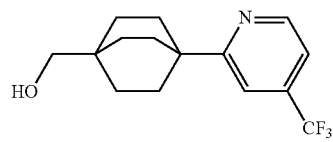

The title compound was prepared according to the method described for the synthesis of Intermediate 1G by substituting Intermediate 240A where appropriate. (370 mg, 1.27 mmol, 80% yield) as brown gummy solid. $^1$H NMR (400 MHz, DMSO-$d_6$) δ 8.78 (d, J=5.0 Hz, 1H), 7.62-7.51 (m, 2H), 4.36 (t, J=5.5 Hz, 1H), 3.10 (d, J=5.5 Hz, 2H), 1.93-1.80 (m, 6H), 1.52-1.41 (m, 6H). MS (ESI) 286 (M+H).

Step C. Intermediate 240C. Preparation of 4-(4-(trifluoromethyl)pyridin-2-yl) bicyclo[2.2.2]octane-1-carbaldehyde

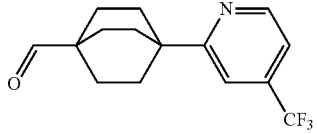 [SMILES: O=CC12CCC(c3cc(C(F)(F)F)ccn3)(CC1)CC2]

The title compound was prepared according to the method described for the synthesis of Intermediate 3C by substituting Intermediate 240B where appropriate. (220 mg, 0.77 mmol, 60% yield) as oily liquid. MS (ESI) 284 (M+H). $^1$H NMR (300 MHz, DMSO-d$_6$) δ 9.45 (s, 1H), 78 (d, J=5.0 Hz, 1H), 7.62-7.51 (m, 2H), 1.93-1.80 (m, 6H), 1.52-1.41 (m, 6H).

(d, J=9.0 Hz, 1H), 3.88 (s, 3H), 3.17 (d, J=5.0 Hz, 1H), 2.90 (d, J=5.5 Hz, 1H), 1.90-1.88 (m, 6H), 1.61-1.59 (m, 6H). MS (ESI) 468 (M+H).

Step E. Example 240. Preparation of N-(3-(2-methoxypyridin-4-yl)phenyl)-N-((4-(4-(trifluoromethyl)pyridin-2-yl)bicyclo[2.2.2]octan-1-yl)methyl)cyclobutanecarboxamide The title compound was prepared according to the method described for the synthesis of Example 3 by substituting Intermediate 240D and cyclobutane carboxylic acid where appropriate. (10 mg, 0.018 mmol, 43% yield). $^1$H NMR (400 MHz, DMSO-d$_6$) δ 8.74 (d, J=5.1 Hz, 1H), 8.25 (d, J=5.4 Hz, 1H), 7.81-7.70 (m, 2H), 7.62-7.48 (m, 3H), 7.42 (d, J=6.8 Hz, 1H), 7.37 (d, J=5.4 Hz, 1H), 7.18 (s, 1H), 3.90 (s, 3H), 3.66 (s, 2H), 3.13 (d, J=6.8 Hz, 1H), 2.21-2.04 (m, 2H), 1.88-1.70 (m, 6H), 1.63 (br. s., 4H), 1.51-1.32 (m, 6H). FXR EC$_{50}$ (nM)=2129; MS (ESI) 550 (M+H).

The following compounds were prepared according to the method described for the synthesis of Example 3 by substituting Intermediate 240D and the corresponding acids where appropriate.

| Ex. No. | Structure | MS (ESI) (M + H) | FXR EC$_{50}$ (nM) |
|---|---|---|---|
| 241 | 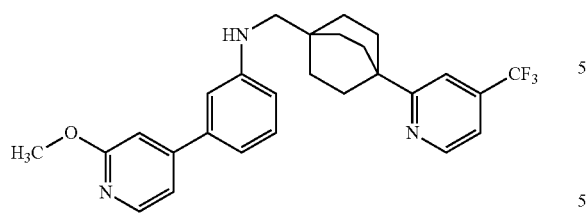 | 580 | 1058 |

241  $^1$HNMR (400 MHz, DMSO-d$_6$) δ 8.76 (d, J = 5.1 Hz, 1H), 8.27 (d, J = 5.4 Hz, 1H), 7.90-7.78 (m, 2H), 7.64-7.53 (m, 3H), 7.50 (d, J = 8.3 Hz, 1H), 7.41 (dd, J = 5.5, 1.6 Hz, 1H), 7.23 (s, 1H), 3.92 (s, 3H), 3.72-3.64 (m, 1H), 3.61 (s, 1H), 1.89-1.71 (m, 12H), 1.48 (d, J = 5.4 Hz, 6H)

Step D. Intermediate 240D. Preparation of 3-(2-methoxypyridin-4-yl)-N-((4-(4-(trifluoromethyl)pyridin-2-yl)bicyclo[2.2.2]octan-1-yl)methyl)aniline The title compound was prepared according to the method described for the synthesis of Intermediate 1I by substituting Intermediate 222A and Intermediate 240C where appropriate. (80 mg, 0.17 mmol, 69% yield) as brown gummy solid. $^1$H NMR (400 MHz, DMSO-d$_6$) δ 8.79 (d, J=5.5 Hz, 1H), 8.20-8.16 (m, 1H), 7.61 (s, 1H), 7.56 (d, J=3.5 Hz, 1H), 7.21 (dd, J=5.5, 1.5 Hz, 1H), 7.18-7.10 (m, 1H), 7.00-6.88 (m, 2H), 6.84 (d, J=5.0 Hz, 1H), 6.72 (d, J=7.5 Hz, 1H), 6.64

Example 242

N-((4-(3-cyclopropyl-1,2,4-oxadiazol-5-yl)bicyclo[2.2.2]octan-1-yl)methyl)-3-fluoro-N-(3-(2-methoxypyrimidin-4-yl)phenyl)bicyclo[1.1.1]pentane-1-carboxamide (242)

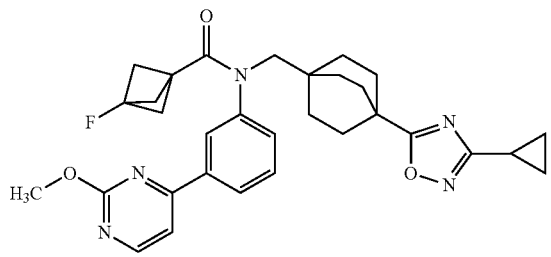

415

Step A. Intermediate 242A. Preparation of 2-chloro-4-(3-nitrophenyl)pyrimidine

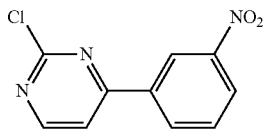 [SMILES: O=[N+]([O-])c1cccc(-c2ccnc(Cl)n2)c1]

To a stirred solution of 2,4-dichloropyrimidine (1 g, 6.71 mmol) in 1,2-dimethoxyethane (15 mL) were added (3-nitrophenyl)boronic acid (1.12 g, 6.71 mmol) and a solution of sodium bicarbonate (1.13 g, 13.43 mmol) in water (1.5 mL). The reaction mixture was degassed and back-filled with argon. Tetrakis(triphenylphosphine)palladium(0) (0.776 g, 0.67 mmol) was added to the reaction mass and heated at 80° C. for 12 h. The reaction mixture was cooled to room temperature, diluted with water (15 mL) and extracted with EtOAc (2×15 mL). The organic layers were combined, dried over anhydrous sodium sulphate and concentrated under reduced pressure. The crude material was purified by flash chromatography (24 g silica gel cartridge; A=Hex, B=EtOAc; 30 min grad.; 0% B to 40% B; flow rate=30 mL/min). The pure fractions were combined, concentrated and dried in vacuo to afford the title compound (1.1 g, 4.43 mmol, 66% yield) as pale yellow solid. The product was confirmed by NOE. $^1$H NMR (400 MHz, DMSO-$d_6$) δ 8.94-8.95 (m, 2H), 8.64 (d, J=7.60 Hz, 1H), 8.44-8.47 (m, 1H), 8.36 (d, J=5.60 Hz, 1H), 7.89 (t, J=8.00 Hz, 1H). MS (ESI) 236 (M+H).

Step B. Intermediate 242B. Preparation of 2-methoxy-4-(3-nitrophenyl)pyrimidine

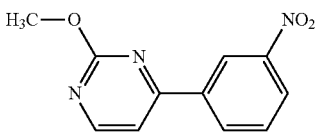 [SMILES: COc1nccc(-c2cccc([N+](=O)[O-])c2)n1]

To a solution of Intermediate 242A (500 mg, 2.122 mmol) in methanol (5 mL) was added sodium methoxide in methanol (1.38 g, 6.37 mmol). The reaction mixture was stirred at 80° C. for overnight. The reaction mixture was concentrated under reduced pressure. The residue was dissolved in EtOAc (20 mL), washed with water (15 mL), brine solution (10 mL), dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated and dried in vacuo to afford the title compound (300 mg, 1.23 mmol, 58% yield) as solid. MS (ESI) 232 (M+H).

416

Step C. Intermediate 242C. Preparation of 3-(2-methoxypyrimidin-4-yl)aniline

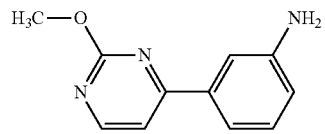

To a stirred solution of Intermediate 242B (0.3 g, 1.3 mmol) in tetrahydrofuran (2 mL) and ethanol (2 mL) were added zinc (1.27 g, 19.46 mmol) and an aqueous solution of ammonium chloride (1.0 g, 19.46 mmol) in water (2 mL). The reaction mixture was stirred at room temperature for 3 h. The reaction mixture was diluted with EtOAc (50 mL), filtered through Celite. The filtrate was washed with water (20 mL), brine solution (20 mL), dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated and dried in vacuo to afford the title compound (230 mg, 1.1 mmol, 84% yield) as solid. MS (ESI) 202 (M+H).

Step D. Intermediate 242D. Preparation of N-((4-(3-cyclopropyl-1,2,4-oxadiazol-5-yl) bicyclo[2.2.2]octan-1-yl)methyl)-3-(2-methoxypyrimidin-4-yl)aniline

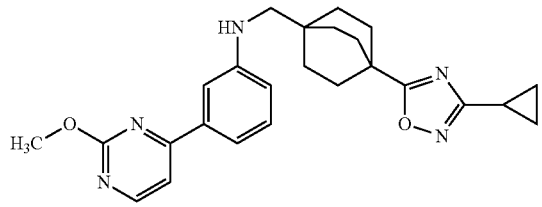

The title compound was prepared according to the method described for the synthesis of Intermediate 1I by substituting Intermediate 242C and Intermediate 4C where appropriate. (160 mg, 0.352 mmol, 71% yield) as yellow solid. MS (ESI) 432 (M+H).

Step E. Example 242. Preparation of N-((4-(3-cyclopropyl-1,2,4-oxadiazol-5-yl)bicyclo[2.2.2]octan-1-yl)methyl)-3-fluoro-N-(3-(2-methoxypyrimidin-4-yl)phenyl)bicyclo[1.1.1]pentane-1-carboxamide The title compound was prepared according to the method described for the synthesis of Example 3 by substituting Intermediate 242D and the corresponding acid where appropriate. (17.3 mg, 0.032 mmol, 55% yield). $^1$H NMR (400 MHz, DMSO-$d_6$) δ 8.72 (d, J=5.4 Hz, 1H), 8.22 (d, J=7.6 Hz, 1H), 8.19-8.13 (m, 1H), 7.83 (d, J=5.1 Hz, 1H), 7.68-7.56 (m, 2H), 4.02 (s, 3H), 3.62 (d, J=4.9 Hz, 2H), 2.09-2.02 (m, 1H), 1.88 (br. s., 6H), 1.82-1.68 (m, 6H), 1.52-1.36 (m, 6H), 1.06-0.95 (m, 2H), 0.87-0.78 (m, 2H). FXR $EC_{50}$ (nM) 276; MS (ESI) 544 (M+H).

The following compounds were prepared according to the method described for the synthesis of Example 3 by substituting Intermediate 242D and the corresponding acids where appropriate.

| Ex. No. | Structure | MS (ESI) (M + H) | FXR EC$_{50}$ (nM) |
|---|---|---|---|
| 243 | | 550 | 428 |
| 244 | | 514 | 576 |
| 245 | | 564 | 538 |

243 $^1$H NMR (400 MHz, DMSO-d$_6$) δ 8.72 (d, J = 5.1 Hz, 1H), 8.25-8.11 (m, 2H), 7.82 (d, J = 5.1 Hz, 1H), 7.69-7.55 (m, 2H), 4.02 (s, 3H), 3.68 (s, 2H), 2.90 (br. s., 1H), 2.78 (d, J = 10.8 Hz, 2H), 2.41-2.32 (m, 2H), 2.09-2.01 (m, 1H), 1.85-1.66 (m, 6H), 1.50-1.32 (m, 6H), 1.07-0.97 (m, 2H), 0.89-0.75 (m, 2H).

244 $^1$H NMR (400 MHz, DMSO-d$_6$) δ 8.69 (d, J = 5.1 Hz, 1H), 8.14 (d, J = 7.6 Hz, 1H), 8.10 (s, 1H), 7.80 (d, J = 5.1 Hz, 1H), 7.59 (t, J = 7.7 Hz, 1H), 7.53 (d, J = 8.3 Hz, 1H), 4.00 (s, 3H), 3.64 (s, 2H), 3.07 (br. s., 1H), 2.22-2.07 (m, 2H), 2.06-1.99 (m, 1H), 1.82-1.71 (m, 6H), 1.64 (br. s., 4H), 1.51-1.32 (m, 6H), 1.06-0.94 (m, 2H), 0.87-0.75 (m, 2H).

245 $^1$H NMR (400 MHz, DMSO-d$_6$) δ 8.72 (d, J = 5.1 Hz, 1H), 8.20 (s, 2H), 7.83 (d, J = 5.4 Hz, 1H), 7.74-7.57 (m, 2H), 4.09 (s, 3H), 3.67 (d, J = 11.0 Hz, 2H), 2.99-2.88 (m, 1H), 2.17-1.99 (m, 3H), 1.98-1.72 (m, 7H), 1.69 (br s., 1H), 1.59 (br. s., 1H), 1.53-1.33 (m, 7H), 1.10-0.93 (m, 2H), 0.91-0.76 (m, 2H).

Example 246

N-((4-(3-cyclopropyl-1,2,4-oxadiazol-5-yl)bicyclo[2.2.2]octan-1-yl)methyl)-3-fluoro-N-(4'-(methylsulfonamido)-[1,1'-biphenyl]-3-yl)bicyclo[1.1.1]pentane-1-carboxamide

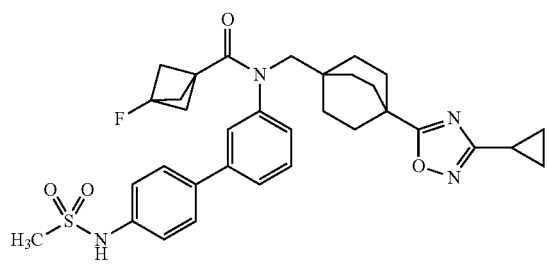

(246)

Step A. Intermediate 246A. Preparation of 3-bromo-N-((4-(3-cyclopropyl-1,2,4-oxadiazol-5-yl)bicyclo[2.2.2]octan-1-yl)methyl)aniline

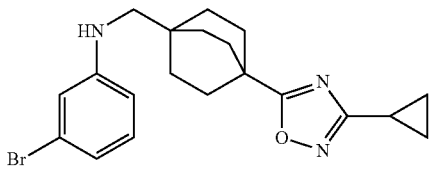 [SMILES: Brc1cccc(NCC23CCC(c4nc(C5CC5)no4)(CC2)CC3)c1]

The title compound was prepared according to the method described for the synthesis of Intermediate 1I by substituting 3-bromoaniline and Intermediate 4C where appropriate. (700 mg, 1.74 mmol, 86% yield) as brown gummy solid. MS (ESI) 402.2 (M+H); $^1$H NMR (400 MHz, DMSO-$d_6$) δ 7.02-6.92 (m, 1H), 6.76 (s, 1H), 6.59 (dd, J=8.0, 2.0 Hz, 2H), 5.80-5.70 (m, 1H), 2.79 (d, J=6.0 Hz, 2H), 2.05 (m, 1H), 1.89-1.77 (m, 6H), 1.59-1.48 (m, 6H), 1.02 (m, 2H), 0.89-0.80 (m, 2H).

Step B. Intermediate 246B. Preparation of N-(3-bromophenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide

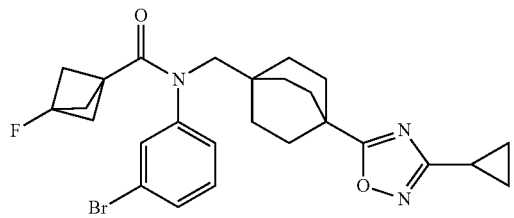

The title compound was prepared according to the method described for the synthesis of Example 3 by substituting Intermediate 246A and 3-fluorobicyclo[1.1.1]pentane-1-carboxylic acid where appropriate. (320 mg, 0.603 mmol, 35% yield) as white solid. MS (ESI) 514.0 (M+H); $^1$H NMR (400 MHz, DMSO-$d_6$) δ 7.69 (s, 1H), 7.60 (d, J=7.0 Hz, 1H), 7.45-7.39 (m, 2H), 3.56 (br. s., 1H), 3.48 (br. s., 1H), 2.08-2.00 (m, 1H), 1.86 (br. s., 6H), 1.81-1.72 (m, 6H), 1.40 (br. s., 6H), 1.01 (m, 2H), 0.86-0.79 (m, 2H).

Step C. Example 246. Preparation of N-((4-(3-cyclopropyl-1,2,4-oxadiazol-5-yl) bicyclo[2.2.2]octan-1-yl)methyl)-3-fluoro-N-(4'-(methylsulfonamido)-[1,1'-biphenyl]-3-yl)bicyclo[1.1.1]pentane-1-carboxamide The title compound was prepared according to the method described for the synthesis of Example 149 by substituting Intermediate 246B and the corresponding boronic acid where appropriate. (16.1 mg, 0.027 mmol, 46% yield). $^1$H NMR (400 MHz, DMSO-$d_6$) δ 9.90 (s, 1H), 7.73 (d, J=8.00 Hz, 2H), 7.66 (t, J=8.00 Hz, 2H), 7.51 (t, J=7.60 Hz, 1H), 7.30-7.35 (m, 3H), 3.58-3.59 (m, 2H), 3.03 (s, 3H), 2.02-2.06 (m, 1H), 1.75-1.86 (m, 12H), 1.42-1.46 (m, 6H), 0.98-1.02 (m, 2H), 0.80-0.84 (m, 2H); FXR EC$_{50}$ (nM)=66; MS (ESI) 605 (M+H).

The following compounds were prepared according to the method described for the synthesis of Example 149 by substituting Intermediate 246B and the corresponding heteroaryl/aryl boronic acids/esters (commercially available).

| Ex. No. | Structure | MS (ESI) (M + H) | FXR EC$_{50}$ (nM) |
|---|---|---|---|
| 247 | 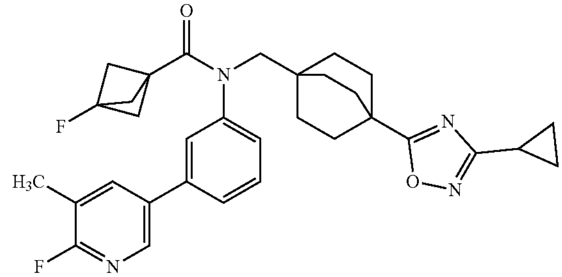 [SMILES: Cc1cc(-c2cccc(N(CC34CCC(c5nc(C6CC6)no5)(CC3)CC4)C(=O)C34CC(F)(C3)C4)c2)cnc1F] | 545 | 341 |

-continued

| Ex. No. | Structure | MS (ESI) (M + H) | FXR EC$_{50}$ (nM) |
|---|---|---|---|
| 248 | 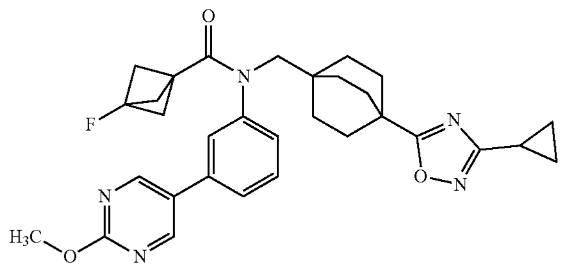 [SMILES: COc1ncc(-c2cccc(N(CC34CCC(c5nc(C6CC6)no5)(CC3)CC4)C(=O)C34CC(F)(C3)C4)c2)cn1] | 544 | 154 |
| 249 | 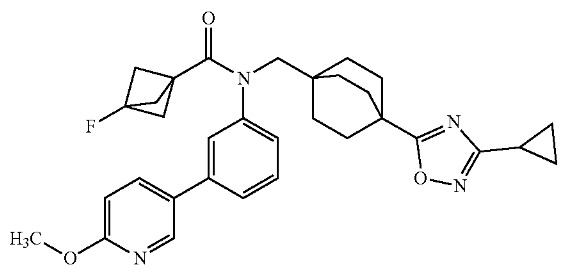 [SMILES: COc1ccc(-c2cccc(N(CC34CCC(c5nc(C6CC6)no5)(CC3)CC4)C(=O)C34CC(F)(C3)C4)c2)cn1] | 543 | 153 |
| 250 | 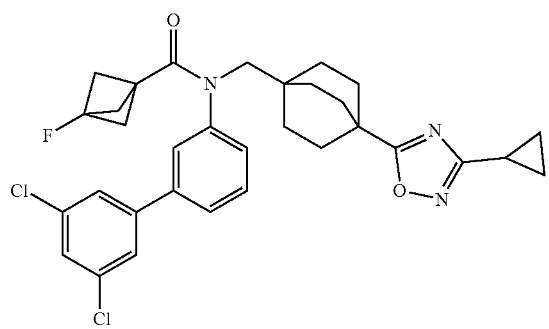 [SMILES: O=C(N(CC12CCC(c3nc(C4CC4)no3)(CC1)CC2)c1cccc(-c2cc(Cl)cc(Cl)c2)c1)C12CC(F)(C1)C2] | 580 | 778 |
| 251 | 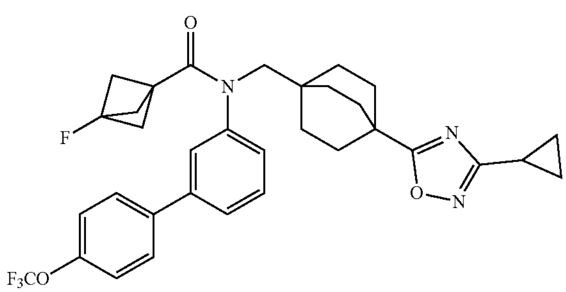 [SMILES: O=C(N(CC12CCC(c3nc(C4CC4)no3)(CC1)CC2)c1cccc(-c2ccc(OC(F)(F)F)cc2)c1)C12CC(F)(C1)C2] | 596 | 277 |
| 252 | 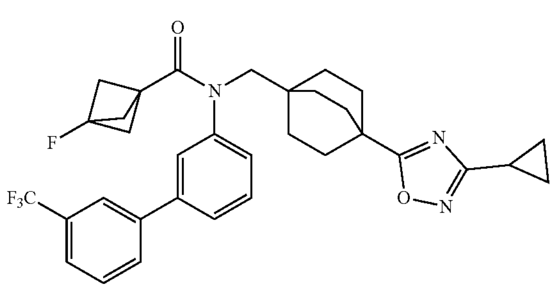 [SMILES: O=C(N(CC12CCC(c3nc(C4CC4)no3)(CC1)CC2)c1cccc(-c2cccc(C(F)(F)F)c2)c1)C12CC(F)(C1)C2] | 580 | 833 |

| Ex. No. | Structure | MS (ESI) (M + H) | FXR EC$_{50}$ (nM) |
|---|---|---|---|
| 253 | 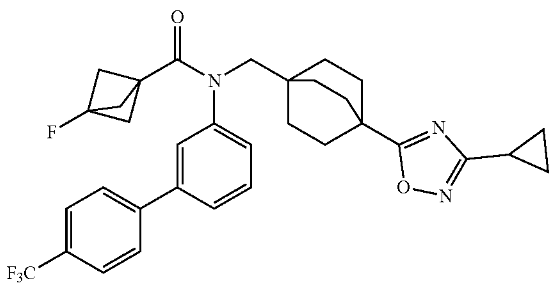 [SMILES: O=C(N(CC12CCC(c3nc(C4CC4)no3)(CC1)CC2)c1cccc(-c2ccc(C(F)(F)F)cc2)c1)C12CC(F)(C1)C2] | 580 | 250 |
| 254 | 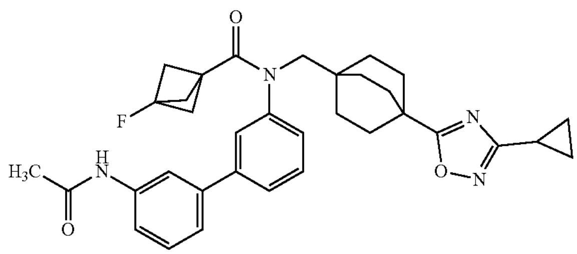 [SMILES: CC(=O)Nc1cccc(-c2cccc(N(CC34CCC(c5nc(C6CC6)no5)(CC3)CC4)C(=O)C34CC(F)(C3)C4)c2)c1] | 569 | 241 |
| 255 | 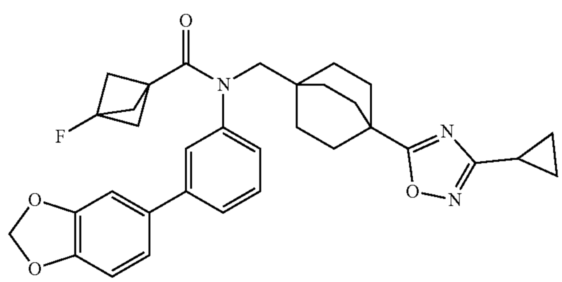 [SMILES: O=C(N(CC12CCC(c3nc(C4CC4)no3)(CC1)CC2)c1cccc(-c2ccc3c(c2)OCO3)c1)C12CC(F)(C1)C2] | 556.3 | 69.80 |
| 256 | 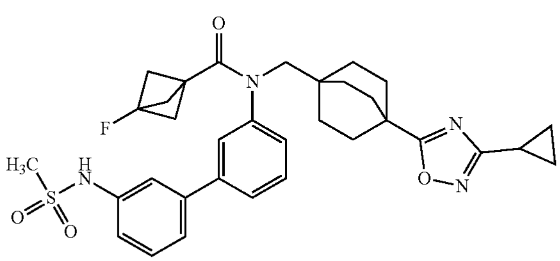 [SMILES: CS(=O)(=O)Nc1cccc(-c2cccc(N(CC34CCC(c5nc(C6CC6)no5)(CC3)CC4)C(=O)C34CC(F)(C3)C4)c2)c1] | 605 | 219 |
| 257 | 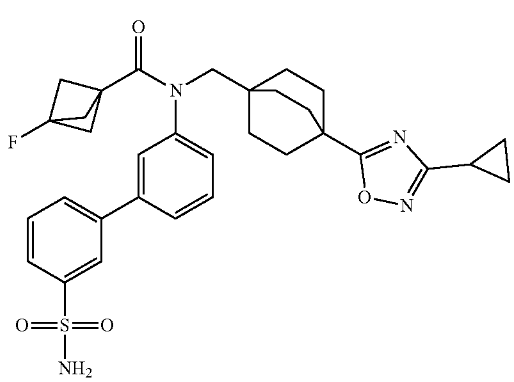 [SMILES: NS(=O)(=O)c1cccc(-c2cccc(N(CC34CCC(c5nc(C6CC6)no5)(CC3)CC4)C(=O)C34CC(F)(C3)C4)c2)c1] | 591 | 521 |

| Ex. No. | Structure | MS (ESI) (M + H) | FXR EC$_{50}$ (nM) |
|---|---|---|---|
| 258 | 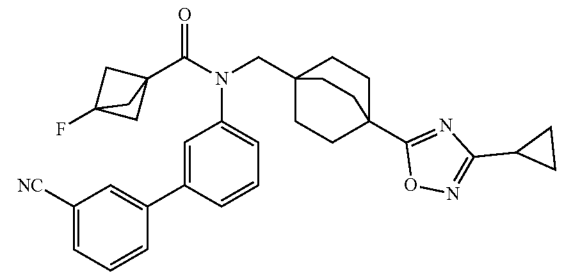 [SMILES: N#Cc1cccc(-c2cccc(N(CC34CCC(c5nc(C6CC6)no5)(CC3)CC4)C(=O)C34CC(F)(C3)C4)c2)c1] | 537 | 479 |
| 259 | 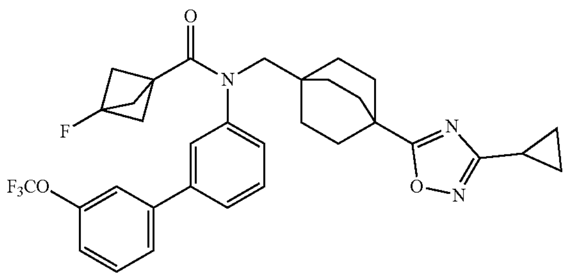 [SMILES: O=C(N(CC12CCC(c3nc(C4CC4)no3)(CC1)CC2)c1cccc(-c2cccc(OC(F)(F)F)c2)c1)C12CC(F)(C1)C2] | 596 | 268 |
| 260 | 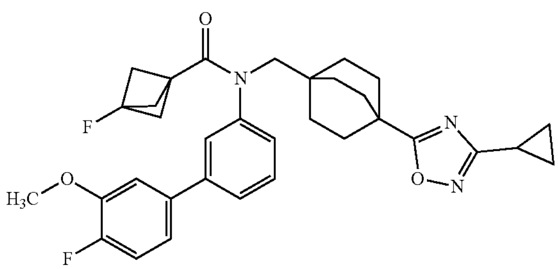 [SMILES: COc1cc(-c2cccc(N(CC34CCC(c5nc(C6CC6)no5)(CC3)CC4)C(=O)C34CC(F)(C3)C4)c2)ccc1F] | 560 | 693 |
| 261 | 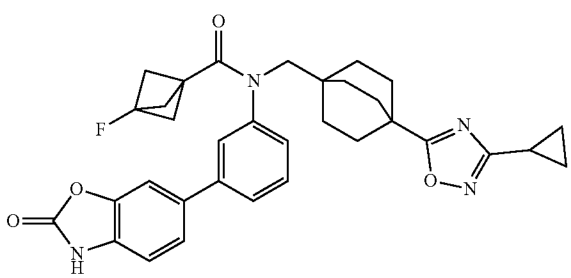 [SMILES: O=C(N(CC12CCC(c3nc(C4CC4)no3)(CC1)CC2)c1cccc(-c2ccc3[nH]c(=O)oc3c2)c1)C12CC(F)(C1)C2] | 569 | 48 |

247 $^1$H NMR (400 MHz, DMSO-d$_6$) δ 8.45 (s, 1H), 8.32-8.18 (m, 1H), 7.84-7.65 (m, 2H), 7.57 (t, J = 7.7 Hz, 1H), 7.44 (d, J = 8.1 Hz, 1H), 3.69 (d, J = 13.9 Hz, 1H), 3.52 (d, J = 14.4 Hz, 1H), 2.34 (s, 3H), 2.13-2.00 (m, 1H), 1.89 (br. s., 3H), 1.87-1.61 (m, 9H), 1.45 (d, J = 6.1 Hz, 6H), 1.08-0.95 (m, 2H), 0.89-0.76 (m, 2H)

248 $^1$H NMR (400 MHz, DMSO-d$_6$) δ 9.03 (s, 2H), 7.82 (s, 1H), 7.78 (d, J = 7.6 Hz, 1H), 7.57 (t, J = 7.8 Hz, 1H), 7.44 (d, J = 7.6 Hz, 1H), 3.99 (s, 3H), 3.70-3.49 (m, 2H), 2.11-2.00 (m, 1H), 1.97-1.68 (m, 12H), 1.57-1.30 (m, 6H), 1.08-0.91 (m, 2H), 0.90-0.79 (m, 2H)

249 $^1$H NMR (400 MHz, DMSO-d$_6$) δ 8.58 (d, J = 2.4 Hz, 1H), 8.11 (dd, J = 8.7, 2.6 Hz, 1H), 7.80-7.63 (m, 2H), 7.54 (t, J = 8.2 Hz, 1H), 7.38 (d, J = 7.6 Hz, 1H), 6.95 (d, J = 8.6 Hz, 1H), 3.91 (s, 3H), 3.60 (d, J = 2.7 Hz, 2H), 2.12-2.00 (m, 1H), 1.97-1.68 (m, 12H), 1.57-1.35 (m, 6H), 1.08-0.96 (m, 2H), 0.89-0.77 (m, 2H)

250 $^1$H NMR (400 MHz, DMSO-d$_6$) δ 7.86 (d, J = 2.0 Hz, 3H), 7.79 (d, J = 7.8 Hz, 1H), 7.64 (t, J = 1.8 Hz, 1H), 7.55 (t, J = 7.8 Hz, 1H), 7.45 (d, J = 8.8 Hz, 1H), 3.74 (d, J = 13.7 Hz, 1H), 3.47 (d, J = 14.2 Hz, 1H), 2.10-1.99 (m, 1H), 1.93-1.85 (m, 3H), 1.84-1.71 (m, 9H), 1.44 (d, J = 8.8 Hz, 6H), 1.05-0.96 (m, 2H), 0.86-0.79 (m, 2H).

251 $^1$H NMR (400 MHz, DMSO-d$_6$) δ 7.91-7.85 (m, 2H), 7.75-7.69 (m, 2H), 7.55 (t, J = 8.2 Hz, 1H), 7.51-7.45 (m, J = 8.1 Hz, 2H), 7.41 (d, J = 7.6 Hz, 1H), 3.68-3.51 (m, 2H), 2.09-1.99 (m, 1H), 1.94-1.69 (m, 12H), 1.50-1.38 (m, 6H), 1.05-0.97 (m, 2H), 0.82 (dd, J = 4.8, 2.6 Hz, 2H).

| Ex. No. | Structure | MS (ESI) (M + H) | FXR EC$_{50}$ (nM) |
|---|---|---|---|
| 252 | $^1$H NMR (400 MHz, DMSO-d$_6$) δ 8.12-8.04 (m, 2H), 7.87-7.70 (m, 4H), 7.58 (t, J = 7.8 Hz, 1H), 7.45 (d, J = 8.5 Hz, 1H), 3.73 (d, J = 13.1 Hz, 1H), 3.50 (d, J = 13.6 Hz, 1H), 2.04 (td, J = 8.7, 4.3 Hz, 1H), 1.90-1.71 (m, 12H), 1.46 (d, J = 7.5 Hz, 6H), 1.05-0.96 (m, 2H), 0.89-0.78 (m, 2H). | | |
| 253 | $^1$H NMR (400 MHz, DMSO-d$_6$) δ 7.99 (d, J = 8.0 Hz, 2H), 7.89-7.75 (m, 4H), 7.59 (t, J = 8.0 Hz, 1H), 7.47 (d, J = 7.5 Hz, 1H), 3.64 (br. s., 1H), 3.58 (br. s., 1H), 2.04 (td, J = 8.7, 4.3 Hz, 1H), 1.95-1.73 (m, 12H), 1.46 (br. s., 6H), 1.06-0.97 (m, 2H), 0.86-0.80 (m, 2H). | | |
| 254 | $^1$H NMR (400 MHz, DMSO-d$_6$) δ 10.03 (s, 1H), 7.95 (s, 1H), 7.67-7.51 (m, 4H), 7.44-7.35 (m, 2H), 3.60 (br. s., 2H), 2.11-1.98 (m, 4H), 1.88 (br. s., 6H), 1.82-1.71 (m, 6H), 1.46 (d, J = 8.0 Hz, 6H), 1.06-0.95 (m, 2H), 0.88-0.79 (m, 2H). | | |
| 255 | $^1$H NMR (400 MHz, DMSO-d$_6$) δ 7.67-7.60 (m, 2H), 7.49 (t, J = 7.8 Hz, 1H), 7.38-7.28 (m, 2H), 7.24 (dd, J = 8.3, 1.8 Hz, 1H), 7.03 (d, J = 8.0 Hz, 1H), 6.08 (s, 2H), 3.59 (d, J = 14.6 Hz, 2H), 2.09-2.00 (m, 1H), 1.94-1.71 (m, 12H), 1.51-1.39 (m, 6H), 1.05-0.97 (m, 2H), 0.88-0.79 (m, 2H). | | |
| 256 | $^1$H NMR (400 MHz, DMSO-d$_6$) δ 9.85 (br. s., 1H), 7.67-7.62 (m, 1H), 7.61-7.53 (m, 2H), 7.51-7.44 (m, 3H), 7.41 (d, J = 8.5 Hz, 1H), 7.26 (dt, J = 5.5, 2.8 Hz, 1H), 3.59 (br. s., 2H), 3.05 (s, 3H), 2.09-1.99 (m, 1H), 1.88 (br. s., 6H), 1.84-1.71 (m, 6H), 1.51-1.40 (m, 6H), 1.01 (dd, J = 8.5, 2.5 Hz, 2H), 0.87-0.79 (m, 2H). | | |
| 257 | $^1$H NMR (400 MHz, DMSO-d$_6$) δ 8.15 (s, 1H), 7.99 (d, J = 7.5 Hz, 1H), 7.86 (d, J = 7.5 Hz, 1H), 7.78-7.67 (m, 3H), 7.61 (t, J = 7.8 Hz, 1H), 7.47 (d, J = 8.0 Hz, 1H), 7.42 (s, 2H), 3.72 (d, J = 14.1 Hz, 1H), 3.55-3.46 (m, 1H), 2.04 (ddd, J = 13.1, 8.3, 4.8 Hz, 1H), 1.90 (br. s., 3H), 1.88-1.73 (m, 9H), 1.46 (d, J = 7.0 Hz, 6H), 1.06-0.97 (m, 2H), 0.86-0.79 (m, 2H). | | |
| 258 | $^1$H NMR (400 MHz, DMSO-d$_6$) δ 8.30 (s, 1H), 8.12 (d, J = 8.0 Hz, 3H), 7.90-7.77 (m, 1H), 7.70 (t, J = 8.0 Hz, 1H), 7.58 (t, J = 7.8 Hz, 1H), 7.45 (d, J = 7.5 Hz, 1H), 3.75-3.64 (m, 1H), 3.55 (br. s., 1H), 2.04 (ddd, J = 13.2, 8.2, 4.8 Hz, 1H), 1.90 (br. s., 3H), 1.87-1.71 (m, 9H), 1.46 (d, J = 8.0 Hz, 6H), 1.05-0.97 (m, 2H), 0.87-0.78 (m, 2H). | | |
| 259 | $^1$H NMR (400 MHz, DMSO-d$_6$) δ 7.84-7.73 (m, 4H), 7.64 (t, J = 8.0 Hz, 1H), 7.56 (t, J = 7.8 Hz, 1H), 7.46-7.39 (m, 2H), 3.70 (d, J = 14.1 Hz, 1H), 3.52 (d, J = 14.1 Hz, 1H), 2.08-2.00 (m, 1H), 1.90 (br. s., 3H), 1.87-1.72 (m, 9H), 1.46 (d, J = 7.0 Hz, 6H), 1.04-0.98 (m, 2H), 0.86-0.80 (m, 2H). | | |
| 260 | $^1$H NMR (400 MHz, DMSO-d$_6$) δ 7.76-7.69 (m, 2H), 7.53 (t, J = 7.8 Hz, 1H), 7.45 (d, J = 7.5 Hz, 1H), 7.38 (d, J = 8.5 Hz, 1H), 7.33-7.27 (m, 2H), 3.96 (s, 3H), 3.69 (br. s., 1H), 3.52 (br. s., 1H), 2.09-2.00 (m, 1H), 1.90 (br. s., 3H), 1.87-1.72 (m, 9H), 1.46 (d, J = 7.0 Hz, 6H), 1.01 (dd, J = 8.5, 2.5 Hz, 2H), 0.87-0.78 (m, 2H). | | |
| 261 | $^1$H NMR (400 MHz, DMSO-d$_6$) δ 11.74 (s, 1H), 7.78-7.60 (m, 3H), 7.58-7.47 (m, 2H), 7.35 (d, J = 7.6 Hz, 1H), 7.19 (d, J = 8.1 Hz, 1H), 3.71-3.61 (m, 1H), 3.60-3.49 (m, 1H), 2.11-1.99 (m, 1H), 1.98-1.71 (m, 12H), 1.47 (d, J = 4.9 Hz, 6H), 1.07-0.95 (m, 2H), 0.92-0.75 (m, 2H) | | |

Example 262

N-((4-(3-cyclopropyl-1,2,4-oxadiazol-5-yl)bicyclo[2.2.2]octan-1-yl)methyl)-3-fluoro-N-(3-(2-(trifluoromethyl)pyrimidin-5-yl)phenyl)bicyclo[1.1.1]pentane-1-carboxamide (262)

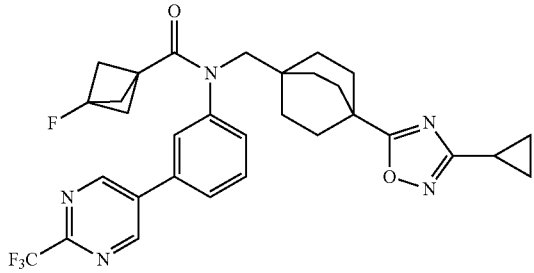

Step A. Intermediate 262A. Preparation of N-((4-(3-cyclopropyl-1,2,4-oxadiazol-5-yl) bicyclo[2.2.2]octan-1-yl)methyl)-N-(3-(5,5-dimethyl-1,3,2-dioxaborinan-2-yl)phenyl)-3-fluorobicyclo[1.1.1]pentane-1-carboxamide

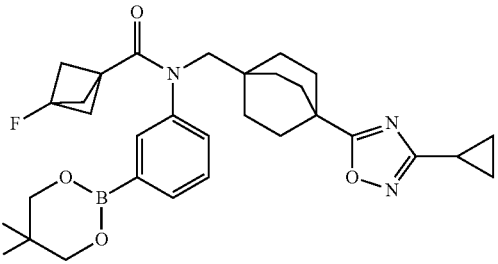

The title compound was prepared according to the method described for the synthesis of Intermediate 149C by substituting Intermediate 246B where appropriate. (45 mg, 0.082 mmol, 85% yield) as brown gummy solid. $^1$H NMR (400 MHz, DMSO-d$_6$) δ 7.68 (s, 1H), 7.55-7.53 (m, 1H), 7.49-7.43 (m, 2H), 3.79 (s, 4H), 2.05-2.00 (m, 1H), 1.84-1.70 (m, 12H), 1.41 (br. s., 6H), 1.01-1.00 (m, 2H), 0.97 (s, 6H), 0.87-0.80 (m, 2H) (2 Protons buried under solvent peak).

Step B. Example 262. Preparation of N-((4-(3-cyclopropyl-1,2,4-oxadiazol-5-yl) bicyclo[2.2.2]octan-1-yl)methyl)-3-fluoro-N-(3-(2-(trifluoromethyl)pyrimidin-5-yl) phenyl)bicyclo[1.1.1]pentane-1-carboxamide The title compound was prepared according to the method described for the synthesis of Example 149 by substituting Intermediate 262A and the corresponding heteroaryl halide where appropriate. (14.6 mg, 0.025 mmol, 69% yield). $^1$H NMR (400 MHz, DMSO-$d_6$) δ 9.50 (s, 2H), 8.01 (s, 1H), 7.96 (d, J=7.6 Hz, 1H), 7.67 (t, J=7.8 Hz, 1H), 7.58 (d, J=7.8 Hz, 1H), 3.65-3.59 (m, 2H), 2.11-2.01 (m, 1H), 1.89-1.76 (m, 12H), 1.56-1.35 (m, 6H), 1.09-0.96 (m, 2H), 0.89-0.76 (m, 2H); FXR EC$_{50}$ (nM)=140; MS (ESI) 582 (M+H).

The following compounds were prepared according to the method described for the synthesis of Example 149 by substituting Intermediate 262A and the corresponding heteroaryl/aryl halides (commercially available).

| Ex. No. | Structure | MS (ESI) (M + H) | FXR EC$_{50}$ (nM) |
|---|---|---|---|
| 263 | 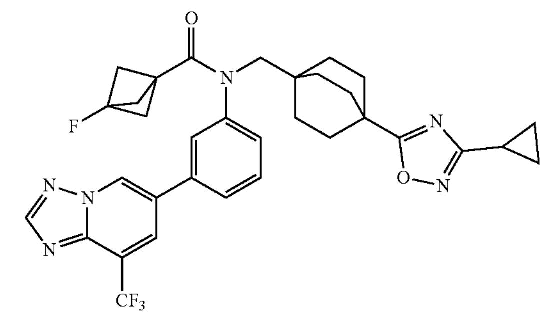 [SMILES: O=C(N(CC12CCC(c3nc(C4CC4)no3)(CC1)CC2)c1cccc(-c2cc(C(F)(F)F)c3ncnn3c2)c1)C12CC(F)(C1)C2] | 621 | 2708 |
| 264 | 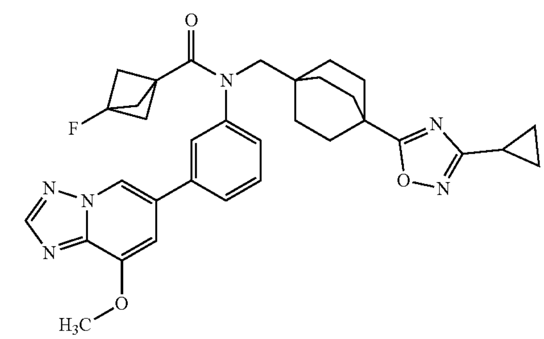 [SMILES: COc1cc(-c2cccc(N(CC34CCC(c5nc(C6CC6)no5)(CC3)CC4)C(=O)C34CC(F)(C3)C4)c2)cn2ncnc12] | 583 | 1505 |
| 265 | 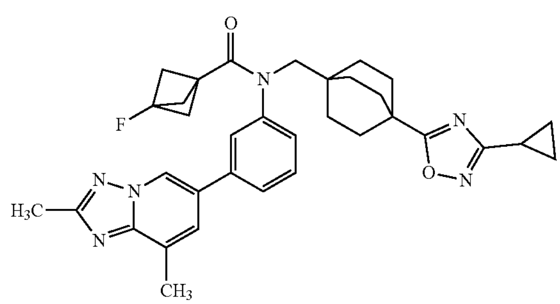 [SMILES: Cc1nc2c(C)cc(-c3cccc(N(CC45CCC(c6nc(C7CC7)no6)(CC4)CC5)C(=O)C45CC(F)(C4)C5)c3)cn2n1] | 581 | 510 |
| 266 | 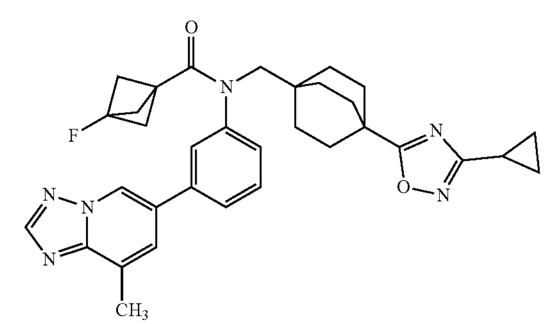 [SMILES: Cc1cc(-c2cccc(N(CC34CCC(c5nc(C6CC6)no5)(CC3)CC4)C(=O)C34CC(F)(C3)C4)c2)cn2ncnc12] | 567 | 690.71 |

| Ex. No. | Structure | MS (ESI) (M + H) | FXR EC$_{50}$ (nM) |
|---|---|---|---|
| 267 | 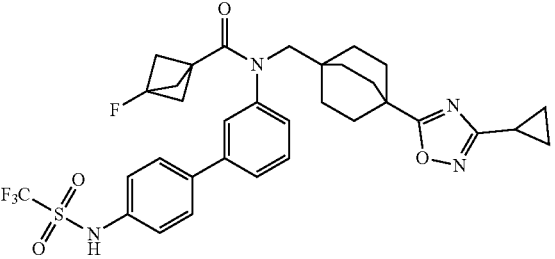 [SMILES: O=C(N(CC12CCC(c3nc(C4CC4)no3)(CC1)CC2)c1cccc(-c2ccc(NS(=O)(=O)C(F)(F)F)cc2)c1)C12CC(F)(C1)C2] | 659 | 46 |
| 268 | 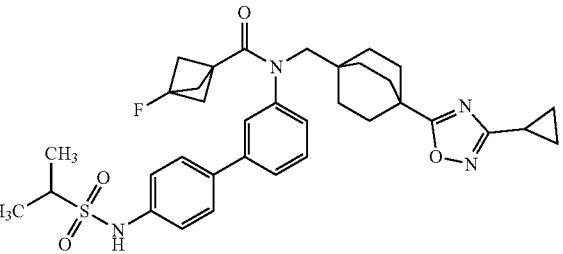 | 633 | 166 |
| 269 | 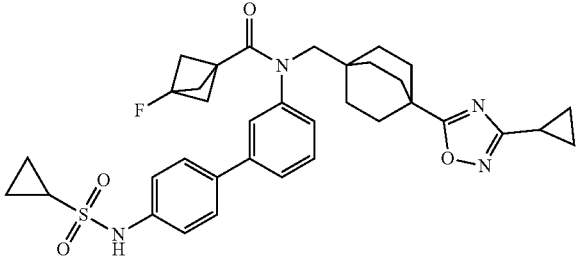 [SMILES: O=C(N(CC12CCC(c3nc(C4CC4)no3)(CC1)CC2)c1cccc(-c2ccc(NS(=O)(=O)C3CC3)cc2)c1)C12CC(F)(C1)C2] | 631 | 142 |
| 270 | 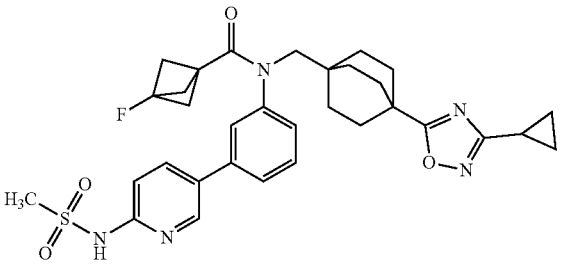 [SMILES: CS(=O)(=O)Nc1ccc(-c2cccc(N(CC34CCC(c5nc(C6CC6)no5)(CC3)CC4)C(=O)C34CC(F)(C3)C4)c2)cn1] | 606 | 442 |
| 271 | 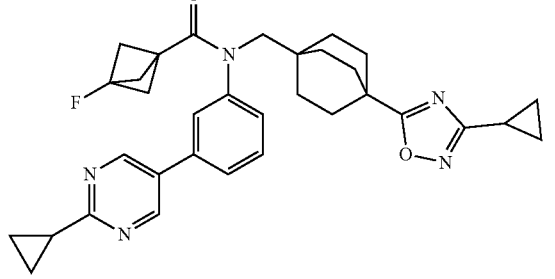 | 554 | 23 |

| Ex. No. | Structure | MS (ESI) (M + H) | FXR EC$_{50}$ (nM) |
|---|---|---|---|
| 272 | 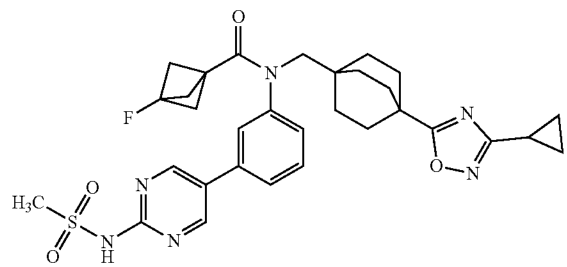 [SMILES: CS(=O)(=O)Nc1ncc(-c2cccc(N(CC34CCC(c5nc(C6CC6)no5)(CC3)CC4)C(=O)C34CC(F)(C3)C4)c2)cn1] | 607 | 559 |
| 273 | 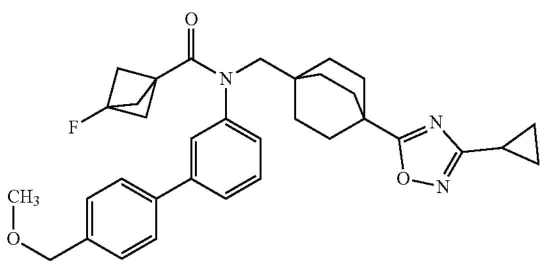 [SMILES: COCc1ccc(-c2cccc(N(CC34CCC(c5nc(C6CC6)no5)(CC3)CC4)C(=O)C34CC(F)(C3)C4)c2)cc1] | 556 | 52 |
| 274 | 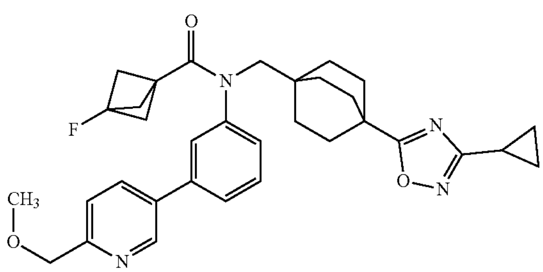 [SMILES: COCc1ccc(-c2cccc(N(CC34CCC(c5nc(C6CC6)no5)(CC3)CC4)C(=O)C34CC(F)(C3)C4)c2)cn1] | 557 | 106 |
| 275 | 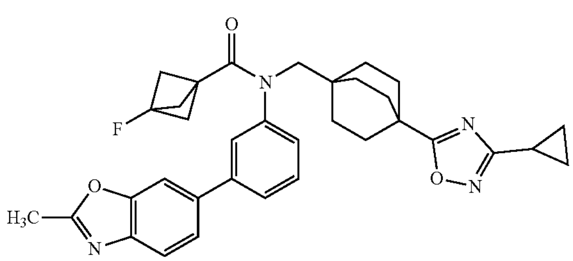 [SMILES: Cc1nc2ccc(-c3cccc(N(CC45CCC(c6nc(C7CC7)no6)(CC4)CC5)C(=O)C45CC(F)(C4)C5)c3)cc2o1] | 567.3 | 58.68 |
| 276 | 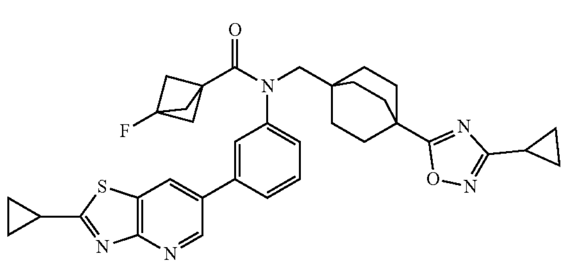 [SMILES: O=C(N(CC12CCC(c3nc(C4CC4)no3)(CC1)CC2)c1cccc(-c2cnc3nc(C4CC4)sc3c2)c1)C12CC(F)(C1)C2] | 610.2 | 77.53 |

| Ex. No. | Structure | MS (ESI) (M + H) | FXR EC$_{50}$ (nM) |
|---|---|---|---|
| 277 | 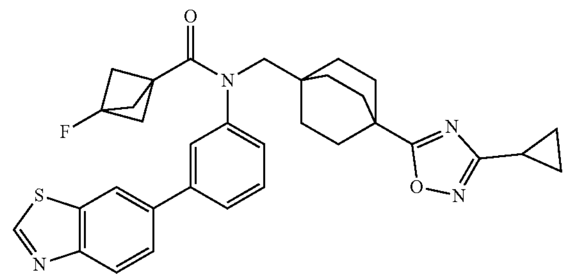 [SMILES: O=C(N(CC12CCC(c3nc(C4CC4)no3)(CC1)CC2)c1cccc(-c2ccc3ncsc3c2)c1)C12CC(F)(C1)C2] | 569 | 35 |
| 278 | 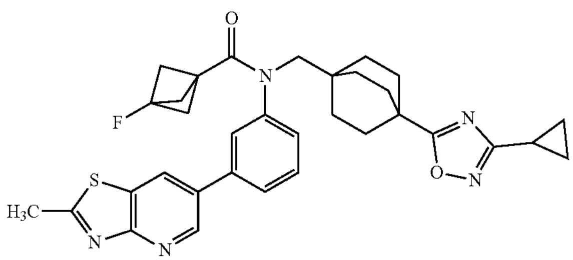 [SMILES: Cc1nc2ncc(-c3cccc(N(CC45CCC(c6nc(C7CC7)no6)(CC4)CC5)C(=O)C45CC(F)(C4)C5)c3)cc2s1] | 584 | 83 |
| 279 | 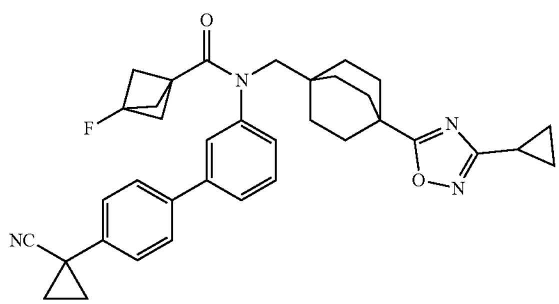 [SMILES: N#CC1(c2ccc(-c3cccc(N(CC45CCC(c6nc(C7CC7)no6)(CC4)CC5)C(=O)C45CC(F)(C4)C5)c3)cc2)CC1] | 577 | 125 |
| 280 | 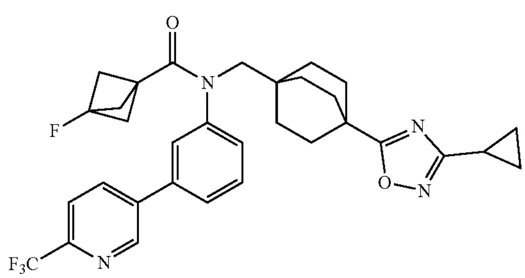 [SMILES: O=C(N(CC12CCC(c3nc(C4CC4)no3)(CC1)CC2)c1cccc(-c2ccc(C(F)(F)F)nc2)c1)C12CC(F)(C1)C2] | 581 | 308 |
| 281 | 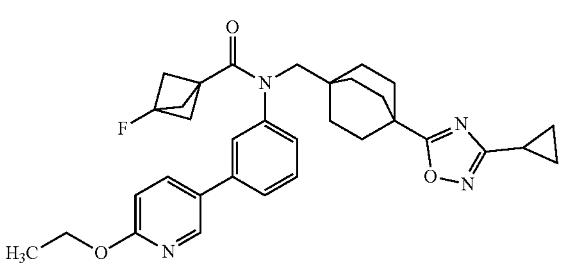 [SMILES: CCOc1ccc(-c2cccc(N(CC34CCC(c5nc(C6CC6)no5)(CC3)CC4)C(=O)C34CC(F)(C3)C4)c2)nn1] | 557 | 66 |

-continued
| Ex. No. | Structure | MS (ESI) (M + H) | FXR EC$_{50}$ (nM) |
|---|---|---|---|
| 282 | 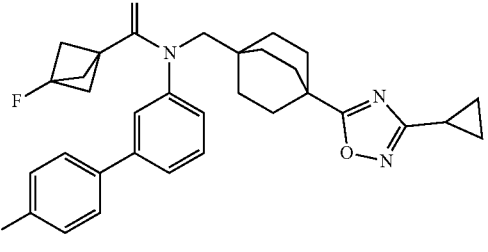 | 542 | 19 |
| 283 | 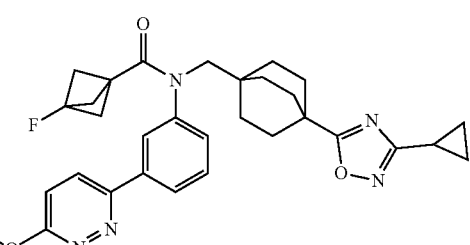 | 558 | 234 |
| 284 | 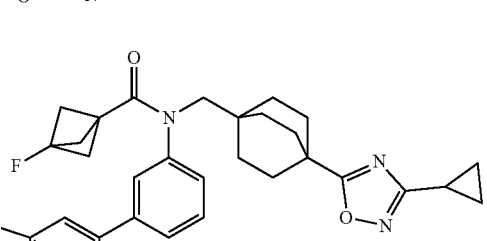 | 592 | 233 |
| 285 | 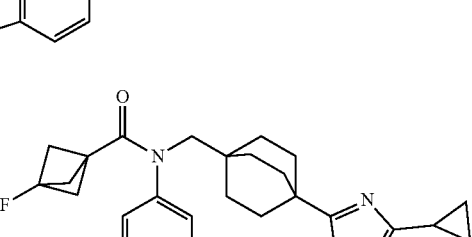 | 540 | 225 |
| 286 | 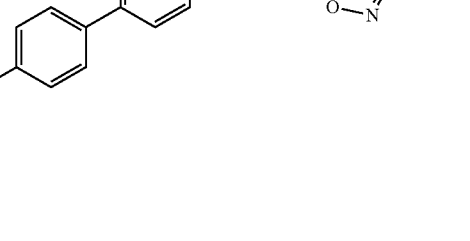 | 580 | 361 |

-continued
| Ex. No. | Structure | MS (ESI) (M + H) | FXR EC$_{50}$ (nM) |
|---|---|---|---|
| 287 | 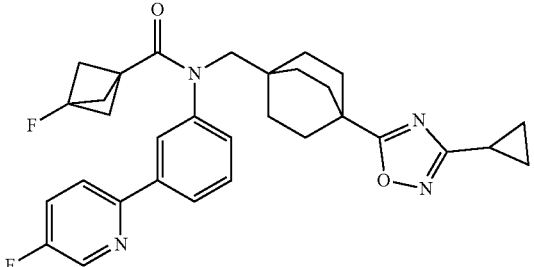 | 531 | 316 |
| 288 | 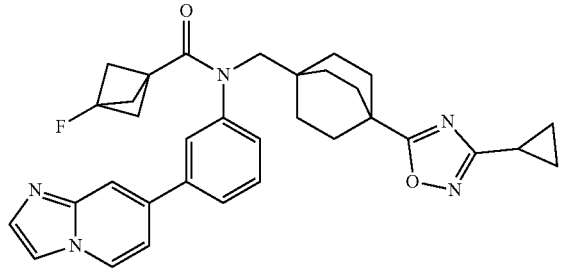 [SMILES: O=C(N(CC12CCC(c3nc(C4CC4)no3)(CC1)CC2)c1cccc(-c2ccn3ccnc3c2)c1)C12CC(F)(C1)C2] | 552 | 539 |
| 289 | 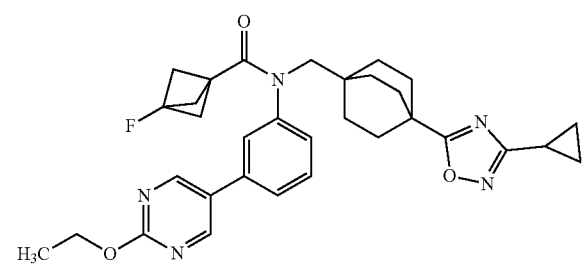 [SMILES: CCOc1ncc(-c2cccc(N(CC34CCC(c5nc(C6CC6)no5)(CC3)CC4)C(=O)C34CC(F)(C3)C4)c2)cn1] | 558 | 48 |
| 290 | 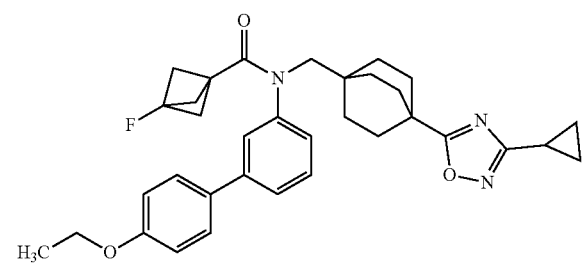 [SMILES: CCOc1ccc(-c2cccc(N(CC34CCC(c5nc(C6CC6)no5)(CC3)CC4)C(=O)C34CC(F)(C3)C4)c2)cc1] | 556 | 60 |
| 291 | 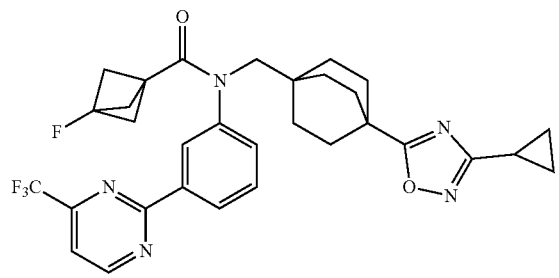 [SMILES: O=C(N(CC12CCC(c3nc(C4CC4)no3)(CC1)CC2)c1cccc(-c2nccc(C(F)(F)F)n2)c1)C12CC(F)(C1)C2] | 582 | 439 |

| Ex. No. | Structure | MS (ESI) (M + H) | FXR EC$_{50}$ (nM) |
|---|---|---|---|
| 292 | 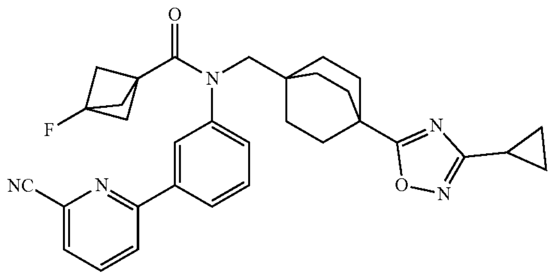 [SMILES: N#Cc1cccc(-c2cccc(N(CC34CCC(c5nc(C6CC6)no5)(CC3)CC4)C(=O)C34CC(F)(C3)C4)c2)n1] | 538 | 148 |
| 293 | 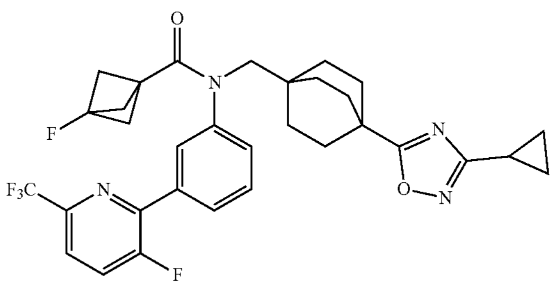 [SMILES: O=C(N(CC12CCC(c3nc(C4CC4)no3)(CC1)CC2)c1cccc(-c2nc(C(F)(F)F)ccc2F)c1)C12CC(F)(C1)C2] | 599.2 | 679.00 |
| 294 | 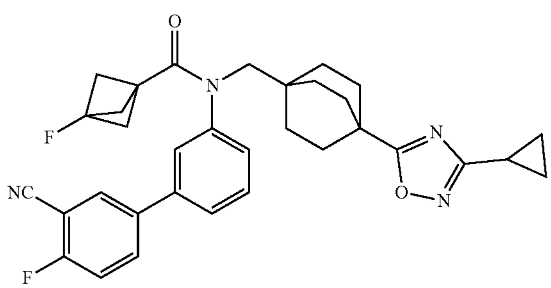 [SMILES: N#Cc1cc(-c2cccc(N(CC34CCC(c5nc(C6CC6)no5)(CC3)CC4)C(=O)C34CC(F)(C3)C4)c2)ccc1F] | 555 | 579 |
| 295 | 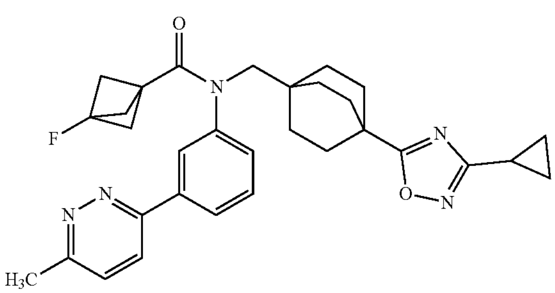 [SMILES: Cc1ccc(-c2cccc(N(CC34CCC(c5nc(C6CC6)no5)(CC3)CC4)C(=O)C34CC(F)(C3)C4)c2)nn1] | 528 | 839 |
| 296 | 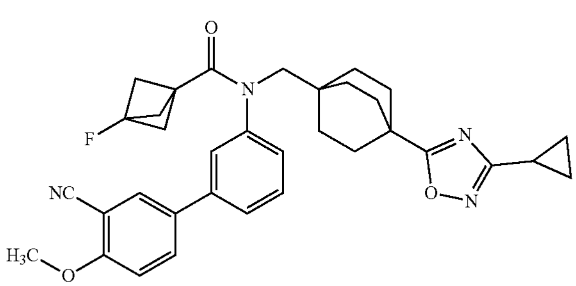 [SMILES: COc1ccc(-c2cccc(N(CC34CCC(c5nc(C6CC6)no5)(CC3)CC4)C(=O)C34CC(F)(C3)C4)c2)cc1C#N] | 567 | 294 |

| Ex. No. | Structure | MS (ESI) (M + H) | FXR EC$_{50}$ (nM) |
|---|---|---|---|
| 297 | 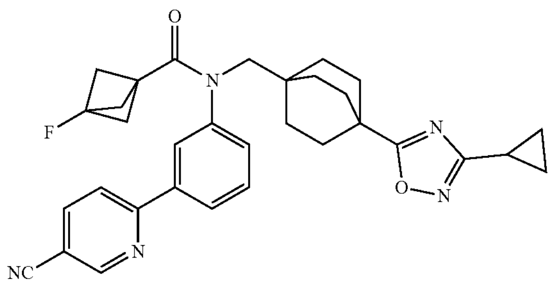 [SMILES: N#Cc1ccc(-c2cccc(N(CC34CCC(c5nc(C6CC6)no5)(CC3)CC4)C(=O)C34CC(F)(C3)C4)c2)nc1] | 538 | 1253 |
| 298 | 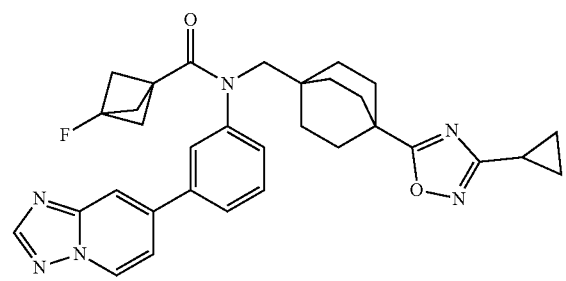 [SMILES: O=C(N(CC12CCC(c3nc(C4CC4)no3)(CC1)CC2)c1cccc(-c2ccn3ncnc3c2)c1)C12CC(F)(C1)C2] | 553 | 1685 |
| 299 | 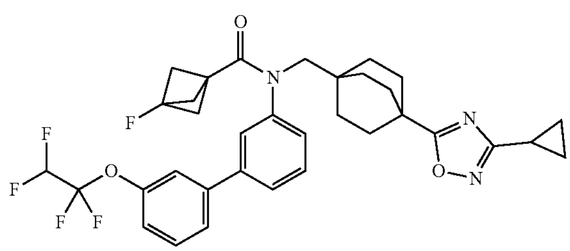 [SMILES: O=C(N(CC12CCC(c3nc(C4CC4)no3)(CC1)CC2)c1cccc(-c2cccc(OC(F)(F)C(F)F)c2)c1)C12CC(F)(C1)C2] | 628 | 660 |
| 300 | 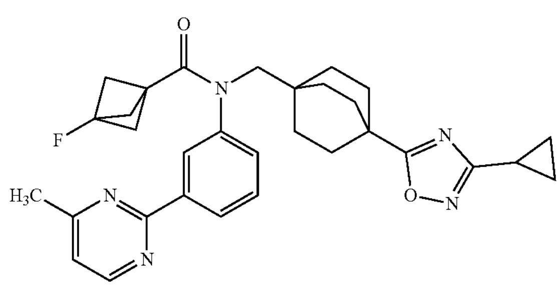 [SMILES: Cc1ccnc(-c2cccc(N(CC34CCC(c5nc(C6CC6)no5)(CC3)CC4)C(=O)C34CC(F)(C3)C4)c2)n1] | 528 | 413 |
| 301 | 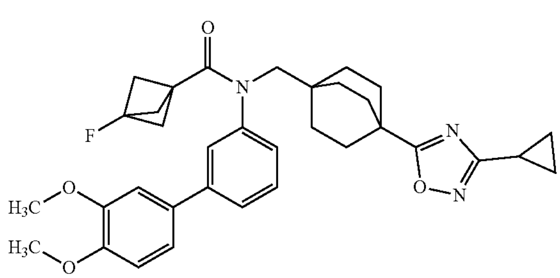 [SMILES: COc1ccc(-c2cccc(N(CC34CCC(c5nc(C6CC6)no5)(CC3)CC4)C(=O)C34CC(F)(C3)C4)c2)cc1OC] | 572 | 519 |

-continued

| Ex. No. | Structure | MS (ESI) (M + H) | FXR EC$_{50}$ (nM) |
|---|---|---|---|
| 302 | 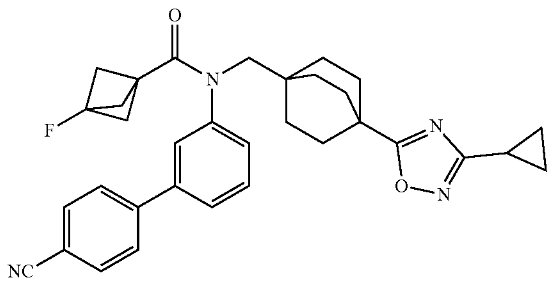 [SMILES: N#Cc1ccc(-c2cccc(N(CC34CCC(c5nc(C6CC6)no5)(CC3)CC4)C(=O)C34CC(F)(C3)C4)c2)cc1] | 537 | 861 |
| 303 | 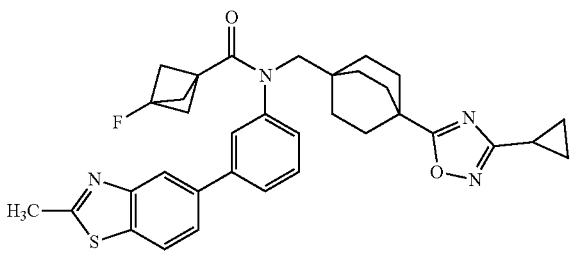 [SMILES: Cc1nc2cc(-c3cccc(N(CC45CCC(c6nc(C7CC7)no6)(CC4)CC5)C(=O)C45CC(F)(C4)C5)c3)ccc2s1] | 583 | 349 |
| 304 | 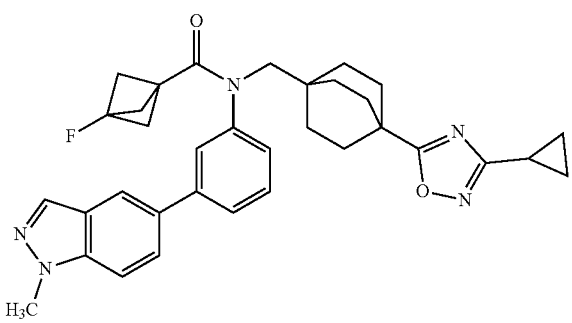 [SMILES: Cn1ncc2cc(-c3cccc(N(CC45CCC(c6nc(C7CC7)no6)(CC4)CC5)C(=O)C45CC(F)(C4)C5)c3)ccc21] | 566 | 248 |
| 305 | 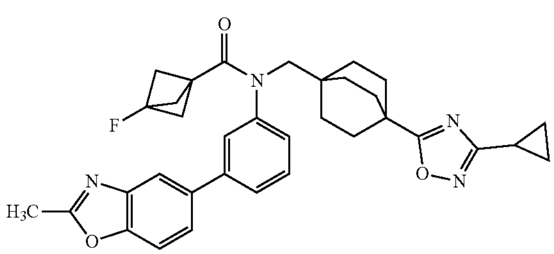 [SMILES: Cc1nc2cc(-c3cccc(N(CC45CCC(c6nc(C7CC7)no6)(CC4)CC5)C(=O)C45CC(F)(C4)C5)c3)ccc2o1] | 567 | 301 |
| 306 | 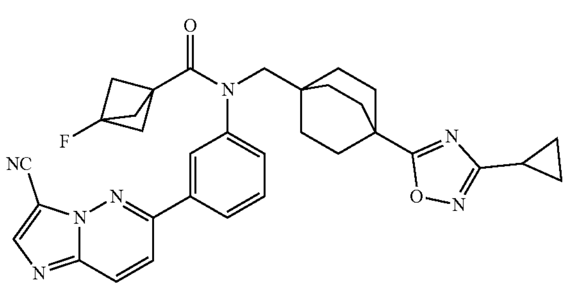 [SMILES: N#Cc1cnc2ccc(-c3cccc(N(CC45CCC(c6nc(C7CC7)no6)(CC4)CC5)C(=O)C45CC(F)(C4)C5)c3)nn12] | 578.2 | 386 |

| Ex. No. | Structure | MS (ESI) (M + H) | FXR EC$_{50}$ (nM) |
|---|---|---|---|
| 307 | 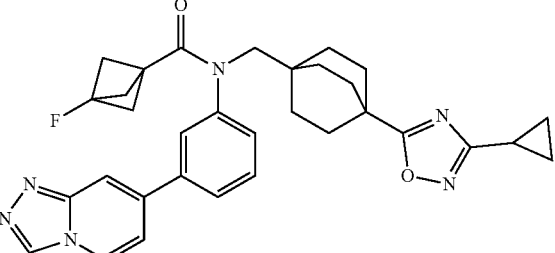 | 553 | 832 |
| 308 | 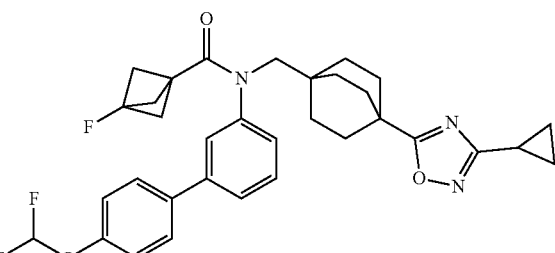 | 578 | 15 |
| 309 | 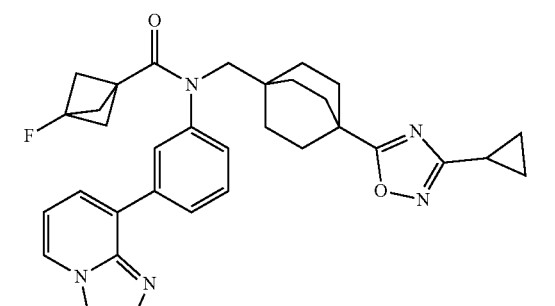 | 553 | 221 |
| 310 | 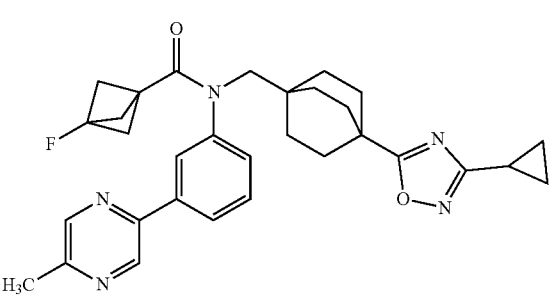 [SMILES: Cc1cnc(-c2cccc(N(CC34CCC(c5nc(C6CC6)no5)(CC3)CC4)C(=O)C34CC(F)(C3)C4)c2)cn1] | 528 | 59 |
| 311 | 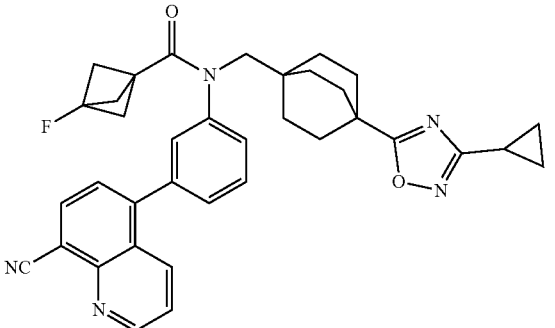 [SMILES: N#Cc1ccc(-c2cccc(N(CC34CCC(c5nc(C6CC6)no5)(CC3)CC4)C(=O)C34CC(F)(C3)C4)c2)c2cccnc12] | 588 | 662 |

| Ex. No. | Structure | MS (ESI) (M + H) | FXR EC$_{50}$ (nM) |
|---|---|---|---|
| 312 | 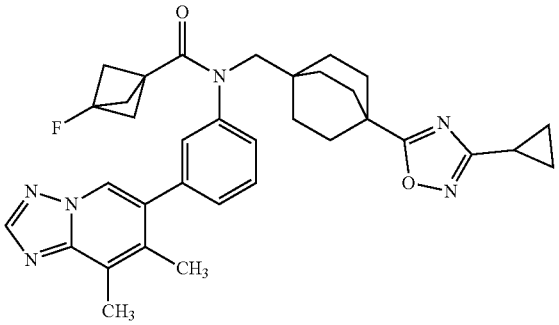 [SMILES: Cc1c(-c2cccc(N(CC34CCC(c5nc(C6CC6)no5)(CC3)CC4)C(=O)C34CC(F)(C3)C4)c2)cn2ncnc2c1C] | 581 | 916 |
| 313 | 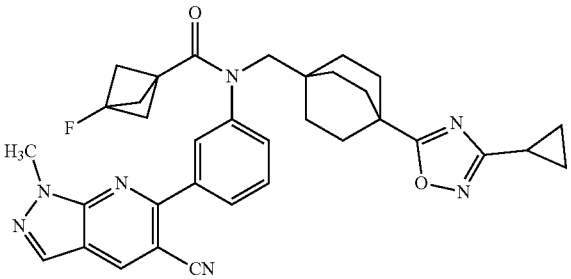 [SMILES: Cn1ncc2cc(C#N)c(-c3cccc(N(CC45CCC(c6nc(C7CC7)no6)(CC4)CC5)C(=O)C45CC(F)(C4)C5)c3)nc21] | 592 | 194 |
| 314 | 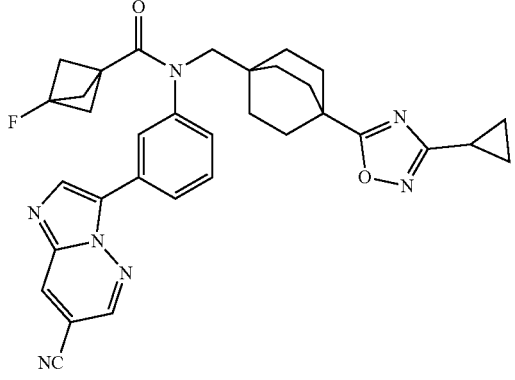 [SMILES: N#Cc1cnn2c(-c3cccc(N(CC45CCC(c6nc(C7CC7)no6)(CC4)CC5)C(=O)C45CC(F)(C4)C5)c3)cnc2c1] | 578 | 504 |
| 315 | 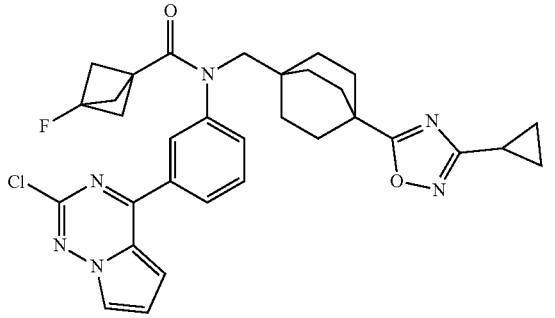 [SMILES: O=C(N(CC12CCC(c3nc(C4CC4)no3)(CC1)CC2)c1cccc(-c2nc(Cl)nn3cccc23)c1)C12CC(F)(C1)C2] | 587.2 | 913 |

| Ex. No. | Structure | MS (ESI) (M + H) | FXR EC$_{50}$ (nM) |
|---|---|---|---|
| 316 | 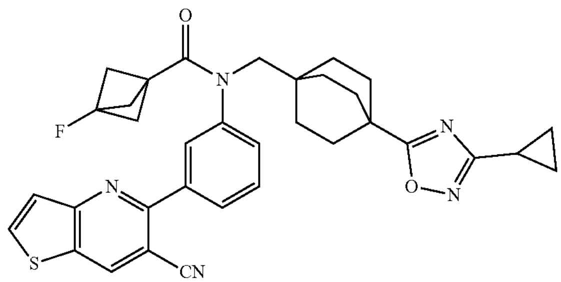 [SMILES: N#Cc1cc2sccc2nc1-c1cccc(N(CC23CCC(c4nc(C5CC5)no4)(CC2)CC3)C(=O)C23CC(F)(C2)C3)c1] | 594 | 138 |
| 317 | 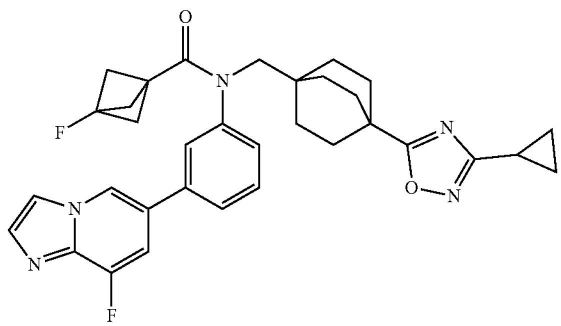 [SMILES: O=C(N(CC12CCC(c3nc(C4CC4)no3)(CC1)CC2)c1cccc(-c2cc(F)c3nccn3c2)c1)C12CC(F)(C1)C2] | 570 | 887 |
| 318 | 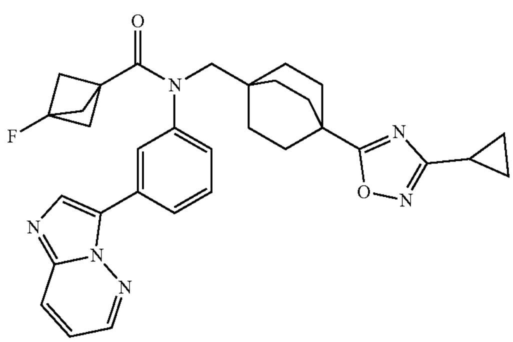 [SMILES: O=C(N(CC12CCC(c3nc(C4CC4)no3)(CC1)CC2)c1cccc(-c2cnc3cccnn23)c1)C12CC(F)(C1)C2] | 553 | 172 |
| 319 | 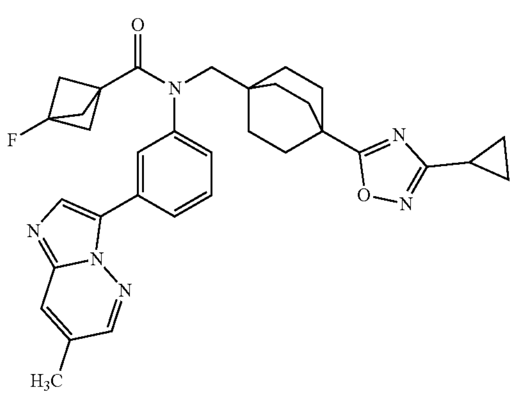 [SMILES: Cc1cnn2c(-c3cccc(N(CC45CCC(c6nc(C7CC7)no6)(CC4)CC5)C(=O)C45CC(F)(C4)C5)c3)cnc2c1] | 567 | 161 |

-continued

| Ex. No. | Structure | MS (ESI) (M + H) | FXR EC$_{50}$ (nM) |
|---|---|---|---|
| 320 | 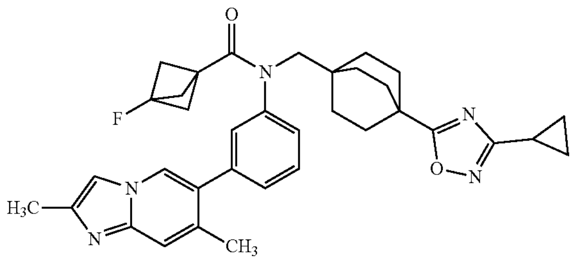 [SMILES: Cc1cn2cc(-c3cccc(N(CC45CCC(c6nc(C7CC7)no6)(CC4)CC5)C(=O)C45CC(F)(C4)C5)c3)c(C)cc2n1] | 580 | 493 |
| 321 | 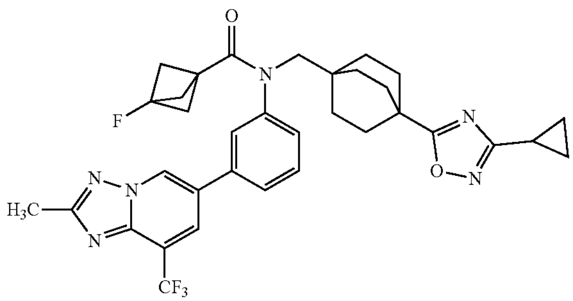 [SMILES: Cc1nc2c(C(F)(F)F)cc(-c3cccc(N(CC45CCC(c6nc(C7CC7)no6)(CC4)CC5)C(=O)C45CC(F)(C4)C5)c3)cn2n1] | 635 | 1464 |
| 322 | 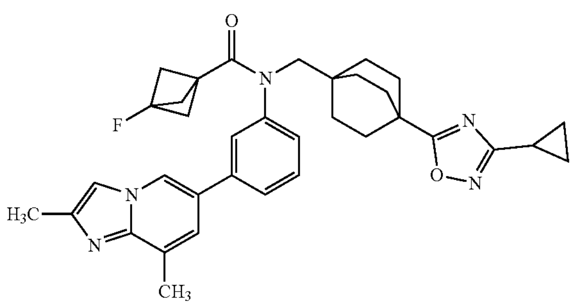 [SMILES: Cc1cn2cc(-c3cccc(N(CC45CCC(c6nc(C7CC7)no6)(CC4)CC5)C(=O)C45CC(F)(C4)C5)c3)cc(C)c2n1] | 580 | 270 |
| 323 | 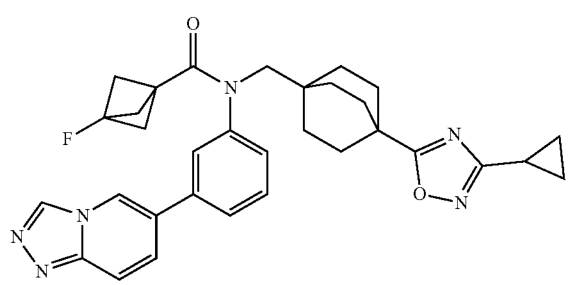 [SMILES: O=C(N(CC12CCC(c3nc(C4CC4)no3)(CC1)CC2)c1cccc(-c2ccc3nncn3c2)c1)C12CC(F)(C1)C2] | 553 | 1626 |
| 324 | 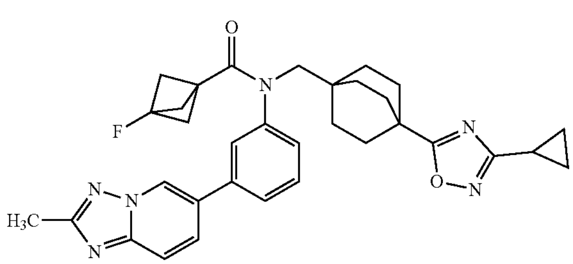 [SMILES: Cc1nc2ccc(-c3cccc(N(CC45CCC(c6nc(C7CC7)no6)(CC4)CC5)C(=O)C45CC(F)(C4)C5)c3)cn2n1] | 567 | 250 |

-continued

| Ex. No. | Structure | MS (ESI) (M + H) | FXR EC$_{50}$ (nM) |
|---|---|---|---|
| 325 | 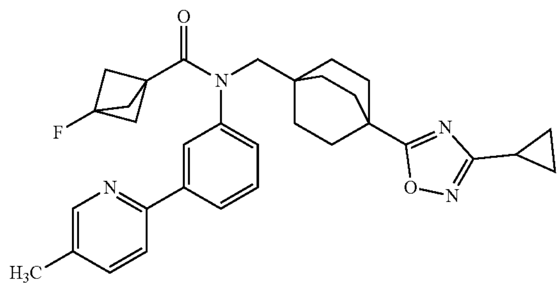 [SMILES: Cc1ccc(-c2cccc(N(CC34CCC(c5nc(C6CC6)no5)(CC3)CC4)C(=O)C34CC(F)(C3)C4)c2)nc1] | 527 | 24 |
| 326 | 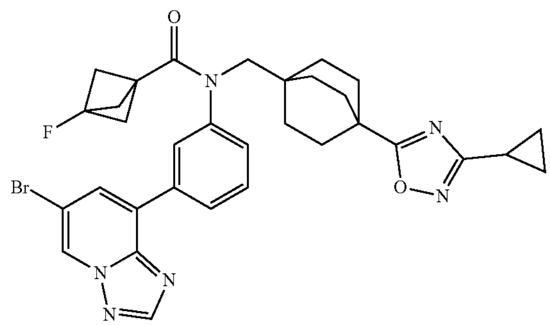 [SMILES: O=C(N(CC12CCC(c3nc(C4CC4)no3)(CC1)CC2)c1cccc(-c2cc(Br)cn3ncnc23)c1)C12CC(F)(C1)C2] | 631 | 782 |
| 327 | 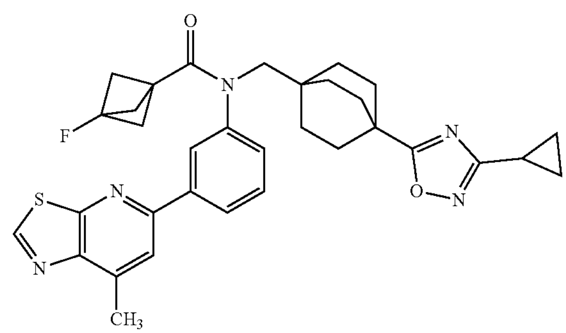 [SMILES: Cc1cc(-c2cccc(N(CC34CCC(c5nc(C6CC6)no5)(CC3)CC4)C(=O)C34CC(F)(C3)C4)c2)nc2scnc12] | 584 | 303 |
| 328 | 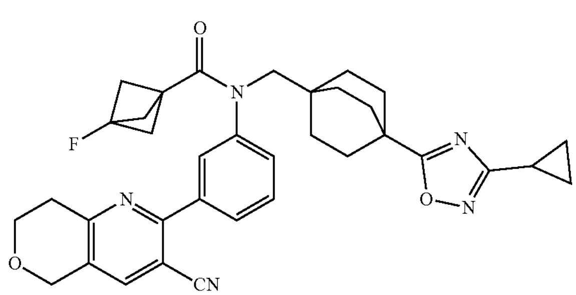 [SMILES: N#Cc1cc2c(nc1-c1cccc(N(CC34CCC(c5nc(C6CC6)no5)(CC3)CC4)C(=O)C34CC(F)(C3)C4)c1)CCOC2] | 594 | 339 |

| Ex. No. | Structure | MS (ESI) (M + H) | FXR EC$_{50}$ (nM) |
|---|---|---|---|
| 329 | 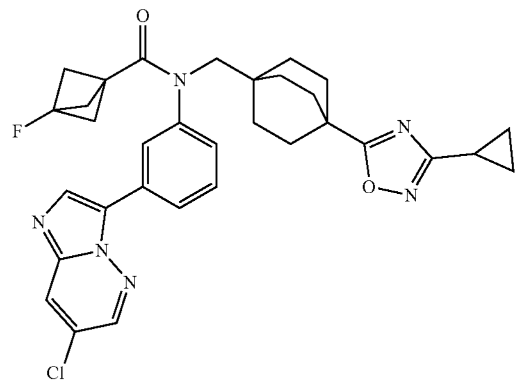 [SMILES: O=C(N(CC12CCC(c3nc(C4CC4)no3)(CC1)CC2)c1cccc(-c2cnc3cc(Cl)cnn23)c1)C12CC(F)(C1)C2] | 587 | 222 |
| 330 | 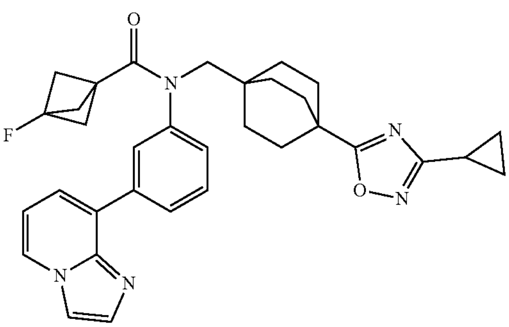 [SMILES: O=C(N(CC12CCC(c3nc(C4CC4)no3)(CC1)CC2)c1cccc(-c2cccn3ccnc23)c1)C12CC(F)(C1)C2] | 552 | 392 |
| 331 | 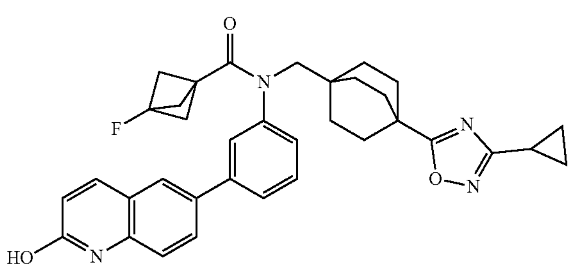 [SMILES: O=C(N(CC12CCC(c3nc(C4CC4)no3)(CC1)CC2)c1cccc(-c2ccc3nc(O)ccc3c2)c1)C12CC(F)(C1)C2] | 579 | 231 |
| 332 | 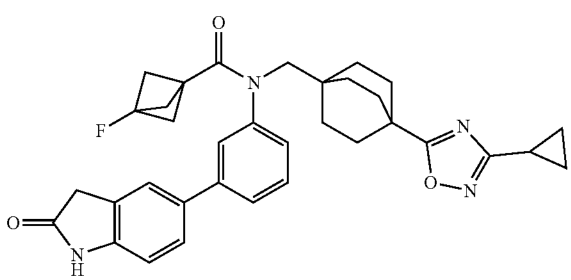 [SMILES: O=C1Cc2cc(-c3cccc(N(CC45CCC(c6nc(C7CC7)no6)(CC4)CC5)C(=O)C45CC(F)(C4)C5)c3)ccc2N1] | 567 | 158 |
| 333 | 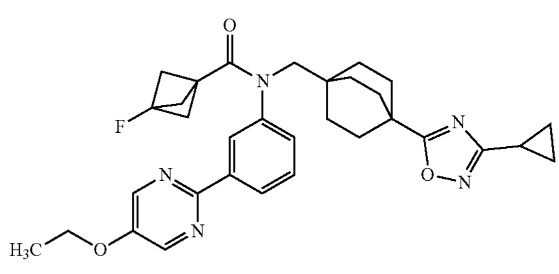 [SMILES: CCOc1cnc(-c2cccc(N(CC34CCC(c5nc(C6CC6)no5)(CC3)CC4)C(=O)C34CC(F)(C3)C4)c2)nc1] | 558 | 302 |

| Ex. No. | Structure | MS (ESI) (M + H) | FXR EC$_{50}$ (nM) |
|---|---|---|---|
| 334 | 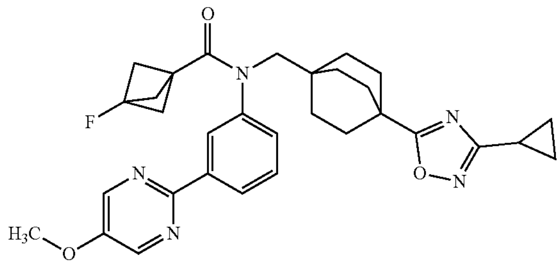 [SMILES: COc1cnc(-c2cccc(N(CC34CCC(c5nc(C6CC6)no5)(CC3)CC4)C(=O)C34CC(F)(C3)C4)c2)nc1] | 544 | 77 |
| 335 | 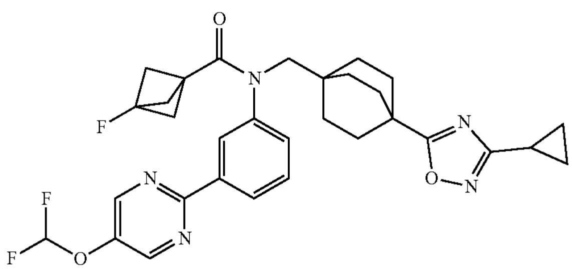 [SMILES: O=C(N(CC12CCC(c3nc(C4CC4)no3)(CC1)CC2)c1cccc(-c2ncc(OC(F)F)cn2)c1)C12CC(F)(C1)C2] | 580 | 26 |
| 336 | 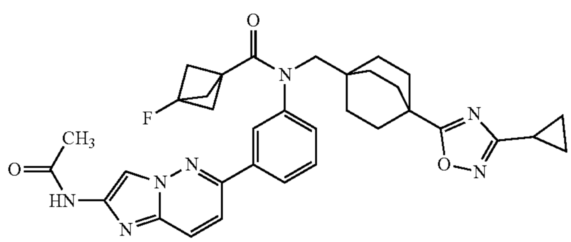 [SMILES: CC(=O)Nc1cn2nc(-c3cccc(N(CC45CCC(c6nc(C7CC7)no6)(CC4)CC5)C(=O)C45CC(F)(C4)C5)c3)ccc2n1] | 610 | 1232 |

263 $^1$H NMR (400 MHz, DMSO-d$_6$) δ 9.79 (s, 1H), 8.75 (s, 1H), 8.52 (s, 1H), 8.05 (s, 1H), 7.96 (d, J = 7.8 Hz, 1H), 7.61 (t, J = 7.9 Hz, 1H), 7.50 (d, J = 8.8 Hz, 1H), 3.76 (d, J = 13.7 Hz, 1H), 3.52 (d, J = 13.7 Hz, 1H), 2.11-2.00 (m, 1H), 1.98-1.89 (m, 3H), 1.89-1.68 (m, 9H), 1.47 (d, J = 8.3 Hz, 6H), 1.07-0.93 (m, 2H), 0.89-0.69 (m, 2H)

264 $^1$H NMR (400 MHz, DMSO-d$_6$) δ 9.08 (d, J = 1.2 Hz, 1H), 8.50 (s, 1H), 7.96 (s, 1H), 7.91 (d, J = 7.8 Hz, 1H), 7.59 (t, J = 7.8 Hz, 1H), 7.46 (d, J = 8.1 Hz, 1H), 7.42 (s, 1H), 4.13 (s, 3H), 3.76 (d, J = 14.2 Hz, 1H), 3.51 (d, J = 13.7 Hz, 1H), 2.11-2.00 (m, 1H), 2.00-1.89 (m, 3H), 1.89-1.64 (m, 9H), 1.47 (d, J = 8.6 Hz, 6H), 1.08-0.91 (m, 2H), 0.91-0.71 (m, 2H)

265 $^1$H NMR (400 MHz, DMSO-d$_6$) δ 9.16 (s, 1H), 7.87 (s, 1H), 7.89 (s, 1H), 7.83 (d, J = 8.1 Hz, 1H), 7.57 (t, J = 7.8 Hz, 1H), 7.43 (d, J = 7.8 Hz, 1H), 3.71 (d, J = 14.2 Hz, 1H), 3.53 (d, J = 14.7 Hz, 1H), 2.59 (s, 3H), 2.5 (s, 3H), 2.12-2.00 (m, 1H), 1.98-1.88 (m, 3H), 1.88-1.65 (m, 9H), 1.46 (d, J = 6.8 Hz, 6H), 1.10-0.95 (m, 2H), 0.89-0.75 (m, 2H)

266 $^1$H NMR (400 MHz, DMSO-d$_6$) δ 9.30 (s, 1H), 8.52 (s, 1H), 7.97 (s, 1H), 7.93-7.89 (m, 1H), 7.86 (d, J = 7.6 Hz, 1H), 7.58 (t, J = 7.8 Hz, 1H), 7.44 (d, J = 9.0 Hz, 1H), 3.73 (d, J = 13.7 Hz, 1H), 3.54 (d, J = 14.4 Hz, 1H), 2.64 (s, 3H), 2.10-2.01 (m, 1H), 1.98-1.88 (m, 3H), 1.88-1.62 (m, 9H), 1.47 (d, J = 7.1 Hz, 6H), 1.10-0.94 (m, 2H), 0.91-0.77 (m, 2H)

267 $^1$H NMR (400 MHz, DMSO-d$_6$) δ 7.80 (d, J = 8.6 Hz, 2H), 7.75-7.63 (m, 2H), 7.55 (t, J = 7.7 Hz, 1H), 7.45-7.29 (m, 3H), 3.60 (q, J = 13.6 Hz, 2H), 2.13-2.00 (m, 1H), 1.96-1.69 (m, 12H), 1.56-1.35 (m, 6H), 1.10-0.96 (m, 2H), 0.89-0.76 (m, 2H)

268 $^1$H NMR (400 MHz, DMSO-d$_6$) δ 9.91 (s, 1H), 7.79-7.59 (m, 4H), 7.52 (t, J = 7.7 Hz, 1H), 7.41-7.25 (m, 3H), 3.91 (s, 1H), 3.59 (br. s., 2H), 3.31-3.25 (m, 1H), 2.10-1.99 (m, 1H), 1.87 (d, J = 8.8 Hz, 6H), 1.83-1.65 (m, 6H), 1.55-1.36 (m, 6H), 1.33-1.14 (m, 6H), 1.06-0.95 (m, 2H), 0.88-0.77 (m, 2H)

269 $^1$H NMR (400 MHz, DMSO-d$_6$) δ 9.88 (s, 1H), 7.80-7.60 (m, 4H), 7.53 (t, J = 7.8 Hz, 1H), 7.46-7.26 (m, 3H), 3.60 (d, J = 8.1 Hz, 2H), 2.71-2.65 (m, 1H), 2.11-2.00 (m, 1H), 1.87 (d, J = 9.8 Hz, 6H), 1.83-1.61 (m, 6H), 1.56-1.34 (m, 6H), 1.12-0.89 (m, 6H), 0.88-0.74 (m, 2H)

270 $^1$H NMR (400 MHz, DMSO-d$_6$) δ 10.75 (br. s., 1H), 8.67 (br. s., 1H), 8.14 (dd, J = 8.6, 2.7 Hz, 1H), 7.77-7.66 (m, 2H), 7.55 (t, J = 7.8 Hz, 1H), 7.39 (d, J = 7.6 Hz, 1H), 7.10 (d, J = 7.8 Hz, 1H), 3.60 (s, 2H), 2.04 (ddd, J = 13.5, 8.6, 5.3 Hz, 1H), 1.96-1.67 (m, 12H), 1.55-1.36 (m, 6H), 1.07-0.97 (m, 2H), 0.90-0.76 (m, 2H)

271 $^1$H NMR (400 MHz, DMSO-d$_6$) δ 9.04 (s, 2H), 7.87-7.81 (m, 1H), 7.80 (d, J = 7.8 Hz, 1H), 7.58 (t, J = 7.8 Hz, 1H), 7.45 (d, J = 7.8 Hz, 1H), 3.60 (d, J = 7.3 Hz, 2H), 2.32-2.23 (m, 1H), 2.10-2.00 (m, 1H), 1.97-1.69 (m, 12H), 1.56-1.31 (m, 6H), 1.16-0.93 (m, 6H), 0.89-0.75 (m, 2H)

272 $^1$H NMR (400 MHz, DMSO-d$_6$) δ 11.48 (s, 1H), 9.04 (s, 2H), 7.77-7.82 (m, 2H), 7.55-7.59 (m, 1H), 7.42-7.44 (m, 1H), 3.58-3.60 (m, 2H), 3.41 (s, 3H), 2.02-2.04 (m, 1H), 1.75-1.87 (m, 12H), 1.43-1.46 (m, 6H), 0.98-1.01 (m, 2H), 0.81-0.84 (m, 2H)

| Ex. No. | Structure | MS (ESI) (M + H) | FXR EC$_{50}$ (nM) |
|---|---|---|---|
| 273 | $^1$H NMR (400 MHz, DMSO-d$_6$) δ 7.81-7.62 (m, 4H), 7.54 (t, J = 7.8 Hz, 1H), 7.44 (d, J = 8.3 Hz, 2H), 7.38 (d, J = 8.3 Hz, 1H), 4.48 (s, 2H), 3.63-3.49 (m, 2H), 2.10-2.00 (m, 1H), 1.96-1.71 (m, 12H), 1.47 (d, J = 5.6 Hz, 6H), 1.07-0.94 (m, 2H), 0.88-0.77 (m, 2H). 3H buried under moisture peak. | | |
| 274 | $^1$H NMR (400 MHz, DMSO-d$_6$) δ 8.92 (d, J = 2.4 Hz, 1H), 8.19 (dd, J = 8.1, 2.4 Hz, 1H), 7.85-7.70 (m, 2H), 7.58 (t, J = 7.8 Hz, 1H), 7.53 (d, J = 8.1 Hz, 1H), 7.44 (d, J = 8.1 Hz, 1H), 4.57 (s, 2H), 3.76-3.60 (m, 1H), 3.60-3.48 (m, 1H), 3.41 (s, 3H), 2.11-1.99 (m, 1H), 1.98-1.69 (m, 12H), 1.57-1.32 (m, 6H), 1.10-0.93 (m, 2H), 0.90-0.74 (m, 2H) | | |
| 275 | $^1$H NMR (400 MHz, DMSO-d$_6$) δ 8.08 (s, 1H), 7.84-7.69 (m, 4H), 7.56 (t, J = 7.8 Hz, 1H), 7.40 (d, J = 8.6 Hz, 1H), 3.64-3.59 (m, 2H), 2.66 (s, 3H), 2.09-2.00 (m, 2H), 1.86 (s, 2H), 1.90 (s, 3H), 1.83-1.67 (m, 7H), 1.48 (d, J = 9.0 Hz, 6H), 1.06-0.94 (m, 2H), 0.89-0.80 (m, 2H). | | |
| 276 | $^1$H NMR (400 MHz, DMSO-d$_6$) δ 9.00 (s, 1H), 8.90 (d, J = 2.2 Hz, 1H), 7.83-7.81 (m, 2H), 7.60 (t, J = 8.2 Hz, 1H), 7.45 (d, J = 8.1 Hz, 1H), 3.91 (s, 1H), 3.67 (d, J = 13.9 Hz, 1H), 3.57 (d, J = 14.4 Hz, 1H), 2.66-2.58 (m, 1H), 2.10-1.99 (m, 1H), 1.86 (s, 2H), 1.91 (s, 3H), 1.83-1.65 (m, 6H), 1.51-1.47 (m, 6H), 1.37-1.17 (m, 4H), 1.07-0.94 (m, 2H), 0.89-0.73 (m, 2H). | | |
| 277 | $^1$H NMR (400 MHz, DMSO-d$_6$) δ 9.48 (s, 1H), 8.48 (s, 1H), 8.30 (d, J = 8.6 Hz, 1H), 7.90 (d, J = 10.3 Hz, 1H), 7.87-7.78 (m, 2H), 7.58 (t, J = 7.9 Hz, 1H), 7.42 (d, J = 7.3 Hz, 1H), 3.70-3.58 (m, 2H), 2.10-2.02 (m, 1H), 1.87-1.85 (m, 3H), 1.91-1.88 (m, 3H), 1.84-1.61 (m, 7H), 1.49 (br. s., 6H), 1.01 (dd, J = 7.9, 2.6 Hz, 2H), 0.88-0.79 (m, 2H). | | |
| 278 | $^1$H NMR (400 MHz, DMSO-d$_6$) δ 9.03 (d, J = 2.0 Hz, 1H), 8.94 (d, J = 2.4 Hz, 1H), 7.86-7.84 (m, 2H), 7.61 (t, J = 7.9 Hz, 1H), 7.47 (d, J = 7.1 Hz, 1H), 3.34-3.67 (m, 2H), 2.91 (s, 3H), 2.10-2.00 (m, 1H), 1.91-1.65 (m, 12H), 1.47-1.44 (m, 6H), 1.07-0.95 (m, 2H), 0.87-0.78 (m, 2H). | | |
| 279 | $^1$H NMR (400 MHz, DMSO-d$_6$) δ 7.85-7.75 (m, J = 8.3 Hz, 2H), 7.75-7.62 (m, 2H), 7.55 (t, J = 7.7 Hz, 1H), 7.50-7.41 (m, J = 8.6 Hz, 2H), 7.39 (d, J = 8.8 Hz, 1H), 3.60 (d, J = 4.2 Hz, 2H), 2.04 (td, J = 8.6, 4.2 Hz, 1H), 1.96-1.66 (m, 14H), 1.60-1.53 (m, 2H), 1.53-1.29 (m, 6H), 1.10-0.96 (m, 2H), 0.89-0.72 (m, 2H) | | |
| 280 | $^1$H NMR (400 MHz, DMSO-d$_6$) δ 9.19 (s, 1H), 8.48 (d, J = 6.8 Hz, 1H), 8.03 (d, J = 8.3 Hz, 1H), 7.92 (s, 1H), 7.88 (d, J = 8.1 Hz, 1H), 7.64 (t, J = 7.9 Hz, 1H), 7.53 (d, J = 8.1 Hz, 1H), 3.65 (br. s., 1H), 3.62-3.52 (m, 1H), 2.08-2.02 (m, 1H), 1.96-1.67 (m, 12H), 1.46 (br. s., 6H), 1.08-0.95 (m, 2H), 0.88-0.77 (m, 2H) | | |
| 281 | $^1$H NMR (400 MHz, DMSO-d$_6$) δ 8.56 (d, J = 2.4 Hz, 1H), 8.10 (dd, J = 8.9, 2.6 Hz, 1H), 7.82-7.61 (m, 2H), 7.54 (t, J = 7.9 Hz, 1H), 7.37 (d, J = 7.8 Hz, 1H), 6.92 (d, J = 8.6 Hz, 1H), 4.37 (q, J = 7.0 Hz, 2H), 3.60 (br. s., 2H), 2.11-2.00 (m, 1H), 1.97-1.67 (m, 12H), 1.46 (d, J = 8.1 Hz, 6H), 1.35 (t, J = 7.0 Hz, 3H), 1.08-0.94 (m, 2H), 0.88-0.79 (m, 2H) | | |
| 282 | $^1$H NMR (400 MHz, DMSO-d$_6$) δ 7.78-7.58 (m, 4H), 7.51 (t, J = 7.7 Hz, 1H), 7.32 (d, J = 7.8 Hz, 1H), 7.06 (d, J = 8.8 Hz, 2H), 3.82 (s, 3H), 3.68-3.49 (m, 2H), 2.11-1.99 (m, 1H), 1.85 (s, 2H), 1.88 (s, 3H), 1.83-1.61 (m, 7H), 1.47 (d, J = 8.1 Hz, 6H), 1.07-0.95 (m, 2H), 0.89-0.74 (m, 2H) | | |
| 283 | $^1$H NMR (400 MHz, DMSO-d$_6$) δ 8.28 (d, J = 9.3 Hz, 1H), 8.16-8.02 (m, 2H), 7.62 (t, J = 8.1 Hz, 1H), 7.52 (d, J = 8.1 Hz, 1H), 7.34 (d, J = 9.3 Hz, 1H), 4.56 (q, J = 7.1 Hz, 2H), 3.66 (br. s., 1H), 3.56 (d, J = 17.4 Hz, 1H), 2.08-1.99 (m, 1H), 1.89 (br. s., 5H), 1.86-1.60 (m, 7H), 1.55-1.26 (m, 9H), 1.01 (dd, J = 8.3, 2.7 Hz, 2H), 0.86-0.79 (m, 2H) | | |
| 284 | $^1$H NMR (400 MHz, DMSO-d$_6$) δ 7.86 (d, J = 2.0 Hz, 1H), 7.73-7.69 (m, 2H), 7.63-7.58 (m, 1H), 7.56-7.49 (m, 2H), 7.39 (d, J = 7.0 Hz, 1H), 3.62 (br. s., 1H), 3.57 (br. s., 1H), 2.09-1.99 (m, 1H), 1.93-1.72 (m, 12H), 1.45 (d, J = 9.5 Hz, 6H), 1.04-0.96 (m, 2H), 0.86-0.79 (m, 2H). | | |
| 285 | $^1$H NMR (400 MHz, DMSO-d$_6$) δ 7.70-7.63 (m, 4H), 7.52 (t, J = 7.8 Hz, 1H), 7.37-7.31 (m, 3H), 3.59 (d, J = 8.0 Hz, 2H), 2.70-2.62 (m, 2H), 2.04 (ddd, J = 13.3, 8.3, 5.0 Hz, 1H), 1.85 (s, 3H), 1.88 (s, 3H), 1.82-1.74 (m, 6H), 1.47 (d, J = 7.0 Hz, 6H), 1.22 (t, J = 7.8 Hz, 3H), 1.05-0.97 (m, 2H), 0.87-0.79 (m, 2H). | | |
| 286 | $^1$H NMR (400 MHz, DMSO-d$_6$) δ 8.10-8.03 (m, 1H), 7.83-7.72 (m, 4H), 7.56 (t, J = 7.8 Hz, 1H), 7.44 (d, J = 9.0 Hz, 1H), 3.68 (br. s., 1H), 3.53 (br. s., 1H), 2.09-2.00 (m, 1H), 1.89 (br. s., 3H), 1.86-1.72 (m, 9H), 1.45 (d, J = 6.5 Hz, 6H), 1.05-0.97 (m, 2H), 0.88-0.80 (m, 2H). | | |
| 287 | $^1$H NMR (400 MHz, DMSO-d$_6$) δ 8.17 (dd, J = 9.0, 4.5 Hz, 1H), 8.10-8.02 (m, 1H), 7.87 (td, J = 8.7, 3.3 Hz, 1H), 7.83-7.72 (m, 2H), 7.61-7.53 (m, 1H), 7.49-7.41 (m, 1H), 3.54 (br. s., 1H), 2.04 (br. s., 1H), 1.95-1.73 (m, 12H), 1.46 (d, J = 8.5 Hz, 6H), 1.01 (d, J = 4.5 Hz, 2H), 0.88-0.80 (m, 2H). | | |
| 288 | $^1$H NMR (400 MHz, DMSO-d$_6$) δ 8.94 (d, J = 7.0 Hz, 1H), 8.30 (s, 1H), 8.22 (s, 1H), 8.13 (s, 1H), 8.01-7.91 (m, 2H), 7.88 (d, J = 7.5 Hz, 1H), 7.66 (t, J = 8.0 Hz, 1H), 7.57 (d, J = 8.5 Hz, 1H), 3.63 (d, J = 17.6 Hz, 2H), 2.04 (ddd, J = 13.2, 8.4, 5.0 Hz, 1H), 1.89 (d, J = 9.0 Hz, 6H), 1.83-1.75 (m, 6H), 1.47 (d, J = 8.0 Hz, 6H), 1.05-0.98 (m, 2H), 0.86-0.79 (m, 2H). | | |
| 289 | $^1$H NMR (400 MHz, DMSO-d$_6$) δ 9.01 (s, 2H), 7.84-7.74 (m, 2H), 7.57 (t, J = 7.8 Hz, 1H), 7.42 (d, J = 9.0 Hz, 1H), 4.42 (q, J = 7.0 Hz, 2H), 3.66-3.53 (m, 2H), 2.09-1.99 (m, 1H), 1.94-1.73 (m, 12H), 1.51-1.41 (m, 6H), 1.38 (t, J = 7.0 Hz, 3H), 1.05-0.97 (m, 2H), 0.86-0.79 (m, 2H) | | |
| 290 | $^1$H NMR (400 MHz, DMSO-d$_6$) δ 7.71-7.59 (m, 4H), 7.50 (t, J = 7.8 Hz, 1H), 7.31 (d, J = 7.5 Hz, 1H), 7.04 (d, J = 9.0 Hz, 2H), 4.14-4.04 (m, 2H), 3.59 (d, J = 4.5 Hz, 2H), 2.09-2.00 (m, 1H), 1.86 (d, J = 9.0 Hz, 6H), 1.83-1.73 (m, 6H), 1.51-1.41 (m, 6H), 1.36 (t, J = 6.8 Hz, 3H), 1.05-0.97 (m, 2H), 0.87-0.79 (m, 2H). | | |
| 291 | $^1$H NMR (400 MHz, DMSO-d$_6$) δ 9.33 (d, J = 5.0 Hz, 1H), 8.44-8.38 (m, 1H), 8.30-8.26 (m, 1H), 8.03 (d, J = 5.0 Hz, 1H), 7.74-7.64 (m, 2H), 3.63 (s, 2H), 2.08-2.00 (m, 1H), 1.90 (br. s., 6H), 1.83-1.71 (m, 6H), 1.50-1.39 (m, 6H), 1.06-0.97 (m, 2H), 0.86-0.78 (m, 2H). | | |
| 292 | $^1$H NMR (400 MHz, DMSO-d$_6$) δ 8.42 (d, J = 8.0 Hz, 1H), 8.19 (t, J = 8.0 Hz, 1H), 8.14 (d, J = 7.5 Hz, 1H), 8.10-8.07 (m, 1H), 8.05 (d, J = 8.0 Hz, 1H), 7.63 (t, J = 7.8 Hz, 1H), 7.56 (d, J = 8.0 Hz, 1H), 3.65 (br. s., 1H), 3.60 (br. s., 1H), 2.09-1.99 (m, 1H), 1.88 (br. s., 6H), 1.82-1.73 (m, 6H), 1.46 (d, J = 7.5 Hz, 6H), 1.05-0.96 (m, 2H), 0.87-0.79 (m, 2H). | | |

| Ex. No. | Structure | MS (ESI) (M + H) | FXR EC$_{50}$ (nM) |
|---|---|---|---|
| 293 | $^1$H NMR (400 MHz, DMSO-d$_6$) δ 8.23-8.15 (m, 1H), 8.10-8.04 (m, 1H), 7.93 (d, J = 7.5 Hz, 1H), 7.86 (s, 1H), 7.70-7.64 (m, 1H), 7.62-7.58 (m, 1H), 3.67 (br. s., 1H), 3.53 (br. s., 1H), 2.04 (ddd, J = 13.3, 8.3, 5.0 Hz, 1H), 1.90-1.93 (m, 6H), 1.81-1.72 (m, 6H), 1.45 (br. s., 6H), 1.05-0.97 (m, 2H), 0.86-0.78 (m, 2H). | | |
| 294 | $^1$H NMR (400 MHz, DMSO-d$_6$) δ 8.40 (dd, J = 6.3, 2.3 Hz, 1H), 8.22-8.16 (m, 1H), 7.83 (s, 1H), 7.78 (d, J = 8.0 Hz, 1H), 7.65 (t, J = 9.0 Hz, 1H), 7.57 (t, J = 7.8 Hz, 1H), 7.45 (d, J = 7.5 Hz, 1H), 3.70 (d, J = 13.6 Hz, 1H), 3.52 (d, J = 13.1 Hz, 1H), 2.04 (td, J = 8.7, 4.3 Hz, 1H), 1.90 (br. s., 3H), 1.86-1.72 (m, 9H), 1.45 (d, J = 6.5 Hz, 6H), 1.06-0.98 (m, 2H), 0.87-0.79 (m, 2H). | | |
| 295 | $^1$H NMR (400 MHz, DMSO-d$_6$) δ 8.25 (d, J = 8.5 Hz, 1H), 8.18-8.12 (m, 2H), 7.71 (d, J = 9.0 Hz, 1H), 7.64 (t, J = 7.5 Hz, 1H), 7.55 (d, J = 8.0 Hz, 1H), 3.63 (d, J = 14.1 Hz, 2H), 2.69 (s, 3H), 2.08-2.01 (m, 1H), 1.89 (br. s., 6H), 1.82-1.73 (m, 6H), 1.50-1.41 (m, 6H), 1.04-0.98 (m, 2H), 0.86-0.79 (m, 2H). | | |
| 296 | $^1$H NMR (400 MHz, DMSO-d$_6$) δ 8.20 (d, J = 2.5 Hz, 1H), 8.08 (dd, J = 8.8, 2.3 Hz, 1H), 7.80-7.72 (m, 2H), 7.53 (t, J = 8.0 Hz, 1H), 7.41-7.34 (m, 2H), 3.98 (s, 3H), 3.68 (d, J = 13.1 Hz, 1H), 3.56-3.49 (m, 1H), 2.09-2.00 (m, 1H), 1.89 (br. s., 3H), 1.86-1.73 (m, 9H), 1.46 (d, J = 7.0 Hz, 6H), 1.06-0.97 (m, 2H), 0.87-0.80 (m, 2H). | | |
| 297 | $^1$H NMR (400 MHz, DMSO-d$_6$) δ 9.14 (d, J = 2.0 Hz, 1H), 8.45 (dd, J = 8.5, 2.0 Hz, 1H), 8.33 (d, J = 8.0 Hz, 1H), 8.21 (d, J = 8.0 Hz, 1H), 8.17 (s, 1H), 7.64 (t, J = 7.8 Hz, 1H), 7.57 (d, J = 8.5 Hz, 1H), 3.62 (s, 2H), 2.09-2.00 (m, 1H), 1.93-1.81 (m, 6H), 1.81-1.73 (m, 6H), 1.50-1.38 (m, 6H), 1.05-0.97 (m, 2H), 0.86-0.79 (m, 2H). | | |
| 298 | $^1$H NMR (400 MHz, DMSO-d$_6$) δ 9.05 (d, J = 7.0 Hz, 1H), 8.56 (s, 1H), 8.32 (s, 1H), 7.99 (s, 1H), 7.94 (d, J = 7.5 Hz, 1H), 7.68-7.56 (m, 1H), 7.52-7.45 (m, 1H), 7.41-7.32 (m, 1H), 3.66 (br. s., 1H), 3.61 (br. s., 1H), 2.08-1.99 (m, 1H), 1.95-1.83 (m, 6H), 1.83-1.73 (m, 6H), 1.52-1.40 (m, 6H), 1.05-0.98 (m, 2H), 0.86-0.79 (m, 2H). | | |
| 299 | $^1$H NMR (400 MHz, DMSO-d$_6$) δ 7.79-7.72 (m, 3H), 7.64-7.60 (m, 1H), 7.60-7.53 (m, 1H), 7.43 (d, J = 8.0 Hz, 1H), 7.34 (d, J = 7.0 Hz, 1H), 6.97 (s, 1H), 6.90-6.71 (m, 1H), 3.68 (br. s., 1H), 3.53 (br. s., 1H), 2.09-2.00 (m, 1H), 1.90 (br. s., 3H), 1.87-1.73 (m, 9H), 1.46 (d, J = 8.0 Hz, 6H), 1.05-0.98 (m, 2H), 0.87-0.80 (m, 2H). | | |
| 300 | $^1$H NMR (400 MHz, DMSO-d$_6$) δ 8.79 (d, J = 5.0 Hz, 1H), 8.39 (d, J = 7.5 Hz, 1H), 8.25 (s, 1H), 7.65-7.53 (m, 2H), 7.39 (d, J = 5.0 Hz, 1H), 3.62 (s, 2H), 2.57 (s, 3H), 2.08-2.00 (m, 1H), 1.88 (br. s., 6H), 1.82-1.73 (m, 6H), 1.49-1.39 (m, 6H), 1.05-0.97 (m, 2H), 0.86-0.79 (m, 2H). | | |
| 301 | $^1$H NMR (400 MHz, DMSO-d$_6$) δ 7.73-7.63 (m, 2H), 7.50 (t, J = 7.8 Hz, 1H), 7.35-7.25 (m, 3H), 7.06 (d, J = 9.0 Hz, 1H), 3.87 (s, 3H), 3.81 (s, 3H), 3.70 (s, 1H), 3.56 (s, 1H), 2.10-1.99 (m, 1H), 1.85-1.89 (m, 6H), 1.78 (t, J = 7.8 Hz, 6H), 1.46 (d, J = 6.5 Hz, 6H), 1.05-0.97 (m, 2H), 0.87-0.79 (m, 2H). | | |
| 302 | $^1$H NMR (400 MHz, DMSO-d$_6$) δ 8.01-7.92 (m, 4H), 7.83-7.76 (m, 2H), 7.59 (t, J = 7.8 Hz, 1H), 7.47 (d, J = 8.5 Hz, 1H), 3.64 (br. s., 1H), 3.55 (d, J = 15.1 Hz, 1H), 2.08-2.00 (m, 1H), 1.93-1.7 (m, 12H), 1.51-1.39 (m, 6H), 1.05-0.97 (m, 2H), 0.86-0.79 (m, 2H). | | |
| 303 | $^1$H NMR (400 MHz, DMSO-d$_6$) δ 8.28 (d, J = 1.5 Hz, 1H), 8.15 (d, J = 8.0 Hz, 1H), 7.83-7.75 (m, 3H), 7.57 (t, J = 8.0 Hz, 1H), 7.40 (d, J = 8.5 Hz, 1H), 3.62 (d, J = 8.0 Hz, 2H), 2.84 (s, 3H), 2.09-1.99 (m, 1H), 1.87-1.90 (m, 6H), 1.84-1.75 (m, 6H), 1.48 (d, J = 8.5 Hz, 6H), 1.06-0.97 (m, 2H), 0.86-0.79 (m, 2H). | | |
| 304 | $^1$H NMR (400 MHz, DMSO-d$_6$) δ 8.12 (d, J = 1.0 Hz, 2H), 7.83-7.70 (m, 4H), 7.54 (t, J = 7.8 Hz, 1H), 7.35 (d, J = 9.0 Hz, 1H), 4.09 (s, 3H), 3.64 (br. s., 1H), 3.59 (br. s., 1H), 2.08-2.00 (m, 1H), 1.87-1.90 (m, 6H), 1.84-1.73 (m, 6H), 1.48 (d, J = 9.5 Hz, 6H), 1.05-0.97 (m, 2H), 0.87-0.79 (m, 2H). | | |
| 305 | $^1$H NMR (400 MHz, DMSO-d$_6$) δ 8.03 (d, J = 1.5 Hz, 1H), 7.79-7.69 (m, 4H), 7.55 (t, J = 8.0 Hz, 1H), 7.38 (d, J = 8.0 Hz, 1H), 3.64 (br. s., 1H), 3.59 (br. s., 1H), 2.65 (s, 3H), 2.09-2.00 (m, 1H), 1.86-1.90 (m, 6H), 1.83-1.74 (m, 6H), 1.47 (d, J = 4.0 Hz, 6H), 1.06-0.97 (m, 2H), 0.87-0.79 (m, 2H). | | |
| 306 | $^1$H NMR (400 MHz, DMSO-d$_6$) δ 8.64 (s, 1H), 8.52 (d, J = 9.5 Hz, 1H), 8.24 (d, J = 9.5 Hz, 1H), 8.17-8.09 (m, 2H), 7.71 (t, J = 7.8 Hz, 1H), 7.64 (d, J = 8.0 Hz, 1H), 3.69 (br. s., 1H), 3.59 (br. s., 1H), 2.03 (td, J = 8.7, 4.3 Hz, 1H), 1.93 (br. s., 6H), 1.83-1.72 (m, 6H), 1.53-1.38 (m, 6H), 1.06-0.97 (m, 2H), 0.86-0.78 (m, 2H). | | |
| 307 | $^1$H NMR (400 MHz, DMSO-d$_6$) δ 9.31 (s, 1H), 8.69 (d, J = 7.2 Hz, 1H), 8.27 (s, 1H), 7.97 (s, 1H), 7.92 (d, J = 7.8 Hz, 1H), 7.61 (t, J = 7.7 Hz, 1H), 7.51 (br. s., 2H), 3.72-3.63 (m, 2H), 2.10-2.00 (m, 1H), 1.95-1.72 (m, 12H), 1.53-1.39 (m, 6H), 1.01 (d, J = 6.2 Hz, 2H), 0.83 (br. s., 2H). | | |
| 308 | $^1$H NMR (400 MHz, DMSO-d$_6$) δ 7.82 (d, J = 8.4 Hz, 2H), 7.74-7.67 (m, 2H), 7.54 (t, J = 7.6 Hz, 1H), 7.39 (d, J = 7.7 Hz, 1H), 7.31 (t, J = 72.00 Hz, 1H), 7.30 (d, J = 8.8 Hz, 2H), 3.69-3.52 (m, 2H), 2.04 (dq, J = 8.4, 4.2 Hz, 1H), 1.94-1.72 (m, 12H), 1.52-1.37 (m, 6H), 1.06-0.96 (m, 2H), 0.87-0.77 (m, 2H). | | |
| 309 | $^1$H NMR (400 MHz, DMSO-d$_6$) δ 9.02 (d, J = 6.6 Hz, 1H), 8.61 (s, 1H), 8.25 (s, 1H), 8.18 (d, J = 7.8 Hz, 1H), 8.07 (d, J = 7.3 Hz, 1H), 7.63 (t, J = 7.9 Hz, 1H), 7.50 (d, J = 7.6 Hz, 1H), 7.35 (t, J = 7.1 Hz, 1H), 3.61 (d, J = 11.7 Hz, 2H), 2.11-2.00 (m, 1H), 1.92 (br. s., 6H), 1.84-1.73 (m, 6H), 1.54-1.40 (m, 6H), 1.01 (d, J = 5.9 Hz, 2H), 0.83 (br. s., 2H). | | |
| 310 | $^1$H NMR (400 MHz, DMSO-d$_6$) δ 9.22 (s, 1H), 8.65 (s, 1H), 8.14 (d, J = 7.7 Hz, 1H), 8.10 (s, 1H), 7.61 (t, J = 7.8 Hz, 1H), 7.51 (d, J = 7.6 Hz, 1H), 3.62 (s, 2H), 2.56 (s, 3H), 2.10-2.00 (m, 1H), 1.88 (br. s., 6H), 1.82-1.72 (m, 6H), 1.52-1.37 (m, 6H), 1.06-0.97 (m, 2H), 0.89-0.78 (m, 2H). | | |
| 311 | $^1$H NMR (400 MHz, DMSO-d$_6$) δ 9.16 (d, J = 4.0 Hz, 1H), 8.48 (d, J = 7.5 Hz, 1H), 8.25 (d, J = 8.7 Hz, 1H), 7.81-7.72 (m, 2H), 7.71-7.64 (m, 1H), 7.62-7.53 (m, 1H), 3.64 (br. s., 1H), 3.59 (br. s., 1H), 2.13-2.01 (m, 1H), 1.94 (br. s., 3H), 1.89 (br. s., 3H), 1.84-1.73 (m, 6H), 1.55-1.39 (m, 6H), 1.02 (d, J = 7.9 Hz, 2H), 0.88-0.79 (m, 2H). | | |
| 312 | $^1$H NMR (400 MHz, DMSO-d$_6$) δ 8.73 (s, 1H), 8.45 (s, 1H), 7.62-7.54 (m, 1H), 7.51-7.39 (m, 3H), 3.60 (d, J = 5.1 Hz, 2H), 2.59 (s, 3H), 2.22 (s, 3H), 2.11-2.01 (m, 1H), 1.88-1.92 (m, 6H), 1.83-1.72 (m, 6H), 1.52-1.36 (m, 6H), 1.02 (d, J = 8.1 Hz, 2H), 0.88-0.79 (m, 2H). | | |

| Ex. No. | Structure | MS (ESI) (M + H) | FXR EC$_{50}$ (nM) |
|---|---|---|---|
| 313 | $^1$H NMR (400 MHz, DMSO-d$_6$) δ 9.05 (s, 1H), 8.41 (s, 1H), 7.95-7.86 (m, 1H), 7.73-7.55 (m, 2H), 7.38 (t, J = 9.0 Hz, 1H), 4.14 (s, 2H), 3.73 (s, 3H), 2.05 (br. s., 1H), 2.00-1.87 (m, 6H), 1.83-1.72 (m, 6H), 1.46 (br. s., 6H), 1.02 (d, J = 6.2 Hz, 2H), 0.83 (br. s., 2H). | | |
| 314 | $^1$H NMR (400 MHz, DMSO-d$_6$) δ 9.06 (s, 2H), 8.72 (s, 1H), 8.26-8.18 (m, 2H), 7.65 (t, J = 8.0 Hz, 1H), 7.50 (d, J = 7.8 Hz, 1H), 3.66 (d, J = 12.5 Hz, 1H), 3.56 (d, J = 13.1 Hz, 1H), 2.10-2.00 (m, 1H),1.91 (br. s., 6H), 1.83-1.73 (m, 6H), 1.46 (br. s., 6H), 1.01 (d, J = 7.6 Hz, 2H), 0.83 (br. s., 2H). | | |
| 315 | $^1$H NMR (400 MHz, DMSO-d$_6$) δ 8.33 (s, 1H), 8.16 (d, J = 6.0 Hz, 1H), 8.04 (s, 1H), 7.78-7.68 (m, 2H), 7.42-7.34 (m, 1H), 7.23 (br. s., 1H), 3.69 (br. s., 1H), 3.58 (br. s., 1H), 2.09-1.99 (m, 1H), 1.91 (br. s., 6H), 1.77 (d, J = 7.0 Hz, 6H), 1.46 (br. s., 6H), 1.01 (d, J = 6.2 Hz, 2H), 0.83 (br. s., 2H). | | |
| 316 | $^1$H NMR (400 MHz, DMSO-d$_6$) δ 9.27 (s, 1H), 8.58 (d, J = 5.5 Hz, 1H), 7.92-7.84 (m, 2H), 7.78 (d, J = 5.4 Hz, 1H), 7.70-7.58 (m, 2H), 3.75-3.64 (m, 1H), 3.64-3.52 (m, 1H), 2.11-2.00 (m, 1H), 1.91 (br. s., 6H), 1.85-1.72 (m, 6H), 1.52-1.38 (m, 6H), 1.01 (d, J = 7.5 Hz, 2H), 0.84 (br. s., 2H). | | |
| 317 | $^1$H NMR (400 MHz, DMSO-d$_6$) δ 8.99 (s, 1H), 8.14 (br s., 1H), 7.83-7.73 (m, 4H), 7.59 (t, J = 7.8 Hz, 1H), 7.45 (d, J = 7.7 Hz, 1H), 3.74-3.66 (m, 2H), 2.08-2.01 (m, 1H), 1.91-1.86 (m, 6H), 1.79 (t, J = 7.6 Hz, 6H), 1.46 (d, J = 5.5 Hz, 6H), 1.05-0.98 (m, 2H), 0.86-0.78 (m, 2H). | | |
| 318 | $^1$H NMR (400 MHz, DMSO-d$_6$) δ 8.69 (d, J = 4.2 Hz, 1H), 8.41 (s, 1H), 8.26 (d, J = 9.3 Hz, 1H), 8.20 (br. s., 2H), 7.61 (t, J = 8.1 Hz, 1H), 7.41 (d, J = 8.1 Hz, 1H), 7.34 (dd, J = 9.1, 4.3 Hz, 1H), 3.70-3.61 (m, 1H), 3.61-3.52 (m, 1H), 2.10-2.00 (m, 1H), 1.92 (br. s., 6H), 1.84-1.72 (m, 6H), 1.54-1.40 (m, 6H), 1.06-0.97 (m, 2H), 0.86-0.78 (m, 2H). | | |
| 319 | $^1$H NMR (400 MHz, DMSO-d$_6$) δ 8.59 (s, 1H), 8.30 (s, 1H), 8.19-8.13 (m, 2H), 8.03 (s, 1H), 7.59 (t, J = 7.9 Hz, 1H), 7.39 (d, J = 7.8 Hz, 1H), 3.67 (d, J = 13.3 Hz, 1H), 3.55 (d, J = 13.4 Hz, 1H), 2.44 (s, 3H), 2.09-2.00 (m, 1H), 1.92 (br. s., 6H), 1.83-1.73 (m, 6H), 1.52-1.41 (m, 6H), 1.01 (d, J = 7.8 Hz, 2H), 0.83 (br. s., 2H). | | |
| 320 | $^1$H NMR (400 MHz, DMSO-d$_6$) δ 8.36 (s, 1H), 7.63 (s, 1H), 7.59-7.52 (m, 1H), 7.47-7.39 (m, 3H), 7.36 (s, 1H), 3.65 (d, J = 13.7 Hz, 1H), 3.52 (d, J = 13.9 Hz, 1H), 2.33 (s, 3H), 2.22 (s, 3H), 2.10-2.00 (m, 1H), 1.86-1.91 (m, 6H), 1.82-1.73 (m, 6H), 1.49-1.39 (m, 6H), 1.06-0.97 (m, 2H), 0.87-0.80 (m, 2H). | | |
| 321 | $^1$H NMR (400 MHz, DMSO-d$_6$) δ 9.66 (s, 1H). 8.44 (s, 1H), 8.02 (s, 1H), 7.93 (d, J = 7.7 Hz, 1H), 7.60 (t, J = 7.8 Hz, 1H), 7.48 (d, J = 7.8 Hz, 1H), 3.75 (d, J = 13.7 Hz, 1H), 3.52 (d, J = 14.1 Hz, 1H), 2.58 (s, 3H), 2.09-2.00 (m, 1H), 1.92-1.82 (m, 6H), 1.79 (t, J = 7.6 Hz, 6H), 1.47 (d, J = 7.8 Hz, 6H), 1.06-0.98 (m, 2H), 0.83 (br. s., 2H). | | |
| 322 | $^1$H NMR (400 MHz, DMSO-d$_6$) δ 8.77 (s, 1H), 7.76-7.67 (m, 3H), 7.55 (t, J = 7.8 Hz, 1H), 7.44 (s, 1H), 7.39 (d, J = 7.7 Hz, 1H), 3.72 (d, J = 13.8 Hz, 1H), 3.51 (d, J = 14.1 Hz, 1H), 2.37 (s, 3H), 2.10-2.00 (m, 1H), 1.91-1.82 (m, 6H), 1.79 (t, J = 7.6 Hz, 6H), 1.46 (d, J = 7.3 Hz, 6H), 1.01 (d, J = 7.9 Hz, 2H), 0.83 (br. s., 2H) (3 Protons are buried under solvent peak). | | |
| 323 | $^1$H NMR (400 MHz, DMSO-d$_6$) δ 9.29 (s, 1H), 9.02 (s, 1H), 7.92 (d, J = 9.5 Hz, 1H), 7.85 (d, J = 9.8 Hz, 1H), 7.82-7.75 (m, 2H), 7.61 (t, J = 7.8 Hz, 1H), 7.47 (d, J = 7.9 Hz, 1H), 3.69-3.64 (m, 2H), 2.09-2.00 (m, 1H), 1.87-1.90 (m, 6H), 1.82-1.74 (m, 6H), 1.51-1.40 (m, 6H), 1.06-0.97 (m, 2H), 0.86-0.80 (m, 2H). | | |
| 324 | $^1$H NMR (400 MHz, DMSO-d$_6$) δ 9.34 (s, 1H), 8.06 (d, J = 9.3 Hz, 1H), 7.89 (s, 1H), 7.83 (t, J = 9.1 Hz, 2H), 7.58 (t, J = 7.8 Hz, 1H), 7.44 (d, J = 7.7 Hz, 1H), 3.72-3.63 (m, 1H), 3.63-3.53 (m, 1H), 2.09-2.00 (m, 1H), 1.86-1.90 (m, 6H), 1.82-1.74 (m, 6H), 1.52-1.39 (m, 6H), 1.06-0.97 (m, 2H), 0.86-0.78 (m, 2H) (3 Protons are buried under solvent peak). | | |
| 325 | $^1$H NMR (400 MHz, DMSO-d$_6$) δ 8.55 (s, 1H), 8.08 (d, J = 7.8 Hz, 1H), 8.04 (s, 1H), 7.98 (d, J = 8.1 Hz, 1H), 7.74 (d, J = 7.8 Hz, 1H), 7.56 (t, J = 7.8 Hz, 1H), 7.43 (d, J = 7.7 Hz, 1H), 3.61 (s, 2H), 2.36 (s, 3H), 2.10-2.00 (m, 1H), 1.87 (br. s., 6H), 1.82-1.72 (m, 6H), 1.50-1.39 (m, 6H), 1.05-0.97 (m, 2H), 0.83 (br. s., 2H). | | |
| 326 | $^1$H NMR (400 MHz, DMSO-d$_6$) δ 9.45 (s, 1H), 8.64 (s, 1H), 8.24 (s, 2H), 8.28 (s, 1H), 7.63 (t, J = 7.8 Hz, 1H), 7.52 (d, J = 7.8 Hz, 1H), 3.62 (d, J = 7.8 Hz, 2H), 2.09-2.02 (m, 1H), 1.92 (br. s., 6H), 1.83-1.74 (m, 6H), 1.52-1.42 (m, 6H), 1.06-0.97 (m, 2H), 0.84 (br. s., 2H). | | |
| 327 | $^1$H NMR (400 MHz, DMSO-d$_6$) δ 9.53 (s, 1H), 8.24-8.16 (m, 2H), 8.14 (s, 1H), 7.61 (t, J = 7.8 Hz, 1H), 7.51 (d, J = 7.9 Hz, 1H), 3.71 (br. s., 1H), 3.58 (br. s., 1H), 2.81 (s, 3H), 2.09-2.00 (m, 1H), 1.89 (br. s., 6H), 1.78 (t, J = 7.5 Hz, 6H), 1.53-1.39 (m, 6H), 1.01 (d, J = 7.7 Hz, 2H), 0.83 (br. s., 2H). | | |
| 328 | $^1$H NMR (400 MHz, DMSO-d$_6$) δ 8.20 (s, 1H), 7.85-7.78 (m, 2H), 7.69-7.57 (m, 2H), 4.81 (s, 2H), 4.05 (t, J = 5.6 Hz, 2H), 3.71-3.62 (m, 1H), 3.62-3.52 (m, 1H), 3.04 (br. s., 2H), 2.11-1.99 (m, 1H), 1.89 (br. s., 6H), 1.83-1.72 (m, 6H), 1.51-1.38 (m, 6H), 1.01 (d, J = 7.6 Hz, 2H), 0.87-0.79 (m, 2H). | | |
| 329 | $^1$H NMR (400 MHz, DMSO-d$_6$) δ 8.83 (s, 1H), 8.56 (s, 1H), 8.43 (s, 1H), 8.19-8.12 (m, 2H), 7.62 (t, J = 7.9 Hz, 1H), 7.43 (d, J = 7.7 Hz, 1H), 3.63 (br. s., 1H), 3.60-3.52 (m, 1H), 2.09-2.00 (m, 1H), 1.91 (br. s., 6H), 1.84-1.73 (m, 6H), 1.51-1.39 (m, 6H), 1.06-0.97 (m, 2H), 0.86-0.79 (m, 2H). | | |
| 330 | $^1$H NMR (400 MHz, DMSO-d$_6$) δ 8.62 (d, J = 6.6 Hz, 1H), 8.26 (s, 1H), 8.15 (d, J = 7.7 Hz, 1H), 8.08 (s, 1H), 7.66 (s, 1H), 7.63-7.55 (m, 2H), 7.44 (d, J = 7.6 Hz, 1H), 7.04 (t, J = 6.9 Hz, 1H), 3.66 (d, J = 13.7 Hz, 1H), 3.55 (d, J = 13.8 Hz, 1H), 2.10-2.00 (m, 1H), 1.93 (d, J = 9.0 Hz, 6H), 1.79 (t, J = 7.7 Hz, 6H), 1.48 (d, J = 4.9 Hz, 6H), 1.01 (d, J = 7.6 Hz, 2H), 0.89-0.79 (m, 2H). | | |
| 331 | $^1$H NMR (400 MHz, DMSO-d$_6$) δ 11.85 (br. s., 1H), 8.09 (s, 1H), 8.00 (d, J = 9.5 Hz, 1H), 7.92 (d, J = 8.7 Hz, 1H), 7.79-7.68 (m, 2H), 7.55 (t, J = 7.8 Hz, 1H), 7.38 (d, J = 7.8 Hz, 1H), 7.41 (d, J = 8.6 Hz, 1H), 6.56 (d, J = 9.4 Hz, 1H), 3.71-3.61 (m, 1H), 3.61-3.50 (m, 1H), 2.11-1.99 (m, 1H), 1.86-1.90 (m, 6H), 1.79 (t, J = 7.5 Hz, 6H), 1.55-1.36 (m, 6H), 1.01 (d, J = 7.7 Hz, 2H), 0.83 (br. s., 2H). | | |
| 332 | $^1$H NMR (400 MHz, DMSO-d$_6$) δ 10.49 (s, 1H), 7.70-7 44 (m, 5H), 7.31 (d, J = 8.0 Hz, 1H), 6.93 (d, J = 8.0 Hz, 1H), 3.69-3.51 (m, 4H), 2.13-2.02 (m, 1H), 1.97-1.67 (m, 12H), 1.58-1.30 (m, 6H), 1.0 (dd, J = 8.0, 2.0 Hz, 2H), 0.89-0.74 (m, 2H) | | |
| 333 | $^1$H NMR (400 MHz, DMSO-d$_6$) δ 8.68 (s, 2H), 8.30 (d, J = 8.1 Hz, 1H), 8.17 (t, J = 1.7 Hz, 1H), 7.59 (t, J = 7.8 Hz, 1H), 7.50 (d, J = 7.6 Hz, 1H), 4.28 (q, J = 7.1 Hz, 2H), 3.71-3.61 (m, 2H), 2.12-1.98 (m, 1H), 1.89 (br. s., 6H), 1.84-1.71 (m, 6H), 1.53-1.31 (m, 9H), 1.06-0.94 (m, 2H), 0.89-0.71 (m, 2H) | | |

| Ex. No. | Structure | MS (ESI) (M + H) | FXR EC$_{50}$ (nM) |
|---|---|---|---|
| 334 | $^1$H NMR (400 MHz, DMSO-d$_6$) δ 8.70 (s, 2H), 8.31 (d, J = 7.8 Hz, 1H), 8.18 (t, J = 1.8 Hz, 1H), 7.68-7.54 (m, 1H), 7.53-7.45 (m, 1H), 3.98 (s, 3H), 3.64 (br. s., 1H), 3.56 (d, J = 15.9 Hz, 1H), 2.09-1.99 (m, 1H), 1.97-1.67 (m, 12H), 1.54-1.35 (m, 6H), 1.06-0.96 (m, 2H), 0.88-0.77 (m, 2H) | | |
| 335 | $^1$H NMR (400 MHz, DMSO-d$_6$) δ 8.93 (s, 2H), 8.36 (d, J = 7.8 Hz, 1H), 8.23 (s, 1H), 7.70-7.50 (m, 2H), 7.5-7.25 (m, 1H), 3.65 (br. s., 1H), 3.59 (br. s., 1H), 2.03 (td, J = 8.6, 4.3 Hz, 1H), 1.89 (br. s., 6H), 1.84-1.59 (m, 6H), 1.55-1.32 (m, 6H), 1.06-0.96 (m, 2H), 0.87-0.78 (m, 2H) | | |
| 336 | $^1$H NMR (400 MHz, DMSO-d$_6$) δ 10.92 (s, 1H), 8.33 (s, 1H), 8.15-8.00 (m, 3H), 7.88 (d, J = 9.5 Hz, 1H), 7.69-7.59 (m, 1H), 7.59-7.48 (m, 1H), 3.64 (br. s., 2H), 2.13 (s, 3H), 2.09-2.00 (m, 1H), 1.91 (s, 6H), 1.83-1.67 (m, 6H), 1.56-1.38 (m, 6H), 1.06-0.96 (m, 2H), 0.86-0.78 (m, 2H) | | |

Example 337

N-(3-(2-cyclopropoxypyrimidin-4-yl)phenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide

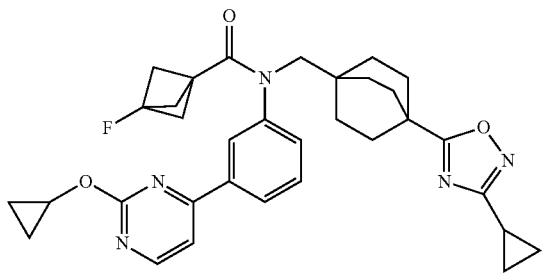

(337)

Step A. Intermediate 337A. Preparation of 2-cyclopropoxy-4-(3-nitrophenyl)pyrimidine

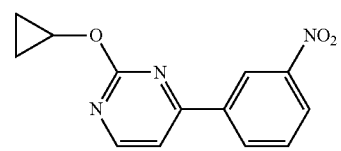 [SMILES: O=[N+]([O-])c1cccc(-c2ccnc(OC3CC3)n2)c1]

To a stirred solution of sodium hydride in mineral oil (138 mg, 3.44 mmol) in tetrahydrofuran (5 mL) was added cyclopropanol (100 mg, 1.722 mmol) at 0° C. The reaction mixture was stirred for 20 min and then Intermediate 40A (406 mg, 1.722 mmol) was added. The reaction mixture was allowed to warm to room temperature and stirred for 1 h. The reaction was quenched with cold water (10 mL) and extracted with EtOAc (2×10 mL). The organic layers were combined, dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated and dried in vacuo to afford (0.3 g, 1.108 mmol, 64% yield) as pale yellow solid. MS (ESI) 258 (M+H).

Step B. Intermediate 337B. Preparation of 3-(2-cyclopropoxypyrimidin-4-yl)aniline

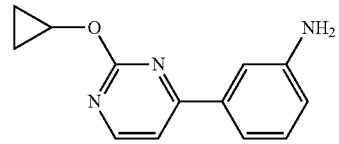

To a stirred solution of Intermediate 337A (300 mg, 1.166 mmol) in mixture of ethanol (2 mL) and Tetrahydrofuran (2 mL) was added zinc (1.2 g, 18 mmol). A solution of ammonium chloride (936 mg, 18 mmol) in water (2 mL) was added to the reaction mixture and stirred at room temperature for 3 h. The reaction mixture was filtered through Celite. The crude material was purified by flash chromatography (12 g silica gel cartridge; A=Hex, B=EtOAc; 30 min grad.; 0% B to 50% B; flow rate=30 mL/min). The pure fractions were combined, concentrated and dried in vacuo to afford (200 mg, 0.836 mmol, 72% yield) as pale yellow solid. MS (ESI) 228 (M+H).

Step C. Intermediate 337C. Preparation of 3-(2-cyclopropoxypyrimidin-4-yl)-N-((4-(3-cyclopropyl-1,2,4-oxadiazol-5-yl)bicyclo[2.2.2]octan-1-yl)methyl)aniline

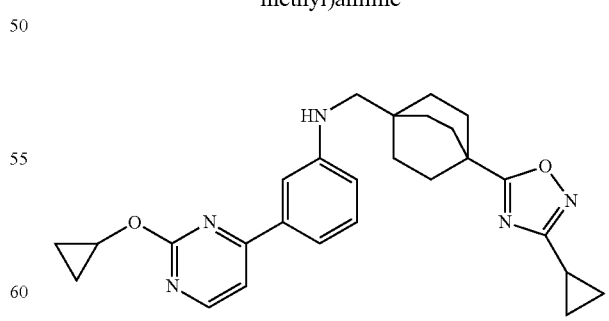

The title compound was prepared according to the method described for the synthesis of Intermediate 1I by substituting Intermediate 337B and Intermediate 4C where appropriate. (130 mg, 0.270 mmol, 53% yield) as pale yellow solid. MS (ESI) 458 (M+H).

Step D. Example 337. Preparation of N-(3-(2-cyclopropoxypyrimidin-4-yl)phenyl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide The title compound was prepared according to the method described for the synthesis of Example 3 by substituting Intermediate 337C and the corresponding acid where appropriate. (10.4 mg, 0.018 mmol, 33% yield). ¹H NMR (400 MHz, DMSO-$d_6$) δ 8.73 (d, J=5.1 Hz, 1H), 8.22 (d, J=7.6 Hz, 1H), 8.18 (s, 1H), 7.86 (d, J=5.1 Hz, 1H), 7.69-7.52 (m, 2H), 4.46-4.39 (m, 1H), 3.62 (d, J=16.4 Hz, 2H), 2.09-2.01 (m, 1H), 1.88 (br. s., 6H), 1.82-1.68 (m, 6H), 1.54-1.36 (m, 6H), 1.08-0.97 (m, 2H), 0.90-0.71 (m, 6H). FXR $EC_{50}$ (nM) 380; MS (ESI) 570 (M+H).

The following compound was prepared according to the method described for the synthesis of Example 3 by substituting Intermediate 337C and the corresponding acid where appropriate.

| Ex. No. | Structure | MS (ESI) (M + H) | FXR $EC_{50}$ (nM) |
|---|---|---|---|
| 338 | ![structure] | 576 | 1365 |

338 ¹H NMR (400 MHz, DMSO-$d_6$) δ 8.73 (d, J = 5.1 Hz, 1H), 8.27-8.09 (m, 2H), 7.85 (d, J = 5.1 Hz, 1H), 7.67-7.52 (m, 2H), 4.44-4.43 (m, 1H), 3.68 (s, 2H), 2.96-2.78 (m, 2H), 2.75 (d, J = 7.3 Hz, 1H), 2.39-2.29 (m, 2H), 2.11-1.99 (m, 1H), 1.89-1.62 (m, 6H), 1.56-1.30 (m, 6H), 1.10-0.94 (m, 2H), 0.89-0.69 (m, 6H).

Example 339

N-((1-(3-cyclopropyl-1,2,4-oxadiazol-5-yl)-2-oxabicyclo[2.2.2]octan-4-yl)methyl)-3-fluoro-N-(3-(2-methoxypyridin-4-yl)phenyl)bicyclo[1.1.1]pentane-1-carboxamide (339)

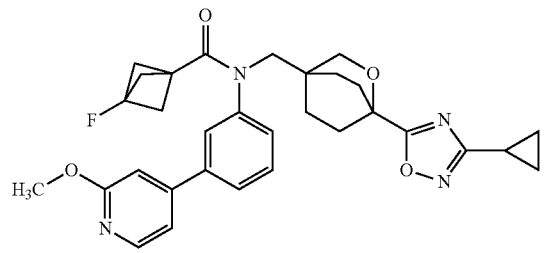

Step A. Intermediate 339A. Preparation of N-((1-(3-cyclopropyl-1,2,4-oxadiazol-5-yl)-2-oxabicyclo[2.2.2]octan-4-yl)methyl)-3-(2-methoxypyridin-4-yl)aniline

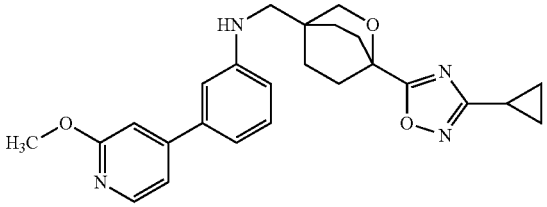 [SMILES: COc1cc(-c2cccc(NCC34CCC(c5nc(C6CC6)no5)(CC3)OC4)c2)ccn1]

The title compound was prepared according to the method described for the synthesis of Intermediate 1I by substituting Intermediate 222A and Intermediate 196K where appropriate. (22 mg, 0.046 mmol, 57% yield) as an off-white solid. MS (ESI) 433.4 (M+H).

Step B. Example 339. Preparation of N-((1-(3-cyclopropyl-1,2,4-oxadiazol-5-yl)-2-oxabicyclo[2.2.2]octan-4-yl)methyl)-3-fluoro-N-(3-(2-methoxypyridin-4-yl)phenyl) bicyclo[1.1.1]pentane-1-carboxamide The title compound was prepared according to the method described for the synthesis of Example 3 by substituting Intermediate 339A and the corresponding acid where appropriate (9.4 mg, 0.017 mmol, 34% yield). ¹H NMR (400 MHz, DMSO-$d_6$) δ 8.27 (d, J=5.1 Hz, 1H), 7.91 (s, 1H), 7.85 (d, J=7.8 Hz, 1H), 7.60 (t, J=7.8 Hz, 1H), 7.52 (d, J=8.6 Hz, 1H), 7.42 (dd, J=5.4, 1.5 Hz, 1H), 7.23 (s, 1H), 3.91 (s, 3H), 3.68 (br. s., 2H), 3.63 (s, 2H), 2.18-2.01 (m, 3H), 1.99-1.76 (m, 8H), 1.70 (br. s., 2H), 1.64-1.47 (m, 2H), 1.12-0.97 (m, 2H), 0.92-0.77 (m, 2H). FXR $EC_{50}$ (nM) 378; MS (ESI) 545 (M+H).

Example 340

N-((4-(3-cyclopropyl-1,2,4-oxadiazol-5-yl)bicyclo[2.2.2]octan-1-yl)methyl)-3-fluoro-N-(2'-methoxy-[4,4'-bipyridin]-2-yl)bicyclo[1.1.1]pentane-1-carboxamide (340)

Step A. Intermediate 340A. Preparation of 4-bromo-N-((4-(3-cyclopropyl-1,2,4-oxadiazol-5-yl)bicyclo[2.2.2]octan-1-yl)methyl)pyridin-2-amine

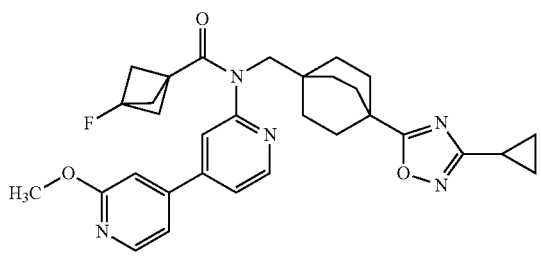

The title compound was prepared according to the method described for the synthesis of Intermediate 1I by substituting 4-bromopyridin-2-amine and Intermediate 4C where appropriate. (550 mg, 1.364 mmol, 67% yield) as gummy liquid. MS (ESI) 404 (M+H).

Step B. Intermediate 340B. Preparation of N-((4-(3-cyclopropyl-1,2,4-oxadiazol-5-yl) bicyclo[2.2.2]octan-1-yl)methyl)-2'-methoxy-[4,4'-bipyridin]-2-amine

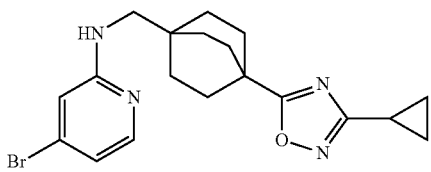 [SMILES: Brc1ccnc(NCC23CCC(c4nc(C5CC5)no4)(CC2)CC3)c1]

The title compound was prepared according to the method described for the synthesis of Example 149 by substituting Intermediate 340A and (2-methoxypyridin-4-yl)boronic acid where appropriate. (40 mg, 0.093 mmol, 75% yield), as brown gummy liquid. MS (ESI) 432 (M+H).

Step C. Example 340. Preparation of N-((4-(3-cyclopropyl-1,2,4-oxadiazol-5-yl) bicyclo[2.2.2]octan-1-yl)methyl)-3-fluoro-N-(2'-methoxy-[4,4'-bipyridin]-2-yl) bicyclo[1.1.1]pentane-1-carboxamide The title compound was prepared according to the method described for the synthesis of Example 3 by substituting Intermediate 340B and the corresponding acid where appropriate. (2 mg, 3.68 μmol, 11% yield). $^1$H NMR (400 MHz, DMSO-$d_6$) δ 8.67 (d, J=5.4 Hz, 1H), 8.35 (d, J=5.9 Hz, 1H), 8.01 (s, 1H), 7.89 (d, J=5.4 Hz, 1H), 7.53 (d, J=4.2 Hz, 1H), 7.40 (s, 1H), 3.94 (s, 3H), 3.72 (s, 2H), 2.07-2.00 (m, 1H), 1.89 (d, J=2.4 Hz, 6H), 1.50-1.30 (m, 6H), 1.17 (t, J=7.3 Hz, 6H), 1.07-0.95 (m, 2H), 0.82 (dd, J=4.5, 2.6 Hz, 2H); FXR $EC_{50}$ (nM)=398; MS (ESI) 544 (M+H).

Example 341

N-((4-(5-cyclopropyl-1,3,4-oxadiazol-2-yl)bicyclo[2.2.2]octan-1-yl)methyl)-3-fluoro-N-(3-(2-methoxypyrimidin-5-yl)phenyl)bicyclo[1.1.1]pentane-1-carboxamide

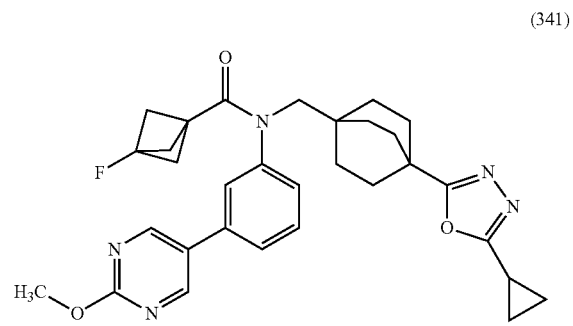 [SMILES: COc1ncc(-c2cccc(N(CC34CCC(c5nnc(C6CC6)o5)(CC3)CC4)C(=O)C34CC(F)(C3)C4)c2)cn1]

(341)

Step A. Intermediate 341A. Preparation of 3-bromo-N-((4-(5-cyclopropyl-1,3,4-oxadiazol-2-yl)bicyclo[2.2.2]octan-1-yl)methyl)aniline

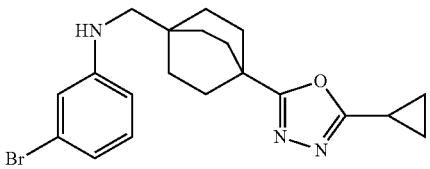 [SMILES: Brc1cccc(NCC23CCC(c4nnc(C5CC5)o4)(CC2)CC3)c1]

The title compound was prepared according to the method described for the synthesis of Intermediate 1I by substituting 3-bromoaniline and Intermediate 133D where appropriate. (120 mg, 0.298 mmol, 74% yield) as gummy liquid. MS (ESI) 404 (M+H).

Step B. Intermediate 341B. Preparation of N-(3-bromophenyl)-N-((4-(5-cyclopropyl-1,3,4-oxadiazol-2-yl)bicyclo[2.2.2]octan-1-yl)methyl)-3-fluoro-bicyclo[1.1.1]pentane-1-carboxamide

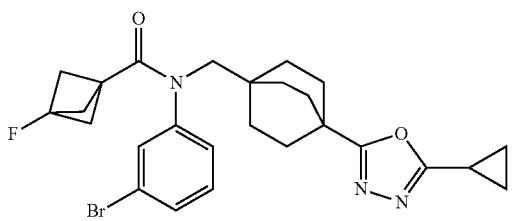 [SMILES: O=C(N(CC12CCC(c3nnc(C4CC4)o3)(CC1)CC2)c1cccc(Br)c1)C12CC(F)(C1)C2]

The title compound was prepared according to the method described for the synthesis of Example 3 by substituting Intermediate 341A and the corresponding acid where appropriate. (120 mg, 0.233 mmol, 85% yield) as gummy liquid. MS (ESI) 514 (M+H).

Step C. Example 341. Preparation of N-((4-(5-cyclopropyl-1,3,4-oxadiazol-2-yl) bicyclo[2.2.2]octan-1-yl)methyl)-3-fluoro-N-(3-(2-methoxypyrimidin-5-yl)phenyl) bicyclo[1.1.1]pentane-1-carboxamide The title compound was prepared according to the method described for the synthesis of Example 149 by substituting Intermediate 341B and (2-methoxypyrimidin-5-yl)boronic acid where appropriate. (8.9 mg, 0.015 mmol, 39% yield). $^1$H NMR (400 MHz, DMSO-$d_6$) δ 9.04 (s, 2H), 7.83 (s, 1H), 7.78 (d, J=7.6 Hz, 1H), 7.58 (t, J=7.9 Hz, 1H), 7.44 (d, J=8.1 Hz, 1H), 3.99 (s, 3H), 3.63 (br. s., 1H), 3.60-3.49 (m, 1H), 2.19-2.09 (m, 1H), 1.85 (s, 3H), 1.89 (s, 3H), 1.75 (d, J=7.1 Hz, 6H), 1.45 (br. s., 6H), 1.08 (dd, J=8.1, 2.4 Hz, 2H), 0.99-0.79 (m, 2H); FXR EC$_{50}$ (nM)=287; MS (ESI) 544 (M+H).

The following compounds were prepared according to the method described for the synthesis of Example 149 by substituting Intermediate 341F and the corresponding Boronic acids.

| Ex. No. | Name | MS (ESI) (M + H) | FXR EC$_{50}$ (nM) |
|---|---|---|---|
| 342 | | 543 | 120 |
| 343 | | 543 | 154 |
| 344 | | 605 | 293 |

342 $^1$H NMR (400 MHz, DMSO-$d_6$) δ 8.27 (d, J = 5.4 Hz, 1H), 7.93-7.76 (m, 2H), 7.58 (t, J = 7.8 Hz, 1H), 7.50 (d, J = 7.6 Hz, 1H), 7.41 (dd, J = 5.4, 1.5 Hz, 1H), 7.23 (s, 1H), 3.92 (s, 3H), 3.70-3.60 (m, 1H), 3.60-3.49 (m, 1H), 2.18-2.06 (m, 1H), 1.83 (s, 3H), 1.87 (s, 3H), 1.80-1.59 (m, 6H),1.55-1.25 (m, 6H), 1.14-1.02 (m, 2H), 0.98-0.82 (m, 2H)

-continued

| Ex. No. | Name | MS (ESI) (M + H) | FXR EC$_{50}$ (nM) |
|---|---|---|---|
| 343 | $^1$H NMR (400 MHz, DMSO-d$_6$) δ 8.58 (d, J = 2.2 Hz, 1H), 8.12 (dd, J = 8.4, 2.6 Hz, 1H), 7.80-7.65 (m, 2H), 7.54 (t, J = 7.8 Hz, 1H), 7.38 (d, J = 7.6 Hz, 1H), 6.95 (d, J = 8.6 Hz, 1H), 3.92 (s, 3H), 3.60 (d, J = 7.6 Hz, 2H), 2.20-2.08 (m, 1H), 1.85 (s, 3H), 1.88 (s, 3H), 1.81-1.62 (m, 6H), 1.46 (d, J = 8.3 Hz, 6H), 1.14-1.01 (m, 2H), 0.98-0.86 (m, 2H) | | |
| 344 | $^1$HNMR (400 MHz, DMSO-d$_6$) δ 9.91 (s, 1H), 7.74 (d, J = 8.8 Hz, 2H), 7.71-7.63 (m, 2H), 7.53 (t, J = 7.8 Hz, 2H), 7.39-7.27 (m, 2H), 3.59 (d, J = 10.3 Hz, 2H), 3.04 (s, 3H), 2.19-2.10 (m, 1H), 1.85 (s, 3H), 1.88 (s, 3H), 1.81-1.58 (m, 6H), 1.46 (d, J = 8.1 Hz, 6H), 1.12-1.02 (m, 2H), 0.98-0.87 (m, 2H) | | |

Example 345

N-((1-(4-(1-Cyanocyclopropyl)phenyl)-2-oxabicyclo[2.2.2]octan-4-yl)methyl)-3-fluoro-N-(4'-(methylsulfonamido)-[1,1'-biphenyl]-3-yl)bicyclo[1.1.1]pentane-1-carboxamide (345)

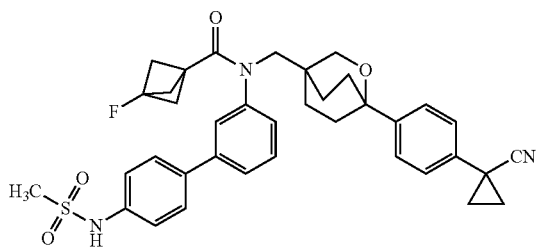

Step A. Intermediate 345A. Preparation of 1-(4-(4-(((3-bromophenyl)amino)methyl)-2-oxabicyclo[2.2.2]octan-1-yl)phenyl)cyclopropane-1-carbonitrile

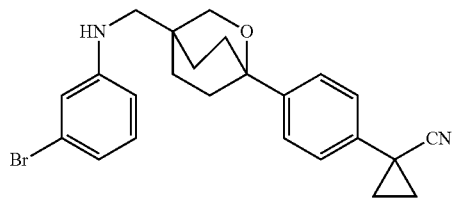 [SMILES: N#CC1(c2ccc(C34CCC(CNc5cccc(Br)c5)(CC3)CO4)cc2)CC1]

The title compound was prepared according to the method described for the synthesis of Intermediate 1I by substituting 3-bromoaniline and Intermediate 141E where appropriate. (250 mg, 0.57 mmol, 80% yield) as white solid. MS (ESI) 437 (M+H). $^1$H NMR (400 MHz, DMSO-d$_6$) δ 7.40 (d, J=8.1 Hz, 2H), 7.26 (d, J=8.3 Hz, 2H), 7.02-6.95 (m, 1H), 6.79 (s, 1H), 6.62 (t, J=6.0 Hz, 2H), 5.81 (t, J=5.7 Hz, 1H), 3.85 (s, 2H), 2.86 (d, J=5.9 Hz, 2H), 2.11-2.02 (m, 2H), 1.86-1.64 (m, 8H), 1.51-1.44 (m, 2H).

Step B. Intermediate 345B. Preparation of N-(3-bromophenyl)-N-((1-(4-(1-cyanocyclopropyl)phenyl)-2-oxabicyclo[2.2.2]octan-4-yl)methyl)-3-fluorobicyclo[1.1.1]pentane-1-carboxamide

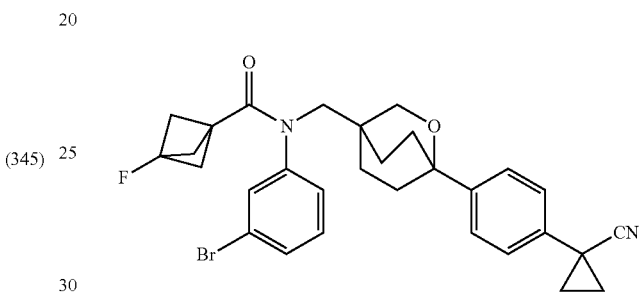

The title compound was prepared according to the method described for the synthesis of Example 3 by substituting Intermediate 345A and the corresponding acid where appropriate. (190 mg, 0.33 mmol, 73% yield) as white solid. $^1$H NMR (400 MHz, DMSO-d$_6$) δ 7.76 (t, J=1.8 Hz, 1H), 7.66-7.61 (m, 1H), 7.51-7.40 (m, 2H), 7.36-7.31 (m, 2H), 7.27-7.21 (m, 2H), 3.68 (s, 2H), 3.59 (br. s., 1H), 3.54 (br. s., 1H), 2.04-1.94 (m, 2H), 1.89 (br. s., 6H), 1.80-1.68 (m, 4H), 1.67-1.50 (m, 4H), 1.49-1.44 (m, 2H). MS (ESI) 549 (M+H).

Step C. Example 345. Preparation of N-((1-(4-(1-Cyanocyclopropyl)phenyl)-2-oxabicyclo[2.2.2]octan-4-yl)methyl)-3-fluoro-N-(4'-(methylsulfonamido)-[1,1'-biphenyl]-3-yl)bicyclo[1.1.1]pentane-1-carboxamide The title compound was prepared according to the method described for the synthesis of Example 149 by substituting Intermediate 345B and 4-(methylsulfonylamino)phenylboronic acid where appropriate. (9.3 mg, 0.015 mmol, 40% yield). $^1$H NMR (400 MHz, DMSO-d$_6$) δ 9.91 (s, 1H), 7.82-7.62 (m, 4H), 7.54 (t, J=8.2 Hz, 1H), 7.39 (d, J=8.6 Hz, 1H), 7.36-7.28 (m, 4H), 7.23 (d, J=8.6 Hz, 2H), 3.72 (br. s., 2H), 3.63 (d, J=4.2 Hz, 2H), 3.04 (s, 3H), 2.05-1.95 (m, 2H), 1.89-1.86 (m, 6H), 1.80-1.64 (m, 6H), 1.60 (d, J=11.0 Hz, 2H), 1.49-1.41 (m, 2H). FXR EC$_{50}$ (nM)=264. MS (ESI) 640 (M+H).

The following compounds were prepared according to the method described for the synthesis of Example 149 by substituting Intermediate 345B and the corresponding heteroaryl boronates.

| Ex. No. | Name | MS (ESI) (M + H) | FXR EC$_{50}$ (nM) |
|---|---|---|---|
| 346 | 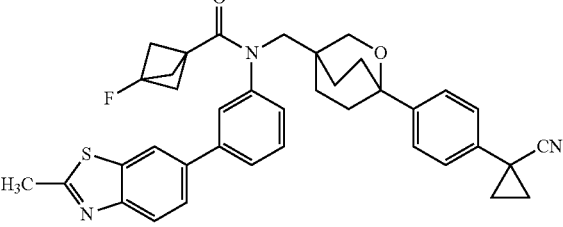 | 618 | 181 |
| 347 | 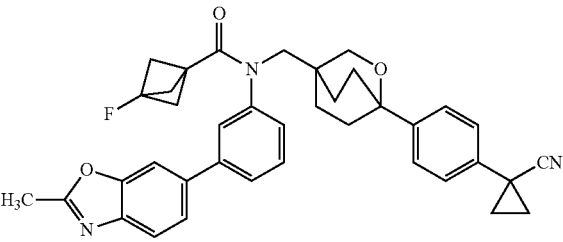 [SMILES: Cc1nc2ccc(-c3cccc(N(CC45CCC(c6ccc(C7(C#N)CC7)cc6)(CC4)OC5)C(=O)C45CC(F)(C4)C5)c3)cc2o1] | 602 | 123 |
| 348 | 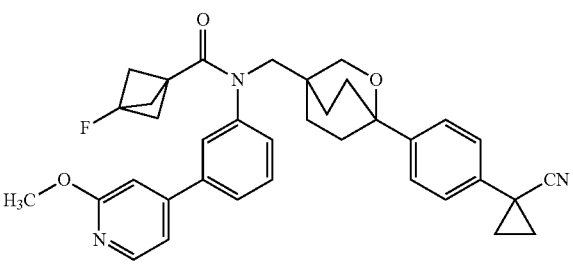 [SMILES: COc1cc(-c2cccc(N(CC34CCC(c5ccc(C6(C#N)CC6)cc5)(CC3)OC4)C(=O)C34CC(F)(C3)C4)c2)ccn1] | 558 | 237 |
| 349 | 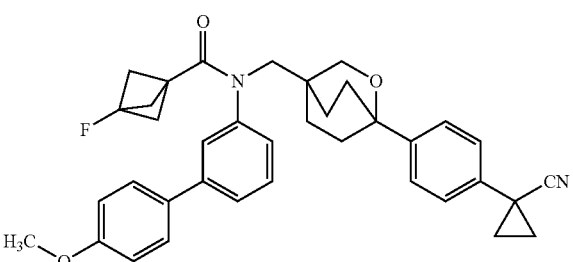 | 577 | 130 |
| 350 | 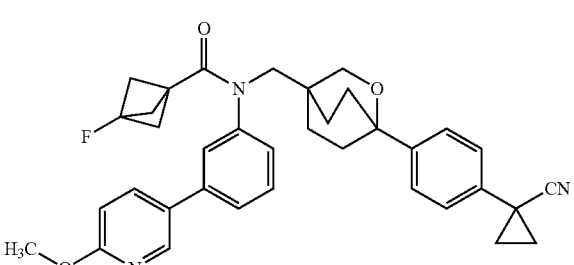 | 578 | 296 |
| 351 | 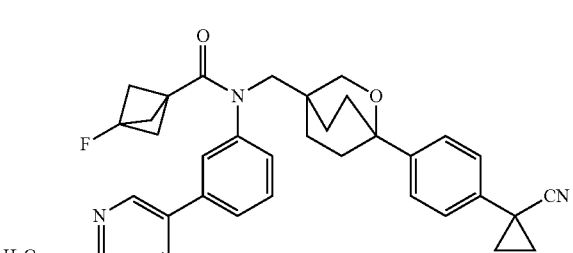 | 579 | 266 |

| Ex. No. | Name | MS (ESI) (M + H) | FXR EC$_{50}$ (nM) |
|---|---|---|---|
| 352 | 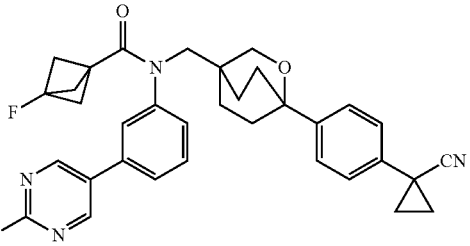 | 593 | 167 |

| | |
|---|---|
| 346 | $^1$H NMR (400 MHz, DMSO-d$_6$) δ 8.48 (d, J = 1.5 Hz, 1H), 8.01 (d, J = 8.6 Hz, 1H), 7.88 (dd, J = 8.6, 1.7 Hz, 1H), 7.85-7.74 (m, 2H), 7.58 (t, J = 7.7 Hz, 1H), 7.44 (d, J = 7.3 Hz, 1H), 7.39-7.28 (m, J = 8.3 Hz, 2H), 7.27-7.13 (m, J = 8.3 Hz, 2H), 3.80-3.65 (m, 3H), 3.65-3.52 (m, 1H), 2.84 (s, 3H), 2.08-1.81 (m, 8H), 1.79-1.64 (m, 6H), 1.59 (br. s., 2H), 1.49-1.38 (m, 2H) |
| 347 | $^1$H NMR (400 MHz, DMSO-d$_6$) δ 8.10 (s, 1H), 7.84-7.78 (m, 2H), 7.78-7.68 (m, 2H), 7.57 (t, J = 7.7 Hz, 1H), 7.43 (d, J = 8.6 Hz, 1H), 7.38-7.29 (m, J = 8.6 Hz, 2H), 7.27-7.14 (m, J = 8.6 Hz, 2H), 3.74 (br. s., 2H), 3.65 (d, J = 19.1 Hz, 2H), 2.65 (s, 3H), 2.05-1.83 (m, 8H), 1.80-1.62 (m, 6H), 1.59 (br. s., 2H), 1.49-1.42 (m, 2H) |
| 348 | $^1$H NMR (400 MHz, DMSO-d$_6$) δ 8.27 (d, J = 5.4 Hz, 1H), 7.90 (s, 1H), 7.85 (d, J = 7.8 Hz, 1H), 7.60 (t, J = 7.8 Hz, 1H), 7.53 (d, J = 8.3 Hz, 1H), 7.42 (dd, J = 5.4, 1.5 Hz, 1H), 7.38-7.29 (m, 2H), 7.28-7.14 (m, 3H), 3.97-3.85 (m, 3H), 3.72 (br. s., 2H), 3.69-3.54 (m, 2H), 2.06-1.94 (m, 2H), 1.89-1.85 (m, 6H), 1.80-1.63 (m, 6H), 1.58 (d, J = 8.6 Hz, 2H), 1.50-1.39 (m, 2H) |
| 349 | $^1$H NMR (400 MHz, DMSO-d$_6$) δ 7.81-7.59 (m, 4H), 7.52 (t, J = 7.8 Hz, 1H), 7.34 (d, J = 8.6 Hz, 3H), 7.23 (d, J = 8.6 Hz, 2H), 7.06 (d, J = 8.8 Hz, 2H), 3.82 (s, 3H), 3.73 (br. s., 2H), 3.62 (d, J = 6.1 Hz, 2H), 2.04-1.94 (m, 2H), 1.89 (d, J = 9.8 Hz, 6H), 1.80-1.64 (m, 6H), 1.60 (d, J = 9.3 Hz, 2H), 1.48-1.37 (m, 2H) |
| 350 | $^1$H NMR (400 MHz, DMSO-d$_6$) δ 8.60 (d, J = 2.4 Hz, 1H), 8.13 (dd, J = 8.7, 2.6 Hz, 1H), 7.81-7.67 (m, 2H), 7.56 (t, J = 7.8 Hz, 1H), 7.41 (d, J = 8.3 Hz, 1H), 7.38-7.28 (m, J = 8.6 Hz, 2H), 7.27-7.14 (m, J = 8.3 Hz, 2H), 6.95 (d, J = 8.6 Hz, 2H), 3.92 (s, 3H), 3.73 (br. s., 2H), 3.63 (d, J = 5.4 Hz, 2H), 2.04-1.94 (m, 2H), 1.87 (s, 3H), 1.90 (s, 3H), 1.79-1.63 (m, 6H), 1.59 (br. s., 2H),1.49-1.41 (m, 2H) |
| 351 | $^1$H NMR (400 MHz, DMSO-d$_6$) δ 9.05 (s, 2H), 7.88 (s, 1H), 7.80 (d, J = 7.3 Hz, 1H), 7.59 (t, J = 7.7 Hz, 1H), 7.47 (d, J = 7.8 Hz, 1H), 7.39-7.29 (m, J = 8.6 Hz, 2H), 7.29-7.14 (m, J = 8.6 Hz, 2H), 3.99 (s, 3H), 3.78-3.63 (m, 3H), 3.63-3.51 (m, 1H), 2.05-1.94 (m, 2H), 1.87 (s, 3H), 1.91 (s, 3H), 1.80-1.62 (m, 6H), 1.58 (br. s., 2H), 1.49-1.38 (m, 2H) |
| 352 | $^1$H NMR (400 MHz, DMSO-d$_6$) δ 9.03 (s, 2H), 7.87 (s, 1H), 7.80 (d, J = 8.3 Hz, 1H), 7.59 (t, J = 7.9 Hz, 1H), 7.46 (d, J = 9.0 Hz, 1H), 7.38-7.29 (m, J = 8.6 Hz, 2H), 7.28-7.15 (m, J = 8.3 Hz, 2H), 4.43 (q, J = 7.0 Hz, 2H), 3.73 (br. s., 2H), 3.69-3.53 (m, 2H), 2.07-1.94 (m, 3H), 1.94-1.79 (m, 6H), 1.79-1.62 (m, 6H), 1.58 (br. s., 2H), 1.50-1.42 (m, 2H), 1.38 (t, J = 7.1 Hz, 2H) |

Example 353

N-((1-(3-cyclopropyl-1,2,4-oxadiazol-5-yl)-2-oxabicyclo[2.2.2]octan-4-yl)methyl)-N-(3-(2-ethoxypyrimidin-5-yl)phenyl)-3-fluorobicyclo[1.1.1]pentane-1-carboxamide

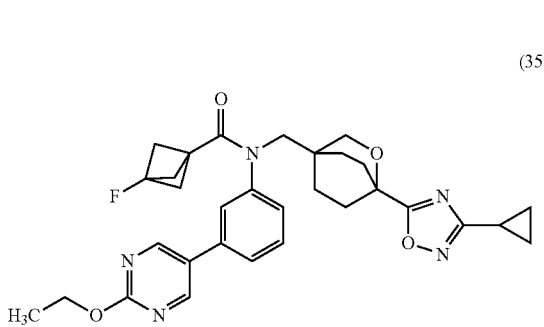

(353)

Step A. Intermediate 353A. Preparation of 3-romo-N-((1-(3-cyclopropyl-1,2,4-oxadiazol-5-yl)-2-oxabicyclo[2.2.2]octan-4-yl)methyl)aniline

The title compound was prepared according to the method described for the synthesis of Intermediate 1I by substituting 3-bromoaniline and Intermediate 196K where appropriate. (50 mg, 0.124 mmol, 77% yield) as gummy liquid. MS (ESI) 404 (M+H).

481

Step B. Intermediate 353B. Preparation of N-(3-bromophenyl)-N-((1-(3-cyclopropyl-1,2,4-oxadiazol-5-yl)-2-oxabicyclo[2.2.2]octan-4-yl)methyl)-3-fluorobicyclo[1.1.1]pentane-1-carboxamide

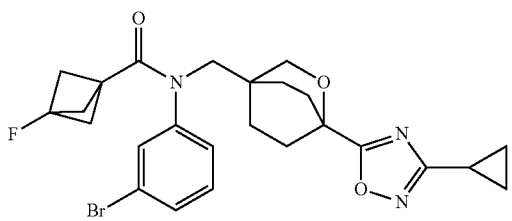

The title compound was prepared according to the method described for the synthesis of Example 3 by substituting Intermediate 353A and the corresponding acid where appropriate. (50 mg, 0.097 mmol, 78% yield) as gummy liquid. MS (ESI) 516 (M+H).

Step C. Example 353. Preparation of N-((1-(3-cyclopropyl-1,2,4-oxadiazol-5-yl)-2-oxabicyclo[2.2.2]octan-4-yl)methyl)-N-(3-(2-ethoxypyrimidin-5-yl)phenyl)-3-fluorobicyclo[1.1.1]pentane-1-carboxamide The title compound was prepared according to the method described for the synthesis of Example 149 by substituting Intermediate 353B and (2-ethoxypyrimidin-5-yl)boronic acid where appropriate. (1.5 mg, 2.68 μmol, 7% yield). $^1$H NMR (400 MHz, DMSO-$d_6$) δ 9.03 (s, 2H), 7.87 (s, 1H), 7.80 (d, J=7.6 Hz, 1H), 7.58 (t, J=7.9 Hz, 1H), 7.46 (d, J=7.8 Hz, 1H), 4.43 (q, J=7.1 Hz, 2H), 3.69 (s, 2H), 3.63 (s, 2H), 2.18-2.03 (m, 3H), 2.01-1.77 (m, 8H), 1.76-1.64 (m, 2H), 1.60 (d, J=6.8 Hz, 2H), 1.38 (t, J=7.1 Hz, 3H), 1.08-0.98 (m, 2H), 0.91-0.78 (m, 2H). FXR EC$_{50}$ (nM)=328. MS (ESI) 560 (M+H).

Example 354

N-(4'-(Cyclopropanesulfonamido)-[1,1'-biphenyl]-3-yl)-3-fluoro-N-((4-(4-(trifluoromethyl)pyridin-2-yl)bicyclo[2.2.2]octan-1-yl)methyl)bicyclo[1.1.1]pentane-1-carboxamide (354)

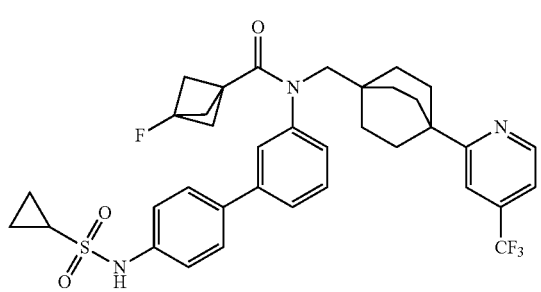

482

Step A. Intermediate 354A. Preparation of 3-bromo-N-((4-(4-(trifluoromethyl)pyridin-2-yl)bicyclo[2.2.2]octan-1-yl)methyl)aniline

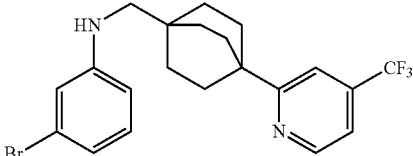

The title compound was prepared according to the method described for the synthesis of Intermediate 1I by substituting 3-bromoaniline and Intermediate 240C where appropriate. (450 mg, 1.01 mmol, 96% yield) as a brown solid. MS (ESI) 439 (M+H).

Step B. Intermediate 354B. Preparation of N-(3-bromophenyl)-3-fluoro-N-((4-(4-(trifluoromethyl)pyridin-2-yl)bicyclo[2.2.2]octan-1-yl)methyl)bicyclo[1.1.1]pentane-1-carboxamide

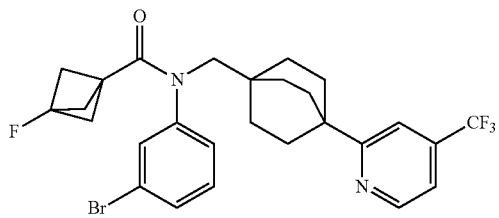 [SMILES: O=C(N(CC12CCC(c3cc(C(F)(F)F)ccn3)(CC1)CC2)c1cccc(Br)c1)C12CC(F)(C1)C2]

The title compound was prepared according to the method described for the synthesis of Example 3 by substituting Intermediate 354A and the corresponding acid where appropriate. (400 mg, 0.73 mmol, 71% yield). $^1$H NMR (400 MHz, DMSO-$d_6$) δ 8.76 (d, J=5.0 Hz, 1H), 7.72-7.68 (m, 1H), 7.62 (dt, J=6.9, 2.1 Hz, 1H), 7.58-7.52 (m, 2H), 7.48-7.41 (m, 2H), 3.60 (br. s., 1H), 3.53 (br. s., 1H), 1.93-1.84 (m, 6H), 1.84-1.76 (m, 6H), 1.49-1.38 (m, 6H). MS (ESI) 553 (M+H).

Step C. Example 354. Preparation of N-(4'-(Cyclopropanesulfonamido)-[1,1'-biphenyl]-3-yl)-3-fluoro-N-((4-(4-(trifluoromethyl)pyridin-2-yl)bicyclo[2.2.2]octan-1-yl)methyl) bicyclo[1.1.1]pentane-1-carboxamide The title compound was prepared according to the method described for the synthesis of Example 149 by substituting Intermediate 354B and (4-(cyclopropanesulfonamido)phenyl)boronic acid where appropriate. (18.4 mg, 0.03 mmol, 61% yield). $^1$H NMR (400 MHz, DMSO-$d_6$) δ 9.88 (br. s., 1H), 8.76 (d, J=4.9 Hz, 1H), 7.80-7.62 (m, 4H), 7.61-7.46 (m, 3H), 7.44-7.29 (m, 3H), 3.63 (d, J=7.3 Hz, 2H), 2.74-2.63 (m, 1H), 2.00-1.70 (m, 12H), 1.60-1.37 (m, 6H), 1.07-0.87 (m, 4H). FXR EC$_{50}$ (nM)=489. MS (ESI) 668 (M+H).

The following compounds were prepared according to the method described for the synthesis of Example 149 by substituting Intermediate 354B and the corresponding boronic acids.

| Ex. No. | Name | MS (ESI) (M + H) | FXR EC$_{50}$ (nM) |
|---|---|---|---|
| 355 | 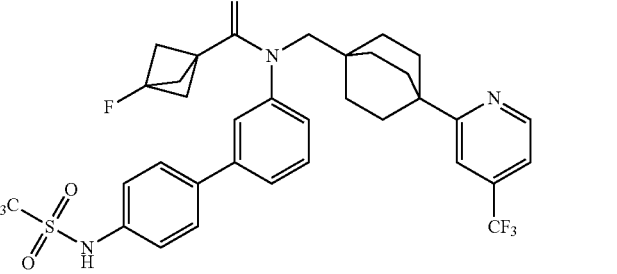 | 642 | 780 |
| 356 | 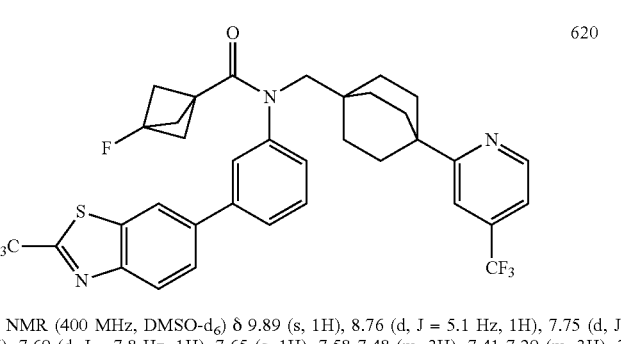 | 620 | 800 |

355 $^1$H NMR (400 MHz, DMSO-d$_6$) δ 9.89 (s, 1H), 8.76 (d, J = 5.1 Hz, 1H), 7.75 (d, J = 8.6 Hz, 2H), 7.69 (d, J = 7.8 Hz, 1H), 7.65 (s, 1H), 7.58-7.48 (m, 3H), 7.41-7.29 (m, 3H), 3.63 (br. s., 2H), 3.04 (s, 3H), 1.99-1.71 (m, 12H), 1.58-1.40 (m, 6H)

356 $^1$H NMR (400 MHz, DMSO-d$_6$) δ 8.76 (d, J = 4.9 Hz, 1H), 8.47 (d, J = 1.5 Hz, 1H), 8.01 (d, J = 8.6 Hz, 1H), 7.86 (dd, J = 8.6, 1.7 Hz, 1H), 7.83-7.73 (m, 2H), 7.64-7.47 (m, 3H), 7.41 (d, J = 8.6 Hz, 1H), 3.71 (d, J = 13.4 Hz, 1H), 3.59 (d, J = 13.2 Hz, 1H), 2.84 (s, 3H), 2.01-1.74 (m, 12H), 1.50 (d, J = 5.6 Hz, 6H)

Example 357

N-((4-(3-(tert-butyl)-1,2,4-oxadiazol-5-yl)bicyclo[2.2.2]octan-1-yl)methyl)-N-(3-(2-ethoxypyrimidin-5-yl)phenyl)-3-fluorobicyclo[1.1.1]pentane-1-carboxamide

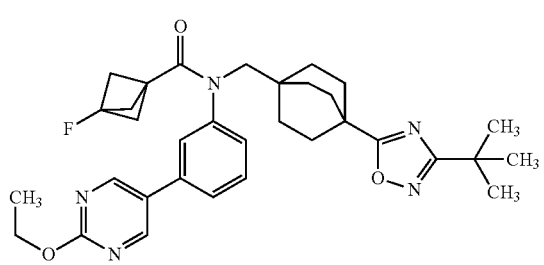

(357)

Step A. Intermediate 357A. Preparation of methyl 4-(((3-bromophenyl)amino) methyl)bicyclo[2.2.2]octane-1-carboxylate

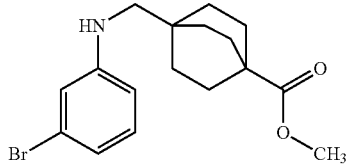

The title compound was prepared according to the method described for the synthesis of Intermediate 1I by substituting 3-bromoaniline and Intermediate 88B where appropriate. (6.4 g, 18.17 mmol, 79% yield) as brown gummy liquid. MS (ESI) 353 (M+H).

Step B. Intermediate 357B. Preparation of methyl 4-((N-(3-bromophenyl)-3-fluorobicyclo[1.1.1]pentane-1-carboxamido)methyl)bicyclo[2.2.2]octane-1-carboxylate

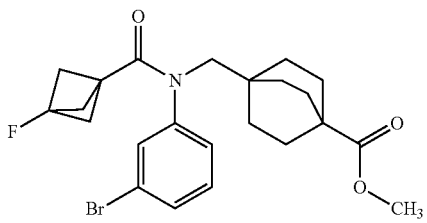 [SMILES: COC(=O)C12CCC(CN(C(=O)C34CC(F)(C3)C4)c3cccc(Br)c3)(CC1)CC2]

The title compound was prepared according to the method described for the synthesis of Example 3 by substituting Intermediate 357A and the corresponding acid where appropriate. (2.5 g, 5.38 mmol, 54% yield) as brown gummy liquid along with minor impurities. MS (ESI) 464 (M+H).

Step C. Intermediate 357C. Preparation of 4-((N-(3-bromophenyl)-3-fluorobicyclo[1.1.1]pentane-1-carboxamido)methyl)bicyclo[2.2.2]octane-1-carboxylic acid

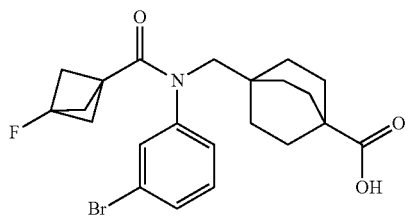 [SMILES: O=C(O)C12CCC(CN(C(=O)C34CC(F)(C3)C4)c3cccc(Br)c3)(CC1)CC2]

The title compound was prepared according to the method described for the synthesis of Intermediate 175B by substituting Intermediate 357B where appropriate. (2.1 g, 4.66 mmol, 98% yield) as brown gummy liquid. MS (ESI) 452 (M+H).

Step D. Intermediate 357D. Preparation of N-(3-bromophenyl)-N-((4-(3-(tert-butyl)-1,2,4-oxadiazol-5-yl)bicyclo[2.2.2]octan-1-yl)methyl)-3-fluorobicyclo[1.1.1]pentane-1-carboxamide

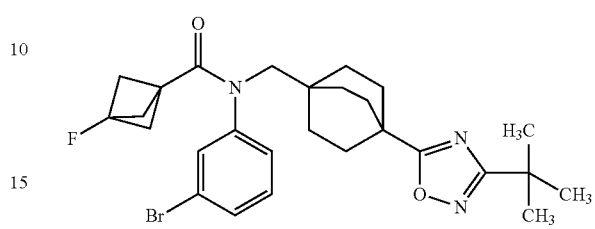

The title compound was prepared according to the method described for the synthesis of Intermediate 3A by substituting Intermediate 357C and (Z)—N'-hydroxypivalimidamide where appropriate. (200 mg, 0.377 mmol, 68% yield) as brown gummy liquid. MS (ESI) 530 (M+H).

Step E. Example 357. Preparation of N-((4-(3-(tert-butyl)-1,2,4-oxadiazol-5-yl) bicyclo[2.2.2]octan-1-yl)methyl)-N-(3-(2-ethoxypyrimidin-5-yl)phenyl)-3-fluorobicyclo [1.1.1]pentane-1-carboxamide The title compound was prepared according to the method described for the synthesis of Example 149 by substituting Intermediate 357D and (2-ethoxypyrimidin-5-yl)boronic acid where appropriate. (11.6 mg, 0.020 mmol, 36% yield). $^1$H NMR (400 MHz, DMSO-d$_6$) δ 9.02 (s, 2H), 7.81 (s, 1H), 7.78 (d, J=7.6 Hz, 1H), 7.57 (t, J=7.8 Hz, 1H), 7.43 (d, J=7.3 Hz, 1H), 4.43 (q, J=7.1 Hz, 2H), 3.61 (d, J=8.6 Hz, 2H), 2.00-1.71 (m, 12H), 1.55-1.41 (m, 6H), 1.38 (t, J=7.1 Hz, 3H), 1.32-1.17 (m, 9H). FXR EC$_{50}$ (nM)=83. MS (ESI) 574 (M+H).

The following compounds were prepared according to the method described for the synthesis of Example 149 by substituting Intermediate 357D and the corresponding aryl/hetero aryl boronates.

| Ex. No. | Name | MS (ESI) (M + H) | FXR EC$_{50}$ (nM) |
| --- | --- | --- | --- |
| 358 | | 570 | 154 |

| Ex. No. | Name | MS (ESI) (M + H) | FXR EC$_{50}$ (nM) |
|---|---|---|---|
| 359 | | 572 | 151 |
| 360 | | 573 | 147 |
| 361 | | 621 | 843 |
| 362 | | 599 | 204 |

358 $^1$H NMR (400 MHz, DMSO-d$_6$) δ 9.04 (s, 2H), 7.88-7.81 (m, 1H), 7.80 (d, J = 7.6 Hz, 1H), 7.59 (t, J = 7.8 Hz, 1H), 7.50-7.31 (m, 1H), 3.61 (d, J = 2.9 Hz, 2H), 2.32-2.23 (m, 1H), 1.99-1.70 (m, 12H), 1.56-1.33 (m, 6H), 1.30-1.19 (m, 9H), 1.18-0.97 (m, 4H)

359 $^1$H NMR (400 MHz, DMSO-d$_6$) δ 7.75-7.63 (m, 3H), 7.63-7.57 (m, 1H), 7.50 (t, J = 7.8 Hz, 1H), 7.31 (d, J = 7.8 Hz, 1H), 7.11-6.97 (m, 2H), 4.09 (q, J = 7.0 Hz, 2H), 3.60 (s, 2H), 2.00-1.71 (m, 12H), 1.58-1.39 (m, 6H), 1.36 (t, J = 7.0 Hz, 3H), 1.31-1.18 (m, 9H)

360 $^1$H NMR (400 MHz, DMSO-d$_6$) δ 8.56 (d, J = 2.2 Hz, 1H), 8.10 (dd, J = 8.7, 2.6 Hz, 1H), 7.77-7.62 (m, 2H), 7.54 (t, J = 8.1 Hz, 1H), 7.42-7.31 (m, 1H), 6.91 (d, J = 8.6 Hz, 1H), 4.37 (q, J = 7.1 Hz, 2H), 3.60 (s, 2H), 1.95-1.72 (m, 12H), 1.57-1.40 (m, 6H), 1.35 (t, J = 7.1 Hz, 3H), 1.30-1.15 (m, 9H)

361 $^1$H NMR (400 MHz, DMSO-d$_6$) δ 9.89 (s, 1H), 7.74 (d, J = 8.8 Hz, 2H), 7.71-7.59 (m, 2H), 7.53 (t, J = 7.8 Hz, 1H), 7.42-7.25 (m, 3H), 3.60 (s, 2H), 3.04 (s, 3H), 1.98-1.73 (m, 12H), 1.58-1.37 (m, 6H), 1.35-1.15 (m, 9H)

362 $^1$H NMR (400 MHz, DMSO-d$_6$) δ 8.46 (d, J = 1.5 Hz, 1H), 8.00 (d, J = 8.6 Hz, 1H), 7.86 (dd, J = 8.6, 2.0 Hz, 1H), 7.83-7.70 (m, 2H), 7.57 (t, J = 7.8 Hz, 1H), 7.40 (d, J = 8.1 Hz, 1H), 3.68 (d, J = 13.9 Hz, 1H), 3.58 (d, J = 13.9 Hz, 1H), 2.83 (s, 3H), 2.00-1.71 (m, 12H), 1.61-1.45 (m, 6H), 1.33-1.15 (m, 9H)

Example 363

N-((4-(3-(tert-butyl)-1,2,4-oxadiazol-5-yl)bicyclo[2.2.2]octan-1-yl)methyl)-3-fluoro-N-(3-(2-methoxypyrimidin-5-yl)phenyl)bicyclo[1.1.1]pentane-1-carboxamide (363)

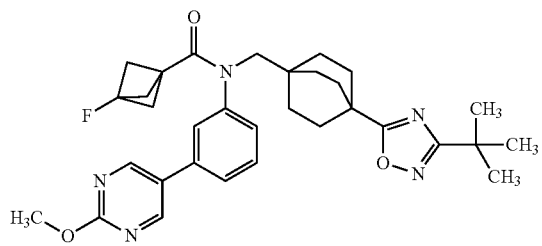

Step A. Intermediate 363A. Preparation of N-((4-(3-(tert-butyl)-1,2,4-oxadiazol-5-yl) bicyclo[2.2.2]octan-1-yl)methyl)-N-(3-(5,5-dimethyl-1,3,2-dioxaborinan-2-yl)phenyl)-3-fluorobicyclo[1.1.1]pentane-1-carboxamide

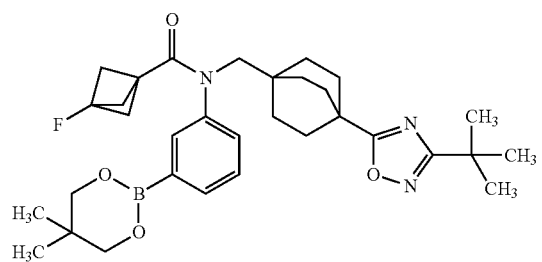 [SMILES: CC1(C)COB(c2cccc(N(CC34CCC(c5nc(C(C)(C)C)no5)(CC3)CC4)C(=O)C34CC(F)(C3)C4)c2)OC1]

The title compound was prepared according to the method described for the synthesis of Intermediate 149C by substituting Intermediate 357D where appropriate. (150 mg, 0.27 mmol, 83% yield) as white solid. MS (ESI) 496 (M+H) (Boronic acid mass).

Step B. Example 363. Preparation of N-((4-(3-(tert-butyl)-1,2,4-oxadiazol-5-yl) bicyclo[2.2.2]octan-1-yl)methyl)-3-fluoro-N-(3-(2-methoxypyrimidin-5-yl) phenyl) bicyclo[1.1.1]pentane-1-carboxamide The title compound was prepared according to the method described for the synthesis of Example 149 by substituting Intermediate 363A and 5-bromo-2-methoxypyrimidine where appropriate. (6.7 mg, 0.012 mmol, 22% yield). $^1$H NMR (400 MHz, DMSO-$d_6$) δ 9.04 (s, 2H), 7.82 (s, 1H), 7.78 (d, J=7.3 Hz, 1H), 7.58 (t, J=7.8 Hz, 1H), 7.44 (d, J=9.0 Hz, 1H), 3.99 (s, 3H), 3.61 (d, J=7.8 Hz, 2H), 1.99-1.69 (m, 12H), 1.59-1.36 (m, 6H), 1.35-1.17 (m, 9H). FXR EC$_{50}$ (nM)=70. MS (ESI) 560 (M+H).

The following compounds were prepared according to the method described for the synthesis of Example 149 by substituting Intermediate 363A and the corresponding aryl/hetero aryl halides.

| Ex. No. | Name | MS (ESI) (M + H) | FXR EC$_{50}$ (nM) |
|---|---|---|---|
| 364 | 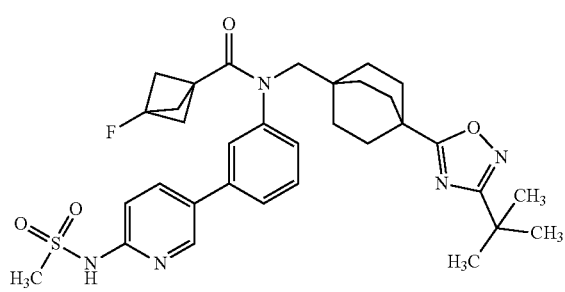 [SMILES: CC(C)(C)c1noc(C23CCC(CN(C(=O)C45CC(F)(C4)C5)c4cccc(-c5ccc(NS(C)(=O)=O)nc5)c4)(CC2)CC3)n1] | 622 | 509 |
| 365 | 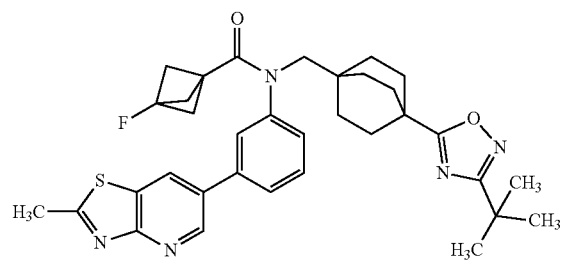 [SMILES: Cc1nc2ncc(-c3cccc(N(CC45CCC(c6nc(C(C)(C)C)no6)(CC4)CC5)C(=O)C45CC(F)(C4)C5)c3)cc2s1] | 600 | 84 |

-continued
| Ex. No. | Name | MS (ESI) (M + H) | FXR EC$_{50}$ (nM) |
|---|---|---|---|
| 366 | 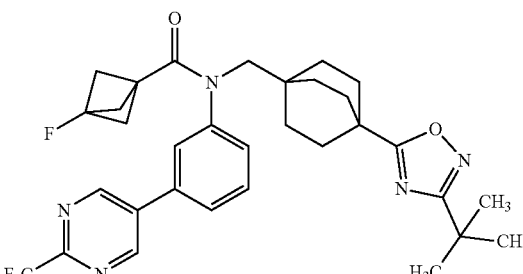 | 598 | 454 |
| 367 | 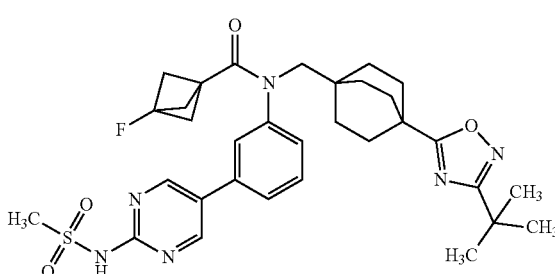 | 623 | 645 |
| 368 | 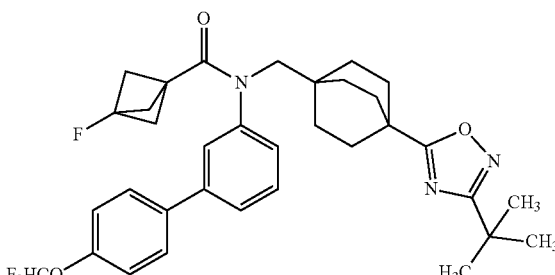 | 594 | 135 |
| 369 | 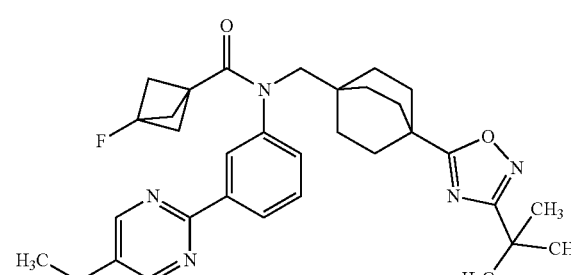 | 560 | 68 |
| 370 | 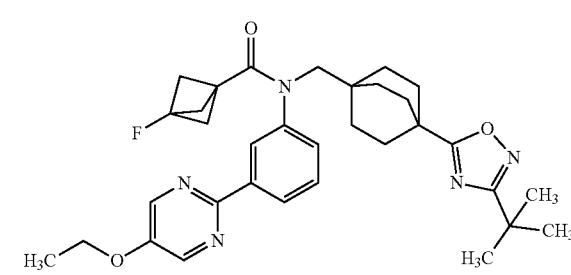 [SMILES: CCOc1cnc(-c2cccc(N(CC34CCC(c5nc(C(C)(C)C)no5)(CC3)CC4)C(=O)C34CC(F)(C3)C4)c2)nc1] | 574 | 121 |

| Ex. No. | Name | MS (ESI) (M + H) | FXR EC$_{50}$ (nM) |
|---|---|---|---|
| 371 | 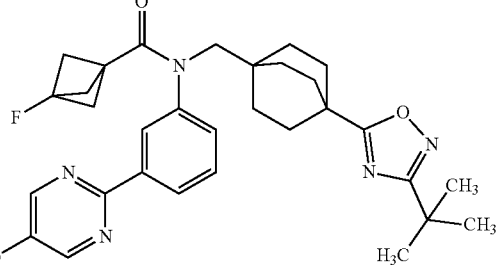 | 596 | 45 |
| 372 | 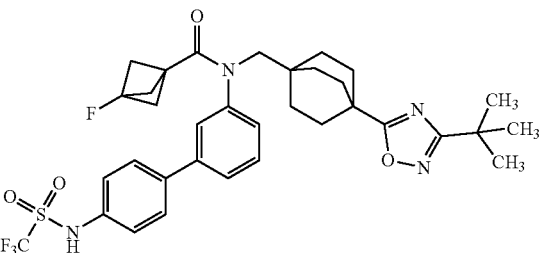 | 675 | 131 |
| 373 | 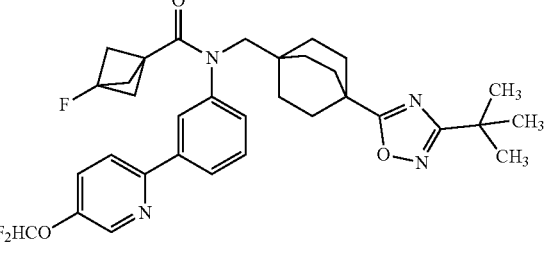 | 595 | 88 |

364 $^1$H NMR (400 MHz, DMSO-d$_6$) δ 10.87 (s, 1H), 8 68 (s, 1H), 8.15 (dd, J = 8.7, 2.6 Hz, 1H), 7.82-7.67 (m, 2H), 7.56 (t, J = 8.1 Hz, 1H), 7.46-7.37(m, 1H), 7.10 (d, J = 8.8 Hz, 1H), 3.91 (s, 3H), 3.61 (s, 2H), 1.97-1.69 (m, 12H), 1.57-1.37 (m, 6H), 1.34-1.22 (m, 9H)

365 $^1$H NMR (400 MHz, DMSO-d$_6$) δ 9.03 (d, J = 2.2 Hz, 1H), 8.94 (d, J = 2.2 Hz, 1H), 7.92-7.81 (m, 2H), 7.61 (t, J = 8.2 Hz, 1H), 7.47 (d, J = 8.6 Hz, 1H), 3.64 (d, J = 19.3 Hz, 2H), 2.91 (s, 3H), 2.00-1.71 (m, 12H), 1.49 (d, J = 7.3 Hz, 6H), 1.33-1.22 (m, 9H)

366 $^1$H NMR (400 MHz, DMSO-d$_6$) δ 9.50 (s, 2H), 8.05-7.99 (m, 1H), 7.97 (d, J = 7.8 Hz, 1H), 7.73-7.63 (m, 1H), 7.58 (d, J = 8.8 Hz, 1H), 3.63 (d, J = 14.9 Hz, 2H), 2.02-1.72 (m, 12H), 1.57-1.37 (m, 6H), 1.35-1.18 (m, 9H)

367 $^1$H NMR (400 MHz, DMSO-d$_6$) δ 11.49 (br. s., 1H), 9.05 (s, 2H), 7.83 (s, 1H), 7.80 (d, J = 8.3 Hz, 1H), 7.59 (t, J = 7 8 Hz, 1H), 7.45 (d, J = 7.8 Hz, 1H), 3.62 (br. s., 2H), 3.42 (s, 3H), 1.99-1.73 (m, 12H), 1.58-1.38 (m, 6H), 1.33-1.21 (m, 9H)

368 $^1$H NMR (400 MHz, DMSO-d$_6$) δ 7.89-7.77 (m, 2H), 7.76-7.64 (m, 2H), 7.55 (t, J = 7.7 Hz, 1H), 7.44-7.34 (m, 1H), 7.34-7.20 (m, 3H), 3.61 (d, J = 10.5 Hz, 2H), 2.01-1.71 (m, 12H), 1.57-1.35 (m, 6H), 1.33-1.16 (m, 9H)

369 $^1$H NMR (400 MHz, DMSO-d$_6$) δ 8.70 (s, 2H), 8.31 (dt, J = 7.8, 1.3 Hz, 1H), 8.19 (t, J = 1.8 Hz, 1H), 7.60 (t, J = 7.8 Hz, 1H), 7.51 (ddd, J = 7.8, 2.2, 1.2 Hz, 1H), 3.98 (s, 3H), 3.66 (br. s., 1H), 3.58 (br. s., 1H), 1.88 (d, J = 9.5 Hz, 6H), 1.84-1.62 (m, 6H), 1.59-1.34 (m, 6H), 1.33-1.18 (m, 9H)

370 $^1$H NMR (400 MHz, DMSO-d$_6$) δ 8.68 (s, 2H), 8.40-8.24 (m, 1H), 8.18 (t, J = 1.8 Hz, 1H), 7.65-7.56 (m, 1H), 7.53-7.43 (m, 1H), 4.28 (q, J = 6.8 Hz, 2H), 3.65 (br. s., 1H), 3.58 (br. s., 1H), 1.88 (d, J = 8.8 Hz, 6H), 1.84-1.60 (m, 6H), 1.57-1.32 (m, 9H), 1.31-1.12 (m, 9H)

371 $^1$H NMR (400 MHz, DMSO-d$_6$) δ 8.93 (s, 2H), 8.36 (dt, J = 7.6, 1.4 Hz, 1H), 8.24 (t, J = 1.7 Hz, 1H), 7.69-7.50 (m, 2H), 7.43 (s, 1H), 3.66 (br. s., 1H), 3.59 (br. s., 1H), 1.89 (br. s., 6H), 1.86-1.61 (m, 6H), 1.57-1.36 (m, 6H), 1.32-1.17 (m, 9H)

372 $^1$H NMR (400 MHz, DMSO-d$_6$) δ 7.79 (d, J = 8.8 Hz, 2H), 7.75-7.64 (m, 2H), 7.54 (t, J = 7.8 Hz, 2H), 7.44-7.30 (m, 3H), 3.60 (d, J = 8.8 Hz, 2H), 1.96-1.72 (m, 12H), 1.55-1.39 (m, 6H), 1.31-1.19 (m, 9H)

373 $^1$H NMR (400 MHz, DMSO-d$_6$) δ 8.61 (d, J = 2.7 Hz, 1H), 8.17 (d, J = 8.8 Hz, 1H), 8.09 (d, J = 7.8 Hz, 1H), 8.05 (t, J = 1.8 Hz, 1H), 7.80 (dd, J = 8.8, 2.9 Hz, 1H), 7.65-7.52 (m, 1H), 7.52-7.42 (m, 1H), 7.38 (s, 1H), 3.62 (br. s., 2H), 1.88 (br. s., 6H), 1.85-1.59 (m, 6H), 1.56-1.33 (m, 6H), 1.32-1.17 (m, 9H)

Example 374

N-(3-(2-ethoxypyrimidin-5-yl)phenyl)-3-fluoro-N-((4-(3-isopropyl-1,2,4-oxadiazol-5-yl) bicyclo[2.2.2]octan-1-yl)methyl)bicyclo[1.1.1]pentane-1-carboxamide (374)

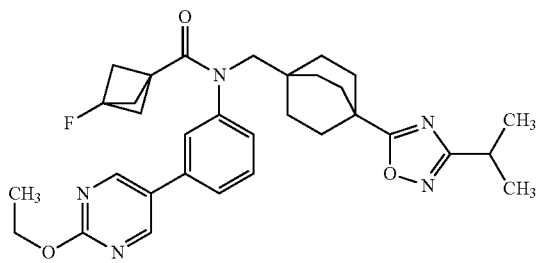

Step A. Intermediate 374A. Preparation of N-(3-bromophenyl)-3-fluoro-N-((4-(3-isopropyl-1,2,4-oxadiazol-5-yl)bicyclo[2.2.2]octan-1-yl)methyl)bicyclo[1.1.1]pentane-1-carboxamide

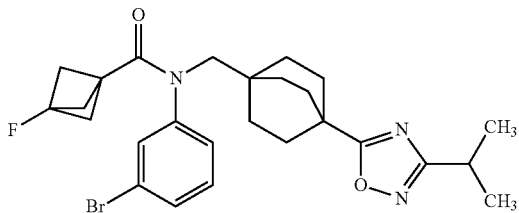 [SMILES: CC(C)c1noc(C23CCC(CN(C(=O)C45CC(F)(C4)C5)c4cccc(Br)c4)(CC2)CC3)n1]

The title compound was prepared according to the method described for the synthesis of Intermediate 3A by substituting Intermediate 357C and (Z)—N'-hydroxyisobutyrimidamide where appropriate. (160 mg, 0.310 mmol, 70% yield) as gray gummy liquid along with minor impurities. MS (ESI) 518 (M+H).

Step B. Example 374. Preparation of N-(3-(2-ethoxypyrimidin-5-yl)phenyl)-3-fluoro-N-((4-(3-isopropyl-1,2,4-oxadiazol-5-yl)bicyclo[2.2.2]octan-1-yl)methyl) bicyclo[1.1.1]pentane-1-carboxamide The title compound was prepared according to the method described for the synthesis of Example 149 by substituting Intermediate 374A and (2-ethoxypyrimidin-5-yl)boronic acid where appropriate. (11 mg, 0.020 mmol, 34% yield). $^1$H NMR (400 MHz, DMSO-$d_6$) δ 9.02 (s, 2H), 7.82 (s, 1H), 7.78 (d, J=7.6 Hz, 1H), 7.57 (t, J=7.8 Hz, 1H), 7.43 (d, J=7.8 Hz, 1H), 4.43 (q, J=6.9 Hz, 2H), 3.61 (d, J=13.7 Hz, 2H), 2.99 (dt, J=13.8, 7.0 Hz, 1H), 1.99-1.71 (m, 12H), 1.56-1.40 (m, 6H), 1.38 (t, J=7.0 Hz, 3H), 1.22 (d, J=6.8 Hz, 6H). FXR EC$_{50}$ (nM)=44. MS (ESI) 560 (M+H).

The following compounds were prepared according to the method described for the synthesis of Example 149 by substituting Intermediate 374A and the corresponding aryl/hetero aryl boronates/boronic acids.

| Ex. No. | Name | MS (ESI) (M + H) | FXR EC$_{50}$ (nM) |
|---|---|---|---|
| 375 | [structure] | 558 | 61 |
| 376 | [structure] | 607.3 | 32 |

| Ex. No. | Name | MS (ESI) (M + H) | FXR EC$_{50}$ (nM) |
|---|---|---|---|
| 377 | 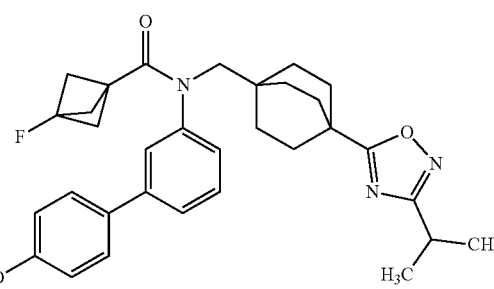 | 544 | 52 |
| 378 | 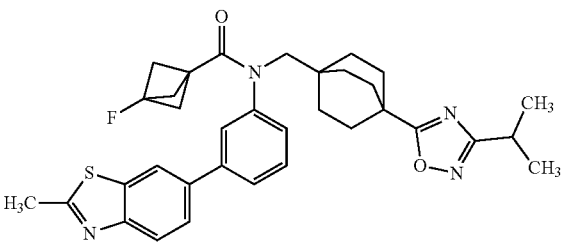 [SMILES: Cc1nc2ccc(-c3cccc(N(CC45CCC(c6nc(C(C)C)no6)(CC4)CC5)C(=O)C45CC(F)(C4)C5)c3)cc2s1] | 585 | 53 |
| 379 | 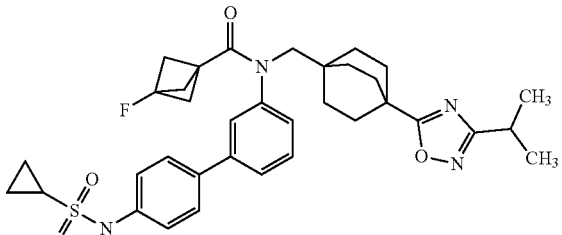 | 633 | 132 |
| 380 | 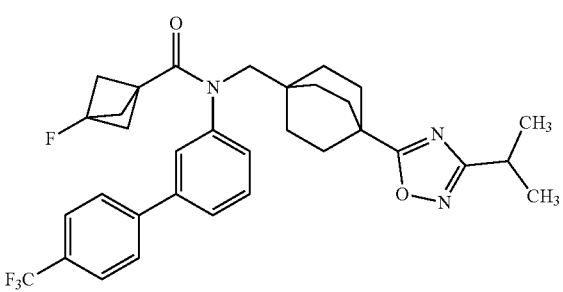 [SMILES: CC(C)c1noc(C23CCC(CN(C(=O)C45CC(F)(C4)C5)c4cccc(-c5ccc(C(F)(F)F)cc5)c4)(CC2)CC3)n1] | 582 | 283 |
| 381 | 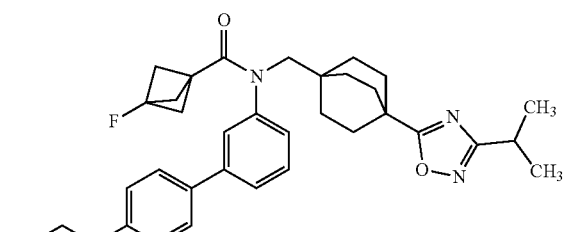 | 559 | 40 |

| Ex. No. | Name | MS (ESI) (M + H) | FXR EC$_{50}$ (nM) |
|---|---|---|---|
| 382 | | 545 | 98 |

375 $^1$H NMR (400 MHz, DMSO-d$_6$) δ 7.72-7.59 (m, 4H), 7.50 (t, J = 7.8 Hz, 1H), 7.31 (d, J = 7.8 Hz, 1H), 7.04 (d, J = 8.8 Hz, 2H), 4.09 (q, J = 6.9 Hz, 2H), 3.60 (d, J = 4.4 Hz, 2H), 2.99 (dt, J = 13.9, 6.9 Hz, 1H), 1.93-1.75 (m, 12H), 1.54-1.42 (m, 6H), 1.36 (t, J = 7.0 Hz, 3H), 1.27-1.18 (m, 6H)

376 $^1$H NMR (400 MHz, DMSO-d$_6$) δ 9.90 (br. s., 1H), 7.74 (d, J = 8.7 Hz, 2H), 7.71-7.63 (m, 2H), 7.53 (t, J = 7.8 Hz, 1H), 7.39-7.29 (m, 3H), 3.60 (d, J = 4.0 Hz, 2H), 3.04 (s, 3H), 3.02-2.94 (m, 1H), 1.94-1.74 (m, 12H), 1.53-1.41 (m, 6H), 1.27-1.17 (m, 6H)

377 $^1$H NMR (400 MHz, DMSO-d$_6$) δ 7.74-7.60 (m, 4H), 7.51 (t, J = 7.8 Hz, 1H), 7.32 (d, J = 8.2 Hz, 1H), 7.06 (d, J = 8.7 Hz, 2H), 3.81 (s, 3H), 3.60 (d, J = 5.7 Hz, 2H), 2.99 (dt, J = 13.8, 7.0 Hz, 1H), 1.94-1.73 (m, 12H), 1.55-1.42 (m, 6H), 1.28-1.17 (m, 6H)

378 $^1$H NMR (400 MHz, DMSO-d$_6$) δ 8.47 (d, J = 1.5 Hz, 1H), 8.00 (d, J = 8.4 Hz, 1H), 7.86 (dd, J = 8.6, 1.8 Hz, 1H), 7.83-7.75 (m, 2H), 7.57 (t, J = 7.8 Hz, 1H), 7.41 (d, J = 8.1 Hz, 1H), 3.68 (d, J = 13.2 Hz, 1H), 3.57 (d, J = 13.7 Hz, 1H), 2.99 (dt, J = 13.8, 7.0 Hz, 1H), 2.84 (s, 3H), 1.97-1.76 (m, 12H), 1.56-1.40 (m, 6H), 1.27-1.18 (m, 6H)

379 $^1$H NMR (400 MHz, DMSO-d$_6$) δ 9.88 (br. s., 1H), 7.77-7.63 (m, 4H), 7.53 (t, J = 7.8 Hz, 1H), 7.35 (d, J = 8.6 Hz, 3H), 3.68-3.52 (m, 2H), 2.99 (dt, J = 13.8, 7.0 Hz, 1H), 2.71-2.64 (m, 1H), 1.95-1.74 (m, 12H), 1.55-1.39 (m, 6H), 1.27-1.17 (m, 6H), 1.02-0.92 (m, 4H)

380 $^1$H NMR (400 MHz, DMSO-d$_6$) δ 7.99 (d, J = 8.1 Hz, 2H), 7.90-7.76 (m, 4H), 7.60 (t, J = 8.1 Hz, 1H), 7.48 (d, J = 7.6 Hz, 1H), 3.71-3.62 (m, 1H), 3.62-3.53 (m, 1H), 2.99 (dt, J = 13.8, 7.0 Hz, 1H), 1.96-1.75 (m, 12H), 1.56-1.40 (m, 6H), 1.28-1.17 (m, 6H)

381 $^1$H NMR (400 MHz, DMSO-d$_6$) δ 8.56 (d, J = 2.0 Hz, 1H), 8.10 (dd, J = 8.8, 2.8 Hz, 1H), 7.75-7.67 (m, 2H), 7.54 (t, J = 8.0 Hz, 1H), 7.37 (d, J = 7.0 Hz, 1H), 6.91 (d, J = 8.5 Hz, 1H), 4.37 (q, J = 7.0 Hz, 2H), 3.61 (s, 2H), 2.99 (dt, J = 13.7, 7.0 Hz, 1H), 1.94-1.75 (m, 12H), 1.52-1.42 (m, 6H), 1.35 (t, J = 7.3 Hz, 3H), 1.26-1.18 (m, 6H)

382 $^1$H NMR (400 MHz, DMSO-d$_6$) δ 8.58 (d, J = 2.5 Hz, 1H), 8.11 (dd, J = 8.5, 2.5 Hz, 1H), 7.74-7.68 (m, 2H), 7.54 (t, J = 8.3 Hz, 1H), 7.38 (d, J = 8.0 Hz, 1H), 6.95 (d, J = 8.5 Hz, 1H), 3.91 (s, 3H), 3.63-3.58 (m, 2H), 2.99 (dt, J = 13.7, 7.0 Hz, 1H), 1.93-1.76 (m, 12H), 1.53-1.42 (m, 6H), 1.26-1.19 (m, 6H)

Example 383

3-Fluoro-N-((4-(3-isopropyl-1,2,4-oxadiazol-5-yl)bicyclo[2.2.2]octan-1-yl)methyl)-N-(3-(2-methoxypyrimidin-5-yl)phenyl)bicyclo[1.1.1]pentane-1-carboxamide (383)

Step A. Intermediate 383A. Preparation of N-(3-(5,5-dimethyl-1,3,2-dioxaborinan-2-yl) phenyl)-3-fluoro-N-((4-(3-isopropyl-1,2,4-oxadiazol-5-yl)bicyclo[2.2.2]octan-1-yl) methyl)bicyclo[1.1.1]pentane-1-carboxamide

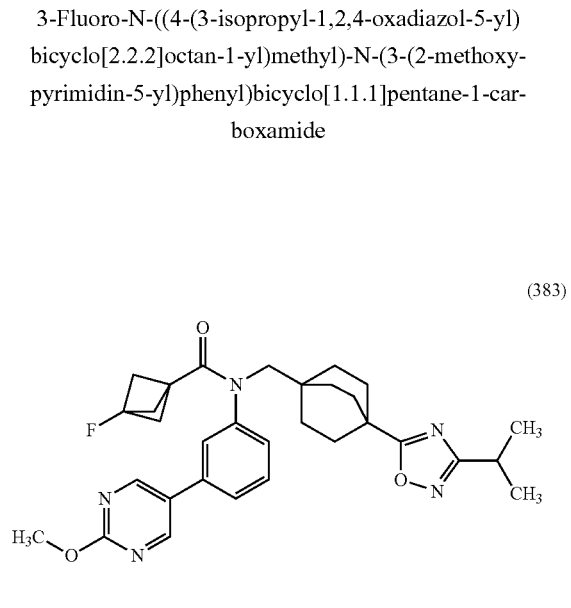

The title compound was prepared according to the method described for the synthesis of Intermediate 262A by substituting Intermediate 374A where appropriate. (90 mg, 0.164 mmol, 70% yield) as white solid. MS (ESI) 482 (M+H) (Boronic acid mass).

Step B. Example 383. Preparation of 3-fluoro-N-((4-(3-isopropyl-1,2,4-oxadiazol-5-yl) bicyclo[2.2.2]octan-1-yl)methyl)-N-(3-(2-methoxypyrimidin-5-yl)phenyl)bicyclo[1.1.1]pentane-1-carboxamide The title compound was prepared according to the method described for the synthesis of Example 149 by substituting Intermediate 383A and 5-bromo-2-methoxypyrimidine where appropriate. (3.7 mg, 6.78 μmol, 12% yield). $^1$H NMR (400 MHz, DMSO-d6) δ 9.03 (s, 2H), 7.87-7.80 (m, 1H), 7.78 (d, J=7.6 Hz, 1H), 7.58 (t, J=7.8 Hz, 1H), 7.44 (d, J=8.8 Hz, 1H), 3.99 (s, 3H), 3.61 (d, J=13.0 Hz, 2H), 2.99 (quin, J=7.0 Hz, 1H), 1.98-1.69 (m, 12H), 1.57-1.36 (m, 6H), 1.28-1.15 (m, 6H). FXR EC$_{50}$ (nM)=47. MS (ESI) 545 (M+H).

The following compounds were prepared according to the method described for the synthesis of Example 149 by substituting Intermediate 383A and the corresponding aryl/hetero aryl halides.

| Ex. No. | Name | MS (ESI) (M + H) | FXR EC$_{50}$ (nM) |
|---|---|---|---|
| 384 | 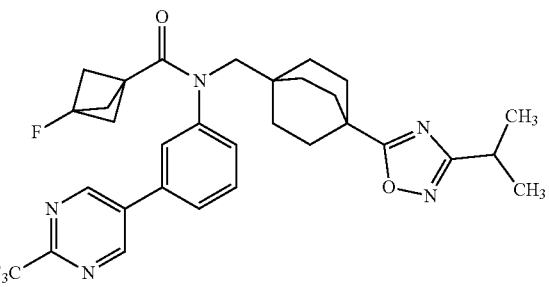 | 584 | 184 |
| 385 | 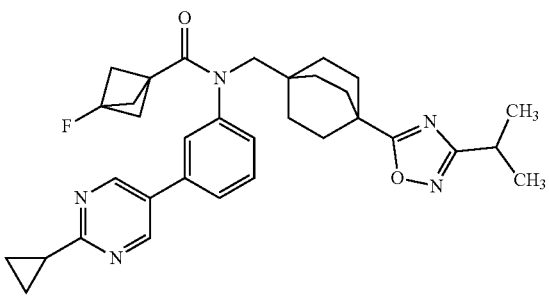 [SMILES: CC(C)c1noc(C23CCC(CN(C(=O)C45CC(F)(C4)C5)c4cccc(-c5cnc(C6CC6)nc5)c4)(CC2)CC3)n1] | 556 | 35 |
| 386 | 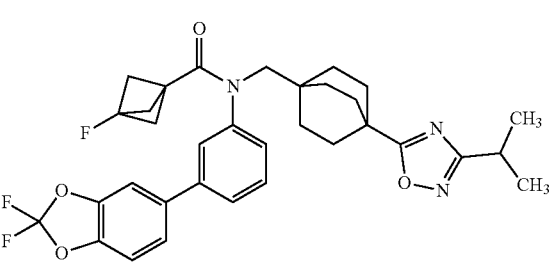 [SMILES: CC(C)c1noc(C23CCC(CN(C(=O)C45CC(F)(C4)C5)c4cccc(-c5ccc6c(c5)OC(F)(F)O6)c4)(CC2)CC3)n1] | 594 | 274 |
| 387 | 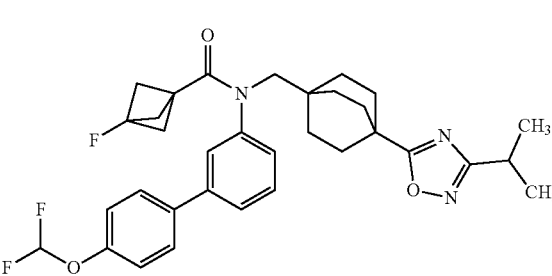 [SMILES: CC(C)c1noc(C23CCC(CN(C(=O)C45CC(F)(C4)C5)c4cccc(-c5ccc(OC(F)F)cc5)c4)(CC2)CC3)n1] | 580 | 47 |

-continued
| Ex. No. | Name | MS (ESI) (M + H) | FXR EC$_{50}$ (nM) |
|---|---|---|---|
| 388 | 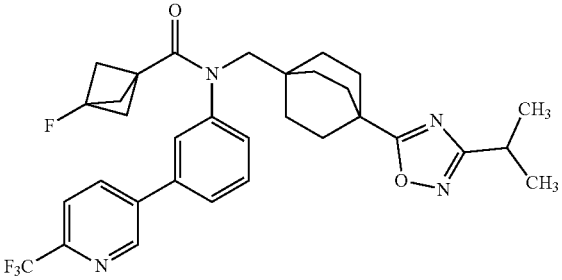 [SMILES: CC(C)c1noc(C23CCC(CN(C(=O)C45CC(F)(C4)C5)c4cccc(-c5ccc(C(F)(F)F)nc5)c4)(CC2)CC3)n1] | 583 | 906 |
| 389 | 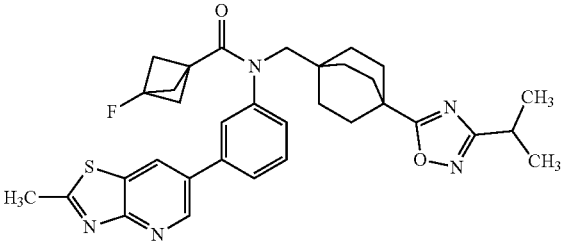 [SMILES: Cc1nc2ncc(-c3cccc(N(CC45CCC(c6nc(C(C)C)no6)(CC4)CC5)C(=O)C45CC(F)(C4)C5)c3)cc2s1] | 586 | 61 |
| 390 | 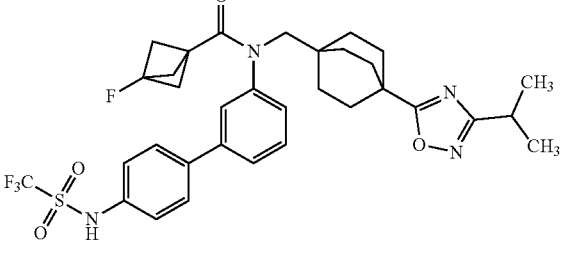 | 661 | 96 |
| 391 | 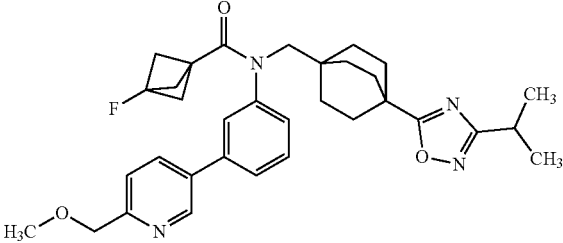 [SMILES: COCc1ccc(-c2cccc(N(CC34CCC(c5nc(C(C)C)no5)(CC3)CC4)C(=O)C34CC(F)(C3)C4)c2)cn1] | 559 | 147 |
| 392 | 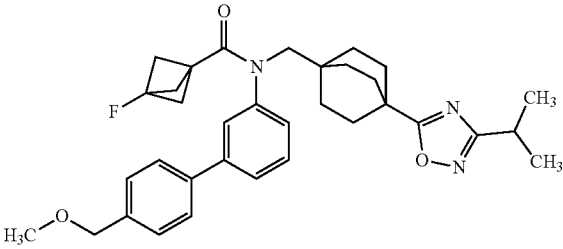 | 558 | 183 |

| Ex. No. | Name | MS (ESI) (M + H) | FXR EC$_{50}$ (nM) |
|---|---|---|---|
| 393 | | 530 | 49 |
| 394 | | 544 | 77 |
| 395 | | 560 | 156 |

384 $^1$H NMR (400 MHz, DMSO-d$_6$) δ 9.50 (s, 2H), 8.01 (s, 1H), 7.97 (d, J = 7.8 Hz, 1H), 7.74-7.62 (m, 1H), 7.61-7.54 (m, 1H), 3.66 (br. s., 1H), 3.61 (br. s., 1H), 2.99 (quin, J = 7.0 Hz, 1H), 2.00-1.71 (m, 12H), 1.59-1.37 (m, 6H), 1.31-1.12 (m, 6H)

385 $^1$H NMR (400 MHz, DMSO-d$_6$) δ 9.04 (s, 2H), 7.84 (d, J = 1.7 Hz, 1H), 7.80 (d, J = 7.8 Hz, 1H), 7.59 (t, J = 7.9 Hz, 1H), 7.46 (d, J = 8.8 Hz, 1H), 3.61 (d, J = 7.1 Hz, 2H), 2.99 (dt, J = 13.9, 6.9 Hz, 1H), 2.31-2.20 (m, 1H), 1.97-1.74 (m, 12H), 1.57-1.38 (m, 6H), 1.27-1.17 (m, 6H), 1.14-0.99 (m, 4H)

386 $^1$H NMR (400 MHz, DMSO-d$_6$) δ 7.87 (d, J = 2.0 Hz, 1H), 7.74-7.69 (m, 2H), 7.61 (dd, J = 8.3, 1.8 Hz, 1H), 7.57-7.49 (m, 2H), 7.43-7.37 (m, 1H), 3.64 (d, J = 13.6 Hz, 1H), 3.56 (d, J = 13.6 Hz, 1H), 2.98 (dt, J = 13.9, 6.8 Hz, 1H), 1.88 (br. s., 4H), 1.85-1.77 (m, 8H), 1.51-1.40 (m, 6H), 1.26-1.18 (m, 6H)

387 $^1$H NMR (400 MHz, DMSO-d$_6$) δ 7.83-7.77 (m, 2H), 7.72-7.66 (m, 2H), 7.53 (t, J = 8.0 Hz, 1H), 7.48-7.11 (m, 4H), 3.66-3.53 (m, 2H), 2.97 (dt, J = 13.7, 7.0 Hz, 1H), 1.91-1.75 (m, 12H), 1.45-1.47 (m, 6H), 1.25-1.17 (m, 6H)

388 $^1$H NMR (400 MHz, DMSO-d$_6$) δ 9.16 (d, J = 2.0 Hz, 1H), 8.45 (dd, J = 8.3, 2.3 Hz, 1H), 8.00 (d, J = 8.5 Hz, 1H), 7.92-7.83 (m, 2H), 7.61 (t, J = 7.8 Hz, 1H), 7.51 (d, J = 8.0 Hz, 1H), 3.68-3.61 (m, 1H), 3.59-3.52 (m, 1H), 2.96 (dt, J = 13.7, 7.0 Hz, 1H), 1.91-1.74 (m, 12H), 1.49-1.40 (m, 6H), 1.23-1.16 (m, 6H)

389 $^1$H NMR (400 MHz, DMSO-d$_6$) δ 9.02 (d, J = 2.5 Hz, 1H), 8.93 (d, J = 2.0 Hz, 1H), 7.87-7.83 (m, 2H), 7.60 (t, J = 8.0 Hz, 1H), 7.48-7.43 (m, 1H), 3.67 (d, J = 13.6 Hz, 1H), 3.58 (d, J = 13.1 Hz, 1H), 2.98 (dt, J = 13.7, 7.0 Hz, 1H), 2.90 (s, 3H), 1.95-1.76 (m, 12H), 1.46 (d, J = 10.5 Hz, 3H), 1.48 (d, J = 9.5 Hz, 3H), 1.25-1.18 (m, 6H)

390 $^1$H NMR (400 MHz, DMSO-d$_6$) δ 7.79 (d, J = 8.0 Hz, 1H), 7.72-7.66 (m, 2H), 7.54 (t, J = 7.5 Hz, 1H), 7.40-7.33 (m, 3H), 3.59 (d, J = 12.5 Hz, 2H), 2.98 (dt, J = 13.9, 6.8 Hz, 1H), 1.93-1.75 (m, 12H), 1.46 (d, J = 8.0 Hz, 6H), 1.25-1.18 (m, 6H)

391 $^1$H NMR (400 MHz, DMSO-d$_6$) δ 8.91 (d, J = 2.5 Hz, 1H), 8.19 (dd, J = 8.0, 2.5 Hz, 1H), 7.81-7.74 (m, 2H), 7.57 (t, J = 7.8 Hz, 1H), 7.52 (d, J = 8.0 Hz, 1H), 7.44 (d, J = 7.5 Hz, 1H), 4.55 (s, 2H), 3.66 (d, J = 13.1 Hz, 1H), 3.56 (d, J = 13.6 Hz, 1H), 3.40 (s, 3H), 2.98 (dt, J = 13.7, 7.0 Hz, 1H), 1.93-1.77 (m, 12H), 1.51-1.42 (m, 6H), 1.25-1.18 (m, 6H)

392 $^1$H NMR (400 MHz, DMSO-d$_6$) δ 7.73 (d, J = 8.0 Hz, 3H), 7.69 (d, J = 5.5 Hz, 1H), 7.53 (t, J = 7.8 Hz, 1H), 7.43 (d, J = 8.0 Hz, 2H), 7.37 (d, J = 9.0 Hz, 1H), 4.46 (s, 2H), 3.65 (d, J = 14.1 Hz, 1H), 3.55 (d, J = 14.1 Hz, 1H), 2.98 (dt, J = 13.7, 7.0 Hz, 1H), 1.93-1.76 (m, 12H), 1.51-1.42 (m, 6H), 1.25-1.17 (m, 6H) (3 Protons buried under solvent)

393 $^1$H NMR (400 MHz, DMSO-d$_6$) δ 8.80 (s, 2H), 8.37 (d, J = 7.5 Hz, 1H), 8.26-8.22 (m, 1H), 7.64-7.58 (m, 1H), 7.57-7.52 (m, 1H), 3.61 (d, J = 15.6 Hz, 2H), 2.97 (dt, J = 13.7, 7.0 Hz, 1H), 2.33 (s, 3H), 1.88 (br. s., 5H), 1.85-1.75 (m, 7H), 1.49-1.41 (m, 6H), 1.25-1.17 (m, 6H)

| Ex. No. | Name | MS (ESI) (M + H) | FXR EC$_{50}$ (nM) |
|---|---|---|---|
| 394 | $^1$H NMR (400 MHz, DMSO-d$_6$) δ 8.84 (s, 2H), 8.37 (d, J = 8.0 Hz, 1H), 8.25 (s, 1H), 7.64-7.59 (m, 1H), 7.57-7.52 (m, 1H), 3.65 (d, J = 15.6 Hz, 2H), 2.97 (dt, J = 13.7, 7.0 Hz, 1H), 2.72-2.65 (m, 2H), 1.93-1.76 (m, 12H), 1.49-1.41 (m, 6H), 1.28-1.18 (m, 9H) | | |
| 395 | $^1$H NMR (400 MHz, DMSO-d$_6$) δ 8.68 (s, 2H), 8.30 (d, J = 8.0 Hz, 1H), 8.17 (t, J = 1.8 Hz, 1H), 7.59 (t, J = 7.8 Hz, 1H), 7.50 (d, J = 7.5 Hz, 1H), 4.27 (q, J = 7.0 Hz, 2H), 3.64 (br. s., 1H), 3.57 (br. s., 1H), 2.97 (dt, J = 13.9, 6.8 Hz, 1H), 1.93-1.75 (m, 12H), 1.49-1.43 (m, 6H), 1.39 (t, J = 7.0 Hz, 3H), 1.26-1.18 (m, 6H) | | |

Example 396

N-(3-(2-ethoxypyrimidin-5-yl)phenyl)-3-fluoro-N-((4-(5-(1-methylcyclopropyl)-1,2,4-oxadiazol-3-yl)bicyclo[2.2.2]octan-1-yl)methyl)bicyclo[1.1.1]pentane-1-carboxamide

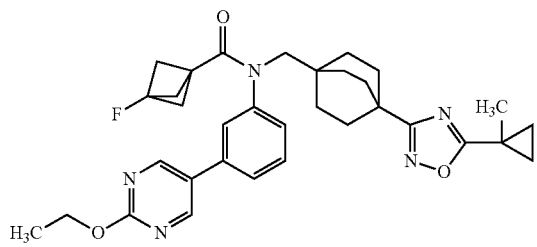

(396)

Step A. Intermediate 396A. Preparation of 4-((N-(3-bromophenyl)-3-fluorobicyclo[1.1.1]pentane-1-carboxamido)methyl)bicyclo[2.2.2]octane-1-carboxamide

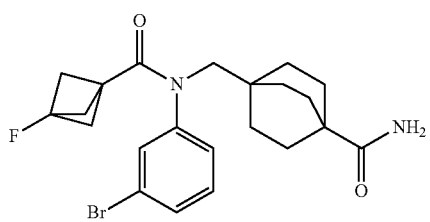 [SMILES: NC(=O)C12CCC(CN(C(=O)C34CC(F)(C3)C4)c3cccc(Br)c3)(CC1)CC2]

To a stirred solution of Intermediate 357C (1.65 g, 3.66 mmol) in DMF (15 mL) were added ammonium chloride (235 mg, 4.40 mmol), TEA (1.5 mL, 10.99 mmol) and BOP (1.78 g, 4.03 mmol). The reaction mixture was stirred at room temperature for 1 h. The reaction mixture was concentrated, diluted with water (50 mL) and extracted with ethyl acetate (2×20 mL). The organic layers were combined, dried over anhydrous sodium sulphate, concentrated and dried in vacuo to afford the title compound (1.6 g, 3.56 mmol, 97% yield). MS (ESI) 450 (M+H).

Step B. Intermediate 396B. Preparation of N-(3-bromophenyl)-N-((4-cyanobicyclo[2.2.2]octan-1-yl)methyl)-3-fluorobicyclo[1.1.1]pentane-1-carboxamide

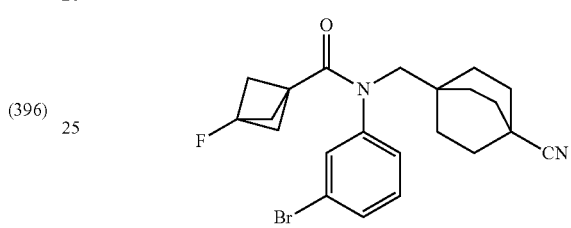

A stirred solution of Intermediate 396A (1.6 g, 3.56 mmol) in pyridine (15 mL) was cooled to 0° C. TFAA (2.51 mL, 17.80 mmol) was added drop wise to the reaction mixture. The reaction mixture was allowed to warm to room temperature and stirred for 30 min. The reaction mixture was diluted with ice cold water (50 mL) and extracted with ethyl acetate (2×20 mL). The organic layers were combined, dried over anhydrous sodium sulphate and concentrated under reduced pressure. The crude material was purified by flash chromatography (24 g silica gel cartridge; A=Hex, B=EtOAc; 30 min grad.; 0% B to 40% B; flow rate=30 mL/min). The pure fractions were combined, concentrated and dried in vacuo to afford the title compound (850 mg, 1.97 mmol, 55% yield) as pale brown gummy liquid. MS (ESI) 431 (M+H).

Step C. Intermediate 396C. Preparation of (E)-N-(3-bromophenyl)-3-fluoro-N-((4-(N'-hydroxycarbamimidoyl)bicyclo[2.2.2]octan-1-yl)methyl)bicyclo[1.1.1]pentane-1-carboxamide

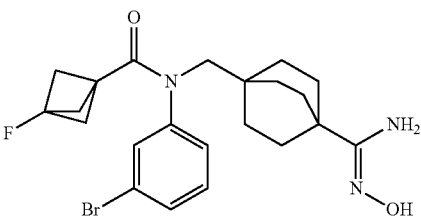 [SMILES: N/C(=N\O)C12CCC(CN(C(=O)C34CC(F)(C3)C4)c3cccc(Br)c3)(CC1)CC2]

The title compound was prepared according to the method described for the synthesis of Intermediate 227F by substituting Intermediate 396B where appropriate. (820 mg, 1.766 mmol, 92% yield) as white solid. MS (ESI) 464 (M+H).

509

Step D. Intermediate 396D. Preparation of N-(3-bromophenyl)-3-fluoro-N-((4-(5-(1-methylcyclopropyl)-1,2,4-oxadiazol-3-yl)bicyclo[2.2.2]octan-1-yl)methyl) bicyclo[1.1.1]pentane-1-carboxamide

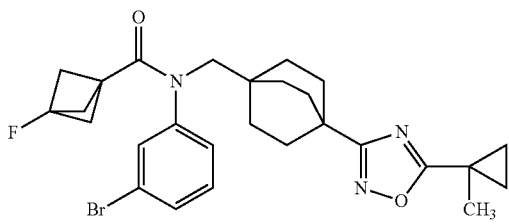 [SMILES: CC1(c2nc(C34CCC(CN(C(=O)C56CC(F)(C5)C6)c5cccc(Br)c5)(CC3)CC4)no2)CC1]

The title compound was prepared according to the method described for the synthesis of Intermediate 3A by substituting Intermediate 396C and the corresponding acid where appropriate. (850 mg, 1.608 mmol, 91% yield) as brown solid. MS (ESI) 528 (M+H).

510

Step E. Example 396. Preparation of N-(3-(2-ethoxypyrimidin-5-yl)phenyl)-3-fluoro-N-((4-(5-(1-methylcyclopropyl)-1,2,4-oxadiazol-3-yl)bicyclo[2.2.2]octan-1-yl)methyl) bicyclo[1.1.1]pentane-1-carboxamide The title compound was prepared according to the method described for the synthesis of Example 149 by substituting Intermediate 396D and (2-ethoxypyrimidin-5-yl)boronic acid where appropriate. (20.7 mg, 0.035 mmol, 62% yield). $^1$H NMR (400 MHz, DMSO-$d_6$) δ 9.02 (s, 2H), 7.82 (d, J=2.0 Hz, 1H), 7.77 (d, J=7.6 Hz, 1H), 7.57 (t, J=7.7 Hz, 1H), 7.43 (d, J=7.8 Hz, 1H), 4.43 (q, J=7.1 Hz, 2H), 3.63 (br. s., 1H), 3.57 (br. s., 1H), 1.85 (s, 3H), 1.89 (s, 3H), 1.78-1.58 (m, 6H), 1.53-1.30 (m, 12H), 1.29-1.18 (m, 2H), 1.11-0.96 (m, 2H). FXR $EC_{50}$ (nM)=46. MS (ESI) 572 (M+H).

The following compounds were prepared according to the method described for the synthesis of Example 149 by substituting Intermediate 396D and the corresponding boronic acids/esters.

| Ex. No. | Name | MS (ESI) (M + H) | FXR $EC_{50}$ (nM) |
|---|---|---|---|
| 397 | | 645 | 183 |
| 398 | | 619 | 93 |
| 399 | | 570 | 58 |

| Ex. No. | Name | MS (ESI) (M + H) | FXR EC$_{50}$ (nM) |
|---|---|---|---|
| 400 | 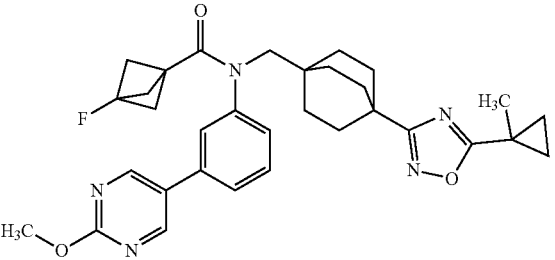 [SMILES: COc1ncc(-c2cccc(N(CC34CCC(c5noc(C6(C)CC6)n5)(CC3)CC4)C(=O)C34CC(F)(C3)C4)c2)cn1] | 558 | 51 |
| 401 | 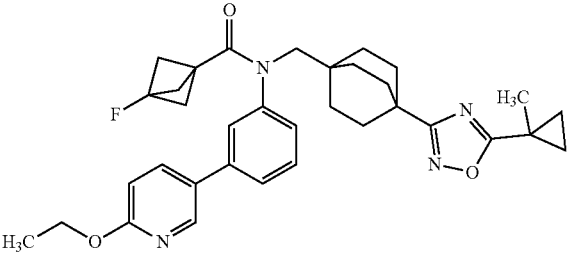 [SMILES: CCOc1ccc(-c2cccc(N(CC34CCC(c5noc(C6(C)CC6)n5)(CC3)CC4)C(=O)C34CC(F)(C3)C4)c2)cn1] | 571 | 42 |
| 402 | 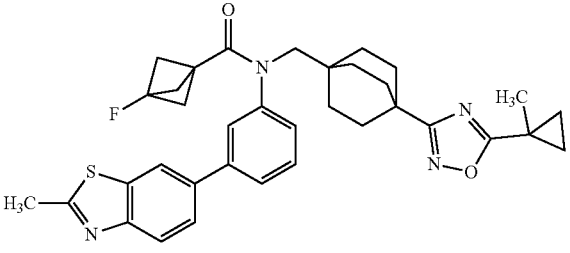 [SMILES: Cc1nc2ccc(-c3cccc(N(CC45CCC(c6noc(C7(C)CC7)n6)(CC4)CC5)C(=O)C45CC(F)(C4)C5)c3)cc2s1] | 597 | 35 |
| 403 | 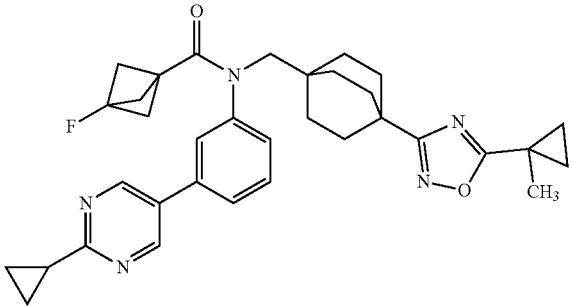 [SMILES: CC1(c2nc(C34CCC(CN(C(=O)C56CC(F)(C5)C6)c5cccc(-c6cnc(C7CC7)nc6)c5)(CC3)CC4)no2)CC1] | 568 | 100 |
| 404 | 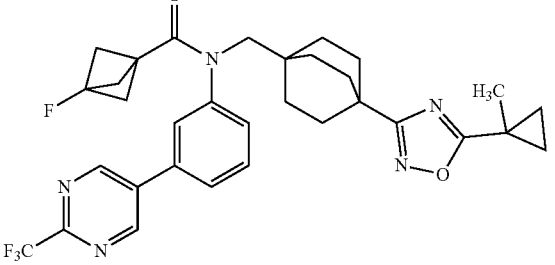 | 596 | 221 |

| Ex. No. | Name | MS (ESI) (M + H) | FXR EC$_{50}$ (nM) |
|---|---|---|---|
| 405 | | 592 | 53 |

397 $^1$H NMR (400 MHz, DMSO-d$_6$) δ 9.87 (s, 1H), 7.80-7.60 (m, 4H), 7.52 (t, J = 7.8 Hz, 1H), 7.36 (d, J = 8.6 Hz, 3H), 3.59 (d, J = 17.9 Hz, 2H), 2.73-2.65 (m, 1H), 1.85 (s, 3H), 1.88 (s, 3H), 1.77-1.63 (m, 6H), 1.45 (s, 8H), 1.27-1.18 (m, 3H), 1.08-1.01 (m, 2H), 1.01-0.90 (m, 4H)
398 $^1$H NMR (400 MHz, DMSO-d$_6$) δ 9.89 (s, 1H), 7.74 (d, J = 8.8 Hz, 2H), 7.71-7.62 (m, 2H), 7.53 (t, J = 7.8 Hz, 1H), 7.39-7.24 (m, 3H), 3.59 (d, J = 12.5 Hz, 2H), 3.04 (s, 3H), 1.86 (s, 3H), 1.88 (s, 3H), 1.78-1.57 (m, 6H), 1.53-1.33 (m, 9H), 1.27-1.19 (m, 2H), 1.08-0.99 (m, 2H)
399 $^1$H NMR (400 MHz, DMSO-d$_6$) δ 7.73-7.56 (m, 4H), 7.50 (t, J = 7.8 Hz, 1H), 7.31 (dd, J = 7.8, 1.0 Hz, 1H), 7.10-6.94 (m, 2H), 4.09 (q, J = 7.0 Hz, 2H), 3.69-3.47 (m, 2H), 1.86 (d, J = 9.5 Hz, 6H), 1.78-1.57 (m, 6H), 1.57-1.38 (m, 9H), 1.36 (t, J = 7.0 Hz, 3H), 1.28-1.19 (m, 2H), 1.08-1.00 (m, 2H).
400 $^1$H NMR (400 MHz, DMSO-d$_6$) δ 9.03 (s, 2H), 7.82 (s, 1H), 7.77 (d, J = 7.6 Hz, 1H), 7.57 (t, J = 7.8 Hz, 1H), 7.43 (d, J = 9.0 Hz, 1H), 3.99 (s, 3H), 3.62 (br. s., 1H), 3.57 (br. s., 1H), 1.85 (s, 3H), 1.88 (s, 3H), 1.77-1.57 (m, 6H), 1.45 (s, 9H), 1.26-1.18 (m, 2H), 1.07-0.98 (m, 2H)
401 $^1$H NMR (400 MHz, DMSO-d$_6$) δ 8.56 (d, J = 2.2 Hz, 1H), 8.09 (dd, J = 8.6, 2.7 Hz, 1H), 7.77-7.62 (m, 2H), 7.53 (t, J = 7.9 Hz, 1H), 7.36 (dd, J = 7.1, 1.2 Hz, 1H), 6.91 (dd, J = 8.7, 0.6 Hz, 1H), 4.37 (q, J = 7.0 Hz, 2H), 3.59 (d, J = 7.6 Hz, 2H), 1.85 (s, 3H), 1.88 (s, 3H), 1.78-1.57 (m, 6H), 1.57-1.38 (m, 9H), 1.35 (t, J = 7.0 Hz, 3H), 1.27-1.18 (m, 2H), 1.09-0.96 (m, 2H)
402 $^1$H NMR (400 MHz, DMSO-d$_6$) δ 8.46 (d, J = 1.7 Hz, 1H), 8.00 (d, J = 8.3 Hz, 1H), 7.85 (dd, J = 8.6, 2.0 Hz, 1H), 7.82-7.71 (m, 2H), 7.56 (t, J = 7.9 Hz, 1H), 7.40 (d, J = 8.3 Hz, 1H), 3.76-3.62 (m, 1H), 3.61-3.47 (m, 1H), 2.83 (s, 3H), 1.86 (s, 3H), 1.90 (s, 3H), 1.79-1.59 (m, 6H), 1.57-1.30 (m, 9H), 1.27-1.16 (m, 2H), 1.08-0.95 (m, 2H)
403 $^1$H NMR (400 MHz, DMSO-d$_6$) δ 9.03 (s, 2H), 7.87-7.81 (m, 1H), 7.79 (d, J = 8.3 Hz, 1H), 7.58 (t, J = 7.8 Hz, 1H), 7.45 (d, J = 8.8 Hz, 1H), 3.68-3.51 (m, 2H), 2.32-2.23 (m, 1H), 1.84 (s, 3H), 1.88 (s, 3H), 1.78-1.60 (m, 6H), 1.54-1.31 (m, 9H), 1.27-1.19 (m, 2H), 1.16-0.93 (m, 6H)
404 $^1$H NMR (400 MHz, DMSO-d$_6$) δ 9.49 (s, 2H), 8.04-7.98 (m, 1H), 7.96 (d, J = 7.8 Hz, 1H), 7.70-7.63 (m, 1H), 7.62-7.55 (m, 1H), 3.66 (br. s., 1H), 3.58 (br. s., 1H), 1.86 (s, 3H), 1.90 (s, 3H), 1.77-1.57 (m, 6H), 1.56-1.31 (m, 9H), 1.26-1.20 (m, 2H), 1.08-1.02 (m, 2H)
405 $^1$H NMR (400 MHz, DMSO-d$_6$) δ 7.88-7.77 (m, 2H), 7.76-7.65 (m, 2H), 7.54 (t, J = 7.8 Hz, 1H), 7.38 (d, J = 8.6 Hz, 1H), 7.34-7.20 (m, 3H), 3.69-3.59 (m, 1H), 3.59-3.48 (m, 1H), 1.85 (s, 3H), 1.88 (s, 3H), 1.79-1.56 (m, 6H), 1.56-1.29 (m, 9H), 1.27-1.17 (m, 2H), 1.07-0.98 (m, 2H)

Example 406

N-((4-(5-cyclopropyl-1-methyl-1H-pyrazol-3-yl)bicyclo[2.2.2]octan-1-yl)methyl)-3-fluoro-N-(4'-(methylsulfonamido)-[1,1'-biphenyl]-3-yl)bicyclo[1.1.1]pentane-1-carboxamide (406)

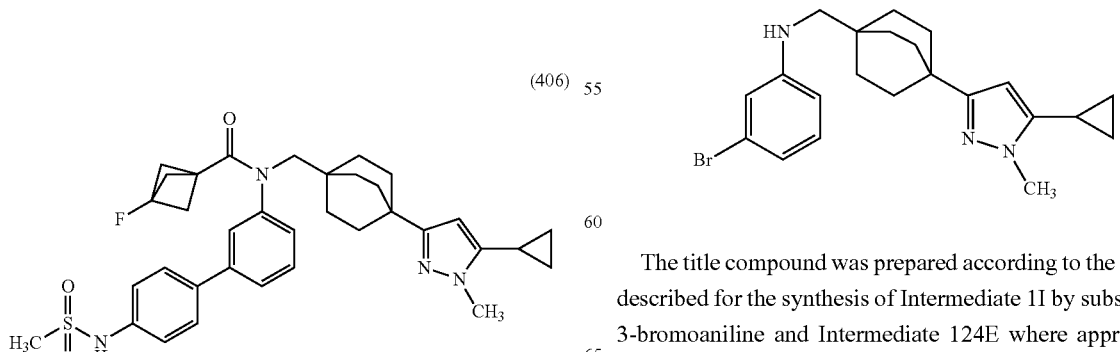

Step A. Intermediate 406A. Preparation of 3-bromo-N-((4-(5-cyclopropyl-1-methyl-1H-pyrazol-3-yl)bicyclo[2.2.2]octan-1-yl)methyl)aniline The title compound was prepared according to the method described for the synthesis of Intermediate 1I by substituting 3-bromoaniline and Intermediate 124E where appropriate. (130 mg, 0.298 mmol, 59% yield) as an off-white solid. MS (ESI) 416 (M+H).

515

Step B. Intermediate 406B. Preparation of N-(3-bromophenyl)-N-((4-(5-cyclopropyl-1-methyl-1H-pyrazol-3-yl)bicyclo[2.2.2]octan-1-yl)methyl)-3-fluorobicyclo[1.1.1]pentane-1-carboxamide

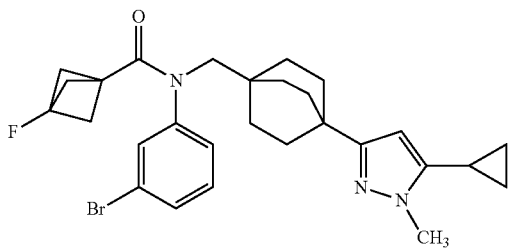 [SMILES: Cn1nc(C23CCC(CN(C(=O)C45CC(F)(C4)C5)c4cccc(Br)c4)(CC2)CC3)cc1C1CC1]

The title compound was prepared according to the method described for the synthesis of Example 3 by substituting Intermediate 406A and the corresponding acid where appropriate. (100 mg, 0.180 mmol, 57% yield) as an off-white solid. MS (ESI) 526 (M+H).

516

Step C. Example 406. Preparation of N-((4-(5-cyclopropyl-1-methyl-1H-pyrazol-3-yl) bicyclo[2.2.2]octan-1-yl)methyl)-3-fluoro-N-(4'-(methylsulfonamido)-[1,1'-biphenyl]-3-yl)bicyclo[1.1.1]pentane-1-carboxamide The title compound was prepared according to the method described for the synthesis of Example 149 by substituting Intermediate 406B and (4-(methylsulfonamido)phenyl)boronic acid where appropriate. (20.3 mg, 0.032 mmol, 68% yield). $^1$H NMR (400 MHz, DMSO-$d_6$) δ 9.87 (br. s., 1H), 7.78-7.71 (m, 2H), 7.67 (d, J=8.1 Hz, 1H), 7.64-7.60 (m, 1H), 7.52 (t, J=7.8 Hz, 1H), 7.33 (d, J=8.6 Hz, 3H), 5.59 (s, 1H), 3.69 (s, 3H), 3.57 (d, J=11.5 Hz, 2H), 3.04 (s, 3H), 1.88-1.85 (m, 6H), 1.78-1.71 (m, 1H), 1.68-1.50 (m, 6H), 1.40-1.38 (m, 6H), 0.88-0.85 (m, 2H), 0.55-0.50 (m, 2H). FXR EC$_{50}$ (nM) 203. MS (ESI) 618 (M+H).

The following compounds were prepared according to the method described for the synthesis of Example 149 by substituting Intermediate 406B and the corresponding boronic acids/esters.

| Ex. No. | Name | MS (ESI) (M + H) | FXR EC$_{50}$ (nM) |
|---|---|---|---|
| 407 | | 570 | 209 |
| 408 | | 554 | 160 |
| 409 | | 595 | 73 |

| Ex. No. | Name | MS (ESI) (M + H) | FXR EC$_{50}$ (nM) |
|---|---|---|---|
| 410 | | 622 | 465 |
| 411 | | 581 | 144 |

407 $^1$H NMR (400 MHz, DMSO-d$_6$) δ 9.00 (s, 2H), 7.79 (d, J = 1.7 Hz, 1H), 7.76 (d, J = 8.1 Hz, 1H), 7.56 (t, J = 7.8 Hz, 1H), 7.40 (d, J = 7.8 Hz, 1H), 5.59 (s, 1H), 4.43 (q, J = 7.1 Hz, 2H), 3.69 (s, 3H), 3.62-3.52 (m, 1H), 1.98-1.78 (m, 7H), 1.78-1.70 (m, 1H), 1.67-1.51 (m, 6H), 1.38-1.35 (m, 9H), 0.87-0.85 (m, 2H), 0.53-0.51 (m, 2H).

408 $^1$H NMR (400 MHz, DMSO-d$_6$) δ 7.72-7.62 (m, 3H), 7.61-7.57 (m, 1H), 7.50 (t, J = 7.8 Hz, 1H), 7.29 (d, J = 7.8 Hz, 1H), 7.06 (d, J = 8.8 Hz, 2H), 5.59 (s, 1H), 3.91 (s, 3H), 3.81 (s, 3H), 3.69-3.57 (m, 2H), 1.87-1.85 (m, 6H), 1.79-1.71 (m, 1H), 1.68-1.52 (m, 6H), 1.40-1.38 (m, 6H), 0.88-0.85 (m, 2H), 0.55-0.52 (m, 2H).

409 $^1$H NMR (400 MHz, DMSO-d$_6$) δ 8.46 (d, J = 1.7 Hz, 1H), 8.00 (d, J = 8.3 Hz, 1H), 7.85 (dd, J = 8.6, 1.7 Hz, 1H), 7.81-7.68 (m, 2H), 7.56 (t, J = 7.8 Hz, 1H), 7.38 (d, J = 7.8 Hz, 1H), 5.59 (s, 1H), 3.73-3.60 (m, 5H), 2.83 (s, 3H), 1.91-1.86 (m, 6H), 1.78-1.71 (m, 1H), 1.68-1.51 (m, 6H), 1.40 (d, J = 5.9 Hz, 6H), 0.87-0.83 (m, 2H), 0.54-0.51 (m, 2H).

410 $^1$H NMR (400 MHz, DMSO-d$_6$) δ 8.98 (d, J = 2.2 Hz, 1H), 8.89 (d, J = 2.2 Hz, 1H), 7.90-7.73 (m, 2H), 7.59 (t, J = 8.2 Hz, 1H), 7.43 (d, J = 8.1 Hz, 1H), 5.59 (s, 1H), 3.78 (s, 3H) 3.57-3.52 (m, 2H), 2.65-2.57 (m, 1H), 1.91-1.86 (m, 6H), 1.78-1.71 (m, 1H), 1.70-1.49 (m, 6H), 1.48-1.28 (m, 8H), 1.28-1.19 (m, 2H), 0.93-0.80 (m, 2H), 0.57-0.46 (m, 2H).

411 $^1$H NMR (400 MHz, DMSO-d$_6$) δ 11.76 (s, 1H), 7.73 (d, J = 1.5 Hz, 1H), 7.71-7.61 (m, 2H), 7.59-7.45 (m, 2H), 7.33 (d, J = 8.8 Hz, 1H), 7.19 (d, J = 8.1 Hz, 1H), 5.59 (s, 1H), 3.69 (s, 3H), 3.63-3.51 (m, 2H), 1.99-1.78 (m, 6H), 1.78-1.71 (m, 1H), 1.69-1.50 (m, 6H), 1.39 (d, J = 6.1 Hz, 6H), 0.94-0.81 (m, 2H), 0.58-0.48 (m, 2H).

Example 412

N-((4-(3-cyclopropyl-1-methyl-1H-pyrazol-5-yl)bicyclo[2.2.2]octan-1-yl)methyl)-3-fluoro-N-(4'-(methylsulfonamido)-[1,1'-biphenyl]-3-yl)bicyclo[1.1.1]pentane-1-carboxamide (412)

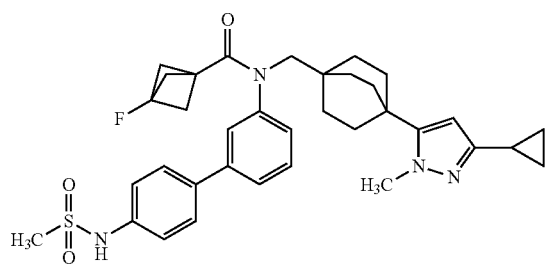

Step A. Intermediate 412A. Preparation of 3-bromo-N-((4-(3-cyclopropyl-1-methyl-1H-pyrazol-5-yl)bicyclo[2.2.2]octan-1-yl)methyl)aniline

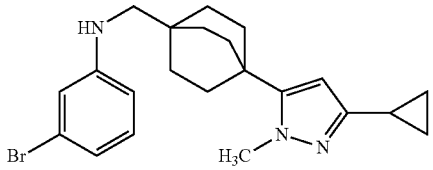

The title compound was prepared according to the method described for the synthesis of Intermediate 1I by substituting 3-bromoaniline and Intermediate 126B where appropriate. (140 mg, 0.321 mmol, 64% yield) as an off-white solid. MS (ESI) 414 (M+H).

Step B. Intermediate 412B. Preparation of N-(3-bromophenyl)-N-((4-(3-cyclopropyl-1-methyl-1H-pyrazol-5-yl)bicyclo[2.2.2]octan-1-yl)methyl)-3-fluorobicyclo[1.1.1]pentane-1-carboxamide

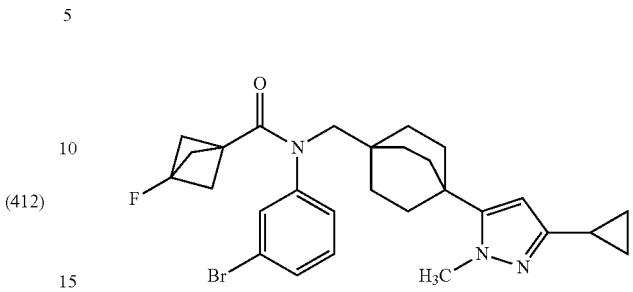

The title compound was prepared according to the method described for the synthesis of Example 3 by substituting Intermediate 412A and the corresponding acid where appropriate. (100 mg, 0.180 mmol, 57% yield) as an off-white solid. MS (ESI) 528 (M+H).

Step C. Example 412. Preparation of N-((4-(3-cyclopropyl-1-methyl-1H-pyrazol-5-yl) bicyclo[2.2.2]octan-1-yl)methyl)-3-fluoro-N-(4'-(methylsulfonamido)-[1,1'-biphenyl]-3-yl)bicyclo[1.1.1]pentane-1-carboxamide The title compound was prepared according to the method described for the synthesis of Example 149 by substituting Intermediate 412B and (4-(methylsulfonamido)phenyl)boronic acid where appropriate. (5.3 mg, 8.59 μmol, 18% yield). $^1$H NMR (400 MHz, DMSO-$d_6$) δ 9.88 (s, 1H), 7.73 (d, J=8.6 Hz, 2H), 7.68 (d, J=8.1 Hz, 1H), 7.66-7.60 (m, 1H), 7.53 (t, J=7.8 Hz, 1H), 7.41-7.26 (m, 3H), 5.62 (s, 1H), 3.72 (s, 3H), 3.58-5.56 (m, 2H), 3.04 (s, 3H), 1.88-1.86 (m, 6H), 1.77-1.60 (m, 7H), 1.45-1.42 (m, 6H), 0.76-0.72 (m, 2H), 0.54-0.52 (m, 2H). FXR EC$_{50}$ (nM) 105. MS (ESI) 617 (M+H).

The following compounds were prepared according to the method described for the synthesis of Example 149 by substituting Intermediate 412B and the corresponding boronic acids/esters.

| Ex. No. | Name | MS (ESI) (M + H) | FXR EC$_{50}$ (nM) |
|---|---|---|---|
| 413 | 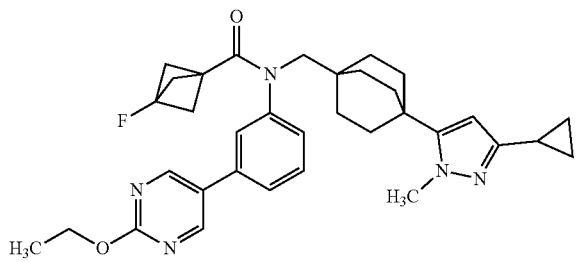 [SMILES: CCOc1ncc(-c2cccc(N(CC34CCC(c5cc(C6CC6)nn5C)(CC3)CC4)C(=O)C34CC(F)(C3)C4)c2)cn1] | 570 | 192 |

| Ex. No. | Name | MS (ESI) (M + H) | FXR EC$_{50}$ (nM) |
|---|---|---|---|
| 414 | | 554 | 85 |
| 415 | | 595 | 125 |

413 $^1$H NMR (400 MHz, DMSO-d$_6$) δ 9.01 (s, 2H), 7.83-7.79 (m, 1H), 7.77 (d, J = 7.6 Hz, 1H), 7.57 (t, J = 7.8 Hz, 1H), 7.42 (dd, J = 7.9, 1.1 Hz, 1H), 5.62 (s, 1H), 4.42 (q, J = 6.9 Hz, 2H), 3.72 (s, 3H), 3.68-3.58 (m, 1H), 3.58-3.45 (m, 1H), 1.89-1.85 (m, 6H), 1.77-1.58 (m, 7H), 1.56-1.29 (m, 9H), 0.75-0.72 (m, 2H), 0.53-0.52 (m, 2H).

414 $^1$H NMR (400 MHz, DMSO-d$_6$) δ 7.70-7.64 (m, 4H), 7.50 (t, J = 7.8 Hz, 1H), 7.31 (dd, J = 7.8, 1.0 Hz, 1H), 7.07-7.01 (m, 2H), 5.62 (s, 1H), 1H), 3.81 (s, 3H), 3.72 (s, 3H), 3.64-3.47 (m, 2H), 1.87-1.81 (s, 6H), 1.76-1.59 (m, 7H), 1.45-1.41 (m, 6H), 0.76-0.73 (m, 2H), 0.54-0.52 (m, 2H).

415 $^1$H NMR (400 MHz, DMSO-d$_6$) δ 8.46 (d, J = 1.7 Hz, 1H), 8.00 (d, J = 8.6 Hz, 1H), 7.85 (dd, J = 8.6, 2.0 Hz, 1H), 7.81-7.76 (m, 2H), 7.57 (t, J = 7.8 Hz, 1H), 7.45-7.40 (m, 1H), 5.60 (s, 1H), 3.71 (s, 3H), 3.63-3.61 (m, 1H), 3.53-3.51 (m, 1H), 2.84 (s, 3H), 1.91-1.73 (m, 6H), 1.73-1.65 (m, 7H), 1.50-1.44 (m, 6H), 0.74-0.72 (m, 2H), 0.54-0.52 (m, 2H).

Example 416

N-((4-(3-cyclopropyl-1,2,4-oxadiazol-5-yl)bicyclo[2.2.2]octan-1-yl)methyl)-3-fluoro-N-(3-(4-methylpiperazin-1-yl)phenyl)bicyclo[1.1.1]pentane-1-carboxamide (416)

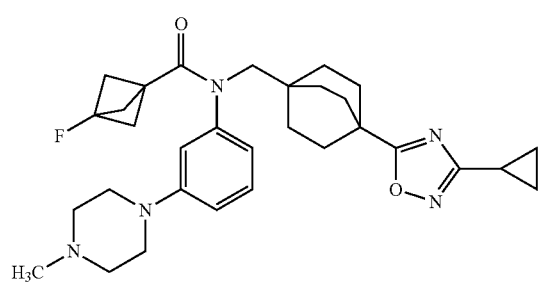

To a stirred solution of Intermediate 246B (20 mg, 0.039 mmol) in 1,4-dioxane (2 mL) were added 1-methylpiperazine (7.79 mg, 0.078 mmol), sodium tert-butoxide (11 mg, 0.117 mmol) and Xantphos (4.5 mg, 7.78 μmol). The reaction mixture was degassed and back-filled with argon. Pd$_2$(dba)$_3$ (3.56 mg, 3.89 μmol) was added to the reaction mixture and the vial (pressure release vial) was sealed under argon atmosphere. The reaction mixture was heated at 110° C. for 16 h. The reaction mixture was cooled to room temperature and concentrated under reduced pressure. The residue was diluted with water (10 mL) and extracted with ethyl acetate ethyl acetate (2×10 mL). The organic layers were combined, dried over anhydrous sodium sulphate and concentrated under reduced pressure. The crude material was purified via preparative LC/MS using following conditions. (Column. Waters XBridge C18, 150 mm×19 mm, 5-μm particles; Mobile Phase A. 5.95 acetonitrile. water with 10-mM ammonium acetate; Mobile Phase B. 95.5 acetonitrile. water with 10-mM ammonium acetate; Gradient. a 5-minute hold at 20% B, 20-58% B over 25 minutes, then a 5-minute hold at 100% B; Flow Rate. 15 mL/min; Column Temperature. 25° C.). Fraction collection was triggered by MS signals. Fractions containing the desired product were combined and dried via centrifugal evaporation to afford the title compound (3 mg, 5.62 μmol, 14% yield). $^1$H NMR (400 MHz, DMSO-d$_6$) δ 7.26 (t, J=8.1 Hz, 1H), 6.95-6.93 (m, 1H), 6.89 (s, 1H), 6.76 (d, J=8.3 Hz, 1H), 3.58-3.44 (m, 2H), 3.27-3.05 (m, 4H), 2.57-2.53 (m, 3H), 2.33-2.29 (m, 4H), 2.11-1.99 (m, 1H), 1.86-1.44 (m, 12H), 1.43-1.40 (m, 6H), 1.03-0.99 (m, 2H), 0.85-0.82 (m, 2H). FXR EC$_{50}$ (nM)=1058. MS (ESI) 534 (M+H).

The following compound was prepared according to the method described for the synthesis of Example 416 by substituting Intermediate 246B and the corresponding amines.

| Ex. No. | Structure | MS (ESI) (M + H) | FXR EC$_{50}$ (nM) |
|---|---|---|---|
| 417 | 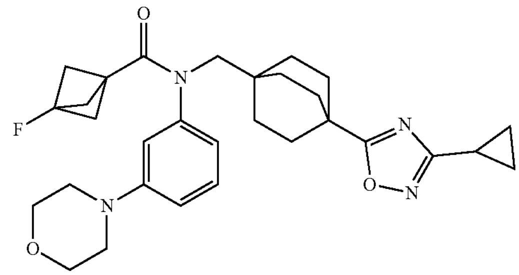 [SMILES: O=C(N(CC12CCC(c3nc(C4CC4)no3)(CC1)CC2)c1cccc(N2CCOCC2)c1)C12CC(F)(C1)C2] | 520 | 207 |

417 $^1$H NMR (400 MHz, DMSO-d$_6$) δ 7.28 (t, J = 8.1 Hz, 1H), 6.95 (dd, J = 8.2, 2.1 Hz, 1H), 6.90 (t, J = 2.0 Hz, 1H), 6.78 (d, J = 7.3 Hz, 1H), 3.75 (t, J = 4.8 Hz, 4H), 3.58-3.45 (m, 2H), 3.21-3.07 (m, 4H), 2.08-2.03 (m, 1H), 1.86-1.70 (m, 12H), 1.49-1.38 (m, 6H), 1.09-0.96 (m, 2H), 0.90-0.82 (m, 2H).

Example 418

N-(3-(2-ethoxypyrimidin-5-yl)phenyl)-3-fluoro-N-((1-(2-(trifluoromethyl)pyrimidin-5-yl)-2-oxabicyclo[2.2.2]octan-4-yl)methyl)bicyclo[1.1.1]pentane-1-carboxamide

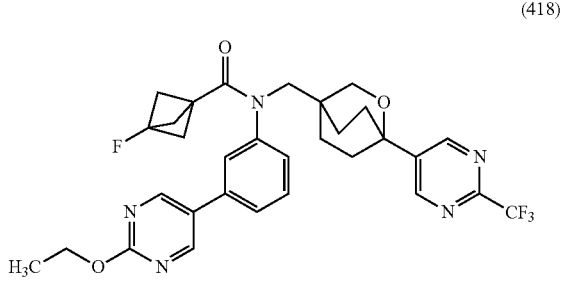 [SMILES: CCOc1ncc(-c2cccc(N(CC34CCC(c5cnc(C(F)(F)F)nc5)(CC3)OC4)C(=O)C34CC(F)(C3)C4)c2)cn1]

(418)

Step A. Intermediate 418A. Preparation of 3-bromo-N-((1-(2-(trifluoromethyl)pyrimidin-5-yl)-2-oxabicyclo[2.2.2]octan-4-yl)methyl)aniline

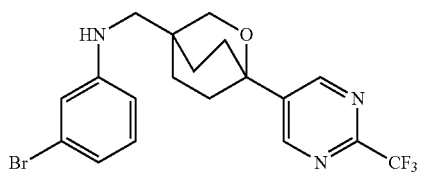 [SMILES: FC(F)(F)c1ncc(C23CCC(CNc4cccc(Br)c4)(CC2)CO3)cn1]

The title compound was prepared according to the method described for the synthesis of Intermediate 1I by substituting 3-bromoaniline and Intermediate 181E where appropriate. (130 mg, 0.270 mmol, 77% yield) as brown solid. $^1$H NMR (400 MHz, DMSO-d$_6$) δ 9.07 (s, 2H), 7.00 (t, J=8.0 Hz, 1H), 6.80 (t, J=2.0 Hz, 1H), 6.67-6.61 (m, 2H), 5.83 (t, J=5.8 Hz, 1H), 3.90 (s, 2H), 2.91 (d, J=6.0 Hz, 2H), 2.28-2.17 (m, 2H), 1.99-1.89 (m, 2H), 1.82-1.69 (m, 4H). MS (ESI) 443 (M+H).

Step B. Intermediate 418B. Preparation of N-(3-bromophenyl)-3-fluoro-N-((1-(2-(trifluoromethyl)pyrimidin-5-yl)-2-oxabicyclo[2.2.2]octan-4-yl)methyl) bicyclo[1.1.1]pentane-1-carboxamide

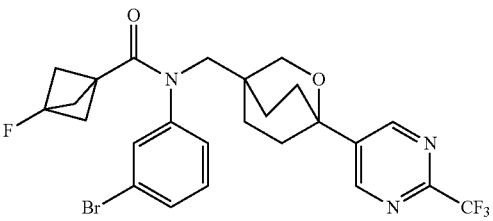 [SMILES: O=C(N(CC12CCC(c3cnc(C(F)(F)F)nc3)(CC1)OC2)c1cccc(Br)c1)C12CC(F)(C1)C2]

The title compound was prepared according to the method described for the synthesis of Example 3 by substituting Intermediate 418A and the corresponding acid where appropriate. (130 mg, 0.234 mmol, 80% yield) as a brown solid. $^1$H NMR (400 MHz, DMSO-d$_6$) δ 9.02 (s, 2H), 7.77-7.74 (m, 1H), 7.64 (d, J=7.5 Hz, 1H), 7.51-7.41 (m, 2H), 3.74 (s, 2H), 3.59 (d, J=14.1 Hz, 2H), 2.20-2.10 (m, 2H), 1.89 (br. s., 8H), 1.68 (br. s., 2H), 1.58 (br. s., 2H). MS (ESI) 556 (M+H).

Step C. Example 418. Preparation of N-(3-(2-ethoxypyrimidin-5-yl)phenyl)-3-fluoro-N-((1-(2-(trifluoromethyl)pyrimidin-5-yl)-2-oxabicyclo[2.2.2]octan-4-yl)methyl) bicyclo[1.1.1]pentane-1-carboxamide The title compound was prepared according to the method described for the synthesis of Example 149 by substituting Intermediate 418B and the corresponding halide where appropriate. (17 mg, 0.028 mmol, 62% yield). $^1$H NMR (400 MHz, DMSO-d$_6$) δ 9.02 (d, J=7.3 Hz, 4H), 7.88 (s, 1H), 7.80 (d, J=8.1 Hz, 1H), 7.59 (t, J=7.8 Hz, 1H), 7.47 (d, J=8.3 Hz, 1H), 4.43 (q, J=7.0 Hz, 2H), 3.78 (br. s., 2H), 3.66 (d, J=13.2 Hz, 2H), 2.23-2.06 (m, 2H), 1.91-1.87 (m, 8H), 1.77-1.67 (m, 2H), 1.63 (d, J=9.3 Hz, 2H), 1.38 (t, J=7.1 Hz, 3H). FXR EC$_{50}$ (nM)=2038. MS (ESI) 598 (M+H).

The following compounds were prepared according to the method described for the synthesis of Example 149 by substituting Intermediate 418B and the corresponding boronates/boronic acids.

| Ex. No. | Name | MS (ESI) (M + H) | FXR EC$_{50}$ (nM) |
|---|---|---|---|
| 419 | | 645 | 523 |
| 420 | | 582 | 802 |
| 421 | | 623 | 2172 |
| 422 | | 596 | 1517 |

419 $^1$H NMR (400 MHz, DMSO-d$_6$) δ 9.87 (br. s., 1H), 9.01 (s, 2H), 7.84-7.61 (m, 4H), 7.59-7.48 (m, 1H), 7.39 (d, J = 8.1 Hz, 1H), 7.33 (d, J = 8.8 Hz, 2H), 3.78 (br. s., 2H), 3.65 (s, 2H), 3.10-2.96 (m, 3H), 2.24-2.07 (m, 2H), 2.03-1.79 (m, 8H), 1.79-1.67 (m, 2H), 1.67-1.51 (m, 2H)

420 $^1$H NMR (400 MHz, DMSO-d$_6$) δ 9.01 (s, 2H), 7.79-7.62 (m, 4H), 7.53 (t, J = 8.2 Hz, 1H), 7.35 (d, J = 8.3 Hz, 1H), 7.15-7.01 (m, 2H), 3.87-3.74 (m, 5H), 3.65 (s, 2H), 2.23-2.07 (m, 2H), 1.89 (d, J = 8.6 Hz, 8H), 1.73 (br. s., 2H), 1.64 (d, J = 7.3 Hz, 2H)

421 $^1$H NMR(400 MHz, DMSO-d$_6$) δ 9.01 (s, 2H), 8.48 (d, J = 1.7 Hz, 1H), 8.01 (d, J = 8.6 Hz, 1H), 7.88 (dd, J = 8.4, 1.8 Hz, 1H), 7.85-7.76 (m, 2H), 7.59 (t, J = 7.8 Hz, 1H), 7.44 (d, J = 7.6 Hz, 1H), 3.80 (br. s., 2H), 3.74-3.68 (m, 1H), 3.68-3.60 (m, 1H), 2.84 (s, 3H), 2.24-2.07 (m, 2H), 1.93-1.89 (m, 4H), 1.74 (br. s., 2H), 1.63 (br. s., 2H)

422 $^1$H NMR (400 MHz, DMSO-d$_6$) δ 9.01 (s, 2H), 7.79-7.58 (m, 4H), 7.52 (t, J = 8.1 Hz, 1H), 7.35 (d, J = 8.3 Hz, 1H), 7.10-6.97 (m, 2H), 4.09 (q, J = 7.1 Hz, 2H), 3.78 (br. s., 2H), 3.65 (s, 2H), 2.23-2.08 (m, 2H), 1.89 (d, J = 8.6 Hz, 8H), 1.72 (br. s., 2H), 1.67-1.53 (m, 2H), 1.36 (t, J = 7.0 Hz, 3H)

Example 423

N-((4-(3-cyclopropyl-1,2,4-oxadiazol-5-yl)bicyclo[2.2.2]octan-1-yl)methyl)-N-(5-(2-ethoxypyrimidin-5-yl)pyridin-3-yl)-3-fluorobicyclo[1.1.1]pentane-1-carboxamide

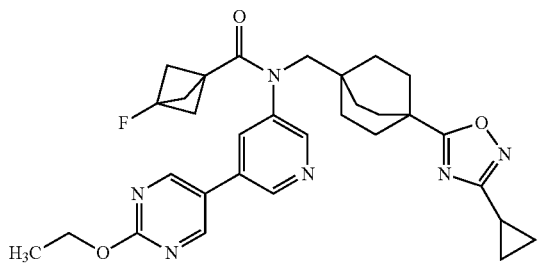

(423)

Step A. Intermediate 423A. Preparation of 5-bromo-N-((4-(3-cyclopropyl-1,2,4-oxadiazol-5-yl)bicyclo[2.2.2]octan-1-yl)methyl)pyridin-3-amine

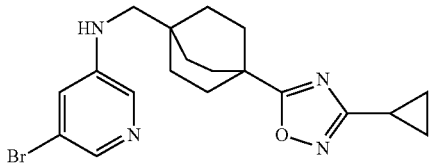 [SMILES: Brc1cncc(NCC23CCC(c4nc(C5CC5)no4)(CC2)CC3)c1]

The title compound was prepared according to the method described for the synthesis of Intermediate 1I by substituting 5-bromopyridin-3-amine and Intermediate 4C where appropriate. (300 mg, 0.744 mmol, 43% yield). MS (ESI) 405 (M+H).

Step B. Intermediate 423B. Preparation of N-(5-bromopyridin-3-yl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide

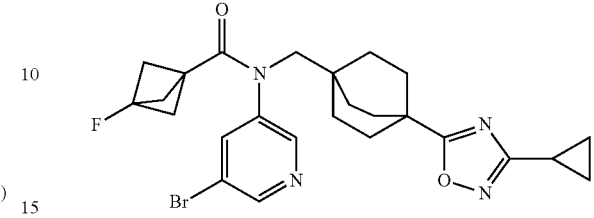

To a stirred solution of Intermediate 423A (300 mg, 0.744 mmol) in DCM (20 mL) was added 3-fluorobicyclo[1.1.1]pentane-1-carboxylic acid (116 mg, 0.893 mmol) followed by pyridine (0.301 mL, 3.72 mmol) and POCl$_3$ (0.139 mL, 1.488 mmol) at 0° C. The reaction mixture was allowed to warm to room temperature and stirred for overnight. The reaction mixture was diluted with DCM (20 mL), washed with water (30 mL) and extracted with EtOAc (2×30 mL). The organic layers were combined, dried over anhydrous sodium sulphate and concentrated under reduced pressure. The crude material was purified by flash chromatography (24 g silica gel cartridge; A=Hex, B=EtOAc; 30 min grad.; 0% B to 30% B; flow rate=30 mL/min). The pure fractions were combined, concentrated and dried in vacuo to afford the title compound (200 mg, 0.361 mmol, 48% yield). MS (ESI) 515 (M+H).

Step C. Example 423. Preparation of N-((4-(3-cyclopropyl-1,2,4-oxadiazol-5-yl) bicyclo[2.2.2]octan-1-yl)methyl)-N-(5-(2-ethoxypyrimidin-5-yl)pyridin-3-yl)-3-fluorobicyclo[1.1.1]pentane-1-carboxamide The title compound was prepared according to the method described for the synthesis of Example 149 by substituting Intermediate 423B and (2-ethoxypyrimidin-5-yl)boronic acid where appropriate. (9.3 mg, 0.017 mmol, 43% yield). $^1$H NMR (400 MHz, DMSO-d$_6$) δ 9.09 (s, 2H), 8.99 (d, J=2.0 Hz, 1H), 8.68 (d, J=2.2 Hz, 1H), 8.32 (t, J=2.2 Hz, 1H), 4.44 (q, J=7.0 Hz, 2H), 3.71 (br. s., 1H), 3.54 (br. s., 1H), 2.08-2.02 (m, 1H), 1.90 (br. s., 6H), 1.85-1.66 (m, 6H), 1.53-1.41 (m, 6H), 1.38 (t, J=7.1 Hz, 3H), 1.06-0.96 (m, 2H), 0.87-0.79 (m, 2H). FXR EC$_{50}$ (nM) 238. MS (ESI) 559 (M+H).

The following compounds were prepared according to the method described for the synthesis of Example 149 by substituting Intermediate 423B and the corresponding boronates.

| Ex. No. | Structure | MS (ESI) (M + H) | FXR EC$_{50}$ (nM) |
|---|---|---|---|
| 424 | 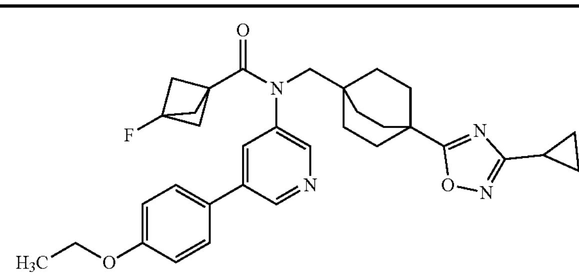 | 557 | 483 |

| Ex. No. | Structure | MS (ESI) (M + H) | FXR EC$_{50}$ (nM) |
|---|---|---|---|
| 425 | | 584 | 198 |
| 426 | | 558 | 417 |
| 427 | | 606 | 671 |
| 428 | | 583 | 3549 |

424 $^1$H NMR (400 MHz, DMSO-d$_6$) δ 8.88 (d, J = 2.0 Hz, 1H), 8.56 (d, J = 2.2 Hz, 1H), 8.15 (t, J = 2.2 Hz, 1H), 7.83-7.69 (m, 2H), 7.16-7.01 (m, 2H), 4.18-4.00 (m, 2H), 3.70 (br. s., 1H), 3.54 (br. s., 1H), 2.09-2.00 (m, 1H), 1.99-1.84 (m, 6H), 1.84-1.58 (m, 6H), 1.46 (d, J = 5.1 Hz, 6H), 1.38-1.29 (m, 3H), 1.09-0.96 (m, 2H), 0.90-0.76 (m, 2H)

425 $^1$H NMR (400 MHz, DMSO-d$_6$) δ 9.00 (d, J = 2.0 Hz, 1H), 8.65 (d, J = 2.2 Hz, 1H), 8.55 (d, J = 1.7 Hz, 1H), 8.30 (t, J = 2.2 Hz, 1H), 8.04 (d, J = 8.3 Hz, 1H), 7.94 (dd, J = 8.6, 2.0 Hz, 1H), 3.76 (d, J = 13.7 Hz, 1H), 3.55 (br. s., 1H), 2.94-2.78 (m, 3H), 2.08-2.02 (m, 1H), 1.89 (s, 3H), 1.93 (s, 3H), 1.85-1.66 (m, 6H), 1.59-1.31 (m, 6H), 1.09-0.96 (m, 2H), 0.87-0.76 (m, 2H)

426 $^1$H NMR (400 MHz, DMSO-d$_6$) δ 8.93 (d, J = 2.0 Hz, 1H), 8.62 (d, J = 2.2 Hz, 1H), 8.64 (d, J = 2.4 Hz, 1H), 8.24 (t, J = 2.1 Hz, 1H), 8.18 (dd, J = 8.7, 2.6 Hz, 1H), 6.95 (d, J = 8.8 Hz, 1H), 4.38 (q, J = 6.9 Hz, 2H), 3.70 (br. s., 1H), 3.55 (br. s., 1H), 2.09-2.01 (m, 1H), 1.90 (br. s., 6H), 1.85-1.57 (m, 6H), 1.55-1.38 (m, 6H), 1.36 (t, J = 7.1 Hz, 3H), 1.07-0.95 (m, 2H), 0.91-0.77 (m, 2H)

427 $^1$H NMR (400 MHz, DMSO-d$_6$) δ 9.96 (s, 1H), 8.91 (d, J = 1.7 Hz, 1H), 8.60 (d, J = 2.2 Hz, 1H), 8.18 (t, J = 2.1 Hz, 1H), 7.90-7.75 (m, J = 8.8 Hz, 2H), 7.45-7.27 (m, J = 8.8 Hz, 2H), 3.70 (br. s., 1H), 3.54 (br. s., 1H), 3.06 (s, 3H), 2.09-2.02 (m, 1H), 1.90 (br. s., 5H), 1.85 -1.58 (m, 7H), 1.45 (d, J = 8.6 Hz, 6H), 1.07-0.95 (m, 2H), 0.88-0.79 (m, 2H)

| Ex. No. | Structure | MS (ESI) (M + H) | FXR EC$_{50}$ (nM) |
|---|---|---|---|
| 428 | $^1$H NMR (400 MHz, DMSO-d$_6$) δ 9.57 (s, 2H), 9.15 (d, J = 2.2 Hz, 1H), 8.82 (d, J = 2.2 Hz, 1H), 8.50 (t, J = 2.2 Hz, 1H), 3.74 (br. s., 1H), 3.56 (br. s., 1H), 2.09-2.01 (m, 1H), 1.92 (br. s., 6H), 1.87-1.60 (m, 6H), 1.60-1.32 (m, 6H), 1.09-0.95 (m, 2H), 0.89 -0.78 (m, 2H) | | |

Example 429

N-(3-(2-ethoxypyrimidin-5-yl)phenyl)-3-fluoro-N-((4-(5-isopropyl-1,2,4-oxadiazol-3-yl)bicyclo[2.2.2]octan-1-yl)methyl)bicyclo[1.1.1]pentane-1-carboxamide

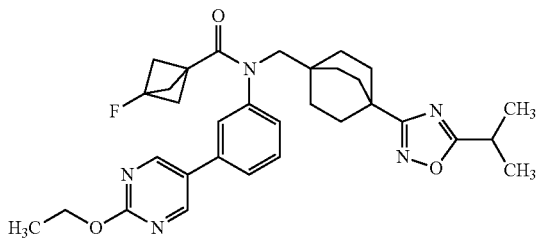
(429)

Step A. Intermediate 429A. Preparation of N-(3-bromophenyl)-3-fluoro-N-((4-(5-isopropyl-1,2,4-oxadiazol-3-yl)bicyclo[2.2.2]octan-1-yl)methyl)bicyclo[1.1.1]pentane-1-carboxamide

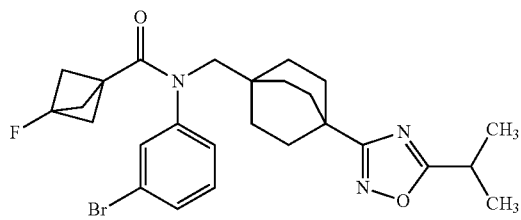 [SMILES: CC(C)c1nc(C23CCC(CN(C(=O)C45CC(F)(C4)C5)c4cccc(Br)c4)(CC2)CC3)no1]

The title compound was prepared according to the method described for the synthesis of Intermediate 1A by substituting Intermediate 396C and the corresponding acid where appropriate. (190 mg, 0.368 mmol, 85% yield). MS (ESI) 516 (M+H).

Step B. Example 429. Preparation of N-(3-(2-ethoxypyrimidin-5-yl)phenyl)-3-fluoro-N-((4-(5-isopropyl-1,2,4-oxadiazol-3-yl)bicyclo[2.2.2]octan-1-yl)methyl) bicyclo[1.1.1]pentane-1-carboxamide The title compound was prepared according to the method described for the synthesis of Example 149 by substituting Intermediate 429A and (2-ethoxypyrimidin-5-yl)boronic acid where appropriate. (10.5 mg, 0.019 mmol, 39% yield). $^1$H NMR (400 MHz, DMSO-d$_6$) δ 9.01 (s, 2H), 7.88-7.79 (m, 1H), 7.77 (d, J=7.6 Hz, 1H), 7.57 (t, J=7.8 Hz, 1H), 7.48-7.37 (m, 1H), 4.43 (q, J=7.0 Hz, 2H), 3.63 (br. s., 1H), 3.60-3.46 (m, 1H), 3.20 (dt, J=13.9, 7.0 Hz, 1H), 1.85 (s, 3H), 1.89 (s, 3H), 1.79-1.61 (m, 6H), 1.56-1.40 (m, 6H), 1.38 (t, J=7.1 Hz, 3H), 1.32-1.24 (m, 6H). FXR EC$_{50}$ (nM)=46. MS (ESI) 560 (M+H).

The following compounds were prepared according to the method described for the synthesis of Example 149 by substituting Intermediate 429A and the corresponding boronic acids/esters.

| Ex. No. | Structure | MS (ESI) (M + H) | FXR EC$_{50}$ (nM) |
|---|---|---|---|
| 430 | 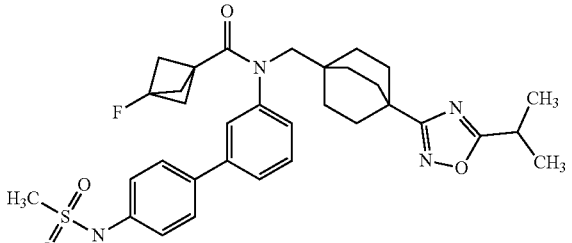 | 607 | 40 |

| Ex. No. | Structure | MS (ESI) (M + H) | FXR EC$_{50}$ (nM) |
|---|---|---|---|
| 431 | 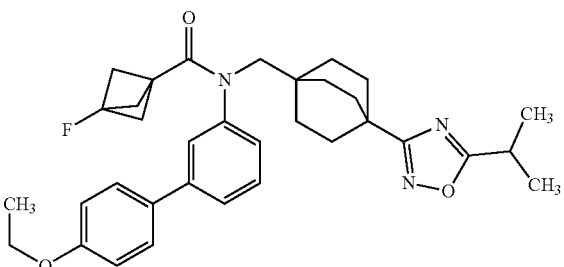 | 558 | 25 |
| 432 | 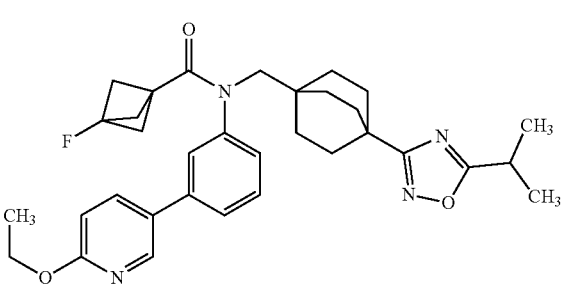 [SMILES: CCOc1ccc(-c2cccc(N(CC34CCC(c5noc(C(C)C)n5)(CC3)CC4)C(=O)C34CC(F)(C3)C4)c2)cn1] | 559 | 51 |
| 433 | 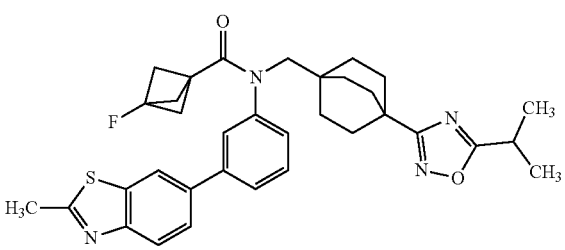 [SMILES: Cc1nc2ccc(-c3cccc(N(CC45CCC(c6noc(C(C)C)n6)(CC4)CC5)C(=O)C45CC(F)(C4)C5)c3)cc2s1] | 585 | 37 |
| 434 | 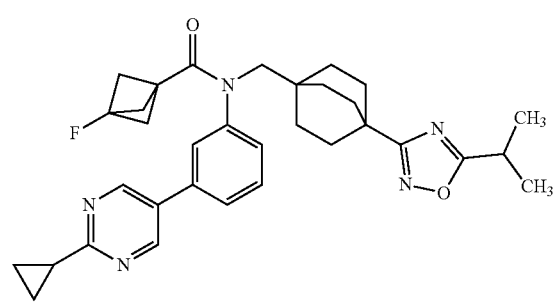 [SMILES: CC(C)c1nc(C23CCC(CN(C(=O)C45CC(F)(C4)C5)c4cccc(-c5cnc(C6CC6)nc5)c4)(CC2)CC3)no1] | 556 | 57 |
| 435 | 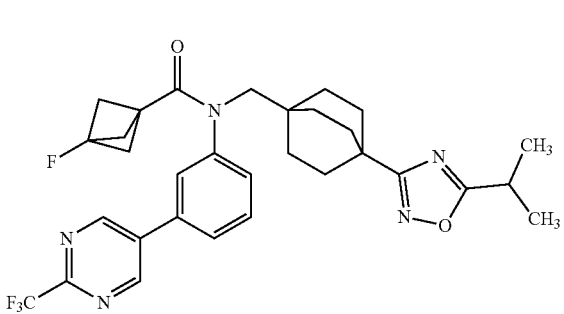 [SMILES: CC(C)c1nc(C23CCC(CN(C(=O)C45CC(F)(C4)C5)c4cccc(-c5cnc(C(F)(F)F)nc5)c4)(CC2)CC3)no1] | 584 | 240 |

| Ex. No. | Structure | MS (ESI) (M + H) | FXR EC$_{50}$ (nM) |
|---|---|---|---|
| 436 | | 580 | 46 |

430 $^1$H NMR (400 MHz, DMSO-d$_6$) δ 9.89 (s, 1H), 7.74 (d, J = 8.6 Hz, 2H), 7.70-7.61 (m, 2H), 7.53 (t, J = 7.8 Hz, 2H), 7.40-7.23 (m, 2H), 3.60 (d, J = 11.5 Hz, 2H), 3.20 (dt, J = 13.9, 7.0 Hz, 1H), 3.04 (s, 3H), 1.85 (s, 3H), 1.88 (s, 3H), 1.79-1.58 (m, 6H), 1.56-1.31 (m, 6H), 1.31-1.20 (m, 6H)

431 $^1$H NMR (400 MHz, DMSO-d$_6$) δ 7.74-7.58 (m, 4H), 7.50 (t, J = 7.8 Hz, 1H), 7.31 (d, J = 7.8 Hz, 1H), 7.12-6.98 (m, 2H), 4.09 (q, J = 7.1 Hz, 2H), 3.59 (d, J = 9.3 Hz, 2H), 3.23-3.17 (m, 1H), 1.85 (s, 3H), 1.88 (s, 3H), 1.79-1.64 (m, 6H), 1.57-1.39 (m, 6H), 1.36 (t, J = 7.0 Hz, 3H), 1.31-1.23 (m, 6H)

432 $^1$H NMR (400 MHz, DMSO-d$_6$) δ 8.56 (d, J = 2.4 Hz, 1H), 8.10 (dd, J = 8.7, 2.6 Hz, 1H), 7.83-7.62 (m, 2H), 7.53 (t, J = 8.1 Hz, 1H), 7.37 (d, J = 8.1 Hz, 1H), 6.91 (d, J = 8.6 Hz, 1H), 4.37 (q, J = 7.1 Hz, 2H), 3.60 (d, J = 7.8 Hz, 2H), 3.20 (dt, J = 13.9, 7.0 Hz, 1H), 1.85 (s, 3H), 1.88 (s, 3H),1.80-1.61 (m, 6H), 1.46 (d, J = 8.3 Hz, 6H), 1.35 (t, J = 7.0 Hz, 3H), 1.31-1.20 (m, 6H)

433 $^1$H NMR (400 MHz, DMSO-d$_6$) δ 8.46 (d, J = 1.5 Hz, 1H), 8.00 (d, J = 8.3 Hz, 1H), 7.85 (dd, J = 8.6, 2.0 Hz, 1H), 7.82-7.71 (m, 2H), 7.57 (t, J = 7.7 Hz, 1H), 7.40 (d, J = 8.3 Hz, 1H), 3.68 (d, J = 13.0 Hz, 1H), 3.55 (d = 13.2 Hz, 1H), 3.19 (dt, J = 14.0, 7.1 Hz, 1H), 2.83 (s, 3H), 1.86 (s, 3H), 1.91 (s, 3H), 1.75 (t, J = 7.7 Hz, 6H), 1.47 (d, J = 5.1 Hz, 6H), 1.27 (d, J = 7.1 Hz, 6H)

434 $^1$H NMR (400 MHz, DMSO-d$_6$) δ 9.03 (s, 2H), 7.84 (s, 1H), 7.79 (d, J = 7.6 Hz, 1H), 7.58 (t, J = 7.8 Hz, 1H), 7.45 (d, J = 7.3 Hz, 1H), 3.70-3.47 (m, 3H), 2.32-2.22 (m, 1H), 2.01-1.80 (m, 6H), 1.80-1.61 (m, 6H), 1.56-1.36 (m, 6H), 1.33-1.23 (m, 6H), 1.18-0.89 (m, 4H)

435 $^1$H NMR (400 MHz, DMSO-d$_6$) δ 9.49 (s, 2H), 8.01 (t, J = 1.8 Hz, 1H), 7.96 (d, J = 7.8 Hz, 1H), 7.73-7.62 (m, 1H), 7.61-7.52 (m, 1H), 3.66 (br. s., 1H), 3.58 (br. s., 1H), 3.23-3.15 (m, 1H), 1.86 (s, 3H), 1.90 (s, 3H), 1.80-1.61 (m, 6H), 1.45 (d, J = 4.6 Hz, 3H), 1.47 (d, J = 4.6 Hz, 3H), 1.32-1.24 (m, 6H)

436 $^1$H NMR (400 MHz, DMSO-d$_6$) δ 7.88-7.77 (m, 2H), 7.75-7.63 (m, 2H), 7.54 (t, J = 7.8 Hz, 1H), 7.39 (d, J = 8.1 Hz, 1H), 7.34-7.20 (m, 3H), 3.63 (br. s., 1H), 3.57 (br. s., 1H), 3.20 (dt, J = 13.9, 7.0 Hz, 1H), 1.85 (s, 3H), 1.88 (s, 3H), 1.81-1.61 (m, 6H), 1.46 (d, J = 9.5 Hz, 6H), 1.33-1.21 (m, 6H)

Example 437

N-((4-(5-(tert-butyl)-1,2,4-oxadiazol-3-yl)bicyclo[2.2.2]octan-1-yl)methyl)-N-(3-(2-ethoxypyrimidin-5-yl)phenyl)-3-fluorobicyclo[1.1.1]pentane-1-carboxamide (437)

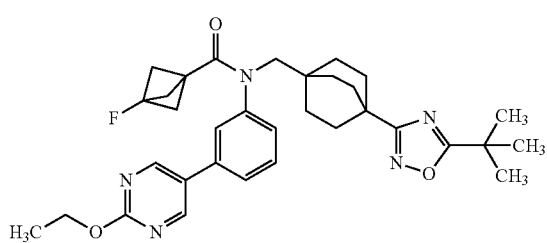

The title compound was prepared according to the method described for the synthesis of Example 149 by substituting Intermediate 194G and (2-ethoxypyrimidin-5-yl)boronic acid where appropriate. (12.9 mg, 0.022 mmol, 47% yield). $^1$H NMR (400 MHz, DMSO-d$_6$) δ 9.01 (s, 2H), 7.82 (s, 1H), 7.77 (d, J=7.8 Hz, 1H), 7.57 (t, J=7.8 Hz, 1H), 7.43 (d, J=8.8 Hz, 1H), 4.43 (q, J=7.0 Hz, 2H), 3.60 (d, J=18.8 Hz, 2H), 1.85 (s, 3H), 1.89 (s, 3H), 1.79-1.63 (m, 6H), 1.57-1.40 (m, 6H), 1.38 (t, J=7.1 Hz, 3H), 1.33 (s, 9H). FXR EC$_{50}$ (nM)=39. MS (ESI) 574 (M+H).

The following compounds were prepared according to the method described for the synthesis of Example 149 by substituting Intermediate 194G and the corresponding boronic acids/esters.

| Ex. No. | Structure | MS (ESI) (M + H) | FXR EC$_{50}$ (nM) |
|---|---|---|---|
| 438 | 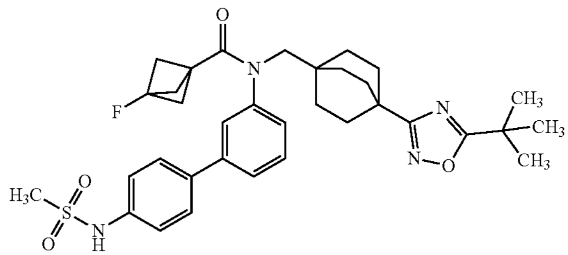 [SMILES: CC(C)(C)c1nc(C23CCC(CN(C(=O)C45CC(F)(C4)C5)c4cccc(-c5ccc(NS(C)(=O)=O)cc5)c4)(CC2)CC3)no1] | 621 | 46 |
| 439 | 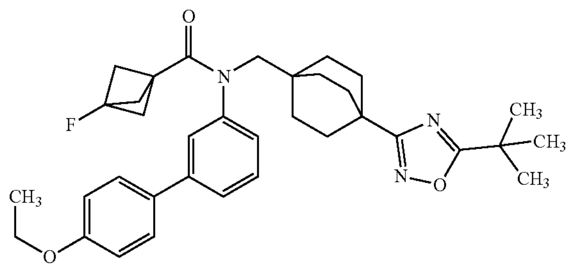 [SMILES: CCOc1ccc(-c2cccc(N(CC34CCC(c5noc(C(C)(C)C)n5)(CC3)CC4)C(=O)C34CC(F)(C3)C4)c2)cc1] | 572 | 70 |
| 440 | 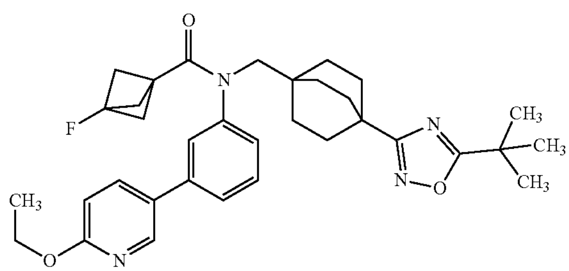 [SMILES: CCOc1ccc(-c2cccc(N(CC34CCC(c5noc(C(C)(C)C)n5)(CC3)CC4)C(=O)C34CC(F)(C3)C4)c2)cn1] | 573 | 103 |
| 441 | 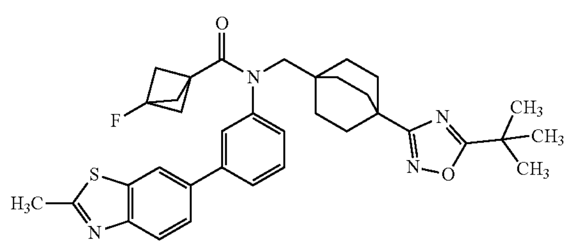 [SMILES: Cc1nc2ccc(-c3cccc(N(CC45CCC(c6noc(C(C)(C)C)n6)(CC4)CC5)C(=O)C45CC(F)(C4)C5)c3)cc2s1] | 599 | 68 |
| 442 | 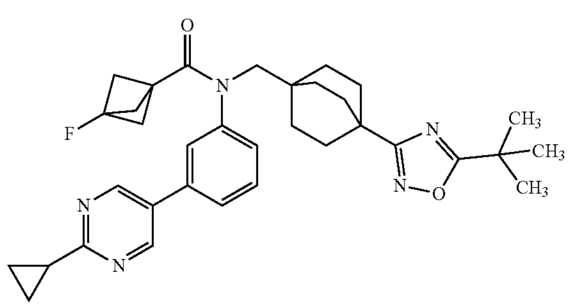 [SMILES: CC(C)(C)c1nc(C23CCC(CN(C(=O)C45CC(F)(C4)C5)c4cccc(-c5cnc(C6CC6)nc5)c4)(CC2)CC3)no1] | 570 | 71 |

| Ex. No. | Structure | MS (ESI) (M + H) | FXR EC$_{50}$ (nM) |
|---|---|---|---|
| 443 | 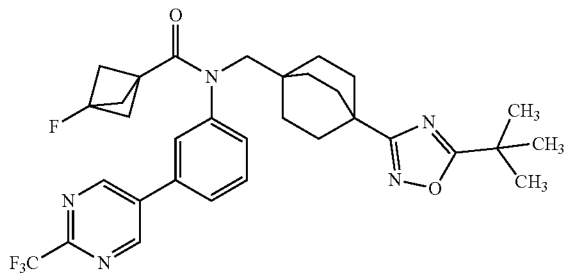 [SMILES: CC(C)(C)c1nc(C23CCC(CN(C(=O)C45CC(F)(C4)C5)c4cccc(-c5cnc(C(F)(F)F)nc5)c4)(CC2)CC3)no1] | 598 | 357 |
| 444 | 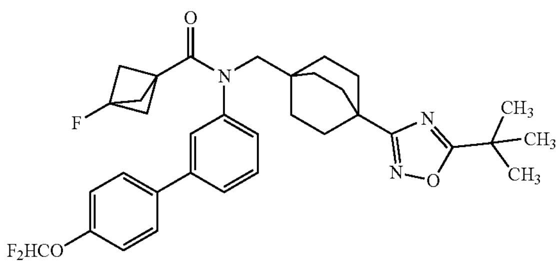 | 594 | 61 |
| 445 | 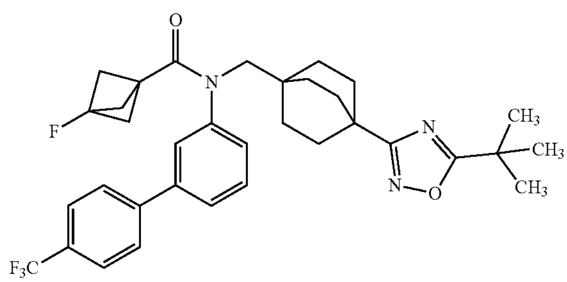 [SMILES: CC(C)(C)c1nc(C23CCC(CN(C(=O)C45CC(F)(C4)C5)c4cccc(-c5ccc(C(F)(F)F)cc5)c4)(CC2)CC3)no1] | 596 | 719 |

438 $^1$H NMR (400 MHz, DMSO-d$_6$) δ 9.89 (s, 1H), 7.74 (d, J = 8.6 Hz, 2H), 7.71-7.61 (m, 2H), 7.53 (t, J = 7.8 Hz, 1H), 7.40-7.27 (m, 3H), 3.60 (d, J = 8.3 Hz, 2H), 3.04 (s, 3H), 1.85 (s, 3H), 1.88 (s, 3H), 1.81-1.63 (m, 6H), 1.53-1.37 (m, 6H), 1.37-1.26 (m, 9H)

439 $^1$H NMR (400 MHz, DMSO-d$_6$) δ 7.76-7.56 (m, 4H), 7.50 (t, J = 7.8 Hz, 1H), 7.31 (d, J = 8.1 Hz, 1H), 7.04 (d, J = 8.8 Hz, 2H), 4.09 (q, J = 7.0 Hz, 2H), 3.59 (d, J = 6.8 Hz, 2H), 1.86 (d, J = 9.3 Hz, 6H), 1.79-1.58 (m, 6H), 1.57-1.39 (m, 6H), 1.39-1.26 (m, 12H)

440 $^1$H NMR (400 MHz, DMSO-d$_6$) δ 8.56 (d, J = 2.0 Hz, 1H), 8.10 (dd, J = 8.7, 2.6 Hz, 1H), 7.79-7.63 (m, 2H), 7.53 (t, J = 8.2 Hz, 1H), 7.42-7.32 (m, 1H), 6.97-6.85 (m, 1H), 4.37 (q, J = 7.1 Hz, 2H), 3.60 (d, J = 5.4 Hz, 2H), 1.85 (s, 3H), 1.88 (s, 3H), 1.79-1.59 (m, 6H), 1.57-1.38 (m, 6H), 1.38-1.25 (m, 12H)

441 $^1$H NMR (400 MHz, DMSO-d$_6$) δ 8.46 (d, J = 1.7 Hz, 1H), 8.00 (d, J = 8.3 Hz, 1H), 7.86 (dd, J = 8.6, 2.0 Hz, 1H), 7.81-7.69 (m, 2H), 7.57 (t, J = 7.7 Hz, 1H), 7.40 (d, J = 7.3 Hz, 1H), 3.68 (d, J = 13.9 Hz, 1H), 3.56 (d, J = 13.4 Hz, 1H), 2.83 (s, 3H), 1.86 (s, 3H), 1.91 (s, 3H), 1.75 (t, J = 7.8 Hz, 6H), 1.47 (d, J = 5.6 Hz, 6H), 1.33 (s, 9H)

442 $^1$H NMR (400 MHz, DMSO-d$_6$) δ 9.03 (s, 2H), 7.88-7.82 (m, 1H), 7.79 (d, J = 7.6 Hz, 1H), 7.58 (t, J = 7.8 Hz, 1H), 7.46 (d, J = 8.1 Hz, 1H), 3.60 (d, J = 12.0 Hz, 2H), 2.31-2.22 (m, 1H), 1.84 (s, 3H), 1.88 (s, 3H), 1.80-1.69 (m, 6H), 1.55-1.36 (m, 6H), 1.33 (s, 9H), 1.14-1.01 (m, 4H)

443 $^1$H NMR (400 MHz, DMSO-d$_6$) δ 9.49 (s, 2H), 8.06-7.99 (m, 1H), 7.96 (d, J = 7.8 Hz, 1H), 7.67 (t, J = 7.8 Hz, 1H), 7.58 (d, J = 8.3 Hz, 1H), 3.66 (br. s., 1H), 3.59 (br. s., 1H), 1.86 (s, 3H), 1.90 (s, 3H), 1.82-1.66 (m, 6H), 1.57-1.37 (m, 6H), 1.33 (s, 9H)

444 $^1$H NMR (400 MHz, DMSO-d$_6$) δ 7.88-7.76 (m, 2H), 7.75-7.62 (m, 2H), 7.54 (t, J = 7.8 Hz, 1H), 7.39 (dd, J = 7.1, 1.2 Hz, 1H), 7.34-7.20 (m, 3H), 3.68-3.60 (m, 1H), 3.60-3.51 (m, 1H), 1.85 (s, 3H), 1.88 (s, 3H), 1.81-1.60 (m, 6H), 1.46 (d, J = 9.5 Hz, 6H), 1.33 (s, 9H)

445 $^1$H NMR (400 MHz, DMSO-d$_6$) δ 8.07-7.93 (m, J = 8.3 Hz, 2H), 7.91-7.82 (m, J = 8.3 Hz, 2H), 7.82-7.71 (m, 2H), 7.60 (t, J = 8.2 Hz, 1H), 7.47 (d, J = 8.3 Hz, 1H), 3.73-3.61 (m, 1H), 3.61-3.52 (m, 1H), 1.85 (s, 3H), 1.89 (s, 3H), 1.80-1.60 (m, 6H), 1.56-1.37 (m, 6H), 1.33 (s, 9H)

Example 346

N-((4-(5-(tert-butyl)-1,2,4-oxadiazol-3-yl)bicyclo[2.2.2]octan-1-yl)methyl)-3-fluoro-N-(4'-((trifluoromethyl)sulfonamido)-[1,1'-biphenyl]-3-yl)bicyclo[1.1.1]pentane-1-carboxamide (446)

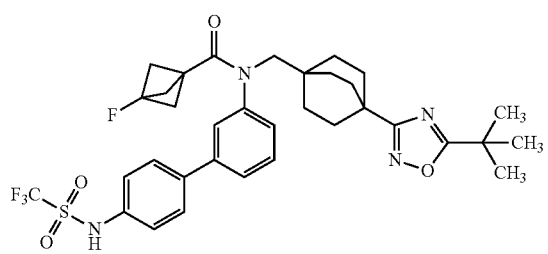

Step A. Intermediate 446A. Preparation of N-((4-(5-(tert-butyl)-1,2,4-oxadiazol-3-yl) bicyclo[2.2.2]octan-1-yl)methyl)-N-(3-(5,5-dimethyl-1,3,2-dioxaborinan-2-yl)phenyl)-3-fluorobicyclo[1.1.1]pentane-1-carboxamide

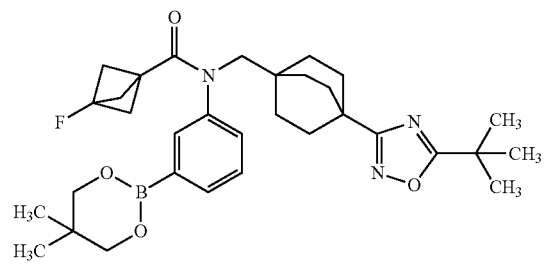 [SMILES: CC1(C)COB(c2cccc(N(CC34CCC(c5noc(C(C)(C)C)n5)(CC3)CC4)C(=O)C34CC(F)(C3)C4)c2)OC1]

The title compound was prepared according to the method described for the synthesis of Intermediate 149C by substituting Intermediate 194G where appropriate. (270 mg, 0.480 mmol, 91% yield) as an off-white solid. MS (ESI) 496 (M+H) (boronic acid mass).

Step B. Example 446. Preparation of N-((4-(5-(tert-butyl)-1,2,4-oxadiazol-3-yl) bicyclo[2.2.2]octan-1-yl)methyl)-3-fluoro-N-(4'-((trifluoromethyl)sulfonamido)-[1,1'-biphenyl]-3-yl)bicyclo[1.1.1]pentane-1-carboxamide The title compound was prepared according to the method described for the synthesis of Example 149 by substituting Intermediate 446A and the corresponding halide where appropriate. (4.7 mg, 7.64 μmol, 17% yield). $^1$H NMR (400 MHz, DMSO-$d_6$) δ 7.79 (d, J=8.8 Hz, 2H), 7.74-7.63 (m, 2H), 7.54 (t, J=7.8 Hz, 1H), 7.44-7.29 (m, 3H), 3.62 (s, 1H), 3.57 (br. s., 1H), 1.85 (s, 3H), 1.88 (s, 3H), 1.79-1.62 (m, 6H), 1.46 (d, J=5.6 Hz, 6H), 1.33 (s, 9H). FXR EC$_{50}$ (nM)=225. MS (ESI) 675 (M+H).

The following compounds were prepared according to the method described for the synthesis of Example 149 by substituting Intermediate 446A and the corresponding aryl/hetero aryl halides.

| Ex. No. | Structure | MS (ESI) (M + H) | FXR EC$_{50}$ (nM) |
|---|---|---|---|
| 447 | 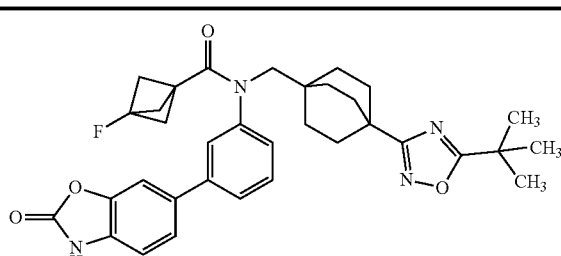 | 585 | 87 |
| 448 | 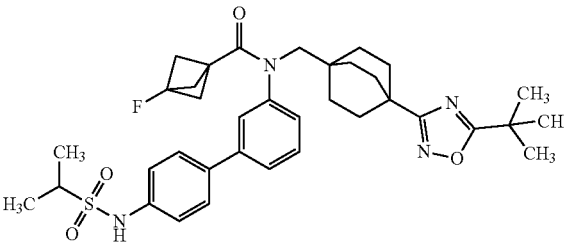 [SMILES: CC(C)S(=O)(=O)Nc1ccc(-c2cccc(N(CC34CCC(c5noc(C(C)(C)C)n5)(CC3)CC4)C(=O)C34CC(F)(C3)C4)c2)cc1] | 649 | 277 |

| Ex. No. | Structure | MS (ESI) (M + H) | FXR EC$_{50}$ (nM) |
|---|---|---|---|
| 449 | 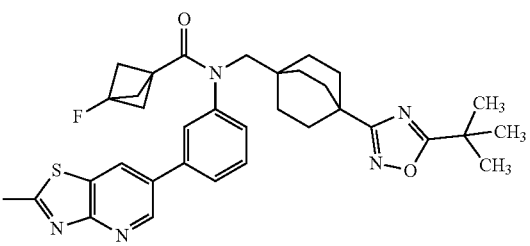 | 600 | 98 |
| 450 | 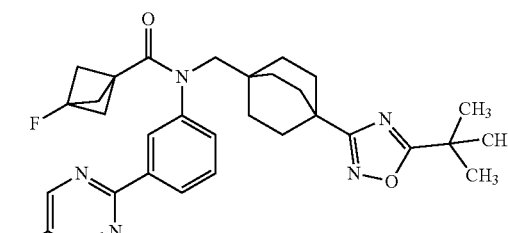 | 560 | 68 |
| 451 | 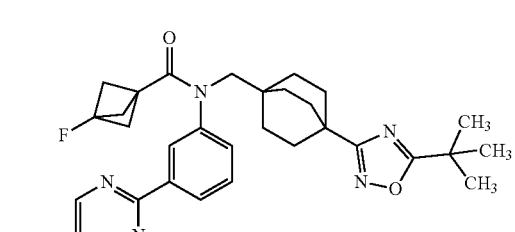 | 574 | 47 |
| 452 | 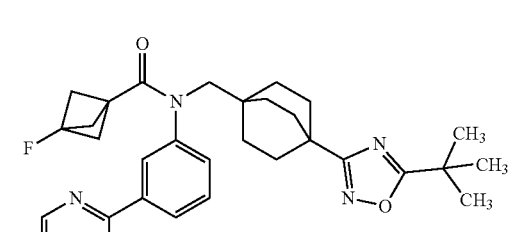 | 596 | 17 |
| 453 | 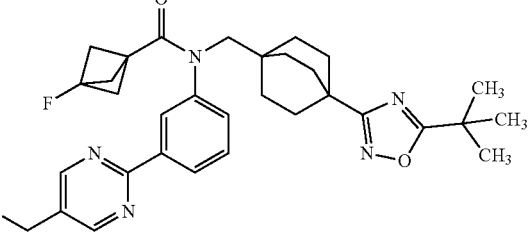 | 558 | 34 |

-continued
| Ex. No. | Structure | MS (ESI) (M + H) | FXR EC$_{50}$ (nM) |
|---|---|---|---|
| 454 | 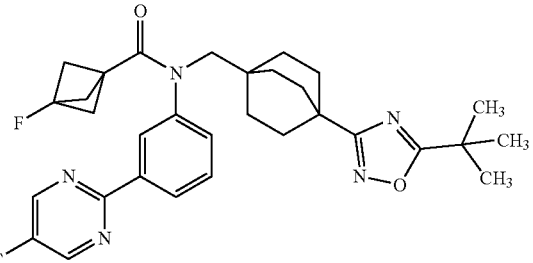 | 544 | 31 |
| 455 | 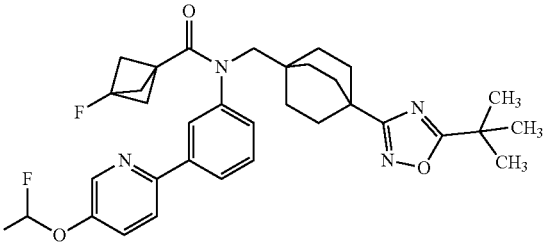 | 595 | 17 |
| 456 | 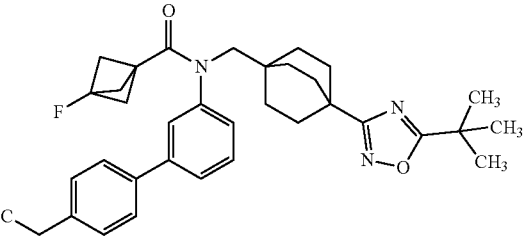 | 556 | 106 |
| 457 | 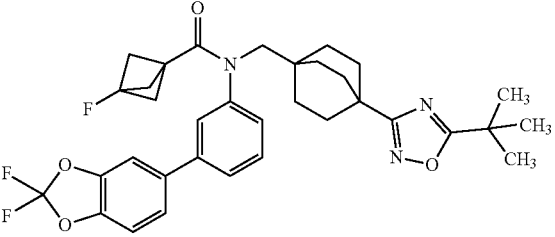 [SMILES: CC(C)(C)c1nc(C23CCC(CN(C(=O)C45CC(F)(C4)C5)c4cccc(-c5ccc6c(c5)OC(F)(F)O6)c4)(CC2)CC3)no1] | 608 | 144 |
| 458 | 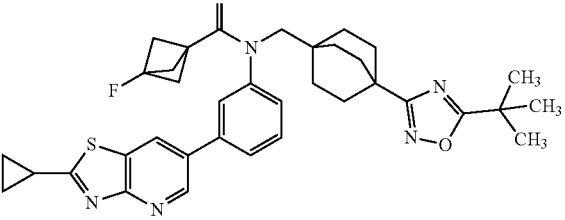 | 626 | 251 |
447 $^1$H NMR (400 MHz, DMSO-d$_6$) δ 11.76 (br. s., 1H), 7.74 (d, J = 1.5 Hz, 1H), 7.72-7.63 (m, 2H), 7.61-7.43 (m, 2H), 7.36 (d, J = 8.1 Hz, 1H), 7.19 (d, J = 8.3 Hz, 1H), 3.65 (d, J = 13.7 Hz, 1H), 3.55 (d, J = 13.9 Hz, 1H), 2.01-1.79 (m, 6H), 1.78-1.67 (m, 6H), 1.45 (d, J = 4.4 Hz, 6H), 1.33 (s, 9H)
448 $^1$H NMR (400 MHz, DMSO-d$_6$) δ 9.93 (s, 1H), 7.77-7.58 (m, 4H), 7.52 (t, J = 7.8 Hz, 1H), 7.35 (d, J = 8.6 Hz, 3H), 3.68-3.50 (m, 2H), 3.28 (dt, J = 13.6, 6.8 Hz, 1H), 1.85 (s, 3H), 1.87 (s, 3H), 1.80-1.59 (m, 6H), 1.57-1.37 (m, 6H), 1.33 (s, 9H), 1.29-1.20 (m, 6H)
449 $^1$H NMR (400 MHz, DMSO-d$_6$) δ 9.03 (d, J = 2.2 Hz, 1H), 8.94 (d, J = 2.2 Hz, 1H), 7.97-7.75 (m, 2H), 7.61 (t, J = 7.9 Hz, 1H), 7.46 (d, J = 8.6 Hz, 1H), 3.73-3.61 (m, 1H), 3.61-3.50 (m, 1H), 2.90 (s, 3H), 2.05-1.80 (m, 6H), 1.80-1.57 (m, 6H), 1.56-1.37 (m, 6H), 1.33 (s, 9H)
450 $^1$H NMR (400 MHz, DMSO-d$_6$) δ 8.71 (s, 2H), 8.31 (d, J = 7.8 Hz, 1H), 8.18 (t, J = 1.7 Hz, 1H), 7.65-7.56 (m, 1H), 7.51 (d, J = 9.0 Hz, 1H), 3.98 (s, 3H), 3.65 (br. s., 1H), 3.57 (br. s., 1H), 1.86 (s, 3H), 1.89 (s, 3H), 1.79-1.59 (m, 6H), 1.55-1.36 (m, 6H), 1.36-1.28 (m, 9H)

-continued

| Ex. No. | Structure | MS (ESI) (M + H) | FXR EC$_{50}$ (nM) |
|---|---|---|---|
| 451 | $^1$H NMR (400 MHz, DMSO-d$_6$) δ 8.69 (s, 2H), 8.30 (d, J = 7.8 Hz, 1H), 8.23-8.13 (m, 1H), 7.60 (t, J = 7.7 Hz, 1H), 7.51 (d, J = 8.1 Hz, 1H), 4.27 (q, J = 7.0 Hz, 2H), 3.65 (br. s., 1H), 3.57 (br. s., 1H), 1.86 (s, 3H), 1.89 (s, 3H), 1.79-1.59 (m, 6H), 1.54-1.34 (m, 9H), 1.33 (s, 9H) | | |
| 452 | $^1$H NMR (400 MHz, DMSO-d$_6$) δ 8.93 (s, 2H), 8.36 (d, J = 7.8 Hz, 1H), 8.24 (t, J = 1.7 Hz, 1H), 7.69-7.51 (m, 3H), 3.65 (br. s., 1H), 3.58 (br. s., 1H), 1.87 (s, 3H), 1.89 (s, 3H), 1.79-1.61 (m, 6H), 1.56-1.35 (m, 6H), 1.33 (s, 9H) | | |
| 453 | $^1$H NMR (400 MHz, DMSO-d$_6$) δ 8.84 (s, 2H), 8.38 (d, J = 7.6 Hz, 1H), 8.26 (t, J = 1.8 Hz, 1H), 7.62 (t, J = 7.8 Hz, 1H), 7.55 (d, J = 8.1 Hz, 1H), 3.65 (br. s., 1H), 3.58 (br. s., 1H), 2.69 (q, J = 7.4 Hz, 2H), 1.86 (s, 3H), 1.89 (s, 3H), 1.79-1.56 (m, 6H), 1.55-1.36 (m, 6H), 1.36-1.28 (m, 9H), 1.28-1.22 (m, 3H) | | |
| 454 | $^1$H NMR (400 MHz, DMSO-d$_6$) δ 8.81 (s, 2H), 8.37 (d, J = 7.8 Hz, 1H), 8.25 (t, J = 1.8 Hz, 1H), 7.61 (t, J = 7.8 Hz, 1H), 7.55 (d, J = 8.3 Hz, 1H), 3.61 (d, J = 17.9 Hz, 2H), 2.34 (s, 3H), 1.87 (d, J = 9.0 Hz, 6H), 1.78-1.57 (m, 6H), 1.55-1.36 (m, 6H), 1.36-1.28 (m, 9H) | | |
| 455 | $^1$H NMR (400 MHz, DMSO-d$_6$) δ 8.61 (d, J = 2.7 Hz, 1H), 8.18 (d, J = 8.8 Hz, 1H), 8.09 (d, J = 8.1 Hz, 1H), 8.05 (s, 1H), 7.80 (dd, J = 8.7, 2.8 Hz, 1H), 7.63-7.20 (m, 3H), 3.61 (s, 2H), 1.88 (br. s., 6H), 1.79-1.65 (m, 6H), 1.55-1.37 (m, 6H), 1.33 (s, 9H). | | |
| 456 | $^1$H NMR (400 MHz, DMSO-d$_6$) δ 7.76-7.58 (m, 4H), 7.53 (t, J = 7.8 Hz, 1H), 7.42-7.30 (m, 3H), 3.60 (d, J = 11.2 Hz, 2H), 2.66 (q, J = 7.6 Hz, 2H), 1.88-1.85 (m, 6H), 1.79-1.62 (m, 6H), 1.56-1.38 (m, 6H), 1.33 (s, 9H), 1.22 (t, J = 7.6 Hz, 3H). | | |
| 457 | $^1$H NMR (400 MHz, DMSO-d$_6$) δ 7.86 (d, J = 1.7 Hz, 1H), 7.77-7.69 (m, 2H), 7.61 (dd, J = 8.6, 2.0 Hz, 1H), 7.58-7.48 (m, 2H), 7.46-7.37 (m, 1H), 3.63 (br. s., 1H), 3.57 (br. s., 1H), 1.89-1.84 (m, 6H), 1.79-1.64 (m, 6H), 1.56-1.38 (m, 6H), 1.33 (s, 9H). | | |
| 458 | $^1$H NMR (400 MHz, DMSO-d$_6$) δ 8.99 (d, J = 2.4 Hz, 1H), 8.90 (d, J = 2.2 Hz, 1H), 7.93-7.79 (m, 2H), 7.60 (t, J = 7.8 Hz, 1H), 7.45 (d, J = 8.3 Hz, 1H), 3.67-3.57 (m, 2H), 2.62-2.58 (m, 1H), 1.90-1.86 (m, 6H), 1.80-1.62 (m, 6H), 1.56-1.37 (m, 6H), 1.37-1.28 (m, 11H), 1.25 (dt, J = 7.5, 2.8 Hz, 2H). | | |

Example 459

N-((4-(5-(difluoromethyl)-1,2,4-oxadiazol-3-yl)bicyclo[2.2.2]octan-1-yl)methyl)-N-(3-(2-ethoxypyrimidin-5-yl)phenyl)-3-fluorobicyclo[1.1.1]pentane-1-carboxamide

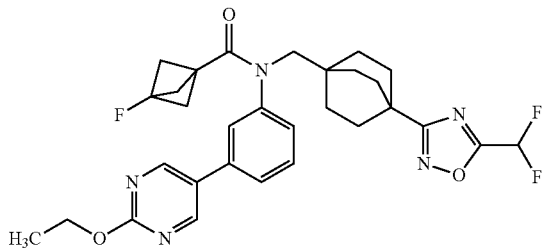

(459)

Step A. Intermediate 459A. Preparation of N-(3-bromophenyl)-N-((4-(5-(difluoromethyl)-1,2,4-oxadiazol-3-yl)bicyclo[2.2.2]octan-1-yl)methyl)-3-fluorobicyclo[1.1.1]pentane-1-carboxamide

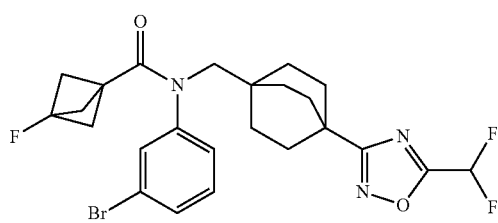 [SMILES: O=C(N(CC12CCC(c3noc(C(F)F)n3)(CC1)CC2)c1cccc(Br)c1)C12CC(F)(C1)C2]

The title compound was prepared according to the method described for the synthesis of Intermediate 1A by substituting Intermediate 396C and the corresponding acid where appropriate. (160 mg, 0.305 mmol, 71% yield). MS (ESI) 524 (M+H).

Step B. Example 459. Preparation of N-((4-(5-(difluoromethyl)-1,2,4-oxadiazol-3-yl) bicyclo[2.2.2]octan-1-yl)methyl)-N-(3-(2-ethoxypyrimidin-5-yl)phenyl)-3-fluorobicyclo[1.1.1]pentane-1-carboxamide The title compound was prepared according to the method described for the synthesis of Example 149 by substituting Intermediate 459A and (2-ethoxypyrimidin-5-yl)boronic acid where appropriate. (8.7 mg, 0.014 mmol, 29% yield). $^1$H NMR (400 MHz, DMSO-d$_6$) δ 9.02 (s, 2H), 7.82 (t, J=1.8 Hz, 1H), 7.77 (d, J=7.8 Hz, 1H), 7.62-7.50 (m, 1H), 7.50-7.33 (m, 2H), 4.43 (q, J=7.0 Hz, 2H), 3.71-3.62 (m, 1H), 3.60-3.52 (m, 1H), 2.00-1.71 (m, 12H), 1.58-1.42 (m, 6H), 1.38 (t, J=7.0 Hz, 3H). FXR EC$_{50}$ (nM)=192. MS (ESI) 568 (M+H).

The following compounds were prepared according to the method described for the synthesis of Example 149 by substituting Intermediate 459A and the corresponding boronic acids/esters.

| Ex. No. | Structure | MS (ESI) (M + H) | FXR EC$_{50}$ (nM) |
|---|---|---|---|
| 460 | 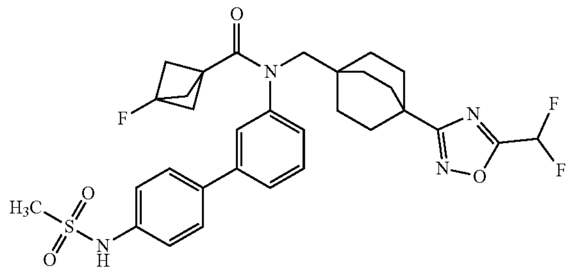 [SMILES: CS(=O)(=O)Nc1ccc(-c2cccc(N(CC34CCC(c5noc(C(F)F)n5)(CC3)CC4)C(=O)C34CC(F)(C3)C4)c2)cc1] | 615 | 338 |
| 461 | 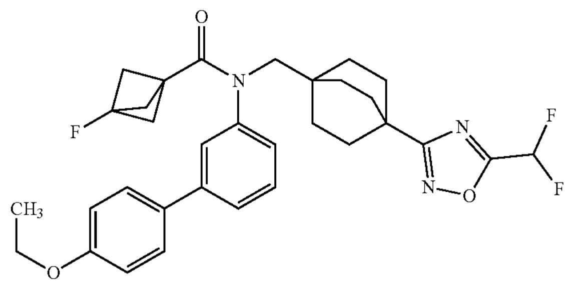 [SMILES: CCOc1ccc(-c2cccc(N(CC34CCC(c5noc(C(F)F)n5)(CC3)CC4)C(=O)C34CC(F)(C3)C4)c2)cc1] | 566 | 603 |
| 462 | 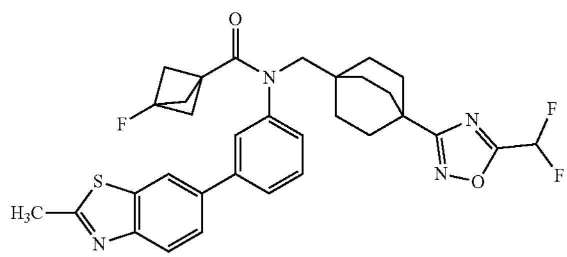 [SMILES: Cc1nc2ccc(-c3cccc(N(CC45CCC(c6noc(C(F)F)n6)(CC4)CC5)C(=O)C45CC(F)(C4)C5)c3)cc2s1] | 593 | 107 |
| 463 | 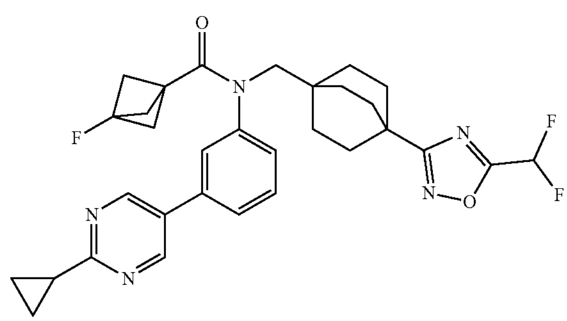 [SMILES: O=C(N(CC12CCC(c3noc(C(F)F)n3)(CC1)CC2)c1cccc(-c2cnc(C3CC3)nc2)c1)C12CC(F)(C1)C2] | 564 | 215 |
| 464 | 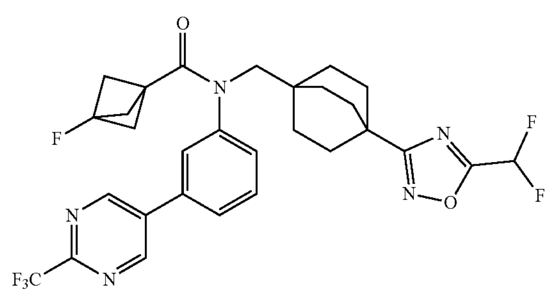 [SMILES: O=C(N(CC12CCC(c3noc(C(F)F)n3)(CC1)CC2)c1cccc(-c2cnc(C(F)(F)F)nc2)c1)C12CC(F)(C1)C2] | 592 | 654 |

-continued

| Ex. No. | Structure | MS (ESI) (M + H) | FXR EC$_{50}$ (nM) |
|---|---|---|---|
| 465 | 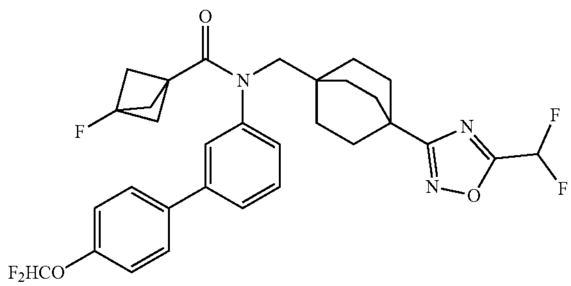 [SMILES: O=C(N(CC12CCC(c3noc(C(F)F)n3)(CC1)CC2)c1cccc(-c2ccc(OC(F)F)cc2)c1)C12CC(F)(C1)C2] | 588 | 180 |

460  $^1$H NMR (400 MHz, DMSO-d$_6$) δ 9.89 (s, 1H), 7.74 (d, J = 8.6 Hz, 2H), 7.70-7.60 (m, 2H), 7.57-7.46 (m, 2H), 7.42 (s, 1H), 7.39-7.24 (m, 2H), 3.61 (d, J = 13.2 Hz, 2H), 3.04 (s, 3H), 1.95-1.70 (m, 12H), 1.49 (d, J = 8.3 Hz, 6H)

461  $^1$H NMR (400 MHz, DMSO-d$_6$) δ 7.78-7.59 (m, 4H), 7.56-7.45 (m, 1H), 7.45-7.35 (m, 1H), 7.34-7.27 (m, 1H), 7.10-6.97 (m, 2H), 4.17-3.99 (m, 2H), 3.61 (d, J = 11.0 Hz, 2H), 1.96-1.70 (m, 12H), 1.49 (d, J = 8.6 Hz, 6H), 1.39-1.29 (m, 3H)

462  $^1$H NMR (400 MHz, DMSO-d$_6$) δ 8.46 (d, J = 1.7 Hz, 1H), 8.00 (d, J = 8.6 Hz, 1H), 7.86 (dd, J = 8.6, 2.0 Hz, 1H), 7.83-7.74 (m, 2H), 7.63-7.48 (m, 1H), 7.48-7.35 (m, 2H), 3.70 (d, J = 13.9 Hz, 1H), 3.57 (d, J = 14.2 Hz, 1H), 2.83 (s, 3H), 1.98-1.70 (m, 12H), 1.50 (d, J = 5.4 Hz, 6H)

463  $^1$H NMR (400 MHz, DMSO-d$_6$) δ 9.04 (s, 2H), 7.89-7.82 (m, 1H), 7.80 (d, J = 7.6 Hz, 1H), 7.63-7.51 (m, 1H), 7.51-7.34 (m, 2H), 3.74-3.51 (m, 2H), 2.32-2.20 (m, 1H), 1.96-1.69 (m, 12H), 1.57-1.33 (m, 6H), 1.21-0.96 (m, 4H)

464  $^1$H NMR (400 MHz, DMSO-d$_6$) δ 9.49 (s, 2H), 8.02 (s, 1H), 7.96 (d, J = 7.6 Hz, 1H), 7.67 (t, J = 7.8 Hz, 1H), 7.59 (d, J = 8.1 Hz, 1H), 7.51-7.33 (m, 1H), 3.68 (br. s., 1H), 3.62-3.54 (m, 1H), 1.97-1.71 (m, 12H), 1.58-1.34 (m, 6H)

465  $^1$H NMR (400 MHz, DMSO-d$_6$) δ 7.87-7.78 (m, 2H), 7.76-7.65 (m, 2H), 7.59-7.51 (m, 1H), 7.46-7.35 (m, 2H), 7.30 (dd, J = 6.8, 1.7 Hz, 3H), 3.69-3.62 (m, 1H), 3.60-3.51 (m, 1H), 1.98-1.70 (m, 12H), 1.57-1.37 (m, 6H)

Example 466

N-(3-(2-cyclopropylpyrimidin-5-yl)phenyl)-N-((4-(3-(difluoromethyl)-1,2,4-oxadiazol-5-yl)bicyclo[2.2.2]octan-1-yl)methyl)-3-fluorobicyclo[1.1.1]pentane-1-carboxamide Step A. Intermediate 466A. Preparation of N-(3-bromophenyl)-N-((4-(3-(difluoromethyl)-1,2,4-oxadiazol-5-yl)bicyclo[2.2.2]octan-1-yl)methyl)-3-fluorobicyclo[1.1.1]pentane-1-carboxamide

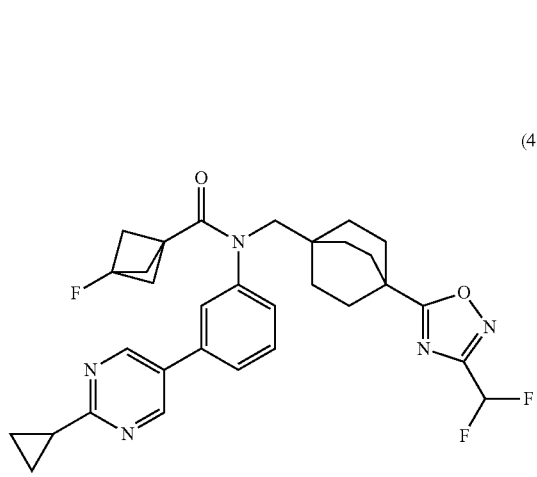

The title compound was prepared according to the method described for the synthesis of Intermediate 1A by substituting Intermediate 357C and (E)-2,2-difluoro-N'-hydroxyacetimidamide where appropriate. (200 mg, 0.381 mmol, 57% yield) as white gummy liquid. MS (ESI) 524 (M+H).

Step B. Example 466. Preparation of N-(3-(2-cyclopropylpyrimidin-5-yl)phenyl)-N-((4-(3-(difluoromethyl)-1,2,4-oxadiazol-5-yl)bicyclo[2.2.2]octan-1-yl)methyl)-3-fluorobicyclo[1.1.1]pentane-1-carboxamide The title compound was prepared according to the method described for the synthesis of Example 149 by substituting Intermediate 466A and 2-cyclopropyl-5-(5,5-dimethyl-1,3,2-dioxaborinan-2-yl)pyrimidine where appropriate. (4.1 mg, 6.55 μmol, 14% yield). $^1$H NMR (400 MHz, DMSO-$d_6$) δ 9.04 (s, 2H), 7.84 (s, 1H), 7.80 (d, J=8.3 Hz, 1H), 7.59 (t, J=7.8 Hz, 1H), 7.53-7.35 (m, 2H), 3.70-3.50 (m, 2H), 2.32-2.23 (m, 1H), 1.97-1.69 (m, 12H), 1.60-1.37 (m, 6H), 1.21-0.96 (m, 4H). FXR EC$_{50}$ (nM)=349. MS (ESI) 564 (M+H).

The following compounds were prepared according to the method described for the synthesis of Example 149 by substituting Intermediate 466A and the corresponding aryl/hetero aryl boronates.

| Ex. No. | Structure | MS (ESI) (M + H) | FXR EC$_{50}$ (nM) |
|---|---|---|---|
| 467 | 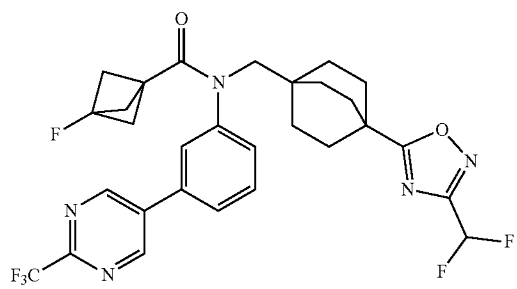 [SMILES: O=C(N(CC12CCC(c3nc(C(F)F)no3)(CC1)CC2)c1cccc(-c2cnc(C(F)(F)F)nc2)c1)C12CC(F)(C1)C2] | 592 | 2110 |
| 468 | 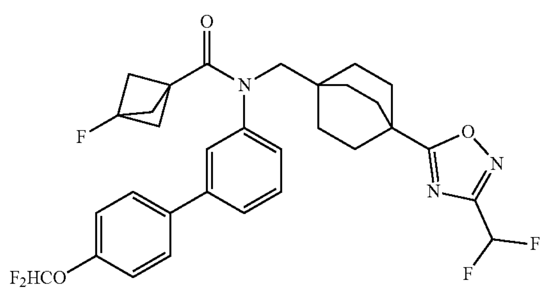 [SMILES: O=C(N(CC12CCC(c3nc(C(F)F)no3)(CC1)CC2)c1cccc(-c2ccc(OC(F)F)cc2)c1)C12CC(F)(C1)C2] | 588 | 184 |
| 469 | 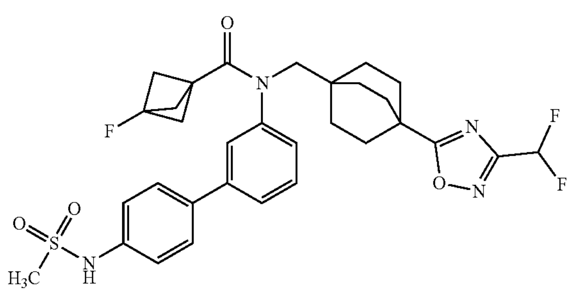 [SMILES: CS(=O)(=O)Nc1ccc(-c2cccc(N(CC34CCC(c5nc(C(F)F)no5)(CC3)CC4)C(=O)C34CC(F)(C3)C4)c2)cc1] | 615 | 654 |
| 470 | 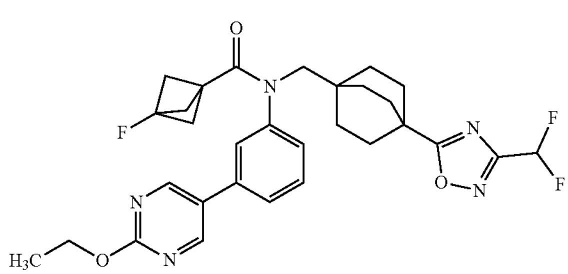 [SMILES: CCOc1ncc(-c2cccc(N(CC34CCC(c5nc(C(F)F)no5)(CC3)CC4)C(=O)C34CC(F)(C3)C4)c2)cn1] | 568 | 164 |

-continued

| Ex. No. | Structure | MS (ESI) (M + H) | FXR EC$_{50}$ (nM) |
|---|---|---|---|
| 471 | | 593 | 135 |

| | |
|---|---|
| 467 | $^1$H NMR (400 MHz, DMSO-d$_6$) δ 9.49 (s, 2H), 8.02 (t, J = 1.8 Hz, 1H), 7.96 (d, J = 7.8 Hz, 1H), 7.73-7.64 (m, 1H), 7.63-7.53 (m, 1H), 7.32 (s, 1H), 3.68 (br. s., 1H), 3.61 (br. s., 1H), 1.99-1.76 (m, 12H), 1.58-1.36 (m, 6H) |
| 468 | $^1$H NMR (400 MHz, DMSO-d$_6$) δ 7.90-7.77 (m, 2H), 7.76-7.65 (m, 2H), 7.55 (t, J = 8.1 Hz, 1H), 7.50-7.35 (m, 2H), 7.35-7.24 (m, 3H), 3.62 (d, J = 16.9 Hz, 2H), 2.02-1.75 (m, 12H), 1.50 (d, J = 9.3 Hz, 6H) |
| 469 | $^1$H NMR (400 MHz, DMSO-d$_6$) δ 9.89 (s, 1H), 7.78-7.71 (m, 2H), 7.68 (d, J = 7.8 Hz, 1H), 7.66 (d, J = 2.0 Hz, 1H), 7.53 (t, J = 7.8 Hz, 1H), 7.41-7.25 (m, 4H), 3.61 (d, J = 7.1 Hz, 2H), 3.04 (s, 3H), 1.87 (d, J = 9.5 Hz, 12H), 1.62-1.39 (m, 6H) |
| 470 | $^1$H NMR (400 MHz, DMSO-d$_6$) δ 9.02 (s, 2H), 7.82 (t, J = 1.8 Hz, 1H), 7.78 (d, J = 8.1 Hz, 1H), 7.57 (t, J = 7.8 Hz, 1H), 7.47-7.32 (m, 2H), 4.43 (q, J = 7.0 Hz, 2H), 3.73-3.48 (m, 2H), 2.04-1.76 (m, 12H), 1.60-1.40 (m, 6H), 1.38 (t, J = 7.0 Hz, 3H) |
| 471 | $^1$H NMR (400 MHz, DMSO-d$_6$) δ 8.46 (d, J = 1.5 Hz, 1H), 8.00 (d, J = 8.6 Hz, 1H), 7.86 (dd, J = 8.6, 2.0 Hz, 1H), 7.82-7.70 (m, 2H), 7.57 (t, J = 8.1 Hz, 1H), 7.48-7.19 (m, 2H), 3.75-3.65 (m, 1H), 3.63-3.54 (m, 1H), 2.84 (s, 3H), 2.04-1.78 (m, 12H), 1.51 (d, J = 5.4 Hz, 6H) |

Example 472

N-((4-(3-(tert-butyl)-1,2,4-oxadiazol-5-yl)bicyclo[2.2.2]octan-1-yl)methyl)-N-(5-(2-ethoxypyrimidin-5-yl)pyridin-3-yl)-3-fluorobicyclo[1.1.1]pentane-1-carboxamide

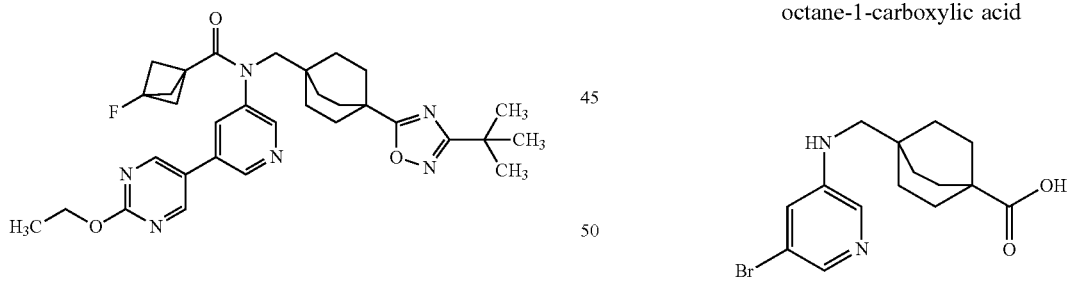
(472)

Step A. Intermediate 472A. Preparation of methyl 4-(((5-bromopyridin-3-yl)amino) methyl)bicyclo[2.2.2]octane-1-carboxylate

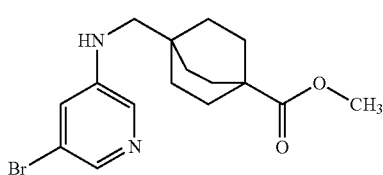 [SMILES: COC(=O)C12CCC(CNc3cncc(Br)c3)(CC1)CC2]

The title compound was prepared according to the method described for the synthesis of Intermediate 1I by substituting 5-bromopyridin-3-amine and Intermediate 88B where appropriate. (800 mg, 2.061 mmol, 36% yield). MS (ESI) 353 (M+H).

Step B. Intermediate 472B. Preparation of 4-(((5-bromopyridin-3-yl)amino)methyl) bicyclo[2.2.2]octane-1-carboxylic acid To a stirred solution of Intermediate 472A (1 g, 2.83 mmol) in THF was added methanol (5 mL), water (2.5 mL) followed by LiOH (0.40 g, 16.98 mmol). The reaction mixture was stirred at room temperature for overnight. The solvent was concentrated, diluted with water (10 mL), acidified with aqueous 1.5 N HCl solution and extracted with ethyl acetate (3×20 mL). The organic layers were combined, dried over anhydrous sodium sulphate, concentrated and dried in vacuo to afford the title compound (700 mg, 2.04 mmol, 72% yield). MS (ESI) 339 (M+H).

Step C. Intermediate 472C. Preparation of 5-bromo-N-((4-(3-(tert-butyl)-1,2,4-oxadiazol-5-yl)bicyclo[2.2.2]octan-1-yl)methyl)pyridin-3-amine

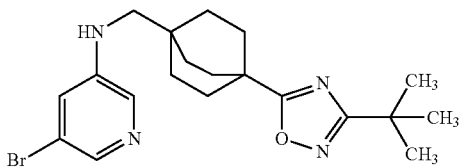 [SMILES: CC(C)(C)c1noc(C23CCC(CNc4cncc(Br)c4)(CC2)CC3)n1]

The title compound was prepared according to the method described for the synthesis of Intermediate 1A by substituting Intermediate 472B and (E)-N'-hydroxypivalimidamide where appropriate. (600 mg, 1.431 mmol, 69% yield). MS (ESI) 419 (M+H).

Step D. Intermediate 472D. Preparation of N-(5-bromopyridin-3-yl)-N-((4-(3-(tert-butyl)-1,2,4-oxadiazol-5-yl)bicyclo[2.2.2]octan-1-yl)methyl)-3-fluorobicyclo[1.1.1]pentane-1-carboxamide

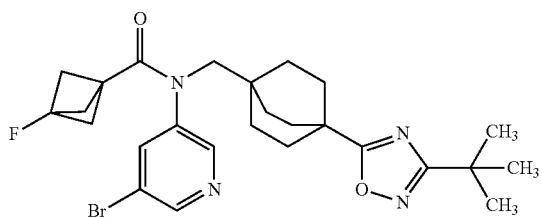 [SMILES: CC(C)(C)c1noc(C23CCC(CN(C(=O)C45CC(F)(C4)C5)c4cncc(Br)c4)(CC2)CC3)n1]

The title compound was prepared according to the method described for the synthesis of Example 323B by substituting Intermediate 472C and the corresponding acid where appropriate. (300 mg, 0.564 mmol, 53% yield). MS (ESI) 531. (M+H).

Step E. Example 472. Preparation of N-((4-(3-(tert-butyl)-1,2,4-oxadiazol-5-yl) bicyclo[2.2.2]octan-1-yl)methyl)-N-(5-(2-ethoxypyrimidin-5-yl)pyridin-3-yl)-3-fluorobicyclo[1.1.1]pentane-1-carboxamide The title compound was prepared according to the method described for the synthesis of Example 149 by substituting Intermediate 472D and (2-ethoxypyrimidin-5-yl)boronic acid where appropriate. (19.1 mg, 0.033 mmol, 70% yield). $^1$H NMR (400 MHz, DMSO-$d_6$) δ 9.10 (s, 2H), 8.99 (d, J=2.0 Hz, 1H), 8.68 (d, J=2.2 Hz, 1H), 8.32 (s, 1H), 4.44 (q, J=7.1 Hz, 2H), 3.72 (br. s., 1H), 3.55 (br. s., 1H), 1.91 (br. s., 5H), 1.87-1.68 (m, 7H), 1.54-1.33 (m, 9H), 1.33-1.09 (m, 9H). FXR $EC_{50}$ (nM) 758. MS (ESI) 575 (M+H).

The following compounds were prepared according to the method described for the synthesis of Example 149 by substituting Intermediate 472D and the corresponding boronates.

| Ex. No. | Structure | MS (ESI) (M + H) | FXR $EC_{50}$ (nM) |
|---|---|---|---|
| 473 | 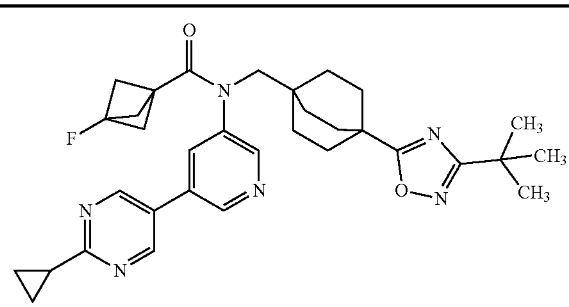 | 571 | 501 |
| 474 | 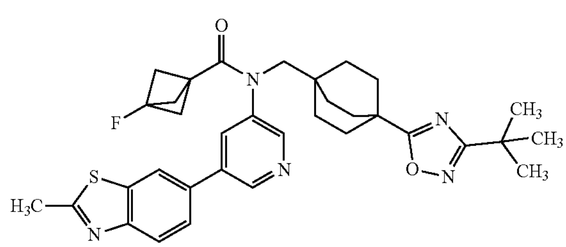 [SMILES: Cc1nc2ccc(-c3cncc(N(CC45CCC(c6nc(C(C)(C)C)no6)(CC4)CC5)C(=O)C45CC(F)(C4)C5)c3)cc2s1] | 600 | 541 |

| Ex. No. | Structure | MS (ESI) (M + H) | FXR EC$_{50}$ (nM) |
|---|---|---|---|
| 475 | 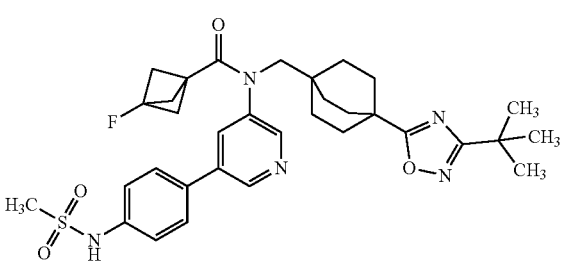 [SMILES: CC(C)(C)c1noc(C23CCC(CN(C(=O)C45CC(F)(C4)C5)c4cncc(-c5ccc(NS(C)(=O)=O)cc5)c4)(CC2)CC3)n1] | 622 | 1596 |
| 476 | 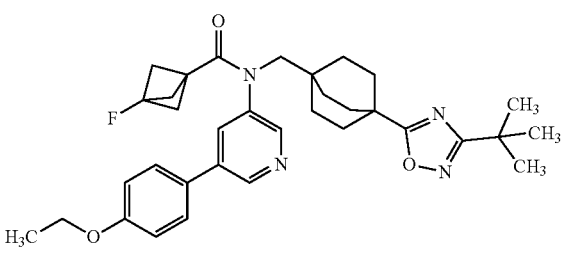 [SMILES: CCOc1ccc(-c2cncc(N(CC34CCC(c5nc(C(C)(C)C)no5)(CC3)CC4)C(=O)C34CC(F)(C3)C4)c2)cc1] | 573 | 560 |
| 477 | 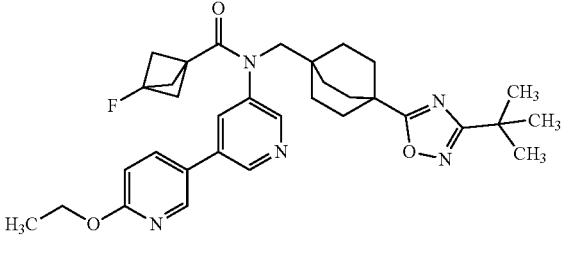 [SMILES: CCOc1ccc(-c2cncc(N(CC34CCC(c5nc(C(C)(C)C)no5)(CC3)CC4)C(=O)C34CC(F)(C3)C4)c2)cn1] | 574 | 485 |

473 $^1$H NMR (400 MHz, DMSO-d$_6$) δ 9.11 (s, 2H), 9.01 (d, J = 2.0 Hz, 1H), 8.70 (d, J = 2.2 Hz, 1H), 8.35 (t, J = 2.0 Hz, 1H), 3.71 (br. s., 1H), 3.56 (br. s., 1H), 2.33-2.23 (m, 1H), 1.90 (br. s., 5H), 1.87-1.57 (m, 7H), 1.55-1.36 (m, 6H), 1.34-1.19 (m, 9H), 1.16-1.03 (m, 4H)

474 $^1$H NMR (400 MHz, DMSO-d$_6$) δ 9.01 (d, J = 2.0 Hz, 1H), 8.66 (d, J = 2.2 Hz, 1H), 8.56 (d, J = 1.7 Hz, 1H), 8.30 (t, J = 2.1 Hz, 1H), 8.05 (d, J = 8.6 Hz, 1H), 7.95 (dd, J = 8.6, 2.0 Hz, 1H), 3.75 (br. s., 1H), 3.56 (br. s., 1H), 2.85 (s, 3H), 1.90 (s, 3H), 1.93 (s, 3H), 1.87-1.59 (m, 6H), 1.57-1.45 (m, 5H), 1.42 (br. s., 1H), 1.35-1.17 (m, 9H)

475 $^1$H NMR (400 MHz, DMSO-d$_6$) δ 9.96 (s, 1H), 8.91 (d, J = 1.7 Hz, 1H), 8.60 (d, J = 2.2 Hz, 1H), 8.18 (t, J = 2.1 Hz, 1H), 7.91-7.76 (m, J = 8.6 Hz, 2H), 7.44-7.28 (m, J = 8.8 Hz, 2H), 3.70 (br. s., 1H), 3.56 (br. s., 1H), 3.06 (s, 3H), 1.90 (br. s., 5H), 1.87-1.59 (m, 7H), 1.57-1.35 (m, 6H), 1.34-1.15 (m, 9H)

476 $^1$H NMR (400 MHz, DMSO-d$_6$) δ 8.89 (d, J = 2.0 Hz, 1H), 8.56 (d, J = 2.2 Hz, 1H), 8.20-8.13 (m, 1H), 7.87-7.72 (m, J = 8.8 Hz, 2H), 7.15-7.00 (m, J = 8.8 Hz, 2H), 4.11 (q, J = 6.8 Hz, 2H), 3.70 (br. s., 1H), 3.55 (br. s., 1H), 1.90 (br. s., 6H), 1.87-1.64 (m, 6H), 1.47 (br. s., 6H), 1.36 (t, J = 7.0 Hz, 3H), 1.30-1.10 (m, 9H)

477 $^1$H NMR (400 MHz, DMSO-d$_6$) δ 8.93 (d, J = 2.0 Hz, 1H), 8.62 (d, J = 2.2 Hz, 1H), 8.65 (d, J = 2.4 Hz, 1H), 8.29-8.21 (m, 1H), 8.19 (dd, J = 8.8, 2.7 Hz, 1H), 6.95 (d, 8.6 Hz, 1H), 4.38 (q, J = 7.1 Hz, 2H), 3.70 (br. s., 1H), 3.57 (br. s., 1H), 1.90 (br. s., 5H), 1.87-1.59 (m, 7H), 1.59-1.39 (m, 6H), 1.36 (t, J = 7.1 Hz, 3H), 1.31-1.11 (m, 9H)

Example 478

N-((4-(5-(tert-butyl)-1,2,4-oxadiazol-3-yl)bicyclo[2.2.2]octan-1-yl)methyl)-N-(5-(2-ethoxypyrimidin-5-yl)pyridin-3-yl)-3-fluorobicyclo[1.1.1]pentane-1-carboxamide

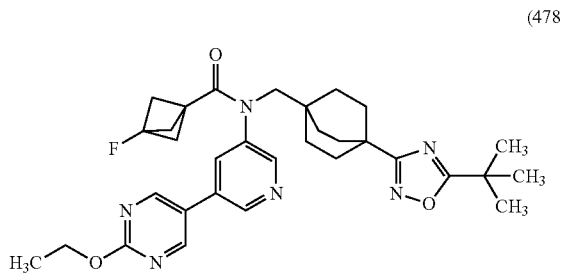 [SMILES: CCOc1ncc(-c2cncc(N(CC34CCC(c5noc(C(C)(C)C)n5)(CC3)CC4)C(=O)C34CC(F)(C3)C4)c2)cn1]
(478)

Step A. Intermediate 478A. Preparation of 4-(((5-bromopyridin-3-yl)amino)methyl) bicyclo[2.2.2]octane-1-carboxamide

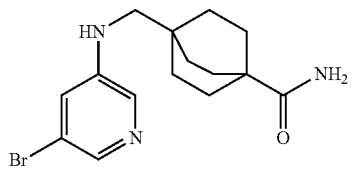 [SMILES: NC(=O)C12CCC(CNc3cncc(Br)c3)(CC1)CC2]

The title compound was prepared according to the method described for the synthesis of Example 144A by substituting Intermediate 472B and ammonium chloride where appropriate. (199 mg, 0.59 mmol, 100% yield). MS (ESI) 338 (M+H).

Step B. Intermediate 478B. Preparation of 4-(((5-bromopyridin-3-yl)amino)methyl) bicyclo[2.2.2]octane-1-carbonitrile

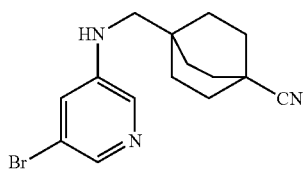 [SMILES: N#CC12CCC(CNc3cncc(Br)c3)(CC1)CC2]

To a stirred solution of Intermediate 478A (200 mg, 0.591 mmol) in pyridine (4 mL) was added imidazole (403 mg, 5.91 mmol) followed by POCl₃ (0.331 mL, 3.55 mmol). The reaction mixture was stirred at room temperature for 12 h. The reaction mixture was cooled to room temperature and poured into crushed ice. The aqueous solution was extracted with EtOAc (2×50 mL). The organic layers were combined, dried over anhydrous sodium sulphate and concentrated under reduced pressure. The crude material was purified by flash chromatography (12 g silica gel cartridge; A=Hex, B=EtOAc; 30 min grad.; 0% to 30% B; flow rate=30 mL/min). The pure fractions were combined, concentrated and dried in vacuo to afford the title compound (100 mg, 0.31 mmol, 52% yield). MS (ESI) 320 (M+H).

Step C. Intermediate 478C. Preparation of (Z)-4-(((5-bromopyridin-3-yl)amino)methyl)-N'-hydroxybicyclo[2.2.2]octane-1-carboximidamide

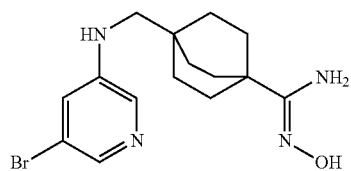 [SMILES: N/C(=N\O)C12CCC(CNc3cncc(Br)c3)(CC1)CC2]

The title compound was prepared according to the method described for the synthesis of Intermediate 88F by substituting Intermediate 478B where appropriate. (100 mg, 0.275 mmol, 88% yield). MS (ESI) 353 (M+H).

Step D. Intermediate 478D. Preparation of 5-bromo-N-((4-(5-(tert-butyl)-1,2,4-oxadiazol-3-yl)bicyclo[2.2.2]octan-1-yl)methyl)pyridin-3-amine

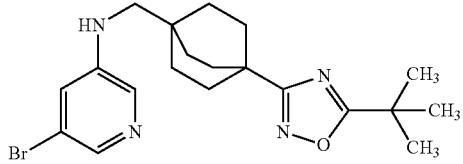 [SMILES: CC(C)(C)c1nc(C23CCC(CNc4cncc(Br)c4)(CC2)CC3)no1]

The title compound was prepared according to the method described for the synthesis of Intermediate 1A by substituting Intermediate 478C and the corresponding acid where appropriate. (90 mg, 0.22 mmol, 76% yield). MS (ESI) 419 (M+H).

Step E. Intermediate 478E. Preparation of N-(5-bromopyridin-3-yl)-N-((4-(5-(tert-butyl)-1,2,4-oxadiazol-3-yl)bicyclo[2.2.2]octan-1-yl)methyl)-3-fluorobicyclo[1.1.1]pentane-1-carboxamide

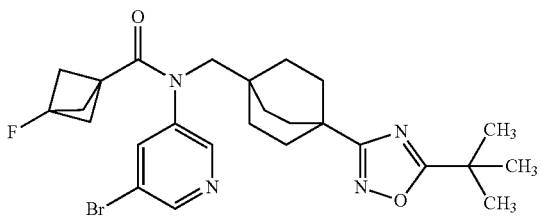 [SMILES: CC(C)(C)c1nc(C23CCC(CN(C(=O)C45CC(F)(C4)C5)c4cncc(Br)c4)(CC2)CC3)no1]

The title compound was prepared according to the method described for the synthesis of Example 423B by substituting Intermediate 478D and the corresponding acid where appropriate. (80 mg, 0.104 mmol, 48% yield). MS (ESI) 531 (M+H).

Step F. Example 478. Preparation of N-((4-(5-(tert-butyl)-1,2,4-oxadiazol-3-yl) bicyclo[2.2.2]octan-1-yl)methyl)-N-(5-(2-ethoxypyrimidin-5-yl)pyridin-3-yl)-3-fluorobicyclo[1.1.1]pentane-1-carboxamide The title compound was prepared according to the method described for the synthesis of Example 149 by substituting Intermediate 478E and (2-ethoxypyrimidin-5-yl)boronic acid where appropriate. (19.3 mg, 0.034 mmol, 59% yield). $^1$H NMR (400 MHz, DMSO-$d_6$) δ 9.10 (s, 2H), 8.99 (d, J=2.0 Hz, 1H), 8.68 (d, J=2.2 Hz, 1H), 8.34 (t, J=2.1 Hz, 1H), 4.44 (q, J=6.9 Hz, 2H), 3.72 (br. s., 1H), 3.52 (d, J=12.7 Hz, 1H), 1.90 (d, J=9.0 Hz, 6H), 1.81-1.64 (m, 6H), 1.56-1.40 (m, 6H), 1.38 (t, J=7.1 Hz, 3H), 1.33 (s, 9H). FXR EC$_{50}$ (nM) 1095. MS (ESI) 575 (M+H).

The following compounds were prepared according to the method described for the synthesis of Example 149 by substituting Intermediate 478E and the corresponding boronates.

| Ex. No. | Structure | MS (ESI) (M + H) | FXR EC$_{50}$ (nM) |
|---|---|---|---|
| 479 | 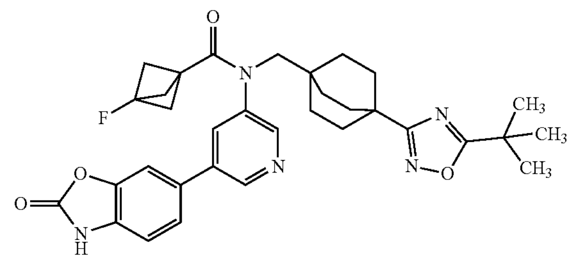 [SMILES: CC(C)(C)c1nc(C23CCC(CN(C(=O)C45CC(F)(C4)C5)c4cncc(-c5ccc6[nH]c(=O)oc6c5)c4)(CC2)CC3)no1] | 586 | 367 |
| 480 | 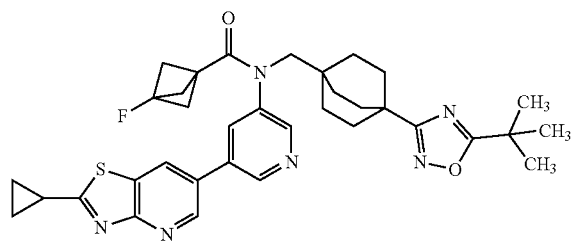 [SMILES: CC(C)(C)c1nc(C23CCC(CN(C(=O)C45CC(F)(C4)C5)c4cncc(-c5cnc6nc(C7CC7)sc6c5)c4)(CC2)CC3)no1] | 627 | 988 |
| 481 | 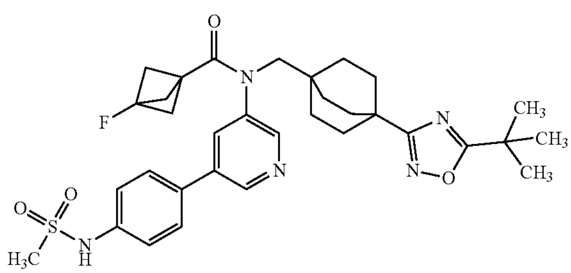 [SMILES: CC(C)(C)c1nc(C23CCC(CN(C(=O)C45CC(F)(C4)C5)c4cncc(-c5ccc(NS(C)(=O)=O)cc5)c4)(CC2)CC3)no1] | 622 | 580 |
| 482 | 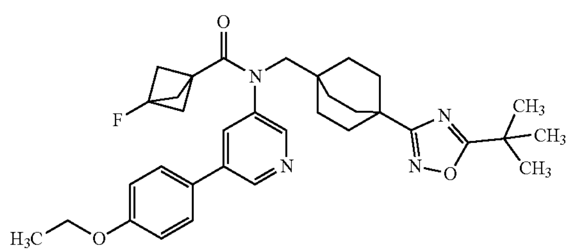 [SMILES: CCOc1ccc(-c2cncc(N(CC34CCC(c5noc(C(C)(C)C)n5)(CC3)CC4)C(=O)C34CC(F)(C3)C4)c2)cc1] | 573 | 322 |
| 483 | 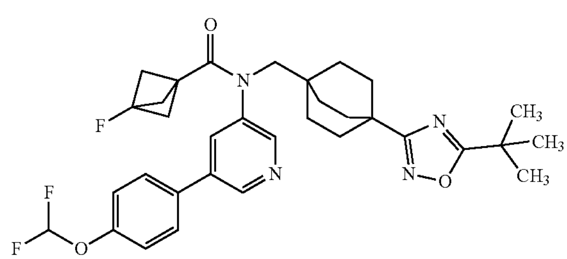 [SMILES: CC(C)(C)c1nc(C23CCC(CN(C(=O)C45CC(F)(C4)C5)c4cncc(-c5ccc(OC(F)F)cc5)c4)(CC2)CC3)no1] | 595.1 | 255 |

-continued

| Ex. No. | Structure | MS (ESI) (M + H) | FXR EC$_{50}$ (nM) |
|---|---|---|---|
| 484 | | 600 | 344 |

479 $^1$H NMR (400 MHz, DMSO-d$_6$) δ 11.76 (s, 1H), 8.92 (d, J = 2.0 Hz, 1H), 8.60 (d, J = 2.2 Hz, 1H), 8.22 (s, 1H), 7.85 (d, J = 1.5 Hz, 1H), 7.68-7.60 (m, 1H), 7.23 (d, J = 8.1 Hz, 1H), 3.73 (br. s., 1H), 3.54 (br. s., 1H), 1.88 (s, 3H), 1.91 (s, 3H), 1.81-1.65 (m, 6H), 1.46 (br. s., 6H), 1.33 (s, 9H)

480 $^1$H NMR (400 MHz, DMSO-d$_6$) δ 9.07 (d, J = 2.2 Hz, 1H), 9.04 (d, J = 2.0 Hz, 1H), 8.98 (d, J = 2.4 Hz, 1H), 8.70 (d, J = 2.2 Hz, 1H), 8.38 (t, J = 2.2 Hz, 1H), 3.74 (br. s., 1H), 3.56 (br. s., 1H), 2.64 (td, J = 8.4, 3.9 Hz, 1H), 1.93 (br. s., 6H), 1.82-1.61 (m, 6H), 1.54-1.39 (m, 6H), 1.39-1.29 (m, 11H), 1.29-1.22 (m, 2H)

481 $^1$H NMR (400 MHz, DMSO-d$_6$) δ 9.96 (s, 1H), 8.91 (d, J = 1.7 Hz, 1H), 8.60 (d, J = 2.2 Hz, 1H), 8.18 (s, 1H), 7.92-7.72 (m, J = 8.6 Hz, 2H), 7.43-7.27 (m, J = 8.8 Hz, 2H), 3.71 (br. s., 1H), 3.54 (br. s., 1H), 3.06 (s, 3H), 1.90 (br. s., 6H), 1.81-1.58 (m, 6H), 1.57-1.37 (m, 6H), 1.33 (s, 9H)

482 $^1$H NMR (400 MHz, DMSO-d$_6$) δ 8.88 (d, J = 1.7 Hz, 1H), 8.56 (d, J = 2.2 Hz, 1H), 8.23-8.08 (m, 1H), 7.89-7.66 (m, 2H), 7.17-7.00 (m, J = 8.8 Hz, 2H), 4.10 (q, J = 6.8 Hz, 2H), 3.70 (br. s., 1H), 3.54 (br. s., 1H), 1.90 (br. s., 6H), 1.80-1.60 (m, 6H), 1.57-1.39 (m, 6H), 1.39-1.29 (m, 12H)

483 $^1$H NMR (400 MHz, DMSO-d$_6$) δ 8.93 (d, J = 2.0 Hz, 1H), 8.64 (d, J = 2.2 Hz, 1H), 8.31-8.17 (m, 1H), 8.01-7.82 (m, 2H), 7.44-7.15 (m, 3H), 3.72 (br. s., 1H), 3.54 (br. s., 1H), 1.91 (br. s., 6H), 1.81-1.61 (m, 6H), 1.58-1.38 (m, 6H), 1.33 (s, 9H)

484 $^1$H NMR (400 MHz, DMSO-d$_6$) δ 9.01 (d, J = 2.0 Hz, 1H), 8.65 (d, J = 2.2 Hz, 1H), 8.56 (d, J = 1.7 Hz, 1H), 8.30 (t, J = 2.2 Hz, 1H), 8.04 (d, J = 8.6 Hz, 1H), 7.95 (dd, J = 8.6, 2.0 Hz, 1H), 3.75 (br. s., 1H), 3.55 (br. s., 1H), 2.85 (s, 3H), 1.90 (s, 3H), 1.93 (s, 3H), 1.81-1.59 (m, 6H), 1.46 (br. s., 6H), 1.33 (s, 9H)

Example 485

N-((4-(5-(tert-butyl)-1,2,4-oxadiazol-3-yl)bicyclo[2.2.2]octan-1-yl)methyl)-N-(5-(5-(difluoromethoxy)pyrimidin-2-yl)pyridin-3-yl)-3-fluorobicyclo[1.1.1]pentane-1-carboxamide (485)

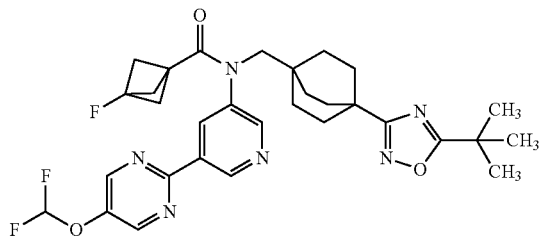

To a stirred solution of Intermediate 478E (20 mg, 0.038 mmol) in toluene (1 mL) was added 5-(difluoromethoxy)-2-(trimethyl stannyl)pyrimidine (12 mg, 0.038 mmol). The reaction mixture was degassed and back-filled with argon. Tetrakis (4.35 mg, 3.76 μmol) was added to the reaction mixture and the reaction vial was sealed (pressure release vial). The reaction mixture was heated at 110° C. for 12 h. The reaction mixture was cooled to room temperature and concentrated under reduced pressure. The crude material was purified via preparative LC/MS using following conditions. (Column. Waters XBridge C18, 150 mm×19 mm, 5-μm particles; Mobile Phase A. 5.95 acetonitrile. water with 10-mM ammonium acetate; Mobile Phase B. 95.5 acetonitrile. water with 10 mM ammonium acetate; Gradient. a 0 minute hold at 20% B, 20-80% B over 25 minutes, then a 5-minute hold at 100% B; Flow Rate. 15 mL/min; Column Temperature. 25° C.). Fraction collection was triggered by signals. Fractions containing the desired product were combined and dried via centrifugal evaporation to afford the title compound (1.2 mg, 1.97 μmol, 5% yield). $^1$H NMR (400 MHz, DMSO-d$_6$) δ 9.46 (s, 1H), 8.98 (s, 2H), 8.84 (d, J=2.2 Hz, 1H), 8.58 (t, J=2.1 Hz, 1H), 7.64 (s, 1H), 7.46-7.28 (m, 1H), 3.66 (br. s., 2H), 1.91 (br. s., 6H), 1.80-1.59 (m, 6H), 1.55-1.37 (m, 6H), 1.33 (s, 9H). FXR EC$_{50}$ (nM) 41. MS (ESI) 597 (M+H).

Example 486

N-((4-(5-(tert-butyl)-1,2,4-oxadiazol-3-yl)bicyclo[2.2.2]octan-1-yl)methyl)-N-(5-(difluoromethoxy)-[2,3'-bipyridin]-5'-yl)-3-fluorobicyclo[1.1.1]pentane-1-carboxamide (486)

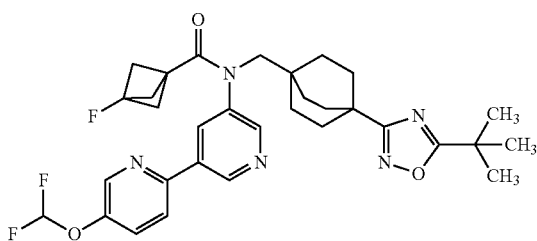

Step A. Intermediate 486A. Preparation of N-((4-(5-(tert-butyl)-1,2,4-oxadiazol-3-yl) bicyclo[2.2.2]octan-1-yl)methyl)-3-fluoro-N-(5-(trimethylstannyl)pyridin-3-yl) bicyclo[1.1.1]pentane-1-carboxamide

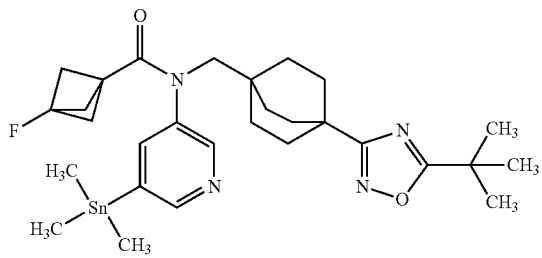 [SMILES: CC(C)(C)c1nc(C23CCC(CN(C(=O)C45CC(F)(C4)C5)c4cnc[c]([Sn]([CH3])([CH3])[CH3])c4)(CC2)CC3)no1]

To a stirred solution of Intermediate 478E (20 mg, 0.038 mmol) in toluene (1 mL) was added hexamethylditin (0.016 mL, 0.075 mmol). The reaction mixture was degassed and back-filled with argon. 1,1'-bis(di-tert-butylphosphino)ferrocene palladium dichloride (2.45 mg, 3.76 µmol) was added to the reaction mass and the reaction vial was sealed. The reaction mixture was heated at 110° C. for 12 h. The reaction mixture was cooled to room temperature and concentrated under reduced pressure. The crude material was purified by flash chromatography (12 g silica gel cartridge; A=Hex, B=EtOAc; 30 min grad.; 0% B to 50% B; flow rate=30 mL/min). The pure fractions were combined, concentrated and dried in vacuo to afford the title compound (25 mg, 93% yield). $^1$H NMR (400 MHz, DMSO-$d_6$) δ 8.54 (d, J=20.00 Hz, 2H), 7.94 (s, 1H), 3.54 (d, J=12.00 Hz, 2H), 1.71-1.81 (m, 12H), 1.40-1.43 (m, 6H), 1.33 (s, 9H), 0.42 (s, 9H).

Step B. Example 386. Preparation of N-((4-(5-(tert-butyl)-1,2,4-oxadiazol-3-yl) bicyclo[2.2.2]octan-1-yl)methyl)-N-(5-(difluoromethoxy)-[2,3'-bipyridin]-5'-yl)-3-fluorobicyclo[1.1.1]pentane-1-carboxamide To a stirred solution of Intermediate 486A (25 mg, 0.041 mmol) in toluene (1 mL) was added 2-bromo-5-(difluoromethoxy)pyridine (18.2 mg, 0.081 mmol). The reaction mixture was degassed and back-filled with argon. Tetrakis (4.69 mg, 4.06 µmol) was added to the reaction mass and the reaction vial was sealed (pressure release vial). The reaction mixture was heated at 110° C. for 12 h. The reaction mixture was cooled to room temperature and concentrated under reduced pressure. The crude material was purified via preparative LC/MS using following conditions. (Column. Waters XBridge C18, 150 mm×19 mm, 5-µm particles; Mobile Phase A. 5.95 acetonitrile. water with 10-mM ammonium acetate; Mobile Phase B. 95.5 acetonitrile. water with 10-mM ammonium acetate; Gradient. a 0-minute hold at 15% B, 15-65% B over 25 minutes, then a 5-minute hold at 100% B; Flow Rate. 15 mL/min; Column Temperature. 25° C.). Fraction collection was triggered by MS signals. Fractions containing the desired product were combined and dried via centrifugal evaporation to afford the title compound (3.5 mg, 5.88 µmol, 14% yield). $^1$H NMR (400 MHz, DMSO-$d_6$) δ 9.26 (d, J=1.7 Hz, 1H), 8.72 (d, J=2.2 Hz, 1H), 8.66 (d, J=2.9 Hz, 1H), 8.48 (t, J=2.2 Hz, 1H), 8.28 (d, J=9.0 Hz, 1H), 7.86 (dd, J=8.7, 3.1 Hz, 1H), 7.4 (t, J=72 Hz, 1H), 3.70 (br. s., 2H), 3.58 (br. s., 1H), 1.90 (br. s., 6H), 1.81-1.64 (m, 6H), 1.56-1.37 (m, 6H), 1.33 (s, 9H). FXR $EC_{50}$ (nM) 89. MS (ESI) 596 (M+H).

Example 487

N-(3-(2-ethoxypyrimidin-5-yl)phenyl)-3-fluoro-N-((4-(5-(trifluoromethyl)pyridin-2-yl)bicyclo[2.2.2]octan-1-yl)methyl)bicyclo[1.1.1]pentane-1-carboxamide

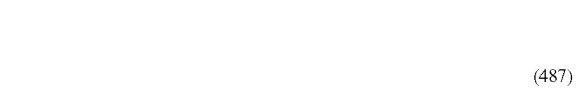

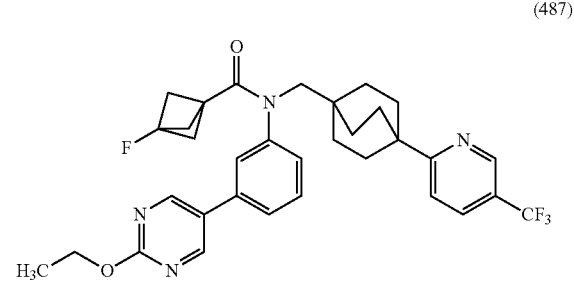 [SMILES: CCOc1ncc(-c2cccc(N(CC34CCC(c5ccc(C(F)(F)F)cn5)(CC3)CC4)C(=O)C34CC(F)(C3)C4)c2)cn1]

Step A. Intermediate 487A. Preparation of 3-bromo-N-((4-(5-(trifluoromethyl)pyridin-2-yl) bicyclo[2.2.2]octan-1-yl)methyl)aniline

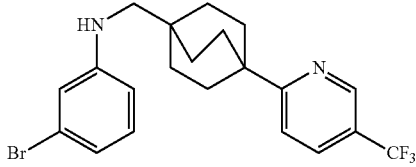 [SMILES: FC(F)(F)c1ccc(C23CCC(CNc4cccc(Br)c4)(CC2)CC3)nc1]

The title compound was prepared according to the method described for the synthesis of Intermediate 1I by substituting 3-bromoaniline and Intermediate 185C where appropriate. (430 mg, 0.959 mmol, 91% yield) as brown solid. $^1$H NMR (400 MHz, DMSO-$d_6$) δ 8.91-8.85 (m, 1H), 8.10 (dd, J=8.5, 2.5 Hz, 1H), 7.59 (d, J=8.5 Hz, 1H), 7.01-6.94 (m, 1H), 6.78 (t, J=2.3 Hz, 1H), 6.64-6.58 (m, 2H), 5.79-5.73 (m, 1H), 2.82 (d, J=5.5 Hz, 2H), 1.93-1.84 (m, 6H), 1.63-1.54 (m, 6H). MS (ESI) 439.2 (M+H).

Step B. Intermediate 487B. Preparation of N-(3-bromophenyl)-3-fluoro-N-((4-(5-(trifluoromethyl)pyridin-2-yl)bicyclo[2.2.2]octan-1-yl)methyl)bicyclo[1.1.1]pentane-1-carboxamide

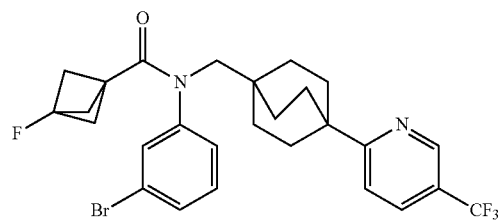

The title compound was prepared according to the method described for the synthesis of Example 3 by substituting Intermediate 487A and the corresponding acid where appropriate. (300 mg, 0.539 mmol, 55% yield) as brown solid. $^1$H NMR (400 MHz, DMSO-d$_6$) δ 8.88-8.82 (m, 1H), 8.08 (dd, J=8.5, 2.5 Hz, 1H), 7.72-7.68 (m, 1H), 7.61 (dt, J=7.4, 1.8 Hz, 1H), 7.53 (d, J=8.0 Hz, 1H), 7.47-7.39 (m, 2H), 3.61 (br. s., 1H), 3.53 (br. s., 1H), 1.88 (br. s., 6H), 1.84-1.75 (m, 6H), 1.50-1.39 (m, 6H). MS (ESI) 553 (M+H).

Step C. Example 487. Preparation of N-(3-(2-ethoxypyrimidin-5-yl)phenyl)-3-fluoro-N-((4-(5-(trifluoromethyl)pyridin-2-yl)bicyclo[2.2.2]octan-1-yl)methyl) bicyclo[1.1.1]pentane-1-carboxamide The title compound was prepared according to the method described for the synthesis of Example 149 by substituting Intermediate 487B and 5-(5,5-dimethyl-1,3,2-dioxaborinan-2-yl)-2-ethoxypyrimidine where appropriate. (18.3 mg, 0.031 mmol, 68% yield). $^1$H NMR (400 MHz, DMSO-d$_6$) δ 9.02 (s, 2H), 8.84 (s, 1H), 8.07 (dd, J=8.6, 2.4 Hz, 1H), 7.83 (s, 1H), 7.78 (d, J=7.8 Hz, 1H), 7.63-7.47 (m, 2H), 7.43 (d, J=7.6 Hz, 1H), 4.43 (q, J=7.1 Hz, 2H), 3.76-3.59 (m, 2H), 1.99-1.71 (m, 12H), 1.49 (d, J=4.4 Hz, 6H), 1.38 (t, J=7.1 Hz, 3H). FXR EC$_{50}$ (nM)=418. MS (ESI) 595 (M+H).

The following compounds were prepared according to the method described for the synthesis of Example 149 by substituting Intermediate 487B and the corresponding boronates/boronic acids.

| Ex. No. | Structure | MS (ESI) (M + H) | FXR EC$_{50}$ (nM) |
|---|---|---|---|
| 488 | 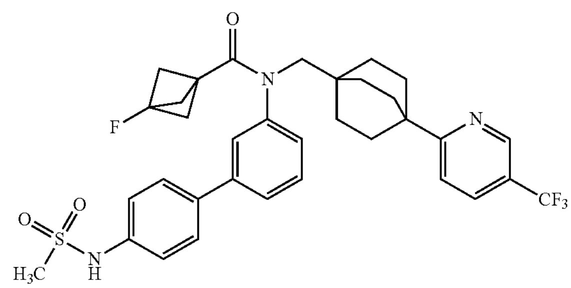 [SMILES: CS(=O)(=O)Nc1ccc(-c2cccc(N(CC34CCC(c5ccc(C(F)(F)F)cn5)(CC3)CC4)C(=O)C34CC(F)(C3)C4)c2)cc1] | 642 | 876 |
| 489 | 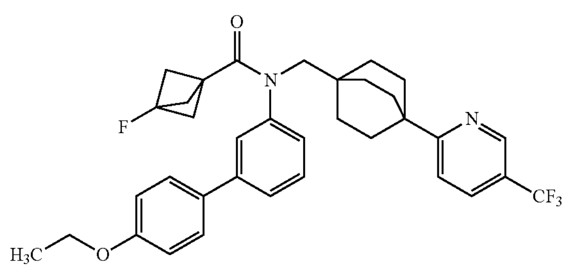 | 593 | 1636 |
| 490 | 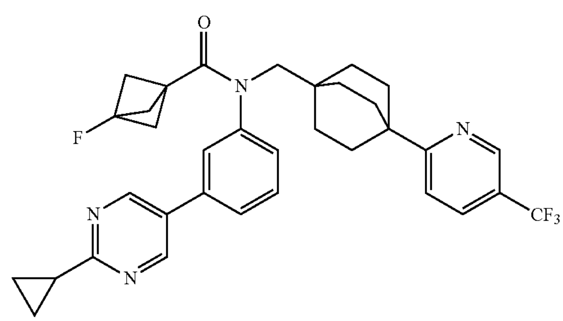 [SMILES: O=C(N(CC12CCC(c3ccc(C(F)(F)F)cn3)(CC1)CC2)c1cccc(-c2cnc(C3CC3)nc2)c1)C12CC(F)(C1)C2] | 591 | 334 |
| 491 | 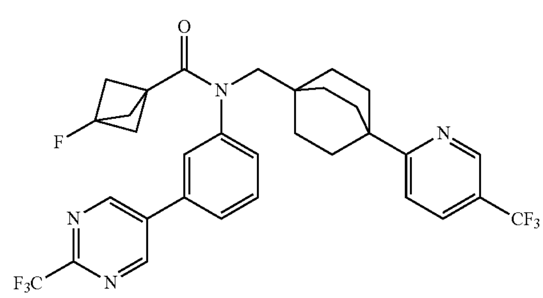 [SMILES: O=C(N(CC12CCC(c3ccc(C(F)(F)F)cn3)(CC1)CC2)c1cccc(-c2cnc(C(F)(F)F)nc2)c1)C12CC(F)(C1)C2] | 619 | 1632 |

| Ex. No. | Structure | MS (ESI) (M + H) | FXR EC$_{50}$ (nM) |
|---|---|---|---|
| 492 | | 594 | 567 |
| 493 | | 615 | 552 |
| 494 | | 581 | 516 |

488 $^1$H NMR (400 MHz, DMSO-d$_6$) δ 9.89 (s, 1H), 8.84 (s, 1H), 8.07 (dd, J = 8.6, 2.2 Hz, 1H), 7.74 (d, J = 8.8 Hz, 2H), 7.71-7.61 (m, 2H), 7.59-7.48 (m, 2H), 7.43-7.26 (m, 3H), 3.62 (d, J = 11.2 Hz, 2H), 3.04 (s, 3H), 2.00-1.70 (m, 12H), 1.58-1.35 (m, 6H)

489 $^1$H NMR (400 MHz, DMSO-d$_6$) δ 8.84 (d, J = 2.4 Hz, 1H), 8.07 (dd, J = 8.6, 2.4 Hz, 1H), 7.75-7.58 (m, 4H), 7.56-7.45 (m, 2H), 7.37-7.26 (m, 1H), 7.04 (d, J = 9.0 Hz, 2H), 4.09 (q, J = 7.1 Hz, 2H), 3.62 (d, J = 10.8 Hz, 2H), 1.99-1.70 (m, 12H), 1.50 (d, J = 8.3 Hz, 6H), 1.36 (t, J = 7.0 Hz, 3H)

490 $^1$H NMR (400 MHz, DMSO-d$_6$) δ 9.04 (s, 2H), 8.85 (s, 1H), 8.08 (d, J = 8.3 Hz, 1H), 7.85 (s, 1H), 7.80 (d, J = 7.8 Hz, 1H), 7.59 (t, J = 7.7 Hz, 1H), 7.53 (d, J = 8.6 Hz, 1H), 7.46 (d, J = 7.8 Hz, 1H), 3.66 (br. s., 1H), 3.60 (br. s., 1H), 2.31-2.23 (m, 1H), 2.00-1.73 (m, 12H), 1.49 (br. s., 6H), 1.19-0.95 (m, 4H)

491 $^1$H NMR (400 MHz, DMSO-d$_6$) δ 9.49 (s, 2H), 8.93-8.79 (m, 1H), 8.08 (dd, J = 8.6, 2.0 Hz, 1H), 8.05-8.00 (m, 1H), 7.96 (d, J = 8.1 Hz, 1H), 7.67 (t, J = 7.8 Hz, 1H), 7.59 (d, J = 8.6 Hz, 1H), 7.53 (d, J = 8.6 Hz, 1H), 3.71-3.50 (m, 2H), 2.00-1.73 (m, 12H), 1.49 (d, J = 4.6 Hz, 6H)

492 $^1$H NMR (400 MHz, DMSO-d$_6$) δ 8.89-8.80 (m, 1H), 8.56 (d, J = 2.2 Hz, 1H), 8.16-8.00 (m, 2H), 7.77-7.63 (m, 2H), 7.60-7.45 (m, 2H), 7.38 (d, J = 7.6 Hz, 1H), 6.98-6.86 (m, 1H), 4.37 (q, J = 7.1 Hz, 2H), 3.62 (d, J = 12.5 Hz, 2H), 1.98-1.71 (m, 12H), 1.50 (d, J = 8.8 Hz, 6H), 1.35 (t, J = 7.0 Hz, 3H)

493 $^1$H NMR (400 MHz, DMSO-d$_6$) δ 8.85 (s, 1H), 8.07 (dd, J = 8.4, 2.1 Hz, 1H), 7.90-7.77 (m, 2H), 7.77-7.63 (m, 2H), 7.60-7.50 (m, 2H), 7.39 (d, J = 8.6 Hz, 1H), 7.35-7.14 (m, 2H), 3.66 (br. s., 1H), 3.60 (br. s., 1H), 1.98-1.70 (m, 12H), 1.59-1.30 (m, 6H)

494 $^1$H NMR (400MHz, DMSO-d$_6$) δ 9.03 (s, 2H), 8.84 (s, 1H), 8.08 (dd, J = 8.3, 2.4 Hz, 1H), 7.83 (d, J = 1.7 Hz, 1H), 7.78 (d, J = 7.8 Hz, 1H), 7.58 (t, J = 7.8 Hz, 1H), 7.53 (d, J = 8.6 Hz, 1H), 7.47-7.40 (m, 1H), 3.99 (s, 3H), 3.68 (br. s., 1H), 3.59 (br. s., 1H), 2.05-1.76 (m, 12H), 1.49 (br. s., 6H)

Example 495

N-(3-(5-(difluoromethoxy)pyridin-2-yl)phenyl)-3-fluoro-N-((4-(5-(trifluoromethyl)pyridin-2-yl)bicyclo[2.2.2]octan-1-yl)methyl)bicyclo[1.1.1]pentane-1-carboxamide (495)

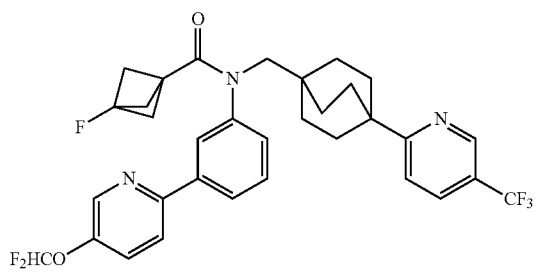

Step A. Intermediate 495A. Preparation of N-(3-(5,5-dimethyl-1,3,2-dioxaborinan-2-yl) phenyl)-3-fluoro-N-((4-(5-(trifluoromethyl)pyridin-2-yl)bicyclo[2.2.2]octan-1-yl)methyl) bicyclo[1.1.1]pentane-1-carboxamide

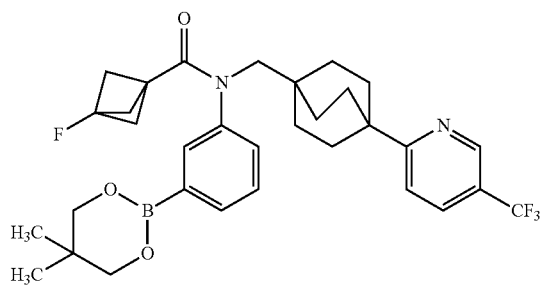 [SMILES: CC1(C)COB(c2cccc(N(CC34CCC(c5ccc(C(F)(F)F)cn5)(CC3)CC4)C(=O)C34CC(F)(C3)C4)c2)OC1]

The title compound was prepared according to the method described for the synthesis of Intermediate 149C by substituting Intermediate 487B where appropriate. (200 mg, 0.311 mmol, 69% yield) as white solid. $^1$H NMR (400 MHz, DMSO-$d_6$) δ 8.85 (s, 1H), 8.07 (d, J=8.5 Hz, 1H), 7.71-7.67 (m, 1H), 7.56-7.50 (m, 2H), 7.49-7.44 (m, 2H), 3.78 (s, 4H), 3.65-3.49 (m, 2H), 1.85-1.74 (m, 12H), 1.45 (d, J=7.5 Hz, 6H), 0.96 (s, 6H).

Step B. Example 495. Preparation of N-(3-(5-(difluoromethoxy)pyridin-2-yl)phenyl)-3-fluoro-N-((4-(5-(trifluoromethyl)pyridin-2-yl)bicyclo[2.2.2]octan-1-yl)methyl) bicyclo[1.1.1]pentane-1-carboxamide The title compound was prepared according to the method described for the synthesis of Example 149 by substituting Intermediate 495A and 2-bromo-5-(difluoromethoxy)pyridine where appropriate. (4.6 mg, 7.17 µmol, 17% yield). $^1$H NMR (400 MHz, DMSO-$d_6$) δ 8.84 (d, J=2.7 Hz, 1H), 8.62 (d, J=2.7 Hz, 1H), 8.18 (d, J=8.6 Hz, 1H), 8.13-7.98 (m, 3H), 7.80 (dd, J=8.8, 2.9 Hz, 1H), 7.65-7.20 (m, 4H), 3.65 (br. s., 2H), 1.89 (br. s., 6H), 1.85-1.62 (m, 6H), 1.58-1.35 (m, 6H). FXR $EC_{50}$ (nM)=271. MS (ESI) 616 (M+H).

The following compounds were prepared according to the method described for the synthesis of Example 149 by substituting Intermediate 495A and the corresponding aryl/hetero aryl halides.

| Ex. No. | Structure | MS (ESI) (M + H) | FXR $EC_{50}$ (nM) |
|---|---|---|---|
| 496 | 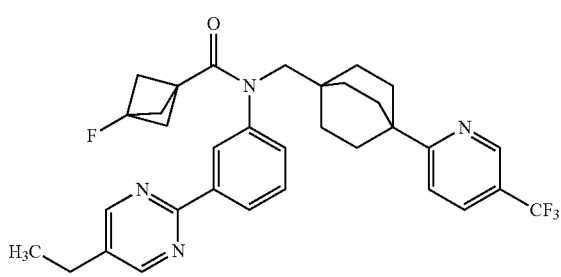 [SMILES: CCc1cnc(-c2cccc(N(CC34CCC(c5ccc(C(F)(F)F)cn5)(CC3)CC4)C(=O)C34CC(F)(C3)C4)c2)nc1] | 59 | 539 |

-continued

| Ex. No. | Structure | MS (ESI) (M + H) | FXR EC$_{50}$ (nM) |
|---|---|---|---|
| 497 | 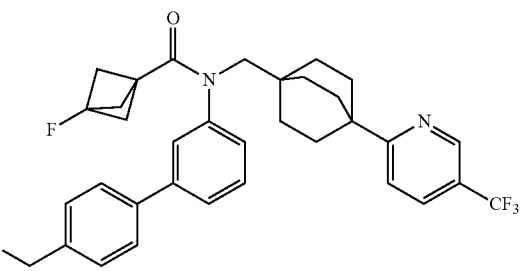 | 577 | 989 |
| 498 | 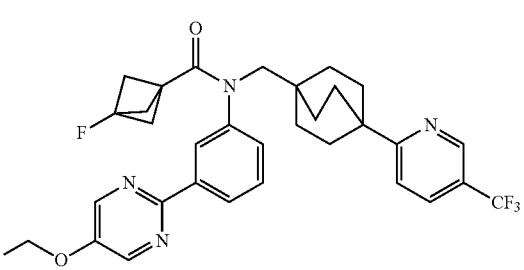 [SMILES: COc1cnc(-c2cccc(N(CC34CCC(c5ccc(C(F)(F)F)cn5)(CC3)CC4)C(=O)C34CC(F)(C3)C4)c2)nc1] | 595 | 524 |
| 499 | 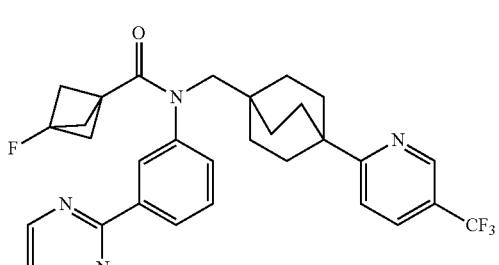 | 617 | 135 |
| 500 | 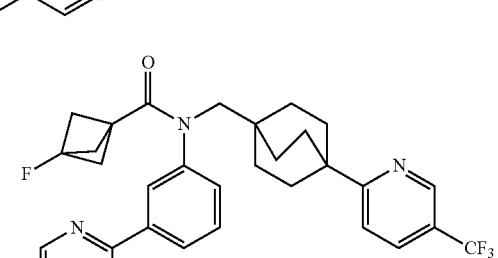 | 581 | 810 |

496 $^1$H NMR (400 MHz, DMSO-d$_6$) δ 8.85 (s, 3H), 8.38 (d, J = 7.6 Hz, 1H), 8.30-8.23 (m, 1H), 8.07 (dd, J = 8.2, 2.3 Hz, 1H), 7.69-7.58 (m, 1H), 7.58-7.45 (m, 2H), 3.69 (br. s., 1H), 3.59 (br. s., 1H), 2.74-2.66 (m, 2H), 1.90 (br. s., 6H), 1.86-1.61 (m, 6H), 1.58-1.36 (m, 6H), 1.30-1.19 (m, 3H)

497 $^1$H NMR (400 MHz, DMSO-d$_6$) δ 8.84 (s, 1H), 8.07 (dd, J = 8.3, 2.2 Hz, 1H), 7.77-7.61 (m, 4H), 7.59-7.47 (m, 2H), 7.40-7.28 (m, 3H), 3.62 (d, J = 14.7 Hz, 2H), 2.66 (q, J = 7.6 Hz, 2H), 2.00-1.70 (m, 12H), 1.50 (d, J = 8.3 Hz, 6H), 1.22 (t, J = 7.6 Hz, 3H)

498 $^1$H NMR (400 MHz, DMSO-d$_6$) δ 8.84 (d, J = 2.4 Hz, 1H), 8.69 (s, 2H), 8.31 (d, J = 7.8 Hz, 1H), 8.19 (t, J = 1.7 Hz, 1H), 8.07 (dd, J = 8.3, 2.2 Hz, 1H), 7.64-7.57 (m, 1H), 7.56-7.41 (m, 2H), 4.28 (q, J = 6.9 Hz, 2H), 3.69 (br. s., 1H), 3.58 (br. s., 1H), 1.87 (s, 3H), 1.90 (s, 3H), 1.84-1.62(m, 6H), 1.59-1.42 (m, 6H), 1.40 (t, J = 7.0 Hz, 3H)

499 $^1$H NMR (400 MHz, DMSO-d$_6$) δ 8.93 (s, 2H), 8.84 (d, J = 2.4 Hz, 1H), 8.43-8.33 (m, 1H), 8.25 (t, J = 1.8 Hz, 1H), 8.07 (dd, J = 8.7, 2.3 Hz, 1H), 7.72-7.55 (m, 2H), 7.52 (d, J = 8.3 Hz, 1H), 7.43 (s, 1H), 3.70 (br. s., 1H), 3.59 (br. s., 1H), 1.90 (br. s., 5H), 1.86-1.57 (m, 7H), 1.57-1.31 (m, 6H)

500 $^1$H NMR (400 MHz, DMSO-d$_6$) δ 8.88-8.81 (m, 1H), 8.71 (s, 2H), 8.36-8.28 (m, 1H), 8.20 (t, J = 1.8 Hz, 1H), 8.07 (dd, J = 8.9, 2.6 Hz, 1H), 7.65-7.57 (m, 1H), 7.56-7.46 (m, 2H), 3.98 (s, 3H), 3.70 (br. s., 1H), 3.58 (br. s., 1H), 1.88 (s, 3H), 1.90 (s, 3H), 1.84-1.60 (m, 6H), 1.58-1.39 (m, 6H)

Example 501

N-((4-(3-(tert-butyl)-1,2,4-oxadiazol-5-yl)bicyclo[2.2.2]octan-1-yl)methyl)-N-(3-(2-ethoxypyrimidin-5-yl)phenyl)-3-hydroxycyclobutane-1-carboxamide

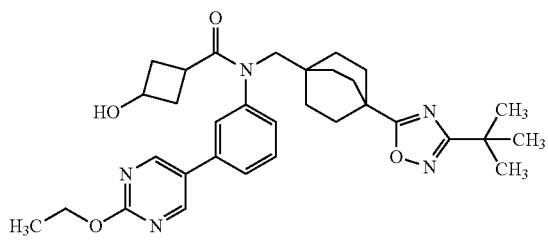

(501)

Step A. Intermediate 501A. Preparation of 3-bromo-N-((4-(3-(tert-butyl)-1,2,4-oxadiazol-5-yl)bicyclo[2.2.2]octan-1-yl)methyl)aniline

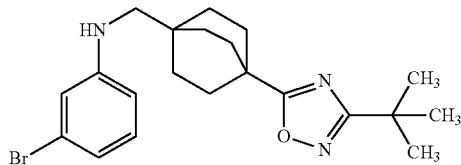 [SMILES: CC(C)(C)c1noc(C23CCC(CNc4cccc(Br)c4)(CC2)CC3)n1]

The title compound was prepared according to the method described for the synthesis of Intermediate 1I by substituting 3-bromoaniline and Intermediate 191C where appropriate. (1.1 g, 2.445 mmol, 64% yield) as brown solid. MS (ESI) 418 (M+H).

Step B. Intermediate 501B. Preparation of N-((4-(3-(tert-butyl)-1,2,4-oxadiazol-5-yl) bicyclo[2.2.2]octan-1-yl)methyl)-3-(2-ethoxypyrimidin-5-yl)aniline

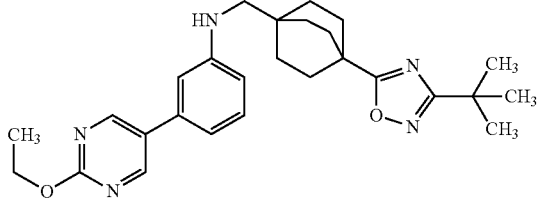 [SMILES: CCOc1ncc(-c2cccc(NCC34CCC(c5nc(C(C)(C)C)no5)(CC3)CC4)c2)cn1]

The title compound was prepared according to the method described for the synthesis of Example 149 by substituting Intermediate 501A and (2-ethoxypyrimidin-5-yl)boronic acid where appropriate. (70 mg, 0.144 mmol, 60% yield) as brown solid. MS (ESI) 462 (M+H).

Step C. Example 501. Preparation of N-((4-(3-(tert-butyl)-1,2,4-oxadiazol-5-yl) bicyclo[2.2.2]octan-1-yl)methyl)-N-(3-(2-ethoxypyrimidin-5-yl)phenyl)-3-hydroxycyclobutane-1-carboxamide The title compound was prepared according to the method described for the synthesis of Example 3 by substituting Intermediate 501B and the corresponding acid where appropriate. (6.6 mg, 0.012 mmol, 17.87% yield). $^1$H NMR (400 MHz, DMSO-$d_6$) δ 8.99 (d, J=3.2 Hz, 2H), 7.83-7.61 (m, 2H), 7.53 (t, J=7.8 Hz, 1H), 7.39-7.26 (m, 1H), 4.96 (br. s., 1H), 4.42 (q, J=7.1 Hz, 2H), 3.71 (br. s., 1H), 3.65 (d, J=4.2 Hz, 2H), 2.45 (d, J=7.8 Hz, 1H), 2.36 (dd, J=10.5, 5.9 Hz, 1H), 1.93 (t, J=8.3 Hz, 2H), 1.86-1.74 (m, 6H), 1.71 (br. s., 1H), 1.53-1.32 (m, 9H), 1.32-1.16 (m, 9H).

The following compounds were prepared according to the method described for the synthesis of Example 3 by substituting Intermediate 501B and the corresponding acids.

| Ex. No. | Structure | MS (ESI) (M + H) | FXR EC$_{50}$ (nM) |
|---|---|---|---|
| 502 | 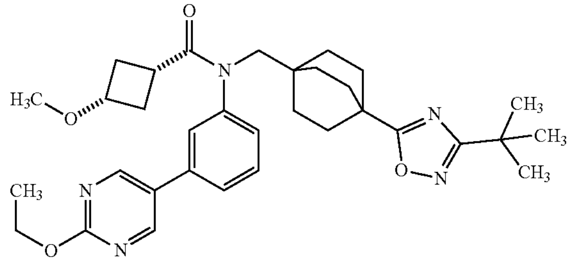 | 574 | 689 |
| 503 | 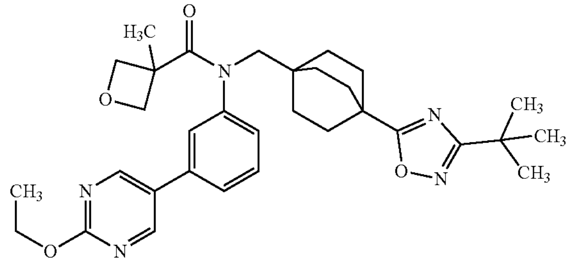 [SMILES: CCOc1ncc(-c2cccc(N(CC34CCC(c5nc(C(C)(C)C)no5)(CC3)CC4)C(=O)C3(C)COC3)c2)cn1] | 560 | 1577 |

| Ex. No. | Structure | MS (ESI) (M + H) | FXR EC$_{50}$ (nM) |
|---|---|---|---|
| 504 | 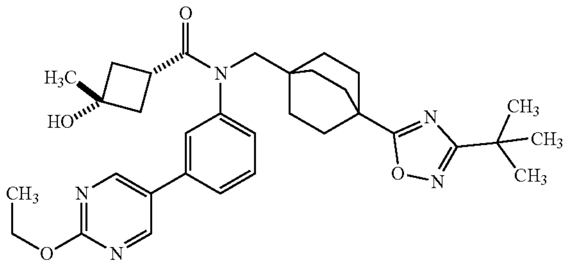 | 475 | 288 |
| 505 | 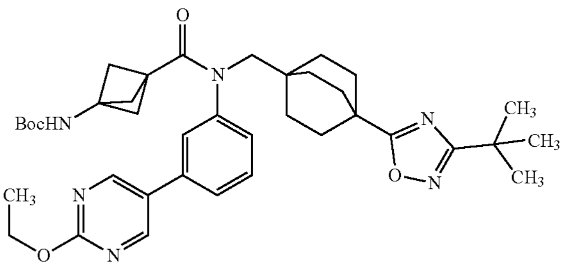 [SMILES: CCOc1ncc(-c2cccc(N(CC34CCC(c5nc(C(C)(C)C)no5)(CC3)CC4)C(=O)C34CC(NC(=O)OC(C)(C)C)(C3)C4)c2)cn1] | 671 | 621 |
| 506 | 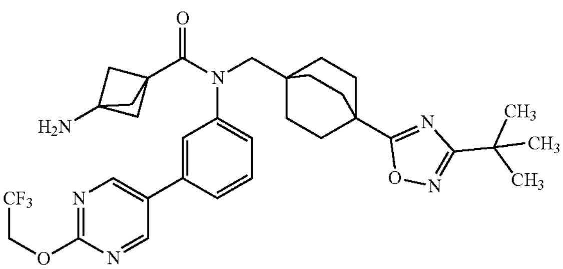 [SMILES: CC(C)(C)c1noc(C23CCC(CN(C(=O)C45CC(N)(C4)C5)c4cccc(-c5cnc(OCC(F)(F)F)nc5)c4)(CC2)CC3)n1] | 571 | 2372 |
| 507 | 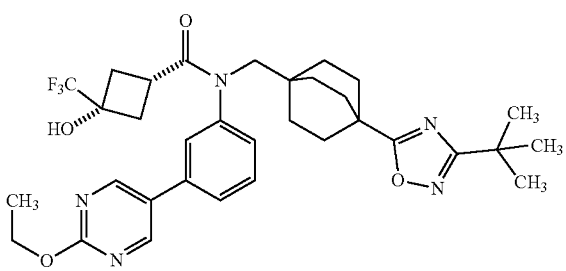 | 628 | 188 |

502 $^1$H NMR (400 MHz, DMSO-d$_6$) δ 9.11-8.92 (m, 2H), 7.76 (s, 1H), 7.70 (d, J = 7.8 Hz, 1H), 7.54 (t, J = 7.8 Hz, 1H), 7.38 (d, J = 9.0 Hz, 1H), 4.42 (q, J = 7.0 Hz, 2H), 3.65 (s, 2H), 3.52 (t, J = 7.3 Hz, 1H), 3.12-2.92 (m, 3H), 2.60 (t, J = 8.9 Hz, 1H), 1.94 (t, J = 7.8 Hz, 4H), 1.87-1.65 (m, 6H), 1.55-1.30 (m, 9H), 1.30-1.16 (m, 9H)

503 $^1$H NMR (400 MHz, DMSO-d$_6$) δ 9.00 (s, 2H), 7.85 (s, 1H), 7.73 (d, J = 8.1 Hz, 1H), 7.54 (t, J = 7.8 Hz, 1H), 7.47 (d, J = 7.6 Hz, 1H), 4.55 (d, J = 5.9 Hz, 2H), 4.42 (q, J = 7.1 Hz, 2H), 3.66 (s, 2H), 3.54 (br. s., 2H), 1.90-1.67 (m, 6H), 1.60 (s, 3H), 1.51-1.31 (m, 9H), 1.31-1.16 (m, 9H)

504 $^1$H NMR (400 MHz, DMSO-d$_6$) δ 9.00 (s, 2H), 7.76 (s, 1H), 7.70 (d, J = 7.3 Hz, 1H), 7.53 (t, J = 7.8 Hz, 1H), 7.36 (d, J = 7.8 Hz, 1H), 4.42 (q, J = 7.1 Hz, 2H), 3.66 (s, 2H), 2.66-2.55 (m, 1H), 2.12 (t, J = 10.3 Hz, 2H), 1.94-1.68 (m, 6H), 1.62 (br. s., 2H), 1.51-1.31 (m, 9H), 1.30-1.19 (m, 9H), 0.99 (s, 3H)

505 $^1$H NMR (400 MHz, DMSO-d$_6$) δ 9.02 (s, 2H), 7.80 (s, 1H), 7.77 (d, J = 7.6 Hz, 1H), 7.56 (t, J = 7.8 Hz, 1H), 7.43-7.38 (m, 1H), 7.28 (br. s., 1H), 4.43 (q, J = 7.1 Hz, 2H), 3.58 (br. s., 2H), 1.88-1.74 (m, 6H), 1.69 (d, J = 6.4 Hz, 6H), 1.53-1.40 (m, 6H), 1.38 (t, J = 7.1 Hz, 3H), 1.33-1.07 (m, 18H)

506 $^1$H NMR (400 MHz, DMSO-d$_6$) δ 9.03 (s, 2H), 8.35 (br. s., 2H), 7.85 (s, 1H), 7.80 (d, J = 7.8 Hz, 1H), 7.59 (t, J = 7.8 Hz, 1H), 7.45 (d, J = 7.6 Hz, 1H), 4.43 (q, J = 7.2 Hz, 2H), 3.65-3.51 (m, 2H), 1.93-1.69 (m, 12H), 1.56-1.40 (m, 6H), 1.38 (t, J = 7.2 Hz, 3H), 1.31-1.19 (m, 9H).

| Ex. No. | Structure | MS (ESI) (M + H) | FXR EC$_{50}$ (nM) |
|---|---|---|---|
| 507 | $^1$H NMR (400 MHz, DMSO-d$_6$) δ 9.00 (s, 2H), 7.83 (s, 1H), 7.72 (d, J = 8.1 Hz, 1H), 7.55 (t, J = 7.8 Hz, 1H), 7.42 (d, J = 7.1 Hz, 1H), 4.42 (q, J = 7.0 Hz, 2H), 3.68 (br. s., 2H), 2.85 (quin, J = 9.0 Hz, 1H), 2.34 (t, J = 10.8 Hz, 2H), 2.06 (d, J = 11.7 Hz, 2H), 1.90-1.69 (m, 6H), 1.55-1.40 (m, 6H), 1.37 (t, J = 7.0 Hz, 3H), 1.31-1.16 (m, 9H) | | |

Example 508

(cis)-N-((4-(5-(tert-butyl)-1,2,4-oxadiazol-3-yl)bicyclo[2.2.2]octan-1-yl)methyl)-N-(3-(2-ethoxypyrimidin-5-yl)phenyl)-3-hydroxy-3-methylcyclobutane-1-carboxamide (508)

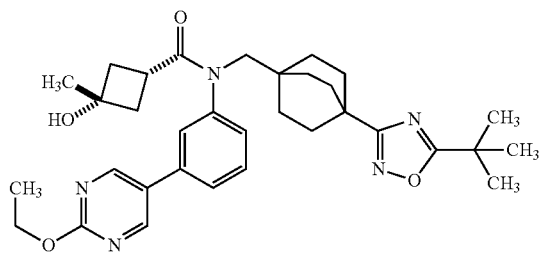

Step A. Intermediate 508A. Preparation of 3-bromo-N-((4-(5-(tert-butyl)-1,2,4-oxadiazol-3-yl)bicyclo[2.2.2]octan-1-yl)methyl)aniline

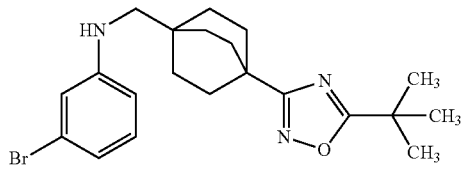

The title compound was prepared according to the method described for the synthesis of Intermediate 1I by substituting 3-bromoaniline and Intermediate 206F where appropriate. (650 mg, 1.55 mmol, 84% yield) as white solid. MS (ESI) 418 (M+H).

Step B. Intermediate 508B. Preparation of N-((4-(5-(tert-butyl)-1,2,4-oxadiazol-3-yl) bicyclo[2.2.2]octan-1-yl)methyl)-3-(2-ethoxypyrimidin-5-yl)aniline

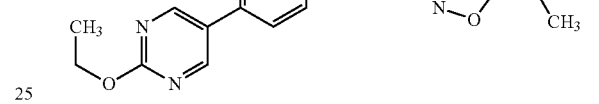

The title compound was prepared according to the method described for the synthesis of Example 149 by substituting Intermediate 508A and (2-ethoxypyrimidin-5-yl)boronic acid where appropriate. (110 mg, 0.236 mmol, 66% yield) as brown solid. MS (ESI) 462 (M+H).

Step C. Example 508. Preparation of (cis)-N-((4-(5-(tert-butyl)-1,2,4-oxadiazol-3-yl) bicyclo[2.2.2]octan-1-yl)methyl)-N-(3-(2-ethoxypyrimidin-5-yl)phenyl)-3-hydroxy-3-methylcyclobutane-1-carboxamide The title compound was prepared according to the method described for the synthesis of Example 3 by substituting Intermediate 508B and the corresponding acid where appropriate. (12.2 mg, 0.021 mmol, 49% yield). $^1$H NMR (400 MHz, DMSO-d$_6$) δ 9.00 (s, 2H), 7.77 (s, 1H), 7.70 (d, J=8.1 Hz, 1H), 7.53 (t, J=7.7 Hz, 1H), 7.36 (d, J=8.8 Hz, 1H), 4.90 (s, 1H), 4.42 (q, J=7.1 Hz, 2H), 3.65 (br. s., 2H), 2.60 (t, J=8.4 Hz, 1H), 2.21-2.01 (m, 2H), 1.84-1.65 (m, 6H), 1.61 (br. s., 2H), 1.45-1.28 (m, 18H), 0.99 (s, 3H). FXR EC$_{50}$ (nM)=210. MS (ESI) 574 (M+H).

The following compounds were prepared according to the method described for the synthesis of Example 3 by substituting Intermediate 508B and the corresponding acids.

| Ex. No. | Structure | MS (ESI) (M + H) | FXR EC$_{50}$ (nM) |
|---|---|---|---|
| 509 | 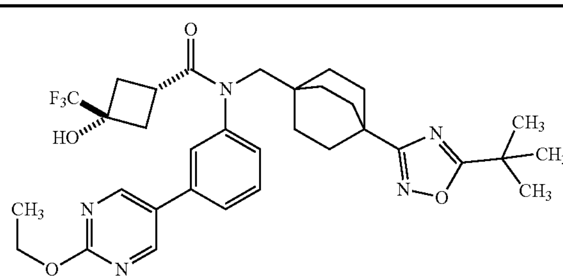 | 628 | 230 |

| Ex. No. | Structure | MS (ESI) (M + H) | FXR EC$_{50}$ (nM) |
|---|---|---|---|
| 510 | 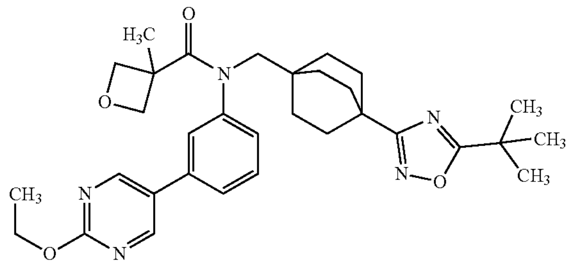 [SMILES: CCOc1ncc(-c2cccc(N(CC34CCC(c5noc(C(C)(C)C)n5)(CC3)CC4)C(=O)C3(C)COC3)c2)cn1] | 560 | 974 |
| 511 | 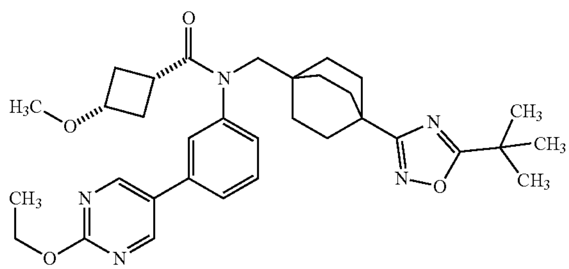 | 574 | 411 |

509 $^1$H NMR (400 MHz, DMSO-d$_6$) δ 9.00 (s, 2H), 7.84 (s, 1H), 7.72 (d, J = 8.1 Hz, 1H), 7.55 (t, J = 7.8 Hz, 1H), 7.42 (d, J = 8.6 Hz, 1H), 6.53 (s, 1H), 4.42 (q, J = 7.1 Hz, 2H), 3.68 (br. s., 2H), 2.85 (t, J = 9.0 Hz, 1H), 2.34 (t, J = 10.4 Hz, 2H), 2.05 (br. s., 2H), 1.86-1.58 (m, 6H), 1.58-1.28 (m, 18H).

510 $^1$H NMR (400 MHz, DMSO-d$_6$) δ 9.01 (s, 2H), 7.87 (s, 1H), 7.73 (d, J = 7.8 Hz, 1H), 7.54 (t, J = 7.8 Hz, 1H), 7.47 (d, J = 7.8 Hz, 1H), 4.54 (d, J = 5.4 Hz, 2H), 4.42 (q, J = 7.0 Hz, 2H), 3.66 (br. s., 2H), 3.53 (br. s., 2H), 1.89-1.63 (m, 6H), 1.60 (s, 3H), 1.49-1.28 (m, 18H).

511 $^1$H NMR (400 MHz, DMSO-d$_6$) δ 9.07-8.96 (m, 2H), 7.77 (s, 1H), 7.70 (d, J = 7.1 Hz, 1H), 7.54 (t, J = 7.8 Hz, 1H), 7.38 (d, J = 8.8 Hz, 1H), 4.42 (q, J = 6.9 Hz, 2H), 3.64 (s, 2H), 3.56-3.47 (m, 1H), 3.09-2.97 (m, 3H), 2.65-2.55 (m, 1H), 1.94 (t, J = 7.8 Hz, 4H), 1.83-1.60 (m, 6H), 1.46-1.28 (m, 18H).

Example 512

(cis)-N-((4-(5-(tert-butyl)-1,2,4-oxadiazol-3-yl)bicyclo[2.2.2]octan-1-yl)methyl)-3-hydroxy-3-methyl-N-(4'-(methylsulfonamido)-[1,1'-biphenyl]-3-yl)cyclobutane-1-carboxamide

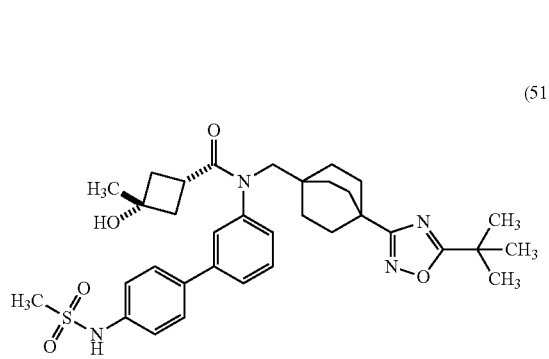

(512)

Step A. Intermediate 512A. Preparation of N-(3'-(((4-(5-(tert-butyl)-1,2,4-oxadiazol-3-yl)bicyclo[2.2.2]octan-1-yl)methyl)amino)-[1,1'-biphenyl]-4-yl)methanesulfonamide

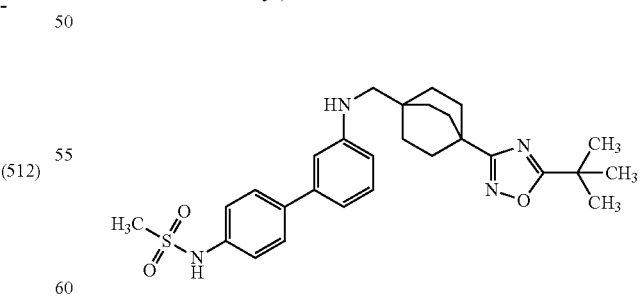

The title compound was prepared according to the method described for the synthesis of Example 149 by substituting Intermediate 508A and (4-(methylsulfonamido)phenyl)boronic acid where appropriate. (130 mg, 0.253 mmol, 71% yield) as white solid. MS (ESI) 509 (M+H).

Step B. Example 512. Preparation of (cis)-N-((4-(5-(tert-butyl)-1,2,4-oxadiazol-3-yl) bicyclo[2.2.2]octan-1-yl)methyl)-3-hydroxy-3-methyl-N-(4'-(methylsulfonamido)-[1,1'-biphenyl]-3-yl)cyclobutane-1-carboxamide The title compound was prepared according to the method described for the synthesis of Example 3 by substituting Intermediate 512A and the corresponding acid where appropriate. (5 mg, 7.72 μmol, 19% yield). $^1$H NMR (400 MHz, DMSO-d$_6$) δ 9.89 (s, 1H), 7.72 (d, J=8.8 Hz, 2H), 7.65-7.53 (m, 2H), 7.49 (t, J=8.1 Hz, 1H), 7.39-7.23 (m, 3H), 4.90 (s, 1H), 3.64 (br. s., 2H), 3.03 (s, 3H), 2.64-2.54 (m, 1H), 2.12 (t, J=10.5 Hz, 2H), 1.83-1.66 (m, 6H), 1.62 (br. s., 2H), 1.49-1.35 (m, 6H), 1.33 (s, 9H). FXR EC$_{50}$ (nM)=909. MS (ESI) 621 (M+H).

The following compounds were prepared according to the method described for the synthesis of Example 3 by substituting Intermediate 512A and the corresponding acids.

Example 515

N-((4-(5-(tert-butyl)-1,2,4-oxadiazol-3-yl)bicyclo[2.2.2]octan-1-yl)methyl)-N-(4'-(difluoromethoxy)-[1,1'-biphenyl]-3-yl)-3-methyloxetane-3-carboxamide (515)

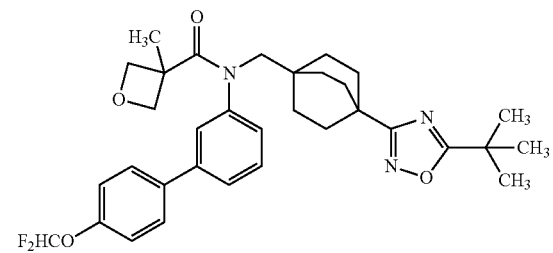

| Ex. No. | Structure | MS (ESI) (M + H) | FXR EC$_{50}$ (nM) |
|---|---|---|---|
| 513 | 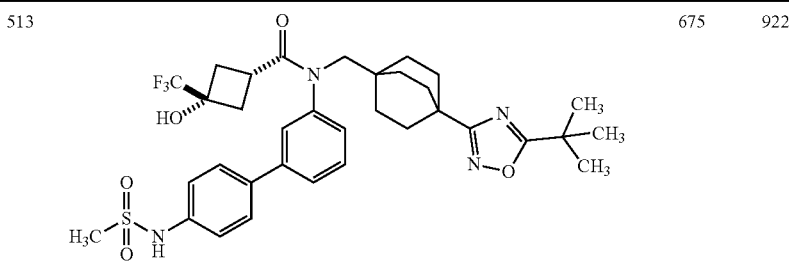 | 675 | 922 |
| 514 | 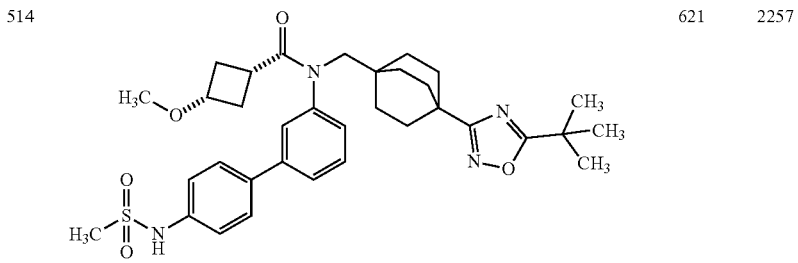 | 621 | 2257 |

513 $^1$H NMR (400 MHz, DMSO-d$_6$) δ 9.89 (s, 1H), 7.72 (d, J = 8.6 Hz, 2H), 7.67 (s, 1H), 7.63 (d, J = 7.8 Hz, 1H), 7.50 (t, J = 7.8 Hz, 1H), 7.42-7.26 (m, 3H), 6.53 (s, 1H), 3.66 (br. s., 2H), 3.03 (s, 3H), 2.90-2.78 (m, 1H), 2.39-2.24 (m, 2H), 2.06 (d, J = 14.4 Hz, 2H), 1.83-1.54 (m, 6H), 1.52-1.35 (m, 6H), 1.33 (s, 9H).

514 $^1$H NMR (400 MHz, DMSO-d$_6$) δ 9.86 (br. s., 1H), 7.72 (d, J = 8.6 Hz, 2H), 7.61 (s, 2H), 7.49 (t, J = 8.2 Hz, 1H), 7.36-7.21 (m, 3H), 3.63-3.49 (m, 3H), 3.09-2.96 (m, 6H), 2.05-1.87 (m, 4H), 1.81-1.67 (m, 6H), 1.42 (d, J = 7.6 Hz, 6H), 1.33 (s, 9H).

Step A. Intermediate 515A. Preparation of N-((4-(5-(tert-butyl)-1,2,4-oxadiazol-3-yl) bicyclo[2.2.2]octan-1-yl)methyl)-4'-(difluoromethoxy)-[1,1'-biphenyl]-3-amine

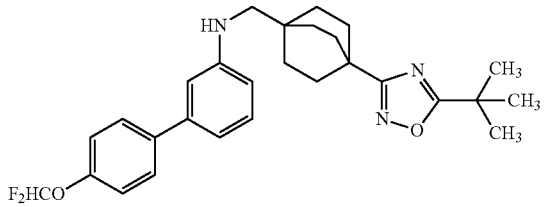 [SMILES: CC(C)(C)c1nc(C23CCC(CNc4cccc(-c5ccc(OC(F)F)cc5)c4)(CC2)CC3)no1]

The title compound was prepared according to the method described for the synthesis of Example 149 by substituting Intermediate 508A and (4-(difluoromethoxy)phenyl)boronic acid where appropriate. (130 mg, 0.267 mmol, 74% yield) as brown solid. $^1$H NMR (400 MHz, DMSO-d$_6$) δ 7.66-7.60 (m, 2H), 7.28-7.20 (m, 3H), 7.16-7.07 (m, 1H), 6.87-6.83 (m, 1H), 6.74 (d, J=8.5 Hz, 1H), 6.63 (dd, J=7.8, 1.8 Hz, 1H), 5.53 (t, J=6.3 Hz, 1H), 2.88 (d, J=6.0 Hz, 2H), 1.89-1.80 (m, 6H), 1.63-1.54 (m, 6H), 1.36 (s, 9H). MS (ESI) 482 (M+H).

Step B. Example 515. Preparation of N-((4-(5-(tert-butyl)-1,2,4-oxadiazol-3-yl) bicyclo[2.2.2]octan-1-yl)methyl)-N-(4'-(difluoromethoxy)-[1,1'-biphenyl]-3-yl)-3-methyloxetane-3-carboxamide The title compound was prepared according to the method described for the synthesis of Example 3 by substituting Intermediate 515A and the corresponding acid where appropriate. (4.7 mg, 8.11 μmol, 19% yield). $^1$H NMR (400 MHz, DMSO-d$_6$) δ 7.87-7.77 (m, 2H), 7.74 (s, 1H), 7.66 (d, J=7.3 Hz, 1H), 7.53-7.12 (m, 5H), 4.55 (d, J=5.4 Hz, 2H), 3.65 (br. s., 2H), 3.53 (br. s., 2H), 1.88-1.65 (m, 6H), 1.60 (s, 3H), 1.51-1.36 (m, 6H), 1.33 (s, 9H). FXR EC$_{50}$ (nM)=357. MS (ESI) 580 (M+H).

The following compounds were prepared according to the method described for the synthesis of Example 3 by substituting Intermediate 515A and the corresponding acids.

| Ex. No. | Structure | MS (ESI) (M + H) | FXR EC$_{50}$ (nM) |
|---|---|---|---|
| 516 | | 648 | 94 |
| 517 | | 594 | 255 |

516 $^1$H NMR (400 MHz, DMSO-d$_6$) δ 7.87-7.76 (m, 2H), 7.71 (s, 1H), 7.65 (d, J = 8.1 Hz, 1H), 7.57-7.44 (m, 1H), 7.38 (d, J = 8.6 Hz, 1H), 7.34-7.20 (m, 3H), 6.53 (s, 1H), 3.67 (br. s., 2H), 2.84 (t, J = 8.9 Hz, 1H), 2.39-2.27 (m, 2H), 2.04 (br. s., 2H), 1.80-1.64 (m, 6H), 1.55-1.35 (m, 6H), 1.33 (s, 9H)

517 $^1$H NMR (400 MHz, DMSO-d$_6$) δ 7.80 (d, J = 8.8 Hz, 2H), 7.70-7.56 (m, 2H), 7.55-7.20 (m, 5H), 3.65 (br. s., 2H), 2.65-2.54 (m, 1H), 2.19-2.05 (m, 2H), 1.82-1.65 (m, 6H), 1.61 (br. s., 2H), 1.46-1.37 (m, 6H), 1.37-1.26 (m, 9H), 0.98 (s, 3H)

Example 518

(cis)-N-(3-(2-ethoxypyrimidin-5-yl)phenyl)-3-methoxy-N-((4-(5-(3-methyloxetan-3-yl)-1,2,4-oxadiazol-3-yl)bicyclo[2.2.2]octan-1-yl)methyl)cyclobutane-1-carboxamide (518)

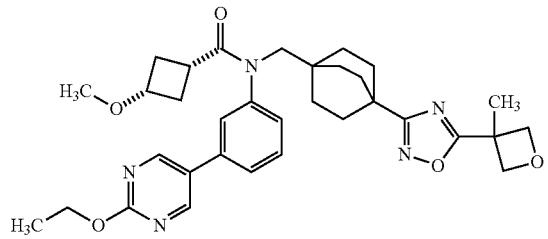

Step A. Intermediate 518A. Preparation of 3-(2-ethoxypyrimidin-5-yl)aniline

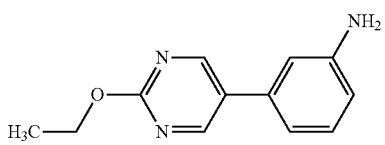

The title compound was prepared according to the method described for the synthesis of Example 149 by substituting 3-bromoaniline and (2-ethoxypyrimidin-5-yl)boronic acid where appropriate. (850 mg, 3.75 mmol, 64% yield) as white solid. MS (ESI) 216 (M+H).

Step B. Intermediate 518B. Preparation of methyl 4-(((3-(2-ethoxypyrimidin-5-yl) phenyl)amino)methyl)bicyclo[2.2.2]octane-1-carboxylate

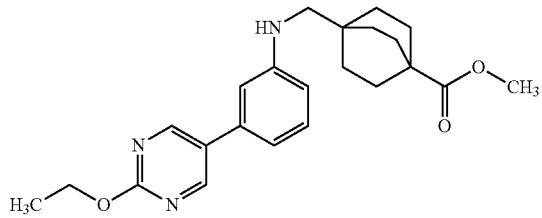 [SMILES: CCOc1ncc(-c2cccc(NCC34CCC(C(=O)OC)(CC3)CC4)c2)cn1]

The title compound was prepared according to the method described for the synthesis of Intermediate 1I by substituting Intermediate 518A and Intermediate 88B where appropriate. (1.3 g, 3.12 mmol, 79% yield) as white solid. MS (ESI) 396 (M+H).

Step C. Intermediate 518C. Preparation of 4-(((3-(2-ethoxypyrimidin-5-yl)phenyl) amino)methyl)bicyclo[2.2.2]octane-1-carboxylic acid

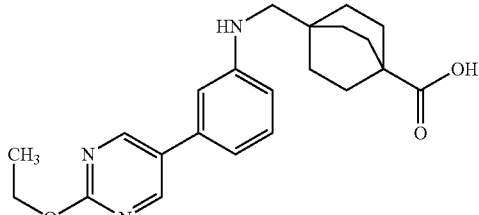

To a solution of Intermediate 518B (1.3 g, 3.29 mmol) in tetrahydrofuran (20 mL) was added a solution of sodium hydroxide (0.39 g, 9.86 mmol) in water (20 mL). The reaction mixture was stirred at 50° C. for overnight. The reaction mixture was concentrated under reduced pressure, the residue was diluted with water (20 mL), acidified (pH ~2) with aqueous 1.5 mL HCl solution and extracted with EtOAc (2×50 mL). The organic layers were combined, dried over anhydrous sodium sulphate, concentrated and dried in vacuo to afford the title compound (1.05 g, 2.61 mmol, 80% yield). MS (ESI) 382 (M+H).

Step D. Intermediate 518D. Preparation of 4-(((3-(2-ethoxypyrimidin-5-yl)phenyl) amino)methyl)bicyclo[2.2.2]octane-1-carboxamide

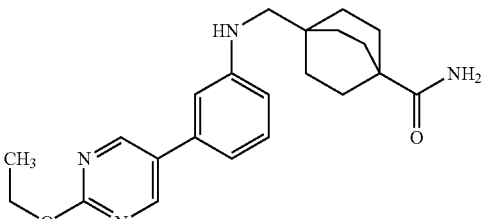

To a stirred solution of Intermediate 518C (850 mg, 2.228 mmol) in dichloromethane (15 mL) were added ammonium chloride (596 mg, 11.14 mmol), BOP (985 mg, 2.228 mmol) followed by TEA (0.95 mL, 6.68 mmol). The reaction mixture was stirred at room temperature for 1 h. The reaction mixture was poured into water (50 mL) and extracted with DCM (2×50 mL). The organic layers were combined, dried over anhydrous sodium sulphate, concentrated and dried in vacuo to afford the title compound (1 g, 2.103 mmol, 94% yield) as an off-white solid. MS (ESI) 381 (M+H).

Step E. Intermediate 518E. Preparation of 4-(((3-(2-ethoxypyrimidin-5-yl)phenyl) amino)methyl)bicyclo[2.2.2]octane-1-carbonitrile

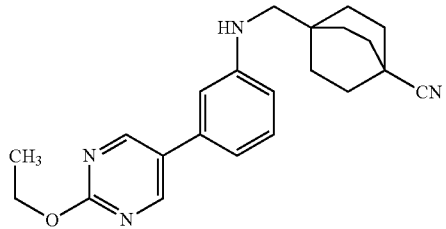 [SMILES: CCOc1ncc(-c2cccc(NCC34CCC(C#N)(CC3)CC4)c2)cn1]

The title compound was prepared according to the method described for the synthesis of Intermediate 194D by substituting Intermediate 516D where appropriate. (110 mg, 0.288 mmol, 18% yield) as an off-white solid. MS (ESI) 363 (M+H).

Step F. Intermediate 518F. Preparation of (Z)-4-(((3-(2-ethoxypyrimidin-5-yl)phenyl) amino)methyl)-N'-hydroxybicyclo[2.2.2]octane-1-carboximidamide

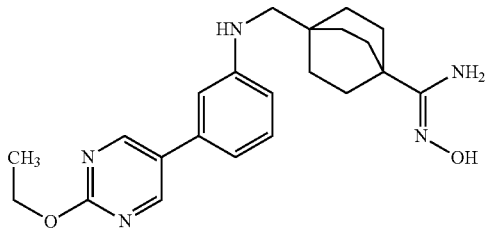 [SMILES: CCOc1ncc(-c2cccc(NCC34CCC(/C(N)=N/O)(CC3)CC4)c2)cn1]

The title compound was prepared according to the method described for the synthesis of Intermediate 88F by substituting Intermediate 518E where appropriate. (120 mg, 0.288 mmol, 95% yield) as an off-white solid. MS (ESI) 396 (M+H).

Step G. Intermediate 518G. Preparation of 3-(2-ethoxypyrimidin-5-yl)-N-((4-(5-(3-methyloxetan-3-yl)-1,2,4-oxadiazol-3-yl)bicyclo[2.2.2]octan-1-yl)methyl)aniline

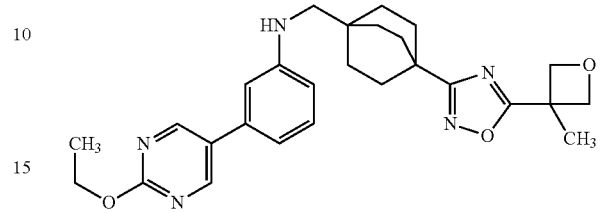

The title compound was prepared according to the method described for the synthesis of Intermediate 1A by substituting Intermediate 518F and the corresponding acid where appropriate. (130 mg, 0.260 mmol, 86% yield) as an off-white solid. MS (ESI) 476 (M+H).

Step H. Example 518. Preparation of (cis)-N-(3-(2-ethoxypyrimidin-5-yl)phenyl)-3-methoxy-N-((4-(5-(3-methyloxetan-3-yl)-1,2,4-oxadiazol-3-yl)bicyclo[2.2.2]octan-1-yl) methyl)cyclobutane-1-carboxamide The title compound was prepared according to the method described for the synthesis of Example 3 by substituting Intermediate 518G and the corresponding acid where appropriate. (7 mg, 0.011 mmol, 22% yield). $^1$H NMR (400 MHz, DMSO-$d_6$) δ 9.09-8.91 (m, 2H), 7.77 (s, 1H), 7.70 (d, J=7.6 Hz, 1H), 7.54 (t, J=7.8 Hz, 1H), 7.38 (d, J=8.3 Hz, 1H), 4.83 (d, J=5.9 Hz, 2H), 4.51 (d, J=5.9 Hz, 2H), 4.42 (q, J=7.1 Hz, 2H), 3.65 (s, 2H), 3.56-3.46 (m, 1H), 3.08-2.96 (m, 3H), 2.66-2.53 (m, 1H), 1.94 (t, J=7.9 Hz, 4H), 1.84-1.58 (m, 9H), 1.54-1.29 (m, 9H). FXR EC$_{50}$ (nM) 1294. MS (ESI) 588 (M+H).

The following compounds were prepared according to the method described for the synthesis of Example 3 by substituting Intermediate 518G and the corresponding acids.

| Ex. No. | Structure | MS (ESI) (M + H) | FXR EC$_{50}$ (nM) |
|---|---|---|---|
| 519 | 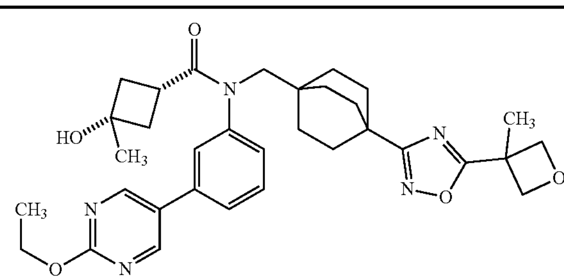 | 588 | 504 |

| Ex. No. | Structure | MS (ESI) (M + H) | FXR EC$_{50}$ (nM) |
|---|---|---|---|
| 520 | | 642 | 449 |
| 519 | <sup>1</sup>H NMR (400 MHz, DMSO-d$_6$) δ 9.00 (s, 2H), 7.77 (s, 1H), 7.70 (d, J = 8.3 Hz, 1H), 7.53 (t, J = 7.8 Hz, 2H), 7.37 (d, J = 8.1 Hz, 1H), 4.87 (s, 1H), 4.83 (d, J = 6.1 Hz, 2H), 4.52 (d, J = 6.1 Hz, 2H), 4.42 (q, J = 7.1 Hz, 2H), 3.67 (br. s., 2H), 2.65-2.57 (m, 1H), 2.19-2.06 (m, 2H), 1.84-1.67 (m, 9H), 1.62 (br. s., 2H), 1.53-1.30 (m, 9H), 0.99 (s, 2H). | | |
| 520 | <sup>1</sup>H NMR (400 MHz, DMSO-d$_6$) δ 9.00 (s, 2H), 7.83 (s, 1H), 7.72 (d, J = 8.1 Hz, 1H), 7.55 (t, J = 7.7 Hz, 1H), 7.42 (d, J = 7.3 Hz, 1H), 6.51 (s, 1H), 4.83 (d, J = 5.9 Hz, 2H), 4.52 (d, J = 6.1 Hz, 2H), 4.42 (q, J = 7.0 Hz, 2H), 3.69 (br. s., 2H), 2.91-2.78 (m, 1H), 2.39-2.26 (m, 2H), 2.06 (d, J = 10.3 Hz, 2H), 1.85-1.72 (m, 6H), 1.71 (s, 3H), 1.54-1.40 (m, 6H), 1.37 (t, J = 7.0 Hz, 3H). | | |

Example 521

N-(4'-ethoxy-[1,1'-biphenyl]-3-yl)-3-fluoro-N-((4-(5-(1-(trifluoromethyl)cyclopropyl)-1,2,4-oxadiazol-3-yl)bicyclo[2.2.2]octan-1-yl)methyl)bicyclo[1.1.1]pentane-1-carboxamide (521)

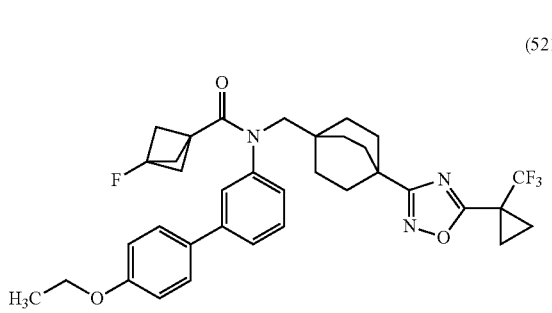

Step A. Intermediate 521A. Preparation of 3-bromo-N-((4-(5-(1-(trifluoromethyl) cyclopropyl)-1,2,4-oxadiazol-3-yl)bicyclo[2.2.2]octan-1-yl) methyl)aniline

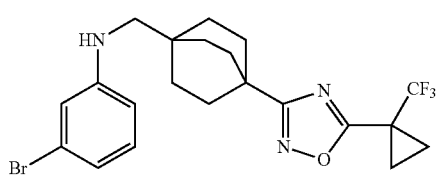 [SMILES: FC(F)(F)C1(c2nc(C34CCC(CNc5cccc(Br)c5)(CC3)CC4)no2)CC1]

The title compound was prepared according to the method described for the synthesis of Intermediate 1A by substituting Intermediate 194E and the corresponding acid where appropriate. (450 mg, 0.957 mmol, 96% yield) as yellow solid. MS (ESI) 470 (M+H).

Step B. Intermediate 521B. Preparation of N-(3-bromophenyl)-3-fluoro-N-((4-(5-(1-(trifluoromethyl) cyclopropyl)-1,2,4-oxadiazol-3-yl)bicyclo[2.2.2] octan-1-yl)methyl) bicyclo[1.1.1]pentane-1-carboxamide The title compound was prepared according to the method described for the synthesis of Example 3 by substituting Intermediate 521A and the corresponding acid where appropriate. (400 mg, 0.687 mmol, 77% yield) as gummy mass. MS (ESI) 582 (M+H).

Step C. Example 521. Preparation of N-(4'-ethoxy-[1,1'-biphenyl]-3-yl)-3-fluoro-N-((4-(5-(1-(trifluoromethyl)cyclopropyl)-1,2,4-oxadiazol-3-yl)bicyclo[2.2.2]octan-1-yl) methyl)bicyclo[1.1.1]pentane-1-carboxamide The title compound was prepared according to the method described for the synthesis of Example 149 by substituting Intermediate 521B and 2-(4-ethoxyphenyl)-5,5-dimethyl-1,3,2-dioxaborinane where appropriate. (8.2 mg, 0.013 mmol, 25% yield). <sup>1</sup>H NMR (400 MHz, DMSO-d$_6$) δ 7.81-7.55 (m, 4H), 7.50 (t, J=7.8 Hz, 1H), 7.31 (d, J=8.8 Hz, 1H), 7.04 (d, J=8.8 Hz, 2H), 4.09 (q, J=7.1 Hz, 2H), 3.59 (d, J=10.0 Hz, 2H), 1.85 (s, 3H), 1.88 (s, 3H), 1.79-1.55 (m, 10H), 1.55-1.39 (m, 6H), 1.36 (t, J=7.0 Hz, 3H). FXR EC$_{50}$ (nM)=112. MS (ESI) 624 (M+H).

The following compounds were prepared according to the method described for the synthesis of Example 149 by substituting Intermediate 521B and the corresponding aryl/hetero aryl boronic acids/esters.

| Ex. No. | Structure | MS (ESI) (M + H) | FXR EC$_{50}$ (nM) |
|---|---|---|---|
| 522 | 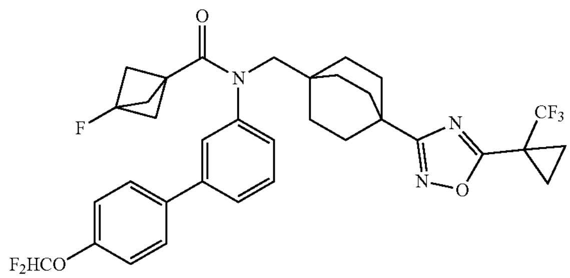 [SMILES: O=C(N(CC12CCC(c3noc(C4(C(F)(F)F)CC4)n3)(CC1)CC2)c1cccc(-c2ccc(OC(F)F)cc2)c1)C12CC(F)(C1)C2] | 646 | 69 |
| 523 | 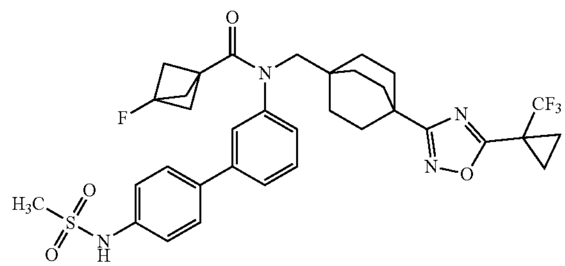 [SMILES: CS(=O)(=O)Nc1ccc(-c2cccc(N(CC34CCC(c5noc(C6(C(F)(F)F)CC6)n5)(CC3)CC4)C(=O)C34CC(F)(C3)C4)c2)cc1] | 673 | 189 |
| 524 | 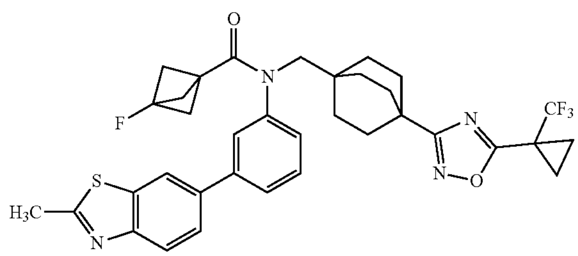 [SMILES: Cc1nc2ccc(-c3cccc(N(CC45CCC(c6noc(C7(C(F)(F)F)CC7)n6)(CC4)CC5)C(=O)C45CC(F)(C4)C5)c3)cc2s1] | 651 | 119 |
| 525 | 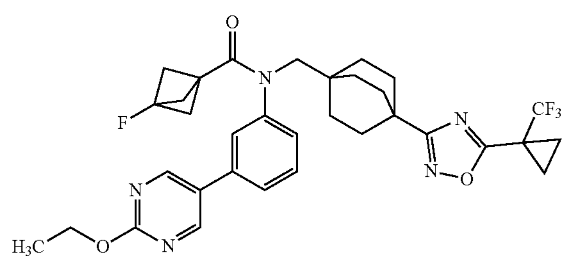 [SMILES: CCOc1ncc(-c2cccc(N(CC34CCC(c5noc(C6(C(F)(F)F)CC6)n5)(CC3)CC4)C(=O)C34CC(F)(C3)C4)c2)cn1] | 626 | 142 |
| 526 | 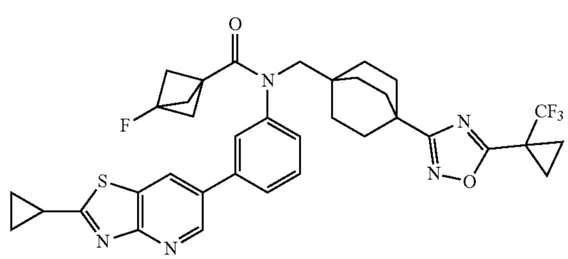 [SMILES: O=C(N(CC12CCC(c3noc(C4(C(F)(F)F)CC4)n3)(CC1)CC2)c1cccc(-c2cnc3nc(C4CC4)sc3c2)c1)C12CC(F)(C1)C2] | 678 | 497 |

522 $^1$H NMR (400 MHz, DMSO-d$_6$) δ 7.89-7.77 (m, 2H), 7.76-7.64 (m, 2H), 7.54 (t, J = 8.1 Hz, 1H), 7.39 (d, J = 8.3 Hz, 1H), 7.34-7.20 (m, 2H), 7.12 (s, 1H), 3.63 (br. s., 1H), 3.60-3.50 (m, 1H), 1.85 (s, 3H), 1.88 (s, 3H), 1.79-1.59 (m, 10H), 1.47 (d, J = 9.5 Hz, 6H)

523 $^1$H NMR (400 MHz, DMSO-d$_6$) δ 9.88 (s, 1H), 7.74 (d, J = 8.6 Hz, 2H), 7.71-7.62 (m, 2H), 7.52 (t, J = 7.8 Hz, 1H), 7.41-7.24 (m, 3H), 3.60 (d, J = 11.5 Hz, 2H), 3.04 (s, 3H), 1.85 (s, 3H), 1.88 (s, 3H), 1.79-1.54 (m, 10H), 1.47 (d, J = 8.1 Hz, 6H)

524 $^1$H NMR (400 MHz, DMSO-d$_6$) δ 8.46 (d, J = 1.7 Hz, 1H), 8.00 (d, J = 8.6 Hz, 1H), 7.86 (dd, J = 8.4, 1.8 Hz, 1H), 7.83-7.71 (m, 2H), 7.56 (t, J = 8.1 Hz, 1H), 7.41 (d, J = 8.1 Hz, 1H), 3.73-3.63 (m, 1H), 3.61-3.49 (m, 1H), 2.83 (s, 3H), 1.86 (s, 3H), 1.91 (s, 3H), 1.79-1.57 (m, 10H), 1.47 (d, J = 4.9 Hz, 6H)

-continued

| Ex. No. | Structure | MS (ESI) (M + H) | FXR EC$_{50}$ (nM) |
|---|---|---|---|
| 525 | $^1$H NMR (400 MHz, DMSO-d$_6$) δ 9.01 (s, 2H), 7.82 (s, 1H), 7.77 (d, J = 8.3 Hz, 1H), 7.57 (t, J = 7.7 Hz, 1H), 7.43 (d, J = 7.8 Hz, 1H), 4.43 (q, J = 6.9 Hz, 2H), 3.66-3.52 (m, 2H), 1.85 (s, 3H), 1.88 (s, 3H), 1.79-1.56 (m, 10H), 1.46 (d, J = 9.0 Hz, 6H), 1.38 (t, J = 7.0 Hz, 3H) | | |
| 526 | $^1$H NMR (400 MHz, DMSO-d$_6$) δ 8.99 (d, J = 2.4 Hz, 1H), 8.89 (d, J = 2.2 Hz, 1H), 7.94-7.70 (m, 2H), 7.60 (t, J = 7.8 Hz, 1H), 7.45 (d, J = 8.3 Hz, 1H), 3.68 (d, J = 13.0 Hz, 1H), 3.57 (d, J = 12.2 Hz, 1H), 2.66-2.58 (m, 1H), 1.86 (s, 3H), 1.91 (s, 3H), 1.80-1.58 (m, 10H), 1.58-1.38 (m, 6H), 1.36-1.30 (m, 2H), 1.28-1.16 (m, 2H) | | |

Example 527

N-((4-(5-(1,1-difluoroethyl)-1,2,4-oxadiazol-3-yl)bicyclo[2.2.2]octan-1-yl)methyl)-N-(4'-ethoxy-[1,1'-biphenyl]-3-yl)-3-fluorobicyclo[1.1.1]pentane-1-carboxamide (527)

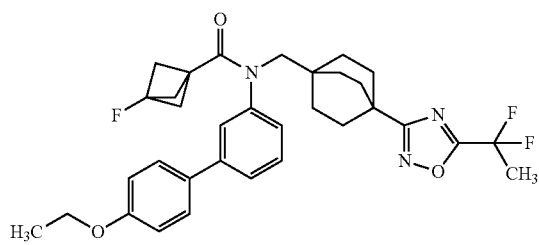

Step A. Intermediate 527A. Preparation of 3-bromo-N-((4-(5-(1,1-difluoroethyl)-1,2,4-oxadiazol-3-yl)bicyclo[2.2.2]octan-1-yl)methyl)aniline

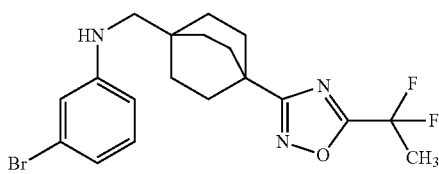

The title compound was prepared according to the method described for the synthesis of Intermediate 1A by substituting Example 194E and the corresponding acid where appropriate. (380 mg, 0.882 mmol, 89% yield) as brown gummy mass. MS (ESI) 426 (M+H).

Step B. Intermediate 527B. Preparation of N-(3-bromophenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide

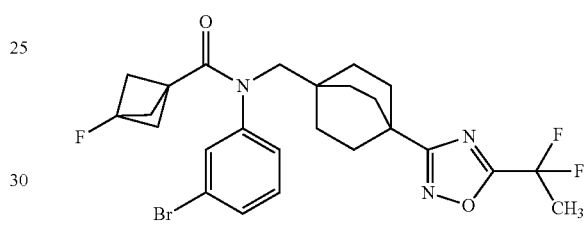

The title compound was prepared according to the method described for the synthesis of Example 3 by substituting Intermediate 527A and the corresponding acid where appropriate. (400 mg, 0.687 mmol, 77% yield) as gummy mass. MS (ESI) 538 (M+H).

Step C. Example 527. Preparation of N-((4-(5-(1,1-difluoroethyl)-1,2,4-oxadiazol-3-yl) bicyclo[2.2.2]octan-1-yl)methyl)-N-(4'-ethoxy-[1,1'-biphenyl]-3-yl)-3-fluorobicyclo [1.1.1]pentane-1-carboxamide The title compound was prepared according to the method described for the synthesis of Example 149 by substituting Intermediate 527B and the corresponding boronic acid where appropriate. (16.6 mg, 0.028 mmol, 50% yield). $^1$H NMR (400 MHz, DMSO-d$_6$) δ 7.76-7.58 (m, 4H), 7.50 (t, J=7.8 Hz, 1H), 7.37-7.27 (m, 1H), 7.13-6.95 (m, 2H), 4.09 (q, J=6.8 Hz, 2H), 3.60 (d, J=8.3 Hz, 2H), 2.14 (t, J=19.7 Hz, 3H), 1.98-1.69 (m, 12H), 1.59-1.38 (m, 6H), 1.38-1.28 (m, 3H). FXR EC$_{50}$ (nM)=103. MS (ESI) 580 (M+H).

The following compounds were prepared according to the method described for the synthesis of Example 149 by substituting Intermediate 527B and the corresponding aryl/hetero aryl boronic acids/esters.

| Ex. No. | Structure | MS (ESI) (M + H) | FXR EC$_{50}$ (nM) |
|---|---|---|---|
| 528 | 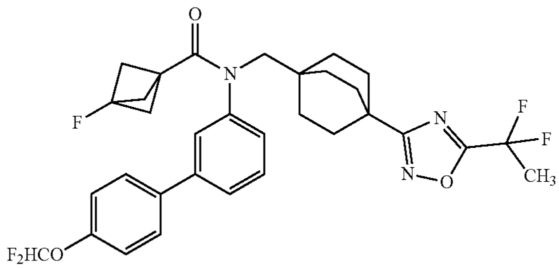 [SMILES: CC(F)(F)c1nc(C23CCC(CN(C(=O)C45CC(F)(C4)C5)c4cccc(-c5ccc(OC(F)F)cc5)c4)(CC2)CC3)no1] | 602 | 73 |
| 529 | 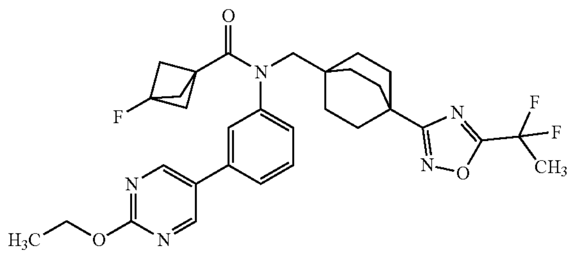 [SMILES: CCOc1ncc(-c2cccc(N(CC34CCC(c5noc(C(C)(F)F)n5)(CC3)CC4)C(=O)C34CC(F)(C3)C4)c2)cn1] | 582 | 106 |
| 530 | 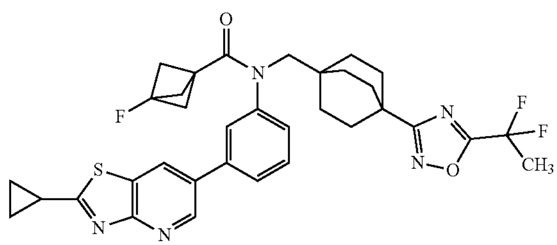 [SMILES: CC(F)(F)c1nc(C23CCC(CN(C(=O)C45CC(F)(C4)C5)c4cccc(-c5cnc6nc(C7CC7)sc6c5)c4)(CC2)CC3)no1] | 634 | 145 |

528 $^1$H NMR (400 MHz, DMSO-d$_6$) δ 7.87-7.77 (m, 2H), 7.76-7.64 (m, 2H), 7.55 (t, J = 8.1 Hz, 1H), 7.40 (d, J = 8.3 Hz, 1H), 7.35-7.21 (m, 3H), 3.71-3.61 (m, 1H), 3.61-3.51 (m, 1H), 2.14 (t, J = 19.6 Hz, 3H), 1.98-1.70 (m, 12H), 1.49 (d, J = 9.5 Hz, 6H)

529 $^1$H NMR (400 MHz, DMSO-d$_6$) δ 9.02 (s, 2H), 7.87-7.80 (m, 1H), 7.78 (d, J = 7.8 Hz, 1H), 7.57 (t, J = 7.8 Hz, 1H), 7.44 (d, J = 7.8 Hz, 1H), 4.43 (q, J = 7.1 Hz, 2H), 3.71-3.51 (m, 2H), 2.14 (t, J = 19.6 Hz, 3H), 2.00-1.70 (m, 12H), 1.47 (d, J = 5.9 Hz, 3H), 1.49 (d, J = 4.9 Hz, 3H), 1.38 (t, J = 7.0 Hz, 3H)

530 $^1$H NMR (400 MHz, DMSO-d$_6$) δ 8.99 (d, J = 2.2 Hz, 1H), 8.90 (d, J = 2.2 Hz, 1H), 7.94-7.77 (m, 2H), 7.60 (t, J = 7.8 Hz, 1H), 7.52-7.41 (m, 1H), 3.74-3.63(m, 1H), 3.62-3.51 (m, 1H), 2.66-2.59 (m, 1H), 2.22-2.05 (m, 3H), 1.99-1.70 (m, 12H), 1.59-1.37 (m, 6H), 1.37-1.17 (m, 4H)

Example 531

N-((4-(5-(tert-butyl)-1,2,4-oxadiazol-3-yl)bicyclo[2.2.2]octan-1-yl)methyl)-N-(4-(2-ethoxypyrimidin-5-yl)pyridin-2-yl)-3-fluorobicyclo[1.1.1]pentane-1-carboxamide (531)

Step A. Intermediate 531A. Preparation of 4-bromo-N-((4-(5-(tert-butyl)-1,2,4-oxadiazol-3-yl)bicyclo[2.2.2]octan-1-yl)methyl)pyridin-2-amine

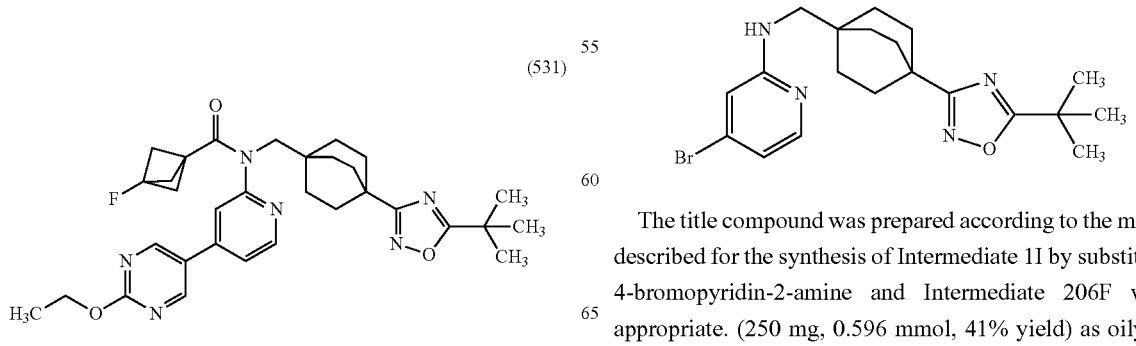

The title compound was prepared according to the method described for the synthesis of Intermediate 1I by substituting 4-bromopyridin-2-amine and Intermediate 206F where appropriate. (250 mg, 0.596 mmol, 41% yield) as oily less liquid. MS (ESI) 419 (M+H).

Step B. Intermediate 531B. Preparation of N-(4-bromopyridin-2-yl)-N-((4-(5-(tert-butyl)-1,2,4-oxadiazol-3-yl)bicyclo[2.2.2]octan-1-yl)methyl)-3-fluorobicyclo[1.1.1]pentane-1-carboxamide

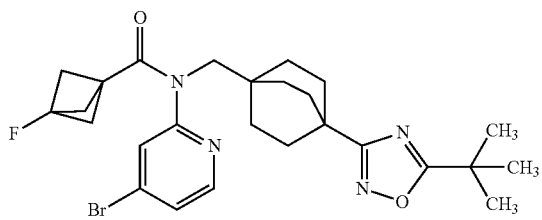 [SMILES: CC(C)(C)c1nc(C23CCC(CN(C(=O)C45CC(F)(C4)C5)c4cc(Br)ccn4)(CC2)CC3)no1]

To a stirred solution of 3-fluorobicyclo[1.1.1]pentane-1-carboxylic acid (84 mg, 0.644 mmol) in acetonitrile (2 mL) was added 1-chloro-n,n,2-trimethylpropenylamine (0.086 mL, 0.644 mmol) drop wise at 0° C. The reaction mixture was stirred at 0° C. for 1 h to get a clear solution. The reaction mixture was cooled to −10° C. A solution of Intermediate 531A (180 mg, 0.429 mmol) in acetonitrile (1 mL) was added to the reaction mixture followed by a solution of 4-methylmorpholine (0.094 mL, 0.858 mmol) in acetonitrile (1 mL). The resulting reaction mixture was stirred at 0° C. for 30 min, then allowed to warm to room temperature and stirred for 4 h. The reaction mixture was diluted with aqueous 10% citric acid (10 mL) and extracted with ethyl acetate (2×10 mL). The organic layers were combined, dried over anhydrous sodium sulphate and concentrated under reduced pressure. The crude material was purified by flash chromatography (12 g silica gel cartridge; A=Hex, B=EtOAc; 30 min grad.; 0% B to 20% B; flow rate=30 mL/min). The pure fractions were combined, concentrated and dried in vacuo to afford the title compound (130 mg, 0.245 mmol, 57% yield) as oily liquid. MS (ESI) 531 (M+H).

Step C. Example 531. Preparation of N-((4-(5-(tert-butyl)-1,2,4-oxadiazol-3-yl) bicyclo[2.2.2]octan-1-yl)methyl)-N-(4-(2-ethoxypyrimidin-5-yl)pyridin-2-yl)-3-fluorobicyclo[1.1.1]pentane-1-carboxamide The title compound was prepared according to the method described for the synthesis of Example 149 by substituting Intermediate 531B and (2-ethoxypyrimidin-5-yl)boronic acid where appropriate. (4.8 mg, 8.35 μmol, 15% yield). $^1$H NMR (400 MHz, DMSO-$d_6$) δ 9.19 (s, 2H), 8.63 (d, J=5.1 Hz, 1H), 7.99 (s, 1H), 7.87 (dd, J=5.3, 1.6 Hz, 1H), 4.45 (q, J=7.1 Hz, 2H), 3.71 (s, 2H), 1.91 (d, J=2.4 Hz, 6H), 1.81-1.59 (m, 6H), 1.58-1.29 (m, 16H), 1.24 (s, 2H). FXR $EC_{50}$ (nM)=159. MS (ESI) 575 (M+H).

The following compounds were prepared according to the method described for the synthesis of Example 149 by substituting Intermediate 531B and the corresponding aryl/hetero aryl boronic acids/esters.

| Ex. No. | Structure | MS (ESI) (M + H) | FXR $EC_{50}$ (nM) |
|---|---|---|---|
| 532 | 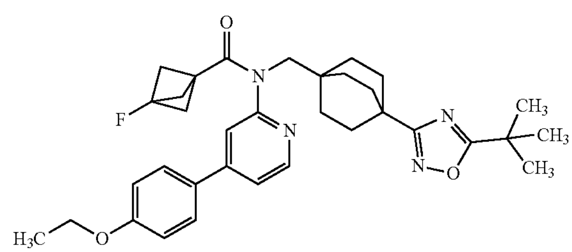 [SMILES: CCOc1ccc(-c2ccnc(N(CC34CCC(c5noc(C(C)(C)C)n5)(CC3)CC4)C(=O)C34CC(F)(C3)C4)c2)cc1] | 573 | 86 |
| 533 | 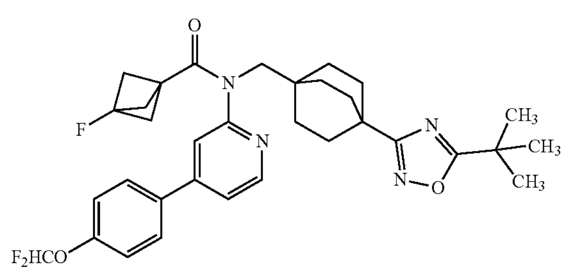 [SMILES: CC(C)(C)c1nc(C23CCC(CN(C(=O)C45CC(F)(C4)C5)c4cc(-c5ccc(OC(F)F)cc5)ccn4)(CC2)CC3)no1] | 595 | 26 |
| 534 | 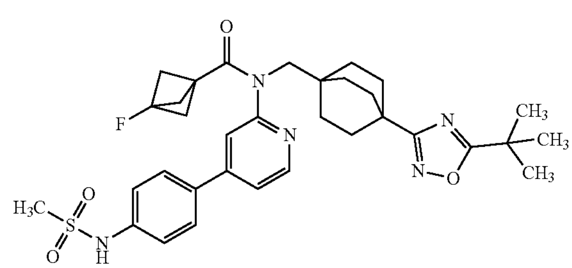 [SMILES: CC(C)(C)c1nc(C23CCC(CN(C(=O)C45CC(F)(C4)C5)c4cc(-c5ccc(NS(C)(=O)=O)cc5)ccn4)(CC2)CC3)no1] | 622 | 77 |

-continued

| Ex. No. | Structure | MS (ESI) (M + H) | FXR EC$_{50}$ (nM) |
|---|---|---|---|
| 535 | 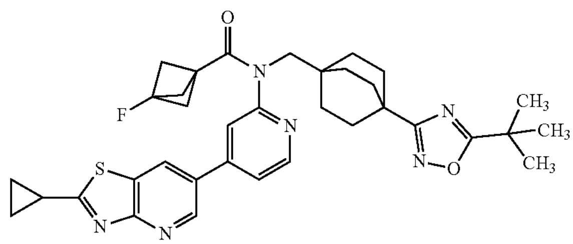 [SMILES: CC(C)(C)c1nc(C23CCC(CN(C(=O)C45CC(F)(C4)C5)c4cc(-c5cnc6nc(C7CC7)sc6c5)ccn4)(CC2)CC3)no1] | 627 | 202 |
| 536 | 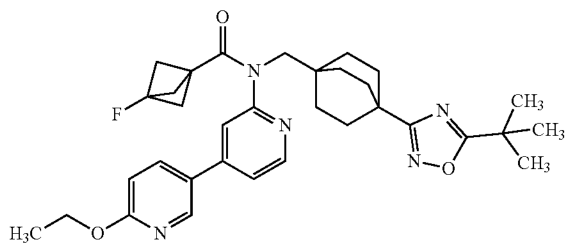 [SMILES: CCOc1ccc(-c2ccnc(N(CC34CCC(c5noc(C(C)(C)C)n5)(CC3)CC4)C(=O)C34CC(F)(C3)C4)c2)cn1] | 574 | 29 |
| 537 | 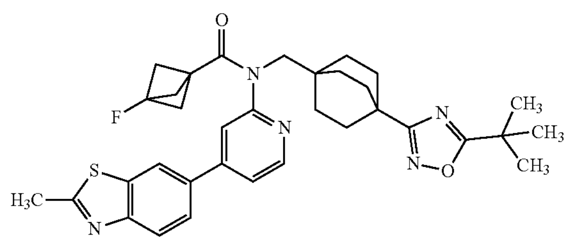 [SMILES: Cc1nc2ccc(-c3ccnc(N(CC45CCC(c6noc(C(C)(C)C)n6)(CC4)CC5)C(=O)C45CC(F)(C4)C5)c3)cc2s1] | 600 | 67 |
| 538 | 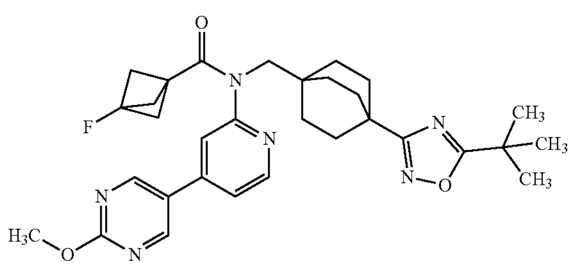 [SMILES: COc1ncc(-c2ccnc(N(CC34CCC(c5noc(C(C)(C)C)n5)(CC3)CC4)C(=O)C34CC(F)(C3)C4)c2)cn1] | 561 | 121 |
| 539 | 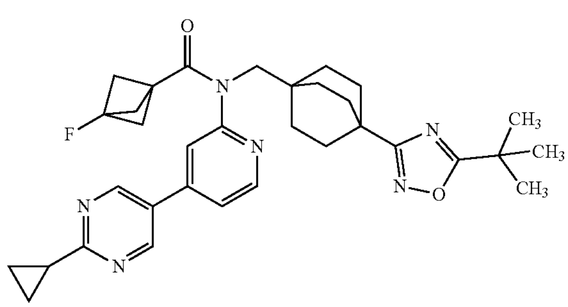 [SMILES: CC(C)(C)c1nc(C23CCC(CN(C(=O)C45CC(F)(C4)C5)c4cc(-c5cnc(C6CC6)nc5)ccn4)(CC2)CC3)no1] | 571 | 119 |

| Ex. No. | Structure | MS (ESI) (M + H) | FXR EC$_{50}$ (nM) |
|---|---|---|---|
| 540 | 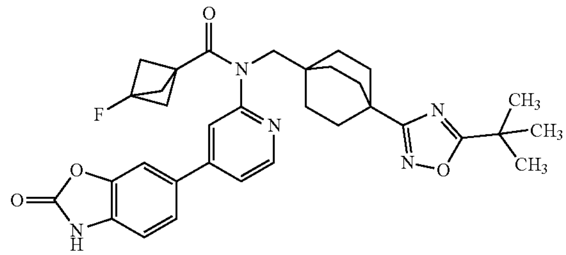 [SMILES: CC(C)(C)c1nc(C23CCC(CN(C(=O)C45CC(F)(C4)C5)c4cc(-c5ccc6[nH]c(=O)oc6c5)ccn4)(CC2)CC3)no1] | 586 | 71 |

532 ¹H NMR (400 MHz, DMSO-d₆) δ 8.54 (d, J = 5.1 Hz, 1H), 7.96-7.85 (m, 2H), 7.82 (s, 1H), 7.73 (dd, J = 5.3, 1.6 Hz, 1H), 7.15-7.01 (m, J = 9.0 Hz, 2H), 4.12 (q, J = 7.0 Hz, 2H), 3.70 (s, 2H), 1.90 (d, J = 2.4 Hz, 6H), 1.79-1.54 (m, 6H), 1.52-1.28 (m, 18H)

533 ¹H NMR (400 MHz, DMSO-d₆) δ 8.60 (d, J = 5.4 Hz, 1H), 8.09-7.94 (m, 2H), 7.89 (s, 1H), 7.79 (dd, J = 5.3, 1.6 Hz, 1H), 7.45-7.26 (m, 3H), 3.71 (s, 2H), 1.90 (d, J = 2.4 Hz, 6H), 1.80-1.58 (m, 6H), 1.51-1.36 (m, 6H), 1.36-1.26 (m, 9H)

534 ¹H NMR (400 MHz, DMSO-d₆) δ 10.06 (s, 1H), 8.57 (d, J = 5.4 Hz, 1H), 8.00-7.86 (m, J = 8.6 Hz, 2H), 7.83 (s, 1H), 7.75 (dd, J = 5.3, 1.6 Hz, 1H), 7.43-7.29 (m, J = 8.8 Hz, 2H), 3.70 (s, 2H), 3.07 (s, 3H), 1.90 (d, J = 2.4 Hz, 6H), 1.80-1.58 (m, 6H), 1.49-1.35 (m, 6H), 1.35-1.25 (m, 9H)

535 ¹H NMR (400 MHz, DMSO-d₆) δ 9.15 (d, J = 2.2 Hz, 1H), 9.07 (d, J = 2.4 Hz, 1H), 8.66 (d, J = 5.4 Hz, 1H), 8.02 (d, J = 1.2 Hz, 1H), 7.92 (dd, J = 5.3, 1.6 Hz, 1H), 3.73 (s, 2H), 2.69-2.63 (m, 1H), 1.92 (d, J = 2.4 Hz, 6H), 1.79-1.62 (m, 6H), 1.48-1.38 (m, 6H), 1.38-1.30 (m, 10H), 1.30-1.19 (m, 3H)

536 ¹H NMR (400 MHz, DMSO-d₆) δ 8.76 (d, J = 2.2 Hz, 1H), 8.58 (d, J = 5.4 Hz, 1H), 8.27 (dd, J = 8.7, 2.6 Hz, 1H), 7.90 (s, 1H), 7.80 (dd, J = 5.3, 1.6 Hz, 1H), 6.97 (d, J = 8.8 Hz, 1H), 4.39 (q, J = 7.1 Hz, 2H), 3.70 (s, 2H), 1.90 (d, J = 2.7 Hz, 6H), 1.81-1.57 (m, 6H), 1.49 (s, 1H), 1.45-1.28 (m, 17H)

537 ¹H NMR (400 MHz, DMSO-d₆) δ 8.67 (d, J = 1.2 Hz, 1H), 8.62 (d, J = 5.4 Hz, 1H), 8.11-7.98 (m, 2H), 7.96 (d, J = 1.0 Hz, 1H), 7.86 (dd, J = 5.3, 1.6 Hz, 1H), 3.73 (s, 2H), 2.86 (s, 3H), 1.92 (d, J = 2.4 Hz, 6H), 1.82-1.59 (m, 6H), 1.50-1.35 (m, 6H), 1.33 (s, 9H)

538 ¹H NMR (400 MHz, DMSO-d₆) δ 9.20 (s, 2H), 8.63 (d, J = 5.4 Hz, 1H), 7.99 (s, 1H), 7.88 (dd, J = 5.4, 1.5 Hz, 1H), 4.01 (s, 3H), 3.71 (s, 2H), 1.91 (d, J = 2.7 Hz, 6H), 1.78-1.59 (m, 6H), 1.49-1.35 (m, 6H), 1.33 (s, 9H)

539 ¹H NMR (400 MHz, DMSO-d₆) δ 9.18 (s, 2H), 8.65 (d, J = 5.4 Hz, 1H), 8.00 (d, J = 1.0 Hz, 1H), 7.89 (dd, J = 5.3, 1.6 Hz, 1H), 3.71 (s, 2H), 2.36-2.25 (m, 1H), 1.90 (d, J = 2.4 Hz, 6H), 1.81-1.56 (m, 6H), 1.53-1.28 (m, 15H), 1.17-1.01 (m, 4H)

540 ¹H NMR (400 MHz, DMSO-d₆) δ 11.89 (s, 1H), 8.57 (d, J = 5.4 Hz, 1H), 7.96 (d, J = 1.5 Hz, 1H), 7.88 (d, J = 1.2 Hz, 1H), 7.83-7.70 (m, 2H), 7.24 (d, J = 8.1 Hz, 1H), 3.71 (s, 2H), 1.96-1.82 (m, 6H), 1.81-1.59 (m, 6H), 1.52-1.34 (m, 6H), 1.33 (s, 7H), 1.30-1.19 (m, 2H)

Example 541

N-((4-(5-(tert-butyl)-1,2,4-oxadiazol-3-yl)bicyclo[2.2.2]octan-1-yl)methyl)-N-(4-(5-(difluoromethoxy)pyrimidin-2-yl)pyridin-2-yl)-3-fluorobicyclo[1.1.1]pentane-1-carboxamide

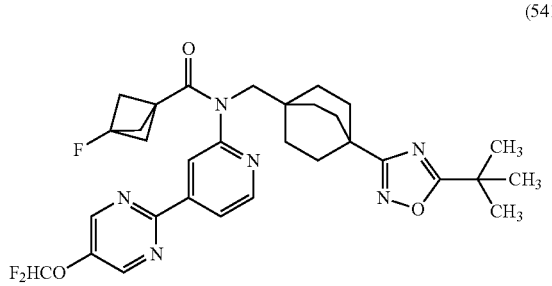

(541)

Step A. Intermediate 541A. Preparation of N-((4-(5-(tert-butyl)-1,2,4-oxadiazol-3-yl) bicyclo[2.2.2]octan-1-yl)methyl)-N-(4-(5,5-dimethyl-1,3,2-dioxaborinan-2-yl)pyridin-2-yl)-3-fluorobicyclo[1.1.1]pentane-1-carboxamide

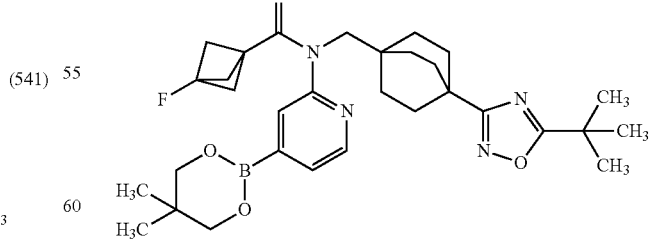

The title compound was prepared according to the method described for the synthesis of Intermediate 149c by substituting Intermediate 531B where appropriate. MS (ESI) 497 (M+H) (boronic acid mass).

Step B. Example 541. Preparation of N-((4-(5-(tert-butyl)-1,2,4-oxadiazol-3-yl) bicyclo[2.2.2]octan-1-yl)methyl)-N-(4-(5-(difluoromethoxy)pyrimidin-2-yl)pyridin-2-yl)-3-fluorobicyclo[1.1.1]pentane-1-carboxamide The title compound was prepared according to the method described for the synthesis of Example 149 by substituting Intermediate 541A and 2-chloro-5-(difluoromethoxy)pyrimidine where appropriate. (3.7 mg, 6.20 µmol, 12% yield). $^1$H NMR (400 MHz, DMSO-d$_6$) δ 9.01 (s, 2H), 8.75 (d, J=5.20 Hz, 1H), 8.25 (d, J=6.80 Hz, 1H), 8.23 (d, J=12.40 Hz, 1H), 7.49 (s, 1H), 3.73 (s, 2H), 1.93 (s, 6H), 1.73-1.69 (m, 6H), 1.41-1.39 (m, 6H), 1.37 (s, 9H). FXR EC$_{50}$ (nM)=18. MS (ESI) 597 (M+H).

The following compounds were prepared according to the method described for the synthesis of Example 149 by substituting Intermediate 541A and the corresponding aryl/hetero aryl halides.

| Ex. No. | Structure | MS (ESI) (M + H) | FXR EC$_{50}$ (nM) |
|---|---|---|---|
| 542 | | 575 | 22 |
| 543 | | 559 | 14 |
| 544 | | 596 | 20 |

| | |
|---|---|
| 542 | $^1$H NMR (400 MHz, DMSO-d$_6$) δ 8.76 (s, 2H), 8.70 (d, J = 5.1 Hz, 1H), 8.20 (dd, J = 5.1, 1.5 Hz, 1H), 8.15 (s, 1H), 4.32 (q, J = 6.8 Hz, 2H), 3.72 (s, 2H), 2.00-1.86 (m, 6H), 1.79-1.64 (m, 6H), 1.48-1.34 (m, 9H), 1.32 (s, 9H) |
| 543 | $^1$H NMR (400 MHz, DMSO-d$_6$) δ 8.93 (s, 2H), 8.73 (dd, J = 5.1, 0.5 Hz, 1H), 8.26 (dd, J = 5.1, 1.5 Hz, 1H), 8.22 (dd, J = 1.5, 0.7 Hz, 1H), 3.73 (s, 2H), 2.73 (q, J = 7.6 Hz, 2H), 1.93 (d, J = 2.4 Hz, 6H), 1.82-1.56 (m, 6H), 1.53-1.36 (m, 6H), 1.35-1.18 (m, 12H) |
| 544 | $^1$H NMR (400 MHz, DMSO-d$_6$) δ 8.75-8.60 (m, 2H), 8.35 (d, J = 8.8 Hz, 1H), 8.13 (s, 1H), 8.09 (dd, J = 5.1, 1.5 Hz, 1H), 7.88 (dd, J = 8.8, 2.9 Hz, 1H), 7.44 (s, 1H), 3.72 (s, 2H), 1.92 (d, J = 2.4 Hz, 6H), 1.80-1.56 (m, 6H), 1.49-1.34 (m, 6H), 1.34-1.28 (m, 9H) |

Example 545

N-((4-(3-cyclopropyl-1-methyl-1H-pyrazol-5-yl)bicyclo[2.2.2]octan-1-yl)methyl)-N-(4-(4-(difluoromethoxy)phenyl)pyridin-2-yl)-3-fluorobicyclo[1.1.1]pentane-1-carboxamide (545)

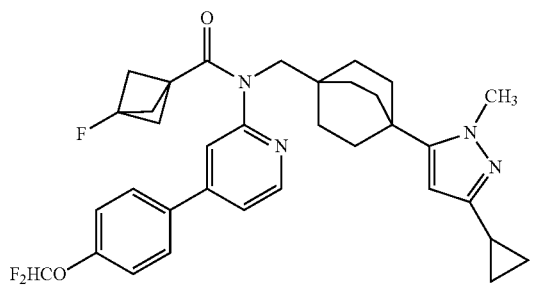

Step A. Intermediate 545A. Preparation of 4-bromo-N-((4-(3-cyclopropyl-1-methyl-1H-pyrazol-5-yl)bicyclo[2.2.2]octan-1-yl)methyl)pyridin-2-amine

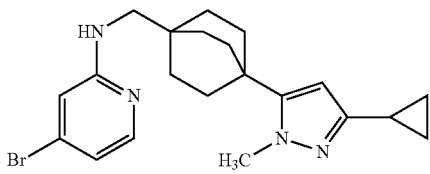 [SMILES: Cn1nc(C2CC2)cc1C12CCC(CNc3cc(Br)ccn3)(CC1)CC2]

The title compound was prepared according to the method described for the synthesis of Intermediate 1I by substituting 4-bromopyridin-2-amine and Intermediate 126B where appropriate. (320 mg, 0.770 mmol, 66% yield) as gummy liquid. MS (ESI) 415 (M+H).

Step B. Intermediate 545B. Preparation of N-(4-bromopyridin-2-yl)-N-((4-(3-cyclopropyl-1-methyl-1H-pyrazol-5-yl)bicyclo[2.2.2]octan-1-yl)methyl)-3-fluorobicyclo[1.1.1]pentane-1-carboxamide

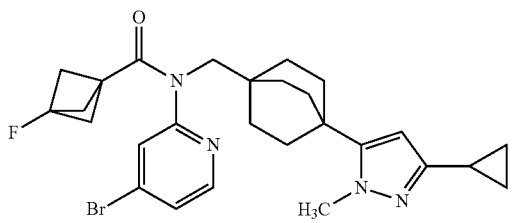 [SMILES: Cn1nc(C2CC2)cc1C12CCC(CN(C(=O)C34CC(F)(C3)C4)c3cc(Br)ccn3)(CC1)CC2]

The title compound was prepared according to the method described for the synthesis of Intermediate 531B by substituting Intermediate 545A and the corresponding acid where appropriate. (200 mg, 0.379 mmol, 52% yield) as colorless liquid. MS (ESI) 527 (M+H).

Step C. Example 545. Preparation of N-((4-(3-cyclopropyl-1-methyl-1H-pyrazol-5-yl) bicyclo[2.2.2]octan-1-yl)methyl)-N-(4-(4-(difluoromethoxy)phenyl)pyridin-2-yl)-3-fluorobicyclo[1.1.1]pentane-1-carboxamide The title compound was prepared according to the method described for the synthesis of Example 149 by substituting Intermediate 545B and 2-(4-(difluoromethoxy)phenyl)-4,4,5,5-tetramethyl-1,3,2-dioxaborolane where appropriate. (12 mg, 0.020 mmol, 43% yield). $^1$H NMR (400 MHz, DMSO-$d_6$) δ 8.60 (d, J=5.4 Hz, 1H), 8.10-7.92 (m, 2H), 7.91-7.83 (m, 1H), 7.78 (dd, J=5.4, 1.7 Hz, 1H), 7.45-7.26 (m, 3H), 5.62 (s, 1H), 3.80-3.63 (m, 5H), 1.91 (d, J=2.4 Hz, 6H), 1.78-1.55 (m, 6H), 1.49-1.26 (m, 6H), 0.80-0.68 (m, 2H), 0.58-0.45 (m, 2H) One proton is buried under moisture approximately at 2.5 ppm. FXR EC$_{50}$ (nM)=115. MS (ESI) 591 (M+H).

The following compounds were prepared according to the method described for the synthesis of Example 149 by substituting Intermediate 545B and the corresponding aryl/hetero aryl boronic acids/esters.

| Ex. No. | Structure | MS (ESI) (M + H) | FXR EC$_{50}$ (nM) |
|---|---|---|---|
| 546 | 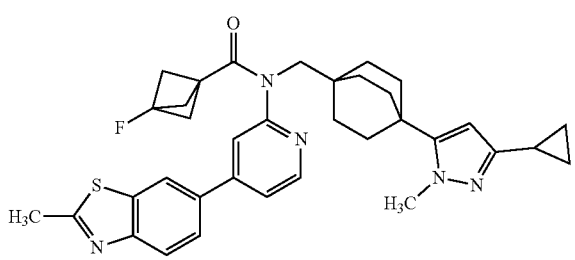 [SMILES: Cc1nc2ccc(-c3ccnc(N(CC45CCC(c6cc(C7CC7)nn6C)(CC4)CC5)C(=O)C45CC(F)(C4)C5)c3)cc2s1] | 596 | 48 |

| Ex. No. | Structure | MS (ESI) (M + H) | FXR EC$_{50}$ (nM) |
|---|---|---|---|
| 547 | 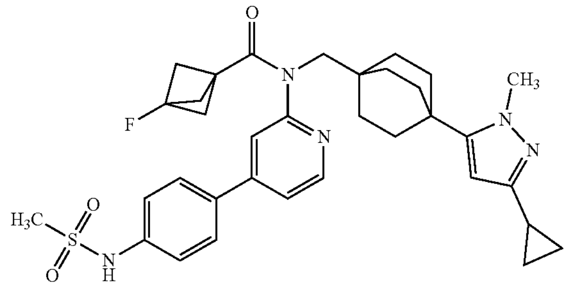 [SMILES: Cn1nc(C2CC2)cc1C12CCC(CN(C(=O)C34CC(F)(C3)C4)c3cc(-c4ccc(NS(C)(=O)=O)cc4)ccn3)(CC1)CC2] | 618 | 251 |

546 $^1$H NMR (400 MHz, DMSO-d$_6$) δ 8.66 (d, J = 1.5 Hz, 1H), 8.62 (d, J = 5.4 Hz, 1H), 8.09-8.03 (m, 1H), 8.03-7.98 (m, 1H), 7.95 (s, 1H), 7.86 (dd, J = 5.3, 1.6 Hz, 1H), 5.62 (s, 1H), 3.71 (s, 5H), 2.86 (s, 3H), 1.92 (d, J = 2.4 Hz, 6H), 1.79-1.61 (m, 6H), 1.51-1.29 (m, 6H), 0.80-0.70 (m, 2H), 0.58-0.46 (m, 2H) (One proton is buried under moisture peak).

547 $^1$H NMR (400 MHz, DMSO-d$_6$) δ 10.06 (s, 1H), 8.57 (d, J = 5.4 Hz, 1H), 7.92 (d, J = 8.8 Hz, 2H), 7.83 (s, 1H), 7.75 (dd, J = 5.4, 1.7 Hz, 1H), 7.36 (d, J = 8.8 Hz, 2H), 5.62 (s, 1H), 3.77-3.67 (m, 5H), 3.07 (s, 3H), 1.91 (d, J = 2.7 Hz, 6H), 1.69 (dd, J = 9.3, 4.4 Hz, 6H), 1.54-1.26 (m, 6H), 0.81-0.68 (m, 2H), 0.60-0.47 (m, 2H). (One proton is buried under moisture peak).

Example 548

N-((4-(3-cyclopropyl-1,2,4-oxadiazol-5-yl)bicyclo[2.2.2]octan-1-yl)methyl)-N-(4-(2-ethoxypyrimidin-5-yl)pyridin-2-yl)-3-fluorobicyclo[1.1.1]pentane-1-carboxamide (548)

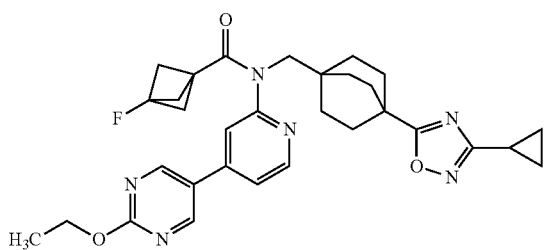

Step A. Intermediate 548A. Preparation of 4-bromo-N-((4-(3-cyclopropyl-1,2,4-oxadiazol-5-yl)bicyclo[2.2.2]octan-1-yl)methyl)pyridin-2-amine

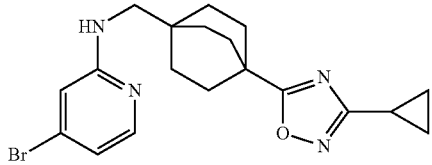

The title compound was prepared according to the method described for the synthesis of Intermediate 1I by substituting 4-bromopyridin-2-amine and Intermediate 4C where appropriate. (400 mg, 0.992 mmol, 49% yield) as brown solid. MS (ESI) 404.0 (M+H). $^1$HNMR (400 MHz, DMSO-d$_6$) δ 7.81 (d, J=5.5 Hz, 1H), 6.76 (d, J=1.5 Hz, 1H), 6.67 (t, J=6.3 Hz, 1H), 6.61 (dd, J=5.5, 1.5 Hz, 1H), 3.10 (dd, J=16.8, 5.8 Hz, 2H), 2.11-2.02 (m, 1H), 1.93-1.75 (m, 6H), 1.54-1.40 (m, 6H), 1.08-0.99 (m, 2H), 0.89-0.82 (m, 2H).

Step B. Intermediate 548B. Preparation of N-(4-bromopyridin-2-yl)-N-((4-(3-cyclopropyl-1,2,4-oxadiazol-5-yl)bicyclo[2.2.2]octan-1-yl)methyl)-3-fluorobicyclo[1.1.1]pentane-1-carboxamide

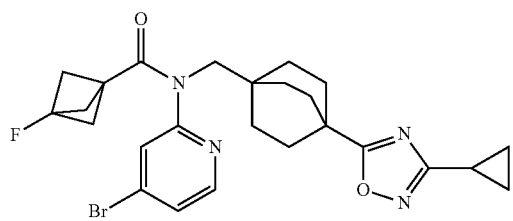 [SMILES: O=C(N(CC12CCC(c3nc(C4CC4)no3)(CC1)CC2)c1cc(Br)ccn1)C12CC(F)(C1)C2]

To a stirred solution of 3-fluorobicyclo[1.1.1]pentane-1-carboxylic acid (206 mg, 1.587 mmol) in DCM (6 mL) was added Intermediate 548A (320 mg, 0.793 mmol) followed by 4-methylmorpholine (0.446 mL, 3.97 mmol). The reaction mixture was cooled to 0° C. POCl$_3$ (0.185 mL, 1.984 mmol) was added to the reaction mass. The reaction mixture was allowed to warm to room temperature and stirred for overnight. The reaction mixture was diluted with DCM (30 mL), washed with aqueous 10% citric acid solution (25 mL), aqueous 10% sodium bicarbonate solution (25 mL) and brine solution (20 mL). The organic layer was dried over anhydrous sodium sulphate and concentrated under reduced pressure. The crude material was purified by flash chromatography (12 g silica gel cartridge; A=Hex, B=EtOAc; 30 min grad.; 0% B to 20% B; flow rate=30 mL/min). The pure fractions were combined, concentrated and dried in vacuo to afford the title compound (50 mg, 0.097 mmol, 12% yield) as brown gummy mass. MS (ESI) 515 (M+H).

Step C. Example 548. Preparation of N-((4-(3-cyclopropyl-1,2,4-oxadiazol-5-yl) bicyclo[2.2.2]octan-1-yl)methyl)-N-(4-(2-ethoxypyrimidin-5-yl)pyridin-2-yl)-3-fluorobicyclo[1.1.1]pentane-1-carboxamide The title compound was prepared according to the method described for the synthesis of Example 149 by substituting Intermediate 548B and (2-ethoxypyrimidin-5-yl)boronic acid where appropriate. (3.5 mg, 6.14 μmol, 16% yield). $^1$H NMR (400 MHz, DMSO-$d_6$) δ 9.18 (s, 2H), 8.62 (d, J=5.4 Hz, 1H), 7.98 (s, 1H), 7.87 (dd, J=5.4, 1.5 Hz, 1H), 4.45 (q, J=7.1 Hz, 2H), 3.71 (s, 2H), 2.09-2.00 (m, 1H), 1.90 (d, J=2.7 Hz, 6H), 1.82-1.63 (m, 6H), 1.49-1.29 (m, 9H), 1.06-0.96 (m, 2H), 0.87-0.77 (m, 2H). FXR $EC_{50}$ (nM)=111. MS (ESI) 559 (M+H).

Example 549

N-((4-(3-cyclopropyl-1,2,4-oxadiazol-5-yl)bicyclo[2.2.2]octan-1-yl)methyl)-3-fluoro-N-(4-(2-methylbenzo[d]thiazol-6-yl)pyridin-2-yl)bicyclo[1.1.1]pentane-1-carboxamide (549)

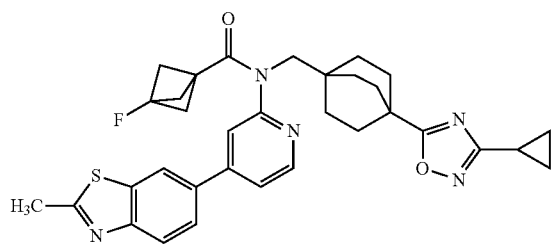

Step A. Intermediate 549A. Preparation of N-((4-(3-cyclopropyl-1,2,4-oxadiazol-5-yl) bicyclo[2.2.2]octan-1-yl)methyl)-4-(2-methylbenzo[d]thiazol-6-yl)pyridin-2-amine

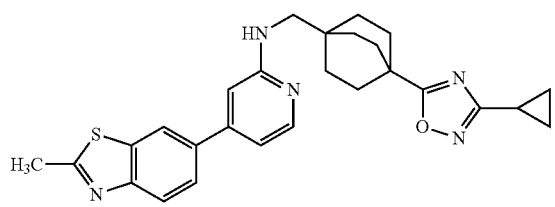 [SMILES: Cc1nc2ccc(-c3ccnc(NCC45CCC(c6nc(C7CC7)no6)(CC4)CC5)c3)cc2o1]

The title compound was prepared according to the method described for the synthesis of Example 149 by substituting Intermediate 548A and 6-(5,5-dimethyl-1,3,2-dioxaborinan-2-yl)-2-methylbenzo[d]thiazole where appropriate. (90 mg, 0.191 mmol, 77% yield) as brown solid. MS (ESI) 472 (M+H).

Step B. Example 549. Preparation of N-((4-(3-cyclopropyl-1,2,4-oxadiazol-5-yl) bicyclo[2.2.2]octan-1-yl)methyl)-3-fluoro-N-(4-(2-methylbenzo[d]thiazol-6-yl)pyridin-2-yl)bicyclo[1.1.1]pentane-1-carboxamide The title compound was prepared according to the method described for the synthesis of Example 3 by substituting Intermediate 549A and the corresponding acid where appropriate. (0.9 mg, 1.459 μmol, 5% yield). $^1$H NMR (400 MHz, DMSO-$d_6$) δ 8.67 (s, 1H), 8.61 (d, J=5.4 Hz, 1H), 8.11-7.98 (m, 2H), 7.95 (s, 1H), 7.86 (d, J=5.1 Hz, 1H), 3.72 (s, 2H), 2.85 (s, 3H), 2.10-1.99 (m, 1H), 1.91 (d, J=2.2 Hz, 6H), 1.83-1.66 (m, 6H), 1.58-1.28 (m, 6H), 1.06-0.95 (m, 2H), 0.89-0.74 (m, 2H). FXR $EC_{50}$ (nM)=36. MS (ESI) 584 (M+H).

Example 550

N-((4-(3-cyclopropyl-1,2,4-oxadiazol-5-yl)bicyclo[2.2.2]octan-1-yl)methyl)-3-fluoro-N-(4-(2-methylbenzo[d]oxazol-6-yl)pyridin-2-yl)bicyclo[1.1.1]pentane-1-carboxamide (550)

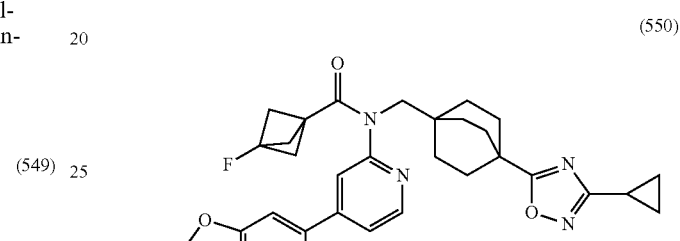

Step A. Intermediate 550A. Preparation of N-((4-(3-cyclopropyl-1,2,4-oxadiazol-5-yl) bicyclo[2.2.2]octan-1-yl)methyl)-4-(2-methylbenzo[d]oxazol-6-yl)pyridin-2-amine

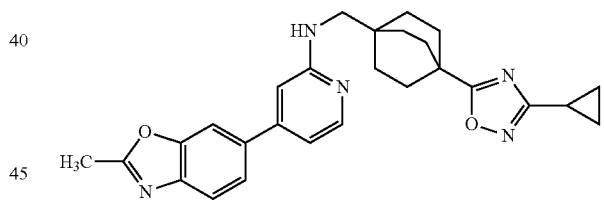

The title compound was prepared according to the method described for the synthesis of Example 149 by substituting Intermediate 548A and 6-(5,5-dimethyl-1,3,2-dioxaborinan-2-yl)-2-methylbenzo[d]oxazole where appropriate. (70 mg, 0.154 mmol, 62% yield) as brown gummy mass. MS (ESI) 456 (M+H).

Step B. Example 550. Preparation of N-((4-(3-cyclopropyl-1,2,4-oxadiazol-5-yl) bicyclo[2.2.2]octan-1-yl)methyl)-3-fluoro-N-(4-(2-methylbenzo[d]oxazol-6-yl)pyridin-2-yl)bicyclo[1.1.1]pentane-1-carboxamide The title compound was prepared according to the method described for the synthesis of Example 3 by substituting Intermediate 550A and the corresponding acid where appropriate. (1.3 mg, 2.290 μmol, 3% yield). $^1$H NMR (400 MHz, DMSO-$d_6$) δ 8.61 (d, J=5.4 Hz, 1H), 8.30 (s, 1H), 7.96 (s, 1H), 7.94-7.89 (m, 1H), 7.87 (d, J=5.4 Hz, 1H), 7.81 (d, J=8.3 Hz, 1H), 3.73 (s, 2H), 2.68 (s, 3H), 2.10-1.99 (m, 1H), 1.92 (d, J=2.4 Hz, 6H), 1.83-1.67 (m, 6H), 1.50-1.35 (m, 6H), 1.07-0.98 (m, 2H), 0.89-0.80 (m, 2H). FXR EC$_{50}$ (nM)=70. MS (ESI) 568 (M+H).

Example 551

N-((4-(3-(tert-butyl)-1,2,4-oxadiazol-5-yl)bicyclo[2.2.2]octan-1-yl)methyl)-3-fluoro-N-(4-(2-methylbenzo[d]thiazol-6-yl)pyridin-2-yl)bicyclo[1.1.1]pentane-1-carboxamide (551)

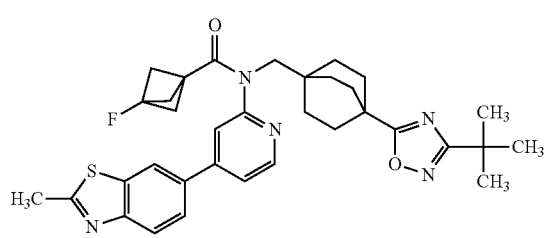

Step A. Intermediate 551A. Preparation of 4-bromo-N-((4-(3-(tert-butyl)-1,2,4-oxadiazol-5-yl)bicyclo[2.2.2]octan-1-yl)methyl)pyridin-2-amine

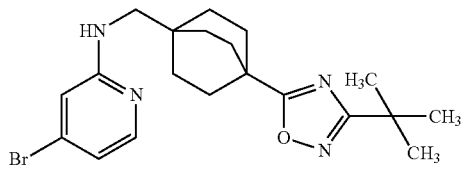 [SMILES: CC(C)(C)c1noc(C23CCC(CNc4cc(Br)ccn4)(CC2)CC3)n1]

The title compound was prepared according to the method described for the synthesis of Intermediate 1I by substituting 4-bromopyridin-2-amine and Intermediate 191C where appropriate. (700 mg, 1.669 mmol, 73% yield) as gummy liquid. MS (ESI) 420 (M+H).

Step B. Intermediate 551B. Preparation of N-(4-bromopyridin-2-yl)-N-((4-(3-(tert-butyl)-1,2,4-oxadiazol-5-yl)bicyclo[2.2.2]octan-1-yl)methyl)-3-fluorobicyclo[1.1.1]pentane-1-carboxamide

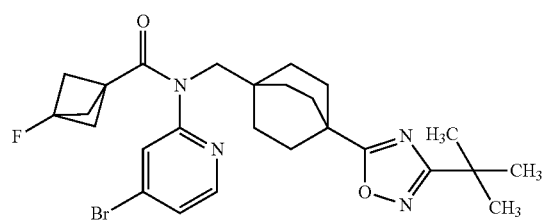 [SMILES: CC(C)(C)c1noc(C23CCC(CN(C(=O)C45CC(F)(C4)C5)c4cc(Br)ccn4)(CC2)CC3)n1]

The title compound was prepared according to the method described for the synthesis of Intermediate 531B by substituting Intermediate 551A and the corresponding acid where appropriate. (70 mg, 0.132 mmol, 34% yield) as colorless liquid. MS (ESI) 531 (M+H).

Step C. Example 551. Preparation of N-((4-(3-(tert-butyl)-1,2,4-oxadiazol-5-yl) bicyclo[2.2.2]octan-1-yl)methyl)-3-fluoro-N-(4-(2-methylbenzo[d]thiazol-6-yl)pyridin-2-yl)bicyclo[1.1.1]pentane-1-carboxamide The title compound was prepared according to the method described for the synthesis of Example 149 by substituting Intermediate 551B and 6-(5,5-dimethyl-1,3,2-dioxaborinan-2-yl)-2-methylbenzo[d]thiazole where appropriate. (13 mg, 0.021 mmol, 38% yield). $^1$H NMR (400 MHz, DMSO-d$_6$) δ 8.68 (d, J=1.2 Hz, 1H), 8.62 (d, J=5.1 Hz, 1H), 8.11-8.00 (m, 2H), 7.97 (d, J=1.0 Hz, 1H), 7.87 (dd, J=5.4, 1.7 Hz, 1H), 3.74 (s, 2H), 2.86 (s, 3H), 1.92 (d, J=2.4 Hz, 6H), 1.86-1.66 (m, 6H), 1.56-1.36 (m, 6H), 1.25 (s, 9H). FXR EC$_{50}$ (nM)=55. MS (ESI) 600 (M+H).

Example 552

N-(3-(2-ethoxypyrimidin-5-yl)phenyl)-3-fluoro-N-((4-(5-methoxypyrimidin-2-yl) bicyclo[2.2.2]octan-1-yl)methyl)bicyclo[1.1.1]pentane-1-carboxamide (552)

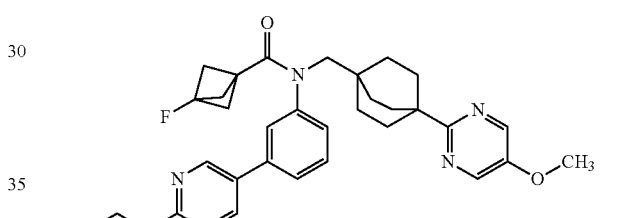

Step A. Intermediate 552A. Preparation of methyl 4-(5-bromopyrimidin-2-yl)bicyclo[2.2.2]octane-1-carboxylate

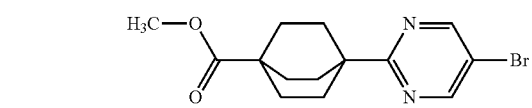

To a stirred solution of 5-bromopyrimidine (1 g, 6.29 mmol) in DCM (55 mL) and water (55 mL) were added 4-(methoxycarbonyl)bicyclo[2.2.2]octane-1-carboxylic acid (1.07 g, 5.03 mmol), potassium persulfate (1.70 g, 6.29 mmol) and silver nitrate (0.21 g, 1.258 mmol). The reaction was stirred at room temperature for 12 h. The reaction mixture was filtered through Celite. The organic layer was separated, washed with water (30 mL), dried over sodium sulphate and concentrated under reduced pressure. The crude material was purified by flash chromatography (24 g silica gel cartridge; A=Hex, B=EtOAc; 30 min grad.; 0% B to 10% B; flow rate=30 mL/min). The pure fractions were combined, concentrated and dried in vacuo to afford the title (250 mg, 0.769 mmol, 12% yield) and methyl 4-(5-bromopyrimidin-4-yl)bicyclo[2.2.2]octane-1-carboxylate (750 mg, 2.306 mmol, 37% yield). MS (ESI) 325 (M+H).

Step B. Intermediate 552B. Preparation of (4-(5-bromopyrimidin-2-yl) bicyclo[2.2.2]octan-1-yl)methanol

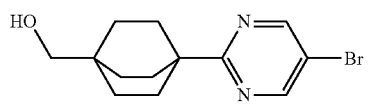 [SMILES: OCC12CCC(c3ncc(Br)cn3)(CC1)CC2]

The title compound was prepared according to the method described for the synthesis of Intermediate 1G by substituting Intermediate 552A where appropriate. (150 mg, 0.505 mmol, 82% yield). $^1$H NMR (400 MHz, DMSO-$d_6$) δ 8.90 (s, 2H), 4.35 (t, J=5.5 Hz, 1H), 3.09 (d, J=5.0 Hz, 2H), 1.91-1.82 (m, 6H), 1.50-1.40 (m, 6H).

Step C. Intermediate 552C. Preparation of 4-(5-bromopyrimidin-2-yl)bicyclo[2.2.2]octane-1-carbaldehyde

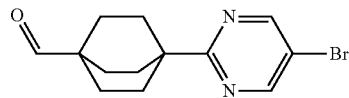

The title compound was prepared according to the method described for the synthesis of Intermediate 3C by substituting Intermediate 552B where appropriate. (130 mg, 0.440 mmol, 87% yield). $^1$H-NMR (400 MHz, DMSO-$d_6$) δ 9.47 (s, 1H), 8.93 (s, 2H), 1.90-1.95 (m, 6H), 1.66-1.71 (m, 6H).

Step D. Intermediate 552D. Preparation of N-((4-(5-bromopyrimidin-2-yl) bicyclo[2.2.2]octan-1-yl)methyl)-3-(2-ethoxypyrimidin-5-yl)aniline

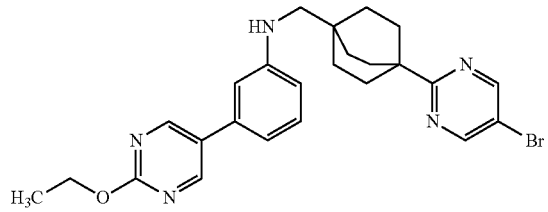 [SMILES: CCOc1ncc(-c2cccc(NCC34CCC(c5ncc(Br)cn5)(CC3)CC4)c2)cn1]

The title compound was prepared according to the method described for the synthesis of Intermediate 1I by substituting Intermediate 518A and Intermediate 552C where appropriate. (70 mg, 0.142 mmol, 40% yield). MS (ESI) 494 (M+H).

Step E. Intermediate 552E. Preparation of N-((4-(5-bromopyrimidin-2-yl) bicyclo[2.2.2]octan-1-yl)methyl)-N-(3-(2-ethoxypyrimidin-5-yl)phenyl)-3-fluorobicyclo[1.1.1]pentane-1-carboxamide

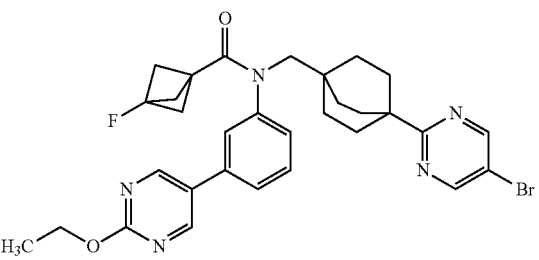 [SMILES: CCOc1ncc(-c2cccc(N(CC34CCC(c5ncc(Br)cn5)(CC3)CC4)C(=O)C34CC(F)(C3)C4)c2)cn1]

The title compound was prepared according to the method described for the synthesis of Example 3 by substituting Intermediate 552D and the corresponding acid where appropriate. (80 mg, 0.070 mmol, 33% yield). MS (ESI) 606 (M+H).

Step F. Example 552. Preparation of N-(3-(2-ethoxypyrimidin-5-yl)phenyl)-3-fluoro-N-((4-(5-methoxypyrimidin-2-yl)bicyclo[2.2.2]octan-1-yl)methyl)bicyclo[1.1.1]pentane-1-carboxamide To a stirred solution of Intermediate 552E (20 mg, 0.033 mmol) in 1,4-dioxane (3 mL) were added methanol (0.027 mL, 0.659 mmol), Cs$_2$CO$_3$ (16 mg, 0.049 mmol) and 2-di-tert-butylphosphino-2',4',6'-triisopropylbiphenyl (2.8 mg, 6.59 μmol). The reaction mixture was degassed and back-filled with argon. Pd$_2$(dba)$_3$ (3.0 mg, 3.30 μmol) was added to the reaction mixture and the reaction vial was sealed. The reaction mixture was stirred at 75° C. for 5 h. The reaction mixture was cooled to room temperature and concentrated under reduced pressure. The crude material was purified via preparative LC/MS using following conditions. (Column. Waters XBridge C18, 150 mm×19 mm, 5-μm particles; Mobile Phase A. 5.95 acetonitrile. water with 10-mM ammonium acetate; Mobile Phase B. 95.5 acetonitrile. water with 10-mM ammonium acetate; Gradient. a 0-minute hold at 25% B, 25-65% B over 25 minutes, then a 5-minute hold at 100% B; Flow Rate. 15 mL/min; Column Temperature. 25° C.). Fraction collection was triggered by signals. Fractions containing the desired product were combined and dried via centrifugal evaporation to afford the title compound (5.6 mg, 9.14 μmol, 28% yield). $^1$H NMR (400 MHz, DMSO-$d_6$) δ 9.01 (s, 2H), 8.43 (s, 2H), 7.87-7.79 (m, 2H), 7.77 (d, J=7.6 Hz, 1H), 7.57 (t, J=7.8 Hz, 1H), 4.43 (q, J=6.9 Hz, 2H), 3.85 (s, 3H), 3.67 (br. s., 1H), 3.55 (d, J=7.6 Hz, 1H), 2.00-1.71 (m, 12H), 1.59-1.40 (m, 6H), 1.38 (t, J=7.1 Hz, 3H). FXR EC$_{50}$ (nM) 359. MS (ESI) 558 (M+H).

Example 553

N-((4-(3-(tert-butyl)-1,2,4-oxadiazol-5-yl)-2-oxabicyclo[2.2.2]octan-1-yl)methyl)-N-(3-(2-ethoxypyrimidin-5-yl)phenyl)-3-fluorobicyclo[1.1.1]pentane-1-carboxamide (553)

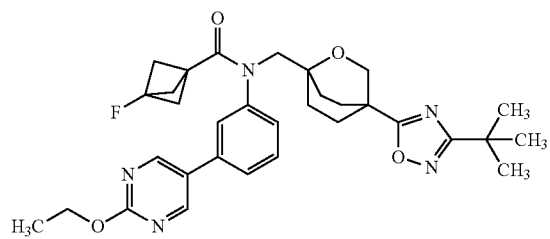

Step A. Intermediate 553A. Preparation of (1-(hydroxymethyl)-2-oxabicyclo[2.2.2]octan-4-yl)methyl 4-methylbenzenesulfonate

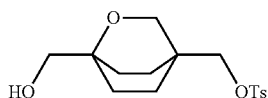

The title compound was prepared according to the method described for the synthesis of Intermediate 88A by substituting Intermediate 196F where appropriate. (900 mg, 2.76 mmol, 52% yield) as white solid. MS (ESI) 344 (M+H). NH₃ adduct

Step B. Intermediate 553B. Preparation of (1-formyl-2-oxabicyclo[2.2.2]octan-4-yl) methyl 4-methylbenzenesulfonate

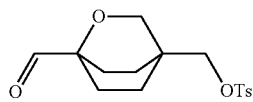

The title compound was prepared according to the method described for the synthesis of Intermediate 208B by substituting Intermediate 553A where appropriate. (430 mg, 1.326 mmol, 72% yield) as white solid. MS (ESI) 342 (M+H). NH₃ adduct

Step C. Intermediate 553C. Preparation of (1-(((3-bromophenyl)amino)methyl)-2-oxabicyclo[2.2.2]octan-4-yl)methyl 4-methylbenzenesulfonate

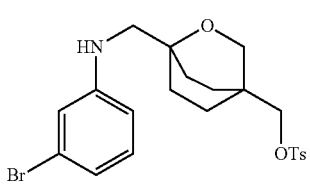 [SMILES: Cc1ccc(S(=O)(=O)OCC23CCC(CNc4cccc(Br)c4)(CC2)OC3)cc1]

The title compound was prepared according to the method described for the synthesis of Intermediate 1I by substituting 3-bromoaniline and Intermediate 553B where appropriate. (440 mg, 0.916 mmol, 79% yield) as brown gummy mass. MS (ESI) 480 (M+H).

Step D. Intermediate 553D. Preparation of (1-((N-(3-bromophenyl)-3-fluorobicyclo[1.1.1]pentane-1-carboxamido)methyl)-2-oxabicyclo[2.2.2]octan-4-yl)methyl 4-methylbenzenesulfonate

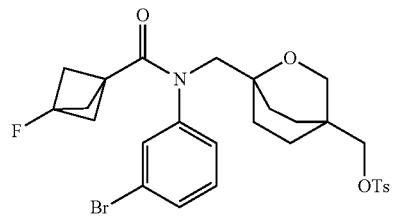 [SMILES: Cc1ccc(S(=O)(=O)OCC23CCC(CN(C(=O)C45CC(F)(C4)C5)c4cccc(Br)c4)(CC2)OC3)cc1]

The title compound was prepared according to the method described for the synthesis of Example 3 by substituting Intermediate 553C and the corresponding acid where appropriate. (330 mg, 0.557 mmol, 61% yield)) as brown gummy mass. MS (ESI) 592 (M+H).

Step E. Intermediate 553E. Preparation of (1-((N-(3-bromophenyl)-3-fluorobicyclo[1.1.1]pentane-1-carboxamido)methyl)-2-oxabicyclo[2.2.2]octan-4-yl)methyl acetate

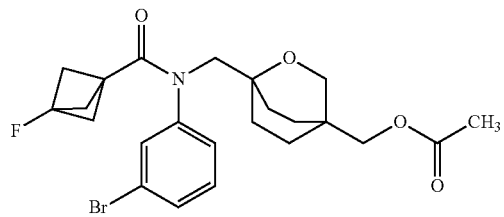 [SMILES: CC(=O)OCC12CCC(CN(C(=O)C34CC(F)(C3)C4)c3cccc(Br)c3)(CC1)OC2]

The title compound was prepared according to the method described for the synthesis of Intermediate 141C by substituting Intermediate 553D where appropriate. (230 mg, 0.479 mmol, 92% yield) as white solid. MS (ESI) 480 (M+H).

Step F. Intermediate 553F. Preparation of N-(3-bromophenyl)-3-fluoro-N-((4-(hydroxymethyl)-2-oxabicyclo[2.2.2]octan-1-yl)methyl)bicyclo[1.1.1]pentane-1-carboxamide

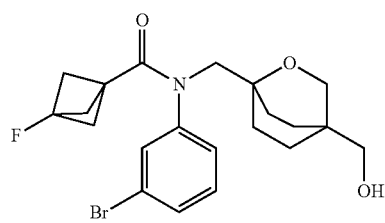 [SMILES: O=C(N(CC12CCC(CO)(CC1)CO2)c1cccc(Br)c1)C12CC(F)(C1)C2]

The title compound was prepared according to the method described for the synthesis of Intermediate 141D by substituting Intermediate 553E where appropriate. (180 mg, 0.411 mmol, 86% yield). MS (ESI) 438 (M+H).

Step G. Intermediate 553G. Preparation of 1-((N-(3-bromophenyl)-3-fluorobicyclo[1.1.1]pentane-1-carboxamido)methyl)-2-oxabicyclo[2.2.2]octane-4-carboxylic acid

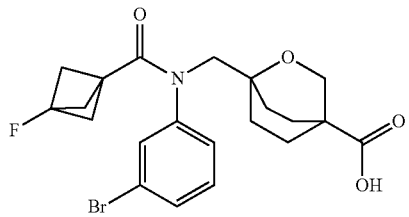 [SMILES: O=C(O)C12CCC(CN(C(=O)C34CC(F)(C3)C4)c3cccc(Br)c3)(CC1)OC2]

A stirred solution of Intermediate 553F (160 mg, 0.365 mmol) in acetone (2 mL) was cooled to 0° C. Chromium trioxide (0.36 mL, 0.730 mmol) was added to the reaction mixture. The reaction mixture was stirred at 0° C. for 15 min. The reaction was quenched with isopropanol (5 mL) and concentrated under reduced pressure. The residue was diluted with water (10 mL), extracted with ethyl acetate (2×10 mL). The organic layers were combined, dried over anhydrous sodium sulphate, concentrated and dried in vacuo to afford the title compound (160 mg, 0.354 mmol, 97% yield. MS (ESI) 452 (M+H).

Step H. Intermediate 553H. Preparation of N-(3-bromophenyl)-N-((4-(3-(tert-butyl)-1,2,4-oxadiazol-5-yl)-2-oxabicyclo[2.2.2]octan-1-yl)methyl)-3-fluorobicyclo[1.1.1]pentane-1-carboxamide

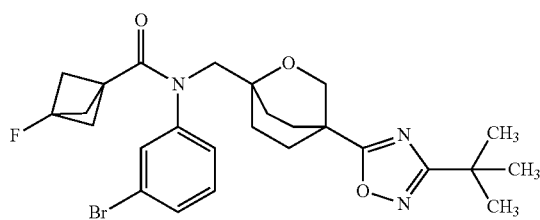 [SMILES: CC(C)(C)c1noc(C23CCC(CN(C(=O)C45CC(F)(C4)C5)c4cccc(Br)c4)(CC2)OC3)n1]

The title compound was prepared according to the method described for the synthesis of Intermediate 1A by substituting Intermediate 553G and (Z)—N'-hydroxypivalimidamide where appropriate. (130 mg, 0.244 mmol, 69% yield) as brown solid. MS (ESI) 532 (M+H).

Step I. Example 553. Preparation of N-((4-(3-(tert-butyl)-1,2,4-oxadiazol-5-yl)-2-oxabicyclo[2.2.2]octan-1-yl)methyl)-N-(3-(2-ethoxypyrimidin-5-yl)phenyl)-3-fluorobicyclo[1.1.1]pentane-1-carboxamide The title compound was prepared according to the method described for the synthesis of Example 149 by substituting Intermediate 553H and (2-ethoxypyrimidin-5-yl)boronic acid where appropriate. (10.8 mg, 0.018 mmol, 38% yield). $^1$H NMR (400 MHz, DMSO-$d_6$) δ 8.98 (s, 2H), 7.82-7.68 (m, 2H), 7.53 (t, J=8.1 Hz, 1H), 7.42-7.35 (m, 1H), 4.42 (q, J=7.0 Hz, 2H), 3.86 (s, 2H), 3.72 (s, 2H), 2.09-1.98 (m, 4H), 1.85 (s, 3H), 1.87 (s, 4H), 1.82-1.70 (m, 3H), 1.37 (t, J=7.0 Hz, 3H), 1.32-1.20 (m, 9H). FXR EC$_{50}$ (nM)=1594. MS (ESI) 576 (M+H).

Example 554

N-((4-(3-cyclopropyl-1,2,4-oxadiazol-5-yl)bicyclo[2.2.2]octan-1-yl)methyl)-3,3-difluoro-N-(3-(2-methylbenzo[d]thiazol-6-yl)phenyl)cyclobutane-1-carboxamide (554)

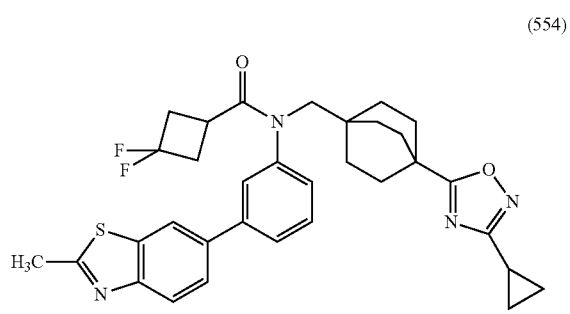 [SMILES: Cc1nc2ccc(-c3cccc(N(CC45CCC(c6nc(C7CC7)no6)(CC4)CC5)C(=O)C4CC(F)(F)C4)c3)cc2s1]

Step A. Intermediate 554A. Preparation of 3-(2-methylbenzo[d]thiazol-6-yl)aniline

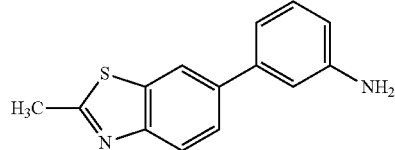 [SMILES: Cc1nc2ccc(-c3cccc(N)c3)cc2s1]

The title compound was prepared according to the method described for the synthesis of Example 149 by substituting 6-bromo-2-methylbenzo[d]thiazole and (3-aminophenyl)boronic acid where appropriate. (60 mg, 0.250 mmol, 57% yield) as white solid. $^1$H NMR (400 MHz, DMSO-$d_6$) δ 8.21 (d, J=1.5 Hz, 1H), 7.94 (d, J=8.5 Hz, 1H), 7.68-7.63 (m, 1H), 7.15-7.09 (m, 1H), 6.90 (t, J=2.0 Hz, 1H), 6.87-6.83 (m, 1H), 6.59 (ddd, J=8.0, 2.0, 1.0 Hz, 1H), 5.19 (s, 2H), 2.82 (s, 3H). MS (ESI) 241 (M+H).

Step B. Intermediate 554B. Preparation of N-((4-(3-cyclopropyl-1,2,4-oxadiazol-5-yl) bicyclo[2.2.2]octan-1-yl)methyl)-3-(2-methylbenzo[d]thiazol-6-yl)aniline

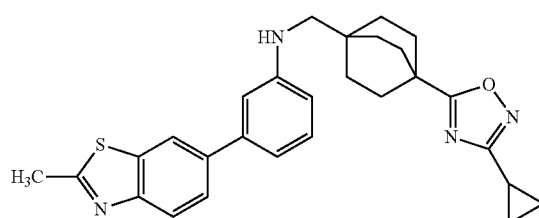

The title compound was prepared according to the method described for the synthesis of Intermediate 1I by substituting Intermediate 554A and Intermediate 4C where appropriate. (90 mg, 0.182 mmol, 87% yield) as an off-white solid. ¹H NMR (400 MHz, DMSO-d₆) δ 8.25 (d, J=1.5 Hz, 1H), 7.94 (d, J=8.5 Hz, 1H), 7.69 (dd, J=8.5, 2.0 Hz, 1H), 7.15 (t, J=7.8 Hz, 1H), 6.94 (s, 1H), 6.84 (d, J=7.5 Hz, 1H), 6.65 (d, J=8.5 Hz, 1H), 5.57 (t, J=6.0 Hz, 1H), 2.90 (d, J=6.0 Hz, 2H), 2.82 (s, 3H), 2.11-2.03 (m, 1H), 1.91-1.83 (m, 6H), 1.64-1.56 (m, 6H), 1.07-1.00 (m, 2H), 0.88-0.83 (m, 2H). MS (ESI) 471 (M+H).

Step C. Example 554. Preparation of N-((4-(3-cyclopropyl-1,2,4-oxadiazol-5-yl) bicyclo[2.2.2]octan-1-yl)methyl)-3,3-difluoro-N-(3-(2-methylbenzo[d]thiazol-6-yl) phenyl)cyclobutane-1-carboxamide The title compounds were prepared according to the method described for the synthesis of Example 3 by substituting Intermediate 554B and the corresponding acids where appropriate. (13.4 mg, 0.023 mmol, 53.6% yield). ¹H NMR (400 MHz, DMSO-d₆) δ 8.46 (d, J=1.5 Hz, 1H), 8.00 (d, J=8.6 Hz, 1H), 7.86 (dd, J=8.4, 1.8 Hz, 1H), 7.81 (s, 1H), 7.75 (d, J=8.1 Hz, 1H), 7.56 (t, J=7.7 Hz, 1H), 7.41 (d, J=8.3 Hz, 1H), 3.69 (br. s., 2H), 2.98 (d, J=5.4 Hz, 1H), 2.84 (s, 3H), 2.78 (d, J=12.0 Hz, 2H), 2.39-2.26 (m, 2H), 2.09-1.98 (m, 1H), 1.84-1.70 (m, 6H), 1.54-1.36 (m, 6H), 1.05-0.96 (m, 2H), 0.85-0.77 (m, 2H). FXR EC₅₀ (nM) 232; MS (ESI) 589 (M+H).

The following compound was prepared according to the method described for the synthesis of Example 3 by substituting Intermediate 554B and the corresponding acid where appropriate.

Example 556

3-Fluoro-N-((1-(4-methoxyphenyl)-2-oxabicyclo[2.2.2]octan-4-yl)methyl)-N-(3-(2-methylbenzo[d]thiazol-6-yl)phenyl)bicyclo[1.1.1]pentane-1-carboxamide (556)

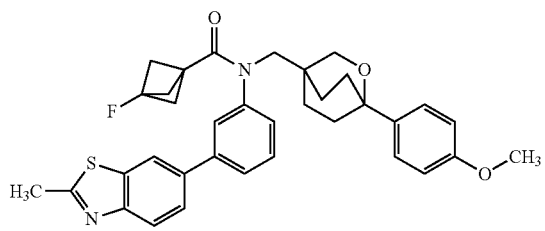

Step A. Intermediate 556A. Preparation of N-((1-(4-methoxyphenyl)-2-oxabicyclo[2.2.2]octan-4-yl)methyl)-3-(2-methylbenzo[d]thiazol-6-yl)aniline

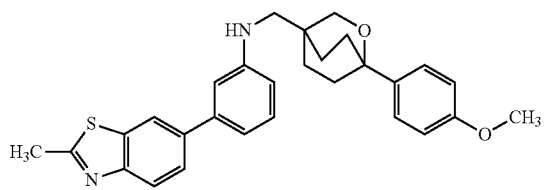

The title compound was prepared according to the method described for the synthesis of Intermediate 1I by substituting Intermediate 554A and Intermediate 128E where appropriate. (70 mg, 0.112 mmol, 69% yield) as brown gummy solid. MS (ESI) 471 (M+H). ¹H NMR (400 MHz, DMSO-d₆) δ 8.27 (d, J=1.5 Hz, 1H), 7.98-7.92 (m, 1H), 7.74-7.63 (m, 1H), 7.33-7.27 (m, 2H), 7.20-7.09 (m, 1H), 6.95 (s, 1H), 6.89-6.82 (m, 3H), 6.66 (d, J=8.5 Hz, 1H), 5.63-5.58 (m, 1H), 3.89 (s, 2H), 3.73 (s, 3H), 2.96 (d, J=6.0 Hz, 2H), 2.82

| Ex. No. | Structure | MS (ESI) (M + H) | FXR EC₅₀ (nM) |
|---|---|---|---|
| 555 | | 583 | 55 |

555 ¹H NMR (400 MHz, DMSO-d₆) δ 8.47 (d, J = 1.7 Hz, 1H), 8.01 (d, J = 8.3 Hz, 1H), 7.86 (dd, J = 8.4, 1.8 Hz, 1H), 7.81-7.71 (m, 2H), 7.57 (t, J = 7.9 Hz, 1H), 7.41 (d, J = 8.1 Hz, 1H), 3.68 (d, J = 14.7 Hz, 1H), 3.56 (d, J = 14.4 Hz, 1H), 2.84 (s, 3H), 2.07-2.00 (m, 1H), 1.98-1.69 (m, 12H), 1.56-1.36 (m, 6H), 1.06-0.94 (m, 2H), 0.90-0.77 (m, 2H).

(s, 3H), 2.42-2.41 (m, 2H), 2.09-1.99 (m, 2H), 1.83 (d, J=11.5 Hz, 2H), 1.76 (br. s., 2H).

Step B. Example 556. Preparation of 3-fluoro-N-((1-(4-methoxyphenyl)-2-oxabicyclo[2.2.2]octan-4-yl)methyl)-N-(3-(2-methylbenzo[d]thiazol-6-yl)phenyl) bicyclo[1.1.1]pentane-1-carboxamide The title compound was prepared according to the method described for the synthesis of Example 3 by substituting Intermediate 556A and the corresponding acid where appropriate. (14 mg, 0.024 mmol, 37% yield). $^1$H NMR (400 MHz, DMSO-$d_6$) δ 8.49 (d, J=1.7 Hz, 1H), 8.01 (d, J=8.6 Hz, 1H), 7.88 (dd, J=8.6, 2.0 Hz, 1H), 7.85-7.74 (m, 2H), 7.58 (t, J=7.9 Hz, 1H), 7.44 (d, J=8.3 Hz, 1H), 7.30-7.16 (m, 2H), 6.90-6.73 (m, 2H), 3.81-3.65 (m, 6H), 3.64-3.55 (m, 1H), 2.84 (s, 3H), 2.03-1.83 (m, 8H), 1.75 (d, J=11.0 Hz, 2H), 1.67 (br. s., 2H), 1.57 (br. s., 2H). FXR $EC_{50}$ (nM)= 815.84. MS (ESI) 583 (M+H).

Example 557

3,3-Difluoro-N-((1-(4-methoxyphenyl)-2-oxabicyclo[2.2.2]octan-4-yl)methyl)-N-(3-(2-methylbenzo[d]thiazol-6-yl)phenyl)cyclobutane-1-carboxamide (557)

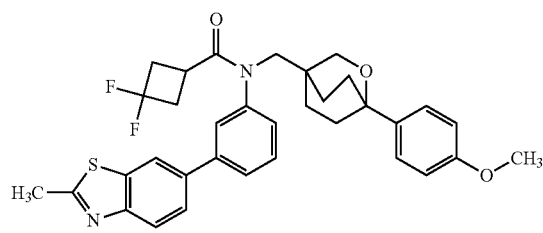

The title compound was prepared according to the method described for the synthesis of Example 3 by substituting Intermediate 556A and the corresponding acid where appropriate. (16 mg, 0.027 mmol, 42% yield). $^1$H NMR (400 MHz, DMSO-$d_6$) δ 8.48 (d, J=1.7 Hz, 1H), 8.01 (d, J=8.6 Hz, 1H), 7.87 (dd, J=8.4, 1.8 Hz, 1H), 7.84 (s, 1H), 7.77 (d, J=7.8 Hz, 1H), 7.58 (t, J=7.8 Hz, 1H), 7.44 (d, J=7.8 Hz, 1H), 7.30-7.11 (m, J=9.0 Hz, 2H), 6.89-6.71 (m, 2H), 3.70 (s, 7H), 3.01 (dd, J=11.7, 8.3 Hz, 1H), 2.84 (s, 3H), 2.77 (br. s., 1H), 2.34 (br. s., 2H), 2.01-1.89 (m, 2H), 1.76 (d, J=5.4 Hz, 2H), 1.70-1.60 (m, 2H), 1.57 (d, J=12.0 Hz, 2H). FXR $EC_{50}$ (nM)=1579. MS (ESI) 589 (M+H).

Example 558

3-Fluoro-N-((1-(2-methoxypyrimidin-5-yl)-2-oxabicyclo[2.2.2]octan-4-yl)methyl)-N-(3-(2-methylbenzo[d]thiazol-6-yl)phenyl)bicyclo[1.1.1]pentane-1-carboxamide (558)

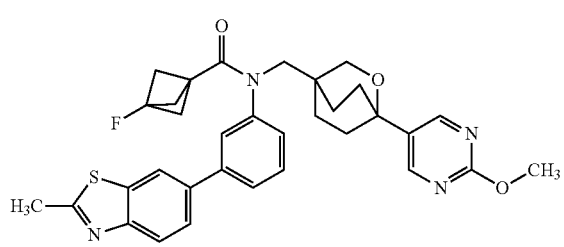

Step A. Intermediate 558A. Preparation of N-((1-(2-methoxypyrimidin-5-yl)-2-oxabicyclo[2.2.2]octan-4-yl)methyl)-3-(2-methylbenzo[d]thiazol-6-yl)aniline

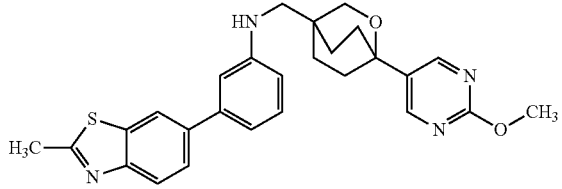

The title compound was prepared according to the method described for the synthesis of Intermediate 1I by substituting Intermediate 554A and Intermediate 140E where appropriate. (20 mg, 0.042 mmol, 35% yield) as brown gummy mass. MS (ESI) 473 (M+H).

Step B. Example 558. Preparation of 3-fluoro-N-((1-(2-methoxypyrimidin-5-yl)-2-oxabicyclo[2.2.2]octan-4-yl)methyl)-N-(3-(2-methylbenzo[d]thiazol-6-yl)phenyl) bicyclo[1.1.1]pentane-1-carboxamide The title compound was prepared according to the method described for the synthesis of Example 3 by substituting Intermediate 558A and the corresponding acid where appropriate. (4 mg, 6.50 μmol, 15% yield). $^1$H NMR (400 MHz, DMSO-$d_6$) δ 8.53 (s, 2H), 8.48 (d, J=1.7 Hz, 1H), 8.01 (d, J=8.6 Hz, 1H), 7.88 (dd, J=8.4, 1.8 Hz, 1H), 7.85-7.75 (m, 2H), 7.59 (t, J=7.8 Hz, 1H), 7.44 (d, J=7.1 Hz, 1H), 3.88 (s, 3H), 3.80-3.66 (m, 3H), 3.66-3.57 (m, 1H), 2.84 (s, 3H), 2.09-1.98 (m, 2H), 1.97-1.77 (m, 8H), 1.76-1.63 (m, 2H), 1.59 (br. s., 2H). FXR $EC_{50}$ (nM)=561. MS (ESI) 585 (M+H).

Example 559

N-((4-(3-Cyclopropyl-1,2,4-oxadiazol-5-yl)bicyclo[2.2.2]octan-1-yl)methyl)-3-fluoro-N-(3-(5-fluorobenzo[d]oxazol-2-yl)phenyl)bicyclo[1.1.1]pentane-1-carboxamide (559)

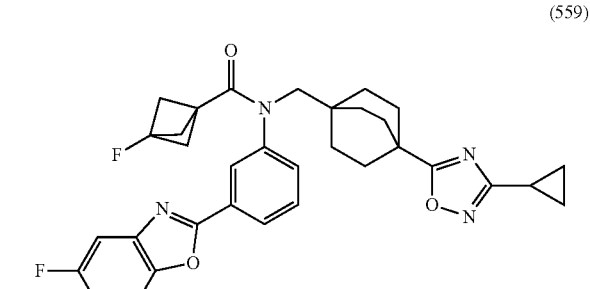

Step A. Intermediate 559A. Preparation of N-(5-fluoro-2-hydroxyphenyl)-3-nitrobenzamide

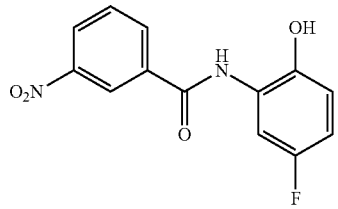 [SMILES: O=C(Nc1cc(F)ccc1O)c1cccc([N+](=O)[O-])c1]

To a stirred solution of 3-nitrobenzoyl chloride (2 g, 10.78 mmol) in THF (40 mL) was added TEA (4.51 mL, 32.3 mmol) followed by 2-amino-4-fluorophenol (1.37 g, 10.78 mmol). The reaction mixture was stirred at room temperature for overnight. The reaction mixture was diluted with ethyl acetate (50 mL), washed with aqueous 10% sodium bicarbonate (2×25 mL). The organic layers were combined, dried over anhydrous sodium sulphate, concentrated and dried in vacuo to afford the title compound (1.7 g, 5.48 mmol, 51% yield) as brown solid. MS (ESI) 277 (M+H).

Step B. Intermediate 559B. Preparation of 5-fluoro-2-(3-nitrophenyl)benzo[d]oxazole

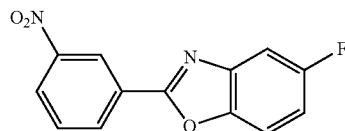

To a stirred solution of Intermediate 559A (1.6 g, 5.79 mmol) in xylene (35 mL) was added p-toluenesulfonic acid monohydrate (0.220 g, 1.158 mmol). The reaction mixture was heated at reflux with Dean-Stark condenser for overnight. The reaction mixture was cooled to room temperature, concentrated, diluted with water (25 mL) and extracted with ethyl acetate (2×30 mL). The organic layers were combined, dried over anhydrous sodium sulphate and concentrated under reduced pressure. The crude material was purified by flash chromatography (40 g silica gel cartridge; A=Hex, B=EtOAc; 30 min grad.; 0% B to 40% B; flow rate=30 mL/min). The pure fractions were combined, concentrated and dried in vacuo to afford the title compound (1.25 g, 4.70 mmol, 81% yield) as brown solid. MS (ESI) 259 (M+H).

Step C. Intermediate 559C. Preparation of 3-(5-fluorobenzo[d]oxazol-2-yl)aniline

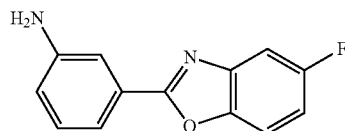

To a stirred solution of Intermediate 559B (1.2 g, 4.65 mmol) in ethanol (30 mL) and tetrahydrofuran (30 mL) was added zinc (4.56 g, 69.7 mmol) followed by a solution of ammonium chloride (3.73 g, 69.7 mmol) in water (10 mL). The reaction mixture was stirred at room temperature for overnight. The reaction mixture was diluted with DCM (50 mL) and filtered through Celite. The filtrate was concentrated under reduced pressure. The crude material was purified by flash chromatography (24 g silica gel cartridge; A=Hex, B=EtOAc; 30 min grad.; 0% B to 50% B; flow rate=30 mL/min). The pure fractions were combined, concentrated and dried in vacuo to afford the title compound (0.5 g, 2.059 mmol, 44% yield) as brown solid. MS (ESI) 229 (M+H).

Step D. Intermediate 559D. Preparation of N-((4-(3-cyclopropyl-1,2,4-oxadiazol-5-yl) bicyclo[2.2.2]octan-1-yl)methyl)-3-(5-fluorobenzo[d]oxazol-2-yl)aniline

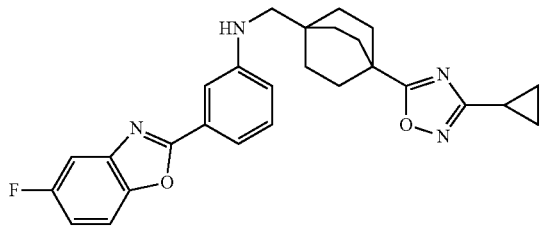 [SMILES: Fc1ccc2oc(-c3cccc(NCC45CCC(c6nc(C7CC7)no6)(CC4)CC5)c3)nc2c1]

The title compound was prepared according to the method described for the synthesis of Intermediate 1I by substituting Intermediate 559C and Intermediate 4C where appropriate. (180 mg, 0.377 mmol, 77% yield) as brown solid. $^1$H NMR (400 MHz, DMSO-d$_6$) δ 7.82 (dd, J=9.0, 4.5 Hz, 1H), 7.68 (dd, J=9.0, 2.5 Hz, 1H), 7.46-7.43 (m, 1H), 7.35-7.25 (m, 3H), 6.90 (dd, J=8.0, 1.0 Hz, 1H), 5.94 (t, J=6.0 Hz, 1H), 2.91 (d, J=6.0 Hz, 2H), 2.12-2.03 (m, 1H), 1.93-1.84 (m, 6H), 1.65-1.55 (m, 6H), 1.08-1.00 (m, 2H), 0.89-0.84 (m, 2H).

Step E. Example 559. Preparation of N-((4-(3-Cyclopropyl-1,2,4-oxadiazol-5-yl) bicyclo[2.2.2]octan-1-yl)methyl)-3-fluoro-N-(3-(5-fluorobenzo[d]oxazol-2-yl)phenyl) bicyclo[1.1.1]pentane-1-carboxamide The title compound was prepared according to the method described for the synthesis of Example 3 by substituting Intermediate 559D and the corresponding acid where appropriate. (15.2 mg, 0.027 mmol, 41% yield). $^1$H NMR (400 MHz, DMSO-d$_6$) δ 8.26-8.16 (m, 1H), 8.12 (s, 1H), 7.88 (dd, J=9.0, 4.4 Hz, 1H), 7.80-7.66 (m, 3H), 7.35 (td, J=9.3, 2.7 Hz, 1H), 3.63 (s, 2H), 2.09-2.01 (m, 1H), 1.91 (br. s., 6H), 1.82-1.65 (m, 6H), 1.55-1.36 (m, 6H), 1.06-0.95 (m, 2H), 0.88-0.74 (m, 2H). FXR EC$_{50}$ (nM)=217. MS (ESI) 571 (M+H).

The following compound was prepared according to the method described for the synthesis of Example 3 by substituting Intermediate 559D and the corresponding acids where appropriate.

| Ex. No. | Structure | MS (ESI) (M + H) | FXR EC$_{50}$ (nM) |
|---|---|---|---|
| 560 | | 577 | 1508 |

560 $^1$HNMR (400 MHz, DMSO-d$_6$) δ 8.24-8.09 (m, 2H), 7.87 (dd, J = 9.0, 4.4 Hz, 1H), 7.79-7.63 (m, 3H), 7.34 (td, J = 9.3, 2.7 Hz, 1H), 3.69 (br. s., 2H), 2.97-2.87 (m, 1H), 2.86-2.70 (m, 2H), 2.41-2.32 (m, 2H), 2.10-2.00 (m, 1H), 1.86-1.67 (m, 6H), 1.56-1.31 (m, 6H), 1.07-0.95 (m, 2H), 0.87-0.77 (m, 2H)

Example 561

N-((4-(5-cyclopropyl-1,3,4-oxadiazol-2-yl)bicyclo[2.2.2]octan-1-yl)methyl)-3-fluoro-N-(3-(2-methylbenzo[d]thiazol-6-yl)phenyl)bicyclo[1.1.1]pentane-1-carboxamide (561)

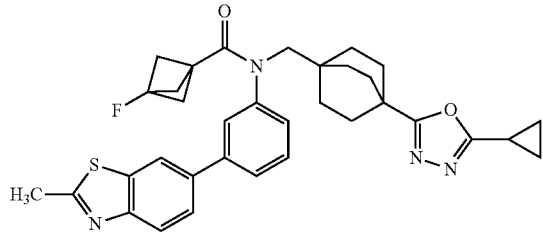

Step A. Intermediate 561A. Preparation of N-((4-(5-cyclopropyl-1,3,4-oxadiazol-2-yl) bicyclo[2.2.2]octan-1-yl)methyl)-3-(2-methylbenzo[d]thiazol-6-yl)aniline

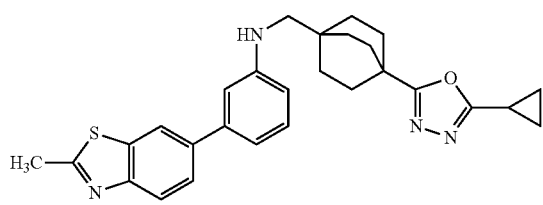 [SMILES: Cc1nc2ccc(-c3cccc(NCC45CCC(c6nnc(C7CC7)o6)(CC4)CC5)c3)cc2s1]

The title compound was prepared according to the method described for the synthesis of Intermediate 1I by substituting Intermediate 554A and Intermediate 133D where appropriate. (90 mg, 0.191 mmol, 67% yield) as gummy liquid. MS (ESI) 471 (M+H).

Step B. Example 561. Preparation of N-((4-(5-cyclopropyl-1,3,4-oxadiazol-2-yl) bicyclo[2.2.2]octan-1-yl)methyl)-3-fluoro-N-(3-(2-methylbenzo[d]thiazol-6-yl)phenyl) bicyclo[1.1.1]pentane-1-carboxamide The title compound was prepared according to the method described for the synthesis of Example 3 by substituting Intermediate 561A and the corresponding acid where appropriate. (4.2 mg, 7.21 μmol, 11% yield). $^1$H NMR (400 MHz, DMSO-d$_6$) δ 8.47 (d, J=1.7 Hz, 1H), 8.01 (d, J=8.3 Hz, 1H), 7.86 (dd, J=8.4, 1.8 Hz, 1H), 7.82-7.74 (m, 2H), 7.57 (t, J=8.1 Hz, 1H), 7.41 (d, J=8.1 Hz, 1H), 3.74-3.62 (m, 1H), 3.61-3.49 (m, 1H), 2.84 (s, 3H), 2.18-2.10 (m, 1H), 1.92 (d, J=8.1 Hz, 3H), 1.85 (d, J=8.8 Hz, 3H), 1.80-1.67 (m, 6H), 1.46 (d, J=4.6 Hz, 6H), 1.11-1.03 (m, 2H), 0.97-0.89 (m, 2H). FXR EC$_{50}$ (nM)=58. MS (ESI) 583 (M+H).

The following compounds were prepared according to the method described for the synthesis of Example 3 by substituting Intermediate 561A and the corresponding acids where appropriate.

| Ex. No. | Structure | MS (ESI) (M + H) | FXR EC$_{50}$ (nM) |
|---|---|---|---|
| 562 | 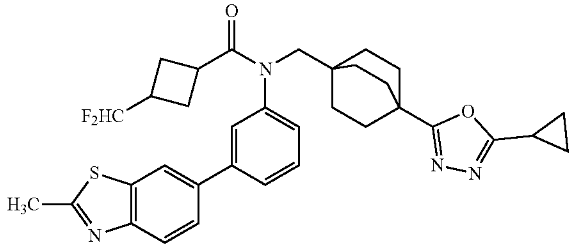 [SMILES: Cc1nc2ccc(-c3cccc(N(CC45CCC(c6nnc(C7CC7)o6)(CC4)CC5)C(=O)C4CC(C(F)F)C4)c3)cc2s1] | 603 | 318 |
| 563 | 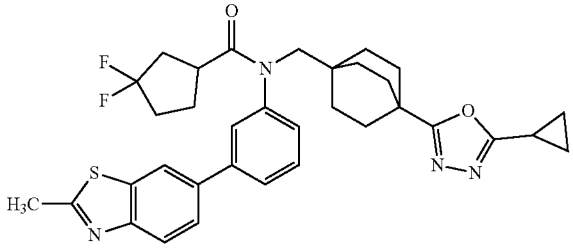 [SMILES: Cc1nc2ccc(-c3cccc(N(CC45CCC(c6nnc(C7CC7)o6)(CC4)CC5)C(=O)C4CCC(F)(F)C4)c3)cc2s1] | 603 | 154 |

562 $^1$H NMR (400 MHz, DMSO-d$_6$) δ 8.45 (dd, J = 7.1, 1.7 Hz, 1H), 8.00 (d, J = 8.3 Hz, 1H), 7.85 (ddd, J = 8.4, 4.8, 2.0 Hz, 1H), 7.80-7.65 (m, 2H), 7.54 (t, J = 7.8 Hz, 1H), 7.45-7.29 (m, 1H), 6.03 (dd, J = 10.4, 4.5 Hz, 1H), 5.96-5.81 (m, 1H), 3.67 (br. s., 2H), 2.84 (s, 3H), 2.29 (d, J = 9.5 Hz, 1H), 2.18-2.00 (m, 3H), 1.85-1.56 (m, 8H), 1.52-1.32 (m, 6H), 1.11-1.02 (m, 2H), 0.96-0.85 (m, 2H) 5.96-5.81 (m, 1H), 563 $^1$H NMR (400 MHz, DMSO-d$_6$) δ 8.45 (s, 1H), 7.99 (d, J = 8.40 Hz, 1H), 7.82-7.86 (m, 2H), 7.75 (d, J = 8.00 Hz, 1H), 7.56 (t, J = 15.60 Hz, 1H), 7.44 (d, J = 7.60 Hz, 1H), 3.81 (s, 2H), 3.02-3.04 (m, 1H), 2.83 (s, 3H), 2.14-2.15 (m, 1H), 2.10-2.15 (m, 3H), 1.83-1.87 (m, 2H), 1.74 (d, J = 15.20 Hz, 7H), 1.43 (s, 6H), 1.06 (d, J = 14.40 Hz, 2H), 0.92 (d, J = 15.60 Hz, 2H)

Example 564

N-((1-(3-cyclopropyl-1,2,4-oxadiazol-5-yl)-2-oxabi-cyclo[2.2.2]octan-4-yl)methyl)-3-fluoro-N-(3-(2-methylbenzo[d]thiazol-6-yl)phenyl)bicyclo[1.1.1] pentane-1-carboxamide (564)

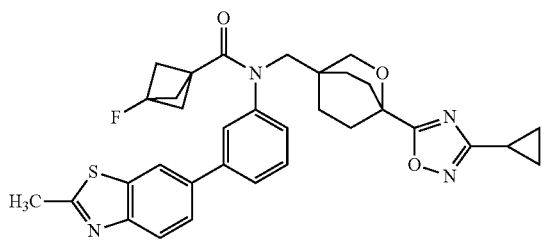

Step A. Intermediate 564A. Preparation of N-((1-(3-cyclopropyl-1,2,4-oxadiazol-5-yl)-2-oxabicyclo [2.2.2]octan-4-yl)methyl)-3-(2-methylbenzo[d]thi-azol-6-yl)aniline

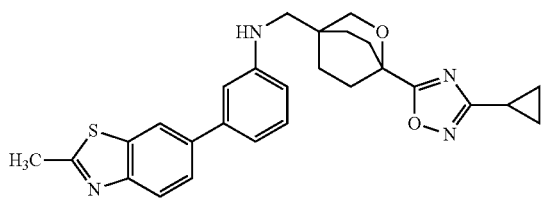

The title compound was prepared according to the method described for the synthesis of Intermediate 1I by substituting Intermediate 554A and Intermediate 196K where appropriate. (32 mg, 0.061 mmol, 76% yield) as an off-white solid. MS (ESI) 473 (M+H).

Step B. Example 564. Preparation of N-((1-(3-cyclopropyl-1,2,4-oxadiazol-5-yl)-2-oxabicyclo[2.2.2] octan-4-yl)methyl)-3-fluoro-N-(3-(2-methylbenzo[d] thiazol-6-yl) phenyl)bicyclo[1.1.1]pentane-1-carboxamide The title compound was prepared according to the method described for the synthesis of Example 3 by substituting Intermediate 564A and the corresponding acid where appropriate. (11.8 mg, 0.020 mmol, 32% yield). $^1$H NMR (400 MHz, DMSO-d$_6$) δ 8.48 (d, J=1.7 Hz, 1H), 8.01 (d, J=8.6 Hz, 1H), 7.87 (dd, J=8.6, 2.0 Hz, 1H), 7.85-7.76 (m, 2H), 7.58 (t, J=7.8 Hz, 1H), 7.44 (d, J=7.8 Hz, 1H), 3.75-3.57 (m, 4H), 2.84 (s, 3H), 2.17-2.02 (m, 3H), 2.02-1.79 (m, 8H), 1.72 (br. s., 2H), 1.61 (d, J=9.3 Hz, 2H), 1.10-0.99 (m, 2H), 0.91-0.77 (m, 2H). FXR EC$_{50}$ (nM) 207. MS (ESI) 585 (M+H).

The following compounds were prepared according to the method described for the synthesis of Example 3 by substituting Intermediate 564A and the corresponding acids where appropriate.

| Ex. No. | Structure | MS (ESI) (M + H) | FXR EC$_{50}$ (nM) |
|---|---|---|---|
| 565 | 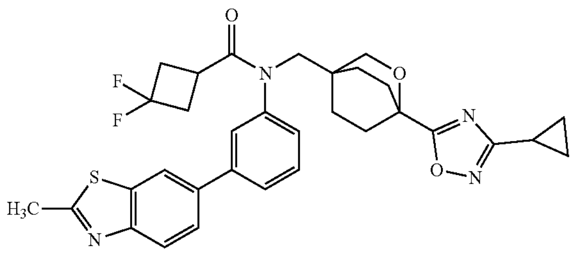 [SMILES: Cc1nc2ccc(-c3cccc(N(CC45CCC(c6nc(C7CC7)no6)(CC4)OC5)C(=O)C4CC(F)(F)C4)c3)cc2s1] | 591 | 947 |
| 566 | 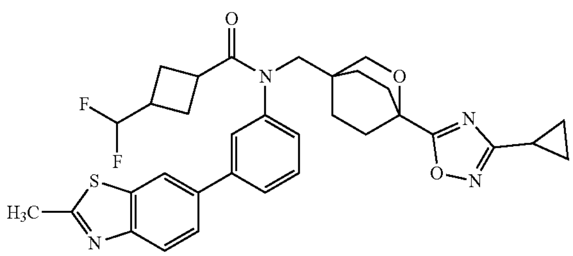 [SMILES: Cc1nc2ccc(-c3cccc(N(CC45CCC(c6nc(C7CC7)no6)(CC4)OC5)C(=O)C4CC(C(F)F)C4)c3)cc2s1] | 605 | 922 |
| 567 | 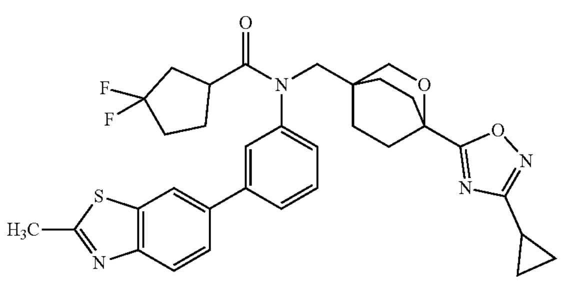 [SMILES: Cc1nc2ccc(-c3cccc(N(CC45CCC(c6nc(C7CC7)no6)(CC4)OC5)C(=O)C4CCC(F)(F)C4)c3)cc2s1] | 605 | 432 |

565  $^1$H NMR (400 MHz, DMSO-d$_6$) δ 8.47 (d, J = 1.7 Hz, 1H), 8.00 (d, J = 8.6 Hz, 1H), 7.93-7.81 (m, 2H), 7.77 (d, J = 8.1 Hz, 1H), 7.57 (t, J = 7.8 Hz, 1H), 7.44 (d, J = 8.8 Hz, 1H), 3.84-3.57 (m, 4H), 2.99 (td, J = 8.6, 2.8 Hz, 1H), 2.91-2.69 (m, 5H), 2.34 (br. s., 2H), 2.17-2.03 (m, 3H), 2.02-1.86 (m, 2H), 1.76-1.63 (m, 2H), 1.63-1.50 (m, 2H), 1.10-0.98 (m, 2H), 0.90-0.78 (m, 2H)

566  $^1$H NMR (400 MHz, DMSO-d$_6$) δ 8.46 (dd, J = 7.3, 1.7 Hz, 1H), 8.00 (d, J = 8.6 Hz, 1H), 7.91-7.66 (m, 3H), 7.55 (t, J = 7.9 Hz, 1H), 7.47-7.33 (m, 1H), 3.81-3.58 (m, 4H), 3.22-3.08 (m, 1H), 2.84 (s, 3H), 2.47 (br. s., 1H), 2.34-2.24 (m, 1H), 2.20-1.99 (m, 4H), 1.99-1.83 (m, 2H), 1.81-1.62 (m, 4H), 1.58 (d, J = 10.0 Hz, 2H), 1.11-0.98 (m, 2H), 0.92-0.72 (m, 2H). 1H buried under DMSO peak.

567  $^1$H NMR (400 MHz, DMSO-d$_6$) δ 8.47 (s, 1H), 8.01 (d, J = 8.6 Hz, 1H), 7.87 (d, J = 2.7 Hz, 1H), 7.78 (d, J = 8.1 Hz, 1H), 7.58 (t, J = 7.8 Hz, 1H), 7.48 (d, J = 7.8 Hz, 1H), 3.91 (s, 1H), 3.68 (s, 4H), 3.08-2.96 (m, 1H), 2.84 (s, 3H), 2.31 (m, 1H), 2.20-2.00 (m, 5H), 2.00-1.89 (m, 3H), 1.85 (d, J = 8.6 Hz, 1H), 1.69 (m, 3H), 1.57 (m, 2H), 1.11-0.96 (m, 2H), 0.92-0.70 (m, 2H)

Examples 568 and 569

N-((1-(4-Cyanophenyl)-2-oxabicyclo[2.2.2]octan-4-yl)methyl)-3-fluoro-N-(3-(2-methylbenzo[d]thiazol-6-yl)phenyl)bicyclo[1.1.1]pentane-1-carboxamide (568) N-((1-(4-(dimethylcarbamoyl)phenyl)-2-oxabicyclo[2.2.2]octan-4-yl)methyl)-3-fluoro-N-(3-(2-methylbenzo[d]thiazol-6-yl)phenyl)bicyclo[1.1.1]pentane-1-carboxamide (569)

(568)

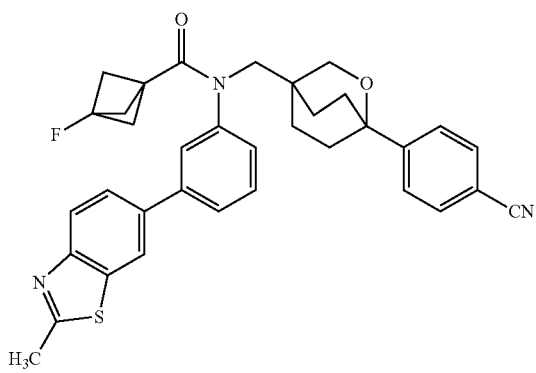

(569)

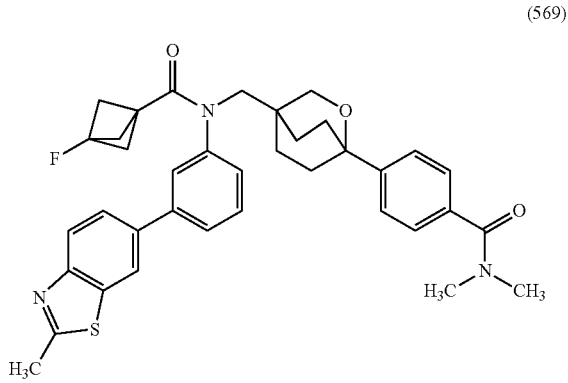

Step A. Intermediate 568A. Preparation of methyl 4-(1-hydroxy-4,4-bis((tosyloxy)methyl)cyclohexyl)benzoate

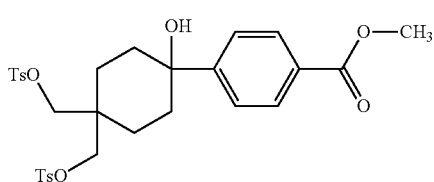 [SMILES: COC(=O)c1ccc(C2(O)CCC(COS(=O)(=O)c3ccc(C)cc3)(COS(=O)(=O)c3ccc(C)cc3)CC2)cc1]

A stirred solution of methyl 4-iodobenzoate (1.755 g, 6.70 mmol) in THF (10 mL) was cooled to 0° C. Isopropyl magnesium chloride (5.36 mL, 6.97 mmol) was added drop wise to the reaction mixture and stirred for 10 min. A solution of (4-oxocyclohexane-1,1-diyl)bis(methylene)bis (4-methyl benzenesulfonate) (2.5 g, 5.36 mmol) (see ACS Medicinal Chemistry Letters, 5(5), 609-614; 2014) in THF (5 mL) was added drop wise to the reaction mixture. The reaction mixture was stirred at 5° C. for 1 h. The solution.

The reaction mixture was quenched with ammonium chloride solution (10 mL), allowed to warm to room temperature and extracted with ethyl acetate (2×25 mL). The organic layers were combined, dried over anhydrous sodium sulphate and concentrated under reduced pressure. The crude material was purified by flash chromatography (40 g silica gel cartridge; A=Hex, B=EtOAc; 30 min grad.; 0% B to 50% B; flow rate=30 mL/min). The pure fractions were combined, concentrated and dried in vacuo to afford the title compound (2.7 g, 2.78 mmol, 52% yield) as yellow solid. MS (ESI) 620 (M+H+17).

Step B. Intermediate 568B. Preparation of 4-(4-((tosyloxy)methyl)-2-oxabicyclo[2.2.2]octan-1-yl)benzoic acid

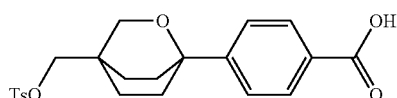

The title compound was prepared according to the method described for the synthesis of Intermediate 141B by substituting Intermediate 568A where appropriate. MS (ESI) 434 (M+H) (NH$_3$ adduct).

Step C. Intermediate 568C. Preparation of methyl 4-(4-((tosyloxy)methyl)-2-oxabicyclo[2.2.2]octan-1-yl)benzoate

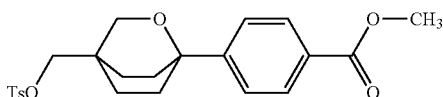

To a stirred solution of Intermediate 568B (1.8 g, 4.32 mmol) in DMF (20 mL) was added K$_2$CO$_3$ (1.19 g, 8.64 mmol). The reaction mixture was stirred for 10 min. MeI (0.540 mL, 8.64 mmol) was added to the reaction mixture and stirred for 1 h. The reaction mixture was concentrated under reduced pressure. The organic layers were combined, dried over anhydrous sodium sulphate and concentrated under reduced pressure. The crude material was purified by flash chromatography (40 g silica gel cartridge; A=Hex, B=EtOAc; 30 min grad.; 0% B to 100% B; flow rate=30 mL/min). The pure fractions were combined, concentrated and dried in vacuo to afford the title compound (1 g, 2.044 mmol, 47% yield) as white solid. MS (ESI) 448 (M+H) (NH$_3$ adduct).

Step D. Intermediate 568D. Preparation of methyl 4-(4-(acetoxymethyl)-2-oxabicyclo[2.2.2]octan-1-yl)benzoate

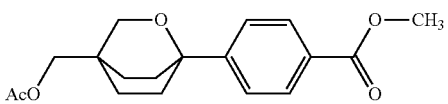

The title compound was prepared according to the method described for the synthesis of Intermediate 141C by substituting Intermediate 568C where appropriate. (660 mg, 1.638 mmol, 78% yield) as brown gummy solid. ¹H NMR (400 MHz, DMSO-d₆) δ 7.90 (dd, J=1.60, 6.80 Hz, 2H), 7.53 (dd, J=1.60, 6.80 Hz, 2H), 3.84 (s, 3H), 3.82 (s, 2H), 2.84 (s, 2H), 2.14-2.08 (m, 2H), 2.04 (s, 3H), 1.85-1.68 (m, 6H). MS (ESI) 319 (M+H).

Step E. Intermediate 568E. Preparation of methyl 4-(4-(hydroxymethyl)-2-oxabicyclo[2.2.2]octan-1-yl)benzoate

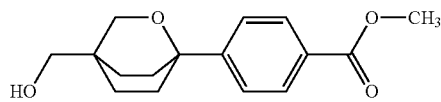

The title compound was prepared according to the method described for the synthesis of Intermediate 141D by substituting Intermediate 568D where appropriate. (550 mg, 1.831 mmol, 88% yield) as white solid. ¹H NMR (400 MHz, DMSO-d₆) δ 7.88 (dd, J=2.00, 5.20 Hz, 2H), 7.53 (dd, J=4.80, 5.20 Hz, 2H), 4.55-4.52 (m, 1H), 3.83 (s, 3H), 3.80 (s, 2H), 3.17 (s, 1H), 3.15 (s, 1H), 2.11-2.05 (m, 2H), 1.82-1.54 (m, 6H). MS (ESI) 277 (M+H).

Step F. Intermediate 568F. Preparation of methyl 4-(4-formyl-2-oxabicyclo[2.2.2]octan-1-yl)benzoate

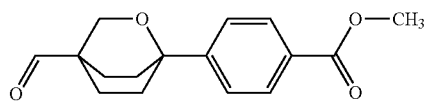

The title compound was prepared according to the method described for the synthesis of Intermediate 3C by substituting Intermediate 568E where appropriate. (170 mg, 0.471 mmol, 65% yield) as white solid. ¹H NMR (400 MHz, DMSO-d₆) δ 9.52 (s, 1H), 7.92 (d, J=8.40 Hz, 2H), 7.55 (d, J=8.00 Hz, 2H), 4.02 (s, 2H), 3.85 (s, 3H), 2.18-2.15 (m, 2H), 1.92-1.90 (m, 6H). MS (ESI) 275 (M+H).

Step G. Intermediate 568G. Preparation of methyl 4-(4-(((3-(2-methylbenzo[d]thiazol-6-yl)phenyl)amino)methyl)-2-oxabicyclo[2.2.2]octan-1-yl)benzoate

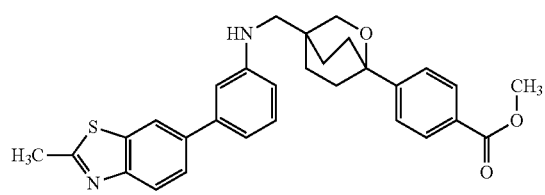

The title compound was prepared according to the method described for the synthesis of Intermediate 1I by substituting Intermediate 554A and Intermediate 568F where appropriate. (40 mg, 0.080 mmol, 73% yield) as brown gummy mass. MS (ESI) 499 (M+H).

Step H. Intermediate 568H. Preparation of methyl 4-(4-((3-fluoro-N-(3-(2-methylbenzo[d]thiazol-6-yl)phenyl)bicyclo[1.1.1]pentane-1-carboxamido)methyl)-2-oxabicyclo[2.2.2]octan-1-yl)benzoate

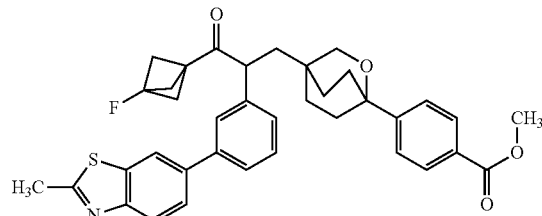

The title compound was prepared according to the method described for the synthesis of Example 3 by substituting Intermediate 568G and the corresponding acid where appropriate. (30 mg, 0.049 mmol, 64% yield) as brown gummy mass. MS (ESI) 611 (M+H).

Step I. Intermediate 568I. Preparation of 4-(4-((3-fluoro-N-(3-(2-methylbenzo[d]thiazol-6-yl)phenyl)bicyclo[1.1.1]pentane-1-carboxamido)methyl)-2-oxabicyclo[2.2.2]octan-1-yl)benzoic acid

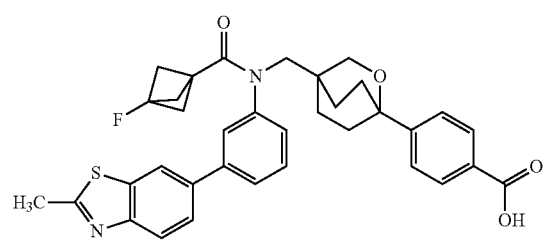 [SMILES: Cc1nc2ccc(-c3cccc(N(CC45CCC(c6ccc(C(=O)O)cc6)(CC4)OC5)C(=O)C45CC(F)(C4)C5)c3)cc2s1]

The title compound was prepared according to the method described for the synthesis of Intermediate 175E by substituting Intermediate 568H where appropriate. (25 mg, 0.036 mmol, 73% yield) as brown gummy mass. MS (ESI) 597 (M+H).

Step J. Intermediate 568J. Preparation of N-((1-(4-carbamoylphenyl)-2-oxabicyclo[2.2.2]octan-4-yl)methyl)-3-fluoro-N-(3-(2-methylbenzo[d]thiazol-6-yl)phenyl)bicyclo[1.1.1]pentane-1-carboxamide

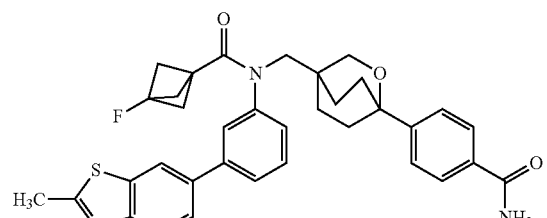

The title compound was prepared according to the method described for the synthesis of Intermediate 114A by substituting Intermediate 568I where appropriate. (35 mg, crude) as brown gummy mass. MS (ESI) 596 (M+H).

Step K. Examples 568 and 569. Preparation of N-((1-(4-Cyanophenyl)-2-oxabicyclo[2.2.2]octan-4-yl)methyl)-3-fluoro-N-(3-(2-methylbenzo[d]thiazol-6-yl) phenyl)bicyclo[1.1.1]pentane-1-carboxamide and N-((1-(4-(dimethylcarbamoyl)phenyl)-2-oxabicyclo[2.2.2]octan-4-yl)methyl)-3-fluoro-N-(3-(2-methylbenzo[d]thiazol-6-yl) phenyl)bicyclo[1.1.1]pentane-1-carboxamide The title compound was prepared according to the method described for the synthesis of Intermediate 114B by substituting Intermediate 568J where appropriate.

Example 568: (2.3 mg, 3.98 μmol, 7% yield). $^1$H NMR (400 MHz, DMSO-d$_6$) δ 8.00 (d, J=8.6 Hz, 1H), 7.87 (d, J=8.6 Hz, 1H), 7.84-7.77 (m, 2H), 7.73 (d, J=8.3 Hz, 2H), 7.62-7.49 (m, 3H), 7.43 (d, J=7.8 Hz, 1H), 3.80-3.65 (m, 3H), 3.65-3.56 (m, 1H), 2.83 (s, 3H), 2.10-1.99 (m, 2H), 1.97-1.82 (m, 6H), 1.80-1.65 (m, 4H), 1.65-1.54 (m, 2H). FXR EC$_{50}$ (nM)=2445. MS (ESI) 578 (M+H).

Example 569: (5.4 mg, 8.66 μmol, 15% yield). $^1$H NMR (400 MHz, DMSO-d$_6$) δ 8.49 (d, J=1.7 Hz, 1H), 8.01 (d, J=8.3 Hz, 1H), 7.88 (dd, J=8.4, 1.8 Hz, 1H), 7.85-7.79 (m, 2H), 7.59 (t, J=7.7 Hz, 1H), 7.44 (d, J=7.3 Hz, 1H), 7.41-7.35 (m, J=8.3 Hz, 2H), 7.33-7.27 (m, J=8.3 Hz, 2H), 3.80-3.66 (m, 3H), 3.66-3.57 (m, 1H), 2.96 (br. s., 3H), 2.89 (br. s., 3H), 2.84 (s, 3H), 2.08-1.97 (m, 2H), 1.97-1.85 (m, 6H), 1.77 (d, J=11.7 Hz, 2H), 1.69 (br. s., 2H), 1.61 (br. s., 2H). FXR EC$_{50}$ (nM)=2222. MS (ESI) 624 (M+H).

Example 570

N-cyclopropyl-4-((3-fluoro-N-(3-(2-methoxypyridin-4-yl)phenyl)bicyclo[1.1.1]pentane-1-carboxamido)methyl)bicyclo[2.2.2]octane-1-carboxamide

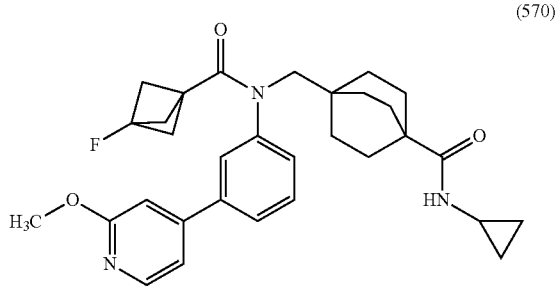 [SMILES: COc1cc(-c2cccc(N(CC34CCC(C(=O)NC5CC5)(CC3)CC4)C(=O)C34CC(F)(C3)C4)c2)ccn1]

(570)

The title compound was synthesized according to the method described for the synthesis of Intermediate 114A by substituting Intermediate 227C and cyclopropylamine where appropriate (7.2 mg, 0.014 mmol, 33.0% yield): $^1$H NMR (400 MHz, DMSO-d$_6$) δ 8.27 (d, J=5.4 Hz, 1H), 7.87-7.75 (m, 2H), 7.57 (t, J=7.7 Hz, 1H), 7.45 (d, J=7.3 Hz, 1H), 7.39 (dd, J=5.4, 1.5 Hz, 1H), 7.26-7.11 (m, 2H), 3.92 (s, 3H), 3.56 (d, J=16.6 Hz, 2H), 2.59-2.55 (m, 1H), 1.94-1.74 (m, 6H), 1.62-1.46 (m, 6H), 1.32 (br. s., 6H), 0.60-0.46 (m, 2H), 0.45-0.29 (m, 2H). FXR EC$_{50}$ (nM)=926. MS (ESI) 518 (M+H).

Example 571

N-(3-cyclopropylphenyl)-N-((4-(5-(1,1-difluoroethyl)-1,2,4-oxadiazol-3-yl) bicyclo[2.2.2]octan-1-yl)methyl)-3-fluorobicyclo[1.1.1]pentane-1-carboxamide

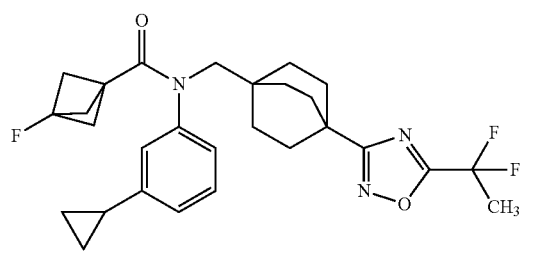

(571)

Step A. Intermediate 571A. Preparation of N-(3-bromophenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide

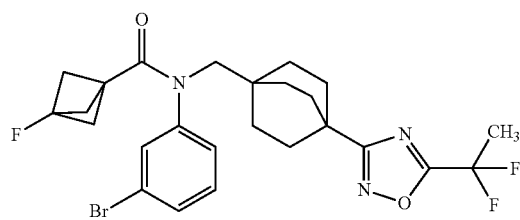 [SMILES: CC(F)(F)c1nc(C23CCC(CN(C(=O)C45CC(F)(C4)C5)c4cccc(Br)c4)(CC2)CC3)no1]

The title compound was prepared according to the method described for the synthesis of Intermediate 1A by substituting Intermediate 396C and the corresponding acid where appropriate. (9.6 mg, 0.017 mmol, 55% yield). $^1$H NMR (400 MHz, DMSO-d$_6$) δ 7.74-7.68 (m, 1H), 7.61 (dt, J=7.3, 1.7 Hz, 1H), 7.49-7.36 (m, 2H), 3.58 (br. s., 1H), 3.51 (br. s., 1H), 2.23-2.05 (m, 3H), 1.88 (br. s., 6H), 1.82-1.69 (m, 6H), 1.53-1.33 (m, 6H).

Step B. Example 571. Preparation of N-(3-cyclopropylphenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide The title compound was prepared according to the method described for the synthesis of Example 149 by substituting Intermediate 571A and cyclopropylboronic acid where appropriate. (7.7 mg, 0.015 mmol, 27% yield). $^1$H NMR (400 MHz, DMSO-d$_6$) δ 7.38-7.25 (m, 1H), 7.19-7.07 (m, 2H), 7.04 (s, 1H), 3.62-3.44 (m, 2H), 2.14 (t, J=19.7 Hz, 3H), 2.04-1.94 (m, 1H), 1.77 (d, J=8.3 Hz, 6H), 1.81 (d, J=7.3 Hz, 6H), 1.45 (d, J=9.0 Hz, 6H), 1.07-0.93 (m, 2H), 0.72 (d, J=4.6 Hz, 2H). FXR EC$_{50}$ (nM)=47. MS (ESI) 500 (M+H).

Example 572

N-(3-cyclopropylphenyl)-3-fluoro-N-((4-(5-(trifluoromethyl)-1,2,4-oxadiazol-3-yl) bicyclo[2.2.2]octan-1-yl)methyl)bicyclo[1.1.1]pentane-1-carboxamide

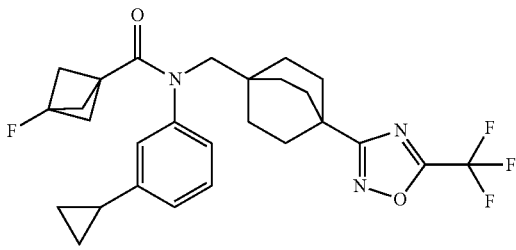

(572)

Step A. Intermediate 572A. Preparation of N-(3-bromophenyl)-3-fluoro-N-((4-(5-(trifluoromethyl)-1,2,4-oxadiazol-3-yl)bicyclo[2.2.2]octan-1-yl)methyl) bicyclo[1.1.1]pentane-1-carboxamide

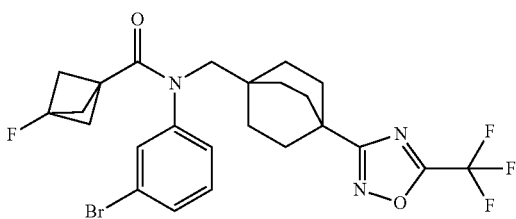 [SMILES: O=C(N(CC12CCC(c3noc(C(F)(F)F)n3)(CC1)CC2)c1cccc(Br)c1)C12CC(F)(C1)C2]

The title compound was prepared according to the method described for the synthesis of Intermediate 1A by substituting Intermediate 396C and the corresponding acid where appropriate: (1.2 g, 2.186 mmol, 78% yield). $^1$H NMR (400 MHz, DMSO-$d_6$) δ 7.71 (t, J=1.8 Hz, 1H), 7.61 (dt, J=7.6, 1.7 Hz, 1H), 7.50-7.37 (m, 2H), 3.59 (br. s., 1H), 3.52 (br. s., 1H), 1.88 (br. s., 6H), 1.84-1.67 (m, 6H), 1.54-1.35 (m, 6H). MS (ESI) 543 (M+H).

Step B. Example 572. Preparation of N-(3-cyclopropylphenyl)-3-fluoro-N-((4-(5-(trifluoromethyl)-1,2,4-oxadiazol-3-yl)bicyclo[2.2.2]octan-1-yl)methyl) bicyclo[1.1.1]pentane-1-carboxamide The title compound was prepared according to the method described for the synthesis of Example 149 by substituting Intermediate 572A and cyclopropylboronic acid where appropriate. (4.5 mg, 8.04 μmol, 15% yield). $^1$H NMR (400 MHz, DMSO-$d_6$) δ 7.35-7.27 (m, 1H), 7.12 (t, J=7.2 Hz, 2H), 7.04 (s, 1H), 3.61-3.52 (m, 1H), 3.52-3.45 (m, 1H), 2.03-1.96 (m, 1H), 1.85-1.60 (m, 12H), 1.56-1.34 (m, 6H), 1.00 (dd, J=8.2, 2.1 Hz, 2H), 0.72 (d, J=4.2 Hz, 2H). FXR EC$_{50}$ (nM)=146. MS (ESI) 504 (M+H).

Example 573

N-(3-cyclopropylphenyl)-3-fluoro-N-((4-(5-(1-fluorocyclopropyl)-1,2,4-oxadiazol-3-yl)bicyclo[2.2.2]octan-1-yl)methyl)bicyclo[1.1.1]pentane-1-carboxamide

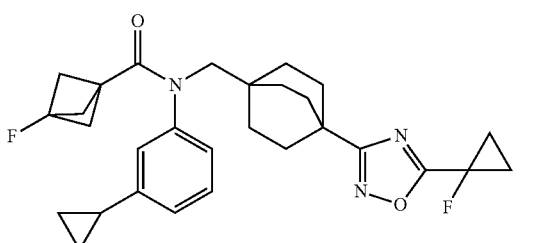

(573)

Step A. Intermediate 573A. Preparation of N-(3-bromophenyl)-3-fluoro-N-((4-(5-(1-fluorocyclopropyl)-1,2,4-oxadiazol-3-yl)bicyclo[2.2.2]octan-1-yl) methyl) bicyclo[1.1.1]pentane-1-carboxamide The title compound was prepared according to the method described for the synthesis of Intermediate 1A by substituting Intermediate 396C and the corresponding acid where appropriate. (450 mg, 0.845 mmol, 65% yield). $^1$H NMR (400 MHz, DMSO-$d_6$) δ 7.75-7.67 (m, 1H), 7.61 (dt, J=7.3, 1.7 Hz, 1H), 7.50-7.36 (m, 2H), 3.58 (br. s., 1H), 3.50 (br. s., 1H), 1.87 (br. s., 6H), 1.81-1.61 (m, 8H), 1.52-1.31 (m, 8H). MS (ESI) 533 (M+H).

Step B. Example 573. Preparation of N-(3-cyclopropylphenyl)-3-fluoro-N-((4-(5-(1-fluorocyclopropyl)-1,2,4-oxadiazol-3-yl)bicyclo[2.2.2]octan-1-yl) methyl) bicyclo[1.1.1]pentane-1-carboxamide The title compound was prepared according to the method described for the synthesis of Example 149 by substituting Intermediate 573A and cyclopropylboronic acid where appropriate. (5.3 mg, 10.74 μmol, 19% yield). $^1$H NMR (400 MHz, DMSO-$d_6$) δ 7.38-7.24 (m, 1H), 7.18-7.06 (m, 2H), 7.06-6.96 (m, 1H), 3.63-3.41 (m, 2H), 2.04-1.93 (m, 1H), 1.93-1.67 (m, 14H), 1.55-1.25 (m, 8H), 1.08-0.91 (m, 2H), 0.72 (d, J=4.4 Hz, 2H). FXR EC$_{50}$ (nM)=44. MS (ESI) 494 (M+H).

Example 574

N-(3-cyclopropyl-4-fluorophenyl)-N-((4-(5-(1,1-difluoroethyl)-1,2,4-oxadiazol-3-yl) bicyclo[2.2.2]octan-1-yl)methyl)-3-fluorobicyclo[1.1.1]pentane-1-carboxamide (574)

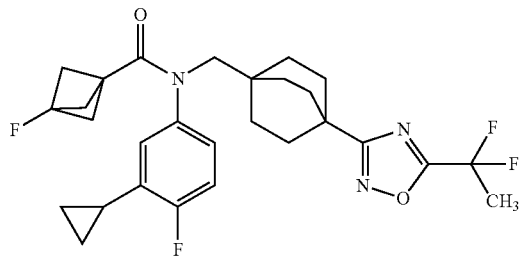

Step A. Intermediate 574A. Preparation of methyl 4-(5-(1,1-difluoroethyl)-1,2,4-oxadiazol-3-yl)bicyclo[2.2.2]octane-1-carboxylate

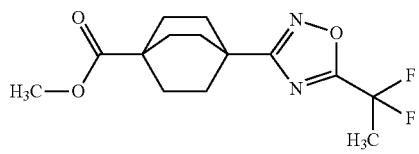 [SMILES: COC(=O)C12CCC(c3noc(C(C)(F)F)n3)(CC1)CC2]

The title compound was prepared according to the method described for the synthesis of Intermediate 1A by substituting Intermediate 206C and the corresponding acid where appropriate. (4.2 g, 11.75 mmol, 53.2% yield) colorless gummy solid. MS (ESI) 301 (M+H).

Step B. Intermediate 574B. Preparation of (4-(5-(1,1-difluoroethyl)-1,2,4-oxadiazol-3-yl)bicyclo[2.2.2]octan-1-yl)methanol

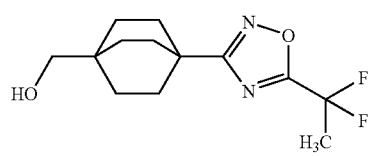 [SMILES: CC(F)(F)c1nc(C23CCC(CO)(CC2)CC3)no1]

The title compound was prepared according to the method described for the synthesis of Intermediate 1G by substituting Intermediate 574A where appropriate. (3000 mg, 10.58 mmol, 76% yield) as colorless liquid. MS (ESI) 273 (M+H).

Step C. Intermediate 574C. Preparation of 4-(5-(1,1-difluoroethyl)-1,2,4-oxadiazol-3-yl) bicyclo[2.2.2]octane-1-carbaldehyde

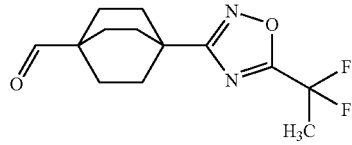 [SMILES: CC(F)(F)c1nc(C23CCC(C=O)(CC2)CC3)no1]

The title compound was prepared according to the method described for the synthesis of Intermediate 3C by substituting Intermediate 574B where appropriate. (2000 mg, 7.40 mmol, 67.2% yield) as colorless white gummy solid. $^1$H NMR (400 MHz, DMSO-$d_6$) δ 9.46 (br. s., 1H), 2.16 (t, J=19.6 Hz, 3H), 1.94-1.76 (m, 12H).

Step D. Intermediate 574D. Preparation of 3-bromo-N-((4-(5-(1,1-difluoroethyl)-1,2,4-oxadiazol-3-yl)bicyclo[2.2.2]octan-1-yl)methyl)-4-fluoroaniline

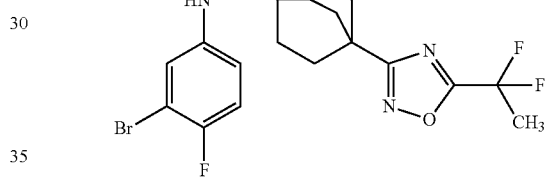

The title compound was prepared according to the method described for the synthesis of Intermediate 1I by substituting Intermediate 574C and 3-bromo-4-fluoro aniline where appropriate. (500 mg, 0.416 mmol, 28% yield) as brown gum. MS (ESI) 444 (M+H).

Step E. Intermediate 574E. Preparation of N-(3-bromo-4-fluorophenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide

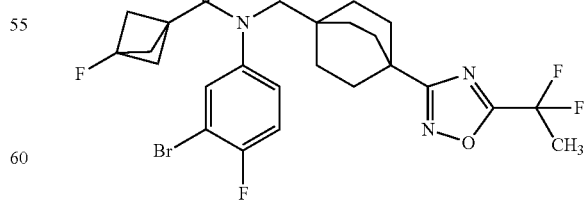

The title compound was prepared according to the method described for the synthesis of Example 3 by substituting Intermediate 574D where appropriate. (160 mg, 0.288 mmol, 85% yield) as brown gum. MS (ESI) 556 (M+H).

Step F. Example 574. Preparation of N-(3-cyclopropyl-4-fluorophenyl)-N-((4-(5-(1,1-difluoroethyl)-1,2,4-oxadiazol-3-yl)bicyclo[2.2.2]octan-1-yl)methyl)-3-fluorobicyclo[1.1.1]pentane-1-carboxamide The title compound was prepared according to the method described for the synthesis of Example 149 by substituting Intermediate 574E and cyclopropylboronic acid where appropriate. (13 mg, 0.024 mmol, 45% yield). $^1$H NMR (400 MHz, DMSO-$d_6$) δ 7.20 (d, J=8.3 Hz, 2H), 6.99 (d, J=7.3 Hz, 1H), 3.56 (d, J=13.2 Hz, 1H), 3.41 (d, J=13.9 Hz, 1H), 2.22-2.02 (m, 4H), 1.96-1.68 (m, 12H), 1.43 (d, J=7.8 Hz, 6H), 1.02 (d, J=8.6 Hz, 2H), 0.85-0.72 (m, 2H). FXR EC$_{50}$ (nM)=244. MS (ESI) 518 (M+H).

Example 575

N-(3-(azetidin-1-yl)-4-fluorophenyl)-N-((4-(5-(1,1-difluoroethyl)-1,2,4-oxadiazol-3-yl) bicyclo[2.2.2]octan-1-yl)methyl)-3-fluorobicyclo[1.1.1]pentane-1-carboxamide (575)

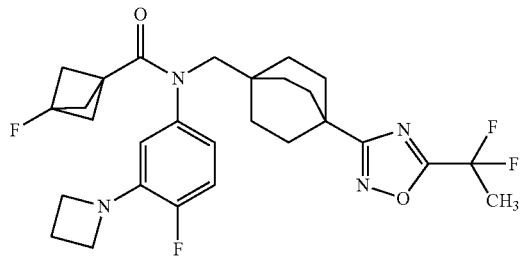

To a stirred solution of Intermediate 574E (30 mg, 0.054 mmol) in 1,4-dioxane (2 mL) was added azetidine (9.24 mg, 0.162 mmol), sodium tert-butoxide (15.55 mg, 0.162 mmol) and XantPhos (6.24 mg, 10.78 μmol). The resulting mixture was evacuated and back-filled with argon for 5 min and then Pd$_2$(dba)$_3$ (4.94 mg, 5.39 μmol) was added under argon atmosphere. After stirring at 110° C. overnight, the reaction mixture was concentrated under reduced pressure. The crude material was purified via preparative LC/MS using following conditions: Column: Waters XBridge C18, 150 mm×19 mm, 5 μm particles; Mobile Phase A: 5:95 acetonitrile:water with 10-mM ammonium acetate; Mobile Phase B: 95:5 acetonitrile:water with 10 mM ammonium acetate; Gradient: a 0 minute hold at 35% B, 35-85% B over 20 minutes, then a 5-minute hold at 100% B; Flow Rate: 15 mL/min; Column Temperature: 25° C. Fraction collection was triggered by signals. Fractions containing the desired product were combined and dried via centrifugal evaporation to afford the title compound (0.9 mg, 1.690 μmol, 3% yield). $^1$H NMR (400 MHz, DMSO-$d_6$) δ 7.07 (dd, J=8.4, 12.3 Hz, 1H), 6.71-6.60 (m, 1H), 6.45 (dd, J=2.6, 8.2 Hz, 1H), 4.00-3.84 (m, 4H), 3.65-3.55 (m, 1H), 3.37 (br s, 1H), 2.32-2.24 (m, 2H), 2.14 (t, J=19.6 Hz, 3H), 1.99-1.82 (m, 6H), 1.82-1.70 (m, 6H), 1.55-1.36 (m, 6H). FXR EC$_{50}$ (nM)=410. MS (ESI) 533 (M+H).

Example 576

(cis)-N-((4-(5-(2-fluoropropan-2-yl)-1,2,4-oxadiazol-3-yl)bicyclo[2.2.2]octan-1-yl) methyl)-3-hydroxy-N-(4'-(2-hydroxypropan-2-yl)-[1,1'-biphenyl]-3-yl)-3-(trifluoromethyl)cyclobutane-1-carboxamide (576)

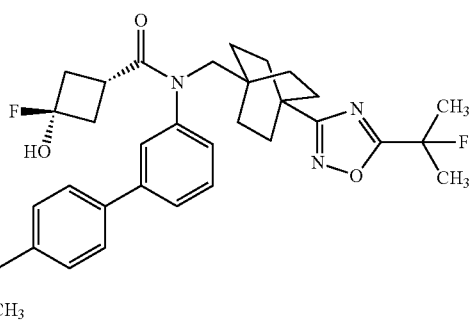

Step A. Intermediate 576A. Preparation of methyl 4-cyanobicyclo[2.2.2]octane-1-carboxylate

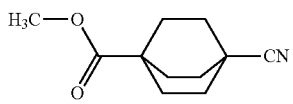

To a stirred solution of 4-(methoxycarbonyl)bicyclo [2.2.2]octane-1-carboxylic acid (15 g, 70.7 mmol) in DCM (225 mL) at room temperature were added ammonium chloride (9.45 g, 177 mmol), BOP (37.5 g, 85 mmol) and Et$_3$N (39.4 mL, 283 mmol). After stirring the reaction mixture for 1 h at room temperature, the reaction mixture was poured into cold water (100 mL) and extracted with DCM (2×150 mL). The combined organic layers were dried over MgSO$_4$, filtered and concentrated under reduced pressure to afford crude compound. The crude material was taken in pyridine (150 mL) at 0° C. and 2,2,2-trifluoroacetic anhydride (50.1 mL, 353 mmol) was added. The reaction mixture was stirred for 30 min at 0° C. The reaction mixture was poured into cold water (100 mL) and extracted with EtOAc (2×500 mL). The combined organic layers were washed with brine solution (250 mL), dried over MgSO$_4$, filtered and concentrated under reduced pressure. The crude product was purified by flash chromatography (120 g silica gel cartridge; A=Hex, B=EtOAc; 30 min grad.; 0% B to 30% B). The pure fractions were combined, concentrated and dried in vacuum to afford methyl 4-cyanobicyclo [2.2.2] octane-1-carboxylate (12 g, 62.1 mmol, 88% yield). as white solid. $^1$H NMR (400 MHz, DMSO-$d_6$) δ=3.58 (s, 3H), 1.93-1.83 (m, 6H), 1.78-1.68 (m, 6H).

Step B. Intermediate 576B. Preparation of methyl (E)-4-(N'-hydroxycarbamimidoyl) bicyclo[2.2.2]octane-1-carboxylate

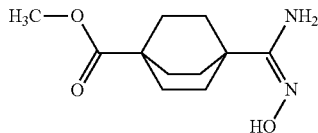 [SMILES: COC(=O)C12CCC(/C(N)=N\O)(CC1)CC2]

To a solution of methyl 4-cyanobicyclo[2.2.2]octane-1-carboxylate (12 g, 62.1 mmol) in ethanol (120 mL) was added aqueous 50% hydroxylamine (19.17 mL, 310 mmol). The reaction mixture was refluxed at 80° C. for 4 h. The reaction mixture was concentrated under reduced pressure and water (30 mL) was added. The reaction mixture was stirred for 10 minutes. The solids were filtered off and dried under vacuum to afford methyl (E)-4-(N'-hydroxycarbamimidoyl)bicyclo[2.2.2]octane-1-carboxylate (10 g, 44.2 mmol, 71% yield) as white solid. $^1$H NMR (400 MHz, CDCL$_3$-d) δ=8.88 (s, 1H), 5.15 (s, 2H), 3.57 (s, 3H), 1.73-1.62 (m, 12H). MS (ESI) 227 (M+H).

Step C. Intermediate 576C. Preparation of methyl 4-(5-(2-fluoropropan-2-yl)-1,2,4-oxadiazol-3-yl)bicyclo[2.2.2]octane-1-carboxylate

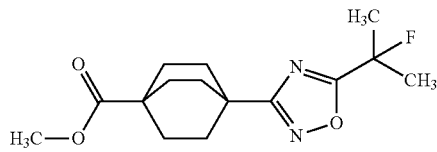

To a stirred solution of methyl (Z)-4-(N'-hydroxycarbamimidoyl) bicyclo[2.2.2]octane-1-carboxylate (10 g, 44.2 mmol) in DMF (100 mL) were added 2-fluoro-2-methylpropanoic acid (5.02 mL, 53.0 mmol) and Et$_3$N (18.48 mL, 133 mmol) followed by BOP (23.46 g, 53.0 mmol). The reaction mixture was stirred at room temperature for 1 h and then overnight at 110° C. The reaction mixture was concentrated, diluted with water (100 mL) and extracted with ethyl acetate (3×100 mL). The combined organic layers were dried over anhydrous sodium sulfate, concentrated under reduced pressure. The crude product was purified by flash chromatography (120 g silica gel cartridge; A=Hex, B=EtOAc; 30 min grad.; 0% B to 30% B). The pure fractions were combined, concentrated and dried in vacuum to afford methyl 4-(5-(2-fluoropropan-2-yl)-1,2,4-oxadiazol-3-yl)bicyclo[2.2.2]octane-1-carboxylate (8.2 g, 27.7 mmol, 63% yield) as colorless gummy solid. $^1$H NMR (400 MHz, DMSO-d$_6$) δ=3.60 (s, 3H), 1.92-1.79 (m, 15H), 1.76 (s, 3H). MS (ESI) 297 (M+H).

Step D. Intermediate 576D. Preparation of (4-(5-(2-fluoropropan-2-yl)-1,2,4-oxadiazol-3-yl)bicyclo[2.2.2]octan-1-yl)methanol

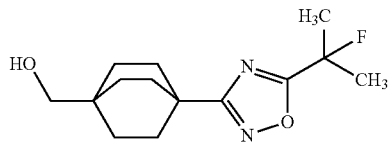 [SMILES: CC(C)(F)c1nc(C23CCC(CO)(CC2)CC3)no1]

To a stirred solution of methyl 4-(5-(2-fluoropropan-2-yl)-1,2,4-oxadiazol-3-yl) bicyclo[2.2.2]octane-1-carboxylate (7.5 g, 25.3 mmol) in THF (75 mL) was added DIBAL-H (63.3 mL, 76 mmol) drop wise at −78° C. The reaction mixture was allowed to warm up to room temperature and continued stirring for at room temperature for 2 h. The reaction mixture was quenched with aqueous 1.5 N HCl (50 mL) and the aqueous solution was extracted with EtOAc (2×100 mL). The combined organic layers were dried over anhydrous sodium sulphate, filtered and concentrated under reduced pressure. The crude product was purified by flash chromatography (40 g silica gel cartridge; A=Hex, B=EtOAc; 30 min grad.; 0% B to 40% B). The pure fractions were combined, concentrated and dried in vacuum to afford (4-(5-(2-fluoropropan-2-yl)-1,2,4-oxadiazol-3-yl)bicyclo[2.2.2]octan-1-yl)methanol (6.5 g, 24.22 mmol, 96% yield) as colorless liquid. $^1$H NMR (300 MHz, DMSO-d$_6$) δ=4.43 (t, J=5.4 Hz, 1H), 3.08 (d, J=5.4 Hz, 2H), 1.88-1.71 (m, 12H), 1.50-1.36 (m, 6H). MS (ESI) 269 (M+H).

Step E. Intermediate 576E. Preparation of 4-(5-(2-fluoropropan-2-yl)-1,2,4-oxadiazol-3-yl)bicyclo[2.2.2]octane-1-carbaldehyde

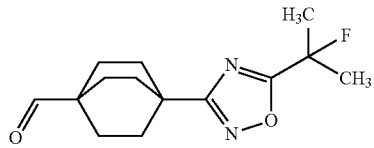 [SMILES: CC(C)(F)c1nc(C23CCC(C=O)(CC2)CC3)no1]

To a stirred solution of (4-(5-(2-fluoropropan-2-yl)-1,2,4-oxadiazol-3-yl) bicyclo[2.2.2]octan-1-yl)methanol (3.00 g, 11.18 mmol) in DCM (30 mL) 0° C. was added Dess-Martin periodinane (5.69 g, 13.42 mmol). The reaction mixture was stirred at 0° C. for 30 min and then diluted with DCM (50 mL). The organic solution was washed with aqueous 10% sodium bicarbonate solution (3×20 mL), dried over anhydrous sodium sulphate and concentrated under reduced pressure. The crude product was purified by flash chromatography (40 g silica gel cartridge; A=Hex, B=EtOAc; 30 min grad.; 0% B to 25% B). The pure fractions were combined, concentrated and dried in vacuum to afford 4-(5-(2-fluoropropan-2-yl)-1,2,4-oxadiazol-3-yl) bicyclo[2.2.2]octane-1-carbaldehyde (1.9 g, 7.13 mmol, 64% yield) as colorless white gummy solid. $^1$H NMR (400 MHz, DMSO-d$_6$) δ=9.50-9.40 (m, 1H), 1.97-1.50 (m, 18H)

Step F. Intermediate 576F. Preparation of 3-bromo-N-((4-(5-(2-fluoropropan-2-yl)-1,2,4-oxadiazol-3-yl)bicyclo[2.2.2]octan-1-yl)methyl)aniline

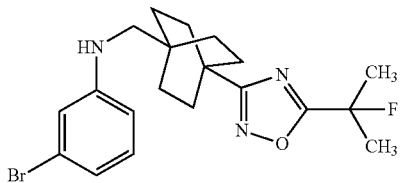 [SMILES: CC(C)(F)c1nc(C23CCC(CNc4cccc(Br)c4)(CC2)CC3)no1]

To a stirred solution of 4-(5-(2-fluoropropan-2-yl)-1,2,4-oxadiazol-3-yl) bicyclo[2.2.2]octane-1-carbaldehyde (1.9 g, 7.13 mmol) in MeOH (20 mL) was added 3-bromoaniline (1.227 g, 7.13 mmol) and AcOH (0.817 mL, 14.27 mmol) followed by 4 Å molecular sieves (100 mg). The reaction mixture was heated overnight at 60° C. The reaction mixture was then cooled to 0° C. and sodium cyanoborohydride (1.345 g, 21.40 mmol) was added to it and the reaction was gradually warmed up to room temperature over 1 h. The reaction mixture was concentrated and the residue was taken up in cold water (50 mL). The aqueous solution was extracted with EtOAc (2×50 mL). The combined organic layers were dried over MgSO$_4$, filtered and concentrated under reduced pressure. The crude material was purified by flash chromatography (40 g silica gel cartridge; A=Hex, B=EtOAc; 30 min grad.; 0% B to 30% B). The pure fractions were combined, concentrated and dried in vacuum to afford 3-bromo-N-((4-(5-(2-fluoropropan-2-yl)-1,2,4-oxadiazol-3-yl)bicyclo[2.2.2]octan-1-yl)methyl)aniline (2.3 g, 5.45 mmol, 76% yield). $^1$H NMR (300 MHz, DMSO-d$_6$) δ=7.01-6.92 (m, 1H), 6.76 (s, 1H), 6.59 (d, J=8.3 Hz, 2H), 5.79 (t, J=5.9 Hz, 1H), 2.80 (d, J=5.8 Hz, 2H), 1.90-1.79 (m, 9H), 1.75 (s, 3H), 1.62-1.48 (m, 6H). MS (ESI) 422 (M+H).

Step G. Intermediate 576G. Preparation of (cis)-N-(3-bromophenyl)-N-((4-(5-(2-fluoropropan-2-yl)-1,2,4-oxadiazol-3-yl)bicyclo[2.2.2]octan-1-yl)methyl)-3-hydroxy-3-(trifluoromethyl)cyclobutane-1-carboxamide

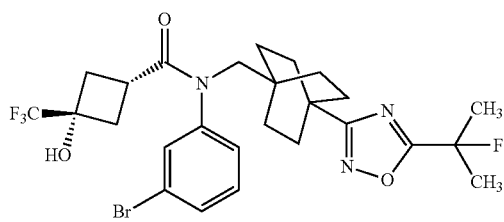 [SMILES: CC(C)(F)c1nc(C23CCC(CN(c4cccc(Br)c4)C(=O)[C@H]4C[C@](O)(C(F)(F)F)C4)(CC2)CC3)no1]

To a stirred solution of 3-bromo-N-((4-(5-(2-fluoropropan-2-yl)-1,2,4-oxadiazol-3-yl)bicyclo[2.2.2]octan-1-yl)methyl)aniline (1.8 g, 4.26 mmol) in DCM (20 mL) was added (cis)-3-hydroxy-3-(trifluoromethyl)cyclobutane-1-carboxylic acid (0.942 g, 5.11 mmol) followed by pyridine (1.724 mL, 21.31 mmol). The reaction mixture was cooled to 0° C. and POCl$_3$ (0.993 mL, 10.65 mmol) was added. After stirring the reaction mixture for 1 h at 0° C., DCM (250 mL) was added. The organic solution was washed with cold water (2×30 mL) followed by brine solution (30 mL). The organic layer was dried over anhydrous sodium sulfate, filtered and concentrated under reduced pressure. The crude material was purified by flash chromatography (40 g silica gel cartridge; A=Hex, B=EtOAc; 30 min grad.; 0% B to 50% B). The pure fractions were combined, concentrated and dried in vacuum to afford (cis)-N-(3-bromophenyl)-N-((4-(5-(2-fluoropropan-2-yl)-1,2,4-oxadiazol-3-yl)bicyclo[2.2.2]octan-1-yl)methyl)-3-hydroxy-3-trifluoromethyl)cyclobutane-1-carboxamide: (1.65 g, 2.80 mmol, 66% yield). $^1$H NMR (300 MHz, DMSO-d$_6$) δ=7.71 (s, 1H), 7.55 (d, J=7.6 Hz, 1H), 7.48-7.35 (m, 2H), 6.57 (s, 1H), 3.59 (br. s., 2H), 2.80-2.64 (m, 1H), 2.39-2.24 (m, 2H), 2.12-1.96 (m, 2H), 1.80 (s, 3H), 1.79-1.67 (m, 9H), 1.45-1.33 (m, 6H). MS (ESI) 588 (M+H).

Step H. Example 576. Preparation of (cis)-N-((4-(5-(2-fluoropropan-2-yl)-1,2,4-oxadiazol-3-1)bicyclo[2.2.2]octan-1-yl)methyl)-3-hydroxy-N-(4'-(2-hydroxypropan-2-yl)-[1,1'-biphenyl]-3-yl)-3-(trifluoromethyl)cyclobutane-1-carboxamide To a stirred solution of (cis)-N-(3-bromophenyl)-N-((4-(5-(2-fluoropropan-2-yl)-1,2,4-oxadiazol-3-yl)bicyclo[2.2.2]octan-1-yl)methyl)-3-hydroxy-3-(trifluoromethyl)cyclobutane-1-carboxamide (20 mg, 0.034 mmol) and (4-(2-hydroxypropan-2-yl)phenyl)boronic acid (6.12 mg, 0.034 mmol) in 1,4-dioxane (1 mL)/H$_2$O (0.1 mL) at room temperature was added K$_2$CO$_3$ (9.39 mg, 0.068 mmol). Argon gas was bubbled through the solution for 5 min and then Pd(dppf)Cl$_2$ (2.5 mg, 0.340 μmol)) was added. The reaction mixture was heated to 100° C. and stirred for 1 h. The reaction mixture was concentrated and the crude material was purified via preparative LC/MS with the following conditions: Column: Waters XBridge C18, 19×150 mm, 5-μm particles; Mobile Phase A: 10-mM ammonium acetate; Mobile Phase B: acetonitrile; Gradient: 40-80% B over 25 minutes, then a 5-minute hold at 100% B; Flow: 15 mL/min. Fractions containing the product were combined and dried via centrifugal evaporation to afford (cis)-N-((4-(5-(2-fluoropropan-2-yl)-1,2,4-oxadiazol-3-1)bicyclo[2.2.2]octan-1-yl) methyl)-3-hydroxy-N-(4'-(2-hydroxypropan-2-yl)-[1,1'-biphenyl]-3-yl)-3-(trifluoromethyl)cyclobutane-1-carboxamide (12.9 mg, 0.019 mmol, 56% yield). $^1$H NMR (400 MHz, DMSO-d$_6$) δ=7.71-7.60 (m, 4H), 7.59-7.54 (m, 2H), 7.51 (t, J=7.8 Hz, 1H), 7.38-7.31 (m, 1H), 6.53 (s, 1H), 5.08 (s, 1H), 3.73-3.62 (m, 2H), 2.85 (quin, J=9.0 Hz, 1H), 2.39-2.27 (m, 2H), 2.10-1.97 (m, 2H), 1.85-1.67 (m, 12H), 1.55-1.35 (m, 12H); FXR EC$_{50}$ (nM)=19; MS (ESI) 644 (M+H).

Example 577

(cis)-N-((4-(5-(2-fluoropropan-2-yl)-1,2,4-oxadiazol-3-yl)bicyclo[2.2.2]octan-1-yl) methyl)-3-hydroxy-N-(4'-(2-hydroxypropan-2-yl)-[1,1'-biphenyl]-3-yl)-3-methylcyclobutane-1-carboxamide

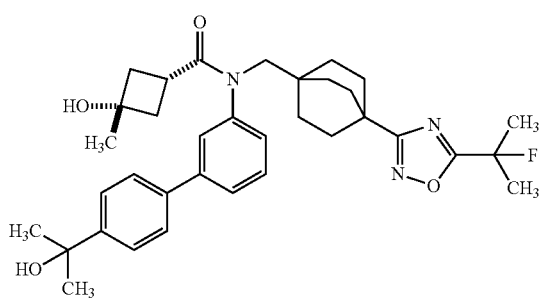

(577)

The title compound was synthesized according to the method described for the synthesis of Example 149 by substituting Intermediate 576E and the corresponding boronic acid where appropriate: (14.2 mg, 0.024 mmol, 51% yield); $^1$H NMR (400 MHz, DMSO-d$_6$) δ 7.65-7.55 (m, 6H), 7.49 (t, J=15.60 Hz, 1H), 7.30 (d, J=8.00 Hz, 1H), 5.05 (s, 1H), 4.88 (s, 1H), 3.65 (s, 2H), 2.62-2.57 (m, 1H), 2.15-2.10 (m, 2H), 1.79-1.73 (m, 12H), 1.65-1.62 (m, 2H), 1.46-1.44 (m, 12H), 0.98 (s, 3H); FXR EC$_{50}$ (nM)=23; MS (ESI) 590 (M+H).

Example 578

(cis)-N-(4'-(1-cyanocyclopropyl)-3'-fluoro-[1,1'-biphenyl]-3-yl)-N-((4-(5-(1-fluorocyclopropyl)-1,2,4-oxadiazol-3-yl)bicyclo[2.2.2]octan-1-yl)methyl)-3-hydroxy-3-(trifluoromethyl)cyclobutane-1-carboxamide (578)

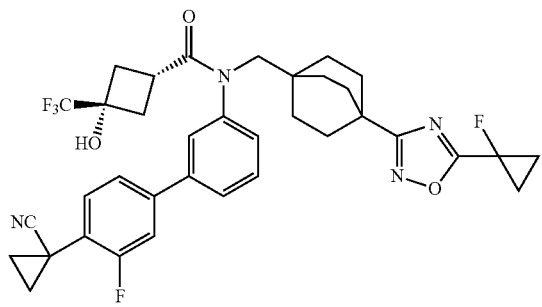

Step A. Intermediate 578A. Preparation of 3-bromo-N-((4-(5-(1-fluorocyclopropyl)-1,2,4-oxadiazol-3-yl)bicyclo[2.2.2]octan-1-yl)methyl)aniline

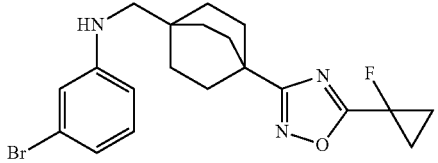 [SMILES: FC1(c2nc(C34CCC(CNc5cccc(Br)c5)(CC3)CC4)no2)CC1]

The title compound was synthesized according to the method described for the synthesis of Intermediate 3A by substituting Intermediate 194E and the corresponding acid where appropriate: (1.1 g, 2.62 mmol, 77% yield). MS (ESI) 420 (M+2).

Step B. Intermediate 578B. Preparation of (cis)-N-(3-bromophenyl)-N-((4-(5-(1-fluorocyclopropyl)-1,2,4-oxadiazol-3-yl)bicyclo[2.2.2]octan-1-yl)methyl)-3-hydroxy-3-(trifluoromethyl)cyclobutane-1-carboxamide

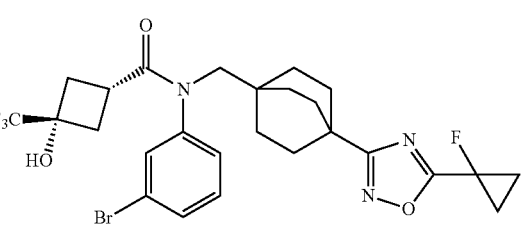

The title compound was synthesized according to the method described for the synthesis of Example 3 by substituting Intermediate 578A and the corresponding acid where appropriate: (420 mg, 0.594 mmol, 50% yield) as brown solid. MS (ESI) 586 (M+H).

Step C. Example 578. Preparation of (cis)-N-(4'-(1-cyanocyclopropyl)-3'-fluoro-[1,1'-biphenyl]-3-yl)-N-((4-(5-(1-fluorocyclopropyl)-1,2,4-oxadiazol-3-yl)bicyclo[2.2.2]octan-1-yl)methyl)-3-hydroxy-3-(trifluoromethyl)cyclobutane-1-carboxamide The title compound was synthesized according to the method described for the synthesis of Example 149 by substituting Intermediate 578B and the corresponding boronate ester where appropriate: (9.8 mg, 0.015 mmol, 43% yield). $^1$H NMR (400 MHz, DMSO-d$_6$) δ 7.81 (s, 1H), 7.72 (t, J=19.60 Hz, 2H), 7.61 (d, J=9.60 Hz, 1H), 7.54 (q, J=22.00 Hz, 2H), 7.43 (d, J=8.00 Hz, 1H), 6.51 (s, 1H), 3.68 (s, 2H), 2.88-2.83 (m, 1H), 2.50-2.30 (m, 2H), 2.08-2.03 (m, 2H), 1.80-1.72 (m, 10H), 1.52-1.44 (m, 10H). FXR EC$_{50}$ (nM)=92; MS (ESI) 667 (M+H).

Example 579

N-(3-(2-cyclopropylpyrimidin-5-yl)phenyl)-3-fluoro-N-((4-(5-(1-fluorocyclopropyl)-1,2,4-oxadiazol-3-yl)bicyclo[2.2.2]octan-1-yl)methyl)bicyclo[1.1.1]pentane-1-carboxamide (579)

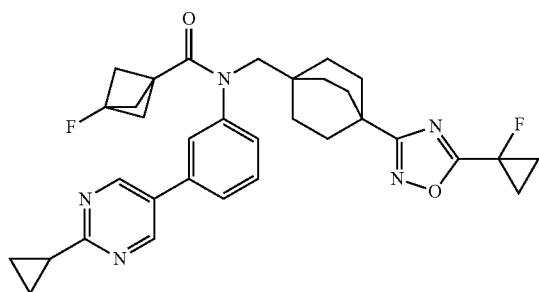

The title compound was synthesized according to the method described for the synthesis of Example 149 by substituting Intermediate 573A and the corresponding boronate ester where appropriate: (9.8 mg, 0.017 mmol, 30% yield). $^1$H NMR (400 MHz, DMSO-d$_6$) δ 9.03 (s, 2H), 7.88-7.81 (m, 1H), 7.79 (d, J=7.8 Hz, 1H), 7.58 (t, J=7.8 Hz, 1H), 7.46 (d, J=9.0 Hz, 1H), 3.60 (d, J=15.7 Hz, 2H), 2.32-2.23 (m, 1H), 1.95-1.80 (m, 6H), 1.79-1.67 (m, 8H), 1.54-1.36 (m, 8H), 1.11-1.05 (m, 4H). FXR EC$_{50}$ (nM)=45; MS (ESI) 572 (M+H).

Example 580

N-(3-(2-cyclopropylpyrimidin-5-yl)phenyl)-3-fluoro-N-((4-(5-(trifluoromethyl)-1,2,4-oxadiazol-3-yl)bicyclo[2.2.2]octan-1-yl)methyl)bicyclo[1.1.1]pentane-1-carboxamide (580)

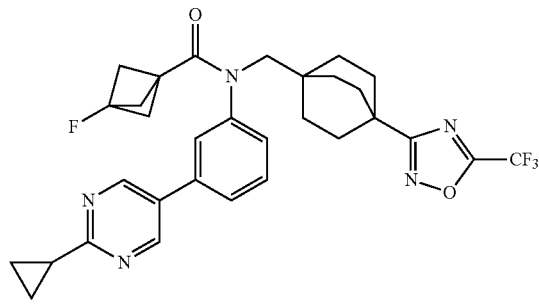

The title compound was synthesized according to the method described for the synthesis of Example 149 by substituting Intermediate 572A and the corresponding boronate ester where appropriate: (2.2 mg, 3.48 μmol, 8% yield). $^1$H NMR (400 MHz, DMSO-d$_6$) δ 9.03 (s, 2H), 7.84 (s, 1H), 7.79 (d, J=7.60 Hz, 1H), 7.58 (t, J=15.60 Hz, 1H), 7.46 (d, J=8.00 Hz, 1H), 3.60 (m, 2H), 2.33-2.32 (m, 1H), 1.88-1.78 (m, 12H), 1.50-1.47 (m, 6H), 1.10-1.04 (m, 4H). FXR EC$_{50}$ (nM)=160; MS (ESI) 582 (M+H).

Example 581

(cis)-N-(6-fluoro-4'-isopropoxy-[1,1'-biphenyl]-3-yl)-N-((4-(5-(1-fluorocyclopropyl)-1,2,4-oxadiazol-3-yl)bicyclo[2.2.2]octan-1-yl)methyl)-3-hydroxy-3-(trifluoromethyl)cyclobutane-1-carboxamide (581)

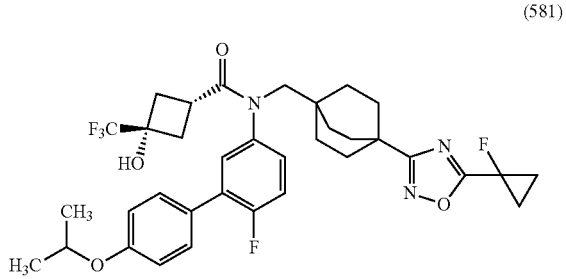 [SMILES: CC(C)Oc1ccc(-c2cc(N(CC34CCC(c5noc(C6(F)CC6)n5)(CC3)CC4)C(=O)[C@H]3C[C@](O)(C(F)(F)F)C3)ccc2F)cc1]

Step A. Intermediate 581A. Preparation of methyl 4-(((3-bromo-4-fluorophenyl)amino) methyl)bicyclo[2.2.2]octane-1-carboxylate

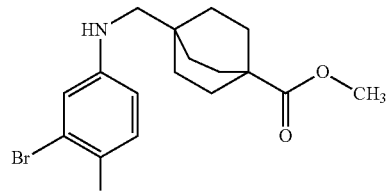

The title compound was synthesized according to the method described for the synthesis of Intermediate 1I by substituting 3-bromo-4-fluoroaniline and Intermediate 88B where appropriate: (1.5 g, 4.05 mmol, 77% yield). MS (ESI) 370 (M+H).

Step B. Intermediate 581B. Preparation of 4-(((3-bromo-4-fluorophenyl)amino) methyl)bicyclo[2.2.2]octane-1-carboxylic acid

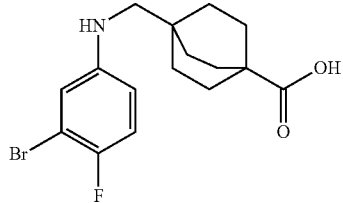

The title compound was synthesized according to the method described for the synthesis of Intermediate 175B by substituting Intermediate 581A where appropriate: (1.2 g, 3.37 mmol, 83% yield) as white solid. MS (ESI) 356 (M+H).

Step C. Intermediate 581C. Preparation of 4-(((3-bromo-4-fluorophenyl)amino) methyl)bicyclo[2.2.2]octane-1-carboxamide

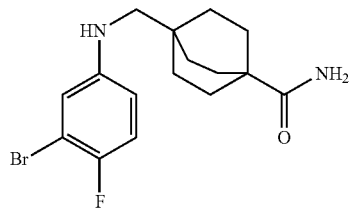 [SMILES: NC(=O)C12CCC(CNc3ccc(F)c(Br)c3)(CC1)CC2]

The title compound was synthesized according to the method described for the synthesis of Intermediate 184A by substituting Intermediate 581B where appropriate: (2 g Crude) as brown wax, which was taken as such for next step. MS (ESI) 355 (M+H).

Step D. Intermediate 581D. Preparation of 4-(((3-bromo-4-fluorophenyl)amino) methyl)bicyclo[2.2.2]octane-1-carbonitrile

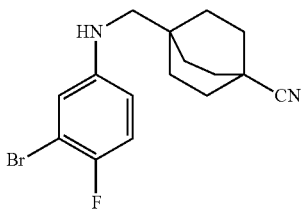 [SMILES: N#CC12CCC(CNc3ccc(F)c(Br)c3)(CC1)CC2]

The title compound was synthesized according to the method described for the synthesis of Intermediate 194D by substituting Intermediate 581C where appropriate; (1.6 g, 4.74 mmol, 84% yield) as white solid. MS (ESI) 339 (M+H).

Step E. Intermediate 581E. Preparation of 4-(((6-fluoro-4'-isopropoxy-[1,1'-biphenyl]-3-yl)amino) methyl)bicyclo[2.2.2]octane-1-carbonitrile

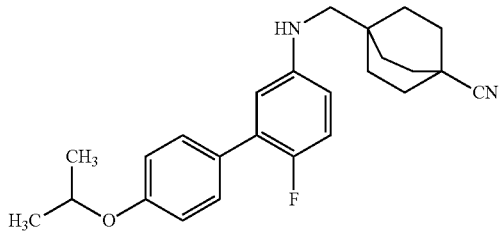 [SMILES: CC(C)Oc1ccc(-c2cc(NCC34CCC(C#N)(CC3)CC4)ccc2F)cc1]

The title compound was synthesized according to the method described for the synthesis of Example 149 by substituting Intermediate 581D where appropriate: (500 mg, 1.274 mmol, 86% yield) as brown wax. MS (ESI) 393 (M+H).

Step F. Intermediate 581F. Preparation of (cis)-N-((4-cyanobicyclo[2.2.2]octan-1-yl) methyl)-N-(6-fluoro-4'-isopropoxy-[1,1'-biphenyl]-3-yl)-3-hydroxy-3-(trifluoromethyl)cyclobutane-1-carboxamide

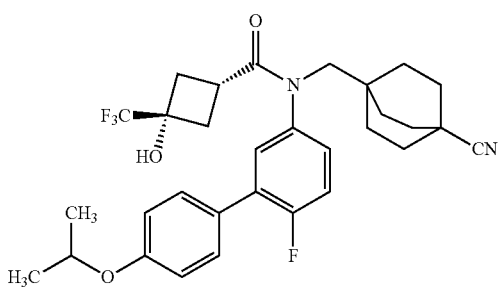 [SMILES: CC(C)Oc1ccc(-c2cc(N(CC34CCC(C#N)(CC3)CC4)C(=O)[C@H]3C[C@](O)(C(F)(F)F)C3)ccc2F)cc1]

The title compound was synthesized according to the method described for the synthesis of Example 3 by substituting Intermediate 581E and the corresponding acid where appropriate: (300 mg, 0.537 mmol, 56% yield) as brown wax. MS (ESI) 559 (M+H).

Step G. Intermediate 581G. Preparation of (cis)-N-(6-fluoro-4'-isopropoxy-[1,1'-biphenyl]-3-yl)-3-hydroxy-N-((4-((Z)—N'-hydroxycarbamimidoyl)bicyclo[2.2.2]octan-1-yl)methyl)-3-(trifluoromethyl)cyclobutane-1-carboxamide

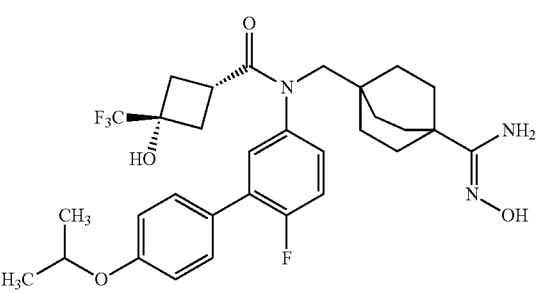 [SMILES: CC(C)Oc1ccc(-c2cc(N(CC34CCC(/C(N)=N/O)(CC3)CC4)C(=O)[C@H]3C[C@](O)(C(F)(F)F)C3)ccc2F)cc1]

The title compound was synthesized according to the method described for the synthesis of Intermediate 88F by substituting Intermediate 581F where appropriate: (240 mg, 0.406 mmol, 60% yield) as white solid. MS (ESI) 592 (M+H).

Step H. Example 581. Preparation of (cis)-N-(6-fluoro-4'-isopropoxy-[1,1'-biphenyl]-3-yl)-N-((4-(5-(1-fluorocyclopropyl)-1,2,4-oxadiazol-3-yl)bicyclo[2.2.2]octan-1-yl) methyl)-3-hydroxy-3-(trifluoromethyl)cyclobutane-1-carboxamide The title compound was synthesized according to the method described for the synthesis of Intermediate 3A by substituting Intermediate 581G and the corresponding acid where appropriate: (16.4 mg, 0.025 mmol, 49% yield). $^1$H NMR (400 MHz, DMSO-d$_6$) δ 7.56 (dd, J=7.09, 2.45 Hz, 1H), 7.50 (d, J=7.58 Hz, 2H), 7.42-7.29 (m, 2H), 7.04 (d, J=8.80 Hz, 2H), 6.52 (s, 1H), 4.69 (dt, J=12.10, 6.17 Hz, 1H), 3.74-3.50 (m, 2H), 2.84 (t, J=8.93 Hz, 1H), 2.39-2.28

(m, 2H), 2.15-2.00 (m, 2H), 1.83-1.68 (m, 8H), 1.52-1.35 (m, 8H), 1.30 (d, J=6.11 Hz, 6H). FXR EC$_{50}$ (nM)=74; MS (ESI) 660 (M+H).

Example 582

(cis)-N-(4'-((2-cyanopropan-2-yl)oxy)-6-fluoro-[1,1'-biphenyl]-3-yl)-N-((4-(5-(2-fluoropropan-2-yl)-1,2,4-oxadiazol-3-yl)bicyclo[2.2.2]octan-1-yl)methyl)-3-hydroxy-3-(trifluoromethyl)cyclobutane-1-carboxamide (582)

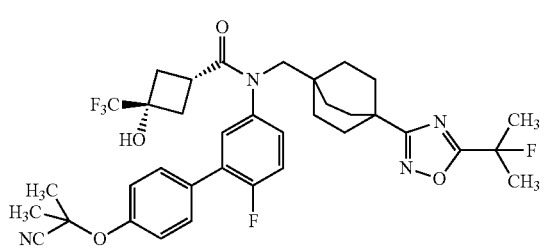

Step A. Intermediate 582A. Preparation of 3-bromo-4-fluoro-N-((4-(5-(2-fluoropropan-2-yl)-1,2,4-oxadiazol-3-yl)bicyclo[2.2.2]octan-1-yl)methyl) aniline

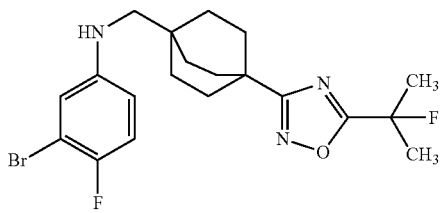 [SMILES: CC(C)(F)c1nc(C23CCC(CNc4ccc(F)c(Br)c4)(CC2)CC3)no1]

The title compound was synthesized according to the method described for the synthesis of Intermediate 1I by substituting 3-bromo-4-fluoroaniline and Intermediate 576C where appropriate: (590 mg, 1.340 mmol, 85% yield) as brown wax. MS (ESI) 440 (M+H).

Step B. Intermediate 582B. Preparation of (cis)-N-(3-bromo-4-fluorophenyl)-N-((4-(5-(2-fluoropropan-2-yl)-1,2,4-oxadiazol-3-yl)bicyclo[2.2.2]octan-1-yl)methyl)-3-hydroxy-3-(trifluoromethyl)cyclobutane-1-carboxamide

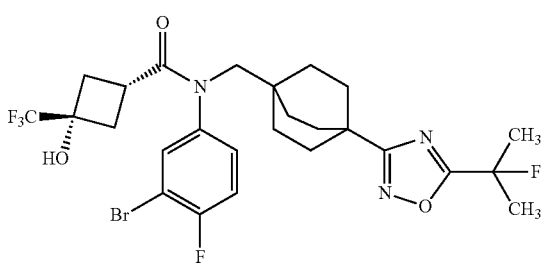 [SMILES: CC(C)(F)c1nc(C23CCC(CN(c4ccc(F)c(Br)c4)C(=O)[C@H]4C[C@](O)(C(F)(F)F)C4)(CC2)CC3)no1]

The title compound was synthesized according to the method described for the synthesis of Example 3 by substituting Intermediate 582A and the corresponding acid where appropriate: (240 mg, 0.396 mmol, 58% yield) as brown wax. MS (ESI) 608 (M+H).

Step C. Intermediate 582C. Preparation of 2-(4-bromophenoxy)-2-methylpropanenitrile

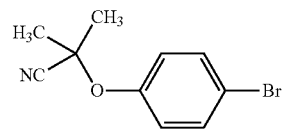

To a stirred solution of 2-(4-bromophenoxy)-2-methylpropanoic acid (2.0 g, 7.72 mmol) and ammonium chloride (2.064 g, 38.6 mmol) in DCM (20 mL) at room temperature was added BOP (5.12 g, 11.58 mmol). The reaction mixture was cooled to 0° C. and TEA (3.23 mL, 23.16 mmol) was added dropwise. After stirring at room temperature for 1 h, the reaction mixture was diluted with water (20 mL), and extracted with DCM (3×50 mL). The combined organic layers were dried over anhydrous sodium sulfate, filtered and concentrated under reduced pressure. The residue obtained was dissolved in pyridine (20 mL) and cooled to 0° C. To this reaction mixture, trifluoroacetic anhydride (2.432 g, 11.58 mmol) was added. The reaction mixture was allowed to warm up to room temperature and stirred for 2 h. The reaction mixture was diluted with water (30 mL) and extracted with ethyl acetate (3×20 mL). The combined organic layers were washed with 1.5 N aqueous HCl (2×50 mL), followed by brine solution (2×20 mL). The organic layer was dried over anhydrous sodium sulfate, filtered and concentrated under reduced pressure. The crude material was purified by flash chromatography (24 g silica gel cartridge; A=Hex, B=EtOAc; 30 min grad.; 0% B to 80% B; flow rate=30 mL/min). The pure fractions were combined, concentrated under reduced pressure and dried in vacuo to afford the title compound (750 mg, 3.12 mmol, 41% yield) as brown oil. $^{1}$H NMR (400 MHz, DMSO-d$_{6}$) δ 7.59-7.57 (m, 2H), 7.15-7.13 (m, 2H), 1.69 (s, 6H).

Step D. Intermediate 582D. Preparation of 2-(4-(5,5-dimethyl-1,3,2-dioxaborinan-2-yl) phenoxy)-2-methylpropanenitrile

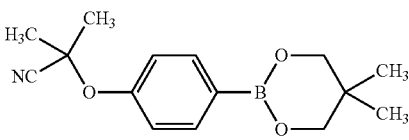 [SMILES: CC1(C)COB(c2ccc(OC(C)(C)C#N)cc2)OC1]

The title compound was synthesized according to the method described for the synthesis of Intermediate 149C by substituting Intermediate 582C and the corresponding acid where appropriate: (1.0 g, 3.66 mmol, 63% yield) as white fluffy solid. $^{1}$H NMR (400 MHz, DMSO-d6) δ 7.71 (d, J=8.00 Hz, 2H), 7.14 (d, J=8.00 Hz, 2H), 3.75 (s, 4H), 1.71 (s, 6H), 0.96 (s, 6H).

Step E. Example 582. Preparation of (cis)-N-(4'-((2-cyanopropan-2-yl)oxy)-6-fluoro-[1,1'-biphenyl]-3-yl)-N-((4-(5-(2-fluoropropan-2-yl)-1,2,4-oxadiazol-3-yl)bicyclo[2.2.2]octan-1-yl)methyl)-3-hydroxy-3-(trifluoromethyl)cyclobutane-1-carboxamide The title compound was synthesized according to the method described for the synthesis of example 149 by substituting Intermediate 582B and Intermediate 582D where appropriate: (12.4 mg, 0.018 mmol, 54% yield). $^1$H NMR (400 MHz, DMSO-$d_6$) δ 7.71-7.59 (m, 3H), 7.51-7.42 (m, 1H), 7.42-7.35 (m, 1H), 7.30 (d, J=8.6 Hz, 2H), 6.53 (s, 1H), 3.80-3.49 (m, 2H), 2.91-2.80 (m, 1H), 2.39-2.28 (m, 2H), 2.16-2.00 (m, 2H), 1.84-1.66 (m, 18H), 1.54-1.37 (m, 6H). FXR EC$_{50}$ (nM)=48; MS (ESI) 687 (M+H).

Example 583

(cis)-N-(4'-((2-cyanopropan-2-yl)oxy)-[1,1'-biphenyl]-3-yl)-N-((4-(5-(1-fluorocyclopropyl)-1,2,4-oxadiazol-3-yl)bicyclo[2.2.2]octan-1-yl)methyl)-3-hydroxy-3-(trifluoromethyl)cyclobutane-1-carboxamide (583)

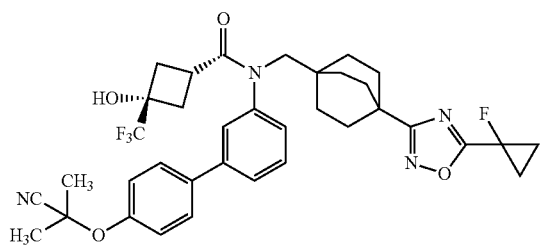

The title compound was synthesized according to the method described for the synthesis of Example 149 by substituting Intermediate 578B and Intermediate 582D where appropriate: (5.8 mg, 8.03 μmol, 24% yield). $^1$H NMR (400 MHz, DMSO-$d_6$) δ 7.77 (d, J=8.8 Hz, 2H), 7.71 (s, 1H), 7.65 (br d, J=7.8 Hz, 1H), 7.51 (t, J=7.9 Hz, 1H), 7.40-7.33 (m, 1H), 7.28 (d, J=8.8 Hz, 2H), 6.52 (s, 1H), 3.76-3.56 (m, 2H), 2.90-2.81 (m, 1H), 2.38-2.28 (m, 2H), 2.10-1.97 (m, 2H), 1.81-1.62 (m, 14H), 1.51-1.33 (m, 8H). FXR EC$_{50}$ (nM)=49; MS (ESI) 667 (M+H).

Example 584

1,1,1-trifluoro-2-methylpropan-2-yl ((4-(5-(2-fluoropropan-2-yl)-1,2,4-oxadiazol-3-yl) bicyclo[2.2.2]octan-1-yl)methyl)(4'-isopropoxy-[1,1'-biphenyl]-3-yl)carbamate (584)

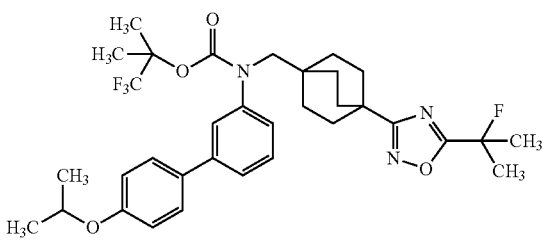

Step A. Intermediate 584A. Preparation of 1,1,1-trifluoro-2-methylpropan-2-yl(3-bromophenyl)((4-(5-(2-fluoropropan-2-yl)-1,2,4-oxadiazol-3-yl)bicyclo[2.2.2]octan-1-yl) methyl)carbamate

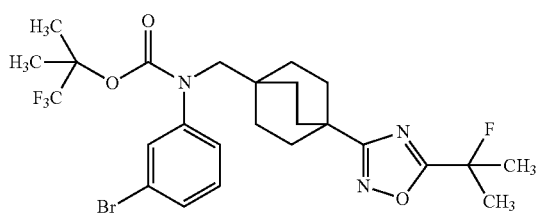 [SMILES: CC(C)(F)c1nc(C23CCC(CN(C(=O)OC(C)(C)C(F)(F)F)c4cccc(Br)c4)(CC2)CC3)no1]

To a stirred solution of Intermediate 576D (200 mg, 0.474 mmol) in tetrahydrofuran (10 mL) at −50° C. was added LiHMDS in THF (1.184 mL, 1.184 mmol). The reaction mixture was stirred at −50° C. for 10 min. A solution of pyridin-2-yl (1,1,1-trifluoro-2-methylpropan-2-yl) carbonate (236 mg, 0.947 mmol) in 0.5 mL of dry THF was added to the above at −50° C. and stirred for 1 h. The reaction mixture was quenched with aqueous saturated NH$_4$Cl solution (25 mL) and extracted with EtOAc (2×25 mL). The combined organic layers were dried over anhydrous sodium sulfate, filtered and concentrated under reduced pressure. The crude material was purified by flash chromatography (12 g silica gel cartridge; A=Hex, B=EtOAc; 30 min grad.; 0% B to 35% B). The pure fractions were combined, concentrated under reduced pressure and dried in vacuo to afford the title compound (150 mg, 0.247 mmol, 52% yield) as off-white solid. $^1$H NMR (300 MHz, DMSO-$d_6$) δ 7.62 (s, 1H), 7.46-7.28 (m, 3H), 3.57 (s, 2H), 1.83-1.68 (m, 12H), 1.64 (s, 6H), 1.51-1.17 (m, 6H). MS (ESI) 576 (M+H).

Step B. Example 584. Preparation of 1,1,1-trifluoro-2-methylpropan-2-yl ((4-(5-(2-fluoropropan-2-yl)-1,2,4-oxadiazol-3-yl)bicyclo[2.2.2]octan-1-yl) methyl)(4'-isopropoxy-[1,1'-biphenyl]-3-yl) carbamate The title compound was synthesized according to the method described for the synthesis of Example 149 by substituting Intermediate 584A and the corresponding boronic acid where appropriate: (13 mg, 0.020 mmol, 47% yield). $^1$H NMR (400 MHz, DMSO-$d_6$) δ 7.68-7.52 (m, 3H), 7.50-7.44 (m, 1H), 7.40 (t, J=7.9 Hz, 1H), 7.27 (br d, J=6.8 Hz, 1H), 7.01 (d, J=8.8 Hz, 2H), 4.67 (td, J=5.9, 12.1 Hz, 1H), 3.63 (s, 2H), 1.85-1.70 (m, 12H), 1.65 (s, 6H), 1.50-1.36 (m, 6H), 1.29 (d, J=6.1 Hz, 6H). FXR EC$_{50}$ (nM)=31; MS (ESI) 632 (M+H).

Example 585

3-cyano-N-((4-(5-(1,1-difluoroethyl)-1,2,4-oxadiazol-3-yl)bicyclo[2.2.2]octan-1-yl) methyl)-N-(4'-(2-hydroxypropan-2-yl)-[1,1'-biphenyl]-3-yl)bicyclo[1.1.1]pentane-1-carboxamide (585)

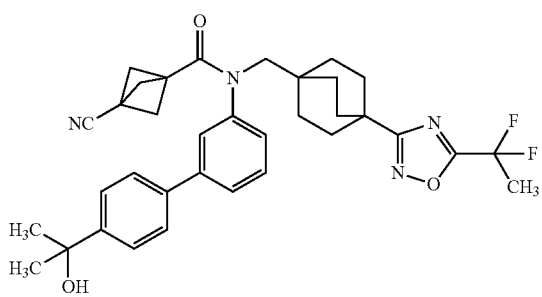

Step A. Intermediate 585A. Preparation of 3-bromo-N-((4-(5-(1,1-difluoroethyl)-1,2,4-oxadiazol-3-yl)bicyclo[2.2.2]octan-1-yl)methyl)aniline

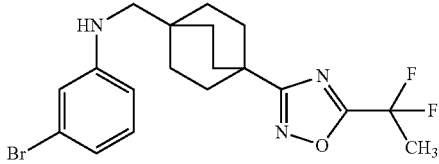 [SMILES: CC(F)(F)c1nc(C23CCC(CNc4cccc(Br)c4)(CC2)CC3)no1]

The title compound was prepared according to the method described for the synthesis of Intermediate 1I by substituting Intermediate 574C and 3-bromo aniline where appropriate. (150 mg, 0.334 mmol, 68% yield) as off-white solid. MS (ESI) 426 (M+H).

Step B. Intermediate 585B. Preparation of methyl 3-((3-bromophenyl)((4-(5-(1,1-difluoroethyl)-1,2,4-oxadiazol-3-yl)bicyclo[2.2.2]octan-1-yl)methyl)carbamoyl) bicyclo[1.1.1]pentane-1-carboxylate

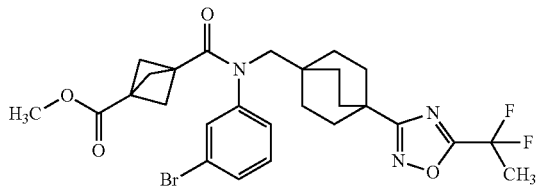 [SMILES: COC(=O)C12CC(C(=O)N(CC34CCC(c5noc(C(C)(F)F)n5)(CC3)CC4)c3cccc(Br)c3)(C1)C2]

The title compound was prepared according to the method described for the synthesis of Example 3 by substituting Intermediate 585A and 3-(methoxycarbonyl) bicyclo[1.1.1]pentane-1-carboxylic acid where appropriate. (120 mg, 0.197 mmol, 84% yield) as off-white solid. MS (ESI) 578 (M+H).

Step C. Intermediate 585C. Preparation of 3-((3-bromophenyl)((4-(5-(1,1-difluoroethyl)-1,2,4-oxadiazol-3-yl)bicyclo[2.2.2]octan-1-yl)methyl)carbamoyl)bicyclo[1.1.1]pentane-1-carboxylic acid

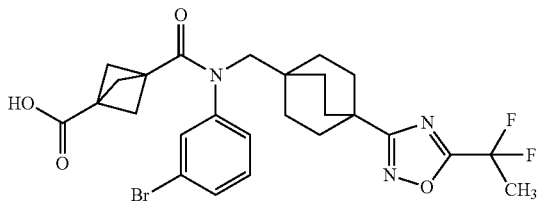 [SMILES: CC(F)(F)c1nc(C23CCC(CN(C(=O)C45CC(C(=O)O)(C4)C5)c4cccc(Br)c4)(CC2)CC3)no1]

The title compound was prepared according to the method described for the synthesis of Intermediate 145B by substituting Intermediate 585B where appropriate. (110 mg, 0.195 mmol, 94% yield) as brown gummy solid. MS (ESI) 564 (M+H).

Step D. Intermediate 585D. Preparation of N1-(3-bromophenyl)-N1-((4-(5-(1,1-difluoroethyl)-1,2,4-oxadiazol-3-yl)bicyclo[2.2.2]octan-1-yl)methyl)bicyclo[1.1.1]pentane-1,3-dicarboxamide

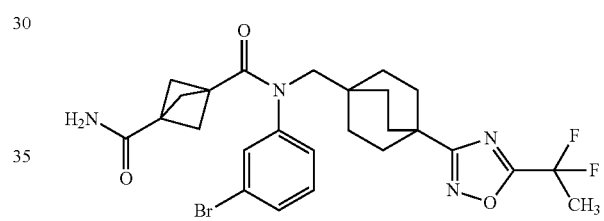

The title compound was prepared according to the method described for the synthesis of Intermediate 114A by substituting Intermediate 585C where appropriate. (100 mg, 0.169 mmol, 87% yield) as off-white solid. MS (ESI) 563 (M+H).

Step E. Intermediate 585E. Preparation of N-(3-bromophenyl)-3-cyano-N-((4-(5-(1,1-difluoroethyl)-1,2,4-oxadiazol-3-yl)bicyclo[2.2.2]octan-1-yl) methyl) bicyclo[1.1.1]pentane-1-carboxamide

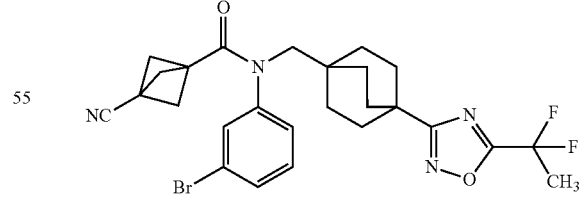

The title compound was prepared according to the method described for the synthesis of Intermediate 114B by substituting Intermediate 585D where appropriate. (80 mg, 0.139 mmol, 79% yield) as white solid. $^1$H NMR (300 MHz, DMSO-$d_6$) δ 7.77-7.72 (m, 1H), 7.62 (br d, J=7.3 Hz, 1H), 7.49-7.39 (m, 2H), 3.66-3.47 (m, 2H), 2.23-1.97 (m, 9H), 1.82-1.72 (m, 6H), 1.46-1.35 (m, 6H). MS (ESI) 545 (M+H).

Step F. Example 585. Preparation of 3-cyano-N-((4-(5-(1,1-difluoroethyl)-1,2,4-oxadiazol-3-yl)bicyclo[2.2.2]octan-1-yl)methyl)-N-(4'-(2-hydroxypropan-2-yl)-[1,1'-biphenyl]-3-yl)bicyclo[1.1.1]pentane-1-carboxamide The title compound was synthesized according to the method described for the synthesis of Example 149 by substituting Intermediate 585E and the corresponding boronic acid where appropriate: (13 mg, 0.021 mmol, 58% yield). $^1$H NMR (400 MHz, DMSO-$d_6$) δ 7.75-7.63 (m, 4H), 7.62-7.51 (m, 3H), 7.38 (br d, J=7.3 Hz, 1H), 5.07 (s, 1H), 3.65-3.49 (m, 2H), 2.20-1.93 (m, 9H), 1.86-1.72 (m, 6H), 1.58-1.28 (m, 12H). FXR $EC_{50}$ (nM)=18; MS (ESI) 601 (M+H).

Example 586

3-(tert-butyl)-1-(6-fluoro-4'-isopropoxy-[1,1'-biphenyl]-3-yl)-1-((4-(5-(1-fluorocyclopropyl)-1,2,4-oxadiazol-3-yl)bicyclo[2.2.2]octan-1-yl)methyl)urea (586)

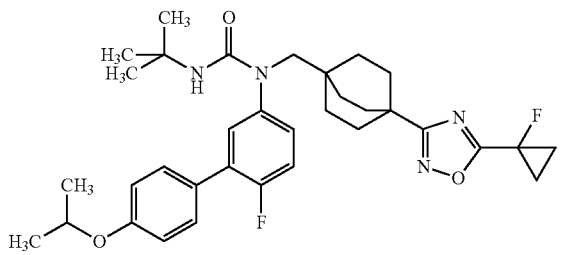

Step A. Intermediate 586A. Preparation of 6-fluoro-4'-isopropoxy-[1,1'-biphenyl]-3-amine

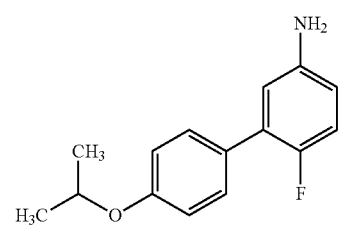 [SMILES: CC(C)Oc1ccc(-c2cc(N)ccc2F)cc1]

The title compound was prepared according to the method described for the synthesis of Example 149 by substituting 3-bromo-4-fluoroaniline and the corresponding boronic acid where appropriate: (1.0 g, 4.08 mmol, 86% yield). MS (ESI) 246 (M+H).

Step B. Intermediate 586B. Preparation of methyl 4-(5-(1-fluorocyclopropyl)-1,2,4-oxadiazol-3-yl)bicyclo[2.2.2]octane-1-carboxylate

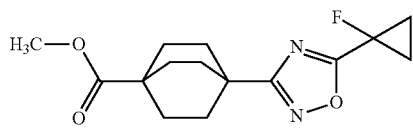 [SMILES: COC(=O)C12CCC(c3noc(C4(F)CC4)n3)(CC1)CC2]

The title compound was prepared according to the method described for the synthesis of Intermediate 3A by substituting Intermediate 206C and the corresponding acid where appropriate: (2.4 g, 8.07 mmol, 91% yield). MS (ESI) 295 (M+H).

Step C. Intermediate 586C. Preparation of (4-(5-(1-fluorocyclopropyl)-1,2,4-oxadiazol-3-yl)bicyclo[2.2.2]octan-1-yl)methanol

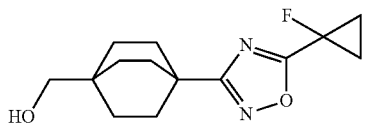 [SMILES: OCC12CCC(c3noc(C4(F)CC4)n3)(CC1)CC2]

The title compound was prepared according to the method described for the synthesis of Intermediate 1G by substituting Intermediate 586B where appropriate: (1.6 g, 6.01 mmol, 80% yield). MS (ESI) 267 (M+H).

Step D. Intermediate 586D. Preparation of 4-(5-(1-fluorocyclopropyl)-1,2,4-oxadiazol-3-yl)bicyclo[2.2.2]octane-1-carbaldehyde

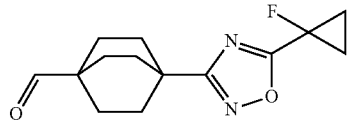 [SMILES: O=CC12CCC(c3noc(C4(F)CC4)n3)(CC1)CC2]

The title compound was prepared according to the method described for the synthesis of Intermediate 3C by substituting Intermediate 586C where appropriate: (1.6 g, 6.05 mmol, 77% yield). MS (ESI) 265 (M+H).

Step E. Intermediate 586E. Preparation of 6-fluoro-N-((4-(5-(1-fluorocyclopropyl)-1,2,4-oxadiazol-3-yl)bicyclo[2.2.2]octan-1-yl)methyl)-4'-isopropoxy-[1,1'-biphenyl]-3-amine

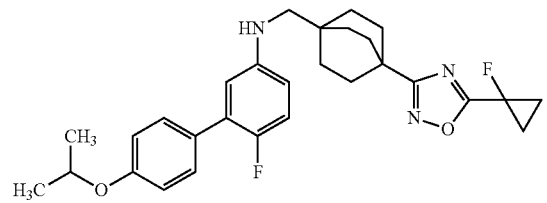 [SMILES: CC(C)Oc1ccc(-c2cc(NCC34CCC(c5noc(C6(F)CC6)n5)(CC3)CC4)ccc2F)cc1]

The title compound was prepared according to the method described for the synthesis of Intermediate 1I by substituting Intermediate 586D and Intermediate 586A where appropriate: (1.6 g, 3.24 mmol, 88% yield) as brown wax. MS (ESI) 494 (M+H).

Step F. Example 586. Preparation of 3-(tert-butyl)-1-(6-fluoro-4'-isopropoxy-[1,1'-biphenyl]-3-yl)-1-((4-(5-(1-fluorocyclopropyl)-1,2,4-oxadiazol-3-yl)bicyclo[2.2.2]octan-1-yl)methyl)urea To a stirred and cooled solution of Intermediate 586E (30 mg, 0.061 mmol) in DCM (1 mL) at 0° C. was added triphosgene (27.1 mg, 0.091 mmol) followed by TEA (0.051 mL, 0.365 mmol). After stirring reaction mixture overnight at room temperature, 2-methylpropan-2-amine (4.45 mg, 0.061 mmol) in THF (2 mL) was added followed by TEA (0.051 mL, 0.365 mmol). The reaction mixture was heated to 50° C. and stirred overnight. The reaction mixture was concentrated under reduced pressure. The crude material was purified via preparative LC/MS with the following conditions: Column: Waters XBridge C18, 150 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 2-minute hold at 15% B, 15-57% B over 25 minutes, then a 5-minute hold at 100% B; Flow Rate: 15 mL/min; Column Temperature: 25° C. Fraction collection was triggered by signals. Fractions containing the product were combined and dried via centrifugal evaporation to afford the title compound (21 mg, 0.034 mmol, 56% yield). $^1$H NMR (400 MHz, DMSO-$d_6$) δ 7.49 (d, J=7.3 Hz, 2H), 7.42 (br d, J=6.8 Hz, 1H), 7.30 (d, J=7.6 Hz, 2H), 7.03 (d, J=8.8 Hz, 2H), 4.75 (s, 1H), 4.68 (td, J=6.0, 12.0 Hz, 1H), 3.54 (s, 2H), 1.87-1.65 (m, 8H), 1.49-1.35 (m, 8H), 1.30 (d, J=5.9 Hz, 6H), 1.21 (s, 9H). FXR $EC_{50}$ (nM)=36; MS (ESI) 593 (M+H).

Example 587

(cis)-N-((4-(5-(2-fluoropropan-2-yl)-1,2,4-oxadiazol-3-yl)bicyclo[2.2.2]octan-1-yl)methyl)-3-hydroxy-N-(4'-(2-hydroxypropan-2-yl)-2',3',4',5'-tetrahydro-[1,1'-biphenyl]-3-yl)-3-(trifluoromethyl)cyclobutane-1-carboxamide (587)

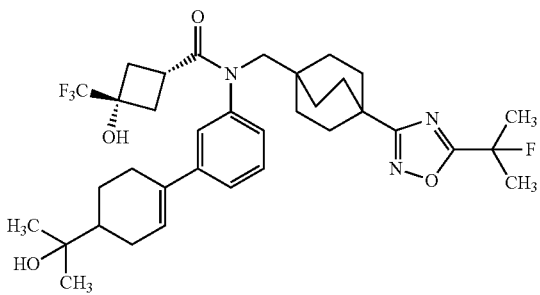

Step A. Intermediate 587A. Preparation of ethyl 3'-((cis)-N-((4-(5-(2-fluoropropan-2-yl)-1,2,4-oxadiazol-3-yl)bicyclo[2.2.2]octan-1-yl)methyl)-3-hydroxy-3-(trifluoromethyl) cyclobutane-1-carboxamido)-2,3,4,5-tetrahydro-[1,1'-biphenyl]-4-carboxylate

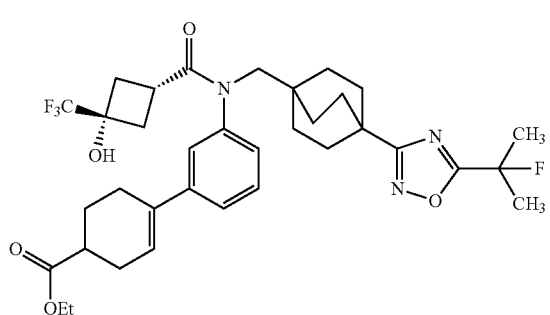 [SMILES: CCOC(=O)C1CC=C(c2cccc(N(CC34CCC(c5noc(C(C)(C)F)n5)(CC3)CC4)C(=O)[C@H]3C[C@](O)(C(F)(F)F)C3)c2)CC1]

The title compound was synthesized according to the method described for the synthesis of Example 149 by substituting Intermediate 576E and the corresponding boronic acid where appropriate: (44 mg, 0.066 mmol, 78% yield); MS (ESI) 662 (M+H).

Step B. Example 587. Preparation of (cis)-N-((4-(5-(2-fluoropropan-2-yl)-1,2,4-oxadiazol-3-yl)bicyclo[2.2.2]octan-1-yl)methyl)-3-hydroxy-N-(4'-(2-hydroxypropan-2-yl)-2',3',4',5'-tetrahydro-[1,1'-biphenyl]-3-yl)-3-(trifluoromethyl)cyclobutane-1-carboxamide A solution of Intermediate 587A (40 mg, 0.060 mmol) in THF (2 mL) was cooled to 0° C. and methylmagnesium bromide (0.201 mL, 0.604 mmol) was added. The reaction mixture was allowed to warm up to room temperature over 1 h. The reaction was quenched with saturated aqueous ammonium chloride solution (5 mL). The aqueous mixture was extracted with EtOAc (15 mL) and the organic layer was washed with brine (5 mL), dried over anhydrous sodium sulfate, filtered and concentrated under reduced pressure to afford a residue. The crude material was purified via preparative LC/MS with the following conditions: Column: Waters XBridge C18, 150 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 15% B, 15-65% B over 25 minutes, then a 5-minute hold at 100% B; Flow Rate: 15 mL/min; Column Temperature: 25° C. Fraction collection was triggered by MS signals. Fractions containing the product were combined and dried via centrifugal evaporation to afford the title compound (12.5 mg, 0.019 mmol, 32% yield); $^1$H NMR (400 MHz, DMSO-$d_6$) δ 7.44-7.29 (m, 3H), 7.26-7.15 (m, 1H), 6.52 (s, 1H), 6.31-6.17 (m, 1H), 4.23-3.99 (m, 1H), 3.76-3.50 (m, 2H), 2.80-2.64 (m, 1H), 2.47-2.22 (m, 4H), 2.12-1.87 (m, 5H), 1.83-1.64 (m, 12H), 1.54-1.33 (m, 6H), 1.31-1.16 (m, 2H), 1.09 (d, J=3.7 Hz, 6H). FXR $EC_{50}$ (nM)=42; MS (ESI) 648 (M+H).

Example 588

(cis)-N-(3-(3,6-dihydro-2H-pyran-4-yl)phenyl)-N-((4-(5-(2-fluoropropan-2-yl)-1,2,4-oxadiazol-3-yl)bicyclo[2.2.2]octan-1-yl)methyl)-3-hydroxy-3-(trifluoromethyl) cyclobutane-1-carboxamide (588)

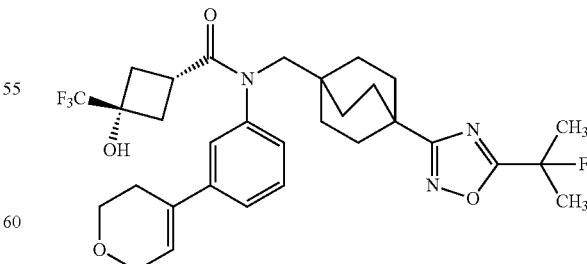

The title compound was synthesized according to the method described for the synthesis of Example 149 by substituting Intermediate 576E and the corresponding boronic acid where appropriate: (4.1 mg, 0.007 mmol, 16% yield). $^1$H NMR (400 MHz, DMSO-d$_6$) δ 7.71-7.33 (m, 4H), 7.30-7.16 (m, 1H), 6.57-6.46 (m, 1H), 6.39-6.29 (m, 1H), 4.50-4.43 (m, 1H), 4.24 (br d, J=2.45 Hz, 1H), 3.83 (t, J=5.50 Hz, 1H), 3.71-3.49 (m, 2H), 3.01-2.83 (m, 1H), 2.79-2.71 (m, 1H), 2.48-2.41 (m, 1H), 2.36-2.27 (m, 2H), 2.10-1.94 (m, 2H), 1.84-1.68 (m, 12H), 1.52-1.31 (m, 6H). FXR EC$_{50}$ (nM)=395; MS (ESI) 592 (M+H).

Example 589

N-((4-(5-(1,1-difluoroethyl)-1,2,4-oxadiazol-3-yl)bicyclo[2.2.2]octan-1-yl)methyl)-3-fluoro-N-(3-(4-hydroxypiperidin-1-yl)phenyl)bicyclo[1.1.1]pentane-1-carboxamide (589)

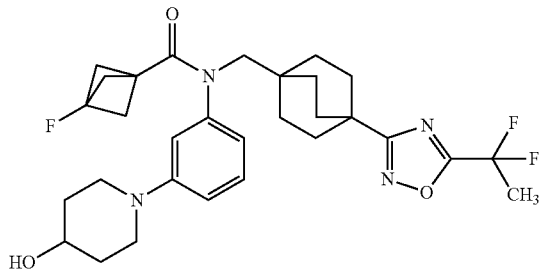

A solution containing Intermediate 527B (70 mg, 0.130 mmol), piperidin-4-ol (15.78 mg, 0.156 mmol), cesium carbonate (127 mg, 0.390 mmol) and (R)-(+)-BINAP (16.19 mg, 0.026 mmol) in 1,4-dioxane (2 mL) was degassed and backfilled with argon for three times and Pd$_2$(dba)$_3$ (11.91 mg, 0.013 mmol) was added. The reaction mixture was heated to 110° C. and stirred for 18 h. The mixture was cooled to room temperature and concentrated under reduced pressure to afford a residue. The crude material was purified via preparative LC/MS with the following conditions: Column: Waters XBridge C18, 150 mm×19 mm, 5-µm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 15% B, 15-50% B over 20 minutes, then a 5-minute hold at 100% B; Flow Rate: 15 mL/min. Fraction collection was triggered by signals. Fractions containing the product were combined and dried via centrifugal evaporation to afford N-((4-(5-(1,1-difluoroethyl)-1,2,4-oxadiazol-3-yl) bicyclo[2.2.2]octan-1-yl)methyl)-3-fluoro-N-(3-(4-hydroxypiperidin-1-yl)phenyl) bicyclo[1.1.1]pentane-1-carboxamide (1.0 mg, 1.679 µmol, 1% yield). $^1$H NMR (400 MHz, DMSO-d$_6$) δ 7.23 (t, J=7.9 Hz, 1H), 6.92 (dd, J=1.7, 8.6 Hz, 1H), 6.86 (s, 1H), 6.73-6.65 (m, 1H), 4.68 (d, J=4.2 Hz, 1H), 3.69-3.62 (m, 1H), 3.62-3.52 (m, 3H), 3.47-3.42 (m, 1H), 2.93-2.84 (m, 2H), 2.13 (t, J=19.7 Hz, 3H), 1.95-1.72 (m, 14H), 1.54-1.37 (m, 8H). FXR EC$_{50}$ (nM)=436; MS (ESI) 559 (M+H).

Example 590

(cis)-N-((4-(5-(2-fluoropropan-2-yl)-1,2,4-oxadiazol-3-yl)bicyclo[2.2.2]octan-1-yl)methyl)-3-hydroxy-N-(3-(6-(2-hydroxypropan-2-yl)spiro[3.3]hept-1-en-2-yl)phenyl)-3-(trifluoromethyl)cyclobutane-1-carboxamide (590)

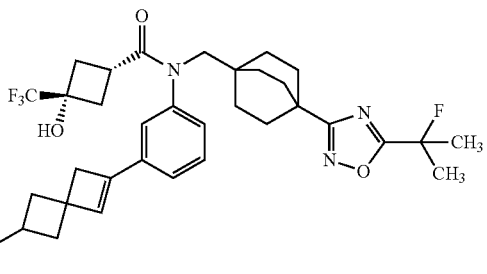

Step A. Intermediate 590A. Preparation of methyl 6-(((trifluoromethyl)sulfonyl)oxy) spiro[3.3]hept-5-ene-2-carboxylate

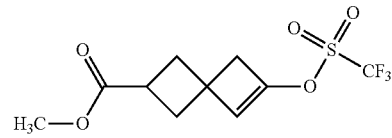 [SMILES: COC(=O)C1CC2(C=C(OS(=O)(=O)C(F)(F)F)C2)C1]

To a stirred solution of LiHMDS (8.92 mL, 8.92 mmol) in THF (2 mL) −78° C. was added a solution of methyl 6-oxospiro[3.3]heptane-2-carboxylate (500 mg, 2.97 mmol) in THF (2 mL) dropwise at −78° C. and stirred for 45 min. Subsequently, a solution of N-(5-chloropyridin-2-yl)-1,1,1-trifluoro-N-((trifluoromethyl)sulfonyl)methanesulfonamide (2.34 g, 5.95 mmol) in THF (5 mL) was added dropwise at −78° C. and the reaction mixture was allowed to warm up to room temperature and stirred for 1 h. The reaction mixture was quenched with water (10 mL) and the reaction mixture was extracted with ethyl acetate (2×20 mL). The combined organic layers were washed with water (10 mL) followed by brine solution (10 mL). The organic layer was dried over anhydrous sodium sulfate, filtered and concentrated under reduced pressure. The crude material was purified by flash chromatography (12 g silica gel cartridge; A=Hex, B=EtOAc; 30 min grad.; 0% B to 50% B). The pure fractions were combined, concentrated under reduced pressure and dried in vacuo to afford methyl 6-(((trifluoromethyl)sulfonyl)oxy)spiro[3.3]hept-5-ene-2-carboxylate (500 mg, 1.665 mmol, 56% yield) as yellow oil. MS (ESI) 318 (M+18).

Step B. Intermediate 590B. Preparation of methyl 6-(4,4,5,5-tetramethyl-1,3,2-dioxaborolan-2-yl)spiro[3.3]hept-5-ene-2-carboxylate

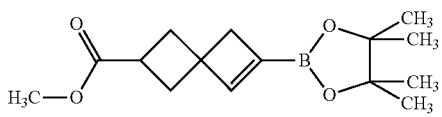

To a stirred solution of Intermediate 590A (300 mg, 0.999 mmol) in 1,4-dioxane (5 mL) at room temperature was added 4,4,4',4',5,5,5',5'-octamethyl-2,2'-bi(1,3,2-dioxaborolane) (507 mg, 1.998 mmol) and potassium acetate (441 mg, 4.50 mmol). The resulting reaction mixture was purged with argon for 5 min and Pd(dppf)Cl$_2$ (36.6 mg, 0.050 mmol) was added. The reaction mixture was heated to 110° C. and stirred for 2 h. The reaction mixture was concentrated under reduced pressure and the residue was diluted with ethyl acetate (20 mL). The resulting solution was washed with water (10 mL) followed by brine solution wash (10 mL). The organic layer was dried over anhydrous sodium sulfate, filtered and concentrated under reduced pressure. The crude material was purified by flash chromatography (12 g silica gel cartridge; A=Hex, B=EtOAc; 30 min grad.; 0% B to 80% B). The pure fractions were combined, concentrated under reduced pressure and dried in vacuo to afford methyl 6-(4,4,5,5-tetramethyl-1,3,2-dioxaborolan-2-yl)spiro[3.3]hept-5-ene-2-carboxylate (150 mg, 0.539 mmol, 54% yield) as brown oil. MS (ESI) 214 (M-64, boronic acid water adduct).

Step C. Example 590. Preparation of (cis)-N-((4-(5-(2-fluoropropan-2-yl)-1,2,4-oxadiazol-3-yl)bicyclo[2.2.2]octan-1-yl)methyl)-3-hydroxy-N-(3-(6-(2-hydroxypropan-2-yl)spiro[3.3]hept-1-en-2-yl)phenyl)-3-(trifluoromethyl)cyclobutane-1-carboxamide The title compound was synthesized according to the method described for the synthesis of Example 149 by substituting Intermediate 576E and Intermediate 590B where appropriate: (7.1 mg, 10.76 µmol, 24% yield). $^1$H NMR (400 MHz, DMSO-d$_6$) δ 7.43-7.32 (m, 2H), 7.30-7.19 (m, 2H), 6.75 (s, 1H), 6.54 (s, 1H), 6.45 (s, 1H), 4.10 (d, J=1.5 Hz, 1H), 3.81-3.43 (m, 2H), 2.78 (s, 1H), 2.74-2.65 (m, 1H), 2.61 (s, 1H), 2.32 (br t, J=10.9 Hz, 2H), 2.26-2.12 (m, 2H), 2.09-1.99 (m, 2H), 1.97-1.90 (m, 2H), 1.84-1.65 (m, 12H), 1.50-1.30 (m, 6H), 1.07-0.98 (m, 6H). FXR EC$_{50}$ (nM)=11; MS (ESI) 660 (M+H).

Example 591

1,1,1-trifluoro-2-methylpropan-2-yl (4'-(1-cyanocyclopropyl)-3'-fluoro-[1,1'-biphenyl]-3-yl)((4-(5-(2-fluoropropan-2-yl)-1,2,4-oxadiazol-3-yl)bicyclo[2.2.2]octan-1-yl)methyl) carbamate (591)

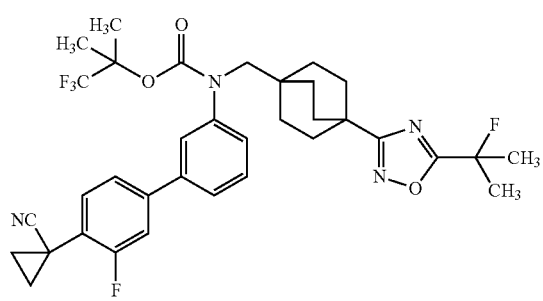

The title compound was synthesized according to the method described for the synthesis of Example 149 by substituting Intermediate 584A and the corresponding boronic acid where appropriate: (20 mg, 0.030 mmol, 70% yield). $^1$H NMR (400 MHz, DMSO-d$_6$) δ 7.78-7.64 (m, 2H), 7.62-7.51 (m, 3H), 7.49-7.42 (m, 1H), 7.41-7.32 (m, 1H), 3.65 (s, 2H), 1.82-1.71 (m, 14H), 1.69-1.60 (m, 6H), 1.53-1.47 (m, 2H), 1.41 (br dd, J=7.1, 7.8 Hz, 6H). FXR EC$_{50}$ (nM)=77; MS (ESI) 657 (M+H).

Example 592

(cis)-N-(3-(2-oxa-6-azaspiro[3.3]heptan-6-yl)phenyl)-N-((4-(5-(2-fluoropropan-2-yl)-1,2,4-oxadiazol-3-yl)bicyclo[2.2.2]octan-1-yl)methyl)-3-hydroxy-3-(trifluoromethyl)cyclobutane-1-carboxamide (592)

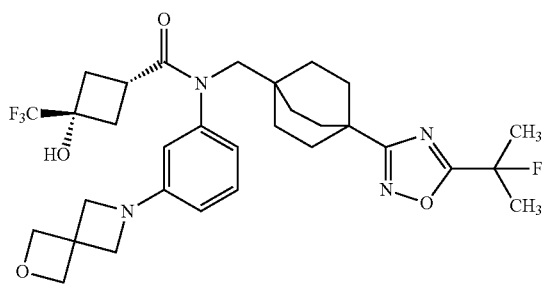

A solution containing Intermediate 576E (25 mg, 0.042 mmol), 2-oxa-6-azaspiro[3.3]heptane hemioxalate (12.25 mg, 0.042 mmol), X-PHOS (4.05 mg, 8.50 mol) and Cs$_2$CO$_3$ (27.7 mg, 0.085 mmol) in 1,4-dioxane (2 mL) was degassed and backfilled with argon for three times and Pd$_2$(dba)$_3$ (3.89 mg, 4.25 µmol) was added. The reaction mixture was heated to 110° C. and stirred for 18 h. The mixture was cooled to room temperature and concentrated under reduced pressure to afford a residue. The crude material was purified via preparative LC/MS using following conditions: Column: Waters XBridge C18, 150 mm×19 mm, 5 µm particles; Mobile Phase A: 5:95 acetonitrile:water with 10-mM ammonium acetate; Mobile Phase B: 95:5 acetonitrile:water with 10 mM ammonium acetate; Gradient: a 0 minute hold at 35% B, 35-85% B over 20 minutes, then a 5-minute hold at 100% B; Flow Rate: 15 mL/min; Column Temperature: 25° C. Fraction collection was triggered by signals. Fractions containing the product were combined and dried via centrifugal evaporation to afford the title compound (14.9 mg, 0.025 mmol, 58% yield). $^1$H NMR (400 MHz, DMSO-d$_6$) δ 7.24-7.14 (m, 1H), 6.62 (d, J=7.6 Hz, 1H), 6.54 (s, 1H), 6.41-6.31 (m, 2H), 4.72 (s, 3H), 3.97 (s, 3H), 3.69-3.43 (m, 4H), 2.82-2.69 (m, 1H), 2.38-2.25 (m, 2H), 2.19-1.98 (m, 2H), 1.83-1.67 (m, 12H), 1.53-1.27 (m, 6H). FXR EC$_{50}$ (nM)=970; MS (ESI) 607 (M+H).

Example 593

(cis)-N-((4-(5-(2-fluoropropan-2-yl)-1,2,4-oxadiazol-3-yl)bicyclo[2.2.2]octan-1-yl)methyl)-3-hydroxy-N-(3-(6-(2-hydroxypropan-2-yl)pyridazin-3-yl)phenyl)-3-(trifluoromethyl)cyclobutane-1-carboxamide

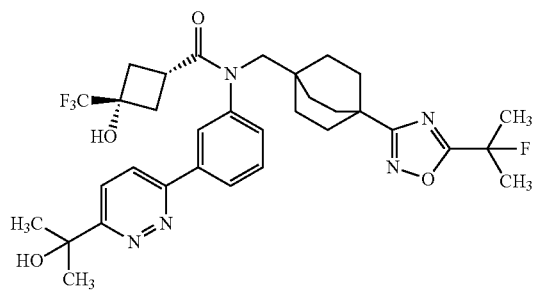

(593)

Step A. Intermediate 593A. Preparation of (cis)-N-((4-(5-(2-fluoropropan-2-yl)-1,2,4-oxadiazol-3-yl)bicyclo[2.2.2]octan-1-yl)methyl)-3-hydroxy-N-(3-(4,4,5,5-tetramethyl-1,3,2-dioxaborolan-2-yl)phenyl)-3-(trifluoromethyl)cyclobutane-1-carboxamide

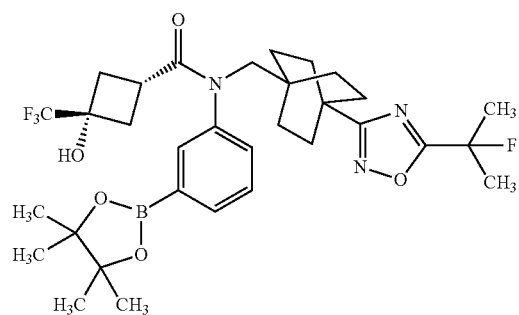 [SMILES: CC(C)(F)c1nc(C23CCC(CN(c4cccc(B5OC(C)(C)C(C)(C)O5)c4)C(=O)[C@H]4C[C@](O)(C(F)(F)F)C4)(CC2)CC3)no1]

A solution of Intermediate 576E (100 mg, 0.170 mmol), 4,4,4',4',5,5,5',5'-octamethyl-2,2'-bi(1,3,2-dioxaborolane) (51.8 mg, 0.204 mmol) and potassium acetate (41.7 mg, 0.425 mmol) in 1,4-dioxane (5 mL) was degassed and backfilled with argon for 5 min and PdCl$_2$(dppf) (9.95 mg, 0.014 mmol) was added. The reaction mixture was heated to 90° C. and stirred for 12 h. The reaction mixture was filtered through celite pad and the celite pad was washed with ethyl acetate (20 mL). The filtrate was concentrated under reduced pressure to afford a residue. The crude material was purified by flash chromatography (12 g silica gel cartridge; A=Hex, B=EtOAc; 30 min grad.; 0% B to 50% B; flow rate=24 mL/min). The pure fractions were combined, concentrated and dried in vacuo to afford the title compound (75 mg, 0.118 mmol, 69% yield). MS (ESI) 636 (M+H).

Step B. Intermediate 593B. Preparation of 2-(6-chloropyridazin-3-yl)propan-2-ol

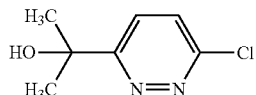

To a stirred solution of methyl magnesium bromide (5.79 mL, 17.38 mmol) in THF (2.5 mL) and toluene (10 mL) at −20° C. under N$_2$ atmosphere was added dropwise a solution of tert-butanol (0.554 mL, 5.79 mmol) in THF (7 mL). The reaction mixture was stirred for 30 min and then methyl 6-chloropyridazine-3-carboxylate (1 g, 5.79 mmol) was added in portions. The solution was allowed to warm up to 0° C. and stirred for 30 min. The reaction was quenched with aqueous 1 N HCl and the resulting solution was extracted with ethyl acetate (2×30 mL). The combined organic layers were washed with aqueous saturated sodium bicarbonate (20 mL) followed by brine solution (20 mL). The organic layer was dried over anhydrous sodium sulfate, filtered and concentrated under reduced pressure. The crude material was purified by flash chromatography (40 g silica gel cartridge; A=Hex, B=EtOAc; 30 min grad.; 0% B to 30% B; flow rate=40 mL/min). The pure fractions were combined, concentrated under reduced pressure to get crude compound to afford the title compound 2-(6-chloropyridazin-3-yl)propan-2-ol (800 mg, 4.63 mmol, 80% yield). MS (ESI) 173 (M+H)

Step C. Example 593. Preparation of (cis)-N-((4-(5-(2-fluoropropan-2-yl)-1,2,4-oxadiazol-3-yl)bicyclo[2.2.2]octan-1-yl)methyl)-3-hydroxy-N-(3-(4,4,5,5-tetramethyl-1,3,2-dioxaborolan-2-yl)phenyl)-3-(trifluoromethyl)cyclobutane-1-carboxamide The title compound was prepared according to the general method described for the synthesis of Example 149 by substituting Intermediate 593 A and Intermediate 593 B where appropriate: (20.5 mg, 0.032 mmol, 58% yield). $^1$H NMR (400 MHz, DMSO-d$_6$) δ 8.34-8.28 (m, 1H), 8.18-8.09 (m, 2H), 8.02-7.96 (m, 1H), 7.67-7.60 (m, 1H), 7.58-7.52 (m, 1H), 6.58-6.53 (m, 1H), 5.59-5.54 (m, 1H), 3.80-3.61 (m, 2H), 2.85-2.77 (m, 1H), 2.37-2.31 (m, 2H), 2.15-2.03 (m, 2H), 1.82-1.70 (m, 12H), 1.61-1.53 (m, 6H), 1.48-1.39 (m, 6H). FXR EC$_{50}$ (nM)=566. MS (ESI) 646 (M+H).

Example 594

3-fluoro-N-((4-(5-(2-fluoropropan-2-yl)-1,2,4-oxadiazol-3-yl)bicyclo[2.2.2]octan-1-yl) methyl)-N-(3-(6-oxo-1,6-dihydropyridazin-4-yl)phenyl)bicyclo[1.1.1]pentane-1-carboxamide

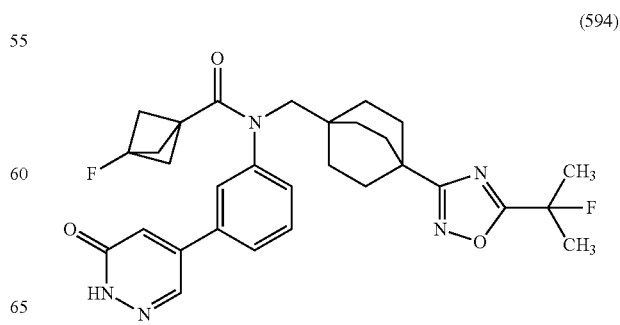

(594)

Step A. Intermediate 594A. Preparation of 5-(3-aminophenyl)pyridazin-3(2H)-one

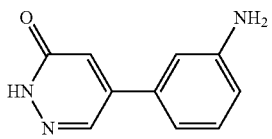 [SMILES: Nc1cccc(-c2cn[nH]c(=O)c2)c1]

The title compound was prepared according to the method described for the synthesis of Example 149 by substituting 5-chloropyridazin-3(2H)-one and (3-aminophenyl)boronic acid where appropriate: (450 mg, 2.404 mmol, 66% yield) as white solid. MS (ESI) 188 (M+H).

Step B. Intermediate 594B. Preparation of 5-(3-(((4-(5-(2-fluoropropan-2-yl)-1,2,4-oxadiazol-3-yl)bicyclo[2.2.2]octan-1-yl)methyl)amino)phenyl)pyridazin-3 (2H)-one

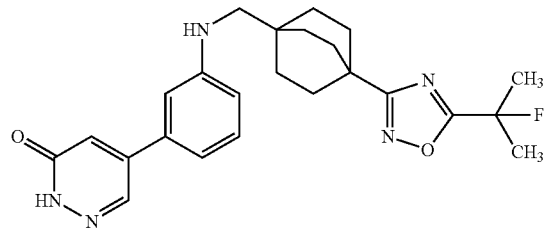 [SMILES: CC(C)(F)c1nc(C23CCC(CNc4cccc(-c5cn[nH]c(=O)c5)c4)(CC2)CC3)no1]

The title compound was prepared according to the method described for the synthesis of Intermediate 1F by substituting Intermediate 594A and Intermediate 576C where appropriate: (110 mg, 0.250 mmol, 47% yield) as an off-white solid. MS (ESI) 438 (M+H).

Step C. Example 594. Preparation of 3-fluoro-N-((4-(5-(2-fluoropropan-2-yl)-1,2,4-oxadiazol-3-yl)bicyclo[2.2.2]octan-1-yl)methyl)-N-(3-(6-oxo-1,6-dihydropyridazin-4-yl)phenyl)bicyclo[1.1.1]pentane-1-carboxamide The title compound was prepared according to the method described for the synthesis of Example 3 by substituting Intermediate 594B and the corresponding acid where appropriate: (10.2 mg, 0.018 mmol, 39% yield). $^1$H NMR (400 MHz, DMSO-$d_6$) δ 13.29-13.04 (m, 1H), 8.39 (d, J=2.0 Hz, 1H), 7.93 (s, 1H), 7.86 (d, J=7.6 Hz, 1H), 7.65-7.49 (m, 2H), 7.28 (d, J=2.0 Hz, 1H), 3.69-3.63 (m, 1H), 3.59-3.53 (m, 1H), 2.29 (d, J=2.7 Hz, 1H), 1.93-1.86 (m, 3H), 1.85-1.67 (m, 14H), 1.54-1.37 (m, 6H). FXR $EC_{50}$ (nM)=1838. MS (ESI) 567 (M+NH$_4$).

Example 595

(cis)-N-((4-(5-(2-fluoropropan-2-yl)-1,2,4-oxadiazol-3-yl)bicyclo[2.2.2]octan-1-yl)methyl)-3-hydroxy-N-(6-(4-(2-hydroxypropan-2-yl)phenyl)pyridin-2-yl)-3-(trifluoromethyl)cyclobutane-1-carboxamide (595)

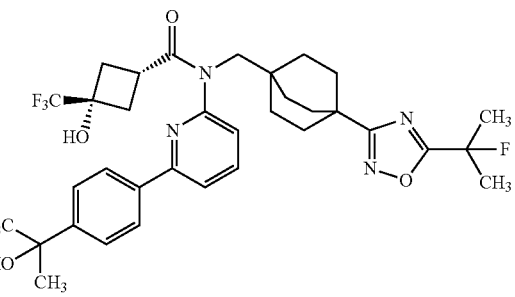

Step A. Intermediate 595A. Preparation of 6-bromo-N-((4-(5-(2-fluoropropan-2-yl)-1,2,4-oxadiazol-3-yl)bicyclo[2.2.2]octan-1-yl)methyl)pyridin-2-amine

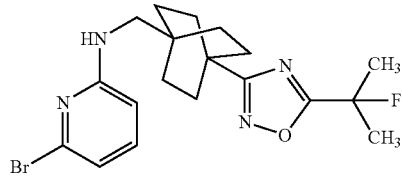 [SMILES: CC(C)(F)c1nc(C23CCC(CNc4cccc(Br)n4)(CC2)CC3)no1]

The title compound was synthesized according to the method described for the synthesis of Intermediate 1I by substituting Intermediate 576C and 6-bromopyridin-2-amine where appropriate: (170 mg, 0.402 mmol, 41% yield). MS (ESI) 423 (M+H).

Step B. Intermediate 595B. Preparation of (cis)-N-(6-bromopyridin-2-yl)-N-((4-(5-(2-fluoropropan-2-yl)-1,2,4-oxadiazol-3-yl)bicyclo[2.2.2]octan-1-yl)methyl)-3-hydroxy-3-(trifluoromethyl)cyclobutane-1-carboxamide

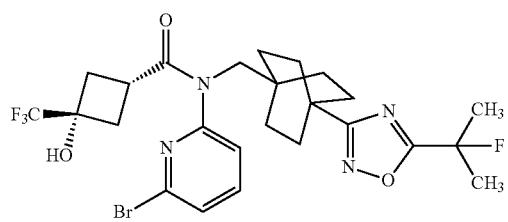 [SMILES: CC(C)(F)c1nc(C23CCC(CN(c4cccc(Br)n4)C(=O)[C@H]4C[C@](O)(C(F)(F)F)C4)(CC2)CC3)no1]

The title compound was synthesized according to the method described for the synthesis of Example 3 by substituting Intermediate 595A and the corresponding acid where appropriate: (200 mg, 0.339 mmol, 72% yield). MS (ESI) 589 (M+H).

Step C. Example 595. Preparation of (cis)-N-((4-(5-(2-fluoropropan-2-yl)-1,2,4-oxadiazol-3-yl)bicyclo[2.2.2]octan-1-yl)methyl)-3-hydroxy-N-(6-(4-(2-hydroxypropan-2-yl)phenyl)pyridin-2-yl)-3-(trifluoromethyl)cyclobutane-1-carboxamide The title compound was synthesized according to the method described for the synthesis of Example 149 by substituting Intermediate 595B and the corresponding boronic acid where appropriate: (12.9 mg, 0.019 mmol, 56% yield); 1H NMR (400 MHz, DMSO-d$_6$) δ 7.94-8.06 (m, 3H) 7.89 (d, J=7.83 Hz, 1H) 7.60 (d, J=8.56 Hz, 2H) 7.44 (d, J=7.83 Hz, 1H) 6.53 (s, 1H) 5.10 (s, 1H) 3.82 (s, 2H) 2.95-3.08 (m, 1H) 2.25-2.38 (m, 2H) 2.02-2.21 (m, 2H) 1.78 (s, 3H) 1.63-1.77 (m, 9H) 1.46 (s, 6H) 1.31-1.44 (m, 6H). FXR EC$_{50}$ (nM)=64; MS (ESI) 645 (M+H).

Example 596

N-((4-(5-(tert-butyl)-1,2,4-oxadiazol-3-yl)bicyclo[2.2.2]octan-1-yl)methyl)-N-(2-(2-ethoxypyrimidin-5-yl)pyridin-4-yl)-3-fluorobicyclo[1.1.1]pentane-1-carboxamide (596)

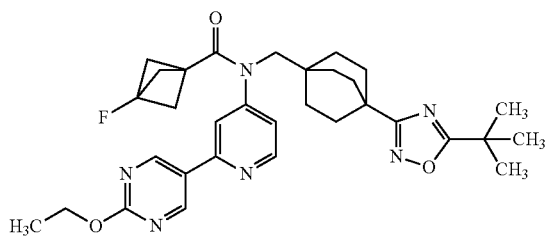

Step A. Intermediate 596A. Preparation of 2-bromo-N-((4-(5-(tert-butyl)-1,2,4-oxadiazol-3-yl)bicyclo[2.2.2]octan-1-yl)methyl)pyridin-4-amine

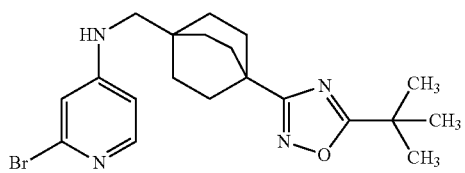 [SMILES: CC(C)(C)c1nc(C23CCC(CNc4ccnc(Br)c4)(CC2)CC3)no1]

The title compound was prepared according to the method described for the synthesis of Intermediate 1I by substituting 2-bromopyridin-4-amine and Intermediate 206F where appropriate: (350 mg, 0.793 mmol, 62% yield). MS (ESI) 421 (M+2H).

Step B. Intermediate 596B. N-(2-bromopyridin-4-yl)-N-((4-(5-(tert-butyl)-1,2,4-oxadiazol-3-yl)bicyclo[2.2.2]octan-1-yl)methyl)-3-fluorobicyclo[1.1.1]pentane-1-carboxamide

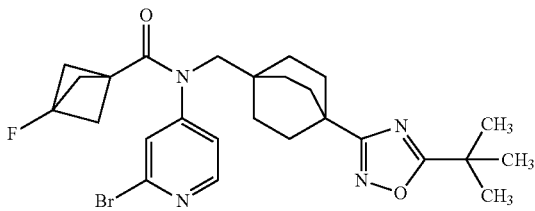 [SMILES: CC(C)(C)c1nc(C23CCC(CN(C(=O)C45CC(F)(C4)C5)c4ccnc(Br)c4)(CC2)CC3)no1]

The title compound was synthesized according to the method described for the synthesis of Example 3 by substituting Intermediate 596B and the corresponding acid where appropriate: (50 mg, 0.085 mmol, 36% yield). MS (ESI) 533 (M+2H).

Step C. Example 596. Preparation of N-((4-(5-(tert-butyl)-1,2,4-oxadiazol-3-yl)bicyclo[2.2.2]octan-1-yl)methyl)-N-(2-(2-ethoxypyrimidin-5-yl)pyridin-4-yl)-3-fluorobicyclo[1.1.1]pentane-1-carboxamide The title compound was synthesized according to the method described for the synthesis of Example 149 by substituting Intermediate 596B and the corresponding boronic acid where appropriate: (9.1 mg, 0.015 mmol, 32% yield). $^1$H NMR (400 MHz, DMSO-d$_6$) δ 9.33 (s, 2H), 8.74 (d, J=5.4 Hz, 1H), 8.18 (d, J=1.7 Hz, 1H), 7.51 (dd, J=5.3, 1.8 Hz, 1H), 4.45 (q, J=7.1 Hz, 2H), 3.65 (s, 2H), 1.98 (d, J=2.4 Hz, 6H), 1.84-1.65 (m, 6H), 1.54-1.34 (m, 9H), 1.33 (s, 9H). FXR EC$_{50}$ (nM)=321; MS (ESI) 575 (M+H).

Example 597

N-((4-(5-(tert-butyl)-1,2,4-oxadiazol-3-yl)bicyclo[2.2.2]octan-1-yl)methyl)-N-(2-(2-cyclopropylpyrimidin-5-yl)pyridin-4-yl)-3-fluorobicyclo[1.1.1]pentane-1-carboxamide (597)

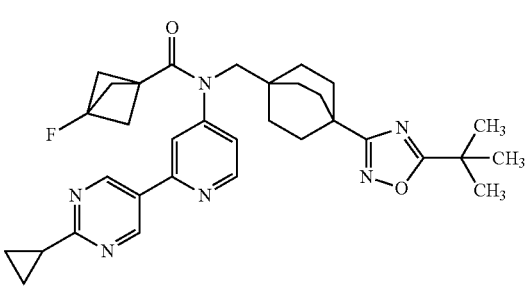

The title compound was synthesized according to the method described for the synthesis of Example 149 by substituting Intermediate 596B and the corresponding boronic acid where appropriate: (12.2 mg, 0.021 mmol, 45% yield). $^1$H NMR (400 MHz, DMSO-d$_6$) δ 9.35 (s, 2H), 8.77 (d, J=5.4 Hz, 1H), 8.21 (d, J=1.5 Hz, 1H), 7.54 (dd, J=5.3, 1.8 Hz, 1H), 3.65 (s, 2H), 2.30 (ddd, J=12.8, 7.9, 5.4 Hz, 1H), 1.97 (d, J=2.4 Hz, 6H), 1.83-1.59 (m, 6H), 1.53-1.36

(m, 6H), 1.33 (s, 9H), 1.20-1.00 (m, 4H). FXR EC$_{50}$ (nM)=226; MS (ESI) 571 (M+H).

Example 598

2-cyanopropan-2-yl ((4-(5-(2-fluoropropan-2-yl)-1, 2,4-oxadiazol-3-yl) bicyclo[2.2.2]octan-1-yl)methyl) (4'-(2-hydroxypropan-2-yl)-[1,1'-biphenyl]-3-yl) carbamate

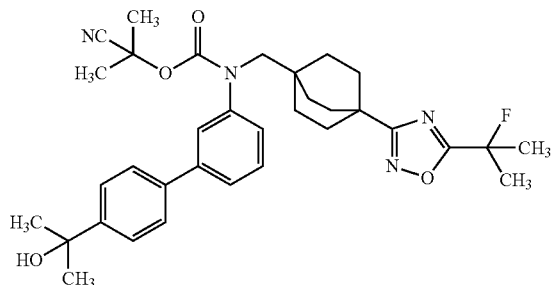

(598)

Step A. Intermediate 598A. Preparation of 2-cyanopropan-2-yl carbonochloridate

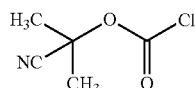

To a stirred solution of phosgene (3.09 mL, 5.88 mmol) under nitrogen at −15° C. was added a solution of 2-hydroxy-2-methylpropanenitrile (500 mg, 5.88 mmol) in pyridine (1 mL). The reaction mixture was allowed to warm up to room temperature and stirred overnight. The reaction mixture was filtered over a celite pad and the filtrate was concentrated to afford 2-cyanopropan-2-yl carbonochloridate (300 mg, 2.040 mmol, 34% yield), which and used in the next step without further purification. $^1$H NMR (400 MHz, DMSO-d$_6$) δ 1.48 (s, 6H).

Step B. Intermediate 598B. Preparation of 2-(3'-(((4-(5-(2-fluoropropan-2-yl)-1,2,4-oxadiazol-3-yl) bicyclo[2.2.2]octan-1-yl)methyl)amino)-[1,1'-biphenyl]-4-yl)propan-2-ol

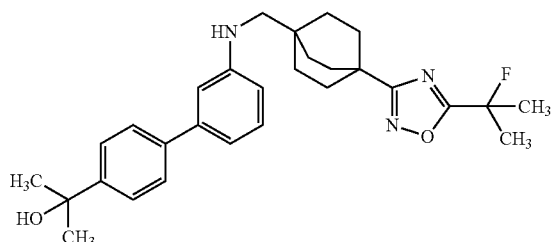

The title compound was synthesized according to the method described for the synthesis of Example 149 by substituting Intermediate 576D and the corresponding boronic acid where appropriate: (160 mg, 0.301 mmol, 64% yield), MS (ESI) 478 (M+H).

Step C. Example 598: Preparation of 2-cyanopropan-2-yl ((4-(5-(2-fluoropropan-2-yl)-1,2,4-oxadiazol-3-yl)bicyclo[2.2.2]octan-1-yl)methyl)(4'-(2-hydroxypropan-2-yl)-[1,1'-biphenyl]-3-yl)carbamate To a stirred solution of Intermediate 598B (30 mg, 0.063 mmol) in DCM (1 mL) at room temperature was added Intermediate 598A (9.27 mg, 0.063 mmol) followed by pyridine (5.08 μL, 0.063 mmol). After stirring for 2 h at room temperature, the reaction mixture was concentrated under reduced pressure. The crude material was purified via preparative LC/MS with the following conditions: Column: Waters XBridge C18, 150 mm×19 mm, 5-μm particles; Mobile Phase A: 5:95 acetonitrile:water with 0.1% trifluoroacetic acid; Mobile Phase B: 95:5 acetonitrile:water with 0.1% trifluoroacetic acid; Gradient: a 0-minute hold at 20% B, 20-70% B over 20 minutes, then a 5-minute hold at 100% B; Flow Rate: 15 mL/min; Column Temperature: 25° C. Fraction collection was triggered by MS signals. Fractions containing the desired product were combined and dried via centrifugal evaporation to afford the title compound (5.7 mg, 9.68 μmol, 15% yield). $^1$H NMR (400 MHz, DMSO-d$_6$) δ 7.70-7.60 (m, 3H), 7.60-7.51 (m, 3H), 7.46 (t, J=7.8 Hz, 1H), 7.40-7.29 (m, 1H), 5.05 (s, 1H), 3.68 (s, 2H), 1.87-1.57 (m, 18H), 1.50-1.35 (m, 12H). FXR EC$_{50}$ (nM)=29. MS (ESI) 589 (M+H).

Example 599

1-((4-(5-(2-fluoropropan-2-yl)-1,2,4-oxadiazol-3-yl) bicyclo[2.2.2]octan-1-yl)methyl)-3-((trans)-4-hydroxy-4-methylcyclohexyl)-1-(4'-(2-hydroxypropan-2-yl)-[1,1'-biphenyl]-3-yl)urea

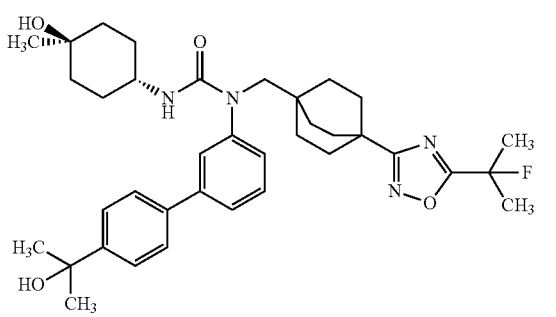

(599)

The title compound was synthesized according to the method described for the synthesis of Example 586 by substituting Intermediate 598B and (trans)-4-amino-1-methylcyclohexan-1-ol where appropriate: (22.1 mg, 0.035 mmol, 38% yield). $^1$H NMR (400 MHz, DMSO-d$_6$) δ 7.63-7.60 (m, 2H), 7.60-7.56 (m, 2H), 7.55 (s, 1H), 7.52 (d, J=11.00 Hz, 1H), 7.49-7.46 (m, 1H), 7.30 (d, J=7.58 Hz, 1H), 5.20-5.15 (m, 1H), 5.06 (s, 1H), 4.17 (s, 1H), 3.60 (s, 2H), 3.53-3.46 (m, 1H), 1.79 (s, 3H), 1.78-1.70 (m, 9H), 1.66-1.59 (m, 2H), 1.46 (s, 6H), 1.45-1.37 (m, 6H), 1.37-1.23 (m, 6H), 0.99 (s, 3H). FXR EC$_{50}$ (nM)=30; MS (ESI) 633 (M+H).

Example 600

1-((4-(5-(2-fluoropropan-2-yl)-1,2,4-oxadiazol-3-yl)bicyclo[2.2.2]octan-1-yl) methyl)-3-(4-hydroxy-4-(trifluoromethyl) cyclohexyl)-1-(4'-(2-hydroxypropan-2-yl)-[1,1'-biphenyl]-3-yl) urea (Isomer-1)

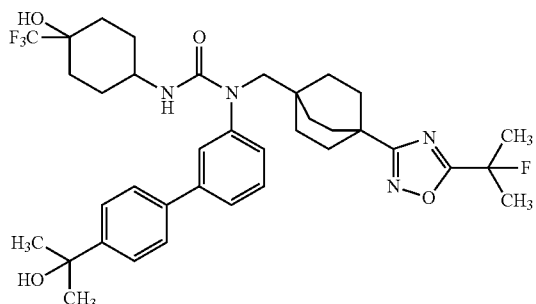

(600)

Step A. Intermediate 600A. Preparation of 8-(trifluoromethyl)-1, 4-dioxaspiro [4.5]decan-8-ol

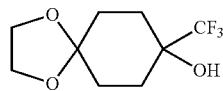

To a stirred solution of 1,4-dioxaspiro[4.5]decan-8-one (3 g, 19.21 mmol) in THF (80 mL) at −10° C., was added (trifluoromethyl)trimethylsilane (5.46 g, 38.4 mmol) dropwise followed by TBAF (1M solution in THF) (38.4 mL, 38.4 mmol). The resulting mixture was allowed to warm to room temperature and stirred for 4 h. Aqueous saturated ammonium chloride solution (30 mL) was added to the reaction mixture and the mixture was stirred for 10 minutes. The resulting solution was extracted with diethylether (3×50 mL). The combined ether extracts were dried over Na$_2$SO$_4$, filtered, and concentrated under reduced pressure to afford the title compound (3.6 g, 15.92 mmol, 83% yield) as a brown oil. $^1$H NMR (400 MHz, DMSO-d$_6$) δ 5.83 (s, 1H), 3.87 (s, 4H), 1.71-1.80 (m, 4H), 1.56-1.67 (m, 4H). MS (ESI) 227 (M+H).

Step B. Intermediate 600B. Preparation of 4-hydroxy-4-(trifluoromethyl) cyclohexan-1-one

To a stirred solution of Intermediate 600A (3 g, 13.26 mmol) in THF (80 mL) at room temperature was added aqueous 1.5N HCl solution (44.2 mL, 66.3 mmol). After stirring at room temperature for 12 h, the reaction mixture was diluted with EtOAc (50 mL). The organic layer was separated and the aqueous layer was extracted with EtOAc (2×30 mL). The combined organic extracts were washed with brine solution (50 mL), dried over sodium sulphate, filtered and concentrated to afford the title compound (2.2 g, 12.08 mmol, 91% yield) as an off-white semi-solid. $^1$H NMR (400 MHz, DMSO-d$_6$) δ 6.30 (s, 1H), 2.63-2.50 (m, 2H), 2.19-2.15 (m, 2H), 2.00-1.91 (m, 4H).

Step C. Intermediate 600C1 and 600C2. Preparation of 4-((4-methoxybenzyl) amino)-1-(trifluoromethyl) cyclohexan-1-ol

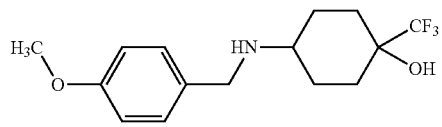

To a solution of Intermediate 600B (1.5 g, 8.24 mmol) in 1,2-dichloroethane (30 mL) were added (4-methoxyphenyl)methanamine (1.356 g, 9.88 mmol), sodium triacetoxyborohydride (5.24 g, 24.71 mmol) and AcOH (0.943 mL, 16.47 mmol). The reaction mixture was heated to 80° C. and stirred for 6 h. The reaction mixture was allowed to cool to room temperature and neutralized by addition of aqueous 10% NaOH solution (20 mL). The resulting solution was extracted with DCM (3×20 mL). The combined organic extracts were dried over anhydrous sodium sulphate, filtered, concentrated under reduced pressure. The crude material was purified by flash chromatography (40 g silica gel cartridge; A=Hex, B=EtOAc; 30 min grad.; 0% B to 30% B; flow rate=40 mL/min). The pure fractions were combined, concentrated under reduced pressure and dried in vacuo to afford Intermediate 600C1 (800 mg, 2.64 mmol, 64% yield), MS (ESI) 304 (M+H) and Intermediate 600C2 (900 mg, 2.97 mmol, 72% yield) MS (ESI) 304 (M+H) as a brown oil.

Step D. Intermediate 600D. Preparation of 4-amino-1-(trifluoromethyl) cyclohexan-1-ol

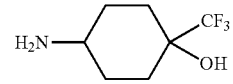

A stirred solution of Intermediate 600C1 (0.8 g, 2.64 mmol) in ethanol (20 mL) was degassed and backfilled with nitrogen three times and 10% Pd/C (0.281 g, 0.264 mmol) was added. The resulting mixture was stirred at room temperature under hydrogen balloon (1 atm) for 12 h. The reaction mixture was filtered over a celite pad and the filtrate was concentrated under reduced pressure to afford the title compound (0.4 g, 2.184 mmol, 83% yield) as an off-white solid. MS (ESI) 184 (M+H).

Step E. Example 600. Preparation of 1-((4-(5-(2-fluoropropan-2-yl)-1,2,4-oxadiazol-3-yl)bicyclo [2.2.2]octan-1-yl) methyl)-3-(4-hydroxy-4-(trifluoromethyl) cyclohexyl)-1-(4'-(2-hydroxypropan-2-yl)-[1,1'-biphenyl]-3-yl)urea The title compound was synthesized according to the method described for the synthesis of Example 586 by substituting Intermediate 598B and 600D where appropriate: (9.9 mg, 0.014 mmol, 15% yield). $^1$H NMR (400 MHz, DMSO-d$_6$) δ 7.66-7.52 (m, 6H), 7.48 (t, J=7.8 Hz, 1H), 7.33 (br d, J=8.3 Hz, 1H), 5.68 (s, 1H), 5.05 (s, 1H), 5.01-4.91 (m, 1H), 3.78-3.70 (m, 1H), 3.62 (s, 2H), 1.82-1.65 (m, 14H), 1.63-1.56 (m, 2H), 1.51-1.39 (m, 14H), 1.37-1.25 (m, 2H). FXR EC$_{50}$ (nM)=16; MS (ESI) 687 (M+H).

Example 601

1-((4-(5-(2-fluoropropan-2-yl)-1,2,4-oxadiazol-3-yl) bicyclo[2.2.2]octan-1-yl) methyl)-3-(4-hydroxy-4-(trifluoromethyl) cyclohexyl)-1-(4'-(2-hydroxypropan-2-yl)-[1,1'-biphenyl]-3-yl) urea (Isomer-2)

(601)

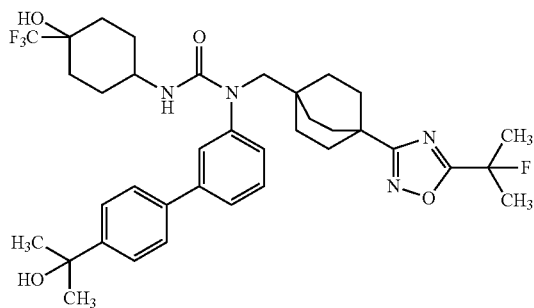

Step A. Intermediate 601A. Preparation of 4-amino-1-(trifluoromethyl) cyclohexan-1-ol

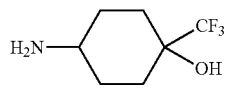

The title compound was prepared according to the method described for the synthesis of Intermediate 600D by using Intermediate 600C2 where appropriate. (0.42 g, 2.293 mmol, 87% yield). MS (ESI) 184 (M+H).

Step G. Example 601. Preparation of 1-((4-(5-(2-fluoropropan-2-yl)-1,2,4-oxadiazol-3-yl)bicyclo [2.2.2]octan-1-yl) methyl)-3-(4-hydroxy-4-(trifluoromethyl) cyclohexyl)-1-(4'-(2-hydroxypropan-2-yl)-[1,1'-biphenyl]-3-yl) urea The title compound was synthesized according to the method described for the synthesis of Example 586 by substituting Intermediate 598B and Intermediate 601A where appropriate: (5.2 mg, 7.27 μmol, 8% yield). $^1$H NMR (400 MHz, DMSO-d$_6$) δ 7.68-7.59 (m, 2H), 7.59-7.50 (m, 4H), 7.50-7.39 (m, 1H), 7.29 (br d, J=7.6 Hz, 1H), 5.62 (s, 1H), 5.42 (d, J=8.3 Hz, 1H), 5.05 (s, 1H), 3.91 (s, 1H), 3.61 (s, 2H), 3.51-3.42 (m, 1H), 1.84-1.58 (m, 17H), 1.55-1.32 (m, 14H). FXR EC$_{50}$ (nM)=246; MS (ESI) 687 (M+H).

Example 602

Isopropyl (4-(((cis)-3-hydroxy-N-(4'-(2-hydroxypropan-2-yl)-[1,1'-biphenyl]-3-yl)-3-(trifluoromethyl) cyclobutane-1-carboxamido)methyl)bicyclo[2.2.2] octan-1-yl)carbamate (602)

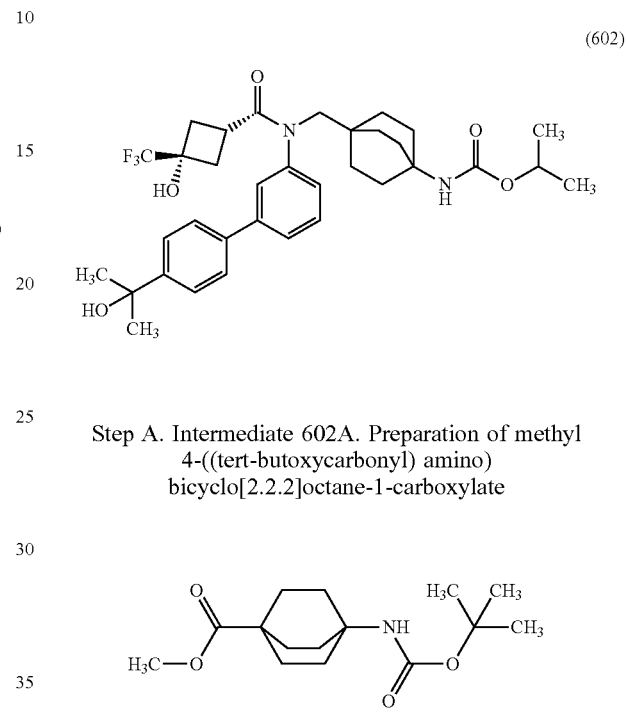

Step A. Intermediate 602A. Preparation of methyl 4-((tert-butoxycarbonyl) amino) bicyclo[2.2.2]octane-1-carboxylate To a solution of 4-(methoxycarbonyl)bicyclo[2.2.2]octane-1-carboxylic acid (5 g, 9.42 mmol) in toluene (50 mL) at 0° C. was added diphenyl phosphoryl azide (5.06 mL, 23.56 mmol) followed by TEA (3.28 mL, 23.56 mmol). The reaction mixture was stirred at room temperature for 1 h, and then heated to 110° C. for 1 h. Tert-butanol (11.27 mL, 118 mmol) was added and the reaction mixture was stirred overnight at 110° C. The reaction mixture was cooled to room temperature and concentrated under reduced pressure to afford a residue. The residue was reconstituted in a mixture of ethyl acetate (50 mL) and water (30 mL). The organic layer was separated and aqueous layer was extracted with ethyl acetate (2×50 mL). The combined organic layers were washed with water (30 mL), brine (30 mL), dried over anhydrous sodium sulfate, filtered and concentrated under reduced pressure to afford a residue. The crude material was purified by flash chromatography (80 g silica gel cartridge; A=Hex, B=EtOAc; 30 min grad.; 0% B to 25% B). The pure fractions were combined, concentrated under reduced pressure and dried in vacuo to afford the title compound (5.2 g, 11.74 mmol, 50% yield) as white solid. $^1$H NMR (400 MHz, DMSO-d$_6$) δ 6.42 (br s, 1H), 3.58-3.38 (m, 3H), 1.83-1.60 (m, 12H), 1.41-1.27 (m, 9H).

Step B. Intermediate 602B. Preparation of tert-butyl (4-formylbicyclo[2.2.2]octan-1-yl) carbamate

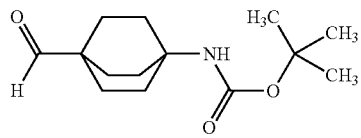 [SMILES: CC(C)(C)OC(=O)NC12CCC(C=O)(CC1)CC2]

To a solution of Intermediate 602A (1.0 g, 3.50 mmol) in tetrahydrofuran (20 mL) at −78° C. was added LAH (5.26 mL, 5.26 mmol). The reaction mixture was stirred at −78° C. for 20 min and quenched with aqueous saturated ammonium chloride solution (10 mL). The mixture was diluted with ethyl acetate (30 mL) and the resulting solution was filtered through celite bed. The organic layer was separated, dried over anhydrous sodium sulfate and concentrated under reduced pressure to afford a residue. The crude material was purified by flash chromatography (24 g silica gel cartridge; A=Hex, B=EtOAc; 30 min grad.; 0% B to 40% B). The pure fractions were combined, concentrated under reduced pressure and dried in vacuo to afford the title compound (0.41 g, 1.618 mmol, 46% yield) as white solid. $^1$H NMR (400 MHz, DMSO-$d_6$) δ 9.40 (s, 1H), 6.51-6.43 (m, 1H), 1.79-1.74 (m, 6H), 1.63-1.57 (m, 6H), 1.36 (s, 9H).

Step C. Intermediate 602C. Preparation of tert-butyl (4-(((3-bromophenyl) amino) methyl)bicyclo[2.2.2] octan-1-yl)carbamate

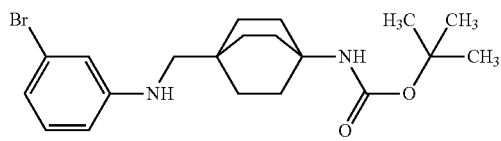

The title compound was prepared according to the method described for the synthesis of Intermediate 1I by using Intermediate 602B and 3-bromoaniline where appropriate: (0.32 g, 0.782 mmol, 40% yield). $^1$H NMR (400 MHz, DMSO-$d_6$) δ 6.96-6.89 (m, 1H), 6.74-6.69 (m, 1H), 6.63-6.50 (m, 2H), 6.32 (br s, 1H), 5.67 (t, J=5.5 Hz, 1H), 2.71 (d, J=6.0 Hz, 2H), 1.80-1.67 (m, 6H), 1.50-1.43 (m, 6H), 1.36 (s, 9H). MS (ESI) 409 (M+H).

Step D. Intermediate 602D. Preparation of tert-butyl(4-(((cis)-N-(3-bromophenyl)-3-hydroxy-3-(trifluoromethyl)cyclobutane-1-carboxamido) methyl)bicyclo[2.2.2]octan-1-yl)carbamate

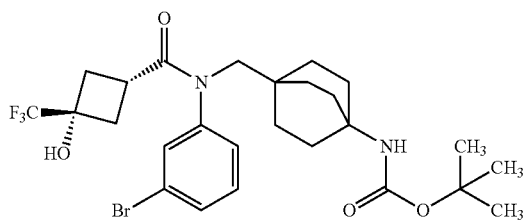 [SMILES: CC(C)(C)OC(=O)NC12CCC(CN(c3cccc(Br)c3)C(=O)[C@H]3C[C@](O)(C(F)(F)F)C3)(CC1)CC2]

The title compound was prepared according to the method described for the synthesis of Example 3 by using Intermediate 602C and the corresponding acid where appropriate: (0.32 g, 0.528 mmol, 72% yield) as an off-white solid. $^1$H NMR (400 MHz, DMSO-$d_6$) δ 7.69-7.61 (m, 1H), 7.53 (br d, J=6.5 Hz, 1H), 7.41-7.34 (m, 2H), 6.52 (s, 1H), 6.29-6.18 (m, 1H), 3.54-3.53 (m, 1H), 3.61-3.47 (m, 1H), 2.74-2.66 (m, 1H), 2.35-2.22 (m, 2H), 2.10-1.99 (m, 2H), 1.70-1.57 (m, 12H), 1.45-1.14 (m, 9H). MS (ESI) 575 (M+H).

Step E. Intermediate 602E. Preparation of tert-butyl (4-(((cis)-3-hydroxy-N-(4'-(2-hydroxypropan-2-yl)-[1,1'-biphenyl]-3-yl)-3-(trifluoromethyl)cyclobutane-1-carboxamido)methyl)bicyclo[2.2.2]octan-1-yl) carbamate

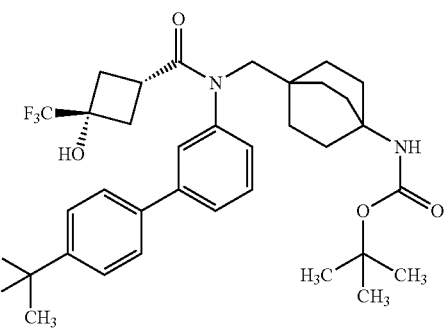

The title compound was prepared according to the method described for the synthesis of Example 149 by using Intermediate 602D and the corresponding boronic acid where appropriate: (0.21 g, 0.306 mmol, 59% yield) as an off-white solid. MS (ESI) 631 (M+H).

Step F. Intermediate 606F. Preparation of (cis)-N-((4-aminobicyclo[2.2.2]octan-1-yl) methyl)-3-hydroxy-N-(4'-(2-hydroxypropan-2-yl)-[1,1'-biphenyl]-3-yl)-3-(trifluoromethyl)cyclobutane-1-carboxamide

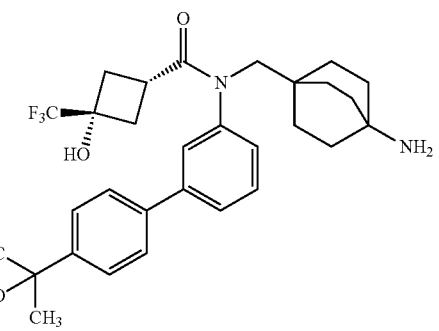

To a stirred solution of Intermediate 602E (100 mg, 0.159 mmol) in 1,4-dioxane (5 mL) at 0° C. was added a solution of 4 M HCl in 1,4-dioxane (0.198 mL, 0.793 mmol). The reaction mixture was allowed to warm up to room temperature and stirred for 1 h. The reaction mixture was concentrated under reduced pressure to afford the title compound (80 mg, 0.053 mmol, 33% yield) as an off-white solid. MS (ESI) 531 (M+H).

Step G: Example 602. Preparation of isopropyl (4-(((cis)-3-hydroxy-N-(4'-(2-hydroxypropan-2-yl)-[1,1'-biphenyl]-3-yl)-3-(trifluoromethyl)cyclobutane-1-carboxamido)methyl)bicyclo[2.2.2]octan-1-yl)carbamate To a stirred solution of Intermediate 602F (50 mg, 0.094 mmol) in dichloromethane (2 mL) at room temperature was added DIPEA (0.016 mL, 0.094 mmol). The reaction mixture was cooled to 0° C. and isopropyl chloroformate (11.55 mg, 0.094 mmol) was added. The reaction mixture was stirred at 0° C. for 3 h. The reaction mixture was diluted with DCM (10 mL) and the organic solution was washed with water (10 mL) followed by brine solution (10 mL). The organic layer was dried over anhydrous sodium sulphate, filtered, and concentrated under reduced pressure to afford a residue. The crude compound was purified via preparative HPLC with the following conditions: (Column: Waters XBridge BEH C18 XP(50×2.1 mm) 2.5 μm; Mobile Phase A: 5:95 acetonitrile:water with 10 mM NH$_4$OAc; Mobile Phase B: 95:5 acetonitrile:water with 10 mM NH$_4$OAc; Temperature: 50° C.; Gradient: 0-100% B over 3 minutes; Flow: 1.1 ml/min). Fractions containing the product were combined and dried via centrifugal evaporation to afford isopropyl (4-(((cis)-3-hydroxy-N-(4'-(2-hydroxypropan-2-yl)-[1,1'-biphenyl]-3-yl)-3-(trifluoromethyl)cyclobutane-1-carboxamido)methyl) bicyclo[2.2.2]octan-1-yl)carbamate (9.6 mg, 0.016 mmol, 17% yield). $^1$H NMR (400 MHz, DMSO-d$_6$) δ 7.66-7.60 (m, 4H), 7.53-7.46 (m, 1H), 7.35-7.27 (m, 1H), 6.58-6.46 (m, 2H), 5.06 (s, 1H), 4.69-4.57 (m, 2H), 3.65-3.51 (m, 2H), 2.91-2.72 (m, 1H), 2.39-2.28 (m, 2H), 2.10-1.97 (m, 2H), 1.70-1.58 (m, 6H), 1.56-1.46 (m, 7H), 1.40-1.31 (m, 6H), 1.11 (d, J=6.11 Hz, 6H). FXR EC$_{50}$ (nM)=142; MS (ESI) 617 (M+H).

Example 603

(cis)-N-(4'-(difluoromethoxy)-[1,1'-biphenyl]-3-yl)-3-hydroxy-3-(trifluoromethyl)-N-((4-(((trifluoromethyl)sulfonamido)bicyclo[2.2.2]octan-1-yl)methyl)cyclobutane-1-carboxamide (603)

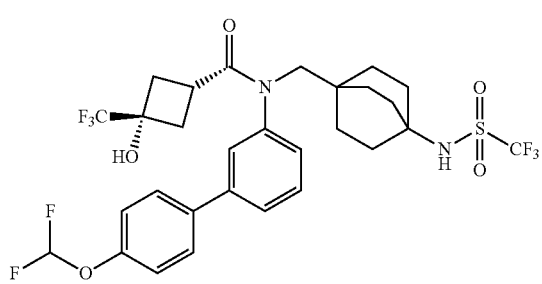

Step A. Intermediate 603A. Preparation of tert-butyl (4-(((cis)-N-(4'-(difluoromethoxy)-[1,1'-biphenyl]-3-yl)-3-hydroxy-3-(trifluoromethyl)cyclobutane-1-carboxamido)methyl)bicyclo[2.2.2]octan-1-yl)carbamate

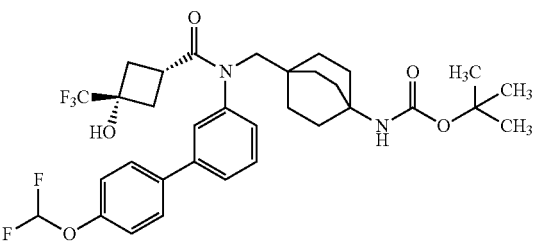 [SMILES: CC(C)(C)OC(=O)NC12CCC(CN(c3cccc(-c4ccc(OC(F)F)cc4)c3)C(=O)[C@H]3C[C@](O)(C(F)(F)F)C3)(CC1)CC2]

The title compound was prepared according to the general method described for the synthesis of Example 149 by using Intermediate 602D and the corresponding boronic acid where appropriate: (350 mg, 0.449 mmol, 53% yield) as an off-white solid. MS (ESI) 639 (M+H).

Step B. Intermediate 603B. Preparation of (cis)-N-((4-aminobicyclo[2.2.2]octan-1-yl) methyl)-N-(4'-(difluoromethoxy)-[1,1'-biphenyl]-3-yl)-3-hydroxy-3-(trifluoromethyl) cyclobutane-1-carboxamide

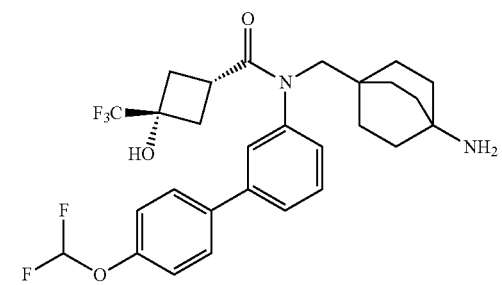 [SMILES: NC12CCC(CN(c3cccc(-c4ccc(OC(F)F)cc4)c3)C(=O)[C@H]3C[C@](O)(C(F)(F)F)C3)(CC1)CC2]

The title compound was prepared according to the general method described for the synthesis of Intermediate 606F by using Intermediate 603A and the corresponding boronic acid where appropriate: (200 mg, 0.260 mmol, 55% yield) as an off-white solid. MS (ESI) 539 (M+H).

Step C. Example 603. Preparation of (cis)-N-(4'-(difluoromethoxy)-[1,1'-biphenyl]-3-yl)-3-hydroxy-3-(trifluoromethyl)-N-((4-(((trifluoromethyl)sulfonamido)bicyclo[2.2.2]octan-1-yl)methyl)cyclobutane-1-carboxamide To a stirred solution of Intermediate 603B (20 mg, 0.037 mmol) in dichloromethane (2 mL) at room temperature was added sodium bicarbonate (3.12 mg, 0.037 mmol). The reaction mixture was cooled to 0° C. and trifluoromethanesulfonic anhydride (11.52 mg, 0.041 mmol) was added. The reaction mixture was stirred at 0° C. for 30 min. The reaction mixture was diluted with DCM (10 mL) and the organic solution was washed with water (10 mL) followed by brine solution (10 mL). The organic layer was dried over anhydrous sodium sulphate, filtered, and concentrated under reduced pressure to afford a residue. The crude compound was purified via preparative HPLC with the following conditions: (Column: Waters XBridge BEH C18 XP (50×2.1 mm) 2.5 μm; Mobile Phase A: 5:95 acetonitrile:water with 10 mM NH₄OAc; Mobile Phase B: 95:5 acetonitrile:water with 10 mM NH₄OAc; Temperature: 50° C.; Gradient: 0-100% B over 3 minutes; Flow: 1.1 ml/min. Fractions containing the desired product were combined and dried via centrifugal evaporation to afford the title compound (8.2 mg, 0.012 mmol, 33% yield). $^1$H NMR (400 MHz, DMSO-$d_6$) δ 8.88 (s, 1H), 7.79 (d, J=8.3 Hz, 2H), 7.69 (s, 1H), 7.64 (d, J=7.8 Hz, 1H), 7.54-7.09 (m, 5H), 6.50 (s, 1H), 3.72-3.50 (m, 2H), 2.87-2.74 (m, 1H), 2.38-2.25 (m, 2H), 2.11-1.97 (m, 2H), 1.81-1.61 (m, 6H), 1.51-1.32 (m, 6H). FXR EC$_{50}$ (nM)=1821; MS (ESI) 671 (M+H).

Example 604

(cis)-3-hydroxy-N-(4'-isopropoxy-[1,1'-biphenyl]-3-yl)-N-((4-(3-isopropylureido) bicyclo[2.2.2]octan-1-yl)methyl)-3-(trifluoromethyl)cyclobutane-1-carboxamide (604)

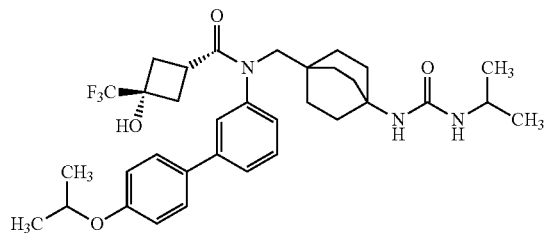

Step A. Intermediate 604A. Preparation of (cis)-N-((4-aminobicyclo[2.2.2]octan-1-yl) methyl)-N-(3-bromophenyl)-3-hydroxy-3-(trifluoromethyl)cyclobutane-1-carboxamide

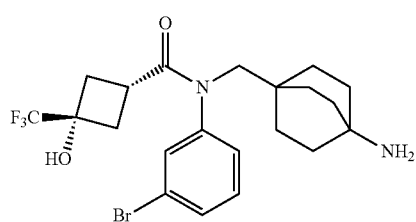 [SMILES: NC12CCC(CN(c3cccc(Br)c3)C(=O)[C@H]3C[C@](O)(C(F)(F)F)C3)(CC1)CC2]

To a stirred solution of Intermediate 602D (100 mg, 0.174 mmol) in dichloromethane (5 mL) at 0° C. was added TFA (0.013 mL, 0.174 mmol). The reaction mixture was stirred at 0° C. for 1 h. The reaction mixture was concentrated under reduced pressure to afford the title compound (75 mg, 0.121 mmol, 70% yield) as pale brown solid. $^1$H NMR (300 MHz, DMSO-$d_6$) δ 7.89-7.68 (m, 4H), 7.61-7.50 (m, 1H), 7.49-7.28 (m, 2H), 2.80-2.62 (m, 1H), 2.40-2.22 (m, 2H), 2.12-1.94 (m, 2H), 1.65-1.51 (m, 6H), 1.47-1.29 (m, 6H). MS (ESI) 475 (M+H).

Step B. Intermediate 604B. Preparation of (cis)-N-(3-bromophenyl)-3-hydroxy-N-((4-(3-isopropylureido)bicyclo[2.2.2]octan-1-yl)methyl)-3-(trifluoromethyl)cyclobutane-1-carboxamide

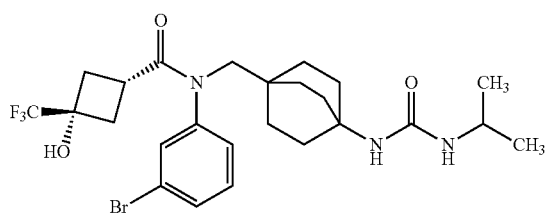 [SMILES: CC(C)NC(=O)NC12CCC(CN(c3cccc(Br)c3)C(=O)[C@H]3C[C@](O)(C(F)(F)F)C3)(CC1)CC2]

To a stirred solution of Intermediate 604A (0.12 g, 0.252 mmol) in dichloromethane (3 mL) at room temperature was added TEA (0.106 mL, 0.757 mmol). The reaction mixture was cooled to 0° C. and 2-isocyanatopropane (0.032 g, 0.379 mmol) was added. The reaction mixture was stirred at 0° C. for 3 h. The reaction mixture was diluted with DCM (20 mL) and the organic solution was washed with water (10 mL) followed by brine solution (10 mL). The organic layer was dried over anhydrous sodium sulphate, filtered, and concentrated under reduced pressure to afford a residue. The crude material was purified by flash chromatography (4 g silica gel cartridge; A=Hex, B=EtOAc; 30 min grad.; 0% B to 35% B). The pure fractions were combined, concentrated under reduced pressure and dried in vacuo to afford the title compound (0.12 g, 0.111 mmol, 44% yield) as a white solid. MS (ESI) 560 (M+H).

Step C. Example 604. Preparation of (cis)-3-hydroxy-N-(4'-isopropoxy-[1,1'-biphenyl]-3-yl)-N-((4-(3-isopropylureido)bicyclo[2.2.2]octan-1-yl)methyl)-3-(trifluoromethyl) cyclobutane-1-carboxamide The title compound was prepared according to the method described for the synthesis of Example 149 by using Intermediate 604B and the corresponding boronic acid where appropriate: (9 mg, 0.015 mmol, 16% yield). $^1$H NMR (400 MHz, DMSO-$d_6$) δ 7.67-7.56 (m, 4H), 7.46 (t, J=7.8 Hz, 1H), 7.26 (d, J=8.3 Hz, 1H), 7.01 (d, J=8.8 Hz, 2H), 6.50 (s, 1H), 5.41 (d, J=7.6 Hz, 1H), 5.27 (s, 1H), 4.68 (td, J=6.0, 12.2 Hz, 1H), 3.64-3.49 (m, 3H), 2.82 (t, J=8.9 Hz, 1H), 2.36-2.27 (m, 2H), 2.11-1.99 (m, 2H), 1.67-1.58 (m, 6H), 1.40-1.27 (m, 12H), 0.96 (d, J=6.6 Hz, 6H). FXR EC$_{50}$ (nM)=968; MS (ESI) 616 (M+H).

Example 605

1,1,1-trifluoro-2-methylpropan-2-yl((4-(5-(1,1-difluoroethyl) pyridin-2-1) bicyclo[2.2.2]octan-1-yl) methyl)(4-(4-(2-hydroxypropan-2-yl)phenyl)pyridin-2-yl)carbamate

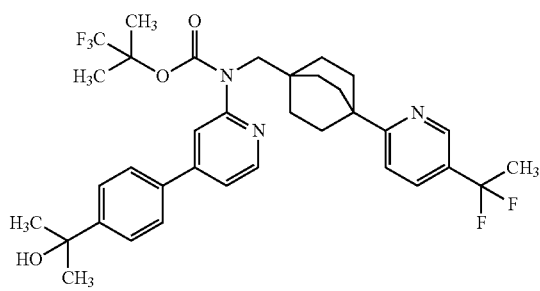

(605)

Step A. Intermediate 605A. Preparation of 3-(1,1-difluoroethyl) pyridine

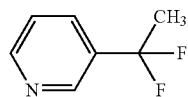

To a stirred solution of 1-(pyridin-3-yl) ethan-1-one (10.00 g, 83 mmol) in DCM (100 mL) in a screw capped reaction vessel was added diethylaminosulfur trifluoride (32.7 mL, 248 mmol). The reaction vessel was screw-capped under nitrogen atmosphere. The reaction mixture was heated overnight at 50° C. The reaction mixture was cooled to room temperature and was added dropwise to cooled aqueous 2 N NaOH solution and extracted with DCM (2×300 mL). The combined organic extracts were washed with brine solution (50 mL), dried over anhydrous sodium sulphate, filtered and concentrated under reduced pressure. The crude material so obtained was purified by flash column chromatography (120 g silica gel cartridge; A=hexanes, B=EtOAc; 30 min grad.; 0% B to 30% B; flow rate=120 mL/min). The pure fractions were combined, concentrated under reduced pressure to afford the title compound (7 g, 48.9 mmol, 59% yield) as pale yellow liquid. $^1$H NMR (400 MHz, DMSO-d$_6$) δ 8.81 (dd, J=1.0, 2.2 Hz, 1H), 8.72 (td, J=0.7, 4.9 Hz, 1H), 8.05-7.96 (m, 1H), 7.58-7.51 (m, 1H), 2.08-1.98 (m, 3H).

Step B. Intermediate 605B. Preparation of methyl 4-(5-(1,1-difluoroethyl) pyridin-2-yl) bicyclo[2.2.2]octane-1-carboxylate

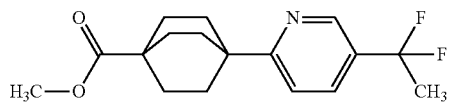

To a stirred solution of 4-(methoxycarbonyl)bicyclo[2.2.2]octane-1-carboxylic acid (2.224 g, 10.48 mmol), N-hydroxyphthalimide (1.710 g, 10.48 mmol) and DMAP (0.043 g, 0.349 mmol) in DMSO (40 mL) was added N,N'-Diisopropylcarbodiimide (1.633 mL, 10.48 mmol). The reaction mixture was stirred at room temperature for 24 h. In another vial, Intermediate 605A (1.00 g, 6.99 mmol) was dissolved in DMSO (20 mL) and TFA (1.076 mL, 13.97 mmol) was added. This mixture was added to the above reaction mixture followed by 2,4,5,6-tetra(9H-carbazol-9-yl)isophthalonitrile (4CZIPN) (0.055 g, 0.070 mmol). The entire stirred reaction mixture was degassed and back-filled with nitrogen and irradiated using two blue LED (34 W) lights for 3 h. The reaction mixture was quenched with aqueous 10% NaHCO$_3$ solution, diluted with water (30 mL) and extracted with ethyl acetate (2×50 mL). The combined organic layers were washed with brine solution (20 mL), dried over anhydrous sodium sulphate, filtered and concentrated under reduced pressure. The crude material so obtained was purified via flash silica gel column chromatography (40 g silica gel cartridge; A=hexanes, B=EtOAc; 30 min grad.; 0% B to 10% B; flow rate=40 mL/min). The pure fractions were combined, concentrated under reduced pressure and dried in vacuo to afford the title compound (1.45 g, 4.69 mmol, 67% yield) as white solid. $^1$H NMR (300 MHz, DMSO-d$_6$) δ 8.70 (dd, J=0.9, 2.5 Hz, 1H), 7.94-7.88 (m, 1H), 7.46 (dd, J=0.8, 8.3 Hz, 1H), 3.60 (s, 3H), 2.10-1.94 (m, 3H), 1.92-1.78 (m, 12H). MS (ESI) 310 (M+H).

Step C. Intermediate 605C. Preparation of (4-(5-(1,1-difluoroethyl) pyridin-2-yl)bicyclo [2.2.2]octan-1-yl) methanol

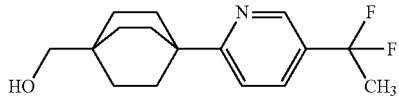

To a stirred solution of Intermediate 605B (4.4 g, 14.22 mmol) in THF (44 mL) was added diisobutylaluminium hydride in THF (1.0 M) (35.6 mL, 35.6 mmol) drop wise at −78° C. The reaction mixture was stirred at −78° C. for 30 min. The reaction was quenched with aqueous saturated ammonium chloride solution. The reaction mixture was extracted with ethyl acetate (2×75 mL), washed the organic layer with aqueous 1.5 N HCl solution (50 mL). The combined organic layers were washed with brine solution (20 mL), dried over anhydrous sodium sulphate, filtered and concentrated under reduced pressure. The crude material was purified via flash silica gel column chromatography (80 g silica gel cartridge; A=hexanes, B=EtOAc; 30 min grad.; 0% B to 30% B; flow rate=80 mL/min). The pure fractions were combined, concentrated under reduced pressure and dried in vacuo to afford the title compound (3.2 g, 11.37 mmol, 80% yield) as a white solid. $^1$H NMR (400 MHz, DMSO-d$_6$) δ 8.72 (br s, 1H), 7.88 (dd, J=2.5, 8.0 Hz, 1H), 7.47-7.40 (m, 1H), 4.38 (t, J=5.5 Hz, 1H), 3.09 (d, J=5.5 Hz, 2H), 2.00 (t, J=19.1 Hz, 3H), 1.87-1.78 (m, 6H), 1.51-1.41 (m, 6H). MS (ESI) 282 (M+H).

Step D. Intermediate 605D. Preparation of 4-(5-(1,1-difluoroethyl) pyridin-2-yl)bicyclo [2.2.2]octane-1-carb aldehyde

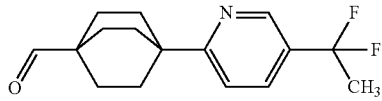

To a stirred solution of Intermediate 605C (3.20 g, 11.37 mmol) in DCM (64 mL) was added Dess-Martin periodinane (4.2 g, 11.37 mmol) at 0° C. The reaction mixture was stirred at 0° C. for 30 min. The reaction mixture was allowed to warm to room temperature, diluted with DCM (50 mL), washed with aqueous 10% sodium bicarbonate solution (2×50 mL). The organic layer was washed with brine solution (50 mL), dried over anhydrous sodium sulphate, filtered and concentrated under reduced pressure. The crude material was purified via flash silica gel column chromatography (24 g silica gel cartridge; A=hexanes, B=EtOAc; 30 min grad.; 0% B to 20% B; flow rate=24 mL/min). The pure fractions were combined, concentrated under reduced pressure and dried in vacuo to afford the title compound (2.25 g, 8.05 mmol, 71% yield) as a white solid. $^1$H NMR (400 MHz, DMSO-$d_6$) δ 9.51-9.45 (m, 1H), 8.73-8.68 (m, 1H), 7.91 (dd, J=2.5, 8.5 Hz, 1H), 7.48 (d, J=7.5 Hz, 1H), 2.01 (t, J=18.8 Hz, 3H), 1.92-1.87 (m, 6H), 1.75-1.67 (m, 6H).

Step E. Intermediate 605E. 4-bromo-N-((4-(5-(1,1-difluoroethyl) pyridin-2-yl)bicyclo [2.2.2]octan-1-yl) methyl) pyridin-2-amine

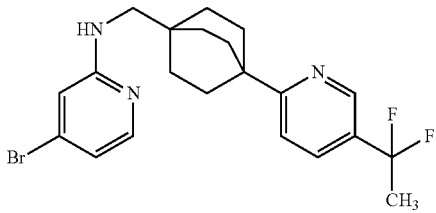 [SMILES: CC(F)(F)c1ccc(C23CCC(CNc4cc(Br)ccn4)(CC2)CC3)nc1]

To a solution of Intermediate 605D (1.0 g, 3.58 mmol) and 4-bromopyridin-2-amine (563 mg, 3.25 mmol) in MeOH (20 mL) was added acetic acid (0.373 mL, 6.51 mmol) followed by molecular sieves 4 Å (100 mg). The reaction mixture was heated to 60° C. and stirred for 16 h. The reaction mixture was cooled to 0° C. and sodium cyanoborohydride (409 mg, 6.51 mmol) was added. The reaction mixture was stirred for 1 h and poured into water (20 mL). The aqueous layer was extracted with ethyl acetate (2×30 mL). The combined organic layers were washed with brine (20 mL), dried over anhydrous sodium sulphate, filtered and concentrated under reduced pressure to afford a residue. The residue was purified via flash column chromatography (12 g silica gel column, conditions: 30% ethyl acetate in pet ether) to afford the title compound (800 mg, 1.833 mmol, 56% yield) as an off-white solid. $^1$H NMR (400 MHz, DMSO-$d_6$) δ 8.70 (dd, J=1.0, 2.5 Hz, 1H), 7.88 (dd, J=2.5, 8.0 Hz, 1H), 7.81 (d, J=5.5 Hz, 1H), 7.45 (d, J=7.5 Hz, 1H), 6.78 (d, J=1.5 Hz, 1H), 6.66 (t, J=6.0 Hz, 1H), 6.61-6.55 (m, 1H), 3.15 (dd, J=5.8, 18.3 Hz, 2H), 2.08-1.93 (m, 3H), 1.88-1.80 (m, 6H), 1.55-1.47 (m, 6H). MS (ESI) 436 (M+H).

Step F. Intermediate 605F. Preparation of 1,1,1-trifluoro-2-methylpropan-2-yl(4-bromopyridin-2-yl) ((4-(5-(1,1-difluoroethyl)pyridin-2-yl)bicyclo[2.2.2] octan-1-yl)methyl) carbamate

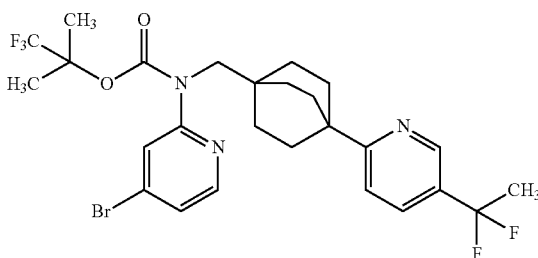 [SMILES: CC(F)(F)c1ccc(C23CCC(CN(C(=O)OC(C)(C)C(F)(F)F)c4cc(Br)ccn4)(CC2)CC3)nc1]

To a stirred solution of Intermediate 605E (0.25 g, 0.573 mmol) in THF (2 mL) cooled −50° C., was added lithium hexamethyldisilazane in THF (1.0 M) (1.432 mL, 1.432 mmol) drop wise over a period of 2 minutes. The reaction mixture was stirred at −50° C. for 10 min. To this reaction mixture, a solution of pyridin-2-yl (1,1,1-trifluoro-2-methylpropan-2-yl)carbonate (0.214 g, 0.859 mmol) in THF (0.5 mL) was added and the reaction mixture was stirred at −50° C. for 1 h. The reaction was quenched with saturated aqueous ammonium chloride solution (10 mL). The reaction mixture was diluted with water (15 mL) and extracted with ethyl acetate (2×25 mL). The combined organic layers were washed with brine solution (15 mL), dried over anhydrous sodium sulfate, filtered and concentrated under reduced pressure. The residue was purified via flash column chromatography (12 g silica gel column, conditions: 30% ethyl acetate in pet ether) to afford the title compound (0.23 g, 0.390 mmol, 68.0% yield) as brown solid. MS (ESI) 590 (M+H).

Step G. Example 605. Preparation of 1,1,1-trifluoro-2-methylpropan-2-yl ((4-(5-(1,1-difluoroethyl) pyridin-2-yl)bicyclo[2.2.2]octan-1-yl)methyl)(4-(4-(2-hydroxypropan-2-yl) phenyl)pyridin-2-yl) carbamate The mixture of Intermediate 605F (30 mg, 0.051 mmol), (4-(2-hydroxypropan-2-yl) phenyl)boronic acid (9.15 mg, 0.051 mmol) and K$_2$CO$_3$ (14.04 mg, 0.102 mmol) in 1,4-dioxane (1 mL) and H$_2$O (0.25 mL) was stirred at room temperature. Argon gas was bubbled through the mixture for 5 min. PdCl$_2$(dppf) (1.859 mg, 2.54 μmol) was added and argon gas was bubbled through the mixture for another 5 min. The reaction mixture was heated at 110° C. for 1 h. The reaction mixture was cooled to room temperature and diluted with EtOAc (10 mL). The organic layer was washed with water (5 mL), brine (5 mL), dried over anhydrous sodium sulfate and concentrated under reduced pressure to afford the residue. The crude material was purified via preparative LC/MS using following conditions: Column: Waters XBridge C18, 19×150 mm, 5-μm particles; Mobile Phase A: 10-mM ammonium acetate; Mobile Phase B: acetonitrile; Gradient: 28-85% B over 20 minutes, then a 5-minute hold at 100% B; Flow: 15 mL/min. Fractions containing the product were combined and dried via centrifugal evaporation, to afford the title compound (18.7 mg, 0.029 mmol, 56% yield). $^1$H NMR (400 MHz, DMSO-$d_6$) δ 8.65 (d, J=1.0 Hz, 1H), 8.45 (d, J=5.1 Hz, 1H), 7.84 (dd, J=2.2, 8.6 Hz, 1H), 7.76 (d, J=8.6 Hz, 3H), 7.62 (d, J=8.3 Hz, 2H), 7.57 (dd, J=1.3, 5.3 Hz, 1H), 7.37 (d, J=8.3 Hz, 1H), 5.14 (s, 1H), 3.89 (d, J=11.0 Hz, 2H), 1.97 (t, J=19.0 Hz, 3H), 1.80-1.68 (m, 12H), 1.46 (s, 6H), 1.44-1.33 (m, 6H). FXR $EC_{50}$ (nM)=52. MS (ESI) 646 (M+H).

Example 606

1,1,1-trifluoro-2-methylpropan-2-yl (4-(4-((2-cyanopropan-2-yl)oxy)phenyl)pyridin-2-yl)((4-(5-(1,1-difluoroethyl)pyridin-2-yl)bicyclo[2.2.2]octan-1-yl)methyl)carbamate (606)

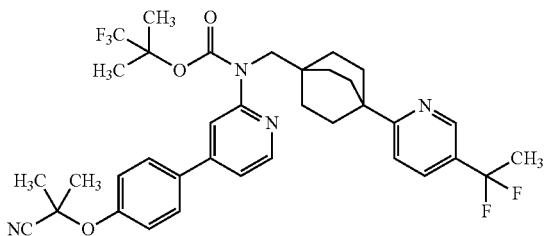

The title compound was synthesized according to the general method described for the synthesis of Example 149 by substituting Intermediate 605F and the corresponding boronic acid where appropriate: (15.9 mg, 0.024 mmol, 47% yield). $^1$H NMR (400 MHz, DMSO-$d_6$) δ 8.65 (s, 1H), 8.46 (d, J=5.4 Hz, 1H), 7.93-7.82 (m, 3H), 7.81 (s, 1H), 7.58 (dd, J=1.5, 5.4 Hz, 1H), 7.37 (d, J=8.3 Hz, 1H), 7.33 (d, J=8.8 Hz, 2H), 3.88 (s, 2H), 1.97 (t, J=19.0 Hz, 3H), 1.83-1.68 (m, 18H), 1.45-1.34 (m, 6H). FXR $EC_{50}$ (nM)=95. MS (ESI) 671 (M+H).

Example 607

1,1,1-trifluoro-2-methylpropan-2-yl ((4-(5-(1,1-difluoroethyl)pyridin-2-yl) bicyclo[2.2.2]octan-1-yl)methyl)(5-(2-hydroxypropan-2-yl)-[2,4'-bipyridin]-2'-yl)carbamate (607)

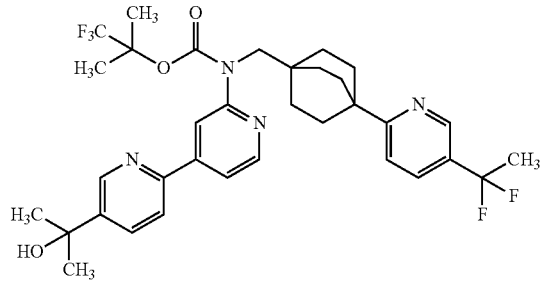

Step A. Intermediate 607A. Preparation of 2-(6-bromopyridin-3-yl) propan-2-ol

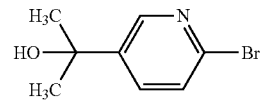

To a stirred solution of methyl 6-bromonicotinate (1 g, 4.63 mmol) in THF (10 mL) cooled at −30° C. was added methyl magnesium bromide in diethyl ether (3M) (6.17 mL, 18.52 mmol) drop wise over a period of 3 minutes. The reaction mixture was gradually warmed to room temperature and stirred at room temperature overnight. The reaction was quenched with saturated aqueous ammonium chloride solution. The reaction mixture was diluted with water (30 mL) and extracted with ethyl acetate (2×50 mL). The combined organic layer was washed with brine solution (20 mL), dried over anhydrous sodium sulphate, filtered and concentrated under reduced pressure. The crude material was purified via flash column chromatography (120 g silica gel column, conditions: 30% ethyl acetate in pet ether) to afford the title compound (brown solid, 0.9 g, 4.17 mmol, 90% yield). $^1$H NMR (300 MHz, DMSO-$d_6$) δ 8.48 (dd, J=0.7, 2.6 Hz, 1H), 7.80 (dd, J=2.6, 8.3 Hz, 1H), 7.57 (dd, J=0.7, 8.3 Hz, 1H), 5.33-5.30 (m, 1H), 1.44 (s, 6H).

Step B. Intermediate 607B. Preparation of 1,1,1-trifluoro-2-methylpropan-2-yl ((4-(5-(1,1-difluoroethyl)pyridin-2-yl)bicyclo[2.2.2]octan-1-yl)methyl)(4-(4,4,5,5-tetramethyl-1,3,2-dioxaborolan-2-yl)pyridin-2-yl)carbamate

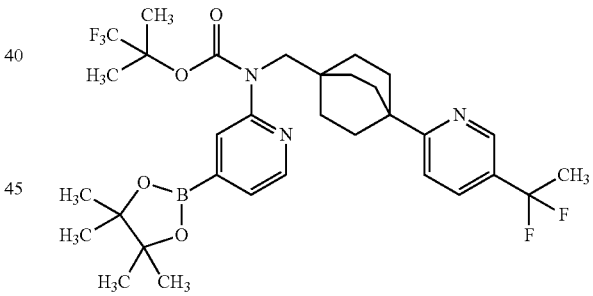

The mixture of Intermediate 605F (150 mg, 0.254 mmol), 4,4,4',4',5,5,5',5'-octamethyl-2,2'-bi(1,3,2-dioxaborolane) (129 mg, 0.508 mmol) and potassium acetate (112 mg, 1.143 mmol) in dioxane (3 mL) was stirred at room temperature. Argon gas was bubbled through the mixture for 5 min. $PdCl_2$(dppf)-$CH_2Cl_2$ adduct (9.29 mg, 0.013 mmol) was added and argon gas was bubbled through the mixture for 5 min. The reaction mixture was heated at 100° C. for 4 h. The reaction mixture was cooled to room temperature and diluted with ethyl acetate (20 mL). The organic layer was washed with water (15 mL), brine (15 mL), dried over anhydrous sodium sulfate and concentrated under reduced pressure to afford a residue. The residue was purified via flash column chromatography (4 g silica gel column, conditions: 30% ethyl acetate in pet ether) to afford the title compound (100 mg, 0.180 mmol, 71% yield) as brown gummy mass. MS (ESI) 556 (M+H).

Step C. Example 607. Preparation of 1,1,1-trifluoro-2-methylpropan-2-yl ((4-(5-(1,1-difluoroethyl)pyridin-2-yl)bicyclo[2.2.2]octan-1-yl)methyl)(5-(2-hydroxypropan-2-yl)-[2,4'-bipyridin]-2'-yl)carbamate The title compound was synthesized according to the general method described for the synthesis of Example 149 by substituting Intermediate 607A and Intermediate 607B where appropriate: (10.1 mg, 0.015 mmol, 31% yield). $^1$H NMR (400 MHz, DMSO-$d_6$) δ 8.85 (d, J=2.0 Hz, 1H), 8.65 (s, 1H), 8.51 (d, J=5.1 Hz, 1H), 8.16 (s, 1H), 8.11-8.05 (m, 1H), 8.04-7.98 (m, 1H), 7.91 (d, J=4.4 Hz, 1H), 7.84 (dd, J=2.0, 8.6 Hz, 1H), 7.38 (d, J=8.3 Hz, 1H), 5.34 (s, 1H), 3.91 (s, 2H), 1.97 (t, J=19.1 Hz, 3H), 1.83-1.66 (m, 12H), 1.50 (s, 6H), 1.44-1.32 (m, 6H). FXR EC$_{50}$ (nM)=96. MS (ESI) 647 (M+H).

Example 608

1,1,1-trifluoro-2-methylpropan-2-yl ((4-(5-(1,1-difluoroethyl)pyridin-2-yl) bicyclo[2.2.2]octan-1-yl)methyl)(4-(5-(2-hydroxypropan-2-yl)pyrimidin-2-yl) pyridin-2-yl) carbamate (608)

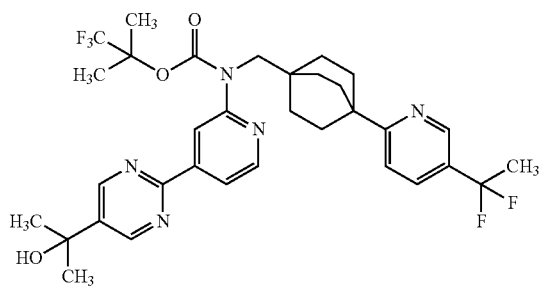

Step A. Intermediate 608A. Preparation of 2-(2-chloropyrimidin-5-yl)propan-2-ol

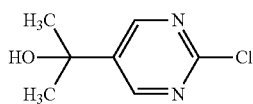

To a stirred solution of methyl 2-chloropyrimidine-5-carboxylate (1 g, 5.79 mmol) in THF (20 mL) was added methyl magnesium bromide in diethyl ether (3 M) (5.79 mL, 17.38 mmol) drop wise at 0° C. The reaction mixture was stirred at 0° C. for 15 min. The reaction was quenched with saturated aqueous ammonium chloride solution. The reaction mixture was diluted with water (30 mL) and extracted with ethyl acetate (2×50 mL). The combined organic layer was washed with brine solution (20 mL), dried over anhydrous sodium sulfate, filtered and concentrated under reduced pressure. The crude material was purified via flash silica gel column chromatography (24 g silica gel column, conditions: 30% ethyl acetate in pet ether) to afford the title compound (brown solid, 750 mg, 4.35 mmol, 75% yield). $^1$H NMR (400 MHz, DMSO-$d_6$) δ 8.83 (s, 2H), 5.33-5.30 (s, 1H), 1.47 (s, 6H).

Step B. Example 608. Preparation of 1,1,1-trifluoro-2-methylpropan-2-yl ((4-(5-(1,1-difluoroethyl)pyridin-2-yl)bicyclo[2.2.2]octan-1-yl)methyl)(4-(5-(2-hydroxypropan-2-yl) pyrimidin-2-yl)pyridin-2-yl) carbamate

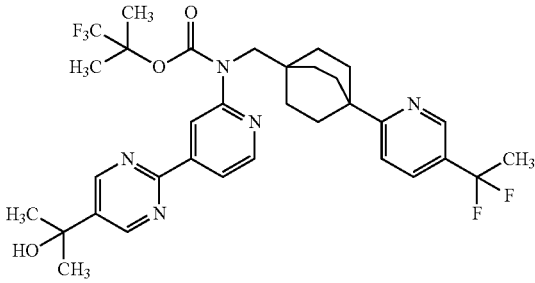 [SMILES: CC(C)(O)c1cnc(-c2ccnc(N(CC34CCC(c5ccc(C(C)(F)F)cn5)(CC3)CC4)C(=O)OC(C)(C)C(F)(F)F)c2)nc1]

The title compound was synthesized according to the general method described for the synthesis of Example 149 by substituting Intermediate 608A and Intermediate 607B where appropriate: (7.3 mg, 0.011 mmol, 24% yield). $^1$H NMR (400 MHz, DMSO-$d_6$) δ 9.07 (s, 2H), 8.65 (d, J=1.2 Hz, 1H), 8.59 (d, J=5.1 Hz, 1H), 8.38 (s, 1H), 8.11 (dd, J=1.3, 5.3 Hz, 1H), 7.84 (dd, J=2.2, 8.6 Hz, 1H), 7.38 (d, J=8.3 Hz, 1H), 5.53 (s, 1H), 3.94 (s, 2H), 1.97 (t, J=19.1 Hz, 3H), 1.84-1.66 (m, 12H), 1.53 (s, 6H), 1.45-1.33 (m, 6H). FXR EC$_{50}$ (nM)=301. MS (ESI) 648 (M+H).

Example 609

1,1,1-trifluoro-2-methylpropan-2-yl((4-(5-(1,1-difluoroethyl)-1,2,4-oxadiazol-3-yl)bicyclo[2.2.2]octan-1-yl)methyl)(4-(4-(2-hydroxypropan-2-yl)phenyl)pyridin-2-yl)carbamate (609)

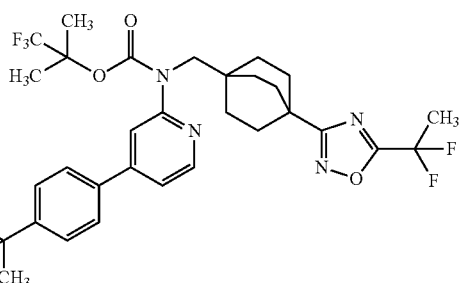

Step A. Intermediate 609A. Preparation of methyl 4-cyanobicyclo[2.2.2]octane-1-carboxylate

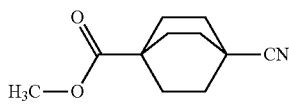

To a stirred solution of 4-(methoxycarbonyl)bicyclo[2.2.2]octane-1-carboxylic acid (5.0 g, 23.56 mmol) in EtOAc (75 mL) were added ammonium chloride (2.52 g, 47.1 mmol), DIPEA (20.57 mL, 118 mmol) and propylphosphonic anhydride solution 50% in EtOAc (45 g, 70.7 mmol) under nitrogen atmosphere. The reaction mixture was stirred at room temperature for 1 h. The reaction mixture was heated at 75° C. for overnight. The reaction mixture was concentrated under reduced pressure. Residue water (100 mL) was added and the reaction mixture was stirred for 30 minutes at room temperature. The solids were filtered, dried under vacuum to afford the title compound (4.4 g, 22.77 mmol, 97% yield) as a brown solid. $^1$H NMR (400 MHz, DMSO-$d_6$) δ 3.60-3.55 (m, 3H), 1.93-1.82 (m, 6H), 1.75-1.68 (m, 6H).

Step B. Intermediate 609B. Preparation of methyl (E)-4-(N'-hydroxycarbamimidoyl) bicyclo[2.2.2]octane-1-carboxylate

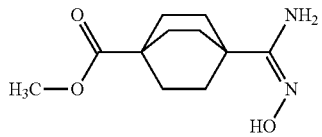 [SMILES: COC(=O)C12CCC(/C(N)=N\O)(CC1)CC2]

To a stirred solution of Intermediate 609A (7.6 g, 39.3 mmol) in ethanol (160 mL) was added hydroxylamine (50% aqueous solution, 12.05 mL, 197 mmol). The reaction mixture was refluxed at 80° C. for 1 h. The reaction mixture was cooled to room temperature, concentrated under reduced pressure and the residue was diluted with water (100 mL). The solids were filtered and dried in vacuo to afford the title compound (8.3 g, 36.7 mmol, 93% yield) as a white solid. $^1$H NMR (400 MHz, DMSO-$d_6$) δ 8.89 (s, 1H), 5.19-5.10 (m, 2H), 3.60-3.54 (m, 3H), 1.73-1.63 (m, 12H). MS (ESI) 227 (M+H).

Step C. Intermediate 609C. Preparation of methyl 4-(5-(1,1-difluoroethyl)-1,2,4-oxadiazol-3-yl)bicyclo[2.2.2]octane-1-carboxylate

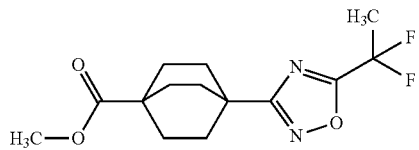

To a stirred solution of Intermediate 609B (2 g, 8.84 mmol) in DMF (40 mL) were added 2,2-difluoropropanoic acid (1.459 g, 13.26 mmol), benzotriazol-1-yl oxytris(dimethylamino)phosphonium hexafluorophosphate (4.3 g, 9.72 mmol) followed by TEA (4.93 mL, 35.4 mmol) at room temperature. The reaction mixture was stirred at room temperature for 1 h and then heated at 110° C. for 4 h. The reaction mixture was cooled to room temperature and diluted with water (50 mL). The aqueous layer was extracted with EtOAc (2×75 mL). The combined organic layers were washed with water (25 mL), brine solution (25 mL), dried over anhydrous sodium sulphate and concentrated under reduced pressure. The crude material was purified via flash column chromatography (40 g silica gel cartridge; A=hexanes, B=EtOAc; 30 min grad.; 0% B to 40% B; flow rate=40 mL/min). The pure fractions were combined, concentrated under reduced pressure and dried in vacuo to afford the title compound (2.1 g, 6.99 mmol, 79% yield) brown gummy mass. $^1$H NMR (400 MHz, DMSO-$d_6$) δ 3.61 (s, 3H), 2.16 (t, J=19.6 Hz, 3H), 1.94-1.78 (m, 12H).

Step D. Intermediate 609D. Preparation of (4-(5-(1,1-difluoroethyl)-1,2,4-oxadiazol-3-yl)bicyclo[2.2.2]octan-1-yl) methanol

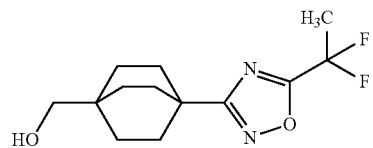 [SMILES: CC(F)(F)c1nc(C23CCC(CO)(CC2)CC3)no1]

To a stirred solution of Intermediate 609C (2.1 g, 6.99 mmol) in THF (20 mL) was added diisobutylaluminium hydride (1.0 M) (17.48 mL, 17.48 mmol) drop wise at −78° C. over a period of 5 minutes. The reaction mixture was stirred at −78° C. for 1 h. The reaction was quenched with saturated aqueous ammonium chloride solution. The reaction mixture was extracted with ethyl acetate (2×50 mL). The organic layer was washed with aqueous 1.5 N HCl solution (50 mL). The combined organic layers were washed with brine solution (20 mL), dried over anhydrous sodium sulphate, filtered and concentrated under reduced pressure. The crude material was purified via flash column chromatography (40 g silica gel cartridge; A=hexanes, B=EtOAc; 30 min grad.; 0% B to 60% B; flow rate=40 mL/min). The pure fractions were combined, concentrated under reduced pressure and dried in vacuo to afford the title compound (1.7 g, 6.24 mmol, 89% yield) colorless oil. $^1$H NMR (400 MHz, DMSO-$d_6$) δ 4.41 (t, J=5.3 Hz, 1H), 3.09 (d, J=5.0 Hz, 2H), 2.15 (t, J=19.6 Hz, 3H), 1.90-1.80 (m, 6H), 1.50-1.41 (m, 6H).

Step E. Intermediate 609E. Preparation of 4-(5-(1,1-difluoroethyl)-1,2,4-oxadiazol-3-yl) bicyclo[2.2.2]octane-1-carbaldehyde

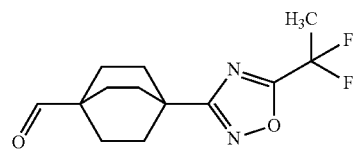 [SMILES: CC(F)(F)c1nc(C23CCC(C=O)(CC2)CC3)no1]

To a stirred solution of Intermediate 609D (1.7 g, 6.24 mmol) in DCM (35 mL) was added Dess-Martin periodinane (3.178 g, 7.49 mmol) at 0° C. The reaction mixture was stirred at 0° C. for 15 min. The reaction mixture was diluted with DCM (50 mL), washed with aqueous 10% sodium bicarbonate solution (3×50 mL). The organic layers were washed with brine solution (20 mL), dried over anhydrous sodium sulphate and concentrated under reduced pressure. The crude material was purified via flash column chromatography (24 g silica gel cartridge; A=hexanes, B=EtOAc; 30 min grad.; 0% B to 25% B; flow rate=24 mL/min). The pure fractions were combined, concentrated under reduced pressure and dried in vacuo to afford the title compound (1.3 g, 4.76 mmol, 76% yield) white solid. $^1$H NMR (300 MHz, DMSO-$d_6$) δ 9.46 (s, 1H), 2.25-2.05 (m, 3H), 1.95-1.83 (m, 6H), 1.74-1.63 (m, 6H).

Step F. Intermediate 609F. Preparation of 4-bromo-N-((4-(5-(1,1-difluoroethyl)-1,2,4-oxadiazol-3-yl)bicyclo[2.2.2]octan-1-yl) methyl) pyridin-2-amine

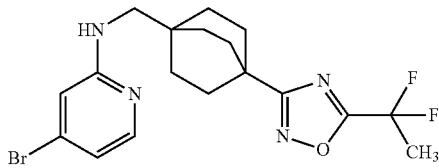

To a stirred solution of Intermediate 609E (10 g, 37 mmol) and 4-bromopyridin-2-amine (5.82 g, 33.6 mmol) in MeOH (200 mL) was added acetic acid (3.85 mL, 67.3 mmol) followed by molecular sieves 4A (500 mg). The reaction mixture was heated to 60° C. and stirred for 16 h. The reaction mixture was cooled to 0° C. and sodium cyanoborohydride (4.23 g, 67.3 mmol) was added. The reaction mixture was stirred for 1 h at room temperature. The reaction mixture was concentrated under reduced pressure, diluted with water (100 mL) and extracted with ethyl acetate (2×100 mL). The combined organic layers were washed with brine (50 mL), dried over anhydrous sodium sulphate, filtered and concentrated under reduced pressure to afford the residue. The residue was purified via flash column chromatography (120 g silica gel column, conditions: 30% ethyl acetate in pet ether) to afford the title compound (9.0 g, 21.06 mmol, 63% yield) as a white solid. $^1$H NMR (300 MHz, DMSO-$d_6$) δ 7.79-7.83 (m, 1H), 6.70 (t, J=5.48 Hz, 1H), 6.76 (d, J=1.51 Hz, 1H), 6.60 (dd, J=5.48, 1.70 Hz, 1H), 3.12-3.19 (m, 2H), 2.08-2.24 (m, 3H), 1.82-1.87 (m, 6H), 1.48-1.56 (m, 6H). MS (ESI) 427 (M+H).

Step G. Intermediate 609G. Preparation of 1,1,1-trifluoro-2-methylpropan-2-yl(4-bromopyridin-2-yl)((4-(5-(1,1-difluoroethyl)-1,2,4-oxadiazol-3-yl)bicyclo[2.2.2]octan-1-yl)methyl)carbamate

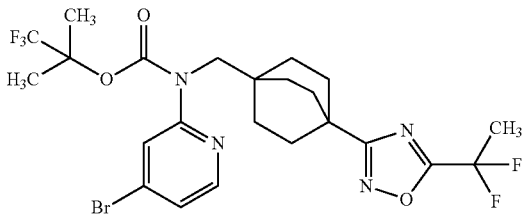 [SMILES: CC(F)(F)c1nc(C23CCC(CN(C(=O)OC(C)(C)C(F)(F)F)c4cc(Br)ccn4)(CC2)CC3)no1]

To a stirred solution of Intermediate 609F (6.0 g, 14.04 mmol) in THF (60 mL) was added LiHMDS in THF (1.0 M) (35.1 mL, 35.1 mmol) drop wise at −50° C. over a period of 5 minutes. The reaction mixture was stirred at −50° C. for 10 min. To this reaction mixture, a solution of pyridin-2-yl (1,1,1-trifluoro-2-methylpropan-2-yl)carbonate (3.5 g, 14.04 mmol) in THF (10 mL) was added. The reaction mixture was stirred at −50° C. for 1 h. The reaction was quenched with saturated aqueous ammonium chloride solution, diluted with water (50 mL) and extracted with ethyl acetate (2×75 mL). The combined organic layers were washed with brine solution (50 mL), dried over anhydrous sodium sulphate, filtered and concentrated under reduced pressure. The crude material was purified via flash column chromatography (120 g silica gel column, conditions: 30% ethyl acetate in pet ether) to afford the title compound (5.8 g, 9.98 mmol, 71% yield) as a pale yellow gummy solid. $^1$H NMR (400 MHz, DMSO-$d_6$) δ 8.32-8.28 (m, 1H), 7.80 (d, J=1.5 Hz, 1H), 7.50 (dd, J=1.8, 5.3 Hz, 1H), 3.86-3.82 (m, 2H), 2.19-2.05 (m, 3H), 1.81-1.72 (m, 6H), 1.68 (s, 6H), 1.41-1.30 (m, 6H). MS (ESI) 581 (M+H).

Step H. Example 609. Preparation of 1,1,1-trifluoro-2-methylpropan-2-yl((4-(5-(1,1-difluoroethyl)-1,2,4-oxadiazol-3-yl)bicyclo[2.2.2]octan-1-yl)methyl)(4-(4-(2-hydroxypropan-2-yl)phenyl)pyridin-2-yl)carbamate

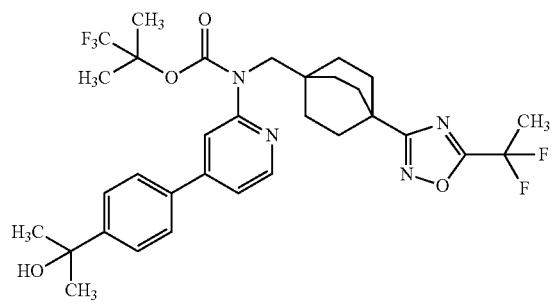 [SMILES: CC(C)(O)c1ccc(-c2ccnc(N(CC34CCC(c5noc(C(C)(F)F)n5)(CC3)CC4)C(=O)OC(C)(C)C(F)(F)F)c2)cc1]

The mixture of Intermediate 609G (25 mg, 0.043 mmol), (4-(2-hydroxypropan-2-yl) phenyl)boronic acid (7.74 mg, 0.043 mmol) and $K_2CO_3$ (11.89 mg, 0.086 mmol) in 1,4-dioxane (1 mL) and $H_2O$ (0.25 mL) was stirred at room temperature. Argon gas was bubbled through the mixture for 5 min. $PdCl_2$(dppf) (1.573 mg, 2.150 μmol) was added and argon gas was bubbled through the mixture for another 5 min. The reaction mixture was heated at 110° C. for 90 min. The reaction mixture was cooled to room temperature and diluted with EtOAc (5 mL). The organic layer was washed with water (5 mL), brine (5 mL), dried over anhydrous sodium sulfate and concentrated under reduced pressure to afford the residue. The crude material was purified via preparative LC/MS using following conditions: Column: Waters XBridge C18, 150 mm×19 mm, 5-μm particles; Mobile Phase A: 5:95 acetonitrile:water with 10-mM ammonium acetate; Mobile Phase B: 95:5 acetonitrile:water with 10-mM ammonium acetate; Gradient: a 0-minute hold at 28% B, 28-80% B over 20 minutes, then a 5-minute hold at 100% B; Flow Rate: 15 mL/min; Column Temperature: 25° C. Fraction collection was triggered by signals. Fractions containing the product were combined and dried via centrifugal evaporation to afford the title compound (11.3 mg, 0.018 mmol, 43% yield). $^1$H NMR (400 MHz DMSO-$d_6$) δ 8.44 (d, J=5.1 Hz, 1H), 7.76 (d, J=8.8 Hz, 3H), 7.62 (d, J=8.3 Hz, 2H), 7.57 (dd, J=1.5, 5.1 Hz, 1H), 5.13 (s, 1H), 3.86 (s, 2H), 2.12 (t, J=19.7 Hz, 3H), 1.80-1.57 (m, 12H), 1.46 (s, 6H), 1.44-1.26 (m, 6H). FXR $EC_{50}$ (nM)=30. MS (ESI) 637 (M+H).

Example 610

1,1,1-trifluoro-2-methylpropan-2-yl ((4-(5-(1,1-difluoroethyl)-1,2,4-oxadiazol-3-yl) bicyclo[2.2.2]octan-1-yl)methyl)(4-(4-isopropoxyphenyl)pyridin-2-yl)carbamate

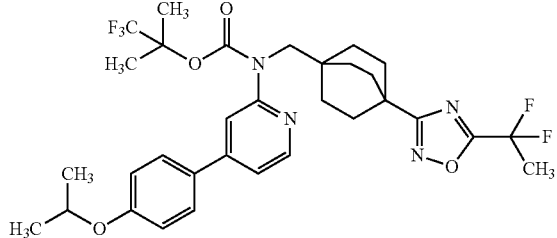

(610)

The title compound was synthesized according to the general method described for the synthesis of Example 149 by substituting Intermediate 609B and the corresponding boronic acid where appropriate: (8.0 mg, 0.013 mmol, 29.2% yield). $^1$H NMR (400 MHz, DMSO-d$_6$) δ 8.40 (d, J=5.4 Hz, 1H), 7.86-7.68 (m, 3H), 7.53 (dd, J=1.5, 5.4 Hz, 1H), 7.06 (d, J=8.8 Hz, 2H), 4.72 (td, J=6.0, 12.0 Hz, 1H), 3.85 (s, 2H), 2.12 (t, J=19.7 Hz, 3H), 1.84-1.72 (m, 6H), 1.70 (m, 6H), 1.46-1.34 (m, 6H), 1.30 (d, J=6.1 Hz, 6H). FXR EC$_{50}$ (nM)=47. MS (ESI) 637 (M+H).

Example 611

3-(tert-butyl)-1-(4'-(2-hydroxypropan-2-yl)-[1,1'-biphenyl]-3-yl)-1-((4-(5-(trifluoromethyl)-1,2,4-oxadiazol-3-yl)bicyclo[2.2.2]octan-1-yl)methyl) urea

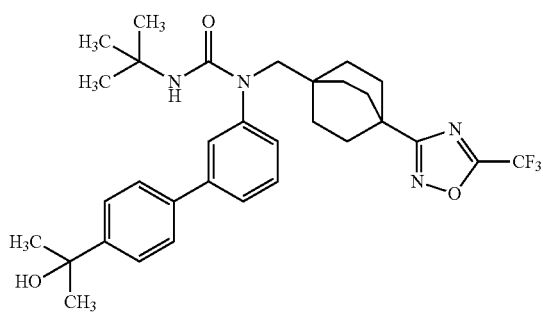

(611)

Step A. Intermediate 611A. Preparation of methyl 4-(5-(trifluoromethyl)-1,2,4-oxadiazol-3-yl)bicyclo[2.2.2]octane-1-carboxylate

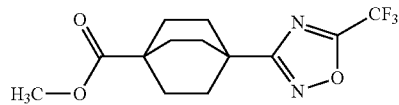

To a stirred solution of Intermediate 206C (7 g, 30.9 mmol) in DMF (70 mL) was added pyridine (5 mL, 61.9 mmol). The reaction mixture was cooled to 0° C. and trifluoroacetic anhydride (6.55 mL, 46.4 mmol) was added drop wise over a period of 10 minutes. The reaction mixture was stirred at room temperature overnight. The reaction mixture was concentrated under reduced pressure. The residue was diluted with ice cold water (50 mL) and extracted with ethyl acetate (2×75 mL). The combined organic layers were washed with aqueous 1 N HCl (2×25 mL) followed by brine solution (20 mL), dried over anhydrous sodium sulfate and concentrated under reduced pressure to afford the residue. The crude material was purified via flash silica gel column chromatography (80 g silica gel cartridge; A=hexanes, B=EtOAc; 30 min grad.; 0% B to 30% B; flow rate=80 mL/min). The pure fractions were combined, concentrated under reduced pressure and dried in vacuo to afford the title compound (colorless liquid, 8 g, 26.3 mmol, 85% yield). $^1$H NMR (400 MHz, DMSO-d$_6$) δ 3.61 (s, 3H), 1.92-1.81 (m, 12H).

Step B. Intermediate 611B. Preparation of (4-(5-(trifluoromethyl)-1,2,4-oxadiazol-3-yl) bicyclo[2.2.2]octan-1-yl) methanol

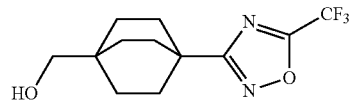 [SMILES: OCC12CCC(c3noc(C(F)(F)F)n3)(CC1)CC2]

The title compound was prepared according to the general method described for the synthesis of Intermediate 1G by substituting Intermediate 611A where appropriate: (colorless liquid, 4 g, 14.48 mmol, 55% yield). $^1$H NMR (400 MHz, DMSO-d$_6$) δ 4.44 (t, J=5.3 Hz, 1H), 3.09 (d, J=5.5 Hz, 2H), 1.88-1.82 (m, 6H), 1.50-1.42 (m, 6H). MS (ESI) 279 (M+H).

Step C. Intermediate 611C. Preparation of 4-(5-(trifluoromethyl)-1,2,4-oxadiazol-3-yl) bicyclo[2.2.2]octane-1-carbaldehyde

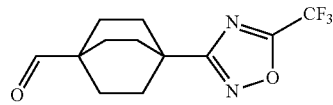 [SMILES: O=CC12CCC(c3noc(C(F)(F)F)n3)(CC1)CC2]

The title compound was prepared according to the general method described for the synthesis of Intermediate 3C by substituting Intermediate 611B where appropriate: (colorless liquid, 1.6 g, 5.83 mmol, 40% yield). $^1$H NMR (400 MHz, DMSO-d$_6$) δ 9.47 (s, 1H), 1.94-1.88 (m, 6H), 1.74-1.67 (m, 6H).

Step D. Intermediate 611D. Preparation of 3-bromo-N-((4-(5-(trifluoromethyl)-1,2,4-oxadiazol-3-yl)bicyclo[2.2.2]octan-1-yl) methyl) aniline

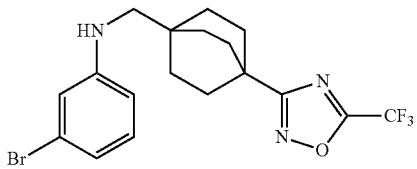 [SMILES: FC(F)(F)c1nc(C23CCC(CNc4cccc(Br)c4)(CC2)CC3)no1]

The title compound was prepared according to the general method described for the synthesis of Intermediate 1I by substituting Intermediate 611C and 3-bromoaniline where appropriate: (Off-white solid, 650 mg, 1.511 mmol, 75% yield). $^1$H NMR (400 MHz, DMSO-$d_6$) δ 7.00-6.93 (m, 1H), 6.80-6.74 (m, 1H), 6.63-6.57 (m, 2H), 5.81-5.74 (m, 1H), 2.81 (d, J=5.9 Hz, 2H), 1.91-1.82 (m, 6H), 1.62-1.48 (m, 6H). MS (ESI) 430 (M+H).

Step E. Intermediate 611E. Preparation of 1-(4-bromopyridin-2-yl)-3-(tert-butyl)-1-((4-(5-(trifluoromethyl)-1,2,4-oxadiazol-3-yl)bicyclo[2.2.2]octan-1-yl) methyl) urea

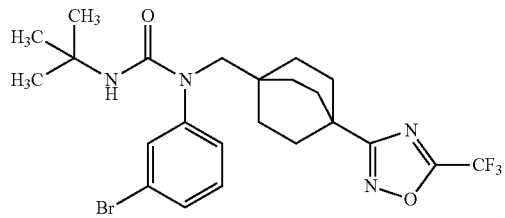 [SMILES: CC(C)(C)NC(=O)N(CC12CCC(c3noc(C(F)(F)F)n3)(CC1)CC2)c1cccc(Br)c1]

The title compound was prepared according to the general method described for the synthesis of Example 586 by substituting Intermediate 611D and the corresponding amine where appropriate: (brown gum, 600 mg, 1.134 mmol, 69% yield). MS (ESI) 529 (M+H).

Step F. Example 611. Preparation of 3-(tert-butyl)-1-(4'-(2-hydroxypropan-2-yl)-[1,1'-biphenyl]-3-yl)-1-((4-(5-(trifluoromethyl)-1,2,4-oxadiazol-3-yl)bicyclo[2.2.2]octan-1-yl) methyl)urea

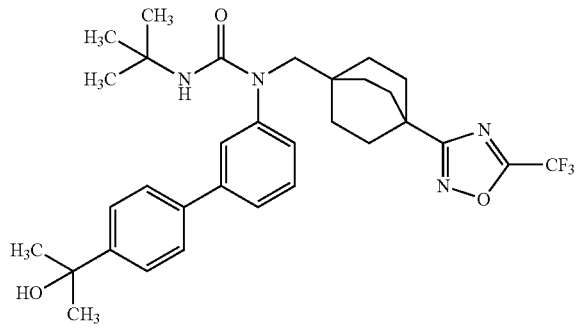 [SMILES: CC(C)(C)NC(=O)N(CC12CCC(c3noc(C(F)(F)F)n3)(CC1)CC2)c1cccc(-c2ccc(C(C)(C)O)cc2)c1]

The title compound was synthesized according to the general method described for the synthesis of Example 149 by substituting Intermediate 611E and the corresponding boronic acid where appropriate: (7.1 mg, 10.81 μmol, 23% yield). $^1$H NMR (400 MHz, DMSO-$d_6$) δ 7.67-7.43 (m, 7H), 7.31 (d, J=7.8 Hz, 1H), 5.18-4.98 (m, 1H), 4.74 (s, 1H), 3.60 (s, 2H), 1.83-1.72 (m, 6H), 1.52-1.39 (m, 12H), 1.21 (s, 9H). FXR EC$_{50}$ (nM)=41. MS (ESI) 585 (M+H).

Example 612

3-(tert-butyl)-1-(4'-(difluoromethoxy)-[1,1'-biphenyl]-3-yl)-1-((4-(5-(trifluoromethyl)-1,2,4-oxadiazol-3-yl)bicyclo[2.2.2]octan-1-yl)methyl)urea

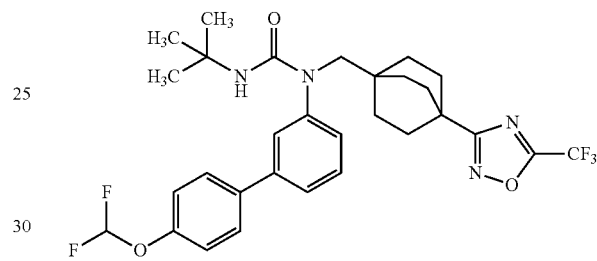

(612)

The title compound was synthesized according to the general method described for the synthesis of Example 149 by substituting Intermediate 611E and the corresponding boronic acid where appropriate: (10 mg, 0.016 mmol, 35% yield). $^1$H NMR (400 MHz, DMSO-$d_6$) δ 7.80-7.72 (m, 2H), 7.62 (s, 1H), 7.58-7.46 (m, 2H), 7.37-7.10 (m, 4H), 4.75 (s, 1H), 3.60 (s, 2H), 1.84-1.68 (m, 6H), 1.51-1.36 (m, 6H), 1.20 (s, 9H). FXR EC$_{50}$ (nM)=65. MS (ESI) 593 (M+H).

Example 613

3-(tert-butyl)-1-(4'-(2-(difluoromethoxy)propan-2-yl)-[1,1'-biphenyl]-3-yl)-1-((4-(5-(trifluoromethyl)-1,2,4-oxadiazol-3-yl)bicyclo[2.2.2]octan-1-yl)methyl) urea

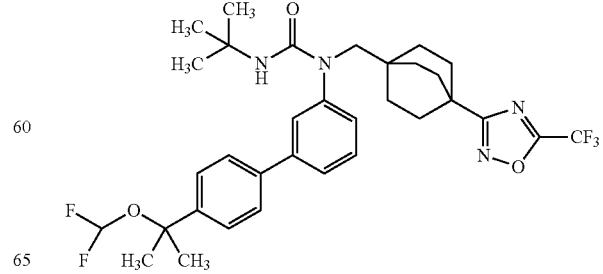

(613)

Step A. Intermediate 613A. Preparation of 2-(4-bromophenyl) propan-2-ol

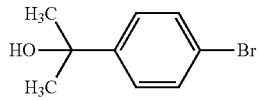

To a stirred solution of methyl 4-bromobenzoate (3 g, 13.95 mmol) in THF (30 mL) was added methyl magnesium bromide in THF (3M) (13.95 mL, 4.19 mmol) drop wise at −10° C. The reaction mixture was gradually warmed to room temperature and stirred at room temperature overnight. The reaction was quenched with saturated aqueous ammonium chloride solution, diluted with water (30 mL) and extracted with ethyl acetate (2×50 mL). The combined organic layer was washed with brine solution (20 mL), dried over anhydrous sodium sulphate, filtered and concentrated under reduced pressure. The crude material was purified via flash silica gel column chromatography (40 g silica gel column, conditions: 30% ethyl acetate in pet ether) to afford the title compound (yellow liquid, 2.5 g, 11.62 mmol, 83% yield). $^1$H NMR (300 MHz, DMSO-$d_6$) δ 7.29-7.55 (m, 4H), 5.11 (s, 1H), 1.32-1.51 (m, 6H).

Step B. Intermediate 613B. Preparation of 1-bromo-4-(2-(difluoromethoxy)propan-2-yl) benzene

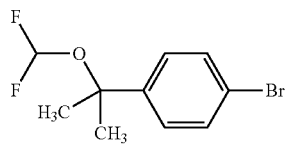

To a stirred solution of 2-(4-bromophenyl) propan-2-ol (1000 mg, 4.65 mmol) in DCM (3 mL) and H$_2$O (3 mL) were added potassium hydrogen fluoride (2905 mg, 37.2 mmol) and (bromodifluoromethyl)trimethylsilane (2.179 mL, 13.95 mmol) under a nitrogen atmosphere. The reaction mixture was stirred at room temperature overnight. The reaction mixture was diluted with water (30 mL) and extracted with DCM (2×30 mL). The combined organic layer was washed with brine solution (20 mL), dried over anhydrous sodium sulphate, filtered and concentrated under reduced pressure. The residue was purified via flash silica gel column chromatography (24 g silica gel column, conditions: 25% ethyl acetate in pet ether) to afford the title compound (350 mg, 1.320 mmol, 28% yield) as colorless liquid $^1$H NMR (300 MHz, DMSO-$d_6$) δ 7.60 (d, J=8.59 Hz, 2H), 7.13-7.33 (m, 3H), 1.63 (s, 6H).

Step C. Intermediate 613C. Preparation of 2-(4-(2-(difluoromethoxy)propan-2-yl) phenyl)-4,4,5,5-tetramethyl-1,3,2-dioxaborolane

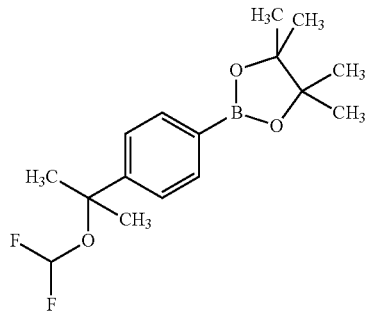 [SMILES: CC(C)(OC(F)F)c1ccc(B2OC(C)(C)C(C)(C)O2)cc1]

The title compound was prepared according to the general method described for the synthesis of Intermediate 607B by substituting Intermediate 613B where appropriate: (0.3 g, 0.961 mmol, 51% yield). $^1$H NMR (300 MHz, DMSO-$d_6$) δ 7.65-7.73 (m, 2H), 7.47 (d, J=8.26 Hz, 2H), 6.27-6.83 (m, 1H), 1.59-1.68 (m, 6H), 1.29 (s, 12H).

Step D. Example 613. Preparation of 3-(tert-butyl)-1-(4'-(2-(difluoromethoxy)propan-2-yl)-[1,1'-biphenyl]-3-yl)-1-((4-(5-(trifluoromethyl)-1,2,4-oxadiazol-3-yl)bicyclo[2.2.2]octan-1-yl)methyl)urea The title compound was synthesized according to the general method described for the synthesis of Example 149 by substituting Intermediate 611E and Intermediate 613C where appropriate: (5.2 mg, 7.87 μmol, 17% yield). $^1$H NMR (400 MHz, DMSO-$d_6$) δ 7.74 (d, J=8.3 Hz, 2H), 7.63 (s, 1H), 7.56 (d, J=8.3 Hz, 3H), 7.54-7.44 (m, 1H), 7.34 (br d, J=7.8 Hz, 1H), 6.80-6.39 (m, 1H), 4.76 (s, 1H), 3.60 (s, 2H), 1.83-1.72 (m, 6H), 1.68 (s, 6H), 1.50-1.36 (m, 6H), 1.21 (s, 9H). FXR EC$_{50}$ (nM)=79. MS (ESI) 635 (M+H).

Example 614

1-(4'-(2-hydroxypropan-2-yl)-[1,1'-biphenyl]-3-yl)-3-(spiro[2.3]hexan-5-ylmethyl)-1-((4-(5-(trifluoromethyl)-1,2,4-oxadiazol-3-yl)bicyclo[2.2.2]octan-1-yl)methyl)urea (614)

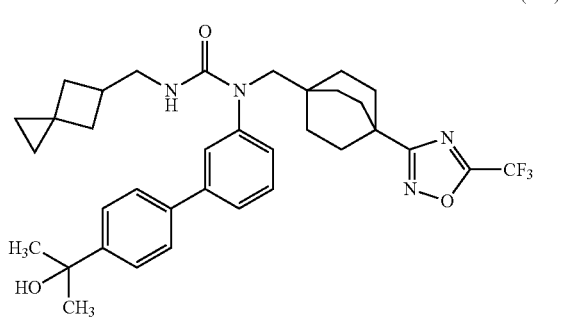

707

Step A. Intermediate 614A. Preparation of 1-(3-bromophenyl)-3-(spiro[2.3]hexan-5-ylmethyl)-1-((4-(5-(trifluoromethyl)-1,2,4-oxadiazol-3-yl)bicyclo[2.2.2]octan-1-yl)methyl) urea

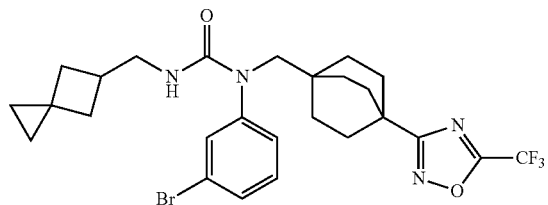 [SMILES: O=C(NCC1CC2(CC2)C1)N(CC12CCC(c3noc(C(F)(F)F)n3)(CC1)CC2)c1cccc(Br)c1]

The title compound was prepared according to the general method described for the synthesis of Example 586 by substituting Intermediate 611D and the corresponding amine where appropriate: (gummy solid, 80 mg, 0.141 mmol, 76% yield). MS (ESI) 567 (M+H).

Step B. Example 614. Preparation of 1-(4'-(2-hydroxypropan-2-yl)-[1,1'-biphenyl]-3-yl)-3-(spiro[2.3]hexan-5-ylmethyl)-1-((4-(5-(trifluoromethyl)-1,2,4-oxadiazol-3-yl) bicyclo[2.2.2]octan-1-yl)methyl) urea The title compound was synthesized according to the general method described for the synthesis of Example 149 by substituting Intermediate 614A and the corresponding boronic acid where appropriate: (5.6 mg, 8.99 μmol, 20.41% yield). $^1$H NMR (400 MHz, DMSO-$d_6$) δ 7.66-7.58 (m, 2H), 7.57-7.50 (m, 4H), 7.50-7.42 (m, 1H), 7.28 (br d, J=7.6 Hz, 1H), 5.66 (t, J=5.6 Hz, 1H), 5.04 (s, 1H), 3.61 (s, 2H), 3.14 (m, 2H), 2.48-2.37 (m, 1H), 2.03-1.94 (m, 2H), 1.84-1.68 (m, 8H), 1.48-1.39 (m, 12H), 0.40-0.17 (m, 4H). FXR EC$_{50}$ (nM)=171. MS (ESI) 623 (M+H).

Example 615

1,1,1-trifluoro-2-methylpropan-2-yl (4-(4-(chlorodifluoromethoxy)phenyl)pyridin-2-yl)((4-(5-(1,1-difluoroethyl)-1,2,4-oxadiazol-3-yl)bicyclo[2.2.2]octan-1-yl)methyl)carbamate (615)

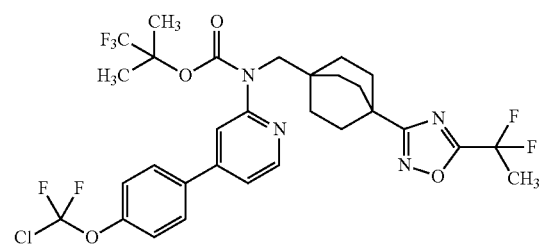

708

Step A. Intermediate 615A. Preparation of 2-(4-(chlorodifluoromethoxy)phenyl)-5,5-dimethyl-1,3,2-dioxaborinane

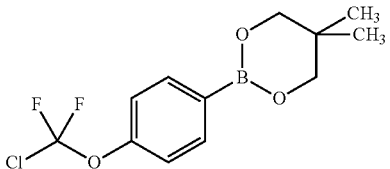 [SMILES: CC1(C)COB(c2ccc(OC(F)(F)Cl)cc2)OC1]

The title compound was prepared according to the general method described for the synthesis of Intermediate 607B by substituting 1-bromo-4-(chlorodifluoromethoxy)benzene where appropriate: (0.3 g, 1.033 mmol, 53% yield) as white fluffy solid. $^1$H NMR (300 MHz, DMSO-$d_6$) δ 7.81 (d, J=8.6 Hz, 2H), 7.33 (dd, J=0.8, 7.8 Hz, 2H), 3.77 (s, 4H), 0.96 (s, 6H).

Step B. Example 615. Preparation of 1,1,1-trifluoro-2-methylpropan-2-yl (4-(4-(chlorodifluoromethoxy)phenyl)pyridin-2-yl)((4-(5-(1,1-difluoroethyl)-1,2,4-oxadiazol-3-yl)bicyclo[2.2.2]octan-1-yl)methyl)carbamate The title compound was synthesized according to the general method described for the synthesis of Example 149 by substituting Intermediate 609B and Intermediate 615A where appropriate: (15.2 mg, 0.021 mmol, 50% yield). $^1$H NMR (400 MHz, DMSO-$d_6$) δ 8.49 (d, J=5.1 Hz, 1H), 8.03-7.92 (m, 2H), 7.85 (s, 1H), 7.61 (dd, J=1.6, 5.3 Hz, 1H), 7.54 (d, J=8.8 Hz, 2H), 3.87 (s, 2H), 2.12 (t, J=19.7 Hz, 3H), 1.83-1.72 (m, 6H), 1.70 (m, 6H), 1.48-1.32 (m, 6H). FXR EC$_{50}$ (nM)=473. MS (ESI) 679 (M+H).

Example 616

1,1,1-trifluoro-2-methylpropan-2-yl((4-(3-cyclopropyl-1,2,4-oxadiazol-5-yl)bicyclo[2.2.2]octan-1-yl)methyl)(5-fluoro-4-(4-(2-hydroxypropan-2-yl)phenyl) pyridin-2-yl)carbamate (616)

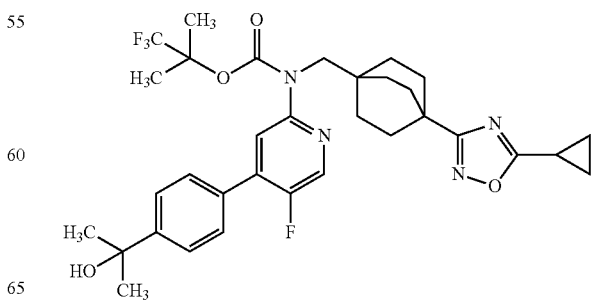

Step A. Intermediate 616A. Preparation of N-((4-(3-cyclopropyl-1,2,4-oxadiazol-5-yl) bicyclo[2.2.2]octan-1-yl)methyl)-5-fluoro-4-iodopyridin-2-amine

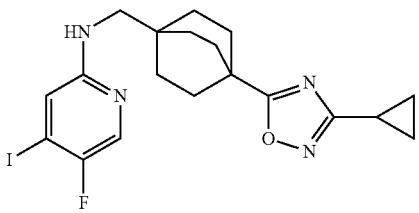 [SMILES: Fc1cnc(NCC23CCC(c4nc(C5CC5)no4)(CC2)CC3)cc1I]

The title compound was prepared according to the general method described for the synthesis of Intermediate 1I by substituting Intermediate 4C and 5-fluoro-4-iodopyridin-2-amine where appropriate: (light yellow colored solid, 300 mg, 0.641 mmol, 20% yield). MS (ESI) 469 (M+H).

Step B. Intermediate 616B. Preparation of 1,1,1-trifluoro-2-methylpropan-2-yl ((4-(3-cyclopropyl-1,2,4-oxadiazol-5-yl)bicyclo[2.2.2]octan-1-yl) methyl)(5-fluoro-4-iodopyridin-2-yl)carbamate

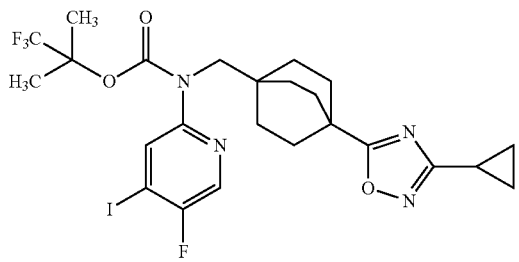 [SMILES: CC(C)(OC(=O)N(CC12CCC(c3nc(C4CC4)no3)(CC1)CC2)c1cc(I)c(F)cn1)C(F)(F)F]

The title compound was synthesized according to the general method described for the synthesis of Intermediate 584A by substituting pyridin-2-yl (1,1,1-trifluoro-2-methylpropan-2-yl)carbonate and Intermediate 616A where appropriate: (Off-white semi-solid, 95 mg, 0.153 mmol, 72% yield). MS (ESI) 623 (M+H).

Step C. Example 616. Preparation of 1,1,1-trifluoro-2-methylpropan-2-yl ((4-(3-cyclopropyl-1,2,4-oxadiazol-5-yl)bicyclo[2.2.2]octan-1-yl)methyl)(5-fluoro-4-(4-(2-hydroxypropan-2-yl)phenyl)pyridin-2-yl)carbamate The title compound was synthesized according to the general method described for the synthesis of Example 149 by substituting Intermediate 616B and the corresponding boronic acid where appropriate: (22.9 mg, 0.036 mmol, 74% yield). $^1$H NMR (400 MHz, DMSO-$d_6$) δ=8.48 (d, J=2.0 Hz, 1H), 7.71 (d, J=5.9 Hz, 1H), 7.67-7.54 (m, 4H), 5.16 (s, 1H), 3.79 (s, 2H), 2.08-1.98 (m, 1H), 1.81-1.72 (m, 6H), 1.68 (s, 6H), 1.47 (s, 6H), 1.42-1.33 (m, 6H), 1.05-0.94 (m, 2H), 0.86-0.72 (m, 2H). FXR EC$_{50}$ (nM)=21. MS (ESI) 631 (M+H).

Example 617

1,1,1-trifluoro-2-methylpropan-2-yl ((4-(3-cyclopropyl-1,2,4-oxadiazol-5-yl) bicyclo[2.2.2]octan-1-yl) methyl)(5-fluoro-4-(4-isopropoxyphenyl)pyridin-2-yl)carbamate

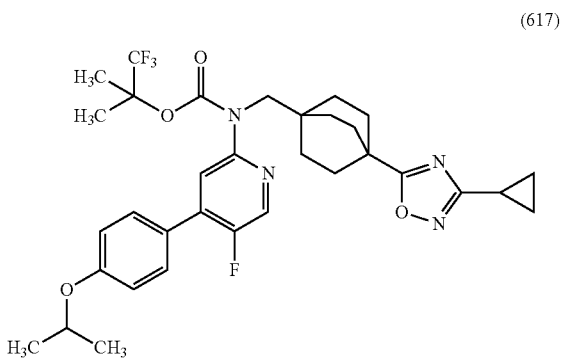 [SMILES: CC(C)Oc1ccc(-c2cc(N(CC34CCC(c5nc(C6CC6)no5)(CC3)CC4)C(=O)OC(C)(C)C(F)(F)F)ncc2F)cc1]

(617)

The title compound was synthesized according to the general method described for the synthesis of Example 149 by substituting Intermediate 616B and the corresponding boronic acid where appropriate: (7.3 mg, 10.70 μmol, 22% yield). $^1$H NMR (400 MHz, DMSO-$d_6$) δ 8.44 (d, J=2.2 Hz, 1H), 7.71-7.66 (m, 1H), 7.63 (d, J=8.1 Hz, 2H), 7.09 (d, J=8.8 Hz, 2H), 4.72 (td, J=6.2, 12.1 Hz, 1H), 3.78 (s, 2H), 2.08-1.98 (m, 1H), 1.81-1.70 (m, 6H), 1.67 (s, 6H), 1.42-1.33 (m, 6H), 1.30 (d, J=5.9 Hz, 6H), 1.04-0.96 (m, 2H), 0.84-0.78 (m, 2H). FXR EC$_{50}$ (nM)=81. MS (ESI) 631 (M+H).

Example 618

1,1,1-trifluoro-2-methylpropan-2-yl((4-(3-cyclopropyl-1,2,4-oxadiazol-5-yl) bicyclo[2.2.2]octan-1-yl) methyl)(5-fluoro-4-(3-fluoro-4-(2-hydroxypropan-2-yl)phenyl)pyridin-2-yl) carbamate

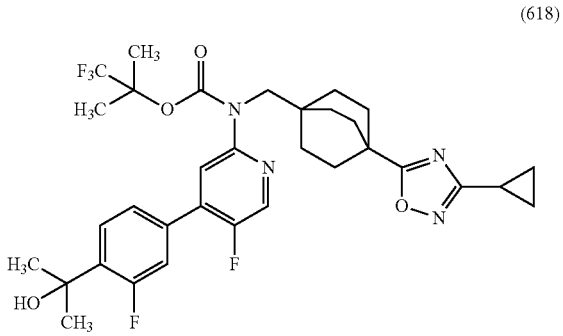 [SMILES: CC(C)(O)c1ccc(-c2cc(N(CC34CCC(c5nc(C6CC6)no5)(CC3)CC4)C(=O)OC(C)(C)C(F)(F)F)ncc2F)cc1F]

(618)

Step A. Intermediate 618A. Preparation of 2-(4-bromo-2-fluorophenyl)propan-2-ol

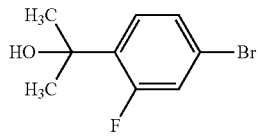

The title compound was prepared according to the general method described for the synthesis of Intermediate 607A by substituting methyl 4-bromo-2-fluorobenzoate where appropriate: (yellow liquid, 2.5 g, 11.62 mmol, 83% yield). $^1$H NMR (400 MHz, DMSO-$d_6$) δ 7.60 (dd, J=7.5, 8.5 Hz, 1H), 7.41 (dd, J=2.0, 11.0 Hz, 1H), 7.25 (dd, J=2.0, 8.5 Hz, 1H), 5.24 (s, 1H), 1.41 (s, 6H).

Step B. Intermediate 618B. Preparation of 2-(2-fluoro-4-(4,4,5,5-tetramethyl-1,3,2-dioxaborolan-2-yl)phenyl)propan-2-ol

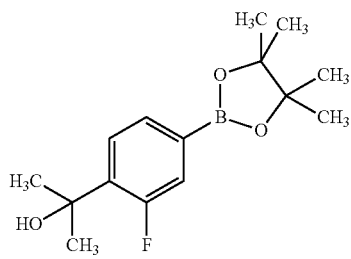 [SMILES: CC(C)(O)c1ccc(B2OC(C)(C)C(C)(C)O2)cc1F]

The title compound was prepared according to the general method described for the synthesis of Intermediate 607B by substituting Intermediate 618A where appropriate: (2.1 g, 6.37 mmol, 59% yield). $^1$H NMR (400 MHz, DMSO-$d_6$) δ 7.69-7.61 (m, 1H), 7.48-7.42 (m, 1H), 7.25 (dd, J=1.0, 12.5 Hz, 1H), 5.29 (s, 1H), 1.47 (d, J=1.0 Hz, 6H), 1.29 (s, 12H).

Step C. Example 618. Preparation of 1,1,1-trifluoro-2-methylpropan-2-yl ((4-(3-cyclopropyl-1,2,4-oxadiazol-5-yl)bicyclo[2.2.2]octan-1-yl)methyl)(5-fluoro-4-(3-fluoro-4-(2-hydroxypropan-2-yl)phenyl) pyridin-2-yl)carbamate The title compound was synthesized according to the general method described for the synthesis of Example 149 by substituting Intermediate 616B and Intermediate 618B where appropriate: (5.2 mg, 7.87 μmol, 17% yield). $^1$H NMR (400 MHz, DMSO-$d_6$) δ 8.50 (d, J=2.2 Hz, 1H), 7.87-7.69 (m, 2H), 7.51 (td, J=1.5, 8.2 Hz, 1H), 7.45 (d, J=13.2 Hz, 1H), 5.46-5.39 (m, 1H), 3.79 (s, 2H), 2.03 (tt, J=4.9, 8.3 Hz, 1H), 1.81-1.72 (m, 6H), 1.68 (s, 6H), 1.52 (s, 6H), 1.44-1.29 (m, 6H), 1.05-0.96 (m, 2H), 0.85-0.77 (m, 2H). FXR EC$_{50}$ (nM)=49. MS (ESI) 649 (M+H).

Example 619

Neopentyl ((4-(5-(1,1-difluoroethyl)-1,2,4-oxadiazol-3-yl)bicyclo[2.2.2]octan-1-yl) methyl) (5-fluoro-4-(4-(2-hydroxypropan-2-yl) phenyl) pyridin-2-yl) carbamate

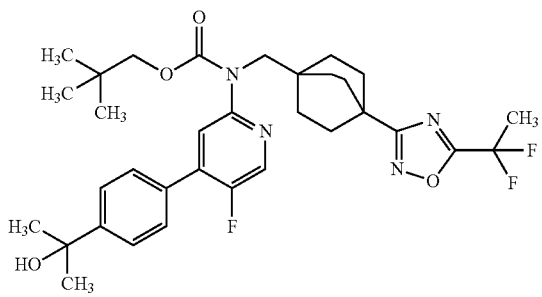

(619)

Step A. Intermediate 619A. Preparation of N-((4-(5-(1,1-difluoroethyl)-1,2,4-oxadiazol-3-yl)bicyclo[2.2.2]octan-1-yl) methyl)-5-fluoro-4-iodopyridin-2-amine

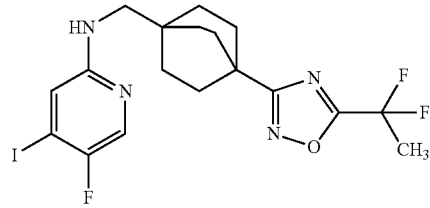 [SMILES: CC(F)(F)c1nc(C23CCC(CNc4cc(I)c(F)cn4)(CC2)CC3)no1]

The title compound was prepared according to the general method described for the synthesis of Intermediate 1I by substituting Intermediate 574C and 5-fluoro-4-iodopyridin-2-amine where appropriate: (brown solid, 850 mg, 1.727 mmol, 62.2% yield). MS (ESI) 493 (M+H).

Step B. Intermediate 619B. Preparation of neopentyl((4-(5-(1,1-difluoroethyl)-1,2,4-oxadiazol-3-yl)bicyclo[2.2.2]octan-1-yl)methyl)(5-fluoro-4-iodopyridin-2-yl)carbamate

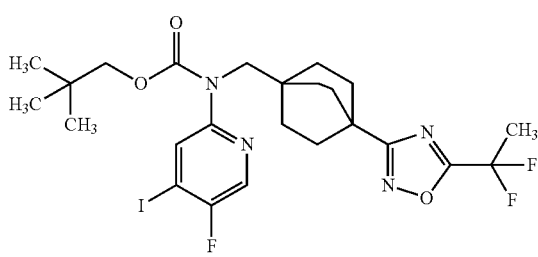 [SMILES: CC(C)(C)COC(=O)N(CC12CCC(c3noc(C(C)(F)F)n3)(CC1)CC2)c1cc(I)c(F)cn1]

To a stirred solution of Intermediate 619A (150 mg, 0.305 mmol) in DCM (1 mL) was added pyridine (0.074 mL, 0.914 mmol). The reaction mixture was cooled to 0° C. and neopentyl carbonochloridate (92 mg, 0.609 mmol) was added. The reaction mixture was stirred at room temperature for 2 h. The reaction mixture was diluted with DCM (25 mL) and the organic solution was washed with 10% aq. sodium bicarbonate solution (2×15 mL) followed by brine solution (15 mL). The organic layer was dried over anhydrous sodium sulphate, filtered, concentrated under reduced pressure to afford a residue. The crude material was purified via flash silica gel column chromatography (4 g silica gel column, conditions: 30% ethyl acetate in pet ether) to afford the title compound (brown solid, 130 mg, 0.214 mmol, 70% yield). MS (ESI) 607 (M+H).

Step C. Example 619. Preparation of neopentyl((4-(5-(1,1-difluoroethyl)-1,2,4-oxadiazol-3-yl)bicyclo[2.2.2]octan-1-yl)methyl)(5-fluoro-4-(4-(2-hydroxypropan-2-yl)phenyl) pyridin-2-yl)carbamate The title compound was synthesized according to the general method described for the synthesis of Example 149 by substituting Intermediate 619B and the corresponding boronic acid where appropriate: (10 mg, 0.016 mmol, 40% yield). $^1$H NMR (400 MHz, DMSO-$d_6$) δ 8.48 (d, J=2.2 Hz, 1H), 7.72 (d, J=5.9 Hz, 1H), 7.68-7.54 (m, 4H), 5.13 (s, 1H), 3.84 (s, 2H), 3.77 (s, 2H), 2.12 (t, J=19.6 Hz, 3H), 1.89-1.69 (m, 6H), 1.46 (s, 6H), 1.44-1.36 (m, 6H), 0.83 (s, 9H). FXR $EC_{50}$ (nM)=28. MS (ESI) 615 (M+H).

Example 620

1,1,1-trifluoro-2-methylpropan-2-yl(5-fluoro-4-(4-(2-hydroxypropan-2-yl)phenyl)pyridin-2-yl)((4-(5-(2-fluoropropan-2-yl)-1,2,4-oxadiazol-3-yl)bicyclo[2.2.2]octan-1-yl)methyl) carbamate

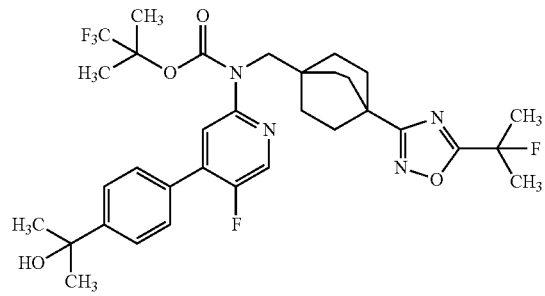

(620)

Step A. Intermediate 620A. Preparation of 5-fluoro-N-((4-(5-(2-fluoropropan-2-yl)-1,2,4-oxadiazol-3-yl)bicyclo[2.2.2]octan-1-yl) methyl)-4-iodopyridin-2-amine

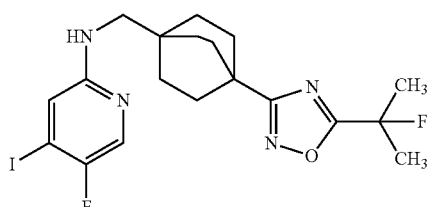

The title compound was prepared according to the general method described for the synthesis of Intermediate 1I by substituting Intermediate 576E and 5-fluoro-4-iodopyridin-2-amine where appropriate: (light yellow colored solid, 200 mg, 0.418 mmol, 56% yield). MS (ESI) 489 (M+H).

Step B. Intermediate 620B. Preparation of 1,1,1-trifluoro-2-methylpropan-2-yl(5-fluoro-4-iodopyridin-2-yl)((4-(5-(2-fluoropropan-2-yl)-1,2,4-oxadiazol-3-yl)bicyclo[2.2.2]octan-1-yl)methyl)carbamate

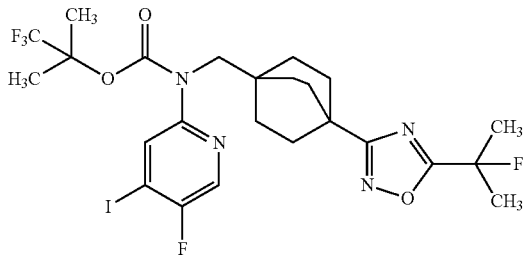 [SMILES: CC(C)(F)c1nc(C23CCC(CN(C(=O)OC(C)(C)C(F)(F)F)c4cc(I)c(F)cn4)(CC2)CC3)no1]

The title compound was synthesized according to the general method described for the synthesis of Intermediate 584A by substituting pyridin-2-yl(1,1,1-trifluoro-2-methylpropan-2-yl)carbonate and Intermediate 620A where appropriate: (Off-white semi-solid, 140 mg, 0.218 mmol, 79% yield). MS (ESI) 643 (M+H).

Step C. Example 620. Preparation of 1,1,1-trifluoro-2-methylpropan-2-yl(5-fluoro-4-(4-(2-hydroxypropan-2-yl)phenyl)pyridin-2-yl)((4-(5-(2-fluoropropan-2-yl)-1,2,4-oxadiazol-3-yl)bicyclo[2.2.2]octan-1-yl)methyl)carbamate The title compound was synthesized according to the general method described for the synthesis of Example 149 by substituting Intermediate 620B and the corresponding boronic acid where appropriate: (12.2 mg, 0.019 mmol, 40% yield). $^1$H NMR (400 MHz, DMSO-$d_6$) δ 8.48 (d, J=2.2 Hz, 1H), 7.72 (d, J=6.1 Hz, 1H), 7.68-7.54 (m, 4H), 5.16 (s, 1H), 3.80 (s, 2H), 1.82-1.70 (m, 12H), 1.68 (s, 6H), 1.46 (s, 6H), 1.43-1.28 (m, 6H). FXR $EC_{50}$ (nM)=29. MS (ESI) 651 (M+H).

Example 621

1,1,1-trifluoro-2-methylpropan-2-yl(5-fluoro-4-(1-(oxetan-3-ylmethyl)-1H-pyrazol-4-yl) pyridin-2-yl)((4-(5-(2-fluoropropan-2-yl)-1,2,4-oxadiazol-3-yl)bicyclo[2.2.2]octan-1-yl) methyl)carbamate

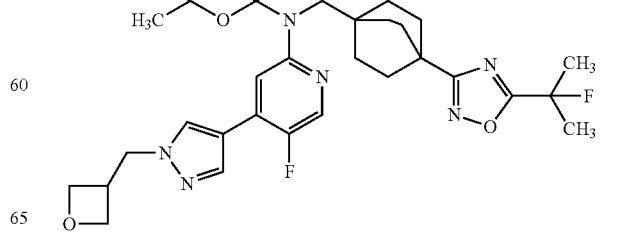

(621)

The title compound was synthesized according to the general method described for the synthesis of Example 149 by substituting Intermediate 620B and the corresponding boronic acid where appropriate: (4.4 mg, 0.006 mmol, 17% yield). $^1$H NMR (400 MHz, DMSO-$d_6$) δ 8.44 (d, J=2.2 Hz, 1H), 8.39 (d, J=2.4 Hz, 1H), 8.09 (s, 1H), 7.81 (d, J=5.4 Hz, 1H), 4.65 (dd, J=6.2, 7.7 Hz, 2H), 4.51 (d, J=7.1 Hz, 2H), 4.44 (t, J=6.1 Hz, 2H), 3.76 (s, 2H), 3.44 (br d, J=7.6 Hz, 1H), 1.81-1.70 (m, 12H), 1.68 (s, 6H), 1.43-1.29 (m, 6H). FXR EC$_{50}$ (nM)=84. MS (ESI) 653 (M+H).

Example 622

1,1,1-trifluoro-2-methylpropan-2-yl(4-(4-((2-cyanopropan-2-yl)oxy)phenyl)pyridin-2-yl) ((4-(3-cyclopropyl-1,2,4-oxadiazol-5-yl)bicyclo[2.2.2]octan-1-yl)methyl)carbamate

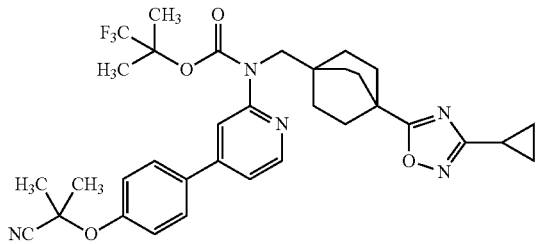

(622)

Step A. Intermediate 622A. Preparation of 4-bromo-N-((4-(3-cyclopropyl-1,2,4-oxadiazol-5-yl)bicyclo[2.2.2]octan-1-yl)methyl)pyridin-2-amine

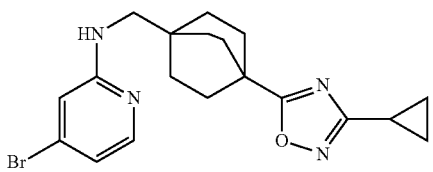

The title compound was prepared according to the general method described for the synthesis of Intermediate 1I by substituting Intermediate 4C and 4-bromopyridin-2-amine where appropriate: (white solid, 1.0 g, 2.479 mmol, 67% yield). $^1$H NMR (400 MHz, DMSO-$d_6$) δ 7.80 (d, J=5.0 Hz, 1H), 6.75 (d, J=1.5 Hz, 1H), 6.71-6.67 (m, 1H), 6.60 (dd, J=2.0, 5.5 Hz, 1H), 3.12 (d, J=6.0 Hz, 2H), 2.06 (tt, J=4.8, 8.3 Hz, 1H), 1.87-1.79 (m, 6H), 1.53-1.45 (m, 6H), 1.06-0.98 (m, 2H), 0.88-0.81 (m, 2H). MS (ESI) 403 (M+H).

Step B. Intermediate 622B. Preparation of 1,1,1-trifluoro-2-methylpropan-2-yl(4-bromopyridin-2-yl) ((4-(3-cyclopropyl-1,2,4-oxadiazol-5-yl)bicyclo[2.2.2]octan-1-yl) methyl)carbamate

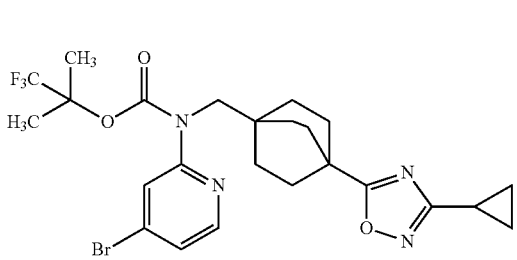 [SMILES: CC(C)(OC(=O)N(CC12CCC(c3nc(C4CC4)no3)(CC1)CC2)c1cc(Br)ccn1)C(F)(F)F]

The title compound was synthesized according to the general method described for the synthesis of Intermediate 584A by substituting pyridin-2-yl (1,1,1-trifluoro-2-methylpropan-2-yl) carbonate and Intermediate 622A where appropriate: (gum, 0.65 mg, 1.166 mmol, 78% yield). $^1$H NMR (400 MHz, DMSO-$d_6$) δ 8.31-8.27 (m, 1H), 7.81-7.79 (m, 1H), 7.52-7.48 (m, 1H), 3.85-3.81 (m, 2H), 2.06-2.01 (m, 1H), 1.79-1.73 (m, 6H), 1.71-1.66 (m, 6H), 1.38-1.30 (m, 6H), 1.03-0.98 (m, 2H), 0.85-0.80 (m, 2H). MS (ESI) 557 (M+H).

Step C. Example 622. Preparation of 1,1,1-trifluoro-2-methylpropan-2-yl (4-(4-((2-cyanopropan-2-yl)oxy)phenyl)pyridin-2-yl)((4-(3-cyclopropyl-1,2,4-oxadiazol-5-yl)bicyclo[2.2.2]octan-1-yl)methyl) carbamate The title compound was synthesized according to the general method described for the synthesis of Example 149 by substituting Intermediate 622B and the corresponding boronate ester where appropriate: (12.1 mg, 0.019 mmol, 42% yield). $^1$H NMR (400 MHz, DMSO-$d_6$) δ 8.45 (d, J=5.20 Hz, 1H), 7.88 (d, J=11.60 Hz, 2H), 7.79 (s, 1H), 7.58 (dd, J=6.80 Hz, 1H), 7.34 (d, J=12.00 Hz, 2H), 3.85 (s, 2H), 2.05-2.01 (m, 1H), 1.77-1.74 (m, 12H), 1.70 (s, 6H), 1.39-1.37 (m, 6H), 1.03-1.01 (m, 2H), 0.82-0.80 (m, 2H). FXR EC$_{50}$ (nM)=34. MS (ESI) 638 (M+H).

Example 623

1,1,1-trifluoro-2-methylpropan-2-yl((4-(3-cyclopropyl-1,2,4-oxadiazol-5-yl) bicyclo[2.2.2]octan-1-yl) methyl)(4'-(2-hydroxypropan-2-yl)-[1,1'-biphenyl]-3-yl)carbamate (623)

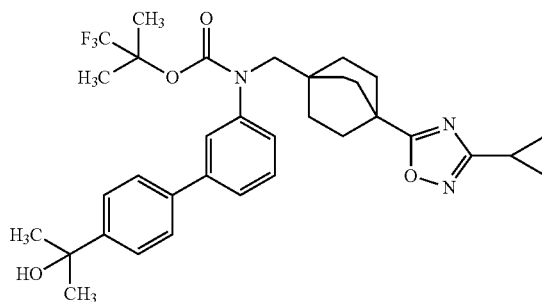

Step A. Intermediate 623A. Preparation of 3-bromo-N-((4-(3-cyclopropyl-1,2,4-oxadiazol-5-yl)bicyclo[2.2.2]octan-1-yl) methyl) aniline

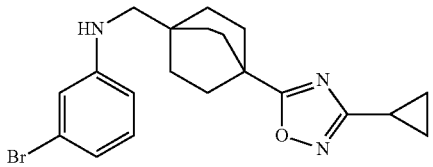 [SMILES: Brc1cccc(NCC23CCC(c4nc(C5CC5)no4)(CC2)CC3)c1]

The title compound was prepared according to the general method described for the synthesis of Intermediate 1I by substituting Intermediate 4C and 3-bromoaniline where appropriate: (brown solid, 0.78 g, 1.745 mmol, 57% yield). MS (ESI) 403 (M+H).

Step B. Intermediate 623B. Preparation of 1,1,1-trifluoro-2-methylpropan-2-yl(3-bromophenyl)((4-(3-cyclopropyl-1,2,4-oxadiazol-5-yl)bicyclo[2.2.2]octan-1-yl)methyl) carbamate

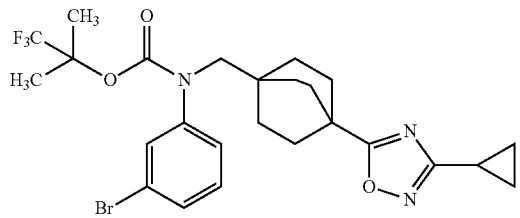 [SMILES: CC(C)(OC(=O)N(CC12CCC(c3nc(C4CC4)no3)(CC1)CC2)c1cccc(Br)c1)C(F)(F)F]

The title compound was synthesized according to the general method described for the synthesis of Intermediate 584A by substituting pyridin-2-yl (1,1,1-trifluoro-2-methylpropan-2-yl)carbonate and Intermediate 623A where appropriate: (gum, 300 mg, 0.539 mmol, 72% yield). MS (ESI) 556 (M+H).

Step C. Example 623. Preparation of 1,1,1-trifluoro-2-methylpropan-2-yl((4-(3-cyclopropyl-1,2,4-oxadiazol-5-yl)bicyclo[2.2.2]octan-1-yl)methyl)(4'-(2-hydroxypropan-2-yl)-[1,1'-biphenyl]-3-yl) carbamate The title compound was synthesized according to the general method described for the synthesis of Example 149 by substituting Intermediate 623B and the corresponding boronic acid where appropriate: (11 mg, 0.018 mmol, 39.9% yield). $^1$H NMR (400 MHz, DMSO-$d_6$) δ 7.61 (d, J=8.40 Hz, 3H), 7.53 (q, J=23.20 Hz, 3H), 7.42 (t, J=15.60 Hz, 1H), 7.36-7.27 (m, 1H), 5.06 (s, 1H), 3.63 (s, 2H), 2.08-2.01 (m, 1H), 1.78-1.74 (m, 6H), 1.65 (s, 6H), 1.45 (s, 6H), 1.41-1.37 (m, 6H), 1.01-0.99 (m, 2H), 0.82-0.80 (m, 2H). FXR $EC_{50}$ (nM)=50. MS (ESI) 612 (M+H).

Example 624

1,1,1-trifluoro-2-methylpropan-2-yl(4-(4-(difluoromethoxy)phenyl)pyridin-2-yl)((4-(5-(1-fluorocyclopropyl)-1,2,4-oxadiazol-3-yl)bicyclo[2.2.2]octan-1-yl)methyl)carbamate

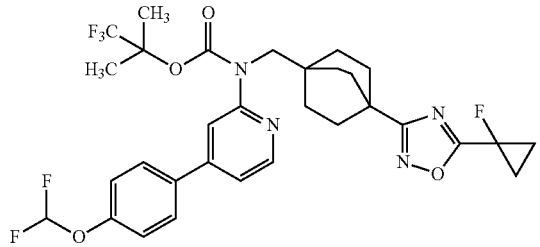

(624)

Step A. Intermediate 624A. Preparation of 4-bromo-N-((4-(5-(1-fluorocyclopropyl)-1,2,4-oxadiazol-3-yl)bicyclo[2.2.2]octan-1-yl) methyl) pyridin-2-amine

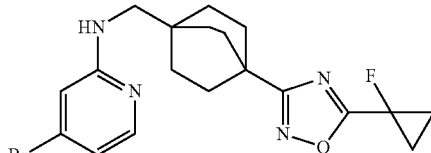

The title compound was prepared according to the general method described for the synthesis of Intermediate 1I by substituting Intermediate 586D and 4-bromopyridin-2-amine where appropriate: (Off-white solid, 100 mg, 0.237 mmol, 63% yield). MS (ESI) 421 (M+H).

Step B. Intermediate 624B. Preparation of 1,1,1-trifluoro-2-methylpropan-2-yl(4-bromopyridin-2-yl)((4-(5-(1-fluorocyclopropyl)-1,2,4-oxadiazol-3-yl)bicyclo[2.2.2]octan-1-yl)methyl)carbamate

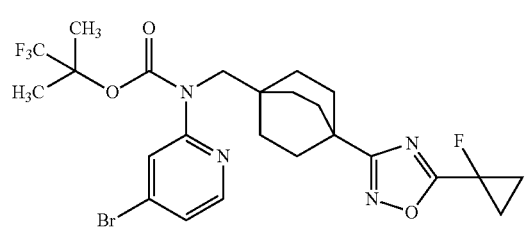 [SMILES: CC(C)(OC(=O)N(CC12CCC(c3noc(C4(F)CC4)n3)(CC1)CC2)c1cc(Br)ccn1)C(F)(F)F]

The title compound was synthesized according to the general method described for the synthesis of Intermediate 584A by substituting pyridin-2-yl (1,1,1-trifluoro-2-methylpropan-2-yl) carbonate and Intermediate 624A where appropriate: (pale yellow liquid, 0.39 g, 0.142 mmol, 12% yield). MS (ESI) 575 (M+H).

Step C. Example 624. Preparation of 1,1,1-trifluoro-2-methylpropan-2-yl(4-(4-(difluoromethoxy)phenyl)pyridin-2-yl)((4-(5-(1-fluorocyclopropyl)-1,2,4-oxadiazol-3-yl) bicyclo[2.2.2]octan-1-yl)methyl) carbamate The title compound was synthesized according to the general method described for the synthesis of Example 149 by substituting Intermediate 624B and the corresponding boronic acid where appropriate: (24.6 mg, 0.039 mmol, 55% yield). $^1$H NMR (400 MHz, DMSO-d$_6$) δ 8.46 (d, J=5.4 Hz, 1H), 7.96-7.86 (m, 2H), 7.80 (s, 1H), 7.58 (dd, J=1.6, 5.3 Hz, 1H), 7.55-7.11 (m, 3H), 3.86 (s, 2H), 1.81-1.61 (m, 14H), 1.48-1.29 (m, 8H). FXR EC$_{50}$ (nM)=50. MS (ESI) 639 (M+H).

Example 625

1,1,1-trifluoro-2-methylpropan-2-yl(4-(4-((2-cyanopropan-2-yl)oxy)phenyl)pyridin-2-yl) ((4-(5-(1-fluorocyclopropyl)-1,2,4-oxadiazol-3-yl)bicyclo[2.2.2]octan-1-yl)methyl) carbamate

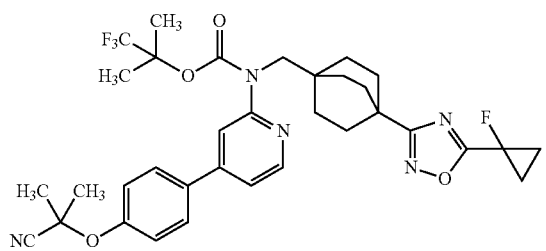

(625)

The title compound was synthesized according to the general method described for the synthesis of Example 149 by substituting Intermediate 624B and the corresponding boronate ester where appropriate: (22.9 mg, 0.035 mmol, 50% yield). $^1$H NMR (400 MHz, DMSO-d$_6$) δ 8.45 (d, J=5.4 Hz, 1H), 7.93-7.82 (m, 2H), 7.80 (s, 1H), 7.58 (dd, J=1.6, 5.3 Hz, 1H), 7.38-7.28 (m, 2H), 3.86 (s, 2H), 1.80-1.63 (m, 20H), 1.48-1.32 (m, 8H). FXR EC$_{50}$ (nM)=18. MS (ESI) 656 (M+H).

Example 626

N-((4-(5-(1,1-difluoroethyl)-1,2,4-oxadiazol-3-yl)bicyclo[2.2.2]octan-1-yl)methyl)-N-(4-(4-isopropoxyphenyl)pyridin-2-yl)morpholine-4-carboxamide

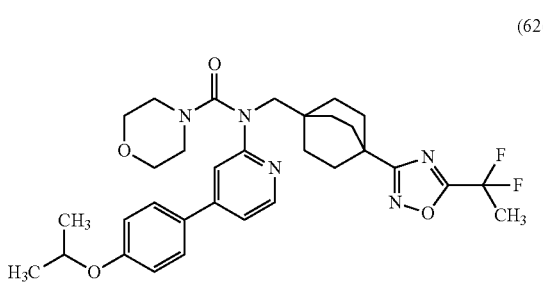

(626)

Step A. Intermediate A. Preparation of N-(4-bromopyridin-2-yl)-N-((4-(5-(1,1-difluoroethyl)-1,2,4-oxadiazol-3-yl)bicyclo[2.2.2]octan-1-yl)methyl)morpholine-4-carboxamide

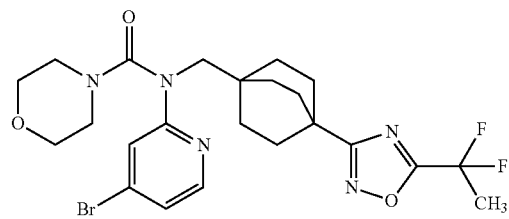 [SMILES: CC(F)(F)c1nc(C23CCC(CN(C(=O)N4CCOCC4)c4cc(Br)ccn4)(CC2)CC3)no1]

The title compound was prepared according to the general method described for the synthesis of Example 586 by substituting Intermediate 609A and the corresponding amine where appropriate: (gummy solid, 100 mg, 0.185 mmol, 99% yield). MS (ESI) 540 (M+H).

Step B. Example 626. Preparation of N-((4-(5-(1,1-difluoroethyl)-1,2,4-oxadiazol-3-yl) bicyclo[2.2.2]octan-1-yl)methyl)-N-(4-(4-isopropoxyphenyl)pyridin-2-yl)morpholine-4-carboxamide The title compound was synthesized according to the general method described for the synthesis of Example 149 by substituting Intermediate 626A and the corresponding boronic acid where appropriate: (6.5 mg, 10.91 μmol, 24% yield). $^1$H NMR (400 MHz, DMSO-d$_6$) δ 8.26 (d, J=5.1 Hz, 1H), 7.75-7.64 (m, 2H), 7.23 (dd, J=1.5, 5.4 Hz, 1H), 7.09-6.97 (m, 3H), 4.69 (td, J=6.1, 12.0 Hz, 1H), 3.68 (s, 2H), 3.51 (t, J=4.8 Hz, 4H), 3.32-3.26 (m, 4H), 2.15 (t, J=19.7 Hz, 3H), 1.93-1.81 (m, 6H), 1.66-1.52 (m, 6H), 1.29 (d, J=6.1 Hz, 6H). FXR EC$_{50}$ (nM)=72. MS (ESI) 596 (M+H).

Example 627 tetrahydro-2H-pyran-4-yl((4-(3-cyclopropyl-1,2,4-oxadiazol-5-yl)bicyclo[2.2.2]octan-1-yl) methyl)(4-(4-isopropoxyphenyl)pyridin-2-yl)carbamate

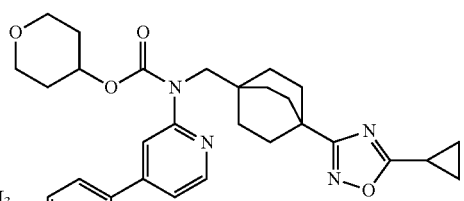

(627)

Step A. Intermediate 627A. Preparation of 4-nitrophenyl (tetrahydro-2H-pyran-4-yl) carbonate

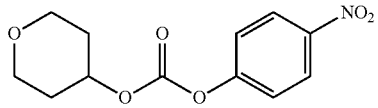 [SMILES: O=C(Oc1ccc([N+](=O)[O-])cc1)OC1CCOCC1]

To a stirred solution of tetrahydro-2H-pyran-4-ol (500 mg, 4.90 mmol) in DCM (10 mL) was added TEA (2.047 mL, 14.69 mmol) followed by 4-nitrophenyl carbonochloridate (1085 mg, 5.39 mmol) added portion wise at 0° C. The reaction mixture was stirred at room temperature for 2 h. The reaction mixture was diluted with DCM (25 mL), washed with water (2×15 mL). The organic layer was washed with brine solution (20 mL), dried over anhydrous sodium sulphate, filtered and concentrated under reduced pressure. The crude material was purified via flash column chromatography (12 g silica gel cartridge; A=hexanes, B=EtOAc; 30 min grad.; 0% B to 30% B; flow rate=12 mL/min). The pure fractions were combined, concentrated under reduced pressure and dried in vacuo to afford the title compound (800 mg, 2.99 mmol, 61% yield) as a white solid. $^1$H NMR (300 MHz, DMSO-d$_6$) δ 8.29-8.35 (m, 2H) 7.55-7.61 (m, 2H), 4.91 (dt, J=8.78, 4.49 Hz, 1H), 3.82 (dt, J=11.90, 4.63 Hz, 2H), 3.49 (ddd, J=11.80, 8.97, 3.02 Hz, 2H), 2.00 (dq, J=13.13, 3.68 Hz, 2H), 1.68 (dtd, J=13.08, 8.95, 8.95, 4.15 Hz, 2H).

Step B. Intermediate 627B. Preparation of tetrahydro-2H-pyran-4-yl (4-bromopyridin-2-yl)((4-(3-cyclopropyl-1,2,4-oxadiazol-5-yl)bicyclo[2.2.2]octan-1-yl)methyl)carbamate

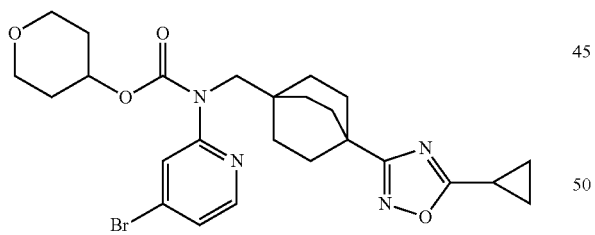

The title compound was synthesized according to the general method described for the synthesis of Intermediate 584A by substituting Intermediate 627A and Intermediate 622A where appropriate: (yellow gum, 100 mg, 0.188 mmol, 76% yield). MS (ESI) 531 (M+H).

Step C. Example 627. Preparation of tetrahydro-2H-pyran-4-yl((4-(3-cyclopropyl-1,2,4-oxadiazol-5-yl)bicyclo[2.2.2]octan-1-yl)methyl)(4-(4-isopropoxyphenyl)pyridin-2-yl) carbamate The title compound was synthesized according to the general method described for the synthesis of Example 149 by substituting Intermediate 627B and the corresponding boronic acid where appropriate: (12.5 mg, 0.021 mmol, 44% yield. $^1$H NMR (400 MHz, DMSO-d$_6$) δ 8.38 (d, J=5.4 Hz, 1H), 7.77 (d, J=1.5 Hz, 1H), 7.76-7.66 (m, 2H), 7.49 (dd, J=1.7, 5.4 Hz, 1H), 7.14-6.97 (m, 2H), 4.92-4.81 (m, 1H), 4.71 (m, 1H), 3.90 (s, 2H), 3.74-3.62 (m, 2H), 3.45 (m, 2H), 2.02 (m, 1H), 1.95-1.84 (m, 2H), 1.82-1.68 (m, 6H), 1.54 (m, 2H), 1.44-1.34 (m, 6H), 1.29 (d, J=6.1 Hz, 6H), 1.05-0.93 (m, 2H), 0.85-0.76 (m, 2H). FXR EC$_{50}$ (nM)=63. MS (ESI) 587 (M+H).

Example 628

(cis)-N-(4'-(2,2-difluoro-1-hydroxyethyl)-[1,1'-biphenyl]-3-yl)-N-((4-(5-(1,1-difluoroethyl)-1,2,4-oxadiazol-3-yl)bicyclo[2.2.2]octan-1-yl)methyl)-3-hydroxy-3-(trifluoromethyl) cyclobutane-1-carboxamide (628)

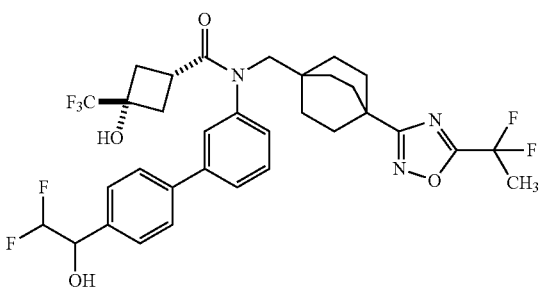

Step A. Intermediate 628A. Preparation of 3-bromo-N-((4-(5-(1,1-difluoroethyl)-1,2,4-oxadiazol-3-yl)bicyclo[2.2.2]octan-1-yl)methyl)aniline

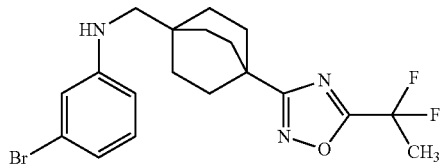 [SMILES: CC(F)(F)c1nc(C23CCC(CNc4cccc(Br)c4)(CC2)CC3)no1]

The title compound was prepared according to the general method described for the synthesis of Intermediate 1I by substituting Intermediate 574C and 3-bromoaniline where appropriate: (white solid, 9.0 g, 21.06 mmol, 63% yield). $^1$H NMR (400 MHz, DMSO-d$_6$) δ 6.98-6.92 (m, 1H), 6.76 (t, J=2.0 Hz, 1H), 6.62-6.55 (m, 2H), 5.79-5.71 (m, 1H), 2.80 (d, J=6.0 Hz, 2H), 2.20-2.08 (m, 3H), 1.90-1.81 (m, 6H), 1.60-1.50 (m, 6H). MS (ESI) 427 (M+H).

Step B. Intermediate 628B. Preparation of (cis)-N-(3-bromophenyl)-N-((4-(5-(1,1-difluoroethyl)-1,2,4-oxadiazol-3-yl)bicyclo[2.2.2]octan-1-yl)methyl)-3-hydroxy-3-(trifluoromethyl)cyclobutane-1-carboxamide

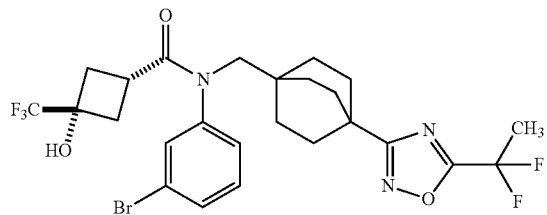

The title compound was prepared according to the general method described for the synthesis of Intermediate 576G by substituting Intermediate 628A where appropriate: (brown solid, 140 mg, 0.236 mmol, 67% yield). MS (ESI) 592 (M+H).

Step C. Intermediate 628C. Preparation of 1-(4-bromophenyl)-2,2-difluoroethan-1-ol (Racemate)

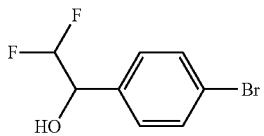 [SMILES: OC(c1ccc(Br)cc1)C(F)F]

To a stirred solution of 4-bromobenzaldehyde (500 mg, 2.70 mmol) and (difluoromethyl)trimethylsilane (671 mg, 5.40 mmol) in DMF (13 mL) was added cesium fluoride (82 mg, 0.540 mmol) under nitrogen atmosphere. The reaction mixture was stirred at room temperature overnight. To this reaction mixture was added TBAF in $H_2O$ (2.97 mL, 8.11 mmol) at 0° C. The reaction mixture was stirred at room temperature for 1 h. The reaction mixture was diluted with water (20 mL) and extracted with ethyl acetate (2×20 mL). The combined organic layer was washed with brine solution (20 mL), dried over anhydrous sodium sulphate, filtered and concentrated under reduced pressure. The residue was purified via flash silica gel column chromatography (12 g silica gel column, conditions: 30% ethyl acetate in pet ether) to afford the title compound (colorless gummy mass, 300 mg, 1.266 mmol, 47% yield). $^1$H NMR (400 MHz, DMSO-$d_6$) δ 7.61-7.56 (m, 2H), 7.38 (d, J=8.5 Hz, 2H), 6.29 (d, J=5.0 Hz, 1H), 6.17-5.86 (m, 1H), 4.84-4.72 (m, 1H).

Step D. Intermediate 628D. Preparation of 2,2-difluoro-1-(4-(4,4,5,5-tetramethyl-1,3,2-dioxaborolan-2-yl)phenyl)ethan-1-ol (Racemate)

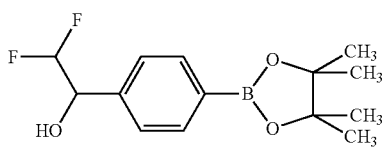 [SMILES: CC1(C)OB(c2ccc(C(O)C(F)F)cc2)OC1(C)C]

The title compound was prepared according to the general method described for the synthesis of Intermediate 607B by substituting Intermediate 628C where appropriate: (grey white solid, 0.26 g, 0.915 mmol, 72% yield). $^1$H NMR (400 MHz, DMSO-$d_6$) δ 7.67 (d, J=8.0 Hz, 2H), 7.43 (d, J=8.0 Hz, 2H), 6.23 (d, J=5.0 Hz, 1H), 6.15-5.78 (m, 1H), 4.83-4.72 (m, 1H), 1.37-1.25 (m, 6H), 1.20-1.11 (m, 6H).

Step E. Example 628. Preparation of (cis)-N-(4'-(2,2-difluoro-1-hydroxyethyl)-[1,1'-biphenyl]-3-yl)-N-((4-(5-(1,1-difluoroethyl)-1,2,4-oxadiazol-3-yl)bicyclo[2.2.2]octan-1-yl) methyl)-3-hydroxy-3-(trifluoromethyl)cyclobutane-1-carboxamide The title compound (racemate) was synthesized according to the general method described for the synthesis of Example 149 by substituting Intermediate 628B and Intermediate 628D where appropriate. The isomers were separated by SFC technique.

Preparative SFC Condition: Column/dimensions: Whelk (R,R) (250×21) mm, 5 μm % $CO_2$: 85% % Co solvent: 15% of 0.2% ammonia in MeOH. Total Flow: 80.0 g/min, Back Pressure: 100 bar; Temperature: 30° C. UV: 240 nm.

First eluting isomer (3.2 mg, 4.78 μmol, 6% yield). $^1$H NMR (400 MHz, DMSO-$d_6$) δ 7.70-7.69 (m, 1H), 7.61-7.59 (m, 3H), 7.57-7.45 (m, 3H), 7.42-7.24 (m, 1H), 6.53 (s, 1H), 6.26 (d, J=5.1 Hz, 1H), 6.23-5.84 (m, 1H), 4.89-4.74 (m, 1H), 3.79-3.59 (m, 2H), 2.85 (br t, J=8.9 Hz, 1H), 2.40-2.27 (m, 2H), 2.19-1.95 (m, 5H), 1.82-1.65 (m, 6H), 1.55-1.35 (m, 6H). FXR $EC_{50}$ (nM)=92. MS (ESI) 670 (M+H). (RT=8.2 min or peak-1).

Second eluting isomer (2.2 mg, 3.29 μmol, 3.89% yield). $^1$H NMR (400 MHz, DMSO-$d_6$) δ 7.81-7.70 (m, 3H), 7.66 (d, J=7.8 Hz, 1H), 7.59-7.47 (m, 3H), 7.38 (dd, J=1.0, 7.8 Hz, 1H), 6.53 (s, 1H), 6.26 (br d, J=4.9 Hz, 1H), 6.21-5.88 (m, 1H), 4.89-4.74 (m, 1H), 3.69 (br dd, J=1.0, 3.2 Hz, 2H), 2.85 (br t, J=9.0 Hz, 1H), 2.39-2.26 (m, 2H), 2.21-1.93 (m, 5H), 1.85-1.72 (m, 6H), 1.57-1.36 (m, 6H). FXR $EC_{50}$ (nM)=128. MS (ESI) 670 (M+H). (RT=10.3 min or peak-2).

Example 629

(cis)-3-hydroxy-3-(trifluoromethyl)cyclobutyl (4-(4-(difluoromethoxy)phenyl)-5-fluoropyridin-2-yl)((4-(5-(2-fluoropropan-2-yl)-1,2,4-oxadiazol-3-yl)bicyclo[2.2.2]octan-1-yl)methyl)carbamate (629)

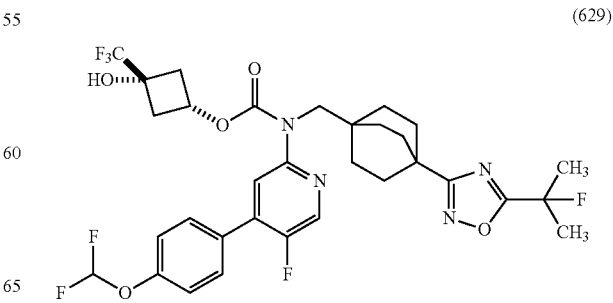

Step A: Intermediate 629A. Preparation of (cis)-3-(benzyloxy)-1-(trifluoromethyl)cyclobutan-1-ol

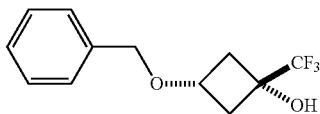

To a stirred solution of 3-(benzyloxy)cyclobutan-1-one (0.50 g, 2.84 mmol) in THF (10 mL) cooled to 0° C. was added (trifluoromethyl)trimethylsilane (2.128 mL, 4.26 mmol) followed by TBAF in THF (0.851 mL, 0.851 mmol). The reaction mixture was gradually warmed to rt and stirred at rt for 2 h. The reaction mixture was quenched with aq. 1.5N HCl solution (15 mL), stirred for 2 h and extracted with ethyl acetate (2×25 mL). Combined organic layers were washed with brine solution (2×20 mL) dried over sodium sulfate and concentrated under reduced pressure to get crude product which was purified by flash column chromatography (15% ethyl acetate: hexane, 12 g silica gel column) to afford to the title compound (490 mg, 1.990 mmol, 70% yield) as brown liquid. $^1$H NMR (400 MHz, CDCl$_3$) δ 7.36 (d, J=2.5 Hz, 5H), 4.47 (s, 2H), 3.94-3.86 (m, 1H), 2.90-2.81 (m, 2H), 2.38-2.34 (m, 1H), 2.32-2.24 (m, 2H).

Step B: Intermediate 629B. Preparation of (cis)-1-(trifluoromethyl)cyclobutane-1,3-diol

To a stirred solution of Intermediate 629A (450 mg, 1.828 mmol) in MeOH (10 mL) was added Pd—C(150 mg, 1.828 mmol). The reaction mixture was stirred at room temperature under 15 Psi hydrogen pressure for 4 h. The reaction mixture was filtered through a celite bed and the filtrate was concentrated under reduced pressure to afford the title compound (270 mg, 1.730 mmol, 95% yield) as a brown solid. $^1$H NMR (400 MHz, DMSO-d$_6$) δ 6.49 (s, 1H), 5.35 (d, J=6.0 Hz, 1H), 3.83 (m, 1H), 2.71-2.63 (m, 2H), 2.11-2.01 (m, 2H).

Step C. Intermediate 629C. Preparation of (cis)-3-hydroxy-3-(trifluoromethyl)cyclobutyl (5-fluoro-4-iodopyridin-2-yl)((4-(5-(2-fluoropropan-2-yl)-1,2,4-oxadiazol-3-yl) bicyclo[2.2.2]octan-1-yl)methyl) carbamate

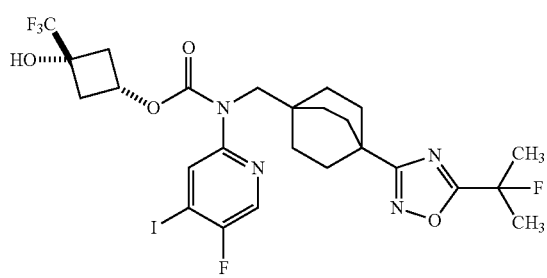

To a stirred solution of Intermediate 620A (450 mg, 0.922 mmol) in DCM (10 mL) were added phosgene (0.585 mL, 1.106 mmol) and TEA (0.642 mL, 4.61 mmol) dropwise at 0° C. The reaction mixture was stirred at room temperature for 2 h. To this reaction mixture were added DCM (5 mL), Intermediate 629B (56.7 mg, 0.363 mmol), and potassium tert-butoxide (102 mg, 0.908 mmol) at 0° C. The reaction mixture was stirred at 0° C. for 10 min. The reaction mixture was diluted with DCM (15 mL), washed with water (2×10 mL) followed by brine solution (10 mL), dried over anhydrous sodium sulphate and concentrated under reduced pressure. The crude material was purified via flash chromatography (12 g silica gel column, conditions: 30% ethyl acetate in pet ether) to afford the title compound (90 mg, 0.063 mmol, 17% yield). MS (ESI) 671 (M+H).

Step D. Example 629. Preparation of (cis)-3-hydroxy-3-(trifluoromethyl)cyclobutyl(4-(4-(difluoromethoxy)phenyl)-5-fluoropyridin-2-yl)((4-(5-(2-fluoropropan-2-yl)-1,2,4-oxadiazol-3-yl)bicyclo[2.2.2]octan-1-yl)methyl)carbamate The title compound was synthesized according to the general method described for the synthesis of Example 149 by substituting Intermediate 629C and the corresponding boronic acid where appropriate: (6.4 mg, 9.32 μmol, 25% yield). $^1$H NMR (400 MHz, DMSO-d$_6$) δ 8.50 (d, J=2.0 Hz, 1H), 7.81 (d, J=5.9 Hz, 1H), 7.79-7.70 (m, 2H), 7.57-7.10 (m, 3H), 6.81 (s, 1H), 4.70 (t, J=7.1 Hz, 1H), 3.87 (s, 2H), 2.91-2.79 (m, 2H), 2.34-2.19 (m, 2H), 1.82-1.68 (m, 12H), 1.49-1.30 (m, 6H). FXR EC$_{50}$ (nM)=99. MS (ESI) 687 (M+H).

Example 630

3,3-difluorocyclobutyl(4-(4-(difluoromethoxy)phenyl)-5-fluoropyridin-2-yl)((4-(5-(2-fluoropropan-2-yl)-1,2,4-oxadiazol-3-yl)bicyclo[2.2.2]octan-1-yl) methyl)carbamate (630)

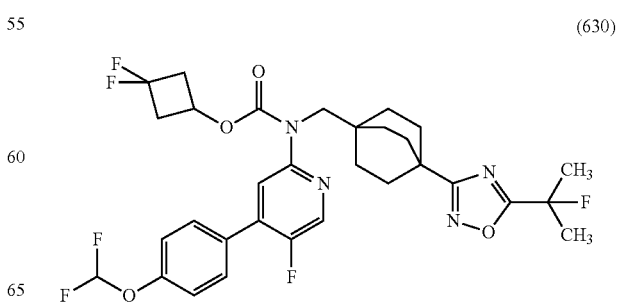

727

Step A. Intermediate 630A. Preparation of 3,3-difluorocyclobutyl(5-fluoro-4-iodopyridin-2-yl)((4-(5-(2-fluoropropan-2-yl)-1,2,4-oxadiazol-3-yl)bicyclo[2.2.2]octan-1-yl)methyl) carbamate

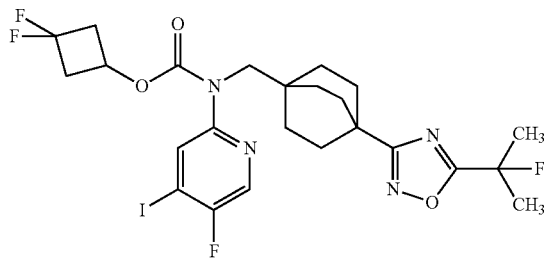 [SMILES: CC(C)(F)c1nc(C23CCC(CN(C(=O)OC4CC(F)(F)C4)c4cc(I)c(F)cn4)(CC2)CC3)no1]

The title compound was synthesized according to the general method described for the synthesis of Intermediate 629C by substituting Intermediate 620A and the corresponding alcohol where appropriate: (white solid, 110 mg, 0.113 mmol, 31% yield). MS (ESI) 623 (M+H).

Step B. Example 630. Preparation of 3,3-difluorocyclobutyl (4-(4-(difluoromethoxy) phenyl)-5-fluoropyridin-2-yl)((4-(5-(2-fluoropropan-2-yl)-1,2,4-oxadiazol-3-yl)bicyclo [2.2.2]octan-1-yl)methyl) carbamate The title compound was synthesized according to the general method described for the synthesis of Example 149 by substituting Intermediate 630A and the corresponding boronic acid where appropriate: (12.1 mg, 0.019 mmol, 47% yield). $^1$H NMR (400 MHz, DMSO-$d_6$) δ 8.49 (d, J=2.0 Hz, 1H), 7.83 (d, J=6.1 Hz, 1H), 7.79-7.71 (m, 2H), 7.58-7.15 (m, 3H), 4.91 (br dd, J=4.9, 7.8 Hz, 1H), 3.87 (s, 2H), 3.13-2.99 (m, 2H), 2.81-2.63 (m, 2H), 1.81-1.68 (m, 12H), 1.48-1.31 (m, 6H). FXR EC$_{50}$ (nM)=160. MS (ESI) 639 (M+H).

Example 631

4,4-difluorocyclohexyl (4-(4-(difluoromethoxy) phenyl)-5-fluoropyridin-2-yl) ((4-(5-(2-fluoropropan-2-yl)-1,2,4-oxadiazol-3-yl)bicyclo[2.2.2]octan-1-yl) methyl) carbamate (631)

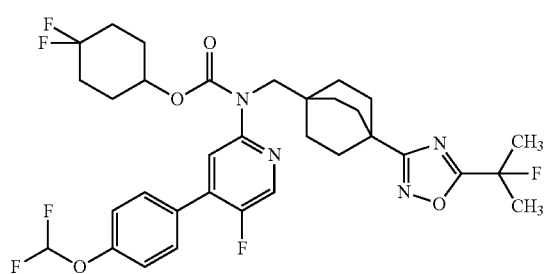

728

Step A. Intermediate 631A. Preparation of 4,4-difluorocyclohexyl (5-fluoro-4-iodopyridin-2-yl)((4-(5-(2-fluoropropan-2-yl)-1,2,4-oxadiazol-3-yl)bicyclo[2.2.2]octan-1-yl)methyl) carbamate

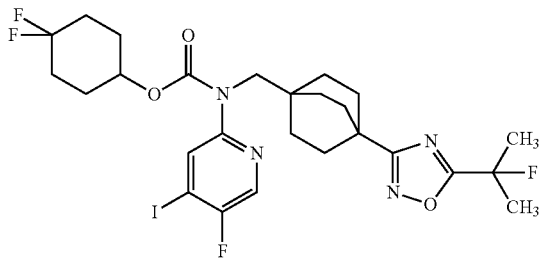 [SMILES: CC(C)(F)c1nc(C23CCC(CN(C(=O)OC4CCC(F)(F)CC4)c4cc(I)c(F)cn4)(CC2)CC3)no1]

The title compound was synthesized according to the general method described for the synthesis of Intermediate 629C by substituting Intermediate 620A and the corresponding alcohol where appropriate: (white solid, 110 mg, 0.12 mmol, 33% yield). MS (ESI) 651 (M+H).

Step B. Example 631. Preparation of 4,4-difluorocyclohexyl (4-(4-(difluoromethoxy) phenyl)-5-fluoropyridin-2-yl)((4-(5-(2-fluoropropan-2-yl)-1,2,4-oxadiazol-3-yl)bicyclo [2.2.2]octan-1-yl)methyl) carbamate The title compound was synthesized according to the general method described for the synthesis of Example 149 by substituting Intermediate 631A and the corresponding boronic acid where appropriate: (8.5 mg, 0.012 mmol, 33% yield). $^1$H NMR (400 MHz, DMSO-$d_6$) δ 8.49 (d, J=2.0 Hz, 1H), 7.80 (d, J=5.9 Hz, 1H), 7.78-7.72 (m, 2H), 7.57-7.11 (m, 3H), 4.86 (br dd, J=1.1, 2.1 Hz, 1H), 3.85 (s, 2H), 1.99-1.65 (m, 20H), 1.47-1.33 (m, 6H). FXR EC$_{50}$ (nM)= 117. MS (ESI) 667 (M+H).

Example 632

3-(trifluoromethyl)oxetan-3-yl ((4-(5-(2-fluoropropan-2-yl)-1,2,4-oxadiazol-3-yl) bicyclo[2.2.2]octan-1-yl)methyl)(4'-isopropoxy-[1,1'-biphenyl]-3-yl) carbamate (632)

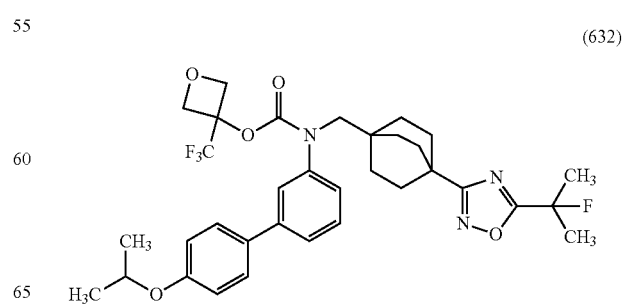

Step A. Intermediate 632A. Preparation of 3-bromo-N-((4-(5-(2-fluoropropan-2-yl)-1,2,4-oxadiazol-3-yl)bicyclo[2.2.2]octan-1-yl)methyl)aniline

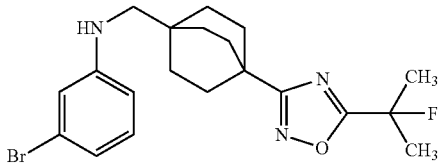 [SMILES: CC(C)(F)c1nc(C23CCC(CNc4cccc(Br)c4)(CC2)CC3)no1]

The title compound was prepared according to the general method described for the synthesis of Intermediate 1I by substituting Intermediate 576E and 3-bromoaniline where appropriate: (light yellow colored solid, 200 mg, 0.418 mmol, 56% yield). MS (ESI) 422 (M+H).

Step B. Intermediate 632B. Preparation of 3-(trifluoromethyl)oxetan-3-ol

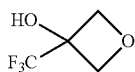

To a stirred solution of oxetan-3-one (2 g, 27.8 mmol) in tetrahydrofuran (80 mL) was added trimethyl(trifluoromethyl)silane (13.88 ml, 13.88 mmol) at 0° C. TBAF in THF (13.88 mL, 27.8 mmol) was added slowly over a period of 10 min under nitrogen atmosphere. The reaction mixture was stirred at room temperature for 16 h. To this reaction mixture, aqueous 1.5 N HCl solution (60 mL) was added at room temperature and the reaction mixture was stirred for another 1 h. The reaction mixture was diluted with water (30 mL) and extracted with EtOAc (2×30 mL). The combined organic layers were washed with brine solution (20 mL), dried over anhydrous sodium sulphate and concentrated under reduced pressure. The residue was purified via flash silica gel column chromatography (24 g silica gel column, conditions: 30% ethyl acetate in pet ether) to afford the title compound (3 g, 20.06 mmol, 72% yield) as a white solid. $^1$H NMR (400 MHz, DMSO-$d_6$) δ 7.55-6.97 (m, 1H), 4.72-4.63 (m, 2H), 4.56 (qd, J=1.7, 8.6 Hz, 2H).

Step C. Intermediate 632C. Preparation of pyridin-2-yl (3-(trifluoromethyl)oxetan-3-yl) carbonate

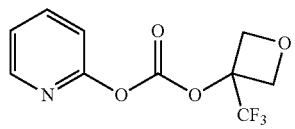 [SMILES: O=C(Oc1ccccn1)OC1(C(F)(F)F)COC1]

Sodium hydride in mineral oil (60%) (141 mg, 3.52 mmol) was added to a solution of Intermediate 632B (500 mg, 3.52 mmol) in tetrahydrofuran (20 mL) at 0° C. The reaction mixture was stirred at the same temperature for 30 min. The solution of di(pyridin-2-yl)carbonate (761 mg, 3.52 mmol) in tetrahydrofuran (20 mL) was added to the above reaction mixture over a period of 5 minutes at 0° C. The reaction mixture was allowed to warm to room temperature and stirred for 2 h. The reaction mixture was quenched with ice, diluted with water (30 mL) and extracted with EtOAc (2×50 mL). The combined organic layers were washed with brine solution (20 mL), dried over anhydrous sodium sulphate and concentrated under reduced pressure. The residue was purified via flash silica gel column chromatography (12 g silica gel column, conditions: 30% ethyl acetate in pet ether) to afford the title compound (450 mg, 1.710 mmol, 49% yield) as a colorless liquid. $^1$H NMR (400 MHz, DMSO-$d_6$) δ 8.45-8.39 (m, 1H), 8.08-8.00 (m, 1H), 7.51-7.35 (m, 2H), 4.86-4.77 (m, 2H), 4.70-4.64 (m, 2H).

Step D. Intermediate 632D. Preparation of 3-(trifluoromethyl)oxetan-3-yl(3-bromophenyl) ((4-(5-(2-fluoropropan-2-yl)-1,2,4-oxadiazol-3-yl)bicyclo[2.2.2]octan-1-yl)methyl) carbamate

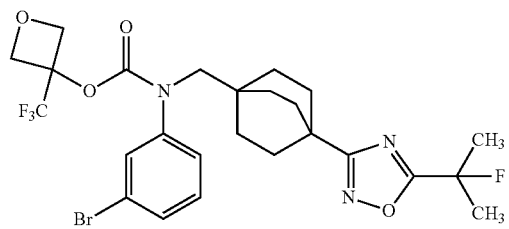 [SMILES: CC(C)(F)c1nc(C23CCC(CN(C(=O)OC4(C(F)(F)F)COC4)c4cccc(Br)c4)(CC2)CC3)no1]

The title compound was synthesized according to the general method described for the synthesis of Intermediate 584A by substituting Intermediate 632A and Intermediate 632C where appropriate: (Off-white solid, 120 mg, 0.193 mmol, 82% yield). MS (ESI) 590 (M+H).

Step E. Example 632. Preparation of 3-(trifluoromethyl)oxetan-3-yl((4-(5-(2-fluoropropan-2-yl)-1,2,4-oxadiazol-3-yl)bicyclo[2.2.2]octan-1-yl)methyl)(4'-isopropoxy-[1,1'-biphenyl]-3-yl)carbamate The title compound was synthesized according to the general method described for the synthesis of Example 149 by substituting Intermediate 632D and the corresponding boronic acid where appropriate: (14 mg, 0.022 mmol, 43% yield). $^1$H NMR (400 MHz, DMSO-$d_6$) δ 7.67 (s, 1H), 7.62 (d, J=8.8 Hz, 2H), 7.48-7.55 (m, 1H), 7.43 (t, J=7.8 Hz, 1H), 7.26-7.37 (m, 1H), 7.01 (d, J=8.8 Hz, 2H), 4.84-5.08 (m, 2H), 4.61-4.82 (m, 3H), 3.58-3.76 (m, 2H), 1.63-1.82 (m, 12H), 1.35-1.51 (m, 6H), 1.29 (d, J=6.1 Hz, 6H). FXR $EC_{50}$ (nM)=222. MS (ESI) 646 (M+H).

Example 633

3-(bicyclo[1.1.1]pentan-1-yl)-1-((4-(5-(1,1-difluoroethyl)-1,2,4-oxadiazol-3-yl) bicyclo[2.2.2]octan-1-yl)methyl)-1-(4-fluoro-3-(1-(2-hydroxy-2-methylpropyl)-1H-pyrazol-4-yl)phenyl)urea

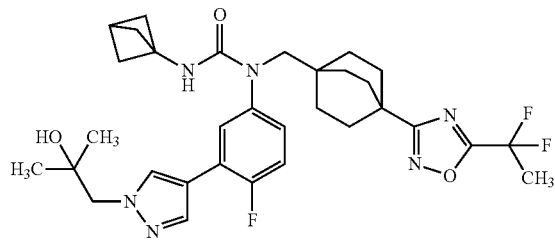

(633)

Step A. Intermediate 633A. Preparation of 3-bromo-N-((4-(5-(1,1-difluoroethyl)-1,2,4-oxadiazol-3-yl)bicyclo[2.2.2]octan-1-yl)methyl)-4-fluoroaniline

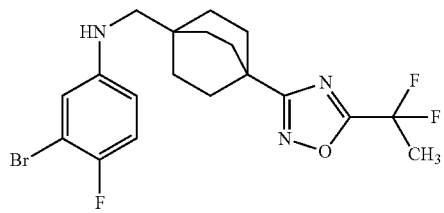 [SMILES: CC(F)(F)c1nc(C23CCC(CNc4ccc(F)c(Br)c4)(CC2)CC3)no1]

The title compound was prepared according to the method described for the synthesis of Intermediate 1I by substituting Intermediate 574C and 3-bromo-4-fluoroaniline where appropriate: (white solid, 9.0 g, 21.06 mmol, 63% yield). MS (ESI) 444 (M+H).

Step B. Intermediate 633B. Preparation of 3-(bicyclo[1.1.1]pentan-1-yl)-1-(3-bromo-4-fluorophenyl)-1-((4-(5-(1,1-difluoroethyl)-1,2,4-oxadiazol-3-yl)bicyclo[2.2.2]octan-1-yl) methyl)urea

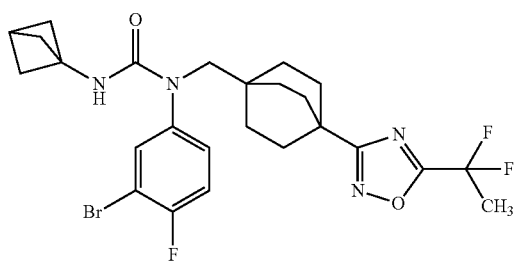 [SMILES: CC(F)(F)c1nc(C23CCC(CN(C(=O)NC45CC(C4)C5)c4ccc(F)c(Br)c4)(CC2)CC3)no1]

The title compound was prepared according to the general method described for the synthesis of Example 586 by substituting Intermediate 633A and the corresponding amine where appropriate: (100 mg, 0.181 mmol, 80% yield) as off-white solid. MS (ESI) 553 (M+H).

Step C. Example 633. Preparation of 3-(bicyclo[1.1.1]pentan-1-yl)-1-((4-(5-(1,1-difluoroethyl)-1,2,4-oxadiazol-3-yl)bicyclo[2.2.2]octan-1-yl)methyl)-1-(4-fluoro-3-(1-(2-hydroxy-2-methylpropyl)-1H-pyrazol-4-yl)phenyl)urea The title compound was synthesized according to the general method described for the synthesis of Example 149 by substituting Intermediate 633B and the corresponding boronic acid where appropriate: (8.3 mg, 0.013 mmol, 23% yield). $^1$H NMR (400 MHz, DMSO-$d_6$) δ 8.15 (d, J=2.2 Hz, 1H), 7.98 (s, 1H), 7.67 (dd, J=2.6, 7.0 Hz, 1H), 7.24 (dd, J=8.8, 10.8 Hz, 1H), 7.15-7.06 (m, 1H), 6.22 (s, 1H), 4.74 (s, 1H), 4.07 (s, 2H), 3.52 (s, 2H), 2.30 (s, 1H), 2.13 (t, J=19.7 Hz, 3H), 1.89 (s, 6H), 1.81-1.69 (m, 6H), 1.48-1.34 (m, 6H), 1.09 (s, 6H). FXR EC$_{50}$ (nM)=32. MS (ESI) 613 (M+H).

Example 634

1,1,1-trifluoro-2-methylpropan-2-yl((4-(5-(2-fluoropropan-2-yl)-1,2,4-oxadiazol-3-yl) bicyclo[2.2.2]octan-1-yl)methyl)(4-(4-(2-hydroxypropan-2-yl)phenyl)pyridin-2-yl) carbamate

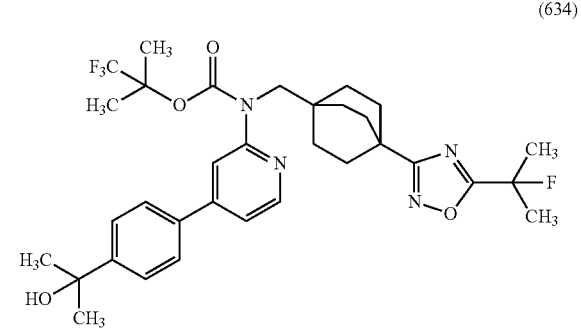 [SMILES: CC(C)(O)c1ccc(-c2ccnc(N(CC34CCC(c5noc(C(C)(C)F)n5)(CC3)CC4)C(=O)OC(C)(C)C(F)(F)F)c2)cc1]

(634)

Step A. Intermediate 634A. Preparation of 4-bromo-N-((4-(5-(2-fluoropropan-2-yl)-1,2,4-oxadiazol-3-yl)bicyclo[2.2.2]octan-1-yl)methyl)pyridin-2-amine

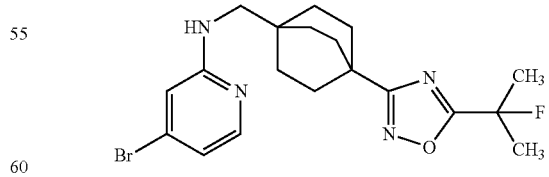

The title compound was prepared according to the general method described for the synthesis of Intermediate 1I by substituting Intermediate 576E and 4-bromopyridin-2-amine where appropriate: (light yellow colored solid, 200 mg, 0.418 mmol, 56% yield). MS (ESI) 423 (M+H).

Step B. Intermediate 634B. Preparation of 1,1,1-trifluoro-2-methylpropan-2-yl(4-bromopyridin-2-yl)((4-(5-(2-fluoropropan-2-yl)-1,2,4-oxadiazol-3-yl)bicyclo[2.2.2]octan-1-yl)methyl)carbamate

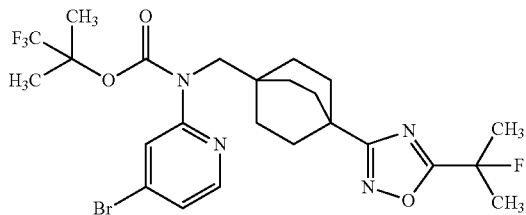

The title compound was synthesized according to the general method described for the synthesis of Intermediate 584A by substituting pyridin-2-yl (1,1,1-trifluoro-2-methylpropan-2-yl)carbonate and Intermediate 634A where appropriate: (Off-white semi-solid, 140 mg, 0.218 mmol, 79% yield). MS (ESI) 577 (M+H).

Step C. Example 634. Preparation of 1,1,1-trifluoro-2-methylpropan-2-yl((4-(5-(2-fluoropropan-2-yl)-1,2,4-oxadiazol-3-yl)bicyclo[2.2.2]octan-1-yl)methyl)(4-(4-(2-hydroxypropan-2-yl)phenyl)pyridin-2-yl)carbamate The title compound was synthesized according to the general method described for the synthesis of Example 149 by substituting Intermediate 634B and the corresponding boronic acid where appropriate: (13.4 mg, 0.021 mmol, 61% yield). $^1$H NMR (400 MHz, DMSO-$d_6$) δ 8.45 (d, J=5.4 Hz, 1H), 7.76 (d, J=8.3 Hz, 3H), 7.62 (d, J=8.3 Hz, 2H), 7.57 (dd, J=1.3, 5.3 Hz, 1H), 5.12 (s, 1H), 3.89-3.79 (m, 2H), 1.89-1.62 (m, 18H), 1.47 (s, 6H), 1.39 (br dd, J=7.3, 8.1 Hz, 6H). FXR EC$_{50}$ (nM)=31. MS (ESI) 633 (M+H).

Example 635

1,1,1-trifluoro-2-methylpropan-2-yl ((4-(5-(2-fluoropropan-2-yl)-1,2,4-oxadiazol-3-yl) bicyclo[2.2.2]octan-1-yl)methyl)(2-(4-(2-hydroxypropan-2-yl)phenyl)pyrimidin-4-yl) carbamate (635)

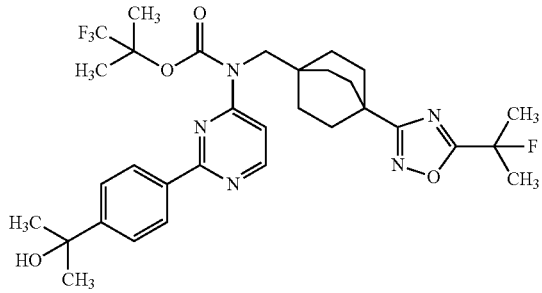

Step A. Intermediate 635A. Preparation of 2-chloro-N-((4-(5-(2-fluoropropan-2-yl)-1,2,4-oxadiazol-3-yl)bicyclo[2.2.2]octan-1-yl)methyl)pyrimidin-4-amine

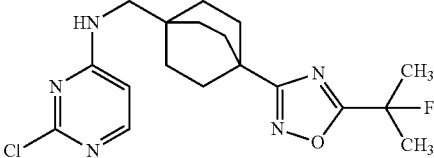 [SMILES: CC(C)(F)c1nc(C23CCC(CNc4ccnc(Cl)n4)(CC2)CC3)no1]

To a stirred solution of 2-chloropyrimidin-4-amine (146 mg, 1.126 mmol) and Intermediate 576E (300 mg, 1.126 mmol) in THF (8 mL) was added titanium(IV) isopropoxide (0.660 mL, 2.253 mmol). The reaction mixture was stirred at room temperature overnight. The reaction mixture was quenched with saturated aqueous ammonium chloride solution (20 mL) and extracted with DCM (2×25 mL). The combined organic layers were dried over sodium sulfate and concentrated under reduced pressure. The crude product was purified by flash chromatography (15% EA:hexane, 12 g silica gel column) to afford the title compound (30 mg, 0.079 mmol, 7% yield) as a white solid. MS (ESI) 380 (M+H).

Step B. Intermediate 635B. Preparation of 1,1,1-trifluoro-2-methylpropan-2-yl (2-chloropyrimidin-4-yl)((4-(5-(2-fluoropropan-2-yl)-1,2,4-oxadiazol-3-yl)bicyclo[2.2.2]octan-1-yl)methyl)carbamate

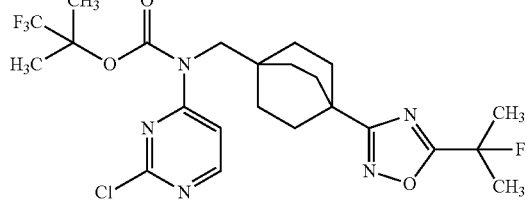

The title compound was synthesized according to the general method described for the synthesis of Intermediate 584A by substituting pyridin-2-yl (1,1,1-trifluoro-2-methylpropan-2-yl) carbonate and Intermediate 635A where appropriate: (brown liquid, 20 mg, 0.037 mmol, 71% yield). MS (ESI) 534 (M+H).

Step C. Example 635. Preparation of 1,1,1-trifluoro-2-methylpropan-2-yl((4-(5-(2-fluoropropan-2-yl)-1,2,4-oxadiazol-3-yl)bicyclo[2.2.2]octan-1-yl)methyl)(2-(4-(2-hydroxypropan-2-yl)phenyl)pyrimidin-4-yl)carbamate The title compound was synthesized according to the general method described for the synthesis of Example 149 by substituting Intermediate 635B and the corresponding boronic acid where appropriate: (12.5 mg, 0.020 mmol, 42% yield). $^1$H NMR (400 MHz, DMSO-$d_6$) δ 8.80 (d, J=5.9 Hz, 1H), 8.32 (d, J=8.6 Hz, 2H), 7.64 (d, J=8.3 Hz, 2H), 7.60 (d, J=5.6 Hz, 1H), 5.12 (s, 1H), 4.13 (s, 2H), 1.84-1.70 (m, 18H), 1.54-1.37 (m, 12H). FXR EC$_{50}$ (nM)=1278. MS (ESI) 634 (M+H).

Example 636

1,1,1-trifluoro-2-methylpropan-2-yl ((4-(5-(2-fluoropropan-2-yl)-1,2,4-oxadiazol-3-yl) bicyclo[2.2.2]octan-1-yl)methyl)(4-(4-isopropoxyphenyl)pyrimidin-2-yl)carbamate

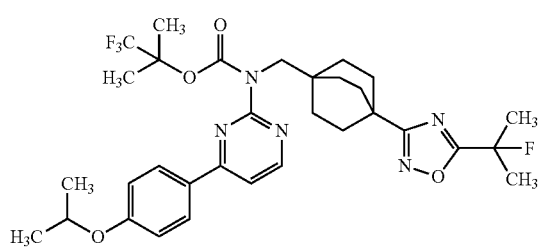

(636)

Step A. Intermediate 636A. Preparation of 4-chloro-N-((4-(5-(2-fluoropropan-2-yl)-1,2,4-oxadiazol-3-yl)bicyclo[2.2.2]octan-1-yl)methyl)pyrimidin-2-amine

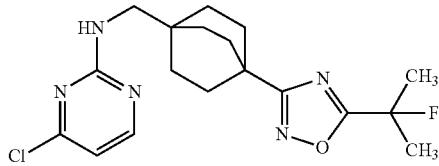 [SMILES: CC(C)(F)c1nc(C23CCC(CNc4nccc(Cl)n4)(CC2)CC3)no1]

The title compound was synthesized according to the general method described for the synthesis of Intermediate 635A by substituting Intermediate 576E and the corresponding aniline where appropriate: (40 mg, 0.095 mmol, 8% yield) as a white solid. MS (ESI) 380 (M+H).

Step B. Intermediate 636B. Preparation of 1,1,1-trifluoro-2-methylpropan-2-yl (4-chloropyrimidin-2-yl)((4-(5-(2-fluoropropan-2-yl)-1,2,4-oxadiazol-3-yl)bicyclo[2.2.2]octan-1-yl)methyl)carbamate

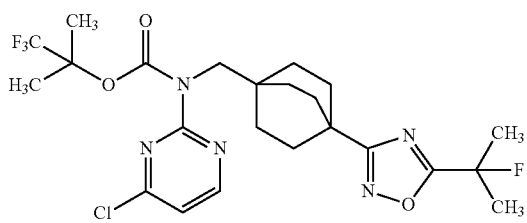 [SMILES: CC(C)(F)c1nc(C23CCC(CN(C(=O)OC(C)(C)C(F)(F)F)c4nccc(Cl)n4)(CC2)CC3)no1]

The title compound was synthesized according to the general method described for the synthesis of Intermediate 584A by substituting pyridin-2-yl (1,1,1-trifluoro-2-methylpropan-2-yl) carbonate and Intermediate 636A where appropriate: (gummy solid, 40 mg, 0.075 mmol, 57% yield). MS (ESI) 534 (M+H).

Step C. Example 636. Preparation of 1,1,1-trifluoro-2-methylpropan-2-yl ((4-(5-(2-fluoropropan-2-yl)-1,2,4-oxadiazol-3-yl)bicyclo[2.2.2]octan-1-yl)methyl)(4-(4-isopropoxyphenyl)pyrimidin-2-yl)carbamate The title compound was synthesized according to the general method described for the synthesis of Example 149 by substituting Intermediate 636B and the corresponding boronic acid where appropriate: (6.2 mg, 9.78 µmol, 21% yield). $^1$H NMR (400 MHz, DMSO-$d_6$) δ 8.74 (d, J=5.1 Hz, 1H), 8.17 (d, J=9.0 Hz, 2H), 7.83 (d, J=5.4 Hz, 1H), 7.09 (d, J=9.0 Hz, 2H), 4.80-4.72 (m, 1H), 3.84 (s, 2H), 1.84-1.65 (m, 18H), 1.46-1.35 (m, 6H), 1.31 (d, J=6.1 Hz, 6H). FXR $EC_{50}$ (nM)=68. MS (ESI) 634 (M+H).

Example 637

N-(4-(((cis)-N-(4'-(difluoromethoxy)-[1,1'-biphenyl]-3-yl)-3-hydroxy-3-(trifluoromethyl) cyclobutane-1-carboxamido) methyl)bicyclo[2.2.2]octan-1-yl)-4-fluorobenzamide

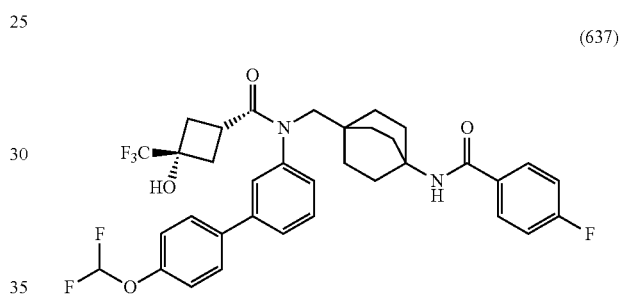

(637)

Step A. Intermediate 637A. Preparation of N-(4-(((cis)-N-(3-bromophenyl)-3-hydroxy-3-(trifluoromethyl)cyclobutane-1-carboxamido)methyl)bicyclo[2.2.2]octan-1-yl)-4-fluorobenzamide

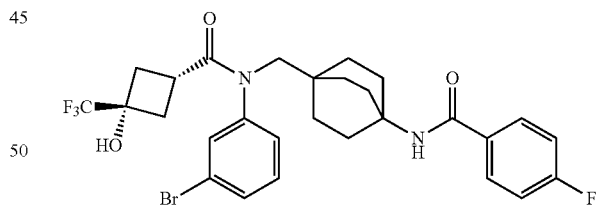

The title compound was prepared according to the general method described for the synthesis of Example 114A by using Intermediate 604A and 4-fluoro benzoic acid where appropriate: (0.08 g, 0.082 mmol, 19% yield) as a pale brown liquid. MS (ESI) 597 (M+H).

Step B. Example 637: Preparation of N-(4-(((cis)-N-(4'-(difluoromethoxy)-[1,1'-biphenyl]-3-yl)-3-hydroxy-3-(trifluoromethyl) cyclobutane-1-carboxamido)methyl)bicyclo[2.2.2]octan-1-yl)-4-fluorobenzamide The title compound was prepared according to the general method described for the synthesis of Example 149 by using Intermediate 637A and the corresponding boronic acid where appropriate: (9.5 mg, 0.014 mmol, 34% yield). $^1$H NMR (400 MHz, DMSO-$d_6$) δ 7.86-7.74 (m, 4H), 7.71 (s, 1H), 7.65 (d, J=8.1 Hz, 1H), 7.60 (s, 1H), 7.55-7.10 (m, 7H), 6.52 (s, 1H), 3.63 (m, 2H), 2.84 (m, 1H), 2.39-2.27 (m, 2H), 2.13-1.96 (m, 2H), 1.91-1.75 (m, 6H), 1.52-1.31 (m, 6H). FXR EC$_{50}$ (nM)=384; MS (ESI) 661 (M+H).

Example 638

N-(cyclopropylsulfonyl)-4-(((cis)-N-(4'-(difluoromethoxy)-[1,1'-biphenyl]-3-yl)-3-hydroxy-3-(trifluoromethyl)cyclobutane-1-carboxamido)methyl)bicyclo[2.2.2]octane-1-carboxamide (638)

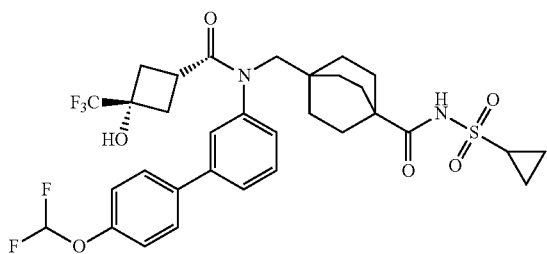

Step A. Intermediate 638A. Preparation of methyl 4-(((3-bromophenyl) amino) methyl) bicyclo[2.2.2]octane-1-carboxylate

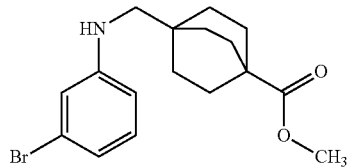 [SMILES: COC(=O)C12CCC(CNc3cccc(Br)c3)(CC1)CC2]

The title compound was synthesized according to the general method described for the synthesis of Intermediate 1I by substituting Intermediate 88B and 3-bromoaniline where appropriate: (900 mg, 2.044 mmol, 33% yield) as an off-white solid. $^1$H NMR (300 MHz, DMSO-$d_6$) δ 6.99-6.91 (m, 1H), 6.76 (s, 1H), 6.58 (br d, J=7.9 Hz, 2H), 5.77-5.65 (m, 1H), 3.56 (s, 3H), 2.78-2.70 (m, 2H), 1.74-1.63 (m, 6H), 1.51-1.38 (m, 6H). MS (ESI) 352 (M+H).

Step B. Intermediate 638B. Preparation of methyl 4-(((cis)-N-(3-bromophenyl)-3-hydroxy-3-(trifluoromethyl)cyclobutane-1-carboxamido)methyl)bicyclo[2.2.2]octane-1-carboxylate

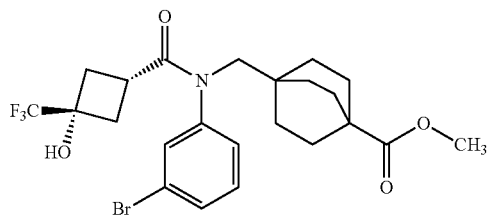 [SMILES: COC(=O)C12CCC(CN(c3cccc(Br)c3)C(=O)[C@H]3C[C@](O)(C(F)(F)F)C3)(CC1)CC2]

The title compound was synthesized according to the general method described for the synthesis of Example 3 by substituting Intermediate 638A and (cis)-3-hydroxy-3-(trifluoromethyl)cyclobutane-1-carboxylic acid where appropriate: (480 mg, 0.694 mmol, 61% yield) as an off-white solid. MS (ESI) 518 (M+H).

Step C. Intermediate 638C. Preparation of 4-(((cis)-N-(3-bromophenyl)-3-hydroxy-3-(trifluoromethyl)cyclobutane-1-carboxamido)methyl)bicyclo[2.2.2]octane-1-carboxylic acid

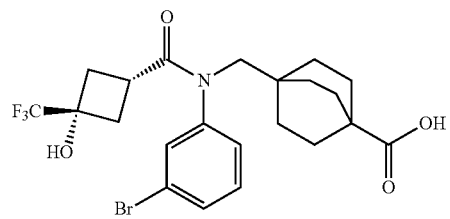 [SMILES: O=C(O)C12CCC(CN(c3cccc(Br)c3)C(=O)[C@H]3C[C@](O)(C(F)(F)F)C3)(CC1)CC2]

To a stirred solution of Intermediate 638B (400 mg, 0.772 mmol) in MeOH (3 mL) and tetrahydrofuran (3 mL) was added a solution of LiOH (92 mg, 3.86 mmol) in H$_2$O (1.5 mL). The reaction mixture was stirred at 0° C. for 2 h. The reaction mixture was concentrated under reduced pressure and diluted with water (10 mL). The aqueous solution was acidified with aqueous 1.5 N HCl and extracted with ethyl acetate (2×20 mL). The combined organic layers were dried over anhydrous sodium sulfate, filtered and concentrated under reduced pressure to afford the title compound (350 mg, 0.541 mmol, 70% yield) as a pale yellow liquid. MS (ESI) 504 (M+H).

Step D. Intermediate 638D. Preparation of 4-(((cis)-N-(3-bromophenyl)-3-hydroxy-3-(trifluoromethyl)cyclobutane-1-carboxamido) methyl)-N-cyclopropylsulfonyl)bicyclo [2.2.2]octane-1-carboxamide

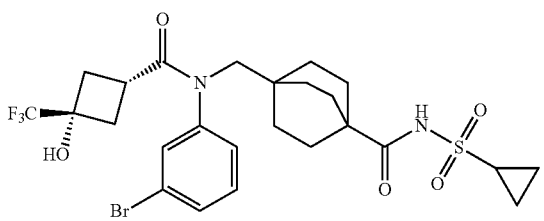 [SMILES: O=C(NS(=O)(=O)C1CC1)C12CCC(CN(c3cccc(Br)c3)C(=O)[C@H]3C[C@](O)(C(F)(F)F)C3)(CC1)CC2]

To a stirred solution of Intermediate 638C (0.2 g, 0.397 mmol) and cyclopropanesulfonamide (48.0 mg, 0.397 mmol) in DCM (5 mL) at room temperature was added DIPEA (0.069 mL, 0.397 mmol). The reaction mixture was cooled to 0° C. and BOP (175 mg, 0.397 mmol) was added. The reaction mixture was stirred at room temperature for 16 h. The reaction mixture was diluted with DCM (20 mL) and the organic solution was washed with water (10 mL) followed by brine solution (10 mL). The organic layer was dried over anhydrous sodium sulphate, filtered, and concentrated under reduced pressure to afford the crude material. The crude material was purified by flash chromatography (4 g silica gel cartridge; A=hexanes, B=EtOAc; 30 min grad.;

0% B to 35% B) to afford the title compound (0.180 g, 0.142 mmol, 36% yield) as a white solid. MS (ESI) 607 (M+H).

Step E. Example 638. Preparation of N-(cyclopropylsulfonyl)-4-(((cis)-N-(4'-(difluoromethoxy)-[1,1'-biphenyl]-3-yl)-3-hydroxy-3-(trifluoromethyl) cyclobutane-1-carboxamido) methyl)bicyclo[2.2.2] octane-1-carboxamide The title compound was prepared according to the general method described for the synthesis of Example 149 by using Intermediate 638D and the corresponding boronic acid where appropriate: (22.8 mg, 0.034 mmol, 52% yield). ¹H NMR (400 MHz, DMSO-d₆) δ 11.02 (s, 1H), 7.79 (d, J=8.8 Hz, 2H), 7.71-7.60 (m, 2H), 7.56-7.06 (m, 5H), 6.58-6.43 (m, 1H), 3.64 (br s, 2H), 2.94-2.82 (m, 2H), 2.37-2.23 (m, 2H), 2.09-1.93 (m, 2H), 1.70-1.51 (m, 6H), 1.40-1.24 (m, 6H), 1.06-0.96 (m, 4H). FXR EC₅₀ (nM)=2000; MS (ESI) 671 (M+H).

Example 639

(cis)-N-(4'-(difluoromethoxy)-[1,1'-biphenyl]-3-yl)-N-((4-(5-(4-fluorophenyl)-1,2,4-oxadiazol-3-yl)bicyclo[2.2.2]octan-1-yl)methyl)-3-hydroxy-3-(trifluoromethyl)cyclobutane-1-carboxamide (639)

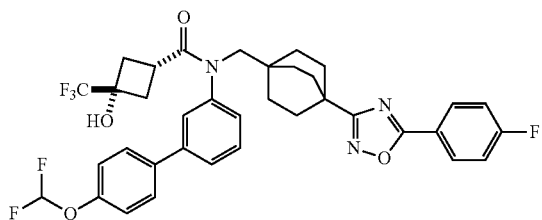

Step A. Intermediate 639A. Preparation of 3-bromo-N-((4-(5-(4-fluorophenyl)-1,2,4-oxadiazol-3-yl)bicyclo[2.2.2]octan-1-yl)methyl)aniline

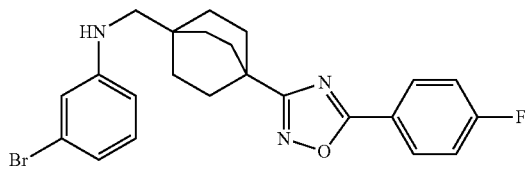 [SMILES: Fc1ccc(-c2nc(C34CCC(CNc5cccc(Br)c5)(CC3)CC4)no2)cc1]

The title compound was synthesized according to the general method described for the synthesis of Intermediate 3A by substituting Intermediate 194E and 4-fluorobenzoic acid where appropriate: (0.27 g, 0.592 mmol, 83% yield) as brown solid. MS (ESI) 456 (M+H).

Step B. Intermediate 639B. Preparation of (cis)-N-(3-bromophenyl)-N-((4-(5-(4-fluorophenyl)-1,2,4-oxadiazol-3-yl)bicyclo[2.2.2]octan-1-yl)methyl)-3-hydroxy-3-(trifluoromethyl)cyclobutane-1-carboxamide

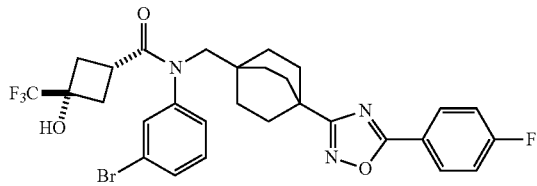

The title compound was synthesized according to the general method described for the synthesis of Example 3 by substituting Intermediate 639A and (cis)-3-hydroxy-3-(trifluoromethyl)cyclobutane-1-carboxylic acid where appropriate: (120 mg, 0.193 mmol, 80% yield) as brown solid. MS (ESI) 622 (M+H).

Step C. Example 639. Preparation of N-(cyclopropylsulfonyl)-4-(((cis)-N-(4'-(difluoromethoxy)-[1,1'-biphenyl]-3-yl)-3-hydroxy-3-(trifluoromethyl) cyclobutane-1-carboxamido) methyl)bicyclo[2.2.2] octane-1-carboxamide The title compound was prepared according to the general method described for the synthesis of Example 149 by using Intermediate 639B and the corresponding boronic acid where appropriate: (22.8 mg, 0.034 mmol, 52% yield). ¹H NMR (400 MHz, DMSO-d₆) δ 8.17-8.05 (m, 2H), 7.85-7.77 (m, 2H), 7.73 (d, J=1.7 Hz, 1H), 7.65 (d, J=8.3 Hz, 1H), 7.56-7.09 (m, 7H), 6.53 (s, 1H), 3.77-3.63 (m, 2H), 2.85 (br t, J=9.2 Hz, 1H), 2.38-2.34 (m, 2H), 2.11-1.98 (m, 2H), 1.90-1.67 (m, 6H), 1.57-1.34 (m, 6H). FXR EC₅₀ (nM)=221; MS (ESI) 686 (M+H).

Example 640

(cis)-N-((4-(5-(1,1-difluoroethyl)pyridin-2-yl)bicyclo[2.2.2]octan-1-yl)methyl)-3-(difluoromethoxy)-N-(4-(4-isopropoxyphenyl)pyridin-2-yl)-3-methylcyclobutane-1-carboxamide (640)

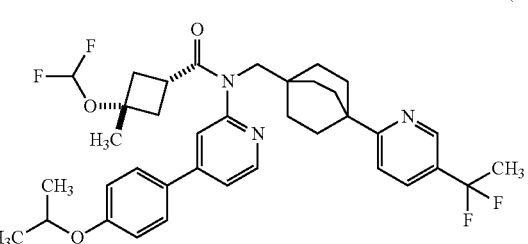

Step A. Intermediate 640A. Preparation of benzyl (cis)-3-(difluoromethoxy)-3-methylcyclobutane-1-carboxylate

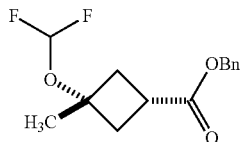

To a stirred solution of benzyl (cis)-3-hydroxy-3-methyl-cyclobutane-1-carboxylate (2 g, 9.08 mmol) in DCM (6 mL) and H₂O (6 mL) was added potassium hydrogen fluoride (5.67 g, 72.6 mmol) followed by (bromodifluoromethyl)trimethylsilane (3.55 mL, 22.70 mmol) under a nitrogen atmosphere. The reaction mixture was stirred at room temperature overnight. The reaction mixture was diluted with DCM (30 mL), washed with water (2×20 mL) followed by brine solution (20 mL), dried over anhydrous sodium sulphate and concentrated under reduced pressure. The residue was purified via flash silica gel column chromatography (24 g silica gel column, conditions: 5-15% ethyl acetate in pet ether) to afford the title compound (colorless liquid, 1.1 g, 4.07 mmol, 45% yield). ¹H NMR (400 MHz, DMSO-d₆) δ 7.42-7.30 (m, 5H), 6.89-6.49 (m, 1H), 5.12 (s, 2H), 3.05-2.95 (m, 1H), 2.46-2.37 (m, 2H), 2.34-2.26 (m, 2H), 1.47 (s, 3H).

Step B: Intermediate 640B. Preparation of (cis)-3-(difluoromethoxy)-3-methylcyclobutane-1-carboxylic acid

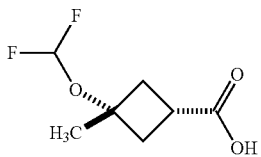

The title compound was prepared according to the general method described for the synthesis of Intermediate 629B by using Intermediate 640A where appropriate: (0.55 g, 3.05 mmol, 75% yield) as colorless liquid. ¹H NMR (400 MHz, DMSO-d₆) δ 12.41-12.27 (m, 1H), 6.90-6.46 (m, 1H), 2.81 (quin, J=8.8 Hz, 1H), 2.36 (br dd, J=9.5, 12.0 Hz, 2H), 2.30-2.16 (m, 2H), 1.49-1.43 (m, 3H).

Step C. Intermediate 640C. Preparation of (cis)-N-(4-bromopyridin-2-yl)-N-((4-(5-(1,1-difluoroethyl)pyridin-2-yl)bicyclo[2.2.2]octan-1-yl)methyl)-3-(difluoromethoxy)-3-methylcyclobutane-1-carboxamide

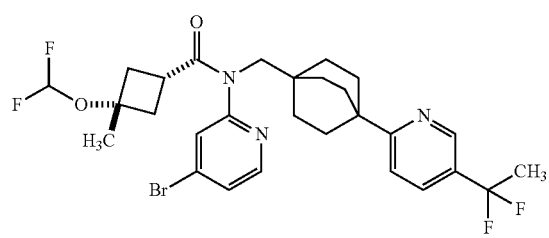

To a stirred solution of Intermediate 605E (100 mg, 0.229 mmol) and Intermediate 640B (49.5 mg, 0.275 mmol) in DCM (3 mL) was added DIPEA (0.200 mL, 1.146 mmol) followed by propylphosphonic anhydride solution (50% in EtOAc) (438 mg, 0.688 mmol). The reaction mixture was stirred at room temperature overnight. The reaction mixture was diluted with DCM (10 mL) and washed with brine solution (10 mL). The organic layer was dried over sodium sulfate and concentrated under reduced pressure to afford crude product which was purified by flash chromatography (10% EA: Hexane, 24 g silica gel column) to afford the title compound (85 mg, 0.142 mmol, 62% yield) as a brown solid. MS (ESI) 598 (M+H).

Step D. Example 640. Preparation of (cis)-N-((4-(5-(1,1-difluoroethyl)pyridin-2-yl) bicyclo[2.2.2]octan-1-yl)methyl)-3-(difluoromethoxy)-N-(4-(4-isopropoxyphenyl)pyridin-2-yl)-3-methylcyclobutane-1-carboxamide The title compound was prepared according to the general method described for the synthesis of Example 149 by using Intermediate 640C and the corresponding boronic acid where appropriate: (120 mg, 0.184 mmol, 73% yield). ¹H NMR (400 MHz, DMSO-d₆) δ 8.66 (s, 1H), 8.49 (d, J=5.20 Hz, 1H), 7.85 (d, J=8.80 Hz, 3H), 7.77 (s, 1H), 7.64 (d, J=6.40 Hz, 1H), 7.38 (d, J=8.40 Hz, 1H), 7.07 (d, J=9.20 Hz, 2H), 6.61 (t, J=152.00 Hz, 1H), 4.73 (m, 1H), 3.81 (s, 2H), 3.05-2.98 (m, 1H), 2.39-2.33 (m, 2H), 2.00 (t, J=19.20 Hz, 3H), 1.88-1.81 (m, 2H), 1.76-1.73 (m, 6H), 1.42-1.38 (m, 6H), 1.31-1.28 (m, 9H). FXR EC₅₀ (nM)=27. MS (ESI) 654 (M+H).

Example 641

N-((4-(5-(2-fluoropropan-2-yl)-1,2,4-oxadiazol-3-yl)bicyclo[2.2.2]octan-1-yl)methyl)-N-(4'-(2-hydroxypropan-2-yl)-[1,1'-biphenyl]-3-yl)-2-thia-6-azaspiro[3.3]heptane-6-carboxamide 2,2-dioxide (641)

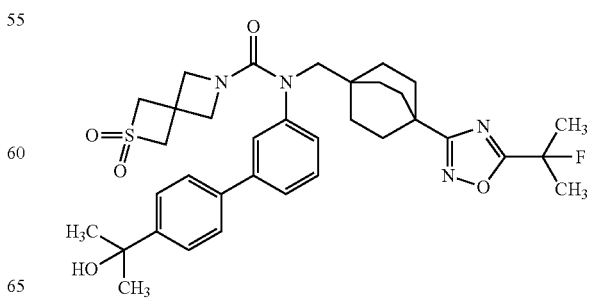

Step A. Intermediate 641A. Preparation of 2-(3'-(((4-(5-(2-fluoropropan-2-yl)-1,2,4-oxadiazol-3-yl)bicyclo[2.2.2]octan-1-yl)methyl)amino)-[1,1'-biphenyl]-4-yl)propan-2-ol

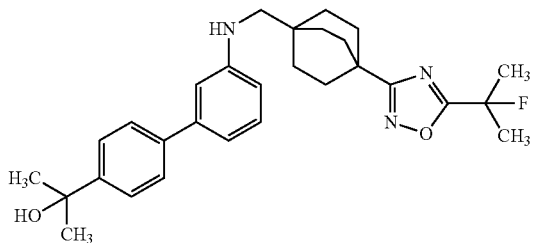 [SMILES: CC(C)(O)c1ccc(-c2cccc(NCC34CCC(c5noc(C(C)(C)F)n5)(CC3)CC4)c2)cc1]

The title compound was synthesized according to the general method described for the synthesis of Example 149 by substituting Intermediate 632A and the corresponding boronic acid where appropriate: (400 mg, 0.837 mmol, 74% yield). MS (ESI) 478 (M+H).

Step B. Example 641. Preparation of N-((4-(5-(2-fluoropropan-2-yl)-1,2,4-oxadiazol-3-yl)bicyclo[2.2.2]octan-1-yl)methyl)-N-(4'-(2-hydroxypropan-2-yl)-[1,1'-biphenyl]-3-yl)-2-thia-6-azaspiro[3.3]heptane-6-carboxamide 2,2-dioxide The title compound was prepared according to the general method described for the synthesis of Example 586 by substituting Intermediate 641A and 2-thia-6-azaspiro[3.3]heptane 2,2-dioxide where appropriate: (2 mg, 3.07 μmol, 7% yield). $^1$H NMR (400 MHz, DMSO-$d_6$) δ 7.53-7.67 (m, 6H) 7.44-7.51 (m, 1H) 7.27-7.34 (m, 1H) 5.07 (s, 1H) 4.24 (s, 4H) 3.58-3.69 (m, 6H) 1.79 (s, 3H) 1.68-1.77 (m, 9H) 1.36-1.50 (m, 12H). FXR $EC_{50}$ (nM)=1302. MS (ESI) 651 (M+H).

The following compounds were synthesized according to the general method described for the synthesis of Example 586 by substituting Intermediate 641A and the corresponding amines where appropriate.

| Ex. No. | Structure | MS (ESI) (M + H) | FXR $EC_{50}$ (nM) |
|---|---|---|---|
| 642 | 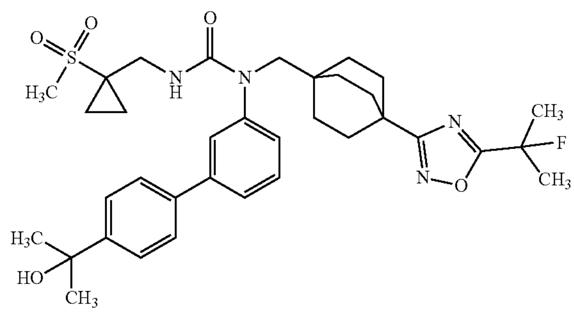 [SMILES: CC(C)(O)c1ccc(-c2cccc(N(CC34CCC(c5noc(C(C)(C)F)n5)(CC3)CC4)C(=O)NCC3(S(C)(=O)=O)CC3)c2)cc1] | 653 | 294 |
| 643 | 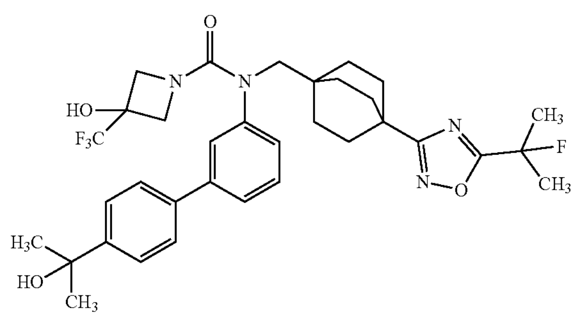 [SMILES: CC(C)(O)c1ccc(-c2cccc(N(CC34CCC(c5noc(C(C)(C)F)n5)(CC3)CC4)C(=O)N3CC(O)(C(F)(F)F)C3)c2)cc1] | 645 | 235 |
| 644 | 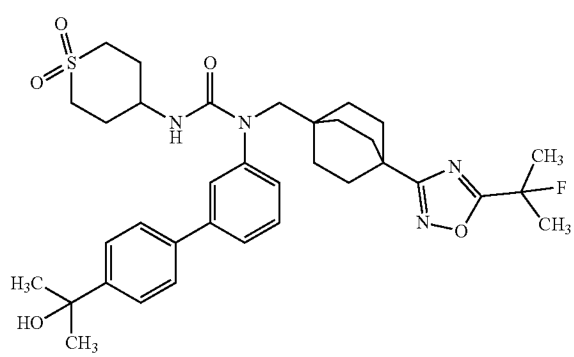 [SMILES: CC(C)(O)c1ccc(-c2cccc(N(CC34CCC(c5noc(C(C)(C)F)n5)(CC3)CC4)C(=O)NC3CCS(=O)(=O)CC3)c2)cc1] | 653 | 743 |

-continued

| Ex. No. | Structure | MS (ESI) (M + H) | FXR EC$_{50}$ (nM) |
|---|---|---|---|
| 645 | 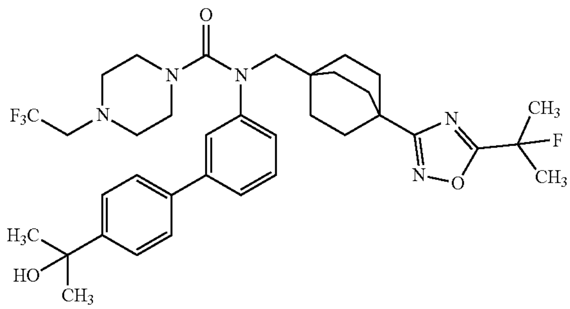 [SMILES: CC(C)(O)c1ccc(-c2cccc(N(CC34CCC(c5noc(C(C)(C)F)n5)(CC3)CC4)C(=O)N3CCN(CC(F)(F)F)CC3)c2)cc1] | 672 | 229 |
| 646 | 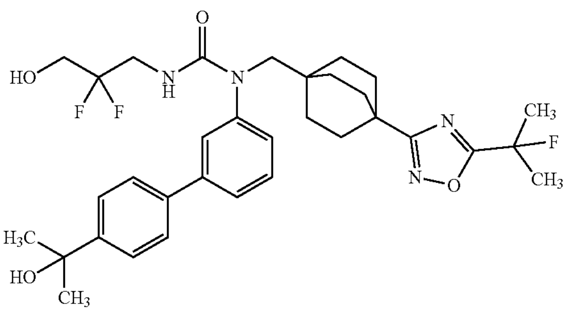 [SMILES: CC(C)(O)c1ccc(-c2cccc(N(CC34CCC(c5noc(C(C)(C)F)n5)(CC3)CC4)C(=O)NCC(F)(F)CO)c2)cc1] | 615 | 270 |
| 647 | 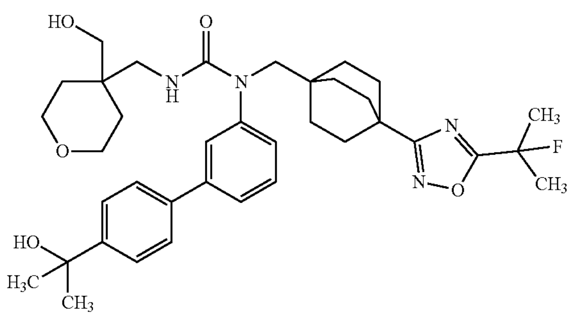 [SMILES: CC(C)(O)c1ccc(-c2cccc(N(CC34CCC(c5noc(C(C)(C)F)n5)(CC3)CC4)C(=O)NCC3(CO)CCOCC3)c2)cc1] | 649 | 581 |
| 648 | 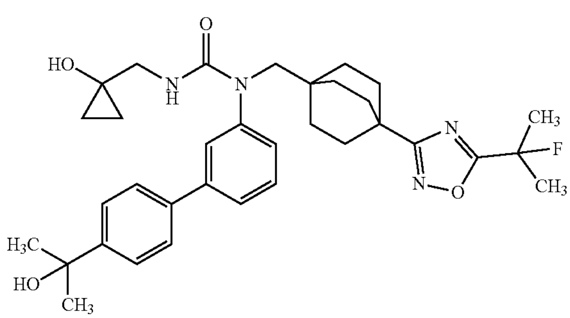 [SMILES: CC(C)(O)c1ccc(-c2cccc(N(CC34CCC(c5noc(C(C)(C)F)n5)(CC3)CC4)C(=O)NCC3(O)CC3)c2)cc1] | 591 | 509 |

| Ex. No. | Structure | MS (ESI) (M + H) | FXR EC$_{50}$ (nM) |
|---|---|---|---|
| 649 | | 634 | 600 |
| 650 | | 633 | 472 |

642 $^1$H NMR (400 MHz, DMSO-d$_6$) δ 7.62-7.66 (m, 2H) 7.54-7.61 (m, 4H) 7.50 (t, J = 7.70 Hz, 1H) 7.31 (d, J = 8.07 Hz, 1H) 5.86 (t, J = 6.11 Hz, 1H) 5.06 (s, 1H) 3.55-3.65 (m, 4H) 2.98 (s, 3H) 1.79 (s, 3H) 1.70-1.78 (m, 9H) 1.36-1.50 (m, 12H) 1.13-1.19 (m, 2H) 1.01-1.06 (m, 2H)

643 $^1$H NMR (400 MHz, DMSO-d$_6$) δ 7.63 (d, J = 8.56 Hz, 3H) 7.58 (s, 1H) 7.53-7.57 (m, 2H) 7.46-7.52 (m, 1H) 7.34 (d, J = 7.83 Hz, 1H) 7.06 (s, 1H) 5.07 (s, 1H) 3.61 (s, 2H) 3.51 (s, 4H) 1.79 (s, 3H) 1.68-1.77 (m, 9H) 1.39-1.50 (m, 12H)

644 $^1$H NMR (400 MHz, DMSO-d$_6$) δ 7.65-7.59 (m, 2H), 7.56 (d, J = 7.8 Hz, 3H), 7.53-7.49 (m, 1H), 7.48-7.41 (m, 1H), 7.28 (d, J = 8.1 Hz, 1H), 5.86 (d, J = 7.8 Hz, 1H), 5.05 (s, 1H), 3.93-3.81 (m, 1H), 3.61 (s, 2H), 3.29-3.16 (m, 2H), 2.97 (br d, J = 11.5 Hz, 2H), 2.04-1.90 (m, 4H), 1.79 (s, 3H), 1.77-1.64 (m, 9H), 1.46 (s, 6H), 1.45-1.33 (m, 6H)

645 $^1$H NMR (400 MHz, DMSO-d$_6$) δ 7.57 (s, 4H), 7.45-7.37 (m, 1H), 7.37-7.29 (m, 1H), 7.20 (s, 1H), 7.04-6.91 (m, 1H), 5.06 (s, 1H), 3.50 (s, 2H), 3.23 (br d, J = 4.6 Hz, 4H), 3.13 (q, J = 10.3 Hz, 2H), 2.48-2.43 (m, 4H), 1.90-1.79 (m, 9H), 1.76 (s, 3H), 1.63-1.52 (m, 6H), 1.46 (s, 6H)

646 $^1$H NMR (400 MHz, DMSO-d$_6$) δ 7.69-7.61 (m, 2H), 7.61-7.54 (m, 4H), 7.54-7.46 (m, 1H), 7.32 (br d, J = 7.8 Hz, 1H), 5.95 (t, J = 6.0 Hz, 1H), 5.39 (t, J = 6.6 Hz, 1H), 5.07 (s, 1H), 3.69-3.60 (m, 2H), 3.60-3.44 (m, 4H), 1.79 (s, 3H), 1.73 (s, 9H), 1.52-1.36 (m, 12H)

647 $^1$H NMR (400 MHz, DMSO-d$_6$) δ 7.69-7.60 (m, 2H), 7.60-7.53 (m, 4H), 7.53-7.43 (m, 1H), 7.31 (br d, J = 7.8 Hz, 1H), 5.75 (t, J = 5.9 Hz, 1H), 5.07 (s, 1H), 4.65 (t, J = 5.7 Hz, 1H), 3.61 (s, 2H), 3.57-3.45 (m, 4H), 3.18 (dd, J = 1.7, 5.6 Hz, 2H), 3.11 (br d, J = 5.6 Hz, 2H), 1.79 (s, 3H), 1.77-1.61 (m, 9H), 1.51-1.34 (m, 12H), 1.31-1.19 (m, 4H)

648 $^1$H NMR (400 MHz, DMSO-d$_6$) δ 7.69-7.59 (m, 3H), 7.55 (d, J = 8.6 Hz, 3H), 7.52-7.45 (m, 1H), 7.33 (d, J = 7.8 Hz, 1H), 5.51 (t, J = 5.6 Hz, 1H), 5.29 (s, 1H), 5.06 (s, 1H), 3.62 (s, 2H), 3.17 (d, J = 5.6 Hz, 2H), 1.78 (s, 3H), 1.76-1.68 (m, 9H), 1.45 (s, 6H), 1.44-1.36 (m, 6H), 0.55-0.28 (m, 4H)

649 $^1$H NMR (400 MHz, DMSO-d$_6$) δ 7.64-7.47 (m, 7H), 7.35-7.30 (m, 1H), 5.54-5.47 (m, 1H), 5.04 (s, 1H), 3.63-3.58 (m, 2H), 3.35 (br s, 4H), 3.14-3.03 (m, 2H), 2.32-2.20 (m, 6H), 1.80-1.66 (m, 12H), 1.48-1.36 (m, 12H)

650 $^1$H NMR (400 MHz, DMSO-d$_6$) δ 7.64-7.60 (m, 2H), 7.56-7.42 (m, 5H), 7.30-7.24 (m, 1H), 5.67-5.60 (m, 1H), 5.05 (s, 1H), 4.06 (s, 1H), 3.59 (s, 2H), 3.14 (q, J = 6.3 Hz, 2H), 1.80-1.67 (m, 12H), 1.65-1.51 (m, 4H), 1.50-1.34 (m, 18H)

Example 651

N-(4'-((2-cyanopropan-2-yl)oxy)-[1,1'-biphenyl]-3-yl)-N-((4-(5-(2-fluoropropan-2-yl)-1,2,4-oxadiazol-3-yl)bicyclo[2.2.2]octan-1-yl)methyl)-4-(2-hydroxypropan-2-yl)piperidine-1-carboxamide (651)

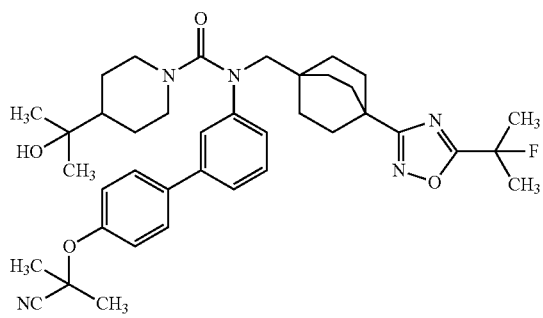

Step A. Intermediate 651A. Preparation of ethyl 1-((3-bromophenyl) ((4-(5-(2-fluoropropan-2-yl)-1,2,4-oxadiazol-3-yl)bicyclo[2.2.2]octan-1-yl) methyl) carbamoyl) piperidine-4-carboxylate

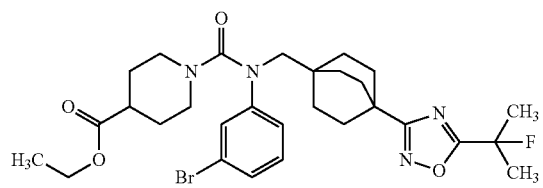 [SMILES: CCOC(=O)C1CCN(C(=O)N(CC23CCC(c4noc(C(C)(C)F)n4)(CC2)CC3)c2cccc(Br)c2)CC1]

The title compound was prepared according to the general method described for the synthesis of Example 586 by substituting Intermediate 632A and ethyl piperidine-4-carboxylate where appropriate: (160 mg, 0.264 mmol, 80% yield) as brown solid. MS (ESI) 605 (M+H).

Step B. Intermediate 651B. Preparation of N-(3-bromophenyl)-N-((4-(5-(2-fluoropropan-2-yl)-1,2,4-oxadiazol-3-yl)bicyclo[2.2.2]octan-1-yl)methyl)-4-(2-hydroxypropan-2-yl) piperidine-1-carboxamide

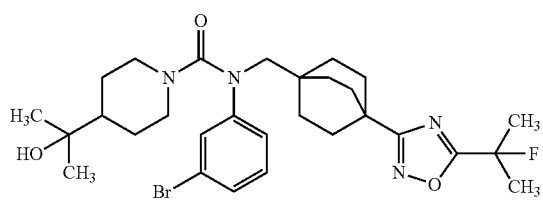 [SMILES: CC(C)(F)c1nc(C23CCC(CN(C(=O)N4CCC(C(C)(C)O)CC4)c4cccc(Br)c4)(CC2)CC3)no1]

To a stirred solution of Intermediate 651A (160 mg, 0.264 mmol) in THF (2 mL) was added methyl magnesium bromide in diethyl ether (3M) (0.264 mL, 0.793 mmol) drop wise at −20° C. The reaction mixture was stirred at room temperature for 1 h. The reaction mixture was quenched with saturated aqueous ammonium chloride solution, diluted with water (30 mL) and extracted with ethyl acetate (2×15 mL). The combined organic layer was washed with brine solution (10 mL), dried over anhydrous sodium sulphate, filtered and concentrated under reduced pressure. The crude material was purified via flash chromatography (4 g silica gel column, conditions: 30% ethyl acetate in pet ether) to afford the title compound (white solid, 120 mg, 0.203 mmol, 77% yield). MS (ESI) 591 (M+H).

Step C. Example 651. Preparation of N-(4'-((2-cyanopropan-2-yl)oxy)-[1,1'-biphenyl]-3-yl)-N-((4-(5-(2-fluoropropan-2-yl)-1,2,4-oxadiazol-3-yl)bicyclo[2.2.2]octan-1-yl)methyl)-4-(2-hydroxypropan-2-yl)piperidine-1-carboxamide The title compound was prepared according to the general method described for the synthesis of Example 149 by substituting Intermediate 651B and the corresponding boronate ester where appropriate: (3.4 mg, 4.91 µmol, 12% yield). $^1$H NMR (DMSO-$d_6$) δ7.73-7.59 (m, 2H), 7.45-7.37 (m, 1H), 7.36-7.31 (m, 1H), 7.30-7.22 (m, 2H), 7.18 (s, 1H), 7.04-6.94 (m, 1H), 4.07 (s, 1H), 4.00-3.91 (m, 2H), 3.53-3.42 (m, 2H), 2.53 (br s, 1H), 1.91-1.79 (m, 9H), 1.78-1.65 (m, 9H), 1.63-1.46 (m, 8H), 1.33-1.18 (m, 2H), 1.00-0.78 (m, 8H). FXR EC$_{50}$ (nM)=273. MS (ESI) 672 (M+H).

Example 652

1-((4-(5-(1,1-difluoroethyl)-1,2,4-oxadiazol-3-yl)bicyclo[2.2.2]octan-1-yl)methyl)-1-(4'-isopropoxy-[1,1'-biphenyl]-3-yl)-3-(tetrahydro-2H-pyran-4-yl)urea (652)

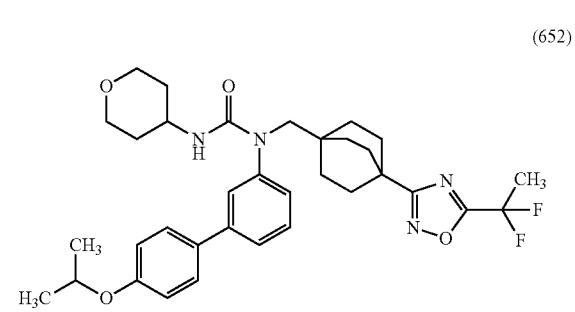 [SMILES: CC(C)Oc1ccc(-c2cccc(N(CC34CCC(c5noc(C(C)(F)F)n5)(CC3)CC4)C(=O)NC3CCOCC3)c2)cc1]

Step A. Intermediate 652A. Preparation of N-((4-(5-(1,1-difluoroethyl)-1,2,4-oxadiazol-3-yl)bicyclo[2.2.2]octan-1-yl)methyl)-4'-isopropoxy-[1,1'-biphenyl]-3-amine

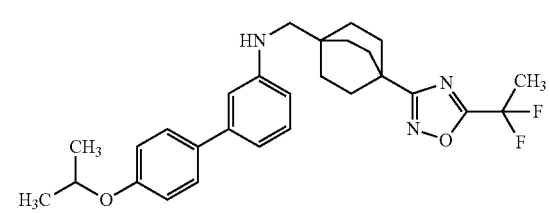 [SMILES: CC(C)Oc1ccc(-c2cccc(NCC34CCC(c5noc(C(C)(F)F)n5)(CC3)CC4)c2)cc1]

The title compound was synthesized according to the general method described for the synthesis of Example 149 by substituting Intermediate 628A and the corresponding boronic acid where appropriate: (210 mg, 0.386 mmol, 93% yield). MS (ESI) 481 (M+H).

Step B. Example 652. Preparation of 1-((4-(5-(1,1-difluoroethyl)-1,2,4-oxadiazol-3-yl) bicyclo[2.2.2]octan-1-yl) methyl)-1-(4'-isopropoxy-[1,1'-biphenyl]-3-yl)-3-(tetrahydro-2H-pyran-4-yl) urea The title compound was prepared according to the general method described for the synthesis of Example 586 by substituting Intermediate 652A and tetrahydro-2H-pyran-4-amine where appropriate: (3.4 mg, 4.91 µmol, 12% yield). $^1$H NMR (400 MHz, DMSO-$d_6$) δ 7.61 (d, J=8.56 Hz, 2H) 7.54 (s, 1H) 7.42-7.51 (m, 2H) 7.25 (d, J=7.58 Hz, 1H) 7.01 (d, J=8.80 Hz, 2H) 5.38 (d, J=7.83 Hz, 1H) 4.67 (quin, J=5.99 Hz, 1H) 3.76 (br d, J=10.52 Hz, 2H) 3.59-3.70 (m, 3H) 3.29 (d, J=1.71 Hz, 1H) 3.27 (s, 1H) 2.18 (s, 1H) 2.13 (s, 1H) 2.08 (s, 1H) 1.71-1.80 (m, 6H) 1.60-1.69 (m, 2H) 1.31-1.46 (m, 8H) 1.29 (d, J=6.11 Hz, 6H). FXR $EC_{50}$ (nM)=379. MS (ESI) 609 (M+H).

Example 653

3-((trans)-4-(difluoromethoxy)-4-methylcyclohexyl)-1-(6-fluoro-4'-isopropoxy-[1,1'-biphenyl]-3-yl)-1-((4-(5-(2-fluoropropan-2-yl)-1,2,4-oxadiazol-3-yl)bicyclo[2.2.2]octan-1-yl)methyl)urea (653)

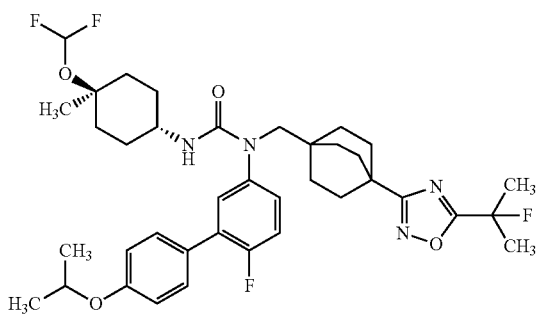

Step A. Intermediate 653A. Preparation of 1-(3-bromo-4-fluorophenyl)-1-((4-(5-(2-fluoropropan-2-yl)-1,2,4-oxadiazol-3-yl)bicyclo[2.2.2]octan-1-yl)methyl)-3-((trans)-4-hydroxy-4-methylcyclohexyl)urea

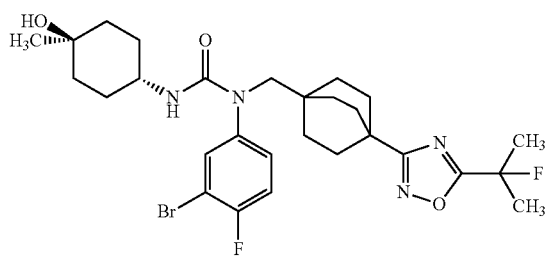 [SMILES: CC(C)(F)c1nc(C23CCC(CN(C(=O)N[C@H]4CC[C@](C)(O)CC4)c4ccc(F)c(Br)c4)(CC2)CC3)no1]

The title compound was prepared according to the general method described for the synthesis of Example 586 by substituting Intermediate 582A and (trans)-4-amino-1-methylcyclohexan-1-ol where appropriate: (400 mg, 0.672 mmol, 75% yield) as an off-white solid. MS (ESI) 595 (M+H).

Step B. Intermediate 653B. Preparation of 1-(3-bromo-4-fluorophenyl)-3-((trans)-4-(difluoromethoxy)-4-methylcyclohexyl)-1-((4-(5-(2-fluoropropan-2-yl)-1,2,4-oxadiazol-3-yl)bicyclo[2.2.2]octan-1-yl)methyl)urea

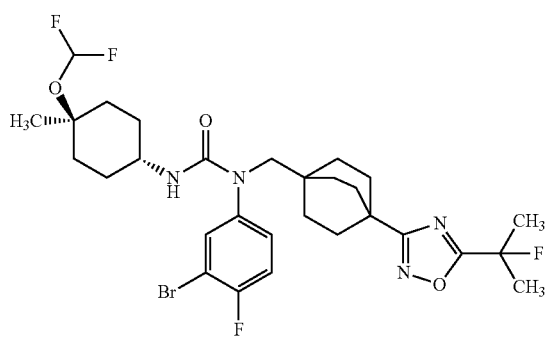 [SMILES: CC(C)(F)c1nc(C23CCC(CN(C(=O)N[C@H]4CC[C@](C)(OC(F)F)CC4)c4ccc(F)c(Br)c4)(CC2)CC3)no1]

To a stirred solution of Intermediate 653A (150 mg, 0.252 mmol) in MeCN (15 mL) was added copper(I) iodide (9.59 mg, 0.050 mmol). The reaction mixture was heated at 50° C. A solution of 2,2-difluoro-2-(fluorosulfonyl)acetic acid (67.3 mg, 0.378 mmol) in 2 mL of acetonitrile was added dropwise over a period of 5 min. The reaction mixture was heated at 50° C. for 30 min. The reaction mixture was concentrated under reduced pressure, the residue was dissolved in ethyl acetate (20 mL), and the insoluble solid was filtered out. The resulting EtOAc solution was concentrated under reduced pressure. The crude material was purified via flash silica gel column chromatography (12 g silica gel column, conditions: 30% ethyl acetate in pet ether) to afford the title compound (off-white semi-solid, 80 mg, 0.124 mmol, 49% yield). MS (ESI) 645 (M+H).

Step C. Example 654. Preparation of 3-((trans)-4-(difluoromethoxy)-4-methylcyclohexyl)-1-(6-fluoro-4'-isopropoxy-[1,1'-biphenyl]-3-yl)-1-((4-(5-(2-fluoropropan-2-yl)-1,2,4-oxadiazol-3-yl)bicyclo[2.2.2]octan-1-yl)methyl)urea The title compound was prepared according to the general method described for the synthesis of Example 149 by substituting Intermediate 653B and the corresponding boronic acid where appropriate: (5.8 mg, 8.28 µmol, 18% yield). $^1$H NMR (400 MHz, DMSO-$d_6$) δ 7.62-7.44 (m, 2H), 7.40 (q, J=6.7 Hz, 1H), 7.35-7.20 (m, 2H), 7.17-6.98 (m, 2H), 6.98-6.47 (m, 1H), 5.46-5.19 (m, 1H), 4.74-4.53 (m, 1H), 3.61-3.46 (m, 3H), 1.88-1.68 (m, 12H), 1.68-1.47 (m, 6H), 1.47-1.33 (m, 8H), 1.33-1.13 (m, 9H). FXR $EC_{50}$ (nM)=145. MS (ESI) 701 (M+H).

Example 654

(cis)-N-(4'-((1-amino-2-methyl-1-oxopropan-2-yl) oxy)-[1,1'-biphenyl]-3-yl)-N-((4-(5-(2-fluoropropan-2-yl)-1,2,4-oxadiazol-3-yl)bicyclo[2.2.2]octan-1-yl) methyl)-3-hydroxy-3-(trifluoromethyl)cyclobutane-1-carboxamide

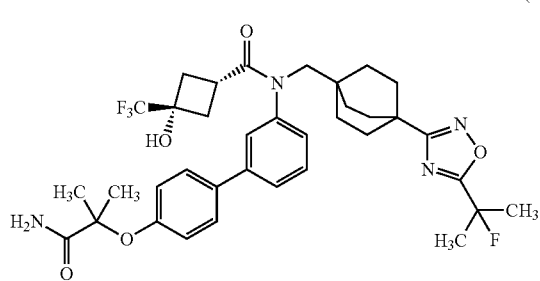

(654)

Step A. Intermediate 654A. Preparation of (cis)-N-(4'-((2-cyanopropan-2-yl)oxy)-[1,1'-biphenyl]-3-yl)-N-((4-(5-(2-fluoropropan-2-yl)-1,2,4-oxadiazol-3-yl) bicyclo[2.2.2]octan-1-yl)methyl)-3-hydroxy-3-(trifluoromethyl)cyclobutane-1-carboxamide

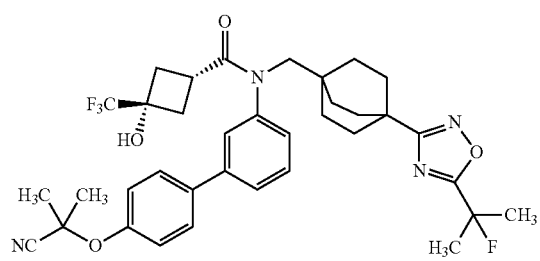 [SMILES: CC(C)(C#N)Oc1ccc(-c2cccc(N(CC34CCC(c5noc(C(C)(C)F)n5)(CC3)CC4)C(=O)[C@H]3C[C@](O)(C(F)(F)F)C3)c2)cc1]

The title compound was prepared according to the general method described for the synthesis of Example 149 by substituting Intermediate 576G and the corresponding boronate ester where appropriate: (35 mg, 0.052 mmol, 77% yield). MS (ESI) 669 (M+H).

Step B. Example 654. Preparation of (cis)-N-(4'-((1-amino-2-methyl-1-oxopropan-2-yl) oxy)-[1,1'-biphenyl]-3-yl)-N-((4-(5-(2-fluoropropan-2-yl)-1,2,4-oxadiazol-3-yl) bicyclo[2.2.2]octan-1-yl)methyl)-3-hydroxy-3-(trifluoromethyl)cyclobutane-1-carboxamide To a stirred solution of Intermediate 654A (30 mg, 0.045 mmol) in DMSO (1 mL) was added $K_2CO_3$ (18.60 mg, 0.135 mmol) followed by $H_2O_2$(0.023 mL, 0.224 mmol) at 10° C. The reaction mixture was stirred at 10° C. for 1 h. The reaction mixture was concentrated under reduced pressure and the crude material was purified via preparative LC/MS with the following conditions: Column: Waters XBridge C18, 19×150 mm, 5-μm particles; Mobile Phase A: 10-mM ammonium acetate; Mobile Phase B: acetonitrile; Gradient: 20-75% B over 25 minutes, then a 5-minute hold at 100% B; Flow: 15 mL/min. Fractions containing the product were combined and dried via centrifugal evaporation to afford the title compound (15.3 mg, 0.124 mmol, 50% yield). $^1$H NMR (400 MHz, DMSO-$d_6$) δ 7.70-7.62 (m, 3H), 7.60 (d, J=7.6 Hz, 1H), 7.56 (s, 1H), 7.48 (t, J=7.8 Hz, 1H), 7.36-7.23 (m, 2H), 7.03-6.91 (m, 2H), 6.51 (s, 1H), 3.76-3.57 (m, 2H), 2.84 (quin, J=8.9 Hz, 1H), 2.38-2.27 (m, 2H), 2.13-1.96 (m, 2H), 1.82-1.67 (m, 12H), 1.53-1.36 (m, 12H). FXR $EC_{50}$ (nM)=169. MS (ESI) 687 (M+H).

Example 655

1,1,1-trifluoro-2-methylpropan-2-yl ((4-(3-(1-fluoro-cyclopropyl)-1-methyl-1H-pyrazol-5-yl)bicyclo [2.2.2]octan-1-yl)methyl)(4'-isopropoxy-[1,1'-biphenyl]-3-yl)carbamate

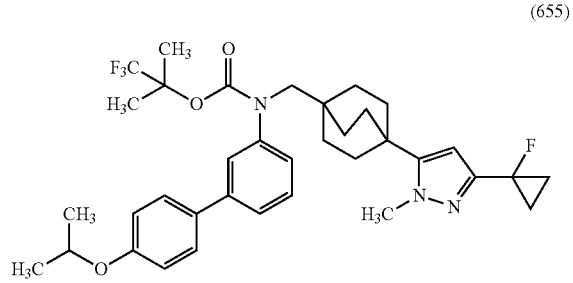 [SMILES: CC(C)Oc1ccc(-c2cccc(N(CC34CCC(c5cc(C6(F)CC6)nn5C)(CC3)CC4)C(=O)OC(C)(C)C(F)(F)F)c2)cc1]

(655)

Step A. Intermediate 655A. Preparation of methyl 4-(1-hydroxyethyl)bicyclo[2.2.2]octane-1-carboxylate

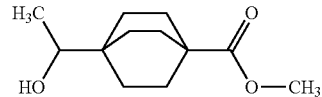

To a stirred solution of Intermediate 88B (500 mg, 2.55 mmol) in THF (5 mL) was added methyl magnesium bromide (3.4 M in diethyl ether) (0.899 mL, 3.06 mmol) drop wise at 0° C. The reaction mixture was stirred at 0° C. for 1 h. The reaction was quenched with saturated aqueous ammonium chloride solution. The reaction mixture was diluted with water (20 mL) and extracted with ethyl acetate (2×30 mL). The combined organic layers were washed with brine solution (20 mL), dried over anhydrous sodium sulphate, filtered and concentrated under reduced pressure. The crude material was purified via flash chromatography (12 g silica gel column, conditions: 40% ethyl acetate in pet ether) to afford the title compound (Brown solid, 350 mg, 1.649 mmol, 64.7% yield). $^1$H NMR (300 MHz, DMSO-$d_6$) δ 4.23 (d, J=5.10 Hz, 1H), 3.57 (s, 3H), 3.19 (m, 1H), 1.63-2.00 (m, 6H), 1.30-1.44 (m, 6H), 0.92 (d, J=6.30 Hz, 3H).

Step B. Intermediate 655B. Preparation of methyl 4-acetylbicyclo[2.2.2]octane-1-carboxylate

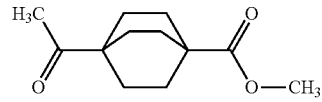

The title compound was synthesized according to the general method described for the synthesis of Intermediate 3C by substituting Intermediate 655A where appropriate: (250 mg, 1.189 mmol, 70% yield) as an off-white solid. $^1$H NMR (400 MHz, DMSO-d$_6$) δ 3.61-3.54 (s, 3H), 2.06-2.01 (s, 3H), 1.75-1.58 (m, 12H).

Step C: Intermediate 655C. Preparation of methyl 4-(3-(1-fluorocyclopropyl)-3-oxopropanoyl)bicyclo[2.2.2]octane-1-carboxylate

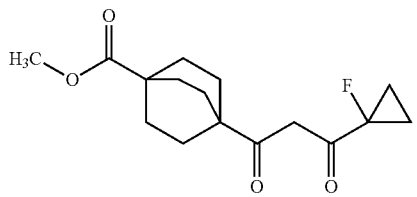 [SMILES: COC(=O)C12CCC(C(=O)CC(=O)C3(F)CC3)(CC1)CC2]

To a stirred solution of 1-fluorocyclopropane-1-carboxylic acid (0.916 g, 8.80 mmol) in THF (18.5 mL) was added 1-chloro-N,N, 2-trimethyl-1-propenylamine (3.03 mL, 22.88 mmol) at room temperature. The reaction mixture was stirred at room temperature for 45 min. The reaction mixture was concentrated under reduced pressure. The crude product was co-distilled twice with DCM to afford 1-fluorocyclopropane-1-carbonyl chloride (1.5 g, 6.63 mmol) as an off-white solid.

To a stirred solution of LiHMDS (26.4 mL, 26.4 mmol) in THF at −78° C. was added Intermediate 655B (1.85 g, 8.80 mmol) and the reaction mixture was stirred at −78° C. for 1 h. A solution of 1-fluorocyclopropane-1-carbonyl chloride (1.5 g, 6.63 mmol) in tetrahydrofuran (18.5 mL) was added to the reaction mixture and stirred for additional 1 h at −78° C. The reaction mixture was gradually warmed to room temperature and stirred at room temperature for 12 h. The reaction was quenched with saturated aqueous ammonium chloride solution (20 mL). The reaction mixture was extracted with EtOAc (2×50 mL). The combined organic layers were dried over anhydrous sodium sulphate, filtered and concentrated under reduced pressure. The crude material was purified via flash silica gel column chromatography (12 g silica gel cartridge; A=hexanes, B=EtOAc; 30 min grad.; 0% B to 40% B; flow rate=12 mL/min) to afford the title compound (1.9 g, 6.41 mmol, 73% yield) as an off-white solid. $^1$H NMR (400 MHz, DMSO-d$_6$) δ 3.59 (s, 3H), 3.58 (s, 2H), 1.76-1.70 (m, 12H), 1.54-1.45 (m, 2H), 1.38-1.31 (m, 2H).

Step D. Intermediate 655D1 and 655D2. Preparation of methyl 4-(5-(1-fluorocyclopropyl)-1-methyl-1H-pyrazol-3-yl)bicyclo[2.2.2]octane-1-carboxylate (655D1) and methyl 4-(3-(1-fluorocyclopropyl)-1-methyl-1H-pyrazol-5-yl)bicyclo [2.2.2]octane-1-carboxylate (655D2)

(655D1)

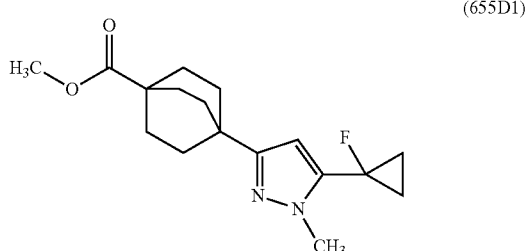

(655D2)

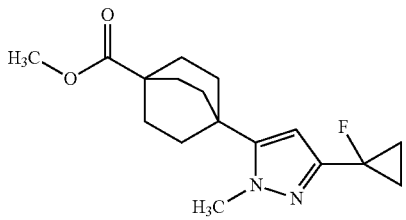

To a solution of Intermediate 655C (1.0 g, 3.37 mmol) in IPA (10 mL) was added methylhydrazine sulfate (0.584, 4.05 mmol) followed by TEA (1.411 mL, 10.12 mmol) drop wise at 0° C. The reaction mixture was gradually warmed to room temperature and stirred at room temperature for 12 h. The reaction mixture was concentrated under reduced pressure. The crude material was poured into water (15 mL) and extracted with EtOAc (25 mL). The organic layer was washed with brine, dried over anhydrous sodium sulfate and concentrated under reduced pressure. The crude material was purified via flash column chromatography (12 g silica gel cartridge; A=hexanes, B=EtOAc; 30 min grad.; 0% B to 40% B; flow rate=12 mL/min). The purified fractions were combined, concentrated under reduced pressure and dried in vacuo to afford the title compounds.

The first eluting isomer was methyl 4-(5-(1-fluorocyclopropyl)-1-methyl-1H-pyrazol-3-yl)bicyclo[2.2.2]octane-1-carboxylate (655D1) (100 mg, 0.326 mmol, 10% yield). MS (ESI) 307 (M+H) (RT=0.78 min or peak-1).

Second eluting isomer was methyl 4-(3-(1-fluorocyclopropyl)-1-methyl-1H-pyrazol-5-yl)bicyclo[2.2.2]octane-1-carboxylate (655D2) (900 mg, 2.94 mmol, 87% yield). MS (ESI) 307 (M+H). (RT=0.82 min or peak-2).

Step E. Intermediate 655E. Preparation of (4-(3-(1-fluorocyclopropyl)-1-methyl-1H-pyrazol-5-yl)bicyclo[2.2.2]octan-1-yl)methanol

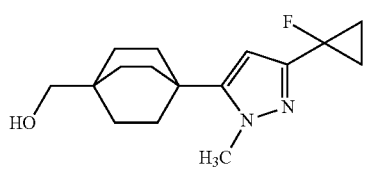 [SMILES: Cn1nc(C2(F)CC2)cc1C12CCC(CO)(CC1)CC2]

The title compound was synthesized according to the general method described for the synthesis of Intermediate 1G by substituting Intermediate 655D2 where appropriate: (720 mg, 2.59 mmol, 79% yield) as an off-white solid. $^1$H NMR (400 MHz, DMSO-d$_6$) δ 6.19-6.15 (m, 1H), 4.33-4.29 (m, 1H), 3.85-3.80 (m, 3H), 3.09-3.02 (m, 2H), 1.73-1.65 (m, 6H), 1.45-1.32 (m, 8H), 1.10-0.99 (m, 2H). MS (ESI) 279 (M+H).

Step F. Intermediate 655F. Preparation of 4-(3-(1-fluorocyclopropyl)-1-methyl-1H-pyrazol-5-yl)bicyclo[2.2.2]octane-1-carbaldehyde

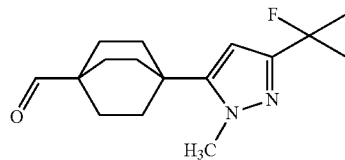 [SMILES: Cn1nc(C2(F)CC2)cc1C12CCC(C=O)(CC1)CC2]

The title compound was synthesized according to the general method described for the synthesis of Intermediate 3C by substituting Intermediate 655E where appropriate: (470 mg, 1.701 mmol, 68% yield) as an off-white solid. $^1$H NMR (400 MHz, DMSO-d$_6$) δ 9.45-9.42 (m, 1H), 6.20 (d, J=2.5 Hz, 1H), 3.84 (d, J=1.0 Hz, 3H), 1.80-1.71 (m, 6H), 1.67-1.59 (m, 6H), 1.45-1.35 (m, 2H), 1.11-1.04 (m, 2H).

Step G. Intermediate 655G. Preparation of 3-bromo-N-((4-(3-(1-fluorocyclopropyl)-1-methyl-1H-pyrazol-5-yl)bicyclo[2.2.2]octan-1-yl) methyl)aniline

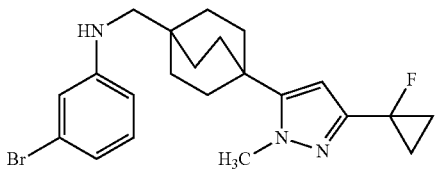 [SMILES: Cn1nc(C2(F)CC2)cc1C12CCC(CNc3cccc(Br)c3)(CC1)CC2]

The title compound was synthesized according to the general method described for the synthesis of Intermediate 1I by substituting Intermediate 655F and 3-bromoaniline where appropriate: (150 mg, 0.347 mmol, 33% yield) as an off-white solid. MS (ESI) 432 (M+H).

Step H. Intermediate 655H. Preparation of 1,1,1-trifluoro-2-methylpropan-2-yl (3-bromophenyl)((4-(3-(1-fluorocyclopropyl)-1-methyl-1H-pyrazol-5-yl)bicyclo[2.2.2]octan-1-yl)methyl)carbamate

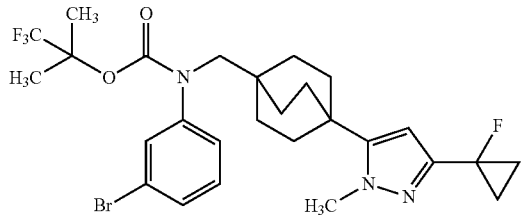 [SMILES: Cn1nc(C2(F)CC2)cc1C12CCC(CN(C(=O)OC(C)(C)C(F)(F)F)c3cccc(Br)c3)(CC1)CC2]

The title compound was synthesized according to the general method described for the synthesis of Intermediate 584A by substituting pyridin-2-yl (1,1,1-trifluoro-2-methyl-propan-2-yl)carbonate and Intermediate 655G where appropriate: (brown solid, 60 mg, 0.102 mmol, 74% yield). MS (ESI) 586 (M+H).

Step I. Example 655. Preparation of 1,1,1-trifluoro-2-methylpropan-2-yl ((4-(3-(1-fluorocyclopropyl)-1-methyl-1H-pyrazol-5-yl)bicyclo[2.2.2]octan-1-yl)methyl)(4'-isopropoxy-[1,1'-biphenyl]-3-yl)carbamate The title compound was synthesized according to the general method described for the synthesis of Example 149 by substituting Intermediate 655H and the corresponding boronic acid where appropriate: (10 mg, 0.016 mmol, 31% yield). $^1$H NMR (400 MHz, DMSO-d$_6$) δ 7.64-7.51 (m, 3H), 7.48-7.43 (m, 1H), 7.39 (t, J=7.9 Hz, 1H), 7.29-7.19 (m, 1H), 7.00 (d, J=8.8 Hz, 2H), 6.12 (d, J=2.2 Hz, 1H), 4.70-4.61 (m, 1H), 3.80 (s, 3H), 3.61 (s, 2H), 1.69-1.56 (m, 12H), 1.46-1.16 (m, 14H), 1.08-0.98 (m, 2H). FXR EC$_{50}$ (nM) 819; MS (ESI) 642 (M+H).

Example 656

1,1,1-trifluoro-2-methylpropan-2-yl ((4-(5-(1,1-difluoroethyl)isoxazol-3-yl) bicyclo[2.2.2]octan-1-yl) methyl)(4'-isopropoxy-[1,1'-biphenyl]-3-yl)carbamate (656)

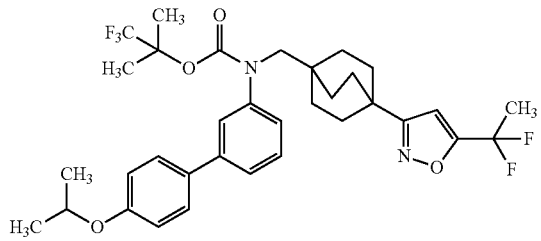

Step A. Intermediate 656A. Preparation of methyl 4-(4,4-difluoro-3-oxopentanoyl)bicyclo[2.2.2]octane-1-carboxylate

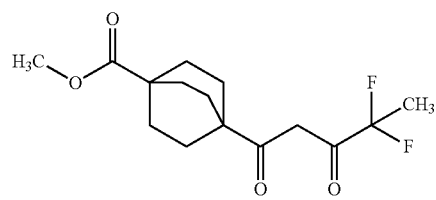 [SMILES: COC(=O)C12CCC(C(=O)CC(=O)C(C)(F)F)(CC1)CC2]

The title compound was synthesized according to the general method described for the synthesis of Intermediate 655C by substituting Intermediate 655B and 2,2-difluoropropanoyl chloride where appropriate: (500 mg, 1.654 mmol, 87% yield) as a gummy liquid. $^1$H NMR (400 MHz, DMSO-d$_6$) δ 3.59 (s, 3H), 1.85-1.58 (m, 15H), 2H buried under moisture peak. MS (ESI) 303 (M+H).

Step B. Intermediate 656B1 & 656B2. Preparation of methyl 4-(5-(1,1-difluoroethyl)-5-hydroxy-4,5-dihydroisoxazol-3-yl)bicyclo[2.2.2]octane-1-carboxylate 656B1 and methyl 4-(3-(1,1-difluoroethyl)-5-hydroxy-4,5-dihydroisoxazol-5-yl)bicyclo[2.2.2]octane-1-carboxylate (656B2)

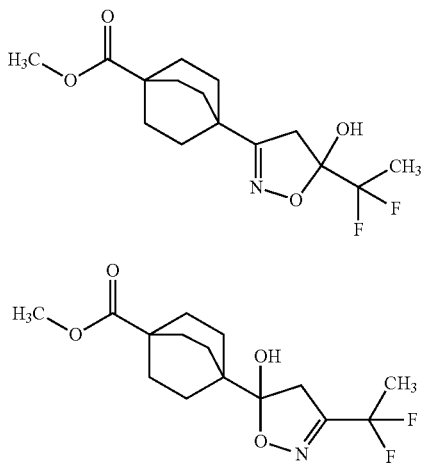

To a solution of Intermediate 656A (1.0 g, 3.31 mmol) in IPA (10 mL) was added hydroxylamine hydrochloride (0.276 g, 3.97 mmol) followed by TEA (1.383 mL, 9.92 mmol) drop wise at 0° C. The reaction mixture was heated to 80° C. and stirred for 12 h. The reaction mixture was concentrated under reduced pressure. The crude material was diluted with water (20 mL) and extracted with EtOAc (2×30 mL). The organic layers were washed with brine, dried over anhydrous sodium sulfate and concentrated under reduced pressure. The crude material was purified via flash column chromatography (12 g silica gel cartridge; A=hexanes, B=EtOAc; 30 min grad.; 0% B to 40% B; flow rate=12 mL/min).

First isomer was methyl 4-(5-(1,1-difluoroethyl)-5-hydroxy-4,5-dihydroisoxazol-3-yl)bicyclo[2.2.2]octane-1-carboxylate (656B1) (Major peak) (830 mg, 2.62 mmol, 79% yield). $^1$H NMR (400 MHz, DMSO-$d_6$) δ 7.50 (d, J=1.00 Hz, 1H) 3.58 (s, 3H) 3.20 (d, J=18.57 Hz, 1H) 2.82 (dd, J=18.32, 2.26 Hz, 1H) 1.56-1.81 (m, 15H). MS (ESI) 318 (M+H).

Second isomer methyl was 4-(3-(1,1-difluoroethyl)-5-hydroxy-4,5-dihydroisoxazol-5-yl)bicyclo[2.2.2]octane-1-carboxylate (656B2) (minor peak) (100 mg, 0.315 mmol, 10% yield). $^1$H NMR (400 MHz, DMSO-$d_6$) 6.87 (s, 1H) 3.52-3.64 (s, 3H) 3.27 (s, 1H) 2.69 (d, J=19.07 Hz, 1H) 1.88 (t, J=19.07 Hz, 3H) 1.65-1.73 (m, 6H) 1.48-1.56 (m, 6H). MS (ESI) 318 (M+H).

Step C. Intermediate 656C. Preparation of methyl 4-(5-(1,1-difluoroethyl)isoxazol-3-yl) bicyclo[2.2.2]octane-1-carboxylate

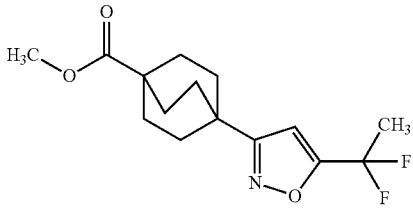 [SMILES: COC(=O)C12CCC(c3cc(C(C)(F)F)on3)(CC1)CC2]

To a solution of Intermediate 656B1 (750 mg, 2.363 mmol) in ACN (20 mL) was added triphenylphosphine (1302 mg, 4.96 mmol) followed by CCl$_4$ (0.684 mL, 7.09 mmol) at room temperature. The reaction mixture was stirred for 1 h at 90° C. The reaction mixture was poured into saturated aqueous ammonium chloride solution, diluted with water (15 mL) and extracted with EtOAc (2×25 mL). The combined organic layers were washed with brine, dried over anhydrous sodium sulfate and concentrated under reduced pressure The crude material was purified via flash column chromatography (12 g silica gel cartridge; A=hexanes, B=EtOAc; 30 min grad.; 0% B to 40% B; flow rate=12 mL/min). The pure fractions were combined, concentrated under reduced pressure and dried in vacuo to afford the title compound: (425 mg, 1.420 mmol, 60% yield). $^1$H NMR (400 MHz, DMSO-$d_6$) δ 7.00-6.98 (m, 1H), 3.59 (s, 3H), 2.09-1.97 (m, 3H), 1.86-1.76 (m, 12H). MS (ESI) 300 (M+H).

Step D. Intermediate 656D. Preparation of (4-(5-(1,1-difluoroethyl)isoxazol-3-yl) bicyclo[2.2.2]octan-1-yl)methanol

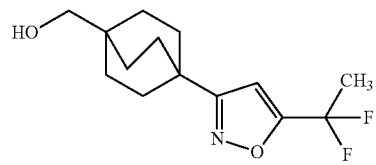 [SMILES: CC(F)(F)c1cc(C23CCC(CO)(CC2)CC3)no1]

The title compound was synthesized according to the general method described for the synthesis of Intermediate 1G by substituting Intermediate 656C where appropriate: (140 mg, 0.516 mmol, 52% yield) as an off-white solid. $^1$H NMR (400 MHz, DMSO-$d_6$) δ 7.02-6.97 (m, 1H), 4.40 (t, J=5.5 Hz, 1H), 3.08 (d, J=5.5 Hz, 2H), 2.11-1.97 (m, 3H), 1.83-1.72 (m, 6H), 1.49-1.38 (m, 6H). MS (ESI) 272 (M+H).

Step E. Intermediate 656E. Preparation of 4-(5-(1,1-difluoroethyl)isoxazol-3-yl) bicyclo[2.2.2]octane-1-carbaldehyde

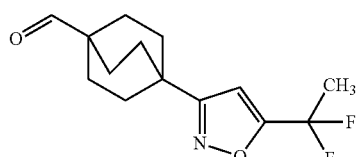

The title compound was synthesized according to the general method described for the synthesis of Intermediate 3C by substituting Intermediate 656D where appropriate: (130 mg, 0.483 mmol, 44% yield) as an off-white solid. ¹H NMR (400 MHz, DMSO-d₆) δ 9.48-9.44 (m, 1H), 7.06-7.02 (m, 1H), 2.11-2.00 (m, 3H), 1.90-1.81 (m, 6H), 1.72-1.63 (m, 6H).

Step F. Intermediate 656F. Preparation of 3-bromo-N-((4-(5-(1,1-difluoroethyl)isoxazol-3-yl)bicyclo[2.2.2]octan-1-yl)methyl)aniline

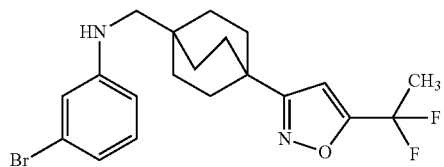 [SMILES: CC(F)(F)c1cc(C23CCC(CNc4cccc(Br)c4)(CC2)CC3)no1]

The title compound was synthesized according to the general method described for the synthesis of Intermediate 1I by substituting Intermediate 656E and 3-bromo aniline where appropriate: (60 mg, 0.141 mmol, 58% yield) as an off-white solid. ¹H NMR (400 MHz, DMSO-d₆) δ 7.02-6.94 (m, 2H), 6.80-6.75 (m, 1H), 6.63-6.53 (m, 2H), 5.80-5.74 (m, 1H), 2.80 (d, J=5.9 Hz, 2H), 2.11-1.98 (m, 3H), 1.86-1.76 (m, 6H), 1.60-1.50 (m, 6H). MS (ESI) 427 (M+H).

Step G. Intermediate 656G. Preparation of 1,1,1-trifluoro-2-methylpropan-2-yl (3-bromophenyl)((4-(5-(1,1-difluoroethyl)isoxazol-3-yl)bicyclo[2.2.2]octan-1-yl)methyl) carbamate

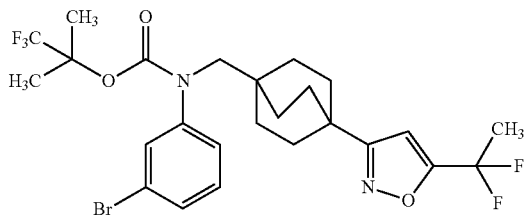 [SMILES: CC(F)(F)c1cc(C23CCC(CN(C(=O)OC(C)(C)C(F)(F)F)c4cccc(Br)c4)(CC2)CC3)no1]

The title compound was synthesized according to the general method described for the synthesis of Intermediate 584A by substituting pyridin-2-yl (1,1,1-trifluoro-2-methylpropan-2-yl)carbonate and Intermediate 656F where appropriate: (solid, 100 mg, 0.173 mmol, 73% yield). ¹H NMR (400 MHz, DMSO-d₆) δ 7.64-7.58 (m, 1H), 7.45-7.29 (m, 3H), 6.97-6.91 (m, 1H), 3.61-3.54 (m, 2H), 2.09-1.95 (m, 3H), 1.79-1.68 (m, 6H), 1.65-1.59 (m, 6H), 1.42-1.31 (m, 6H). MS (ESI) 579 (M+H).

Step H. Example 656. Preparation of 1,1,1-trifluoro-2-methylpropan-2-yl ((4-(5-(1,1-difluoroethyl)isoxazol-3-yl)bicyclo[2.2.2]octan-1-yl)methyl)(4'-isopropoxy-[1,1'-biphenyl]-3-yl)carbamate The title compound was synthesized according to the general method described for the synthesis of Example 149 by substituting Intermediate 656G and the corresponding boronic acid where appropriate: (17.7 mg, 0.028 mmol, 54% yield. ¹H NMR (400 MHz, DMSO-d₆) δ 7.66-7.50 (m, 3H), 7.50-7.44 (m, 1H), 7.40 (t, J=7.8 Hz, 1H), 7.27 (br d, J=2.2 Hz, 1H), 7.06-6.97 (m, 2H), 6.95-6.88 (m, 1H), 4.67 (td, J=6.1, 12.0 Hz, 1H), 3.63 (s, 2H), 2.02 (t, J=19.2 Hz, 3H), 1.79-1.54 (m, 12H), 1.51-1.35 (m, 6H), 1.29 (d, J=6.1 Hz, 6H). FXR EC₅₀ (nM) 1063; MS (ESI) 635 (M+H).

Example 657

1,1,1-trifluoro-2-methylpropan-2-yl ((4-(3-(1,1-difluoroethyl)-1-methyl-1H-pyrazol-5-yl)bicyclo[2.2.2]octan-1-yl)methyl)(4-(4-isopropoxyphenyl)pyridin-2-yl)carbamate

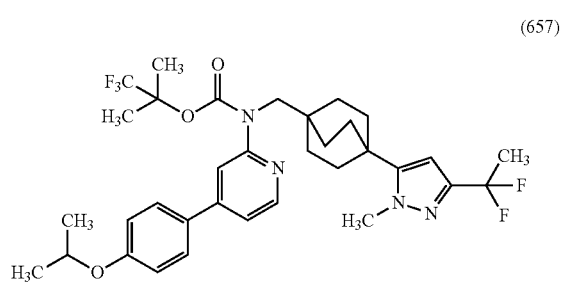 [SMILES: CC(C)Oc1ccc(-c2ccnc(N(CC34CCC(c5cc(C(C)(F)F)nn5C)(CC3)CC4)C(=O)OC(C)(C)C(F)(F)F)c2)cc1]

(657)

Step A. Intermediate 657A1 and 657A2. Preparation of methyl 4-(5-(1,1-difluoroethyl)-1-methyl-1H-pyrazol-3-yl)bicyclo[2.2.2]octane-1-carboxylate and methyl 4-(3-(1,1-difluoroethyl)-1-methyl-1H-pyrazol-5-yl)bicyclo[2.2.2]octane-1-carboxylate

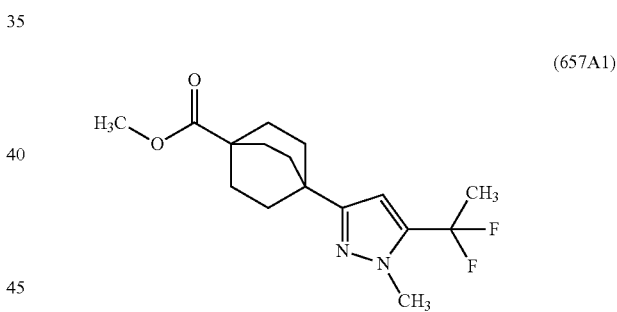

(657A1)

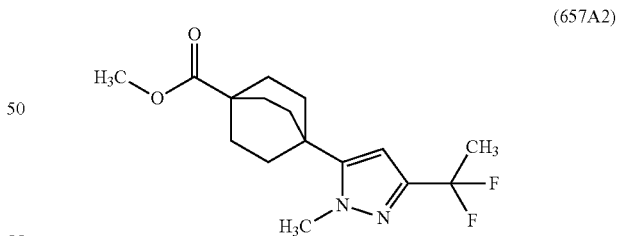

(657A2)

To a solution of Intermediate 656A (2.0 g, 6.62 mmol) in IPA (15 mL) was added methylhydrazine sulfate (1.144 g, 7.94 mmol) followed by TEA (2.77 mL, 19.85 mmol) drop wise at 0° C. The reaction mixture was heated to 80° C. and stirred for 12 h. The reaction mixture was concentrated under reduced pressure. The crude material was diluted with water (30 mL) and extracted with EtOAc (2×30 mL). The combined organic layers were washed with brine, dried over anhydrous sodium sulfate and concentrated under reduced pressure. The crude material was purified via flash silica gel column chromatography (40 g silica gel cartridge;

A=hexanes, B=EtOAc; 30 min grad.; 0% B to 10% B; flow rate=40 mL/min). The pure fractions were combined, concentrated under reduced pressure and dried in vacuo to afford the title compounds.

The first eluting isomer was methyl 4-(5-(1,1-difluoroethyl)-1-methyl-1H-pyrazol-3-yl)bicyclo[2.2.2]octane-1-carboxylate (657A1) (550 mg, 1.761 mmol, 27% yield). $^1$H NMR (400 MHz, DMSO-d$_6$) δ 6.46-6.37 (m, 1H), 3.83 (s, 3H), 3.64-3.54 (m, 3H), 2.09-1.95 (m, 3H), 1.77 (s, 12H). MS (ESI) 313 (M+H) (RT=1.72 min or peak-1).

Second eluting isomer was methyl 4-(3-(1,1-difluoroethyl)-1-methyl-1H-pyrazol-5-yl)bicyclo[2.2.2]octane-1-carboxylate (657A2) (950 mg, 3.04 mmol, 46% yield). $^1$H NMR (400 MHz, DMSO-d$_6$) δ 6.21 (s, 1H), 3.91 (s, 3H), 3.60 (s, 3H), 1.91 (s, 3H), 1.88-1.75 (m, 12H). MS (ESI) 313 (M+H) (RT=1.65 min or peak-2).

Step B. Intermediate 657B. Preparation of (4-(3-(1,1-difluoroethyl)-1-methyl-1H-pyrazol-5-yl)bicyclo[2.2.2]octan-1-yl)methanol

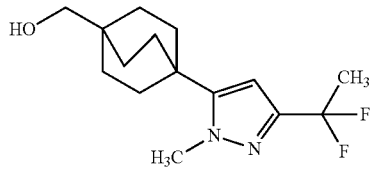

The title compound was synthesized according to the general method described for the synthesis of Intermediate 1G by substituting Intermediate 657A2 where appropriate: (0.42 g, 1.477 mmol, 49% yield) as a colorless liquid. $^1$H NMR (400 MHz, DMSO-d$_6$) δ 6.20-6.16 (m, 1H), 4.43-4.38 (m, 1H), 3.91 (s, 3H), 3.08 (d, J=5.6 Hz, 2H), 1.98-1.86 (m, 3H), 1.86-1.78 (m, 6H), 1.49-1.40 (m, 6H).

Step C. Intermediate 657C. Preparation of 4-(3-(1,1-difluoroethyl)-1-methyl-1H-pyrazol-5-yl)bicyclo[2.2.2]octane-1-carbaldehyde

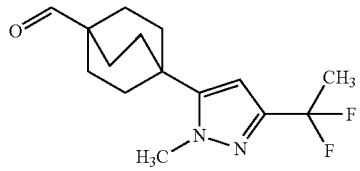 [SMILES: Cn1nc(C(C)(F)F)cc1C12CCC(C=O)(CC1)CC2]

The title compound was synthesized according to the general method described for the synthesis of Intermediate 3C by substituting Intermediate 657B where appropriate: (0.4 g, 1.417 mmol, 50% yield) as white gummy solid. $^1$H NMR (400 MHz, DMSO-d$_6$) δ 9.48-9.44 (m, 1H), 6.22 (s, 1H), 3.92 (s, 3H), 1.99-1.91 (m, 3H), 1.90-1.81 (m, 6H), 1.72-1.65 (m, 6H).

Step D. Intermediate 657D. Preparation of 4-bromo-N-((4-(3-(1,1-difluoroethyl)-1-methyl-1H-pyrazol-5-yl)bicyclo[2.2.2]octan-1-yl)methyl)pyridin-2-amine

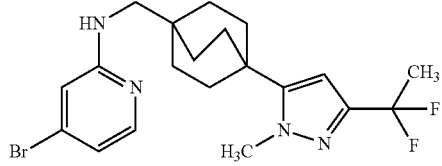

The title compound was synthesized according to the general method described for the synthesis of Intermediate 1I by substituting Intermediate 657C and 4-bromopyridin-2-amine where appropriate: (290 mg, 0.660 mmol, 93% yield) as an off-white solid. $^1$H NMR (400 MHz, CHLOROFORM-d) δ 7.94-7.87 (m, 1H), 6.84-6.78 (m, 1H), 6.74-6.70 (m, 1H), 6.59 (d, J=1.5 Hz, 1H), 6.20-6.15 (m, 1H), 4.00-3.96 (m, 3H), 3.10 (d, J=6.0 Hz, 2H), 2.11-1.99 (m, 3H), 1.98-1.88 (m, 6H), 1.67-1.53 (m, 6H).

Step E. Intermediate 657E. Preparation of 1,1,1-trifluoro-2-methylpropan-2-yl (4-bromopyridin-2-yl)((4-(3-(1,1-difluoroethyl)-1-methyl-1H-pyrazol-5-yl)bicyclo[2.2.2]octan-1-yl)methyl)carbamate

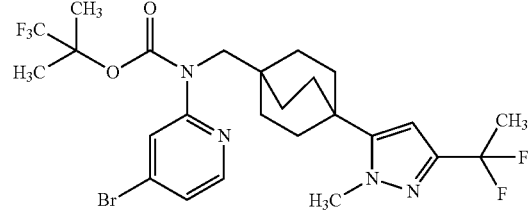 [SMILES: Cn1nc(C(C)(F)F)cc1C12CCC(CN(C(=O)OC(C)(C)C(F)(F)F)c3cc(Br)ccn3)(CC1)CC2]

The title compound was synthesized according to the general method described for the synthesis of Intermediate 584A by substituting pyridin-2-yl (1,1,1-trifluoro-2-methylpropan-2-yl) carbonate and Intermediate 657D where appropriate: (solid, 0.1 g, 0.169 mmol, 74% yield). $^1$H NMR (400 MHz, DMSO-d$_6$) δ 8.32-8.28 (m, 1H), 7.79 (s, 1H), 7.52-7.48 (m, 1H), 6.13 (s, 1H), 3.87-3.82 (m, 5H), 1.89-1.84 (m, 3H), 1.79-1.72 (m, 6H), 1.69 (s, 6H), 1.38-1.31 (m, 6H). MS (ESI) 593 (M+H).

Step F. Example 657. Preparation of 1,1,1-trifluoro-2-methylpropan-2-yl ((4-(3-(1,1-difluoroethyl)-1-methyl-1H-pyrazol-5-yl)bicyclo[2.2.2]octan-1-yl)methyl)(4-(4-isopropoxyphenyl)pyridin-2-yl)carbamate The title compound was synthesized according to the general method described for the synthesis of Example 149 by substituting Intermediate 657E and the corresponding boronic acid where appropriate: (15.9 mg, 0.025 mmol, 49% yield). $^1$H NMR (400 MHz, DMSO-d$_6$) δ 8.40 (d, J=5.4 Hz, 1H), 7.81-7.63 (m, 3H), 7.52 (dd, J=1.5, 5.4 Hz, 1H), 7.07 (d, J=8.8 Hz, 2H), 6.11 (s, 1H), 4.72 (td, J=6.0, 12.0 Hz, 1H), 3.89-3.73 (m, 5H), 1.88 (t, J=18.7 Hz, 3H), 1.79-1.62 (m, 12H), 1.44-1.33 (m, 6H), 1.30 (d, J=5.9 Hz, 6H). FXR EC$_{50}$ (nM) 67; MS (ESI) 649 (M+H).

Example 658

1,1,1-trifluoro-2-methylpropan-2-yl ((4-(5-(1,1-difluoroethyl)-1-methyl-1H-pyrazol-3-yl) bicyclo[2.2.2]octan-1-yl)methyl)(4'-isopropoxy-[1,1'-biphenyl]-3-yl)carbamate

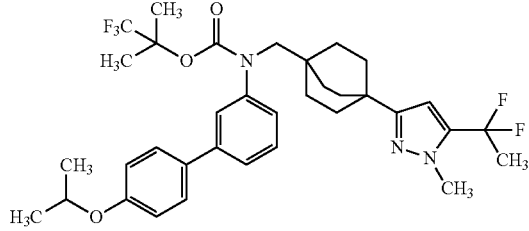
(658)

Step A. Intermediate 658A. Preparation of (4-(5-(1,1-difluoroethyl)-1-methyl-1H-pyrazol-3-yl)bicyclo[2.2.2]octan-1-yl)methanol

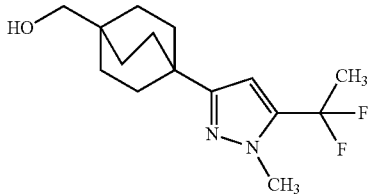 [SMILES: Cn1nc(C23CCC(CO)(CC2)CC3)cc1C(C)(F)F]

The title compound was synthesized according to the general method described for the synthesis of Intermediate 1G by substituting Intermediate 657A1 where appropriate: (0.41 g, 1.442 mmol, 85% yield) as a colorless liquid. $^1$H NMR (400 MHz, DMSO-$d_6$) δ 6.43-6.37 (m, 1H), 4.37-4.30 (m, 1H), 3.83 (s, 3H), 3.06 (d, J=5.5 Hz, 2H), 2.04 (t, J=19.1 Hz, 3H), 1.77-1.66 (m, 6H), 1.45-1.36 (m, 6H).

Step B. Intermediate 658B. Preparation of 4-(5-(1,1-difluoroethyl)-1-methyl-1H-pyrazol-3-yl)bicyclo[2.2.2]octane-1-carbaldehyde

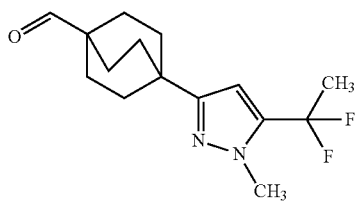 [SMILES: Cn1nc(C23CCC(C=O)(CC2)CC3)cc1C(C)(F)F]

The title compound was synthesized according to the general method described for the synthesis of Intermediate 3C by substituting Intermediate 658A where appropriate: (0.22 g, 0.779 mmol, 55% yield) as white gummy solid. $^1$H NMR (400 MHz, DMSO-$d_6$) δ 9.47-9.44 (m, 1H), 6.46-6.43 (m, 1H), 3.85 (s, 3H), 2.10-1.98 (m, 3H), 1.81-1.74 (m, 6H), 1.69-1.60 (m, 6H).

Step C. Intermediate 658C. Preparation of 3-bromo-N-((4-(5-(1,1-difluoroethyl)-1-methyl-1H-pyrazol-3-yl)bicyclo[2.2.2]octan-1-yl)methyl)aniline

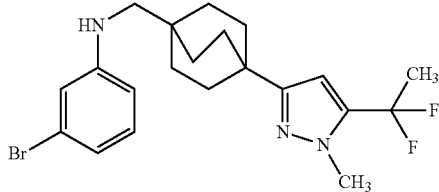 [SMILES: Cn1nc(C23CCC(CNc4cccc(Br)c4)(CC2)CC3)cc1C(C)(F)F]

The title compound was synthesized according to the general method described for the synthesis of Intermediate 1I by substituting Intermediate 658B and 3-bromo aniline where appropriate: (162 mg, 0.370 mmol, 87% yield) as an off-white solid. MS (ESI) 438 (M+H). $^1$H NMR (400 MHz, CHLOROFORM-d) δ 7.04-6.98 (m, 1H), 6.90-6.83 (m, 1H), 6.81-6.75 (m, 2H), 6.55-6.48 (m, 1H), 6.17 (t, J=1.5 Hz, 1H), 3.98 (s, 3H), 2.88 (s, 2H), 2.09-1.96 (m, 3H), 1.91-1.84 (m, 6H), 1.63-1.55 (m, 6H).

Step D. Intermediate 658D. Preparation of 1,1,1-trifluoro-2-methylpropan-2-yl (3-bromophenyl)((4-(5-(1,1-difluoroethyl)-1-methyl-1H-pyrazol-3-yl)bicyclo[2.2.2]octan-1-yl) methyl)carbamate

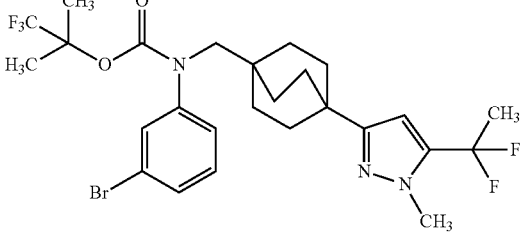

The title compound was synthesized according to the general method described for the synthesis of Intermediate 584A by substituting pyridin-2-yl (1,1,1-trifluoro-2-methylpropan-2-yl)carbonate and Intermediate 658C where appropriate: (solid, 100 mg, 0.169 mmol, 74% yield). $^1$H NMR (400 MHz, DMSO-$d_6$) δ 7.60 (br s, 1H), 7.47-7.35 (m, 2H), 7.35-7.22 (m, 1H), 6.37 (s, 1H), 3.81 (s, 3H), 3.62-3.51 (m, 2H), 2.02 (t, J=19.0 Hz, 3H), 1.74-1.55 (m, 12H), 1.41-1.25 (m, 6H). MS (ESI) 592 (M+H).

Step E. Example 658. Preparation of 1,1,1-trifluoro-2-methylpropan-2-yl ((4-(5-(1,1-difluoroethyl)-1-methyl-1H-pyrazol-3-yl)bicyclo[2.2.2]octan-1-yl) methyl) (4'-isopropoxy-[1,1'-biphenyl]-3-yl) carbamate The title compound was synthesized according to the general method described for the synthesis of Example 149 by substituting Intermediate 658D and the corresponding boronic acid where appropriate: (13 mg, 0.020 mmol, 40% yield). $^1$H NMR (400 MHz, DMSO-$d_6$) δ 7.67-7.50 (m, 3H), 7.49-7.43 (m, 1H), 7.39 (t, J=7.8 Hz, 1H), 7.32-7.20 (m, 1H), 7.07-6.88 (m, 2H), 6.36 (s, 1H), 4.67 (m, 1H), 3.80 (s, 3H), 3.61 (s, 2H), 2.01 (t, J=19.0 Hz, 3H), 1.76-1.52 (m, 12H), 1.44-1.32 (m, 6H), 1.29 (d, J=5.9 Hz, 6H). FXR EC$_{50}$ (nM) 917; MS (ESI) 648 (M+H).

Example 659

3-(tert-butyl)-1-((4-(3-(1,1-difluoroethyl)-1-methyl-1H-pyrazol-5-yl)bicyclo[2.2.2]octan-1-yl)methyl)-1-(4'-isopropoxy-[1,1'-biphenyl]-3-yl)urea (659)

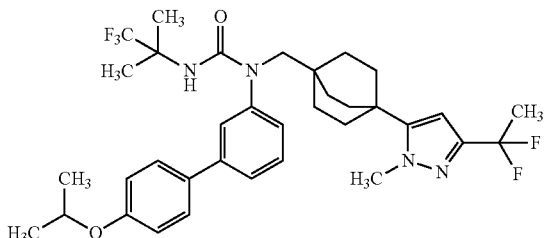

Step A. Intermediate 659A. Preparation of 3-bromo-N-((4-(3-(1,1-difluoroethyl)-1-methyl-1H-pyrazol-5-yl)bicyclo[2.2.2]octan-1-yl)methyl)aniline

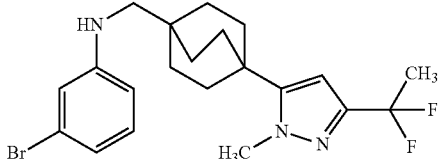

The title compound was synthesized according to the general method described for the synthesis of Intermediate 1I by substituting Intermediate 657C and 3-bromo aniline where appropriate: (290 mg, 0.660 mmol, 93% yield) as an off-white solid. MS (ESI) 438 (M+H).

Step B. Intermediate 659B. Preparation of 1-(3-bromophenyl)-3-(tert-butyl)-1-((4-(3-(1,1-difluoroethyl)-1-methyl-1H-pyrazol-5-yl)bicyclo[2.2.2]octan-1-yl)methyl)urea

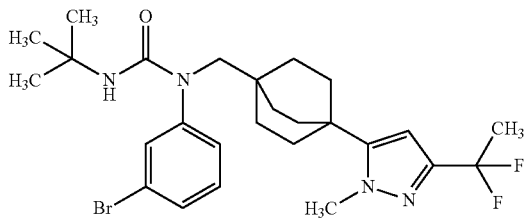 [SMILES: Cn1nc(C(C)(F)F)cc1C12CCC(CN(C(=O)NC(C)(C)C)c3cccc(Br)c3)(CC1)CC2]

The title compound was prepared according to the general method described for the synthesis of Example 586 by substituting Intermediate 659A and 2-methylpropan-2-amine where appropriate: (90 mg, 0.167 mmol, 92% yield) as an off-white solid. MS (ESI) 537 (M+H).

Step C. Example 659. Preparation of 3-(tert-butyl)-1-((4-(3-(1,1-difluoroethyl)-1-methyl-1H-pyrazol-5-yl)bicyclo[2.2.2]octan-1-yl) methyl)-1-(4'-isopropoxy-[1,1'-biphenyl]-3-yl) urea The title compound was synthesized according to the general method described for the synthesis of Example 149 by substituting Intermediate 659B and the corresponding boronic acid where appropriate: (14.4 mg, 0.024 mmol, 44% yield. $^1$H NMR (400 MHz, DMSO-d$_6$) δ 7.65-7.58 (m, 2H), 7.56-7.52 (m, 1H), 7.51-7.41 (m, 2H), 7.26 (d, J=8.1 Hz, 1H), 7.01 (d, J=8.8 Hz, 2H), 6.13 (s, 1H), 4.76-4.63 (m, 2H), 3.86 (s, 3H), 3.58 (s, 2H), 1.96-1.82 (m, 3H), 1.79-1.70 (m, 6H), 1.47-1.36 (m, 6H), 1.29 (d, J=6.1 Hz, 6H), 1.20 (s, 9H). FXR EC$_{50}$ (nM) 53; MS (ESI) 593 (M+H).

Example 660

3-(tert-butyl)-1-(5-(4-(difluoromethoxy)phenyl) pyridazin-3-yl)-1-((4-(5-(2-fluoropropan-2-yl)-1,2,4-oxadiazol-3-yl)bicyclo[2.2.2]octan-1-yl)methyl)urea (660)

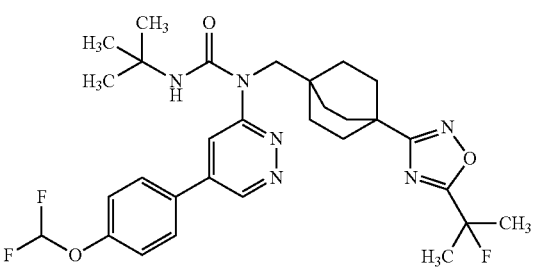

Step A. Intermediate 660A. Preparation of 2-((4-(5-(2-fluoropropan-2-yl)-1,2,4-oxadiazol-3-yl)bicyclo [2.2.2]octan-1-yl)methyl)isoindoline-1,3-dione

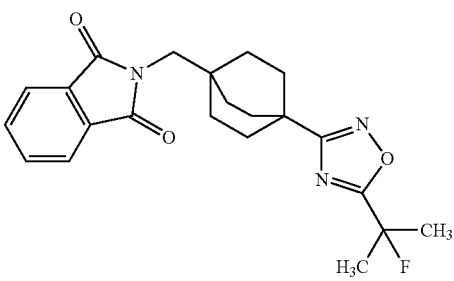 [SMILES: CC(C)(F)c1nc(C23CCC(CN4C(=O)c5ccccc5C4=O)(CC2)CC3)no1]

To a stirred solution of Intermediate 576D (500 mg, 1.863 mmol) in THF (10 mL) was added isoindoline-1,3-dione (0.302 g, 2.050 mmol), triphenylphosphine (0.977 g, 3.73 mmol) followed by DIAD (1.087 mL, 5.59 mmol) at 0° C. The reaction mixture was stirred at room temperature for 12 h. The reaction mixture was diluted with DCM (30 mL) and washed with saturated sodium bicarbonate solution (2×15 mL). The organic layer was washed with brine, dried over anhydrous sodium sulfate and concentrated under reduced pressure. The crude material was purified via flash silica gel column chromatography (40 g silica gel cartridge;

A=hexanes, B=EtOAc; 30 min grad.; 0% B to 30% B; flow rate=12 mL/min). The pure fractions were combined, concentrated under reduced pressure and dried in vacuo to afford the title compound: (0.5 g, 1.258 mmol, 68% yield). MS (ESI) 398 (M+H).

Step B. Intermediate 660B. Preparation of (4-(5-(2-fluoropropan-2-yl)-1,2,4-oxadiazol-3-yl)bicyclo[2.2.2]octan-1-yl)methanamine

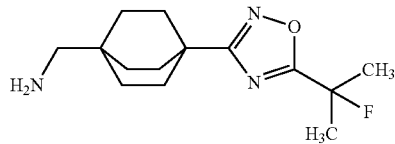 [SMILES: CC(C)(F)c1nc(C23CCC(CN)(CC2)CC3)no1]

To a stirred solution of Intermediate 660A (500 mg, 1.258 mmol) in ethanol (10 mL) was added hydrazine hydrate (0.611 mL, 12.58 mmol) at room temperature. The reaction mixture was refluxed for 12 h. The reaction mixture was filtered, washed with ethanol. The combined organic layer was dried over anhydrous sodium sulfate and concentrated under reduced pressure to afford the title compound (335 mg, 1.25 mmol, 67% yield) as a semi solid. $^1$H NMR (400 MHz, DMSO-$d_6$) δ 2.28-2.22 (m, 2H), 1.85-1.74 (m, 6H), 1.47-1.35 (m, 6H), 1.22-1.05 (m, 6H).

Step C. Intermediate 660C. Preparation of 3-chloro-5-(4-(difluoromethoxy)phenyl) pyridazine

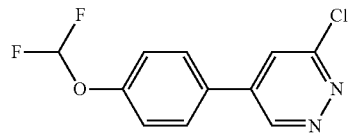 [SMILES: FC(F)Oc1ccc(-c2cnnc(Cl)c2)cc1]

To a stirred solution of 3,5-dichloropyridazine (100 mg, 0.671 mmol) in toluene (2 mL) were added (4-(difluoromethoxy)phenyl)boronic acid (107 mg, 0.571 mmol) and potassium phosphate (285 mg, 1.343 mmol). The resulting reaction mixture was degassed and back-filled with argon and bis(tri-tert-butylphosphine) palladium(0) (34.3 mg, 0.067 mmol) was added. The reaction mixture was heated at 75° C. for 12 h. The reaction mixture was concentrated under reduced pressure; the residue was diluted with water (10 mL) and extracted with EtOAc (2×15 mL). The organic layer was washed with brine, dried over anhydrous sodium sulfate and concentrated under reduced pressure. The crude material was purified via flash silica gel column chromatography (12 g silica gel cartridge; A=hexanes, B=EtOAc; 30 min grad.; 0% B to 40% B; flow rate=12 mL/min). The pure fractions were combined, concentrated under reduced pressure and dried in vacuo to afford the title compound: (25 mg, 0.097 mmol, 15% yield). MS (ESI) 257 (M+H).

Step D. Intermediate 660D. Preparation of 5-(4-(difluoromethoxy) phenyl)-N-((4-(5-(2-fluoropropan-2-yl)-1,2,4-oxadiazol-3-yl)bicyclo[2.2.2]octan-1-yl)methyl)pyridazin-3-amine

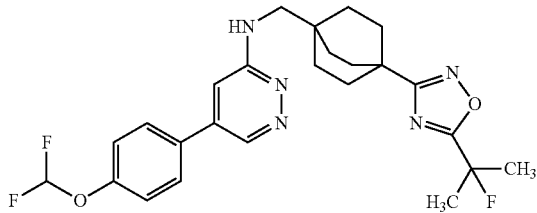 [SMILES: CC(C)(F)c1nc(C23CCC(CNc4cc(-c5ccc(OC(F)F)cc5)cnn4)(CC2)CC3)no1]

To a stirred solution of Intermediate 660C (100 mg, 0.390 mmol) in toluene (2 mL) were added Intermediate 660B (104 mg, 0.390 mmol) and sodium tert-butoxide (112 mg, 1.169 mmol). The resulting reaction mixture was degassed and back-filled with argon, and Pd$_2$(dba)$_3$ (35.7 mg, 0.039 mmol) and t-Bu Xphos (33.1 mg, 0.078 mmol) were added. The reaction mixture was heated at 110° C. for 12 h. The reaction mixture was concentrated under reduced pressure; the residue was diluted with water (10 mL) and extracted with EtOAc (2×15 mL). The organic layer was washed with brine, dried over anhydrous sodium sulfate and concentrated under reduced pressure. The crude material was purified via flash silica gel column chromatography (12 g silica gel cartridge; A=hexanes, B=EtOAc; 30 min grad.; 0% B to 40% B; flow rate=12 mL/min). The pure fractions were combined, concentrated under reduced pressure and dried in vacuo to afford the title compound: (80 mg, 0.164 mmol, 42% yield). MS (ESI) 488 (M+H).

Step E. Example 660. Preparation of N-((4-(5-(2-fluoropropan-2-yl)-1,2,4-oxadiazol-3-yl)bicyclo[2.2.2]octan-1-yl)methyl)-N-(4'-(2-hydroxypropan-2-yl)-[1,1'-biphenyl]-3-yl)-2-thia-6-azaspiro[3.3]heptane-6-carboxamide 2,2-dioxide The title compound was prepared according to the general method described for the synthesis of Example 586 by substituting Intermediate 660D and 2-methylpropan-2-amine where appropriate: (2.8 mg, 4.58 μmol, 7% yield). $^1$H NMR (400 MHz, DMSO-$d_6$) δ 9.27 (d, J=1.7 Hz, 1H), 8.29 (s, 1H), 7.92 (d, J=2.0 Hz, 1H), 7.83-7.76 (m, 1H), 7.61-7.13 (m, 2H), 7.07 (d, J=2.0 Hz, 1H), 6.80-6.69 (m, 1H), 4.00 (s, 2H), 1.91-1.69 (m, 8H), 1.61-1.54 (m, 4H), 1.51-1.43 (m, 6H), 1.32 (s, 9H). FXR EC$_{50}$ (nM)=2188. MS (ESI) 587 (M+H).

Example 661

1,1,1-trifluoro-2-methylpropan-2-yl (4-(4-(2-hydroxypropan-2-yl)phenyl)pyridin-2-yl)((4-(3-isopropyl-1-methyl-1H-pyrazol-5-yl)bicyclo[2.2.2]octan-1-yl)methyl)carbamate (661)

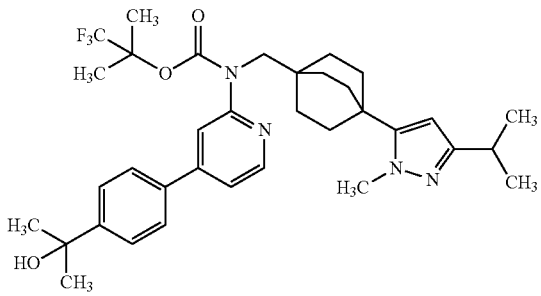

Step A: Intermediate 661A. Preparation of methyl 4-(4-methyl-3-oxopentanoyl)bicyclo[2.2.2]octane-1-carboxylate

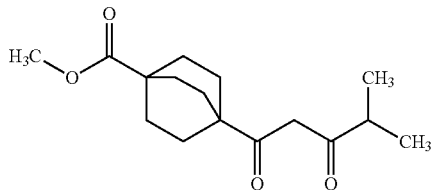 [SMILES: COC(=O)C12CCC(C(=O)CC(=O)C(C)C)(CC1)CC2]

The title compound was synthesized according to the general method described for the synthesis of Intermediate 655C by substituting Intermediate 655B and isobutyryl chloride where appropriate: (650 mg, 2.318 mmol, 49% yield) as a gum. $^1$H NMR (400 MHz, DMSO-d$_6$) δ 3.58-3.55 (m, 3H), 2.56-2.51 (m, 1H), 1.77-1.64 (m, 12H), 1.06 (d, J=7.0 Hz, 6H), 2H buried under moisture peak.

Step B. Intermediates 661B1 and 661B2. Preparation of methyl 4-(5-isopropyl-1-methyl-1H-pyrazol-3-yl)bicyclo[2.2.2]octane-1-carboxylate and methyl 4-(3-isopropyl-1-methyl-1H-pyrazol-5-yl)bicyclo[2.2.2]octane-1-carboxylate (661B1)

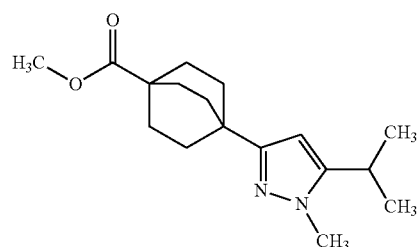

(661B2)

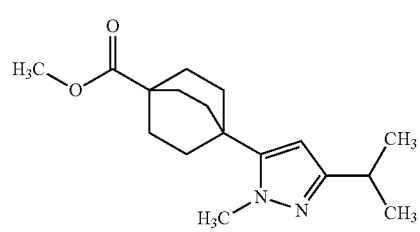

The title compound was synthesized according to the general method described for the synthesis of Intermediate 124C by substituting Intermediate 661A where appropriate. The compound containing fractions were concentrated to yield a mixture of compounds. The mixture was purified by SFC to yield the individual regio isomers. Column Name: Lux Cellulose C4 (250*4.6) mm. 5 μm, Flow Rate: 3 mL/min, Co-Solvent: 15% Vial No: LA5, Co-Solvent: 0.2% ammonia in methanol; Injected Volume: 10 μL, Outlet Pressure: 100 bar, Temperature: 40° C.

The first eluting isomer was methyl 4-(5-isopropyl-1-methyl-1H-pyrazol-3-yl) bicyclo[2.2.2]octane-1-carboxylate (661B1) (120 mg, 0.413 mmol, 24% yield). $^1$H NMR (400 MHz, DMSO-d$_6$) δ 5.82-5.79 (m, 1H), 3.64 (s, 3H), 3.58 (s, 3H), 2.91 (td, J=6.8, 13.6 Hz, 1H), 1.79-1.68 (m, 12H), 1.15 (d, J=6.5 Hz, 6H). MS (ESI) 291 (M+H) (RT=1.68 min or peak-1).

Second eluting isomer was methyl 4-(3-isopropyl-1-methyl-1H-pyrazol-5-yl) bicyclo[2.2.2]octane-1-carboxylate (661B2) (190 mg, 0.654 mmol, 37% yield). MS (ESI) 291 (M+H). $^1$H NMR (400 MHz, DMSO-d$_6$) δ 5.79 (s, 1H), 3.79 (s, 3H), 3.59 (s, 3H), 2.74 (td, J=6.8, 13.9 Hz, 1H), 1.87-1.76 (m, 12H), 1.13 (d, J=7.0 Hz, 6H). MS (ESI) 291 (M+H). (RT=1.71 min or peak-2).

Step C. Intermediate 661C. Preparation of (4-(3-isopropyl-1-methyl-1H-pyrazol-5-yl) bicyclo[2.2.2]octan-1-yl)methanol

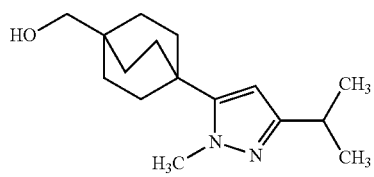 [SMILES: CC(C)c1cc(C23CCC(CO)(CC2)CC3)n(C)n1]

The title compound was synthesized according to the general method described for the synthesis of Intermediate 1G by substituting Intermediate 661B2 where appropriate: (0.1 g, 0.381 mmol, 58% yield) as a colorless liquid. $^1$H NMR (400 MHz, DMSO-d$_6$) δ 5.79-5.75 (m, 1H), 4.38-4.33 (m, 1H), 3.82-3.76 (m, 3H), 3.09-3.04 (m, 2H), 2.78-2.69 (m, 1H), 1.83-1.74 (m, 6H), 1.48-1.39 (m, 6H), 1.17-1.08 (m, 6H).

Step D. Intermediate 661D. Preparation of 4-(3-isopropyl-1-methyl-1H-pyrazol-5-yl) bicyclo[2.2.2]octane-1-carbaldehyde

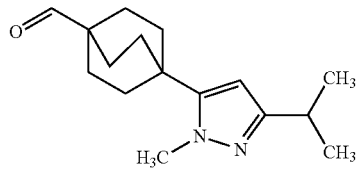 [SMILES: CC(C)c1cc(C23CCC(C=O)(CC2)CC3)n(C)n1]

The title compound was synthesized according to the general method described for the synthesis of Intermediate 3C by substituting Intermediate 661C where appropriate: (50 mg, 0.192 mmol, 50% yield) as a white solid. $^1$H NMR (400 MHz, CHLOROFORM-d) δ 9.52-9.49 (m, 1H), 5.81 (s, 1H), 3.91 (s, 3H), 2.94-2.85 (m, 1H), 2.00-1.93 (m, 6H), 1.81-1.74 (m, 6H), 1.23 (d, J=7.0 Hz, 6H).

Step E. Intermediate 661E. Preparation of 4-bromo-N-((4-(3-isopropyl-1-methyl-1H-pyrazol-5-yl)bicyclo[2.2.2]octan-1-yl)methyl)pyridin-2-amine

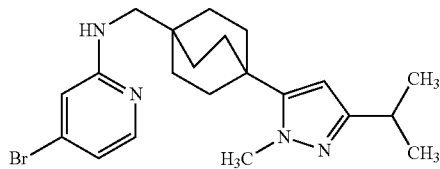 [SMILES: CC(C)c1cc(C23CCC(CNc4cc(Br)ccn4)(CC2)CC3)n(C)n1]

The title compound was synthesized according to the general method described for the synthesis of Intermediate 11 by substituting Intermediate 661D and 4-bromopyridin-2-amine where appropriate: (15 mg, 0.036 mmol, 37% yield) as an off-white solid. MS (ESI) 417 (M+H).

Step F. Intermediate 661F. Preparation of 1,1,1-trifluoro-2-methylpropan-2-yl (4-bromopyridin-2-yl)((4-(3-isopropyl-1-methyl-1H-pyrazol-5-yl)bicyclo[2.2.2]octan-1-yl) methyl)carbamate

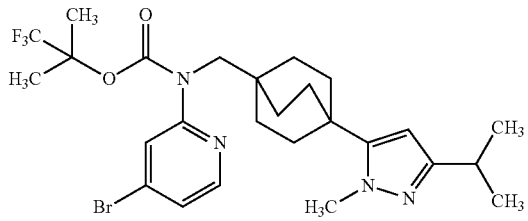 [SMILES: CC(C)c1cc(C23CCC(CN(C(=O)OC(C)(C)C(F)(F)F)c4cc(Br)ccn4)(CC2)CC3)n(C)n1]

The title compound was synthesized according to the general method described for the synthesis of Intermediate 584A by substituting pyridin-2-yl (1,1,1-trifluoro-2-methylpropan-2-yl)carbonate and Intermediate 661E where appropriate: (solid, 22 mg, 0.038 mmol, 56% yield). MS (ESI) 571 (M+H).

Step G. Example 661. Preparation of 1,1,1-trifluoro-2-methylpropan-2-yl (4-(4-(2-hydroxypropan-2-yl)phenyl)pyridin-2-yl)((4-(3-isopropyl-1-methyl-1H-pyrazol-5-yl) bicyclo[2.2.2]octan-1-yl)methyl) carbamate The title compound was synthesized according to the general method described for the synthesis of Example 149 by substituting Intermediate 661F and the corresponding boronic acid where appropriate: (5.4 mg, 0.008 mmol, 24% yield). $^1$H NMR (400 MHz, DMSO-d$_6$) δ 8.44 (d, J=5.1 Hz, 1H), 7.79-7.68 (m, 3H), 7.66-7.58 (m, 2H), 7.56 (dd, J=1.6, 5.3 Hz, 1H), 5.70 (s, 1H), 5.13 (s, 1H), 3.84 (s, 2H), 3.56 (s, 3H), 2.75-2.65 (m, 1H), 1.77-1.61 (m, 12H), 1.46 (s, 6H), 1.40-1.29 (m, 6H), 1.09 (d, J=6.8 Hz, 6H). FXR EC$_{50}$ (nM) 53; MS (ESI) 627 (M+H).

Example 662

(cis)-N-(4'-(4-amino-1,2,5-oxadiazol-3-yl)-[1,1'-biphenyl]-3-yl)-N-((4-(5-(2-fluoropropan-2-yl)-1,2,4-oxadiazol-3-yl)bicyclo[2.2.2]octan-1-yl)methyl)-3-hydroxy-3-(trifluoromethyl)cyclobutane-1-carboxamide (662)

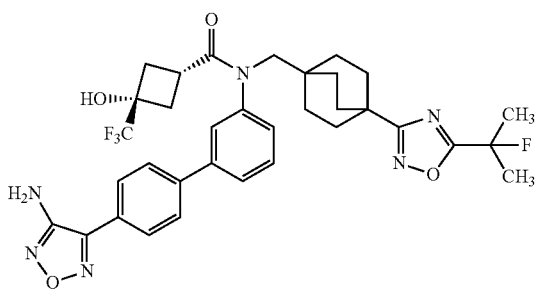

Step A. Intermediate 662A. Preparation of (Z)-4-bromo-N-hydroxybenzimidoyl cyanide

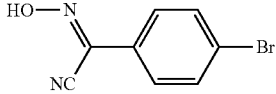

To a stirred solution of 2-(4-bromophenyl)acetonitrile (3 g, 15.30 mmol) in DMF (75 mL) was added potassium tert-butoxide (18.36 mL, 18.36 mmol) at 0° C. The reaction mixture was stirred for 5 min. Tert-butyl Nitrite (3.16 g, 30.6 mmol) was added at 0° C. The reaction mixture was stirred at room temperature for 1 h. The reaction was quenched with 1.5 N HCl (5 mL). The reaction mixture was diluted with water (5 mL) and extracted with ethyl acetate (2×10 mL). The combined organic layers were washed with brine solution (5 mL), dried over anhydrous sodium sulphate and concentrated under reduced pressure to afford the residue. The crude material was purified via flash silica gel column chromatography (12 g silica gel cartridge; A=hexanes, B=EtOAc; 30 min grad.; 0% B to 30% B; flow rate=80 mL/min). The pure fractions were combined, concentrated and dried in vacuo to afford the title compound (colorless liquid, 3.1 g, 13.78 mmol, 90% yield). $^1$H NMR (400 MHz, DMSO-d$_6$) δ 13.93 (d, J=1.7 Hz, 1H), 7.77-7.70 (m, 2H), 7.69-7.64 (m, 2H).

Step B. Intermediate 662B. Preparation of 4-(4-bromophenyl)-1,2,5-oxadiazol-3-amine

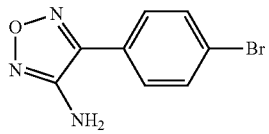

To a stirred solution of Intermediate 662A (3.25 g, 14.44 mmol) in MeOH (50 mL) was added hydroxylamine (0.954 g, 28.9 mmol). The reaction mixture was heated at 40° C. for 12 h. The reaction mixture was concentrated under reduced pressure and co-distilled with dichloromethane (3 mL). The solid obtained was dissolved in tetrahydrofuran (50 mL) and CDI (3.51 g, 21.66 mmol) was added. The reaction mixture was stirred at room temperature for 1 h. The reaction mixture was concentrated under reduced pressure. The crude material was purified via flash silica gel column chromatography (12 g silica gel cartridge; A=hexanes, B=EtOAc; 30 min grad.; 0% B to 30% B; flow rate=12 mL/min). The pure fractions were combined, concentrated and dried in vacuo to afford the title compound: (2.0 g, 8.33 mmol, 58% yield). $^1$H NMR (300 MHz, DMSO-d$_6$) δ 7.79-7.69 (m, 4H), 6.27 (s, 2H).

Step C. Example 662. Preparation of (cis)-N-(4'-(4-amino-1,2,5-oxadiazol-3-yl)-[1,1'-biphenyl]-3-yl)-N-((4-(5-(2-fluoropropan-2-yl)-1,2,4-oxadiazol-3-yl)bicyclo[2.2.2]octan-1-yl)methyl)-3-hydroxy-3-(trifluoromethyl)cyclobutane-1-carboxamide The title compound was synthesized according to the general method described for the synthesis of Example 149 by substituting Intermediate 662B and Intermediate 593A where appropriate: (7.2 mg, 0.0107 mmol, 26% yield). $^1$H NMR (400 MHz, DMSO-d$_6$) δ 8.03-7.91 (m, 2H), 7.91-7.84

(m, 2H), 7.81 (s, 1H), 7.74 (d, J=7.8 Hz, 1H), 7.57 (t, J=7.8 Hz, 1H), 7.50-7.41 (m, 1H), 6.54 (s, 1H), 6.27 (s, 2H), 3.80-3.54 (m, 2H), 3.01-2.77 (m, 1H), 2.40-2.24 (m, 2H), 2.13-1.91 (m, 2H), 1.85-1.65 (m, 12H), 1.56-1.37 (m, 6H). FXR EC$_{50}$ (nM) 574; MS (ESI) 669 (M+H).

Example 663

3-fluoro-N-((4-(5-(2-fluoropropan-2-yl)-1,2,4-oxadiazol-3-yl)bicyclo[2.2.2]octan-1-yl) methyl)-N-(3-(1-(2-hydroxy-2-methylpropyl)-1,2,3,6-tetrahydropyridin-4-yl)phenyl) bicyclo[1.1.1]pentane-1-carboxamide (663)

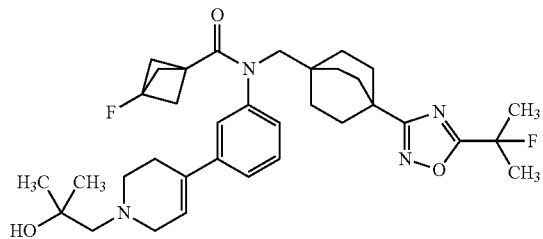

Step A. Intermediate 663A. Preparation of tert-butyl 4-(3-aminophenyl)-3,6-dihydropyridine-1 (2H)-carboxylate

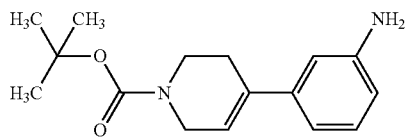 [SMILES: CC(C)(C)OC(=O)N1CC=C(c2cccc(N)c2)CC1]

The title compound was prepared according to the general method described for the synthesis of Example 149 by substituting 3-bromoaniline and 5-tert-butyl 4-(4,4,5,5-tetramethyl-1,3,2-dioxaborolan-2-yl)-3,6-dihydropyridine-1 (2H)-carboxylate where appropriate: (pale yellow liquid, 1.1 g, 4.01 mmol, 69% yield). $^1$H NMR (300 MHz, DMSO-d$_6$) δ 6.97 (t, J=7.8 Hz, 1H), 6.64-6.52 (m, 2H), 6.50-6.41 (m, 1H), 5.99 (br s, 1H), 5.08-4.96 (m, 2H), 3.95 (s, 2H), 3.50 (br t, J=5.6 Hz, 2H), 2.37 (br s, 2H), 1.46-1.35 (m, 9H). MS (ESI) 275 (M+H).

Step B. Intermediate 663B. Preparation of tert-butyl 4-(3-(((4-(5-(2-fluoropropan-2-yl)-1,2,4-oxadiazol-3-yl)bicyclo[2.2.2]octan-1-yl)methyl)amino)phenyl)-3,6-dihydropyridine-1 (2H)-carboxylate

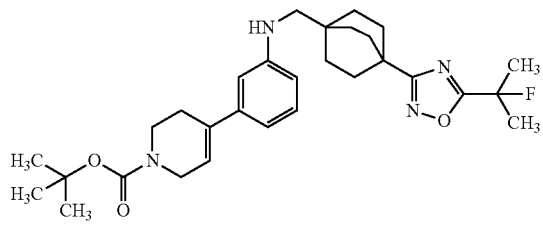 [SMILES: CC(C)(C)OC(=O)N1CC=C(c2cccc(NCC34CCC(c5noc(C(C)(C)F)n5)(CC3)CC4)c2)CC1]

The title compound was prepared according to the general method described for the synthesis of Intermediate 1I by substituting Intermediate 576E and 663A where appropriate: (Pale brown liquid, 620 mg, 1.087 mmol, 58% yield). $^1$H NMR (300 MHz, CHLOROFORM-d) δ 7.26 (s, 1H), 7.13 (t, J=7.8 Hz, 1H), 6.72-6.67 (m, 1H), 6.60 (s, 1H), 6.55-6.49 (m, 1H), 4.05 (br s, 3H), 3.65-3.57 (m, 4H), 2.92 (s, 2H), 2.01-1.92 (m, 6H), 1.86 (s, 3H), 1.79 (s, 3H), 1.66-1.56 (m, 6H), 1.49 (s, 9H). MS (ESI) 525 (M+H).

Step C. Intermediate 663C. Preparation of tert-butyl 4-(3-(3-fluoro-N-((4-(5-(2-fluoropropan-2-yl)-1,2,4-oxadiazol-3-yl)bicyclo[2.2.2]octan-1-yl)methyl) bicyclo[1.1.1]pentane-1-carboxamido)phenyl)-3,6-dihydropyridine-1 (2H)-carboxylate

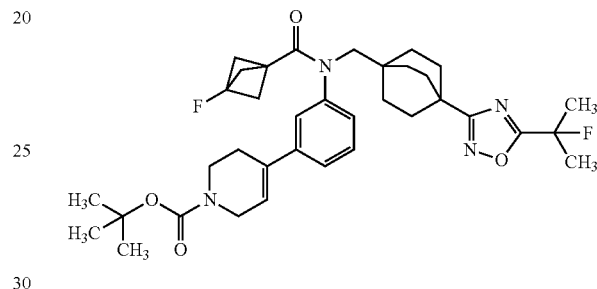

The title compound was prepared according to the general method described for the synthesis of Intermediate 576G by substituting Intermediate 663B where appropriate. (gummy liquid, 0.18 g, 0.260 mmol, 68% yield). MS (ESI) 637 (M+H).

Step D. Intermediate 663D. Preparation of 3-fluoro-N-((4-(5-(2-fluoropropan-2-yl)-1,2,4-oxadiazol-3-yl)bicyclo[2.2.2]octan-1-yl)methyl)-N-(3-(1,2,3,6-tetrahydropyridin-4-yl) phenyl)bicyclo[1.1.1]pentane-1-carboxamide

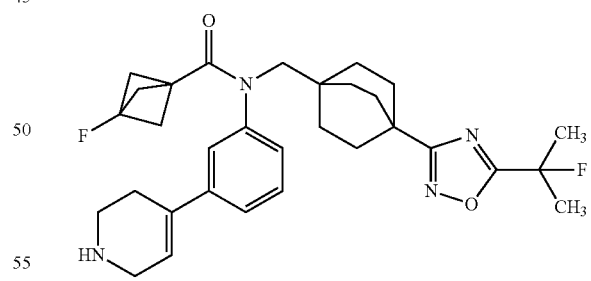

To a stirred solution of Intermediate 663C (100 mg, 0.157 mmol) in DCM (5 mL) was added TFA (0.06 mL, 0.785 mmol) at 0° C. The reaction mixture was stirred at 0° C. for 30 min. The reaction mixture was concentrated under reduced pressure to afford the title compound (70 mg, 0.130 mmol, 70% yield). $^1$H NMR (400 MHz, DMSO-d$_6$) δ 7.50-7.36 (m, 3H), 7.27 (br d, J=7.6 Hz, 1H), 6.34 (br s, 1H), 3.56 (br s, 2H), 3.46 (br d, J=1.2 Hz, 3H), 3.00 (br t, J=5.7 Hz, 2H), 2.46-2.31 (m, 2H), 1.96-1.68 (m, 18H), 1.53-1.38 (m, 6H). MS (ESI) 537 (M+H).

Step E. Example 663. Preparation of 3-fluoro-N-((4-(5-(2-fluoropropan-2-yl)-1,2,4-oxadiazol-3-yl)bicyclo[2.2.2]octan-1-yl)methyl)-N-(3-(1-(2-hydroxy-2-methylpropyl)-1,2,3,6-tetrahydropyridin-4-yl) phenyl)bicyclo[1.1.1]pentane-1-carboxamide To a stirred solution of Intermediate 663D (20 mg, 0.037 mmol) in isobutylene oxide (2 mL) was added cesium carbonate (1.214 mg, 3.73 µmol) at room temperature. The reaction mixture was stirred at 110° C. in microwave at 70 W for 2 h. The reaction mixture was concentrated under reduced pressure. The crude material was purified via preparative LC/MS using following conditions: Column: Waters XBridge C18, 19×150 mm, 5-µm particles; Mobile Phase A: 10-mM ammonium acetate; Mobile Phase B: acetonitrile; Gradient: 28-85% B over 20 minutes, then a 5-minute hold at 100% B; Flow: 15 mL/min. Fractions containing the product were combined and dried via centrifugal evaporation to afford the title compound (9.1 mg, 0.015 mmol, 40% yield). $^1$H NMR (400 MHz, DMSO-$d_6$) δ 7.50-7.32 (m, 3H), 7.24 (br d, J=7.6 Hz, 1H), 6.27 (br s, 1H), 4.23-4.09 (m, 1H), 3.65-3.56 (m, 1H), 3.54-3.46 (m, 1H), 3.26 (br s, 2H), 2.87-2.72 (m, 2H), 2.47-2.40 (m, 2H), 2.37-2.24 (m, 2H), 1.93-1.65 (m, 18H), 1.54-1.34 (m, 6H), 1.12 (s, 6H). FXR $EC_{50}$ (nM)=159. MS (ESI) 609 (M+H).

Example 664

1-((4-(5-(2-fluoropropan-2-yl)-1,2,4-oxadiazol-3-yl)bicyclo[2.2.2]octan-1-yl)methyl)-1-(4'-(2-hydroxypropan-2-yl)-[1,1'-biphenyl]-3-yl)-3-((2S,4S,6S)-6-hydroxyspiro[3.3]heptan-2-yl)urea

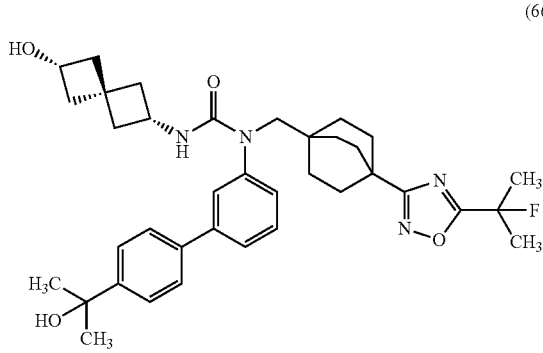

(664)

Step A. Intermediate 664A. Preparation of 1-(3-bromophenyl)-1-((4-(5-(2-fluoropropan-2-yl)-1,2,4-oxadiazol-3-yl)bicyclo[2.2.2]octan-1-yl)methyl)-3-((2S,4S,6S)-6-hydroxyspiro[3.3]heptan-2-yl)urea

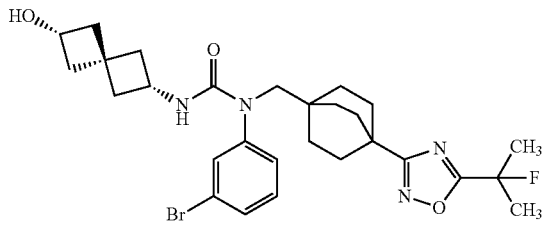

The title compound was prepared according to the general method described for the synthesis of Example 586 by substituting Intermediate 632A and (2S,4S,6S)-6-aminospiro[3.3]heptan-2-ol hydrochloride where appropriate: (50 mg, 0.087 mmol, 61.2% yield) as a brown wax. MS (ESI) 575 (M+H).

Step B. Example 664. Preparation of 1-((4-(5-(2-fluoropropan-2-yl)-1,2,4-oxadiazol-3-yl)bicyclo[2.2.2]octan-1-yl)methyl)-1-(4'-(2-hydroxypropan-2-yl)-[1,1'-biphenyl]-3-yl)-3-((2S,4s,6S)-6-hydroxyspiro[3.3]heptan-2-yl)urea The title compound was prepared according to the general method described for the synthesis of Example 149 by substituting Intermediate 664A and the corresponding boronic acid where appropriate: (13.2 mg, 0.021 mmol, 30% yield). $^1$H NMR (400 MHz, DMSO-$d_6$) δ 7.64-7.60 (m, 2H), 7.58-7.51 (m, 4H), 7.49-7.44 (m, 1H), 7.28-7.19 (m, 1H), 5.71 (d, J=7.8 Hz, 1H), 5.06 (s, 1H), 4.84 (d, J=6.4 Hz, 1H), 4.06-3.99 (m, 1H), 3.94-3.86 (m, 1H), 3.58 (s, 2H), 2.31-2.25 (m, 1H), 2.18-2.09 (m, 1H), 2.08-1.98 (m, 2H), 1.91-1.81 (m, 2H), 1.79 (s, 4H), 1.76-1.70 (m, 10H), 1.46 (s, 6H), 1.43-1.36 (m, 6H). FXR $EC_{50}$ (nM)=47. MS (ESI) 631 (M+H).

Example 665

1,1,1-trifluoro-2-methylpropan-2-yl (4-(4-cyanobicyclo[2.2.2]octan-1-yl)pyrimidin-2-yl)((4-(3-cyclopropyl-1,2,4-oxadiazol-5-yl)bicyclo[2.2.2]octan-1-yl)methyl)carbamate

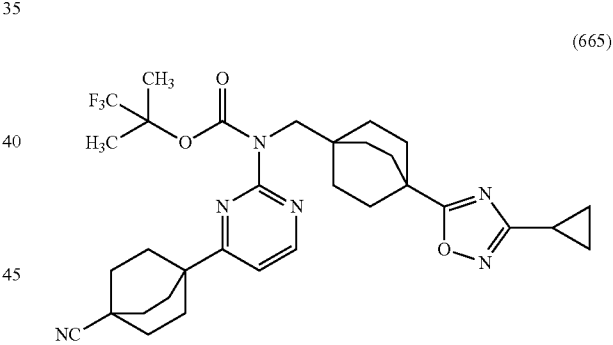

(665)

Step A. Intermediate 665A. Preparation of methyl 4-(2-chloropyrimidin-4-yl)bicyclo[2.2.2]octane-1-carboxylate

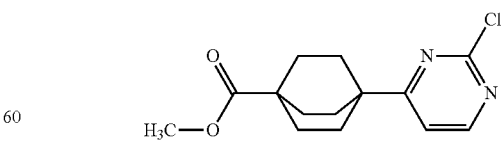

To a stirred solution of 4-(methoxycarbonyl)bicyclo[2.2.2]octane-1-carboxylic acid (1 g, 4.71 mmol) and 2-chloropyrimidine (0.594 g, 5.18 mmol) in DCM (183 mL) and water (183 mL) was added ammonium persulfate (1.075 g, 4.71 mmol) followed by silver nitrate (0.480 g, 2.83 mmol). The reaction mixture was stirred at room temperature for 3 days. The reaction mixture was diluted with DCM (100 mL) and filtered through celite. The organic layer was washed with brine, dried over anhydrous sodium sulfate and concentrated under reduced pressure. The crude material was purified via flash silica gel column chromatography (24 g silica gel cartridge; A=hexanes, B=EtOAc; 30 min grad.; 0% B to 30% B; flow rate=24 mL/min). The pure fractions were combined, concentrated and dried in vacuo to afford the title compound: (800 mg, 2.85 mmol, 61% yield) as a white solid. MS (ESI) 281 (M+H).

Step B. Intermediate 665B. Preparation of 2-((4-(3-cyclopropyl-1,2,4-oxadiazol-5-yl) bicyclo[2.2.2]octan-1-yl)methyl)isoindoline-1,3-dione

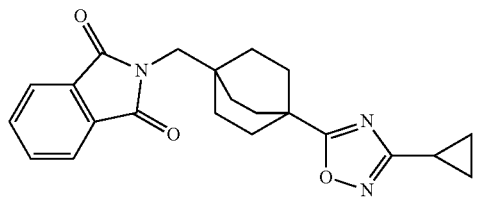 [SMILES: O=C1c2ccccc2C(=O)N1CC12CCC(c3nc(C4CC4)no3)(CC1)CC2]

To a stirred solution of Intermediate 4B (1.1 g, 4.43 mmol) in THF (22 mL) was added phthalimide (0.782 g, 5.32 mmol) followed by triphenylphosphine (1.394 g, 5.32 mmol). The reaction mixture was cooled to 0° C., and DEAD (0.842 mL, 5.32 mmol) was added drop wise over a period of 2 minutes. The reaction mixture was gradually warmed to room temperature and stirred at room temperature overnight. The reaction mixture was diluted with ethyl acetate (20 mL) and washed with water (20 mL) followed by brine solution (20 mL). The organic layer was dried over sodium sulfate and concentrated under reduced pressure to get crude product which was purified by flash chromatography (25% EA: Hexane, 24 g silica gel column) to afford the title compound (1.2 g, 3.18 mmol, 72% yield) as a white solid. MS (ESI) 378 (M+H).

Step C. Intermediate 665C. Preparation of (4-(3-cyclopropyl-1,2,4-oxadiazol-5-yl) bicyclo[2.2.2]octan-1-yl)methanamine

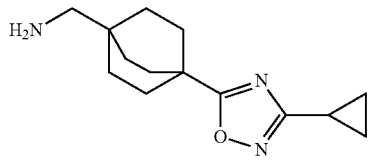 [SMILES: NCC12CCC(c3nc(C4CC4)no3)(CC1)CC2]

The title compound was synthesized according to the general method described for the synthesis of Intermediate 660B by substituting Intermediate 665B where appropriate: $^1$H NMR (400 MHz, DMSO-$d_6$) δ 2.31 (s, 2H), 2.06 (tt, J=8.3, 4.8 Hz, 1H), 1.88-1.76 (m, 6H), 1.48-1.36 (m, 6H), 1.06-0.97 (m, 2H), 0.89-0.80 (m, 2H).

Step D. Intermediate 665D. Preparation of methyl 4-(2-(((4-(3-cyclopropyl-1,2,4-oxadiazol-5-yl)bicyclo[2.2.2]octan-1-yl)methyl)amino)pyrimidin-4-yl)bicyclo[2.2.2]octane-1-carboxylate

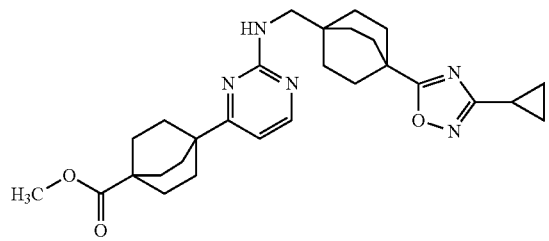 [SMILES: COC(=O)C12CCC(c3ccnc(NCC45CCC(c6nc(C7CC7)no6)(CC4)CC5)n3)(CC1)CC2]

To a stirred solution of Intermediate 665A (600 mg, 2.137 mmol) in 2-propanol (12 mL) was added Intermediate 665C (529 mg, 2.137 mmol) followed by DIPEA (1.120 mL, 6.41 mmol). The reaction mixture was heated to 110° C. for overnight. The reaction mixture was concentrated under reduced pressure. The crude material was diluted with water (20 mL) and extracted with EtOAc (2×30 mL). The organic layer was washed with brine, dried over anhydrous sodium sulfate and concentrated under reduced pressure. The crude material was purified via flash silica gel column chromatography (12 g silica gel cartridge; A=hexanes, B=EtOAc; 30 min grad.; 0% B to 40% B; flow rate=12 mL/min). The pure fractions were combined, concentrated under reduced pressure and dried in vacuo to afford the title compound (250 mg, 0.509 mmol, 24% yield) as a brown solid. MS (ESI) 492 (M+H).

Step E. Intermediate 665E. Preparation of methyl 4-(2-(((4-(3-cyclopropyl-1,2,4-oxadiazol-5-yl)bicyclo[2.2.2]octan-1-yl)methyl)(((1,1,1-trifluoro-2-methylpropan-2-yl) oxy)carbonyl)amino)pyrimidin-4-yl)bicyclo[2.2.2]octane-1-carboxylate

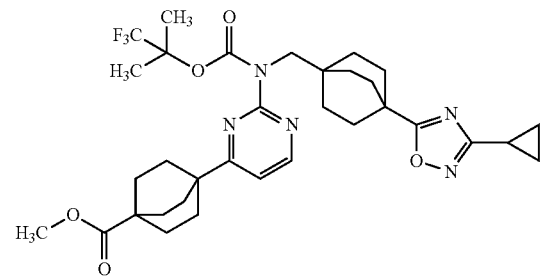 [SMILES: COC(=O)C12CCC(c3ccnc(N(CC45CCC(c6nc(C7CC7)no6)(CC4)CC5)C(=O)OC(C)(C)C(F)(F)F)n3)(CC1)CC2]

The title compound was synthesized according to the general method described for the synthesis of Intermediate 584A by substituting pyridin-2-yl (1,1,1-trifluoro-2-methylpropan-2-yl) carbonate and Intermediate 665D where appropriate: (white solid, 150 mg, 0.232 mmol, 76% yield). MS (ESI) 646 (M+H).

Step F. Intermediate 665F. Preparation of 4-(2-(((4-(3-cyclopropyl-1,2,4-oxadiazol-5-yl) bicyclo[2.2.2]octan-1-yl)methyl)(((1,1,1-trifluoro-2-methylpropan-2-yl)oxy)carbonyl) amino)pyrimidin-4-yl)bicyclo[2.2.2]octane-1-carboxylic acid

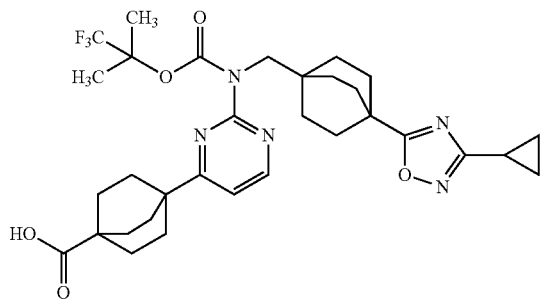 [SMILES: CC(C)(OC(=O)N(CC12CCC(c3nc(C4CC4)no3)(CC1)CC2)c1nccc(C23CCC(C(=O)O)(CC2)CC3)n1)C(F)(F)F]

The title compound was synthesized according to the general method described for the synthesis of Intermediate 88E by substituting Intermediate 665E where appropriate (colorless liquid, 5.4 mg, 8.55 μmol, 37% yield). $^1$H NMR (400 MHz, DMSO-d$_6$) δ 8.66 (d, J=5.4 Hz, 1H), 7.28 (d, J=5.4 Hz, 1H), 3.72 (s, 2H), 2.08-1.98 (m, 1H), 1.90-1.77 (m, 12H), 1.77-1.69 (m, 12H), 1.64 (s, 6H), 1.05-0.94 (m, 2H), 0.86-0.76 (m, 2H). MS (ESI) 632 (M+H).

Step G. Intermediate 665G. Preparation of 1,1,1-trifluoro-2-methylpropan-2-yl (4-(4-carbamoylbicyclo[2.2.2]octan-1-yl)pyrimidin-2-yl)((4-(3-cyclopropyl-1,2,4-oxadiazol-5-yl)bicyclo[2.2.2]octan-1-yl)methyl)carbamate

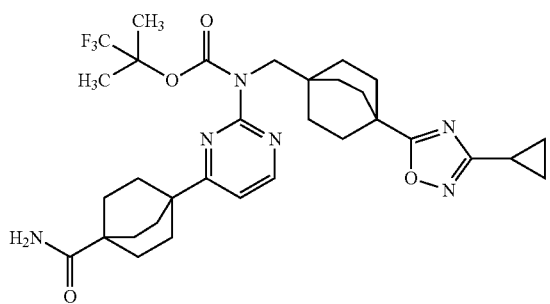 [SMILES: CC(C)(OC(=O)N(CC12CCC(c3nc(C4CC4)no3)(CC1)CC2)c1nccc(C23CCC(C(N)=O)(CC2)CC3)n1)C(F)(F)F]

The title compound was synthesized according to the general method described for the synthesis of Intermediate 114A by substituting Intermediate 665F where appropriate: (white solid, 7 mg, 10.8 μmol, 46% yield). $^1$H NMR (400 MHz, DMSO-d$_6$) δ 8.65 (d, J=5.1 Hz, 1H), 7.28 (d, J=5.4 Hz, 1H), 6.98 (s, 1H), 6.75 (s, 1H), 3.72 (s, 2H), 2.09-1.97 (m, 1H), 1.87-1.68 (m, 18H), 1.65 (s, 6H), 1.37-1.22 (m, 6H), 1.04-0.96 (m, 2H), 0.86-0.77 (m, 2H). MS (ESI) 631 (M+H).

Step H. Intermediate 665. Preparation of 1,1,1-trifluoro-2-methylpropan-2-yl (4-(4-cyanobicyclo[2.2.2]octan-1-yl)pyrimidin-2-yl)((4-(3-cyclopropyl-1,2,4-oxadiazol-5-yl) bicyclo[2.2.2]octan-1-yl)methyl)carbamate The title compound was synthesized according to the general method described for the synthesis of Intermediate 114B by substituting Intermediate 665G where appropriate: (8 mg, 0.013 mmol, 28% yield). $^1$H NMR (400 MHz, DMSO-d$_6$) δ 8.68 (d, J=5.1 Hz, 1H), 7.28 (d, J=5.1 Hz, 1H), 3.72 (s, 2H), 2.10-1.95 (m, 7H), 1.92-1.80 (m, 6H), 1.79-1.68 (m, 6H), 1.64 (s, 6H), 1.32-1.28 (m, 6H), 1.06-0.93 (m, 2H), 0.86-0.70 (m, 2H)). FXR EC$_{50}$ (nM)=2000. MS (ESI) 613 (M+H).

Example 666

1,1,1-trifluoro-2-methylpropan-2-yl ((4-(3-cyclopropyl-1,2,4-oxadiazol-5-yl) bicyclo[2.2.2]octan-1-yl)methyl)(4-(4-(2-hydroxypropan-2-yl)bicyclo[2.2.2]octan-1-yl) pyrimidin-2-yl)carbamate (666)

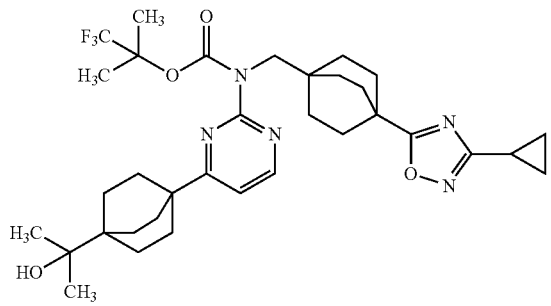

Step A. Intermediate 666A. Preparation of 2-(4-(2-((((4-(3-cyclopropyl-1,2,4-oxadiazol-5-yl)bicyclo[2.2.2]octan-1-yl)methyl)amino)pyrimidin-4-yl)bicyclo[2.2.2]octan-1-yl)propan-2-ol

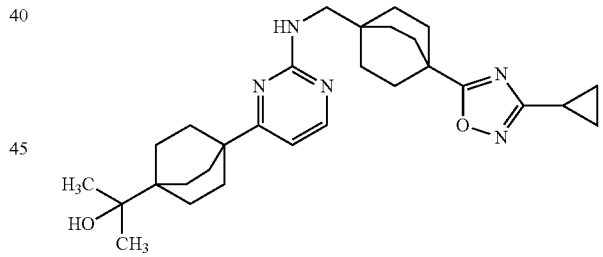

The title compound was synthesized according to the general method described for the synthesis of Intermediate 607A by substituting Intermediate 665D where appropriate: (white solid, 35 mg, 0.071 mmol, 50% yield). MS (ESI) 492 (M+H).

Step B. Example 666. Preparation of 1,1,1-trifluoro-2-methylpropan-2-yl ((4-(3-cyclopropyl-1,2,4-oxadiazol-5-yl)bicyclo[2.2.2]octan-1-yl)methyl)(4-(4-(2-hydroxypropan-2-yl)bicyclo[2.2.2]octan-1-yl) pyrimidin-2-yl)carbamate The title compound was synthesized according to the general method described for the synthesis of Intermediate 584A by substituting pyridin-2-yl (1,1,1-trifluoro-2-methylpropan-2-yl) carbonate and Intermediate 666A where appropriate: (white solid, 13 mg, 0.020 mmol, 33% yield). $^1$H NMR (400 MHz, DMSO-d$_6$) δ 8.63 (d, J=5.4 Hz, 1H), 7.26 (d, J=5.4 Hz, 1H), 3.89 (s, 1H), 3.72 (s, 2H), 2.07-1.96 (m, 1H), 1.82-1.68 (m, 12H), 1.64 (s, 6H), 1.59-1.49 (m, 6H), 1.38-1.21 (m, 6H), 1.07-0.93 (m, 8H), 0.86-0.72 (m, 2H). FXR EC$_{50}$ (nM)=496. MS (ESI) 646 (M+H).

BIOLOGICAL EVALUATION

The exemplified compounds of the present invention were tested in the transient human FXR/Gal4-luciferase reporter assay, and assay results were described in Table 1.

A Gal4-hFXR fusion construct reporter system was used as the primary assay to characterize compound activity. A construct including 5 copies of the Gal4 promoter response element upstream of a firefly luciferase reporter cDNA was stably expressed in HEK293 cells. This reporter cell line was maintained in Dulbecco's Modified Eagle's medium (DMEM; Gibco) supplemented with 1% penicillin-streptomycin (P/S) solution, 500 µg/mL Zeocin and 10% charcoal/dextran-treated fetal bovine serum (cs-FBS) at 37° C. in a humidified 5% CO$_2$ atmosphere. Another plasmid was constructed in which the human cytomegalovirus promoter in the pcDNA3.1 vector directs the expression of the cDNA encoding a fusion protein comprised of the DNA binding domain from the Gal4 transcription factor fused to the ligand binding domain from human FXR.

The day prior to transfection, the reporter cells in culture are detached from the plate with trypsin and plated into a T75 flask at a sufficient density to achieve approximately 90% confluence the next morning. The transfection reagents are prepared by separately diluting 25 µg of the pcDNA3.1-Gal4-FXR plasmid into 1.87 mL of Opti-MEM (Thermo-Fisher), and 40 µL of Lipofectamine 2000 (Thermo-Fisher) into 1.87 mL of Opti-MEM, and then adding the diluted DNA solution into the diluted Lipofectamine 2000 solution and incubating at room temperature for 15-20 minutes. The mixture is further diluted with 10 mL of a solution comprised of DMEM, 10% cs-FBS, and 1% P/S immediately prior to transferring to the cells. The maintenance culture media is aspirated from the cells and the final transfection mixture is added before the cells are incubated overnight at 37° C. in a humidified 5% CO$_2$ atmosphere. This protocol can be scaled up, and the transiently transfected cells can be cryopreserved in an assay-ready format.

For compound testing, 100 nL of the compounds (serial dilutions in DMSO) are dispensed with an Echo acoustic dispenser (Labcyte) into the wells of a Corning/Costar clear bottom 384-well white plate. The transfected cells are harvested, counted, and diluted such that 10-25,000 cells in 25 µL are plated into each well of the 384-well compound assay plate. The compound-treated cells are incubated overnight at 37° C. in a humidified 5% CO$_2$ atmosphere. The next morning 25 µL of Steady-Glo (Promega) are added to each well of the plate, the mixture is incubated for 15 min. with shaking, and luminescence is measured on an Envision (Perkin Elmer) plate reader. Background counts from cells treated with DMSO alone are subtracted from all raw counts, and the corrected values are converted to a percentage of the control response attained with 8 µM GW-4064. These data are fit to a 4-parameter log agonist-response equation to calculate an EC$_{50}$ value.

Acute Mouse In Vivo Assay:

Male, C57BL6/NTac mice, weighing 25-28 g, are purchased from Taconic Labs (Hudson, N.Y.) and maintained on Teklad Global 18% Protein Rodent Diet (Harlan Laboratories). After 1 week acclimation, mice are sorted into groups based upon body weight. Mice are administered a single oral dose of vehicle or experimental compound. Systemic compound exposure is evaluated in plasma derived from blood collected via the submandibular vein at 1 hour post-dose, and at study termination (6 h). At study termination, the animals are euthanized and rapidly dissected. The medial lobe of the liver is divided, with one half being homogenized and analyzed for compound exposure, and the other half saved in RNAlater (Thermo-Fisher Scientific). The ileum is also dissected and preserved in RNAlater. Tissue samples in RNAlater are homogenized with MP Biomedicals' beads. RNA is extracted using the MagMax-96 Total RNA Isolation kit (Thermo-Fisher Scientific) according to the manufacturer's protocol. RNA Concentration is determined with the Nano-Drop 8000 Spectrophotometer (Thermo Fisher). Reverse transcription is done with Invitrogen's SuperScript® VILO cDNA Synthesis Kit according to the manufacturer's protocol. Real time PCR is done with Applied Biosystems' Taqman PCR master mixture according to the manufacturer's protocol. All primers are purchased from Thermo-Fisher Scientific. Mouse genes analyzed include Nr0b2 (which encodes the small heterodimer partner, SHP), Abcb11 (which encodes the bile salt excretion pump, BSEP), Cyp7a1, & Cyp8b1 in liver, and Fgf15, Fabp6 (which encodes ileal bile acid binding protein, I-BABP), Slc51a (which encodes organic solute transporter alpha subunit, OSTA), and Slc51b (which encodes organic solute transporter beta subunit, OSTB) in the ileum. The statistical significant changes in FGF15 gene expression are expressed as fold increase and CYP$_{7A1}$ expression as a percent reduction relative to vehicle control.

Other features of the invention should become apparent in the course of the above descriptions of exemplary embodiments that are given for illustration of the invention and are not intended to be limiting thereof. The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

BIOLOGICAL EVALUATION

The exemplified compounds of the present invention were tested in the transient human FXR/Gal4-luciferase reporter assay, and assay results were described in the EXAMPLES section hereinbefore.

A Gal4-hFXR fusion construct reporter system was used as the primary assay to characterize compound activity. A construct including 5 copies of the Gal4 promoter response element upstream of a firefly luciferase reporter cDNA was stably expressed in HEK293 cells. This reporter cell line was maintained in Dulbecco's Modified Eagle's medium (DMEM; Gibco) supplemented with 1% penicillin-streptomycin (P/S) solution, 500 µg/mL Zeocin and 10% charcoal/dextran-treated fetal bovine serum (cs-FBS) at 37° C. in a humidified 5% CO$_2$ atmosphere. Another plasmid was constructed in which the human cytomegalovirus promoter in the pcDNA3.1 vector directs the expression of the cDNA encoding a fusion protein comprised of the DNA binding domain from the Gal4 transcription factor fused to the ligand binding domain from human FXR.

The day prior to transfection, the reporter cells in culture are detached from the plate with trypsin and plated into a T75 flask at a sufficient density to achieve approximately 90% confluence the next morning. The transfection reagents are prepared by separately diluting 25 μg of the pcDNA3.1-Gal4-FXR plasmid into 1.87 mL of Opti-MEM (Thermo-Fisher), and 40 μL of Lipofectamine 2000 (Thermo-Fisher) into 1.87 mL of Opti-MEM, and then adding the diluted DNA solution into the diluted Lipofectamine 2000 solution and incubating at room temperature for 15-20 minutes. The mixture is further diluted with 10 mL of a solution comprised of DMEM, 10% cs-FBS, and 1% P/S immediately prior to transferring to the cells. The maintenance culture media is aspirated from the cells and the final transfection mixture is added before the cells are incubated overnight at 37° C. in a humidified 5% $CO_2$ atmosphere. This protocol can be scaled up, and the transiently transfected cells can be cryopreserved in an assay-ready format.

For compound testing, 100 nL of the compounds (serial dilutions in DMSO) are dispensed with an Echo acoustic dispenser (Labcyte) into the wells of a Corning/Costar clear bottom 384-well white plate. The transfected cells are harvested, counted, and diluted such that 10-25,000 cells in 25 μL are plated into each well of the 384-well compound assay plate. The compound-treated cells are incubated overnight at 37° C. in a humidified 5% $CO_2$ atmosphere. The next morning 25 μL of Steady-Glo (Promega) are added to each well of the plate, the mixture is incubated for 15 min. with shaking, and luminescence is measured on an Envision (Perkin Elmer) plate reader. Background counts from cells treated with DMSO alone are subtracted from all raw counts, and the corrected values are converted to a percentage of the control response attained with 8 μM GW-4064. These data are fit to a 4-parameter log agonist-response equation to calculate an $EC_{50}$ value.

In Vivo Testing Example: Acute Mouse PK/PD

Male, C57BL6/NTac mice, weighing 25-28 g, are purchased from Taconic Labs (Hudson, N.Y.) and maintained on Teklad Global 18% Protein Rodent Diet (Harlan Laboratories). After 1 week acclimation, mice are sorted into groups based upon body weight. Mice are administered a single oral dose of vehicle or experimental compound. Systemic compound exposure is evaluated in plasma derived from blood collected via the submandibular vein at 1 hour post-dose, and at study termination (6 h). At study termination, the animals are euthanized and rapidly dissected. The medial lobe of the liver is divided, with one half being homogenized and analyzed for compound exposure, and the other half saved in RNAlater (Thermo-Fisher Scientific). The ileum is also dissected and preserved in RNAlater. Tissue samples in RNAlater are homogenized with MP Biomedicals' beads. RNA is extracted using the MagMax-96 Total RNA Isolation kit (Thermo-Fisher Scientific) according to the manufacturer's protocol. RNA Concentration is determined with the Nano-Drop 8000 Spectrophotometer (Thermo Fisher). Reverse transcription is done with Invitrogen's SuperScript® VILO cDNA Synthesis Kit according to the manufacturer's protocol. Real time PCR is done with Applied Biosystems' Taqman PCR master mixture according to the manufacturer's protocol. All primers are purchased from Thermo-Fisher Scientific. Mouse genes analyzed include Nr0b2 (which encodes the small heterodimer partner, SHP), Abcb11 (which encodes the bile salt excretion pump, BSEP), Cyp7a1, & Cyp8b1 in liver, and Fgf15, Fabp6 (which encodes ileal bile acid binding protein, I-BABP), Slc51a (which encodes organic solute transporter alpha subunit, OSTA), and Slc51b (which encodes organic solute transporter beta subunit, OSTB) in the ileum. The statistical significant changes in FGF15 gene expression are expressed as fold increase and $CYP_{7A1}$ expression as a percent reduction relative to vehicle control.

Other features of the invention should become apparent in the course of the above descriptions of exemplary embodiments that are given for illustration of the invention and are not intended to be limiting thereof. The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional embodiments. It is also understood that each individual element of the embodiments is its own independent embodiment. Furthermore, any element of an embodiment is meant to be combined with any and all other elements from any embodiment to describe an additional embodiment.

What is claimed is:
1. A compound of Formula (I):

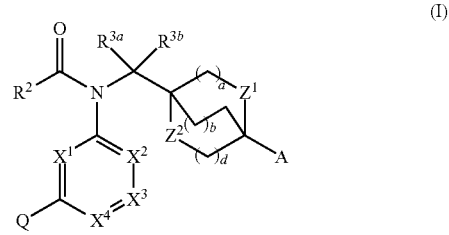

or a stereoisomer, or a salt or solvate thereof, wherein:
$X^1$ is CH;
$X^2$ is CH or N;
$X^3$ is CH;
$X^4$ is CH;
$Z^1$ and $Z^2$ are each $CH_2$;
a is 1;
b is 1;
d is 1;
Q is phenyl substituted with $R^1$;
$R^1$ is $C_{1-4}$ alkyl, $C_{1-2}$ fluoroalkyl, —$CH_2Cl$, $C_{1-4}$ hydroxyalkyl, —$C(CH_3)_2CN$, or —$CH(OH)CHF_2$;
$R^2$ is:
  (i) $C_{1-4}$ alkyl, $C_{1-5}$ alkoxy, or —$NH(C_{1-6}$ alkyl), wherein each of said alkyl and alkoxy is substituted with zero to 4 $R^{2a}$; or
  (ii) $C_{3-6}$ cycloalkyl substituted with zero to 3 $R^{2b}$;
each $R^{2a}$ is independently F, cyano, hydroxyl, $C_{1-2}$ alkoxy, or —$NH_2$;
each $R^{2b}$ is independently F, cyano, hydroxyl, $C_{1-3}$ alkyl, $C_{1-2}$ fluoroalkyl, $C_{1-3}$ hydroxyalkyl, $C_{1-2}$ alkoxy, $C_{1-2}$ fluoroalkoxy, or —$NH_2$;
$R^{3a}$ is hydrogen;
$R^{3b}$ is hydrogen;
A is oxadiazolyl substituted with $R^{4a}$;
$R^{4a}$ is $C_{1-4}$ alkyl substituted with zero to 4 $R^{4d}$; and
each $R^{4d}$ is independently F, Cl, hydroxyl, —$NH_2$, cyano, $C_{1-3}$ alkoxy, or $C_{1-3}$ fluoroalkoxy.

2. The compound according to claim 1 or a stereoisomer, or a salt or solvate thereof, having the structure:

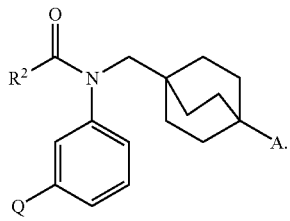

3. The compound according to claim 1 or a stereoisomer, or a salt or solvate thereof, having the structure:

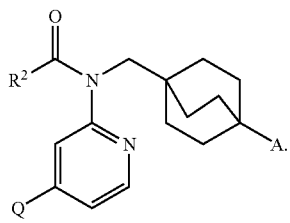

4. A compound having the structure:

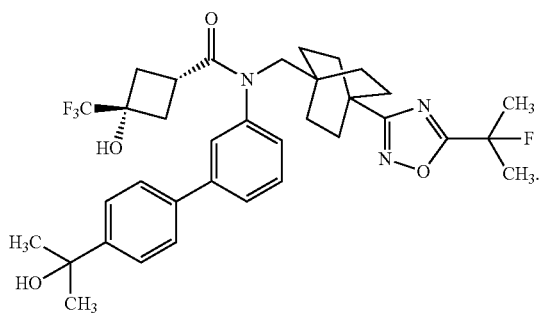 [SMILES: CC(C)(O)c1ccc(-c2cccc(N(CC34CCC(c5noc(C(C)(C)F)n5)(CC3)CC4)C(=O)[C@H]3C[C@](O)(C(F)(F)F)C3)c2)cc1]

5. A pharmaceutically acceptable salt of a compound having the structure:

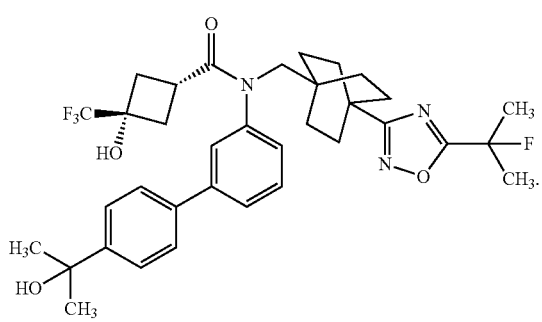 [SMILES: CC(C)(O)c1ccc(-c2cccc(N(CC34CCC(c5noc(C(C)(C)F)n5)(CC3)CC4)C(=O)[C@H]3C[C@](O)(C(F)(F)F)C3)c2)cc1]

6. A compound having the structure:

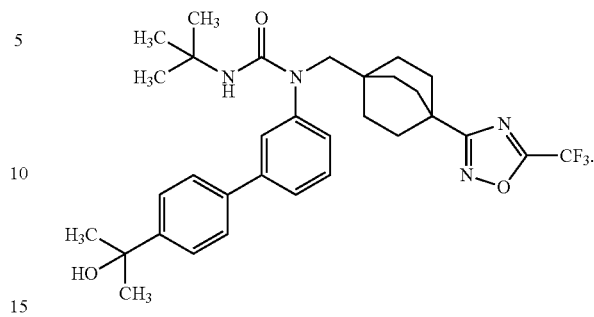

7. A pharmaceutically acceptable salt of a compound having the structure:

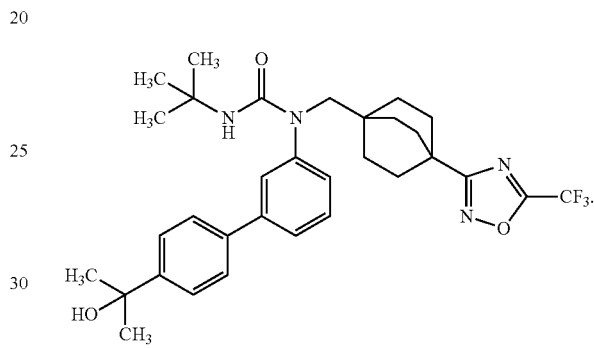

8. A compound having the structure:

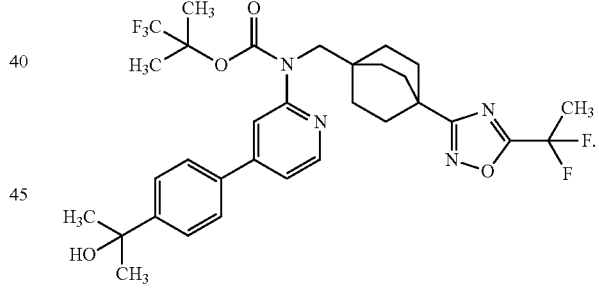

9. A pharmaceutically acceptable salt of a compound having the structure:

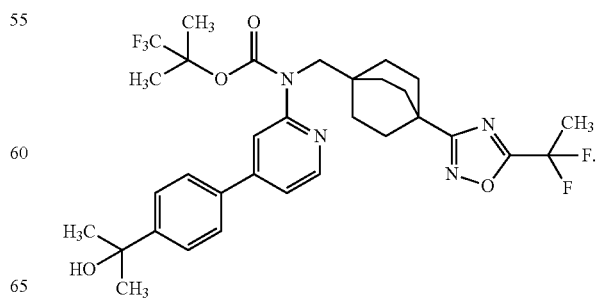

10. A pharmaceutical composition comprising a pharmaceutically acceptable carrier and a compound according to claim 1, or a stereoisomer, or a pharmaceutically acceptable salt or solvate thereof.

11. A pharmaceutical composition comprising a pharmaceutically acceptable carrier and said compound according to claim 4.

12. A pharmaceutical composition comprising a pharmaceutically acceptable carrier and said pharmaceutically acceptable salt of the compound according to claim 5.

13. A pharmaceutical composition comprising a pharmaceutically acceptable carrier and said compound according to claim 6.

14. A pharmaceutical composition comprising a pharmaceutically acceptable carrier and said pharmaceutically acceptable salt of the compound according to claim 7.

15. A pharmaceutical composition comprising a pharmaceutically acceptable carrier and said compound according to claim 8.

16. A pharmaceutical composition comprising a pharmaceutically acceptable carrier and said pharmaceutically acceptable salt of the compound according to claim 9.

17. A method of treating a disease or disorder, comprising administering to a mammalian patent a compound according to claim 1 or a pharmaceutically acceptable salt thereof, wherein said disease or disorder is pathological fibrosis, metabolic disorders, or cholestatic disorders.

18. The method according to claim 17, wherein the pathological fibrosis is liver fibrosis, renal fibrosis, biliary fibrosis, or pancreatic fibrosis.

19. The method according to claim 17, wherein said disease or disorder is nonalcoholic steatohepatitis (NASH), non-alcoholic fatty liver disease (NAFLD), chronic kidney disease, diabetic kidney disease, primary sclerosing cholangitis (PSC), or primary biliary cirrhosis (PBC).

20. The method according to claim 17, wherein said disease or disorder is idiopathic pulmonary fibrosis (IPF).

21. A method of treating a disease or disorder, comprising administering to a mammalian patent the compound according to claim 4, wherein said disease or disorder is liver fibrosis, renal fibrosis, biliary fibrosis, pancreatic fibrosis, nonalcoholic steatohepatitis (NASH), non-alcoholic fatty liver disease (NAFLD), chronic kidney disease, diabetic kidney disease, primary sclerosing cholangitis (PSC), or primary biliary cirrhosis (PBC).

22. A method of treating a disease or disorder, comprising administering to a mammalian patent the pharmaceutically acceptable salt of the compound according to claim 5, wherein said disease or disorder is liver fibrosis, renal fibrosis, biliary fibrosis, pancreatic fibrosis, nonalcoholic steatohepatitis (NASH), non-alcoholic fatty liver disease (NAFLD), chronic kidney disease, diabetic kidney disease, primary sclerosing cholangitis (PSC), or primary biliary cirrhosis (PBC).

23. A method of treating a disease or disorder, comprising administering to a mammalian patent the compound according to claim 6, wherein said disease or disorder is liver fibrosis, renal fibrosis, biliary fibrosis, pancreatic fibrosis, nonalcoholic steatohepatitis (NASH), non-alcoholic fatty liver disease (NAFLD), chronic kidney disease, diabetic kidney disease, primary sclerosing cholangitis (PSC), or primary biliary cirrhosis (PBC).

24. A method of treating a disease or disorder, comprising administering to a mammalian patent the pharmaceutically acceptable salt of the compound according to claim 7, wherein said disease or disorder is liver fibrosis, renal fibrosis, biliary fibrosis, pancreatic fibrosis, nonalcoholic steatohepatitis (NASH), non-alcoholic fatty liver disease (NAFLD), chronic kidney disease, diabetic kidney disease, primary sclerosing cholangitis (PSC), or primary biliary cirrhosis (PBC).

25. A method of treating a disease or disorder, comprising administering to a mammalian patent the compound according to claim 8, wherein said disease or disorder is liver fibrosis, renal fibrosis, biliary fibrosis, pancreatic fibrosis, nonalcoholic steatohepatitis (NASH), non-alcoholic fatty liver disease (NAFLD), chronic kidney disease, diabetic kidney disease, primary sclerosing cholangitis (PSC), or primary biliary cirrhosis (PBC).

26. A method of treating a disease or disorder, comprising administering to a mammalian patent the pharmaceutically acceptable salt of the compound according to claim 9, wherein said disease or disorder is liver fibrosis, renal fibrosis, biliary fibrosis, pancreatic fibrosis, nonalcoholic steatohepatitis (NASH), non-alcoholic fatty liver disease (NAFLD), chronic kidney disease, diabetic kidney disease, primary sclerosing cholangitis (PSC), or primary biliary cirrhosis (PBC).

* * * * *